United States Patent
Vandyck et al.

(10) Patent No.: US 11,952,365 B2
(45) Date of Patent: Apr. 9, 2024

(54) ANTI-VIRAL COMPOUNDS

(71) Applicants: Aligos Therapeutics, Inc., South San Francisco, CA (US); Katholieke Universiteit Leuven, Leuven (BE)

(72) Inventors: Koen Vandyck, Paal (BE); Pierre Jean-Marie Bernard Raboisson, Wavre (BE); Leonid Beigelman, San Mateo, CA (US); Vladimir Serebryany, Burlingame, CA (US); Antitsa Dimitrova Stoycheva, Half Moon Bay, CA (US); Dorothée Alice Marie-Eve Bardiot, Leuven (BE); Sandro Boland, Leuven (BE); Arnaud Didier Marie Marchand, Leuven (BE)

(73) Assignees: Aligos Therapeutics, Inc., South San Francisco, CA (US); Katholieke Universiteit Leuven, Leuven (BE)

( * ) Notice: Subject to any disclaimer, the term of this patent is extended or adjusted under 35 U.S.C. 154(b) by 138 days.

(21) Appl. No.: 17/303,815

(22) Filed: Jun. 8, 2021

(65) Prior Publication Data

US 2022/0009903 A1 Jan. 13, 2022

Related U.S. Application Data

(60) Provisional application No. 63/155,113, filed on Mar. 1, 2021, provisional application No. 63/125,562, filed on Dec. 15, 2020, provisional application No. 63/086,787, filed on Oct. 2, 2020, provisional application No. 63/085,871, filed on Sep. 30, 2020, provisional application No. 63/055,679, filed on Jul. 23, 2020, provisional application No. 63/037,200, filed on Jun. 10, 2020.

(51) Int. Cl.
| | |
|---|---|
| C07D 401/14 | (2006.01) |
| A61K 31/404 | (2006.01) |
| A61K 31/4178 | (2006.01) |
| A61K 31/428 | (2006.01) |
| A61K 31/437 | (2006.01) |
| A61K 31/454 | (2006.01) |
| A61K 31/675 | (2006.01) |
| A61K 45/06 | (2006.01) |
| A61P 31/14 | (2006.01) |
| C07D 403/14 | (2006.01) |
| C07D 405/14 | (2006.01) |
| C07D 409/14 | (2006.01) |
| C07D 417/14 | (2006.01) |
| C07D 471/04 | (2006.01) |
| C07F 9/6558 | (2006.01) |

(52) U.S. Cl.
CPC .......... *C07D 401/14* (2013.01); *A61K 31/404* (2013.01); *A61K 31/4178* (2013.01); *A61K 31/428* (2013.01); *A61K 31/437* (2013.01); *A61K 31/454* (2013.01); *A61K 31/675* (2013.01); *A61K 45/06* (2013.01); *A61P 31/14* (2018.01); *C07D 403/14* (2013.01); *C07D 405/14* (2013.01); *C07D 409/14* (2013.01); *C07D 417/14* (2013.01); *C07D 471/04* (2013.01); *C07F 9/65583* (2013.01)

(58) Field of Classification Search
None
See application file for complete search history.

(56) References Cited

U.S. PATENT DOCUMENTS

| | | | |
|---|---|---|---|
| 4,388,305 | A | 6/1983 | Trouet et al. |
| 4,639,456 | A | 1/1987 | Trouet et al. |
| 4,970,297 | A | 1/1990 | Castelhano et al. |
| 5,147,865 | A | 9/1992 | Habich et al. |
| 5,364,931 | A | 11/1994 | Haebich et al. |
| 5,514,694 | A | 5/1996 | Powers et al. |
| 5,756,528 | A | 5/1998 | Anthony et al. |
| 5,847,135 | A | 12/1998 | Bemis et al. |
| 5,856,309 | A | 1/1999 | Konetschny-Rapp et al. |
| 5,874,424 | A | 2/1999 | Batchelor et al. |
| 6,162,791 | A | 12/2000 | Karimian et al. |
| 6,174,887 | B1 | 1/2001 | Haruta et al. |
| 11,124,497 | B1 * | 9/2021 | Arnold .............. C07D 401/12 |
| 2004/0110945 | A1 | 6/2004 | Nakayama et al. |
| 2004/0171489 | A1 | 9/2004 | Hacker et al. |
| 2006/0111303 | A1 | 5/2006 | Hatayama et al. |
| 2007/0238769 | A1 | 10/2007 | Ochi et al. |

(Continued)

FOREIGN PATENT DOCUMENTS

| | | |
|---|---|---|
| AU | 2002318741 | 3/2003 |
| CA | 2851462 | 7/2004 |

(Continued)

OTHER PUBLICATIONS

CAS Reg. No. 1040187-41-4, Entry Date Aug. 11, 2008.
CAS Reg. No. 1212645-49-2, Entry Date Mar. 21, 2010.
CAS Reg. No. 1240410-37-0, Entry Date Sep. 9, 2010.
Calaza et al., "Synthesis of [c]-Fused Bicyclic Proline Analogues" Eur. J. Org. Chem. (2015), 2015(8):1633-1658.

(Continued)

*Primary Examiner* — Zinna Northington Davis
(74) *Attorney, Agent, or Firm* — Knobbe Martens Olson & Bear LLP

(57) ABSTRACT

Provided herein are compounds of Formula (I), or pharmaceutically acceptable salts thereof, pharmaceutical compositions that include a compound described herein (including pharmaceutically acceptable salts of a compound described herein) and methods of synthesizing the same. Also provided herein are methods of treating diseases and/or conditions with a compound of Formula (I), or a pharmaceutically acceptable salt thereof.

18 Claims, No Drawings

(56) References Cited

U.S. PATENT DOCUMENTS

| | | |
|---|---|---|
| 2013/0109661 A1 | 5/2013 | Hermann et al. |
| 2013/0178478 A1 | 7/2013 | Hermann et al. |
| 2014/0194386 A1 | 7/2014 | Burns et al. |
| 2014/0374657 A1 | 12/2014 | Matsuyama et al. |
| 2017/0324007 A1 | 11/2017 | Pentlehmer |

FOREIGN PATENT DOCUMENTS

| | | |
|---|---|---|
| CN | 103254129 | 8/2013 |
| CN | 103288832 | 9/2013 |
| DE | 4016994 | 11/1991 |
| EP | 472077 | 2/1992 |
| EP | 472078 | 2/1992 |
| EP | 520336 | 12/1992 |
| EP | 525420 | 2/1993 |
| EP | 1217000 | 6/2002 |
| EP | 2270025 | 1/2011 |
| EP | 3835296 | 6/2021 |
| JP | 63144084 | 6/1988 |
| JP | 06192199 | 7/1994 |
| JP | 04334357 | 11/1995 |
| JP | 09124571 | 5/1997 |
| JP | 2002145848 | 5/2002 |
| JP | 2005336172 | 12/2005 |
| JP | 2006232707 | 9/2006 |
| JP | 2013032343 | 2/2013 |
| JP | 2015174929 | 10/2015 |
| WO | WO 89/04833 | 6/1989 |
| WO | WO 92/00954 | 1/1992 |
| WO | WO 92/20357 | 11/1992 |
| WO | WO 93/12796 | 7/1993 |
| WO | WO 95/07294 | 3/1995 |
| WO | WO 95/09858 | 4/1995 |
| WO | WO 95/12611 | 5/1995 |
| WO | WO 95/35308 | 12/1995 |
| WO | WO 96/16981 | 6/1996 |
| WO | WO 96/39137 | 12/1996 |
| WO | WO 96/40732 | 12/1996 |
| WO | WO 97/08133 | 3/1997 |
| WO | WO 97/22619 | 6/1997 |
| WO | WO 97/31939 | 9/1997 |
| WO | WO 98/53814 | 12/1998 |
| WO | WO 98/53817 | 12/1998 |
| WO | WO 99/67230 | 12/1999 |
| WO | WO 2000/016627 | 3/2000 |
| WO | WO 2000/071572 | 11/2000 |
| WO | WO 01/79167 | 10/2001 |
| WO | WO 2002/085899 | 10/2001 |
| WO | WO 2002/053534 | 7/2002 |
| WO | WO 2003/008380 | 1/2003 |
| WO | WO 2003/039529 | 5/2003 |
| WO | WO 2003/091202 | 11/2003 |
| WO | WO 2004/032846 | 4/2004 |
| WO | WO 2004/046107 | 6/2004 |
| WO | WO 2004/062601 | 7/2004 |
| WO | WO 2005/014532 | 2/2005 |
| WO | WO 2005/061475 | 7/2005 |
| WO | WO 2005/102381 | 11/2005 |
| WO | WO 2007/022459 | 2/2007 |
| WO | WO 2007/067836 | 6/2007 |
| WO | WO 2008/074035 | 6/2008 |
| WO | WO 2008/121065 | 10/2008 |
| WO | WO 2008/154642 | 12/2008 |
| WO | WO 2009/043889 | 4/2009 |
| WO | WO 2009/105782 | 8/2009 |
| WO | WO 2010/077836 | 7/2010 |
| WO | WO 2010/126881 | 11/2010 |
| WO | WO 2011/043994 | 4/2011 |
| WO | WO 2011/048390 | 4/2011 |
| WO | WO 2011/050160 | 4/2011 |
| WO | WO 2011/082337 | 7/2011 |
| WO | WO 2012/058645 | 5/2012 |
| WO | WO 2012/065963 | 5/2012 |
| WO | WO 2012/083048 | 6/2012 |
| WO | WO 2012/123938 | 9/2012 |
| WO | WO 2012/163724 | 12/2012 |
| WO | WO 2013/003720 | 1/2013 |
| WO | WO 2013/133178 | 9/2013 |
| WO | WO 2013/178816 | 12/2013 |
| WO | WO 2014/151958 | 9/2014 |
| WO | WO 2016/075150 | 5/2016 |
| WO | WO 2017/091616 | 6/2017 |
| WO | WO 2017/197377 | 11/2017 |
| WO | WO 2018/045084 | 3/2018 |
| WO | WO 2018/064119 | 4/2018 |
| WO | WO 2018/112626 | 6/2018 |
| WO | WO 2018/167269 | 9/2018 |
| WO | WO 2019/190885 | 10/2019 |
| WO | WO 2019/190999 | 10/2019 |
| WO | WO 2020/006294 | 1/2020 |
| WO | WO 2020/030143 | 2/2020 |
| WO | WO 2020/123675 | 6/2020 |
| WO | WO 2020/160707 | 8/2020 |
| WO | WO 2020/185830 | 9/2020 |
| WO | WO 2021/151265 | 8/2021 |
| WO | WO 2021/151387 | 8/2021 |
| WO | WO 2021/250648 | 12/2021 |
| WO | WO 2021/252644 | 12/2021 |

OTHER PUBLICATIONS

Cox et al., "Escaping form Flatland: Substituted Bridged Pyrrolidine Fragments with Inherent Three-Dimensional Character" ACS Med. Chem. Lett. (2020) 11(6):1185-1190.

Eiden et al., "Synthesis of a 3-Amino-2,3-dihdropyrid-4-one and Related Heterocyclic Anaalogues as Mechanism-Based Inhibitors of BioA, a Pyridoxal Phosphate-Dependent Enzyme" J. Org. Chem. (2017) 82(15):7806-7819.

Gupton et al., "Application of 2-Substituted Vinamidinium Salts to the Synthesis of 2,4-Disubstituted Pyrroles" J. Org. Chem. (1990) 55(15):4735-4740.

Hoffmann et al., "SARS-COV-2 Cell Entry Depends onACE2 and TMPRSS2 and Is Blocked by a Clinically Proven Protease Inhibitor" Cell (2020) 181:271-280.

Kim et al., "Broad-Spectrum Antivirals against 3C or 3C-Like Proteases of Picornaviruses, Noroviruses, and Coronaviruses" Journal of Virology (2012) 86(21):11754-11762.

Liu et al., "Modular and Stereoselective Synthesis of Tetrasubstituted Helical Alkenes via a Palladium-Catalyzed Domino Reaction" Org. Lett. (2012) 14(14):3648-3651.

Mellott et al., "A cysteine protease inhibitor blocks SARS-COV-2 infection of human and monkey cells" bioRxiv (2020) 2020.2010. 2023.347534.

Mulamreddy et al., "4-Vinylproline" J. Org. Chem. (2018) 83(21):13580-13586.

Roy et al., "The Hemetsberger-Knittel Synthesis of Substituted 5-,6-, and 7-Azaindoles" Synthesis (2005) 16:2751-2757.

Shang et al., "Cell entry mechanisms of SARS-COV-2" PNAS (2020) 117(21):11727-11734.

Steuten et al., "Challenges for targeting SARS-COV-2 proteases as a therapeutic strategy for COVID-19" bioRxiv (2020) 2020.2011. 2021.392753.

Zhang et al., "α-Ketoamides as Broad-Spectrum Inhibitors of Coronavirus and Enterovirus Replication: Structure-Based Design, Synthesis, and Activity Assessment" J. Med. Chem. (2020) 63:4562-4578.

https://www.cdc.gov/coronavirus/2019-ncov/need-extra-precautions/groups-at-higher-risk.html, (2019).

International Search Report and Written Opinion dated Jul. 26, 2021 for PCT Application No. PCT/US2021/036403, filed Jun. 8, 2021.

International Preliminary Report on Patentability dated Dec. 13, 2022 for PCT Application No. PCT/US2021/036403, filed Jun. 8, 2021.

* cited by examiner

ANTI-VIRAL COMPOUNDS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application No. 63/037,200, filed Jun. 10, 2020, 63/055,679, filed Jul. 23, 2020, 63/085,871, filed Sep. 30, 2020, 63/086,787, filed Oct. 2, 2020, 63/125,562, filed Dec. 15, 2020 and 63/155,113, filed Mar. 1, 2021.

BACKGROUND

Field

The present application relates to the fields of chemistry, biochemistry and medicine. Disclosed herein are compounds of Formula (I), or pharmaceutically acceptable salt thereof, pharmaceutical compositions that include a compound described herein (including pharmaceutically acceptable salts of a compound described herein) and methods of synthesizing the same. Also disclosed herein are methods of treating diseases and/or conditions with a compound of Formula (I), or a pharmaceutically acceptable salt thereof.

Description

A positive-sense single-stranded RNA virus ((+)ssRNA virus) is a virus that uses positive sense, single stranded, RNA as its genetic material. Positive-sense single-stranded RNA viruses can be enveloped or non-enveloped. Coronaviridae, Picornaviridae and Norviruses are each a (+)ssRNA virus. Each of the aforementioned viruses are known to infect mammals, including humans.

SUMMARY

Some embodiments disclosed herein relate to a compound of Formula (I), or a pharmaceutically acceptable salt thereof.

Some embodiments disclosed herein relate to a pharmaceutical composition that can contain an effective amount of a compound of Formula (I), or a pharmaceutically acceptable salt thereof.

Some embodiments described herein relate to a method of treating a coronavirus infection that can include administering to a subject identified as suffering from the coronavirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a coronavirus infection.

Some embodiments disclosed herein relate to a method of inhibiting replication of a coronavirus that can include contacting a cell infected with the coronavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication a coronavirus.

Some embodiments described herein relate to a method of treating a picornavirus infection that can include administering to a subject identified as suffering from the picornavirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a picornavirus infection.

Some embodiments disclosed herein relate to a method of inhibiting replication of a picornavirus that can include contacting a cell infected with the picornavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication a picornavirus.

Some embodiments described herein relate to a method of treating a norovirus infection that can include administering to a subject identified as suffering from the norovirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a norovirus infection.

Some embodiments disclosed herein relate to a method of inhibiting replication of a norovirus that can include contacting a cell infected with the norovirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication a norovirus.

These are other embodiments are described in greater detail below.

DETAILED DESCRIPTION

Coronaviridae viruses are a family of enveloped, positive-stranded, single-stranded, spherical RNA viruses. Coronaviruses are named for the crown-like spikes on their surface. The Coronaviridae family includes two sub-families, Coronavirus and Torovirus. The Coronavirus genus has a helical nucleocapsid, and Torovirus genus has a tubular nucleocapsid. The Coronaviridae family of viruses includes Middle East respiratory syndrome coronavirus (MERS-CoV), SARS and SARS-CoV-2.

Coronavirus disease 2019 (COVID-19) (also referred to as novel coronavirus pneumonia or 2019-nCoV acute respiratory disease) is an infectious disease caused by the virus severe respiratory syndrome coronavirus 2 (SARS-CoV-2) (also referred to as novel coronavirus 2019, or 2019-nCoV). The disease was first identified in December 2019 and spread globally, causing a pandemic. Symptoms of COVID-19 include fever, cough, shortness of breath, fatigue, headache, loss of smell, nasal congestion, sore throat, coughing up sputum, pain in muscles or joints, chills, nausea, vomiting, and diarrhea. In severe cases, symptoms can include difficulty waking, confusion, blueish face or lips, coughing up blood, decreased white blood cell count, and kidney failure. Complications can include pneumonia, viral sepsis, acute respiratory distress syndrome, and kidney failure.

COVID-19 is especially threatening to public health. The virus is highly contagious, and studies currently indicate that it can be spread by asymptomatic carriers or by those who are pre-symptomatic. Likewise, the early stage of the disease is slow-progressing enough that carriers do not often realize they are infected, leading them to expose numerous others to the virus. The combination of COVID-19's ease of transmission, its high rate of hospitalization of victims, and its death rate make the virus a substantial public health risk, especially for countries without a healthcare system equipped to provide supportive care to pandemic-level numbers of patients. There is not yet a vaccine or specific antiviral treatment for COVID-19 and accordingly, there is a pressing need for treatments or cures.

SARS-CoV-2 is not the only coronavirus that causes disease. It is a β-coronavirus, a genus of coronaviruses that includes other human pathogens, including SARS-CoV (the causative agent of SARS), MERS-CoV (the causative agent of MERS), and HCoV-OC43 (a causative agent of the common cold). The infectivity of these viruses, and the severity of the diseases they cause, varies widely. β-coronavirus can also manifest as zoonotic infections, spread to and from humans and animals. Additionally, non-human species such as camels, bats, tigers, non-human primates, and rabbits can be susceptible to β-coronavirus. Accordingly, there is a pressing need for treatments or cures to multiple coronaviruses.

The present disclosure provides molecules useful against coronaviruses, and especially SARS-CoV-2, the causative agent of COVID-19 in humans. Accordingly, the present disclosure fulfills the need in the art for compounds that can be safely and effectively treat or prevent coronavirus infections in humans.

Picornaviruses are a family of positive strand RNA, nonenveloped viruses. A picornavirus has 60 identical subunits (vertices) which contain five protomers. Each protomer is made up of one copy of four proteins, named VP1, VP2, VP3 and VP4. There are several genera of picornaviruses, including, Enterovirus, Aphthovirus, Cardiovirus, and Hepatovirus. Enteroviruses known to infect human include, but are not limited to, Rhinovirus A, Rhinovirus B, Rhinovirus C, Coxsackievirus A, Coxsackievirus B and Poliovirus. There is no specific treatment for a picornavirus infection.

Noroviruses are single-stranded positive-sense RNA, non-enveloped viruses belonging to the Caliciviridae family. Noroviruses are often spread by the fecal-oral route, and are a common cause of gastroenteritis. Infected subjects can experience nausea, non-bloody diarrhea, vomiting and/or abdominal pain. Those suffering from a norovirus infection can become severely dehydrated and require medical attention. As with a picornavirus infection, there is no specific treatment for a norovirus infection. Accordingly, there is a need for compounds that effectively treat or prevent a picornavirus and/or a norovirus infection.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) (such as 1, 2 or 3) individually and independently selected from deuterium, alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, C-amido(alkyl), isocyanato, thiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amine and a di-substituted amine.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The length of an alkenyl can vary. For example, the alkenyl can be a $C_{2-4}$ alkenyl, $C_{2-6}$ alkenyl or $C_{2-8}$ alkenyl. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. The length of an alkynyl can vary. For example, the alkynyl can be a $C_{2-4}$ alkynyl, $C_{2-6}$ alkynyl or $C_{2-8}$ alkynyl. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused- or spiro-fashion. Cycloalkyl groups can contain 3 to 10 atoms in the ring(s). 3 to 8 atoms in the ring(s) or 3 to 6 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused- or spiro-fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to a monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The number of atoms in the ring(s) of a heterocyclyl group can vary. For example, the heterocyclyl group can contain 4 to 14 atoms in the ring(s), 5 to 10 atoms in the ring(s) or 5 to 6 atoms in the ring(s). The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl groups may be unsubstituted or substituted. Examples of such "heterocyclyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl), and their benzo-fused analogs.

A "(heterocyclyl)alkyl" refer to a heterocyclic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin- 4-yl(ethyl), piperidin-4-yl(propyl), tetrahydro-2H-thiopyran-4-yl(methyl) and 1,3-thiazinan-4-yl(methyl).

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—) and butylene (—CH$_2$CH$_2$CH$_2$CH$_2$—). A lower alkylene group can be substituted by replacing one or more hydrogen of the lower alkylene group with a substituent(s) listed under the definition of "substituted." Further, when a lower alkylene group is substituted, the lower alkylene can be substituted by replacing both hydrogens on the same carbon with a cycloalkyl group

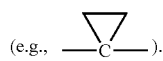

(e.g., ).

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzyloxy. In some instances, an alkoxy can be —OR, wherein R is an unsubstituted C$_{1-4}$ alkyl. An alkoxy may be substituted or unsubstituted.

As used herein, "acyl" refers to a hydrogen, an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) connected, as substituents, via a carbonyl group. Examples include formyl, acetyl, propanoyl, benzoyl and acryl. An acyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group and O-monocyclic cycloalkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy, 2-fluoroisobutoxy, chloro-substituted cyclopropyl, fluoro-substituted cyclopropyl, chloro-substituted cyclobutyl and fluoro-substituted cyclobutyl. In some instances, a haloalkoxy can be —OR, wherein R is a C$_{1-4}$ alkyl substituted by 1, 2 or 3 halogens. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein each X is a halogen.

A "trihalomethanesulfonamido" group refers to an "X$_3$CS(O)$_2$N(R$_A$)—" group wherein each X is a halogen, and R$_A$ is hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a —C(=O)— group.

An "S-sulfonamido" group refers to a "—SO$_2$N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "—OC(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "ROC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "—OC(=S)—N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "ROC(=S)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(=O)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

A "mono-substituted amine" refers to a "—$NHR_A$" in which $R_A$ can be independently alkyl, alkenyl, alkynyl, cycloalkyl, cycloalkenyl, aryl, heteroaryl, heterocyclyl, aryl(alkyl), heteroaryl(alkyl) or heterocyclyl(alkyl). A mono-substituted amine may be substituted or unsubstituted. In some instances, a mono-substituted amine can be —$NHR_A$, wherein $R_A$ can be an unsubstituted $C_{1-6}$ alkyl or an unsubstituted or a substituted benzyl.

A "di-substituted amine" refers to a "—$NR_AR_B$" in which $R_A$ and $R_B$ can be independently can be independently alkyl, alkenyl, alkynyl, cycloalkyl, cycloalkenyl, aryl, heteroaryl, heterocyclyl, aryl(alkyl), heteroaryl(alkyl) or heterocyclyl (alkyl). A mono-substituted amine may be substituted or unsubstituted. In some instances, a mono-substituted amine can be —$NR_AR_B$, wherein $R_A$ and $R_B$ can be independently an unsubstituted $C_{1-6}$ alkyl or an unsubstituted or a substituted benzyl.

A "ketoamide" group refers to a —C(=O)—C(=O)N($R_AR_B$) group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A ketoamide may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof. In addition, the term "comprising" is to be interpreted synonymously with the phrases "having at least" or "including at least". When used in the context of a compound or composition, the term "comprising" means that the compound or composition includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality.

It is understood that, in any compound described herein having one or more chiral centers, if an absolute stereochemistry is not expressly indicated, then each center may independently be of (R)-configuration or (S)-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof:

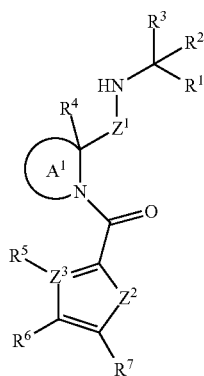

(I)

wherein: $Z^1$ can be —C(=O)— or —CH(CF$_3$)—; $Z^2$ can be O (oxygen), S (sulfur) or NR$^8$, wherein R$^8$ can be H or an unsubstituted C$_{1-4}$ alkyl; $Z^3$ can be N (nitrogen) or C (carbon), and when $Z^3$ is N, then R$^5$ is absent; Ring A$^1$ can be selected from an unsubstituted or a substituted azetidine, an unsubstituted or a substituted pyrrolidine and an unsubstituted or a substituted piperidine, wherein the azetidine, the pyrrolidine and the piperidine can be optionally substituted with one or more R$^x$ groups independently selected from deuterium, halogen, an unsubstituted or a substituted C$_{1-4}$ alkyl, an unsubstituted or a substituted C$_{2-4}$ alkenyl, an unsubstituted or a substituted C$_{1-8}$ alkoxy, an unsubstituted or a substituted C$_{3-6}$ cycloalkyl, an unsubstituted or a substituted aryl, an unsubstituted or a substituted heteroaryl, an unsubstituted or a substituted heterocyclyl and an unsubstituted C$_{1-4}$ haloalkyl, and wherein the azetidine, the pyrrolidine and the piperidine can be connected to a cyclic moiety selected from a monocyclic C$_{3-7}$ cycloalkyl, a bicyclic C$_{5-9}$ cycloalkyl, a monocyclic C$_{3-7}$ cycloalkenyl, a bicyclic C$_{5-9}$ cycloalkenyl and phenyl, wherein the cyclic moiety is connected to the azetidine, the pyrrolidine and the piperidine in a fused-fashion or a spiro-fashion that can be optionally substituted with one or more moieties independently selected from the group consisting of halogen, an unsubstituted C$_{1-4}$ alkyl, an unsubstituted C$_{2-4}$ alkenyl and an unsubstituted or a substituted C$_{3-6}$ monocyclic cycloalkyl; R$^1$ can be selected from cyano, an unsubstituted or a substituted C$_{2-5}$ alkynyl, an unsubstituted or a substituted acyl, an unsubstituted or a substituted ketoamide, an unsubstituted or a substituted —C(=O)—N— sulfonamido, —CH(OH)—(S(=O)$_2$—O$^−$), —CH(OH)((P=O)(OR$^9$)$_2$), —C(=O)CH$_2$—O—((P=O)(OR$^{10}$)$_2$), —C(=O)CH$_2$—O—C(R$^{11A}$)$_2$—O—((P=O)(OR$^{11B}$)$_2$), —C(=O)CH$_2$—O—C(R$^{12A}$)$_2$—O—C(=O)—OR$^{12B}$ and —C(=O)CH$_2$—O—C(R$^{13A}$)$_2$—O—C(=O)—R$^{13B}$, wherein each R$^9$, each R$^{10}$, each R$^{11B}$ and R$^{12B}$ and R$^{13B}$ can be independently hydrogen, an unsubstituted C$_{1-6}$ alkyl, an unsubstituted C$_{2-6}$ alkenyl, an unsubstituted C$_{1-6}$ haloalkyl, an unsubstituted or a substituted aryl or an unsubstituted or a substituted aryl(C$_{1-4}$ alkyl); each R$^{11A}$, each R$^{12A}$ and each R$^{13A}$ can be independently hydrogen or an unsubstituted C$_{1-4}$ alkyl; R$^2$ can be hydrogen, deuterium or halogen; R$^3$ can be an unsubstituted or a substituted C-amido(C$_{1-4}$ alkyl), an unsubstituted or a substituted monocyclic nitrogen-containing heteroaryl(C$_{1-4}$ alkyl), an unsubstituted or a substituted monocyclic nitrogen-containing heterocyclyl(C$_{1-4}$ alkyl), an unsubstituted or a substituted bicyclic nitrogen-containing heteroaryl(C$_{1-4}$ alkyl) or an unsubstituted or a substituted bicyclic nitrogen-containing heterocyclyl(C$_{1-4}$ alkyl); R$^4$ can be hydrogen, deuterium or halogen; R$^5$ can be selected from hydrogen, deuterium, halogen, an unsubstituted C$_{1-6}$ alkyl and an unsubstituted C$_{1-4}$ haloalkyl; and R$^6$ and R$^7$ can be independently selected from hydrogen, deuterium, halogen, an unsubstituted C$_{1-6}$ alkyl or a substituted C$_{1-6}$ alkyl, an unsubstituted or a substituted phenyl, an unsubstituted or a substituted acyl, an unsubstituted or a substituted C-carboxy and an unsubstituted or a substituted sulfonyl; or R$^6$ and R$^7$ can be taken together with the carbon to which R$^6$ and R$^7$ are each attached to form an optionally substituted 4-9 membered saturated or unsaturated ring or ring system that can optionally contain 1 or 2 ring heteroatoms selected from O (oxygen), N (nitrogen) and S (sulfur).

The substituent R$^1$ can be various moieties. In some embodiments, R$^1$ can be an unsubstituted ketoamide. In some embodiments, R$^1$ can be a substituted ketoamide. The ketoamide can have the structure —C(=O)—C(=O)NR$^{y1}$R$^{z1}$. In some embodiments, R$^1$ can be an acyl, for example, R$^1$ can be —C(=O)H, —C(=O)(an unsubstituted C$_{1-4}$ alkyl), —C(=O)(an unsubstituted to a substituted benzyl), —C(=O)(an unsubstituted to a substituted monocyclic heteroaryl) or —C(=O)(an unsubstituted to a substituted bicyclic heteroaryl). In some embodiments, R$^1$ can be a substituted acyl. The acyl for R$^1$ can have the structure —C(=O)R$^{y2}$. When the acyl is substituted, the possible groups that can be present on the acyl include hydroxy, a substituted or an unsubstituted alkoxy (such as —O-(an unsubstituted C$_{1-4}$ alkyl), —O-(an unsubstituted C$_{3-6}$ cycloalkyl), a substituted or an unsubstituted phenoxy or a substituted or an unsubstituted benzyloxy) or —O—(C=O)-(an unsubstituted C$_{1-6}$ alkyl). In some embodiments, R$^1$ can be an unsubstituted can be —C(=O)—N-sulfonamido. In other embodiments, R$^1$ can be a substituted can be —C(=O)—N-sulfonamido. As described herein, a N-sulfonamido can have the structure "RSO$_2$N(R$_A$)—," such that R$^1$ can be —C(=O)—N(R$^{y3}$)SO$_2$R$^{y4}$.

R$^{y1}$, R$^{y2}$, R$^{y3}$, R$^{y4}$ and R$^{z1}$ can be a variety of groups. In some embodiments, R$^{y1}$, R$^{y2}$, R$^{y3}$, R$^{y4}$ and R$^{z1}$ can be independently selected from hydrogen, C$_{1-8}$ alkyl, C$_{2-8}$ alkenyl, C$_{2-8}$ alkynyl, C$_{3-8}$ cycloalkyl (for example, a monocyclic C$_{3-8}$ cycloalkyl), C$_{3-8}$ cycloalkenyl (such as a monocyclic C$_{3-8}$ cycloalkenyl), aryl (such as phenyl or naphthyl), heteroaryl (including a monocyclic or a bicyclic heteroaryl), heterocyclyl (for example, a monocyclic or a bicyclic heterocyclyl), aryl(alkyl) (such as benzyl), heteroaryl(alkyl) (including a monocyclic heteroaryl(CH$_2$)— and a monocyclic (heteroaryl(CH$_2$CH$_2$)—) or heterocyclyl(alkyl) (such as a monocyclic heterocyclyl(CH$_2$)— and a monocyclic heterocyclyl(CH$_2$CH$_2$)—), wherein each of the aforementioned R$^{y1}$, R$^{y2}$, R$^{y3}$, R$^{y4}$ and R$^{z1}$ groups can be unsubstituted or substituted. In some embodiments, R$^{y1}$, R$^{y2}$ and R$^{z1}$ can be independently selected from H, C$_{1-8}$ alkyl, an unsubstituted C$_{1-4}$ haloalkyl (including —CF$_3$, —CCl$_3$, —CHF$_2$, —C(CH$_3$)F$_2$, —CHCl$_2$, —CH$_2$F, —CH(CH$_3$)F, —CH$_2$CF$_3$, —CH$_2$C$_1$, —CH$_2$CH$_2$F, —CH$_2$CH$_2$C$_1$, —CH$_2$CH$_2$CH$_2$F and —CH$_2$CH$_2$CH$_2$C$_1$), —C$_{1-4}$ alkyl(OH) (including —CH$_2$OH, —CH$_2$CH$_2$OH and —CH(CH$_3$)OH), —C$_{1-4}$ alkyl(C$_{1-4}$ alkoxy) (such as —CH$_2$O(an unsubstituted C$_{1-4}$ alkyl) and —CH$_2$CH$_2$O(an unsubstituted C$_{1-4}$ alkyl)), —$C_{1-4}$ alkyl-O-(a monocyclic $C_{3-6}$ cycloalkyl) (such as —$CH_2O$(a monocyclic $C_{3-6}$ cycloalkyl), —$CH_2CH_2O$(a monocyclic $C_{3-6}$ cycloalkyl)), —$C_{1-4}$ alkyl-O-(phenyl) (for example, —$CH_2O$(phenyl) and —$CH_2CH_2O$(phenyl)), —$C_{1-4}$ alkyl-O-(5- to 6-membered monocyclic heteroaryl) (such as —$CH_2O$(5- to 6-membered monocyclic heteroaryl) and —$CH_2CH_2O$(5- to 6-membered monocyclic heteroaryl)), —$C_{1-4}$ alkyl-O-(5- to 6-membered monocyclic heterocyclyl) (for example, —$CH_2O$(5- to 6-membered monocyclic heterocyclyl) and —$CH_2CH_2O$(5- to 6-membered monocyclic heterocyclyl)), —$C_{1-4}$ alkyl-O-(a monocyclic $C_{3-6}$ cycloalkyl($C_{1-4}$ alkyl) (such as —$C_{1-4}$ alkyl-O—$CH_2$-(monocyclic $C_{3-6}$ cycloalkyl) and —$C_{1-4}$ alkyl-O—$CH_2CH_2$-(monocyclic $C_{3-6}$ cycloalkyl)), —$C_{1-4}$ alkyl-O-(benzyl) (for example, —$CH_2O$(benzyl) and —$CH_2CH_2O$(benzyl)), —$C_{1-4}$ alkyl-O-(5- to 6-membered monocyclic heteroaryl($C_{1-4}$ alkyl), —$C_{1-4}$ alkyl-O-(5- to 6-membered monocyclic heterocyclyl($C_{1-4}$ alkyl), —$C_{1-4}$ alkyl-O(C=O) (an unsubstituted $C_{1-6}$ alkyl) (for example, —$CH_2O$(C=O) (an unsubstituted $C_{1-6}$ alkyl)), a monocyclic $C_{3-8}$ cycloalkyl (such as cyclopropyl, cyclobutyl, cyclopentyl, cyclohexyl, cycloheptyl and cyclooctyl), a monocyclic heteroaryl (such as imidazole, 1,3,4-oxadiazole and pyridinyl), a monocyclic heterocyclyl (for example, tetrahydrofuran and tetrahydropyran), a bicyclic heteroaryl (for example, benzothiazole, benzoimidazole and benzooxazole), a bicyclic heterocyclyl, a monocyclic $C_{3-6}$ cycloalkyl(alkyl), aryl(alkyl) (such as benzyl), heteroaryl(alkyl) (for example, a monocyclic heteroaryl-($CH_2$)—, such as pyridinyl-($CH_2$)—) and heterocyclyl(alkyl) (for example, a monocyclic heterocyclyl-($CH_2$)—), wherein each of the aforementioned $R^{y1}$, $R^{y2}$ and $R^{z1}$ groups can be unsubstituted or substituted.

In some embodiments, $R^1$ can be —$C(=O)R^{y2}$, wherein $R^{y2}$ can be —$C_{1-4}$ alkyl(OH) (such as —$CH_2OH$). In some embodiments, $R^1$ can be —$C(=O)$—$C(=O)NR^{y1}R^{z1}$; wherein $R^{y1}$ can be H; and $R^{z1}$ can be any of the moieties listed for $R^{z1}$ in the previous paragraph. In some embodiments, $R^1$ can be —$C(=O)$—$C(=O)NR^{y1}R^{z1}$; wherein $R^{y1}$ can be H; and $R^{z1}$ can be a monocyclic $C_{3-8}$ cycloalkyl (for example, cyclopropyl, cyclobutyl, cyclopentyl, cyclohexyl, cycloheptyl and cyclooctyl).

Prodrug-type and phosphate-containing moieties can be present at $R^1$. In some embodiments, $R^1$ can be —CH(OH)—(S(=O)$_2$—O$^-$). In other embodiments, $R^1$ can be —CH(OH)((P=O)(OR$^9$)$_2$), wherein each $R^9$ can be independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl). In still other embodiments, $R^1$ can be —$C(=O)CH_2$—O—((P=O)(OR$^{10}$)$_2$), wherein each $R^{10}$ can be independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl). In yet still other embodiments, $R^1$ can be —$C(=O)CH_2$—O—$C(R^{11A})_2$—O—((P=O)(OR$^{11B}$)$_2$), wherein each $R^{11A}$ is independently hydrogen or an unsubstituted $C_{1-4}$ alkyl; and each $R^{11B}$ can be independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl). In some embodiments, $R^1$ can be —$C(=O)CH_2$—O—$C(R^{12A})_2$—O—$C(=O)$—OR$^{12B}$ wherein each $R^{12A}$ is independently hydrogen or an unsubstituted $C_{1-4}$ alkyl; and $R^{12B}$ can be independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl). In some embodiments, each $R^9$ can be hydrogen. In some embodiments, each $R^{10}$ can be hydrogen. In some embodiments, each $R^{11A}$ can be hydrogen. In some embodiments, each $R^{11B}$ can be an unsubstituted $C_{1-6}$ alkyl. In some embodiments, each $R^{12A}$ can be hydrogen. In some embodiments, $R^{12B}$ can be an unsubstituted $C_{1-6}$ alkyl. In some embodiments, $R^1$ can be —$C(=O)CH_2$—O—$C(R^{13A})_2$—O—$C(=O)$—R$^{13B}$, wherein each $R^{13A}$ is independently hydrogen or an unsubstituted $C_{1-4}$ alkyl; and $R^{13B}$ can be independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl). In some embodiments, each $R^{13A}$ can be hydrogen. Examples of suitable unsubstituted $C_{1-6}$ alkyl for each $R^{11B}$, $R^{12B}$ and/or $R^{13B}$ include methyl, ethyl, n-propyl, iso-propyl, n-butyl, sec-butyl, iso-butyl, tert-butyl, pentyl (branched and straight-chained) and hexyl (branched and straight-changed). In some embodiments, $R^1$ can be —$C(=O)CH_2$—O—((P=O)(OH)$_2$). Other examples of $R^9$, $R^{10}$, $R^{11B}$ and $R^{12B}$ groups include methyl, ethyl, n-propyl, iso-propyl, n-butyl, iso-butyl, sec-butyl, tert-butyl, pentyl (straight-chained and branched), hexyl (straight-chained and branched), ethenyl, propenyl, butenyl, pentenyl, hexenyl, chloromethyl, fluoromethyl, difluoromethyl, dichloromethyl, trifluoromethyl, trichloromethyl, an unsubstituted or a substituted phenyl and an unsubstituted or a substituted benzyl.

In some embodiments, $R^1$ can be cyano. In other embodiments, $R^1$ can be an unsubstituted $C_{2-5}$ alkynyl. In still other embodiments, $R^1$ can be a substituted $C_{2-5}$ alkynyl. The $C_{2-5}$ alkynyl can have various structures. For example, the $C_{2-5}$ alkynyl can have the structure —($CH_2$)$_1$—$C_{2-4}$ alkynyl or —($CH_2$)$_2$—$C_{2-3}$ alkynyl.

As provided herein, $Z^1$ can be —$C(=O)$—, such that a compound of Formula (I) can have the structure of a compound of Formula (Ia). Also, as provided herein, $Z^1$ can be —CH(CF$_3$)— such that a compound of Formula (I) can have the structure of a compound of Formula (Ib).

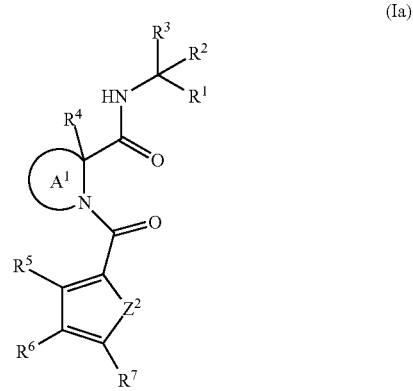

(Ia)

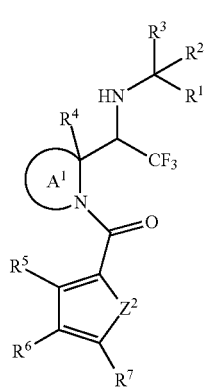

(Ib)

rings C₁ and C₂ are joined in a spiro-fashion. When Ring $A^1$ and a cyclic moiety described herein are connected in a fused-fashion, Ring $A^1$ and the cyclic moiety are connected by two or more ring atoms. In some instances, Ring $A^1$ and a cyclic moiety described herein can be connected by two adjacent ring atoms. As an example, rings D1 and D1 are connected in a fused-fashion by two adjacent ring atoms

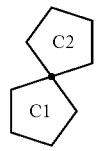

Ring $A^1$ can be azetidine, pyrrolidine or piperidine. Each of azetidine, pyrrolidine or piperidine can be optionally substituted. In some embodiments, Ring $A^1$ can be an unsubstituted azetidine. In other embodiments, Ring $A^1$ can be an unsubstituted pyrrolidine. In still other embodiments, Ring $A^1$ can be an unsubstituted piperidine. As provided herein, Ring $A^1$ can be substituted. For example, in some embodiments, Ring $A^1$ can be a substituted azetidine. In other embodiments, Ring $A^1$ can be a substituted pyrrolidine. In still other embodiments, Ring $A^1$ can be a substituted piperidine.

When Ring $A^1$ is substituted, the ring can be substituted with one or more $R^x$ groups independently selected from deuterium, halogen (such as fluoro and chloro), an unsubstituted or a substituted $C_{1-4}$ alkyl (including methyl, ethyl, n-propyl, isopropyl, n-butyl, sec-butyl, iso-butyl and tert-butyl), an unsubstituted or a substituted $C_{2-4}$ alkenyl (such as —CH═CH₂, —CH₂CH═CH₂, —CH═CHCH₃, —CH₂CH₂CH═CH₂, —CH₂CH═CHCH₃ and —CH═CH₂CHCH₃) an unsubstituted or a substituted $C_{1-8}$ alkoxy (such as (including methoxy, ethoxy, n-propoxy, isopropoxy, n-butoxy, sec-butoxy, iso-butoxy, tert-butoxy, pentoxy (branched and straight-chained), hexoxy (branched and straight-chained) and $C_{3-8}$ cycloalkyloxy (including a monocyclic $C_{3-8}$ cycloalkyloxy)), an unsubstituted or a substituted $C_{3-6}$ cycloalkyl (such as cyclopropyl, cyclobutyl, cyclopentyl and cyclohexyl), an unsubstituted or a substituted aryl, an unsubstituted or a substituted heteroaryl, an unsubstituted or a substituted heterocyclyl and an unsubstituted $C_{1-4}$ haloalkyl (for example, CF₃, CHF₂, CH₂F and CCl₃). The $C_{3-6}$ cycloalkyl, aryl, heteroaryl and heterocyclyl for $R^x$ can be monocyclic. For example, each $R^x$ can be independently, an unsubstituted or a substituted cyclopropyl, an unsubstituted or a substituted cyclobutyl, an unsubstituted or a substituted cyclopentyl, an unsubstituted or a substituted cyclohexyl, an unsubstituted or a substituted phenyl, an unsubstituted or a substituted 5- or 6-membered monocyclic heteroaryl or an unsubstituted or a substituted 5- or 6-membered monocyclic heterocyclyl.

Ring $A^1$ can be connected to an unsubstituted or a substituted a cyclic moiety described herein in a fused-fashion or a spiro-fashion. As described herein, the cyclic moiety can be selected from a monocyclic $C_{3-7}$ cycloalkyl, a bicyclic $C_{5-9}$ cycloalkyl, a monocyclic $C_{3-7}$ cycloalkenyl, a bicyclic $C_{5-9}$ cycloalkenyl and a phenyl. Those skilled in the art understand that when Ring $A^1$ and a cyclic moiety described herein are connected in a spiro-fashion, Ring $A^1$ and the cyclic moiety can be connected by a single ring atom. For example, in the structure

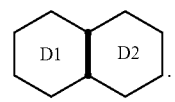

In some instances, Ring $A^1$ and a cyclic moiety described herein can be connected by three or more atoms are shared between the two rings. The following structure:

is an example of two rings being connected by three or more ring atoms. When two rings are connected by three or more ring atoms, the three or more ring atoms connecting the two rings would be referred to by those skilled in the art as "bridging" atoms. Further, those skilled in the art would understand based on the disclosure provided herein that two rings connected in a "bridged" fashion is an example of two rings connected in a fused-fashion.

In some embodiments, Ring $A^1$ can be an unsubstituted or a substituted azetidine, wherein the azetidine can be connected to a monocyclic $C_{3-7}$ cycloalkyl in a fused-fashion. In other embodiments, Ring $A^1$ can be an unsubstituted or a substituted azetidine, wherein the azetidine can be connected to a monocyclic $C_{3-7}$ cycloalkyl in a spiro-fashion. In some embodiments, Ring $A^1$ can be an unsubstituted or a substituted pyrrolidine, wherein the pyrrolidine can be connected to a monocyclic $C_{3-7}$ cycloalkyl in a fused-fashion. In other embodiments, Ring $A^1$ can be an unsubstituted or a substituted pyrrolidine, wherein the pyrrolidine can be connected to a monocyclic $C_{3-7}$ cycloalkyl in a spiro-fashion. In some embodiments, Ring $A^1$ can be an unsubstituted or a substituted piperidine, wherein the piperidine can be connected to a monocyclic $C_{3-7}$ cycloalkyl in a fused-fashion. In other embodiments, Ring $A^1$ can be an unsubstituted or a substituted piperidine, wherein the piperidine can be connected to a monocyclic $C_{3-7}$ cycloalkyl in a spiro-fashion.

In some embodiments, Ring $A^1$ can be an unsubstituted or a substituted azetidine, wherein the azetidine can be connected to a bicyclic $C_{5-9}$ cycloalkyl in a fused-fashion. In other embodiments, Ring $A^1$ can be an unsubstituted or a substituted azetidine, wherein the azetidine can be connected to a bicyclic $C_{5-9}$ cycloalkyl in a spiro-fashion. In some embodiments, Ring $A^1$ can be an unsubstituted or a substituted pyrrolidine, wherein the pyrrolidine can be connected to a bicyclic C<sub>5-9</sub> cycloalkyl in a fused-fashion. In other embodiments, Ring A¹ can be an unsubstituted or a substituted pyrrolidine, wherein the pyrrolidine can be connected to a bicyclic C$_{5-9}$ cycloalkyl in a spiro-fashion. In some embodiments, Ring A¹ can be an unsubstituted or a substituted piperidine, wherein the piperidine can be connected to a bicyclic C$_{5-9}$ cycloalkyl in a fused-fashion. In other embodiments, Ring A¹ can be an unsubstituted or a substituted piperidine, wherein the piperidine can be connected to a bicyclic C$_{5-9}$ cycloalkyl in a spiro-fashion.

In some embodiments, Ring A¹ can be an unsubstituted or a substituted azetidine, wherein the azetidine can be connected to a monocyclic C$_{3-7}$ cycloalkenyl in a fused-fashion. In other embodiments, Ring A¹ can be an unsubstituted or a substituted azetidine, wherein the azetidine can be connected to a monocyclic C$_{3-7}$ cycloalkenyl in a spiro-fashion. In some embodiments, Ring A¹ can be an unsubstituted or a substituted pyrrolidine, wherein the pyrrolidine can be connected to a monocyclic C$_{3-7}$ cycloalkenyl in a fused-fashion. In other embodiments, Ring A¹ can be an unsubstituted or a substituted pyrrolidine, wherein the pyrrolidine can be connected to a monocyclic C$_{3-7}$ cycloalkenyl in a spiro-fashion. In some embodiments, Ring A¹ can be an unsubstituted or a substituted piperidine, wherein the piperidine can be connected to a monocyclic C$_{3-7}$ cycloalkenyl in a fused-fashion. In other embodiments, Ring A¹ can be an unsubstituted or a substituted piperidine, wherein the piperidine can be connected to a monocyclic C$_{3-7}$ cycloalkenyl in a spiro-fashion.

In some embodiments, Ring A¹ can be an unsubstituted or a substituted azetidine, wherein the azetidine can be connected to a bicyclic C$_{5-9}$ cycloalkenyl in a fused-fashion. In other embodiments, Ring A¹ can be an unsubstituted or a substituted azetidine, wherein the azetidine can be connected to a bicyclic C$_{5-9}$ cycloalkenyl in a spiro-fashion. In some embodiments, Ring A¹ can be an unsubstituted or a substituted pyrrolidine, wherein the pyrrolidine can be connected to a bicyclic C$_{5-9}$ cycloalkenyl in a fused-fashion. In other embodiments, Ring A¹ can be an unsubstituted or a substituted pyrrolidine, wherein the pyrrolidine can be connected to a bicyclic C$_{5-9}$ cycloalkenyl in a spiro-fashion. In some embodiments, Ring A¹ can be an unsubstituted or a substituted piperidine, wherein the piperidine can be connected to a bicyclic C$_{5-9}$ cycloalkenyl in a fused-fashion. In other embodiments, Ring A¹ can be an unsubstituted or a substituted piperidine, wherein the piperidine can be connected to a bicyclic C$_{5-9}$ cycloalkenyl in a spiro-fashion. Examples of monocyclic C$_{3-7}$ cycloalkyls, bicyclic C$_{5-9}$ cycloalkyls, monocyclic C$_{3-7}$ cycloalkenyls and bicyclic C$_{5-9}$ cycloalkenyl include cyclopropyl, cyclobutyl, cyclopentyl, cyclohexyl, cycloheptyl, bicyclo[3.1.0]hexane, spiro[2.2]pentane, spiro[2.4]heptane, bicyclo[2.2.1]heptane, bicyclo[2.2.1]hept-2-ene, bicyclo[2.2.2]octane, bicyclo[2.2.2]oct-2-ene, bicyclo[2.2.2]octane and bicyclo[2.2.2]oct-2-ene.

In some embodiments, Ring A¹ can be an unsubstituted or a substituted azetidine, wherein the azetidine can be connected to a phenyl in a fused-fashion. In some embodiments, Ring A¹ can be an unsubstituted or a substituted pyrrolidine, wherein the pyrrolidine can be connected to a phenyl in a fused-fashion. In some embodiments, Ring A¹ can be an unsubstituted or a substituted piperidine, wherein the piperidine can be connected to a phenyl in a fused-fashion.

As provided herein the cyclic moiety (such as a monocyclic C$_{3-7}$ cycloalkyl, a bicyclic C$_{5-9}$ cycloalkyl, a monocyclic C$_{3-7}$ cycloalkenyl, a bicyclic C$_{5-9}$ cycloalkenyl and phenyl) connected to the azetidine, the pyrrolidine or the piperidine, can be unsubstituted or can be substituted with one or more moieties. Each moiety that can be present on the cyclic moieties can be independently selected from halogen (for example, fluoro or chloro), an unsubstituted C$_{1-4}$ alkyl (such as methyl, ethyl, n-propyl, iso-propyl, n-butyl, iso-butyl, sec-butyl or tert-butyl), an unsubstituted C$_{2-4}$ alkenyl (such as ethenyl, propenyl and butenyl) and an unsubstituted or a substituted monocyclic C$_{3-6}$ cycloalkyl (such as cyclopropyl, cyclobutyl, cyclopentyl and cyclohexyl along with halo-substituted versions of these monocyclic C$_{3-6}$ cycloalkyls). Examples of Ring A¹ with a monocyclic C$_{3-7}$ cycloalkyl. a bicyclic C$_{5-9}$ cycloalkyl, a monocyclic C$_{3-7}$ cycloalkenyl or a bicyclic C$_{5-9}$ cycloalkenyl that is connected in a fused-fashion (including bridged-fashion) or a spiro-fashion include, but are not limited, to the following:

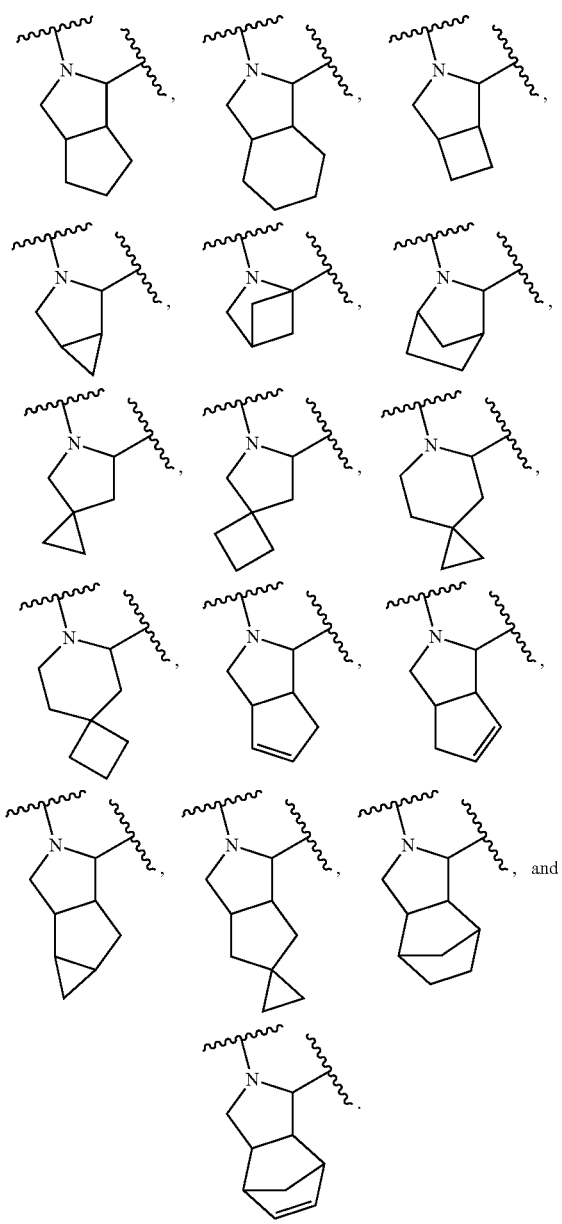

Exemplary bicyclic rings with Ring $A^1$ and a phenyl that is connected in a fused-fashion are

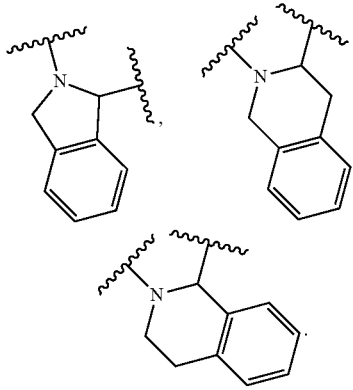

In some embodiments, $R^4$ can be hydrogen. In other embodiments, $R^4$ can be deuterium. In still other embodiments, $R^4$ can be halogen (such as fluoro or chloro).

The 5-membered ring that includes $Z^2$ and $Z^3$ can be a furan ring when $Z^2$ is O (oxygen) and $Z^3$ is C. When $Z^2$ is S and $Z^3$ is C, the 5-membered ring that includes $Z^2$ and $Z^3$ can be a thiophene ring. The 5-membered ring that includes $Z^2$ and $Z^3$ can also be a pyrrole ring when $Z^3$ is C, and where the nitrogen of $Z^2$ can be bonded to a hydrogen or an unsubstituted $C_{1-4}$ alkyl ($Z^2$ is $NR^8$, wherein $R^8$ can be H or an unsubstituted $C_{1-4}$ alkyl). When $Z^2$ is $NR^8$ and $Z^3$ is N, the 5-membered ring that includes $Z^2$ and $Z^3$ can be an imidazole. Examples of Formula (I) where $Z^2$ is O, S or $NR^8$ and $Z^3$ is N or $CR^5$ are shown below in Formulae (Ic), (Id), (Ie), (If), (Ig) and (Ih), respectively.

(Ic)

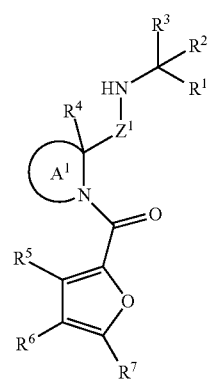

(Id)

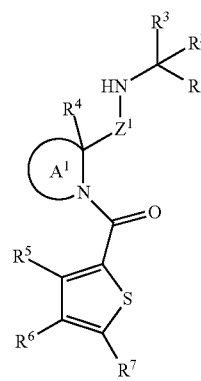

(Ie)

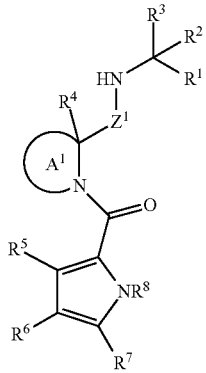

(If)

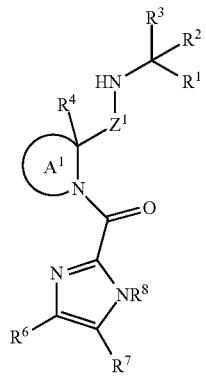

(Ig)

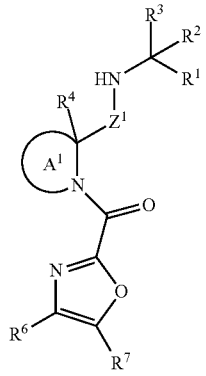

(Ih)

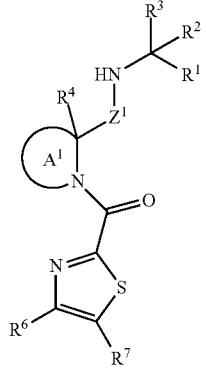

In some embodiments, $Z^1$ can be —C(=O)— in Formula (Ic), Formula (Id), Formula (Ie) and/or Formula (If). In other embodiments, $Z^1$ can be —CH(CF$_3$)— in Formula (Ic), Formula (Id), Formula (Ie) and/or (If).

The 5-membered ring that includes $Z^2$ and $Z^3$ can be unsubstituted or substituted. When substituted, the 5-membered ring that includes $Z^2$ and $Z^3$ can be substituted with deuterium, halogen and/or an unsubstituted $C_{1-6}$ alkyl. In some embodiments, $R^5$, $R^6$ and $R^7$ can be each hydrogen. In other embodiments, at least one of $R^5$, $R^6$ and $R^7$ can be deuterium, halogen, an unsubstituted $C_{1-6}$ alkyl or an unsubstituted $C_{1-4}$ haloalkyl. In some embodiments, one of $R^5$, $R^6$ and $R^7$ can be deuterium, halogen, an unsubstituted $C_{1-6}$ alkyl or an unsubstituted $C_{1-4}$ haloalkyl. In other embodiments, two of $R^5$, $R^6$ and $R^7$ can be deuterium, halogen, an unsubstituted $C_{1-6}$ alkyl or an unsubstituted $C_{1-4}$ haloalkyl. In still other embodiments, all of $R^5$, $R^6$ and $R^7$ can be deuterium, halogen, an unsubstituted $C_{1-6}$ alkyl or an unsubstituted $C_{1-4}$ haloalkyl. The halogen for $R^5$, $R^6$ and/or $R^7$ can be fluoro or chloro. The unsubstituted $C_{1-6}$ alkyl for $R^5$, $R^6$ and/or $R^7$ can be methyl, ethyl, n-propyl, iso-propyl, n-butyl, iso-butyl, sec-butyl, tert-butyl, pentyl (branched or straight-chained) or hexyl (branched or straight-chained). Exemplary an unsubstituted $C_{1-4}$ haloalkyls for $R^5$, $R^6$ and/or $R^7$ include $CF_3$, $CHF_2$, $CH_2F$, $CCl_3$, $CHCl_2$ and $CH_2Cl$. In some embodiments, $Z^3$ is $CR^5$; $R^5$ can be selected from hydrogen, deuterium, halogen, an unsubstituted $C_{1-6}$ alkyl and an unsubstituted $C_{1-4}$ haloalkyl; $R^6$ can be selected from halogen, an unsubstituted $C_{1-6}$ alkyl, an unsubstituted or a substituted phenyl, an unsubstituted or a substituted acyl, an unsubstituted or a substituted C-carboxy and an unsubstituted or a substituted sulfonyl; and $R^7$ can be selected from hydrogen, deuterium, halogen, an unsubstituted $C_{1-6}$ alkyl, an unsubstituted or a substituted phenyl, an unsubstituted or a substituted acyl, an unsubstituted or a substituted C-carboxy and an unsubstituted or a substituted sulfonyl.

The 5-membered ring that includes $Z^2$ and $Z^3$ can be fused to a 4-9 membered saturated or unsaturated ring or ring system that can optionally contain 1 or 2 ring heteroatoms selected from O (oxygen), N (nitrogen) and S (sulfur). When the ring or ring system includes one or more sulfurs, each sulfur can be oxidized to a sulfoxide (S(=O)) or a sulfone (S(=O)$_2$). The 4-9 membered saturated or unsaturated ring can be formed by taking $R^6$ and $R^7$ together along with each carbon to which $R^6$ and $R^7$ are attached. In some embodiments, $R^6$ and $R^7$ can be taken together with each carbon to which $R^6$ and $R^7$ are attached to form an optionally substituted 4-9 membered saturated ring that can optionally contain 1 or 2 ring heteroatoms selected from O, N and S. For example, $R^6$ and $R^7$ can be taken together with each carbon to which $R^6$ and $R^7$ are attached to form an optionally substituted 4-9 membered monocyclic cycloalkyl ring.

In some embodiments, $R^6$ and $R^7$ can be taken together with each carbon to which $R^6$ and $R^7$ are attached to form an optionally substituted 4-9 membered unsaturated ring that can optionally contain 1 or 2 ring heteroatoms selected from O, N and S. In some embodiments, the 4-9 membered saturated or unsaturated ring can be a substituted or an unsubstituted 4-9 membered monocyclic cycloalkyl ring, a substituted or an unsubstituted 4-9 membered monocyclic cycloalkenyl ring, a substituted or an unsubstituted 4-9 membered monocyclic heterocyclyl ring, a substituted or an unsubstituted phenyl ring or a substituted or an unsubstituted 4-9 membered monocyclic heteroaryl ring. In some embodiment, $R^6$ and $R^7$ can be taken together with each carbon to which $R^6$ and $R^7$ are attached to form a substituted or an unsubstituted 4-9 membered monocyclic cycloalkyl ring. In some embodiment, $R^6$ and $R^7$ can be taken together with each carbon to which $R^6$ and $R^7$ are attached to form a substituted or an unsubstituted 4-9 membered monocyclic cycloalkenyl ring. In some embodiment, $R^6$ and $R^7$ can be taken together with each carbon to which $R^6$ and $R^7$ are attached to form a substituted or an unsubstituted 5- to 6-membered monocyclic heterocyclyl ring. In some embodiment, $R^6$ and $R^7$ can be taken together with each carbon to which $R^6$ and $R^7$ are attached to form a substituted or an unsubstituted phenyl. In some embodiment, $R^6$ and $R^7$ can be taken together with each carbon to which $R^6$ and $R^7$ are attached to form a substituted or an unsubstituted 5- or 6-membered monocyclic heteroaryl. In some embodiment, $R^6$ and $R^7$ can be taken together with each carbon to which $R^6$ and $R^7$ are attached to form a substituted or an unsubstituted 4-9 membered bicyclic cycloalkyl, a substituted or an unsubstituted 4-9 membered bicyclic cycloalkenyl, a substituted or an unsubstituted 4-9 membered bicyclic heteroaryl or a substituted or an unsubstituted 4-9 membered bicyclic heterocyclyl. The 4-9 membered saturated or unsaturated ring can be formed by taking $R^6$ and $R^7$ together along with each carbon to which $R^6$ and $R^7$ are attached can be unsubstituted or substituted.

The ring system that can be formed by taking $R^6$ and $R^7$ together with each the carbon to which $R^6$ and $R^7$ are attached can be an unsubstituted or a substituted bicyclic ring system, wherein the ring system can be a 4-9 membered saturated or unsaturated ring system that can optionally contain 1 or 2 ring heteroatoms selected from O, N and S. In some embodiments, the 4-9 membered saturated or unsaturated ring system can be a saturated bicyclic ring system. In other embodiments, the 4-9 membered saturated or unsaturated ring system can be an unsaturated bicyclic ring system. As described herein, the ring system can be a ring system where the ring atoms are carbons. The ring system can be also a ring system that contains 1 or 2 ring heteroatoms selected from O, N and S. As examples, the ring system formed by $R^6$ and $R^7$ together with the carbon to which $R^6$ and $R^7$ are each attached can be a bicyclic cycloalkyl, a bicyclic cycloalkenyl, a bicyclic aryl, a bicyclic heteroaryl or a bicyclic heterocyclyl.

An example of an optionally substituted 4-9 membered cycloalkyl ring that can be formed by taking $R^6$ and $R^7$ together with each carbon to which $R^6$ and $R^7$ are attached is an optionally substituted 4-9 membered monocyclic cycloalkyl ring, such as an optionally substituted cyclobutyl, an optionally substituted cyclopentyl, an optionally substituted cyclohexyl and an optionally substituted cycloheptyl. As provided, the ring system formed by $R^6$ and $R^7$ together with each carbon to which $R^6$ and $R^7$ are attached can be a bicyclic hydrocarbon ring system, such as bicyclo[2.2.1]heptane. Examples of 4-9 membered heterocyclyl, 4-7 membered aryl and 4-7 membered heteroaryl rings include, but are not limited to, phenyl, furan, thiophene, pyridine, piperazine, pyridazine, pyrimidine, pyridin-2-one, tetrahydrothiophene 1,1-dioxide and tetrahydro-2H-thiopyran 1,1-dioxide.

When substituted, the 5-membered ring that includes $Z^2$ and $Z^3$ and/or the 4-9 membered saturated or unsaturated ring or ring system that is formed by taking $R^6$ and $R^7$ together with each carbon to which $R^6$ and $R^7$ are attached can be substituted with one or more moieties independently selected from deuterium, halogen (for example, fluoro, chloro and bromo), cyano, an unsubstituted $C_{1-6}$ alkyl (including methyl, ethyl, n-propyl, iso-propyl, n-butyl, sec-butyl, iso-butyl, tert-butyl, pentyl (branched and straight-chained) and hexyl (branched and straight-chained)), an unsubstituted $C_{2-6}$ alkenyl an unsubstituted $C_{2-6}$ alkynyl, an unsubstituted or a substituted $C_{3-6}$ cycloalkyl (such as an unsubstituted or a substituted monocyclic $C_{3-6}$ cycloalkyl— including cyclopropyl, cyclobutyl, cyclopentyl and cyclohexyl), an unsubstituted or a substituted phenyl, an unsubstituted or a substituted 5- or 6-membered monocyclic heteroaryl (for example, a 5- or 6-membered monocyclic heteroaryl that includes 1, 2 or 3 heteroatoms selected from O, S and N—including pyrazole and pyridine), an unsubstituted or a substituted 5- or 6-membered monocyclic heterocyclyl (for example, a 5- or 6-membered monocyclic heterocyclyl that includes 1, 2 or 3 heteroatoms selected from O, S and N), an unsubstituted $C_{1-4}$ alkoxy (for example, methoxy, ethoxy, n-propoxy, isopropoxy, n-butoxy, isobutoxy, sec-butoxy and tert-butoxy), an unsubstituted or a substituted $C_{3-6}$ cycloalkoxy (for example, an unsubstituted or a substituted monocyclic $C_{3-6}$ cycloalkoxy—including cyclopropoxy, cyclobutoxy, cyclopentoxy and cyclohexoxy), an unsubstituted or a substituted phenoxy, an unsubstituted or a substituted benzyloxy, an unsubstituted or a substituted —O—CH$_2$-heteroaryl (such as an unsubstituted or a substituted —O—CH$_2$-monocyclic heteroaryl), an unsubstituted or a substituted —O—CH$_2$-heterocyclyl (such as an unsubstituted or a substituted —O—CH$_2$-monocyclic heterocyclyl), an unsubstituted $C_{1-4}$ haloalkyl (including —CF$_3$, —CCl$_3$, —CHF$_2$, —C(CH$_3$)F$_2$, —CHCl$_2$, —CH$_2$F, —CH(CH$_3$)F, —CH$_2$CF$_3$ and —CH$_2$C$_1$), an unsubstituted $C_{1-4}$ haloalkoxy (such as —OCF$_3$, —OCHF$_2$, —OCH$_2$F, —OCCl$_3$, —OCHCl$_2$ and —OCH$_2$C$_1$), an unsubstituted or a substituted acyl (such as —C(=O)H and —C(=O)(an unsubstituted $C_{1-4}$ alkyl)), an unsubstituted or a substituted C-carboxy (for example —C(=O)OH and —C(=O)—O-(an unsubstituted $C_{1-4}$ alkyl)), an unsubstituted sulfenyl (for example, —S(an unsubstituted $C_{1-4}$ alkyl)), —SF$_5$, —SCF$_3$, an unsubstituted sulfonyl (such as, —S(=O)$_2$(an unsubstituted $C_{1-4}$ alkyl)), —NH(an unsubstituted $C_{1-4}$ alkyl), —O—S(=O)$_2$(an unsubstituted $C_{1-4}$ alkyl), -(an unsubstituted $C_{1-4}$ alkyl)-O—P—(OH)$_2$ and -(an unsubstituted $C_{1-4}$ alkyl)-O—P—(O(an unsubstituted $C_{1-4}$ alkyl))$_2$. Examples of -(an unsubstituted $C_{1-4}$ alkyl)-O—P—(OH)$_2$ and -(an unsubstituted $C_{1-4}$ alkyl)-O—P—(O(an unsubstituted $C_{1-4}$ alkyl))$_2$ include —CH$_2$—O—P—(OH)$_2$ and —CH$_2$—O—P—(OCH$_3$)$_2$.

In some embodiments, the 5-membered ring that includes $Z^2$ and $Z^3$ and the 5-membered ring that includes $Z^2$ and $Z^3$ fused to a 4-7 membered saturated or unsaturated ring or ring system that can optionally contain 1 or 2 ring heteroatoms selected from O, N and S, can be mono-substituted, di-substituted or tri-substituted. In other embodiments, the 5-membered ring that includes $Z^2$ and $Z^3$ and the 5-membered ring that includes $Z^2$ and $Z^3$ fused to a 4-7 membered saturated or unsaturated ring or ring system that can optionally contain 1 or 2 ring heteroatoms selected from O, N and S, can be unsubstituted. Various saturated and unsaturated ring or ring systems are described herein. Possible substituents that can be present on the ring and/or ring systems referred to in this paragraph can be independently selected from deuterium, halogen (for example, fluoro, chloro and bromo), cyano, an unsubstituted $C_{1-6}$ alkyl (including methyl, ethyl, n-propyl, iso-propyl, n-butyl, sec-butyl, iso-butyl, tert-butyl, pentyl (branched and straight-chained) and hexyl (branched and straight-chained)), an unsubstituted $C_{2-6}$ alkenyl an unsubstituted $C_{2-6}$ alkynyl, an unsubstituted or a substituted $C_{3-6}$ cycloalkyl (such as an unsubstituted or a substituted monocyclic $C_{3-6}$ cycloalkyl—including cyclopropyl, cyclobutyl, cyclopentyl and cyclohexyl), an unsubstituted or a substituted phenyl, an unsubstituted or a substituted 5- or 6-membered monocyclic heteroaryl (for example, a 5- or 6-membered nitrogen-containing monocyclic heteroaryl including pyrazole and pyridine), an unsubstituted $C_{1-4}$ alkoxy (for example, methoxy, ethoxy, n-propoxy, isopropoxy, n-butoxy, isobutoxy, sec-butoxy and tert-butoxy), an unsubstituted or a substituted $C_{3-6}$ cycloalkoxy (for example, an unsubstituted or a substituted monocyclic $C_{3-6}$ cycloalkoxy—including cyclopropoxy, cyclobutoxy, cyclopentoxy and cyclohexoxy), an unsubstituted or a substituted phenoxy, an unsubstituted or a substituted benzyloxy, an unsubstituted $C_{1-4}$ haloalkyl (including —CF$_3$, —CCl$_3$, —CHF$_2$, —C(CH$_3$)F$_2$, —CHCl$_2$, —CH$_2$F, —CH(CH$_3$)F, —CH$_2$CF$_3$ and —CH$_2$C$_1$), an unsubstituted $C_{1-4}$ haloalkoxy (such as —OCF$_3$, —OCHF$_2$, —OCH$_2$F, —OCCl$_3$, —OCHCl$_2$ and —OCH$_2$C$_1$), an unsubstituted or a substituted acyl (such as —C(=O)H and —C(=O)(an unsubstituted $C_{1-4}$ alkyl)), an unsubstituted or a substituted C-carboxy (for example —C(=O)OH and —C(=O)—O-(an unsubstituted $C_{1-4}$ alkyl)), an unsubstituted sulfenyl (for example, —S(an unsubstituted $C_{1-4}$ alkyl)), an unsubstituted sulfonyl (such as, —S(=O)$_2$(an unsubstituted $C_{1-4}$ alkyl)), —NH(an unsubstituted $C_{1-4}$ alkyl), —O—S(=O)$_2$(an unsubstituted $C_{1-4}$ alkyl), -(an unsubstituted $C_{1-4}$ alkyl)-O—P—(OH)$_2$ and -(an unsubstituted $C_{1-4}$ alkyl)-O—P—(O(an unsubstituted $C_{1-4}$ alkyl))$_2$. Examples of -(an unsubstituted $C_{1-4}$ alkyl)-O—P—(OH)$_2$ and -(an unsubstituted $C_{1-4}$ alkyl)-O—P—(O(an unsubstituted $C_{1-4}$ alkyl))$_2$ include —CH$_2$—O—P—(OH)$_2$ and —CH$_2$—O—P—(OCH$_3$)$_2$.

Exemplary fused rings from the 5-membered ring that includes $Z^2$ and $Z^3$ and a 4-7 membered saturated or unsaturated ring or ring system that can optionally contain 1 or 2 ring heteroatoms selected from O, N and S includes an optionally substituted 4,5,6,7-tetrahydro-1H-indole, an optionally substituted indolyl, an optionally substituted benzofuran, an optionally substituted benzo[b]thiophene, an optionally substituted benzoimidazole, an optionally substituted benzo[d]oxazole, an optionally substituted benzo[d]thiazole, an optionally substituted pyrrolo[2,3-b]pyridine, an optionally substituted pyrrolo[2,3-c]pyridine, an optionally substituted pyrrolo[3,2-b]pyridine, an optionally substituted pyrrolo[3,2-c]pyridine, an optionally substituted 1,5-dihydro-4H-pyrrolo[3,2-c]pyridin-4-one, an optionally substituted 6H-thieno[2,3-b]pyrrole, an optionally substituted 3,4-dihydro-2H-thieno[3,2-b]pyrrole 1,1-dioxide, an optionally substituted 1,5,6,7-tetrahydrothiopyrano[3,2-b]pyrrole 4,4-dioxide, an optionally substituted 4,5,6,7-tetrahydro-1H-4,7-methanoindole and an optionally substituted 3,6-dihydro-2H-furo[2,3-e]indole, such as:

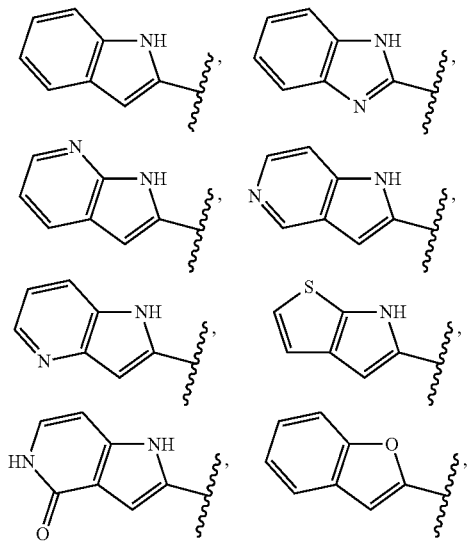

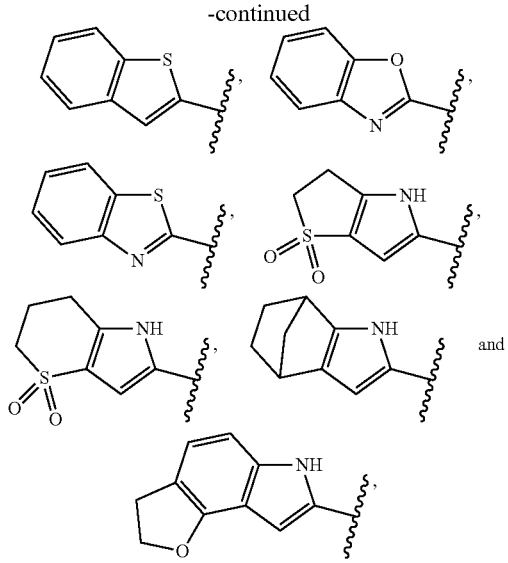

wherein each of these moieties can be unsubstituted or substituted as described herein.

As provided herein $R^3$ can be a non-hydrogen substituent selected from an unsubstituted or a substituted C-amido($C_{1-4}$ alkyl), an unsubstituted or a substituted monocyclic nitrogen-containing heteroaryl($C_{1-4}$ alkyl) and an unsubstituted or a substituted monocyclic nitrogen-containing heterocyclyl($C_{1-4}$ alkyl). In some embodiments, $R^3$ can be an unsubstituted C-amido($C_{1-4}$ alkyl). In other embodiments, $R^3$ can be a substituted C-amido($C_{1-4}$ alkyl). In still other embodiments, $R^3$ can be an unsubstituted monocyclic nitrogen-containing heteroaryl($C_{1-4}$ alkyl). In yet still other embodiments, $R^3$ can be a substituted monocyclic nitrogen-containing heteroaryl($C_{1-4}$ alkyl). The number of ring atoms can vary for a monocyclic nitrogen-containing heteroaryl($C_{1-4}$ alkyl). For example, the unsubstituted or substituted monocyclic nitrogen-containing heteroaryl($C_{1-4}$ alkyl) can be a 5-membered or a 6-membered heteroaryl($C_{1-4}$ alkyl). In some embodiments, $R^3$ can be an unsubstituted monocyclic nitrogen-containing heterocyclyl($C_{1-4}$ alkyl). In other embodiments, $R^3$ can be a substituted monocyclic nitrogen-containing heterocyclyl($C_{1-4}$ alkyl). In still other embodiments, $R^3$ can be an unsubstituted bicyclic nitrogen-containing heteroaryl($C_{1-4}$ alkyl). In yet still other embodiments, $R^3$ can be a substituted bicyclic nitrogen-containing heteroaryl ($C_{1-4}$ alkyl). In some embodiments, $R^3$ can be an unsubstituted bicyclic nitrogen-containing heterocyclyl($C_{1-4}$ alkyl). In other embodiments, $R^3$ can be a substituted bicyclic nitrogen-containing heterocyclyl($C_{1-4}$ alkyl). When $R^3$ is a bicyclic nitrogen-containing heteroaryl($C_{1-4}$ alkyl), the two rings of the bicyclic heteroaryl can be connected in a fused-fashion (including bridged-fashion). When $R^3$ is a bicyclic nitrogen-containing heterocyclyl($C_{1-4}$ alkyl), the two rings of the bicyclic heterocyclyl can be connected in a fused-fashion (including bridged-fashion) or a spiro-fashion.

The number of ring atoms for a monocyclic and a bicyclic nitrogen-containing heteroaryl($C_{1-4}$ alkyl) and a monocyclic and a bicyclic nitrogen-containing heterocyclyl($C_{1-4}$ alkyl) can vary. Non-limiting examples include an unsubstituted or a substituted 5-membered monocyclic nitrogen-containing heteroaryl($C_{1-4}$ alkyl), an unsubstituted or a substituted 6-membered monocyclic nitrogen-containing heteroaryl ($C_{1-4}$ alkyl), an unsubstituted or a substituted 5-membered monocyclic nitrogen-containing heterocyclyl($C_{1-4}$ alkyl), 6-membered monocyclic nitrogen-containing heterocyclyl ($C_{1-4}$ alkyl), an unsubstituted or a substituted 9-membered bicyclic nitrogen-containing heteroaryl($C_{1-4}$ alkyl), an unsubstituted or a substituted 10-membered bicyclic nitrogen-containing heteroaryl($C_{1-4}$ alkyl), an unsubstituted or a substituted 9-membered bicyclic nitrogen-containing heterocyclyl($C_{1-4}$ alkyl) and 10-membered bicyclic nitrogen-containing heterocyclyl($C_{1-4}$ alkyl). Examples of suitable $R^3$ groups include the following: ($C_{1-4}$ alkyl)$_2$NC(=O)—CH$_2$—, ($C_{1-4}$ alkyl)$_2$NC(=O)—CH$_2$CH$_2$—, ($C_{1-4}$ alkyl)$_2$NC(=O)—CH$_2$CH$_2$CH$_2$—, pyrrolidin-2-one($C_{1-4}$ alkyl), piperidin-2-one($C_{1-4}$ alkyl), azepan-2-one($C_{1-4}$ alkyl), imidazolidin-2-one($C_{1-4}$ alkyl), tetrahydropyrimidin-2-one ($C_{1-4}$ alkyl), 1,3-dihydro-2H-imidazol-2-one($C_{1-4}$ alkyl), imidazole($C_{1-4}$ alkyl), pyrazole($C_{1-4}$ alkyl),

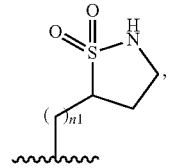

wherein n1 can be 1, 2, 3, or 4,

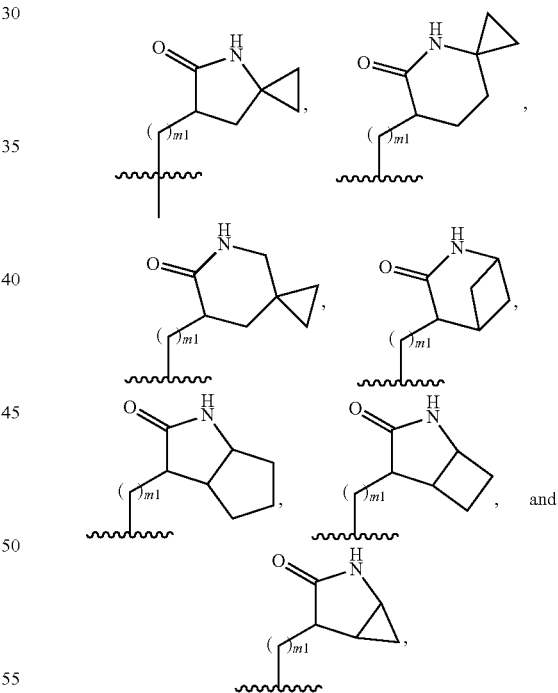

wherein each m1 can be independently 1, 2, 3 or 4, (including substituted or unsubstituted versions of the aforementioned). The $R^3$ groups provided herein can be substituted with one or more moieties independently selected from those listed for "optionally substituted." In some embodiments, a $R^3$ group provided herein can be substituted with one or more moieties selected from halogen, hydroxy, an unsubstituted $C_{1-4}$ alkyl, an unsubstituted $C_{2-4}$ alkenyl an unsubstituted $C_{1-4}$ alkoxy, amino, -(an unsubstituted $C_{1-4}$ alkyl)-O—P—(OH)$_2$ (such as —CH$_2$—O—P—(OH)$_2$) and -(an unsubstituted $C_{1-4}$ alkyl)-O—P—(O(an unsubstituted $C_{1-4}$ alkyl))$_2$ (such as —CH$_2$—O—P—(OCH$_3$)$_2$).

Non-limiting examples of R$^3$ moieties include the following:

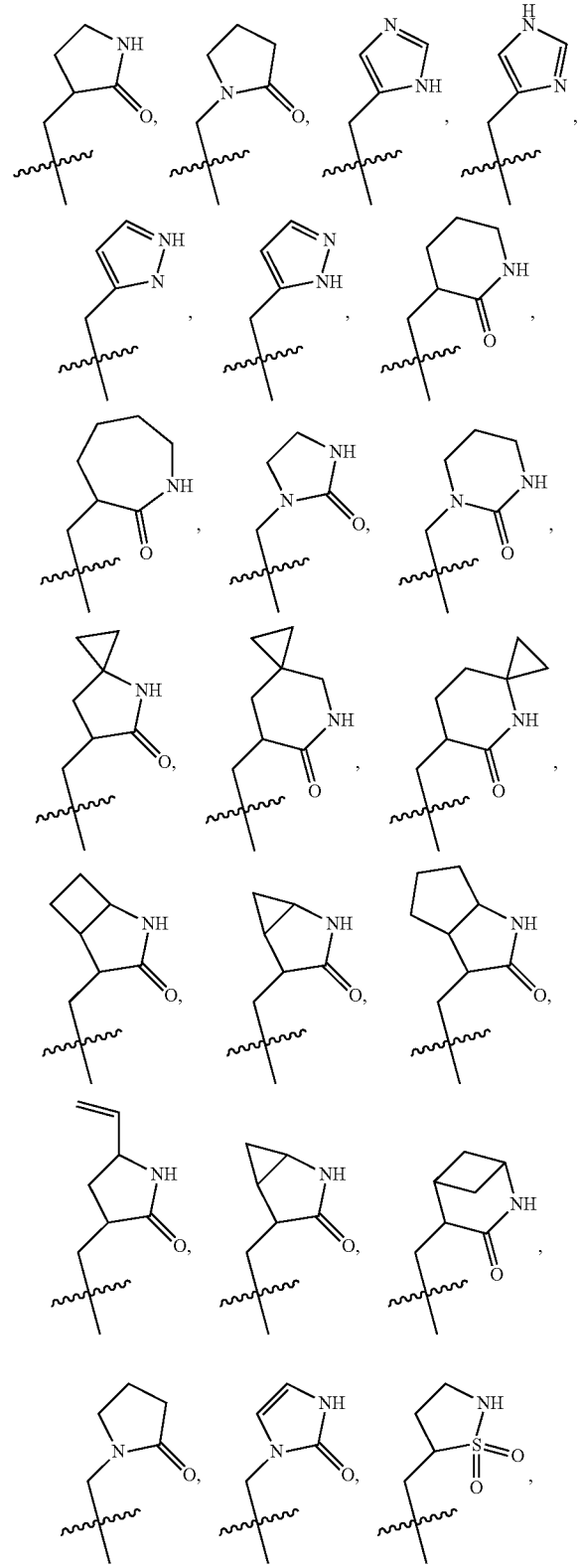

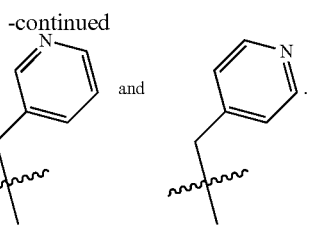

In some embodiments, R$^2$ can be hydrogen. In other embodiments, R$^2$ can be deuterium. In still other embodiments, R$^2$ can be halogen (for example, fluoro or chloro).

In some embodiments, R$^1$ can be an unsubstituted or a substituted ketoamide, R$^2$ can be hydrogen; R$^3$ can be monocyclic nitrogen-containing heterocyclyl(C$_{1-4}$ alkyl); Ring A$^1$ can be an unsubstituted or a substituted pyrrolidine, wherein the pyrrolidine can be connected to an optionally substituted monocyclic C$_{3-7}$ cycloalkyl (for example, an optionally substituted cyclopentyl or an optionally substituted cyclohexyl); and

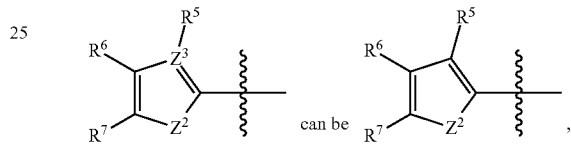

wherein R$^6$ and R$^7$ together with each carbon to which R$^6$ and R$^7$ are attached can be a substituted or an unsubstituted phenyl ring or a substituted or an unsubstituted 5- to 6-membered monocyclic heteroaryl ring. In other embodiments, R$^1$ can be a hydroxy-substituted acyl (for example, R$^1$ can be —C(=O)CH$_2$OH), R$^2$ can be hydrogen; R$^3$ can be monocyclic nitrogen-containing heterocyclyl(C$_{1-4}$ alkyl); Ring A$^1$ can be an unsubstituted or a substituted pyrrolidine, wherein the pyrrolidine can be connected to an optionally substituted monocyclic C$_{3-7}$ cycloalkyl (for example, an optionally substituted cyclopentyl or an optionally substituted cyclohexyl); and


can be

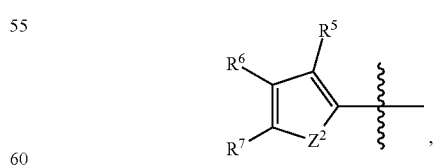

wherein R$^6$ and R$^7$ together with each carbon to which R$^6$ and R$^7$ are attached can be a substituted or an unsubstituted phenyl ring or a substituted or an unsubstituted 5- to 6-membered monocyclic heteroaryl ring. In still other embodiments, R$^1$ can be —C(=O)CH$_2$—O—((P=O)(OR$^{10}$)$_2$) (such as, —C(=O)CH$_2$—O—((P=O)(OH)$_2$)), R$^2$ can be hydrogen; R³ can be monocyclic nitrogen-containing heterocyclyl(C₁₋₄ alkyl); Ring A¹ can be an unsubstituted or a substituted pyrrolidine, wherein the pyrrolidine can be connected to an optionally substituted monocyclic C₃₋₇ cycloalkyl (for example, an optionally substituted cyclopentyl or an optionally substituted cyclohexyl); and

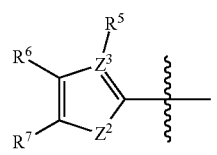

can be

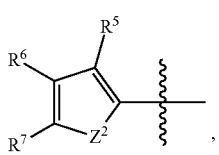

wherein R⁶ and R⁷ together with each carbon to which R⁶ and R⁷ are attached can be a substituted or an unsubstituted phenyl ring or a substituted or an unsubstituted 5- to 6-membered monocyclic heteroaryl ring.

In some embodiments, R¹ can be —C(=O)R^{y2}, R^{y2} can be a moiety as described herein (for example, —C₁₋₄ alkyl (OH)— such as —CH₂OH); R² can be hydrogen; R³ can be selected from

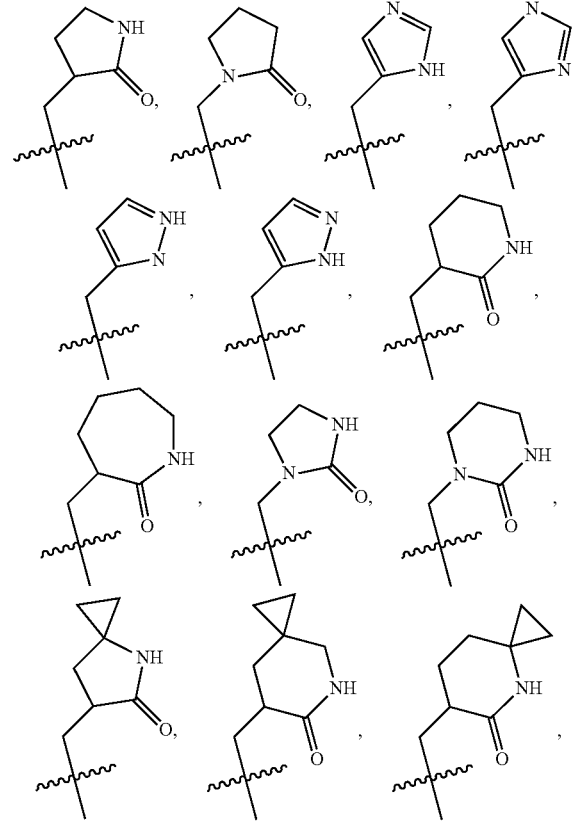

-continued

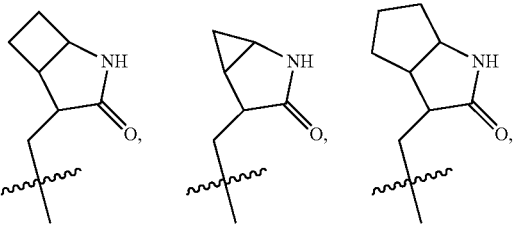

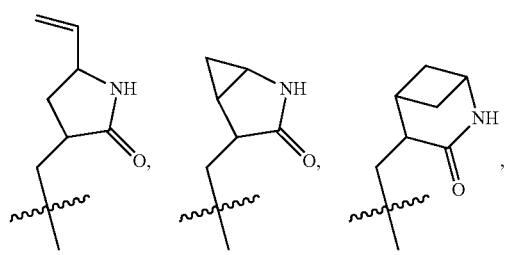

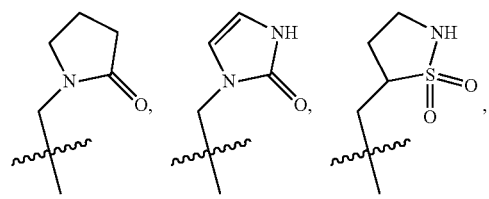

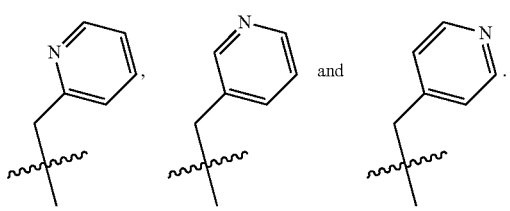

wherein R³ can be unsubstituted or substituted as described herein; Ring A¹ can be selected from

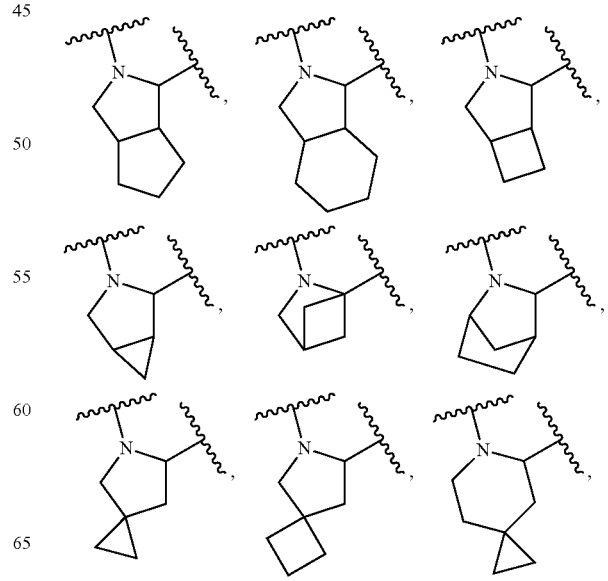

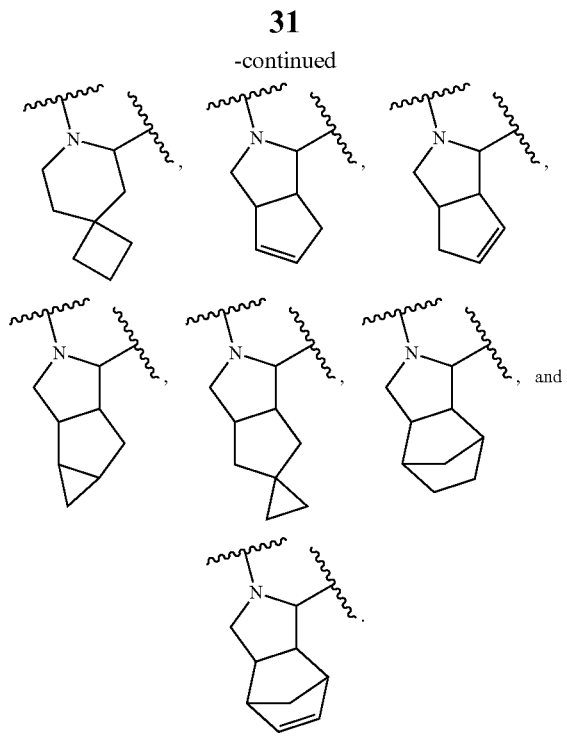

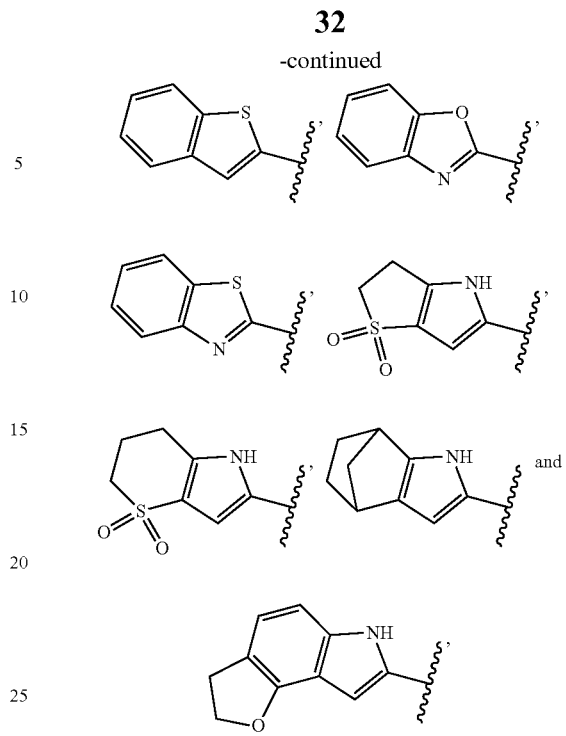

wherein Ring $A^1$ can be unsubstituted or substituted as described herein (for example, substituted with 1 or 2 fluoros); and

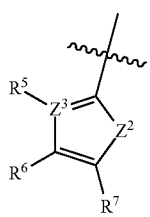

can be selected from

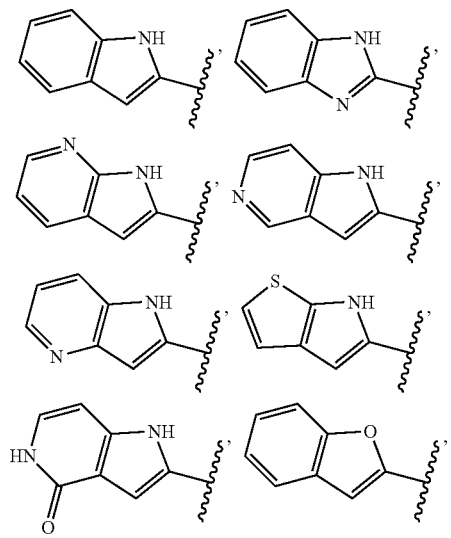

wherein each of the moieties can be unsubstituted or substituted as described herein (such as substituted 1, 2 or 3 times with a substituent selected from halogen, an unsubstituted $C_{1-4}$ alkyl, —O-(an unsubstituted $C_{1-4}$ alkyl) and an unsubstituted $C_{1-4}$ haloalkyl). In some embodiments, $R^1$ can be —C(=O)—C(=O)NR$^{y1}$R$^{z1}$; R$^{y1}$ can be H; and R$^{z1}$ can be any of the moieties provided for R$^{z1}$ as described herein. In some embodiments, $R^1$ can be —C(=O)—C(=O)NR$^{y1}$R$^{z1}$; R$^{y1}$ can be H; R$^{z1}$ can be a monocyclic $C_{3-8}$ cycloalkyl (such as cyclopropyl, cyclobutyl, cyclopentyl, cyclohexyl, cycloheptyl and cyclooctyl); $R^2$ can be hydrogen; $R^3$ can be selected from

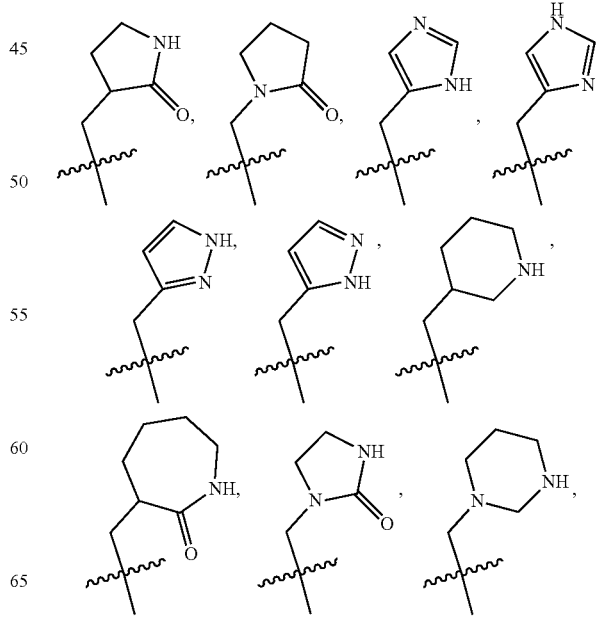

-continued
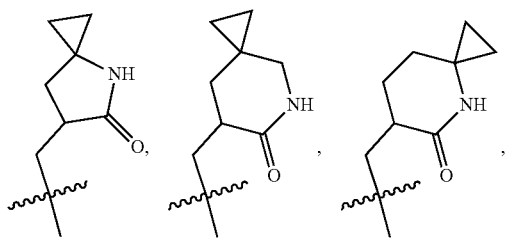
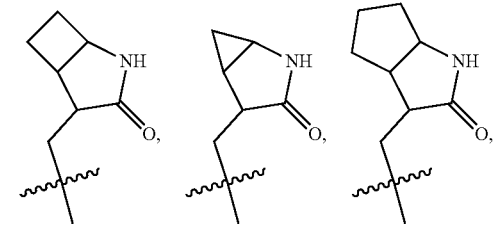
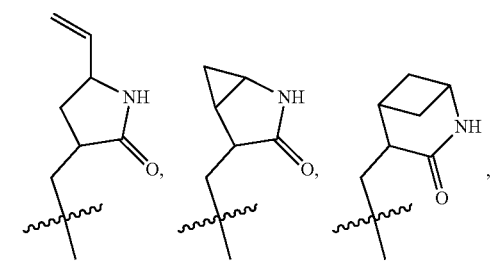
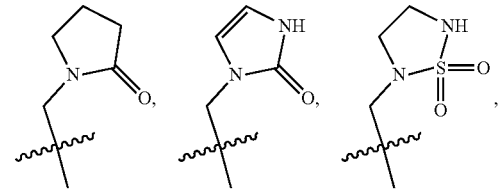
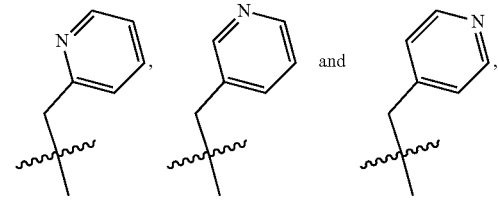
wherein R³ can be unsubstituted or substituted as described herein; Ring A¹ can be selected from
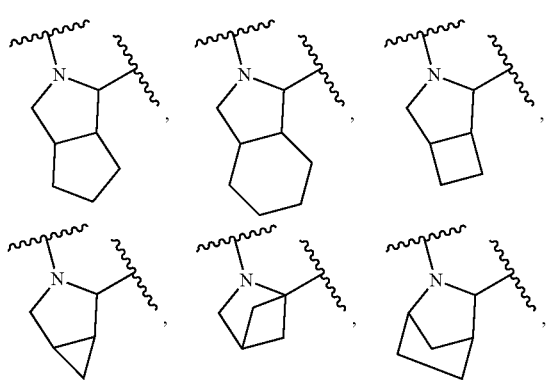
-continued
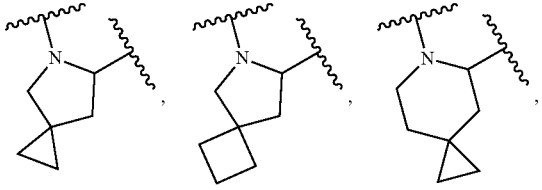
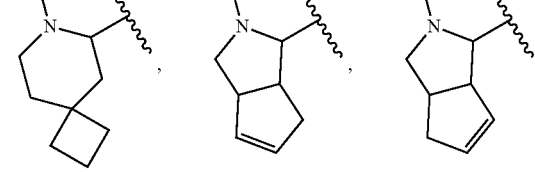
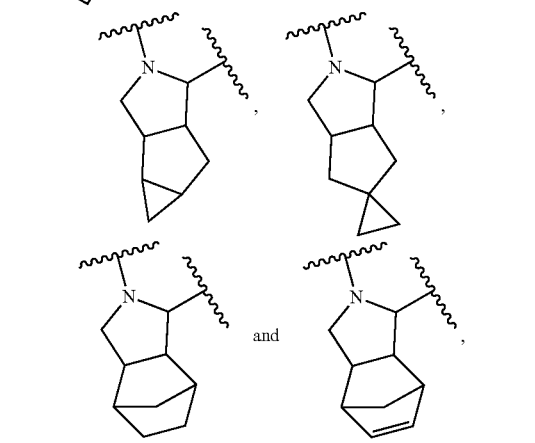
wherein Ring A¹ can be unsubstituted or substituted as described herein (for example, substituted with 1 or 2 fluoros); and
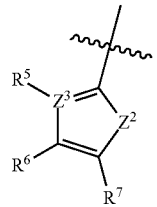
can be selected from
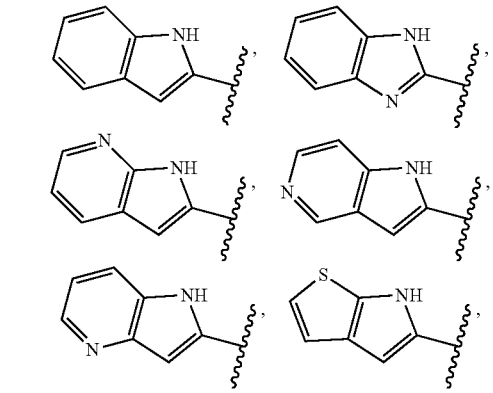

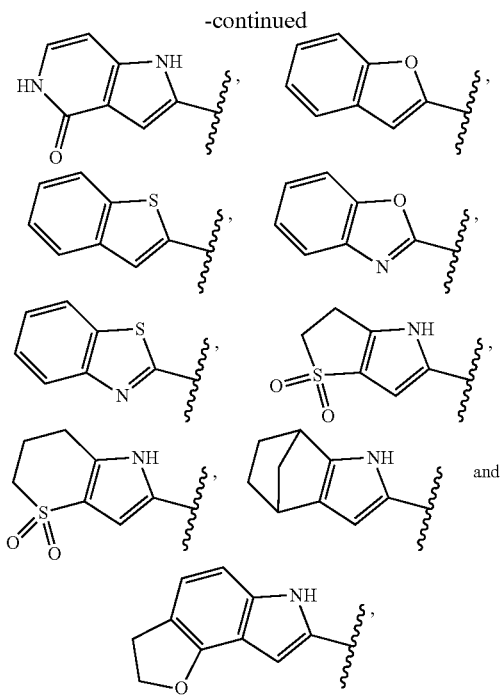

wherein each of the moieties can be unsubstituted or substituted as described herein (such as substituted 1, 2 or 3 times with a substituent selected from halogen, an unsubstituted $C_{1-4}$ alkyl, —O-(an unsubstituted $C_{1-4}$ alkyl) and an unsubstituted $C_{1-4}$ haloalkyl).

In some embodiments, a compound of Formula (I), or a pharmaceutically acceptable salt thereof, can be where $Z^1$ can be —C(=O)— or —CH(CF$_3$)—; $Z^2$ can be O, S or NR$^8$, wherein R$^8$ can be H or an unsubstituted $C_{1-4}$ alkyl; $Z^3$ can be C; Ring $A^1$ can be selected from an unsubstituted or a substituted azetidine, an unsubstituted or a substituted pyrrolidine and an unsubstituted or a substituted piperidine, wherein the azetidine, the pyrrolidine and the piperidine can be optionally substituted with one or more $R^x$ groups independently selected from deuterium, halogen, an unsubstituted or a substituted $C_{1-4}$ alkyl, an unsubstituted or a substituted $C_{1-8}$ alkoxy, an unsubstituted or a substituted $C_{3-6}$ cycloalkyl, an unsubstituted or a substituted aryl, an unsubstituted or a substituted heteroaryl and an unsubstituted or a substituted heterocyclyl, and wherein the azetidine, the pyrrolidine and the piperidine can be connected to a monocyclic $C_{4-7}$ cycloalkyl in a fused-fashion or a spiro-fashion that can be optionally substituted with one or more moieties independently selected from halogen and an unsubstituted $C_{1-4}$ alkyl; $R^1$ can be selected from cyano, an unsubstituted or a substituted $C_{2-5}$ alkynyl, an unsubstituted or a substituted acyl, an unsubstituted or a substituted ketoamide, an unsubstituted or a substituted —C(=O)—N-sulfonamido, —CH(OH)—(S(=O)$_2$—O$^-$) and —CH(OH)((P=O)(OR$^9$)$_2$), wherein each R$^9$ can be independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl); $R^2$ can be hydrogen, deuterium or halogen; $R^3$ can be an unsubstituted or a substituted C-amido($C_{1-4}$ alkyl), an unsubstituted or a substituted monocyclic nitrogen-containing heteroaryl($C_{1-4}$ alkyl), an unsubstituted or a substituted monocyclic nitrogen-containing heterocyclyl($C_{1-4}$ alkyl), an unsubstituted or a substituted bicyclic nitrogen-containing heteroaryl($C_{1-4}$ alkyl) or an unsubstituted or a substituted bicyclic nitrogen-containing heterocyclyl($C_{1-4}$ alkyl); $R^4$ can be hydrogen, deuterium or halogen; $R^5$ can be selected from hydrogen, deuterium, halogen and an unsubstituted $C_{1-6}$ alkyl; and $R^6$ and $R^7$ can be independently selected from hydrogen, deuterium, halogen and an unsubstituted $C_{1-6}$ alkyl; or $R^6$ and $R^7$ can be taken together with the carbon to which $R^6$ and $R^7$ are each attached to form a 4-7 membered saturated or unsaturated ring that can optionally contain 1 or 2 heteroatoms selected from O, N and S.

In some embodiments, a compound of Formula (I), or a pharmaceutically acceptable salt thereof, can be where $Z^1$ can be —C(=O)— or —CH(CF$_3$)—; $Z^2$ can be O, S or NR$^8$, wherein R$^8$ can be H or an unsubstituted $C_{1-4}$ alkyl; $Z^3$ can be C; Ring $A^1$ can be selected from an unsubstituted or a substituted azetidine, an unsubstituted or a substituted pyrrolidine and an unsubstituted or a substituted piperidine, wherein the azetidine, the pyrrolidine and the piperidine can be optionally substituted with one or more $R^x$ groups independently selected from deuterium, halogen, an unsubstituted or a substituted $C_{1-4}$ alkyl, an unsubstituted or a substituted $C_{2-4}$ alkenyl, an unsubstituted or a substituted $C_{1-8}$ alkoxy, an unsubstituted or a substituted $C_{3-6}$ cycloalkyl, an unsubstituted or a substituted aryl, an unsubstituted or a substituted heteroaryl and an unsubstituted or a substituted heterocyclyl and an unsubstituted $C_{1-4}$ haloalkyl, and wherein the azetidine, the pyrrolidine and the piperidine can be connected to a monocyclic $C_{3-7}$ cycloalkyl in a fused-fashion or a spiro-fashion that can be optionally substituted with one or more moieties independently selected from halogen and an unsubstituted $C_{1-4}$ alkyl; $R^1$ can be selected from cyano, an unsubstituted or a substituted $C_{2-5}$ alkynyl, an unsubstituted or a substituted acyl, an unsubstituted or a substituted ketoamide, an unsubstituted or a substituted —C(=O)—N-sulfonamido, —CH(OH)—(S(=O)$_2$—O$^-$) and —CH(OH)((P=O)(OR$^9$)$_2$), wherein each R$^9$ can be independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl); $R^2$ can be hydrogen, deuterium or halogen; $R^3$ can be an unsubstituted or a substituted C-amido($C_{1-4}$ alkyl), an unsubstituted or a substituted monocyclic nitrogen-containing heteroaryl($C_{1-4}$ alkyl), an unsubstituted or a substituted monocyclic nitrogen-containing heterocyclyl($C_{1-4}$ alkyl), an unsubstituted or a substituted bicyclic nitrogen-containing heteroaryl($C_{1-4}$ alkyl) or an unsubstituted or a substituted bicyclic nitrogen-containing heterocyclyl($C_{1-4}$ alkyl); $R^4$ can be hydrogen, deuterium or halogen; $R^5$ can be selected from hydrogen, deuterium, halogen and an unsubstituted $C_{1-6}$ alkyl; and $R^6$ and $R^7$ can be independently selected from hydrogen, deuterium, halogen and an unsubstituted $C_{1-6}$ alkyl; or $R^6$ and $R^7$ can be taken together with the carbon to which $R^6$ and $R^7$ are each attached to form an optionally substituted 4-7 membered saturated or unsaturated ring that can optionally contain 1 or 2 heteroatoms selected from O, N and S.

In some embodiments, a compound of Formula (I), or a pharmaceutically acceptable salt thereof, can be where $Z^1$ can be —C(=O)— or —CH(CF$_3$)—; $Z^2$ can be O, S or NR$^8$, wherein R$^8$ can be H or an unsubstituted $C_{1-4}$ alkyl; $Z^3$ can be N (nitrogen) or C (carbon), and when $Z^3$ is N, then $R^5$ is absent; Ring $A^1$ can be selected from an unsubstituted or a substituted azetidine, an unsubstituted or a substituted pyrrolidine and an unsubstituted or a substituted piperidine, wherein the azetidine, the pyrrolidine and the piperidine can be optionally substituted with one or more $R^x$ groups independently selected from deuterium, halogen, an unsubstituted or a substituted $C_{1-4}$ alkyl, an unsubstituted or a substituted $C_{2-4}$ alkenyl, an unsubstituted or a substituted $C_{1-8}$ alkoxy, an unsubstituted or a substituted $C_{3-6}$ cycloalkyl, an unsubstituted or a substituted aryl, an unsubstituted or a substituted heteroaryl, an unsubstituted or a substituted heterocyclyl and an unsubstituted $C_{1-4}$ haloalkyl, and wherein the azetidine, the pyrrolidine and the piperidine can be connected to a monocyclic $C_{3-7}$ cycloalkyl in a fused-fashion or a spiro-fashion that can be optionally substituted with one or more moieties independently selected from halogen and an unsubstituted $C_{1-4}$ alkyl; $R^1$ can be selected from cyano, an unsubstituted or a substituted $C_{2-5}$ alkynyl, an unsubstituted or a substituted acyl, an unsubstituted or a substituted ketoamide, an unsubstituted or a substituted —C(=O)—N-sulfonamido, —CH(OH)—(S(=O)$_2$—O$^-$) and —CH(OH)((P=O)(OR$^9$)$_2$), wherein each $R^9$ can be independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl); $R^2$ can be hydrogen, deuterium or halogen; $R^3$ can be an unsubstituted or a substituted C-amido($C_{1-4}$ alkyl), an unsubstituted or a substituted monocyclic nitrogen-containing heteroaryl($C_{1-4}$ alkyl), an unsubstituted or a substituted monocyclic nitrogen-containing heterocyclyl($C_{1-4}$ alkyl), an unsubstituted or a substituted bicyclic nitrogen-containing heteroaryl($C_{1-4}$ alkyl) or an unsubstituted or a substituted bicyclic nitrogen-containing heterocyclyl($C_{1-4}$ alkyl); $R^4$ can be hydrogen, deuterium or halogen; $R^5$ can be selected from hydrogen, deuterium, halogen and an unsubstituted $C_{1-6}$ alkyl; and $R^6$ and $R^7$ can be independently selected from hydrogen, deuterium, halogen and an unsubstituted $C_{1-6}$ alkyl; or $R^6$ and $R^7$ can be taken together with the carbon to which $R^6$ and $R^7$ are each attached to form an optionally substituted 4-7 membered saturated or unsaturated ring that can optionally contain 1 or 2 heteroatoms selected from O, N and S.

In some embodiments, a compound of Formula (I), or a pharmaceutically acceptable salt thereof, can be where $Z^1$ can be —C(=O)— or —CH(CF$_3$)—; $Z^2$ can be O, S or NR$^8$, wherein R$^8$ can be H or an unsubstituted $C_{1-4}$ alkyl; $Z^3$ can be N or C, and when $Z^3$ is N, then $R^5$ is absent; Ring A$^1$ can be selected from an unsubstituted or a substituted azetidine, an unsubstituted or a substituted pyrrolidine and an unsubstituted or a substituted piperidine, wherein the azetidine, the pyrrolidine and the piperidine can be optionally substituted with one or more $R^x$ groups independently selected from deuterium, halogen, an unsubstituted or a substituted $C_{1-4}$ alkyl, an unsubstituted or a substituted $C_{2-4}$ alkenyl, an unsubstituted or a substituted $C_{1-8}$ alkoxy, an unsubstituted or a substituted $C_{3-6}$ cycloalkyl, an unsubstituted or a substituted aryl, an unsubstituted or a substituted heteroaryl, an unsubstituted or a substituted heterocyclyl and an unsubstituted $C_{1-4}$ haloalkyl, and wherein the azetidine, the pyrrolidine and the piperidine can be connected to a cyclic moiety selected from a monocyclic $C_{3-7}$ cycloalkyl, a monocyclic $C_{3-7}$ cycloalkenyl and phenyl, wherein the cyclic moiety is connected to the azetidine, the pyrrolidine and the piperidine in a fused-fashion or a spiro-fashion that can be optionally substituted with one or more moieties independently selected from the group consisting of halogen, an unsubstituted $C_{1-4}$ alkyl and an unsubstituted $C_{2-4}$ alkenyl; $R^1$ can be selected from cyano, an unsubstituted or a substituted $C_{2-5}$ alkynyl, an unsubstituted or a substituted acyl, an unsubstituted or a substituted ketoamide, an unsubstituted or a substituted —C(=O)—N-sulfonamido, —CH(OH)—(S(=O)$_2$—O$^-$), —CH(OH)((P=O)(OR$^9$)$_2$) and —C(=O)CH$_2$—O—((P=O)(OR$^{10}$)$_2$), wherein each $R^9$ and $R^{10}$ can be independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl); $R^2$ can be hydrogen, deuterium or halogen; $R^3$ can be an unsubstituted or a substituted C-amido($C_{1-4}$ alkyl), an unsubstituted or a substituted monocyclic nitrogen-containing heteroaryl($C_{1-4}$ alkyl), an unsubstituted or a substituted monocyclic nitrogen-containing heterocyclyl($C_{1-4}$ alkyl), an unsubstituted or a substituted bicyclic nitrogen-containing heteroaryl($C_{1-4}$ alkyl) or an unsubstituted or a substituted bicyclic nitrogen-containing heterocyclyl($C_{1-4}$ alkyl); $R^4$ can be hydrogen, deuterium or halogen; $R^5$ can be selected from hydrogen, deuterium, halogen and an unsubstituted $C_{1-6}$ alkyl; and $R^6$ and $R^7$ can be independently selected from hydrogen, deuterium, halogen and an unsubstituted $C_{1-6}$ alkyl; or $R^6$ and $R^7$ can be taken together with the carbon to which $R^6$ and $R^7$ are each attached to form an optionally substituted 4-7 membered saturated or unsaturated ring that can optionally contain 1 or 2 ring heteroatoms selected from O, N and S.

In some embodiments, a compound of Formula (I), or a pharmaceutically acceptable salt thereof, can be where $Z^1$ can be —C(=O)— or —CH(CF$_3$)—; $Z^2$ can be O, S or NR$^8$, wherein R$^8$ can be H or an unsubstituted $C_{1-4}$ alkyl; $Z^3$ can be N or C, and when $Z^3$ is N, then $R^5$ is absent; Ring A$^1$ can be selected from an unsubstituted or a substituted azetidine, an unsubstituted or a substituted pyrrolidine and an unsubstituted or a substituted piperidine, wherein the azetidine, the pyrrolidine and the piperidine can be optionally substituted with one or more $R^x$ groups independently selected from deuterium, halogen, an unsubstituted or a substituted $C_{1-4}$ alkyl, an unsubstituted or a substituted $C_{2-4}$ alkenyl, an unsubstituted or a substituted $C_{1-8}$ alkoxy, an unsubstituted or a substituted $C_{3-6}$ cycloalkyl, an unsubstituted or a substituted aryl, an unsubstituted or a substituted heteroaryl, an unsubstituted or a substituted heterocyclyl and an unsubstituted $C_{1-4}$ haloalkyl, and wherein the azetidine, the pyrrolidine and the piperidine can be connected to a cyclic moiety selected from a monocyclic $C_{3-7}$ cycloalkyl, a bicyclic $C_{5-9}$ cycloalkyl, a monocyclic $C_{3-7}$ cycloalkenyl, a bicyclic $C_{5-9}$ cycloalkenyl and phenyl, wherein the cyclic moiety is connected to the azetidine, the pyrrolidine and the piperidine in a fused-fashion or a spiro-fashion that can be optionally substituted with one or more moieties independently selected from the group consisting of halogen, an unsubstituted $C_{1-4}$ alkyl, an unsubstituted $C_{2-4}$ alkenyl and an unsubstituted or a substituted $C_{3-6}$ monocyclic cycloalkyl; $R^1$ can be selected from cyano, an unsubstituted or a substituted $C_{2-5}$ alkynyl, an unsubstituted or a substituted acyl, an unsubstituted or a substituted ketoamide, an unsubstituted or a substituted —C(=O)—N-sulfonamido, —CH(OH)—(S(=O)$_2$—O$^-$), —CH(OH)((P=O)(OR$^9$)$_2$), —C(=O)CH$_2$—O—((P=O)(OR$^{10}$)$_2$), —C(=O)CH$_2$—O—C(R$^{11A}$)$_2$—O—((P=O)(OR$^{11B}$)$_2$) and —C(=O)CH$_2$—O—C(R$^{12A}$)$_2$—O—C(=O)—OR$^{12B}$, wherein each R$^9$, each R$^{10}$, each R$^{11B}$ and each R$^{12B}$ are independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl); each R$^{11A}$ and each R$^{12A}$ can be independently hydrogen or an unsubstituted $C_{1-4}$ alkyl; $R^2$ can be hydrogen, deuterium or halogen; $R^3$ can be an unsubstituted or a substituted C-amido($C_{1-4}$ alkyl), an unsubstituted or a substituted monocyclic nitrogen-containing heteroaryl($C_{1-4}$ alkyl), an unsubstituted or a substituted monocyclic nitrogen-containing heterocyclyl($C_{1-4}$ alkyl), an unsubstituted or a substituted bicyclic nitrogen-containing heteroaryl($C_{1-4}$ alkyl) or an unsubstituted or a substituted bicyclic nitrogen-containing heterocyclyl($C_{1-4}$ alkyl); $R^4$ can be hydrogen, deuterium or halogen; $R^5$ can be selected from hydrogen, deuterium, halogen, an unsubstituted $C_{1-6}$ alkyl and an unsubstituted $C_{1-4}$ haloalkyl; and $R^6$ and $R^7$ can be independently selected from hydrogen, deuterium, halogen, an unsubstituted or a substituted $C_{1-6}$ alkyl, an unsubstituted or a substituted phenyl, an unsubstituted or a substituted acyl, an unsubstituted or a substituted C-carboxy and an unsubstituted or a substituted sulfonyl; or $R^6$ and $R^7$ can be taken together with the carbon to which $R^6$ and $R^7$ are each attached to form an optionally substituted 4-9 membered saturated or unsaturated ring or ring system that can optionally contain 1 or 2 ring heteroatoms selected from O, N and S.

Examples of compounds of Formula (I), include the following:

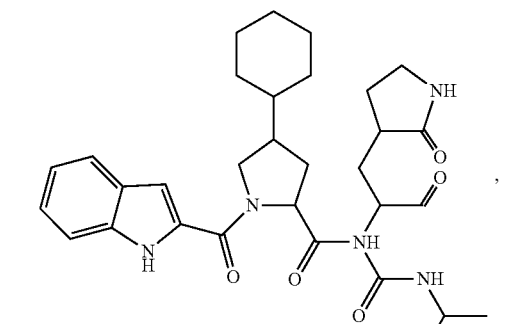

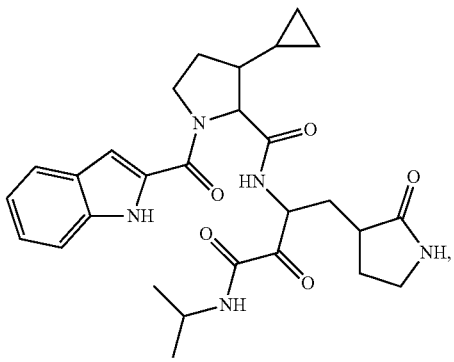

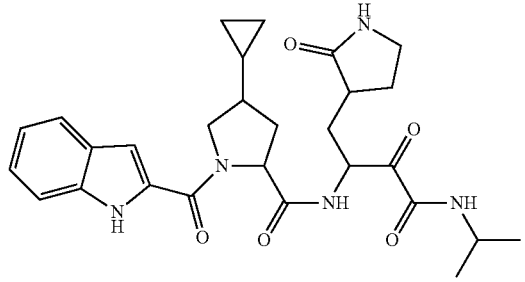

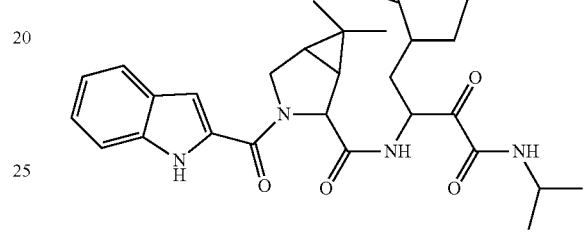

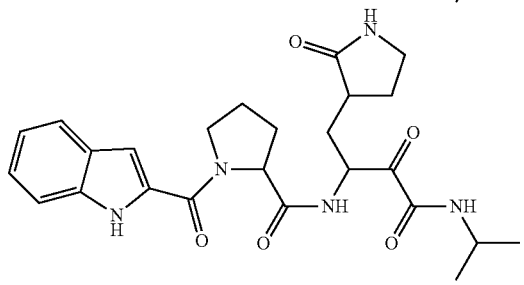

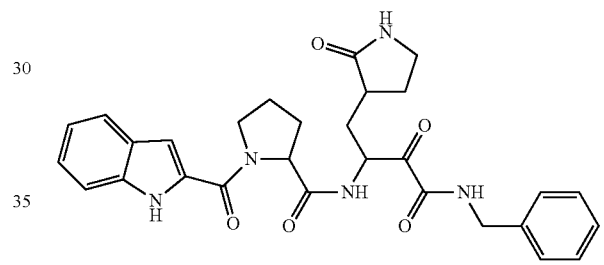

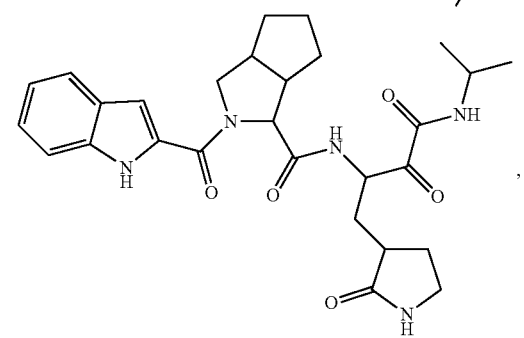

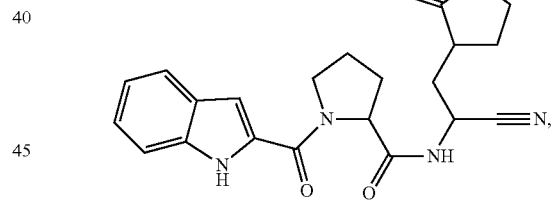

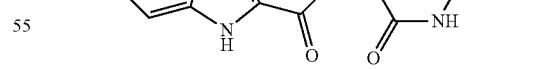

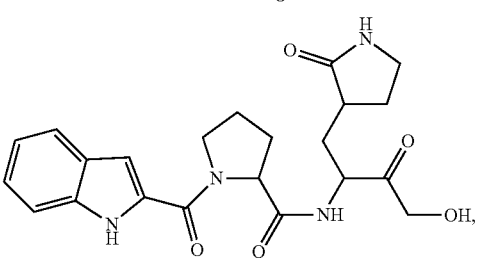

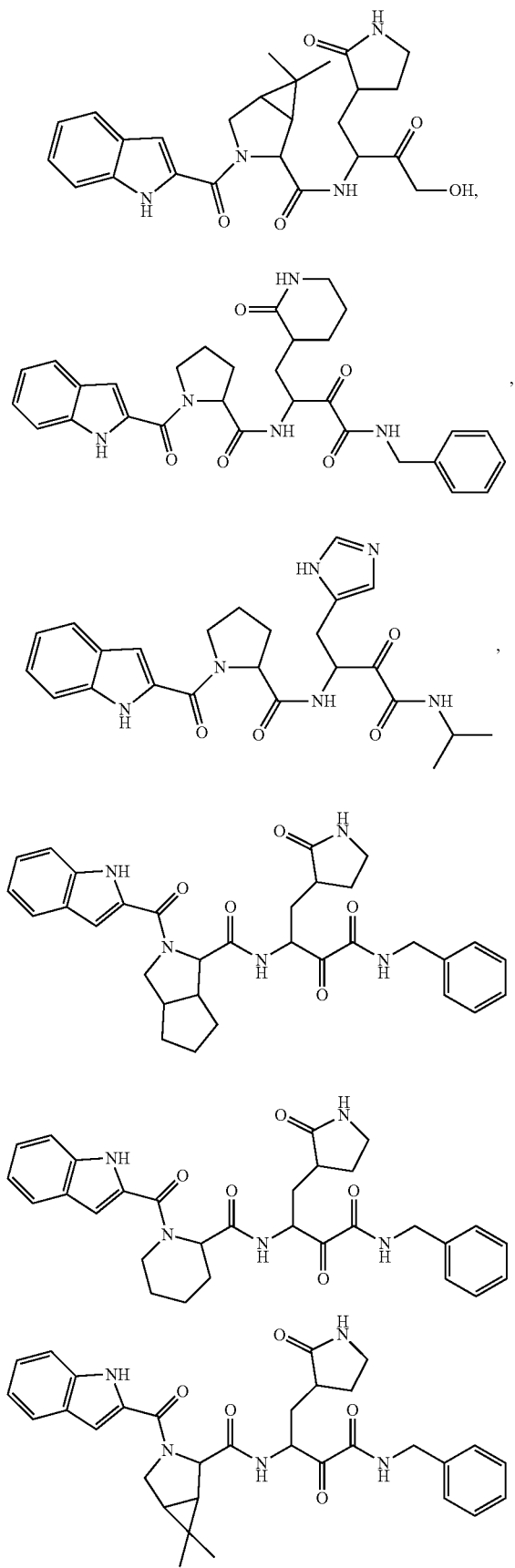
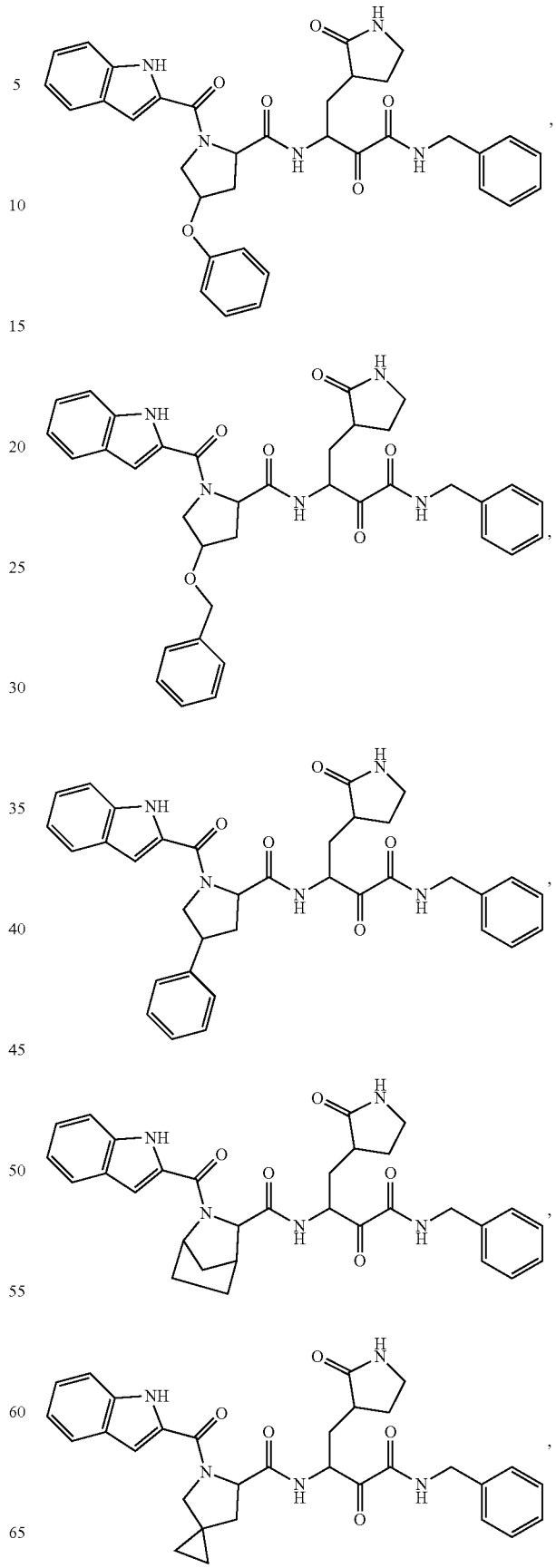

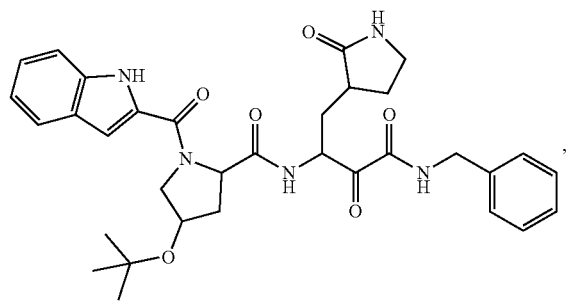
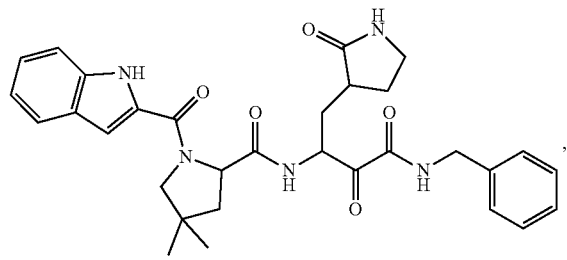
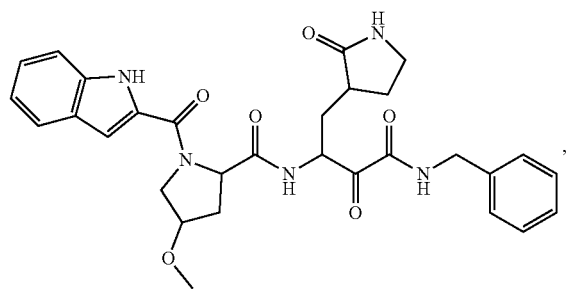
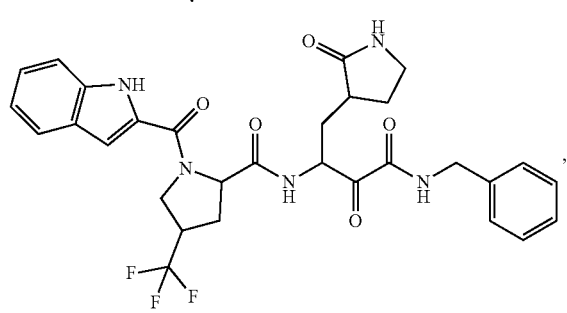
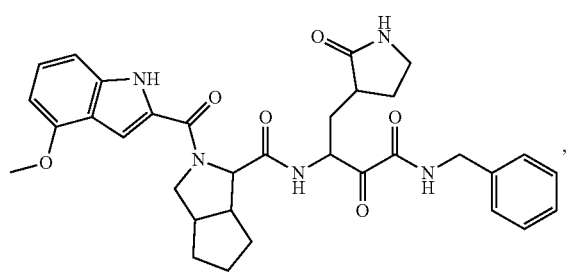
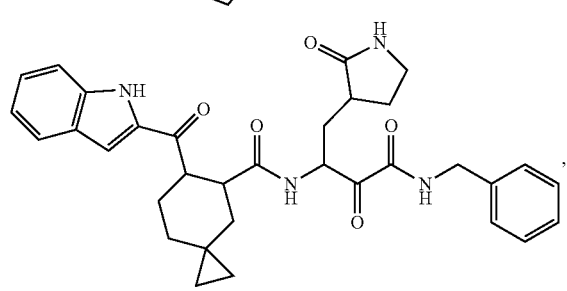
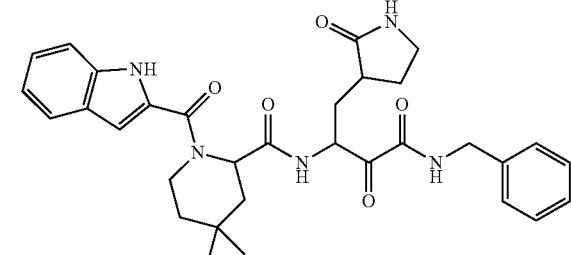
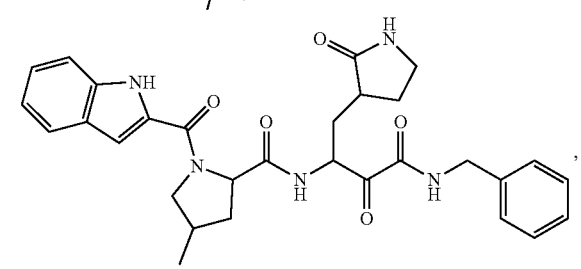
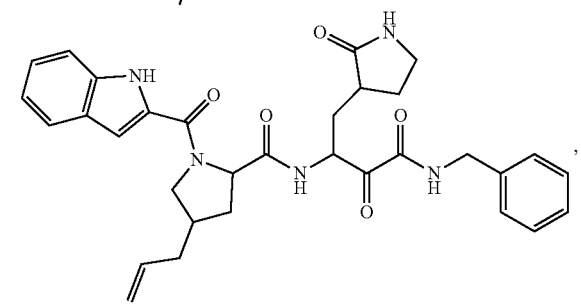
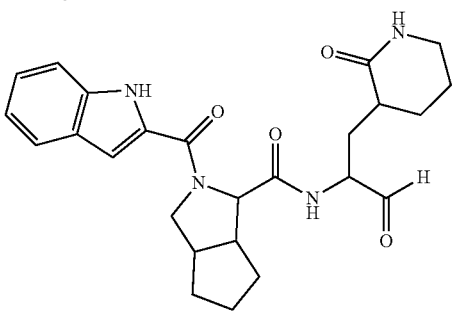
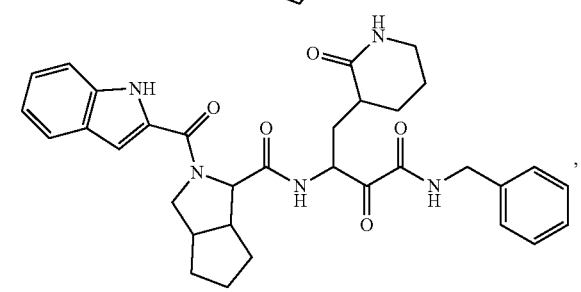
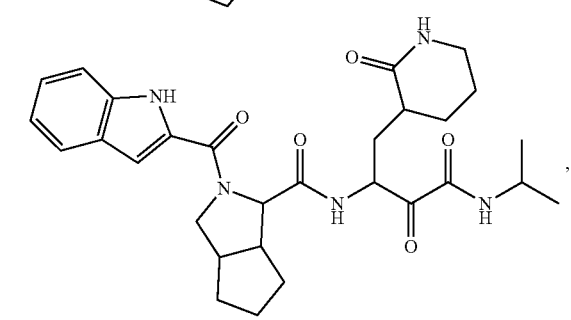

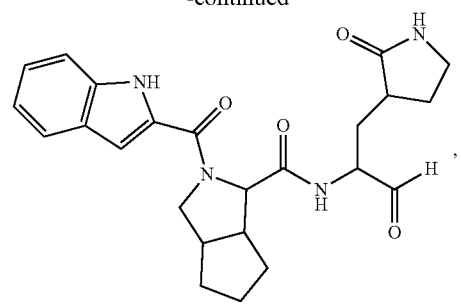
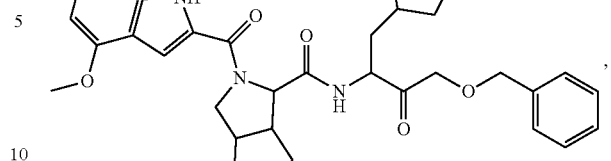
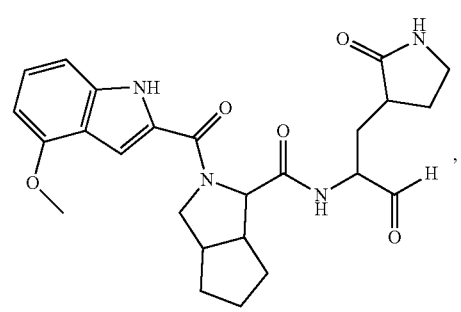
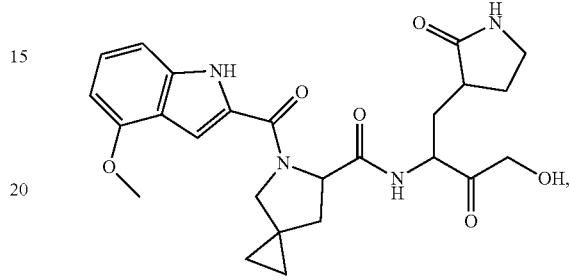
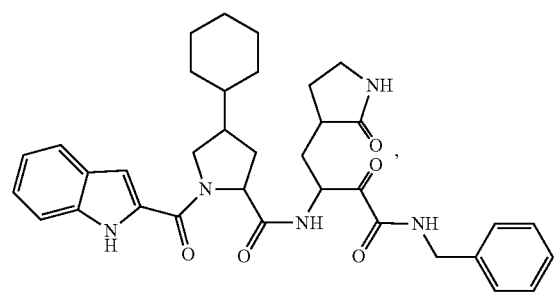
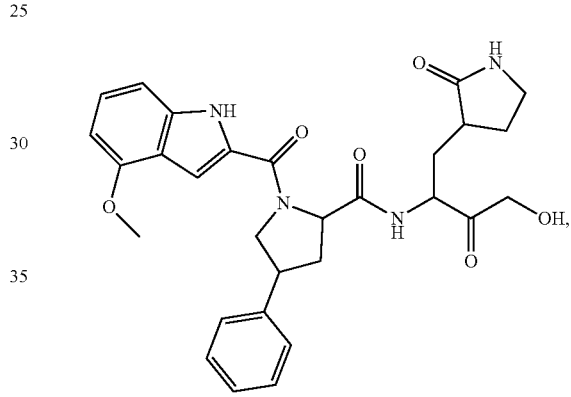
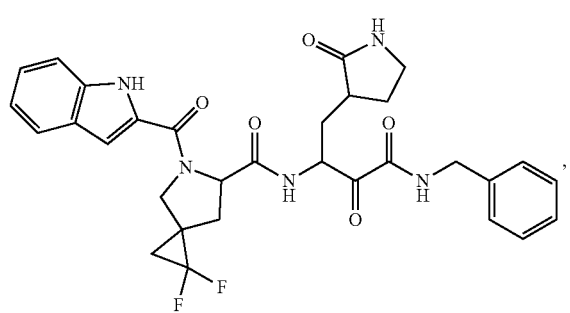
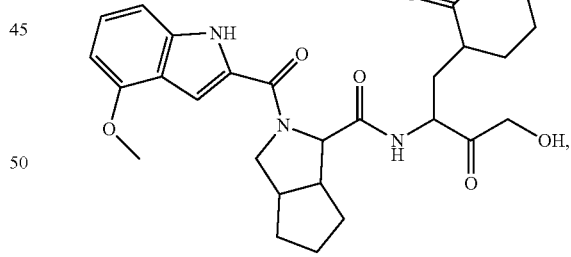
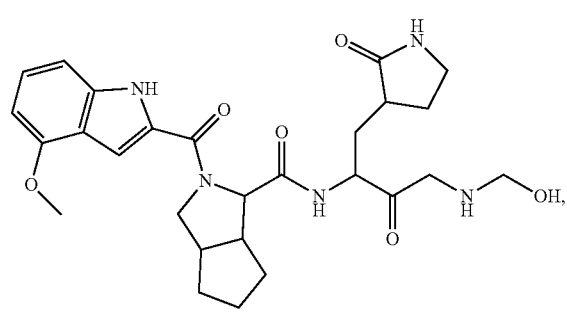
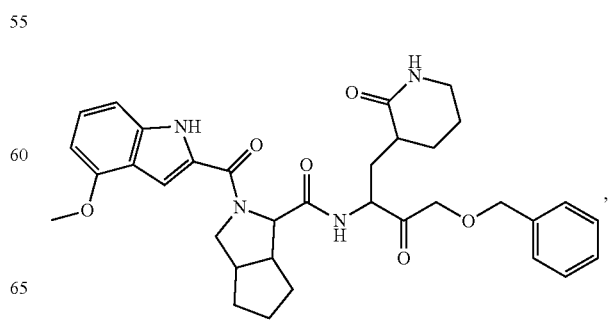

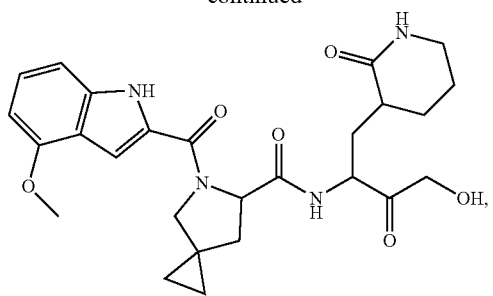
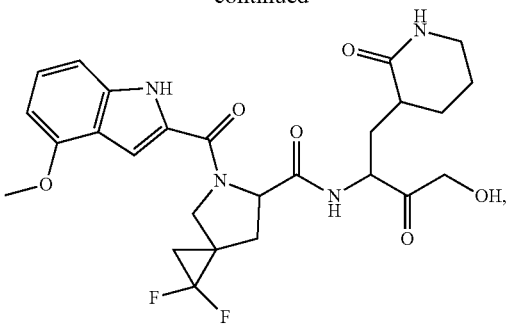
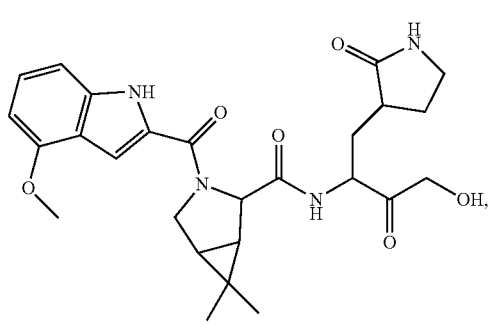
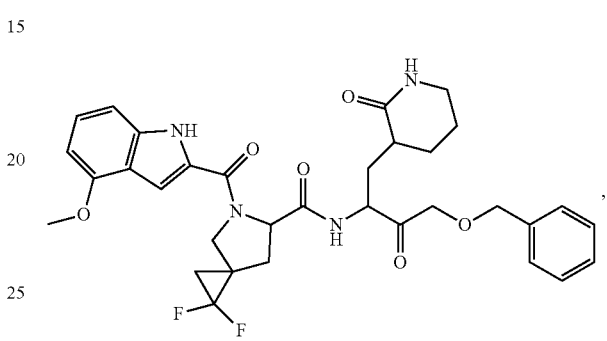
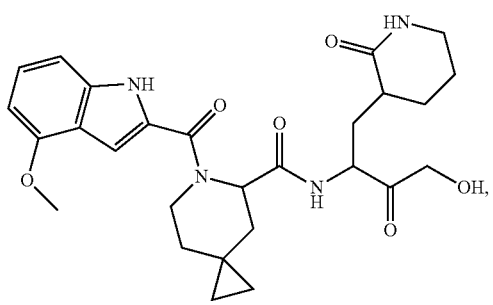
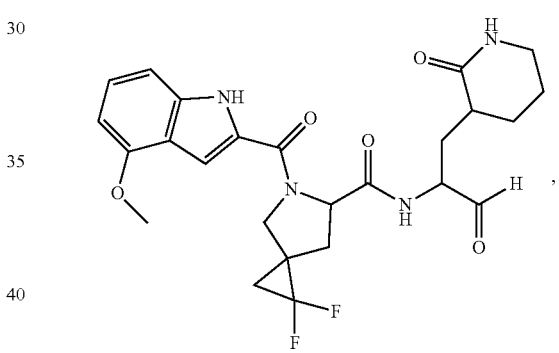
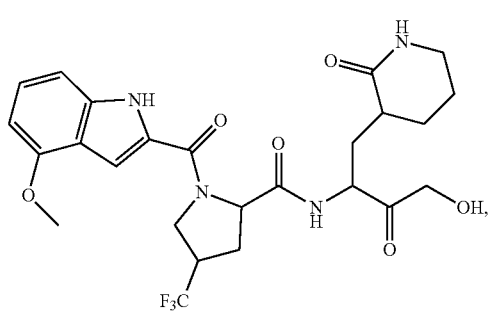
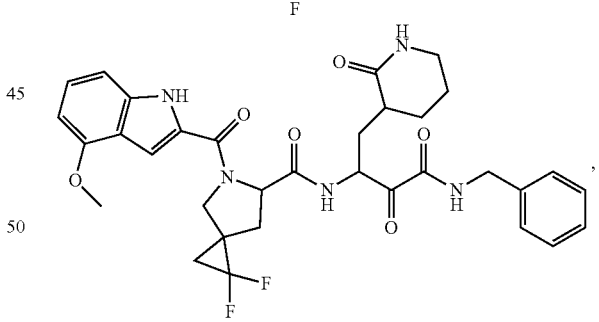
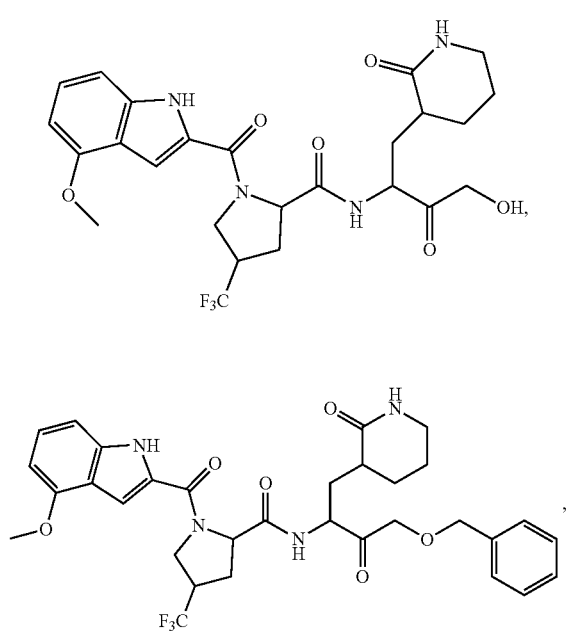
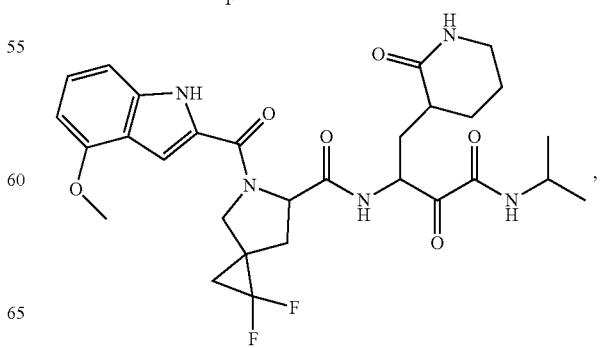

49
-continued
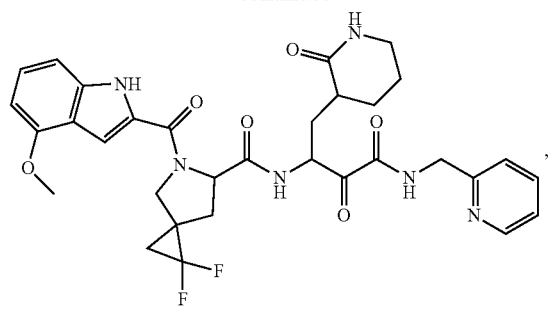
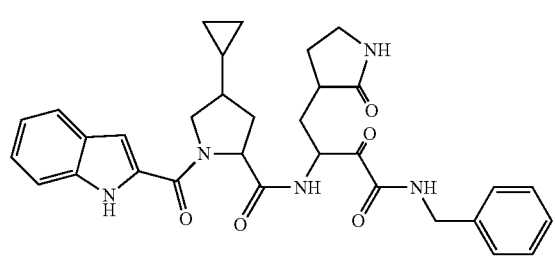
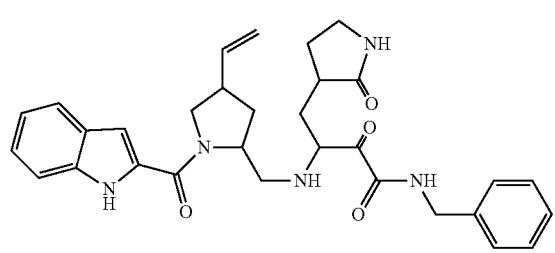
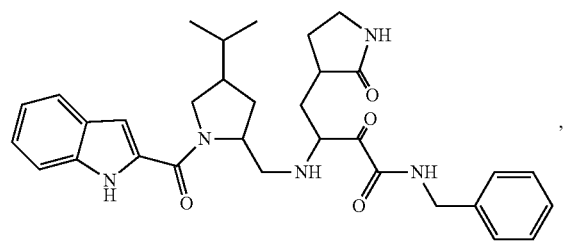
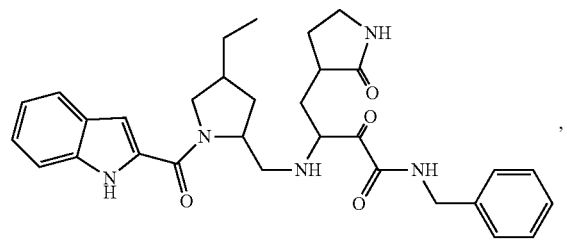
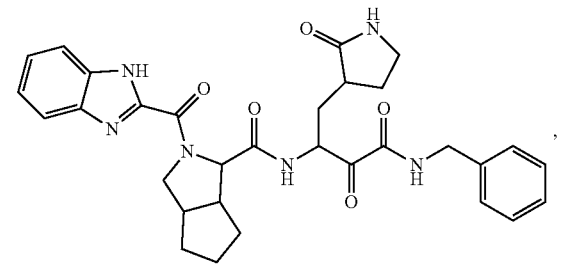
50
-continued
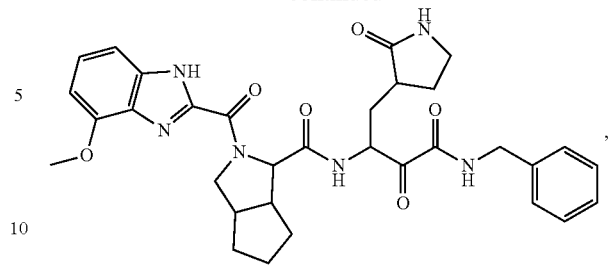
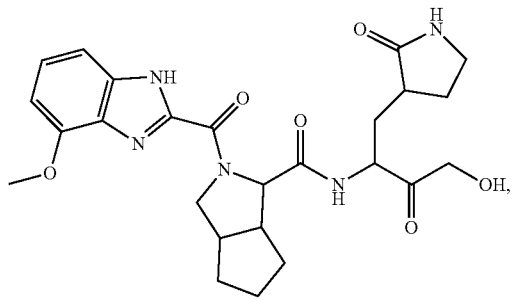
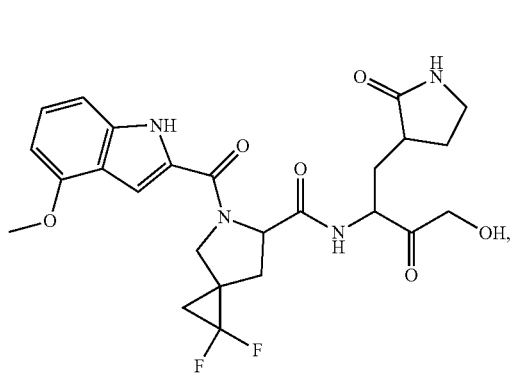
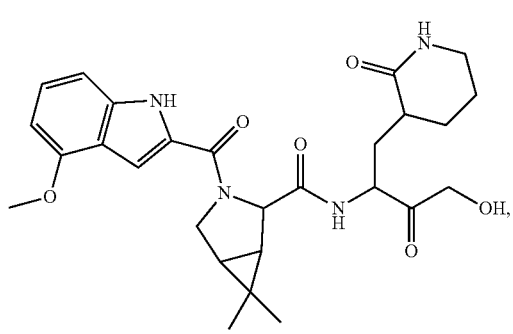
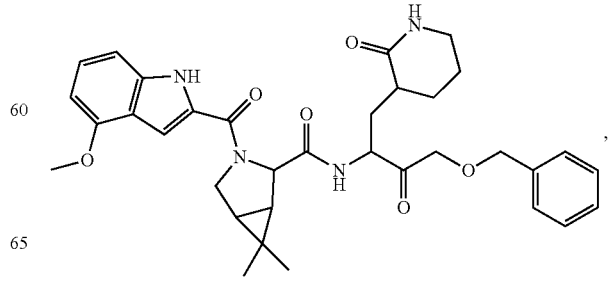

51
-continued
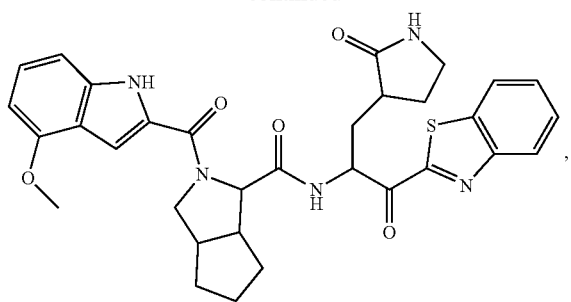
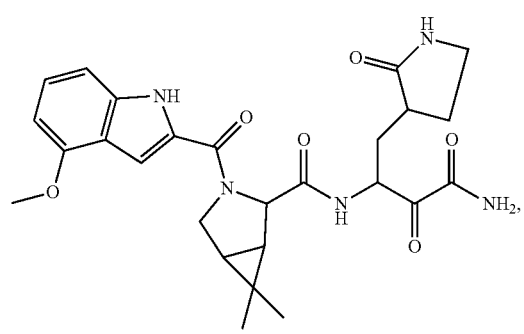
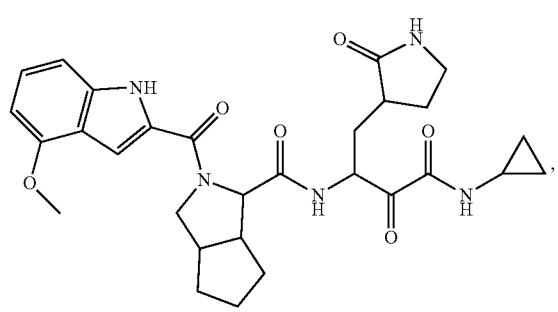
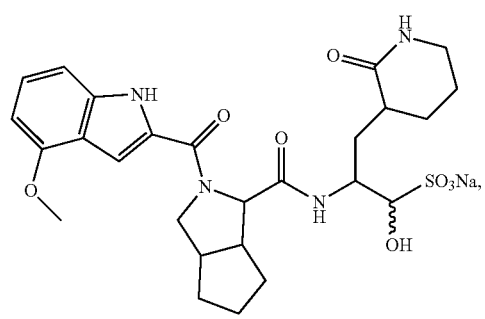
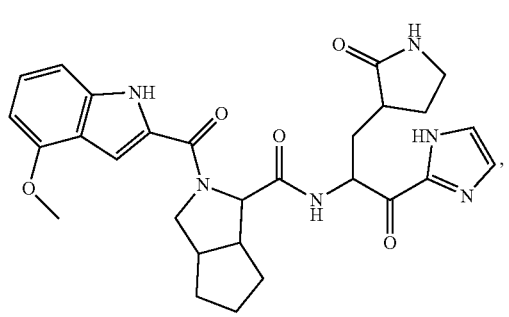
52
-continued
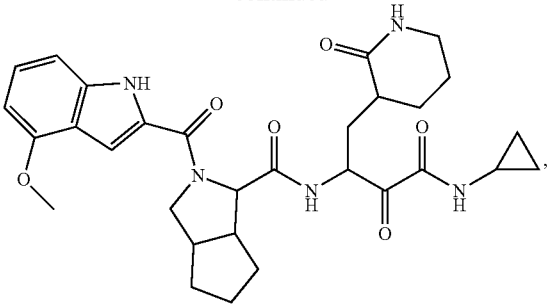
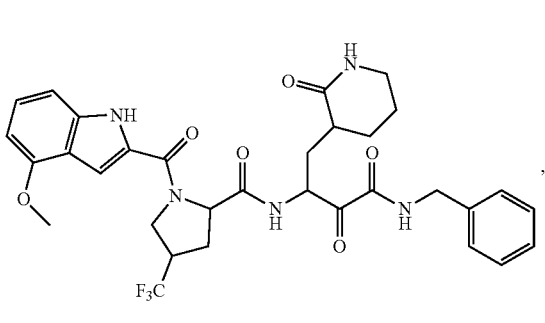
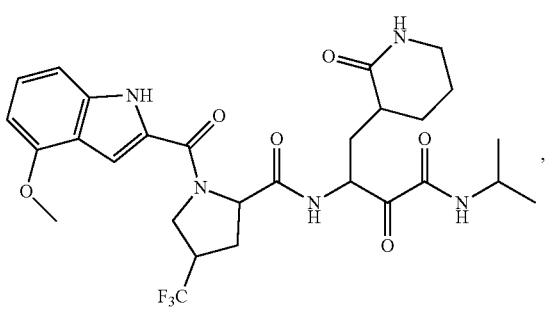
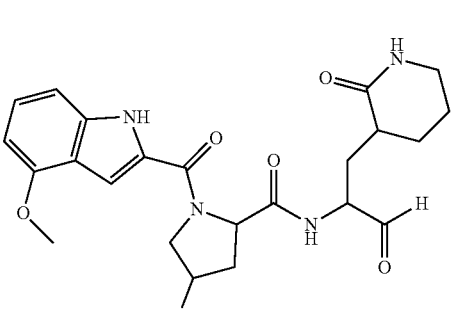
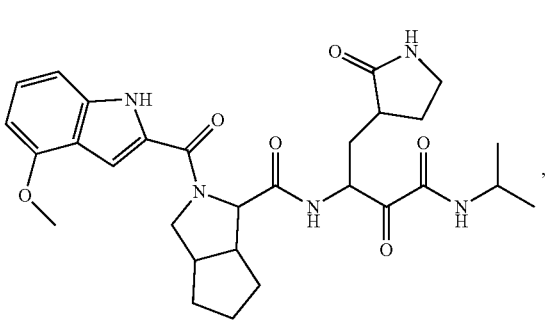

53
-continued
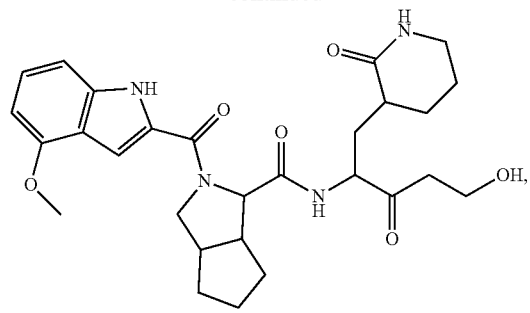
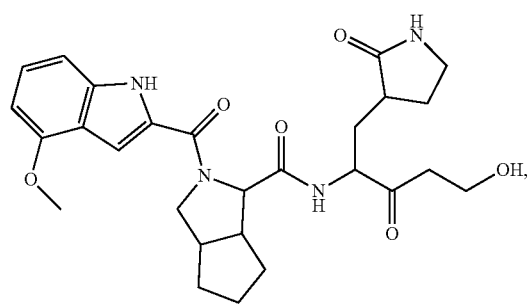
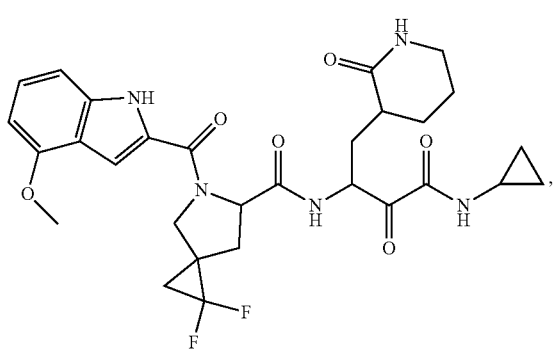
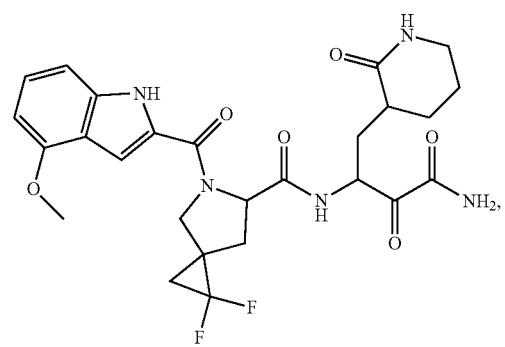
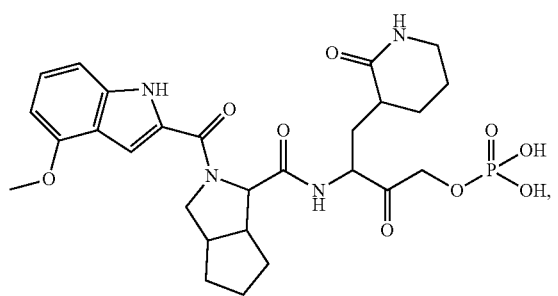
54
-continued
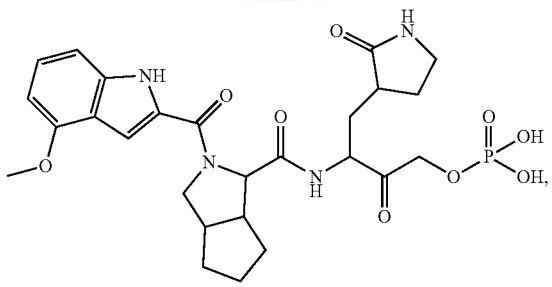
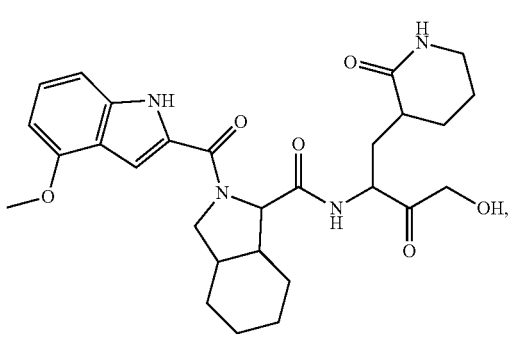
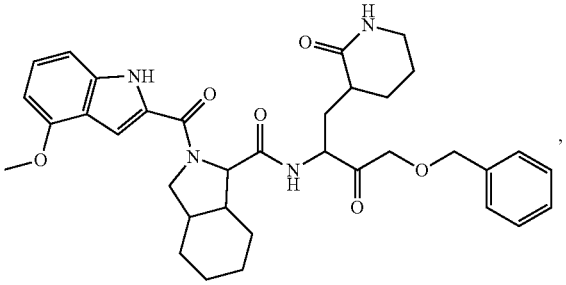
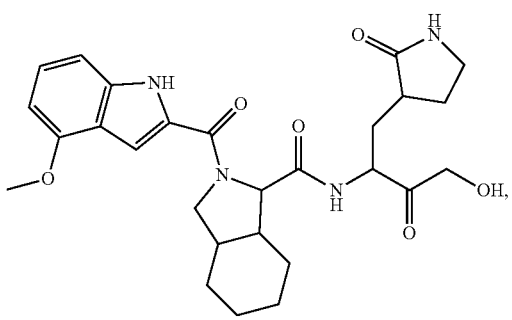
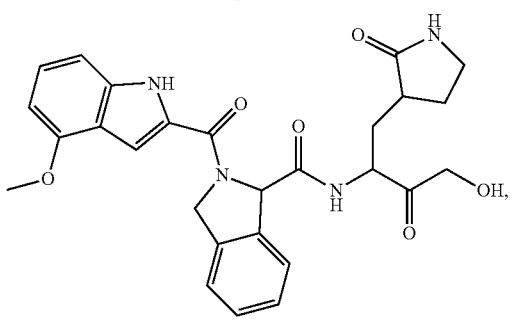

55
-continued
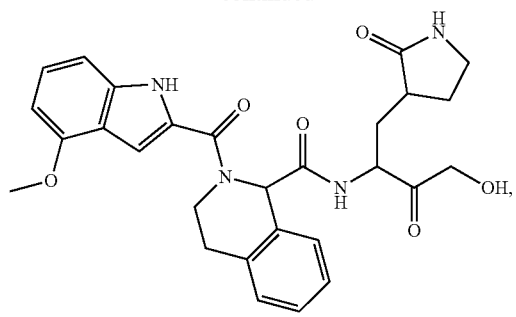
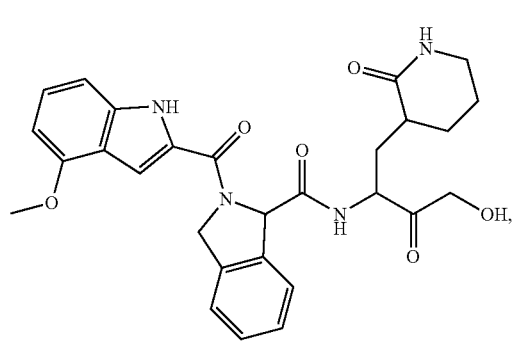
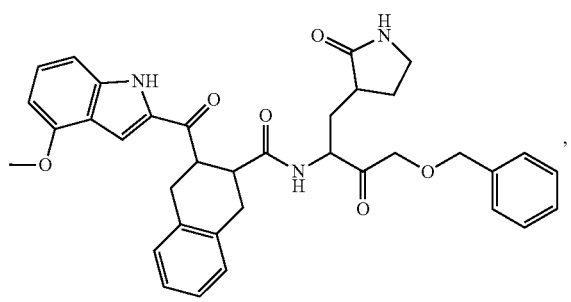
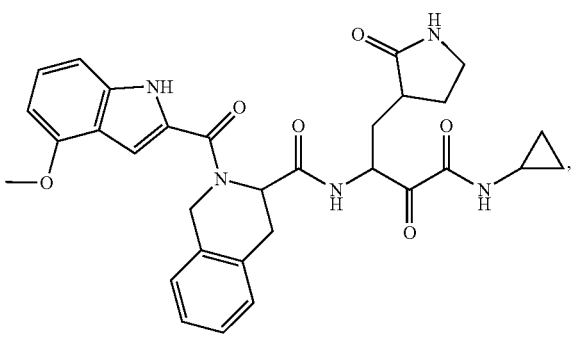
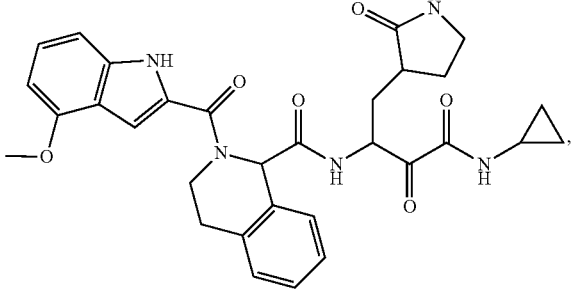
56
-continued
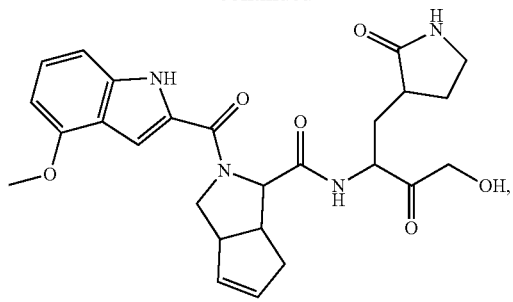
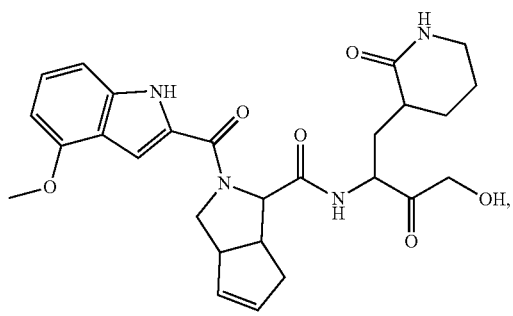
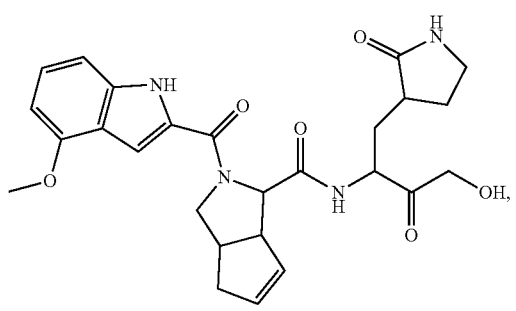
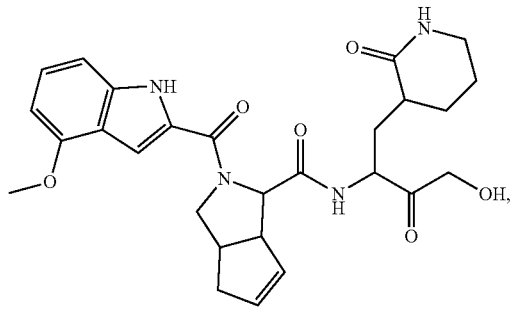
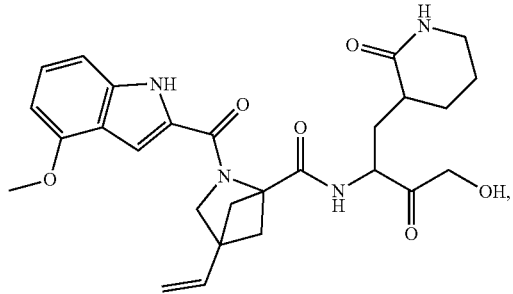

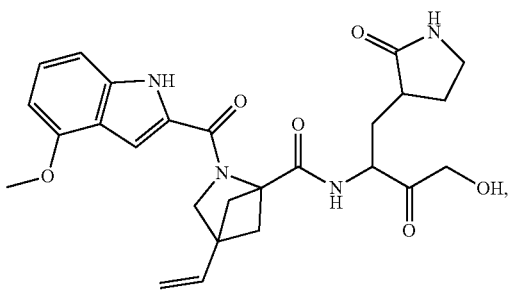
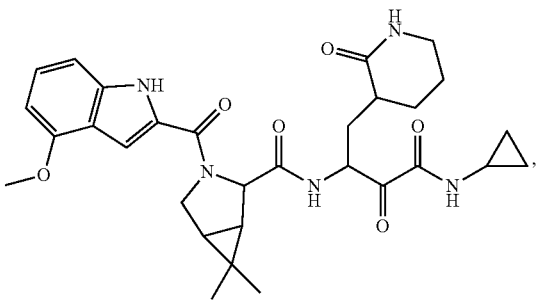
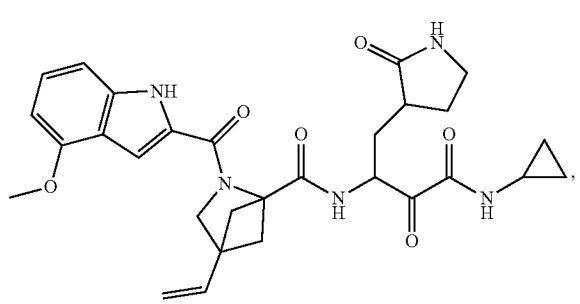
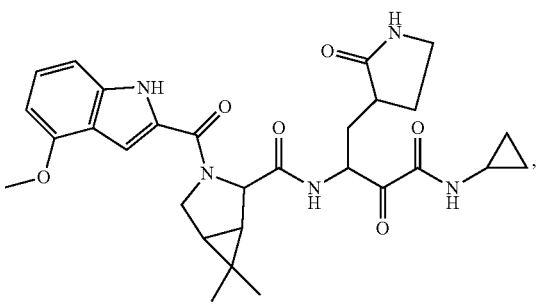
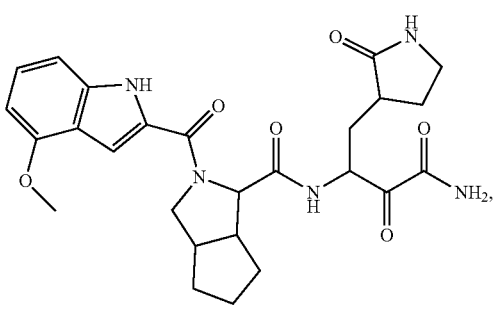
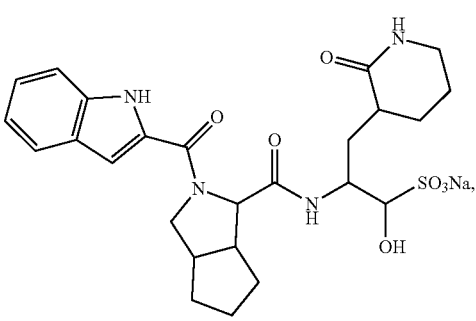
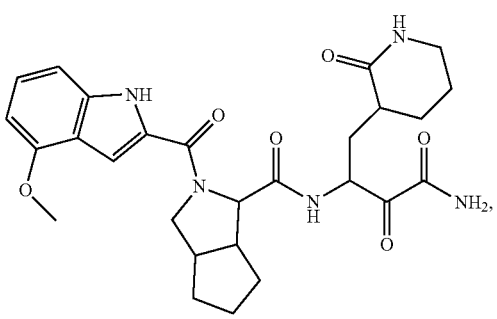
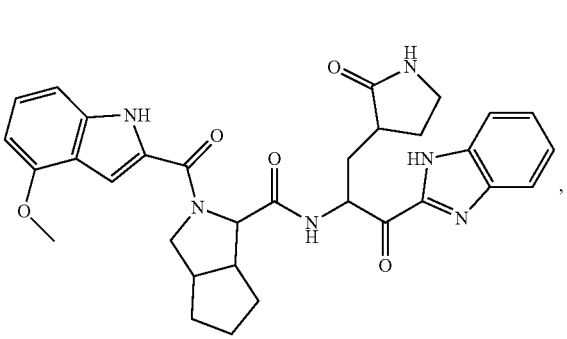
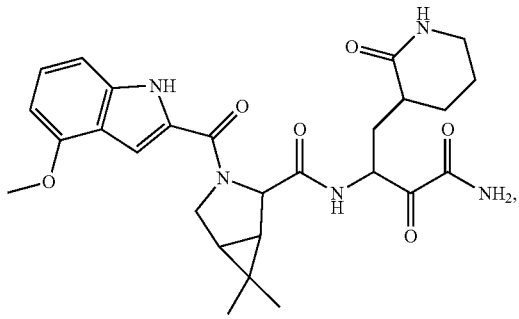
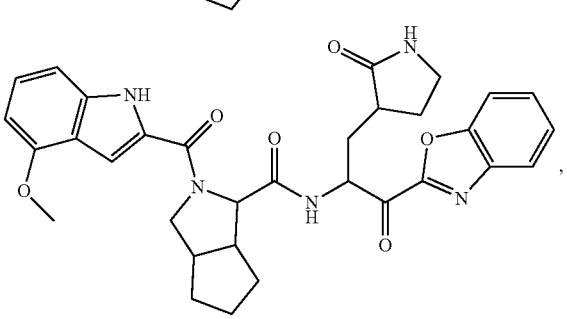

59
-continued
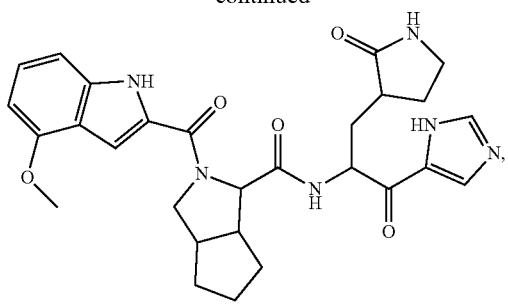
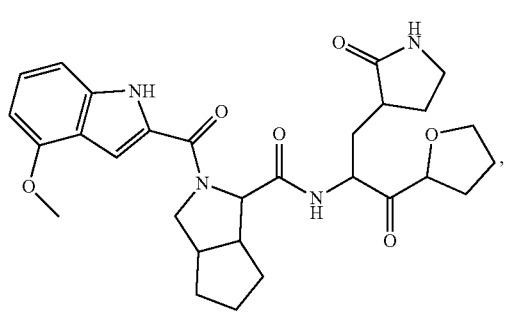
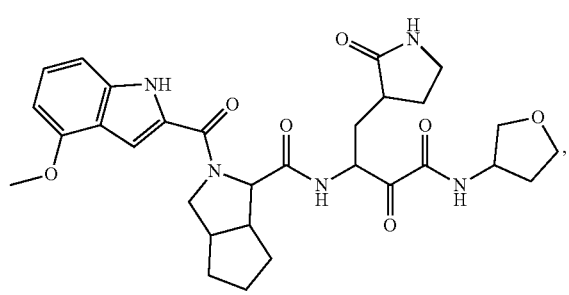
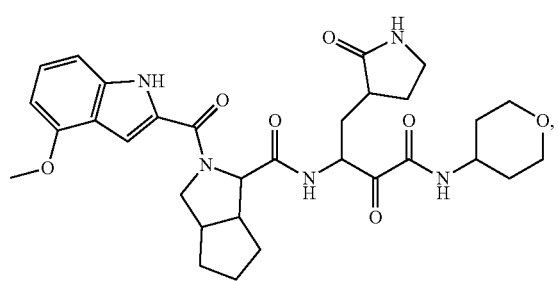
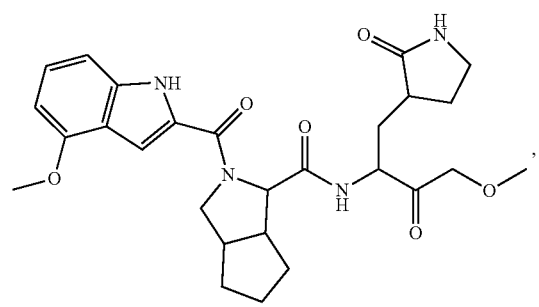
60
-continued
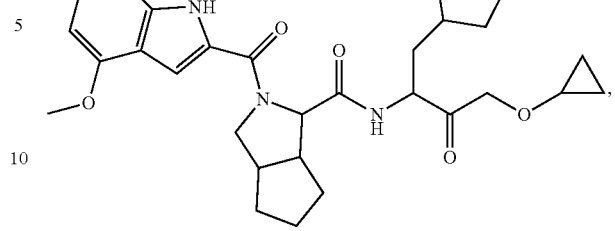
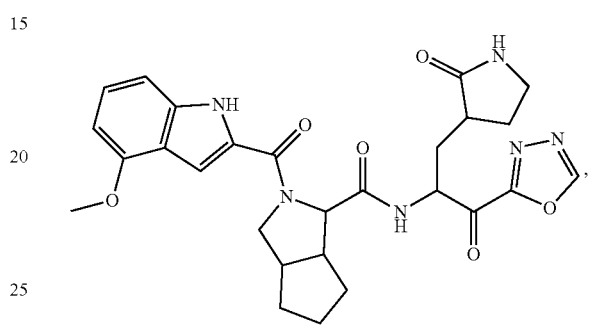
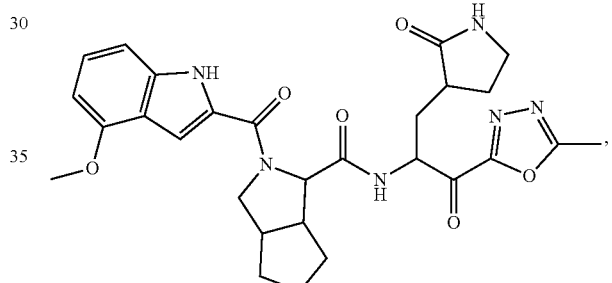
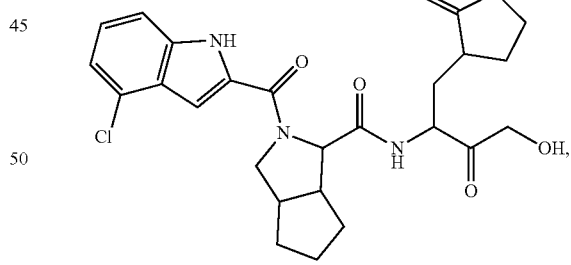
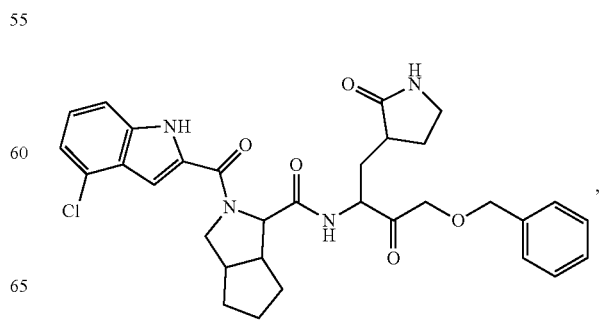

61
-continued
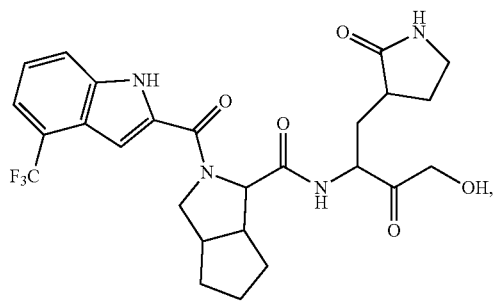
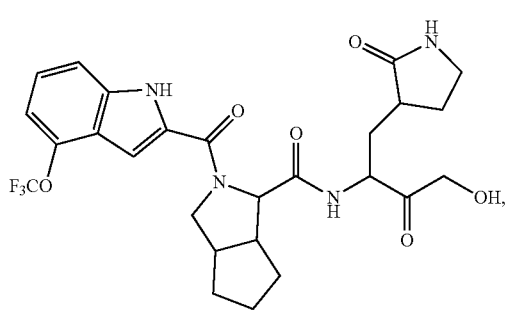
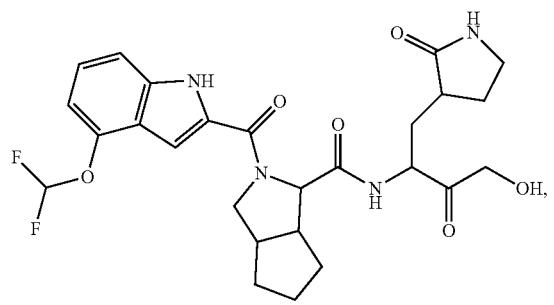
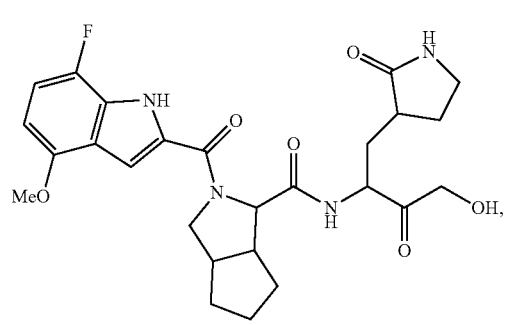
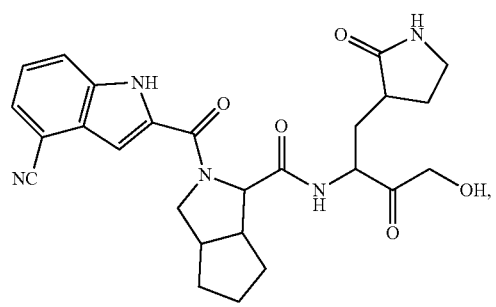
62
-continued
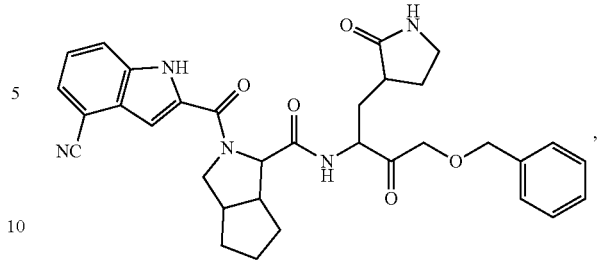
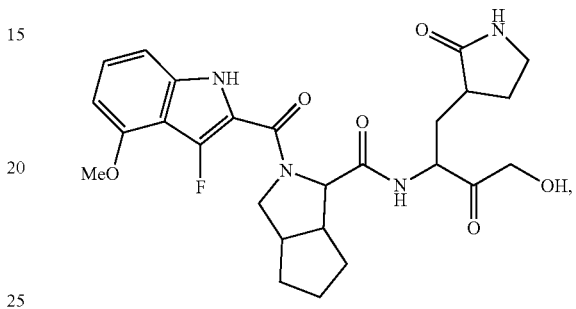
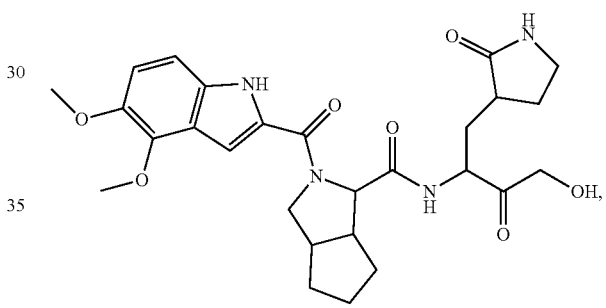
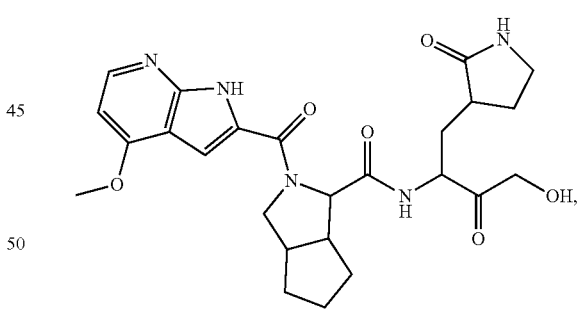
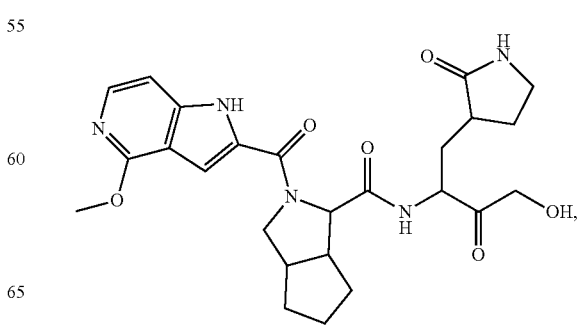

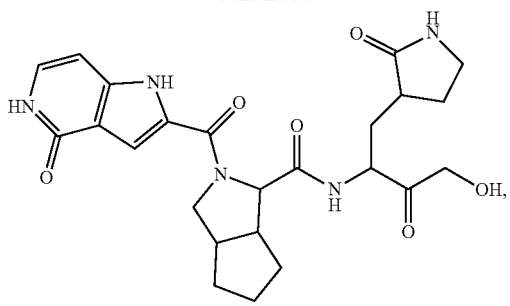
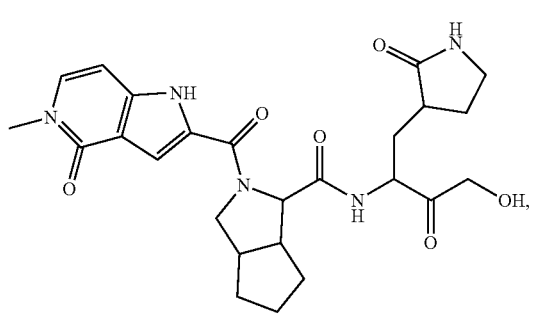
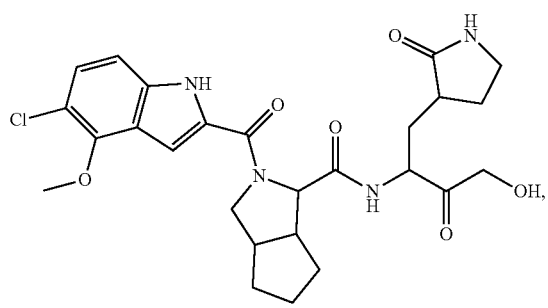
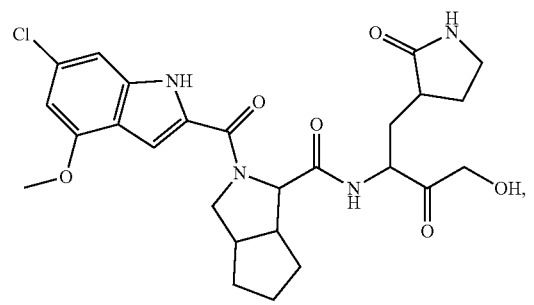
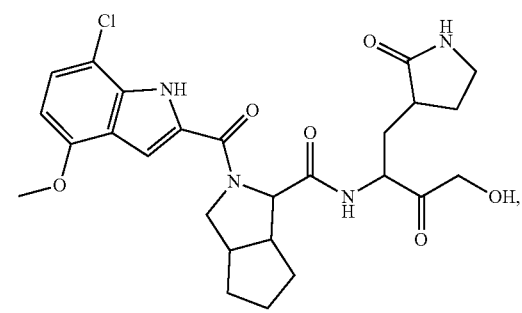
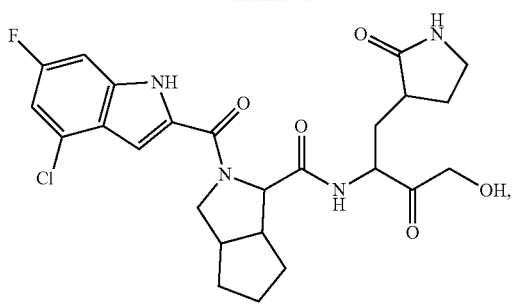
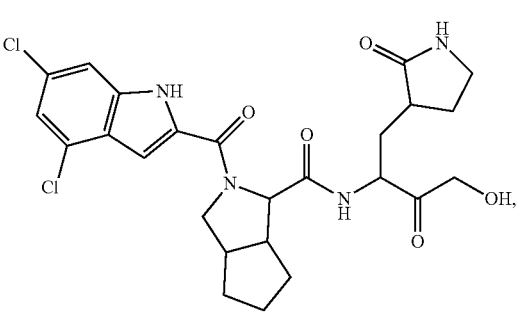
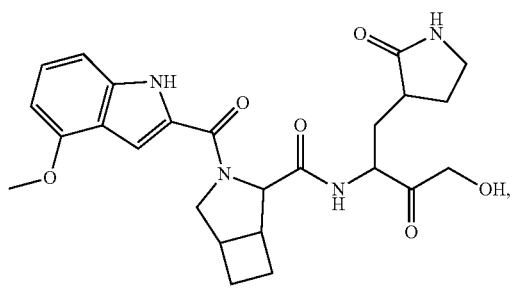
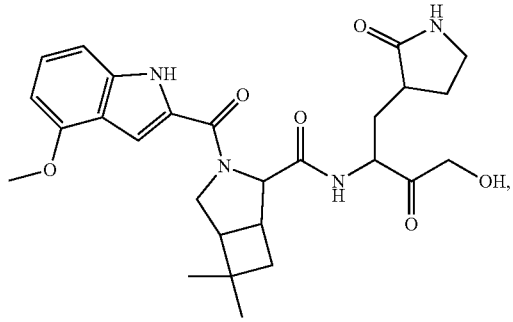
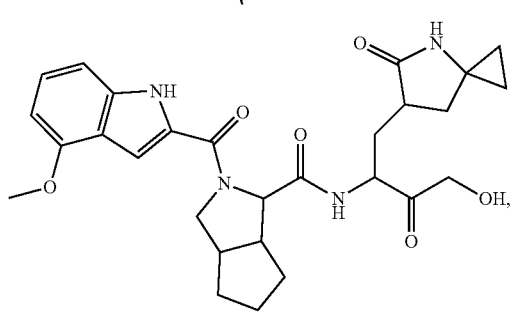

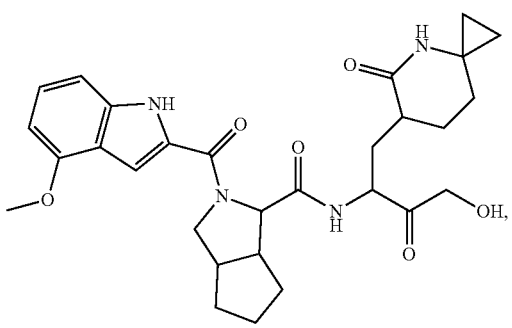
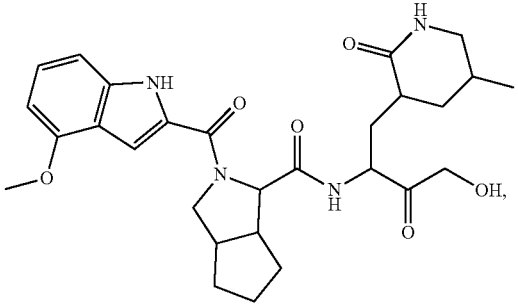
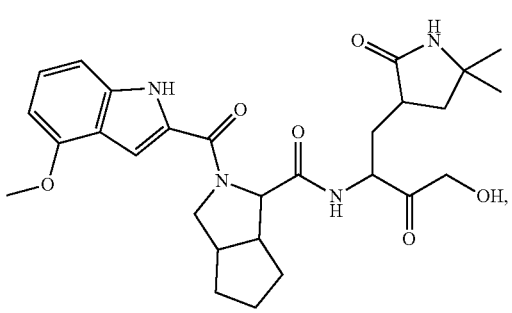
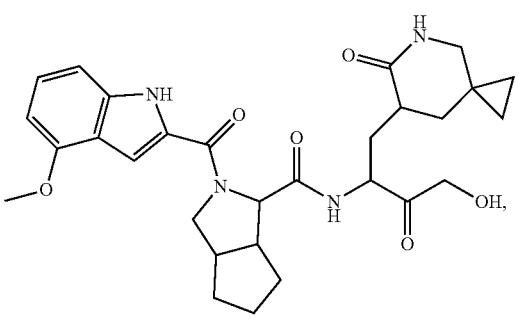
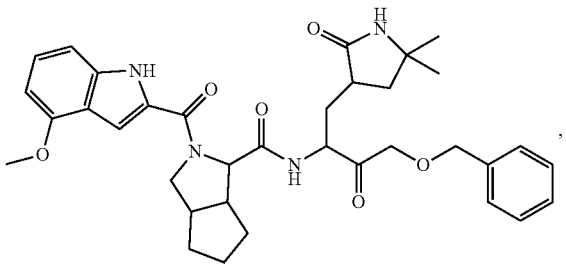
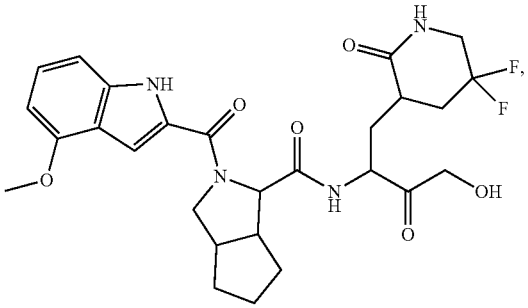
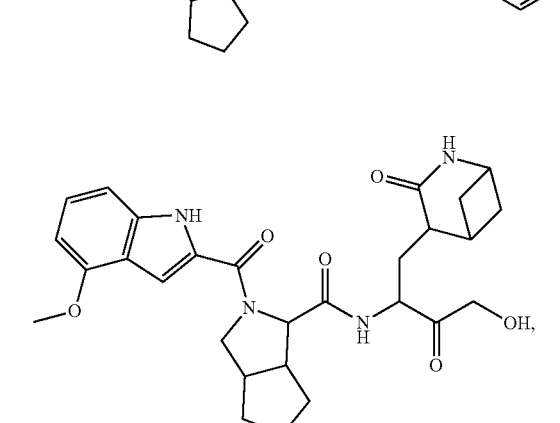
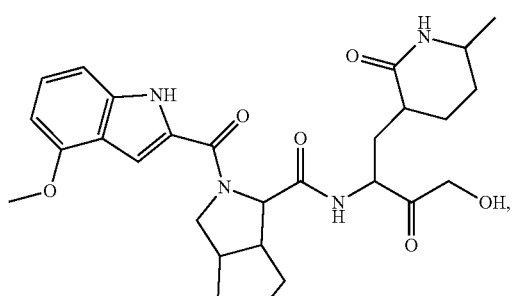
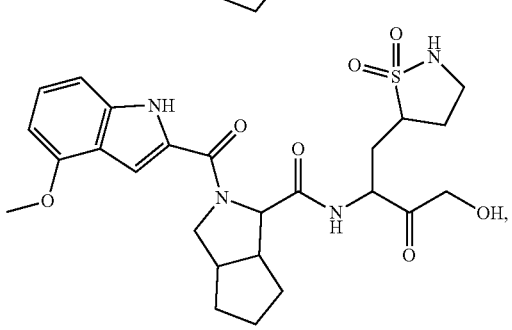
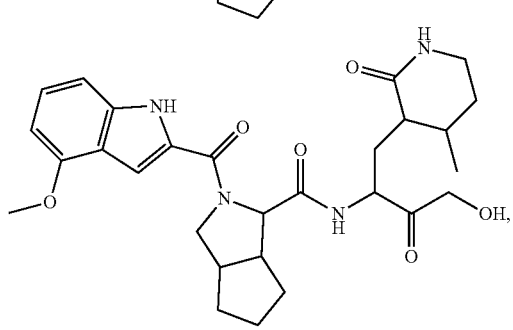

67
-continued
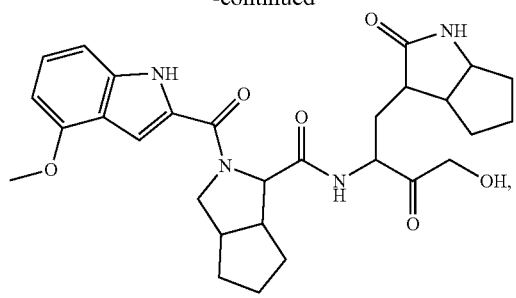
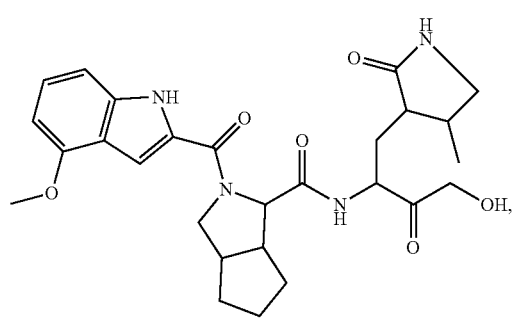
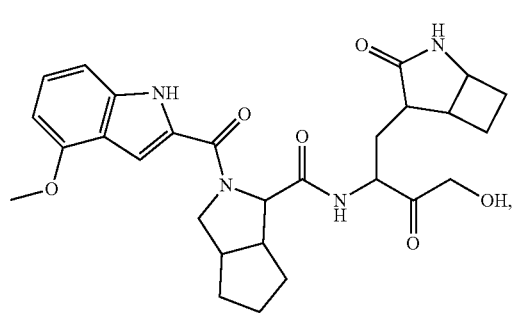
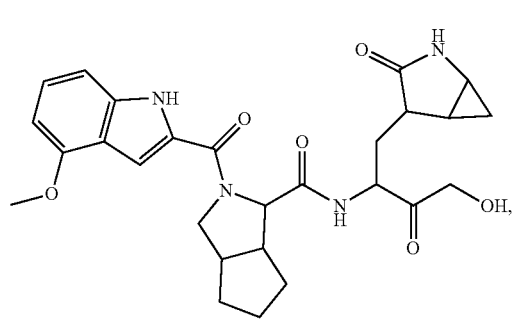
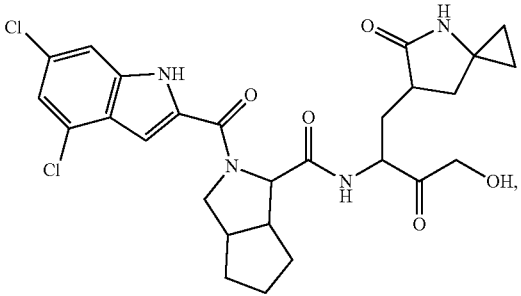
68
-continued
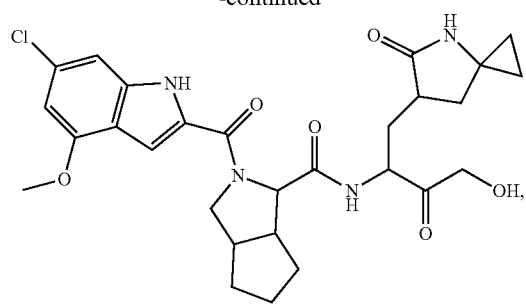
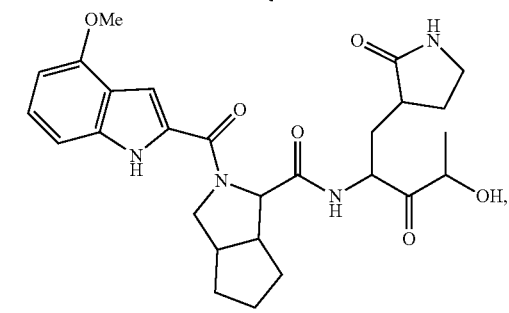
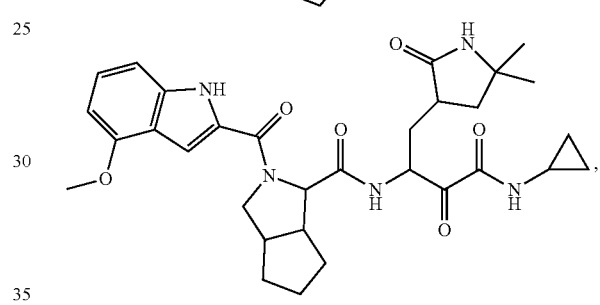
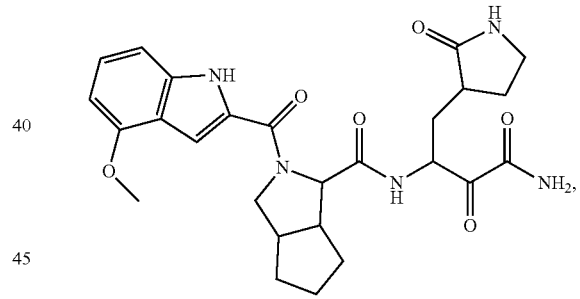
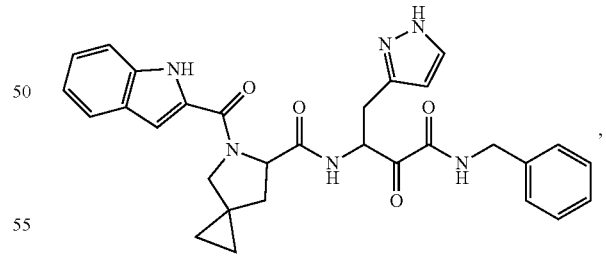
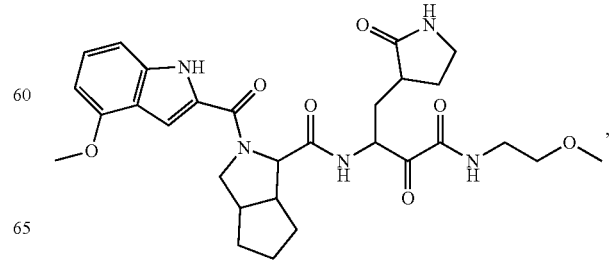

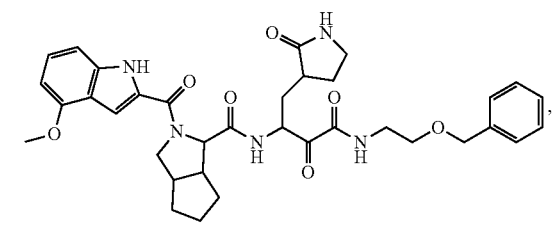
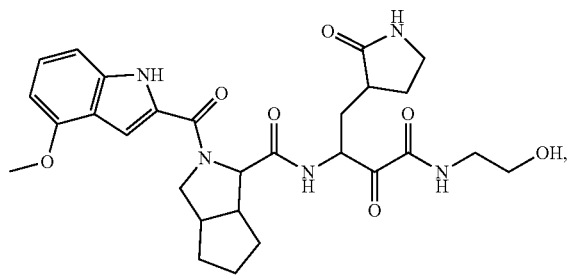
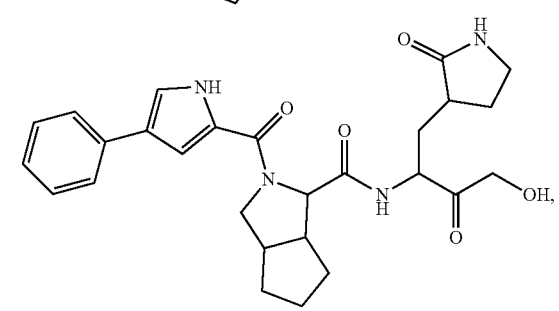
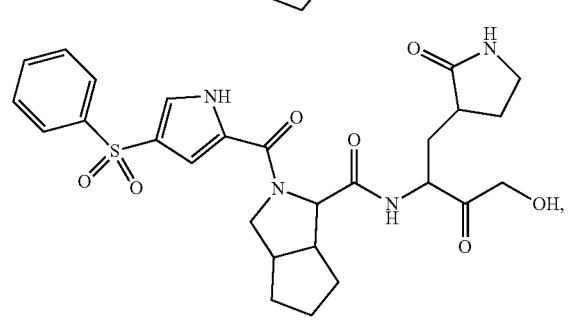
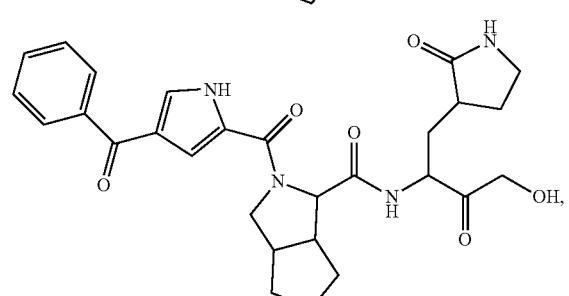
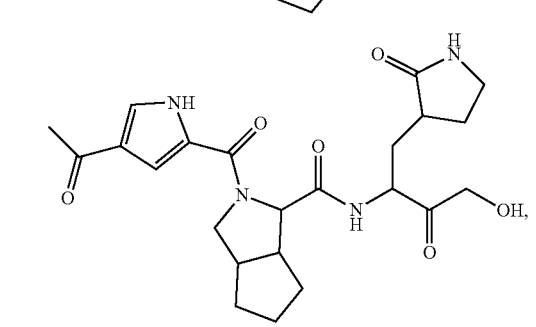
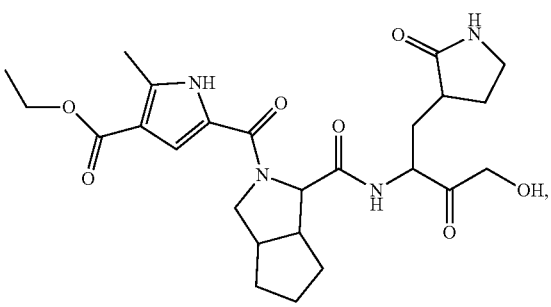
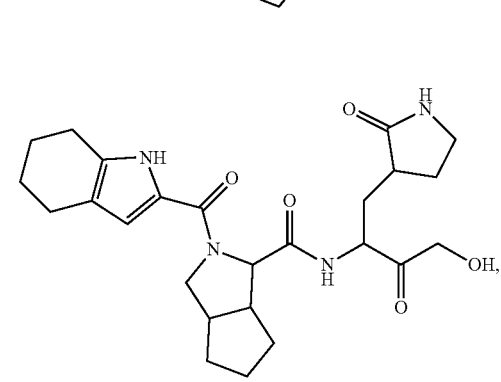
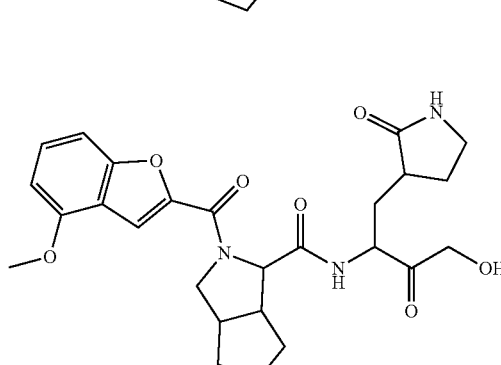
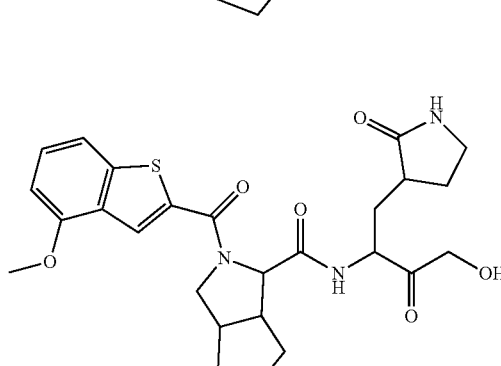
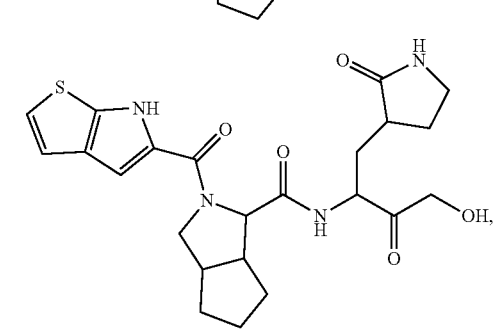

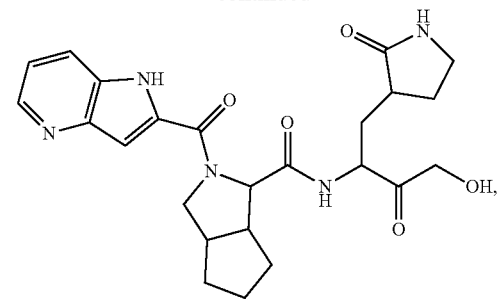
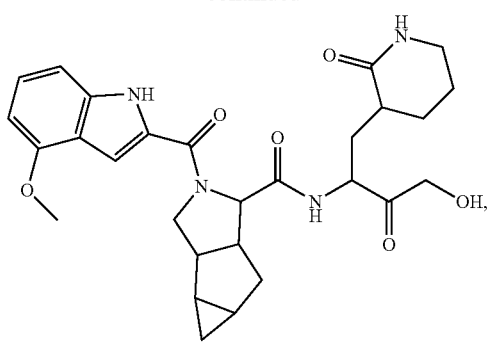
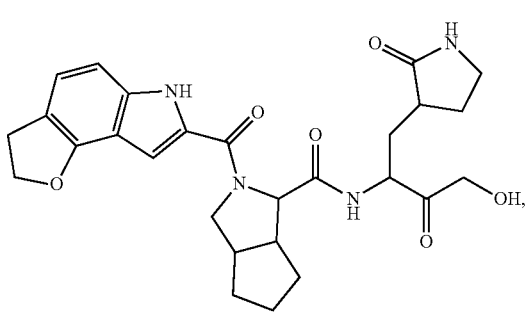
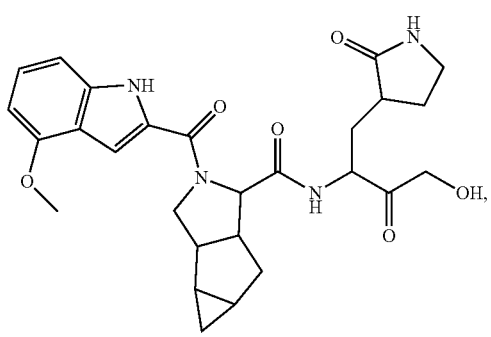
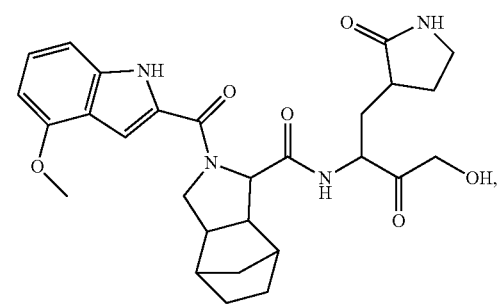
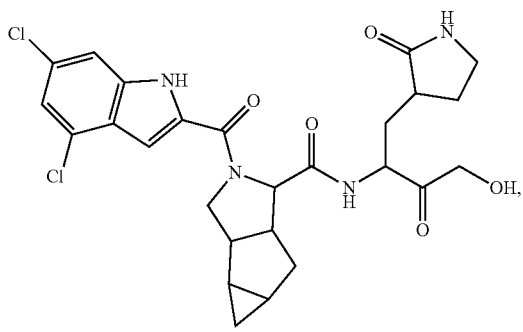
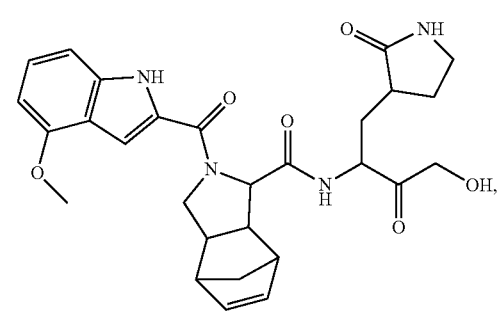
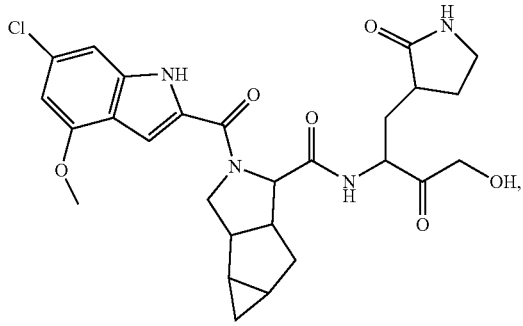
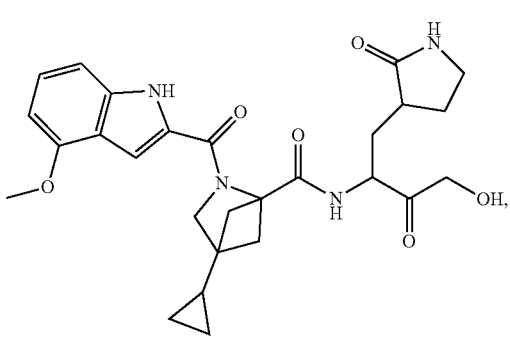
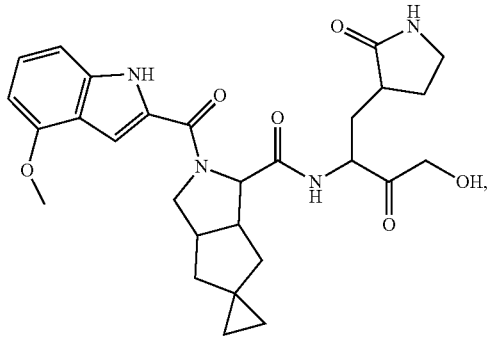

73
-continued
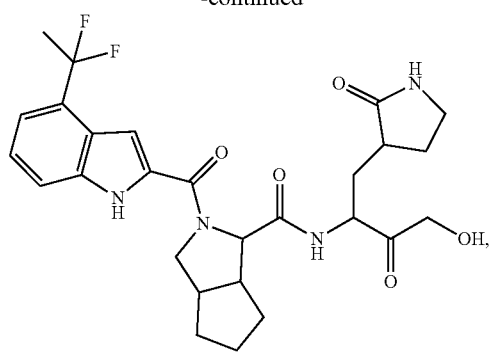
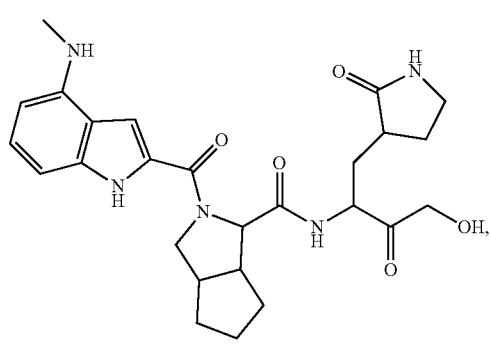
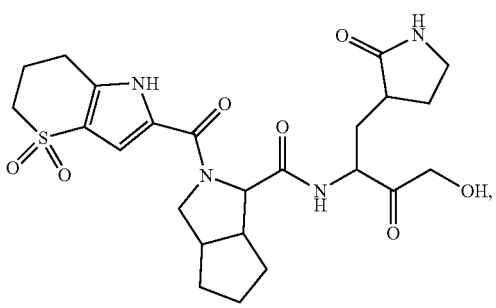
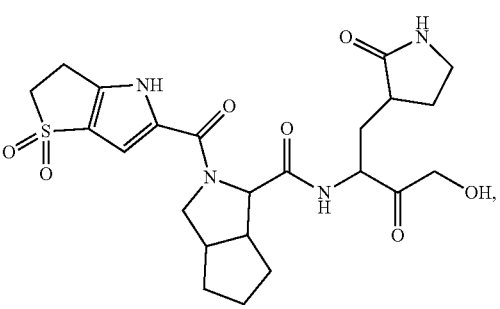
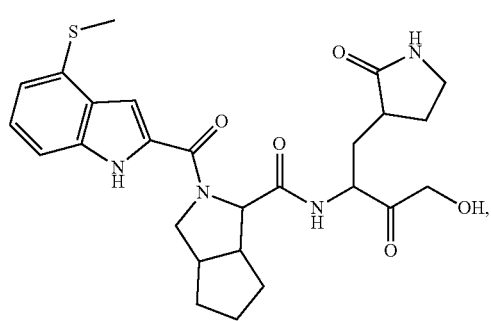
74
-continued
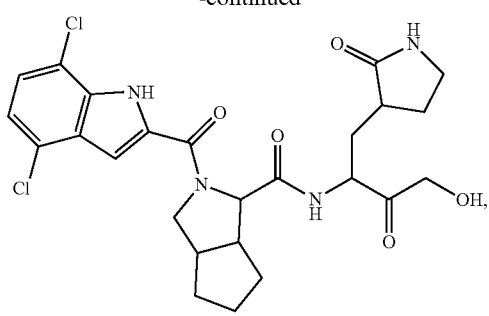
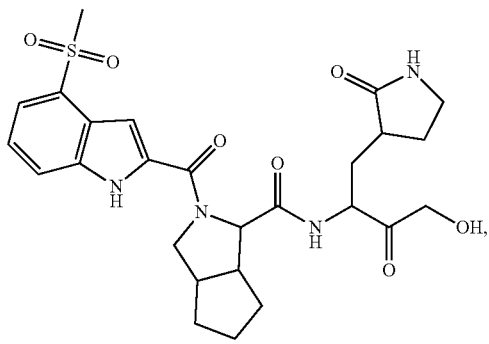
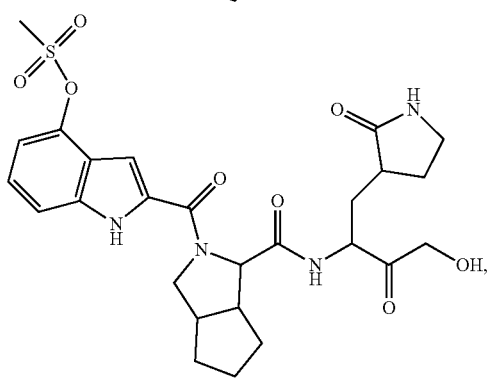
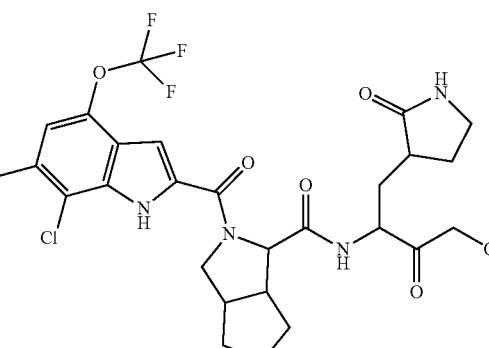
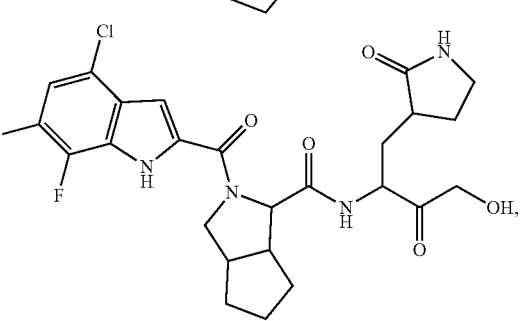

75
-continued
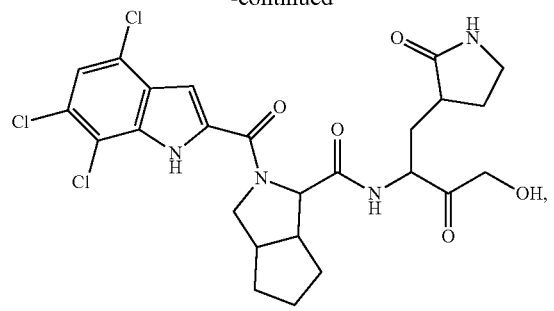
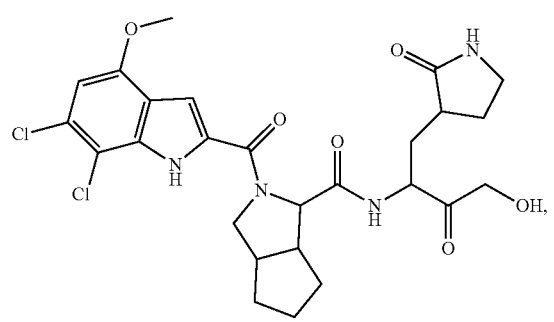
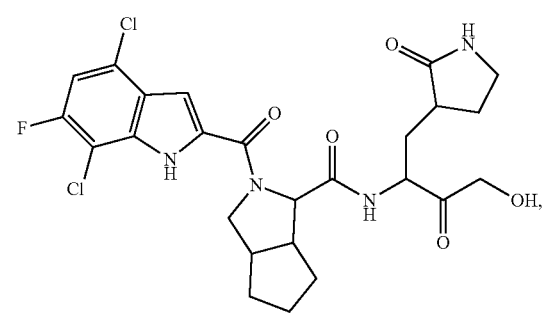
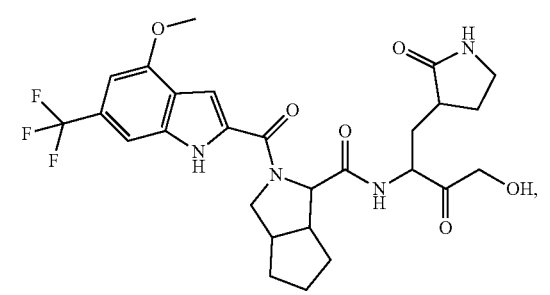
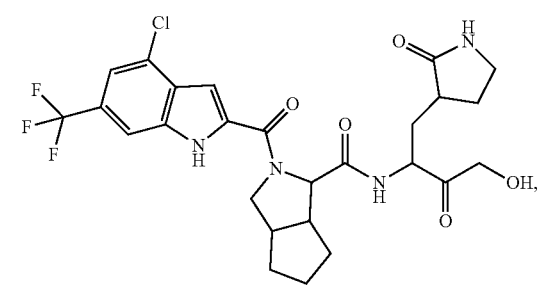
76
-continued
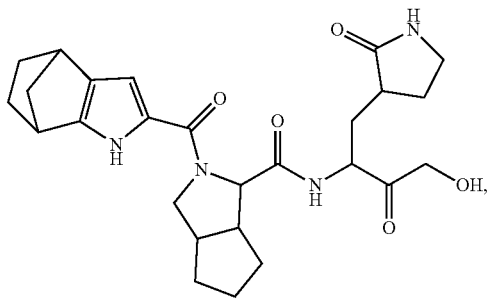
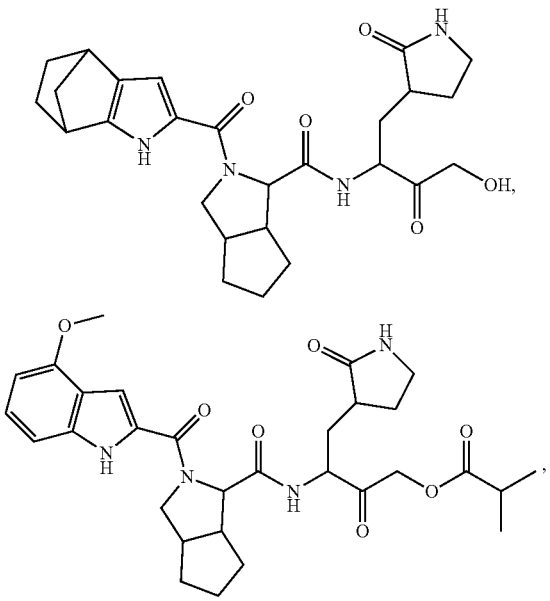
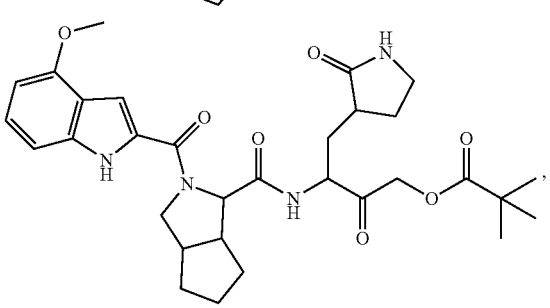
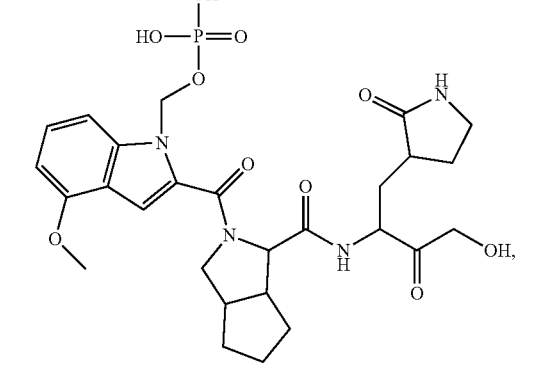
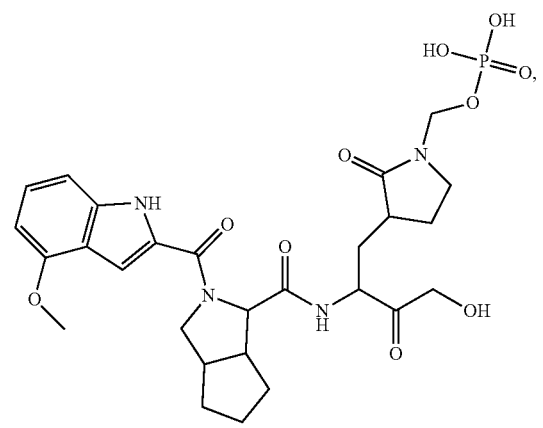

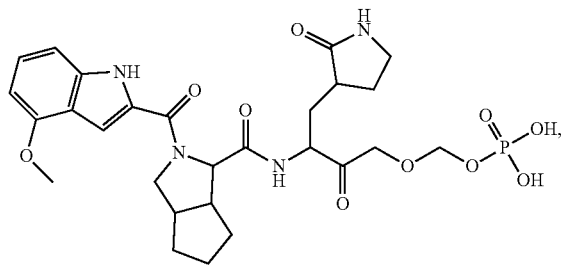
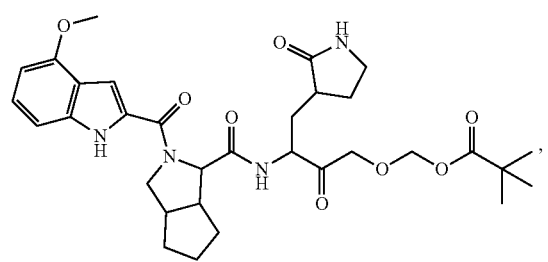
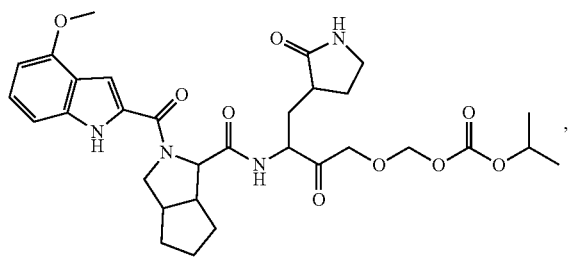
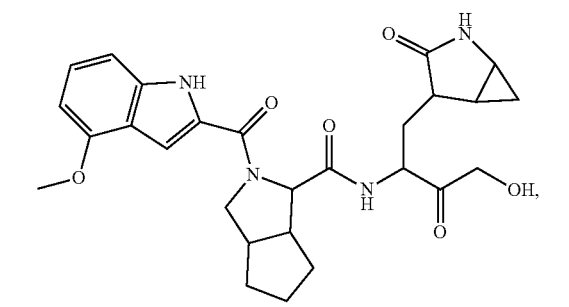
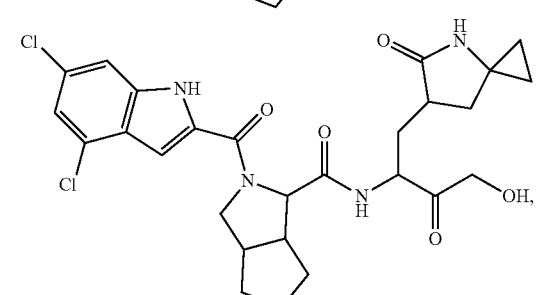
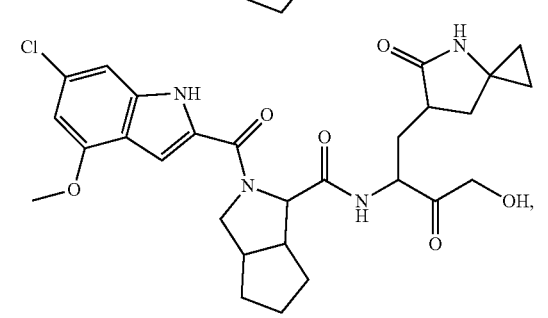
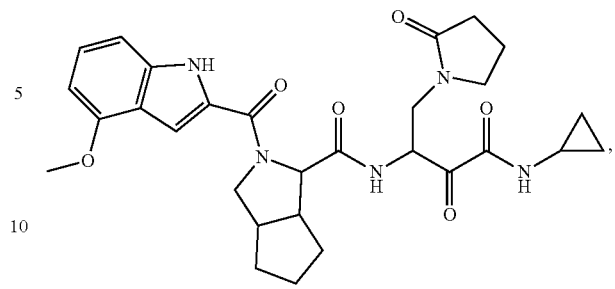
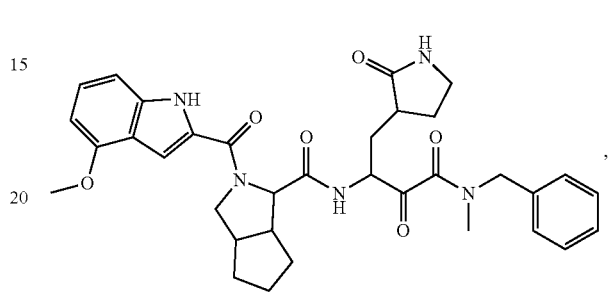
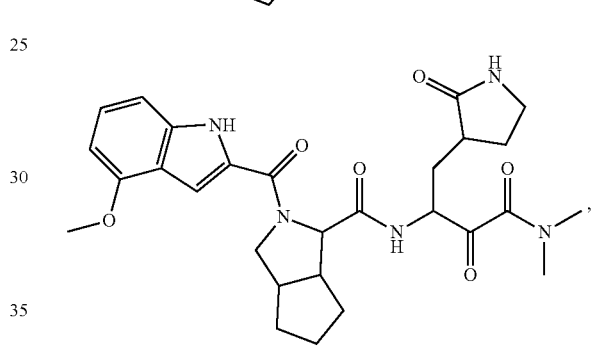
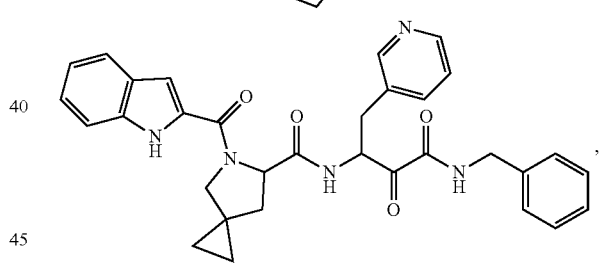
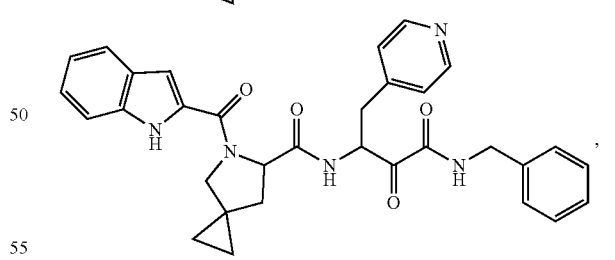
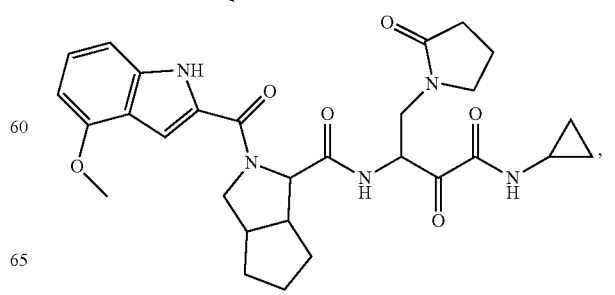

79
-continued
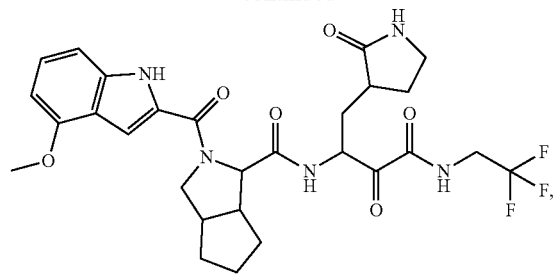
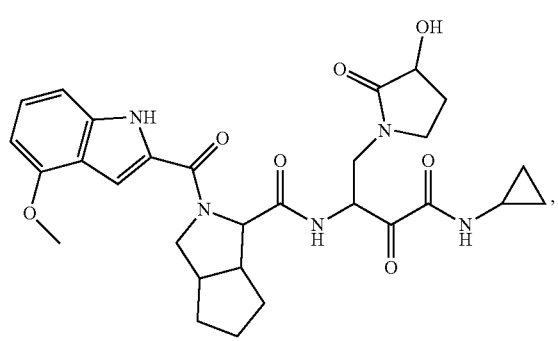
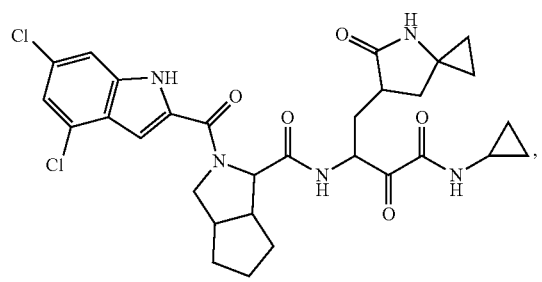
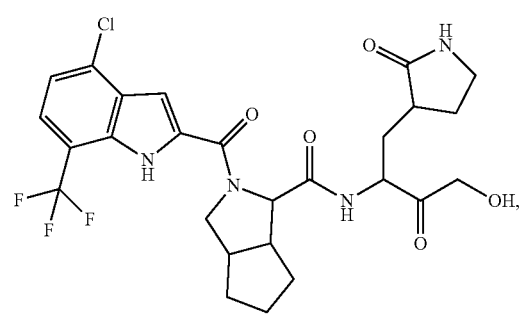
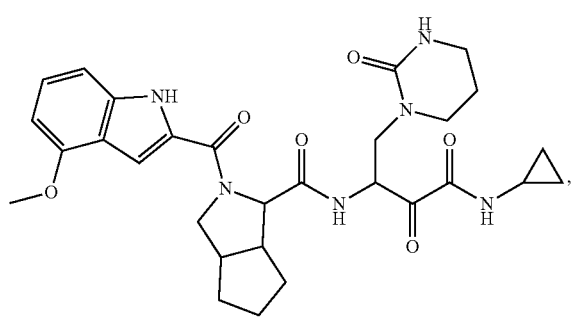
80
-continued
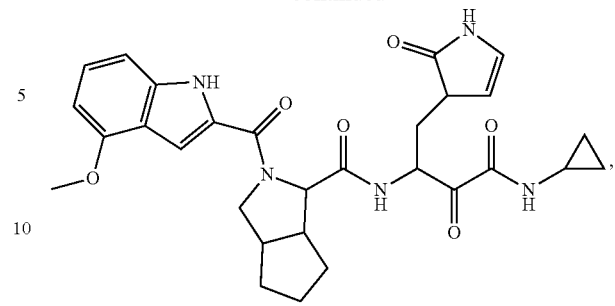
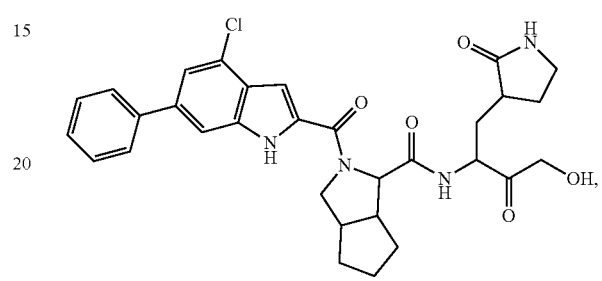
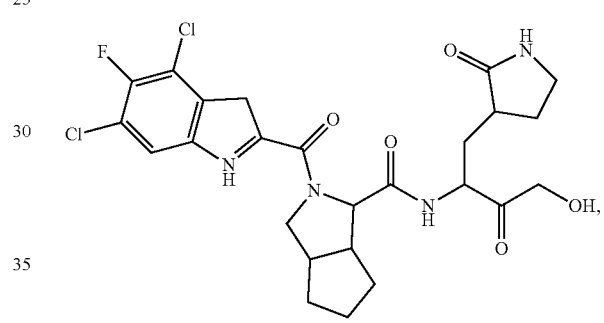
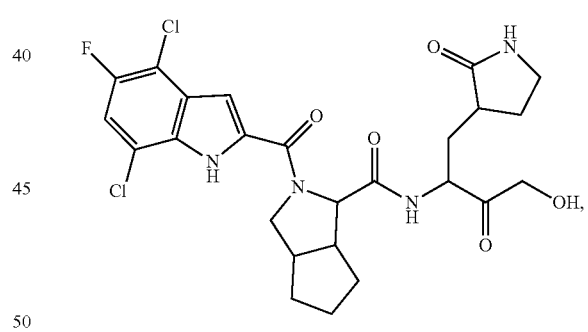
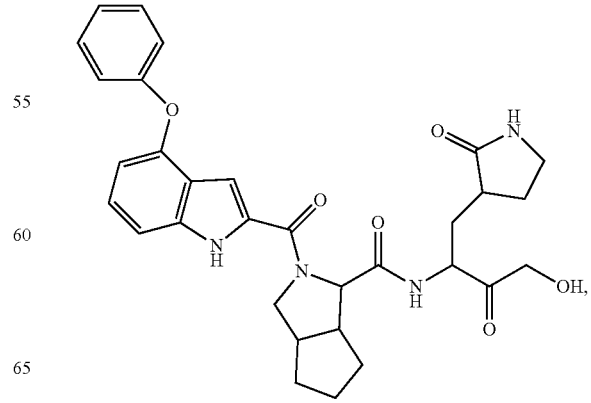

-continued
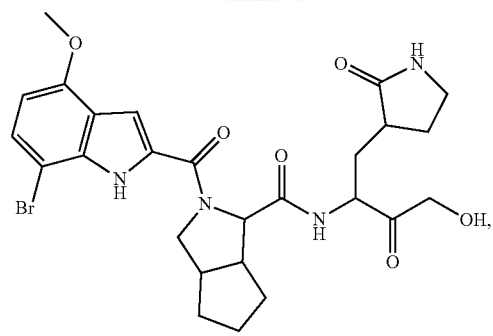
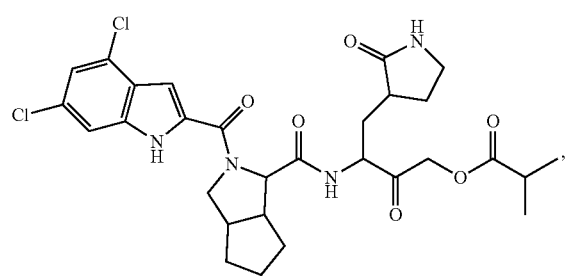
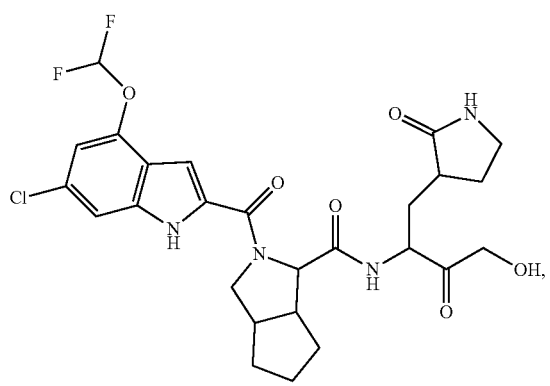
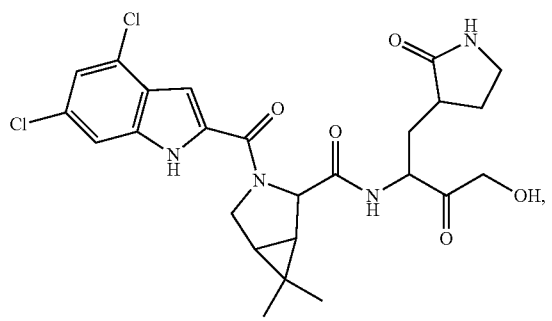
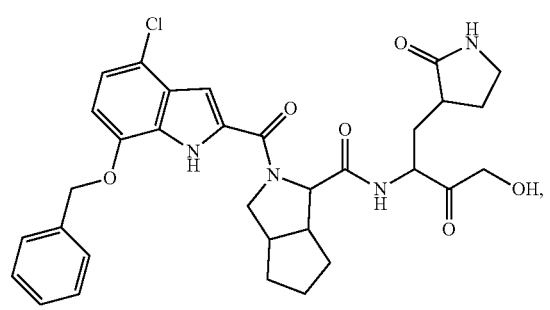
-continued
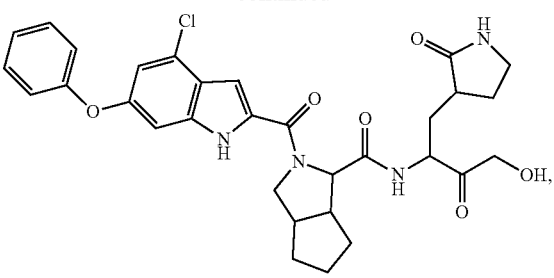
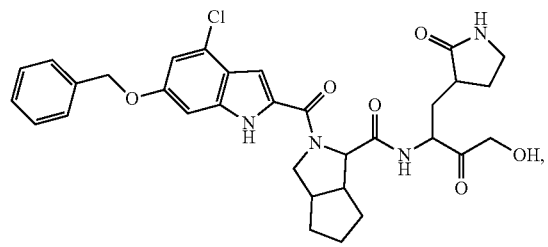
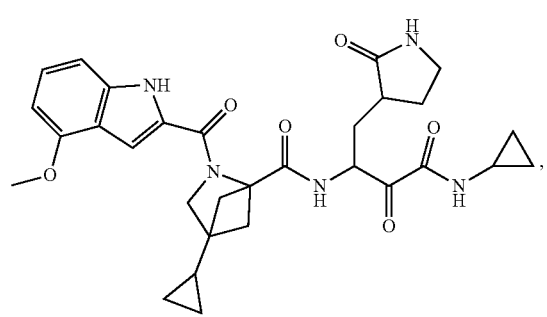
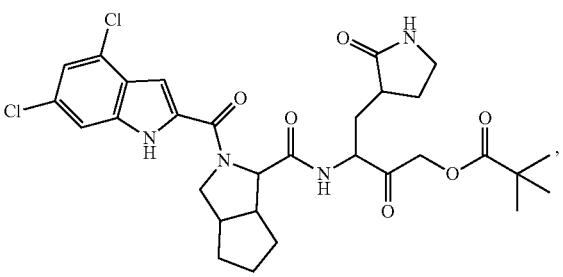
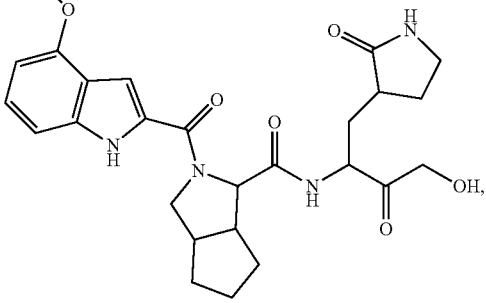

83
-continued
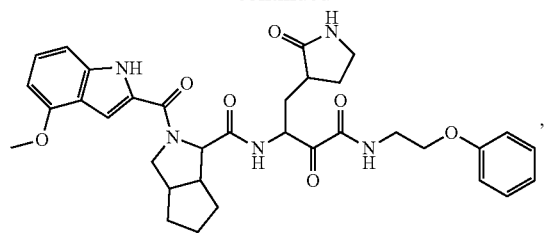
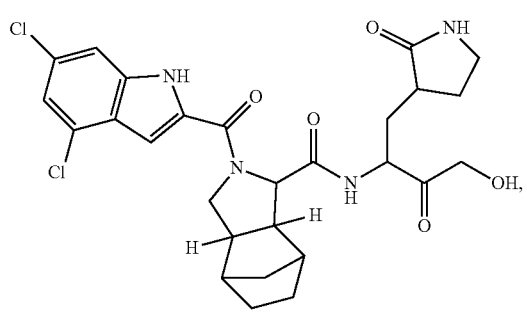
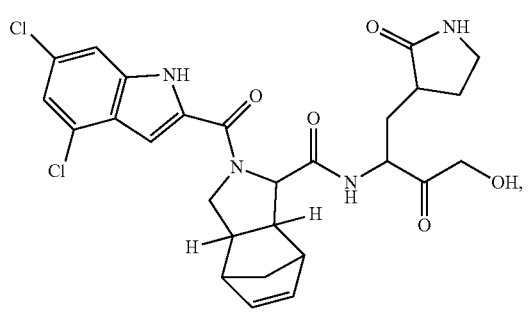
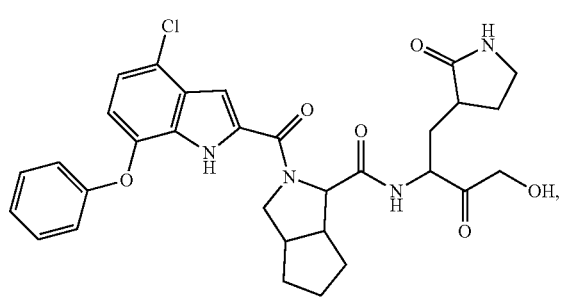
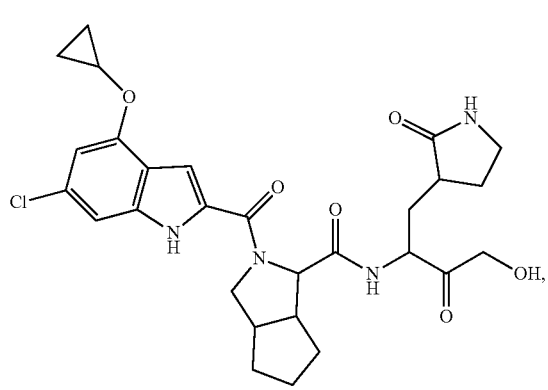
84
-continued
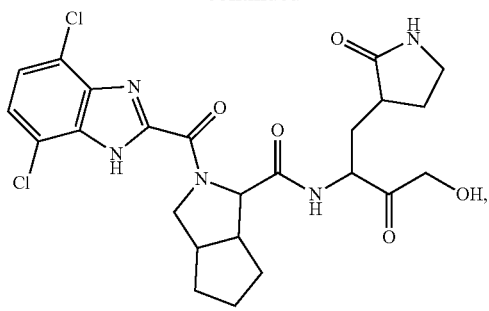
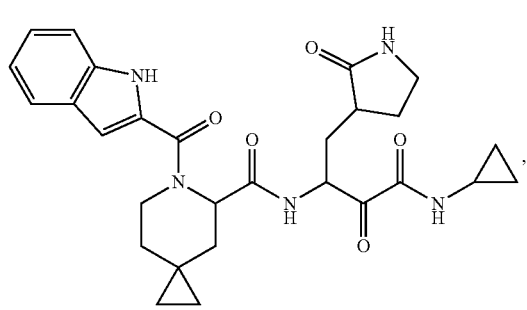
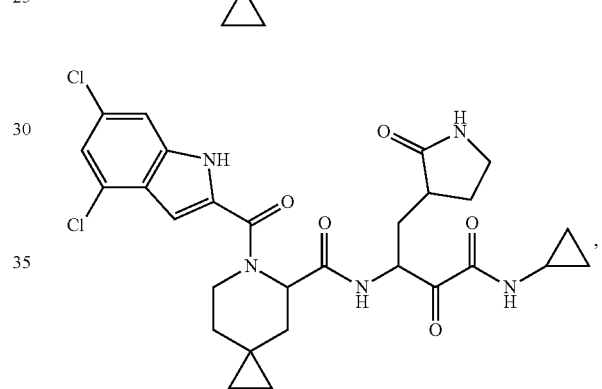
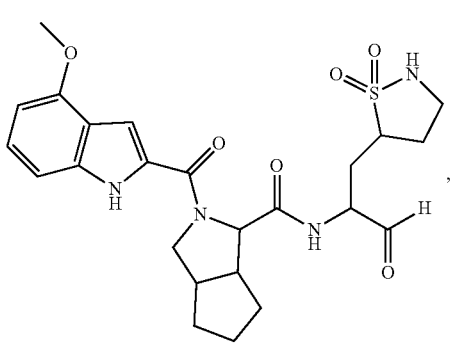
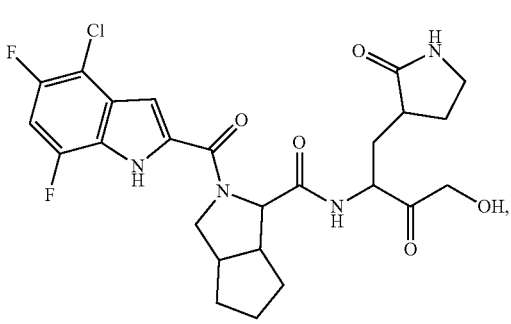

85
-continued
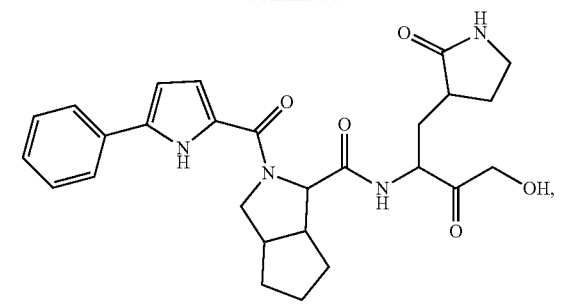
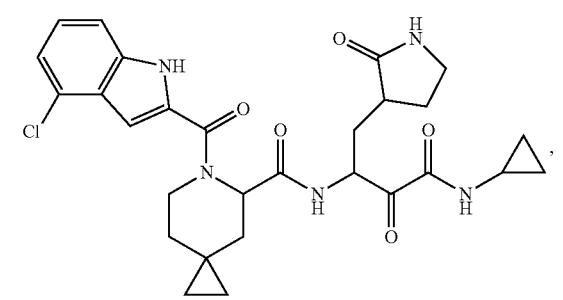
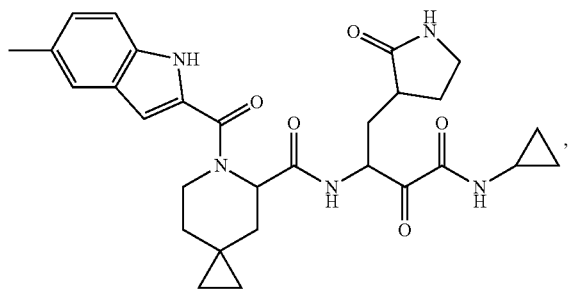
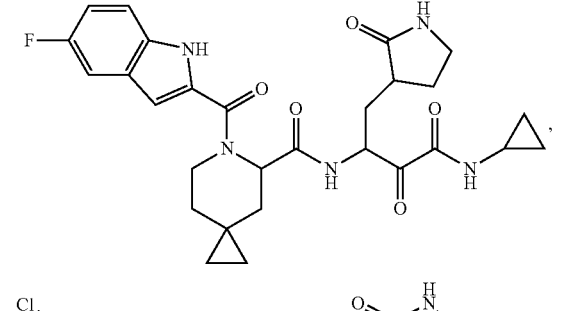
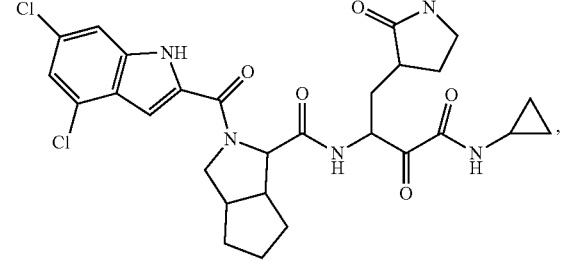
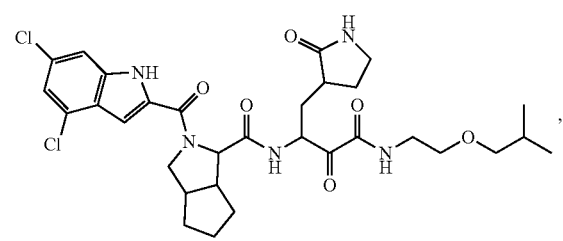
86
-continued
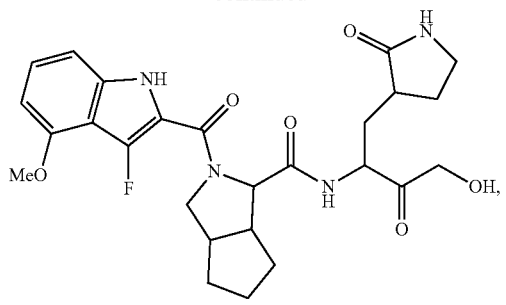
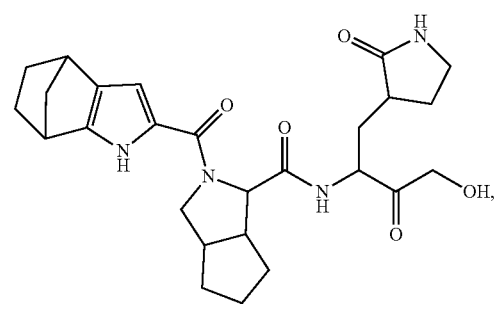
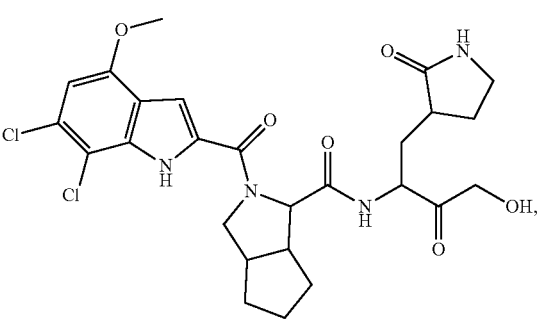
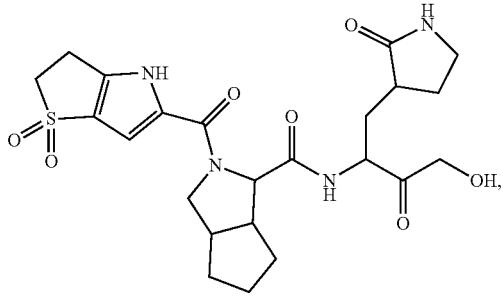
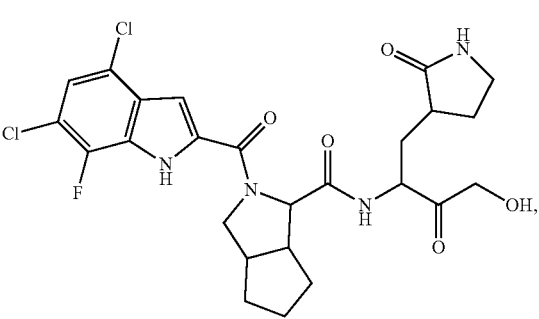

87
-continued
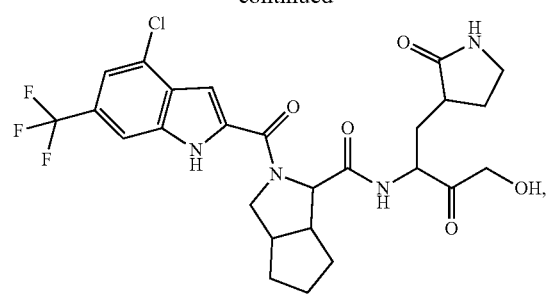
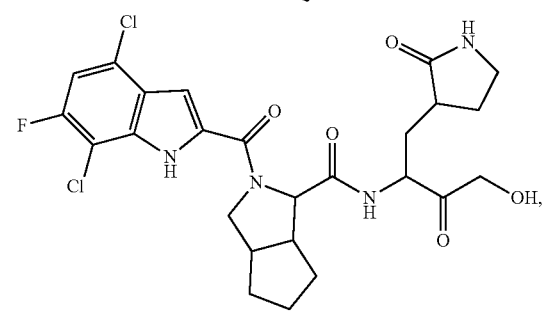
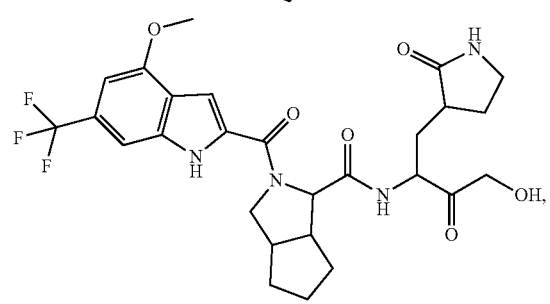
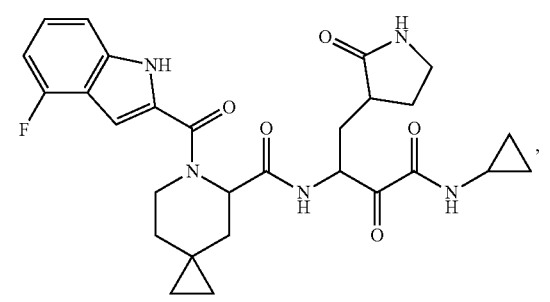
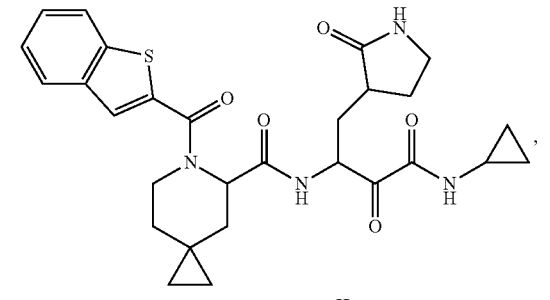
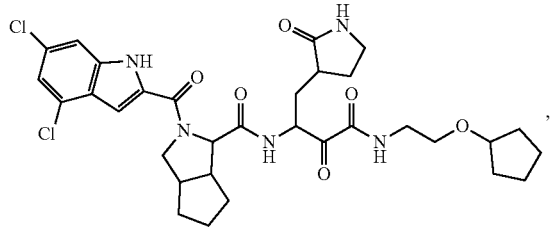
88
-continued
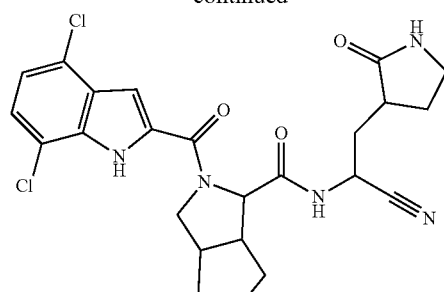
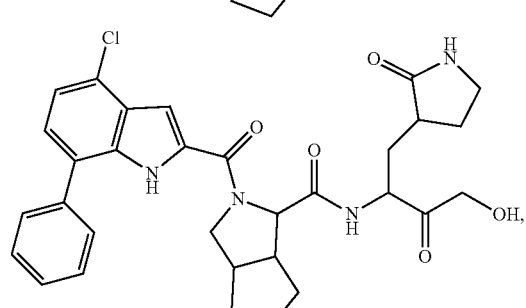
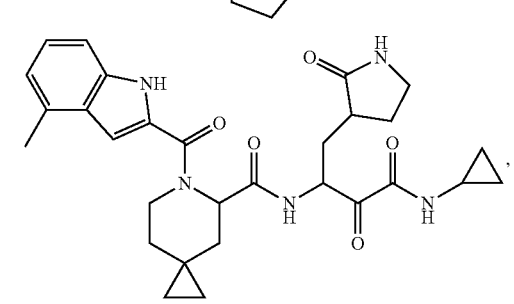
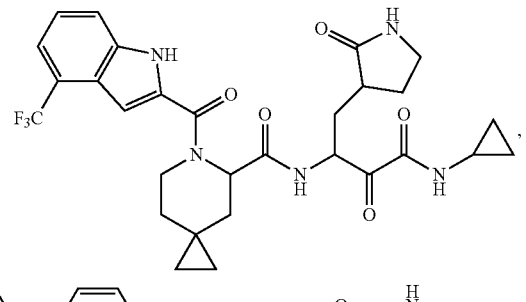
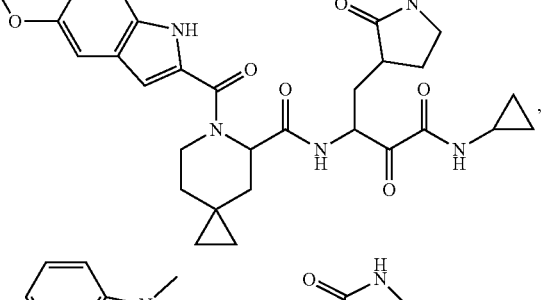
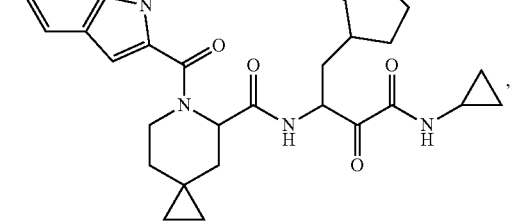

89
-continued
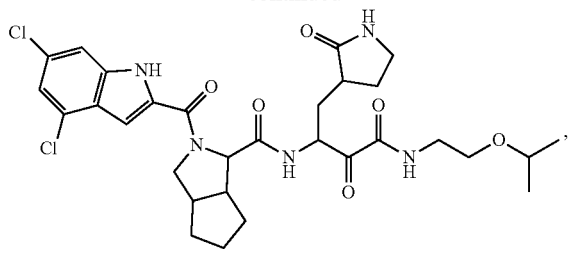
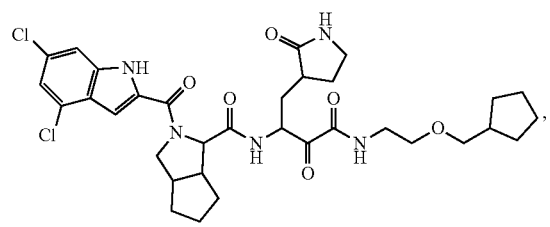
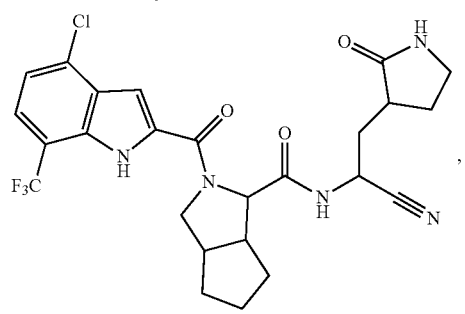
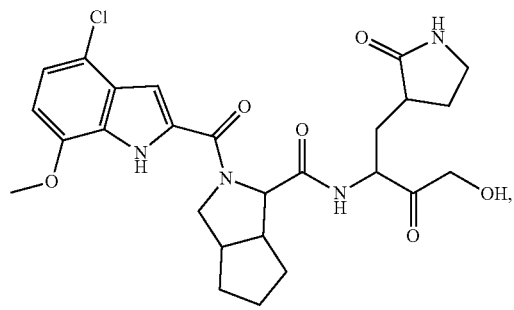
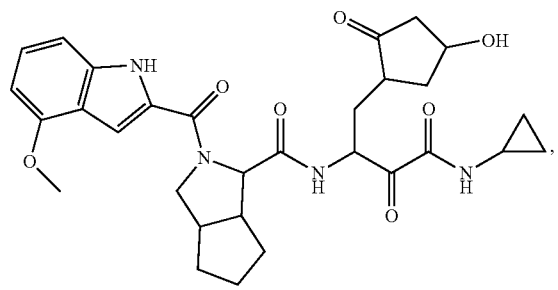
90
-continued
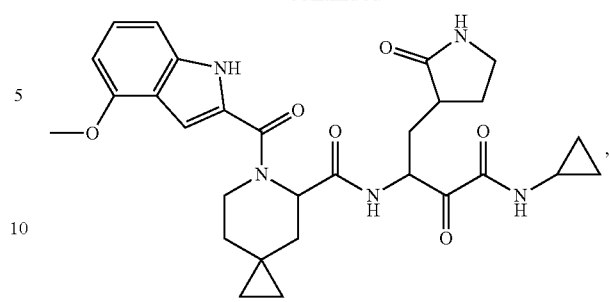
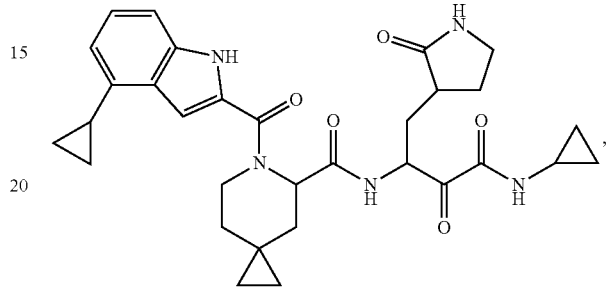
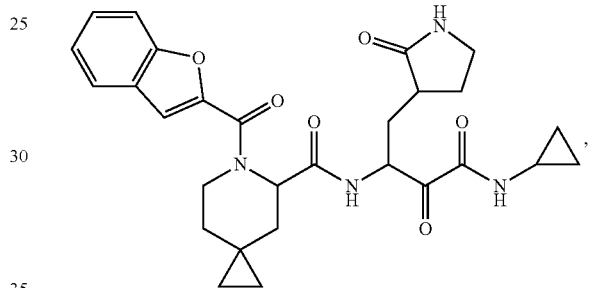

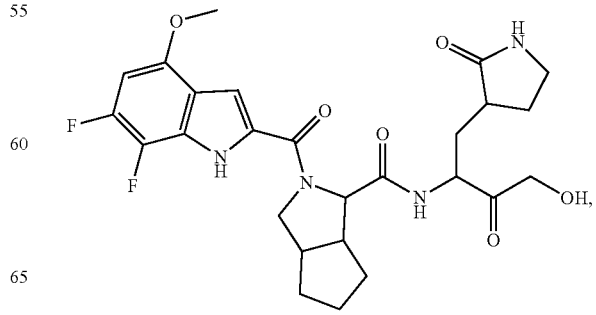

91
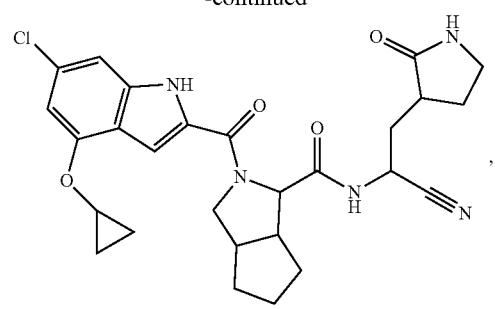
,
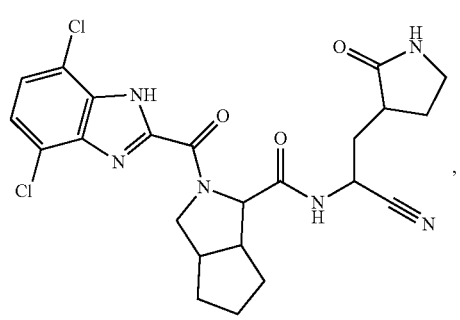
,
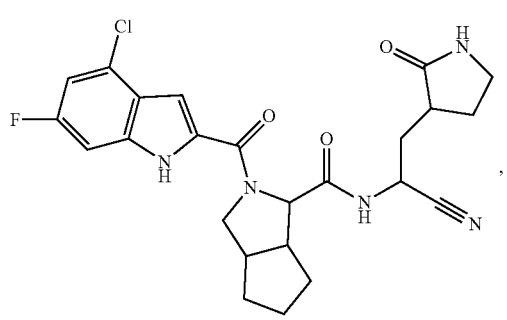
,
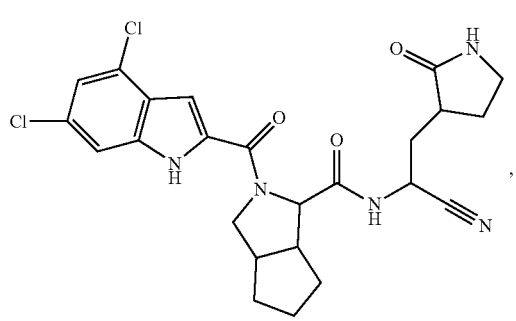
,
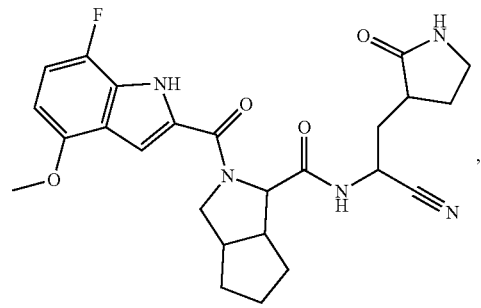
,
92
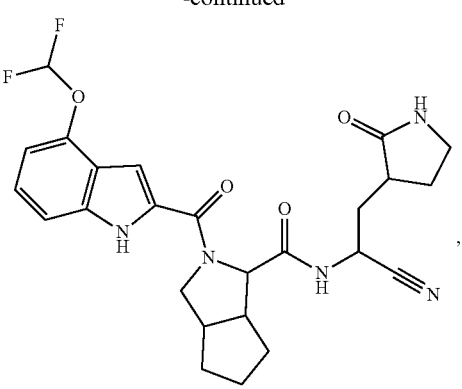
,
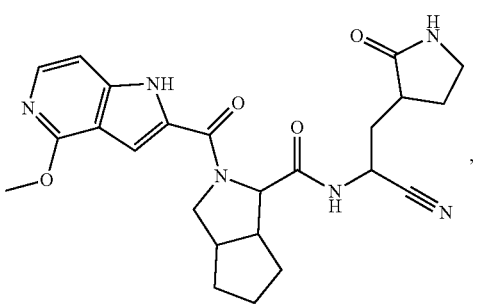
,
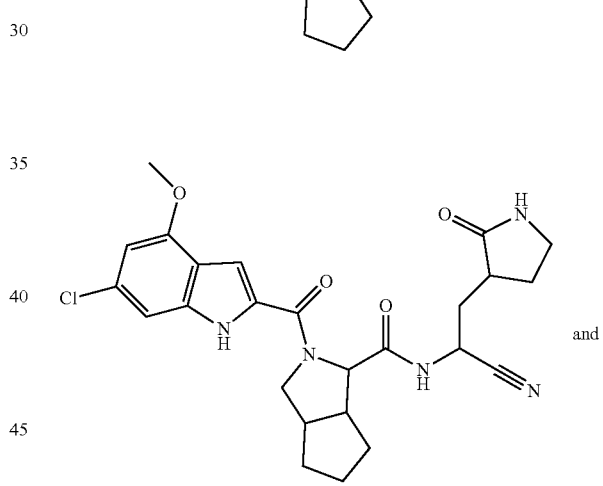
and
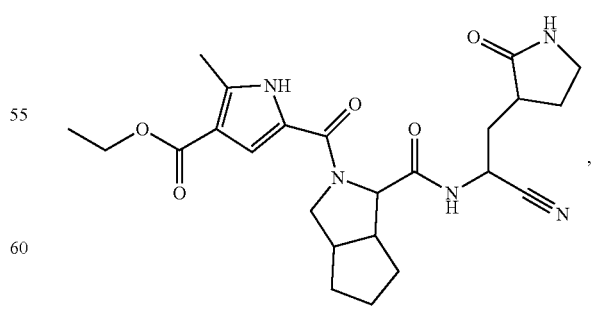
,
or pharmaceutically acceptable salt of any of the foregoing.
Additional examples of compounds of Formula (I), include the following:

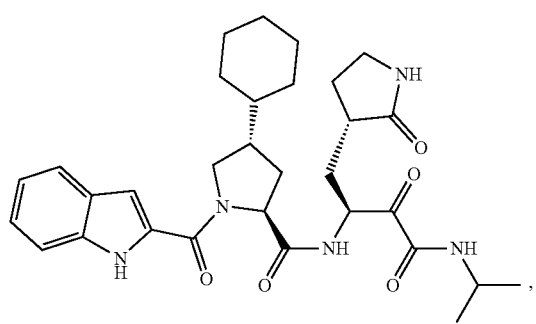
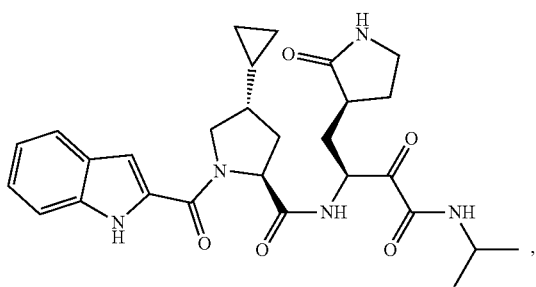
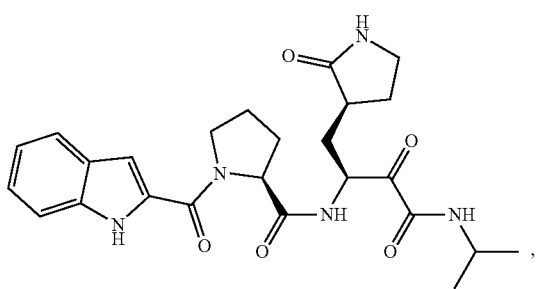
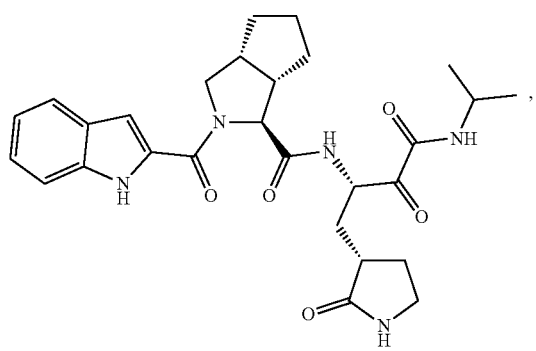
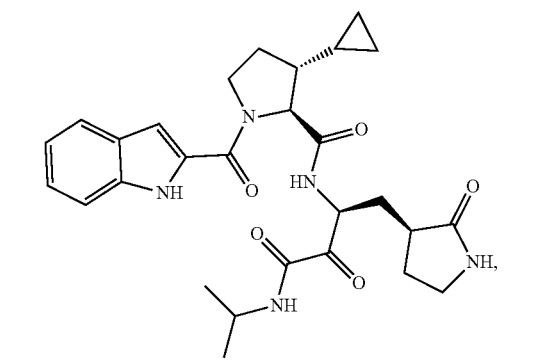
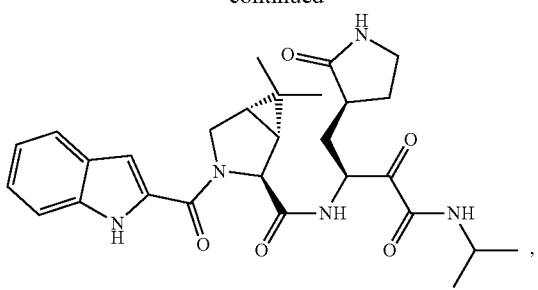
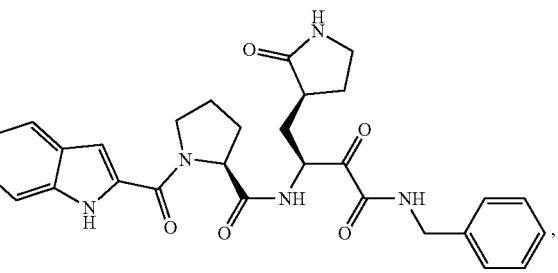
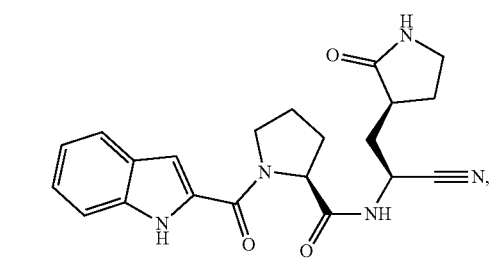
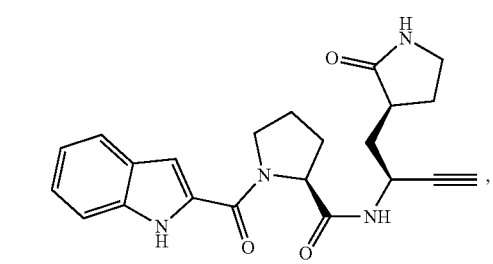
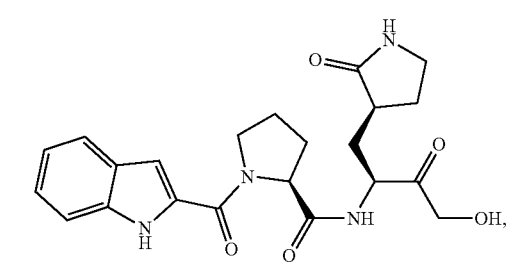
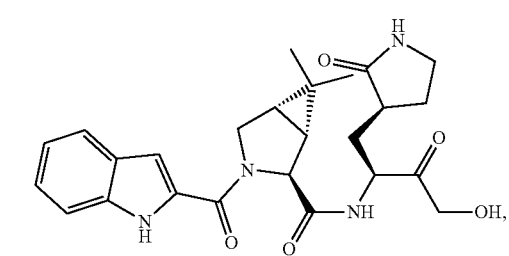

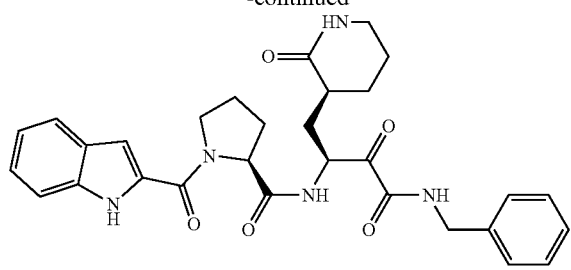
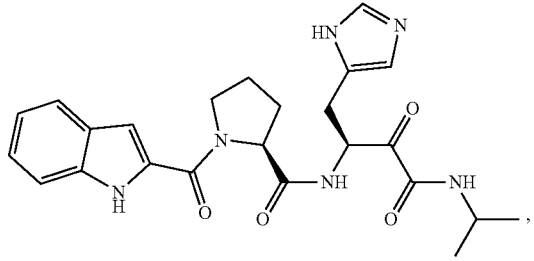
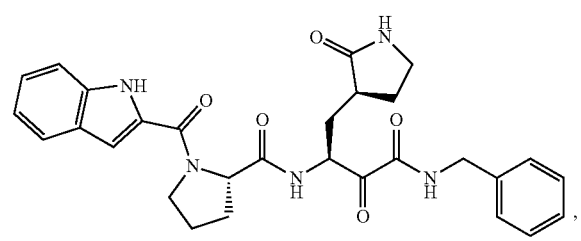
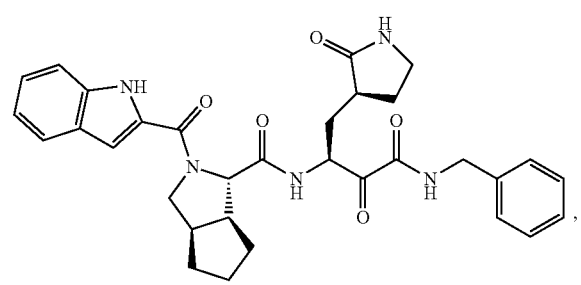
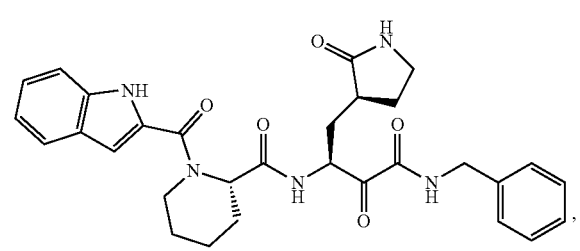
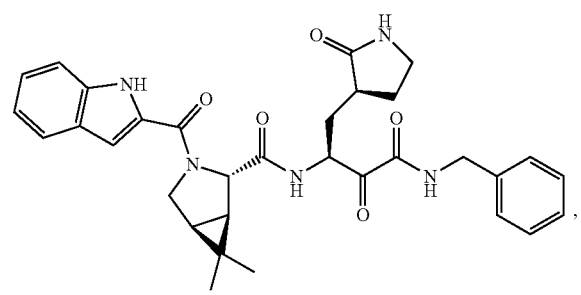
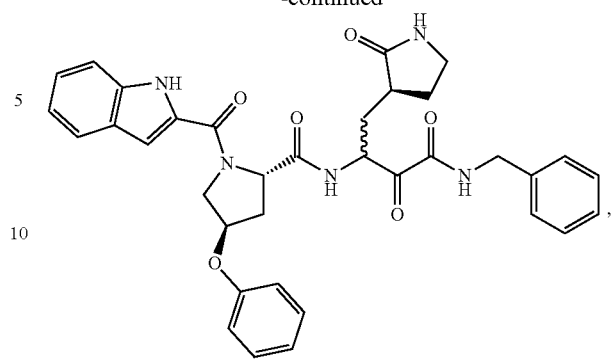
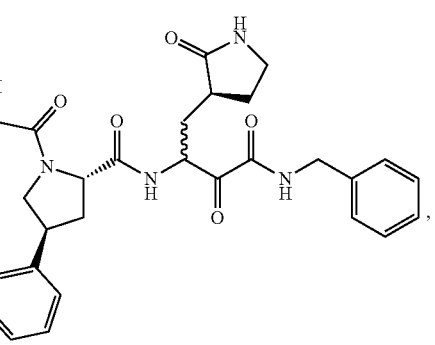
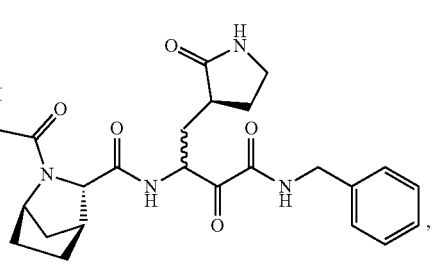
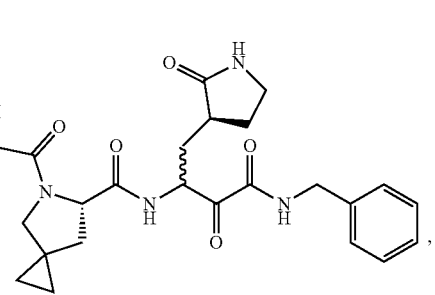

97
-continued
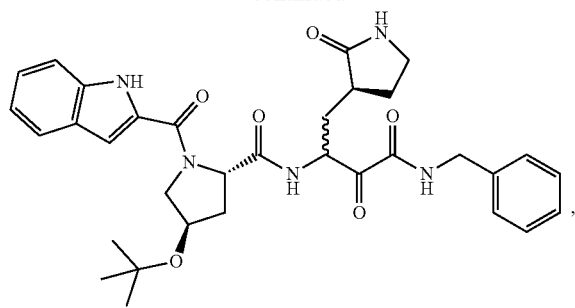
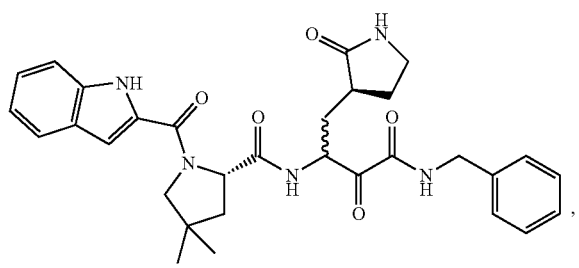
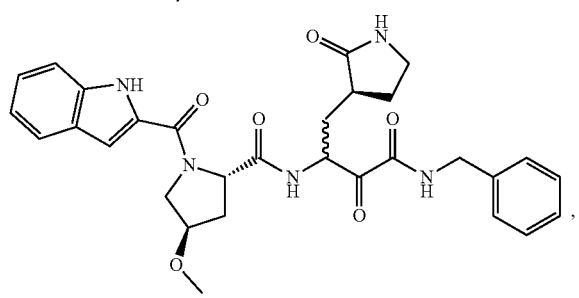
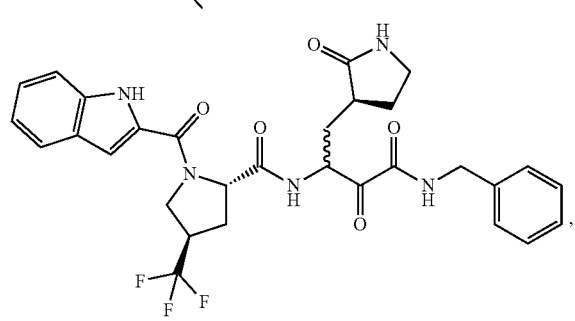
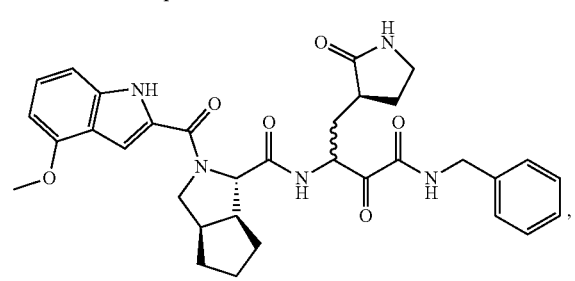
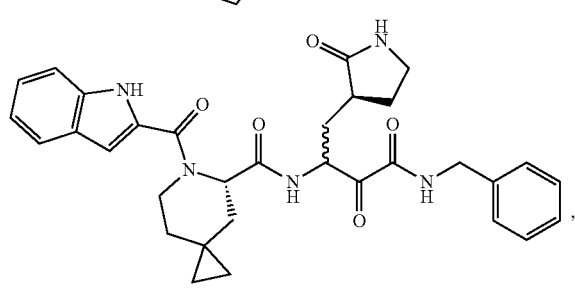
98
-continued
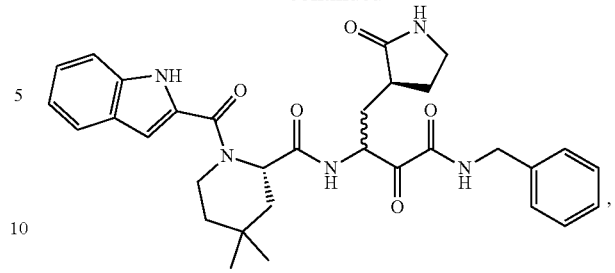
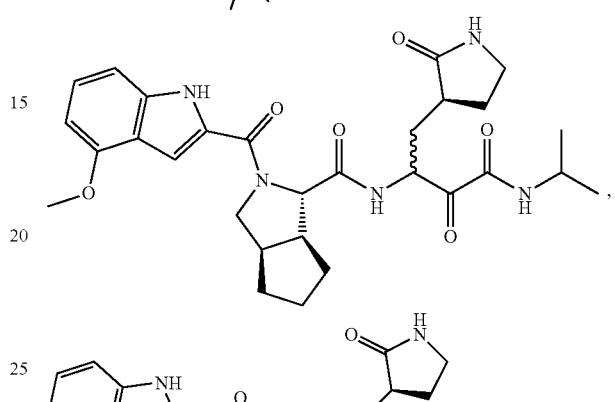
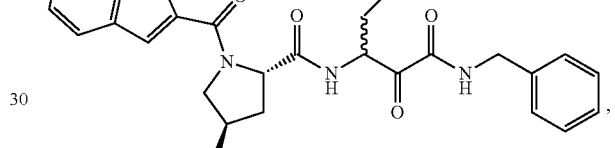
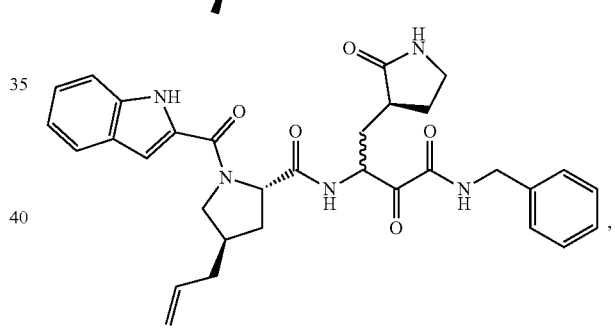
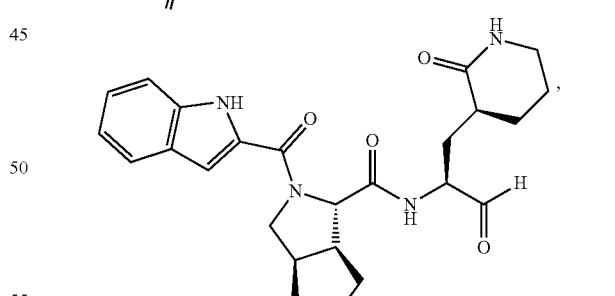
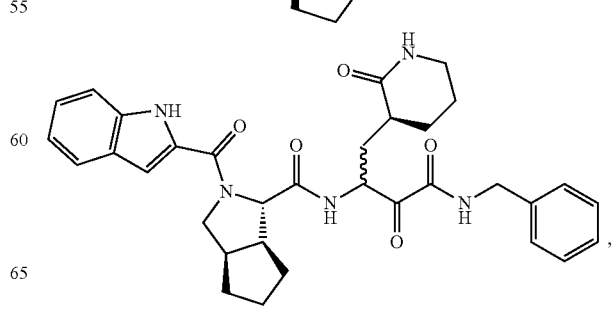

99
-continued
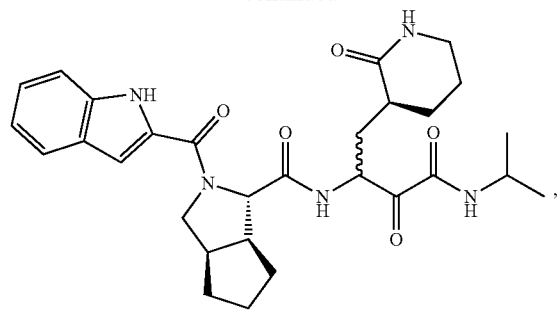
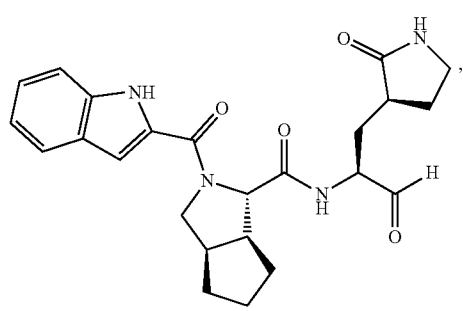
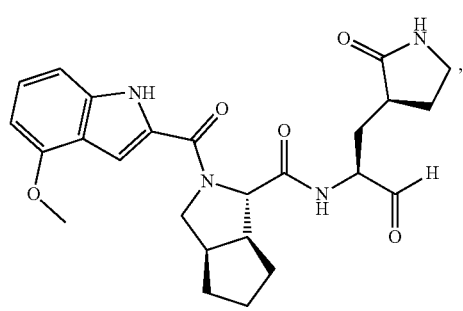
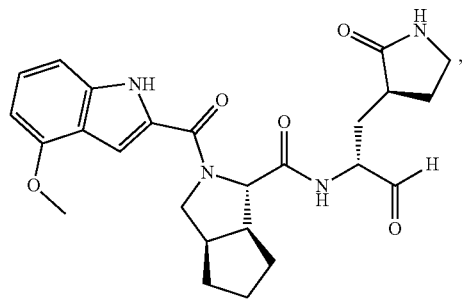
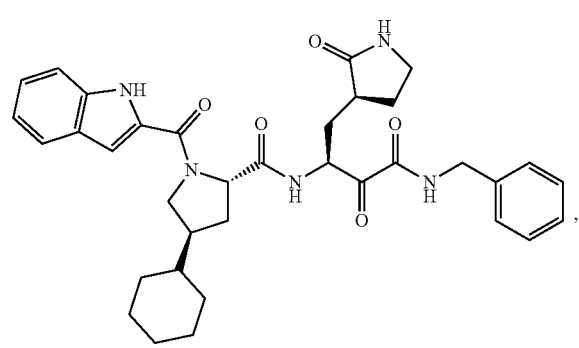
100
-continued
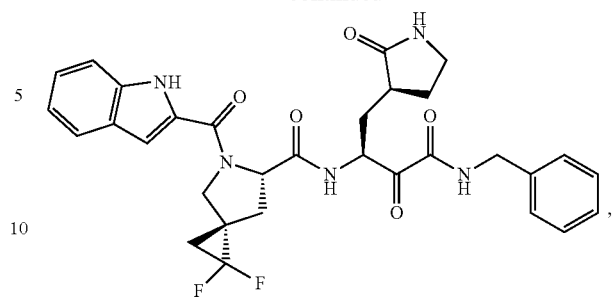
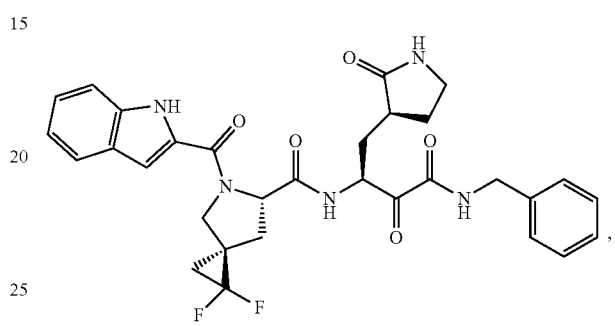
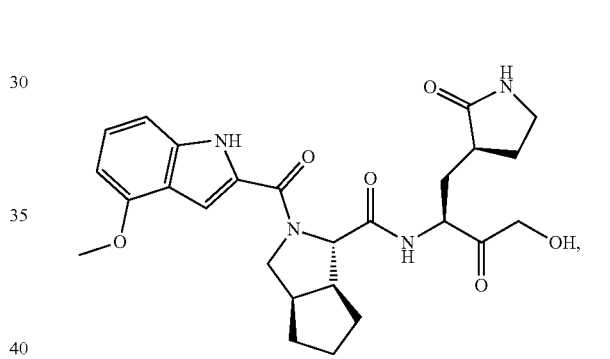
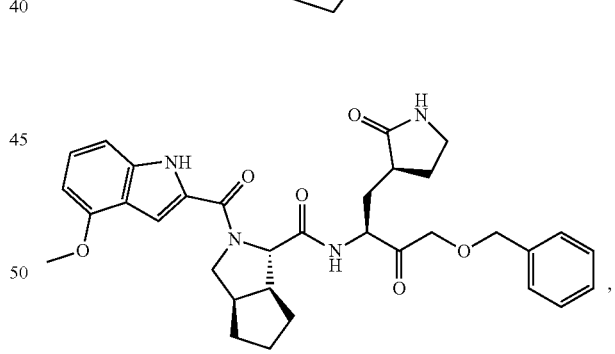
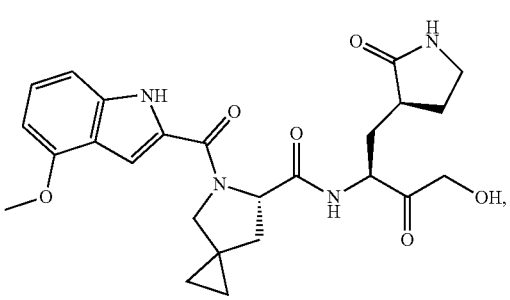

101
-continued
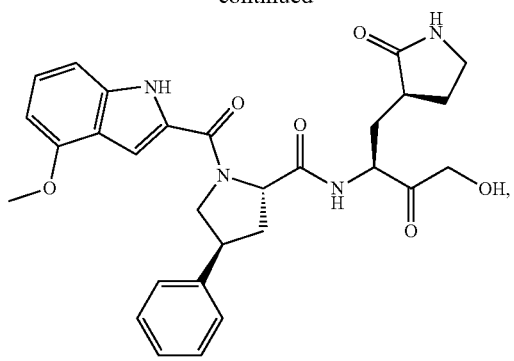
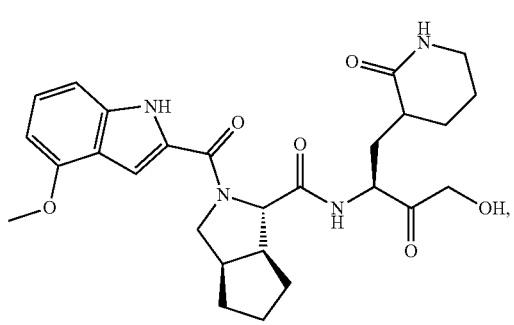
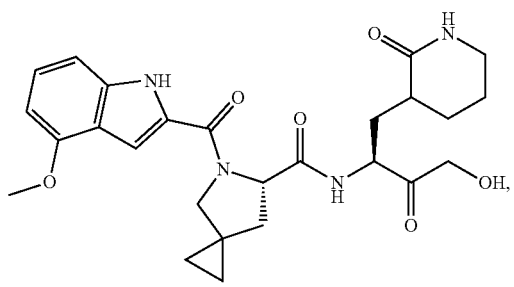
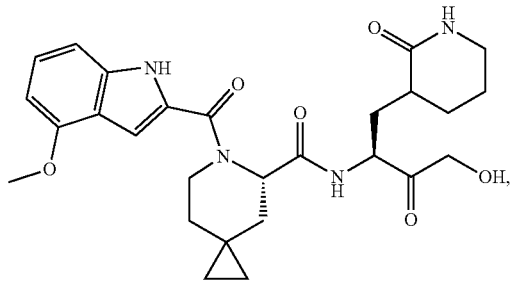
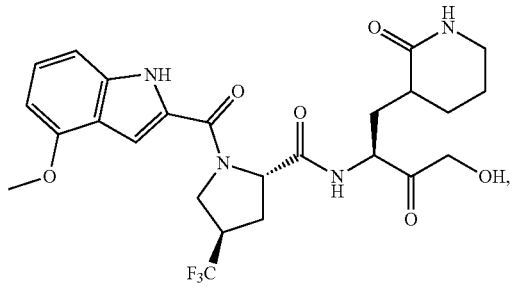
102
-continued
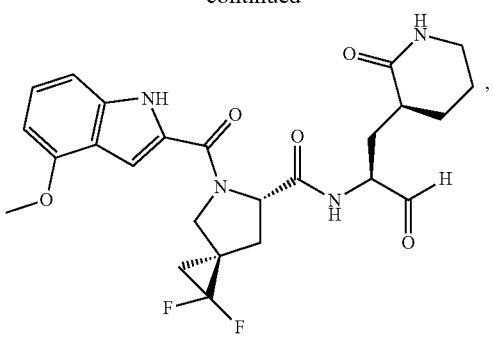
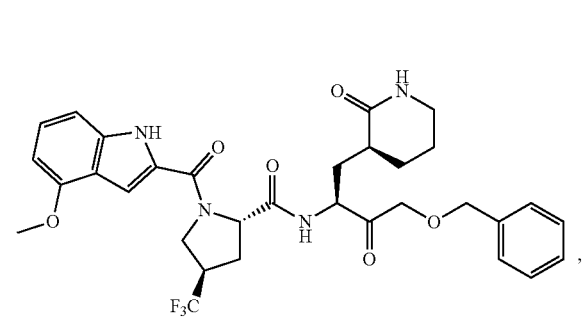
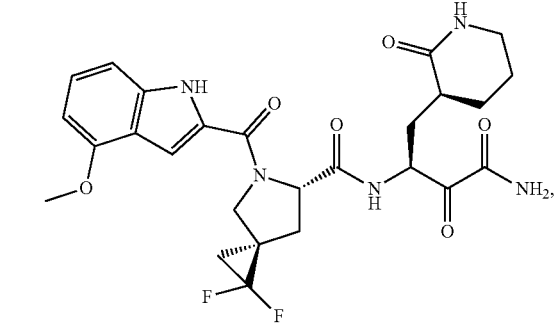
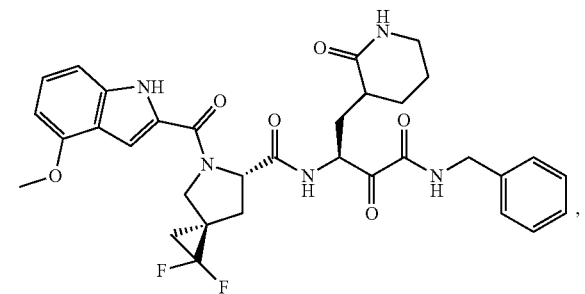
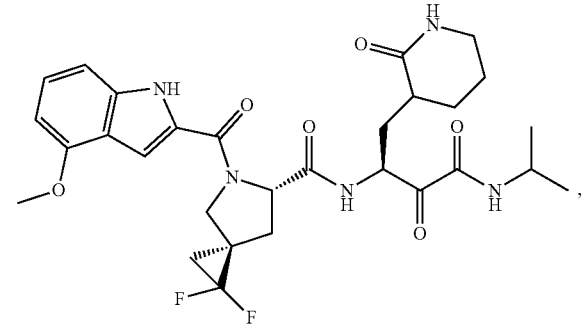

-continued
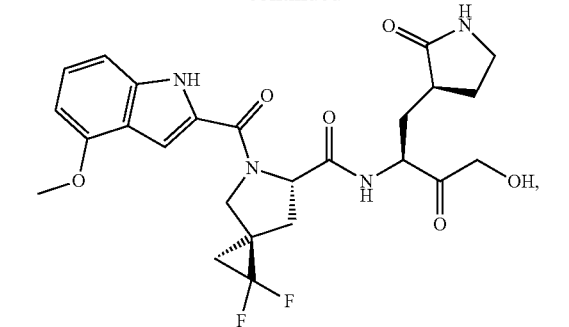
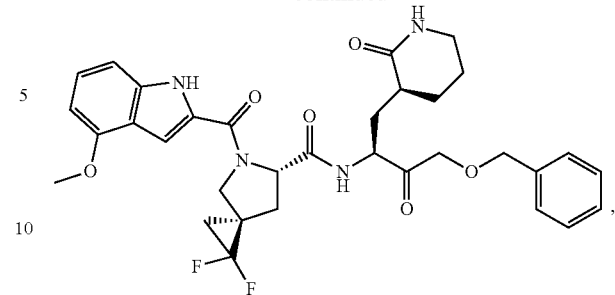
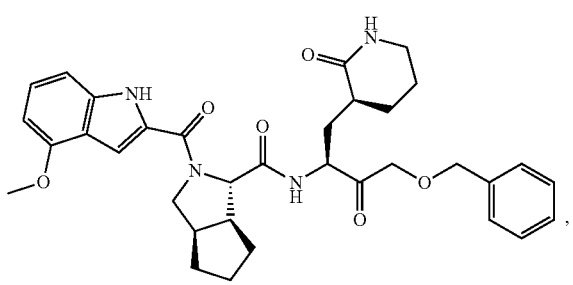
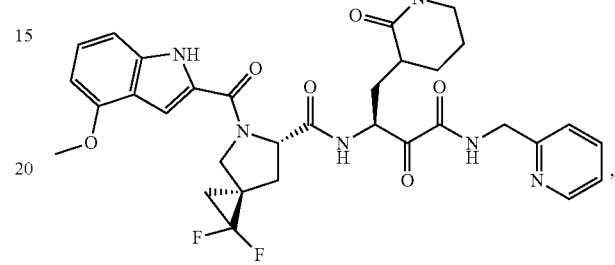
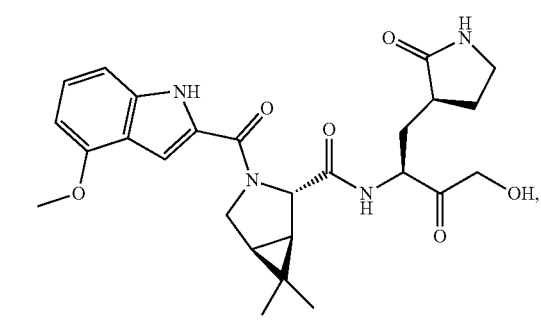
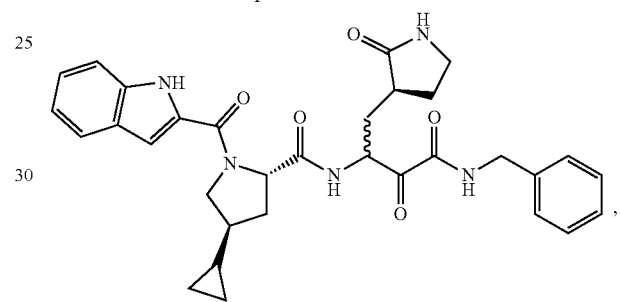
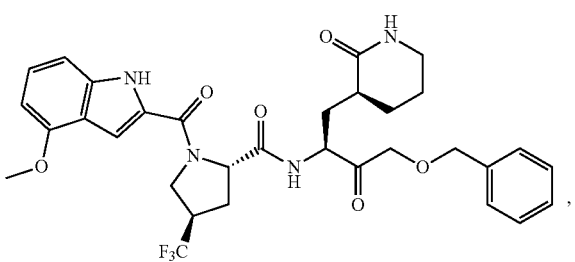
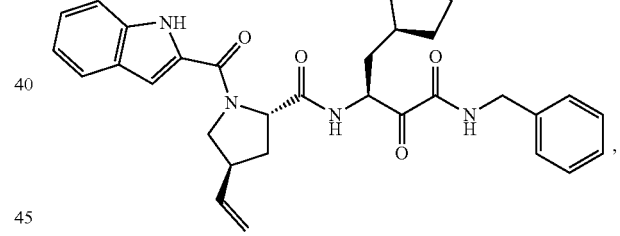
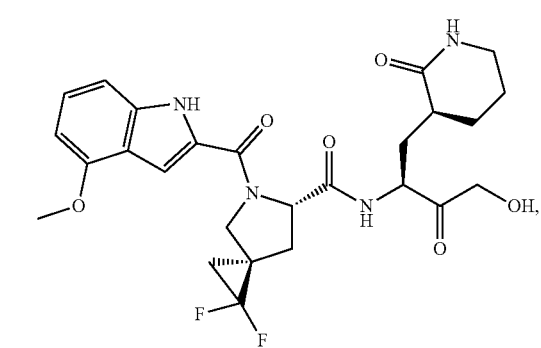
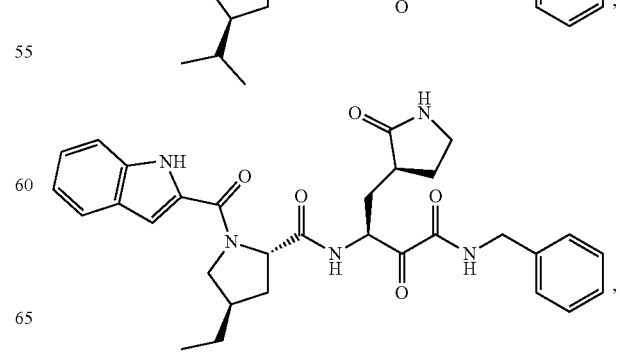

105
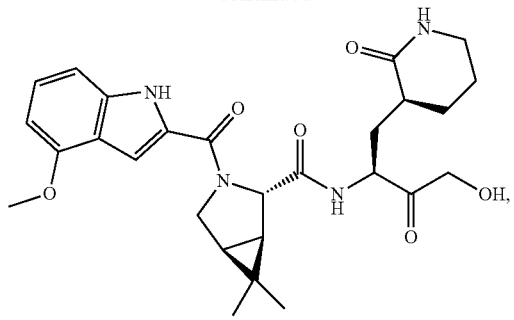
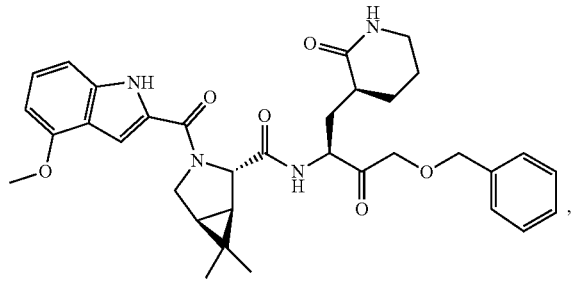
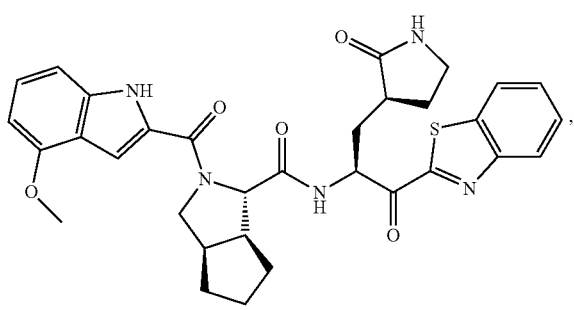
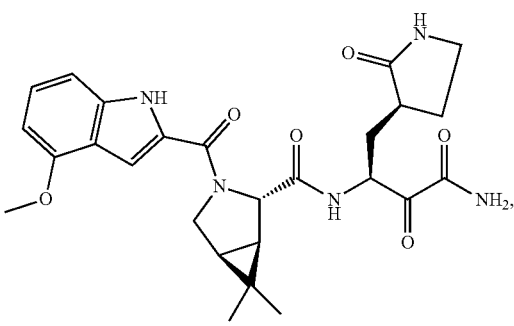
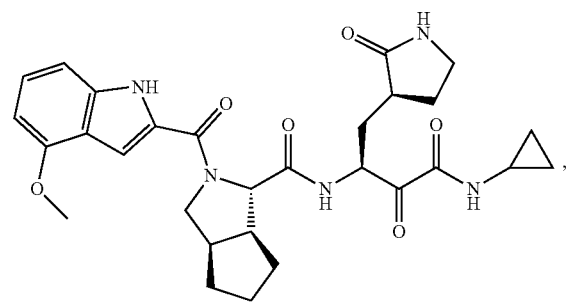
106
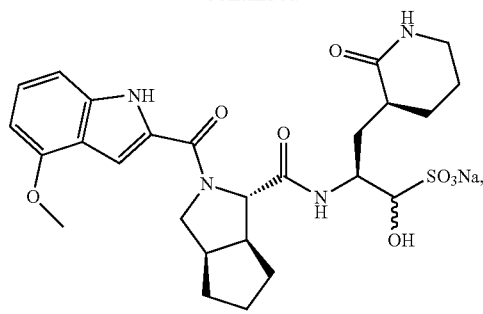
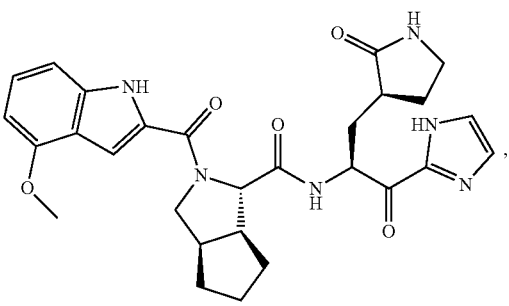
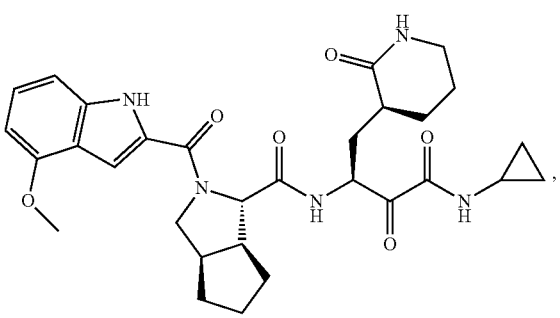
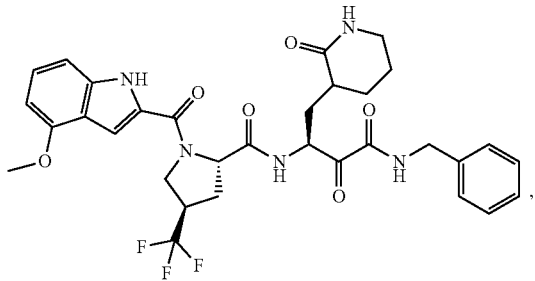
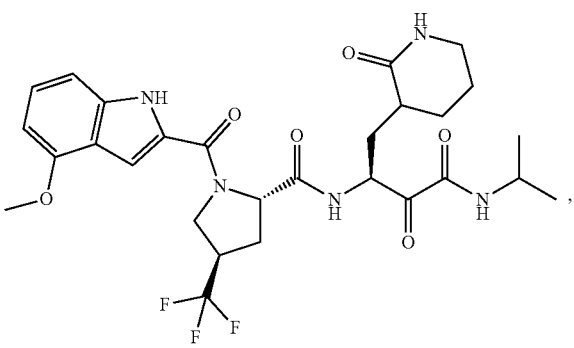

107
-continued
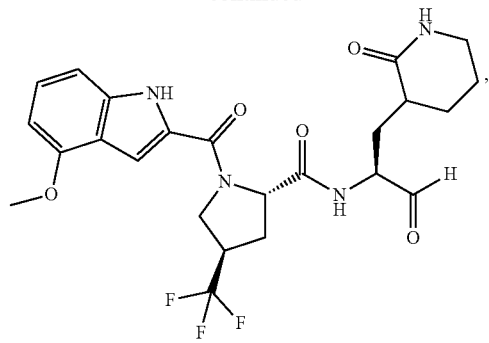
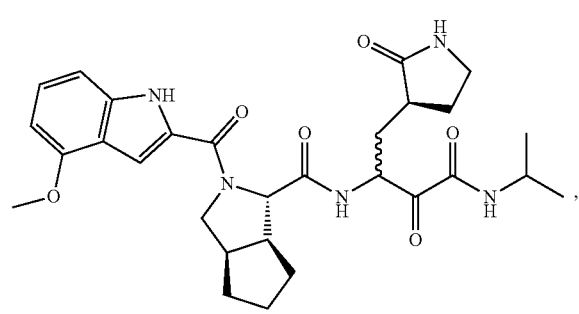
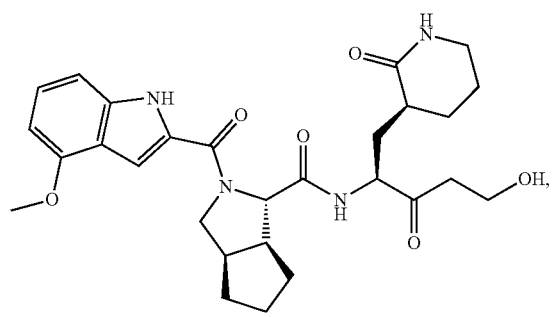
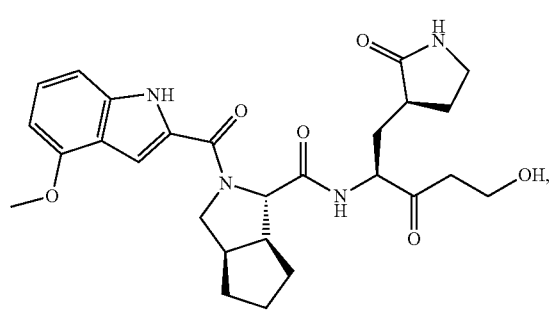
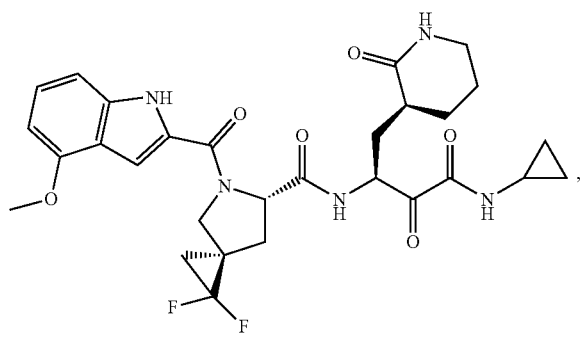
108
-continued
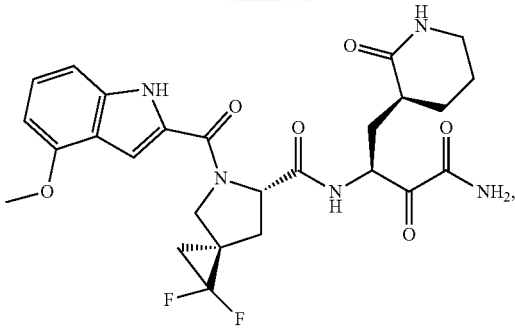
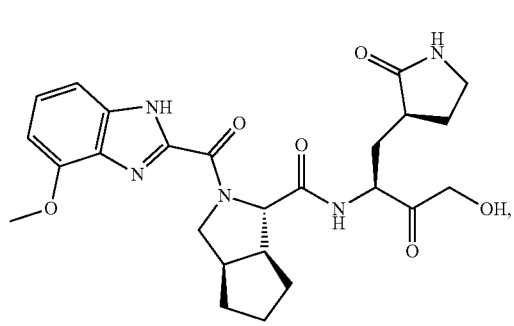
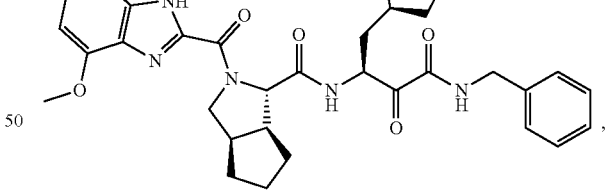
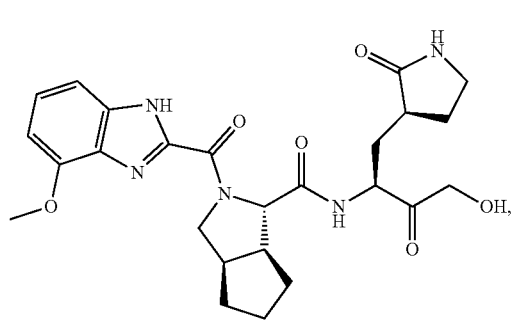

| 109 | 110 |
|---|---|
| -continued | -continued |
| 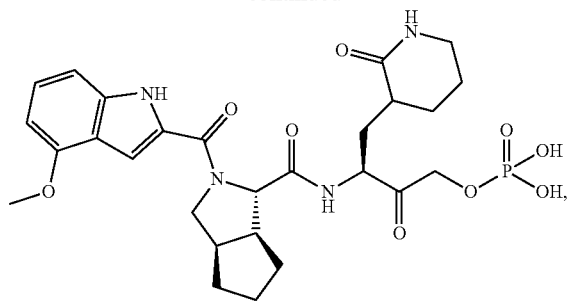 | 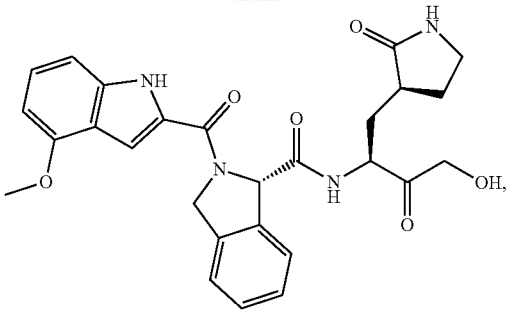 |
| 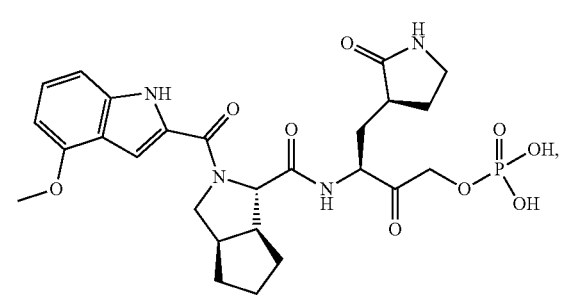 | 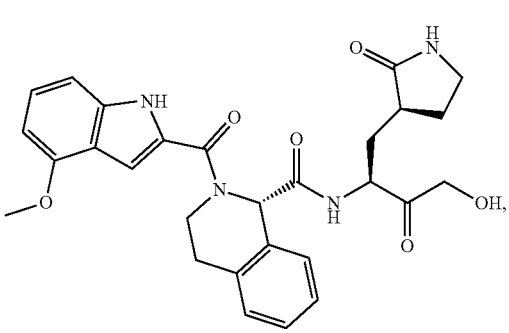 |
| 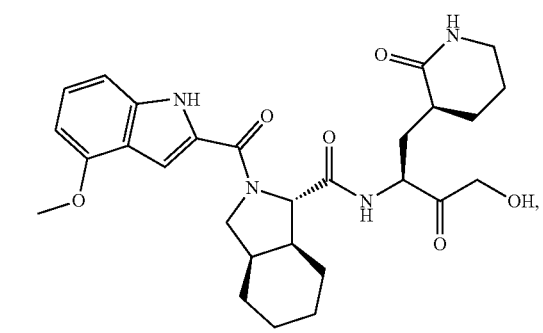 | 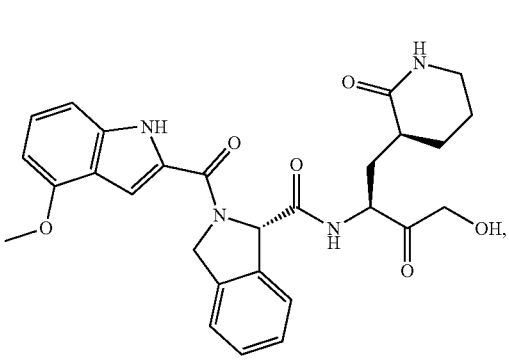 |
| 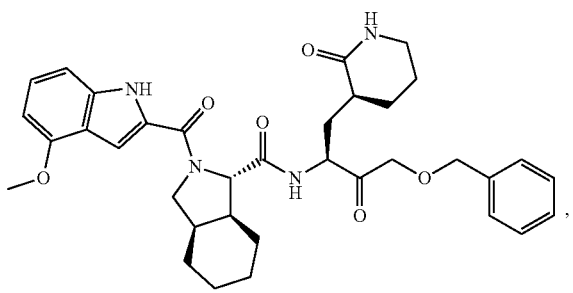 | 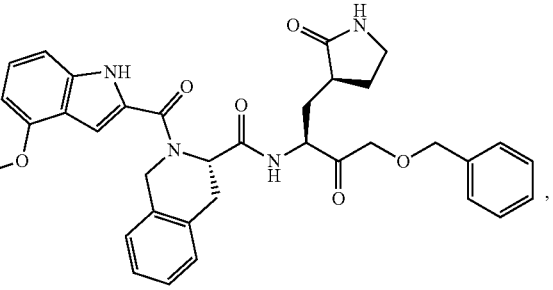 |
| 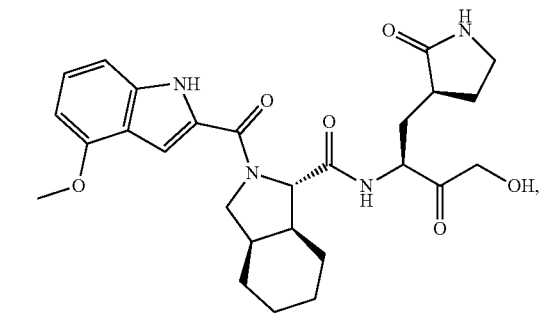 | 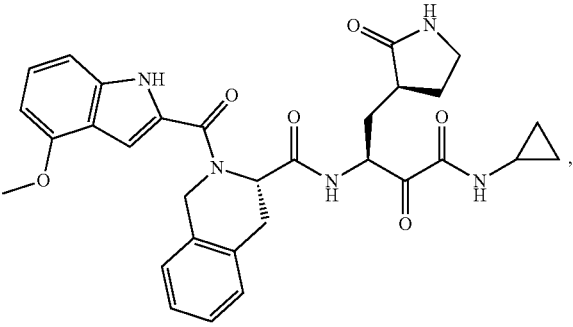 |

111
-continued
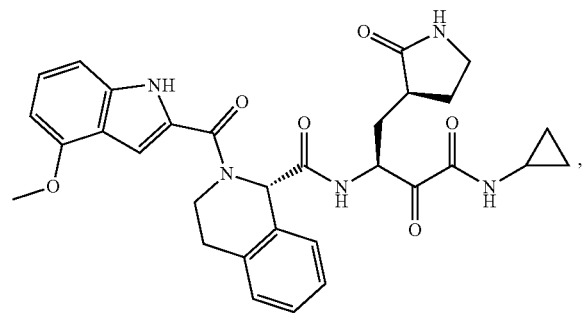
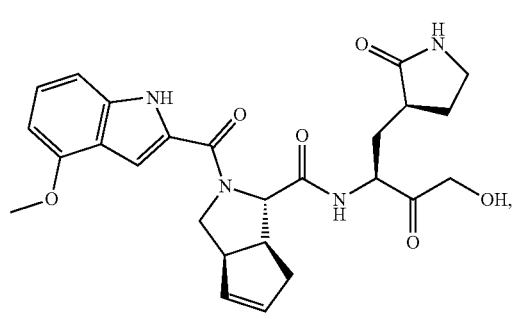
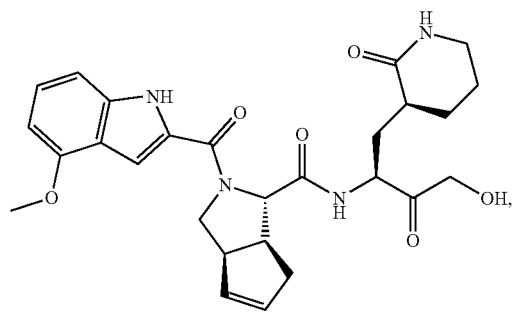
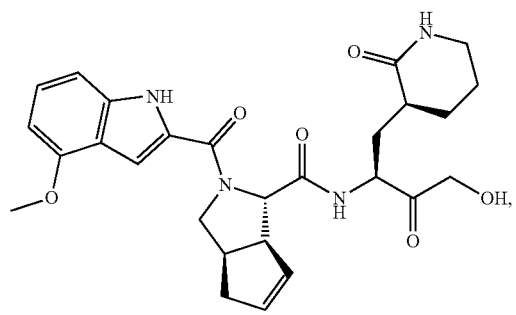
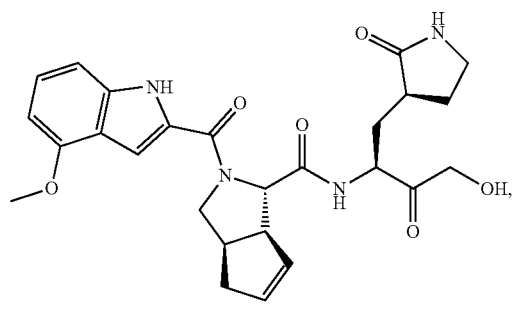
112
-continued
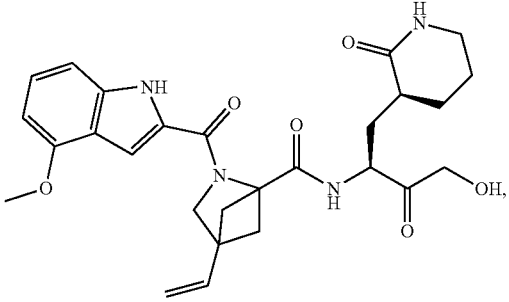
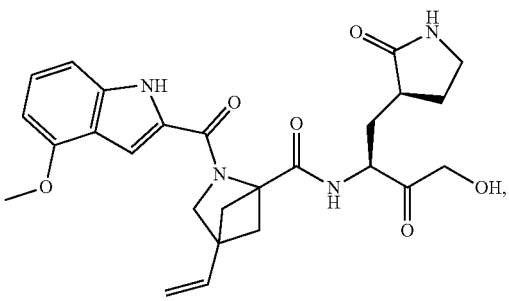
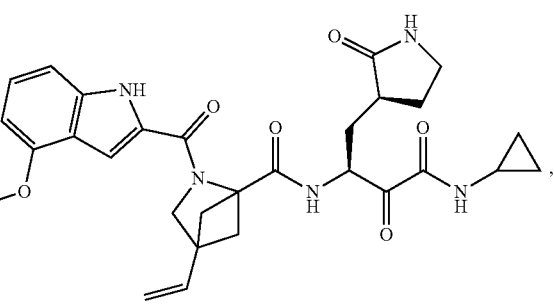
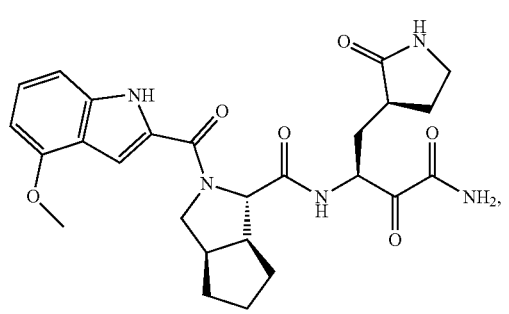
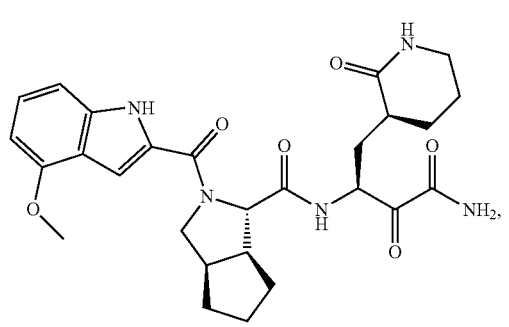

113
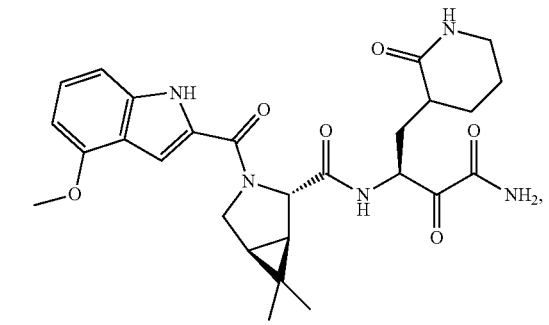
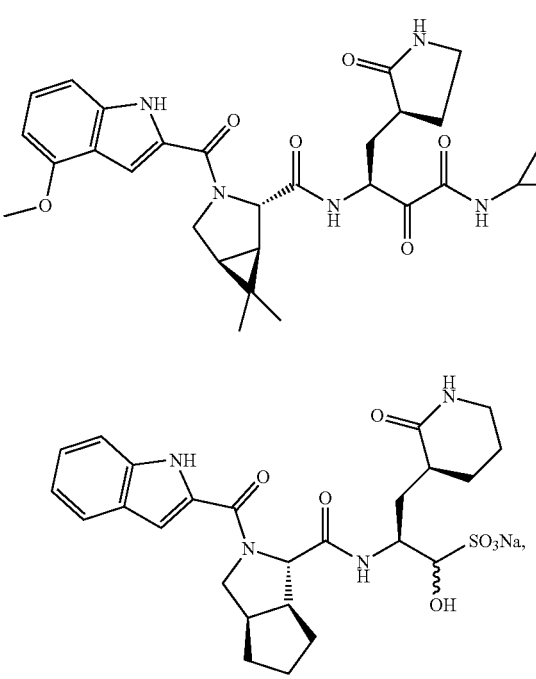
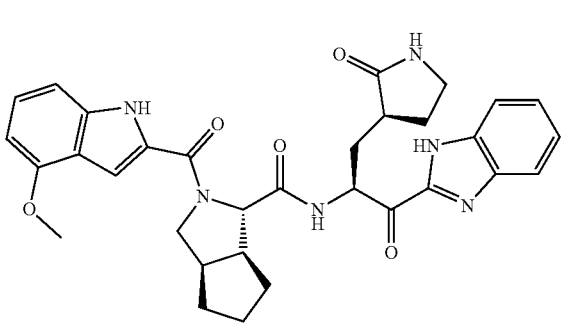
114
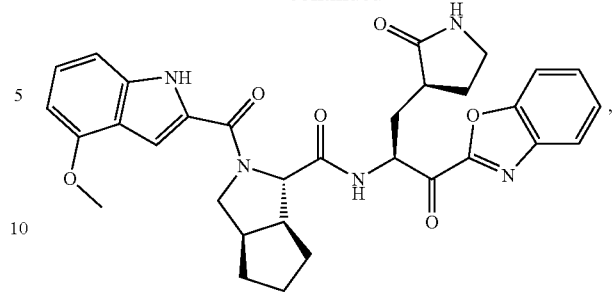
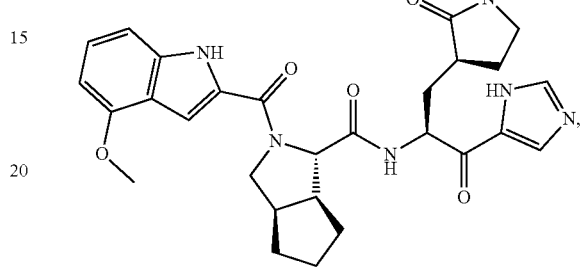
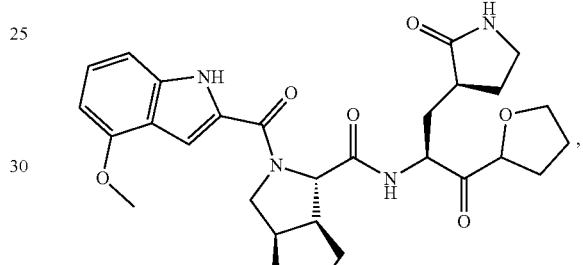
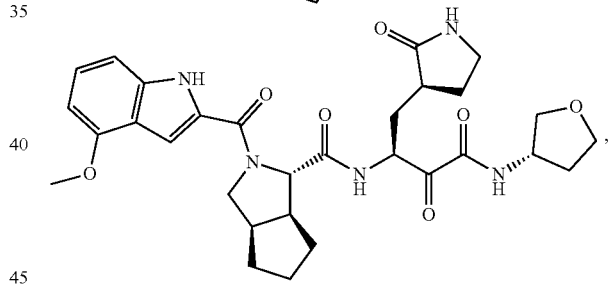
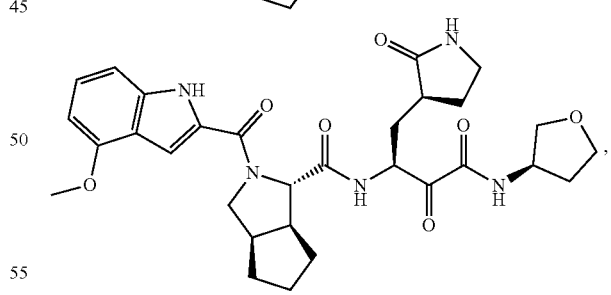

115
-continued
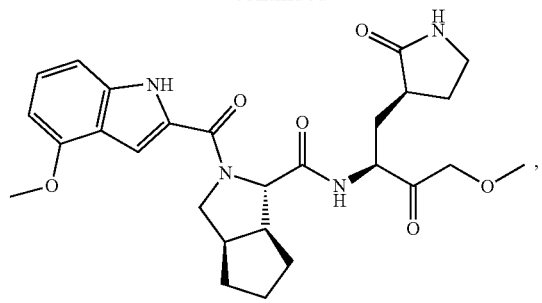
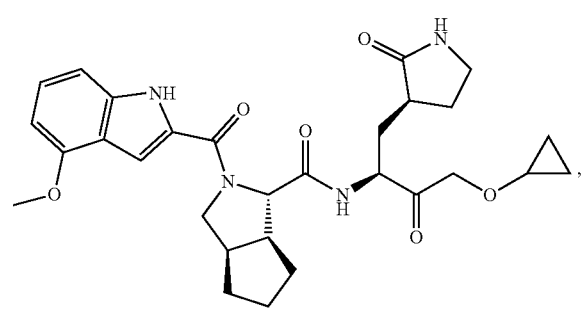
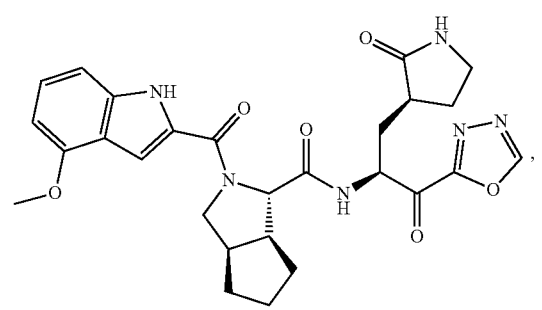
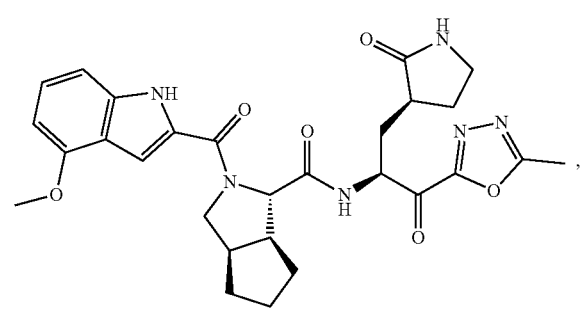
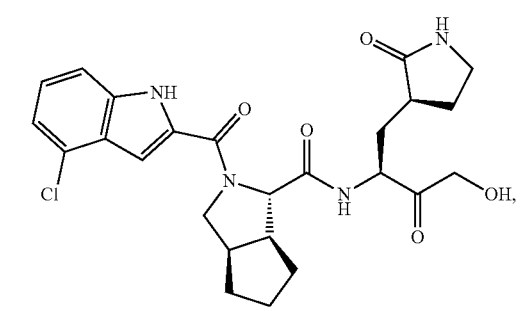
116
-continued
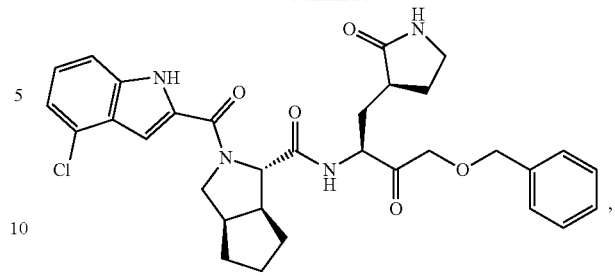
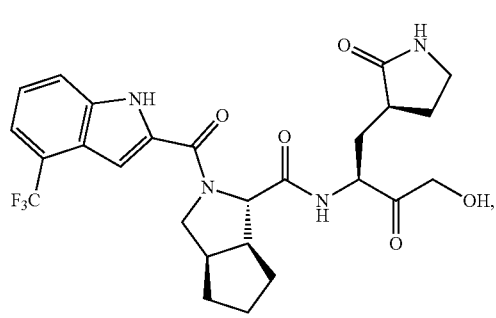
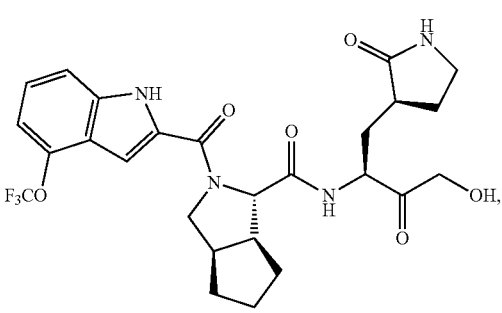
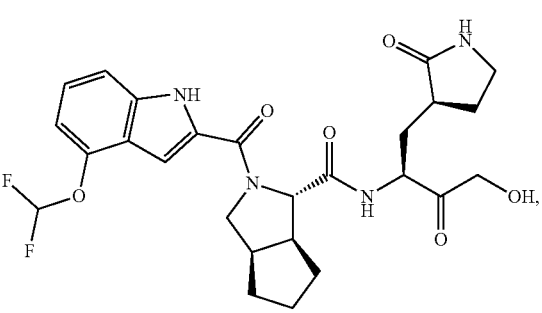
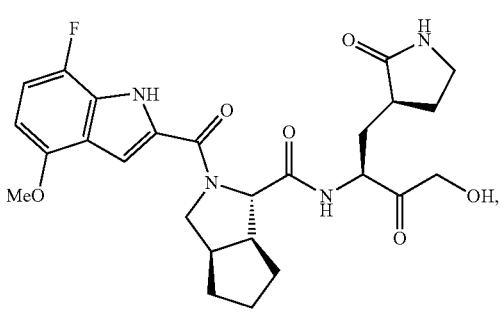

117
-continued
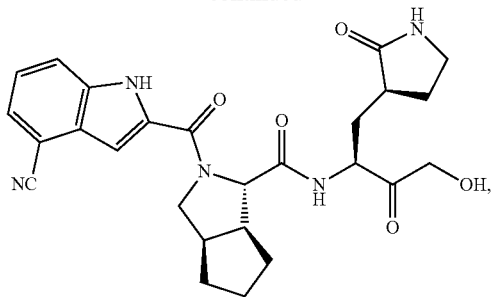
118
-continued
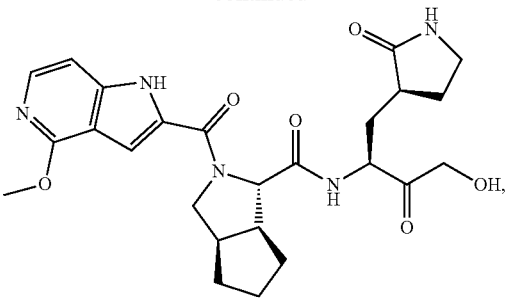

119
-continued
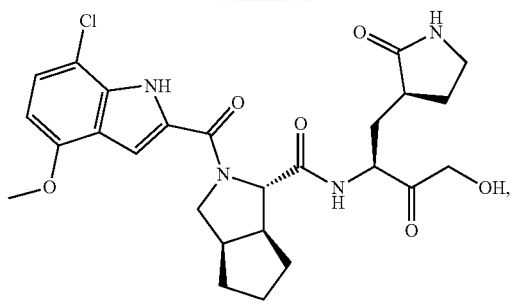
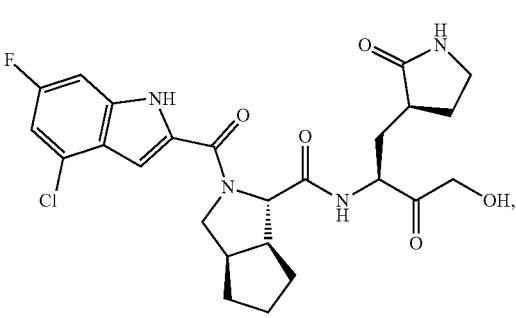
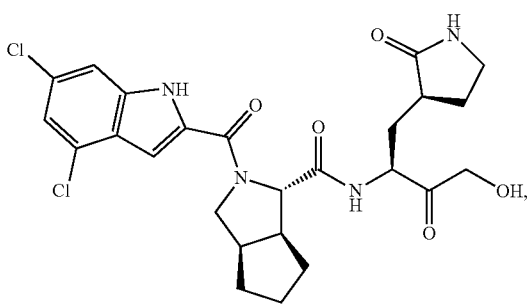
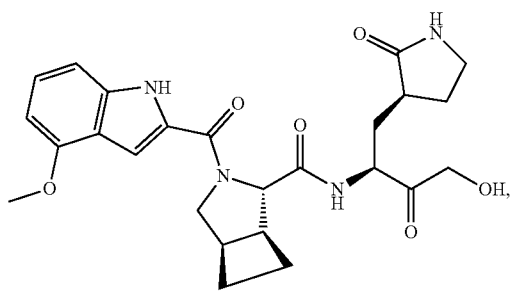
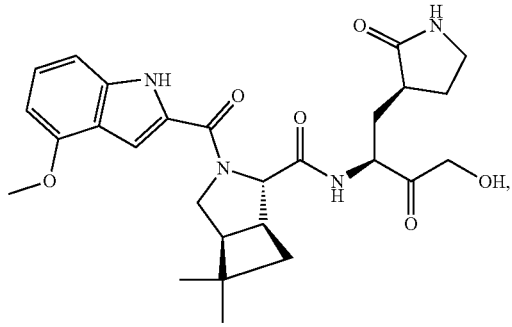
120
-continued
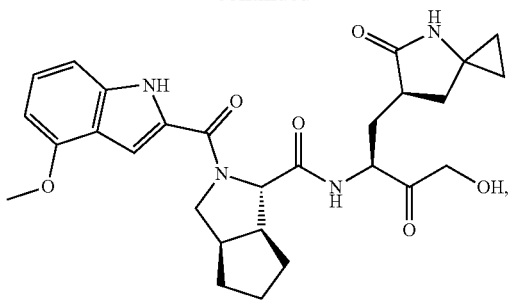
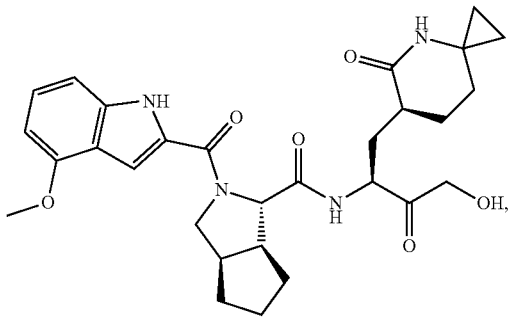
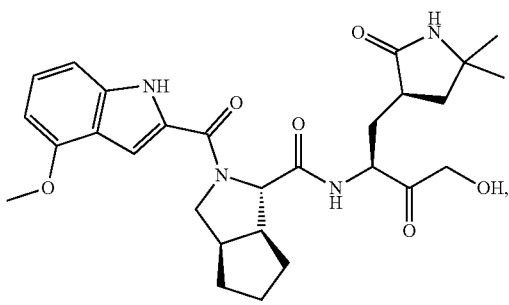
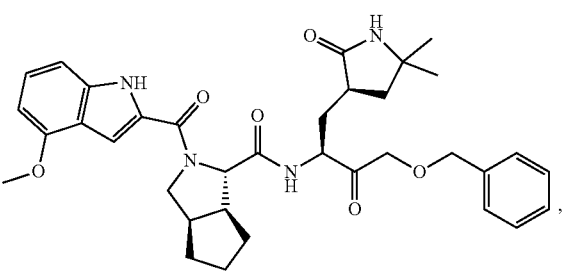
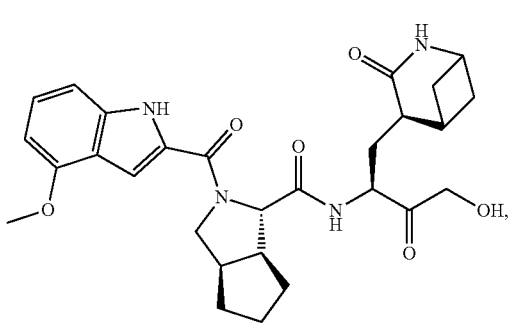

121
-continued
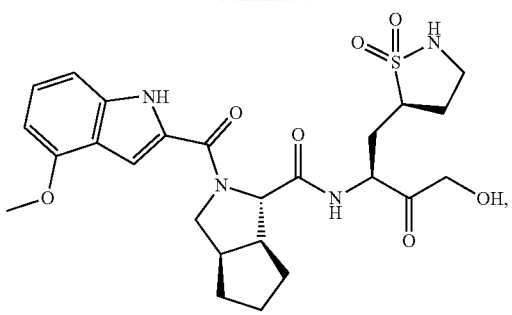
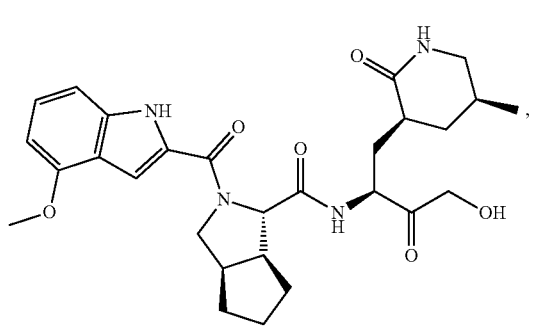
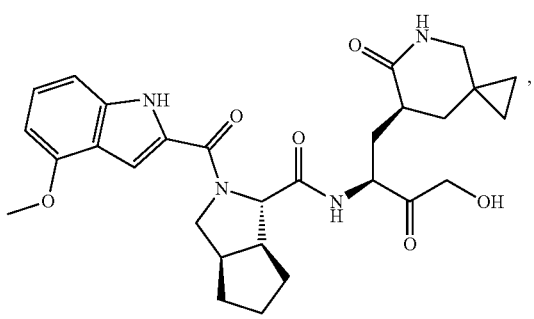
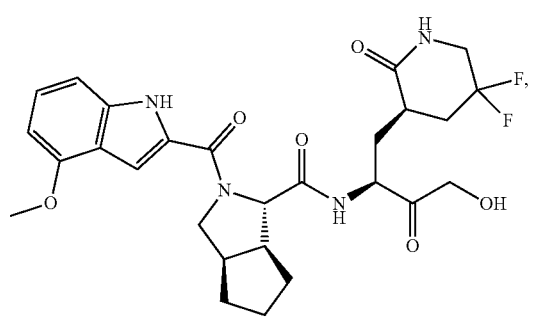
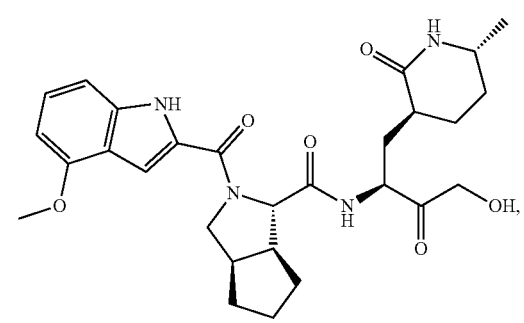
122
-continued
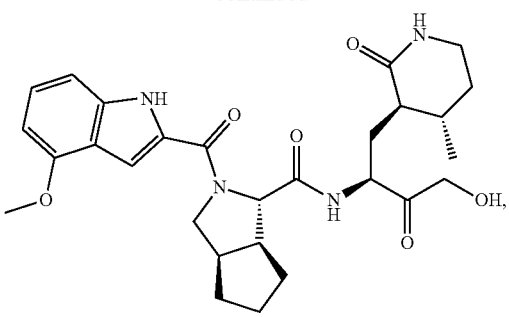
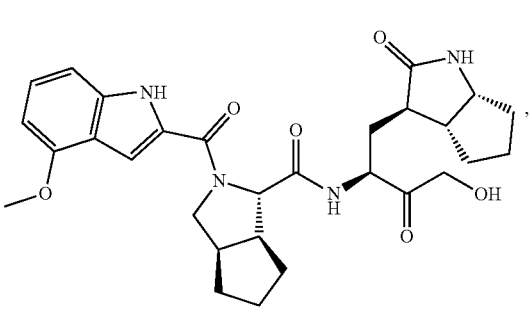
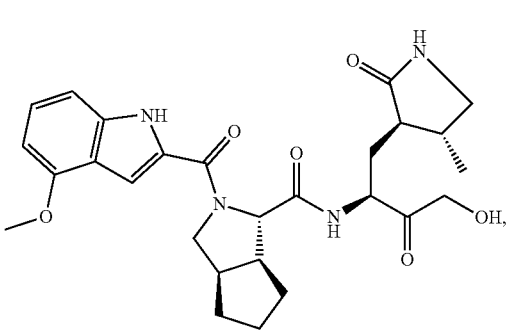
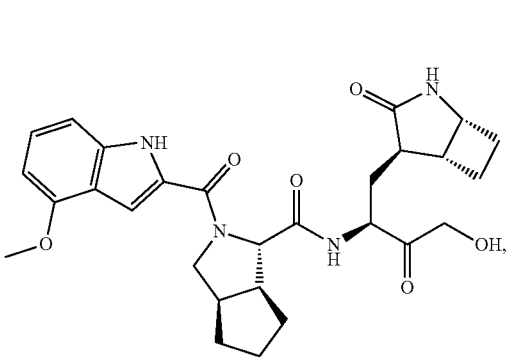

123
-continued
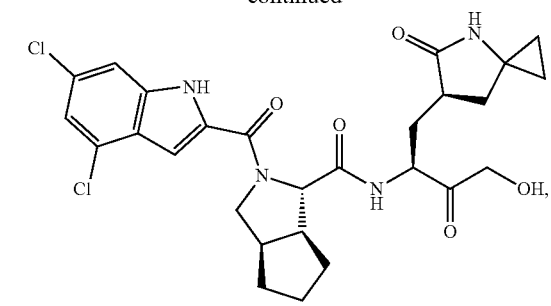
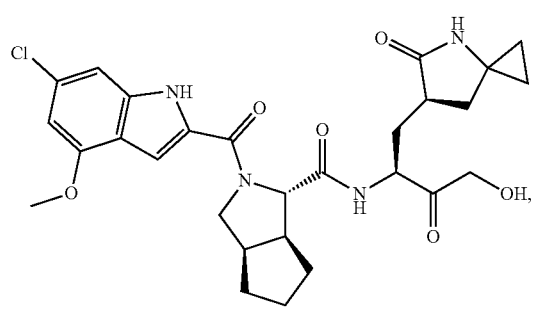
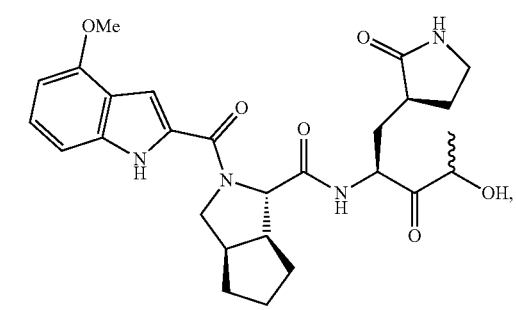
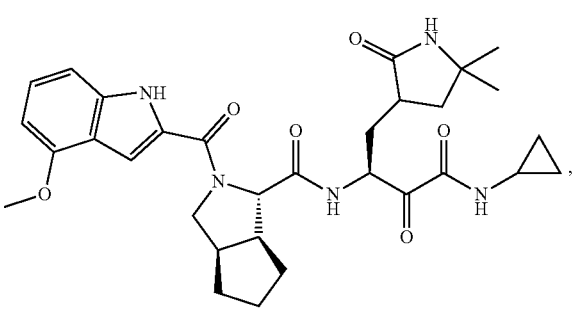
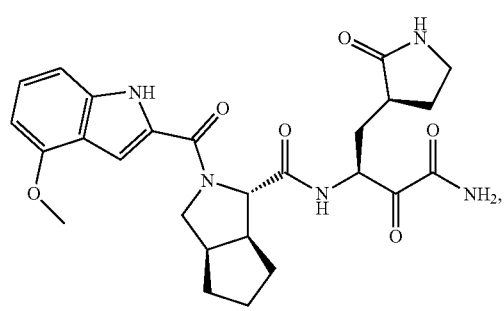
124
-continued
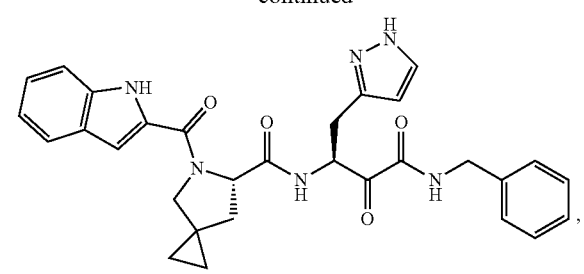
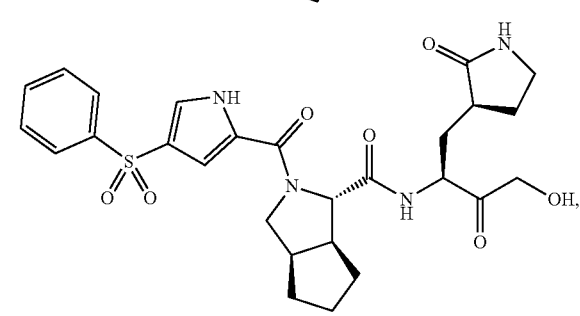

125
-continued
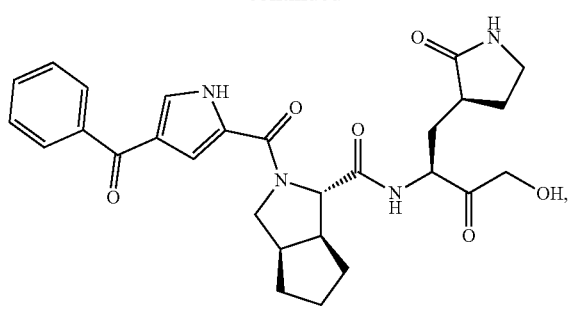
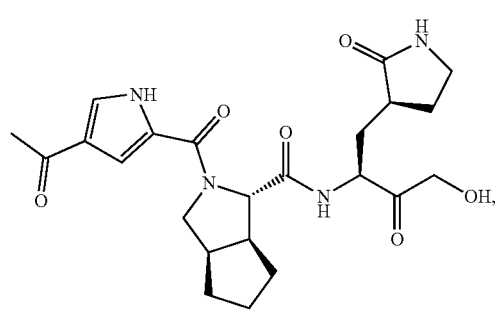
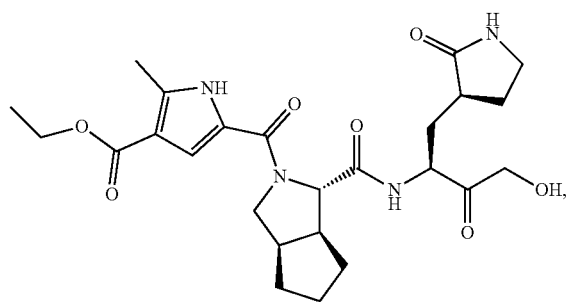
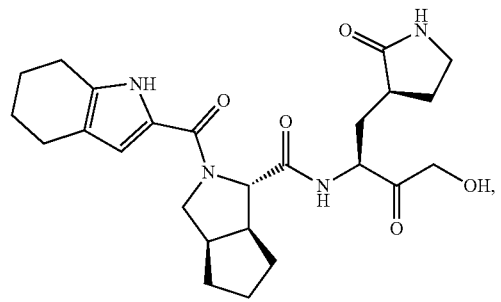
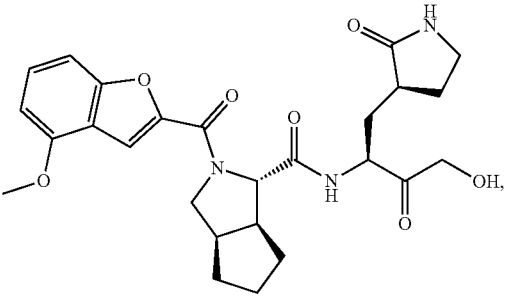
126
-continued
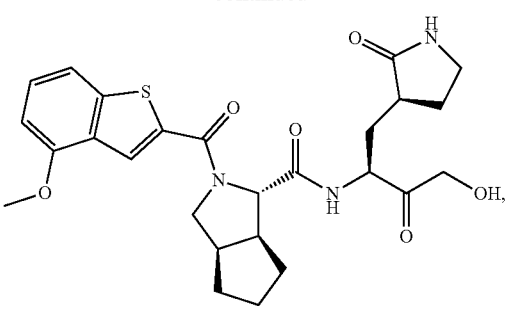
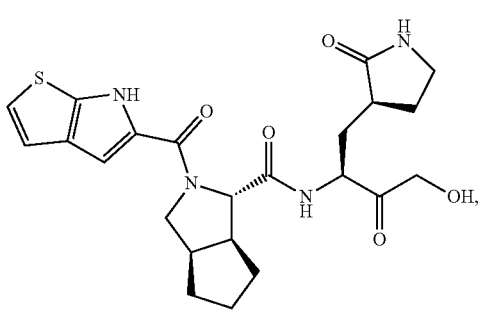
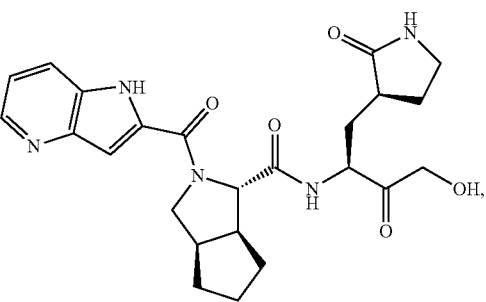
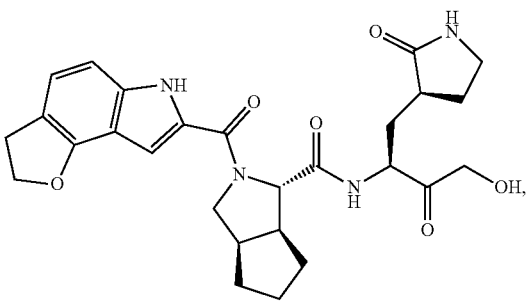
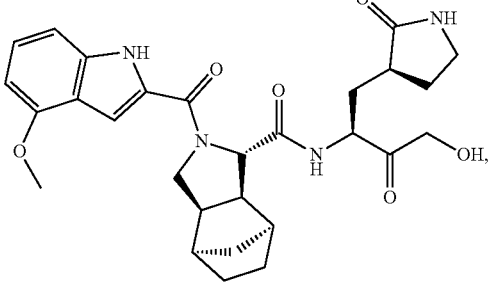

127
-continued
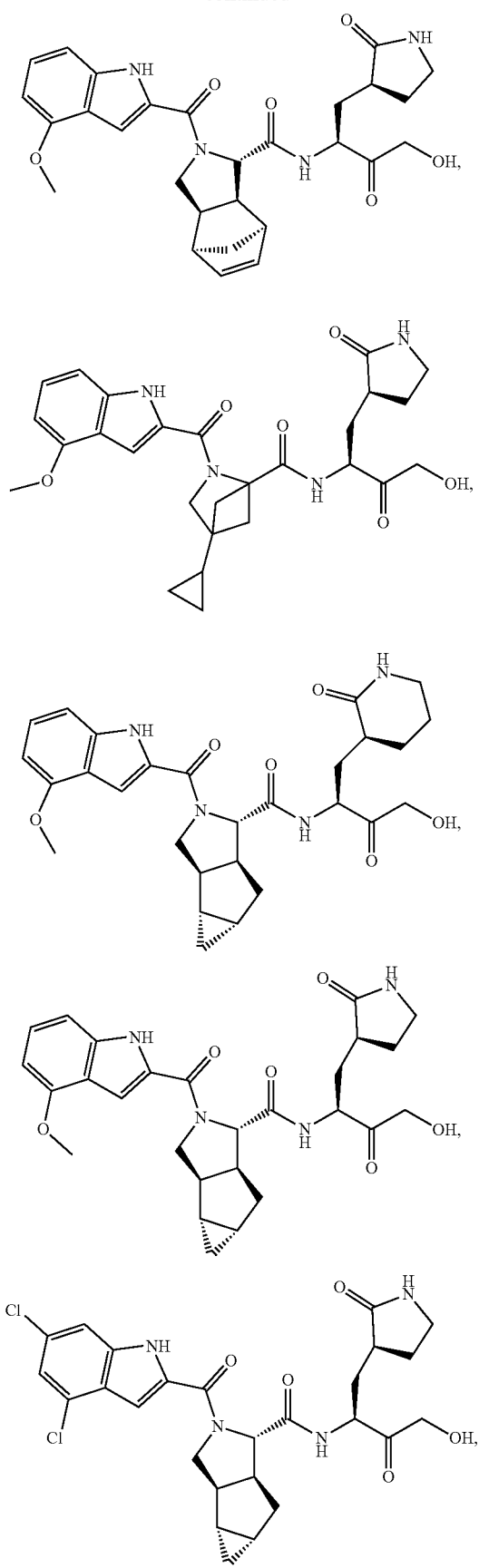
128
-continued
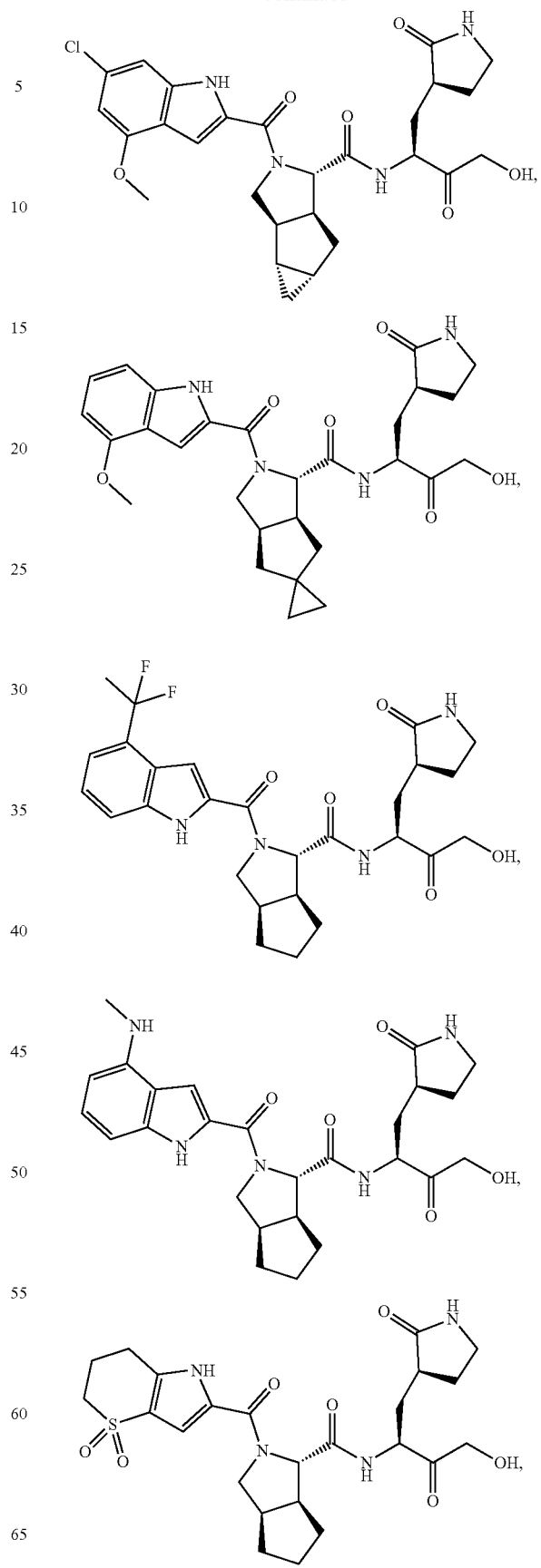

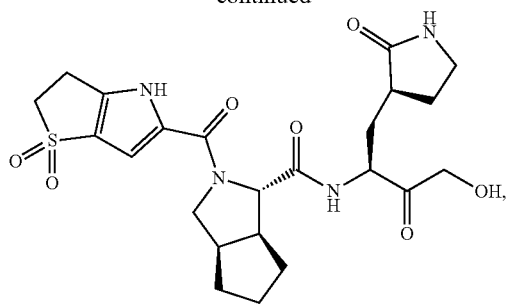
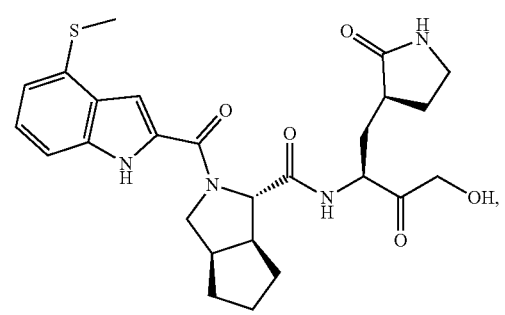
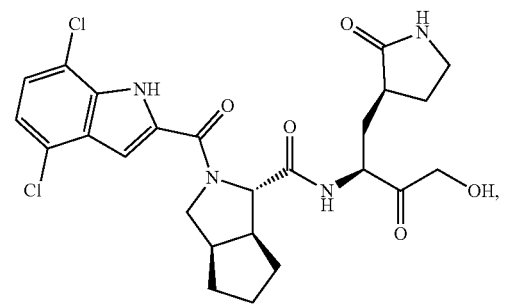
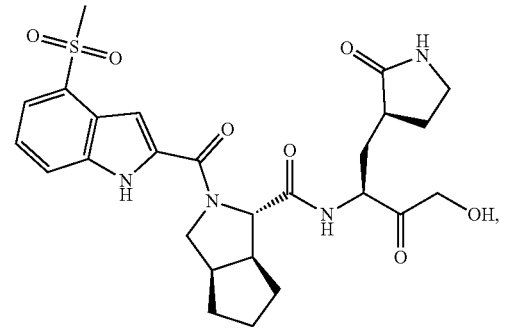
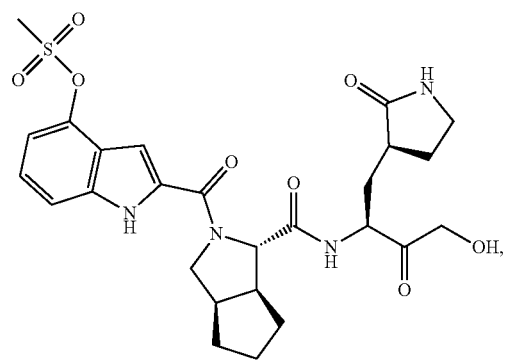
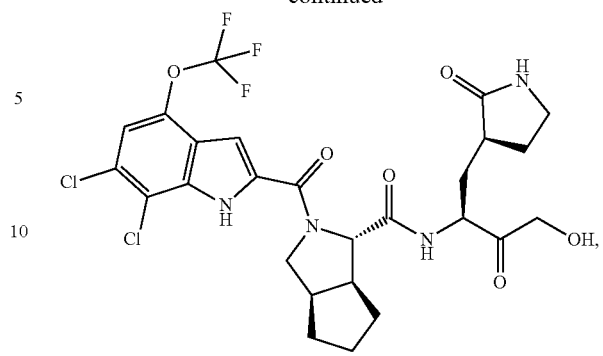
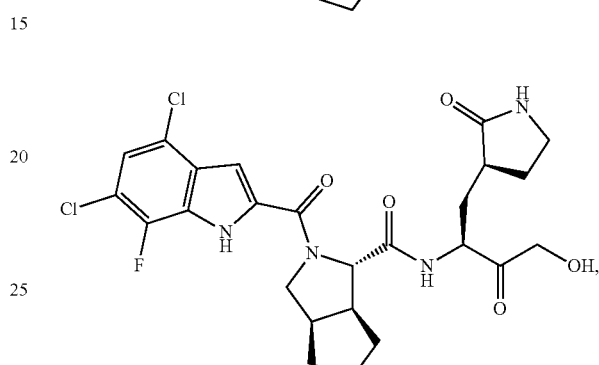
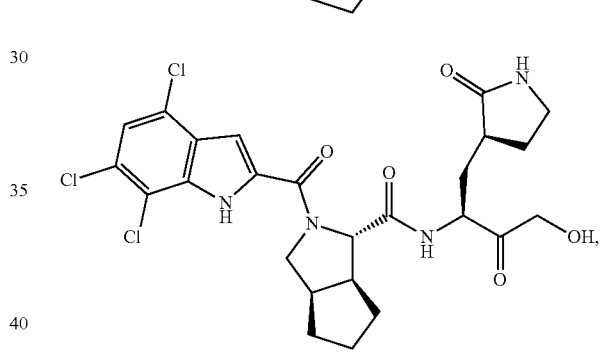
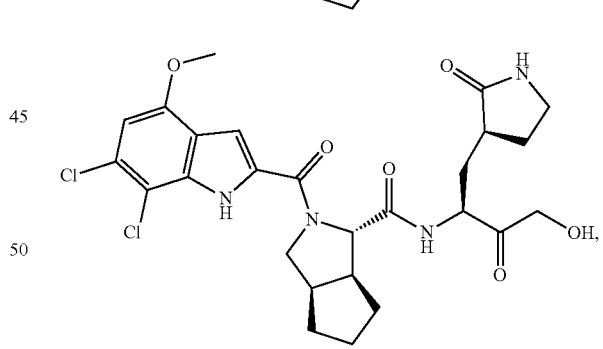
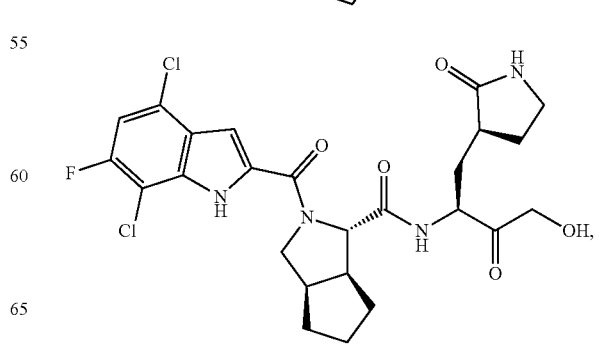

131
-continued
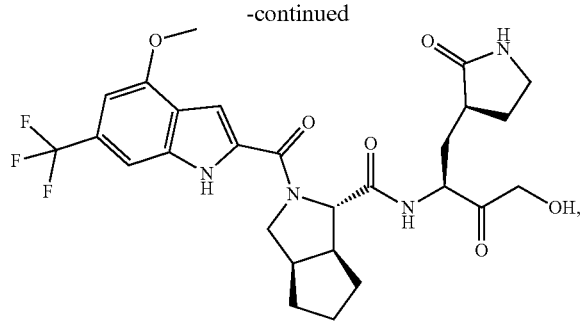
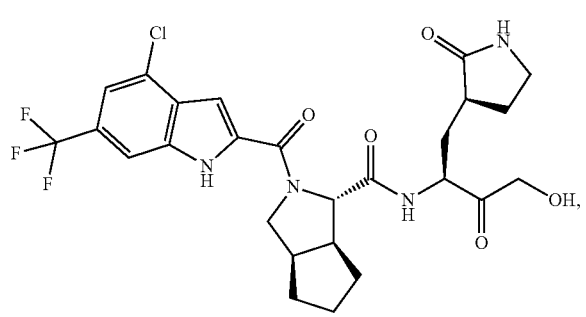
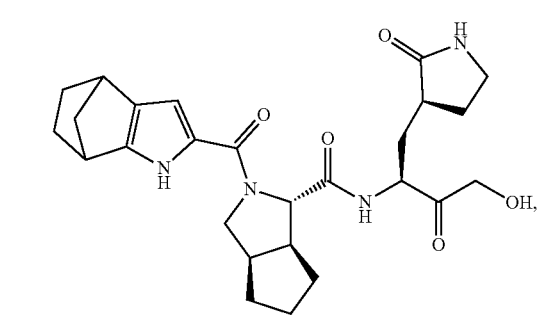
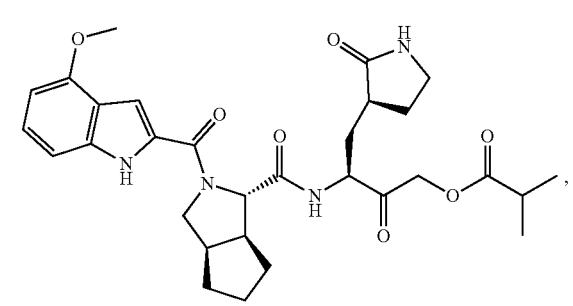
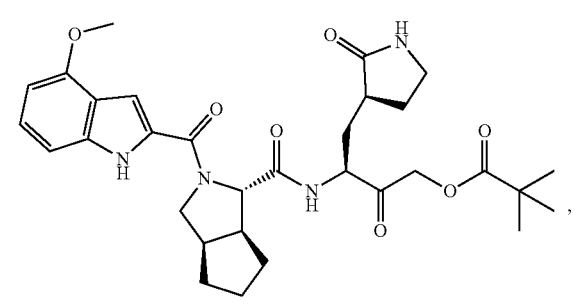
132
-continued
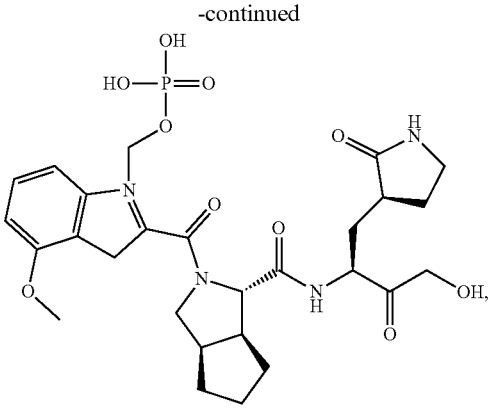
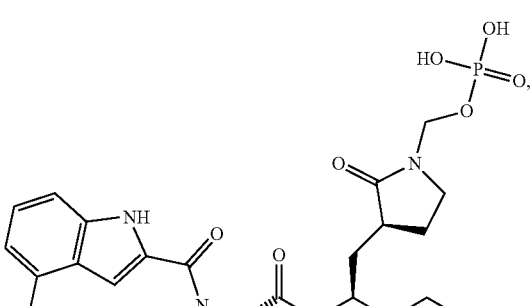
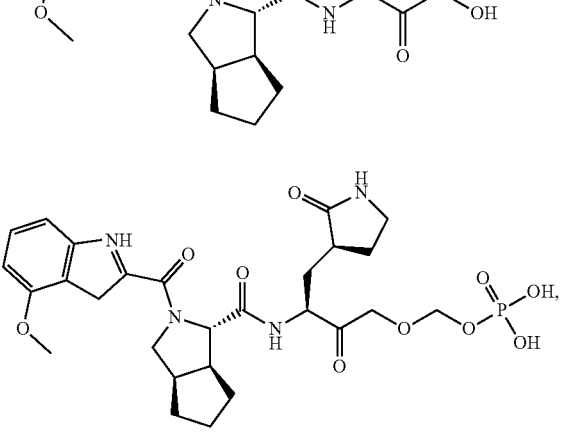
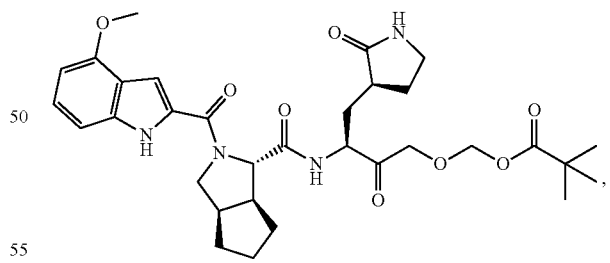
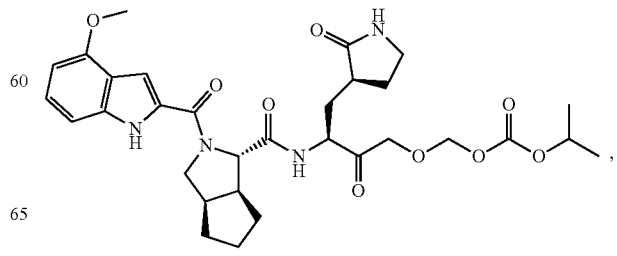

133
-continued
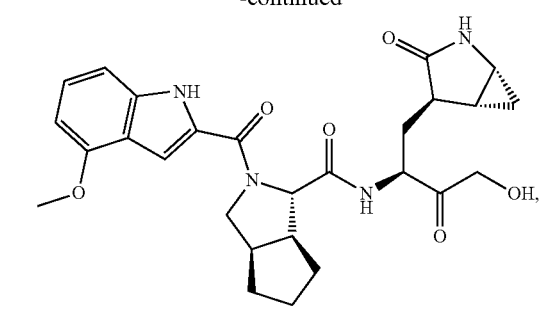
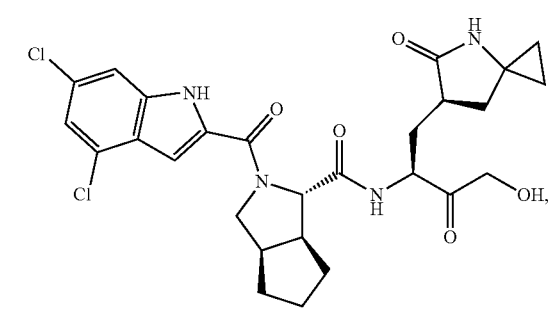
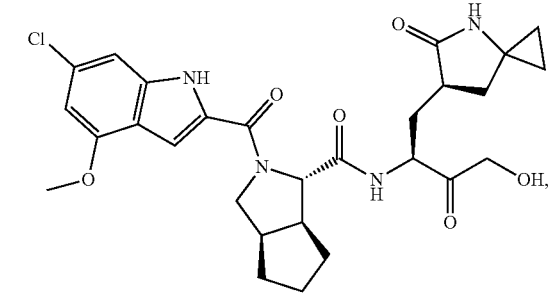
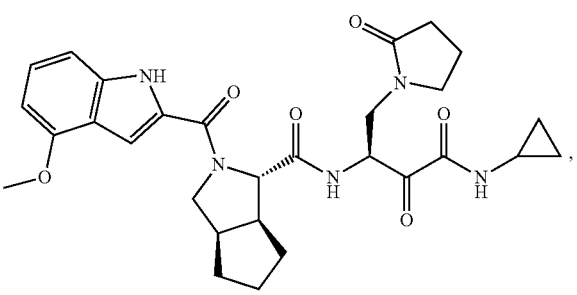
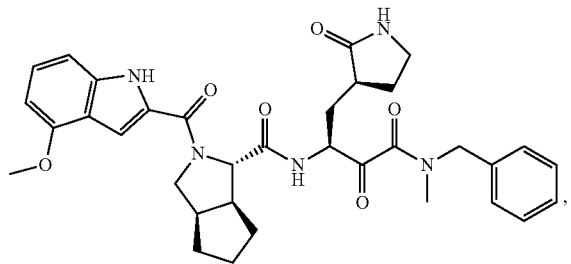
134
-continued
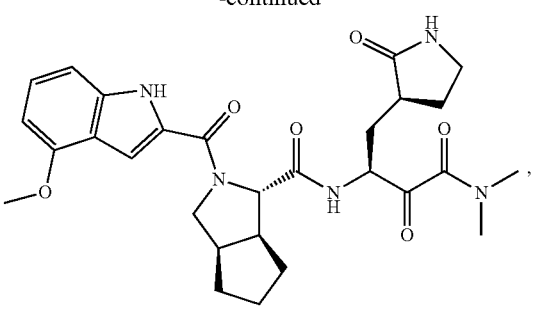
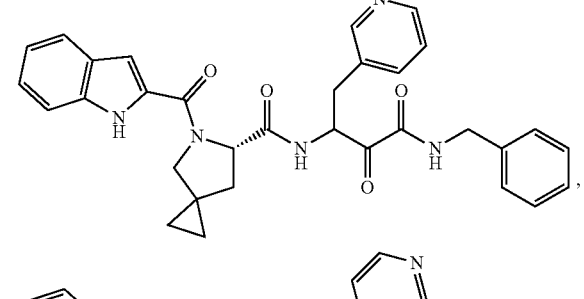
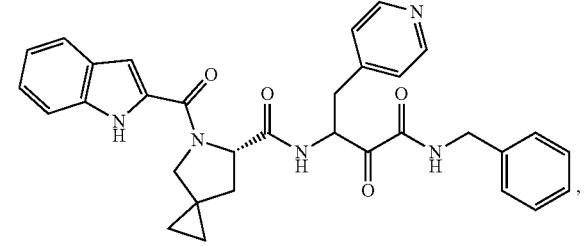
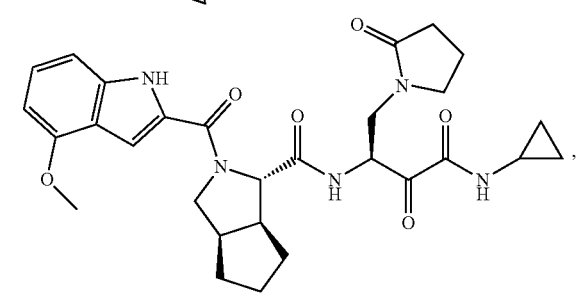
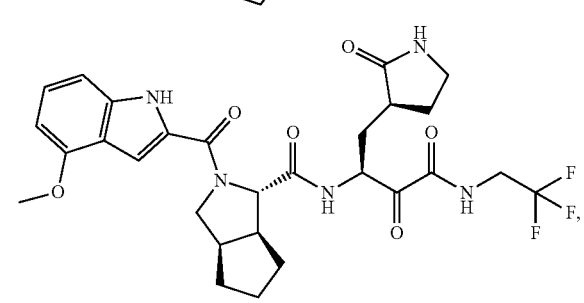
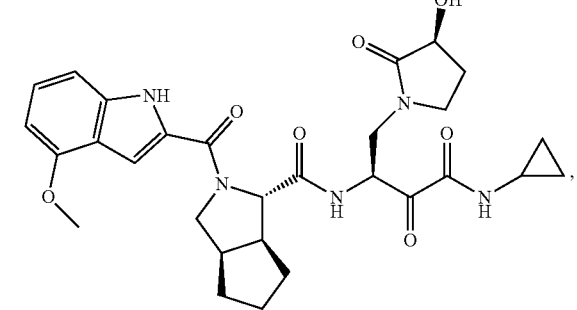

135
-continued
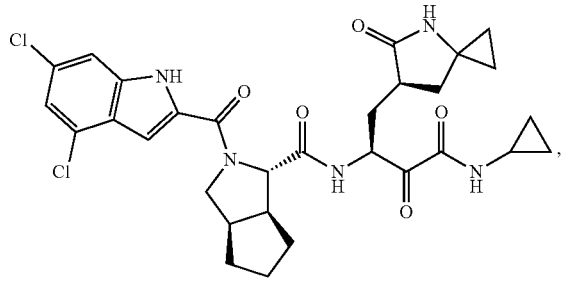
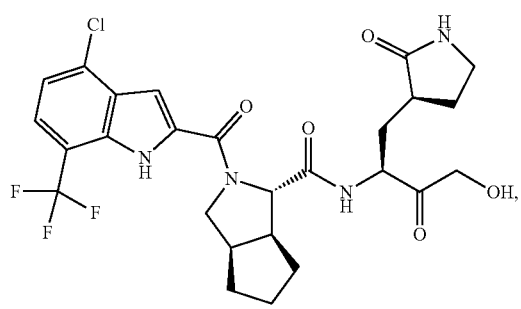
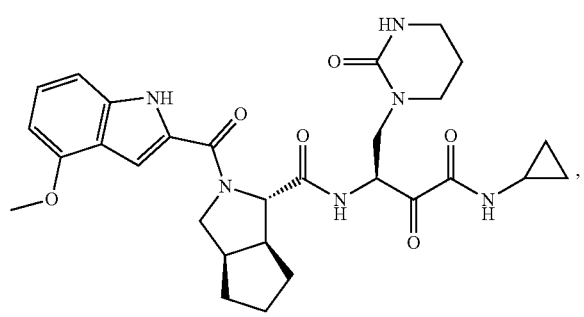
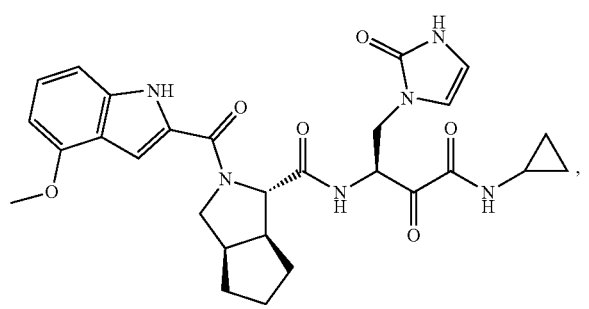
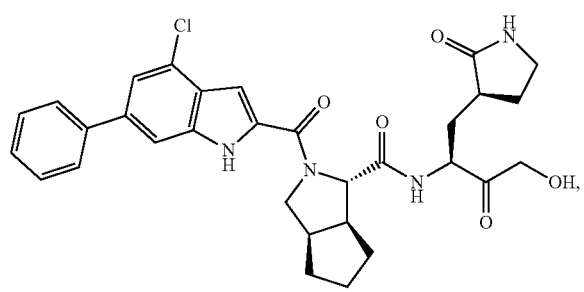
136
-continued
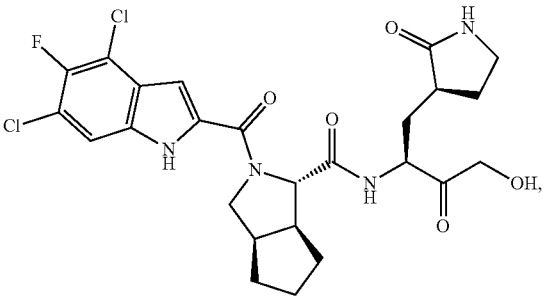
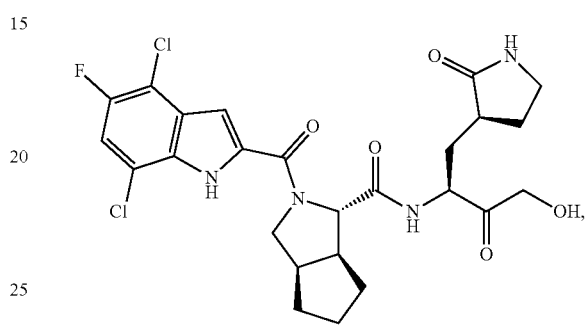
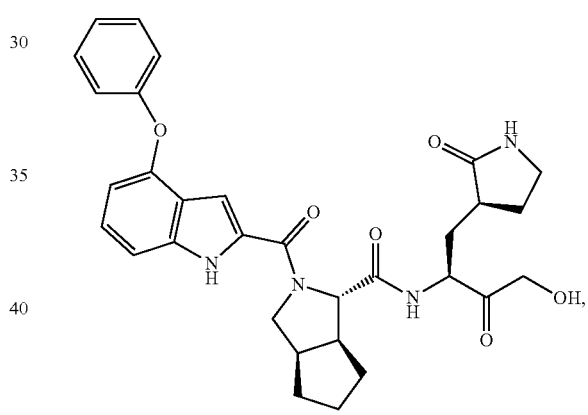
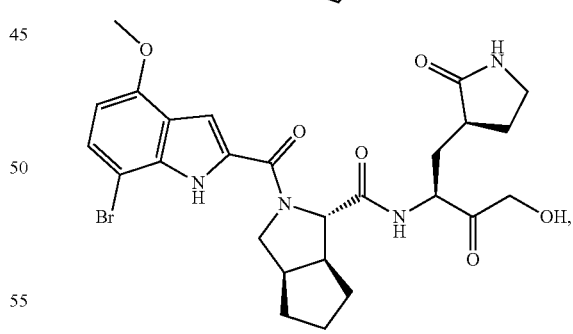
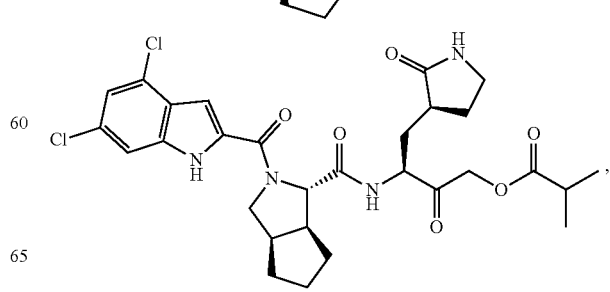

137
-continued
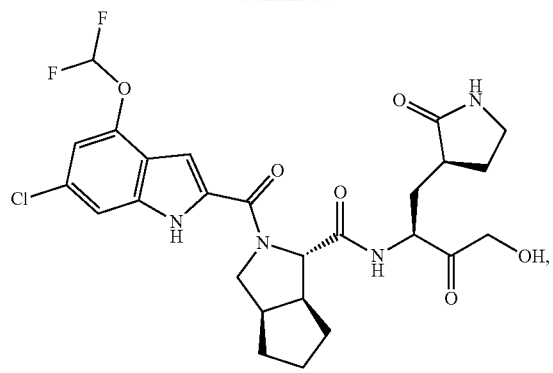
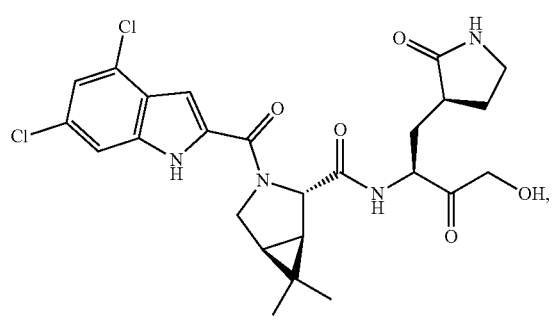
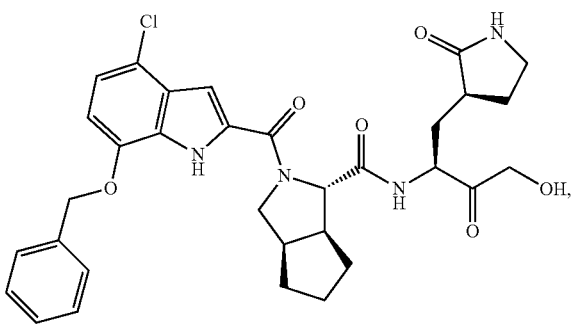
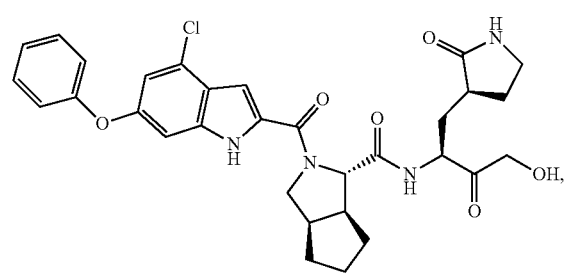
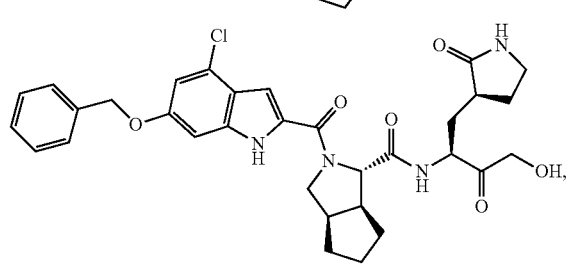
138
-continued
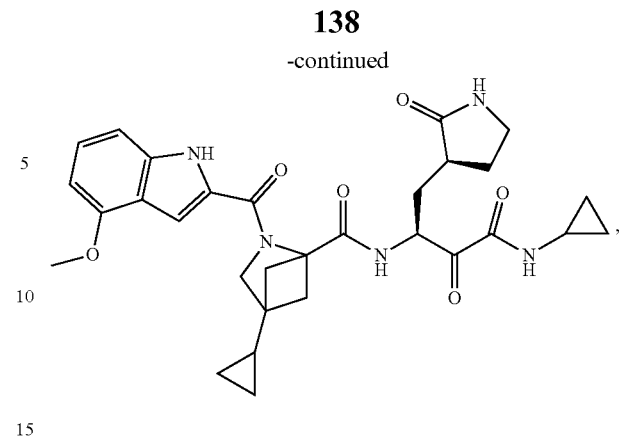
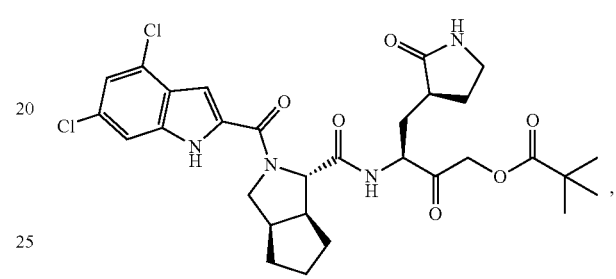
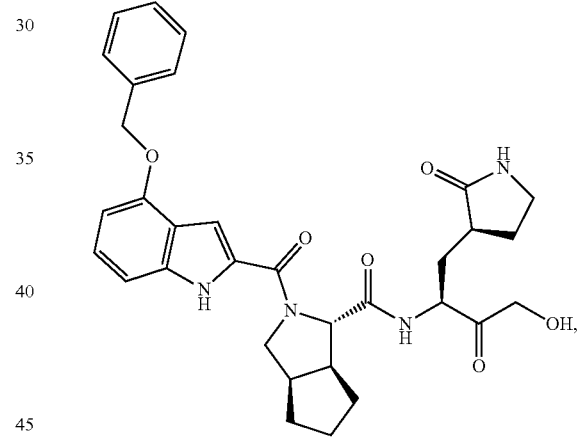
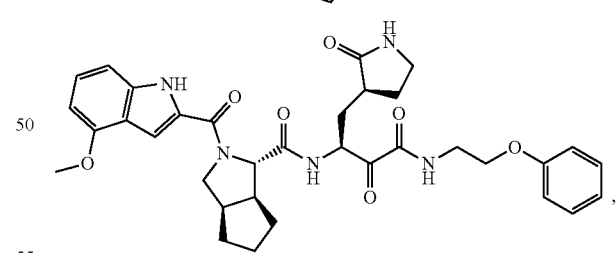
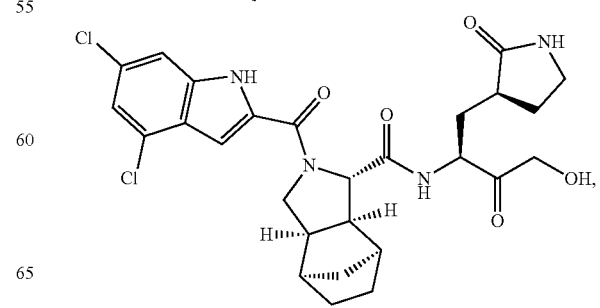

139
-continued
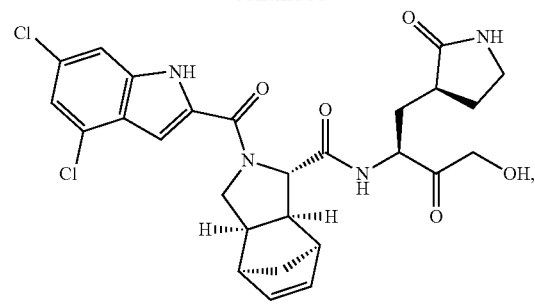
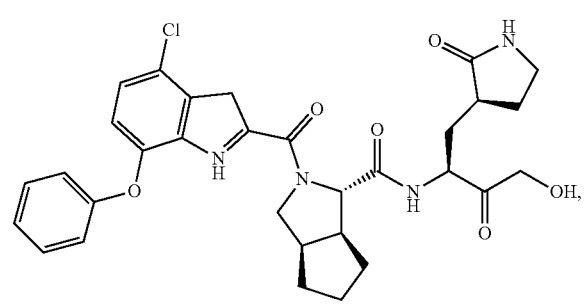
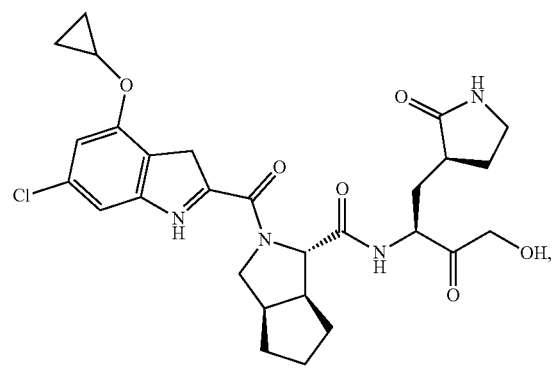
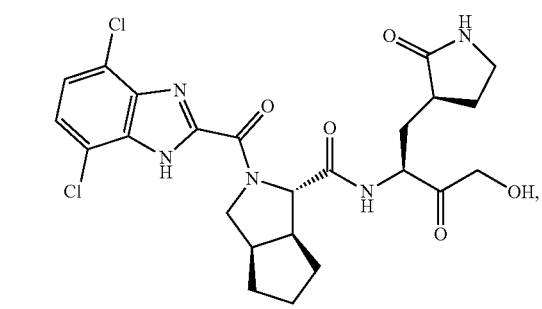
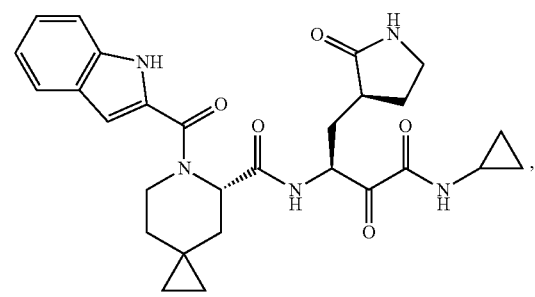
140
-continued
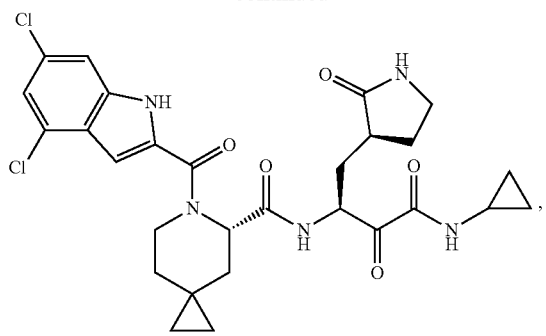
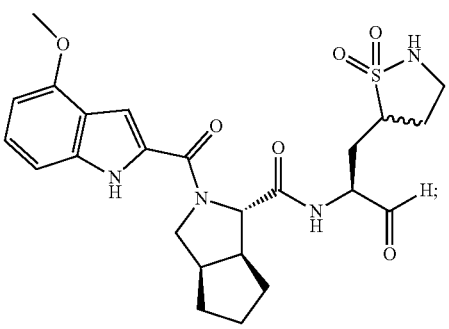
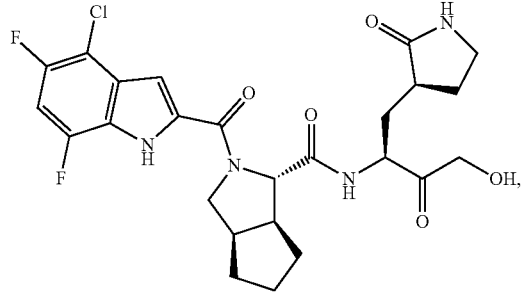
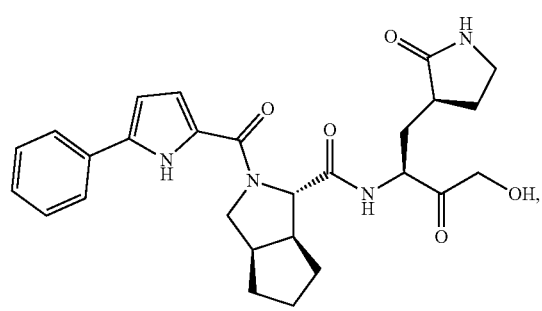
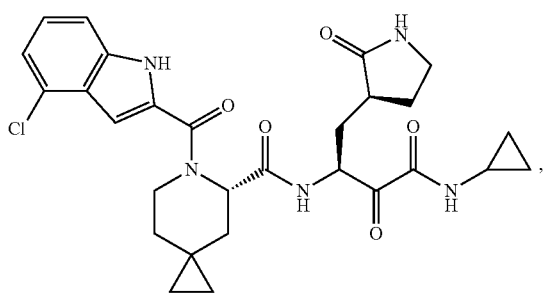

141
-continued
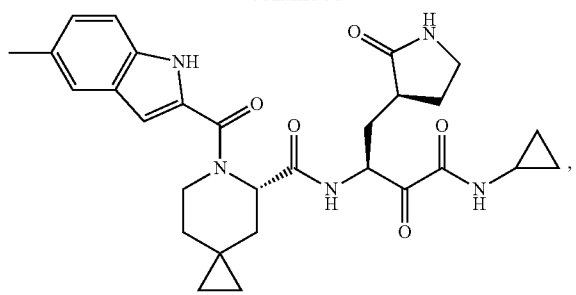
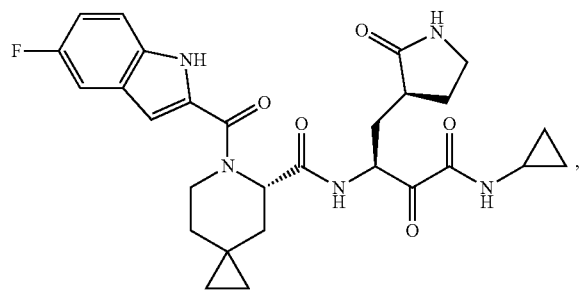
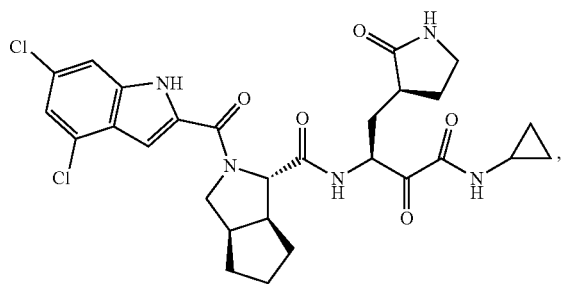
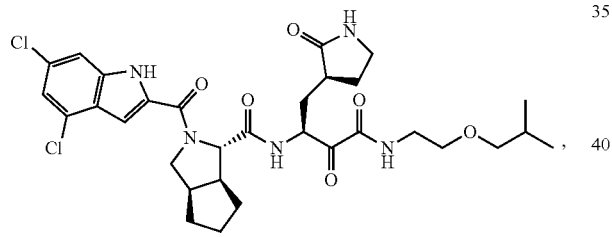
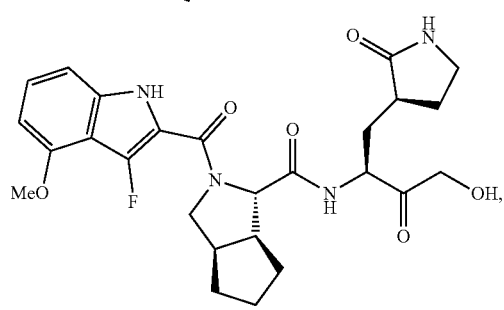
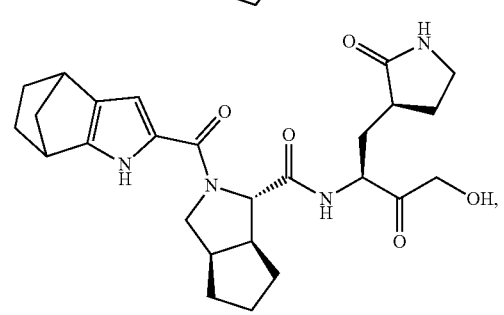
142
-continued
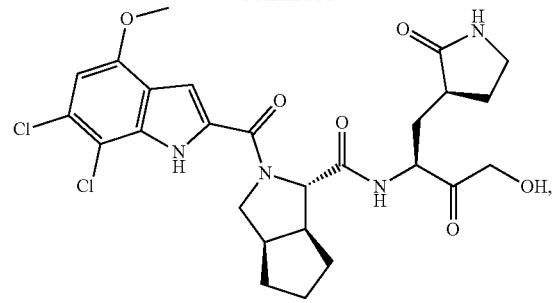
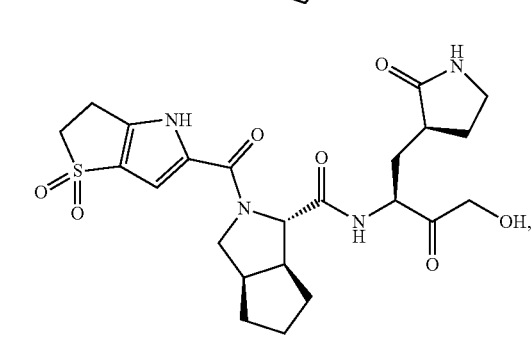
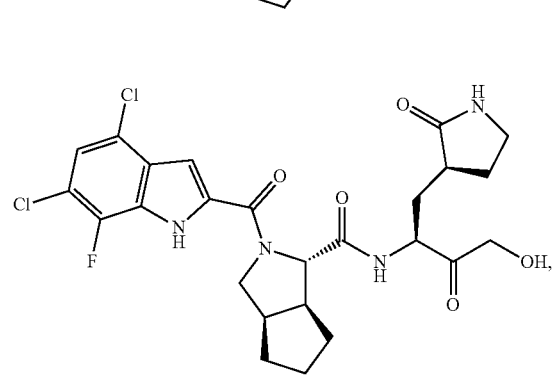
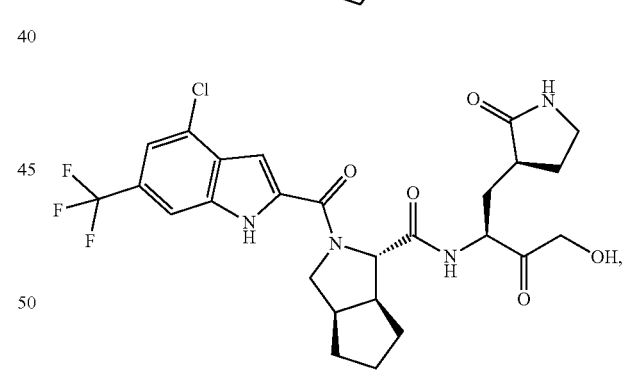
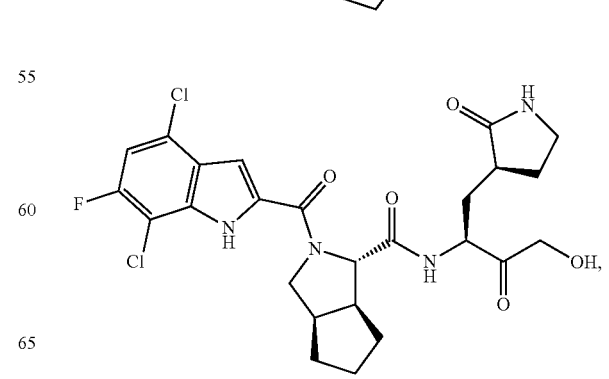

143
-continued
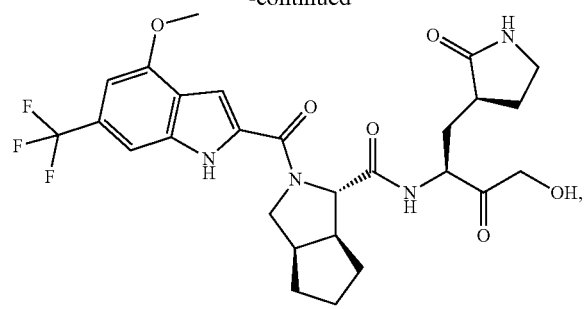
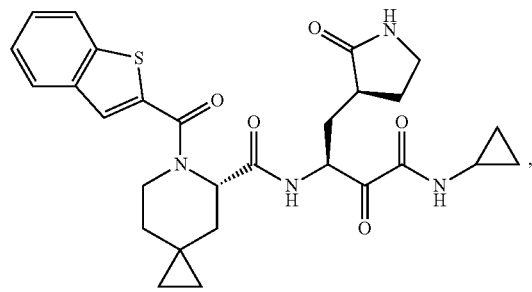
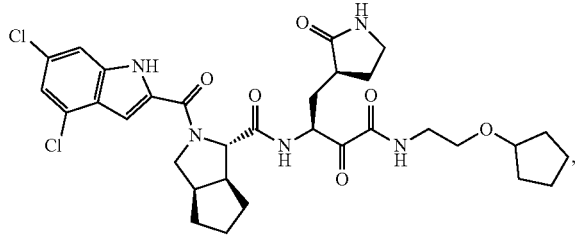
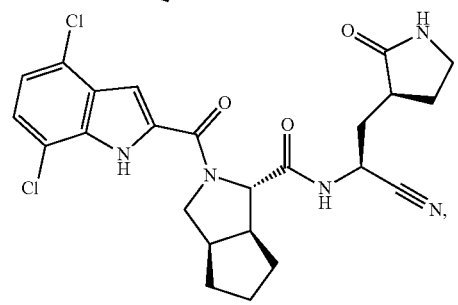
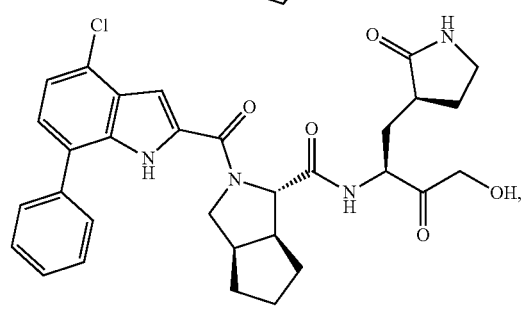
144
-continued
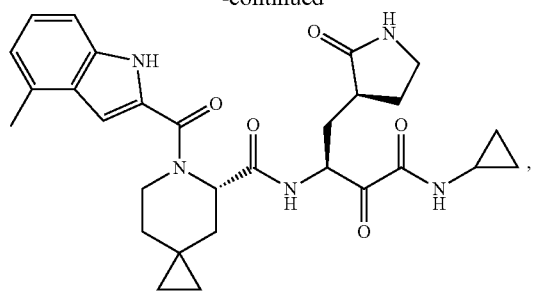
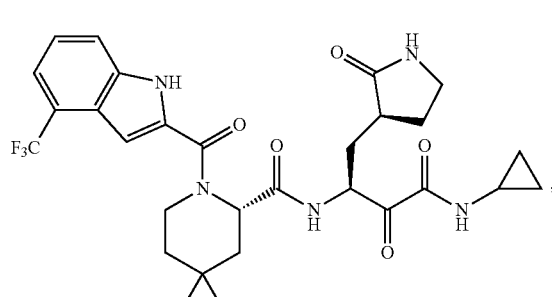
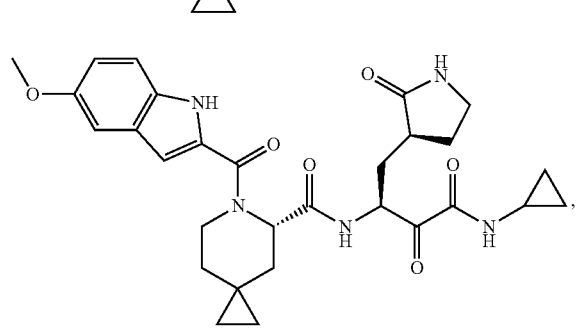
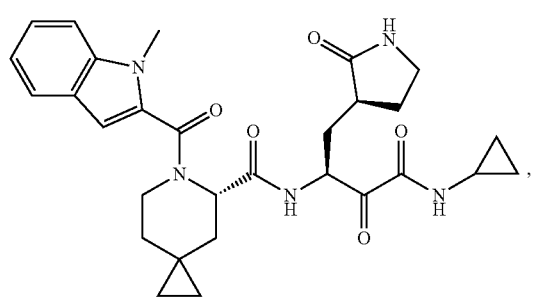
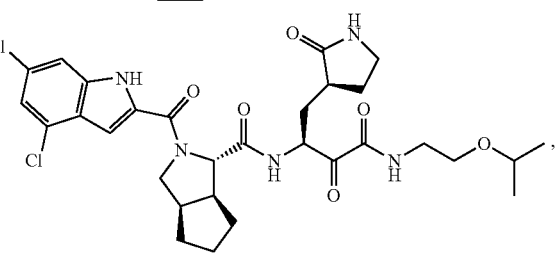
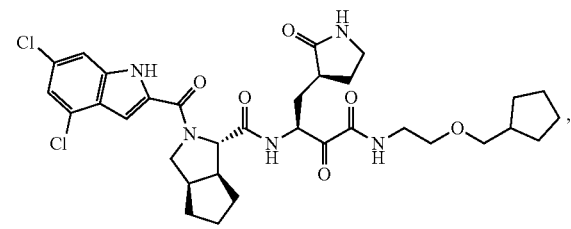

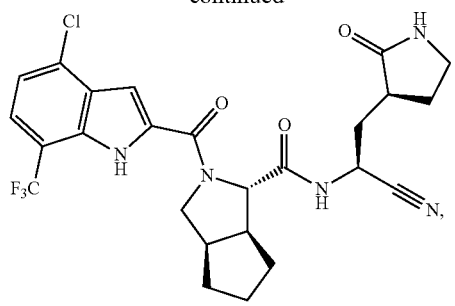
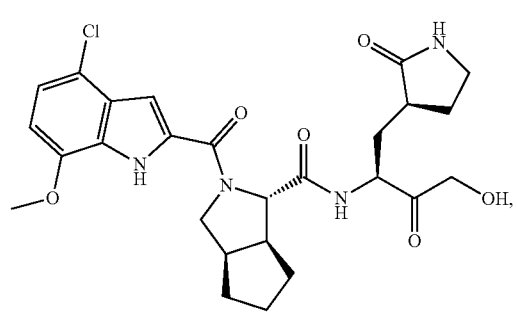
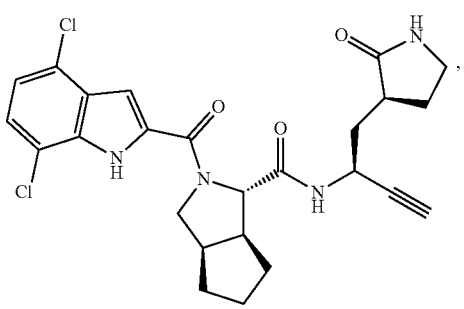
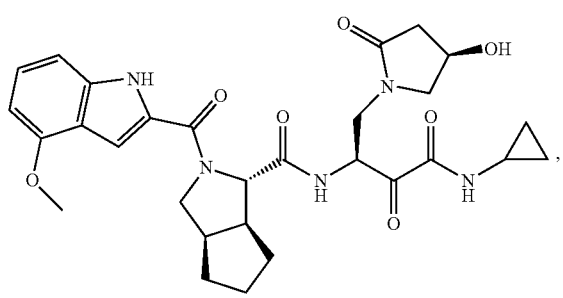
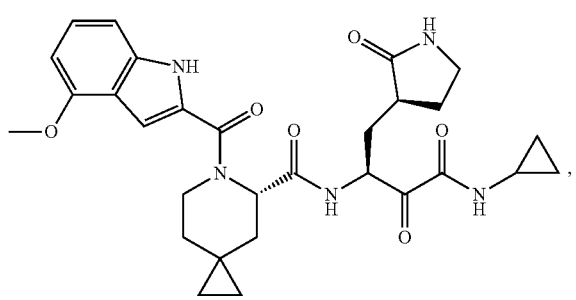
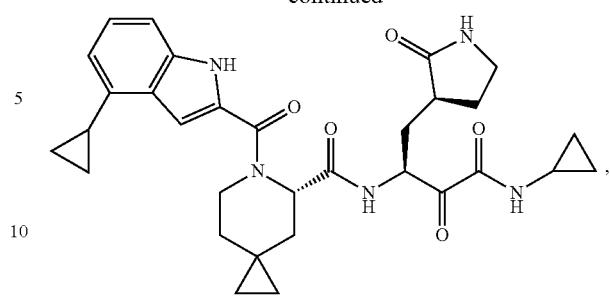
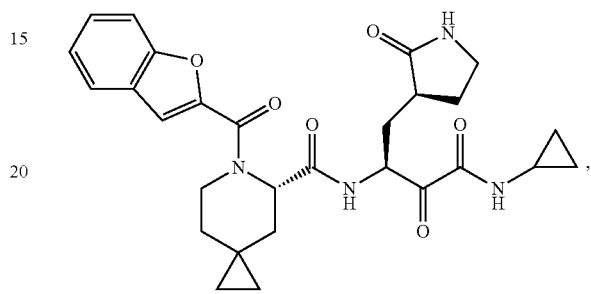
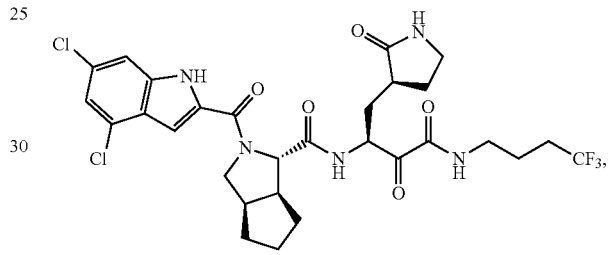
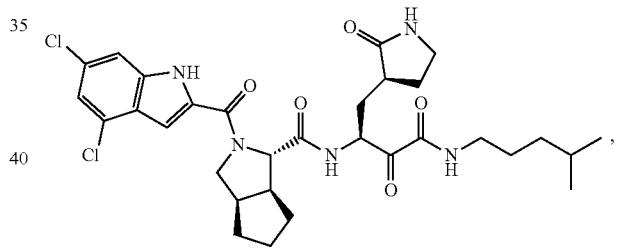
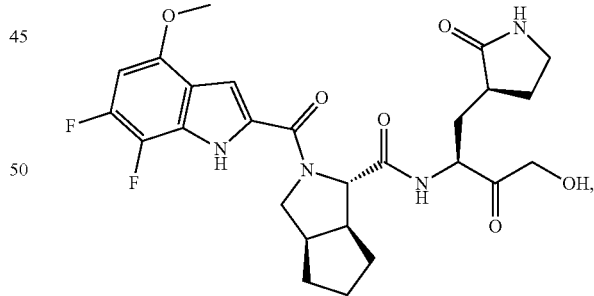
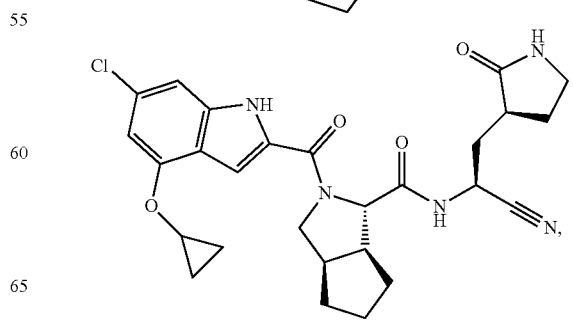

147

-continued

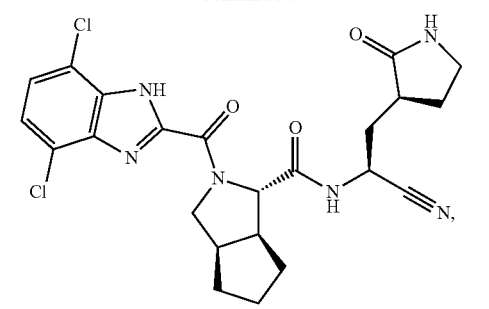

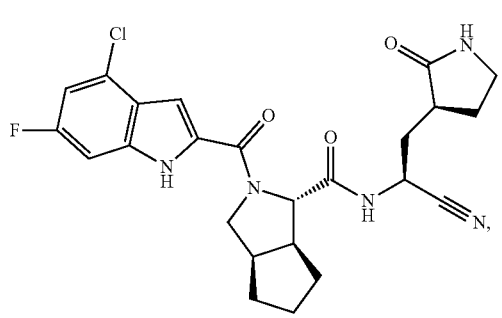

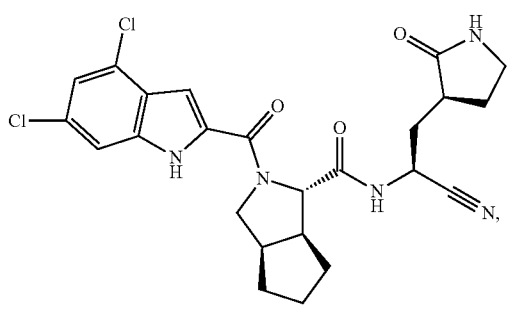

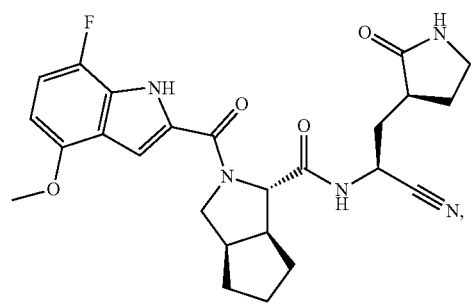

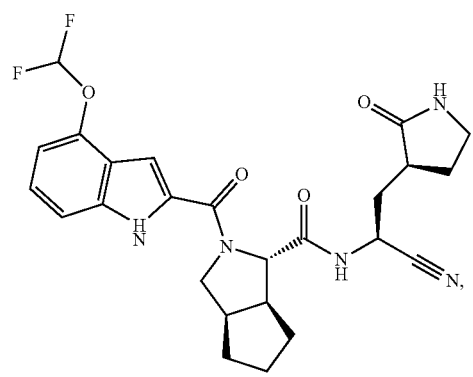

148

-continued

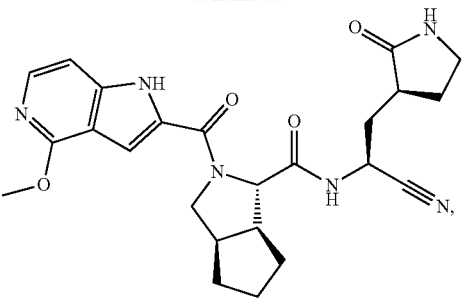

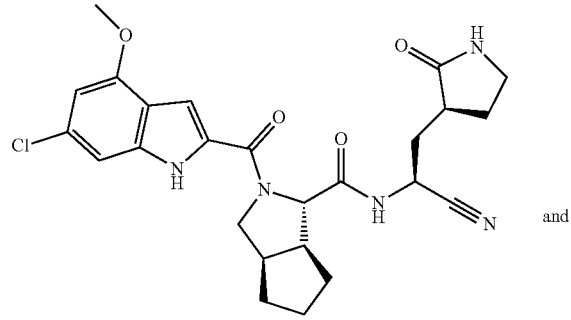

and

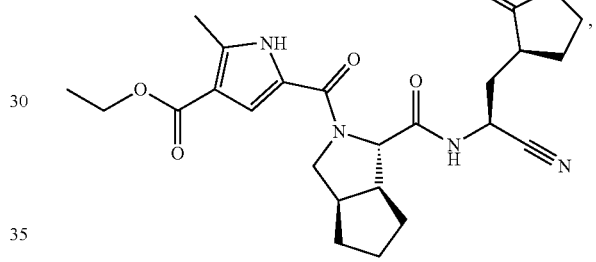

or pharmaceutically acceptable salt of any of the foregoing.

In some embodiments, $R^1$ cannot be an unsubstituted or a substituted acyl. For example, in some embodiments, $R^1$ cannot be an unsubstituted acyl, such as —C(=O)H. In some embodiments, when $R^1$ is an unsubstituted or a substituted acyl (for example, —C(=O)H), then $R^3$ cannot be an unsubstituted or a substituted

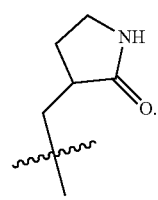 [SMILES: *CC1CCNC1=O]

In some embodiments, when $R^1$ is an unsubstituted or a substituted acyl (such as —C(=O)H), then

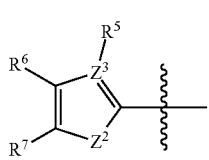

cannot be

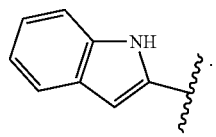 [SMILES: *c1cc2ccccc2[nH]1]

In some embodiments, when R¹ is an unsubstituted or a substituted acyl (such as —C(=O)H), and

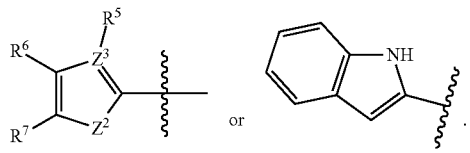

then R³ cannot be an unsubstituted or a substituted pyrrolidin-2-one($C_{1-4}$ alkyl) (such as an unsubstituted or a substituted

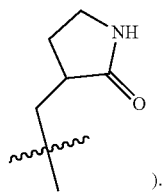 [SMILES: *CC1CCNC1=O]

).

In some embodiments, when R¹ is an unsubstituted or a substituted acyl (for example, —C(=O)H), then Ring A¹ cannot be

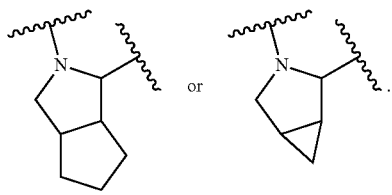 [SMILES: *C1C2CCCC2CN1* ; *C1C2CC2CN1*]

In some embodiments, when R¹ is an unsubstituted or a substituted acyl (for example, —C(=O)H), then Ring A¹ cannot be an unsubstituted $C_{1-4}$ alkyl-substituted version of

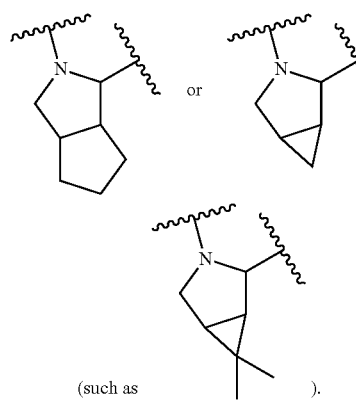

(such as ).

Synthesis

Compounds of Formula (I) along with those described herein may be prepared in various ways. General synthetic routes for preparing compounds of Formula (I) are shown and described herein along with some examples of starting materials used to synthesize compounds described herein. Additionally, for the purpose of the general synthetic routes, the structures depicted are appropriately protected, as known by one skilled in the art and the generic structures are meant to include these protecting groups. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Scheme A

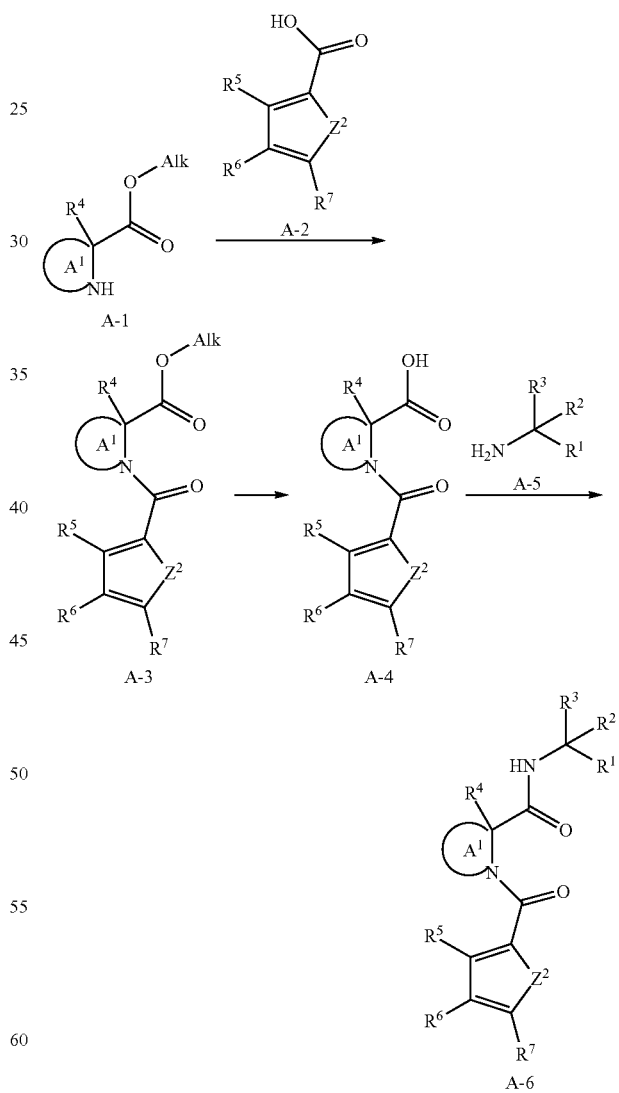

Scheme A describes the synthesis of compounds of general Formula (A-6). An amino ester of general Formula (A-1) (Alk represents alkyl) with an acid of general Formula (A-2), either by activating the carboxylic acid by converting it to an acid chloride, followed by reaction with the amino acid in the presence of a base, or by activation of the acid with a coupling reagent (such as HATU) followed by coupling with the amino ester in the presence of a base (such as DIPEA), resulting in a compound of general Formula (A-3). The ester functionality of general Formula (A-3) can be hydrolyzed, for example, under basic conditions of —OAlk is —OMe, using LiOH in MeOH, providing in a compound of general Formula (A-4). Further coupling of the carboxylic acid of general Formula (A-4) with an amine of general Formula (A-5), can provide a compound of general Formula (A-6). For the purpose of the generic synthesis, $R^1$ might be a latent functionality, converted to a functionality as described herein for $R^1$.

DIPEA). The obtained compound of general Formula (B-2) can be oxidized, providing in a compound of general Formula (B-3). In Scheme B, $R^{y1}$ is part of the ketoamide described herein with respect to $R^1$.

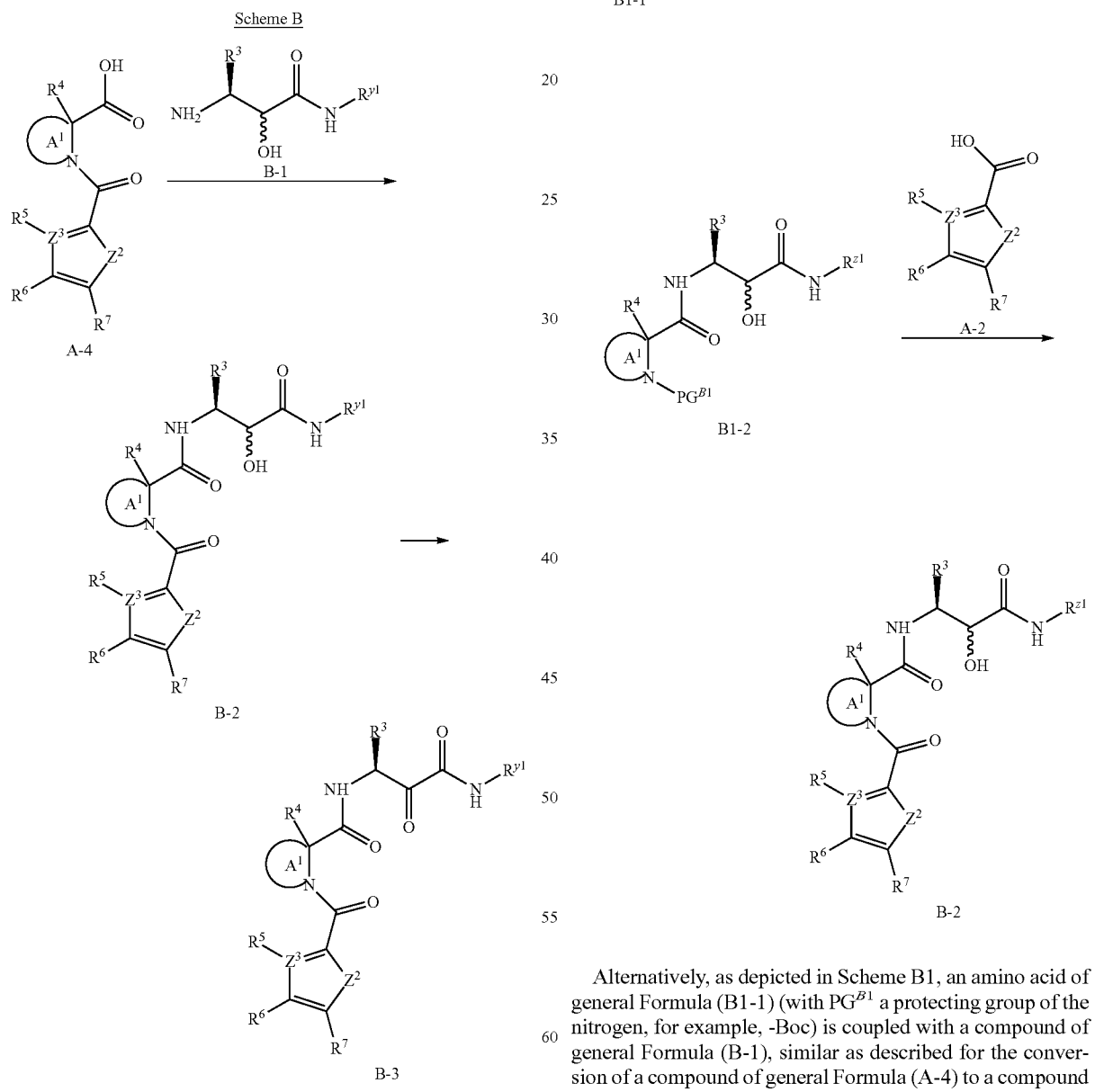

An example is given in Scheme B, where a carboxylic acid of general Formula A-4 is coupled with an amino acid of general Formula (B-1), for example, under the influence of a coupling reagent (such as T3P) and a base (for example, Alternatively, as depicted in Scheme B1, an amino acid of general Formula (B1-1) (with $PG^{B1}$ a protecting group of the nitrogen, for example, -Boc) is coupled with a compound of general Formula (B-1), similar as described for the conversion of a compound of general Formula (A-4) to a compound of general Formula (B-2). The protecting group can be then removed, for example, by treatment with acid in case of $PG^{B1}$ equaling Boc, followed by coupling with a compound of general Formula (A-2), resulting in the formation of a compound of general formula (B-2).

Scheme B2

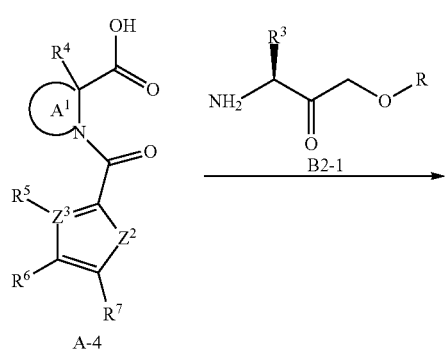

A-4

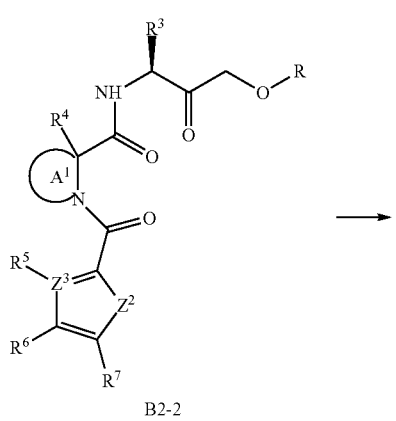

B2-2

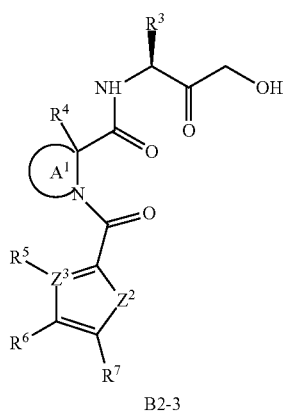

B2-3

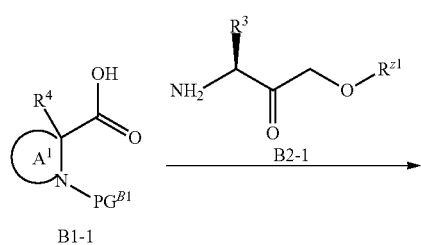

B1-1

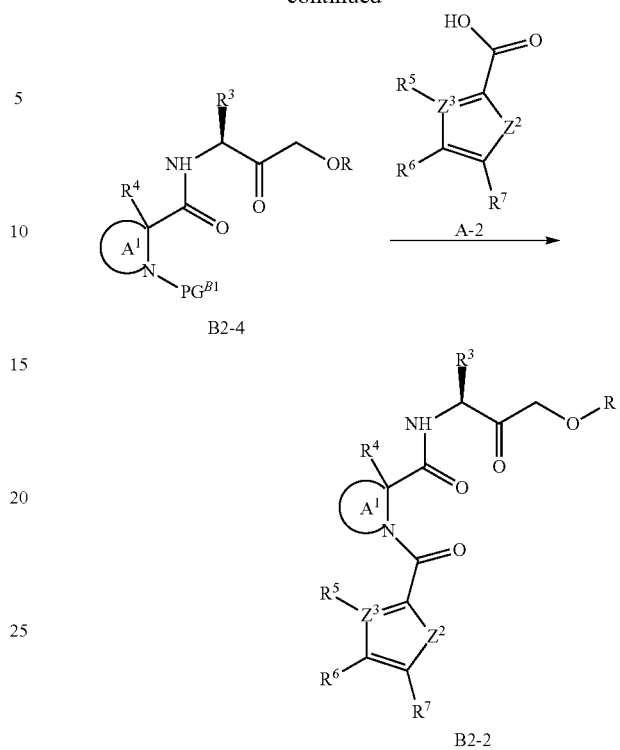

B2-4

B2-2

As described herein, $R^1$ can be a substituted acyl, where the possible groups that can be present on the acyl include hydroxy, a substituted or an unsubstituted alkoxy (for example, —O-(an unsubstituted $C_{1-4}$ alkyl) and —O-(an unsubstituted $C_{3-6}$ cycloalkyl)), an unsubstituted $C_{1-4}$ alkyl (such as a heteroaryl substituted with an unsubstituted $C_{1-4}$ alkyl), a substituted or an unsubstituted phenoxy or a substituted or an unsubstituted benzyloxy). In Scheme B2, R can represent any of the aforementioned moieties that can be present on a substituted acyl for $R^1$. Compounds of general Formulae (B2-2) and (B2-3) can be prepared as described in Scheme B2. An amino-ketone compound of general Formula (B2-1) can be coupled to a carboxylic acid of general Formula (A-4) or (B1-1) under typical amide coupling conditions. A compound of general Formula (B2-2) can be optionally further converted in a hydroxyketone of general Formula (B2-3), for example, in case where R represents a benzyl group, by catalytic hydrogenolysis. The $PG^{B1}$ of a compound of general Formula (B2-4) can be deprotected (for example in the case wherein $PG^{B1}$ is a Boc-group, by treatment with HCl in $Et_2O$). The amine can then be coupled with a carboxylic acid of general Formula (A-2) under typical amide bound formation conditions, to provide a compound of general Formula (B2-2).

Scheme C

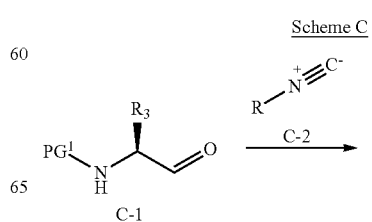

C-1

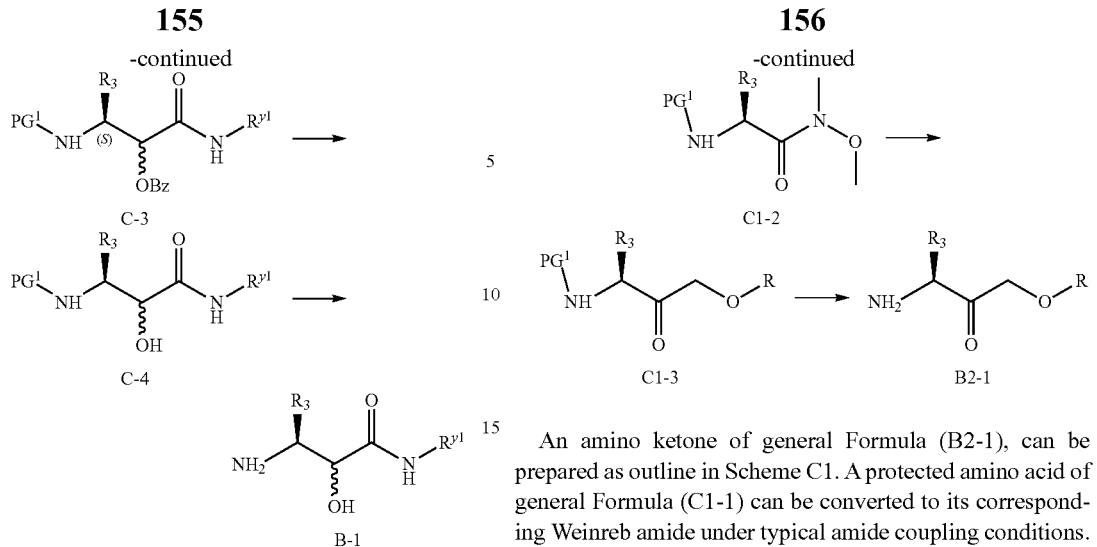

A compound of general Formula (B-1) can be prepared as outlined in Scheme C. An aldehyde of general Formula C-1 (PG¹ can be a nitrogen protecting group, for example -Boc) and an isonitrile of general Formula (C-2), in the presence of a carboxylic acid (for example, benzoic acid), can be condensed in a passerini-like reaction towards a compound of general Formula (C-3). After hydrolysis, a compound of general Formula (C-4) can be obtained. The PG¹ can be removed, for example, by treatment with HCl when PG¹ is Boc.

Scheme C1

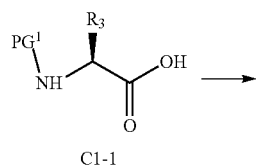

C1-1

An amino ketone of general Formula (B2-1), can be prepared as outline in Scheme C1. A protected amino acid of general Formula (C1-1) can be converted to its corresponding Weinreb amide under typical amide coupling conditions. Addition of an organometallic reagent to the Weinreb amide, followed by work-up, results in the ketone of general Formula (C1-3). An example, wherein R can be benzyl, is the formation of an organometallic reagent by mixing Mg, HgCl₂ and benzylchloromethyl ether, followed by addition to a Weinreb amide of general Formula (C1-2), and then followed by work-up with saturated ammonium chloride. The protecting group (PG¹) can be removed (for example, when PG¹ is Boc, the protecting group can be removed using HCl) resulting in the formation of an amino ketone of general Formula (B2-1). When HCl is used for the deprotection, a compound of general Formula (B2-1) can be obtained as a HCl salt. Examples of C1-1 are (S)-2-((tert-butoxycarbonyl)amino)-3-((S)-2-oxopiperidin-3-yl)propanoic acid and (S)-2-((tert-butoxycarbonyl)amino)-3-((S)-2-oxopyrrolidin-3-yl)propanoic acid, prepared as provided in the synthesis of intermediates and example 42.

Scheme D1

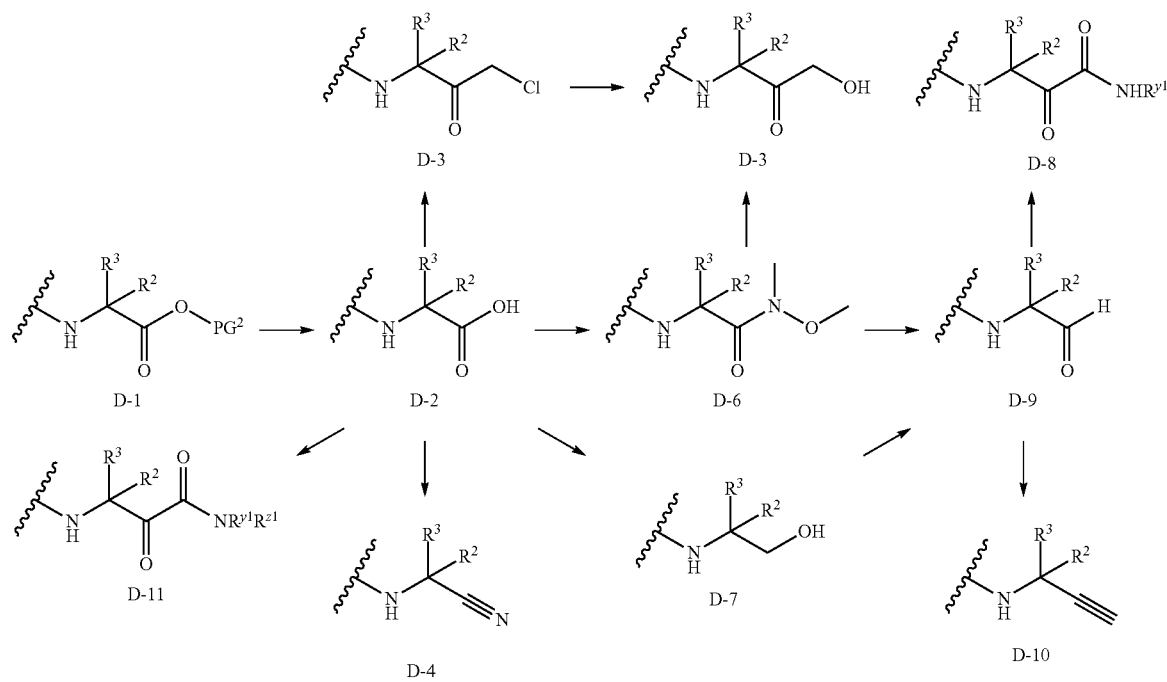

Scheme D2

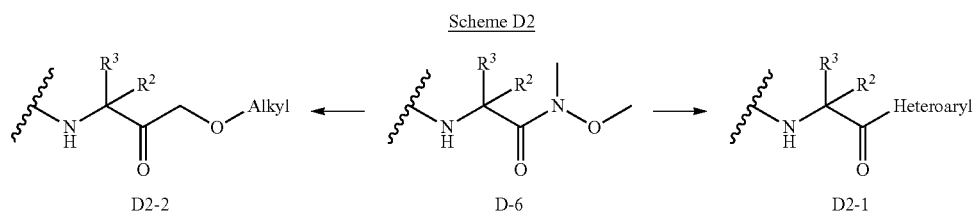

Other conversions for $R^1$ described herein are shown in Scheme D1 and D2. In Schemes D1 and D2, $PG^2$ represents an appropriate protecting group, and $R^{z1}$ and $R^{y1}$ are part of the ketoamide described herein with respect to $R^1$.

Scheme E

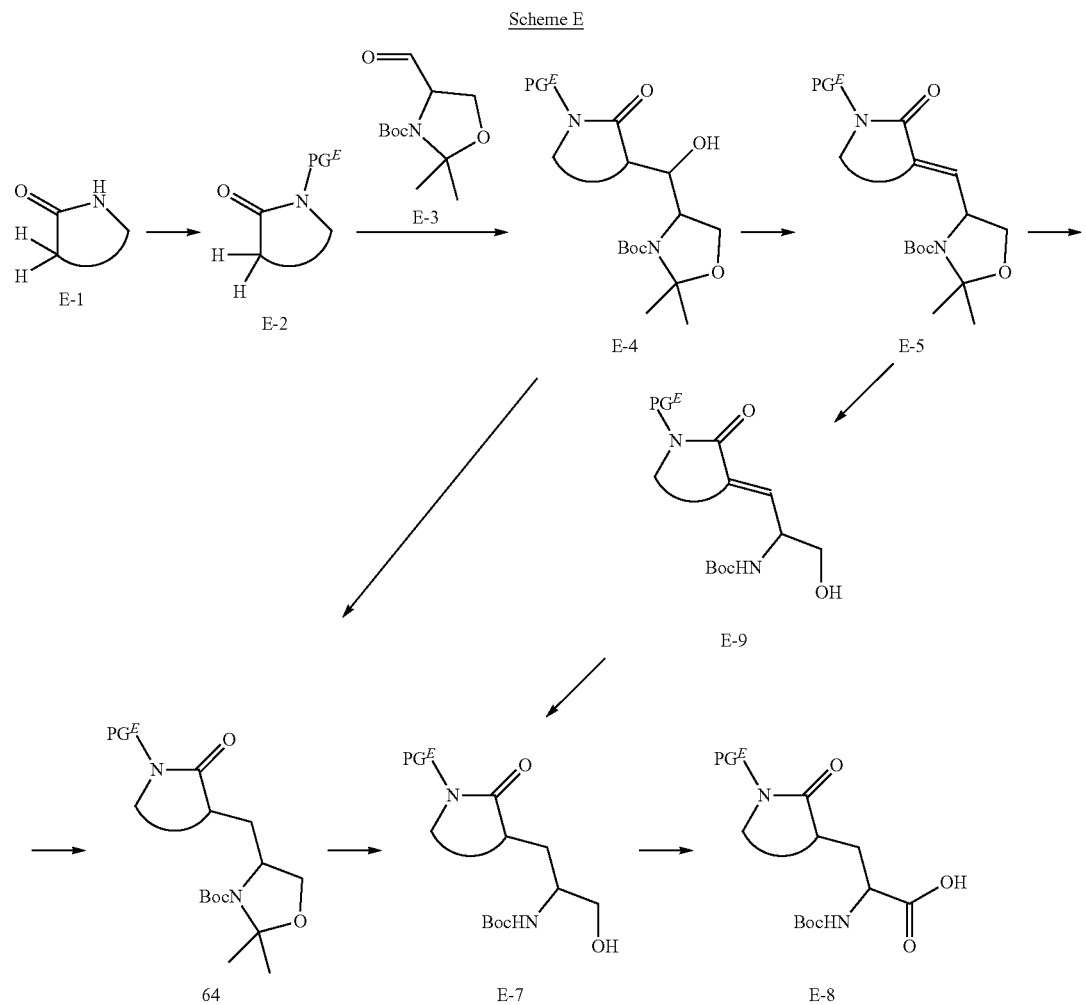

A method for preparing a subgroup of amino acids of general Formula (E-8) is described in Scheme E. A lactam of general Formula (E-1) can be protected with a suitable protecting group, $PG^E$. An example of such a $PG^E$ group is a Boc-group. For the purpose of the Scheme E, this protecting group can be removed at any relevant stage; and therefore, $PG^E$ can be hydrogen for any of compounds of general Formulae (E-4), (E-5), (E-6), (E-7), (E-8) and (E-9). The lactam of general Formula (E-2) can be reacted with an aldehyde of general Formula (E-3) (S or R-garner's aldehyde). The resulting alcohol of general Formula (E-4) can be eliminated to provide an alkene compound of general Formula (E-5) (for example, by sequential conversion of the hydroxy to a corresponding mesylate, followed by elimination under basic conditions). The double bond can be reduced (for example, by hydrogenation, under influence of a homogeneous or a heterogenous catalyst, optionally diastereoselective) to provide a compound of general Formula (E-6). Removal of the acetonide in a compound of general Formula (E-6) to the Boc-protected amino alcohol of general Formula (E-7) can be followed by the oxidation to the carboxylic acid of general Formula (E-8). Alternatively, the acetonide can be deprotected in a compound of general Formula (E-5) to obtain a compound of general Formula (E-9). Reduction of the double bond of a compound of general Formula (E-9) (for example, by hydrogenation under influence of a homogeneous or a heterogenous catalyst, optionally diastereoselective) can be used to obtain a compound of general Formula (E-7). A compound of general Formula (E-4) can be deoxygenated, for example, by a Barton-type deoxygenation, to provide a compound of general Formula (E-6). A similar synthetic strategy can be used starting from a cyclic sulfonamide instead of a lactam of general Formula (E-1).

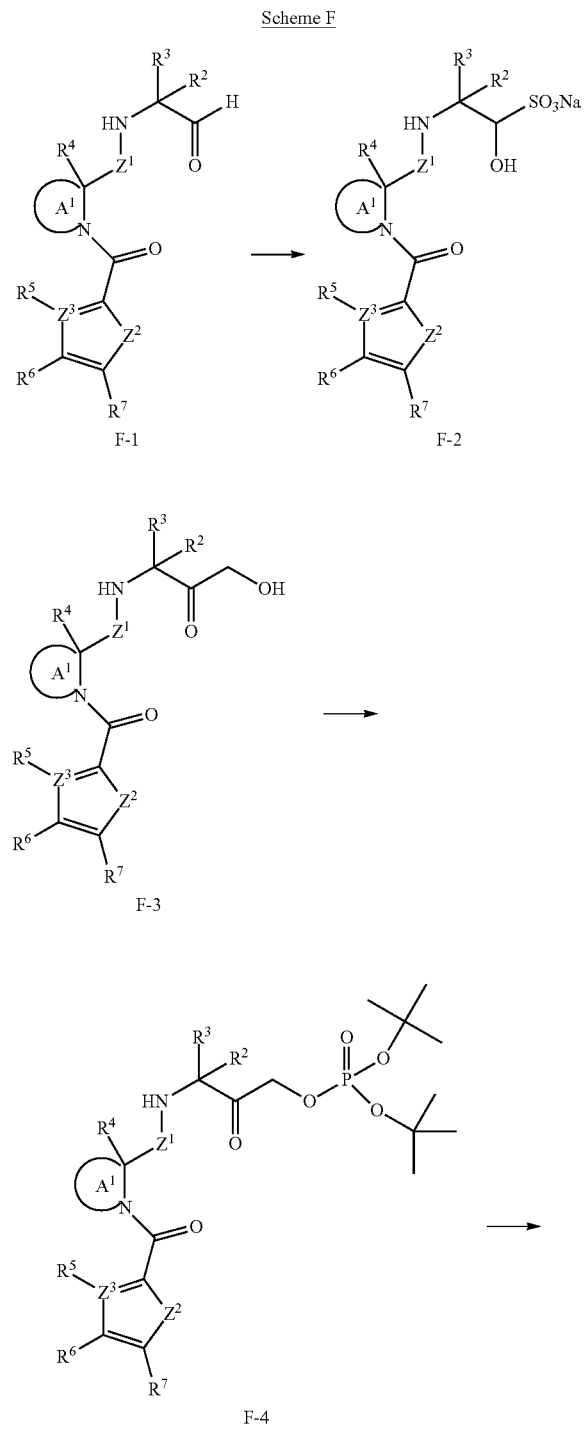

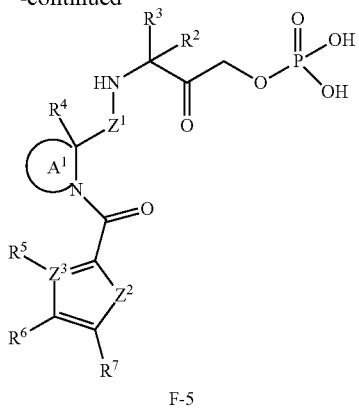

Compounds of Formula (I) can include a prodrug moieties. A method for including a prodrug moiety is depicted in Scheme F. For example an aldehyde of general Formula (F-1) can be transformed into the corresponding bisulfite adduct of general Formula (F-2), by treatment with $NaHSO_3$. A hydroxyketone of general Formula (F-3), can be transformed to the corresponding phosphate of general Formula (F-5), for example, by treatment with di-tert-butyl N,N-dipropan-2-ylphosphoramidite and tetrazole followed by oxidation with $H_2O_2$, that can provide a compound of general Formula (F-4). A compound of general Formula (F-4) can be deprotected (for example by treatment with TFA) to provide a compound of general Formula (F-5).

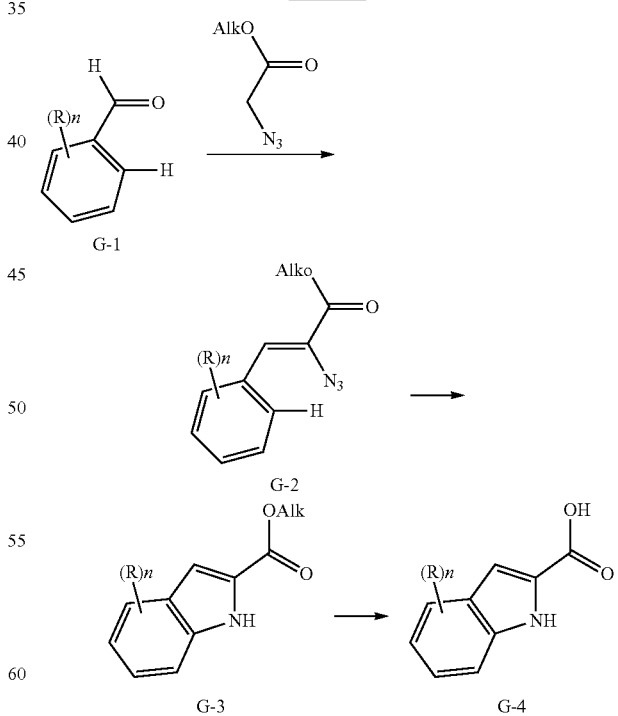

As a subgroup of a carboxylic acid of general Formula (A-2), the indole carboxylic acid of general Formula (G-4), among other methodologies, can be prepared via a Hemetsberger indole synthesis. In Scheme G, "R" represents possible substituent(s) that can be present on the shown ring(s). An aromatic aldehyde of general Formula (G-1) can be condensed with an alkyl (Alk) 2-azidoacetate, for example, under influence of sodium methoxide in methanol at −10° C. The azide of general Formula (G-2) can be thermally converted into a compound general Formula (G-3), for example, by heating at 120° C. in xylene. The alkyl (Alk) ester G-3 can be hydrolyzed to the carboxylic acid of general Formula (G-4), for example, by the treatment with NaOH in THF/H$_2$O. This methodology can be extended to 5-, 6-, and 7-azaindoles related to (G-4) (See Roy et al., Synthesis 2005(16):2751-2757) and other heteroaryls.

Scheme H

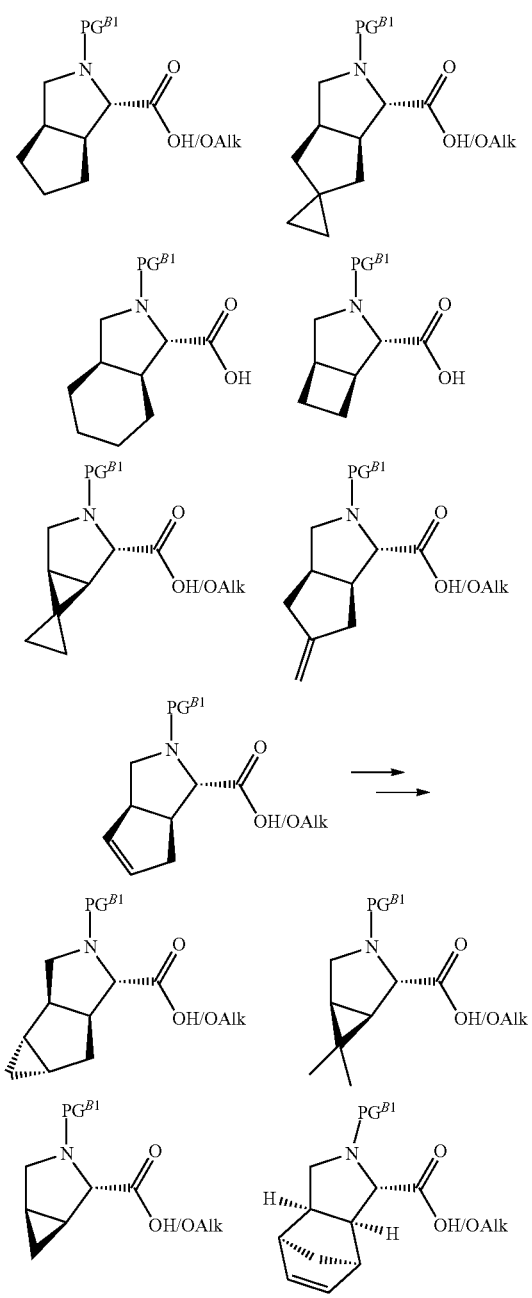

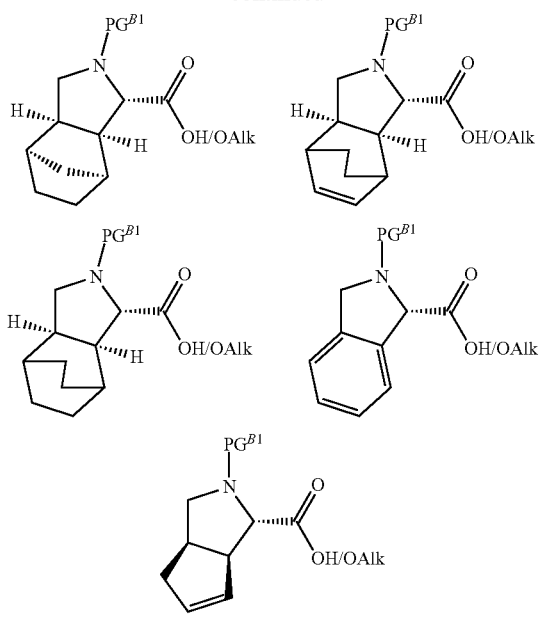

Scheme H depicts several examples of the amino acids/esters of the general Formulae (A-1) and (B1-1). Examples are, but are not limited to, proline derivatives, depicted, obtained from intermediates, or obtained according to methodology, as outlined in Calaza et al., European Journal of Organic Chemistry (2015), 2015(8):1633-1658.

Scheme I

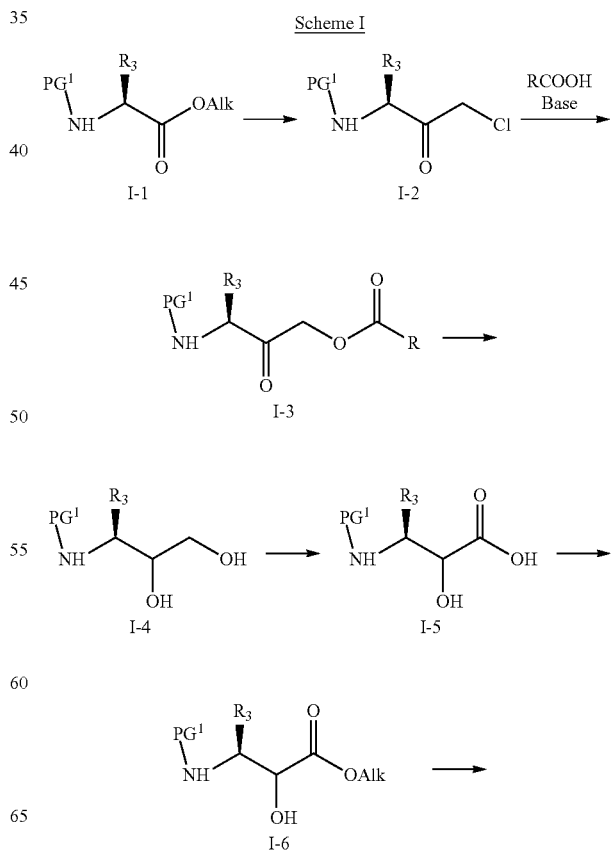

-continued

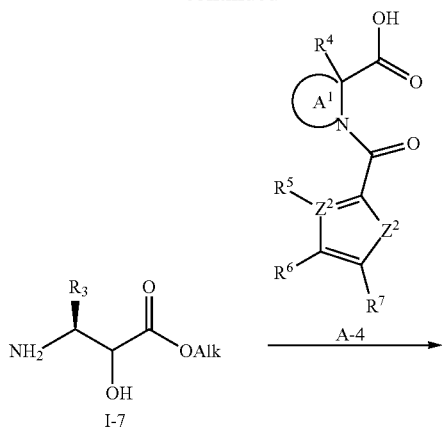
I-7

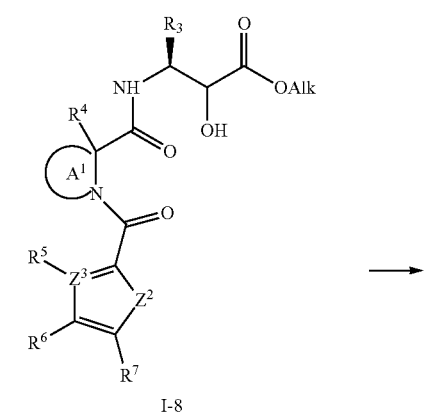
I-8

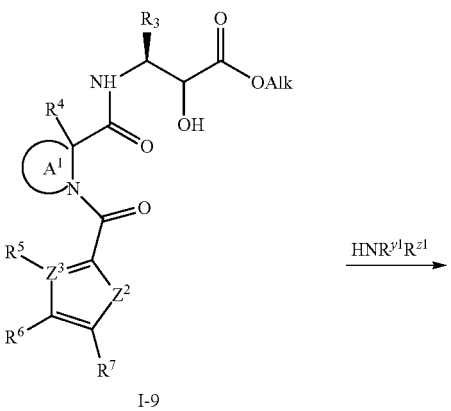
I-9

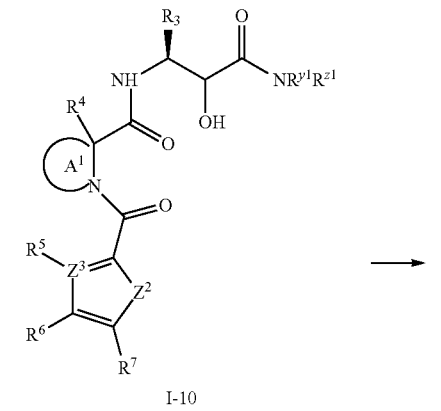
I-10

-continued

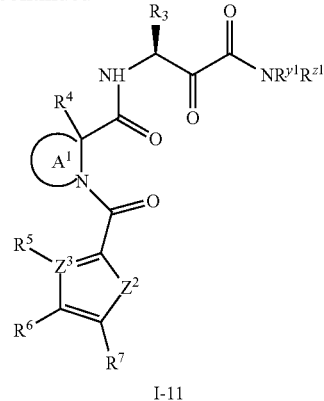
I-11

Scheme I describes the synthesis of general Formula (I-11) where $R^{y1}$ and $R^{z1}$ are part of the ketoamide described herein with respect to $R^1$. An aminoester of general Formula (I-1) ($PG^1$ can be a nitrogen protecting group, for example, Boc and Alk represents an alkyl group) is converted into a chloromethylketone of general Formula (I-2). After chlorine displacement with a carboxylate salt (for instance, R is phenyl) and reduction, a diol of general Formula (I-4) can be obtained. Selective primary alcohol oxidation (such as with TEMPO, $NaClO_2$ and NaOCl) results in α-hydroxyacid of general Formula (I-5). The α-hydroxyacid can be converted into an α-hydroxyester of general Formula (I-6). $PG^1$ can be removed, for example, in acidic conditions in case when $PG^1$ is Boc. The amine of general Formula (I-7) can be coupled with a carboxylic acid of general Formula (A-4) in presence of coupling agents (such as EDC and HOAt) and a base (such as DIPEA) to provide a compound of general Formula (I-8). After ester hydrolysis, a compound of general Formula (I-9) can be coupled with an amine under typical amide bound formation conditions. The obtained α-hydroxyamide of general Formula (I-10) can be oxidized, providing a compound of general Formula (I-11).

Pharmaceutical Compositions

Some embodiments described herein relate to a pharmaceutical composition, that can include an effective amount of a compound described herein (e.g., a compound, or a pharmaceutically acceptable salt thereof, as described herein) and a pharmaceutically acceptable carrier, excipient or combination thereof. A pharmaceutical composition described herein is suitable for human and/or veterinary applications.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

Proper formulation is dependent upon the route of administration chosen. Techniques for formulation and administration of the compounds described herein are known to those skilled in the art. Multiple techniques of administering a compound exist in the art including, but not limited to, oral, rectal, topical, aerosol, injection, inhalation and parenteral delivery, including intramuscular, subcutaneous, intravenous, intramedullary injections, intrathecal, direct intraventricular, intraperitoneal, intranasal and intraocular injections. Pharmaceutical compositions will generally be tailored to the specific intended route of administration.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes may be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

Methods of Use

Some embodiments described herein relate to a method of treating a coronavirus infection that can include administering to a subject identified as suffering from the coronavirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a coronavirus infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a coronavirus infection.

Some embodiments disclosed herein relate to a method of treating a coronavirus infection that can include contacting a cell infected with the coronavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a coronavirus infection. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating a coronavirus infection.

Some embodiments disclosed herein relate to a method of inhibiting replication of a coronavirus that can include contacting a cell infected with the coronavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of a coronavirus. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of a coronavirus.

In some embodiments, the coronavirus can be an α-coronavirus or a β-coronavirus. In some embodiments, the coronavirus can be selected from CoV 229E, CoV NL63, CoV OC43, CoV HKU1, Middle East Respiratory Syndrome (MERS)-CoV, Severe Acute Respiratory Syndrome (SARS)-CoV, and SARS-CoV-2.

Some embodiments described herein relate to a method of treating a picornavirus infection that can include administering to a subject identified as suffering from the picornavirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a picornavirus infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a picornavirus infection.

Some embodiments disclosed herein relate to a method of treating a picornavirus infection that can include contacting a cell infected with the picornavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a picornavirus infection. Still other embodiments described herein relate to the use of a compound, or a pharmaceutically acceptable salt thereof, as described herein described herein, or a pharmaceutical composition that includes an effective amount of a compound, or a pharmaceutically acceptable salt thereof, as described herein for treating a picornavirus infection.

Some embodiments disclosed herein relate to a method of inhibiting replication of a picornavirus that can include contacting a cell infected with the picornavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of a picornavirus. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of a picornavirus.

In some embodiments, the picornavirus can be a rhinovirus, including rhinovirus A, B and/or C. In some embodiments, a compound described herein, including a compound of Formula (I), or a pharmaceutically acceptable salt thereof, can be used to treat one or serotypes of a rhinovirus.

Some embodiments described herein relate to a method of treating a norovirus infection that can include administering to a subject identified as suffering from the norovirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a norovirus infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a norovirus infection.

Some embodiments disclosed herein relate to a method of treating a norovirus infection that can include contacting a cell infected with the norovirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a norovirus infection. Still other embodiments described herein relate to the use of a compound, or a pharmaceutically acceptable salt thereof, as described herein described herein, or a pharmaceutical composition that includes an effective amount of a compound, or a pharmaceutically acceptable salt thereof, as described herein for treating a norovirus infection.

Some embodiments disclosed herein relate to a method of inhibiting replication of a norovirus that can include contacting a cell infected with the norovirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of a norovirus. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of a norovirus.

Some embodiments disclosed herein relate to a method of treating a respiratory condition that is developed because of a coronavirus and/or a picornavius infection that can include administering to a subject suffering from the respiratory condition and/or contacting a cell infected with the coronavirus and/or the picornavirus in a subject suffering from the respiratory condition with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a respiratory condition due to a coronavirus infection and/or a picornavius infection with an effective amount of the compound, or a pharmaceutically acceptable salt thereof. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating a respiratory condition due to a coronavirus infection and/or a picornavius infection.

A subject infected with a coronavirus can be asymptotic. A coronavirus infection can manifest itself via one or more symptoms. Examples of symptoms include, but are not limited to, coughing, sore throat, runny nose, sneezing, headache, fever, shortness of breath, myalgia, abdominal pain, fatigue, difficulty breathing, persistent chest pain or pressure, difficulty waking, loss of smell and taste, muscle or joint pain, chills, nausea or vomiting, nasal congestion, diarrhea, haemoptysis, conjunctival congestion, sputum production, chest tightness and/or palpitations. A coronavirus infection can cause complications. A non-limiting list of complications include, but are not limited to, sinusitis, otitis media, pneumonia, acute respiratory distress syndrome, disseminated intravascular coagulation, pericarditis and/or kidney failure.

As with a coronavirus, a subject infected with a picornavirus can be asymptotic. Alternatively, a subject can exhibit one or more of symptoms. Examples of symptoms of a picornavirus infection include, but are not limited to, aseptic meningitis, rash, conjunctivitis, runny nose a headache a cough a fever a sore throat, chest and/or abdominal pain and paralysis. As provided herein, subjects infected with a norovirus can exhibit one or more the symptoms including, but not limited to, nausea, non-bloody diarrhea, vomiting and abdominal pain. An example of a complication that can be attributed to a norovirus infection is dehydration, including severe dehydration.

Various indicators for determining the effectiveness of a method for treating a coronavirus, picornavirus and/or norovirus infection are also known to those skilled in the art. Examples of suitable indicators include, but are not limited to, a reduction in viral load indicated by reduction in coronavirus (or load) (e.g., reduction<$10^5$ copies/mL in serum), a reduction in plasma viral load, a reduction in viral replication, a reduction in time to seroconversion (virus undetectable in patient serum), an increase in the rate of sustained viral response to therapy a reduction of morbidity or mortality in clinical outcomes, reduction in the need for a ventilator and/or total time on a ventilator, reduction in hospitalization rates and/or reduction in time in an ICU (intensive care unit) and/or hospital.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, camels, non-human primates, such as monkeys, chimpanzees, and apes, and, in particular, humans. In some embodiments, the subject can be human, for example a human subject that is 60 years old or older.

The term "effective amount" is used to indicate an amount of an active compound, or pharmaceutical agent, that elicits the biological or medicinal response indicated. For example, an effective amount of compound can be the amount needed to alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In some embodiments, the subject can be asymptomatic, for example, the subject can be infected with coronavirus but does not exhibit any symptoms of the viral infection. In some embodiments, the subject can be have a pre-existing condition, such as asthma, hypertension, immunocomprised subjects (such as subjects with cancer, HIV and/or genetic immune deficiencies, bone marrow transplant subjects, solid organ transplant subjects, subjects who have had stem cells for cancer treatment and/or subjects who use oral or intravenous corticosteroids or other medicines called immunosuppressants), liver disease, subjects at risk for severe illness, chronic kidney disease being treated with dialysis, chronic lung disease, diabetes, hemoglobin disorders, serious heart conditions (for example, heart failure, coronary artery disease, congenital heart disease, cardiomyopathies, and pulmonary hypertension), severe obesity (such as subjects with a body mass index (BMI) of 40 or above) and people who live in a nursing home or long-term care facility. Additional examples and/or further information is provided by the CDC (https://www.cdc.gov/coronavirus/2019-ncov/need-extra-precautions/groups-at-higher-risk.html).

A compound described herein, including a compound of Formula (I), or a pharmaceutically acceptable salt thereof, can be administered after a subject is infected with a coronavirus. In addition and/or alternatively, a compound described herein, including a compound of Formula (I), or a pharmaceutically acceptable salt thereof, can be administered prophylactically.

Examples of agents that have been used to treat a coronavirus infection include Remdesivir. However, there can be drawbacks associated with compounds being used to treat a coronavirus including, but not limited to, one or more adverse side effects, the need for subcutaneous administration and/or high cost. Potential advantages of a compound of Formula (I), or a pharmaceutically acceptable salt thereof, can be less adverse side effects, delay in the onset of an adverse side effect and/or reduction in the severity of an adverse side effect.

A coronavirus infection can be treated by inhibiting certain mechanisms. In some embodiments, a compound described herein (such as a compound of Formula (I), or a pharmaceutically acceptable salt thereof) can be selective for a coronavirus protease. For example, a compound of Formula (I), or a pharmaceutically acceptable salt thereof, can be selective for a coronavirus protease compared to a host protease, for example, one or more host proteases selected from Cathepsin L, Cathepsin B, Cathepsin D, Leukocyte Elastase, Chymotrypsin, Trypsin, Thrombin, Pepsin, Caspase 2, Elastase and Calpain. In some embodiments, the selectivity for a coronavirus protease over a host protease (such as those described herein) can be >2-fold. In some embodiments, the selectivity for a coronavirus protease over a host protease (such as those described herein) can be >10-fold. In some embodiments, the selectivity for a coronavirus protease over a host protease (such as those described herein) can be >100-fold.

Studies have shown that the entry of SARS-CoV-2 into the target cells is a process that can be mediated by multiple proteases including cysteine cathepsins L and/or transmembrane protease serine 2 (TMPRSS2) (Shang et al., PNAS (2020) 117:11727, and Hoffmann et al., Cell (2020) 181:271-280). The cathepsin L inhibitor K117777, which lacks an inhibitory effect on the 3CLpro, can result in potent inhibition of SARS-CoV-2 in VeroE6, A549-ACE2 and/or HeLa-ACE2 (Mellott et al., bioRxiv (2020) 2020.2010.2023.347534). It has also been shown that the potent antiviral effect of K117777 is abolished when TMPRSS2 was expressed in A549-ACE2 (Steuten et al., bioRxiv (2020) 2020.2011.2021.392753). Off target activity of 3CLpro inhibitors, for example, on cathepsin L, may lead to an inaccurate assessment of the 3CLpro component of a compound's cellular potency. As an example, a compound described herein (such as a compound of Formula (I), or a pharmaceutically acceptable salt thereof) can have greater selectivity for a coronavirus protease over a host protease, such as cathepsin L. The selectivity can be determined by those skilled in the art, for example, using $IC_{50}$ and/or Ki values. In some embodiments, a compound described herein does not significantly inhibit cathepsin L (for example, $IC_{50} \geq 10000$ nM or >3.3 µM), but inhibits a coronavirus protease (for example, SARS-Cov-2 3Clpro).

A drawback with anti-viral treatment can be the development of resistance, including cross-resistance. Resistance can be a cause for treatment failure. The term "resistance" as used herein refers to a viral strain displaying a delayed, lessened and/or null response to an anti-viral agent. In some embodiments, a compound, or a pharmaceutically acceptable salt thereof, as described herein can be provided to a subject infected with a coronavirus strain that is resistant to one or more other anti-viral agents. In some embodiments, development of coronavirus resistant strains is delayed when a subject is treated with a compound, or a pharmaceutically acceptable salt thereof, as described herein compared to the development of a coronavirus resistant strain when treated with one or more other anti-viral agents.

Combination Therapies

In some embodiments, a compound, or a pharmaceutically acceptable salt thereof, as described herein can be used in combination with one or more additional agent(s) for treating and/or inhibiting replication a coronavirus. Additional agents include, but are not limited to, an ACE inhibitor, an anticoagulant, an anti-inflammatory, an ARB, an ASO, a Covid-19 convalescent plasma, an entry inhibitor, an H₂ pump antagonist, an H-conducting channel, an HIV protease inhibitor, an HMG-CoA reductase inhibitor, an immune globulin, an immunosuppressant, an immunotherapeutic agent, a monoclonal antibody, a neuraminidase inhibitor, a nucleoside inhibitor, a nucleoside analog inhibitor, a polymerase inhibitor, a protease inhibitor, an siRNA, a statin, a tissue plasminogen activator, an antibiotic, an antimicrobial and a vaccine. Examples of additional agents include Ascorbic acid, Anakin, Azithromycin, Baloxavir, Baricitinib, Chloroquine Phosphate, Colchicine, a corticosteroid, Epoprostenol, Famotidine, Favipiravir, an IGIV, an interferon (for example, recombinant interferon alpha 2b, IFN-α and/or PEG-IFN-α-2a), an IVIG, Ivermectin, γ-globulin, lopinavir, Methylprednisolone, Molnupiravir (MK-4482 or EIDD-2801), Niclosamide, Nitazoxanide, Nitric oxide, Oseltamivir, Peramivir, RANTES, ribavirin, Remdesivir, Ruxolitinib, Sarilumab, Siltuximab, Sirolimus, a statin, Tacrolimus, Tocilizumab, Umifenovir, Zanamivir, Casirivimab, imdevimab, bamlanivimab, etesevimab and Molnupiravir.

In some embodiments, a compound, or a pharmaceutically acceptable salt thereof, as described herein can be administered with one or more additional agent(s) together in a single pharmaceutical composition. In some embodiments, a compound, or a pharmaceutically acceptable salt thereof, can be administered with one or more additional agent(s) as two or more separate pharmaceutical compositions. Further, the order of administration of a compound, or a pharmaceutically acceptable salt thereof, as described herein with one or more additional agent(s) can vary.

EXAMPLES

Additional embodiments are disclosed in further detail in the following examples, which are not in any way intended to limit the scope of the claims.

Example 1

Compounds

Compounds of Formula (I), along with pharmaceutically acceptable salts thereof, can be prepared in various ways, including those synthetic schemes shown and described herein, are provided below. Those skilled in the art will be able to recognize modifications of the disclosed syntheses and to devise routes based on the disclosures herein; all such modifications and alternate routes are within the scope of the claims.

Synthesis of Intermediates

Intermediate 1

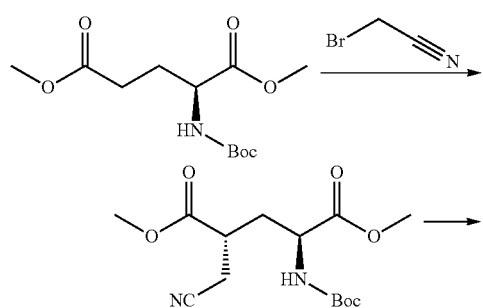

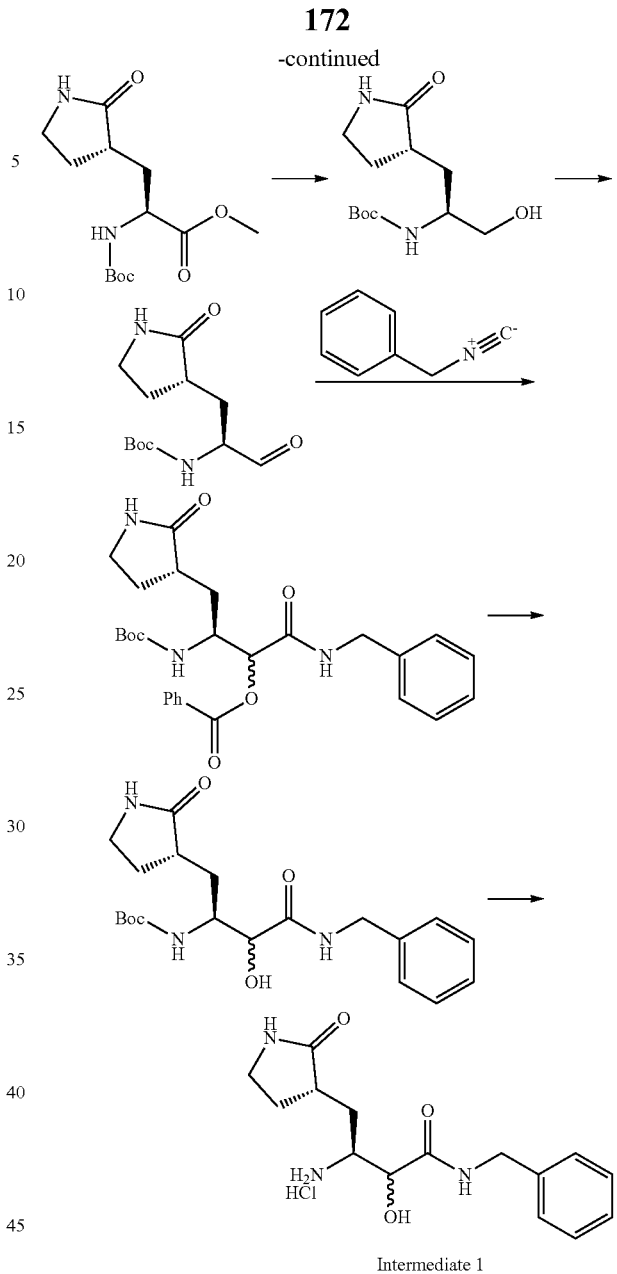

Intermediate 1

To a mixture of 1,5-dimethyl (2S)-2-[(tert-butoxycarbonyl)amino]pentanedioate (75.0 g, 272 mmol, 1.0 eq.) in tetrahydrofuran (1.2 L) was added dropwise lithium bis(trimethylsilyl)amide (599 mL, 599 mmol, 2.2 eq.) at −78° C. under N₂. After stirred for 1 h at −78° C., 2-bromoacetonitrile (35.9 g, 300 mmol, 1.1 eq.) was added. The mixture was stirred for 2 h at −78° C. under N₂. The reaction was quenched with methanol (200 mL) and hydrochloric acid (1.00 L, 2M). The mixture was extracted with ethyl acetate (EA) (3×1.20 L). The organic layers were combined, washed with brine (2×1.20 L), dried over anhydrous sodium sulfate, filtered and concentrated under reduced pressure to afford the crude product. After removing the dichloromethane, the crude product was diluted with dichloromethane (2.00 L) and made into a slurry with 100~200 silicagel mesh (200 g). The sample was purified by column chromatography (Column size 6×24 cm, column volume: 600 mL, silicagel size (100~200 mesh) quantity: 330 g) and eluted with ethyl acetate (EA):petroleum ether (PE) (0%~50% over 30 min). The collected fractions: 35%~37% EA:PE fractions were chosen as pure fractions. Those fractions were combined and concentrated under reduced pressure to provide 1,5-dimethyl (2S,4R)-2-[(tert-butoxycarbonyl)amino]-4-(cyanomethyl)pentanedioate (65.2 g, 69%) as yellow oil. LCMS (ESI, m/z): 215 [M−100+H]+.

To a mixture of 1,5-dimethyl (2S,4R)-2-[(tert-butoxycarbonyl)amino]-4-(cyanomethyl)pentanedioate (65.2 g, 207 mmol, 1.0 eq.) in methanol (650 mL):chloroform (65 mL) was added platinum dioxide (6.59 g). The mixture was stirred for 36 h at room temperature (rt) under hydrogen. The mixture was filtered through a celite pad and washed with methanol (200 mL). To the filtrate was added sodium carbonate (48.8 g, 460 mmol, 2.2 eq.), and the mixture was reflux for 6 h. The mixture was filtered, and the filtrate was concentrated under reduced pressure to afford the crude product. The crude product was diluted with dichloromethane (1.50 L). After removing the dichloromethane, a slurry with 100~200 silicagel mesh (150 g) was made. The sample was purified by column chromatography (Column size 6×24 cm, column volume: 600 mL, silicagel size (100~200 mesh) quantity: 330 g) and eluted with methanol:dichloromethane (0%-20% over 30 min). The collected fractions: 12%-13% methanol:dichloromethane fractions were chosen as pure fractions. Those fractions were combined and concentrated under reduced pressure to provide methyl (2S)-2-[(tert-butoxycarbonyl)amino]-3-[(3S)-2-oxopyrrolidin-3-yl]propanoate (30.8 g, 37%) as a yellow semi-solid. LCMS (ESI, m/z): 187 [M−100+H]+.

To a mixture of methyl (2S)-2-[(tert-butoxycarbonyl)amino]-3-[(3S)-2-oxopyrrolidin-3-yl]propanoate (29.0 g, 101 mmol, 1.0 eq.) in tetrahydrofuran (1.00 L) was added dropwise lithium borohydride (253 mL, 506 mmol, 5.0 eq., 2 M in tetrahydrofuran) at 0° C. The mixture was stirred for 2 h at rt. The reaction was quenched with water (500 mL). The mixture was extracted with chloroform:isopropyl alcohol (5:1, 3×500 mL). The organic layers were combined, washed with brine (2×500 mL), dried over anhydrous sodium sulfate, filtered and concentrated under reduced pressure to afford the crude product. The crude product was diluted with dichloromethane (600 mL). After removing the dichloromethane, a slurry with 100~200 silicagel mesh (60 g) was made. The sample was purified by column chromatography (Column size 6×24 cm, column volume: 600 mL, silicagel size (100~200 mesh) quantity: 330 g) and eluted with methanol:dichloromethane (0%~20% over 30 min). The collected fractions: 13%-14% methanol:dichloromethane fractions were chosen as pure fractions. Those fractions were combined and concentrated under reduced pressure to provide the crude product (24.2 g). The crude product was triturated with EA:n-hexane (300 mL/60 mL) to provide tert-butyl N-[(2S)-1-hydroxy-3-[(3S)-2-oxopyrrolidin-3-yl]propan-2-yl]carbamate (12.4 g, 45%) as a white solid. LCMS (ESI, m/z): 159 [M−100+H]+.

To a mixture of tert-butyl N-[(2S)-1-hydroxy-3-[(3S)-2-oxopyrrolidin-3-yl]propan-2-yl]carbamate (7.00 g, 27.1 mmol, 1.0 eq.) in dichloromethane (100 mL) was added sodium bicarbonate (2.28 g, 27.1 mmol, 1.0 eq.) and Dess-Martin periodinane (11.5 g, 27.1 mmol, 1.0 eq.) at rt. The mixture was stirred for 1 h at rt. The product used directly for the next step. LCMS (ESI, m/z): 257 [M+H]+.

(Isocyanomethyl)Benzene (3.81 g, 32.5 mmol, 1.2 eq.) and benzoic acid (21.5 g, 176 mmol, 6.5 eq.) was added to above mixture. The mixture was stirred overnight at rt. The reaction was quenched with water (200 mL). The mixture was extracted with EA (3×200 mL). The organic layers were combined, washed with saturated aqueous sodium bicarbonate (200 mL), brine (2×200 mL), dried over anhydrous sodium sulfate, filtered and concentrated under reduced pressure to afford the crude product. The crude product was diluted with dichloromethane (200 mL). After removing the dichloromethane, a slurry with 100~200 silicagel mesh (20 g) was made. The sample was purified by column chromatography (Column size 6×24 cm, column volume: 600 mL, silicagel size (100~200 mesh) quantity: 330 g) and eluted with methanol:dichloromethane (0%~20% over 30 min). The collected fractions: 12%-13% methanol:dichloromethane fractions were chosen as pure fractions. Those fractions were combined and concentrated under reduced pressure to provide (S)-1-(benzylamino)-3-(tert-butoxycarbonylamino)-1-oxo-4-((S)-2-oxopyrrolidin-3-yl)butan-2-yl benzoate (9.70 g, 67%) as a off-white solid. LCMS (ESI, m/z): 496 [M+H]+.

To a mixture of (S)-1-(benzylamino)-3-(tert-butoxycarbonylamino)-1-oxo-4-((S)-2-oxopyrrolidin-3-yl)butan-2-yl benzoate (8.20 g, 16.5 mmol, 1.0 eq.) in tetrahydrofuran (70 mL):water (70 mL) was added lithiumol (793 mg, 33.1 mmol, 2.0 e q). The mixture was stirred for 1 h at rt. The reaction was quenched with water (150 mL), and the mixture was extracted with EA (3×200 mL). The organic layers were combined, washed with brine (2×200 mL), dried over anhydrous sodium sulfate, filtered and concentrated under reduced pressure to afford the crude product. The crude product was diluted with dichloromethane (200 mL). After removing the dichloromethane, a slurry with 100~200 silicagel mesh (15 g) was made. The sample was purified by column chromatography (Column size 6×24 cm, column volume: 600 mL, silicagel size (100~200 mesh) quantity: 330 g) and eluted with methanol:dichloromethane (0%~20% over 20 min). The collected fractions: 15%-17% methanol:dichloromethane fractions were chosen as pure fractions. Those fractions were combined and concentrated under reduced pressure to provide tert-butyl (S)-4-(benzylamino)-3-hydroxy-4-oxo-1-((S)-2-oxopyrrolidin-3-yl)butan-2-ylcarbamate (5.60 g, 83%) as a off-white solid. $^1$H NMR (300 MHz, DMSO-$d_6$) δ 8.29-8.39 (m, 1H), 7.51-7.62 (m, 1H), 7.17-7.34 (m, 5H), 6.13-6.67 (m, 1H), 5.68-5.75 (m, 1H), 4.21-4.41 (m, 2H), 3.80-4.05 (m, 2H), 3.03-3.22 (m, 2H), 2.04-2.35 (m, 2H), 1.82-1.99 (m, 1H), 1.56-1.73 (m, 1H), 1.36-1.45 (m, 9H), 0.90-1.34 (m, 1H). LCMS (ESI, m/z): 392 [M+H]+.

To a mixture of tert-butyl (S)-4-(benzylamino)-3-hydroxy-4-oxo-1-((S)-2-oxopyrrolidin-3-yl)butan-2-ylcarbamate (5.50 g, 14.1 mmol, 1.0 eq.) in DCM (10 mL):EA (67.5 mL) was added HCl (14.1 mL, 56.2 mmol, 4.0 eq., 4 M in dioxane) at 0° C. The mixture was stirred overnight at rt. The mixture was concentrated under reduced pressure to afford crude (S)-3-amino-N-benzyl-2-hydroxy-4-((S)-2-oxopyrrolidin-3-yl)butanamide hydrochloride (5.2 g, crude) as an off-white solid. LCMS (ESI, m/z): 292 [M+H]+.

Synthesis of methyl (S)-2-amino-3-((S)-2-oxopiperidin-3-yl)propanoate

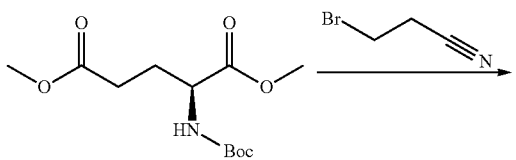

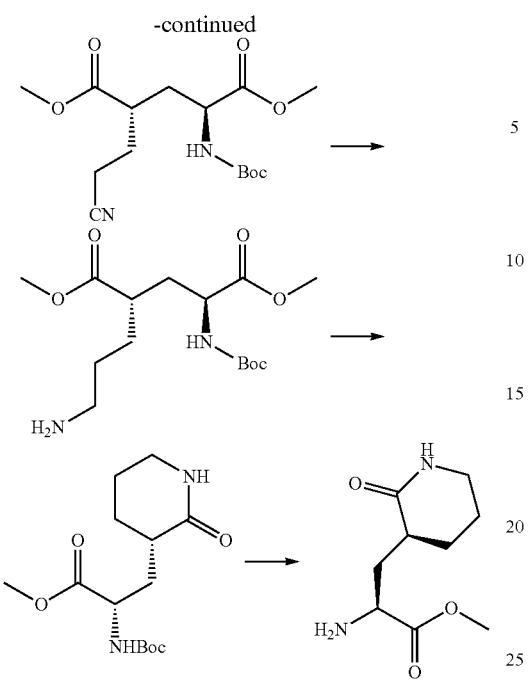

A 1000 mL 3-necked round-bottom flask was charged with dimethyl (tert-butoxycarbonyl)-L-glutamate (50.0 g, 182 mmol, 1.0 eq.) in THF (500 mL) under $N_2$. Lithium bis(trimethylsilyl)amide (363 mL, 363 mmol, 2.0 eq., 1M in THF) was added dropwise at −78° C. The reaction was stirred for 2 h at −78° C. 3-bromopropanenitrile (48.7 g, 363 mmol, 2.0 eq.) was added dropwise at −78° C. over 1 h. The reaction was stirred for 2 h at −78° C. The reaction was quenched with pre-cooled methanol (75 mL) and pre-cooled acetic acid in THF (12.5 mL/100 mL). The reaction was stirred for 30 min at −78° C. The reaction was allowed to warm up to 0° C. and concentrated under reduced pressure. The residue was dissolved in EA (200 mL), washed with brine (2×100 mL), dried over anhydrous sodium sulfate, filtered and concentrated under reduced pressure. The residue was chromatographed on a silica gel column with EA:PE (4:6) to provide dimethyl (2S,4S)-2-((tert-butoxycarbonyl)amino)-4-(2-cyanoethyl)pentanedioate (19 g, 29%) as a yellow oil. LCMS (ESI, m/z): 329 [M+H]⁺.

A 1000 mL round-bottom flask was charged with dimethyl (2S,4S)-2-((tert-butoxycarbonyl)amino)-4-(2-cyanoethyl)pentanedioate (27.6 g, 84.0 mmol, 1.0 eq.) in methanol (300 mL). Chloroform (30 mL) and platinum dioxide (2.70 g) was added. The contents of the flask were placed under an atmosphere of $H_2$ (3 atm). The reaction was stirred for 36 h at rt. The solids were filtered out. The organic layer was concentrated under reduced pressure to provide dimethyl (2S,4S)-2-(3-aminopropyl)-4-((tert-butoxycarbonyl)amino) pentanedioate ((30 g, 89% (ELSD)) as an off-white solid. LCMS (ESI, m/z): 333 [M+H]⁺.

A 500 mL round-bottom flask was charged with dimethyl (2S,4S)-2-(3-aminopropyl)-4-((tert-butoxycarbonyl)amino) pentanedioate (28 g, 84.2 mmol, 1.0 eq.), methanol (250 mL) and sodium carbonate (19.6 g, 185 mmol, 2.2 eq.) was added. The reaction was stirred for 4 h at 70° C. The solids were filtered out and concentrated under reduced pressure. The residue was diluted with EA (50 mL), washed with water (2×20 mL), washed with brine (2×20 mL), dried over anhydrous sodium sulfate, filtered and concentrated under reduced pressure. The residue was chromatographed on a silica gel column with EA:dichloromethane (2:3) then methanol:dichloromethane (4:96) to provide methyl (S)-2-((tert-butoxycarbonyl)amino)-3-((S)-2-oxopiperidin-3-yl) propanoate (7.2 g, 27%) as a yellow oil. LCMS (ESI, m/z): 301 [M+H]⁺.

A 100 mL round-bottom flask was charged with methyl (S)-2-((tert-butoxycarbonyl)amino)-3-((S)-2-oxopiperidin-3-yl)propanoate (1.0 g, 3.33 mmol, 1.0 eq.), dichloromethane (10 mL). Trifluoroacetic acid (3 mL) was added dropwise at 0° C. The reaction was stirred for 1 h at rt. The reaction was concentrated under reduced pressure to provide methyl (S)-2-amino-3-((S)-2-oxopiperidin-3-yl)propanoate (0.7 g, crude) as a yellow oil. LCMS (ESI, m/z): 201 [M+H]⁺.

Synthesis of (S)-3-((S)-2-amino-4-(benzyloxy)-3-oxobutyl)pyrrolidin-2-one hydrochloride

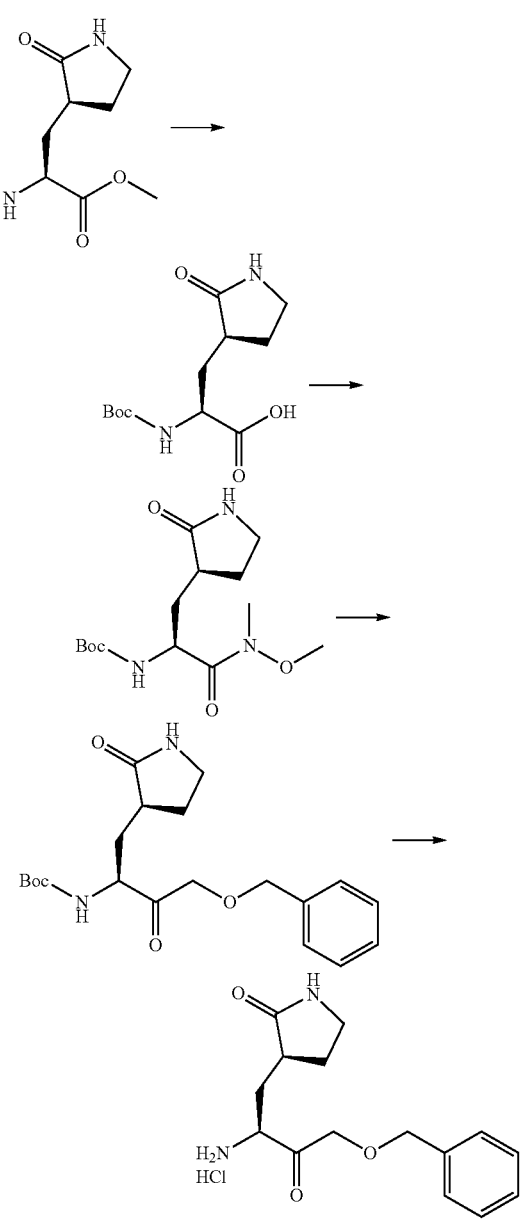

To a mixture of methyl (2S)-2-[(tert-butoxycarbonyl)amino]-3-[(3S)-2-oxopyrrolidin-3-yl]propanoate (4.00 g, 14.0 mmol, 1.0 eq.) in methanol (20 mL) was added sodium hydroxide (19 mL, 57.0 mmol, 4.0 eq., 3 M in water). The mixture was stirred for 1 h at 0° C. The mixture was concentrated under reduced pressure to remove the methanol, and the pH was adjusted to 6 with HCl (2 M). The mixture was extracted with EA (3×30 mL). The organic layers were combined, washed with brine (2×20 mL), dried over anhydrous sodium sulfate, filtered and concentrated under reduced pressure to provide (2S)-2-[(tert-butoxycarbonyl)amino]-3-[(3S)-2-oxopyrrolidin-3-yl]propanoic acid (3.56 g, 88%) as a light yellow solid.

To a mixture of (2S)-2-[(tert-butoxycarbonyl)amino]-3-[(3S)-2-oxopyrrolidin-3-yl]propanoic acid (3.56 g, 13.1 mmol, 1.0 eq.) in dichloromethane (50 mL) was added N,O-dimethylhydroxylamine hydrochloride (1.28 g, 13.1 mmol, 1.0 eq.), N-methylmorphline (3.97 g, 39.0 mmol, 3.0 eq.), 1-hydroxybenzotriazole (1.77 g, 13.1 mmol, 1.0 eq.) and 1-(3-dimethylaminopropyl)-3-ethylcarbodiimide hydrochloride (2.76 g, 14.4 mmol, 1.1 eq.) at 0° C. The mixture was stirred for 2 h at 0° C. under N₂. The reaction was quenched with water (40 mL). The organic layers were washed with HCl (2×40 mL, 1 M), water (40 mL), sat. aq. sodium bicarbonate (2×40 mL) and brine (40 mL), dried over anhydrous sodium sulfate, filtered and concentrated under reduced pressure to provide tert-butyl N-[(1S)-1-[methoxy(methyl)carbamoyl]-2-[(3S)-2-oxopyrrolidin-3-yl]ethyl]carbamate (3.43 g, 81%) as a light yellow solid.

To a mixture of magnesium (2.36 g, 97.0 mmol, 9.0 eq.) and mercury dichloride (1.76 g, 6.47 mmol, 0.6 eq.) in THF (120 mL) was added benzylchloromethyl ether (15.2 g, 97.0 mmol, 9.0 eq.) at −45° C. under N₂. The mixture was stirred for 5 h from −45° C. to 5° C. Then the mixture was cooled to −45° C., and tert-butyl N-[(1S)-1-[methoxy(methyl)carbamoyl]-2-[(3S)-2-oxopyrrolidin-3-yl]ethyl]carbamate (3.40 g, 10.8 mmol, 1.0 eq.) was added. The mixture was stirred overnight at rt under N₂. The reaction was quenched with sat. aq. ammonium chloride (200 mL). The mixture was extracted with EA (3×200 mL). The organic layers were combined, washed with brine (2×200 mL), dried over anhydrous sodium sulfate, filtered and concentrated under reduced pressure to afford the crude product. The crude product was diluted with dichloromethane (100 mL). A slurry was made with 100~200 silica gel mesh (10 g) and then loaded onto a column after removing the dichloromethane. The sample was purified by column chromatography (Column size 5×24 cm, column volume: 600 mL, silica gel size (100~200 mesh) quantity: 330 g) and eluted with methanol:dichloromethane (0%~5% over 20 min). Collected fractions: 3%-4% methanol:dichloromethane fractions were chosen as pure fractions. Those fractions were combined and concentrated under reduced pressure to provide tert-butyl N-[(2S)-4-(benzyloxy)-3-oxo-1-[(3S)-2-oxopyrrolidin-3-yl]butan-2-yl]carbamate (2.15 g, 45%) as a light yellow oil. ¹H NMR (300 MHz, CDCl₃-d) δ 7.30-7.42 (m, 5H), 6.21 (s, 1H), 5.82 (d, J=7.9 Hz, 1H), 4.52-4.69 (m, 3H), 4.18-4.37 (m, 2H), 3.23-3.34 (m, 2H), 2.32-2.54 (m, 2H), 1.72-2.06 (m, 3H), 1.44 (s, 9H). LCMS (ESI, m/z): 277 [M−100+H]⁺.

To a mixture of tert-butyl N-[(2S)-4-(benzyloxy)-3-oxo-1-[(3S)-2-oxopyrrolidin-3-yl]butan-2-yl]carbamate (800 mg, 2.125 mmol, 1.00 eq.) in 1,4-dioxane (8 mL) was added HCl (8 mL, 4 M in 1,4-dioxane) at 0° C. The mixture was stirred for 1 h at rt, and then concentrated under reduced pressure to afford (3S)-3-[(2S)-2-amino-4-(benzyloxy)-3-oxobutyl]pyrrolidin-2-one hydrochloride (664 mg, crude) as a yellow semi-solid. LCMS (ESI, m/z): 277 [M+H]⁺.

Synthesis of (3S)-3-amino-N-cyclopropyl-2-hydroxy-4-((S)-2-oxopyrrolidin-3-yl)butanamide

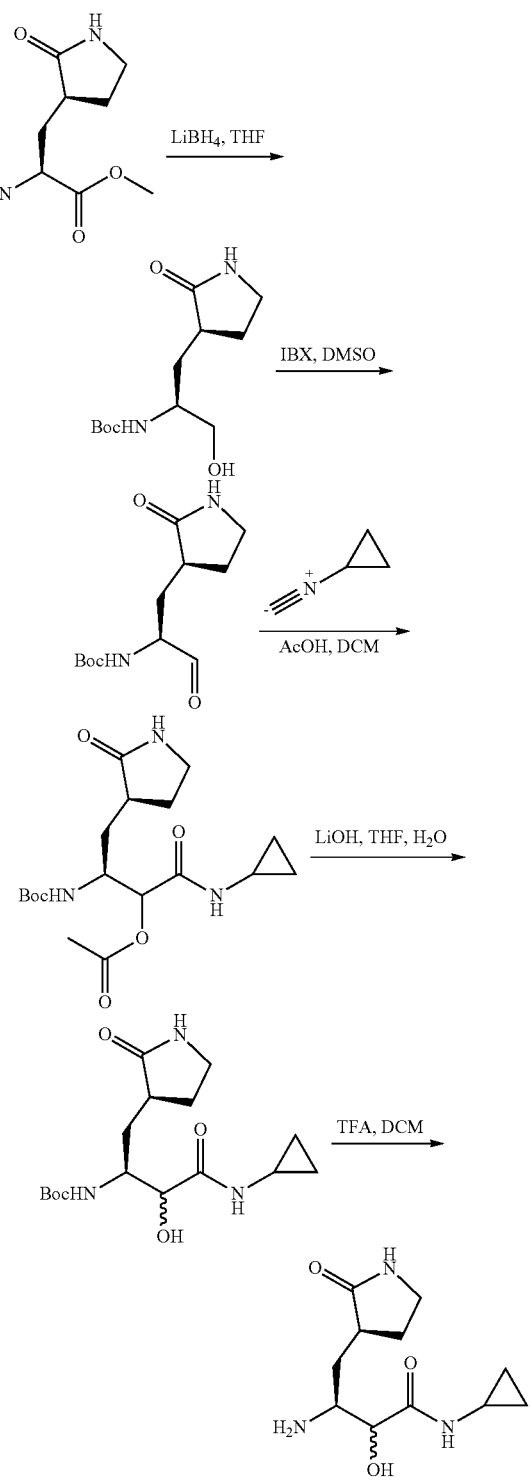

To a stirred mixture of methyl (2S)-2-[(tert-butoxycarbonyl)amino]-3-[(3S)-2-oxopyrrolidin-3-yl]propanoate (3.0 g, 10.5 mmol, 1.0 eq.) in tetrahydrofuran (50 mL) was added lithium borohydride (26.2 mL, 52.4 mmol, 5.0 eq.) dropwise at 0° C. The mixture was stirred for 1 h at 0° C. and concentrated under reduced pressure. The mixture was then diluted with water (20 mL), and extracted with isopropanol: trichloromethane (1:5, 4×50 mL). The organic layers were combined, dried over anhydrous sodium sulfate, filtered and concentrated under reduced pressure. The residue was purified by silica gel column chromatography, eluted with dichloromethane:methanol (19:1) to afford tert-butyl N-[(2S)-1-hydroxy-3-[(3S)-2-oxopyrrolidin-3-yl]propan-2-yl]carbamate (2.6 g, crude) as a white solid. The crude product was precipitated by the addition of PE:EA (4:1, 40 mL) to afford tert-butyl N-[(2S)-1-hydroxy-3-[(3S)-2-oxopyrrolidin-3-yl]propan-2-yl]carbamate (2.4 g, 79%) as a white solid. LC-MS (ESI, m/z): 259 [M+H]$^+$.

To a stirred mixture of tert-butyl N-[(2S)-1-hydroxy-3-[(3S)-2-oxopyrrolidin-3-yl]propan-2-yl]carbamate (2.4 g, 9.29 mmol, 1.0 eq.) in dimethyl sulfoxide (40 mL) was added 2-iodoxybenzoic acid (7.80 g, 27.8 mmol, 3.0 eq.) in portions at rt. The mixture was stirred for 3 h at rt, and then basified pH=8 with sat. sodium bicarbonate (aq.). The mixture was diluted with water (20 mL) and extracted with EA (4×200 mL). The organic layers were combined, washed with brine (3×100 mL), dried over anhydrous sodium sulfate, filtered and concentrated under reduced pressure to afford tert-butyl N-[(2S)-1-oxo-3-[(3S)-2-oxopyrrolidin-3-yl]propan-2-yl]carbamate (1.5 g, 63%) as a yellow solid. LC-MS (ESI, m/z): 257 [M+H]$^+$.

To a stirred mixture of tert-butyl N-[(2S)-1-oxo-3-[(3S)-2-oxopyrrolidin-3-yl]propan-2-yl]carbamate (900 mg, 3.51 mmol, 1.0 eq.) in dichloromethane (10 mL) was added isocyanocyclopropane (471 mg, 7.02 mmol, 2.0 eq.) and acetic acid (633 mg, 10.5 mmol, 3.0 eq.) dropwise at 0° C. The mixture was stirred for 5 h at rt and concentrated under reduced pressure. The residue was purified by silica gel column chromatography, eluted with dichloromethane:methanol (49:1) to afford (2S)-2-[(tert-butoxycarbonyl)amino]-1-(cyclopropylcarbamoyl)-3-[(3S)-2-oxopyrrolidin-3-yl]propyl acetate (820 mg, 55%) as a yellow solid. LC-MS (ESI, m/z): 384 [M+H]$^+$.

To a stirred mixture of (2S)-2-[(tert-butoxycarbonyl)amino]-1-(cyclopropylcarbamoyl)-3-[(3S)-2-oxopyrrolidin-3-yl]propyl acetate (810 mg, 2.11 mmol, 1.0 eq.) in tetrahydrofuran (8 mL) was added lithium hydroxide (253 mg, 10.5 mmol, 5.0 eq., in water 8 mL) at 0° C. The mixture was stirred for 1 h at 0° C. The mixture was acidified to pH=6 with hydrochloric acid (2M). The mixture was extracted with EA (4×60 mL). The organic layers were combined, dried over anhydrous sodium sulfate, filtered and concentrated under reduced pressure to afford tert-butyl N-[(2S)-1-(cyclopropylcarbamoyl)-1-hydroxy-3-[(3S)-2-oxopyrrolidin-3-yl]propan-2-yl]carbamate (680 mg, 94%) as a yellow solid. LCMS (ESI, m/z): 342[M+H]$^+$.

To a stirred mixture of tert-butyl N-[(2S)-1-(cyclopropylcarbamoyl)-1-hydroxy-3-[(3S)-2-oxopyrrolidin-3-yl]propan-2-yl]carbamate (400 mg, 1.17 mmol, 1.0 eq.) in dichloromethane (6 mL) was added trifluoroacetic acid (2 mL) dropwise at rt. The mixture was stirred for 1 h at rt and concentrated under reduced pressure to afford (3S)-3-amino-N-cyclopropyl-2-hydroxy-4-[(3S)-2-oxopyrrolidin-3-yl]butanamide (290 mg, crude) as a brown solid. LC-MS (ESI, m/z): 242[M+H]$^+$.

Synthesis of (3S)-3-amino-2-hydroxy-4-((S)-2-oxopyrrolidin-3-yl)butanamide

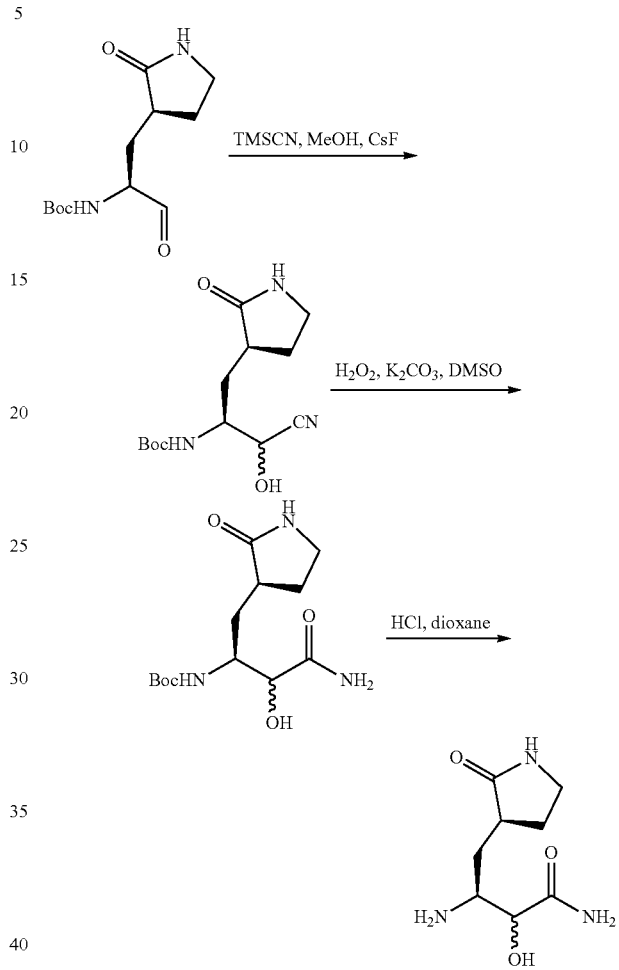

To a solution of tert-butyl N-[(2S)-1-oxo-3-[(3S)-2-oxopyrrolidin-3-yl]propan-2-yl]carbamate (1.8 g, 7.02 mmol, 1.0 eq.) in MeOH (21 mL) was added CsF (0.53 g, 3.51 mmol, 0.5 eq.) and then trimethylsilyl cyanide (0.84 g, 8.43 mmol, 1.2 eq.) was added at 0° C. slowly. The mixture was stirred at rt overnight, and the reaction was quenched with water (15 mL). The mixture was extracted with EtOAc (6×20 mL). The organic layers were combined, dried over anhydrous sodium sulfate, filtered and concentrated under reduced pressure. The residue was chromatographed on a C18 column with water:MeCN (9:1) to provide tert-butyl N-[(2S)-1-cyano-1-hydroxy-3-[(3S)-2-oxopyrrolidin-3-yl]propan-2-yl]carbamate (1.3 g, 49%) as a white solid. LC-MS (ESI, m/z): 284 [M+H]$^+$.

To a solution of tert-butyl N-[(2S)-1-cyano-1-hydroxy-3-[(3S)-2-oxopyrrolidin-3-yl]propan-2-yl]carbamate (1.2 g, 4.24 mmol, 1.0 eq.) in DMSO (13 mL) was added K$_2$CO$_3$ (1.17 g, 8.47 mmol, 2.0 eq.) and H$_2$O$_2$ (0.72 g, 21.2 mmol, 5.0 eq.). The mixture was stirred at rt for 3 h, and the reaction was quenched with water (10 mL). The mixture was extracted with EtOAc (5×20 mL). The organic layers were combined, dried over anhydrous sodium sulfate, filtered and concentrated under reduced pressure. The residue was chromatographed on a C18 column with water:MeCN (9:1) to provide tert-butyl N-[(2S)-1-carbamoyl-1-hydroxy-3-[(3S)-

2-oxopyrrolidin-3-yl]propan-2-yl]carbamate (460 mg, 32%) as a white solid. LC-MS (ESI, m/z): 302 [M+H]+.

A solution of tert-butyl N-[(2S)-1-carbamoyl-1-hydroxy-3-[(3S)-2-oxopyrrolidin-3-yl]propan-2-yl]carbamate (460 mg, 1.53 mmol, 1.0 eq.) in hydrochloric acid (6 mL, 4M in dioxane) was stirred at rt for 3 h and then concentrated under reduced pressure to provide (3S)-3-amino-2-hydroxy-4-[(3S)-2-oxopyrrolidin-3-yl]butanamide (300 mg, 68%) as an off-white solid. LC-MS (ESI, m/z): 202 [M+H]+.

Synthesis of (3S)-3-amino-N-cyclopropyl-2-hydroxy-4-((S)-2-oxopiperidin-3-yl)butanamide

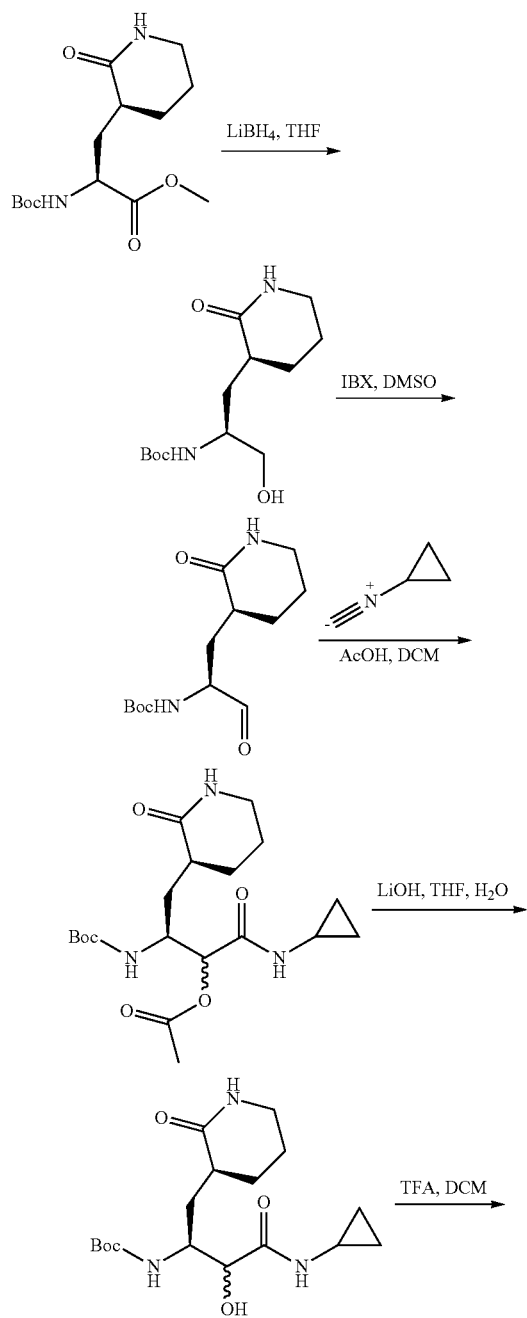

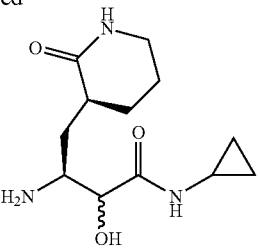

To a solution of methyl (2S)-2-[(tert-butoxycarbonyl)amino]-3-[(3S)-2-oxopiperidin-3-yl]propanoate (3 g, 9.99 mmol, 1.0 eq.) in tetrahydrofuran (30 mL) was added a solution of lithium borohydride (10 mL, 19.9 mmol, 2.0 eq., 2M in THF) at 0° C. The mixture was stirred for 1 h at 0° C., and the reaction was quenched with sat. ammonium chloride solution (10 mL). The mixture was extracted with isopropanol:trichloromethane (1:3, 3×40 mL). The organic layers were combined, washed with brine (2×40 mL), dried over anhydrous sodium sulfate, filtered and concentrated under reduced pressure to afford the crude product. The crude product was purified by silica gel column chromatography, eluted with DCM:MeOH (9:1) to afford tert-butyl N-[(2S)-1-hydroxy-3-[(3S)-2-oxopiperidin-3-yl]propan-2-yl]carbamate (2.0 g, 73%) as a white solid. LC-MS (ESI, m/z): 273 [M+H]+.

To a solution of tert-butyl N-[(2S)-1-hydroxy-3-[(3S)-2-oxopiperidin-3-yl]propan-2-yl]carbamate (2.0 g, 7.34 mmol, 1.0 eq.) in DMSO (20 mL) was added 2-Iodoxybenzoic acid (4.10 g, 14.7 mmol, 2.0 eq.) at rt. The mixture was stirred overnight, and the reaction was quenched with sat. sodium bicarbonate solution (5 mL). The mixture was extracted with EtOAc (4×40 mL). The organic layers were combined, washed with brine (2×40 mL), dried over anhydrous sodium sulfate, filtered and concentrated under reduced pressure to afford tert-butyl N-[(2S)-1-oxo-3-[(3S)-2-oxopiperidin-3-yl]propan-2-yl]carbamate (crude, 1.3 g, 67%) as a white solid. LC-MS (ESI, m/z): 271 [M+H]+.

To a solution of tert-butyl N-[(2S)-1-oxo-3-[(3S)-2-oxopiperidin-3-yl]propan-2-yl]carbamate (1.3 g, 4.80 mmol, 1.0 eq.) in DCM (4 mL) was added AcOH (866 mg, 14.4 mmol, 3.0 eq.) and isocyanocyclopropane (645 mg, 9.62 mmol, 2.0 eq.). The mixture was stirred for 5 h at rt and concentrated under reduced pressure to afford the crude product. LC-MS (ESI, m/z): 398 [M+H]+.

To a solution of (2S)-2-[(tert-butoxycarbonyl)amino]-1-(cyclopropylcarbamoyl)-3-[(3S)-2-oxopiperidin-3-yl]propyl acetate (1.90 g, 4.78 mmol, 1.0 eq.) in THF (10 mL) was lithium hydroxide (286 mg, 12.0 mmol, 2.5 eq., in water 10 mL). The mixture was stirred for 1 h at 0° C. and acidified to pH=6 with hydrochloric acid (2M). The mixture was extracted with EA (4×50 mL). The organic layers were combined, dried over anhydrous sodium sulfate, filtered and concentrated under reduced pressure to afford the crude product. The crude product was purified by silica gel column chromatography and eluted with dichloromethane:methanol (33:1) to afford tert-butyl N-[(2S)-1-(cyclopropylcarbamoyl)-1-hydroxy-3-[(3S)-2-oxopiperidin-3-yl]propan-2-yl]carbamate (953 mg, 56%) as a yellow solid.

To a solution of tert-butyl N-[(2S)-1-(cyclopropylcarbamoyl)-1-hydroxy-3-[(3S)-2-oxopiperidin-3-yl]propan-2-yl]carbamate (270 mg, 0.760 mmol, 1.0 eq.) in DCM (9 mL) was added trifluoroacetic acid (3 mL). The mixture was stirred for 1 h at rt and concentrated under reduced pressure to afford (3S)-3-amino-N-cyclopropyl-2-hydroxy-4-[(3S)-2-oxopiperidin-3-yl]butanamide (260 mg, crude). LC-MS (ESI, m/z): 256 [M+H]$^+$.

Example 2

COMPOUND 1

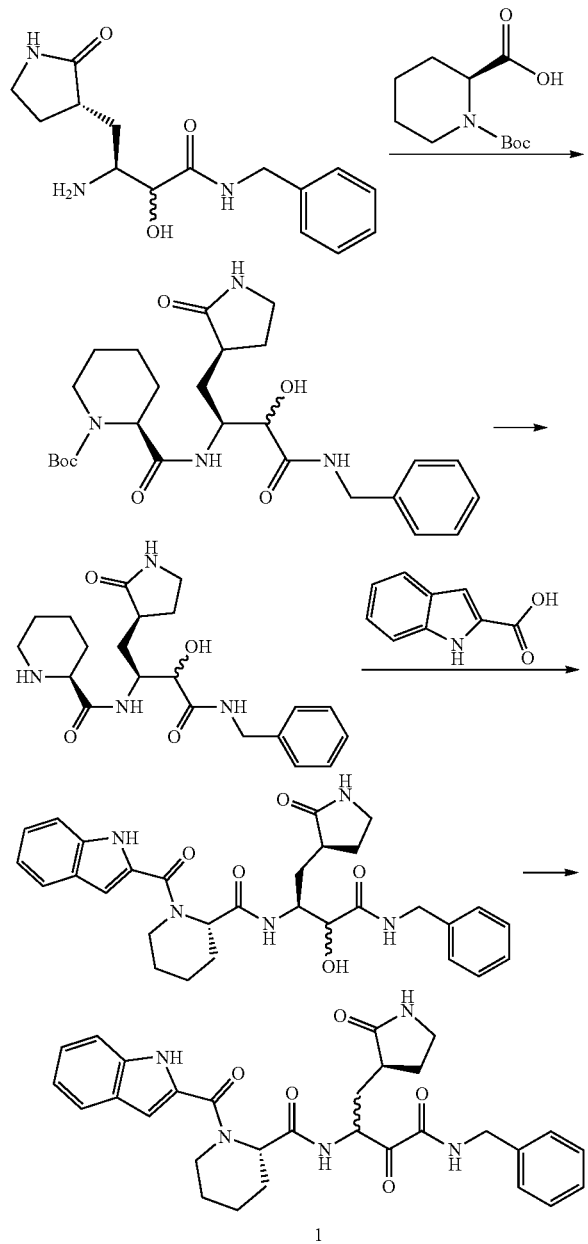

To a stirred mixture of (S)-1-(tert-butoxycarbonyl)piperidine-2-carboxylic acid (260 mg, 1.13 mmol, 1.1 eq.) in N,N-dimethylformamide (10 mL) was added o-(7-azabenzotriazol-1-yl)-N,N,N',N'-tetramethyluronium hexafluorophosphate (509 mg, 1.33 mmol, 1.3 eq.) and N,N-diisopropylethylamine (532 mg, 4.12 mmol, 4.0 eq.) at 0° C. The mixture was stirred for 20 min at 0° C. (3S)-3-amino-N-benzyl-2-hydroxy-4-((S)-2-oxopyrrolidin-3-yl)butanamide (300 mg, 1.03 mmol, 1.0 eq.) was added at 0° C. The mixture was stirred for 1 h at rt, and the reaction was quenched with water (30 mL) at rt. The residue was extracted with EA (3×40 mL). The organic layers were combined, washed with brine (6×40 mL), dried over anhydrous sodium sulfate, filtered and concentrated under reduced pressure. The residue was purified by silica gel column chromatography, eluted with dichloromethane:methanol (19:1) to afford tert-butyl (2S)-2-(((2S)-4-(benzylamino)-3-hydroxy-4-oxo-1-((S)-2-oxopyrrolidin-3-yl)butan-2-yl)carbamoyl)piperidine-1-carboxylate (380 mg, 66%) as a yellow solid. LCMS (ESI, m/z): 503 [M+H]$^+$.

To a stirred solution of tert-butyl (2S)-2-(((2S)-4-(benzylamino)-3-hydroxy-4-oxo-1-((S)-2-oxopyrrolidin-3-yl)butan-2-yl)carbamoyl)piperidine-1-carboxylate (370 mg, 0.740 mmol, 1.0 eq.) in dichloromethane (20 mL) was added trifluoroacetic acid (5 mL) dropwise at rt. The mixture was stirred for 1 h at rt and concentrated under reduced pressure to afford (2S)—N-((2S)-4-(benzylamino)-3-hydroxy-4-oxo-1-((S)-2-oxopyrrolidin-3-yl)butan-2-yl)piperidine-2-carboxamide (300 mg, 67%) as a yellow solid. LCMS (ESI, m/z): 403 [M+H]$^+$.

To a stirred mixture of indole-2-carboxylic acid (120 mg, 0.740 mmol, 1.0 eq.) in N,N-dimethylformamide (10 mL) were added o-(7-azabenzotriazol-1-yl)-N,N,N',N'-tetramethyluronium hexafluorophosphate (368 mg, 0.970 mmol, 1.3 eq.) and N,N-diisopropylethylamine (289 mg, 2.24 mmol, 3.0 eq.) in portions at 0° C. The mixture was stirred for 20 min at 0° C. (2S)—N-((2S)-4-(benzylamino)-3-hydroxy-4-oxo-1-((S)-2-oxopyrrolidin-3-yl)butan-2-yl)piperidine-2-carboxamide (300 mg, 0.750 mmol, 1.0 eq.) was added at 0° C. The mixture was stirred for 1 h at rt, and the reaction was quenched with water (30 mL) at rt. The mixture was extracted with EA (3×40 mL). The organic layers were combined, washed with brine (4×40 mL), dried over anhydrous sodium sulfate, filtered and concentrated under reduced pressure. The residue was purified by silica gel column chromatography, eluted with dichloromethane (DCM):methanol (MeOH) (16:1) to afford (2S)—N-((2S)-4-(benzylamino)-3-hydroxy-4-oxo-1-((S)-2-oxopyrrolidin-3-yl)butan-2-yl)-1-(1H-indole-2-carbonyl)piperidine-2-carboxamide (173 mg, crude) as a white solid. LCMS (ESI, m/z): 546 [M+H]$^+$.

To a stirred mixture of (2S)—N-((2S)-4-(benzylamino)-3-hydroxy-4-oxo-1-((S)-2-oxopyrrolidin-3-yl)butan-2-yl)-1-(1H-indole-2-carbonyl)piperidine-2-carboxamide (50.0 mg, 0.092 mmol, 1.0 eq.) in dichloromethane (3 mL) was added Dess-Martin periodinane (58.0 mg, 0.140 mmol, 1.5 eq.) in portions at 0° C. The reaction was quenched with sat. sodium bicarbonate (5 mL) at 0° C. The residue was extracted with EA (3×30 mL). The organic layers were combined, washed with brine (2×20 mL), dried over anhydrous sodium sulfate, filtered and concentrated under reduced pressure. The residue was purified by TLC (dichloromethane:methanol:10:1) to afford (2S)—N-(4-(benzylamino)-3,4-dioxo-1-((S)-2-oxopyrrolidin-3-yl)butan-2-yl)-1-(1H-indole-2-carbonyl)piperidine-2-carboxamide (6.3 mg, 12%) as a light yellow solid. LCMS (ESI, m/z): 544 [M+H]$^+$.

Example 3

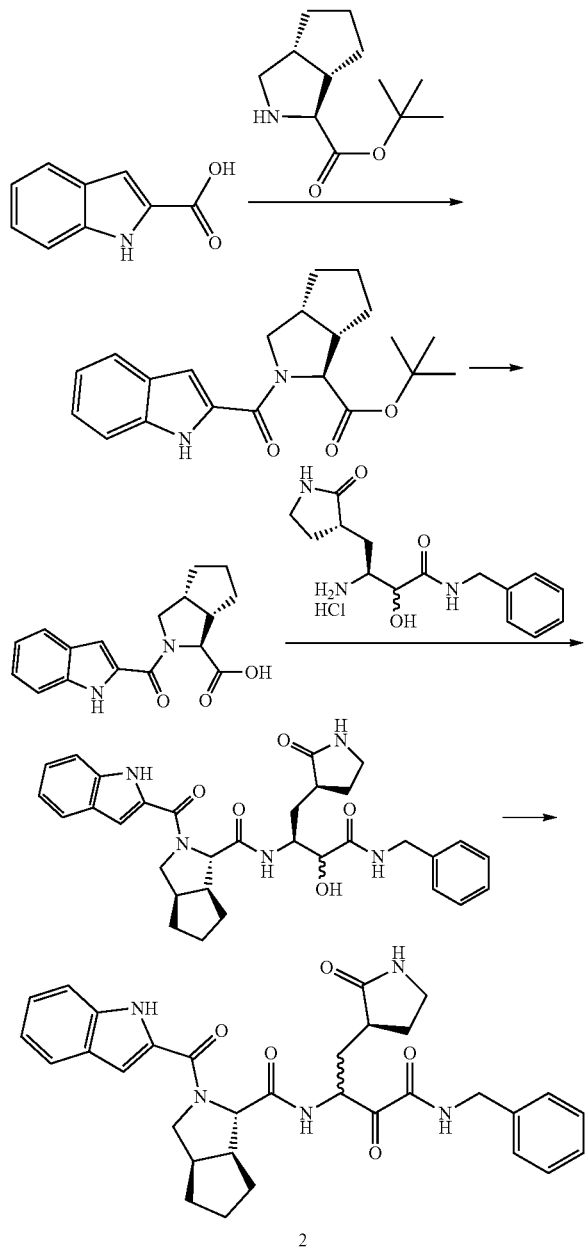

2

To a mixture of 1H-indole-2-carboxylic acid (600 mg, 3.72 mmol, 1.0 eq.), (1S,3aR,6aS)-tert-butyl octahydrocyclopenta[c]pyrrole-1-carboxylate (787 mg, 3.72 mmol, 1.0 eq.) and o-(7-azabenzotriazol-1-yl)-N,N,N',N'-tetramethyluronium hexafluorophosphate (2.12 g, 5.59 mmol, 1.5 eq.) in N,N-dimethylformamide (10 mL) was added N-ethyl-N-isopropylpropan-2-amine (1.44 g, 11.2 mmol, 3.0 eq.). The mixture was stirred overnight at rt, and the reaction was quenched with water (20 mL). The mixture was extracted with EA (3×30 mL). The organic layers were combined, washed with brine (2×20 mL), dried over anhydrous sodium sulfate, filtered and concentrated under reduced pressure to afford the crude product. The crude product was diluted with DCM (20 mL). After removing the DCM, a slurry with 100~200 silicagel mesh (1.2 g) was made and purified by column chromatography (Column size 5×24 cm, column volume: 300 mL, silica gel size (100~200 mesh) quantity: 120 g) and eluted with EA:PE (0%~50% over 30 min). Collected fractions: 21%-23% EA:PE fractions were chosen as pure fractions, and those fractions were combined and concentrated under reduced pressure to provide (1S,3aR,6aS)-tert-butyl 2-(1H-indole-2-carbonyl)-octahydrocyclopenta[c]pyrrole-1-carboxylate (865 mg, 62%) as a white solid. $^1$H NMR (300 MHz, DMSO-$d_6$) δ 11.60 (s, 1H), 7.65 (d, J=8.1 Hz, 1H), 7.44 (d, J=8.2 Hz, 1H), 7.21 (t, J=7.6 Hz, 1H), 6.72-7.10 (m, 2H), 4.23-4.74 (m, 1H), 3.58-4.18 (m, 2H), 2.54-2.96 (m, 2H), 1.22-2.04 (m, 15H). LCMS (ESI, m/z): 299 [M−56+H]$^+$.

To a solution of (1S,3aR,6aS)-tert-butyl 2-(1H-indole-2-carbonyl)-octahydrocyclopenta[c]pyrrole-1-carboxylate (300 mg, 0.846 mmol, 1.0 eq.) in DCM (3 mL) was added trifluoroacetic acid (1 mL) at rt. The mixture was stirred for 1 h at rt and concentrated under reduced pressure to afford the crude (1S,3aR,6aS)-2-(1H-indole-2-carbonyl)octahydrocyclopenta[c]pyrrole-1-carboxylic acid as yellow oil. $^1$H NMR (300 MHz, DMSO-$d_6$) δ 12.57 (br, 1H), 11.57 (s, 1H), 7.61-7.68 (m, 1H), 7.42-7.48 (m, 1H), 7.16-7.25 (m, 1H), 7.00-7.10 (m, 2H), 4.34-4.41 (m, 1H), 4.06-4.18 (m, 1H), 3.76-3.86 (m, 1H), 2.78-2.88 (m, 1H), 2.59-2.71 (m, 1H), 1.46-1.92 (m, 6H). LCMS (ESI, m/z): 299 [M+H]$^+$.

To a mixture of (3S)-3-amino-N-benzyl-2-hydroxy-4-[(3S)-2-oxopyrrolidin-3-yl]butanamide hydrochloride (250 mg, 0.763 mmol, 1.0 eq.), (1S,3aR,6aS)-2-(1H-indole-2-carbonyl)-octahydrocyclopenta[c]pyrrole-1-carboxylic acid (250 mg, 0.839 mmol, 1.1 eq.) and N-ethyl-N-isopropylpropan-2-amine (394 mg, 3.051 mmol, 4.0 eq.) in DCM (10 mL) was added 2,4,6-tripropyl-1,3,5,2,4,6-trioxatriphosphorinane-2,4,6-trioxide (1.07 g, 1.679 mmol, 2.2 eq., 50% in EA) at 0° C. The mixture was stirred for 2 h at 0° C., and the reaction was quenched with water (20 mL). The mixture was extracted with EA (3×20 mL). The organic layers were combined, washed with brine (2×20 mL), dried over anhydrous sodium sulfate, filtered and concentrated under reduced pressure to afford the crude product. The crude product was diluted with dichloromethane (10 mL). After removing the DCM, a slurry with 100~200 silica gel mesh (500 mg) was made. The sample was purified by column chromatography (Column size 4×24 cm, column volume: 200 mL, silica gel size (100~200 mesh) quantity: 80 g) and eluted with MeOH:DCM (0%~15% over 20 min). The collected fractions: 11%-12% MeOH:DCM fractions were chosen as pure fractions. Those fractions were combined and concentrated under reduced pressure to provide (1S,3aR, 6aS)—N—((S)-4-(benzylamino)-3-hydroxy-4-oxo-1-((S)-2-oxopyrrolidin-3-yl)butan-2-yl)-2-(1H-indole-2-carbonyl)-octahydrocyclopenta[c]pyrrole-1-carboxamide (180 mg, 35%) as a yellow solid. LCMS (ESI, m/z): 572 [M+H]$^+$.

To a mixture of (1S,3aR,6aS)—N—((S)-4-(benzylamino)-3-hydroxy-4-oxo-1-((S)-2-oxopyrrolidin-3-yl)butan-2-yl)-2-(1H-indole-2-carbonyl)-octahydrocyclopenta[c]pyrrole-1-carboxamide (180 mg, 0.315 mmol, 1.0 eq.) in DCM (5 mL) was added Dess-Martin periodinane (200 mg, 0.472 mmol, 1.5 eq.) at 0° C. The mixture was stirred for 1 h at 0° C. The reaction was quenched with sat. aq. sodium thiosulfate (5 mL) and sat. aq. sodium bicarbonate (5 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by TLC (Mobile phase: MeOH:DCM=1:11; Rf=0.5; detection: UV) to provide (1S,3aR, 6aS)—N-(4-(benzylamino)-3,4-dioxo-1-((S)-2-oxopyrrolidin-3-yl)butan-2-yl)-2-(1H-indole-2-carbonyl)-octahydrocyclopenta[c]pyrrole-1-carboxamide (28.2 mg, 15%) as an off-white solid. $^1$H NMR (300 MHz, DMSO-$d_6$) δ 11.30-13.70 (m, 1H), 8.98-9.35 (m, 1H), 8.45-8.90 (m, 1H), 7.10-7.95 (m, 9H), 6.45-7.09 (m, 2H), 5.12-4.66 (m, 1H), 4.03-4.52 (m, 4H), 3.57-3.89 (m, 1H), 2.93-3.15 (m, 2H), 2.60-2.86 (m, 2H), 2.10-2.35 (m, 2H), 1.40-2.08 (m, 9H). LCMS (ESI, m/z): 570 [M+H]$^+$.

Example 4

COMPOUND 3

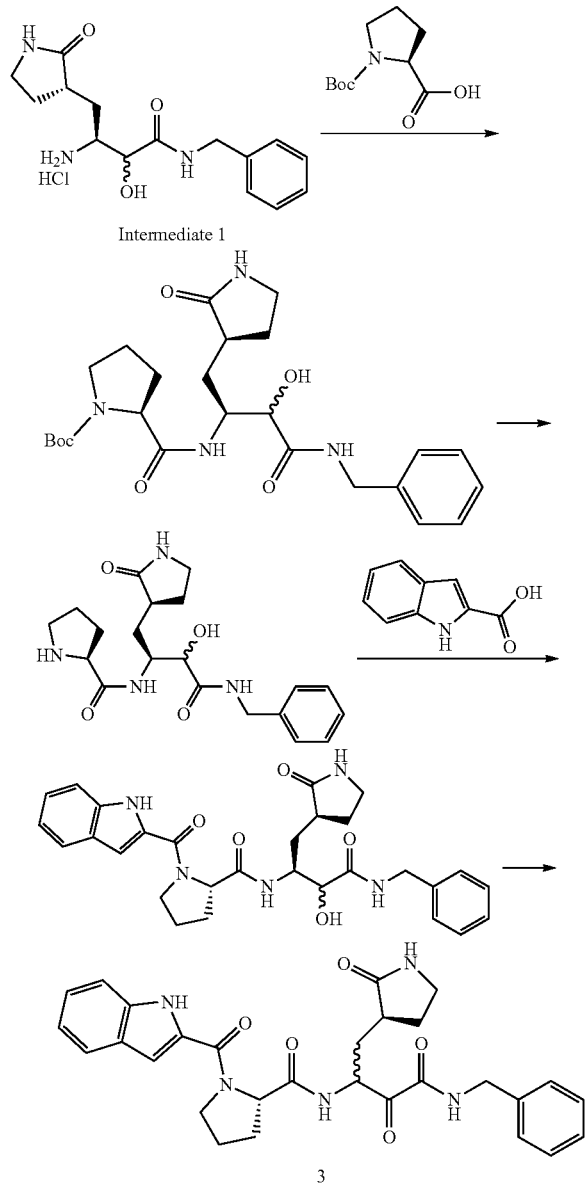

To a mixture of (2S)-1-(tert-butoxycarbonyl)pyrrolidine-2-carboxylic acid (341 mg, 1.59 mmol, 1.3 eq.) in acetonitrile (6 mL) was added and N,N,N',N'-tetramethylchloroformamidinium hexafluorophosphate (445 mg, 1.59 mmol, 1.3 eq.) and N-methylimidazole (351 mg, 4.27 mmol, 3.5 eq.) at 0° C. The mixture was stirred for 15 min at 0° C. (3S)-3-amino-N-benzyl-2-hydroxy-4-[(3S)-2-oxopyrrolidin-3-yl]butanamide hydrochloride (400 mg, 1.22 mmol, 1.0 eq.) was added. The mixture stirred for 2 h at rt, and the reaction was quenched with water (10 mL). The mixture was extracted with EA (3×15 mL). The organic layers were combined, washed with brine (2×10 mL), dried over anhydrous sodium sulfate, filtered and concentrated under reduced pressure to afford the crude product. The crude product was diluted with DCM (10 mL). After the removal of the DCM, a slurry with 100~200 silica gel mesh (1 g) was made. The sample was purified by column chromatography (Column size 4×24 cm, column volume: 200 mL, silica gel size (100~200 mesh) quantity: 80 g) and eluted with MeOH:DCM (0%~15% over 20 min). Collected fractions: 6%-7% MeOH:DCM fractions were chosen as pure fractions. Those fractions were combined and concentrated under reduced pressure to provide tert-butyl (2S)-2-[[(2S)-1-(benzylcarbamoyl)-1-hydroxy-3-[(3S)-2-oxopyrrolidin-3-yl]propan-2-yl]carbamoyl]pyrrolidine-1-carboxylate (280 mg, 43%) as a white solid. LCMS (ESI, m/z): 489 [M+H]$^+$.

To a mixture of tert-butyl (2S)-2-[[(2S)-1-(benzylcarbamoyl)-1-hydroxy-3-[(3S)-2-oxopyrrolidin-3-yl]propan-2-yl]carbamoyl]pyrrolidine-1-carboxylate (230 mg, 0.471 mmol, 1.0 eq.) in DCM (4 mL) was added trifluoroacetic acid (1 mL) at rt. The mixture was stirred for 1 h and concentrated under reduced pressure to afford crude (3S)—N-benzyl-2-hydroxy-4-[(3S)-2-oxopyrrolidin-3-yl]-3-[(2S)-pyrrolidin-2-ylformamido]butanamide (180 mg, crude) as a yellow semi-solid. LCMS (ESI, m/z): 389 [M+H]$^+$.

A mixture of indole-2-carboxylic acid (82.1 mg, 0.510 mmol, 1.1 eq.), N-ethyl-N-isopropylpropan-2-amine (180 mg, 1.39 mmol, 3.0 eq.) and o-(7-Azabenzotriazol-1-yl)-N,N,N',N'-tetramethyluronium hexafluorophosphate (229 mg, 0.602 mmol, 1.3 eq.) in N,N-dimethylformamide (2 mL) was stirred for 15 min at 0° C. (3S)—N-benzyl-2-hydroxy-4-[(3S)-2-oxopyrrolidin-3-yl]-3-[(2S)-pyrrolidin-2-ylformamido]butanamide (180 mg, 0.463 mmol, 1.0 eq.) was added. The mixture was stirred for 2 h at rt. The reaction was quenched with water (5 mL). The mixture was extracted with EA (3×5 mL). The organic layers were combined, washed with brine (2×5 mL), dried over anhydrous sodium sulfate, filtered and concentrated under reduced pressure to afford the crude product. The crude product was diluted with DCM (10 mL). After the removal of the DCM, a slurry with 100~200 silica gel mesh (500 mg) was made. The sample was purified by column chromatography (Column size 4×24 cm, column volume: 200 mL, silica gel size (100~200 mesh) quantity: 80 g) and eluted with MeOH:DCM (0%~10% over 20 min). Collected fractions: 5%-7% MeOH:DCM fractions were chosen as pure fractions. Those fractions were combined and concentrated under reduced pressure to provide (3S)—N-benzyl-2-hydroxy-3-[[(2S)-1-(1H-indole-2-carbonyl)pyrrolidin-2-yl]formamido]-4-[(3S)-2-oxopyrrolidin-3-yl]butanamide (160 mg, 62%) as a light-yellow solid. LCMS (ESI, m/z): 532 [M+H]$^+$.

To a mixture of (3S)—N-benzyl-2-hydroxy-3-[[(2S)-1-(1H-indole-2-carbonyl)pyrrolidin-2-yl]formamido]-4-[(3S)-2-oxopyrrolidin-3-yl]butanamide (100 mg, 0.188 mmol, 1.0 eq.) in DCM (2 mL) was added Dess-Martin periodinane (120 mg, 0.282 mmol, 1.5 eq.) at 0° C. The mixture was stirred for 1 h at 0° C. The reaction was quenched with sat. aq. sodium bicarbonate (3 mL) and sat. aq. sodium thiosulfate (3 mL). The mixture was extracted with EA (3×3 mL). The organic layers were combined, washed with brine (2×3 mL), dried over anhydrous sodium sulfate, filtered and concentrated under reduced pressure to afford the crude product. The crude product was purified by TLC (Mobile phase: MeOH:DCM=1:11; Rf=0.3; detection: UV) to provide N-benzyl-3-[[(2S)-1-(1H-indole-2-carbonyl)pyrrolidin-2-yl]formamido]-2-oxo-4-[(3S)-2-oxopyrrolidin-3-yl]butanamide (10.1 mg, 9%) as a light yellow solid. $^1$H NMR (300 MHz, DMSO-$d_6$) δ 11.32-13.58 (m, 1H), 8.95-9.30 (m, 1H), 8.52-8.88 (m, 1H), 7.36-7.82 (m, 3H), 7.10-7.35 (m, 6H), 6.60-7.09 (m, 2H), 4.76-5.12 (m, 1H), 4.45-4.70 (m, 1H), 4.15-4.35 (m, 2H), 3.85-4.05 (m, 1H), 3.58-4.04 (m, 1H), 3.00-3.20 (m, 2H), 1.50-2.35 (m, 9H). LCMS (ESI, m/z): 530 [M+H]$^+$.

Example 5

COMPOUND 4

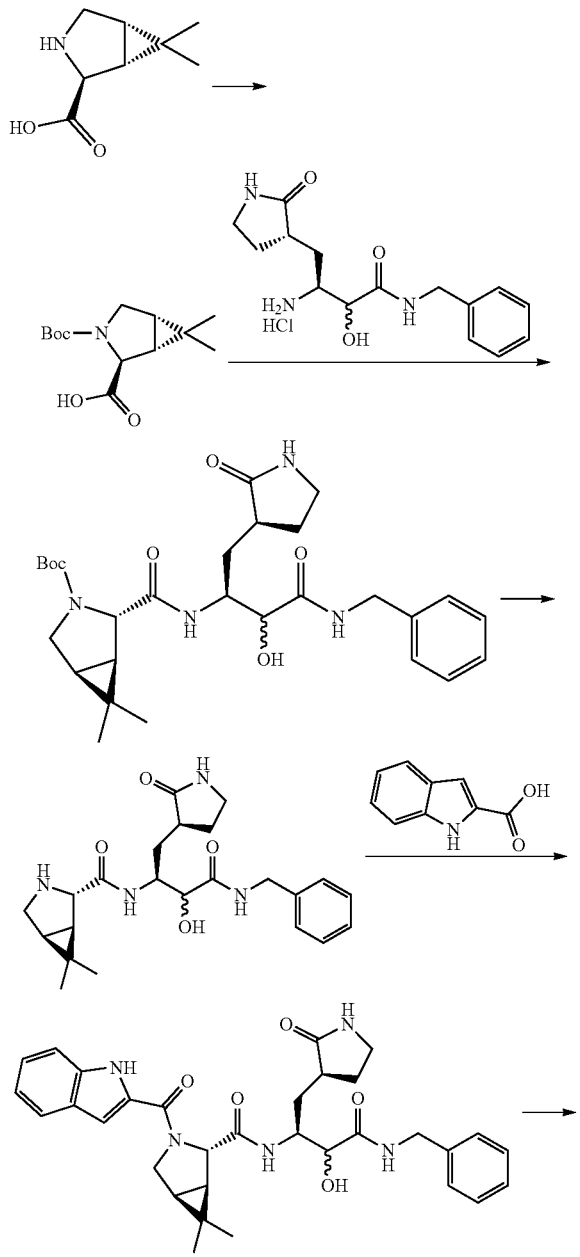

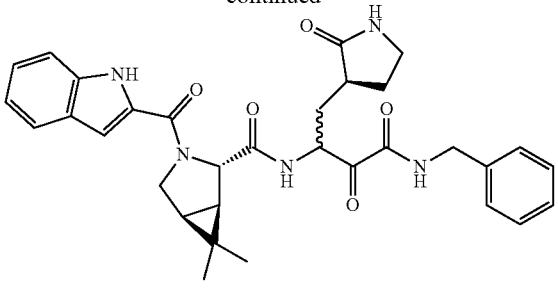

To a mixture of (1R,2S,5S)-6,6-dimethyl-3-azabicyclo[3.1.0]hexane-2-carboxylic acid (100 mg, 0.644 mmol, 1.0 eq.) and di-tert-butyl decarbonate (155 mg, 0.709 mmol, 1.1 eq.) in DCM (2 mL) was added triethylamine (72.0 mg, 0.709 mmol, 1.1 eq.). The mixture was stirred for 2 h at rt and the concentrated under reduced pressure to afford crude (1R,2S,5S)-3-(tert-butoxycarbonyl)-6,6-dimethyl-3-azabicyclo[3.1.0]hexane-2-carboxylic acid (165 mg, crude) as a yellow oil. LCMS (ESI, m/z): 200 [M−56+H]$^+$.

A mixture of (1R,2S,5S)-3-(tert-butoxycarbonyl)-6,6-dimethyl-3-azabicyclo[3.1.0]hexane-2-carboxylic acid (154 mg, 0.604 mmol, 1.1 eq.), o-(7-azabenzotriazol-1-yl)-N,N,N',N'-tetramethyluronium hexafluorophosphate (313 mg, 0.824 mmol, 1.5 eq.) and N-ethyl-N-isopropylpropan-2-amine (284 mg, 2.20 mmol, 4.0 eq.) in N,N-dimethylformamide (3 mL) was stirred for 0.5 h at 0° C. (3S)-3-amino-N-benzyl-2-hydroxy-4-[(3S)-2-oxopyrrolidin-3-yl]butanamide hydrochloride (180 mg, 0.549 mmol, 1.00 eq.) was added. The mixture was stirred for 1 h at rt, and the reaction was quenched with water (10 mL). The mixture was extracted with EA (3×10 mL). The organic layers were combined, washed with brine (2×10 mL), dried over anhydrous sodium sulfate, filtered and concentrated under reduced pressure to afford the crude product. The crude product was diluted with DCM (10 mL). After removal of the DCM, a slurry with 100~200 silica gel mesh (500 mg) was made. The sample was purified by column chromatography (Column size 4×24 cm, column volume: 200 mL, silica gel size (100~200 mesh) quantity: 80 g) and eluted with MeOH:DCM (0%~15% over 20 min). Collected fractions: 6%-7% MeOH:DCM fractions were chosen as pure fractions. Those fractions were combined and concentrated under reduced pressure to provide tert-butyl (1R,2S,5S)-2-[[(2S)-1-(benzylcarbamoyl)-1-hydroxy-3-[(3S)-2-oxopyrrolidin-3-yl]propan-2-yl]carbamoyl]-6,6-dimethyl-3-azabicyclo[3.1.0]hexane-3-carboxylate (230 mg, 71%) as a yellow solid. LCMS (ESI, m/z): 529 [M+H]$^+$.

To a mixture of tert-butyl (1R,2S,5S)-2-[[(2S)-1-(benzylcarbamoyl)-1-hydroxy-3-[(3S)-2-oxopyrrolidin-3-yl]propan-2-yl]carbamoyl]-6,6-dimethyl-3-azabicyclo[3.1.0]hexane-3-carboxylate (150 mg, 0.284 mmol, 1.0 eq.) in DCM (3 mL) was added trifluoroacetic acid (1 mL). The mixture was stirred for 1 h at rt and concentrated under reduced pressure to afford crude (3S)—N-benzyl-3-[[(1R,2S,5S)-6,6-dimethyl-3-azabicyclo[3.1.0]hexan-2-yl]formamido]-2-hydroxy-4-[(3S)-2-oxopyrrolidin-3-yl]butanamide (120 mg, crude) as a yellow semi-solid. LCMS (ESI, m/z): 429 [M+H]$^+$.

To a mixture of indole-2-carboxylic acid (49.6 mg, 0.308 mmol, 1.1 eq.) and o-(7-azabenzotriazol-1-yl)-N,N,N',N'-tetramethyluronium hexafluorophosphate (160 mg, 0.420 mmol, 1.5 eq.) in N,N-dimethylformamide (3 mL) was added N-ethyl-N-isopropylpropan-2-amine (145 mg, 1.12 mmol, 4.0 eq.) at 0° C. The mixture was stirred for 0.5 h at 0° C., and then (3S)—N-benzyl-3-[[(1R,2S,5S)-6,6-dimethyl-3-azabicyclo[3.1.0]hexan-2-yl]formamido]-2-hydroxy-4-[(3S)-2-oxopyrrolidin-3-yl]butanamide (120 mg, 0.280 mmol, 1.0 eq.) was added. The mixture was stirred for 1 h at rt, and the reaction was quenched with water (10 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by TLC (Mobile phase: MeOH: DCM=1:12; Rf=0.3; detection: UV) to provide (3S)—N-benzyl-2-hydroxy-3-[[(1R,2S,5S)-3-(1H-indole-2-carbonyl)-6,6-dimethyl-3-azabicyclo[3.1.0]hexan-2-yl]formamido]-4-[(3S)-2-oxopyrrolidin-3-yl]butanamide (70.0 mg, 39.8%) as a yellow solid. LCMS (ESI, m/z): 572 [M+H]+.

To a mixture of (3S)—N-benzyl-2-hydroxy-3-[[(1R,2S,5S)-3-(1H-indole-2-carbonyl)-6,6-dimethyl-3-azabicyclo[3.1.0]hexan-2-yl]formamido]-4-[(3S)-2-oxopyrrolidin-3-yl]butanamide (70.0 mg, 0.122 mmol, 1.0 eq.) in DCM (3 mL) was added Dess-Martin periodinane (104 mg, 0.245 mmol, 2.0 eq.) at 0° C. The mixture was stirred for 3 h at rt. The reaction was quenched with sat. aq. sodium thiosulfate (2 mL) and sat. aq. sodium bicarbonate (2 mL). The mixture was extracted with EA (3×3 mL). The organic layers were combined, washed with brine (2×2 mL), dried over anhydrous sodium sulfate, filtered and concentrated under reduced pressure to afford the crude product. The crude product was purified by TLC (Mobile phase: MeOH: DCM=1:12; Rf=0.4; detection: UV) to provide N-benzyl-3-[[(1R,2S,5S)-3-(1H-indole-2-carbonyl)-6,6-dimethyl-3-azabicyclo[3.1.0]hexan-2-yl]formamido]-2-oxo-4-[(3S)-2-oxopyrrolidin-3-yl]butanamide (15.5 mg, 20.3%) as a white solid. LCMS (ESI, m/z): 570 [M+H]+.

Example 6

COMPOUND 5

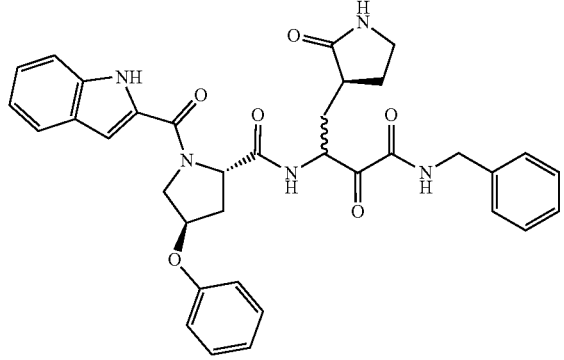

Compound 5 was prepared similarly as described for Compound 1, using (2S,4R)-1-(tert-butoxycarbonyl)-4-phenoxypyrrolidine-2-carboxylic acid in place of (S)-1-(tert-butoxycarbonyl)piperidine-2-carboxylic acid. LCMS (ESI, m/z): 622 [M+H]+.

Example 7

COMPOUND 6

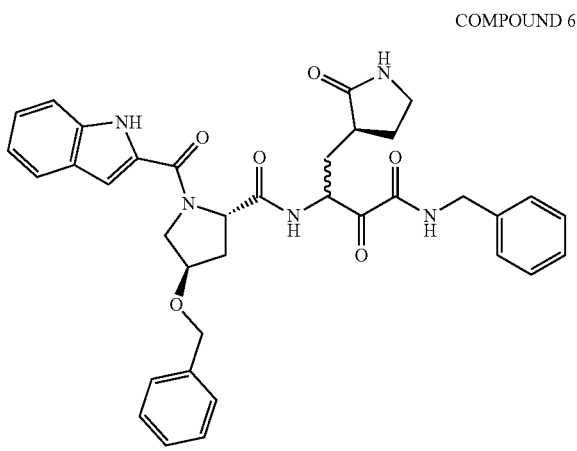 [SMILES: O=C(NCc1ccccc1)C(=O)C(C[C@@H]1CCNC1=O)NC(=O)[C@@H]1C[C@@H](OCc2ccccc2)CN1C(=O)c1cc2ccccc2[nH]1]

Compound 6 was prepared similarly as described for Compound 1, using (2S,4R)-4-(benzyloxy)-1-(tert-butoxycarbonyl)pyrrolidine-2-carboxylic acid in place of (S)-1-(tert-butoxycarbonyl)piperidine-2-carboxylic acid. LCMS (ESI, m/z): 636 [M+H]+.

Example 8

COMPOUND 7

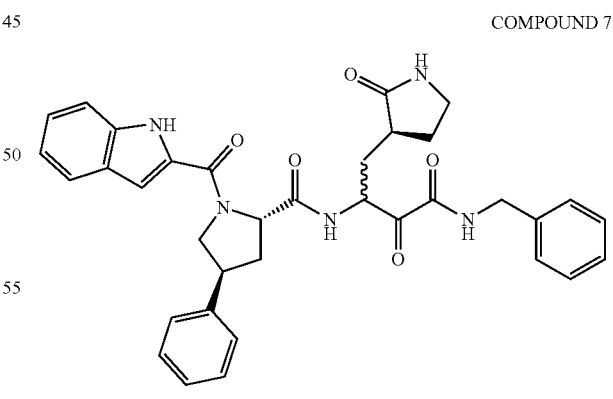

Compound 7 was prepared similarly as described for Compound 1, using (2S,4S)-1-(tert-butoxycarbonyl)-4-phenylpyrrolidine-2-carboxylic acid in place of (S)-1-(tert-butoxycarbonyl)piperidine-2-carboxylic acid. LCMS (ESI, m/z): 606 [M+H]+.

Example 9

COMPOUND 8

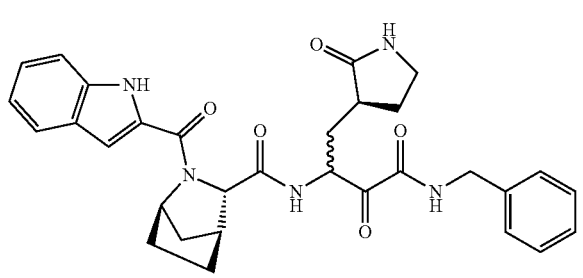

Compound 8 was prepared similarly as described for Compound 1, using (1R,3S,4S)-2-(tert-butoxycarbonyl)-2-azabicyclo[2.2.1]heptane-3-carboxylic acid in place of (S)-1-(tert-butoxycarbonyl)piperidine-2-carboxylic acid. LCMS (ESI, m/z): 556 [M+H]$^+$.

Example 10

COMPOUND 9

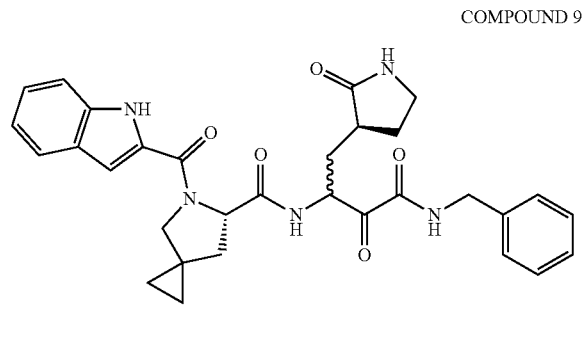 [SMILES: O=C(NCc1ccccc1)C(=O)C(C[C@@H]1CCNC1=O)NC(=O)[C@@H]1CC2(CC2)CN1C(=O)c1cc2ccccc2[nH]1]

Compound 9 was prepared similarly as described for Compound 1, using (S)-5-(tert-butoxycarbonyl)-5-azaspiro[2.4]heptane-6-carboxylic acid in place of (S)-1-(tert-butoxycarbonyl)piperidine-2-carboxylic acid. LCMS (ESI, m/z): 556 [M+H]$^+$.

Example 11

COMPOUND 10

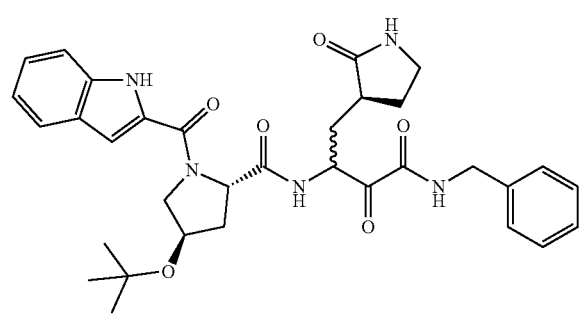

Compound 10 was prepared similarly as described for Compound 1, using (2S,4R)-4-(tert-butoxy)-1-(tert-butoxycarbonyl)pyrrolidine-2-carboxylic acid in place of (S)-1-(tert-butoxycarbonyl)piperidine-2-carboxylic acid. Boc deprotection was done with HCl in dioxane. LCMS (ESI, m/z): 602 [M+H]$^+$.

Example 12

COMPOUND 11

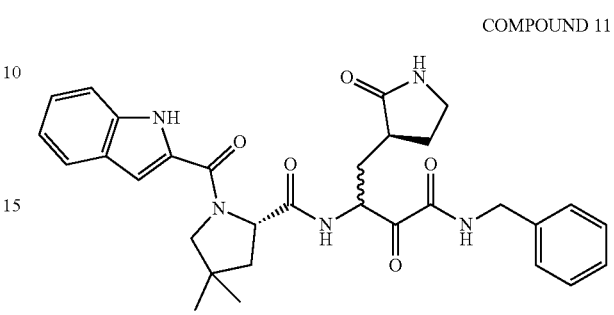

Compound 11 was prepared similarly as described for Compound 10, using (S)-1-(tert-butoxycarbonyl)-4,4-dimethylpyrrolidine-2-carboxylic acid in place of (2S,4R)-4-(tert-butoxy)-1-(tert-butoxycarbonyl)pyrrolidine-2-carboxylic acid. LCMS (ESI, m/z): 558 [M+H]$^+$.

Example 13

COMPOUND 12

Compound 12 was prepared similarly as described for Compound 10, using (2S,4R)-1-(tert-butoxycarbonyl)-4-methoxypyrrolidine-2-carboxylic acid in place of (2S,4R)-4-(tert-butoxy)-1-(tert-butoxycarbonyl)pyrrolidine-2-carboxylic acid. LCMS (ESI, m/z): 560 [M+H]$^+$.

Example 14

COMPOUND 13

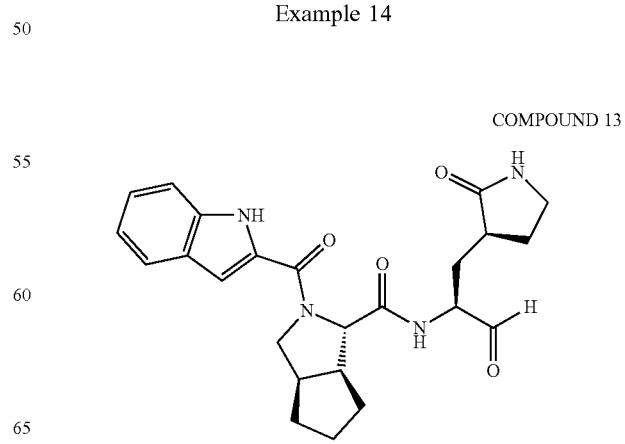

To a mixture of (1S,3aR,6aS)-2-(1H-indole-2-carbonyl)-hexahydro-1H-cyclopenta[c]pyrrole-1-carboxylic acid (317 mg, 1.06 mmol, 1.1 eq.), methyl (2S)-2-amino-3-[(3S)-2-oxopyrrolidin-3-yl]propanoate (180 mg, 0.967 mmol, 1.0 eq.) and N-ethyl-N-isopropylpropan-2-amine (500 mg, 3.87 mmol, 4.0 eq.) in dichloromethane (10 mL) was added 2,4,6-tripropyl-1,3,5,2,4,6-trioxatriphosphorinane-2,4,6-trioxide (1.35 g, 2.13 mmol, 2.2 eq., 50% in EA) at 0° C. The mixture was stirred for 2 h at 0° C., and the reaction was quenched with water (20 mL). The mixture was extracted with EA (3×20 mL). The organic layers were combined, washed with brine (2×20 mL), dried over anhydrous sodium sulfate, filtered and concentrated under reduced pressure to afford the crude product. The crude product was purified by TLC (Mobile phase: methanol:dichloromethane=1:11; Rf=0.4; detection: UV) to provide methyl (2S)-2-[[(1S,3aR,6aS)-2-(1H-indole-2-carbonyl)-hexahydro-1H-cyclopenta[c]pyrrol-1-yl]formamido]-3-[(3S)-2-oxopyrrolidin-3-yl]propanoate (110 mg, 22%) as an off-white solid.

To a mixture of methyl (2S)-2-[[(1S,3aR,6aS)-2-(1H-indole-2-carbonyl)-hexahydro-1H-cyclopenta[c]pyrrol-1-yl]formamido]-3-[(3S)-2-oxopyrrolidin-3-yl]propanoate (100 mg, 0.214 mmol, 1.0 eq.) in THF (1 mL) was added LiBH$_4$ (0.32 mL, 0.642 mmol, 3.0 eq., 2 M in THF) at 0° C. The mixture was stirred for 1 h at rt, and the reaction was quenched with sat. aq. ammonium chloride (3 mL). The mixture was extracted with chloroform:isopropyl alcohol (5:1, 3×3 mL). The organic layers were combined, washed with brine (2×3 mL), dried over anhydrous sodium sulfate, filtered and concentrated under reduced pressure to afford the crude product. The crude product was purified by TLC (Mobile phase: methanol:dichloromethane=1:11; Rf=0.4; detection: UV) to provide (1S,3aR,6aS)—N-[(2S)-1-hydroxy-3-[(3S)-2-oxopyrrolidin-3-yl]propan-2-yl]-2-(1H-indole-2-carbonyl)-hexahydro-1H-cyclopenta[c]pyrrole-1-carboxamide (50.0 mg, 48%) as an off-white solid.

To a mixture of (1S,3aR,6aS)—N-[(2S)-1-hydroxy-3-[(3S)-2-oxopyrrolidin-3-yl]propan-2-yl]-2-(1H-indole-2-carbonyl)-hexahydro-1H-cyclopenta[c]pyrrole-1-carboxamide (50.0 mg, 0.114 mmol, 1.0 eq.) in dichloromethane (1.00 mL) was added Dess-Martin periodinane (96.7 mg, 0.228 mmol, 2.0 eq.) at 0° C. The mixture was stirred for 3 h at rt, and the reaction was quenched sat. aq. sodium bicarbonate (1 mL) and sat. aq. sodium thiosulfate (1 mL). The mixture was extracted with dichloromethane (3×3 mL). The organic layers were combined, washed with brine (2×2 mL), dried over anhydrous sodium sulfate, filtered and concentrated under reduced pressure to afford the crude product (45 mg). The crude product was purified by TLC (Column: XBridge Prep C18 OBD Column, 19×150 mm 5 μm; Mobile Phase A: Water (0.05% NH$_3$·H$_2$O), Mobile Phase B: ACN; Flow rate: 25 mL/min; Gradient: 20 B to 35 B in 9 min, 35 B to B in min, B to B in min, B to B in min, B to B in min; 210 nm; RT: 7.33); to provide (1S,3aR,6aS)-2-(1H-indole-2-carbonyl)-N-[(2S)-1-oxo-3-[(3S)-2-oxopyrrolidin-3-yl]propan-2-yl]-hexahydro-1H-cyclopenta[c]pyrrole-1-carboxamide (8.3 mg, 15%) as a white solid. LCMS (ESI, m/z): 437 [M+H]$^+$.

Example 15

COMPOUND 14A

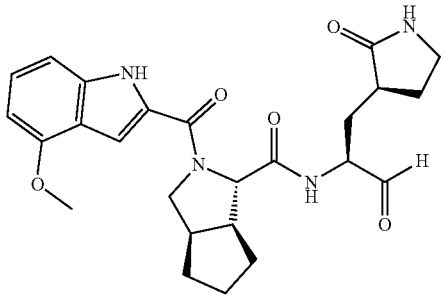

A 40 mL vial was charged with 4-methoxy-1H-indole-2-carboxylic acid (348 mg, 1.82 mmol, 1.1 eq.), o-(7-azabenzotriazol-1-yl)-N,N,N',N'-tetramethyluronium hexafluorophosphate (693 mg, 1.82 mmol, 1.1 eq.), N,N-dimethylformamide (5 mL) and N-ethyl-N-isopropylpropan-2-amine (643 mg, 4.97 mmol, 3.0 eq.). The reaction was stirred for 30 min, and then tert-butyl (1S,3aR,6aS)-octahydrocyclopenta[c]pyrrole-1-carboxylate oxalate (500 mg, 1.65 mmol, 1.0 eq.) was added. The mixture was stirred for 3 h at rt, and the reaction was quenched with water (20 mL). The mixture was extracted with EA (3×50 mL). The organic layers were combined, washed with brine (2×30 mL), dried over anhydrous sodium sulfate, filtered and concentrated under reduced pressure to afford the crude product. The crude product was diluted with dichloromethane (5 mL). A slurry was made with 100~200 silicagel mesh (4 g) and then loaded onto a column after removing the dichloromethane. The sample was purified by column chromatography (Column size 4×24 cm, column volume: 200 mL, silicagel size (100~200 mesh) quantity: 80 g) and eluted with EA:PE (0%~30% over 30 min). The collected fractions: 13% EA:PE fractions were chosen as the pure fractions. Those fractions were combined and concentrated under reduced pressure to provide tert-butyl (1S,3aR,6aS)-2-(4-methoxy-1H-indole-2-carbonyl)-hexahydro-1H-cyclopenta[c]pyrrole-1-carboxylate (530 mg, 78%) as white solid. LCMS (ESI, m/z): 329 [M+H−56]$^+$.

A 40 mL vial was charged with tert-butyl (1S,3aR,6aS)-2-(4-methoxy-1H-indole-2-carbonyl)-hexahydro-1H-cyclopenta[c]pyrrole-1-carboxylate (200 mg, 0.520 mmol, 1.0 eq.), dichloromethane (3 mL). Trifluoroacetic acid (1 mL) was then added at 0° C. The mixture was stirred for 1 h at rt and concentrated under reduced pressure to afford (1S,3aR,6aS)-2-(4-methoxy-1H-indole-2-carbonyl)-hexahydro-1H-cyclopenta[c]pyrrole-1-carboxylic acid (230 mg, crude) as yellow solid. LCMS (ESI, m/z): 329 [M+H]$^+$.

To a solution of methyl (2S)-2-amino-3-[(3S)-2-oxopyrrolidin-3-yl]propanoate (100 mg, 0.537 mmol, 1.0 eq.), (1S,3aR,6aS)-2-(4-methoxy-1H-indole-2-carbonyl)-hexahydro-1H-cyclopenta[c]pyrrole-1-carboxylic acid (211 mg, 0.644 mmol, 1.2 eq.), N,N,N,N-tetramethylchloroformamidinium hexafluorophosphate (165 mg, 0.591 mmol, 1.1 eq.) in acetonitrile (3 mL) was added 1-methylimidazole (136 mg, 1.66 mmol, 3.1 eq.). The mixture was stirred at 0° C. The mixture was then stirred for overnight at rt, and the reaction was quenched with water (10 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by TLC (Mobile phase: methanol:dichloromethane=1:10; Rf=0.4; detection: UV) to provide the desired product methyl (2S)-2-[[(1S,3aR,6aS)-2-(4-methoxy-1H-indole-2-carbonyl)-hexahydro-1H-cyclopenta[c]pyrrol-1-yl]formamido]-3-[(3S)-2-oxopyrrolidin-3-yl]propanoate 60 mg, 20%) as yellow solid. LCMS (ESI, m/z): 497 [M+H]$^+$.

To a solution of methyl (2S)-2-[[(1S,3aR,6aS)-2-(4-methoxy-1H-indole-2-carbonyl)-hexahydro-1H-cyclopenta[c]pyrrol-1-yl]formamido]-3-[(3S)-2-oxopyrrolidin-3-yl]propanoate (60.0 mg, 0.121 mmol, 1.0 eq.) in THF (2 mL) was added lithium borohydride (7.90 mg, 0.363 mmol, 3.0 eq.). The mixture was stirred at 0° C., and then stirred for 2 h at rt. The reaction was quenched with sat. aq. ammonium chloride (10 mL). The mixture was extracted with chloroform:isopropanol (5:1, 3×20 mL). The organic layers were combined, washed with brine (2×10 mL), dried over anhydrous sodium sulfate, filtered and concentrated under reduced pressure to afford the crude product. The crude product was purified by TLC (Mobile phase: methanol:dichloromethane=1:11; Rf=0.4; detection: UV) to provide (1S,3aR,6aS)—N-[(2S)-1-hydroxy-3-[(3S)-2-oxopyrrolidin-3-yl]propan-2-yl]-2-(4-methoxy-1H-indole-2-carbonyl)-hexahydro-1H-cyclopenta[c]pyrrole-1-carboxamide (36 mg, 57%) as a light yellow solid. LCMS (ESI, m/z): 469 [M+H]$^+$.

To a solution of (1S,3aR,6aS)—N-[(2S)-1-hydroxy-3-[(3S)-2-oxopyrrolidin-3-yl]propan-2-yl]-2-(4-methoxy-1H-indole-2-carbonyl)-hexahydro-1H-cyclopenta[c]pyrrole-1-carboxamide (35.0 mg, 0.075 mmol, 1.0 eq.) in dichloromethane (1 mL) was added Dess-Martin periodinane (63.3 mg, 0.149 mmol, 2.0 eq.). The mixture was stirred at rt for 24 h. The reaction was quenched with sat. sodium bicarbonate (10 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by preparative HPLC (Column: XBridge Prep C18 OBD Column, 19×150 mm 5 μm; Mobile Phase A: Water (0.05% NH$_3$·H$_2$O), Mobile Phase B: ACN; Flow rate: 25 mL/min; Gradient: 24 B to 42 B in 9 min; 210 nm; RT1 (min): 5.48; RT2 (min): 7.43) to provide (1S,3aR,6aS)-2-(4-methoxy-1H-indole-2-carbonyl)-N-[(2S)-1-oxo-3-[(3S)-2-oxopyrrolidin-3-yl]propan-2-yl]-hexahydro-1H-cyclopenta[c]pyrrole-1-carboxamide (14A, 4.5 mg, 12%) as a white solid and a stereoisomer 14B (1.6 mg, 4%) as a white solid.

Example 16

COMPOUND 15

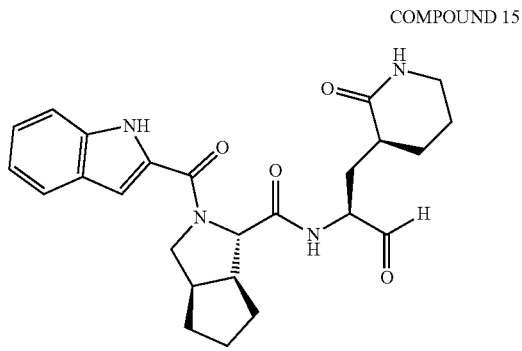 [SMILES: O=C[C@H](C[C@@H]1CCCNC1=O)NC(=O)[C@@H]1[C@H]2CCC[C@H]2CN1C(=O)c1cc2ccccc2[nH]1]

A 100 mL round-bottom flask was charged with (1S,3aR,6aS)-2-(1H-indole-2-carbonyl)octahydrocyclopenta[c]pyrrole-1-carboxylic acid (840 mg, 2.82 mmol, 1.0 eq.), methyl (S)-2-amino-3-((S)-2-oxopiperidin-3-yl)propanoate (676 mg, 3.38 mmol, 1.2 eq.), acetonitrile (20 mL) and N,N,N',N'-Tetramethylchloroformamidinium hexafluorophosphate (869 mg, 3.10 mmol, 1.1 eq.). 1-Methyl-1H-imidazole (717 mg, 8.73 mmol, 3.1 eq.) was added at 0° C. The mixture was stirred overnight at rt. The reaction was quenched with water (10 mL). The resulting solution was extracted with EA (3×30 mL). The organic layers were combined, washed with brine (2×30 mL), dried over anhydrous sodium sulfate, filtered and concentrated under reduced pressure. The residue was chromatographed on a silica gel column with EA:PE (2:1) to provide methyl (S)-2-((1S,3aR,6aS)-2-(1H-indole-2-carbonyl)octahydrocyclopenta[c]pyrrole-1-carboxamido)-3-((S)-2-oxopiperidin-3-yl)propanoate (780 mg, 53%) as a yellow semi-solid. LCMS (ESI, m/z): 481 [M+H]$^+$.

A 40 mL vial was charged with methyl (S)-2-((1S,3aR,6aS)-2-(1H-indole-2-carbonyl)octahydrocyclopenta[c]pyrrole-1-carboxamido)-3-((S)-2-oxopiperidin-3-yl)propanoate (780 mg, 1.62 mmol, 1.0 eq.) in THF (10 mL). Lithium borohydride (2.43 mL, 4.87 mmol, 3.0 eq., 2M in THF) was added dropwise at 0° C. The mixture was stirred for 30 mins, and ethanol (5 mL) was added. The mixture was stirred for 2 h at rt. The pH value of the reaction was adjusted to 3 with potassium bisulfate (1 mol/L). The resulting solution was extracted with dichloromethane (5×40 mL). The organic layers were combined, washed with brine (2×50 mL), dried over anhydrous sodium sulfate, filtered and concentrated under reduced pressure. The residue was chromatographed on a silica gel column with dichloromethane:methanol (95:5) to provide (1S,3aR,6aS)—N—((S)-1-hydroxy-3-((S)-2-oxopiperidin-3-yl)propan-2-yl)-2-(1H-indole-2-carbonyl)octahydrocyclopenta[c]pyrrole-1-carboxamide (600 mg, 76%) as a white solid. LCMS (ESI, m/z): 453 [M+H]$^+$.

A 40 mL vial was charged with (1S,3aR,6aS)—N—((S)-1-hydroxy-3-((S)-2-oxopiperidin-3-yl)propan-2-yl)-2-(1H-indole-2-carbonyl)octahydrocyclopenta[c]pyrrole-1-carboxamide (100 mg, 0.221 mmol, 1.0 eq.), dichloromethane (5 mL). Dess-Martin periodinane (187 mg, 0.442 mmol, 2.0 eq.) was added at 0° C. The mixture was stirred for 2 h at rt. The reaction was diluted with sodium thiosulfate (1M) and sat. sodium bicarbonate solution. The resulting solution was extracted with dichloromethane (6×10 mL). The organic layers was combined and concentrated under reduced pressure. The crude product was purified by prep-HPLC using the following gradient conditions: Column: XBridge Prep C18 OBD Column, 150 mm 5 μm; Mobile Phase A: Water (0.05% NH$_3$·H$_2$O), Mobile Phase B: ACN (1S,3aR,6aS)-2-(1H-indole-2-carbonyl)-N—((S)-1-oxo-3-((S)-2-oxopiperidin-3-yl)propan-2-yl)octahydrocyclopenta[c]pyrrole-1-carboxamide (24 mg, 24%) was obtained as a white solid. $^1$H NMR (400 MHz, DMSO-d$_6$, 80° C.) δ 11.25 (s, 1H), 9.44 (s, 1H), 8.47 (s, 1H), 7.61 (d, J=7.6 Hz, 1H), 7.48 (d, J=8.0 Hz, 1H), 7.18-7.22 (m, 2H), 7.04 (t, J=7.4 Hz, 1H), 6.93 (br, 1H), 4.60-4.80 (m, 1H), 4.25 (br, 1H), 4.07 (br, 1H), 3.74-3.78 (m, 1H), 2.72-3.80 (m, signal partially under H$_2$O peak), 2.28 (m, 1H), 2.10-2.12 (m, 1H), 1.36-1.99 (m, 13H). LCMS (ESI, m/z): 451 [M+H]$^+$.

Example 17

COMPOUND 16

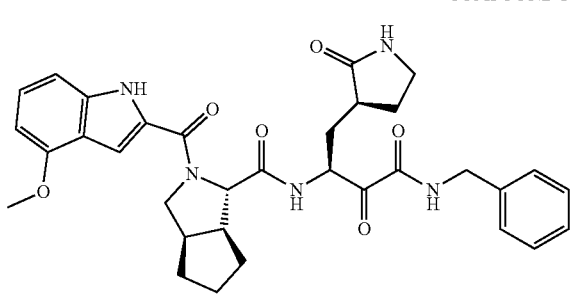

To a solution of (3S)-3-amino-N-benzyl-2-hydroxy-4-[(3S)-2-oxopyrrolidin-3-yl]butanamide hydrochloride (250 mg, 0.763 mmol, 1.0 eq.), (1S,3aR,6aS)-2-(4-methoxy-1H-indole-2-carbonyl)-hexahydro-1H-cyclopenta[c]pyrrole-1-carboxylic acid (275 mg, 0.839 mmol, 1.1 eq.), N,N,N,N-tetramethylchloroformamidinium hexafluorophosphate (235 mg, 0.839 mmol, 1.1 eq.) in acetonitrile (8 mL) was added 1-methylimidazole (313 mg, 3.81 mmol, 5.0 eq.). The mixture was stirred at 0° C., and then for overnight at rt. The reaction was quenched with water (20 mL). The mixture was extracted with EA (3×50 mL). The organic layers were combined, washed with brine (2×20 mL), dried over anhydrous sodium sulfate, filtered and concentrated under reduced pressure to afford the crude product. The crude product was purified by TLC (Mobile phase: methanol:dichloromethane=1:13; Rf=0.4; detection: UV) to provide (3S)-3-[[(1S,3aR,6aS)-2-(4-methoxy-1H-indole-2-carbonyl)-hexahydro-1H-cyclopenta[c]pyrrol-1-yl]formamido]-N-benzyl-2-hydroxy-4-[(3S)-2-oxopyrrolidin-3-yl]butanamide (70.0 mg, 13%) as a yellow solid. LCMS (ESI, m/z): 602 [M+H]⁺.

To a solution of (3S)-3-[[(1S,3aR,6aS)-2-(4-methoxy-1H-indole-2-carbonyl)-hexahydro-1H-cyclopenta[c]pyrrol-1-yl]formamido]-N-benzyl-2-hydroxy-4-[(3S)-2-oxopyrrolidin-3-yl]butanamide (60.0 mg, 0.100 mmol, 1.0 eq.) in dichloromethane (2 mL) was added Dess-Martin periodinane (84.5 mg, 0.200 mmol, 2.0 eq.). The mixture was stirred for 3 h at rt. The reaction was quenched with sat. aq. sodium bicarbonate (10 mL) and 10% sodium thiosulfate solution (10 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by prep-HPLC (Column: XBridge Prep C18 OBD Column, 19×150 mm 5 µm; Mobile Phase A: Water (0.05% NH₃·H₂O), Mobile Phase B: ACN; Flow rate: 25 mL/min; Gradient: 25 B to 52 B in 7 min; 210 nm; RT1 (min): 6.32) to provide 3-[[(1S,3aR,6aS)-2-(4-methoxy-1H-indole-2-carbonyl)-hexahydro-1H-cyclopenta[c]pyrrol-1-yl]formamido]-N-benzyl-2-oxo-4-[(3S)-2-oxopyrrolidin-3-yl]butanamide (9.3 mg, 15%) as an off-white solid. LCMS (ESI, m/z): 600 [M+H]⁺.

Example 18

COMPOUND 17

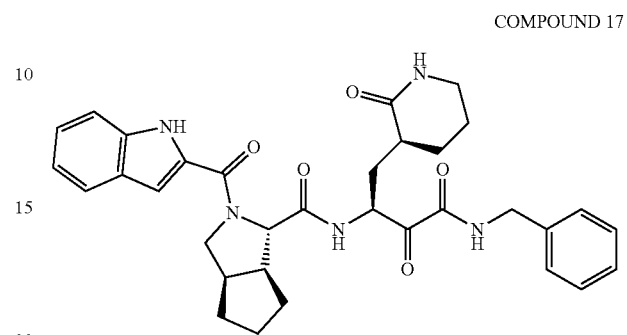

A 40 mL vial was charged with (1S,3aR,6aS)-2-(1H-indole-2-carbonyl)-N—((S)-1-oxo-3-((S)-2-oxopiperidin-3-yl)propan-2-yl)octahydrocyclopenta[c]pyrrole-1-carboxamide (150 mg, 0.333 mmol, 1.0 eq.) in dichloromethane (2 mL). (Isocyanomethyl)benzene (78.0 mg, 0.666 mmol, 2.0 eq.) in dichloromethane (1 mL) was added dropwise at 0° C. Pyridine (105 mg, 1.33 mmol, 4.0 eq.) in dichloromethane (1 mL) was added dropwise at 0° C. Trifluoroacetic acid (114 mg, 0.999 mmol, 3.0 eq.) in dichloromethane (1 mL) was added dropwise at 0° C. The reaction was stirred for 50 min at 0° C., and then stirred overnight at rt. The reaction was concentrated under reduced pressure. The residue was purified by C18 column with acetonitrile:water (0.05% TFA) (30/70) to provide (1S,3aR,6aS)—N-((2S)-4-(benzylamino)-3-hydroxy-4-oxo-1-((S)-2-oxopiperidin-3-yl)butan-2-yl)-2-(1H-indole-2-carbonyl)octahydrocyclopenta[c]pyrrole-1-carboxamide (30 mg) as a white solid. LCMS (ESI, m/z): 586 [M+H]⁺.

A 8 mL vial was charged with (1S,3aR,6aS)—N-((2S)-4-(benzylamino)-3-hydroxy-4-oxo-1-((S)-2-oxopiperidin-3-yl)butan-2-yl)-2-(1H-indole-2-carbonyl)octahydrocyclopenta[c]pyrrole-1-carboxamide (30.0 mg, 0.051 mmol, 1.0 eq.), dichloromethane (2 mL). Dess-Martin periodinane (43.4 mg, 0.102 mmol, 2.0 eq.) was added at 0° C. The reaction was stirred for 2 h at rt. The reaction was diluted with sodium thiosulfate (1M) and sat. sodium bicarbonate solution. The resulting solution was extracted with dichloromethane (6×10 mL). The organic layers was combined and concentrated under reduced pressure. The crude product was purified by prep-HPLC using the following gradient conditions: Column: XBridge Prep Phenyl OBD Column, 150 mm 5 m 13 nm; Mobile Phase A: Water (0.05% NH₃·H₂O), Mobile Phase B: ACN; Purification resulted in (1S,3aR,6aS)—N-(4-(benzylamino)-3,4-dioxo-1-((S)-2-oxopiperidin-3-yl)butan-2-yl)-2-(1H-indole-2-carbonyl)octahydrocyclopenta[c]pyrrole-1-carboxamide (1.3 mg, 4.1%) as a white solid. LCMS (ESI, m/z): 584 [M+H]⁺.

Example 19

COMPOUND 18

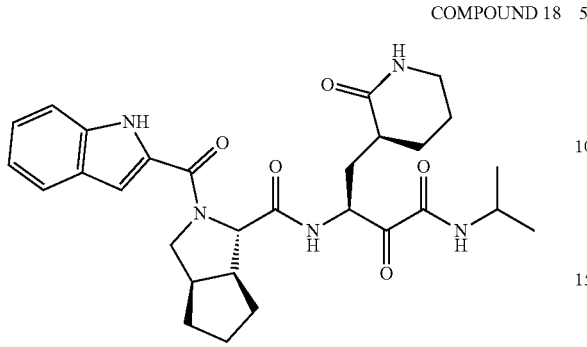

A 40 mL vial was charged with (1S,3aR,6aS)-2-(1H-indole-2-carbonyl)-N—((S)-1-oxo-3-((S)-2-oxopiperidin-3-yl)propan-2-yl)octahydrocyclopenta[c]pyrrole-1-carboxamide (70.0 mg, 0.155 mmol, 1.0 eq.) in dichloromethane (1 mL). 2-Isocyanopropane (21.5 mg, 0.311 mmol, 2.0 eq.) in dichloromethane (1 mL) was added dropwise at 0° C. Pyridine (49.2 mg, 0.621 mmol, 4.0 eq.) in dichloromethane (1 mL) was added dropwise at 0° C. Trifluoroacetic acid (53.2 mg, 0.466 mmol, 3.0 eq.) in dichloromethane (1 mL) was added dropwise at 0° C. The reaction was stirred for 50 min at 0° C., and then stirred overnight at rt. The reaction was quenched with water (5 mL). The resulting solution was extracted with dichloromethane (3×10 mL). The organic layers were combined, washed with brine (2×5 mL), dried over anhydrous sodium sulfate, filtered and concentrated under reduced pressure. The residue was chromatographed on a silica gel column with dichloromethane:methanol (93:7) to provide (1S,3aR,6aS)—N-((2S)-3-hydroxy-4-(isopropylamino)-4-oxo-1-((S)-2-oxopiperidin-3-yl)butan-2-yl)-2-(1H-indole-2-carbonyl)octahydrocyclopenta[c]pyrrole-1-carboxamide (40 mg, 40%) as an off-white solid. LCMS (ESI, m/z): 538 [M+H]$^+$.

A 8 mL vial was charged with (1S,3aR,6aS)—N-((2S)-3-hydroxy-4-(isopropylamino)-4-oxo-1-((S)-2-oxopiperidin-3-yl)butan-2-yl)-2-(1H-indole-2-carbonyl)octahydrocyclopenta[c]pyrrole-1-carboxamide (30.0 mg, 0.056 mmol, 1.0 eq.), dichloromethane (2 mL). Dess-Martin periodinane (47.3 mg, 0.112 mmol, 2.0 eq.) was added at 0° C. The reaction was stirred for 2 h at rt. The reaction was diluted with sodium thiosulfate (1M) and sat. sodium bicarbonate solution. The resulting solution was extracted with dichloromethane (6×10 mL). The organic layers was combined and concentrated under reduced pressure. The crude product was purified by prep-HPLC using the following gradient conditions: Column: XBridge Prep C18 OBD Column, 19×150 mm Sum; Mobile Phase A: Water (0.05% NH$_3$·H$_2$O), Mobile Phase B: ACN; Flow rate: 25 mL/min; Gradient: 25 B to 50 B in 7 min, 210 nm; RT1 (min): 6.32. Purification resulted (1S,3aR,6aS)-2-(1H-indole-2-carbonyl)-N-(4-(isopropylamino)-3,4-dioxo-1-((S)-2-oxopiperidin-3-yl)butan-2-yl)octahydrocyclopenta[c]pyrrole-1-carboxamide (7.8 mg, 25%) as a white solid. LCMS (ESI, m/z): 536 [M+H]$^+$.

Example 20

COMPOUND 19

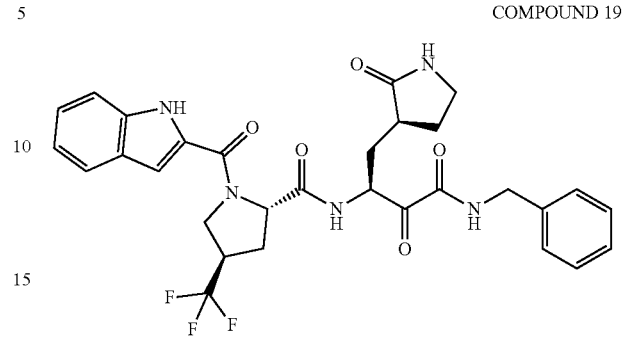

To a mixture of (2S,4R)-1-(tert-butoxycarbonyl)-4-(trifluoromethyl)pyrrolidine-2-carboxylic acid (190 mg, 0.671 mmol, 1.1 eq.), o-(7-Azabenzotriazol-1-yl)-N,N,N',N'-tetramethyluronium hexafluorophosphate (278 mg, 0.732 mmol, 1.2 eq.) and N-ethyl-N-isopropylpropan-2-amine (315 mg, 2.44 mmol, 4.0 eq.) in N,N-dimethylformamide (5 mL) was stirred for 20 min at 0° C. (3S)-3-amino-N-benzyl-2-hydroxy-4-[(3S)-2-oxopyrrolidin-3-yl]butanamide hydrochloride (200 mg, 0.610 mmol, 1.0 eq.) was added. The mixture was stirred for 2 h at rt, and the reaction was quenched with water (100 mL). The mixture was then extracted with EA (3×100 mL). The organic layers were combined, washed with brine (2×100 mL), dried over anhydrous sodium sulfate, filtered and concentrated under reduced pressure to afford the crude product. The crude product was diluted with dichloromethane (20 mL) and a slurry was made with 100~200 silicagel mesh (2 g) loaded onto a column after removing the dichloromethane. The sample was purified by column chromatography (Column size 5×24 cm, column volume: 300 mL, silicagel size (100~200 mesh) quantity: 120 g) and eluted with methanol:dichloromethane (0%~12% over 30 min). The collected fractions: 6%-11% methanol:dichloromethane fractions were chosen as the pure fractions, and those fractions were combined and concentrated under reduced pressure to provide tert-butyl (2S,4R)-2-[[(2S)-1-(benzylcarbamoyl)-1-hydroxy-3-[(3S)-2-oxopyrrolidin-3-yl]propan-2-yl]carbamoyl]-4-(trifluoromethyl)pyrrolidine-1-carboxylate (190 mg, 50%) as a light yellow solid. LCMS (ESI, m/z): 557 [M+H]$^+$.

To a mixture of tert-butyl (2S,4R)-2-[[(2S)-1-(benzylcarbamoyl)-1-hydroxy-3-[(3S)-2-oxopyrrolidin-3-yl]propan-2-yl]carbamoyl]-4-(trifluoromethyl)pyrrolidine-1-carboxylate (190 mg, 0.341 mmol, 1.0 eq.) in dichloromethane (4 mL) was added trifluoroacetic acid (1 mL). The mixture was stirred for 2 h at rt and then concentrated under reduced pressure to provide (3S)—N-benzyl-2-hydroxy-4-[(3S)-2-oxopyrrolidin-3-yl]-3-[[(2S,4R)-4-(trifluoromethyl)pyrrolidin-2-yl]formamido]butanamide (210 mg, crude) as a brown solid. LCMS (ESI, m/z): 457 [M+H]$^+$.

To a mixture of indole-2-carboxylic acid (81.6 mg, 0.506 mmol, 1.1 eq.), o-(7-Azabenzotriazol-1-yl)-N,N,N',N'-tetramethyluronium hexafluorophosphate (209 mg, 0.552 mmol, 1.2 eq.) and N-ethyl-N-isopropylpropan-2-amine (297 mg, 2.30 mmol, 5.0 eq.) in N,N-dimethylformamide (5 mL) was stirred for 20 min at 0° C. Then (3S)—N-benzyl-2-hydroxy-4-[(3S)-2-oxopyrrolidin-3-yl]-3-[[(2S,4R)-4-(trifluoromethyl)pyrrolidin-2-yl]formamido]butanamide (210 mg, 0.460 mmol, 1.0 eq.) was added. The mixture was stirred for 2 h at rt, and the reaction was quenched with water (100 mL). The mixture was extracted with EA (3×100 mL). The organic layers were combined, washed with brine (2×100 mL), dried over anhydrous sodium sulfate, filtered and concentrated under reduced pressure to afford the crude product. The crude product was diluted with dichloromethane (20 mL) and a slurry was made with 100~200 silicagel mesh (2 g) loaded onto a column after removing the dichloromethane. The sample was purified by column chromatography (Column size 5×24 cm, column volume: 300 mL, silicagel size (100~200 mesh) quantity: 120 g) and eluted with methanol:dichloromethane (0%~12% over 30 min). The collected fractions: 5%-9% methanol:dichloromethane fractions were chosen as the pure fractions, and those fractions were combined and concentrated under reduced pressure to provide (3S)—N-benzyl-2-hydroxy-3-[[(2S,4R)-1-(1H-indole-2-carbonyl)-4-(trifluoromethyl)pyrrolidin-2-yl]formamido]-4-[(3S)-2-oxopyrrolidin-3-yl]butanamide (180 mg, 60%) as a light brown solid. LCMS (ESI, m/z): 600 [M+H]$^+$.

To a mixture of (3S)—N-benzyl-2-hydroxy-3-[[(2S,4R)-1-(1H-indole-2-carbonyl)-4-(trifluoromethyl)pyrrolidin-2-yl]formamido]-4-[(3S)-2-oxopyrrolidin-3-yl]butanamide (100 mg, 0.167 mmol, 1.0 eq.) in dichloromethane (5 mL) was added Dess-Martin periodinane (141 mg, 0.334 mmol, 2.0 eq.) at 0° C. The mixture was stirred for 2 h at rt, and the reaction was quenched with sat. aq. sodium bicarbonate (10 mL) and 10% sodium thiosulfate solution (10 mL). The mixture was extracted with EA (3×30 mL). The organic layers were combined, washed with brine (2×30 mL), dried over anhydrous sodium sulfate, filtered and concentrated under reduced pressure to afford the crude product. The crude product (100 mg) was purified by prep-HPLC with the following conditions (Column: XBridge Prep C18 OBD Column, 19×150 mm 5 μm; Mobile Phase A: Water (0.05% NH$_3$·H$_2$O), Mobile Phase B: ACN; to afford N-benzyl-3-[[(2S,4R)-1-(1H-indole-2-carbonyl)-4-(trifluoromethyl)pyrrolidin-2-yl]formamido]-2-oxo-4-[(3S)-2-oxopyrrolidin-3-yl]butanamide (29.6 mg, 28%) as a light pink solid. LCMS (ESI, m/z): 598 [M+H]$^+$.

Example 21

COMPOUND 20

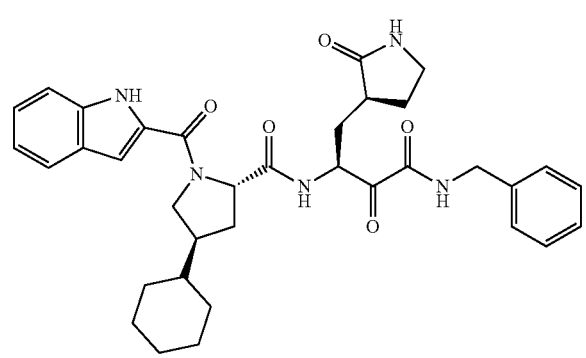

Compound 20 was prepared similarly as described for Compound 19, using (2S,4S)-1-(tert-butoxycarbonyl)-4-cyclohexylpyrrolidine-2-carboxylic acid in place of (2S,4R)-1-(tert-butoxycarbonyl)-4-(trifluoromethyl)pyrrolidine-2-carboxylic acid. LCMS (ESI, m/z): 612 [M+H]$^+$.

Example 22

COMPOUND 21

Compound 21 was prepared similarly as described for Compound 19, using (2S,4R)-1-(tert-butoxycarbonyl)-4-(prop-2-en-1-yl)pyrrolidine-2-carboxylic acid in place of (2S,4R)-1-(tert-butoxycarbonyl)-4-(trifluoromethyl)pyrrolidine-2-carboxylic acid. LCMS (ESI, m/z): 570 [M+H]$^+$.

Example 23

COMPOUND 22

Compound 22 was prepared similarly as described for Compound 19 using (3R,6S)-5-(tert-butoxycarbonyl)-1,1-difluoro-5-azaspiro[2.4]heptane-6-carboxylic acid in place of (2S,4R)-1-(tert-butoxycarbonyl)-4-(trifluoromethyl)pyrrolidine-2-carboxylic acid. LCMS (ESI, m/z): 592 [M+H]$^+$.

Example 24

COMPOUND 23

Compound 23 was prepared similarly as described for Compound 19 using (3S,6S)-5-(tert-butoxycarbonyl)-1,1-difluoro-5-azaspiro[2.4]heptane-6-carboxylic acid in place of (2S,4R)-1-(tert-butoxycarbonyl)-4-(trifluoromethyl)pyrrolidine-2-carboxylic acid. LCMS (ESI, m/z): 592 [M+H]+.

Example 25

COMPOUND 24

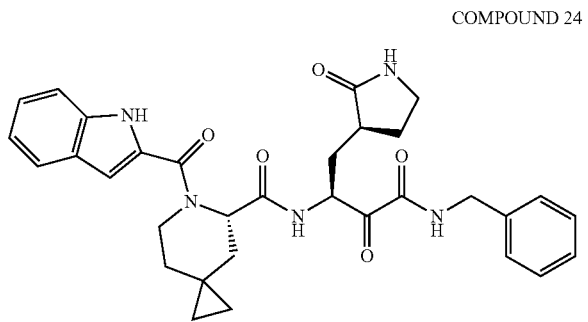 [SMILES: O=C(NCc1ccccc1)C(=O)[C@H](C[C@@H]1CCNC1=O)NC(=O)[C@@H]1CC2(CCN1C(=O)c1cc3ccccc3[nH]1)CC2]

Compound 24 was prepared similarly as described for Compound 19 using (5S)-6-(tert-butoxycarbonyl)-6-azaspiro[2.5]octane-5-carboxylic acid in place of (2S,4R)-1-(tert-butoxycarbonyl)-4-(trifluoromethyl)pyrrolidine-2-carboxylic acid. LCMS (ESI, m/z): 570 [M+H]+.

Example 26

COMPOUND 25

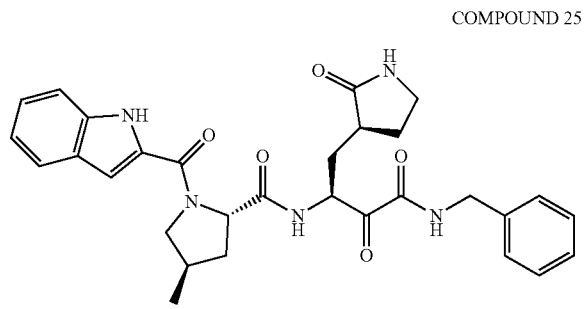 [SMILES: C[C@@H]1C[C@@H](C(=O)N[C@@H](C[C@@H]2CCNC2=O)C(=O)C(=O)NCc2ccccc2)N(C(=O)c2cc3ccccc3[nH]2)C1]

Compound 25 was prepared similarly as described for Compound 19 using (2S,4R)-1-(tert-butoxycarbonyl)-4-methylpyrrolidine-2-carboxylic acid in place of (2S,4R)-1-(tert-butoxycarbonyl)-4-(trifluoromethyl)pyrrolidine-2-carboxylic acid. LCMS (ESI, m/z): 544 [M+H]+.

Example 27

COMPOUND 26

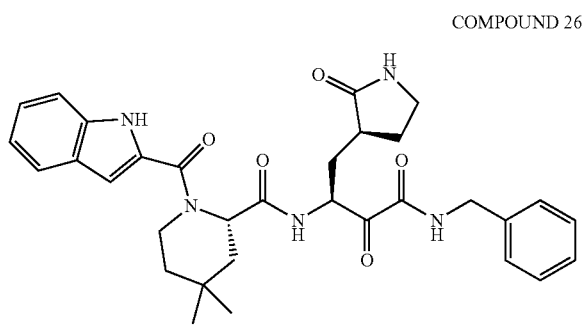 [SMILES: CC1(C)CCN(C(=O)c2cc3ccccc3[nH]2)[C@H](C(=O)N[C@@H](C[C@@H]2CCNC2=O)C(=O)C(=O)NCc2ccccc2)C1]

To a solution of (5S)-6-(tert-butoxycarbonyl)-6-azaspiro[2.5]octane-5-carboxylic acid (250 mg, 0.98 mmol, 1.0 eq.) in EA (3 mL) and acetic acid (3 mL) was added PtO2 (178 mg, 0.78 mmol, 0.8 eq.). Hydrogen (3 atm) was introduced. The mixture was stirred overnight at rt. The mixture was filtered, and the filtrate was collected and concentrated under reduced pressure. The residue was chromatographed on a C18 column with MeCN:water (2:3) to provide (2S)-1-(tert-butoxycarbonyl)-4,4-dimethylpiperidine-2-carboxylic acid (180 mg, 61%) as a white solid. LCMS (ESI, m/z): 258 [M+H]+.

To a solution of (2S)-1-(tert-butoxycarbonyl)-4,4-dimethylpiperidine-2-carboxylic acid (155 mg, 0.60 mmol, 1.0 eq.) in N,N-dimethylformamide (4 mL) was added N,N,N',N'-Tetramethyl-O-(7-azabenzotriazol-1-yl)uronium hexafluorophospate (344 mg, 0.91 mmol, 1.5 eq.) and N,N-diisopropylethylamine (390 mg, 3.02 mmol, 5.0 eq.). The mixture was stirred at 0° C. for 30 min. (3S)-3-amino-N-benzyl-2-hydroxy-4-((S)-2-oxopyrrolidin-3-yl)butanamide (107 mg, 0.66 mmol, 1.1 eq.) was added. The mixture was stirred at 0° C. for 1 h, and the reaction was quenched with water (4 mL). The mixture was extracted with EA (3×10 mL). The organic layers were combined, dried over anhydrous sodium sulfate, filtered and concentrated under reduced pressure. The residue was chromatographed on a silica gel column with methanol:dichloromethane (1:18) to provide tert-butyl (2S)-2-(((2S)-4-(benzylamino)-3-hydroxy-4-oxo-1-((S)-2-oxopyrrolidin-3-yl)butan-2-yl)carbamoyl)-4,4-dimethylpiperidine-1-carboxylate (180 mg, 57%) as a yellow solid. LCMS (ESI, m/z): 531 [M+H]+.

To a solution of tert-butyl (2S)-2-(((2S)-4-(benzylamino)-3-hydroxy-4-oxo-1-((S)-2-oxopyrrolidin-3-yl)butan-2-yl)carbamoyl)-4,4-dimethylpiperidine-1-carboxylate (270 mg, 0.51 mmol, 1.0 eq.) in dichloromethane (6 mL) was added trifluoroacetic acid (2 mL). The mixture was stirred at rt for 2 h and then concentrated under reduced pressure to provide (2S)—N-((2S)-4-(benzylamino)-3-hydroxy-4-oxo-1-((S)-2-oxopyrrolidin-3-yl)butan-2-yl)-4,4-dimethylpiperidine-2-carboxamide (260 mg, crude) as a colorless oil. LCMS (ESI, m/z): 431 [M+H]+.

To a solution of 1H-indole-2-carboxylic acid (107 mg, 0.66 mmol, 1.1 eq.) in N,N-dimethylformamide (4 mL) was added N,N-diisopropylethylamine (390 mg, 3.02 mmol, 5.0 eq.) and N,N,N',N'-Tetramethyl-O-(7-azabenzotriazol-1-yl) uronium hexafluorophospate (344 mg, 0.91 mmol, 1.5 eq.). The mixture was stirred at 0° C. for 30 min. (2S)—N-((2S)-4-(benzylamino)-3-hydroxy-4-oxo-1-((S)-2-oxopyrrolidin-3-yl)butan-2-yl)-4,4-dimethylpiperidine-2-carboxamide (260 mg, 0.6 mmol, 1.0 eq.) was added. The mixture was stirred at rt for 2 h, and the reaction was quenched with water (4 mL). The mixture was extracted with EA (3×6 mL). The organic layers were combined, dried over anhydrous sodium sulfate, filtered and concentrated under reduced pressure. The residue was chromatographed on a silica gel column with methanol:dichloromethane (1:18) to provide (2S)—N-((2S)-4-(benzylamino)-3-hydroxy-4-oxo-1-((S)-2-oxopyrrolidin-3-yl)butan-2-yl)-1-(1H-indole-2-carbonyl)-4,4-dimethylpiperidine-2-carboxamide (150 mg, 49%) as a yellow solid. LCMS (ESI, m/z): 574 [M+H]+.

To a solution of (2S)—N-((2S)-4-(benzylamino)-3-hydroxy-4-oxo-1-((S)-2-oxopyrrolidin-3-yl)butan-2-yl)-1-(1H-indole-2-carbonyl)-4,4-dimethylpiperidine-2-carboxamide (100 mg, 0.17 mmol, 1.0 eq.) in DMSO (10 mL) was added IBX (97.6 mg, 0.35 mmol, 2.0 eq.). The mixture was stirred overnight at rt, and the reaction was quenched with sodium bicarbonate solution (2 mL). The resulting solution was extracted with EA (3×10 mL). The organic layers were combined, dried over anhydrous sodium sulfate, filtered and concentrated under reduced pressure. The residue was purified by pre-TLC with methanol:dichloromethane (1:18) to provide (2S)—N-(4-(benzylamino)-3,4-dioxo-1-((S)-2-oxopyrrolidin-3-yl)butan-2-yl)-1-(1H-indole-2-carbonyl)-4,4-dimethylpiperidine-2-carboxamide (18 mg, 24%) as a white solid. LCMS (ESI, m/z): 572 [M+H]⁺.

Example 28

COMPOUND 27A AND 27

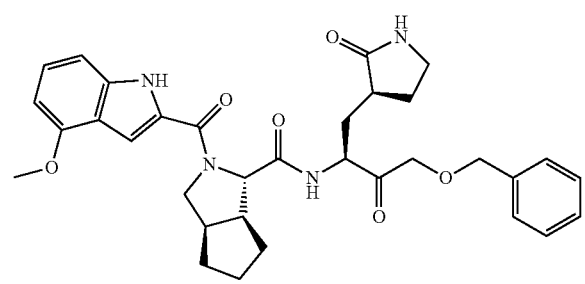

27A

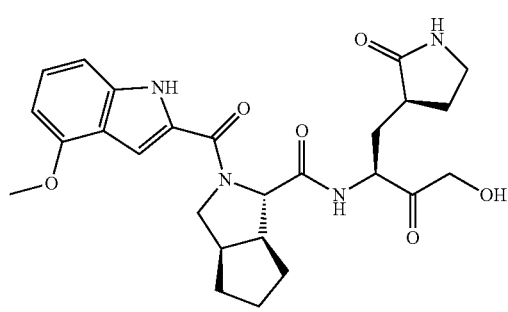

27

To a mixture of (3S)-3-[(2S)-2-amino-4-(benzyloxy)-3-oxobutyl]pyrrolidin-2-one hydrochloride (342 mg, 1.09 mmol, 1.0 eq.) and (1S,3aR,6aS)-2-(4-methoxy-1H-indole-2-carbonyl)-hexahydro-1H-cyclopenta[c]pyrrole-1-carboxylic acid (359 mg, 1.09 mmol, 1.0 eq.) in N,N-dimethylformamide (5 mL) was added o-(7-azabenzotriazol-1-yl)-N,N,N',N'-tetramethyluronium hexafluorophosphate (499 mg, 1.312 mmol, 1.2 eq.) and N-ethyl-N-isopropylpropan-2-amine (424 mg, 3.28 mmol, 3.0 eq.) at 0° C. The mixture was stirred for 1 h at rt under nitrogen. The reaction was quenched with water (10 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by TLC (Mobile phase: methanol:dichloromethane=1:13; Rf=0.4; detection: UV) to provide (1S,3aR,6aS)—N-[(2S)-4-(benzyloxy)-3-oxo-1-[(3S)-2-oxopyrrolidin-3-yl]butan-2-yl]-2-(4-methoxy-1H-indole-2-carbonyl)-hexahydro-1H-cyclopenta[c]pyrrole-1-carboxamide (27A, 145 mg, 21%) as a yellow solid. ¹H NMR (400 MHz, 353K, DMSO-d₆) δ 11.37 (s, 1H), 8.30-8.80 (m, 1H), 7.35-7.60 (m, 1H), 7.20-7.38 (m, 5H), 7.00-7.15 (m, 2H), 6.75-6.99 (m, 1H), 6.51 (d, J=6.8 Hz, 1H), 4.00-5.02 (m, 7H), 3.87 (s, 3H), 3.55-3.80 (m, 1H), 2.86-3.16 (m, 2H), 2.55-2.85 (m, 2H), 2.30-2.40 (m, 1H), 1.35-2.20 (m, 10H). LC-MS (ESI, m/z): 587 [M+H]⁺. LCMS (ESI, m/z): 587 [M+H]⁺.

To a mixture of (1S,3aR,6aS)—N-[(2S)-4-(benzyloxy)-3-oxo-1-[(3S)-2-oxopyrrolidin-3-yl]butan-2-yl]-2-(4-methoxy-1H-indole-2-carbonyl)-hexahydro-1H-cyclopenta[c]pyrrole-1-carboxamide (140 mg, 0.239 mmol, 1.0 eq.) in ethanol (5 mL) was added 10% Pd/C (140 mg). The mixture was stirred overnight at rt under H₂ atmosphere. The mixture was filtered through a celite pad and washed with ethanol (2×5 mL). The filtrate was concentrated under reduced pressure to afford the crude product. The crude product was purified by TLC (Mobile phase: methanol:dichloromethane=1:14; Rf=0.4; detection: UV) to provide (1S,3aR,6aS)—N-[(2S)-4-hydroxy-3-oxo-1-[(3S)-2-oxopyrrolidin-3-yl]butan-2-yl]-2-(4-methoxy-1H-indole-2-carbonyl)-hexahydro-1H-cyclopenta[c]pyrrole-1-carboxamide (43.9 mg, 34%) as a white solid. ¹H NMR (400 MHz, DMSO-d₆, 353K) δ 11.22 (s, 1H), 8.38 (br, 1H), 7.29 (s, 1H), 7.00-7.15 (m, 2H), 6.87 (s, 1H), 6.49 (d, J=7.6 Hz, 1H), 4.50-4.70 (m, 1H), 4.35-4.49 (m, 1H), 4.10-4.30 (m, 2H), 3.90-4.08 (m, 1H), 3.75-3.89 (m, 3H), 3.60-3.74 (m, 1H), 2.82-3.00 (m, signal under H₂O peak), 2.60-2.80 (m, 2H), 2.30-2.43 (m, 1H), 1.45-2.00 (m, 10H). LCMS (ESI, m/z): 497 [M+H]⁺.

Example 29

COMPOUND 28

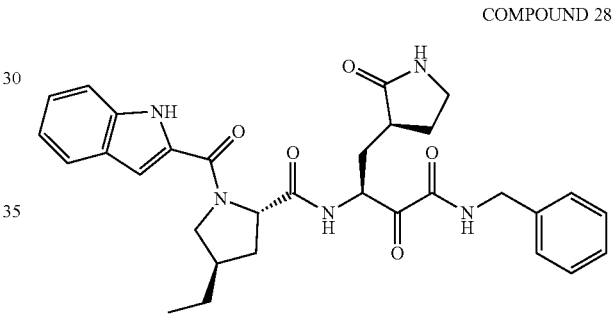

Compound 28 was prepared similarly as described for Compound 26 using (2S,4R)-1-(tert-butoxycarbonyl)-4-ethylpyrrolidine-2-carboxylic acid in place of (2S)-1-(tert-butoxycarbonyl)-4,4-dimethylpiperidine-2-carboxylic acid. LCMS (ESI, m/z): 558 [M+H]⁺.

(2S,4R)-1-(tert-butoxycarbonyl)-4-ethylpyrrolidine-2-carboxylic acid: To a mixture of 1-tert-butyl 2-methyl (2S,4S)-4-ethenylpyrrolidine-1,2-dicarboxylate (Mulamreddy et al., J. Org. Chem. (2018) 83(21):13580-13586) (500 mg, 1.96 mmol, 1.0 eq.) in methanol (10 mL) was added Pd/C (200 mg). The mixture was stirred for 4 h at rt under H₂. The mixture was filtered through a celite pad and washed with methanol (2×5 mL). The filtrate was concentrated under reduced pressure to afford crude 1-tert-butyl 2-methyl (2S,4R)-4-ethylpyrrolidine-1,2-dicarboxylate (500 mg, crude) as light yellow oil. LCMS (ESI, m/z): 158 [M−100+H]⁺.

To a mixture of 1-tert-butyl 2-methyl (2S,4R)-4-ethylpyrrolidine-1,2-dicarboxylate (500 mg, 1.94 mmol, 1.0 eq.) in 1,4-dioxane (5 mL) was added hydrogen chloride (5 mL, 6 M in water). The mixture was stirred for 2 h at 80° C. and concentrated under reduced pressure to afford (2S,4R)-4-ethylpyrrolidine-2-carboxylic acid (278 mg, crude) as a light yellow oil. LCMS (ESI, m/z): 144 [M+H]⁺.

To a mixture of (2S,4R)-4-ethylpyrrolidine-2-carboxylic acid (278 mg, 1.942 mmol, 1.00 eq.) in dichloromethane (10 mL) was added di-tert-butyl dicarbonate (847 mg, 3.88 mmol, 2.0 eq.) and triethylamine (589 mg, 5.83 mmol, 3.0 eq.). The mixture was stirred overnight at rt and concentrated under reduced pressure to afford (2S,4R)-1-(tert-butoxycarbonyl)-4-ethylpyrrolidine-2-carboxylic acid (470 mg, crude) as a light yellow oil. LCMS (ESI, m/z): 188 [M−56+H]⁺.

Example 30

COMPOUND 29

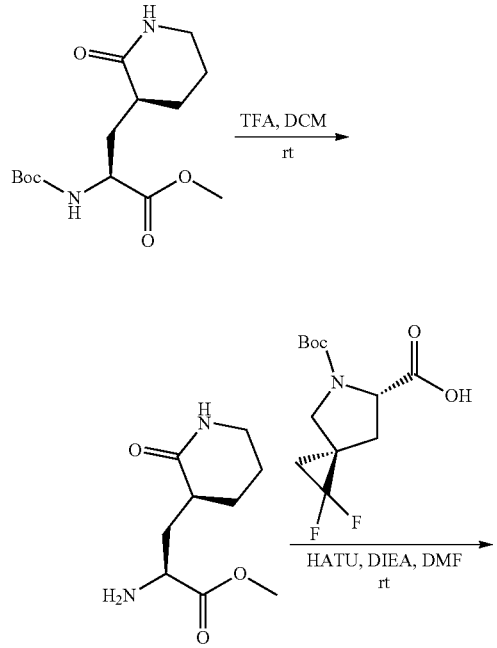

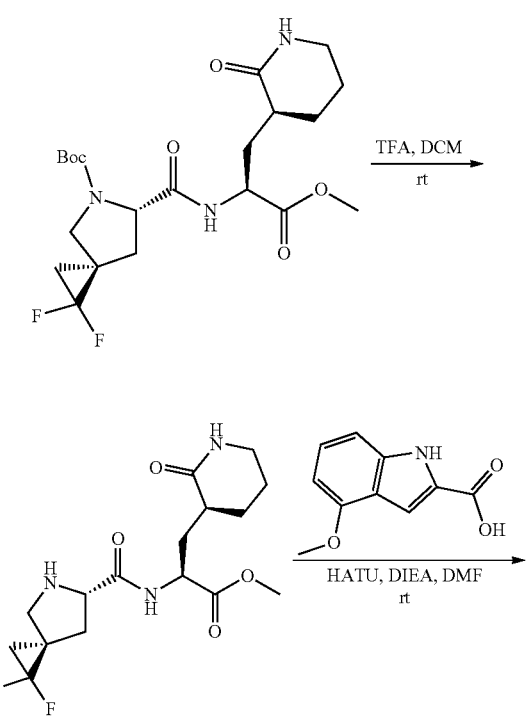

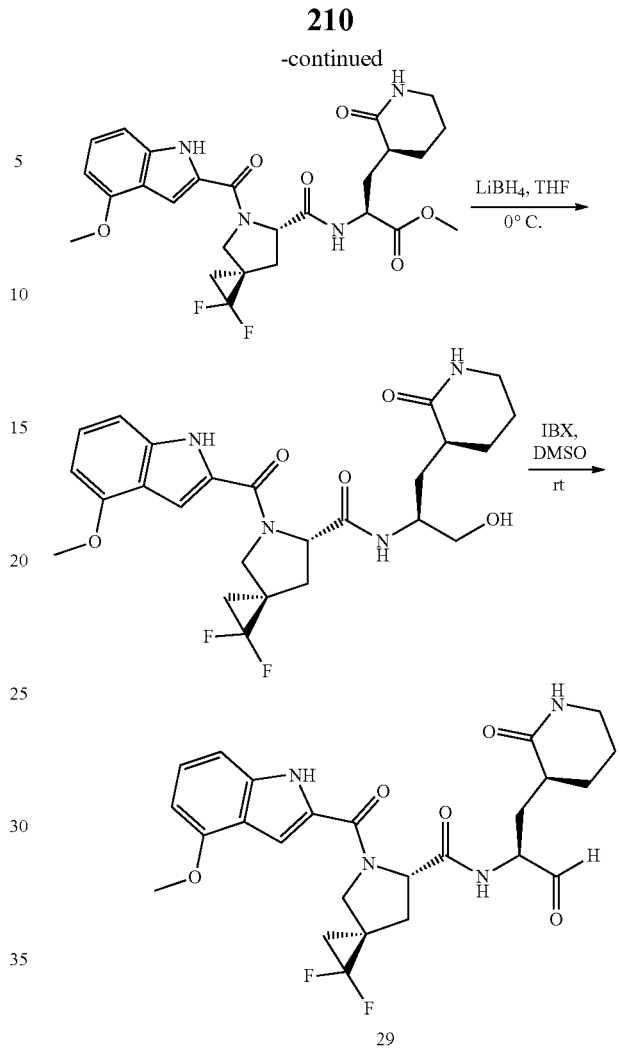

To a solution of methyl (2S)-2-[(tert-butoxycarbonyl)amino]-3-[(3S)-2-oxopiperidin-3-yl]propanoate (960 mg, 3.2 mmol, 1.0 eq.) in dichloromethane (12 mL) was added trifluoroacetic acid (4 mL). The mixture was stirred at rt for 1 h and concentrated under reduced pressure to provide methyl (2S)-2-amino-3-[(3S)-2-oxopiperidin-3-yl]propanoate (780 mg, 85%) as an orange oil. LCMS (ESI, m/z): 201 [M+H]⁺.

To a solution of (3S,6S)-5-(tert-butoxycarbonyl)-1,1-difluoro-5-azaspiro[2.4]heptane-6-carboxylic acid (780 mg, 2.81 mmol, 1.0 eq.) in N,N-dimethylformamide (10 mL) was added N,N,N',N'-Tetramethyl-O-(7-azabenzotriazol-1-yl)uronium hexafluorophospate (1.6 g, 4.22 mmol, 1.5 eq.) and N,N-diisopropylethylamine (2.18 g, 16.9 mmol, 6.0 eq.). The mixture was stirred at 0° C. for 30 min. Methyl (2S)-2-amino-3-[(3S)-2-oxopiperidin-3-yl]propanoate (619.63 mg, 3.094 mmol, 1.1 eq.) was added. The mixture was stirred at 0° C. for 1 h, and the reaction was quenched with water (15 mL). The mixture was extracted with EA (3×20 mL). The organic layers were combined, dried over anhydrous sodium sulfate, filtered and concentrated under reduced pressure. The residue was chromatographed on a silica gel column with methanol:dichloromethane (1:22) to provide tert-butyl (3S,6S)-1,1-difluoro-6-{[(2S)-1-methoxy-1-oxo-3-[(3S)-2-oxopiperidin-3-yl]propan-2-yl]carbamoyl}-5-azaspiro[2.4]heptane-5-carboxylate (1.07 g, 66%) as a yellow solid. LCMS (ESI, m/z): 460 [M+H]⁺.

To a solution of tert-butyl (3S,6S)-1,1-difluoro-6-{[(2S)-1-methoxy-1-oxo-3-[(3S)-2-oxopiperidin-3-yl]propan-2-yl]carbamoyl}-5-azaspiro[2.4]heptane-5-carboxylate (1.07 g, 2.33 mmol, 1.0 eq.) in dichloromethane (12 mL) was added trifluoroacetic acid (4 mL). The mixture was stirred at rt for 1 h and concentrated under reduced pressure to provide methyl (2S)-2-{[(3S,6S)-1,1-difluoro-5-azaspiro[2.4]heptan-6-yl]formamido}-3-[(3S)-2-oxopiperidin-3-yl]propanoate (1.0 g, 83%) as an orange oil. LCMS (ESI, m/z): 360 [M+H]+.

To a solution of 4-methoxy-1H-indole-2-carboxylic acid (486 mg, 2.54 mmol, 1.1 eq.) in N,N-dimethylformamide (12 mL) was added N,N,N',N'-Tetramethyl-O-(7-azabenzotriazol-1-yl)uronium hexafluorophospate (1.32 mg, 3.47 mmol, 1.5 eq.) and N,N-diisopropylethylamine (1.79 mg, 13.9 mmol, 6.0 eq.). The mixture was stirred at 0° C. for 30 min. Methyl (2S)-2-{[(3S,6S)-1,1-difluoro-5-azaspiro[2.4]heptan-6-yl]formamido}-3-[(3S)-2-oxopiperidin-3-yl]propanoate (830 mg, 2.31 mmol, 1.0 eq.) was added. The mixture was stirred at 0° C. for 1 h, and the reaction was quenched with water (15 mL). The mixture was extracted with EA (3×20 mL). The organic layers were combined, dried over anhydrous sodium sulfate, filtered and concentrated under reduced pressure. The residue was chromatographed on a silica gel column with methanol:dichloromethane (1:18) to provide methyl (2S)-2-{[(3S,6S)-1,1-difluoro-5-(4-methoxy-1H-indole-2-carbonyl)-5-azaspiro[2.4]heptan-6-yl]formamido}-3-[(3S)-2-oxopiperidin-3-yl]propanoate (950 mg, 62%) as a yellow solid. LCMS (ESI, m/z): 533 [M+H]+.

To a solution of methyl (2S)-2-{[(3S,6S)-1,1-difluoro-5-(4-methoxy-1H-indole-2-carbonyl)-5-azaspiro[2.4]heptan-6-yl]formamido}-3-[(3S)-2-oxopiperidin-3-yl]propanoate (950 mg, 1.78 mmol, 1.0 eq.) in THF (10 mL) was added lithium borohydride (1.79 mL, 2M in tetrahydrofuran, 3.57 mmol, 2.0 eq.) was added slowly at 0° C. The mixture was stirred for 1.5 h at 0° C. The reaction was quenched with water (8 mL), and the mixture was extracted with EA (3×15 mL). The organic layers were combined, dried over anhydrous sodium sulfate, filtered and concentrated under reduced pressure. The residue was chromatographed on a silica gel column with methanol:dichloromethane (1:16) to provide (3S,6S)-1,1-difluoro-N-[(2S)-1-hydroxy-3-[(3S)-2-oxopiperidin-3-yl]propan-2-yl]-5-(4-methoxy-1H-indole-2-carbonyl)-5-azaspiro[2.4]heptane-6-carboxamide (700 mg, 70%) as a white solid. LCMS (ESI, m/z): 505 [M+H]+.

To a solution of (3S,6S)-1,1-difluoro-N-[(2S)-1-hydroxy-3-[(3S)-2-oxopiperidin-3-yl]propan-2-yl]-5-(4-methoxy-1H-indole-2-carbonyl)-5-azaspiro[2.4]heptane-6-carboxamide (60 mg, 0.12 mmol, 1.0 eq.) in dimethyl sulfoxide (2 mL) was added IBX (66.6 mg, 0.24 mmol, 2.0 eq.). The mixture was stirred at rt overnight, and the reaction was quenched with sodium bicarbonate solution (2 mL). The resulting solution was extracted with EA (3×5 mL). The organic layers were combined, dried over anhydrous sodium sulfate, filtered and concentrated under reduced pressure. The residue was purified by TLC with methanol:dichloromethane (1:18) to provide (3S,6S)-1,1-difluoro-5-(4-methoxy-1H-indole-2-carbonyl)-N-(1-oxo-3-((S)-2-oxopiperidin-3-yl)propan-2-yl)-5-azaspiro[2.4]heptane-6-carboxamide (14.6 mg, 24%) as a white solid. LCMS (ESI, m/z): 503 [M+H]+.

Example 31

COMPOUND 30

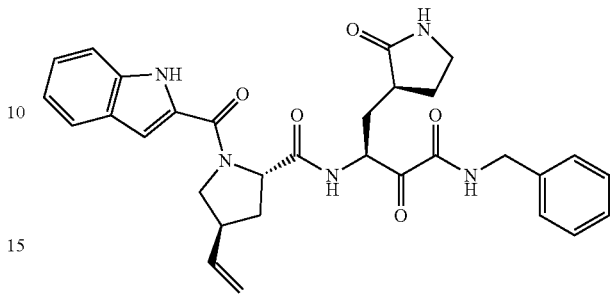

Compound 30 was prepared similarly as described for Compound 26 using (2S,4S)-1-(tert-butoxycarbonyl)-4-vinylpyrrolidine-2-carboxylic acid in place of (2S)-1-(tert-butoxycarbonyl)-4,4-dimethylpiperidine-2-carboxylic acid. LCMS (ESI, m/z): 556 [M+H]+.

(2S,4S)-1-(tert-butoxycarbonyl)-4-vinylpyrrolidine-2-carboxylic acid: To a mixture of 1-tert-butyl 2-methyl (2S,4S)-4-ethenylpyrrolidine-1,2-dicarboxylate (Mulamreddy et al., J. Org. Chem. (2018) 83(21):13580-13586) (1.00 g, 3.92 mmol, 1.0 eq.) in 1,4-dioxane (5 mL) was added hydrogen chloride (5 mL, 6M) at rt. The mixture was stirred for 3 h at 80° C. and concentrated under reduced pressure to remove 1,4-dioxane. The mixture was diluted with water (20 mL) and extracted with EA (3×20 mL). The water layers were combined and concentrated under reduced pressure to afford (2S,4S)-4-ethenylpyrrolidine-2-carboxylic acid (crude) as an off-white semi-solid. The crude product was used in the next step directly without further purification. LCMS (ESI, m/z): 142 [M+H]+.

To a mixture of (2S,4S)-4-ethenylpyrrolidine-2-carboxylic acid (1.00 g, 7.08 mmol, 1.0 eq.) in dichloromethane (10 mL) was added triethylamine (2.15 g, 21.3 mmol, 3.0 eq.) and di-tert-butyl dicarbonate (2.32 g, 10.6 mmol, 1.5 eq.) at rt. The mixture was stirred for 2 h at rt, and the reaction was quenched with water (50 mL). The mixture was extracted with EA (3×70 mL). The water layers were combined and concentrated under reduced pressure to afford (2S,4S)-1-(tert-butoxycarbonyl)-4-ethenylpyrrolidine-2-carboxylic acid (1.1 g, crude) as an off-semi-white solid. LCMS (ESI, m/z): 186 [M+H−56]+.

Example 32

COMPOUND 31A AND COMPOUND 31

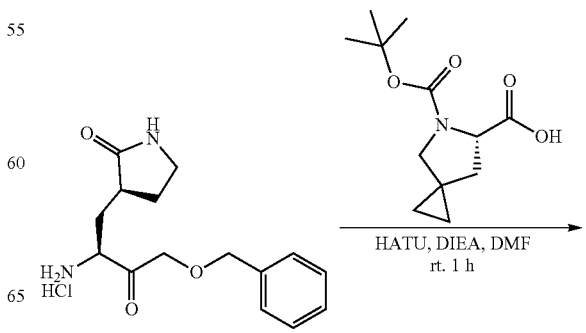

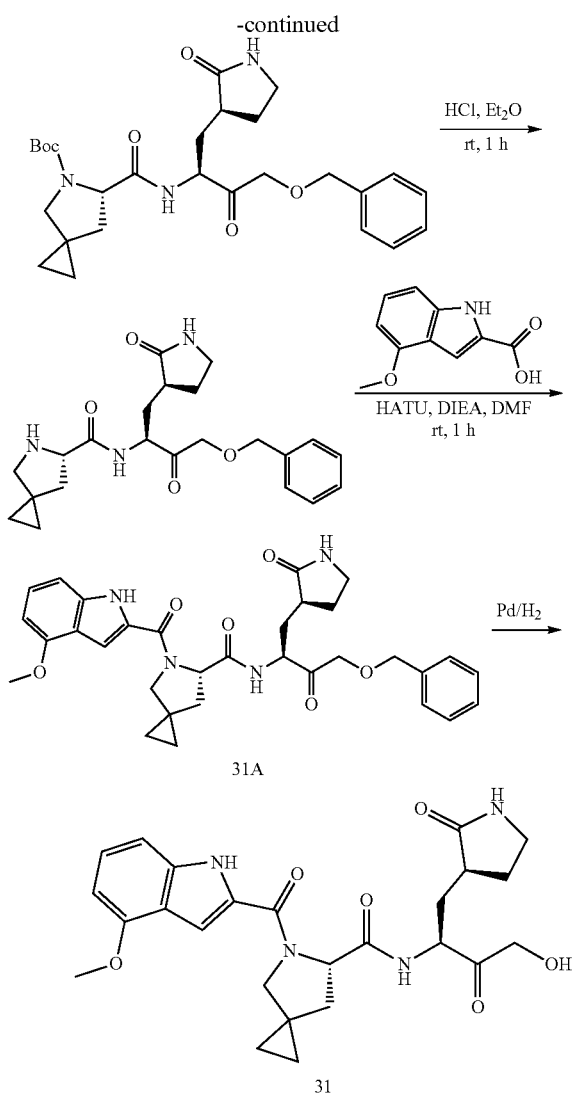

31A

31

To a mixture of (3S)-3-[(2S)-2-amino-4-(benzyloxy)-3-oxobutyl]pyrrolidin-2-one hydrochloride (250 mg, 0.799 mmol, 1.0 eq.) and (6S)-5-(tert-butoxycarbonyl)-5-azaspiro[2.4]heptane-6-carboxylic acid (193 mg, 0.799 mmol, 1.0 eq.) in N,N-dimethylformamide (3 mL) was added o-(7-azabenzotriazol-1-yl)-N,N,N',N'-tetramethyluronium hexafluorophosphate (456 mg, 1.20 mmol, 1.5 eq.) and N-ethyl-N-isopropylpropan-2-amine (310 mg, 2.40 mmol, 3.0 eq.) at 0° C. The mixture was stirred for 1 h at rt, and the reaction was quenched with water (5 mL). The mixture was extracted with EA (3×5 mL). The organic layers were combined, washed with brine (2×5 mL), dried over anhydrous sodium sulfate, filtered and concentrated under reduced pressure to afford crude product. The crude product was purified by TLC (Mobile phase: methanol:dichloromethane=1:15; Rf=0.4; detection: UV) to provide the desired product tert-butyl (6S)-6-{[(2S)-4-(benzyloxy)-3-oxo-1-[(3S)-2-oxopyrrolidin-3-yl]butan-2-yl]carbamoyl}-5-azaspiro[2.4]heptane-5-carboxylate (200 mg, 46%) as colorless semi-solid. LCMS (ESI, m/z): 500 [M+H]⁺.

A mixture of tert-butyl (6S)-6-{[(2S)-4-(benzyloxy)-3-oxo-1-[(3S)-2-oxopyrrolidin-3-yl]butan-2-yl]carbamoyl}-5-azaspiro[2.4]heptane-5-carboxylate (140 mg, 0.280 mmol, 1.0 eq.) in hydrogen chloride (5 mL, 2 M in diethyl ether) at 0° C. The mixture was stirred for 1 h at rt and then concentrated under reduced pressure to afford (6S)—N-[(2S)-4-(benzyloxy)-3-oxo-1-[(3S)-2-oxopyrrolidin-3-yl]butan-2-yl]-5-azaspiro[2.4]heptane-6-carboxamide hydrochloride (122 mg, crude) as a white solid. LCMS (ESI, m/z): 400 [M+H]⁺.

To a mixture of (6S)—N-[(2S)-4-(benzyloxy)-3-oxo-1-[(3S)-2-oxopyrrolidin-3-yl]butan-2-yl]-5-azaspiro[2.4]heptane-6-carboxamide hydrochloride (122 mg, 0.280 mmol, 1.0 eq.) and 4-methoxy-1H-indole-2-carboxylic acid (54.0 mg, 0.280 mmol, 1.0 eq.) in N,N-dimethylformamide (3 mL) was added o-(7-azabenzotriazol-1-yl)-N,N,N',N'-tetramethyluronium hexafluorophosphate (160 mg, 0.420 mmol, 1.5 eq.) and N-ethyl-N-isopropylpropan-2-amine (109 mg, 0.840 mmol, 3.0 eq.) at 0° C. The mixture was stirred for 1 h at rt, and the reaction was quenched with water (5 mL). The mixture was extracted with EA (3×5 mL). The organic layers were combined, washed with brine (2×5 mL), dried over anhydrous sodium sulfate, filtered and concentrated under reduced pressure to afford crude product. The crude product was purified by TLC (Mobile phase: methanol:dichloromethane=1:14; Rf=0.4; detection: UV) to provide (6S)—N-[(2S)-4-(benzyloxy)-3-oxo-1-[(3S)-2-oxopyrrolidin-3-yl]butan-2-yl]-5-(4-methoxy-1H-indole-2-carbonyl)-5-azaspiro[2.4]heptane-6-carboxamide (70 mg, 40%) as a light yellow solid. LCMS (ESI, m/z): 573 [M+H]⁺.

To a mixture of (6S)—N-[(2S)-4-(benzyloxy)-3-oxo-1-[(3S)-2-oxopyrrolidin-3-yl]butan-2-yl]-5-(4-methoxy-1H-indole-2-carbonyl)-5-azaspiro[2.4]heptane-6-carboxamide (65.0 mg, 0.114 mmol, 1.0 eq.) in ethanol (3 mL) was added Pd/C (65.0 mg). The mixture was stirred overnight at rt under H₂. The mixture was filtered through a celite pad, and the filtrate was concentrated under reduced pressure to afford crude product. The crude product was purified by prep-HPLC (Column: X Bridge Prep Phenyl OBD Column, 5 um, 19*250 mm; Water (0.05% TFA), Mobile Phase B: ACN; Flow rate: 25 mL/min; Gradient: 20 B to 40 B in 7 min; 210 nm; RT: 6.35) to provide (6S)—N-[(2S)-4-hydroxy-3-oxo-1-[(3S)-2-oxopyrrolidin-3-yl]butan-2-yl]-5-(4-methoxy-1H-indole-2-carbonyl)-5-azaspiro[2.4]heptane-6-carboxamide (10.5 mg, 19%) as a white solid. ¹H NMR (400 MHz, 353K, DMSO-d₆) δ 11.24 (s, 1H), 8.30 (br, 1H), 7.30 (s, 1H), 7.00-7.20 (m, 2H), 6.86 (s, 1H), 6.49 (d, J=7.2 Hz, 1H), 4.83 (br, 1H), 4.35-4.55 (m, 1H), 4.10-4.30 (m, 2H), 3.72-3.92 (m, 5H), 3.00-3.12 (m, signal under H₂O peak), 2.20-2.40 (m, 2H), 1.80-2.15 (m, 3H), 1.50-1.70 (m, 2H), 0.50-0.70 (m, 4H). LCMS (ESI, m/z): 483 [M+H]⁺.

Example 33

COMPOUND 32

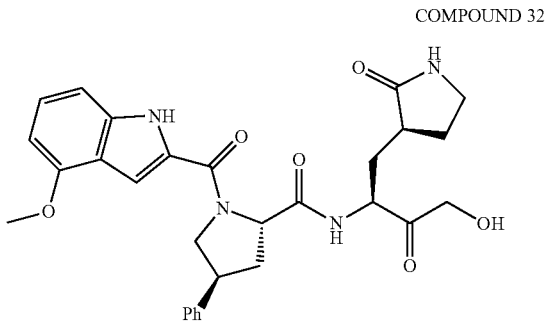 [SMILES: COc1cccc2[nH]c(C(=O)N3C[C@H](c4ccccc4)C[C@H]3C(=O)N[C@@H](C[C@@H]3CCNC3=O)C(=O)CO)cc12]

Compound 32 was prepared similarly as described for Compound 31, using (2S,4S)-1-(tert-butoxycarbonyl)-4-phenylpyrrolidine-2-carboxylic acid in place of (S)-5-(tert-butoxycarbonyl)-5-azaspiro[2.4]heptane-6-carboxylic acid. LCMS (ESI, m/z): 533 [M+H]+.

Example 34

COMPOUND 33

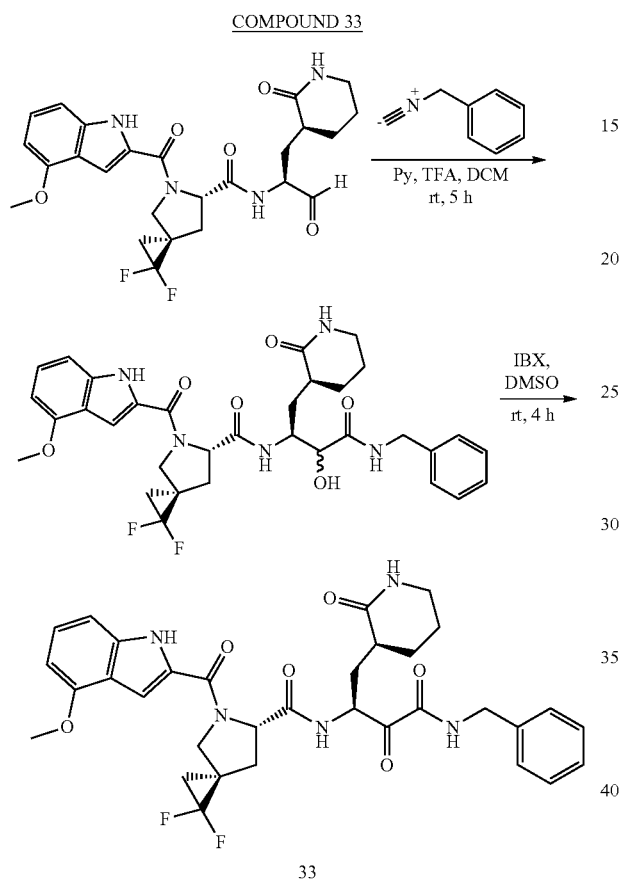

33

Compound 33 was prepared according to synthetic scheme provided above starting from Compound 29.

A 8 mL vial was charged with (3S,6S)-1,1-difluoro-5-(4-methoxy-1H-indole-2-carbonyl)-N-(1-oxo-3-((S)-2-oxopiperidin-3-yl)propan-2-yl)-5-azaspiro[2.4]heptane-6-carboxamide (150 mg, 0.30 mmol, 1.0 eq.) in DCM (1 mL). (isocyanomethyl)benzene (69.8 mg, 0.60 mmol, 2.0 eq.) in dichloromethane (0.5 mL) was added dropwise at 0° C. Pyridine (94.3 mg, 1.19 mmol, 4.0 eq.) in DCM (0.5 mL) was added dropwise at 0° C. Trifluoroacetic acid (102 mg, 0.89 mmol, 3.0 eq.) in DCM (1 mL) was added dropwise at 0° C. The reaction was stirred for 50 min at 0° C. and stirred for 5 h at rt. The reaction was concentrated under reduced pressure. The residue was purified by a C18 column with MeCN:H2O (0.05% TFA) (3:7) to provide (3S)—N-benzyl-3-{[(3S,6S)-1,1-difluoro-5-(4-methoxy-1H-indole-2-carbonyl)-5-azaspiro[2.4]heptan-6-yl]formamido}-2-hydroxy-4-[(3S)-2-oxopiperidin-3-yl]butanamide (53 mg, 22%) of as a white solid. LC-MS (ESI, m/z): 638 [M+H]+.

To a solution of (3S)—N-benzyl-3-{[(3S,6S)-1,1-difluoro-5-(4-methoxy-1H-indole-2-carbonyl)-5-azaspiro[2.4]heptan-6-yl]formamido}-2-hydroxy-4-[(3S)-2-oxopiperidin-3-yl]butanamide (50 mg, 0.08 mmol, 1.0 eq.) in DMSO (2 mL) was added IBX (43.9 mg, 0.16 mmol, 2.0 eq.). The mixture was stirred at rt for 4 h, and the reaction was quenched with sodium bicarbonate solution (2 mL). The solution was extracted with EA (3×10 mL). The organic layers were combined, dried over anhydrous sodium sulfate, filtered and concentrated under reduced pressure. The residue was purified by pre-TLC with MeOH/DCM (1/18) to provide N-benzyl-3-{[(3S,6S)-1,1-difluoro-5-(4-methoxy-1H-indole-2-carbonyl)-5-azaspiro[2.4]heptan-6-yl]formamido}-2-oxo-4-[(3S)-2-oxopiperidin-3-yl]butanamide (11.9 mg, 23%) of as a white solid. LCMS (ESI, m/z): 636 [M+H]+.

Example 35

COMPOUND 34

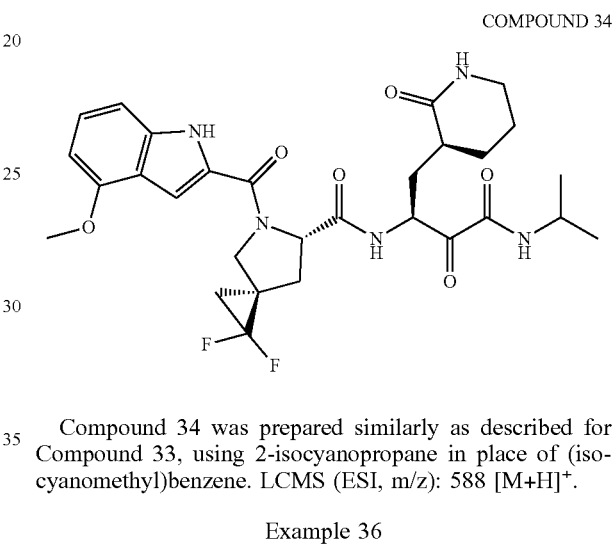

Compound 34 was prepared similarly as described for Compound 33, using 2-isocyanopropane in place of (isocyanomethyl)benzene. LCMS (ESI, m/z): 588 [M+H]+.

Example 36

COMPOUND 35

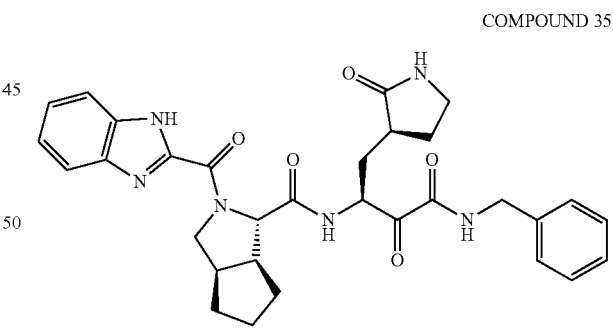

Compound 35 was prepared similar as described for Compound 16 using (1S,3aR,6aS)-2-(1H-1,3-benzodiazole-2-carbonyl)-hexahydro-1H-cyclopenta[c]pyrrole-1-carboxylic acid in place of (1S,3aR,6aS)-2-(4-methoxy-1H-indole-2-carbonyl)octahydrocyclopenta[c]pyrrole-1-carboxylic acid. LCMS (ESI, m/z): 571 [M+H]+.

Synthesis of (1S,3aR,6aS)-2-(1H-1,3-benzodiazole-2-carbonyl)-hexahydro-1H-cyclopenta[c]pyrrole-1-carboxylic acid: To a solution of 1H-1,3-benzodiazole-2-carboxylic acid (295 mg, 1.82 mmol, 1.1 eq.), o-(7-azabenzotriazol-1-yl)-N,N,N',N'-tetramethyluronium hexafluorophosphate (693 mg, 1.82 mmol, 1.1 eq.) in N,N-dimethylformamide (6 mL) was added N-ethyl-N-isopropylpropan-2-amine (643 mg, 4.97 mmol, 3.0 eq.) stirred for 30 min at rt. Then tert-butyl (1S,3aR,6aS)-octahydrocyclopenta[c]pyrrole-1-carboxylate oxalate (500 mg, 1.65 mmol, 1.00 eq.) was added. The mixture was stirred for 3 h at rt. The reaction was quenched with water (20 mL). The mixture was extracted with EA (3×50 mL). The organic layers were combined, washed with brine (2×20 mL), dried over anhydrous sodium sulfate, filtered and concentrated under reduced pressure to afford the crude product. The crude product was diluted with dichloromethane (5 mL) and a slurry was made with 100~200 silicagel mesh (2 g) loaded onto a column after removing the dichloromethane. The sample was purified by column chromatography (Column size 4×24 cm, column volume: 200 mL, silicagel size (100~200 mesh) quantity: 80 g) and eluted with EA:PE (0%~40% over 30 min). Collected fractions: 18% EA:PE fractions were chosen as the pure fractions. Those fractions were combined and concentrated under reduced pressure to provide tert-butyl (1S,3aR,6aS)-2-(1H-1,3-benzodiazole-2-carbonyl)-hexahydro-1H-cyclopenta[c]pyrrole-1-carboxylate (230 mg, 37%) as a colorless oil. LCMS (ESI, m/z): 356 [M+H]$^+$.

To a solution of tert-butyl (1S,3aR,6aS)-2-(1H-1,3-benzodiazole-2-carbonyl)-hexahydro-1H-cyclopenta[c]pyrrole-1-carboxylate (190 mg, 0.535 mmol, 1.0 eq.) in dichloromethane (3 mL) was added trifluoroacetic acid (1 mL). The mixture was stirred for 1 h at rt. The mixture was concentrated under reduced pressure to afford the crude product (1S,3aR,6aS)-2-(1H-1,3-benzodiazole-2-carbonyl)-hexahydro-1H-cyclopenta[c]pyrrole-1-carboxylic acid (280 mg, crude) as a yellow oil. LCMS (ESI, m/z): 300 [M+H]$^+$.

Example 37

COMPOUND 36

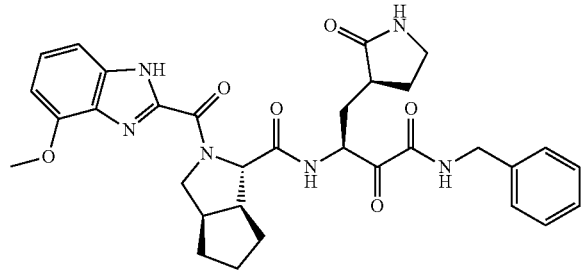

To a mixture of 3-methoxybenzene-1,2-diamine (500 mg, 3.62 mmol, 1.0 eq.) and methyl 2,2,2-trichloroethanimidate (830 mg, 4.70 mmol, 1.3 eq.) in dichloromethane (10 mL) was added trifluoroacetic acid (1.03 g, 9.05 mmol, 2.5 eq.). The mixture was stirred for 2 h at rt under N$_2$ atmosphere. LCMS confirmed the product. LCMS (ESI, m/z): 265 [M+H]$^+$.

To a mixture of 4-methoxy-2-(trichloromethyl)-1H-1,3-benzodiazole (956 mg, 3.60 mmol, 1.0 eq.) in dichloromethane (10 mL) was added aq. sodium hydroxide (5 mL, 2 M in water). The mixture was concentrated under reduced pressure to remove dichloromethane and methanol (5 mL) was added. The mixture was stirred overnight at rt. The mixture was concentrated under reduced pressure to remove the methanol and the pH has adjusted to 6 with HCl (2 M). 4-methoxy-1H-1,3-benzodiazole-2-carboxylic acid (530 mg, 72%) was obtained by filtration as a light yellow solid. LCMS (ESI, m/z): 193 [M+H]$^+$.

To a mixture of 4-methoxy-1H-1,3-benzodiazole-2-carboxylic acid (500 mg, 2.60 mmol, 1.0 eq.) and o-(7-azabenzotriazol-1-yl)-N,N,N',N'-tetramethyluronium hexafluorophosphate (1.48 g, 3.90 mmol, 1.5 eq.) in N,N-dimethylformamide (10 mL) was added N-ethyl-N-isopropylpropan-2-amine (1.35 g, 10.4 mmol, 4.0 eq.) at 0° C. After stirred for 15 min, (1S,3aR,6aS)-tert-butyl octahydrocyclopenta[c]pyrrole-1-carboxylate oxalate (784 mg, 2.60 mmol, 1.0 eq.) was added. The mixture was stirred for 1 h at rt. The reaction was quenched with water (20 mL). The mixture was extracted with EA (3×20 mL). The organic layers were combined, washed with brine (2×20 mL), dried over anhydrous sodium sulfate, filtered and concentrated under reduced pressure to afford the crude product. The crude product was diluted with dichloromethane (20 mL) and a slurry was made with 100~200 silicagel mesh (1 g) loaded to a column after removing the dichloromethane. The sample was purified by column chromatography (Column size 4×24 cm, column volume: 200 mL, silicagel size (100~200 mesh) quantity: 80 g) and eluted with EA:PE (0%~50% over 30 min). Collected fractions: 20%-22% EA:PE fractions were chosen as the pure fractions. Those fractions were combined and concentrated under reduced pressure to provide tert-butyl (1S,3aR,6aS)-2-(4-methoxy-1H-1,3-benzodiazole-2-carbonyl)-hexahydro-1H-cyclopenta[c]pyrrole-1-carboxylate (340 mg, 31%) as a yellow semi-solid. LCMS (ESI, m/z): 386 [M+H]$^+$.

To a mixture of tert-butyl (1S,3aR,6aS)-2-(4-methoxy-1H-1,3-benzodiazole-2-carbonyl)-hexahydro-1H-cyclopenta[c]pyrrole-1-carboxylate (150 mg, 0.389 mmol, 1.0 eq.) in dichloromethane (3 mL) was added trifluoroacetic acid (1 mL). The mixture was stirred for 1 h at rt and then concentrated under reduced pressure to afford crude (1S,3aR,6aS)-2-(4-methoxy-1H-1,3-benzodiazole-2-carbonyl)-hexahydro-1H-cyclopenta[c]pyrrole-1-carboxylic acid (128 mg, crude) as a yellow semi-solid. LCMS (ESI, m/z): 330 [M+H]$^+$.

To a mixture of (3S)-3-amino-N-benzyl-2-hydroxy-4-[(3S)-2-oxopyrrolidin-3-yl]butanamide hydrochloride (128 mg, 0.390 mmol, 1.0 eq.), (1S,3aR,6aS)-2-(4-methoxy-1H-1,3-benzodiazole-2-carbonyl)-hexahydro-1H-cyclopenta[c]pyrrole-1-carboxylic acid (129 mg, 0.390 mmol, 1.0 eq.) and o-(7-azabenzotriazol-1-yl)-N,N,N',N'-tetramethyluronium hexafluorophosphate (223 mg, 0.586 mmol, 1.5 eq.) in N,N-dimethylformamide (3 mL) was added N-ethyl-N-isopropylpropan-2-amine (202 mg, 1.56 mmol, 4.0 eq.). The mixture was stirred for 1 h at rt. The reaction was quenched with water (5 mL). The mixture was extracted with EA (3×5 mL). The organic layers were combined, washed with brine (2×5 mL), dried over anhydrous sodium sulfate, filtered and concentrated under reduced pressure to afford the crude product. The crude product was purified by TLC (Mobile phase: methanol:dichloromethane=1:15; Rf=0.3; detection: UV) to provide (3S)-3-[[(1S,3aR,6aS)-2-(4-methoxy-1H-1,3-benzodiazole-2-carbonyl)-hexahydro-1H-cyclopenta[c]pyrrol-1-yl]formamido]-N-benzyl-2-hydroxy-4-[(3S)-2-oxopyrrolidin-3-yl]butanamide (45 mg, 18%) as a light yellow solid. LCMS (ESI, m/z): 603 [M+H]$^+$.

To a mixture of (3S)-3-[[(1S,3aR,6aS)-2-(4-methoxy-1H-1,3-benzodiazole-2-carbonyl)-hexahydro-1H-cyclopenta[c]pyrrol-1-yl]formamido]-N-benzyl-2-hydroxy-4-[(3S)-2-oxopyrrolidin-3-yl]butanamide (45.0 mg, 0.075 mmol, 1.0 eq.) in dichloromethane (1 mL) was added Dess-Martin periodinane (64.0 mg, 0.149 mmol, 2.0 eq.) at 0° C. The mixture was stirred for 4 h at rt. The reaction was quenched sat. aq. sodium bicarbonate (1 mL) and sat. aq. sodium thiosulfate (1 mL). The mixture was stirred for 15 min. The mixture was then extracted with EA (3×2 mL). The organic layers were combined, washed with brine (2×2 mL), dried over anhydrous sodium sulfate, filtered and concentrated under reduced pressure to afford the crude product. The crude product was purified by TLC (Column: XBridge Prep Phenyl OBD Column, 5 μm, 19*250 mm; Mobile Phase A: Water (0.05% NH$_3$·H$_2$O), Mobile Phase B: ACN; Flow rate: 25 mL/min; Gradient: 35 B to 45 B in 7 min, 210 nm; RT: 6.35); to provide 3-[[(1S,3aR,6aS)-2-(4-methoxy-1H-1,3-benzodiazole-2-carbonyl)-hexahydro-1H-cyclopenta[c]pyrrol-1-yl]formamido]-N-benzyl-2-oxo-4-[(3S)-2-oxopyrrolidin-3-yl]butanamide (8.2 mg, 17%) as a white solid. LCMS (ESI, m/z): 601 [M+H]$^+$.

Example 38

COMPOUND 37

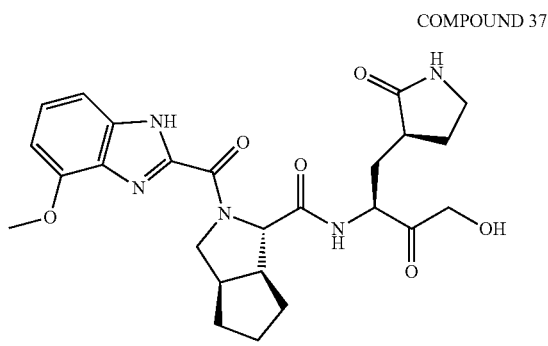 [SMILES: COc1cccc2[nH]c(C(=O)N3C[C@@H]4CCC[C@@H]4[C@H]3C(=O)N[C@@H](C[C@@H]3CCNC3=O)C(=O)CO)nc12]

Compound 37 was prepared similar as described for Compound 27, using (1S,3aR,6aS)-2-(4-methoxy-1H-1,3-benzodiazole-2-carbonyl)-hexahydro-1H-cyclopenta[c]pyrrole-1-carboxylic acid in place of (1S,3aR,6aS)-2-(4-methoxy-1H-indole-2-carbonyl)-hexahydro-1H-cyclopenta[c]pyrrole-1-carboxylic acid. LCMS (ESI, m/z): 498 [M+H]$^+$.

Example 39

COMPOUND 38

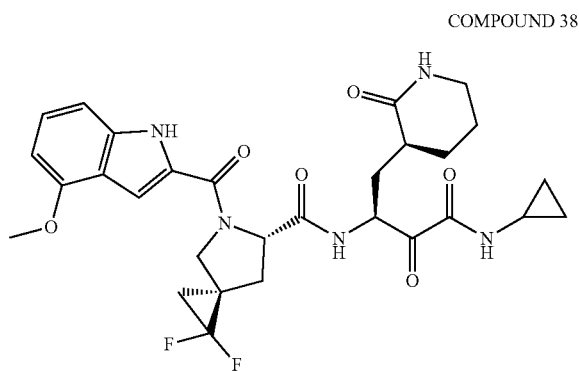 [SMILES: COc1cccc2[nH]c(C(=O)N3C[C@]4(C[C@H]3C(=O)N[C@@H](C[C@@H]3CCCNC3=O)C(=O)C(=O)NC3CC3)CC4(F)F)cc12]

To (3S,6S)-1,1-difluoro-5-(4-methoxy-1H-indole-2-carbonyl)-N-[(2S)-1-oxo-3-[(3S)-2-oxopiperidin-3-yl]propan-2-yl]-5-azaspiro[2.4]heptane-6-carboxamide (60 mg, 0.12 mmol, 1.0 eq.) in DCM (1 mL) was added dropwise isocyanocyclopropane (16 mg, 0.24 mmol, 2.0 eq.) in DCM (0.5 mL) at 0° C. Acetic acid (21.5 mg, 0.36 mmol, 3.0 eq.) in DCM (0.5 mL) was added dropwise at 0° C. The reaction was stirred for 50 min at 0° C. and stirred for 5 h at rt. The mixture was concentrated under reduced pressure to provide (2S)-1-(cyclopropylcarbamoyl)-2-{[(3S,6S)-1,1-difluoro-5-(4-methoxy-1H-indole-2-carbonyl)-5-azaspiro[2.4]heptan-6-yl]formamido}-3-[(3S)-2-oxopiperidin-3-yl]propyl acetate (60 mg crude, 48%) of as an yellow oil. LC-MS (ESI, m/z): 630 [M+H]$^+$.

To a solution of (2S)-1-(cyclopropylcarbamoyl)-2-{[(3S,6S)-1,1-difluoro-5-(4-methoxy-1H-indole-2-carbonyl)-5-azaspiro[2.4]heptan-6-yl]formamido}-3-[(3S)-2-oxopiperidin-3-yl]propyl acetate (60 mg, 0.10 mmol, 1.0 eq.) in THF (2 mL) was added lithium hydroxide (4.56 mg, 0.19 mmol, 2.0 eq.) in water (2 mL) dropwise at 0° C. The mixture was stirred at 0° C. for 1 h, and the reaction was quenched with hydrochloric acid (2 mL, 2 mol/L). The resulting solution was extracted with EA (3×10 mL). The organic layers were combined, dried over anhydrous sodium sulfate, filtered and concentrated under reduced pressure. The residue was chromatographed on a silica gel column with methanol:dichloromethane (1:22) to provide (3S)—N-cyclopropyl-3-{[(3S,6S)-1,1-difluoro-5-(4-methoxy-1H-indole-2-carbonyl)-5-azaspiro[2.4]heptan-6-yl]formamido}-2-hydroxy-4-[(3S)-2-oxopiperidin-3-yl]butanamide (40 mg, 66%) as a white solid. LC-MS (ESI, m/z): 588 [M+H]$^+$.

To a solution of (3S)—N-cyclopropyl-3-{[(3S,6S)-1,1-difluoro-5-(4-methoxy-1H-indole-2-carbonyl)-5-azaspiro[2.4]heptan-6-yl]formamido}-2-hydroxy-4-[(3S)-2-oxopiperidin-3-yl]butanamide (40 mg, 0.07 mmol, 1.0 eq.) in DMSO (2 mL) was added IBX (38.1 mg, 0.14 mmol, 2.0 eq.). The mixture was stirred at rt for 2 h, and the reaction was quenched with sodium bicarbonate solution (2 mL). The resulting solution was extracted with EA (3×10 mL). The organic layers were combined, dried over anhydrous sodium sulfate, filtered and concentrated under reduced pressure. The residue was purified by pre-TLC with MeOH:DCM (1:18) to provide N-cyclopropyl-3-{[(3S,6S)-1,1-difluoro-5-(4-methoxy-1H-indole-2-carbonyl)-5-azaspiro[2.4]heptan-6-yl]formamido}-2-oxo-4-[(3S)-2-oxopiperidin-3-yl]butanamide (14.6 mg, 35%) as a white solid. LC-MS (ESI, m/z): 586 [M+H]$^+$.

Example 40

COMPOUND 39

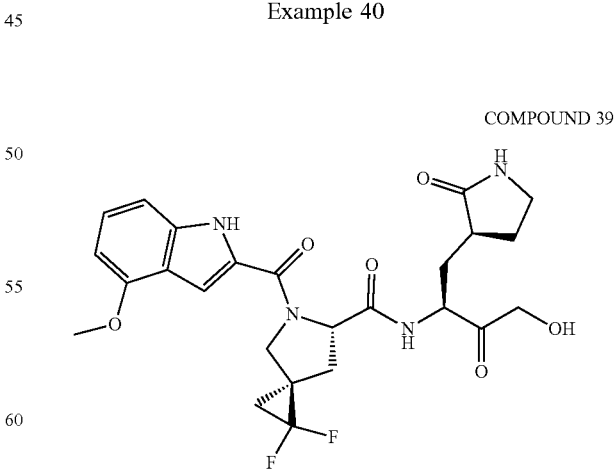

Compound 39 was prepared similarly as described for Compound 31, using (3S,6S)-5-(tert-butoxycarbonyl)-1,1-difluoro-5-azaspiro[2.4]heptane-6-carboxylic acid in place of (S)-5-(tert-butoxycarbonyl)-5-azaspiro[2.4]heptane-6- carboxylic acid. $^1$H NMR (400 MHz, 353K, DMSO-d$_6$) δ 11.32 (s, 1H), 8.40-8.44 (m, 1H), 7.30 (s, 1H), 7.00-7.18 (m, 2H), 6.88 (s, 1H), 6.50 (d, J=6.8 Hz, 1H), 4.95 (br, 1H), 4.70-4.85 (m, 1H), 4.40-4.55 (m, 1H), 4.10-4.30 (m, 2H), 4.02-4.09 (m, 1H), 3.80-4.00 (m, 4H), 3.05-3.15 (m, 2H), 2.50-2.70 (m, 1H), 2.30-2.40 (m, 1H), 1.85-2.10 (m, 3H), 1.50-1.75 (m, 4H). LCMS (ESI, m/z): 519 [M+H]$^+$.

Example 41

COMPOUND 40

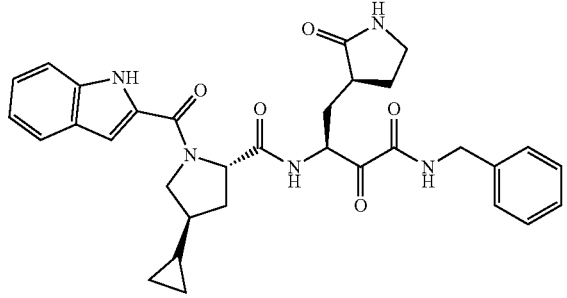

To a mixture of 1-tert-butyl 2-methyl (2S,4S)-4-ethenylpyrrolidine-1,2-dicarboxylate (Mulamreddy et al., J. Org. Chem. (2018) 83(21):13580-13586) in 1,4-dioxane (50 mL) was added hydrochloric acid (30 mL, 4 M in 1,4-dioxane). The mixture was stirred overnight at rt. The mixture was concentrated under reduced pressure and re-dissolved in dichloromethane (65 mL). Potassium carbonate (15.4 g, 111 mmol, 5.0 eq.) and silver nitrate (3.03 g, 17.8 mmol, 0.8 eq.) was added. The mixture was stirred for 2 h at rt. Benzyl chloroformate (4.56 g, 26.7 mmol, 1.2 eq.) was added, and the mixture was stirred for 1 h at rt. The mixture was filtered. The filtrate was washed with sat. aq. sodium bicarbonate (60 mL) and brine (60 mL), dried over anhydrous sodium sulfate, filtered and concentrated under reduced pressure to afford the crude product. The crude product was purified by C18 column with CH$_3$CN:Water (0.05% TFA), and the fraction was concentrated under reduced pressure to provide 1-benzyl 2-methyl (2S,4S)-4-ethenylpyrrolidine-1,2-dicarboxylate (4.66 g, 54%) as a light yellow oil. LCMS (ESI, m/z): 290 [M+H]$^+$.

To a mixture of diethylzinc (69 mL, 69.1 mmol, 20.0 eq., 1 M in hexane) in dichloromethane (24 mL) was added dropwise a solution of trifluoroacetic acid (7.88 g, 69.1 mmol, 20.0 eq.) in dichloromethane (16 mL) at 0° C. under N$_2$. The mixture was stirred for 30 min at 0° C. Diiodomethane (18.5 g, 69.1 mmol, 20.0 eq.) in dichloromethane (16 mL) was added dropwise. After stirred for 30 min at 0° C., a solution of 1-benzyl 2-methyl (2S,4S)-4-ethenylpyrrolidine-1,2-dicarboxylate (1 g, 3.46 mmol, 1.0 eq.) in dichloromethane (40 mL) was added. The mixture was stirred for 3 days at rt. The reaction was quenched with sat. aq. sodium bicarbonate (60 mL), and the mixture was extracted with dichloromethane (3×60 mL). The organic layers were combined, washed with brine (2×50 mL), dried over anhydrous sodium sulfate, filtered and concentrated under reduced pressure to afford crude product. The crude product was purified by C18 column with CH$_3$CN:Water (0.05% TFA), and the fraction was concentrated under reduced pressure to provide 1-benzyl 2-methyl (2S,4S)-4-cyclopropylpyrrolidine-1,2-dicarboxylate (500 mg, 42%) as a light yellow oil. $^1$H NMR (300 MHz, CDCl$_3$-d) δ 7.29-7.45 (m, 5H), 5.03-5.28 (m, 2H), 4.38-4.54 (m, 1H), 3.56-3.87 (m, 4H), 3.18-3.34 (m, 1H), 1.96-2.21 (m, 2H), 1.62-1.84 (m, 1H), 0.57-0.73 (m, 1H), 0.42-0.54 (m, 2H), 0.08-0.25 (m, 2H). LCMS (ESI, m/z): 304 [M+H]$^+$.

To a mixture of 1-benzyl 2-methyl (2S,4S)-4-cyclopropylpyrrolidine-1,2-dicarboxylate (200 mg, 0.659 mmol, 1.0 eq.) in 1,4-dioxane (3 mL) was added hydrogen chloride (3 mL, 6 M in water) at rt. The mixture was stirred for 1 h at 80° C. and concentrated under reduced pressure to afford (2S,4S)-1-[(benzyloxy)carbonyl]-4-cyclopropylpyrrolidine-2-carboxylic acid (190 mg, crude) as a yellow oil. LCMS (ESI, m/z): 290 [M+H]$^+$.

To a mixture of (3S)-3-amino-N-benzyl-2-hydroxy-4-[(3S)-2-oxopyrrolidin-3-yl]butanamide hydrochloride (216 mg, 0.659 mmol, 1.0 eq.) and (2S,4S)-1-[(benzyloxy)carbonyl]-4-cyclopropylpyrrolidine-2-carboxylic acid (190 mg, 0.659 mmol, 1.0 eq.) in dimethylformamide (3 mL) was added o-(7-azabenzotriazol-1-yl)-N,N,N',N'-tetramethyluronium hexafluorophosphate (376 mg, 0.989 mmol, 1.5 eq.) and N-ethyl-N-isopropylpropan-2-amine (255 mg, 1.98 mmol, 3.0 eq.) at 0° C. The mixture was stirred for 1 h at rt. The reaction was quenched with water (5 mL), and the mixture was extracted with EA (3×5 mL). The organic layers were combined, washed with brine (2×5 mL), dried over anhydrous sodium sulfate, filtered and concentrated under reduced pressure to afford crude product. The crude product was purified by TLC (Mobile phase: methanol:dichloromethane=1:15; Rf=0.5; detection: UV) to provide benzyl (2S,4S)-2-{[(2S)-1-(benzylcarbamoyl)-1-hydroxy-3-[(3S)-2-oxopyrrolidin-3-yl]propan-2-yl]carbamoyl}-4-cyclopropylpyrrolidine-1-carboxylate (160 mg, 38%) as a light yellow solid. LCMS (ESI, m/z): 563 [M+H]$^+$.

To a mixture of benzyl (2S,4S)-2-{[(2S)-1-(benzylcarbamoyl)-1-hydroxy-3-[(3S)-2-oxopyrrolidin-3-yl]propan-2-yl]carbamoyl}-4-cyclopropylpyrrolidine-1-carboxylate (115 mg, 0.204 mmol, 1.0 eq.) in EA (5 mL) was added Pd/C (120 mg). The mixture was stirred overnight at rt under H$_2$. The mixture was filtered through a celite pad and washed with EA (3×5 mL). The filtrate was concentrated under reduced pressure to afford (3S)—N-benzyl-3-{[(2S,4S)-4-cyclopropylpyrrolidin-2-yl]formamido}-2-hydroxy-4-[(3S)-2-oxopyrrolidin-3-yl]butanamide (80 mg, crude) as a yellow solid. LCMS (ESI, m/z): 429 [M+H]$^+$.

To a mixture of (3S)—N-benzyl-3-{[(2S,4S)-4-cyclopropylpyrrolidin-2-yl]formamido}-2-hydroxy-4-[(3S)-2-oxopyrrolidin-3-yl]butanamide (80.0 mg, 0.187 mmol, 1.0 eq.) and indole-2-carboxylic acid (30.0 mg, 0.187 mmol, 1.0 eq.) in dimethylformamide (2 mL) was added O-(7-azabenzotriazol-1-yl)-N,N,N',N'-tetramethyluronium hexafluorophosphate (54.0 mg, 0.224 mmol, 1.2 eq.) and N-ethyl-N-isopropylpropan-2-amine (60.0 mg, 0.468 mmol, 2.5 eq.). The mixture was stirred for 1 h at rt, and the reaction was quenched with water (5 mL). The mixture was extracted with EA (3×5 mL). The organic layers were combined, washed with brine (2×5 mL), dried over anhydrous sodium sulfate, filtered and concentrated under reduced pressure to afford crude product. The crude product was purified by TLC (Mobile phase: methanol:dichloromethane=1:15; Rf=0.4; detection: UV) to provide (3S)—N-benzyl-3-{[(2S,4S)-4-cyclopropyl-1-(1H-indole-2-carbonyl)pyrrolidin-2-yl]formamido}-2-hydroxy-4-[(3S)-2-oxopyrrolidin-3-yl]butanamide (30 mg, 25%) as a light yellow solid. LCMS (ESI, m/z): 572 [M+H]$^+$.

To a mixture of (3S)—N-benzyl-3-{[(2S,4S)-4-cyclopropyl-1-(1H-indole-2-carbonyl)pyrrolidin-2-yl]formamido}-2-hydroxy-4-[(3S)-2-oxopyrrolidin-3-yl]butanamide (30.0 mg, 0.052 mmol, 1.0 eq.) in dimethylsulfoxide (1 mL) was added 2-Iodoxybenzoic acid (29.0 mg, 0.104 mmol, 2.0 eq.). The mixture was stirred for 6 h at rt, and the reaction was quenched with sat. aq. sodium bicarbonate (3 mL). The mixture was extracted with EA (3×3 mL). The organic layers were combined, washed with brine (2×3 mL), dried over anhydrous sodium sulfate, filtered and concentrated under reduced pressure to afford crude product. The crude product was purified by TLC (Mobile phase: methanol:dichloromethane=1:14; Rf=0.4; detection: UV) to provide N-benzyl-3-{[(2S,4S)-4-cyclopropyl-1-(1H-indole-2-carbonyl)pyrrolidin-2-yl]formamido}-2-oxo-4-[(3S)-2-oxopyrrolidin-3-yl]butanamide (8.0 mg, 26%) as a white solid. LCMS (ESI, m/z): 570 [M+H]⁺.

Example 42

COMPOUND 41A AND 41

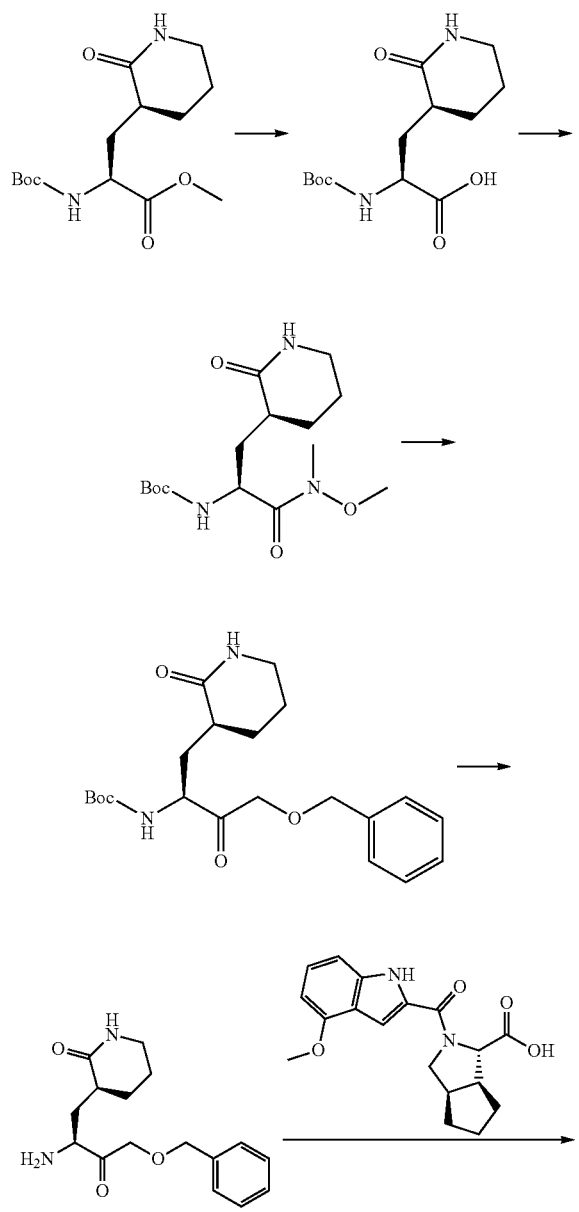

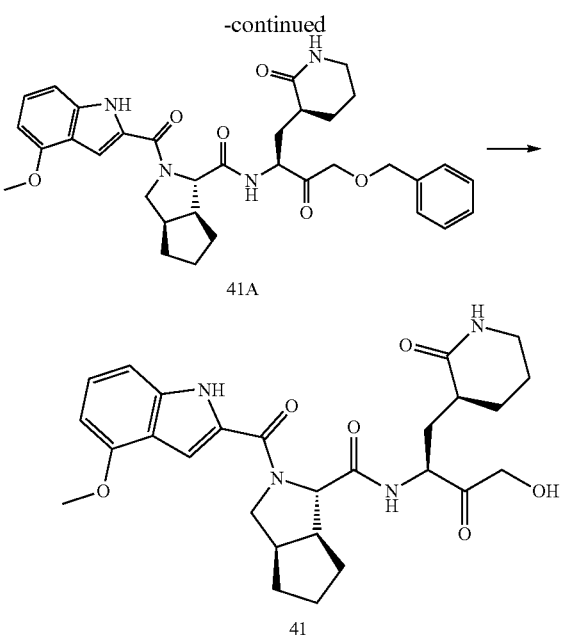

To a mixture of methyl (S)-2-((tert-butoxycarbonyl)amino)-3-((S)-2-oxopiperidin-3-yl)propanoate (3.00 g, 10.0 mmol, 1.0 eq.) in methanol (15 mL) was added aqueous sodium hydroxide (15 mL, 45.0 mmol, 4.0 eq., 3 M in water). The mixture was stirred for 1 h at 0° C. The mixture was concentrated under reduced pressure to remove methanol and the pH was adjusted to 6 with HCl (2 M). The mixture was extracted with EA (3×30 mL). The organic layers were combined, washed with brine (2×20 mL), dried over anhydrous sodium sulfate, filtered and concentrated under reduced pressure to provide (S)-2-((tert-butoxycarbonyl)amino)-3-((S)-2-oxopiperidin-3-yl)propanoic acid (1.70 g, 60%) as a white solid. LC-MS (ESI, m/z): 287 [M+H]⁺.

To a mixture of (S)-2-((tert-butoxycarbonyl)amino)-3-((S)-2-oxopiperidin-3-yl)propanoic acid (1.70 g, 5.93 mmol, 1.0 eq.) in dichloromethane (25 mL) was added N,O-Dimethylhydroxylamine hydrochloride (0.575 g, 5.93 mmol, 1.0 eq.), NMM (1.80 g, 17.8 mmol, 3.0 eq.), HOBt (0.800 g, 5.93 mmol, 1.0 eq.) and EDCI (1.25 g, 6.53 mmol, 1.1 eq.) at 0° C. The mixture was stirred for 1 h at 0° C. under nitrogen atmosphere. The reaction was quenched with water (20 mL). The organic layers were washed with HCl (2×20 mL, 1 M), water (20 mL), sat. aq. sodium bicarbonate (2×20 mL) and brine (20 mL), dried over anhydrous sodium sulfate, filtered and concentrated under reduced pressure to provide tert-butyl ((S)-1-(methoxy(methyl)amino)-1-oxo-3-((S)-2-oxopiperidin-3-yl)propan-2-yl)carbamate (1.29 g, 66%) as a light yellow solid. LC-MS (ESI, m/z): 330 [M+H]⁺.

To a mixture of Mg (1.39 g, 57.3 mmol, 9.0 eq.) and HgCl₂ (1.04 g, 3.83 mmol, 0.6 eq.) in tetrahydrofuran (50 mL) was added Benzylchloromethyl ether (8.99 g, 57.4 mmol, 9.0 eq.) at −45° C. under N₂ atmosphere. The mixture was stirred for 5 h from −45° C. to 5° C. The mixture was re-cooled to −45° C., tert-butyl ((S)-1-(methoxy(methyl)amino)-1-oxo-3-((S)-2-oxopiperidin-3-yl)propan-2-yl)carbamate (2.10 g, 6.37 mmol, 1.0 eq.) was added. The mixture was stirred overnight at rt under N₂ atmosphere. The reaction was quenched with sat. aq. ammonium chloride (30 mL). The mixture was extracted with EA (3×50 mL). The organic layers were combined, washed with brine (2×50 mL), dried over anhydrous sodium sulfate, filtered and concentrated under reduced pressure to afford the crude product. The crude product was diluted with dichloromethane (20 mL) and then a slurry was made with 100~200 silicagel mesh (5 g). The slurry was loaded onto a column after removing dichloromethane. The sample was purified by column chromatography (Column size 4×24 cm, column volume: 200 mL, silicagel size (100~200 mesh) quantity: 80 g) and eluted with methanol:dichloromethane (0%~5% over 20 min). Collected fractions: 3%~4% methanol:dichloromethane fractions were chosen as pure fractions and those fractions were combined and concentrated under reduced pressure to provide tert-butyl ((S)-4-(benzyloxy)-3-oxo-1-((S)-2-oxopiperidin-3-yl)butan-2-yl)carbamate (700 mg, 28%) as a light yellow oil. LC-MS (ESI, m/z): 391 [M+H]⁺.

To a mixture of tert-butyl ((S)-4-(benzyloxy)-3-oxo-1-((S)-2-oxopiperidin-3-yl)butan-2-yl)carbamate (300 mg, 0.768 mmol, 1.0 eq.) in dioxane (3 mL) was added hydrogen chloride (3 mL, 4 M in 1,4-dioxane) at 0° C. The mixture was stirred for 1 h at rt. The mixture was concentrated under reduced pressure to afford (S)-3-((S)-2-amino-4-(benzyloxy)-3-oxobutyl)piperidin-2-one (250 mg, crude) as a yellow semi-solid. LC-MS (ESI, m/z): 291 [M+H]⁺.

To a mixture of (S)-3-((S)-2-amino-4-(benzyloxy)-3-oxobutyl)piperidin-2-one (250 mg, 0.861 mmol, 1.0 eq.), (1S,3aR,6aS)-2-(4-methoxy-1H-indole-2-carbonyl)octahydrocyclopenta[c]pyrrole-1-carboxylic acid (310 mg, 0.947 mmol, 1.1 eq.) and TCFH (265 mg, 0.947 mmol, 1.1 eq.) in acetonitrile (6 mL) was added NMI (353 mg, 4.31 mmol, 5.0 eq.) at 0° C. The mixture was stirred for 1 h at rt. The reaction was quenched with water (3 mL) and extracted with EA (3×20 mL). The organic layers were combined, washed with brine (2×20 mL), dried over anhydrous sodium sulfate, filtered and concentrated under reduced pressure to afford the crude product. The crude product was purified by TLC (Mobile phase: methanol:dichloromethane=1:20; Rf=0.4; detection: UV) to provide (1S,3aR,6aS)—N—((S)-4-(benzyloxy)-3-oxo-1-((S)-2-oxopiperidin-3-yl)butan-2-yl)-2-(4-methoxy-1H-indole-2-carbonyl)octahydrocyclopenta[c]pyrrole-1-carboxamide (95 mg, 18%) as a light yellow oil. LC-MS (ESI, m/z): 601 [M+H]⁺.

To a mixture of (1S,3aR,6aS)—N—((S)-4-(benzyloxy)-3-oxo-1-((S)-2-oxopiperidin-3-yl)butan-2-yl)-2-(4-methoxy-1H-indole-2-carbonyl)octahydrocyclopenta[c]pyrrole-1-carboxamide (90.0 mg, 0.150 mmol, 1.0 eq.) in ethanol (5 mL) was added palladium carbon (90.0 mg). The mixture was stirred overnight at rt under H₂. The mixture was filtered through a celite pad and washed with ethanol (20 mL). The filtrate was concentrated under reduced pressure to afford the crude product. The crude product was diluted with DMF (2 mL) and purified by prep-HPLC (Column: XSelect CSH Prep C18 OBD Column, 19*250 mm, 5 μm; Water (0.1% TFA), Mobile Phase B: ACN; Flow rate: 25 mL/min; Gradient: 30 B to 52 B in 7 min; 254 nm; RT1 (min): 5.70, 6.40) to provide (1S,3aR,6aS)—N-[(2S)-4-hydroxy-3-oxo-1-[(3S)-2-oxopiperidin-3-yl]butan-2-yl]-2-(4-methoxy-1H-indole-2-carbonyl)-hexahydro-1H-cyclopenta[c]pyrrole-1-carboxamide (11.0 mg, 14%) as a white solid.

Example 43

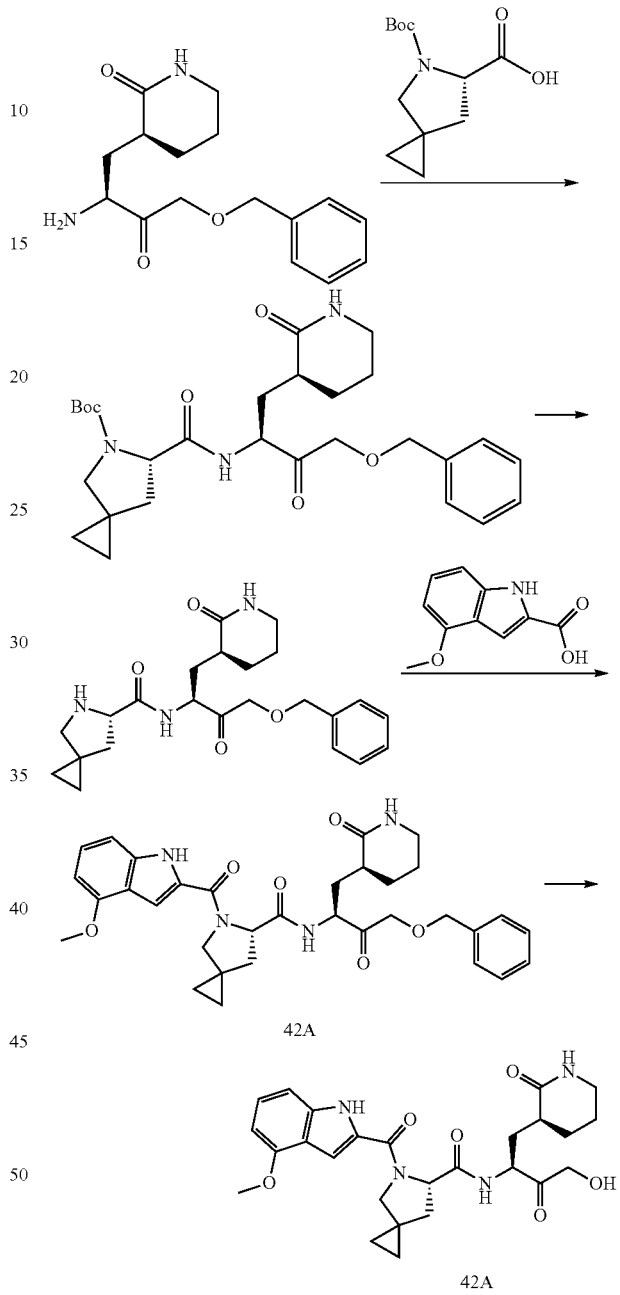

42A

42A

A 40 mL vial was charged with (S)-5-(tert-butoxycarbonyl)-5-azaspiro[2.4]heptane-6-carboxylic acid (164 mg, 0.682 mmol, 1.1 eq.), N,N,N',N'-tetramethyl-O-(7-azabenzotriazol-1-yl)uronium hexafluorophospate (259 mg, 0.682 mmol, 1.1 eq.), N,N-diisopropylethylamine (240 mg, 1.86 mmol, 3.0 eq.) and DMF (5 mL). The mixture was stirred for 30 min at rt. (S)-3-((S)-2-amino-4-(benzyloxy)-3-oxobutyl)piperidin-2-one (180 mg, 0.620 mmol, 1.0 eq.) was added. The mixture was stirred for 1 h rt. The reaction was quenched with water (10 mL). The resulting solution was extracted with EA (3×20 mL). The organic layers were combined, washed with brine (2×10 mL), dried over anhydrous sodium sulfate, filtered and concentrated under reduced pressure. The residue was chromatographed on a silica gel column with DCM:MeOH (95:5) to provide tert-butyl (S)-6-(((S)-4-(benzyloxy)-3-oxo-1-((S)-2-oxopiperidin-3-yl)butan-2-yl)carbamoyl)-5-azaspiro[2.4]heptane-5-carboxylate (120 mg, 28%) as a yellow oil. LC-MS (ESI, m/z): 514 [M+H]$^+$.

A 50 mL round-bottom flask was charged with tert-butyl (S)-6-(((S)-4-(benzyloxy)-3-oxo-1-((S)-2-oxopiperidin-3-yl)butan-2-yl)carbamoyl)-5-azaspiro[2.4]heptane-5-carboxylate (100 mg, 0.195 mmol, 1.0 eq.) and DCM (5 mL). HCl (5 mL, 2M in ether) was added dropwise at 0° C. The mixture was stirred for 1 h at rt. The mixture was concentrated under reduced pressure at rt to provide (S)—N—((S)-4-(benzyloxy)-3-oxo-1-((S)-2-oxopiperidin-3-yl)butan-2-yl)-5-azaspiro[2.4]heptane-6-carboxamide (100 mg, crude) as a yellow solid. LC-MS (ESI, m/z): 414 [M+H]$^+$.

A 8 mL vial was charged with 4-methoxy-1H-indole-2-carboxylic acid (44.4 mg, 0.232 mmol, 1.2 eq.), N,N,N',N'-tetramethyl-O-(7-azabenzotriazol-1-yl)uronium hexafluorophosphate (88.3 mg, 0.232 mmol, 1.2 eq.), DMF (2.5 mL) and N,N-diisopropylethylamine (75.0 mg, 0.579 mmol, 3.0 eq.). The mixture was stirred for 30 min at rt. (S)—N—((S)-4-(benzyloxy)-3-oxo-1-((S)-2-oxopiperidin-3-yl)butan-2-yl)-5-azaspiro[2.4]heptane-6-carboxamide (80 mg, 0.193 mmol, 1.0 eq.) was added. The mixture was stirred for 1 h at rt. The reaction was quenched with water (10 mL). The resulting solution was extracted with EA (3×20 mL). The organic layers were combined, washed with brine (2×10 mL), dried over anhydrous sodium sulfate, filtered and concentrated under reduced pressure. The residue was chromatographed on a silica gel column with DCM:MeOH (92:8) to provide (S)—N—((S)-4-(benzyloxy)-3-oxo-1-((S)-2-oxopiperidin-3-yl)butan-2-yl)-5-(4-methoxy-1H-indole-2-carbonyl)-5-azaspiro[2.4]heptane-6-carboxamide (110 mg, 87%) of as a yellow solid. LC-MS (ESI, m/z): 587 [M+H]$^+$.

A 8 mL vial was charged with (S)—N—((S)-4-(benzyloxy)-3-oxo-1-((S)-2-oxopiperidin-3-yl)butan-2-yl)-5-(4-methoxy-1H-indole-2-carbonyl)-5-azaspiro[2.4]heptane-6-carboxamide (100 mg, 0.017 mmol, 1.0 eq.), palladium carbon (120 mg) and EtOH (5 mL). The contents of the flask were placed under an atmosphere of H$_2$ (3 atm). The mixture was stirred overnight at rt. The solids were filtered off. The organic layer was concentrated under reduced pressure to provide a crude product. The crude product was purified by prep-HPLC using the following gradient conditions: Column: XBridge Prep OBD C18 Column, 19*250 mm, 5 μm; Mobile Phase A: Water (0.1% TFA), Mobile Phase B: ACN; Flow rate: 25 mL/min; Gradient: 27 B to 49 B in 7 min; 254 nm; RT1 (min): 4.82. Purification resulted in (S)—N—((S)-4-hydroxy-3-oxo-1-((S)-2-oxopiperidin-3-yl)butan-2-yl)-5-(4-methoxy-1H-indole-2-carbonyl)-5-azaspiro[2.4]heptane-6-carboxamide (16.0 mg, 18% as a white solid. $^1$H NMR (400 MHz, DMSO-d$_6$, 80° C.) δ 11.24 (s, 1H), 8.31-8.47 (m, 1H), 7.05-7.15 (m, 3H), 6.87 (s, 1H), 6.50 (d, J=7.6 Hz, 1H), 4.82 (br. s, 1H), 4.55-4.70 (m, 1H), 4.46-4.52 (m, 1H), 4.12-4.25 (m, 2H), 3.88 (s, 3H), 3.81-3.82 (m, 2H), 3.05-3.15 (m, signal partially under H$_2$O peak), 2.21-2.31 (m, 2H), 2.07-2.14 (m, 1H), 1.84-1.88 (m, 2H), 1.66-1.73 (m, 2H), 1.35-1.60 (m, 2H), 0.67 (s, 2H), 0.57 (s, 2H). LC-MS (ESI, m/z): 497 [M+H]$^+$.

Example 44

COMPOUND 43A AND COMPOUND 43

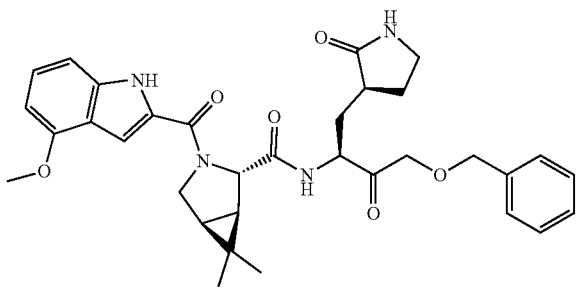

43A

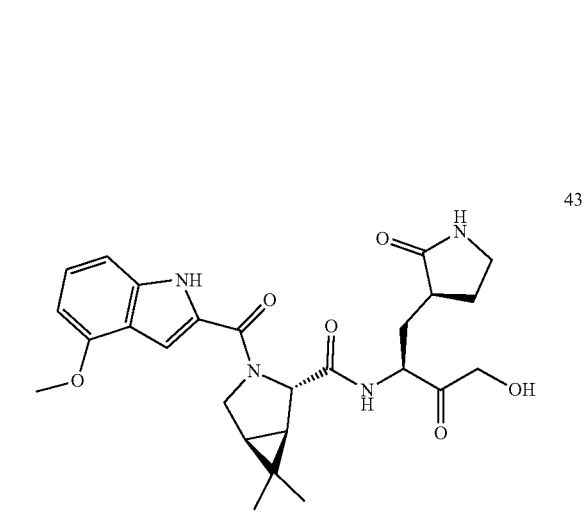

43

Compound 43A (LC-MS (ESI, m/z): 587 [M+H]$^+$) and Compound 43 (LC-MS (ESI, m/z): 497 [M+H]$^+$) were prepared in a similar manner as described for Compounds 31A and 31, using (1R,2S,5S)-3-(tert-butoxycarbonyl)-6,6-dimethyl-3-azabicyclo[3.1.0]hexane-2-carboxylic acid in place of (S)-5-(tert-butoxycarbonyl)-5-azaspiro[2.4]heptane-6-carboxylic acid.

Example 45

COMPOUND 44A AND COMPOUND 44

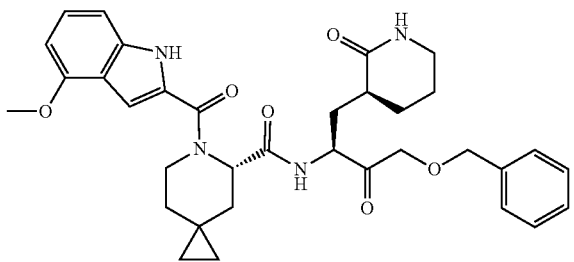

44A

44

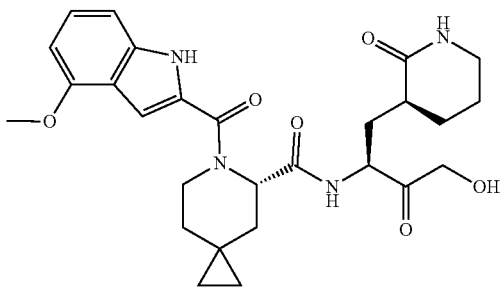

Compound 44A (LC-MS (ESI, m/z): 601 [M+H]+) and Compound 44 were prepared similarly as described for Compounds 42A and 42 using (S)-6-(tert-butoxycarbonyl)-6-azaspiro[2.5]octane-5-carboxylic acid in place of (S)-5-(tert-butoxycarbonyl)-5-azaspiro[2.4]heptane-6-carboxylic acid. Compound 44: $^1$H NMR (400 MHz, DMSO-$d_6$, 80° C.) δ 11.31 (s, 1H), 8.30 (d, J=8.0 Hz, 1H), 7.22 (s, 1H), 7.06-7.13 (m, 2H), 6.75-6.76 (m, 1H), 6.53 (d, J=5.6 Hz, 1H), 5.16-5.17 (m, 1H), 4.62 (br, 1H), 4.64-4.69 (m, 1H), 4.45-4.48 (m, 1H), 4.19-4.30 (m, 2H), 3.89 (s, 3H), 3.44-3.51 (m, 1H), 3.12-3.16 (m, 2H), 2.22-2.33 (m, 1H), 2.06-2.20 (m, 2H), 1.55-1.99 (m, 2H), 1.69-1.82 (m, 3H), 1.54-1.62 (m, 1H), 1.42-1.51 (m, 1H), 1.00-1.04 (m, 1H), 0.47-0.50 (m, 1H), 0.28-0.34 (m, 3H). LC-MS (ESI, m/z): 511 [M+H]+.

Example 46

COMPOUND 45A AND COMPOUND 45

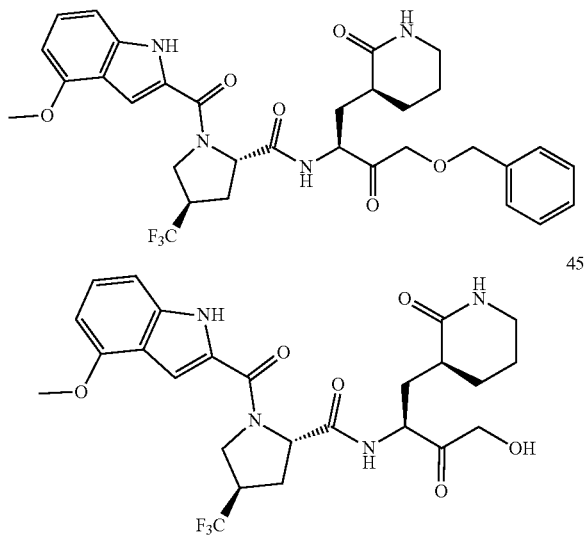

Compound 45A and Compound 45 were prepared similarly as described for Compounds 42A and 42 using (2S,4R)-1-(tert-butoxycarbonyl)-4-(trifluoromethyl)pyrrolidine-2-carboxylic acid in place of (S)-5-(tert-butoxycarbonyl)-5-azaspiro[2.4]heptane-6-carboxylic acid.

Compound 45A: $^1$H NMR (400 MHz, DMSO-$d_6$, 80° C.) δ 11.34 (s, 1H), 8.57 (br, 1H), 7.26-7.36 (m, 5H), 7.07-7.17 (m, 3H), 6.92 (s, 1H), 6.53 (d, J=7.2 Hz, 1H), 4.90-5.10 (m, 1H), 4.48-4.56 (m, 3H), 4.24-4.36 (m, 2H), 4.03-4.19 (m, 1H), 3.95-4.05 (m, 1H), 3.90 (s, 3H), 3.20-3.40 (m, 1H), 3.05-3.15 (m, 2H), 2.35-2.50 (m, 1H), 2.19-2.33 (m, 2H), 2.08-2.18 (m, 1H), 1.69-1.87 (m, 2H), 1.55-1.68 (m, 1H), 1.25-1.50 (m, 2H). LC-MS (ESI, m/z): 629 [M+H]+.

Compound 45: $^1$H NMR (400 MHz, DMSO-$d_6$, 80° C.) δ 11.34 (s, 1H), 8.53 (br, 1H), 7.06-7.24 (m, 3H), 6.92 (s, 1H), 6.53 (d, J=7.6 Hz, 1H), 5.00 (br, 1H), 4.75-4.85 (m, 1H), 4.51-4.57 (m, 1H), 4.15-4.22 (m, 3H), 3.92-4.01 (m, 1H), 3.90 (s, 3H), 3.35 (br, 1H), 3.05-3.15 (m, partially under H$_2$O signal), 2.45-2.47 (m, 1H), 2.22-2.23 (m, 2H), 2.08-2.16 (m, 1H), 1.71-1.90 (m, 2H), 1.62-1.63 (m, 1H), 1.34-1.51 (m, 2H). LC-MS (ESI, m/z): 539 [M+H]+.

Example 47

COMPOUND 46

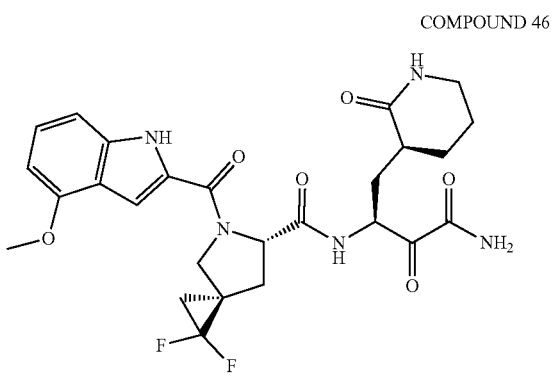 [SMILES: COc1cccc2[nH]c(C(=O)N3C[C@]4(C[C@H]3C(=O)N[C@@H](C[C@@H]3CCCNC3=O)C(=O)C(N)=O)CC4(F)F)cc12]

To a solution of (3S,6S)-1,1-difluoro-5-(4-methoxy-1H-indole-2-carbonyl)-N-[(2S)-1-oxo-3-[(3S)-2-oxopiperidin-3-yl]propan-2-yl]-5-azaspiro[2.4]heptane-6-carboxamide (80 mg, 0.16 mmol, 1.0 eq.) in MeOH (2 mL) was added CsF (12 mg, 0.08 mmol, 0.5 eq.) and trimethylsilyl cyanide (19 mg, 0.19 mmol, 1.2 eq.) at 0° C. The mixture was stirred at rt for overnight, and the reaction was quenched with water (2 mL). The resulting solution was extracted with EA (3×5 mL). The organic layers were combined, dried over anhydrous sodium sulfate, filtered and concentrated under reduced pressure. The residue was chromatographed on a C18 column with H$_2$O:MeCN (2:3) to provide (3S,6S)—N-[(2S)-1-cyano-1-hydroxy-3-[(3S)-2-oxopiperidin-3-yl]propan-2-yl]-1,1-difluoro-5-(4-methoxy-1H-indole-2-carbonyl)-5-azaspiro[2.4]heptane-6-carboxamide (70 mg, 75%) as a white solid. LC-MS (ESI, m/z): 530 [M+H]+.

To a solution of (3S,6S)—N-[(2S)-1-cyano-1-hydroxy-3-[(3S)-2-oxopiperidin-3-yl]propan-2-yl]-1,1-difluoro-5-(4-methoxy-1H-indole-2-carbonyl)-5-azaspiro[2.4]heptane-6-carboxamide (60 mg, 0.11 mmol, 1.0 eq.) in MeOH (2 mL), was added lithium hydroxide (3.26 mg, 0.136 mmol, 1.2 eq.) and H$_2$O$_2$ (38.5 mg, 1.13 mmol, 10 eq.). The mixture was stirred at rt for 2 h, and the reaction was quenched with water (2 mL). The resulting solution was extracted with EA (3×4 mL). The organic layers were combined, dried over anhydrous sodium sulfate, filtered and concentrated under reduced pressure. The residue was chromatographed on a silica gel column with MeOH:DCM (1:25) to provide (3S)-3-{[(3S,6S)-1,1-difluoro-5-(4-methoxy-1H-indole-2-carbonyl)-5-azaspiro[2.4]heptan-6-yl]formamido}-2-hydroxy-4-[(3S)-2-oxopiperidin-3-yl]butanamide (25 mg, 32%) as a white solid. LC-MS (ESI, m/z): 548 [M+H]+.

To a solution of (3S)-3-{[(3S,6S)-1,1-difluoro-5-(4-methoxy-1H-indole-2-carbonyl)-5-azaspiro[2.4]heptan-6-yl]formamido}-2-hydroxy-4-[(3S)-2-oxopiperidin-3-yl]butanamide (10 mg, 0.02 mmol, 1.0 eq.) in DMSO (1 mL) was added IBX (10.2 mg, 0.04 mmol, 2.0 eq.). The mixture was stirred at rt for 3 h, and the reaction quenched with sodium bicarbonate solution (2 mL). The resulting solution was extracted with EA (3×5 mL). The organic layers were combined, dried over anhydrous sodium sulfate, filtered and concentrated under reduced pressure. The residue was purified by pre-TLC with MeOH:DCM (1:18) to provide (3S,6S)—N-(4-amino-3,4-dioxo-1-((S)-2-oxopiperidin-3-yl)butan-2-yl)-1,1-difluoro-5-(4-methoxy-1H-indole-2-carbonyl)-5-azaspiro[2.4]heptane-6-carboxamide (3.3 mg, 32%) as a white solid. LC-MS (ESI, m/z): 546 [M+H]$^+$.

Example 48

COMPOUND 47A AND 47

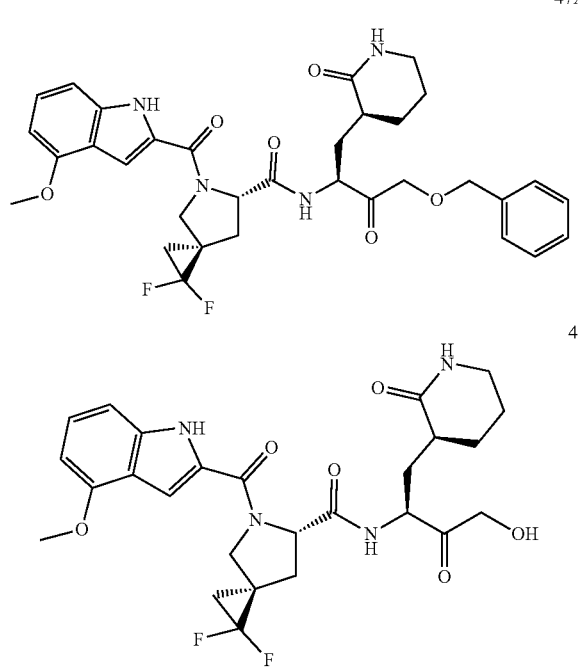

47A

47

To a mixture of (3S)-3-[(2S)-2-amino-4-(benzyloxy)-3-oxobutyl]piperidin-2-one hydrochloride (250 mg, 0.765 mmol, 1.0 eq.) and (3S,6S)-5-(tert-butoxycarbonyl)-1,1-difluoro-5-azaspiro[2.4]heptane-6-carboxylic acid (234 mg, 0.842 mmol, 1.1 eq.) in DMF (3 mL) was added o-(7-azabenzotriazol-1-yl)-N,N,N',N'-tetramethyluronium hexafluorophosphate (436 mg, 1.15 mmol, 1.5 eq.) and N-ethyl-N-isopropylpropan-2-amine (296 mg, 2.29 mmol, 3.0 eq.). The mixture was stirred for 1 h at rt. The reaction was quenched with water (5 mL). The mixture was extracted with EA (3×5 mL). The organic layers were combined, washed with brine (2×5 mL), dried over anhydrous sodium sulfate, filtered and concentrated under reduced pressure to afford crude product. The crude product was purified by TLC (Mobile phase: MeOH:DCM=1:15; Rf=0.6; detection: UV) to provide tert-butyl (3S,6S)-6-{[(2S)-4-(benzyloxy)-3-oxo-1-[(3S)-2-oxopiperidin-3-yl]butan-2-yl]carbamoyl}-1,1-difluoro-5-azaspiro[2.4]heptane-5-carboxylate (280 mg, 51%) as a yellow solid. LC-MS (ESI, m/z): 550 [M+H]$^+$.

A mixture of tert-butyl (3S,6S)-6-{[(2S)-4-(benzyloxy)-3-oxo-1-[(3S)-2-oxopiperidin-3-yl]butan-2-yl]carbamoyl}-1,1-difluoro-5-azaspiro[2.4]heptane-5-carboxylate (250 mg, 0.455 mmol, 1.0 eq.) in hydrogen chloride (3 mL, 2 M in Et$_2$O) was stirred for 1 h at rt. The mixture was concentrated under reduced pressure to afford (3S,6S)—N-[(2S)-4-(benzyloxy)-3-oxo-1-[(3S)-2-oxopiperidin-3-yl]butan-2-yl]-1,1-difluoro-5-azaspiro[2.4]heptane-6-carboxamide hydrochloride (220 mg, crude) as a yellow solid. LC-MS (ESI, m/z): 450 [M+H]$^+$.

To a mixture of 4-methoxy-1H-indole-2-carboxylic acid (95.0 mg, 0.498 mmol, 1.1 eq.), o-(7-azabenzotriazol-1-yl)-N,N,N',N'-tetramethyluronium hexafluorophosphate (258 mg, 0.679 mmol, 1.5 eq.) and N-ethyl-N-isopropylpropan-2-amine (176 mg, 1.36 mmol, 3.0 eq.) in DMF (3 mL) was added (3S,6S)—N-[(2S)-4-(benzyloxy)-3-oxo-1-[(3S)-2-oxopiperidin-3-yl]butan-2-yl]-1,1-difluoro-5-azaspiro[2.4]heptane-6-carboxamide hydrochloride (220 mg, 0.453 mmol, 1.0 eq.) at 0° C. The mixture was stirred for 1 h at rt., and the reaction was quenched with water (5 mL). The mixture was extracted with EA (3×5 mL). The organic layers were combined, washed with brine (2×5 mL), dried over anhydrous sodium sulfate, filtered and concentrated under reduced pressure to afford the crude product. The crude product was purified by TLC (Mobile phase: MeOH:DCM=1:15; Rf=0.4; detection: UV) to provide (3S,6S)—N-[(2S)-4-(benzyloxy)-3-oxo-1-[(3S)-2-oxopiperidin-3-yl]butan-2-yl]-1,1-difluoro-5-(4-methoxy-1H-indole-2-carbonyl)-5-azaspiro[2.4]heptane-6-carboxamide (140 mg, 44%) as a yellow solid.

And 40 mg above of product was purified by prep-HPLC (Column: XBridge Shield RP18 OBD Column, 19×250 mm, 10 μm; Water (0.1% TFA), Mobile Phase B:ACN; Flow rate: 25 mL/min; Gradient: 51 B to 71 B in 7 min; 254 nm; RT: 4.72) to provide (3S,6S)—N-[(2S)-4-(benzyloxy)-3-oxo-1-[(3S)-2-oxopiperidin-3-yl]butan-2-yl]-1,1-difluoro-5-(4-methoxy-1H-indole-2-carbonyl)-5-azaspiro[2.4]heptane-6-carboxamide (19.4 mg, 52%) as a white solid. $^1$H NMR (400 MHz, DMSO-d$_6$, 80° C.) δ 11.34 (s, 1H), 8.50-8.53 (m, 1H), 7.25-7.40 (m, 5H), 7.00-7.24 (m, 3H), 6.91 (s, 1H), 6.53 (d, J=7.6 Hz, 1H), 4.90-5.05 (m, 1H), 4.44-4.60 (m, 3H), 4.20-4.43 (m, 2H), 4.05-4.19 (m, 1H), 3.75-4.03 (m, 4H), 3.05-3.15 (m, 2H), 2.55-2.65 (m, 1H), 2.15-2.30 (m, 1H), 1.95-2.14 (m, 2H), 1.25-1.85 (m, 7H). LC-MS (ESI, m/z): 623 [M+H]$^+$.

To a mixture of (3S,6S)—N-[(2S)-4-(benzyloxy)-3-oxo-1-[(3S)-2-oxopiperidin-3-yl]butan-2-yl]-1,1-difluoro-5-(4-methoxy-1H-indole-2-carbonyl)-5-azaspiro[2.4]heptane-6-carboxamide (100 mg, 0.161 mmol, 1.0 eq.) in EtOH (3 mL) was added Pd/C (120 mg). The mixture was stirred overnight at rt under H$_2$ atmosphere. The mixture was filtered through a celite pad, and the filtrate was concentrated under reduced pressure to afford the crude product. The crude product was purified by prep-HPLC (column: XBridge Prep OBD C18 Column, 19×250 mm, 5 μm; Mobile Phase A: Water (0.1% TFA), Mobile Phase B: ACN; Flow rate: 25 Ml/min; Gradient: 25 B to 50 B in 7 min; 254 nm; RT: 6.65) to provide (3S,6S)-1,1-difluoro-N-[(2S)-4-hydroxy-3-oxo-1-[(3S)-2-oxopiperidin-3-yl]butan-2-yl]-5-(4-methoxy-1H-indole-2-carbonyl)-5-azaspiro[2.4]heptane-6-carboxamide (49.7 mg, 56%) as a white solid. $^1$H NMR (400 MHz, DMSO-d$_6$, 80° C.) δ 11.33 (s, 1H), 8.35-8.50 (m, 1H), 7.05-7.20 (m, 3H), 6.90 (s, 1H), 6.53 (d, J=7.6 Hz, 1H), 4.85-5.05 (m, 1H), 4.65-4.80 (m, 1H), 4.45-4.60 (m, 1H), 4.12-4.28 (m, 2H), 4.02-4.10 (m, 1H), 3.80-4.00 (m, 4H), 3.05-3.15 (m, 2H), 2.55-2.65 (m, 1H), 2.20-2.30 (m, 1H), 2.00-2.19 (m, 2H), 1.80-1.95 (m, 1H), 1.65-1.75 (m, 2H), 1.60-1.64 (m, 1H), 1.50-1.59 (m, 1H), 1.42-1.49 (m, 1H), 1.25-1.40 (m, 1H). LC-MS (ESI, m/z): 533 [M+H]$^+$.

Example 49

COMPOUND 48

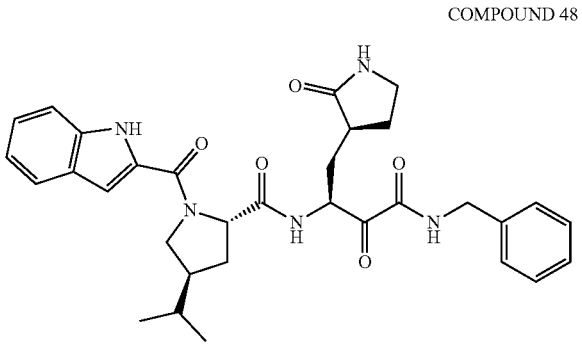 [SMILES: CC(C)[C@@H]1C[C@@H](C(=O)N[C@@H](C[C@@H]2CCNC2=O)C(=O)C(=O)NCc2ccccc2)N(C(=O)c2cc3ccccc3[nH]2)C1]

To a mixture of 1-benzyl 2-methyl (2S,4S)-4-cyclopropylpyrrolidine-1,2-dicarboxylate (500 mg, 1.65 mmol, 1.0 eq.) in EA (5 mL) was added Pd/C (300 mg). The mixture was stirred overnight at rt under H$_2$. The mixture was filtered through a celite pad, and the filtrate was concentrated under reduced pressure to provide methyl (2S,4S)-4-cyclopropylpyrrolidine-2-carboxylate (240 mg, crude) as a light yellow oil. LC-MS (ESI, m/z): 170 [M+H]$^+$.

To a mixture of methyl (2S,4S)-4-cyclopropylpyrrolidine-2-carboxylate (240 mg, 1.42 mmol, 1.0 eq.) in DCM (5 mL) was added di-tert-butyl dicarbonate (619 mg, 2.84 mmol, 2.0 eq.) and triethylamine (430 mg, 4.25 mmol, 3.0 eq.). The mixture was stirred for 2 h at rt and concentrated under reduced pressure to afford 1-tert-butyl 2-methyl (2S,4S)-4-cyclopropylpyrrolidine-1,2-dicarboxylate (380 mg, crude) as a colorless oil. LC-MS (ESI, m/z): 214 [M−56+H]$^+$.

To a mixture of 1-tert-butyl 2-methyl (2S,4S)-4-cyclopropylpyrrolidine-1,2-dicarboxylate (380 mg, 1.41 mmol, 1.0 eq.) in EA (3 mL)/acetic acid (3 mL) was added PtO$_2$ (256 mg, 1.13 mmol, 0.8 eq.). The mixture was stirred overnight at rt under H$_2$. The mixture was filtered through a celite pad and washed with EA (2×5 mL). The filtrate was concentrated under reduced pressure to afford 1-tert-butyl 2-methyl (2S, 4S)-4-isopropylpyrrolidine-1,2-dicarboxylate (380 mg, crude) as a colorless oil. LC-MS (ESI, m/z): 272 [M+H]$^+$.

To a mixture of 1-tert-butyl 2-methyl (2S,4S)-4-isopropylpyrrolidine-1,2-dicarboxylate (380 mg, 1.40 mmol, 1.0 eq.) in 1,4-dioxane (2 mL) was added hydrochloride acid (2 mL, 6 M in water). The mixture was stirred for 2 h at 80° C. and concentrated under reduced pressure to afford (2S,4S)-4-isopropylpyrrolidine-2-carboxylic acid (220 mg, crude) as yellow oil. LC-MS (ESI, m/z): 158 [M+H]$^+$.

To a mixture of (2S,4S)-4-isopropylpyrrolidine-2-carboxylic acid (220 mg, 1.40 mmol, 1.0 eq.) in DCM (5 mL) was added di-tert-butyl dicarbonate (611 mg, 2.80 mmol, 2.0 eq.) and triethylamine (425 mg, 4.20 mmol, 3.0 eq.). The mixture was stirred for 2 h at rt and concentrated under reduced pressure to afford (2S,4S)-1-(tert-butoxycarbonyl)-4-isopropylpyrrolidine-2-carboxylic acid (360 mg, crude) as an off-white semi-solid. LC-MS (ESI, m/z): 202 [M−56+H]$^+$.

To a mixture of (2S,4S)-1-(tert-butoxycarbonyl)-4-isopropylpyrrolidine-2-carboxylic acid (314 mg, 1.22 mmol, 1.0 eq.), o-(7-azabenzotriazol-1-yl)-N,N,N',N'-tetramethyluronium hexafluorophosphate (696 mg, 1.83 mmol, 1.5 eq.) and N-ethyl-N-isopropylpropan-2-amine (473 mg, 3.66 mmol, 3.0 eq.) in DMF (6 mL) was added (3S)-3-amino-N-benzyl-2-hydroxy-4-[(3S)-2-oxopyrrolidin-3-yl]butanamide hydrochloride (400 mg, 1.22 mmol, 1.0 eq.) at 0° C. The mixture was stirred for 1 h at rt, and the reaction quenched with water (10 mL). The mixture was extracted with EA (3×10 mL). The organic layers were combined, washed with brine (2×10 mL), dried over anhydrous sodium sulfate, filtered and concentrated under reduced pressure to afford crude product. The crude product was diluted with dichloromethane (10 mL). A slurry was made with 100~200 silica gel mesh (1 g) and loaded to a column after removing the dichloromethane. The sample was purified by column chromatography (Column size 4×24 cm, column volume: 200 mL, silica gel size (100~200 mesh) quantity: 80 g) and eluted with MeOH:DCM (0%~10% over 20 min). Collected fractions: 3%-4% MeOH:DCM fractions were chosen as pure fractions, and those fractions were combined and concentrated under reduced pressure to provide tert-butyl (2S,4S)-2-{[(2S)-1-(benzylcarbamoyl)-1-hydroxy-3-[(3S)-2-oxopyrrolidin-3-yl]propan-2-yl]carbamoyl}-4-isopropylpyrrolidine-1-carboxylate (330 mg, 40%) as a yellow solid. LC-MS (ESI, m/z): 531 [M+H]$^+$.

A mixture of tert-butyl (2S,4S)-2-{[(2S)-1-(benzylcarbamoyl)-1-hydroxy-3-[(3S)-2-oxopyrrolidin-3-yl]propan-2-yl]carbamoyl}-4-isopropylpyrrolidine-1-carboxylate (320 mg, 0.603 mmol, 1.0 eq.) in trifluoroacetic acid (2 mL):DCM (6 mL) was stirred for 1 h at rt. The mixture was concentrated under reduced pressure to afford (3S)—N-benzyl-2-hydroxy-3-{[(2S,4S)-4-isopropylpyrrolidin-2-yl]formamido}-4-[(3S)-2-oxopyrrolidin-3-yl]butanamide (260 mg, crude) as a yellow oil. LC-MS (ESI, m/z): 431 [M+H]$^+$.

To a mixture of indole-2-carboxylic acid (97.0 mg, 0.604 mmol, 1.0 eq.), o-(7-azabenzotriazol-1-yl)-N,N,N',N'-tetramethyluronium hexafluorophosphate (344 mg, 0.906 mmol, 1.5 eq.) and N-ethyl-N-isopropylpropan-2-amine (234 mg, 1.81 mmol, 3.0 eq.) in DMF (5 mL) was added (3S)—N-benzyl-2-hydroxy-3-{[(2S,4S)-4-isopropylpyrrolidin-2-yl]formamido}-4-[(3S)-2-oxopyrrolidin-3-yl]butanamide (260 mg, 0.604 mmol, 1.0 eq.) at 0° C. The mixture was stirred for 1 h at rt, and the reaction was quenched with water (10 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by TLC (Mobile phase: MeOH:DCM=1:15; Rf=0.3; detection: UV) to provide (3S)—N-benzyl-2-hydroxy-3-{[(2S,4S)-1-(1H-indole-2-carbonyl)-4-isopropylpyrrolidin-2-yl]formamido}-4-[(3S)-2-oxopyrrolidin-3-yl]butanamide (180 mg, 42%) as a yellow solid. LC-MS (ESI, m/z): 574 [M+H]$^+$.

To a mixture of (3S)—N-benzyl-2-hydroxy-3-{[(2S,4S)-1-(1H-indole-2-carbonyl)-4-isopropylpyrrolidin-2-yl]formamido}-4-[(3S)-2-oxopyrrolidin-3-yl]butanamide (160 mg, 0.279 mmol, 1.0 eq.) in DMSO (5 mL) was added 2-Iodoxybenzoic acid (156 mg, 0.558 mmol, 2.0 eq.). The mixture was stirred overnight at rt, and the reaction was quenched with sat. aq. sodium bicarbonate solution (5 mL). The mixture was extracted with EA (3×5 mL). The organic layers were combined, washed with brine (2×5 mL), dried over anhydrous sodium sulfate, filtered and concentrated under reduced pressure to afford the crude product. The crude product was purified by TLC (Mobile phase: MeOH:DCM=1:15; Rf=0.3; detection: UV) to provide N-benzyl-3-{[(2S,4S)-1-(1H-indole-2-carbonyl)-4-isopropylpyrrolidin-2-yl]formamido}-2-oxo-4-[(3S)-2-oxopyrrolidin-3-yl]butanamide (25.2 mg, 14%) as a white solid. LC-MS (ESI, m/z): 572 [M+H]⁺.

Example 50

COMPOUND 49A AND COMPOUND 49

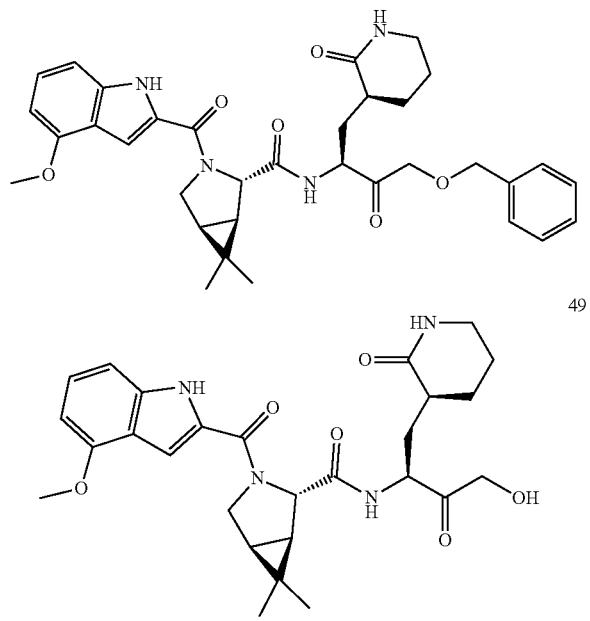

To a mixture of (1R,2S,5S)-3-(tert-butoxycarbonyl)-6,6-dimethyl-3-azabicyclo[3.1.0]hexane-2-carboxylic acid (215 mg, 0.842 mmol, 1.1 eq.), o-(7-azabenzotriazol-1-yl)-N,N,N',N'-tetramethyluronium hexafluorophosphate (436 mg, 1.15 mmol, 1.5 eq.) and N-ethyl-N-isopropylpropan-2-amine (297 mg, 2.30 mmol, 3.0 eq.) in DMF (3 mL) was added (3S)-3-[(2S)-2-amino-4-(benzyloxy)-3-oxobutyl]piperidin-2-one hydrochloride (250 mg, 0.765 mmol, 1.0 eq.) at 0° C. The mixture was stirred for 1 h at rt. The reaction was quenched with water (5 mL), and the mixture was extracted with EA (3×5 mL). The organic layers were combined, washed with brine (2×5 mL), dried over anhydrous sodium sulfate, filtered and concentrated under reduced pressure to afford the crude product. The crude product was purified by TLC (Mobile phase: methanol:dichloromethane=1:15; Rf=0.6; detection: UV) to provide tert-butyl (1R,2S,5S)-2-{[(2S)-4-(benzyloxy)-3-oxo-1-[(3S)-2-oxopiperidin-3-yl]butan-2-yl]carbamoyl}-6,6-dimethyl-3-azabicyclo[3.1.0]hexane-3-carboxylate (320 mg, 55%) as a yellow semi-solid. LC-MS (ESI, m/z): 528 [M+H]⁺. A mixture of tert-butyl (1R,2S,5S)-2-{[(2S)-4-(benzyloxy)-3-oxo-1-[(3S)-2-oxopiperidin-3-yl]butan-2-yl]carbamoyl}-6,6-dimethyl-3-azabicyclo[3.1.0]hexane-3-carboxylate (220 mg, 0.417 mmol, 1.0 eq.) in hydrogen chloride (3 mL, 2 M in Et₂O) was stirred for 1 h at rt, and then concentrated under reduced pressure to afford (1R,2S,5S)—N-[(2S)-4-(benzyloxy)-3-oxo-1-[(3S)-2-oxopiperidin-3-yl]butan-2-yl]-6,6-dimethyl-3-azabicyclo[3.1.0]hexane-2-carboxamide hydrochloride (200 mg, crude) as a yellow solid. LC-MS (ESI, m/z): 428 [M+H]⁺.

To a mixture of 4-methoxy-1H-indole-2-carboxylic acid (91.0 mg, 0.474 mmol, 1.1 eq.), o-(7-azabenzotriazol-1-yl)-N,N,N',N'-tetramethyluronium hexafluorophosphate (246 mg, 0.646 mmol, 1.5 eq.) and N-ethyl-N-isopropylpropan-2-amine (167 mg, 1.29 mmol, 3.0 eq.) in DMF (3 mL) was added (1R,2S,5S)—N-[(2S)-4-(benzyloxy)-3-oxo-1-[(3S)-2-oxopiperidin-3-yl]butan-2-yl]-6,6-dimethyl-3-azabicyclo[3.1.0]hexane-2-carboxamide hydrochloride (200 mg, 0.431 mmol, 1.0 eq.) at 0° C. The mixture was stirred for 1 h at rt, and the reaction was quenched with water (5 mL). The mixture was extracted with EA (3×5 mL). The organic layers were combined, washed with brine (2×5 mL), dried over anhydrous sodium sulfate, filtered and concentrated under reduced pressure to afford the crude product. The crude product was purified by TLC (Mobile phase: MeOH:DCM=1:15; Rf=0.4; detection: UV) to provide (1R,2S,5S)—N-[(2S)-4-(benzyloxy)-3-oxo-1-[(3S)-2-oxopiperidin-3-yl]butan-2-yl]-3-(4-methoxy-1H-indole-2-carbonyl)-6,6-dimethyl-3-azabicyclo[3.1.0]hexane-2-carboxamide (180 mg, 64%) as a yellow solid.

50 mg above of product was purified by prep-HPLC (Column: XBridge Shield RP18 OBD Column, 19×250 mm, 10 μm; Mobile Phase A: Water (0.1% TFA), Mobile Phase B: ACN; Flow rate: 25 mL/min; Gradient: 45 B to 75 B in 7 min, 254 nm; RT: 5.6) to provide (1R,2S,5S)—N-[(2S)-4-(benzyloxy)-3-oxo-1-[(3S)-2-oxopiperidin-3-yl]butan-2-yl]-3-(4-methoxy-1H-indole-2-carbonyl)-6,6-dimethyl-3-azabicyclo[3.1.0]hexane-2-carboxamide (27.5 mg, 58%) as a white solid. ¹H NMR (400 MHz, DMSO-d₆) δ 11.24 (s, 1H), 8.30-8.80 (m, 1H), 7.22-7.42 (m, 5H), 7.00-7.20 (m, 3H), 6.75-6.99 (m, 1H), 6.40-6.60 (m, 1H), 4.10-4.95 (m, 7H), 3.75-3.95 (m, 4H), 3.05-3.20 (m, 2H), 2.18-2.30 (m, 1H), 2.05-2.17 (m, 1H), 1.16-1.95 (m, 7H), 1.08 (s, 3H), 0.92 (s, 3H). LC-MS (ESI, m/z): 601 [M+H]⁺.

To a mixture of (1R,2S,5S)—N-[(2S)-4-(benzyloxy)-3-oxo-1-[(3S)-2-oxopiperidin-3-yl]butan-2-yl]-3-(4-methoxy-1H-indole-2-carbonyl)-6,6-dimethyl-3-azabicyclo[3.1.0]hexane-2-carboxamide (130 mg, 0.216 mmol, 1.0 eq.) in ethanol (3 mL) was added Pd/C (160 mg). The mixture was stirred overnight at rt under hydrogen. The mixture was filtered through a celite pad, and the filtrate was concentrated under reduced pressure to afford the crude product. The crude product was purified by prep-HPLC (Column: XBridge Shield RP18 OBD Column, 19×250 mm, 10 μm; Water (0.1% TFA), Mobile Phase B: ACN; Flow rate: 25 mL/min; Gradient: 25 B to 50 B in 7 min, 254 nm; RT: 6.87) to provide (1R,2S,5S)—N-[(2S)-4-hydroxy-3-oxo-1-[(3S)-2-oxopiperidin-3-yl]butan-2-yl]-3-(4-methoxy-1H-indole-2-carbonyl)-6,6-dimethyl-3-azabicyclo[3.1.0]hexane-2-carboxamide (57.6 mg, 51%) as a white solid. ¹H NMR (400 MHz, DMSO-d₆) δ 11.25 (s, 1H), 8.25-8.80 (m, 1H), 6.75-7.30 (m, 4H), 6.52 (s, 1H), 4.70-5.00 (m, 1H), 4.45-4.69 (m, 2H), 4.05-4.35 (m, 3H), 3.75-3.95 (m, 4H), 3.10-3.25 (m, 2H), 2.18-2.30 (m, 1H), 2.00-2.17 (m, 1H), 1.15-1.99 (m, 7H), 1.09 (s, 3H), 0.92 (s, 3H). LC-MS (ESI, m/z): 511 [M+H]⁺.

Example 51

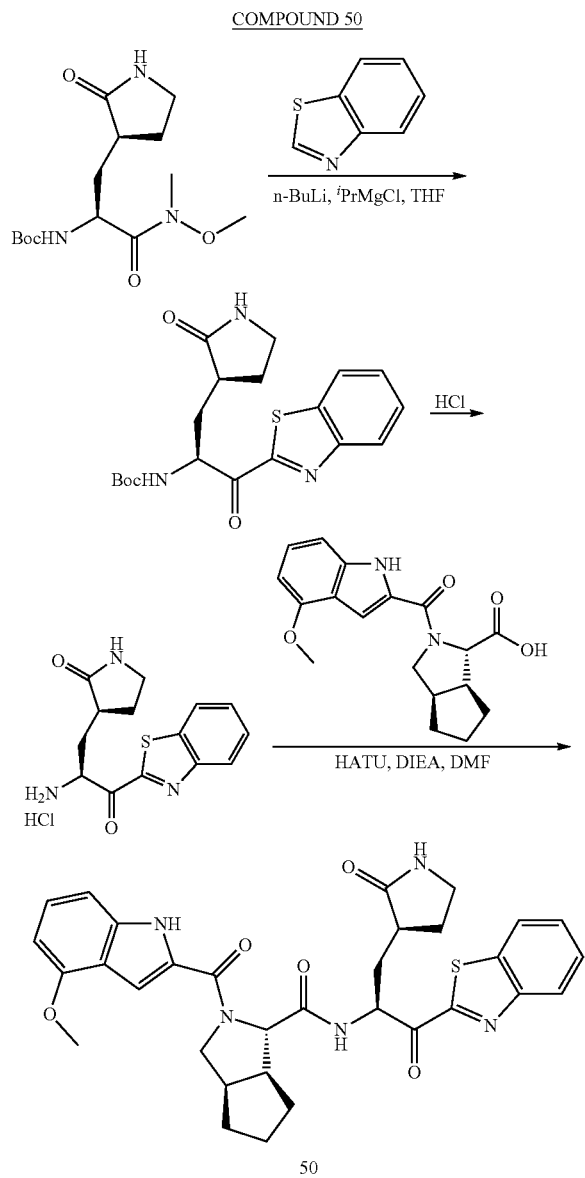

To a solution of benzothiazole (1.07 g, 7.93 mmol, 5.0 eq.) in THF (10 mL) was added n-butyllithium (3.2 mL, 7.93 mmol, 5.0 eq.) at −78° C. and stirred for 1 h at −78° C. under nitrogen. To a solution of tert-butyl N-[(1S)-1-[methoxy (methyl)carbamoyl]-2-[(3S)-2-oxopyrrolidin-3-yl]ethyl] carbamate (500 mg, 1.59 mmol, 1.0 eq.) in THF (5 mL) was added isopropylmagnesium chloride (1.6 mL, 3.17 mmol, 2.0 eq., 2 M in THF) at −15° C. under nitrogen, and the mixture was stirred for 20 min at −15° C. This mixture was added to the above solution, and the resulting mixture was stirred for 3 h at −78° C. under nitrogen. The reaction was quenched with sat. ammonium chloride solution (5 mL). The mixture was extracted with EtOAc (3×10 mL). The organic layers were combined, washed with brine (2×10 mL), dried over anhydrous sodium sulfate, filtered and concentrated under reduced pressure. The product was diluted with DCM (30 mL) and a slurry was made with 100~200 silica gel mesh (3 g) and then loaded to a column after removing the DCM. The sample was purified by column chromatography (Column size 5×24 cm, column volume: 300 mL, silica gel size (100~200 mesh) quantity: 120 g) and eluted with MeOH: DCM (0%~10% over 15 min). The collected fractions: 9% MeOH/DCM fractions were chosen as pure fractions, and those fractions were combined and concentrated under reduced pressure to provide tert-butyl N-[(2S)-1-(1,3-benzothiazol-2-yl)-1-oxo-3-[(3S)-2-oxopyrrolidin-3-yl]propan-2-yl]carbamate (457 mg 87% pure) as a yellow solid. LC-MS (ESI, m/z): 290 [M−100+H]$^+$.

To a solution of tert-butyl N-[(2S)-1-(1,3-benzothiazol-2-yl)-1-oxo-3-[(3S)-2-oxopyrrolidin-3-yl]propan-2-yl]carbamate (427 mg, 1.10 mmol, 1.0 eq.) in DCM (3 mL) was added hydrochloric acid (4.3 mL, 2 M in Et$_2$O). The mixture was stirred for 1 h at rt. The mixture was concentrated under reduced pressure to afford (S)-3-((S)-2-amino-3-(benzo[d] thiazol-2-yl)-3-oxopropyl)pyrrolidin-2-one hydrochloride (400 mg crude). LC-MS (ESI, m/z): 290 [M+H]$^+$.

To a mixture of (S)-3-((S)-2-amino-3-(benzo[d]thiazol-2-yl)-3-oxopropyl)pyrrolidin-2-one hydrochloride (400 mg crude) (317 mg, 1.10 mmol, 1.0 eq.) in DMF (4 mL) was (1S,3aR,6aS)-2-(4-methoxy-1H-indole-2-carbonyl)-hexahydro-1H-cyclopenta[c]pyrrole-1-carboxylic acid (360 mg, 1.10 mmol, 1.0 eq.) in DMF (4 mL), o-(7-azabenzotriazol-1-yl)-N,N,N',N'-tetramethyluronium hexafluorophosphate (584 mg, 1.53 mmol, 1.4 eq.) and N-ethyl-N-isopropylpropan-2-amine (708 mg, 5.48 mmol, 5.0 eq.). The mixture was stirred for 1 h at rt, and the reaction was quenched with water (10 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by HPLC (Column: XBridge Shield RP18 OBD Column, 19×250 mm, 10 μm; Mobile Phase A: Water (0.1% TFA), Mobile Phase B: ACN; Flow rate: 25 mL/min; Gradient: 40% B to 60% B in 10 min, 60% B; Wave Length: 254 nm; RT1 (min): 8.87) to provide (1S,3aR,6aS)—N-[(2S)-1-(1,3-benzothiazol-2-yl)-1-oxo-3-[(3S)-2-oxopyrrolidin-3-yl]propan-2-yl]-2-(4-methoxy-1H-indole-2-carbonyl)-hexahydro-1H-cyclopenta[c]pyrrole-1-carboxamide (57 mg, 8%) as a light yellow solid. $^1$H NMR (400 MHz, DMSO-d$_6$) δ 10.87-11.53 (s, 1H), 8.45-9.11 (br, 1H), 8.09-8.30 (m, 2H), 7.53-7.72 (m, 2H), 7.20-7.50 (s, 1H), 7.01-7.15 (m, 2H), 6.80-7.00 (m, 1H), 6.40-6.61 (m, 1H), 5.29-5.62 (m, 1H), 4.52-4.92 (m, 1H), 3.80-4.10 (m, 1H), 3.89 (s, 3H), 3.58-3.72 (m, 1H), 3.08-3.22 (m, 1H), 2.85-3.01 (m, 1H), 2.51-2.79 (m, 3H), 1.40-2.25 (m, 10H). LC-MS (ESI, m/z): 600 [M+H]$^+$.

Example 52

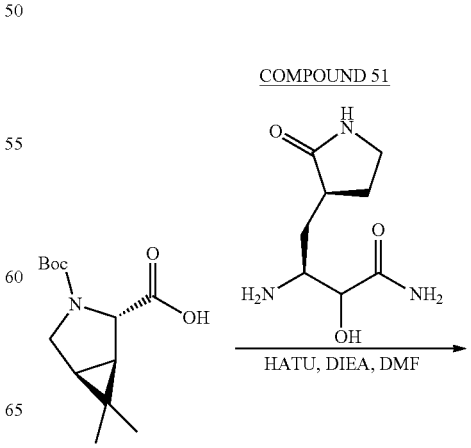

239
-continued

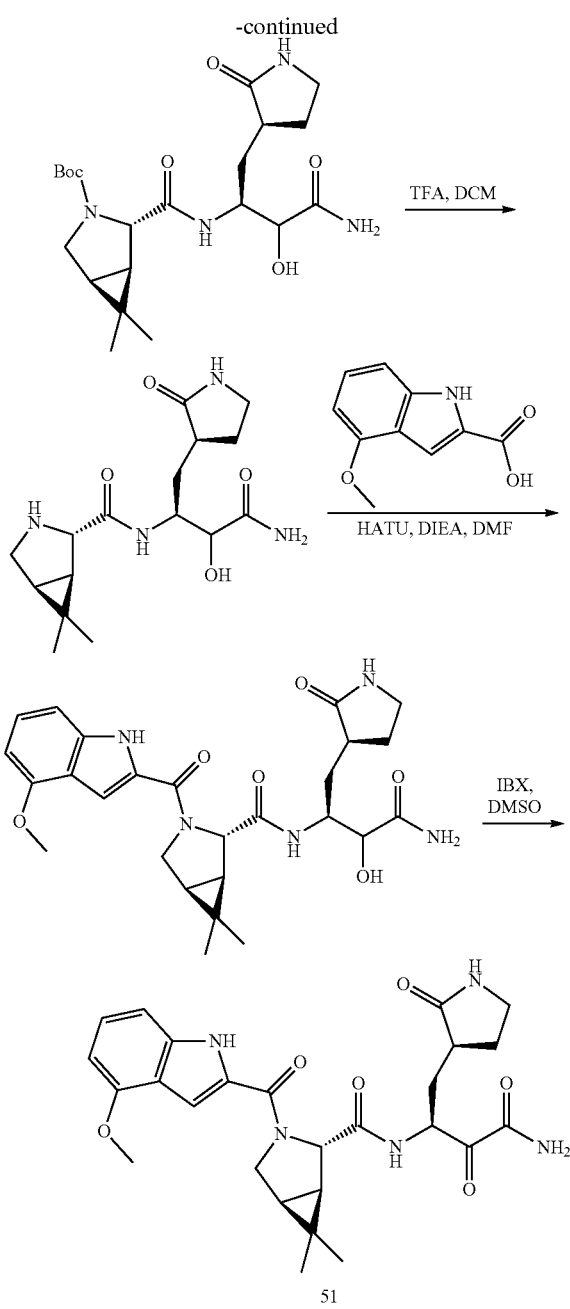

51

To a solution of (1R,2S,5S)-3-(tert-butoxycarbonyl)-6,6-dimethyl-3-azabicyclo[3.1.0]hexane-2-carboxylic acid (209 mg, 0.82 mmol, 1.1 eq.) in DMF (5 mL) was added o-(7-azabenzotriazol-1-yl)-N,N,N',N'-tetramethyluronium hexafluorophosphate (425 mg, 1.12 mmol, 1.5 eq.) and N-ethyl-N-isopropylpropan-2-amine (674 mg, 5.22 mmol, 7.0 eq.). The mixture was stirred at 0° C. for 30 min, and (3S)-3-amino-2-hydroxy-4-[(3S)-2-oxopyrrolidin-3-yl]butanamide (150 mg, 0.75 mmol, 1.0 eq.) was added. The mixture was stirred at rt for 2 h. The reaction was quenched with water (20 mL), and the resulting solution was extracted with EtOAc (3×35 mL). The organic layers were combined, washed with brine (70 mL), dried over anhydrous sodium sulfate, filtered and concentrated under reduced pressure. The residue was chromatographed on a silica gel column with methanol:dichloromethane (9:91) to provide tert-butyl

240

(1R,2S,5S)-2-{[(2S)-1-carbamoyl-1-hydroxy-3-[(3S)-2-oxopyrrolidin-3-yl]propan-2-yl]carbamoyl}-6,6-dimethyl-3-azabicyclo[3.1.0]hexane-3-carboxylate (130 mg, 39%) of as a light yellow oil. LC-MS (ESI, m/z): 439 [M+H]$^+$.

To a solution of tert-butyl (1R,2S,5S)-2-{[(2S)-1-carbamoyl-1-hydroxy-3-[(3S)-2-oxopyrrolidin-3-yl]propan-2-yl]carbamoyl}-6,6-dimethyl-3-azabicyclo[3.1.0]hexane-3-carboxylate (130 mg, 0.30 mmol, 1.0 eq.) in DCM (3 mL) was added TFA (1 mL). The mixture was stirred at rt for 2 h, and then concentrated under reduced pressure to get (3S)-3-{[(1R,2S,5S)-6,6-dimethyl-3-azabicyclo[3.1.0]hexan-2-yl]formamido}-2-hydroxy-4-[(3S)-2-oxopyrrolidin-3-yl]butanamide (130 mg, 91%) as a yellow oil. LC-MS (ESI, m/z): 339 [M+H]$^+$.

To a solution of 4-methoxy-1H-indole-2-carboxylic acid (62 mg, 0.33 mmol, 1.1 eq.) in DMF (5 mL) was added o-(7-azabenzotriazol-1-yl)-N,N,N',N'-tetramethyluronium hexafluorophosphate (168 mg, 0.44 mmol, 1.5 eq.) and N-ethyl-N-isopropylpropan-2-amine (267 mg, 2.07 mmol, 7.0 eq.). The mixture was stirred at 0° C. for 30 min. (3S)-3-{[(1R,2S,5S)-6,6-dimethyl-3-azabicyclo[3.1.0]hexan-2-yl]formamido}-2-hydroxy-4-[(3S)-2-oxopyrrolidin-3-yl]butanamide (100 mg, 0.30 mmol, 1.0 eq.) was added. The mixture was stirred at rt for 2 h, and the reaction was quenched with water (10 mL). The resulting solution was extracted with EtOAc (3×30 mL). The organic layers were combined, washed with brine (60 mL), dried over anhydrous sodium sulfate, filtered and concentrated under reduced pressure. The residue was chromatographed on a silica gel column with MeOH:DCM (3:25) to provide (3S)-2-hydroxy-3-{[(1R,2S,5S)-3-(4-methoxy-1H-indole-2-carbonyl)-6,6-dimethyl-3-azabicyclo[3.1.0]hexan-2-yl]formamido}-4-[(3S)-2-oxopyrrolidin-3-yl]butanamide (30 mg, 17%) as a light yellow oil. LC-MS (ESI, m/z): 512 [M+H]$^+$.

To a solution of (3S)-2-hydroxy-3-{[(1R,2S,5S)-3-(4-methoxy-1H-indole-2-carbonyl)-6,6-dimethyl-3-azabicyclo[3.1.0]hexan-2-yl]formamido}-4-[(3S)-2-oxopyrrolidin-3-yl]butanamide (30 mg, 0.06 mmol, 1.0 eq.) in DMSO (2 mL) was added IBX (32.8 mg, 0.12 mmol, 2.0 eq.). The mixture was stirred at rt for 2 h, and the reaction was quenched with a sodium bicarbonate solution (2 mL). The solution was extracted with EtOAc (3×5 mL). The organic layers were combined, dried over anhydrous sodium sulfate, filtered and concentrated under reduced pressure. The residue was purified by pre-TLC with MeOH:DCM (1:9) to provide (3S)-3-{[(1R,2S,5S)-3-(4-methoxy-1H-indole-2-carbonyl)-6,6-dimethyl-3-azabicyclo[3.1.0]hexan-2-yl]formamido}-2-oxo-4-[(3S)-2-oxopyrrolidin-3-yl]butanamide (0.8 mg, 3%) as a white solid. LC-MS (ESI, m/z): 510 [M+H]$^+$ Example 53

COMPOUND 52

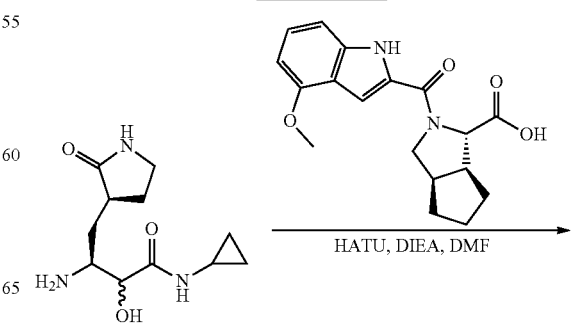

241

-continued

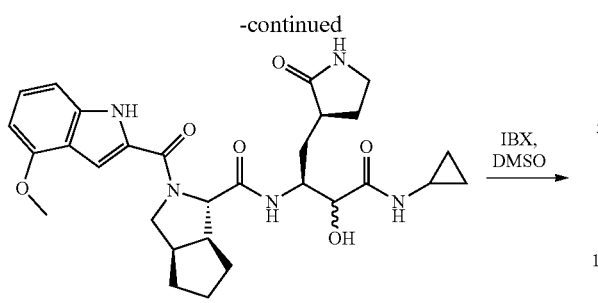

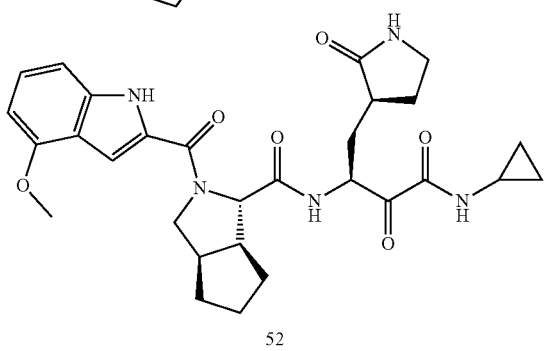

52

To a stirred solution of (1S,3aR,6aS)-2-(4-methoxy-1H-indole-2-carbonyl)-hexahydro-1H-cyclopenta[c]pyrrole-1-carboxylic acid (400 mg, 1.22 mmol, 1.0 eq.) and (3S)-3-amino-N-cyclopropyl-2-hydroxy-4-[(3S)-2-oxopyrrolidin-3-yl]butanamide (295 mg, 1.22 mmol, 1.0 eq.) in N,N-dimethylformamide (15 mL) was added O-(7-Aza-1H-benzotriazol-1-yl)-N,N,N',N'-tetramethyluronium hexafluorophosphate (594 mg, 1.56 mmol, 1.3 eq.) and N,N-diisopropylethylamine (621 mg, 4.81 mmol, 4.0 eq.) in portions at rt. The mixture was stirred for 1 h at rt, and the reaction was quenched with water (30 mL) at rt. The mixture was extracted with EA (3×60 mL). The organic layers were combined, washed with brine (3×40 mL), dried over anhydrous sodium sulfate, filtered and concentrated under reduced pressure. The residue was purified by Prep-TLC (dichloromethane:methanol, 8:1) to afford (3S)-3-1{[(1S,3aR,6aS)-2-(4-methoxy-1H-indole-2-carbonyl)-hexahydro-1H-cyclopenta[c]pyrrol-1-yl]formamido}-N-cyclopropyl-2-hydroxy-4-[(3S)-2-oxopyrrolidin-3-yl]butanamide (320 mg, 46%) as a yellow solid. LC-MS (ESI, m/z): 552 [M+H]⁺.

To a stirred mixture of (3S)-3-{[(1S,3aR,6aS)-2-(4-methoxy-1H-indole-2-carbonyl)-hexahydro-1H-cyclopenta[c]pyrrol-1-yl]formamido}-N-cyclopropyl-2-hydroxy-4-[(3S)-2-oxopyrrolidin-3-yl]butanamide (300 mg, 0.540 mmol, 1.0 eq.) in dimethyl sulfoxide (10 mL) was added 2-Iodoxybenzoic acid (457 mg, 1.63 mmol, 3.0 eq.) in portions at rt. The mixture was stirred for 6 h at rt, and the reaction was quenched with sat. sodium bicarbonate (5 mL). The mixture was diluted with water (15 mL) and extracted with EA (3×60 mL). The organic layers were combined, washed with brine (3×50 mL), dried over anhydrous sodium sulfate, filtered and concentrated under reduced pressure. The residue was purified by Prep-TLC (dichloromethane:methanol, 8:1) to afford 3-{[(1S,3aR,6aS)-2-(4-methoxy-

242

1H-indole-2-carbonyl)-hexahydro-1H-cyclopenta[c]pyrrol-1-yl]formamido}-N-cyclopropyl-2-oxo-4-[(3S)-2-oxopyrrolidin-3-yl]butanamide (100.3 mg, 32%) as a white solid. LC-MS (ESI, m/z): 550 [M+H]⁺.

Example 54

COMPOUND 53A AND COMPOUND 53

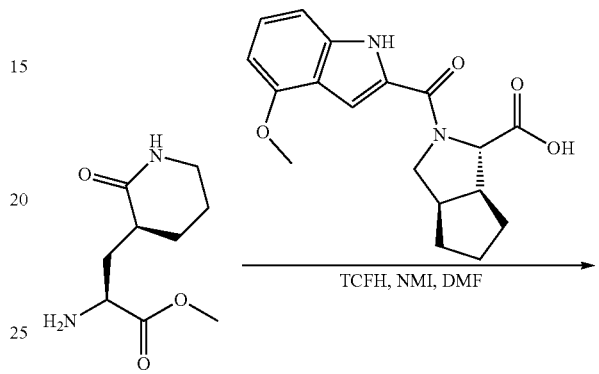

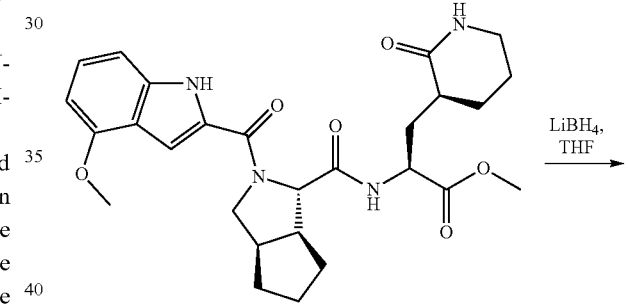

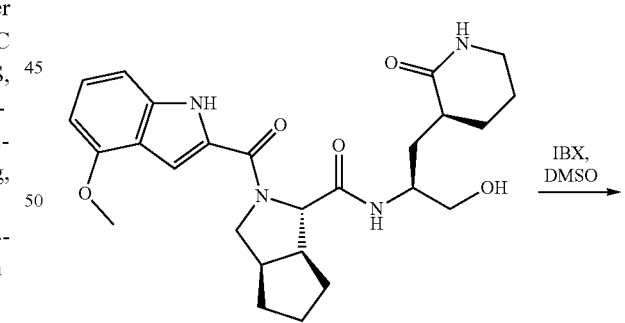

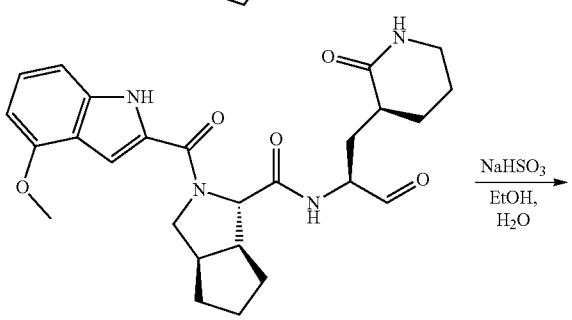

-continued

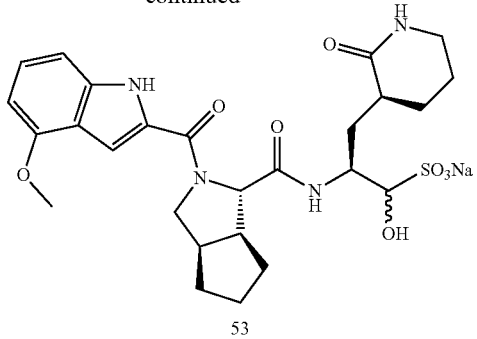

53

To a mixture of methyl (2S)-2-[(tert-butoxycarbonyl)amino]-3-[(3S)-2-oxopiperidin-3-yl]propanoate (800 mg, 2.66 mmol, 1.0 eq.) in DCM (10 mL) was added trifluoroacetic acid (3 mL). The mixture was stirred for 1 h at rt. The mixture was concentrated under reduced pressure to afford methyl (2S)-2-amino-3-[(3S)-2-oxopiperidin-3-yl]propanoate (533 mg, crude) as a yellow oil. LC-MS (ESI, m/z): 201 [M+H]$^+$.

To a mixture of methyl (2S)-2-amino-3-[(3S)-2-oxopiperidin-3-yl]propanoate (533 mg, 2.66 mmol, 1.0 eq.), (1S,3aR,6aS)-2-(4-methoxy-1H-indole-2-carbonyl)-hexahydro-1H-cyclopenta[c]pyrrole-1-carboxylic acid (874 mg, 2.66 mmol, 1.0 eq.) and N,N,N',N'-Tetramethylchloroformamidinium hexafluorophosphate (971 mg, 3.46 mmol, 1.3 eq.) in DMF (10 mL) was added N-methylimidazole (1.75 g, 21.3 mmol, 8.0 eq.) at 0° C. The mixture was stirred for 2 h at rt. The reaction was quenched with water (20 mL). The mixture was extracted with EtOAc (3×20 mL). The organic layers were combined, washed with brine (2×20 mL), dried over anhydrous sodium sulfate, filtered and concentrated under reduced pressure to afford the crude product. The crude product was diluted with DCM (20 mL). A slurry was made with 100~200 silicagel mesh (2 g) and loaded to a column after removing the dichloromethane. The sample was purified by column chromatography (Column size 5×24 cm, column volume: 300 mL, silicagel size (100~200 mesh) quantity: 120 g) and eluted with MeOH:DCM (0%~8% over 20 min). The collected fractions: 3%-4% MeOH:DCM fractions were chosen as pure fractions, and those fractions were combined and concentrated under reduced pressure to provide methyl (2S)-2-{[(1S,3aR,6aS)-2-(4-methoxy-1H-indole-2-carbonyl)-hexahydro-1H-cyclopenta[c]pyrrol-1-yl]formamido}-3-[(3S)-2-oxopiperidin-3-yl]propanoate (870 mg, 60%) as a yellow solid. LC-MS (ESI, m/z): 511 [M+H]$^+$.

To a mixture of methyl (2S)-2-{[(1S,3aR,6aS)-2-(4-methoxy-1H-indole-2-carbonyl)-hexahydro-1H-cyclopenta[c]pyrrol-1-yl]formamido}-3-[(3S)-2-oxopiperidin-3-yl]propanoate (800 mg, 1.57 mmol, 1.0 eq.) in THF (10 mL) was added dropwise lithium borohydride (2.35 mL, 4.70 mmol, 3.0 eq., 2 M in THF) at 0° C. After stirred for 30 min at 0° C., ethanol (5 mL) was added. The mixture was stirred for 2 h at 0° C. The reaction was quenched with potassium bisulfate (20 mL, 1 M in water). The mixture was extracted with DCM (3×20 mL). The organic layers were combined, dried over anhydrous sodium sulfate, filtered and concentrated under reduced pressure to afford crude product. The crude product was purified by TLC (Mobile phase: MeOH:DCM=1:15; Rf=0.3; detection: UV) to provide (1S,3aR,6aS)—N-[(2S)-1-hydroxy-3-[(3S)-2-oxopiperidin-3-yl]propan-2-yl]-2-(4-methoxy-1H-indole-2-carbonyl)-hexahydro-1H-cyclopenta[c]pyrrole-1-carboxamide (420 mg, 51%) as an off-white solid. LC-MS (ESI, m/z): 483 [M+H]$^+$.

To a mixture of (1S,3aR,6aS)—N-[(2S)-1-hydroxy-3-[(3S)-2-oxopiperidin-3-yl]propan-2-yl-2-(4-methoxy-1H-indole-2-carbonyl)-hexahydro-1H-cyclopenta[c]pyrrole-1-carboxamide (320 mg, 0.663 mmol, 1.0 eq.) in DMSO (5 mL) was added 2-iodoxybenzoic acid (557 mg, 1.99 mmol, 3.0 eq.). The mixture was stirred for 6 h at rt. The reaction was quenched with sat. aq. sodium bicarbonate (15 mL). The mixture was extracted with EtOAc (3×10 mL). The organic layers were combined, washed with brine (2×10 mL), dried over anhydrous sodium sulfate, filtered and concentrated under reduced pressure to afford crude product. The crude product was purified by TLC (Mobile phase: MeOH:DCM=1:15; Rf=0.4; detection: UV) to provide (1S,3aR,6aS)-2-(4-methoxy-1H-indole-2-carbonyl)-N-[(2S)-1-oxo-3-[(3S)-2-oxopiperidin-3-yl]propan-2-yl]-hexahydro-1H-cyclopenta[c]pyrrole-1-carboxamide (53A, 130 mg, 39%) as a white solid. LC-MS (ESI, m/z): 481 [M+H]$^+$.

To a mixture of (1S,3aR,6aS)-2-(4-methoxy-1H-indole-2-carbonyl)-N-[(2S)-1-oxo-3-[(3S)-2-oxopiperidin-3-yl]propan-2-yl]-hexahydro-1H-cyclopenta[c]pyrrole-1-carboxamide (90 mg, 0.187 mmol, 1.0 eq.) in ethanol (0.8 mL)/EtOAc (1.6 mL) was added a solution of NaHSO$_3$ (26.0 mg, 0.244 mmol, 1.3 eq.) in water (0.4 mL). The mixture was stirred for 1 h at 50° C. The mixture was filtered. and the filtrate was concentrated under reduced pressure to afford the crude product. The crude product was triturated with EtOAc (2 mL) to provide sodium (2S)-2-{[(1S,3aR,6aS)-2-(4-methoxy-1H-indole-2-carbonyl)-hexahydro-1H-cyclopenta[c]pyrrol-1-yl]formamido}-1-hydroxy-3-[(3S)-2-oxopiperidin-3-yl]propane-1-sulfonate (37.8 mg, 33%) as a white solid. $^1$H NMR (400 MHz, DMSO-d$_6$, 353K) δ 11.10-11.70 (m, 1H), 7.25-8.05 (m, 1H), 7.00-7.20 (m, 3H), 6.70-6.99 (m, 1H), 6.42-6.60 (m, 1H), 4.80-5.50 (m, 1H), 4.35-4.79 (m, 1H), 4.25-4.34 (m, 1H), 4.08-4.24 (m, 1H), 3.90-4.07 (m, 1H), 3.79-3.89 (m, 3H), 3.60-3.75 (m, 1H), 2.88-3.10 (m, 2H), 2.60-2.87 (m, 2H), 2.05-2.30 (m, 2H), 1.10-1.95 (m, 11H).

Example 55

COMPOUND 54

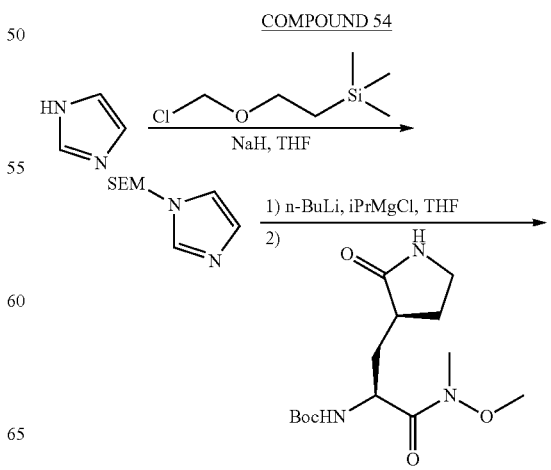

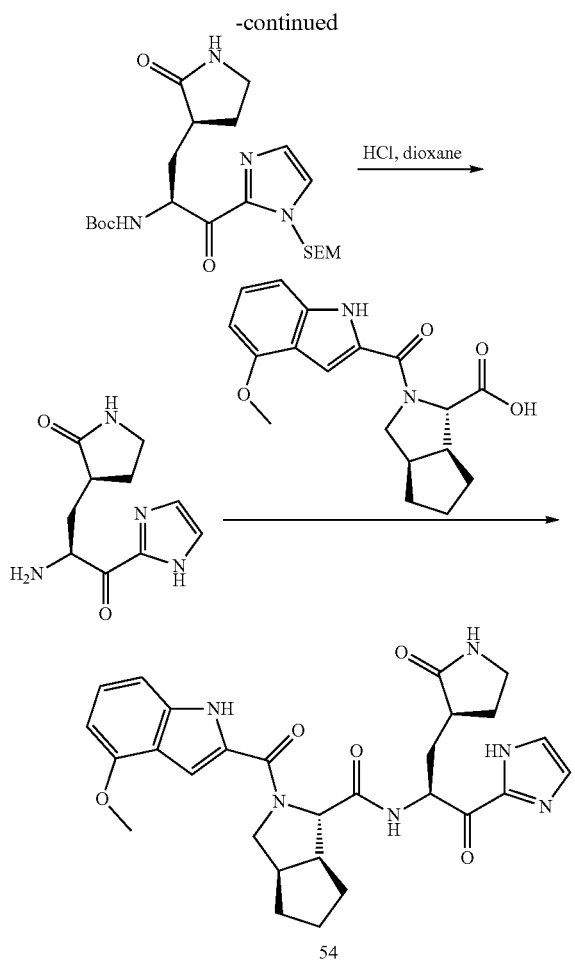

and concentrated under reduced pressure. The residue was chromatographed on a silica gel column with methanol:dichloromethane (3:97) to provide tert-butyl N-[(2S)-1-oxo-3-[(3S)-2-oxopyrrolidin-3-yl]-1-(1-{[2-(trimethylsilyl)ethoxy]methyl}imidazol-2-yl)propan-2-yl]carbamate (294 mg, 37%) as a light yellow oil. LC-MS (ESI, m/z): 453 [M+H]$^+$.

To a solution of tert-butyl N-[(2S)-1-oxo-3-[(3S)-2-oxopyrrolidin-3-yl]-1-(1-{[2-(trimethylsilyl)ethoxy]methyl}imidazol-2-yl)propan-2-yl]carbamate (250 mg, 0.55 mmol, 1.0 eq.) in dioxane was added hydrogen chloride (10 mL, 4M in dioxane). The mixture was stirred at rt for 2 h and then concentrated under reduced pressure to get (3S)-3-[(2S)-2-amino-3-(1H-imidazol-2-yl)-3-oxopropyl]pyrrolidin-2-one (125 mg, crude) as a yellow oil. LC-MS (ESI, m/z): 223 [M+H]$^+$ To a solution of (3S)-3-[(2S)-2-amino-3-(1H-imidazol-2-yl)-3-oxopropyl]pyrrolidin-2-one (100 mg, 0.45 mmol, 1.0 eq.) in DMF (8 mL) was added (1S,3aR,6aS)-2-(4-methoxy-1H-indole-2-carbonyl)-hexahydro-1H-cyclopenta[c]pyrrole-1-carboxylic acid (163 mg, 0.50 mmol, 1.1 eq.), N-ethyl-N-isopropylpropan-2-amine (407 mg, 3.15 mmol, 7.0 eq.) and o-(7-azabenzotriazol-1-yl)-N,N,N',N'-tetramethyluronium hexafluorophosphate (222 mg, 0.59 mmol, 1.3 eq.). The mixture was stirred at rt for 2 h, and the reaction was quenched with water (10 mL). The solution was extracted with EtOAc (3×15 mL). The organic layers were combined, washed with brine (30 mL), dried over anhydrous sodium sulfate, filtered and concentrated under reduced pressure. The residue was purified by pre-TLC with methanol:dichloromethane (3:47) to provide (1S,3aR,6aS)—N-[(2S)-1-(1H-imidazol-2-yl)-1-oxo-3-[(3S)-2-oxopyrrolidin-3-yl]propan-2-yl]-2-(4-methoxy-1H-indole-2-carbonyl)-hexahydro-1H-cyclopenta[c]pyrrole-1-carboxamide (8.4 mg, 3%) as a white solid. LC-MS (ESI, m/z): 533 [M+H]$^+$.

To a solution of NaH (1.76 g, 60% in mineral oil, 44.1 mmol, 1.5 eq.) in THF (160 mL) was added imidazole (2 g, 29.4 mmol, 1.0 eq.) slowly at 0° C. under N$_2$. The mixture was stirred at rt for 1 h, and then [2-(chloromethoxy)ethyl]trimethylsilane (7.4 g, 44.1 mmol, 1.5 eq.) was added slowly at 0° C. The mixture was stirred at rt for overnight, and the reaction was quenched with water (100 mL). The solution was extracted with EtOAc (3×60 mL). The organic layers were combined, washed with brine (150 mL), dried over anhydrous sodium sulfate, filtered and concentrated under reduced pressure. The residue was chromatographed on a silica gel column with EA:PE (3:7) to provide 1-{[2-(trimethylsilyl)ethoxy]methyl}imidazole (4 g, 25%) as a light yellow oil. LC-MS (ESI, m/z): 199 [M+H]$^+$.

To a solution of 1-{[2-(trimethylsilyl)ethoxy]methyl}imidazole (1.57 g, 7.93 mmol, 5.0 eq.) in THF (10 mL) was added n-butyllithium (3.2 mL, 2.5M in hexane, 7.93 mmol, 5.0 eq.) slowly at −78° C. under N$_2$. The mixture was stirred at −78° C. for 1 h. To a solution of tert-butyl N-[(1S)-1-[methoxy(methyl)carbamoyl]-2-[(3S)-2-oxopyrrolidin-3-yl]ethyl]carbamate (500 mg, 1.59 mmol, 1.0 eq.) in THF (10 mL) was slowly added i-PrMgCl (1.6 mL, 2M in THF, 3.18 mmol, 2.0 eq.) at −15° C. under N$_2$. The mixture stirred at −15° C. for 20 min and added into the above solution at −78° C. The mixture was stirred at −78° C. for 3 h, and the reaction was quenched with ammonium chloride (2 mL). The solution was extracted with EtOAc (3×15 mL). The organic layers were combined, washed with brine (30 mL), dried over anhydrous sodium sulfate, filtered

Example 56

COMPOUND 55

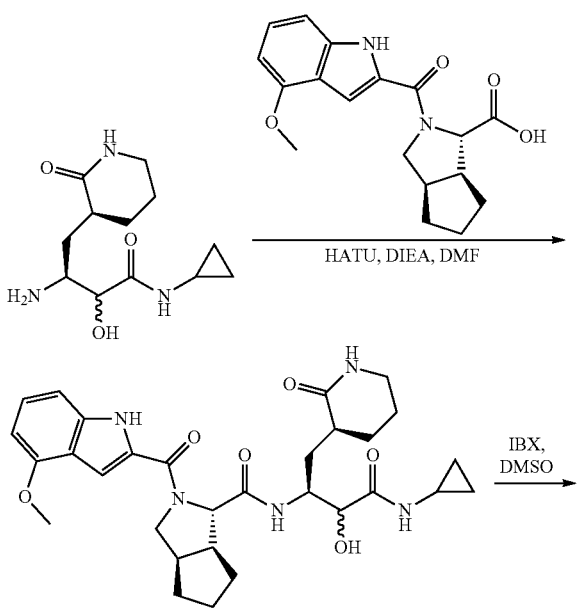

-continued

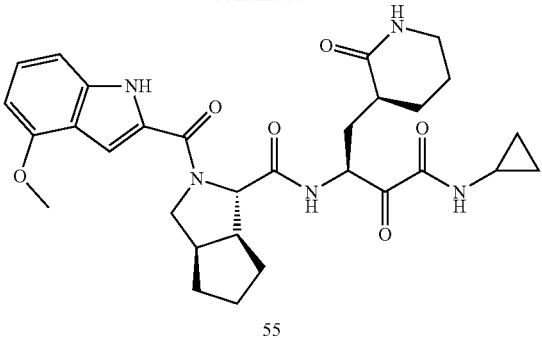

55

To a solution of (3S)-3-amino-N-cyclopropyl-2-hydroxy-4-[(3S)-2-oxopiperidin-3-yl]butanamide (194 mg, 0.760 mmol, 1.0 eq.) and (1S,3aR,6aS)-2-(4-methoxy-1H-indole-2-carbonyl)-hexahydro-1H-cyclopenta[c]pyrrole-1-carboxylic acid (250 mg, 0.760 mmol, 1.0 eq.) in DMF (15 mL) was added o-(7-azabenzotriazol-1-yl)-N,N,N',N'-tetramethyluronium hexafluorophosphate (405 mg, 1.06 mmol, 1.4 eq.) and N-ethyl-N-isopropylpropan-2-amine (491 mg, 3.80 mmol, 5.0 eq.) at rt. The mixture was stirred for 1 h at rt, and the reaction was quenched with water (30 mL) at rt. The mixture was extracted with EA (3×60 mL). The organic layers were combined, washed with brine (3×40 mL), dried over anhydrous sodium sulfate, filtered and concentrated under reduced pressure. The residue was purified by TLC (Mobile phase: MeOH:DCM=1:11; Rf=0.5; detection: UV) to afford (3S)-3-1{[(1S,3aR,6aS)-2-(4-methoxy-1H-indole-2-carbonyl)-hexahydro-1H-cyclopenta[c]pyrrol-1-yl]formamido}-N-cyclopropyl-2-hydroxy-4-[(3S)-2-oxopiperidin-3-yl]butanamide (190 mg, 44%). LC-MS (ESI, m/z): 566 [M+H]$^+$.

To a solution of (3S)-3-{[(1S,3aR,6aS)-2-(4-methoxy-1H-indole-2-carbonyl)-hexahydro-1H-cyclopenta[c]pyrrol-1-yl]formamido}-N-cyclopropyl-2-hydroxy-4-[(3S)-2-oxopiperidin-3-yl]butanamide (170 mg, 0.301 mmol, 1.0 eq.) in DMSO (5 mL) was added 2-Iodoxybenzoic acid (253 mg, 0.903 mmol, 3.0 eq.) with stirring at rt. The mixture was stirred for 20 h at rt. The reaction was quenched with a baking soda solution (5 mL). The mixture was extracted with EA (4×40 mL). The organic layers were combined, washed with brine (2×40 mL), dried over anhydrous sodium sulfate, filtered and concentrated under reduced pressure to afford the crude product. The crude product was purified by TLC (Mobile phase: MeOH:DCM=1:11; Rf=0.6; detection: UV) to provide 3-{[(1S,3aR,6aS)-2-(4-methoxy-1H-indole-2-carbonyl)-hexahydro-1H-cyclopenta[c]pyrrol-1-yl]formamido}-N-cyclopropyl-2-oxo-4-[(3S)-2-oxopiperidin-3-yl]butanamide (96.9 mg, 56%) as a white solid. LC-MS (ESI, m/z): 564 [M+H]$^+$.

Example 57

COMPOUND 56

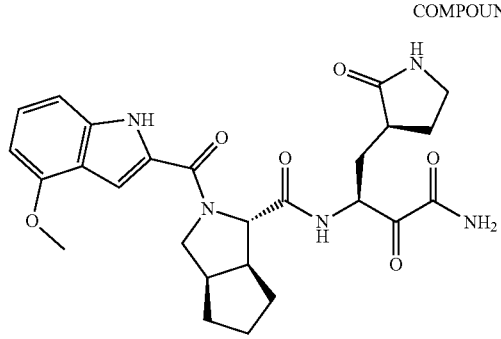

To a solution of (1S,3aR,6aS)-2-{-1[(benzyloxy)carbonyl]-4-methoxyindole-2-carbonyl}-hexahydro-1H-cyclopenta[c]pyrrole-1-carboxylic acid (253 mg, 0.55 mmol, 1.1 eq.) in DMF (3 mL) was added N,N,N',N'-Tetramethyl-O-(7-azabenzotriazol-1-yl)uronium hexafluorophospate (283 mg, 0.75 mmol, 1.5 eq.) and N,N-diisopropylethylamine (450 mg, 3.48 mmol, 7.0 eq.). The mixture was stirred at 0° C. for 30 min. (3S)-3-amino-2-hydroxy-4-[(3S)-2-oxopyrrolidin-3-yl]butanamide (100 mg, 0.50 mmol, 1.0 eq.) was added. The mixture was stirred at 0° C. for 1 h, and the reaction quenched with water (2 mL). The mixture was extracted with EtOAc (3×5 mL). The organic layers were combined, dried over anhydrous sodium sulfate, filtered and concentrated under reduced pressure. The residue was chromatographed on a silica gel column with MeOH:DCM (1:25) to provide benzyl 2-[(1S,3aR,6aS)-1-{[(2S)-1-carbamoyl-1-hydroxy-3-[(3S)-2-oxopyrrolidin-3-yl]propan-2-yl]carbamoyl}-hexahydro-1H-cyclopenta[c]pyrrole-2-carbonyl]-4-methoxyindole-1-carboxylate (105 mg, 33%) as a yellow solid. LC-MS (ESI, m/z): 646 [M+H]$^+$.

2-[(1S,3aR,6aS)-1-{[(2S)-1-carbamoyl-1-hydroxy-3-[(3S)-2-oxopyrrolidin-3-yl]propan-2-yl]carbamoyl}-hexahydro-1H-cyclopenta[c]pyrrole-2-carbonyl]-4-methoxyindole-1-carboxylate (80 mg, 0.12 mmol, 1.0 eq.) in EtOH (2 mL) was added 10% palladium on active carbon (40 mg). The mixture was stirred at rt for 2 h. The resulting solution was filtered, and the filtrate was concentrated under reduced pressure to provide (3S)-3-1{[(1S,3aR,6aS)-2-(4-methoxy-1H-indole-2-carbonyl)-hexahydro-1H-cyclopenta[c]pyrrol-1-yl]formamido}-2-hydroxy-4-[(3S)-2-oxopyrrolidin-3-yl]butanamide (60 mg, 66%) as a white solid. LC-MS (ESI, m/z): 512 [M+H]$^+$.

To a solution of (3S)-3-{[(1S,3aR,6aS)-2-(4-methoxy-1H-indole-2-carbonyl)-hexahydro-1H-cyclopenta[c]pyrrol-1-yl]formamido}-2-hydroxy-4-[(3S)-2-oxopyrrolidin-3-yl]butanamide (52 mg, 0.10 mmol, 1.0 eq.) in DMSO (2 mL) was added IBX (56.9 mg, 0.20 mmol, 2.0 eq.). The mixture was stirred overnight at rt, and the reaction quenched with a sodium bicarbonate solution (2 mL). The solution was extracted with EtOAc (3×5 mL). The organic layers were combined, dried over anhydrous sodium sulfate, filtered and concentrated under reduced pressure. The residue was purified by Pre-TLC to provide 3-{[(1S,3aR,6aS)-2-(4-methoxy-1H-indole-2-carbonyl)-hexahydro-1H-cyclopenta[c]pyrrol-1-yl]formamido}-2-oxo-4-[(3S)-2-oxopyrrolidin-3-yl]butanamide (1.3 mg, 2%) as a white solid. LC-MS (ESI, m/z): 510 [M+H]$^+$.

Example 58

COMPOUND 57

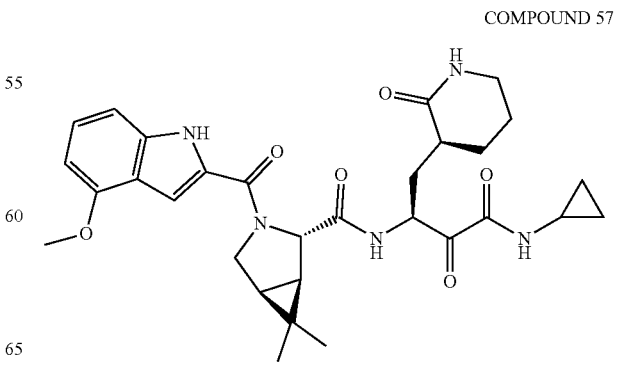

To a solution of (1R,2S,5S)-3-(tert-butoxycarbonyl)-6,6-dimethyl-3-azabicyclo[3.1.0]hexane-2-carboxylic acid (360 mg, 1.41 mmol, 1.0 eq.) in DMF (5 mL) was added o-(7-azabenzotriazol-1-yl)-N,N,N',N'-tetramethyluronium hexafluorophosphate (750 mg, 1.97 mmol, 1.4 eq.) and N-ethyl-N-isopropylpropan-2-amine (911 mg, 7.05 mmol, 5.0 eq.) at 0° C. The mixture was stirred for 15 min at 0° C. (3S)-3-amino-N-cyclopropyl-2-hydroxy-4-[(3S)-2-oxopiperidin-3-yl]butanamide (360 mg, 1.41 mmol) was added. The mixture was stirred for 1 h at rt, and the reaction was quenched with water (10 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by TLC (Mobile phase: MeOH:DCM=1:11; Rf=0.4; detection: UV) to provide tert-butyl (1R,2S,5S)-2-{[(2S)-1-(cyclopropylcarbamoyl)-1-hydroxy-3-[(3S)-2-oxopiperidin-3-yl]propan-2-yl]carbamoyl}-6,6-dimethyl-3-azabicyclo[3.1.0]hexane-3-carboxylate (600 mg, 85%). LC-MS (ESI, m/z): 493 [M+H]⁺.

To a solution of tert-butyl (1R,2S,5S)-2-{[(2S)-1-(cyclopropylcarbamoyl)-1-hydroxy-3-[(3S)-2-oxopiperidin-3-yl]propan-2-yl]carbamoyl}-6,6-dimethyl-3-azabicyclo[3.1.0]hexane-3-carboxylate (600 mg) in DCM (3 mL) was added HCl (6 mL, 2M in Et₂O). The mixture was stirred for 1 h rt, and then concentrated under reduced pressure to afford (3S)—N-cyclopropyl-3-{[(1R,2S,5S)-6,6-dimethyl-3-azabicyclo[3.1.0]hexan-2-yl]formamido}-2-hydroxy-4-[(3S)-2-oxopiperidin-3-yl]butanamide hydrochloride (crude). LC-MS (ESI, m/z): 393 [M+H]⁺.

To a solution of 4-methoxy-1H-indole-2-carboxylic acid (233 mg, 1.22 mmol, 1.0 eq.) in DMF (10 mL) was added o-(7-azabenzotriazol-1-yl)-N,N,N',N'-tetramethyluronium hexafluorophosphate (648 mg, 1.70 mmol, 1.4 eq.) and N-ethyl-N-isopropylpropan-2-amine (786 mg, 6.09 mmol, 5.0 eq.) at 0° C. The mixture was stirred for 15 min at 0° C. (3S)—N-cyclopropyl-3-{[(1R,2S,5S)-6,6-dimethyl-3-azabicyclo[3.1.0]hexan-2-yl]formamido}-2-hydroxy-4-[(3S)-2-oxopiperidin-3-yl]butanamide hydrochloride (522 mg, 1.22 mmol, 1.00 eq.) was added. The mixture was stirred for 1 h at rt, and the reaction was quenched with water (10 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by TLC (Mobile phase: MeOH:DCM=1:11; Rf=0.3; detection: UV) to provide (3S)—N-cyclopropyl-2-hydroxy-3-{[(1R,2S,5S)-3-(4-methoxy-1H-indole-2-carbonyl)-6,6-dimethyl-3-azabicyclo[3.1.0]hexan-2-yl]formamido}-4-[(3S)-2-oxopiperidin-3-yl]butanamide (165 mg, 32%). LC-MS (ESI, m/z): 566 [M+H]⁺.

To a solution of (3S)—N-cyclopropyl-2-hydroxy-3-{[(1R,2S,5S)-3-(4-methoxy-1H-indole-2-carbonyl)-6,6-dimethyl-3-azabicyclo[3.1.0]hexan-2-yl]formamido}-4-[(3S)-2-oxopiperidin-3-yl]butanamide (150 mg, 0.265 mmol, 1.00 eq.) in DMSO (2 mL) was added 2-iodoxybenzoic acid (223 mg, 0.795 mmol, 3.0 eq.). The mixture was stirred for 8 h at rt, and the reaction was quenched with sat. sodium bicarbonate (5 mL). The mixture was extracted with EA (3×5 mL). The organic layers were combined, washed with brine (2×5 mL), dried over anhydrous sodium sulfate, filtered and concentrated under reduced pressure to afford the crude product. The crude product was purified by TLC (Mobile phase: MeOH:DCM=1:11; Rf=0.5; detection: UV) to provide (3S)—N-cyclopropyl-3-{[(1R,2S,5S)-3-(4-methoxy-1H-indole-2-carbonyl)-6,6-dimethyl-3-azabicyclo[3.1.0]hexan-2-yl]formamido}-2-oxo-4-[(3S)-2-oxopiperidin-3-yl]butanamide (56.4 mg, 37%) as a white solid. LC-MS (ESI, m/z): 564 [M+H]⁺.

Example 59

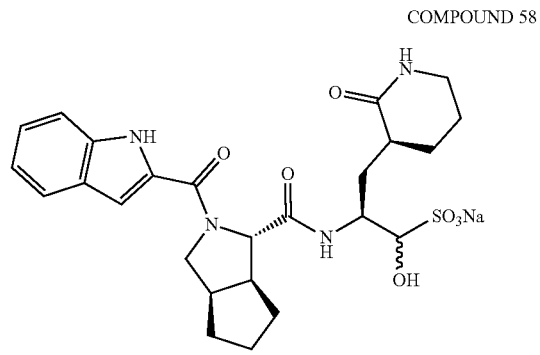

COMPOUND 58

A 100 mL round-bottom flask was charged with (1S,3aR,6aS)-2-(1H-indole-2-carbonyl)-hexahydro-1H-cyclopenta[c]pyrrole-1-carboxylic acid (15.6 g, 52.3 mmol, 1.0 eq.), methyl (2S)-2-amino-3-[(3S)-2-oxopiperidin-3-yl]propanoate (13.3 g, 66.4 mmol, 1.27 eq.), 1-Methyl-1H-imidazole (42.9 g, 523 mmol, 10.0 eq.) and N,N,N',N'-Tetramethylchloroformamidinium hexafluorophosphate (19.1 g, 68.0 mmol, 1.3 eq.) was added at 0° C. The mixture was stirred overnight at rt. The reaction was quenched with water (150 mL). The solution was extracted with EA (5×300 mL). The organic layers were combined, washed with brine (2×100 mL), dried over anhydrous sodium sulfate, filtered and concentrated under reduced pressure. The residue was chromatographed on a silica gel column with dichloromethane:methanol (96:4) to provide methyl (2S)-2-{[(1S,3aR,6aS)-2-(1H-indole-2-carbonyl)-hexahydro-1H-cyclopenta[c]pyrrol-1-yl]formamido}-3-[(3S)-2-oxopiperidin-3-yl]propanoate (17.5 g, 64%) as a yellow semi-solid. LC-MS (ESI, m/z): 481 [M+H]⁺.

A 250 mL round-bottom flask was charged with methyl (2S)-2-{[(1S,3aR,6aS)-2-(1H-indole-2-carbonyl)-hexahydro-1H-cyclopenta[c]pyrrol-1-yl]formamido}-3-[(3S)-2-oxopiperidin-3-yl]propanoate (4.2 g, 8.74 mmol, 1.0 eq.), ethanol (40 mL), THF (20 mL), CaCl₂ (1.94 g, 17.5 mmol, 2.0 eq.) and NaBH₄ (1.32 g, 35.0 mmol, 4.0 eq.) was added at 0° C. The mixture was stirred for 2 h at rt, and then carefully poured into excess 1 M citric acid/ice (80 mL). The solution was extracted with dichloromethane (5×100 mL). The organic layers were combined, washed with brine (2×50 mL), dried over anhydrous sodium sulfate, filtered and concentrated under reduced pressure. The residue was chromatographed on a silica gel column with dichloromethane:methanol (95:5) to provide (1S,3aR,6aS)—N-[(2S)-1-hydroxy-3-[(3S)-2-oxopiperidin-3-yl]propan-2-yl]-2-(1H-indole-2-carbonyl)-hexahydro-1H-cyclopenta[c]pyrrole-1-carboxamide (3.4 g, 84%) as a semi-solid. LC-MS (ESI, m/z): 453 [M+H]⁺.

A 50 mL round-bottom flask was charged with (1S,3aR,6aS)—N-[(2S)-1-hydroxy-3-[(3S)-2-oxopiperidin-3-yl]propan-2-yl]-2-(1H-indole-2-carbonyl)-hexahydro-1H-cyclopenta[c]pyrrole-1-carboxamide (2 g, 4.42 mmol, 1.0 eq.), DMSO (40 mL) and IBX (3.71 g, 13.3 mmol, 3.0 eq.). The mixture was stirred for 2 h at rt, and the reaction was quenched with sodium thiosulfate (1M, 20 mL) and a sat. sodium bicarbonate solution (20 mL). The solution was extracted with EA (5×100 mL). The organic layers was combined, washed with brine (2×50 mL), dried over anhydrous sodium sulfate, filtered and concentrated under reduced pressure. The residue was chromatographed on a silica gel column with dichloromethane:methanol (95:5) to provide (1S,3aR,6aS)-2-(1H-indole-2-carbonyl)-N-[(2S)-1-oxo-3-[(3S)-2-oxopiperidin-3-yl]propan-2-yl]-hexahydro-1H-cyclopenta[c]pyrrole-1-carboxamide (1.1 g, 50%) as a yellow oil. LC-MS (ESI, m/z): 451 [M+H]$^+$.

A 40 mL vial was charged with (1S,3aR,6aS)-2-(1H-indole-2-carbonyl)-N-[(2S)-1-oxo-3-[(3S)-2-oxopiperidin-3-yl]propan-2-yl]-hexahydro-1H-cyclopenta[c]pyrrole-1-carboxamide (300 mg, 0.666 mmol, 1.00 eq.), EA (20 mL), ethyl alcohol (7.5 mL). Sulfur trioxide sodium hydride (92 mg, 0.886 mmol, 1.3 eq.) in H$_2$O (3.75 mL) was added. The mixture was stirred for 1.5 h at 50° C. The mixture was allowed to cool to rt and then filtered. The solid was thoroughly washed with absolute ethanol (50 mL). The filtrate was dried over anhydrous sodium sulfate, filtered and concentrated to yield a yellowish oil. The oily product was treated with ethyl ether (2×50 mL) to form sodium (2S)-2-{[(1S,3aR,6aS)-2-(1H-indole-2-carbonyl)-hexahydro-1H-cyclopenta[c]pyrrol-1-yl]formamido}-1-hydroxy-3-[(3S)-2-oxopiperidin-3-yl]propane-1-sulfonate (206 mg, 48%) as an off-yellow solid. $^1$H NMR (400 MHz, DMSO-d$_6$) δ 11.42-11.53 (m, 1H), 7.40-8.20 (m, 3H), 6.70-7.38 (m, 4H), 5.23-5.58 (m, 1H), 3.62-4.89 (m, 5H), 2.59-3.21 (m, 4H), 1.29-2.32 (m, 13H).

Example 60

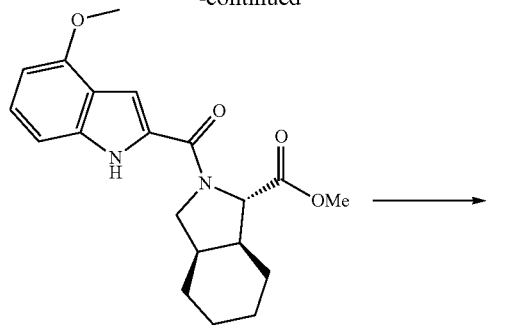

racemic

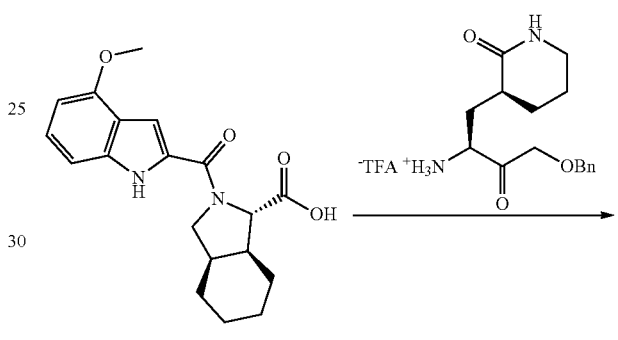

racemic

COMPOUND 59_1, 59_2, 59A_1 AND 59A_2

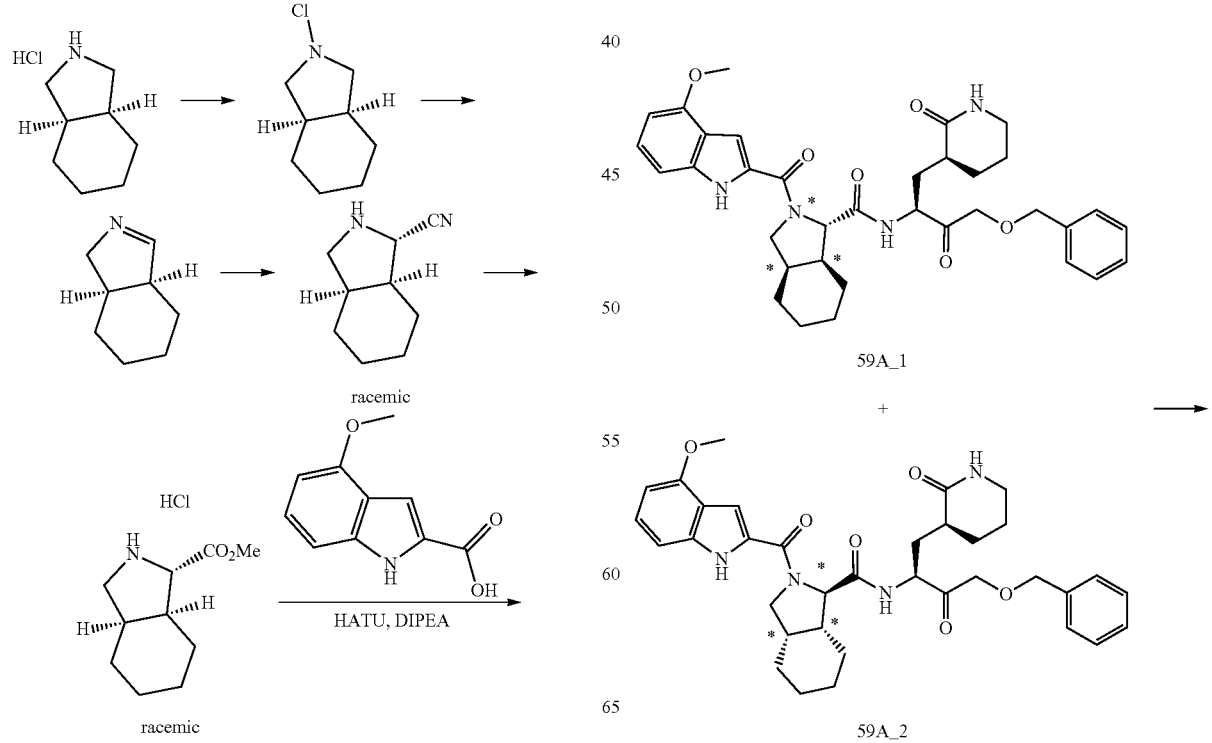

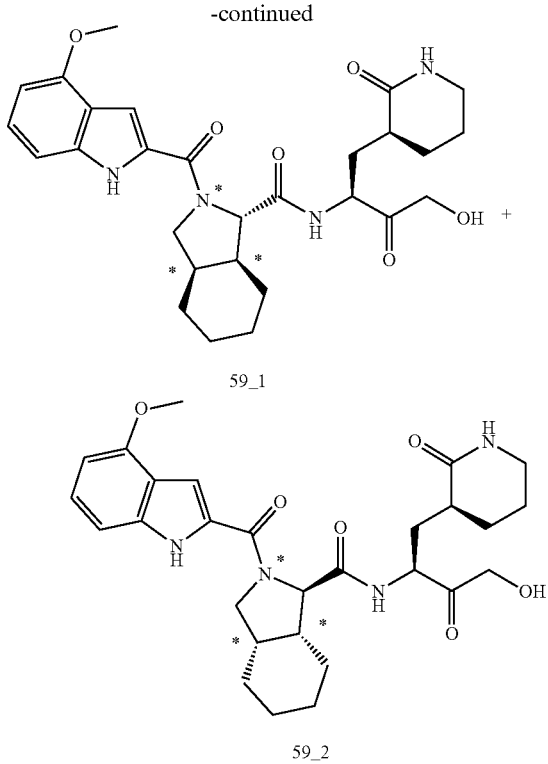

59_1

59_2

The absolute configuration of the chiral centers noted with "*" are tentatively assigned.

To a stirred slurry of cis-2,3,3a,4,5,6,7,7a-octahydro-1H-isoindole hydrochloride 1 (1.62 g, 10 mmol) in MTBE (15 mL) was added an aqueous solution of sodium hydroxide (5 mL, 2N, 10 mmol, 1 eq). The resulting biphasic mixture was treated with ~10% solution of sodium hypochlorite (13 mL, ~20 mmol, ~2 eq), and the mixture was stirred until the starting material was consumed as detected by TLC (~15 min). The organic phase was separated, washed with brine, dried over sodium sulfate and concentrated to ~10 mL to provide a MTBE solution of (3aR,7aS)-2-chlorooctahydro-1H-isoindole, which was used on the next step without further purification.

DBU (1.5 mL, 10 mmol, 1 eq.) was added to the solution rel-(3aR,7aS)-2-chlorooctahydro-1H-isoindole, and the mixture was stirred at 40° C. for 3 h until the starting material could not be detected by TLC. The mixture was washed with brine and concentrated to furnish (3aS,7aR)-3a,4,5,6,7,7a-hexahydro-1H-isoindole as a yellow oil. The oil was dissolved in DCM 15 mL) and methanol (1.6 mL, 40 mmol, 10 eq.). The resulting solution was treated with trimethylsilyl cyanide (2.5 mL, 20 mmol, 2 eq.) while stirring at 0° C. After 15 min, the mixture was washed with an aq. sodium bicarbonate solution, dried over sodium sulfate and concentrated under reduced pressure. Racemic (1S,3aR,7aS)-octahydro-1H-isoindole-1-carbonitrile was isolated by silica gel column chromatography in 3 to 7% methanol-DCM, and provided a pale yellow oil (900 mg, 60%). LC-MS (ESI, m/z): 151.15 [M+H]$^+$.

Racemic (1S,3aR,7aS)-octahydro-1H-isoindole-1-carbonitrile (900 mg, 6 mmol) was dissolved in methanol (5 mL). The solution was treated with 4M solution of hydrogen chloride in dioxane (5 mL). After 5 h at 50° C., the mixture was filtered. The filtrate was concentrated under reduced pressure to give a brown oil. The oil was dissolved in acetone (~10 mL), and the solution was decolorized with activated charcoal. After being filtered, the pale-yellow filtrate was concentrated to dryness to provide racemic methyl rel-(1S,3aR,7aS)-octahydro-1H-isoindole-1-carboxylate, HCl salt (980 mg, 74%) as a yellow oil. $^1$H-NMR (400 MHz, DMSO-d$_6$-D$_2$O), δ: 4.17 (d, 1H), 3.77 (s, 3H), 3.30 (dd, 1H), 3.03 (dd, 1H), 2.41-2.44 (m, 1H), 2.28-2.29 (m, 1H), 1.26-1.39 (m, 8H). LC-MS (ESI, m/z): 184.1 [M+H]$^+$.

To a stirred solution of methyl rel-(1S,3aR,7aS)-octahydro-1H-isoindole-1-carboxylate, HCl salt (90 mg, 0.41 mmol, 1 eq.) and 4-methoxy-1H-indole-2-carboxylic acid (86 mg, 0.45 mmol, 1.1 eq.) in DMF (2 mL) 0° C. was added DIPEA (0.36 mL, 2.05 mmol, 5 eq.) followed by HATU (202 mg, 0.53 mmol, 1.3 eq.). The mixture was stirred for 1 h, and the reaction was quenched with 2M hydrochloric acid (1 mL). The mixture was diluted with EA. The resulting solution was washed with brine, sodium bicarbonate solution, dried over sodium sulfate and concentrated under reduced pressure. Racemic methyl rel-(1S,3aR,7aS)-2-(4-methoxy-1H-indole-2-carbonyl)octahydro-1H-isoindole-1-carboxylate (101 mg, 69%) was isolated as an off-white foam by column chromatography on silica gel in EA:hexane (10-50%). $^1$H-NMR (400 MHz, DMSO-d$_6$), δ: 9.33 (s, 1H), 7.24 (dd, 1H), 7.09 (d, 1H), 7.05 (d, 1H), 6.53 (d, 1H), 4.52 (d, 1H), 4.12 (m, 1H), 4.00 (s, 3H), 3.90 (m, 1H), 3.78 (s, 3H), 2.59 (m, 1H), 2.37 (m, 1H), 1.76 (m, 1H), 1.61-1.44 (m, 7H). LC-MS (ESI, m/z): 357.25 [M+H]$^+$.

To a solution of Racemic methyl rel-(1S,3aR,7aS)-2-(4-methoxy-1H-indole-2-carbonyl)octahydro-1H-isoindole-1-carboxylate (101 mg, 0.28 mmol) in dioxane (3 mL) was added 6N aqueous hydrochloric acid. The mixture was heated at 95° C. for 4 h. The solvent was removed under vacuum, and the product was azeotropically dried by co-evaporation with isopropyl acetate (2×). The resulting crude racemic Rel-(1S,3aR,7aS)-2-(4-methoxy-1H-indole-2-carbonyl)octahydro-1H-isoindole-1-carboxylic acid was used in the next step without any further purification. LC-MS (ESI, m/z): 343.05 [M+H]$^+$.

A solution of tert-butyl ((S)-4-(benzyloxy)-3-oxo-1-((S)-2-oxopiperidin-3-yl)butan-2-yl)carbamate (75 mg, 0.19 mmol) in DCM (1 mL) was treated with TFA (0.2 mL). After 1 h, the solution was diluted with DCM and concentrated under reduced pressure to dryness. The obtained TFA salt was combined with Rel-(1S,3aR,7aS)-2-(4-methoxy-1H-indole-2-carbonyl)octahydro-1H-isoindole-1-carboxylic acid (~0.28 mmol) and DMF (2 mL). The solution was cooled to −25° C. and treated with N,N-diisopropylethylamine (0.174 mL, 1 mmol) and HATU (84 mg, 0.22 mmol). The mixture was to 0° C. over 1 h, and the reaction was quenched with 0.1 N hydrochloric acid (10 mL). The mixture was taken up into EA, and the aqueous phase was separated. The organic layer was washed successively with brine and an aq. sodium bicarbonate solution. After drying over sodium sulfate, the solution was concentrated and the diastereomeric mixture of (1S,3aR,7aS)—N—((S)-4-(benzyloxy)-3-oxo-1-((S)-2-oxopiperidin-3-yl)butan-2-yl)-2-(4-methoxy-1H-indole-2-carbonyl)octahydro-1H-isoindole-1-carboxamide and (1R,3aS,7aR)—N—((S)-4-(benzyloxy)-3-oxo-1-((S)-2-oxopiperidin-3-yl)butan-2-yl)-2-(4-methoxy-1H-indole-2-carbonyl)octahydro-1H-isoindole-1-carboxamide (50 mg, 41%) was isolated by column chromatography on silica gel in 2 to 10% methanol in DCM. Half of the diastereomeric mixture (25 mg) was separated by prep-HPLC in 25 to 95% 0.1% aqueous formic acid in acetonitrile over 25 min. 59A_1 (first eluting peak): 5.7 mg; LC-MS (ESI, m/z):

615.45 [M+H]⁺. 59A_2 (second eluting peak): 6.0 mg; LC-MS (ESI, m/z): 615.45 [M+H]⁺.

A solution of a mixture of (1S,3aR,7aS)—N—((S)-4-(benzyloxy)-3-oxo-1-((S)-2-oxopiperidin-3-yl)butan-2-yl)-2-(4-methoxy-1H-indole-2-carbonyl)octahydro-1H-isoindole-1-carboxamide and (1R,3aS,7aR)—N—((S)-4-(benzyloxy)-3-oxo-1-((S)-2-oxopiperidin-3-yl)butan-2-yl)-2-(4-methoxy-1H-indole-2-carbonyl)octahydro-1H-isoindole-1-carboxamide (25 mg, 0.04 mmol) in methanol (2 mL) was hydrogenated over Pd—C(20 mg) at atmospheric pressure (balloon) overnight. After the catalyst was filtered off, the filtrate was concentrated under reduced pressure. The mixture of (1S,3aR,7aS)—N—((S)-4-hydroxy-3-oxo-1-((S)-2-oxopiperidin-3-yl)butan-2-yl)-2-(4-methoxy-1H-indole-2-carbonyl)octahydro-1H-isoindole-1-carboxamide and (1R,3aS,7aR)—N—((S)-4-hydroxy-3-oxo-1-((S)-2-oxopiperidin-3-yl)butan-2-yl)-2-(4-methoxy-1H-indole-2-carbonyl)octahydro-1H-isoindole-1-carboxamide was separated by prep-HPLC in 25 to 95% 0.1% aqueous formic acid in acetonitrile over 25 min. 59_1: 3.9 mg; LC-MS (ESI, m/z): 525.25 [M+H]⁺. 59_2: 4.1 mg; LC-MS (ESI, m/z): 525.35 [M+H]⁺.

Example 61

COMPOUND 60A AND 60

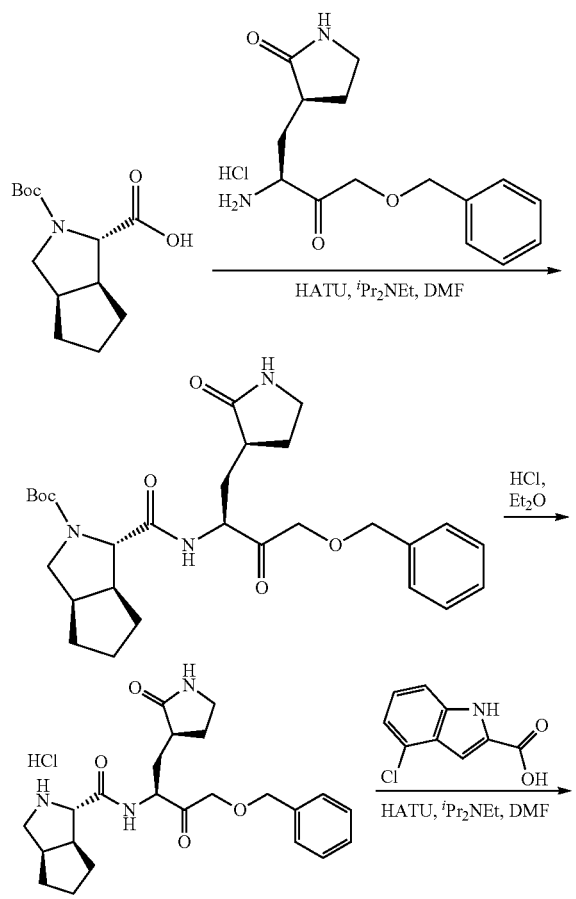

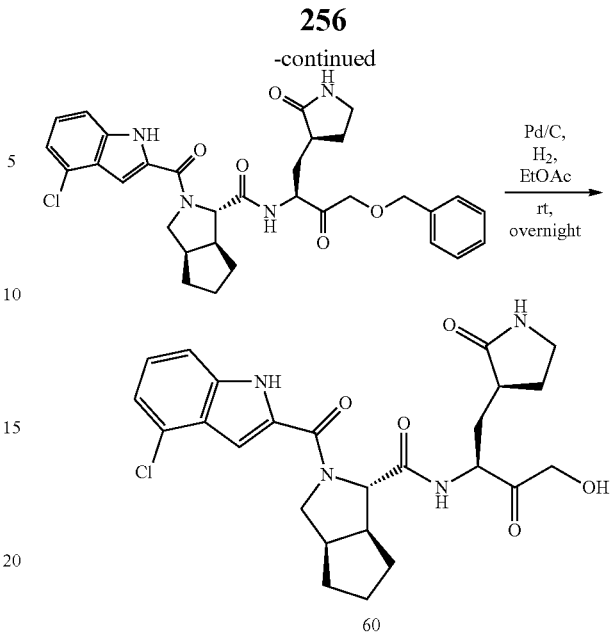

To a mixture of (3S)-3-[(2S)-2-amino-4-(benzyloxy)-3-oxobutyl]pyrrolidin-2-one hydrochloride (2.50 g, 7.99 mmol, 1.0 eq.), (1S,3aR,6aS)-2-(tert-butoxycarbonyl)-hexahydro-1H-cyclopenta[c]pyrrole-1-carboxylic acid (2.04 g, 7.99 mmol, 1.0 eq.) and o-(7-azabenzotriazol-1-yl)-N,N,N',N'-tetramethyluronium hexafluorophosphate (4.56 g, 12.0 mmol, 1.5 eq.) in DMF (50 mL) was added N-ethyl-N-isopropylpropan-2-amine (3.10 g, 24.0 mmol, 3.0 eq.) at 0° C. The mixture was stirred for 1 h at rt, and the reaction quenched with water (60 mL). The mixture was extracted with EtOAc (3×60 mL). The organic layers were combined, washed with brine (2×60 mL), dried over anhydrous sodium sulfate, filtered and concentrated under reduced pressure to afford the crude product. The crude product was diluted with DCM (60 mL) and made into a slurry with 100~200 silica gel mesh (6 g), and then loaded to a column after removing the dichloromethane. The sample was purified by column chromatography (Column size 6×24 cm, column volume: 600 mL, silica gel size (100~200 mesh) quantity: 330 g) and eluted with MeOH:DCM (0%~5% over 20 min). The collected fractions: 3% MeOH:DCM fractions were chosen as the pure fractions. Those fractions were combined and concentrated under reduced pressure to provide tert-butyl (1S,3aR,6aS)-1-{[(2S)-4-(benzyloxy)-3-oxo-1-[(3S)-2-oxopyrrolidin-3-yl]butan-2-yl]carbamoyl}-hexahydro-1H-cyclopenta[c]pyrrole-2-carboxylate (2.2 g, 50%) as a yellow semi-solid. LC-MS (ESI, m/z): 514 [M+H]⁺.

A mixture of tert-butyl (1S,3aR,6aS)-1-{[(2S)-4-(benzyloxy)-3-oxo-1-[(3S)-2-oxopyrrolidin-3-yl]butan-2-yl]carbamoyl}-hexahydro-1H-cyclopenta[c]pyrrole-2-carboxylate (220 mg, 0.428 mmol, 1.0 eq.) in hydrogen chloride (5 mL, 2 M in Et₂O) was stirred for 1 h at rt, and then concentrated under reduced pressure to afford (1S,3aR,6aS)—N-[(2S)-4-(benzyloxy)-3-oxo-1-[(3S)-2-oxopyrrolidin-3-yl]butan-2-yl]-octahydrocyclopenta[c]pyrrole-1-carboxamide hydrochloride (200 mg, crude) as a yellow solid. LC-MS (ESI, m/z): 414 [M+H]⁺.

To a mixture of 4-chloro-1H-indole-2-carboxylic acid (87.0 mg, 0.444 mmol, 1.0 eq.), o-(7-azabenzotriazol-1-yl)-N,N,N',N'-tetramethyluronium hexafluorophosphate (254 mg, 0.666 mmol, 1.5 eq.) and N-ethyl-N-isopropylpropan-2-amine (172 mg, 1.33 mmol, 3.0 eq.) in DMF (5 mL) was added (1S,3aR,6aS)—N-[(2S)-4-(benzyloxy)-3-oxo-1-[(3S)-2-oxopyrrolidin-3-yl]butan-2-yl]-octahydrocyclopenta[c]pyrrole-1-carboxamide hydrochloride (200 mg, 0.444 mmol, 1.0 eq.) at 0° C. The mixture was stirred for 1 h at rt, and the reaction was quenched with water (10 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by TLC (Mobile phase: MeOH:DCM=1:15; Rf=0.5; detection: UV) to provide (1S,3aR,6aS)—N-[(2S)-4-(benzyloxy)-3-oxo-1-[(3S)-2-oxopyrrolidin-3-yl]butan-2-yl]-2-(4-chloro-1H-indole-2-carbonyl)-hexahydro-1H-cyclopenta[c]pyrrole-1-carboxamide (170 mg, 60%) as a yellow solid. The product (40 mg) was purified by prep-HPLC (Column: XBridge Shield RP18 OBD Column, 19×250 mm, 10 μm; Mobile Phase A: Water (0.1% TFA), Mobile Phase B: ACN; Flow rate: 25 mL/min; Gradient: 44% B to 54% B in 10 min, 54% B; Wave Length: 254 nm; RT: 8.78 min) to provide (1S,3aR,6aS)—N-[(2S)-4-(benzyloxy)-3-oxo-1-[(3S)-2-oxopyrrolidin-3-yl]butan-2-yl]-2-(4-chloro-1H-indole-2-carbonyl)-hexahydro-1H-cyclopenta[c]pyrrole-1-carboxamide (16.1 mg, 41%) as a white solid. LC-MS (ESI, m/z): 591 [M+H]$^+$.

To a mixture of (1S,3aR,6aS)—N-[(2S)-4-(benzyloxy)-3-oxo-1-[(3S)-2-oxopyrrolidin-3-yl]butan-2-yl]-2-(4-chloro-1H-indole-2-carbonyl)-hexahydro-1H-cyclopenta[c]pyrrole-1-carboxamide (90.0 mg, 0.152 mmol, 1.0 eq.) in EtOAc (2 mL) was added 10% Palladium on activated carbon (80 mg). The mixture was stirred overnight at rt under hydrogen. The mixture was filtered through a celite pad, and the filtrate was concentrated under reduced pressure to afford the crude product. The crude product was purified by prep-HPLC (Column: XBridge Shield RP18 OBD Column, 19×250 mm, 10 μm; Mobile Phase A: Water (0.1% TFA), Mobile Phase B: ACN; Flow rate: 25 mL/min; Gradient: 25% B to 42% B in 10 min, 42% B; Wave Length: 254 nm; RT: 10.12 min) to provide (1S,3aR,6aS)-2-(4-chloro-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (20.2 mg, 26%) as a white solid. $^1$H NMR (400 MHz, DMSO-d$_6$) δ 11.66 (s, 1H), 8.42 (bs, 1H), 7.45 (d, J=8.4 Hz, 1H), 7.33 (s, 1H), 7.19 (t, J=7.6 Hz, 1H), 7.11 (d, J=7.2 Hz, 1H), 6.90 (s, 1H), 4.35-4.90 (m, 3H), 3.90-4.30 (m, 3H), 3.70-3.85 (m, 1H), 3.05-3.20 (m, 2H), 2.60-2.89 (m, 2H), 2.30-2.40 (m, 1H), 1.43-2.18 (m, 10H). LC-MS (ESI, m/z): 501 [M+H]$^+$.

Example 62

COMPOUND 61

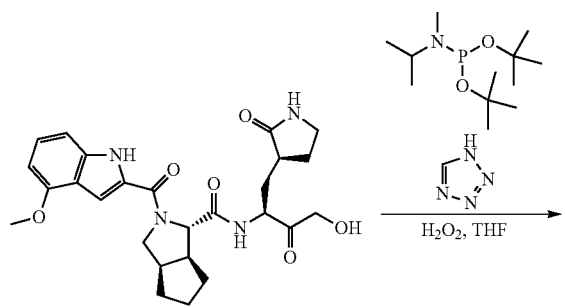

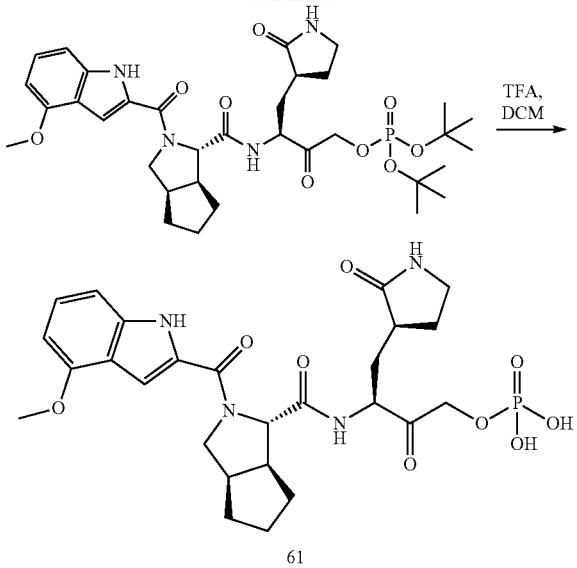

61

To a mixture of (1S,3aR,6aS)—N-[(2S)-4-hydroxy-3-oxo-1-[(3S)-2-oxopyrrolidin-3-yl]butan-2-yl]-2-(4-methoxy-1H-indole-2-carbonyl)-hexahydro-1H-cyclopenta[c]pyrrole-1-carboxamide (300 mg, 0.604 mmol, 1.0 eq.) in THF (3 mL) was added tetrazole (4.03 mL, 1.81 mmol, 3.0 eq., 0.45 M in ACN) and [bis(tert-butoxy)phosphanyl]diisopropylamine (168 mg, 0.603 mmol, 3.0 eq.) at 0° C. The mixture was stirred overnight from 0° C. to rt. Hydrogen peroxide (0.6 mL, 30% in water) was added at 0° C., and the mixture was stirred for 0.5 h at 0° C. The reaction was quenched with water (10 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by TLC (Mobile phase: MeOH:DCM=1:15; Rf=0.4; detection: UV) to provide (3S)-3-{[(1S,3aR,6aS)-2-(4-methoxy-1H-indole-2-carbonyl)-hexahydro-1H-cyclopenta[c]pyrrol-1-yl]formamido}-2-oxo-4-[(3S)-2-oxopyrrolidin-3-yl]butyl di-tert-butyl phosphate (180 mg, 35%) as an off-white solid. LC-MS (ESI, m/z): 689 [M+H]$^+$.

To a mixture of (3S)-3-{[(1S,3aR,6aS)-2-(4-methoxy-1H-indole-2-carbonyl)-hexahydro-1H-cyclopenta[c]pyrrol-1-yl]formamido}-2-oxo-4-[(3S)-2-oxopyrrolidin-3-yl]butyl di-tert-butyl phosphate (140 mg, 0.203 mmol, 1.0 eq.) in DCM (1.5 mL) was added trifluoroacetic acid (0.5 mL). The mixture was stirred for 1 h at rt, and then concentrated under reduced pressure to afford the crude product. The crude product was purified by prep-HPLC (Column: XBridge Shield RP18 OBD Column, 19×250 mm, 10 μm; Mobile Phase A: Water (0.05% TFA), Mobile Phase B: ACN; Flow rate: 25 mL/min; Gradient: 20% B to 30% B in 10 min, 30% B; Wave Length: 25 nm; RT(min): 7.33) to provide (3S)-3-1{[(1S,3aR,6aS)-2-(4-methoxy-1H-indole-2-carbonyl)-hexahydro-1H-cyclopenta[c]pyrrol-1-yl]formamido}-2-oxo-4-[(3S)-2-oxopyrrolidin-3-yl]butoxyphosphonic acid (52.7 mg, 44%) as an off-white solid. $^1$H NMR (400 MHz, DMSO-d$_6$) δ 11.26 (s, 1H), 8.46 (br, 1H), 7.32 (s, 1H), 7.00-7.20 (m, 2H), 6.90 (s, 1H), 6.52 (d, J=7.2 Hz, 1H), 4.42-4.75 (m, 4H), 3.96-4.22 (m, 1H), 3.89 (s, 3H), 3.65-3.76 (m, 1H), 2.85-3.20 (m, 2H), 2.60-2.84 (m, 2H), 2.28-2.44 (m, 1H), 1.40-2.25 (m, 10H). LC-MS (ESI, m/z): 577 [M+H]$^+$.

Example 63

COMPOUND 62

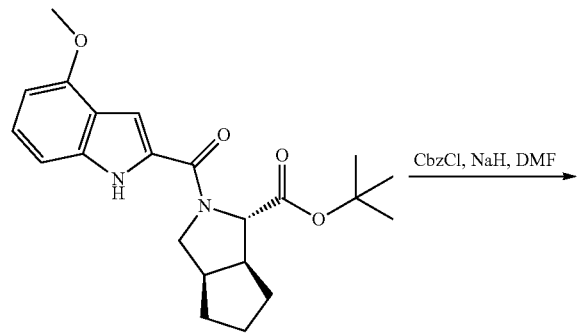

CbzCl, NaH, DMF →

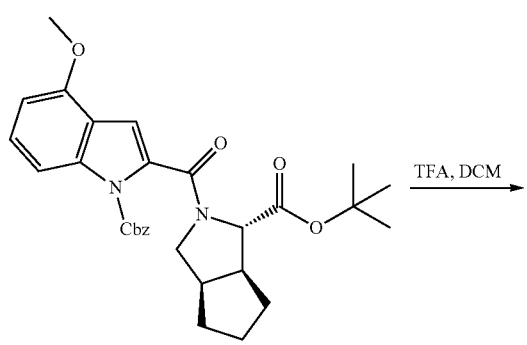

TFA, DCM →

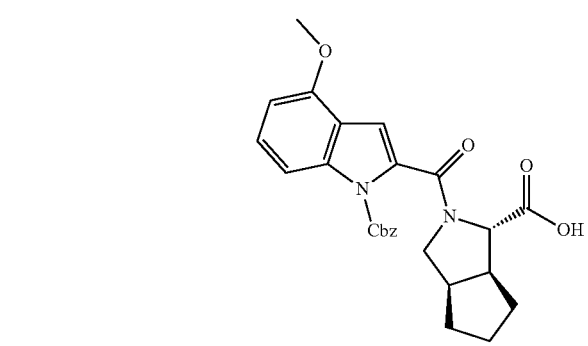

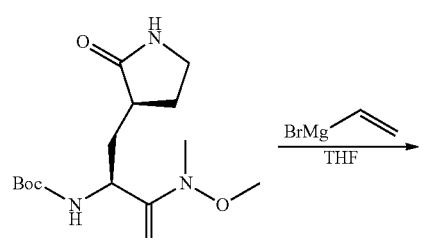

BrMg⏤ / THF →

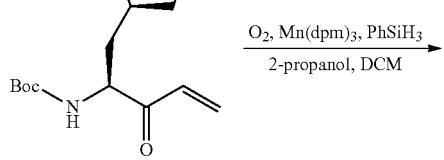

O₂, Mn(dpm)₃, PhSiH₃ / 2-propanol, DCM →

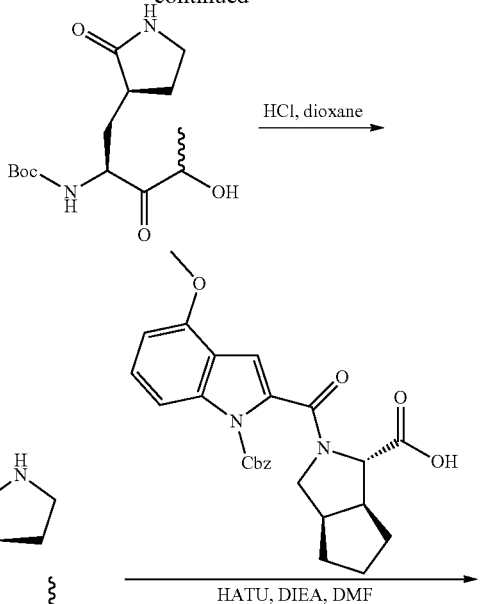

HCl, dioxane →

HATU, DIEA, DMF →

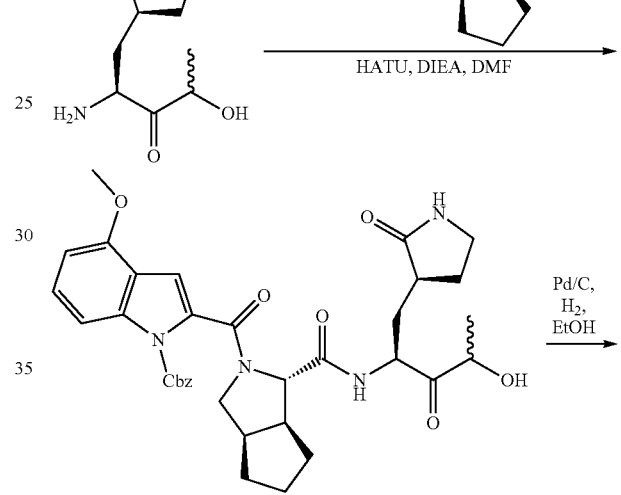

Pd/C, H₂, EtOH →

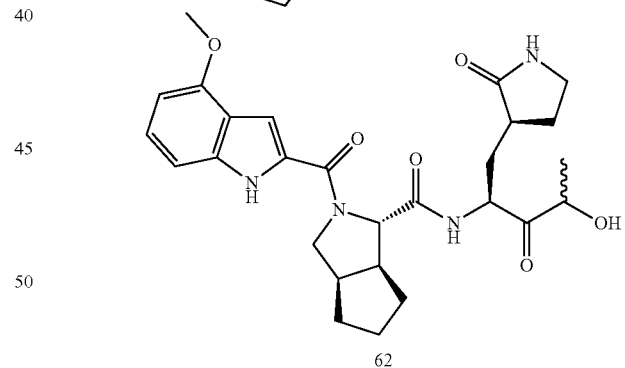

62

To a solution of tert-butyl (1S,3aR,6aS)-2-(4-methoxy-1H-indole-2-carbonyl)-hexahydro-1H-cyclopenta[c]pyrrole-1-carboxylate (1.50 g, 3.90 mmol, 1.0 eq.) in DMF (20 mL) was added sodium hydride (0.203 g, 60% in mineral oil, 5.07 mmol, 1.3 eq.) at 0° C. The mixture was stirred at 0° C. for 30 min. Benzyl carbonochloridate (0.87 g, 5.07 mmol, 1.3 eq.) was added at 0° C. The solution was stirred at 0° C. for 1 h, and the reaction was quenched with water (10 mL). The resulting solution was extracted with EtOAc (3×30 mL). The organic layers were combined, dried over anhydrous sodium sulfate, filtered and concentrated under reduced pressure. The residue was chromatographed on a C18 column with H₂O:MeCN (2:3) to provide benzyl 2-[(1S,3aR,6aS)-1-(tert-butoxycarbonyl)-hexahydro-1H-cyclopenta[c]pyrrole-2-carbonyl]-4-methoxyindole-1-carboxylate (200 mg, 9%) as a yellow oil. LC-MS (ESI, m/z): 519 [M+H]⁺.

To a solution of benzyl 2-[(1S,3aR,6aS)-1-(tert-butoxycarbonyl)-hexahydro-1H-cyclopenta[c]pyrrole-2-carbonyl]-4-methoxyindole-1-carboxylate (200 mg, 0.386 mmol, 1.0 eq.) in DCM (1 mL) was added TFA (3 mL). The mixture was stirred at rt for 2 h, and then concentrated under reduced pressure to provide (1S,3aR,6aS)-2-{1-[(benzyloxy)carbonyl]-4-methoxyindole-2-carbonyl}-hexahydro-1H-cyclopenta[c]pyrrole-1-carboxylic acid (150 mg, 61%) as an off-white solid. LC-MS (ESI, m/z): 463 [M+H]⁺.

To a solution of tert-butyl N-[(1S)-1-[methoxy(methyl)carbamoyl]-2-[(3S)-2-oxopyrrolidin-3-yl]ethyl]carbamate (1.8 g, 5.7 mmol, 1.0 eq.) in THF (18 mL) was added bromo(ethenyl)magnesium (40 mL, 1M in THF, 40 mmol, 7.0 eq.) slowly at 0° C. under N₂. The mixture was stirred for 2 h and then poured into hydrochloric acid (40 mL, 2M) slowly at 0° C. The resulting solution was extracted with EtOAc (3×20 mL). The organic layers were combined, dried over anhydrous sodium sulfate, filtered and concentrated under reduced pressure. The residue was chromatographed on a silica gel column with MeOH:DCM (1:25) to provide tert-butyl N-[(2S)-3-oxo-1-[(3S)-2-oxopyrrolidin-3-yl]pent-4-en-2-yl]carbamate (1 g, 56%) as a yellow oil. LC-MS (ESI, m/z): 283 [M+H]⁺.

To a solution of tert-butyl N-[(2S)-3-oxo-1-[(3S)-2-oxopyrrolidin-3-yl]pent-4-en-2-yl]carbamate (800 mg, 2.83 mmol, 1.0 eq.) in DCM (8 mL) and 2-propanol (8 mL) was added tris(2,2,6,6-tetramethyl-3,5-heptanedionato)manganese(III) (34.3 mg, 0.057 mmol, 0.02 eq.). Phenylsilane (2.15 g, 19.8 mmol, 7.0 eq.) was added at 0° C. under an oxygen atmosphere. The mixture was stirred at rt overnight, and the reaction was quenched with sat. sodium thiosulfate (5 mL). The resulting solution was extracted with EtOAc (3×20 mL). The organic layers were combined, dried over anhydrous sodium sulfate, filtered and concentrated under reduced pressure. The residue was chromatographed on a silica gel column with MeOH:DCM (1:24) to provide tert-butyl N-[(2S)-4-hydroxy-3-oxo-1-[(3S)-2-oxopyrrolidin-3-yl]pentan-2-yl]carbamate (270 mg, 27%) as a white solid. LC-MS (ESI, m/z): 301 [M+H]⁺.

To a solution of tert-butyl N-[(2S)-4-hydroxy-3-oxo-1-[(3S)-2-oxopyrrolidin-3-yl]pentan-2-yl]carbamate (100 mg, 0.33 mmol, 1.0 eq.) in hydrochloric acid (1 mL, 4M in dioxane) was stirred at rt for 2 h, and then concentrated under reduced pressure to provide (3S)-3-[(2S)-2-amino-4-hydroxy-3-oxopentyl]pyrrolidin-2-one (70 mg, 73%) as an off-white solid. LC-MS (ESI, m/z): 201 [M+H]⁺.

To a solution of (1S,3aR,6aS)-2-{1-[(benzyloxy)carbonyl]-4-methoxyindole-2-carbonyl}-hexahydro-1H-cyclopenta[c]pyrrole-1-carboxylic acid (178 mg, 0.385 mmol, 1.1 eq.) in DMF (3 mL) was added N,N,N',N'-Tetramethyl-O-(7-azabenzotriazol-1-yl)uronium hexafluorophosphate (199 mg, 0.525 mmol, 1.5 eq.) and N,N-diisopropylethylamine (316 mg, 2.45 mmol, 7.0 eq.). The mixture was stirred at 0° C. for 30 min and (3S)-3-[(2S)-2-amino-4-hydroxy-3-oxopentyl]pyrrolidin-2-one (70 mg, 0.35 mmol, 1.0 eq.) was added. The mixture was stirred at 0° C. for 1 h, and the reaction was quenched with water (2 mL). The mixture was extracted with EtOAc (3×3 mL). The organic layers were combined, dried over anhydrous sodium sulfate, filtered and concentrated under reduced pressure. The residue was chromatographed on a silica gel column with MeOH:DCM (1:24) to provide benzyl 2-((1S,3aR,6aS)-1-((4-hydroxy-3-oxo-1-((S)-2-oxopyrrolidin-3-yl)pentan-2-yl)carbamoyl)octahydrocyclopenta[c]pyrrole-2-carbonyl)-4-methoxy-1H-indole-1-carboxylate (100 mg, 30%) as a yellow solid. LCMS (ESI, m/z): 645 [M+H]⁺.

To a solution of benzyl 2-((1S,3aR,6aS)-1-((4-hydroxy-3-oxo-1-((S)-2-oxopyrrolidin-3-yl)pentan-2-yl)carbamoyl)octahydrocyclopenta[c]pyrrole-2-carbonyl)-4-methoxy-1H-indole-1-carboxylate (80 mg, 0.14 mmol, 1.0 eq.) in EtOH (3 mL) was added 10% Palladium on activated carbon (40 mg). The mixture was stirred rt under hydrogen (3 atm) for 4 h. The resulting solution was filtered. The filtrate was concentrated under reduced pressure to get a residue. The residue was purified by Prep-HPLC (Column: XBridge Shield RP18 OBD Column, 19*250 mm, 10 μm; Water (0.1% TFA), Mobile Phase B: ACN; Flow rate: 25 mL/min; Gradient: 25 B to 40 B in 10 min; 254 nm; RT1 (min): 9.38) to provide (1S,3aR,6aS)—N-(4-hydroxy-3-oxo-1-((S)-2-oxopyrrolidin-3-yl)pentan-2-yl)-2-(4-methoxy-1H-indole-2-carbonyl)octahydrocyclopenta[c]pyrrole-1-carboxamide (8 mg, 12%) as a white solid. LC-MS (ESI, m/z): 511 [M+H]⁺.

Example 64

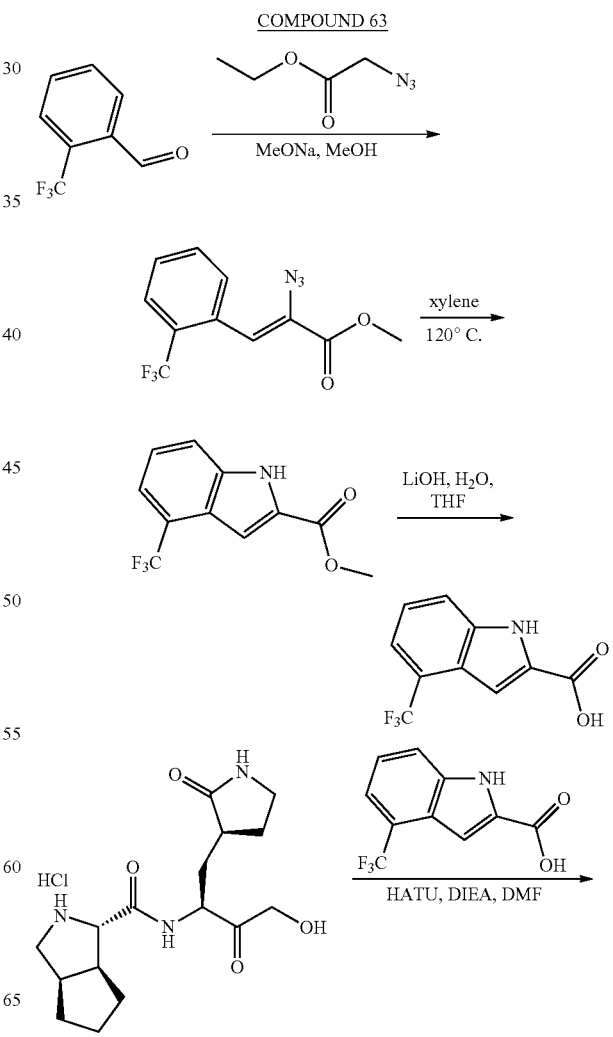

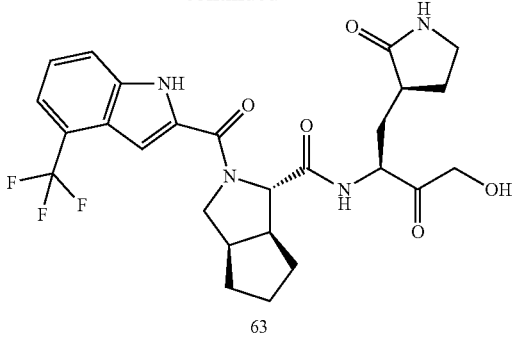

63

To a stirred mixture of sodium methanolate (8.27 g, 46.0 mmol, 4.0 eq.) in methanol (20 mL) was added a mixture of 2-(trifluoromethyl)benzaldehyde (2.00 g, 11.5 mmol, 1.0 eq.) and ethyl 2-azidoacetate (5.93 g, 46.0 mmol, 4.0 eq.) in methanol (20 mL) at −10° C. for 1.5 h. The mixture was stirred for 1.5 h at −10° C., and the reaction was quenched with water/ice (50 mL) at 0° C. The mixture was extracted with EA (3×200 mL). The organic layers were combined, washed with brine (2×80 mL), dried over anhydrous sodium sulfate, filtered and concentrated under reduced pressure. The residue was purified by silica gel column chromatography, eluted with PE:EA (12:1) to afford methyl 2-azido-3-[2-(trifluoromethyl)phenyl]prop-2-enoate (1.17 g, 37%) as a yellow solid.

A solution of methyl (2Z)-2-azido-3-[2-(trifluoromethyl)phenyl]prop-2-enoate (1.00 g, 3.68 mmol, 1.0 eq.) in xylene (20 mL) was stirred for 2 h at 120° C., and then concentrated under reduced pressure. The residue was purified by silica gel column chromatography and eluted with PE:EA (12:1) to afford methyl 4-(trifluoromethyl)-1H-indole-2-carboxylate (840 mg, 88%) as a yellow solid. LC-MS (ESI, m/z): 242 [M−H]⁻.

To a stirred mixture of methyl 4-(trifluoromethyl)-1H-indole-2-carboxylate (400 mg, 1.64 mmol, 1.0 eq.) in tetrahydrofuran (5 mL) was added lithium hydroxide (197 mg, 8.22 mmol, 5.0 eq.) in water (5 mL) dropwise at rt. The mixture was stirred for 4 h at rt, and then diluted with water (20 mL). The mixture was extracted with EA (30 mL). The water layers were acidified to pH=3 with hydrochloric acid (2M). The mixture was extracted with EA (3×50 mL). The organic layers were combined, washed with brine (2×30 mL), dried over anhydrous sodium sulfate, filtered and concentrated under reduced pressure to afford 4-(trifluoromethyl)-1H-indole-2-carboxylic acid (300 mg, 77%) as a yellow solid. $^1$H NMR (400 MHz, DMSO-d$_6$) δ 13.33 (s, 1H), 12.38 (s, 1H), 7.73-7.77 (m, 1H), 7.39-7.50 (m, 2H), 7.09-7.12 (m, 1H). LC-MS (ESI, m/z): 228 [M−H]⁻.

To a stirred mixture of 4-(trifluoromethyl)-1H-indole-2-carboxylic acid (91.0 mg, 0.397 mmol, 1.2 eq.) and N,N-diisopropylethylamine (128 mg, 0.990 mmol, 3.0 eq.) in DMF (8 mL) was added o-(7-aza-1H-benzotriazol-1-yl)-N,N,N',N'-tetramethyluronium hexafluorophosphate (164 mg, 0.430 mmol, 1.3 eq.) in portions at 0° C. The mixture was stirred for 10 min at 0° C. (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (119 mg, 0.331 mmol, 1.0 eq.) was added. The mixture was stirred for 1 h at rt, and the reaction was quenched with water (20 mL) at rt. The mixture was extracted with EA (3×50 mL). The organic layers were combined, washed with brine (2×40 mL), dried over anhydrous sodium sulfate, filtered and concentrated under reduced pressure. The residue was purified by Prep-TLC (dichloromethane:methanol, 12:1) to afford (1S,3aR,6aS)—N-[(2S)-4-hydroxy-3-oxo-1-[(3S)-2-oxopyrrolidin-3-yl]butan-2-yl]-2-[4-(trifluoromethyl)-1H-indole-2-carbonyl]-hexahydro-1H-cyclopenta[c]pyrrole-1-carboxamide (80 mg) as a yellow solid. The crude product (80 mg) was purified by Prep-HPLC with the following conditions (Column: XBridge Prep Phenyl OBD Column, 19*250 mm, 5 μm; Mobile Phase A: Water (0.05% TFA), Mobile Phase B: ACN; Flow rate: 25 mL/min; Gradient: 35% B to 45% B in 10 min, 45% B; Wave Length: 254 nm; RT1 (min): 8.13, 9.10) to afford (1S,3aR,6aS)—N-[(2S)-4-hydroxy-3-oxo-1-[(3S)-2-oxopyrrolidin-3-yl]butan-2-yl]-2-[4-(trifluoromethyl)-1H-indole-2-carbonyl]-hexahydro-1H-cyclopenta[c]pyrrole-1-carboxamide (29.0 mg, 16%) as a white solid. $^1$H NMR (353K, 400 MHz, DMSO-d$_6$) δ 11.87 (s, 1H), 8.39-8.41 (m, 1H), 7.76-7.79 (m, 1H), 7.32-7.45 (m, 3H), 6.93 (s, 1H), 4.43-4.75 (m, 3H), 4.11-4.27 (m, 3H), 3.71-3.74 (m, 1H), 3.07-3.18 (m, 2H), 2.66-2.81 (m, 2H), 2.21-2.41 (m, 1H), 1.91-2.21 (m, 3H), 1.82-1.90 (m, 1H), 1.58-1.81 (m, 5H), 1.45-1.57 (m, 1H). LC-MS (ESI, m/z): 535 [M+H]⁺.

Example 65

COMPOUND 64

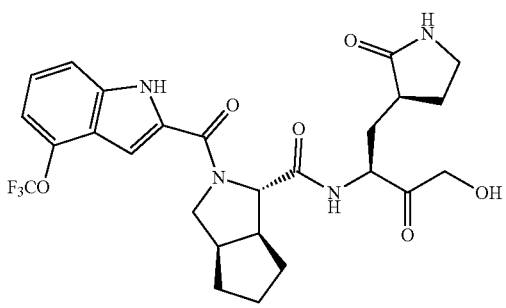

To a mixture of 4-(trifluoromethoxy)-1H-indole-2-carboxylic acid (89.0 mg, 0.361 mmol, 1.0 eq.), o-(7-azabenzotriazol-1-yl)-N,N,N',N'-tetramethyluronium hexafluorophosphate (206 mg, 0.541 mmol, 1.5 eq.) and N-ethyl-N-isopropylpropan-2-amine (140 mg, 1.08 mmol, 3.0 eq.) in DMF (3.00 mL) was added (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (130 mg, 0.361 mmol, 1.0 eq.) at 0° C. The mixture was stirred for 1 h at rt. The reaction was quenched with water (5 mL). The mixture was extracted with EtOAc (3×5 mL). The organic layers were combined, washed with brine (2×5 mL), dried over anhydrous sodium sulfate, filtered and concentrated under reduced pressure to afford the crude product. The crude product was purified by TLC (Mobile phase: MeOH:DCM=1:14; Rf=0.4; detection: UV) to provide the crude product. The crude product was purified by preparative HPLC (Column: XBridge Shield RP18 OBD Column, 19×250 mm, 10 μm; Mobile Phase A: Water (0.1% TFA), Mobile Phase B: ACN; Flow rate: 25 mL/min; Gradient: 40% B to 67% B in 7 min, 67% B; Wave Length: 254 nm; RT: 5.12 min) to provide (1S,3aR,6aS)—N-[(2S)-4-hydroxy-3-oxo-1-[(3S)-2-oxopyrrolidin-3-yl]butan-2-yl]-2-[4-(trifluoromethoxy)-1H-indole-2-carbonyl]-hexahydro-1H-cyclopenta[c]pyrrole-1-carboxamide (42.7 mg, 21%) as a white solid. $^1$H NMR (353K, 400 MHz, DMSO-d$_6$) δ

11.74 (s, 1H), 8.39 (s, 1H), 7.40-7.50 (m, 1H), 7.15-7.39 (m, 2H), 6.75-7.05 (m, 2H), 4.34-5.00 (m, 3H), 3.82-4.33 (m, 3H), 3.55-3.81 (m, 1H), 3.10-3.20 (m, 2H), 2.60-2.89 (m, 2H), 2.23-2.45 (m, 1H), 1.42-2.29 (m, 10H). LC-MS (ESI, m/z): 551 [M+H]⁺.

Example 66

COMPOUND 65

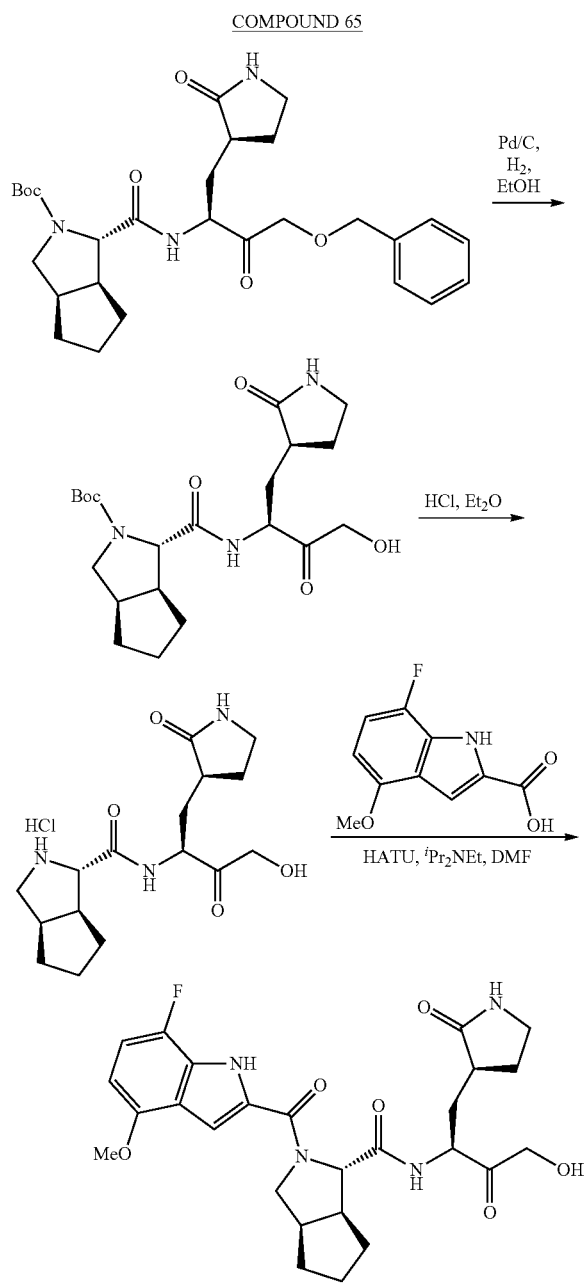 [SMILES: CC(C)(C)OC(=O)N1C[C@@H]2CCC[C@@H]2[C@H]1C(=O)N[C@@H](C[C@@H]1CCNC1=O)C(=O)COCc1ccccc1 ; CC(C)(C)OC(=O)N1C[C@@H]2CCC[C@@H]2[C@H]1C(=O)N[C@@H](C[C@@H]1CCNC1=O)C(=O)CO ; O=C1NCC[C@H]1C[C@H](NC(=O)[C@H]1NC[C@@H]2CCC[C@@H]21)C(=O)CO ; Cl ; COc1ccc(F)c2[nH]c(C(=O)O)cc12 ; COc1ccc(F)c2[nH]c(C(=O)N3C[C@@H]4CCC[C@@H]4[C@H]3C(=O)N[C@@H](C[C@@H]3CCNC3=O)C(=O)CO)cc12]

To a mixture of tert-butyl (1S,3aR,6aS)-1-{[(2S)-4-(benzyloxy)-3-oxo-1-[(3S)-2-oxopyrrolidin-3-yl]butan-2-yl]carbamoyl}-hexahydro-1H-cyclopenta[c]pyrrole-2-carboxylate (2.00 g, 3.89 mmol, 1.0 eq.) in ethanol (30 mL) was added 10% palladium on activated carbon (2 g). The mixture was stirred overnight at rt under a hydrogen atmosphere. The mixture was filtered through a celite pad. The filtrate was concentrated under reduced pressure to provide tert-butyl (1S,3aR,6aS)-1-{[(2S)-4-hydroxy-3-oxo-1-[(3S)-2-oxopyrrolidin-3-yl]butan-2-yl]carbamoyl}-hexahydro-1H-cyclopenta[c]pyrrole-2-carboxylate (1.68 g, 92%) as an off-white solid. LC-MS (ESI, m/z): 424 [M+H]⁺.

A mixture of tert-butyl (1S,3aR,6aS)-1-{[(2S)-4-hydroxy-3-oxo-1-[(3S)-2-oxopyrrolidin-3-yl]butan-2-yl]carbamoyl}-hexahydro-1H-cyclopenta[c]pyrrole-2-carboxylate (1.68 g, 3.97 mmol, 1.0 eq.) in hydrogen chloride (20 mL, 2 M in Et₂O) was stirred for 1 h at rt, and then concentrated under reduced pressure to afford (1S,3aR,6aS)-N-[(2S)-4-hydroxy-3-oxo-1-[(3S)-2-oxopyrrolidin-3-yl]butan-2-yl]-octahydrocyclopenta[c]pyrrole-1-carboxamide hydrochloride (1.2 g, crude) as an off-white solid. LC-MS (ESI, m/z): 324 [M+H]⁺.

To a mixture of 7-fluoro-4-methoxy-1H-indole-2-carboxylic acid (70.0 mg, 0.333 mmol, 1.0 eq.), o-(7-azabenzotriazol-1-yl)-N,N,N',N'-tetramethyluronium hexafluorophosphate (190 mg, 0.500 mmol, 1.5 eq.) and N-ethyl-N-isopropylpropan-2-amine (129 mg, 0.999 mmol, 3.0 eq.) in DMF (3 mL) was added (1S,3aR,6aS)-N-[(2S)-4-hydroxy-3-oxo-1-[(3S)-2-oxopyrrolidin-3-yl]butan-2-yl]-octahydrocyclopenta[c]pyrrole-1-carboxamide hydrochloride (120 mg, 0.333 mmol, 1.0 eq.) at 0° C. The mixture was stirred for 1 h at rt, and the reaction was quenched with water (5 mL). The mixture was extracted with EtOAc (3×5 mL). The organic layers were combined, washed with brine (2×5 mL), dried over anhydrous sodium sulfate, filtered and concentrated under reduced pressure to afford the crude product. The crude product was purified by TLC (Mobile phase: MeOH:DCM=1:14; Rf=0.4; detection: UV) to provide the crude product. The crude product was purified by prep-HPLC (Column: XBridge Shield RP18 OBD Column, 19×250 mm, 10 μm; Mobile Phase A: Water (0.1% TFA), Mobile Phase B: ACN; Flow rate: 25 mL/min; Gradient: 27% B to 50% B in 7 min, 50% B; Wave Length: 254 nm; RT: 6 min) to provide (1S,3aR,6aS)-2-(7-fluoro-4-methoxy-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (37.7 mg, 21%) as a white solid. ¹H NMR (353K, 400 MHz, DMSO-d₆) δ 11.61 (s, 1H), 8.39 (s, 1H), 7.31 (s, 1H), 6.75-7.05 (m, 2H), 6.30-6.50 (m, 1H), 4.55-4.95 (m, 2H), 4.40-4.54 (m, 1H), 4.12-4.30 (m, 2H), 3.93-4.10 (m, 1H), 3.88 (s, 3H), 3.60-3.75 (m, 1H), 3.05-3.25 (m, 2H), 2.60-2.80 (m, 2H), 2.22-2.45 (m, 1H), 1.45-2.06 (m, 10H). LC-MS (ESI, m/z): 515 [M+H]⁺.

Example 67

COMPOUND 66A AND COMPOUND 66

66A

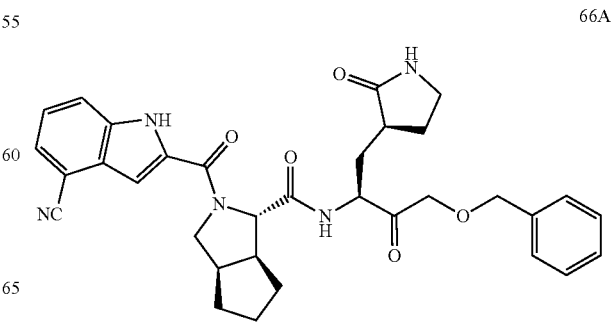

-continued

66

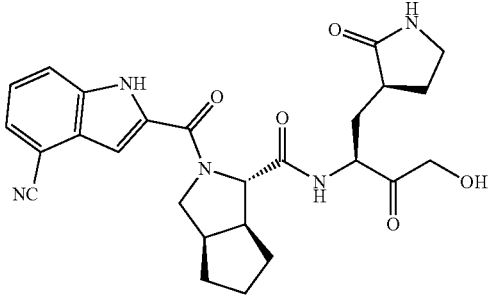

To a stirred mixture of 4-cyano-1H-indole-2-carboxylic acid (82.6 mg, 0.444 mmol, 1.0 eq.) and N,N-diisopropylethylamine (172 mg, 1.33 mmol, 3.0 eq.) in N,N-dimethylformamide (10 mL) was added O-(7-Aza-1H-benzotriazol-1-yl)-N,N,N',N'-tetramethyluronium hexafluorophosphate (253 mg, 0.660 mmol, 1.5 eq.) in portions at 0° C. The mixture was stirred for 10 min at 10° C., and then (1S,3aR,6aS)—N-[(2S)-4-(benzyloxy)-3-oxo-1-[(3S)-2-oxopyrrolidin-3-yl]butan-2-yl]-octahydrocyclopenta[c]pyrrole-1-carboxamide hydrochloride (200 mg, 0.444 mmol, 1.0 eq.) was added. The mixture was stirred for 1 h at rt, and the reaction was quenched with water (20 mL). The mixture was extracted with EA (3×40 mL). The organic layers were combined, washed with brine (3×30 mL), dried over anhydrous sodium sulfate, filtered and concentrated under reduced pressure. The residue was purified by Prep-TLC (dichloromethane:methanol, 1:1) to afford (1S,3aR,6aS)—N-[4-(benzyloxy)-3-oxo-1-[(3S)-2-oxopyrrolidin-3-yl]butan-2-yl]-2-(4-cyano-1H-indole-2-carbonyl)-hexahydro-1H-cyclopenta[c]pyrrole-1-carboxamide (80 mg) as a yellow solid. The crude product (30 mg) was purified by Prep-HPLC with the following conditions (Column: XBridge Shield RP18 OBD Column, 19*250 mm, 10 μm; Mobile Phase A: Water (0.1% TFA), Mobile Phase B: ACN; Flow rate: 25 mL/min; Gradient: 35% B to 58% B in 10 min, 58% B; Wave Length: 254 nm; RT1 (min): 8.55) to afford (1S,3aR,6aS)—N-[4-(benzyloxy)-3-oxo-1-[(3S)-2-oxopyrrolidin-3-yl]butan-2-yl]-2-(4-cyano-1H-indole-2-carbonyl)-hexahydro-1H-cyclopenta[c]pyrrole-1-carboxamide (7 mg) as a white solid. $^1$H-NMR (353K, 400 MHz, DMSO-$d_6$) δ 12.22 (s, 1H), 8.47 (s, 1H), 7.79-7.82 (m, 1H), 7.55-7.58 (m, 1H), 7.19-7.44 (m, 7H), 7.00 (s, 1H), 3.91-4.84 (m, 7H), 3.60-3.86 (m, 1H), 3.07-3.25 (m, 2H), 2.71-2.86 (m, 1H), 2.58-2.70 (m, 1H), 2.17-2.38 (m, 1H), 1.48-2.01 (m, 10H). LC-MS (ESI, m/z): 582 [M+H]$^+$.

To a stirred mixture of (1S,3aR,6aS)—N-[(2S)-4-(benzyloxy)-3-oxo-1-[(3S)-2-oxopyrrolidin-3-yl]butan-2-yl]-2-(4-cyano-1H-indole-2-carbonyl)-hexahydro-1H-cyclopenta[c]pyrrole-1-carboxamide (30.0 mg, 0.052 mmol, 1.0 eq.) in EA (10 mL) was added 10% Palladium on activated carbon (30.0 mg) at rt. The mixture was stirred for 2 days at rt under hydrogen. The mixture was filtered, and the filter cake was washed with EA (3×20 mL). The filtrate was concentrated under reduced pressure. The crude product (30 mg) was purified by Prep-HPLC with the following conditions (Column: XBridge Shield RP18 OBD Column, 19*250 mm, 10 μm; Mobile Phase A: Water (0.1% TFA), Mobile Phase B: ACN; Flow rate: 25 mL/min; Gradient: 23% B to 48% B in 7 min, 48% B; Wave Length: 254 nm; RT1 (min): 6.63) to afford (1S,3aR,6aS)-2-(4-cyano-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (1.9 mg, 7%) as a white solid. LC-MS (ESI, m/z): 492 [M+H]$^+$.

Alternative Synthesis of Compound 66:

To a stirred mixture of 4-cyano-1H-indole-2-carboxylic acid (52.5 mg, 0.282 mmol, 1.2 eq.) and N,N-diisopropylethylamine (91.1 mg, 0.705 mmol, 3.0 eq.) in N,N-dimethylformamide (8 mL) was added O-(7-Aza-1H-benzotriazol-1-yl)-N,N,N',N'-tetramethyluronium hexafluorophosphate (134 mg, 0.352 mmol, 1.5 eq.) in portions at 0° C. The mixture was stirred for 10 min at 0° C., and then (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide (76.0 mg, 0.235 mmol, 1.00 eq.) was added. The mixture was stirred for 1 h at rt. The reaction was quenched with water (15 mL) at rt. The mixture was extracted with EA (3×100 mL). The organic layers were combined, washed with brine (3×50 mL), dried over anhydrous sodium sulfate, filtered and concentrated under reduced pressure. The residue was purified by Prep-TLC dichloromethane:methanol, 12:1) to afford (1S,3aR,6aS)-2-(4-cyano-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (50 mg) as a yellow oil. The crude product (50 mg) was purified by Prep-HPLC with the following conditions (Column: XBridge Prep Phenyl OBD Column, 19*250 mm, 5 μm; Mobile Phase A: Water (0.05% TFA), Mobile Phase B: ACN; Flow rate: 25 mL/min; Gradient: 28% B to 38% B in 10 min, 38% B; Wave Length: 254 nm; RT1 (min): 7.42, 8.52) to afford (1S,3aR,6aS)-2-(4-cyano-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (5.5 mg, 4%) as a white solid. LC-MS (ESI, m/z): 492 [M+H]$^+$.

Example 68

COMPOUND 67

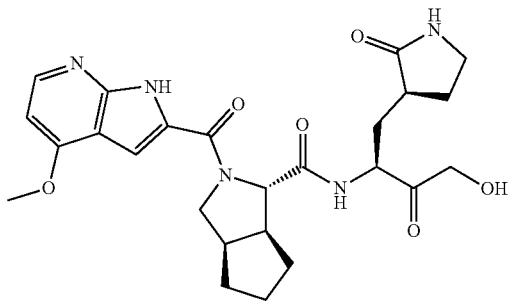

To a mixture of 4-methoxy-1H-pyrrolo[2,3-b]pyridine-2-carboxylic acid (70.0 mg, 0.361 mmol, 1.0 eq.), o-(7-azabenzotriazol-1-yl)-N,N,N',N'-tetramethyluronium hexafluorophosphate (165 mg, 0.433 mmol, 1.2 eq.) and N-ethyl-N-isopropylpropan-2-amine (140 mg, 1.08 mmol, 3.0 eq.) in DMF (3 mL) was added (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (130 mg, 0.361 mmol, 1.0 eq.) at 0° C. The mixture was stirred for 1 h at rt. The mixture was purified by C18 column with CH$_3$CN:Water (0.05% TFA), and the fraction was concentrated under reduced pressure to afford the crude product (100 mg). The crude product was purified by TLC (Mobile phase: MeOH:DCM=1:11; Rf=0.3; detection: UV) to afford the crude product (40 mg). The crude product was purified by prep-HPLC (Column: XBridge Shield RP18 OBD Column, 19×250 mm, 10 μm; Mobile Phase A: Water (0.1% TFA), Mobile Phase B: ACN; Flow rate: 25 mL/min; Gradient: 13% B to 35% B in 7 min, 35% B; Wave Length: 254 nm; RT: 5.23 min) to provide (1S,3aR,6aS)—N-[(2S)-4-hydroxy-3-oxo-1-[(3S)-2-oxopyrrolidin-3-yl]butan-2-yl]-2-{4-methoxy-1H-pyrrolo[2,3-b]pyridine-2-carbonyl}-hexahydro-1H-cyclopenta[c]pyrrole-1-carboxamide (17.0 mg, 9%) as a white solid. $^1$H NMR (353K, 400 MHz, DMSO-$d_6$) δ 11.60 (s, 1H), 8.38 (br, 1H), 8.22 (d, J=5.2 Hz, 1H), 7.31 (s, 1H), 6.86 (s, 1H), 6.67 (d, J=5.2 Hz, 1H), 4.38-5.00 (m, 3H), 4.10-4.35 (m, 2H), 3.86-4.09 (m, 4H), 3.60-3.75 (m, 1H), 2.82-3.05 (m, 2H), 2.60-2.80 (m, 2H), 2.25-2.40 (m, 1H), 1.45-2.20 (m, 10H). LC-MS (ESI, m/z): 498 [M+H]$^+$.

Example 69

COMPOUND 68

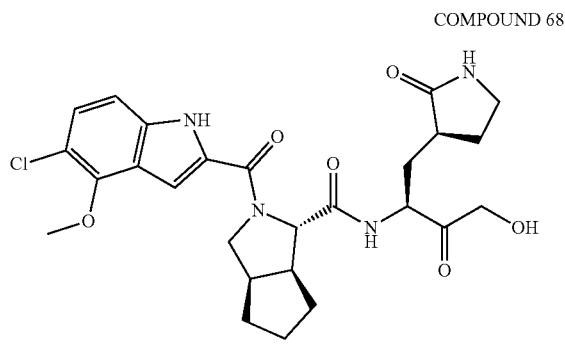 [SMILES: COc1c(Cl)ccc2[nH]c(C(=O)N3C[C@@H]4CCC[C@@H]4[C@H]3C(=O)N[C@@H](C[C@@H]3CCNC3=O)C(=O)CO)cc12]

A 40 mL vial was charged with sodium methoxide (8.45 mL, 30% in methanol, 46.9 mmol, 4.0 eq.) in MeOH (10 mL). 3-chloro-2-methoxybenzaldehyde (2 g, 11.7 mmol, 1.0 eq.) and azido(methoxy)methanone (4.74 g, 46.9 mmol, 4.0 eq.) in MeOH (4 mL) was added dropwise at −10° C. over 1.5 h. The mixture was stirred for 1.5 h at −10° C. The mixture was poured into ice-water (30 mL). The resulting solution was extracted with EA (3×30 mL). The organic layers were combined, washed with brine (2×30 mL), dried over anhydrous sodium sulfate, filtered and concentrated under reduced pressure. The residue was chromatographed on a silica gel column with EA:PE (5:95) to provide methyl 2-azido-3-(3-chloro-2-methoxyphenyl)acrylate (1.37 g, 41%) as a yellow solid. LC-MS (ESI, m/z): 268 [M+H]$^+$.

A 250 mL round-bottom flask was charged with methyl 2-azido-3-(3-chloro-2-methoxyphenyl)acrylate (1.27 g, 4.74 mmol, 1.0 eq.) and xylene (127 mL). The mixture was stirred for 1 h at 140° C. under N$_2$. The mixture was concentrated under reduced pressure. The residue was chromatographed on a silica gel column with EA:PE (10:90) to provide methyl 5-chloro-4-methoxy-1H-indole-2-carboxylate (770 mg, 66%) as a yellow solid. $^1$H NMR (300 MHz, DMSO-$d_6$) δ 12.23 (s, 1H), 7.31-7.32 (m, 1H), 7.27 (s, 1H), 7.15-7.18 (m, 1H), 4.07 (s, 3H), 3.89 (s, 3H). LC-MS (ESI, m/z): 240 [M+H]$^+$.

A 40 mL vial was charged with methyl 5-chloro-4-methoxy-1H-indole-2-carboxylate (770 mg, 3.21 mmol, 1.0 eq.), LiOH (385 mg, 16.1 mmol, 5.0 eq.), THF (8 mL) and H$_2$O (2 mL). The mixture was stirred overnight at 60° C. The pH value of the solution was adjusted to 5 with concentrated hydrochloric acid (1 mol/L). The resulting solution was extracted with dichloromethane (3×20 mL). The organic layers were combined, washed with brine (20 mL), dried over anhydrous sodium sulfate, filtered and concentrated under reduced pressure to provide 5-chloro-4-methoxy-1H-indole-2-carboxylic acid (350 mg, 47%) as a yellow solid. $^1$H NMR (300 MHz, DMSO-$d_6$) δ 13.16 (s, 1H), 12.06 (s, 1H), 7.22-7.26 (m, 2H), 7.13-7.17 (m, 1H), 4.06 (s, 3H). LC-MS (ESI, m/z): 226 [M+H]$^+$.

A 40 mL vial was charged with 5-chloro-4-methoxy-1H-indole-2-carboxylic acid (80 mg, 0.355 mmol, 1.0 eq.), HATU (202 mg, 0.532 mmol, 1.5 eq.), DIEA (137 mg, 1.06 mmol, 3.0 eq.) and DMF (5 mL). The mixture was stirred for 30 min at 0° C. (1S,3aR,6aS)—N—((S)-4-hydroxy-3-oxo-1-((S)-2-oxopyrrolidin-3-yl)butan-2-yl)octahydrocyclopenta[c]pyrrole-1-carboxamide hydrochloride (102 mg, 0.284 mmol, 0.8 eq.) was added. The mixture was stirred for 1 h at 0° C. The reaction was quenched by water (10 mL). The resulting solution was extracted with EA (3×20 mL). The organic layers were combined, washed with brine (20 mL), dried over anhydrous sodium sulfate, filtered and concentrated under reduced pressure. The residue was purified by TLC to provide the crude product (60 mg). The crude product was purified by prep-HPLC using the following gradient conditions: Column: XBridge Shield RP18 OBD Column, 19*250 mm, 10 m; Mobile Phase A: Water (0.1% TFA), Mobile Phase B: ACN; Flow rate: 25 mL/min; Gradient: 30% B to 43% B in 10 min; Wave Length: 254 nm; RT1 (min): 8.72) to provide (1S,3aR,6aS)-2-(5-chloro-4-methoxy-1H-indole-2-carbonyl)-N—((S)-4-hydroxy-3-oxo-1-((S)-2-oxopyrrolidin-3-yl)butan-2-yl)octahydrocyclopenta[c]pyrrole-1-carboxamide (11.6 mg, 6%) as a white solid. $^1$H NMR (353K, 400 MHz, DMSO-$d_6$) δ 11.56 (s, 1H), 8.40 (br, 1H), 7.25-7.40 (m, 1H), 7.10-7.25 (m, 2H), 7.00 (m, 1H), 4.46-4.75 (m, 3H), 4.15-4.22 (m, 3H), 4.05 (s, 3H), 3.60-3.85 (m, 1H), 3.05-3.20 (m, 2H), 2.71-2.85 (m, 1H), 2.55-2.70 (m, 1H), 2.20-2.40 (m, 1H), 1.40-2.10 (m, 10H). LC-MS (ESI, m/z): 531 [M+H]$^+$.

Example 70

COMPOUND 69

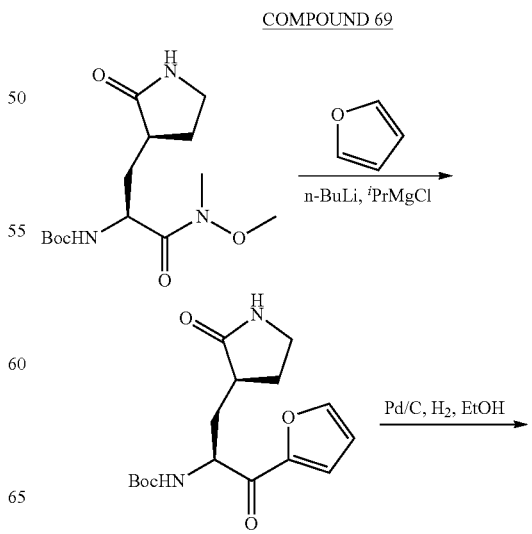

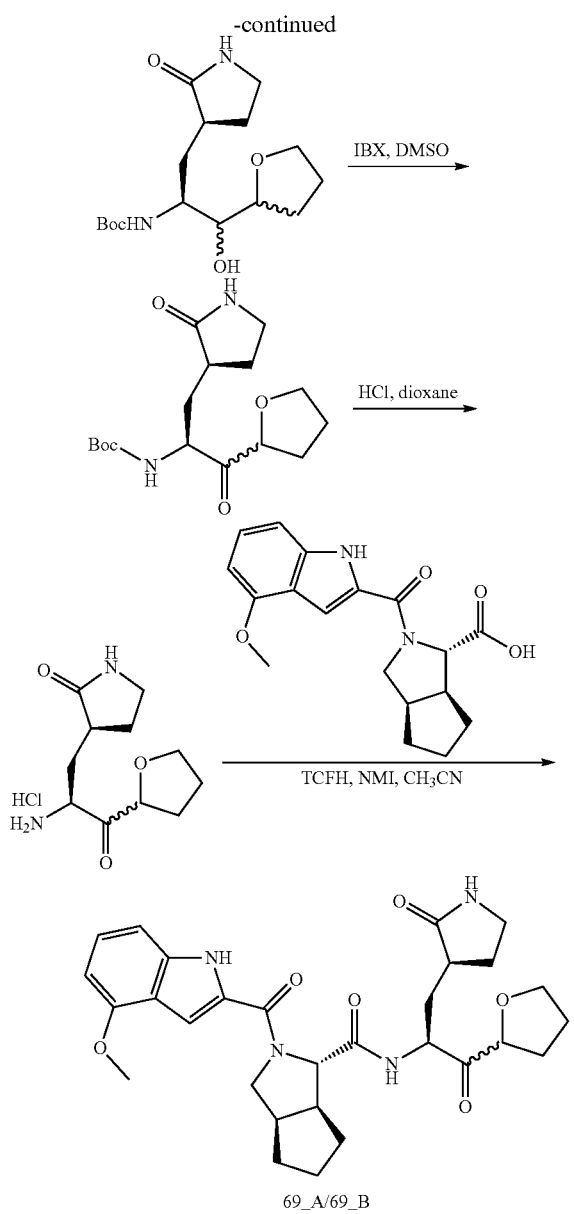

69_A/69_B

To a solution of furan (648 mg, 9.51 mmol, 6.0 eq.) in THF (5 mL) was added n-butyllithium (4.2 mL, 10.5 mmol, 6.6 eq., 2.5 M in hexane) slowly at −78° C. under nitrogen. The mixture was stirred for 1 h at −78° C. To a solution of tert-butyl ((S)-1-(methoxy(methyl)amino)-1-oxo-3-((S)-2-oxopyrrolidin-3-yl)propan-2-yl)carbamate (500 mg, 1.59 mmol, 1.0 eq.) in THF (3 mL) was added $^{i}$PrMgCl (1.59 mL, 3.18 mmol, 2.0 eq., 2 M in THF) slowly at −15° C. under nitrogen. The mixture stirred for 20 min at −15° C. and then added into the above solution. The resulting solution was stirred for 3 h at −78° C., and the reaction was quenched with sat. aq. ammonium chloride (10 mL). The mixture was extracted with EA (3×20 mL). The organic layers were combined, washed with brine (2×20 mL), dried over anhydrous sodium sulfate, filtered and concentrated under reduced pressure to afford the crude product. The crude product was purified by TLC (Mobile phase: methanol: dichloromethane=1:20; Rf=0.5; detection: UV) to provide tert-butyl ((S)-1-(furan-2-yl)-1-oxo-3-((S)-2-oxopyrrolidin-3-yl)propan-2-yl)carbamate (350 mg, 68%) as a yellow solid. LC-MS (ESI, m/z): 323 [M+H]$^+$.

To a mixture of tert-butyl ((S)-1-(furan-2-yl)-1-oxo-3-((S)-2-oxopyrrolidin-3-yl)propan-2-yl)carbamate (350 mg, 1.09 mmol, 1.0 eq.) in ethanol (5 mL) was added 10% palladium on activated carbon (300 mg). The mixture was stirred 8 h at 60° C. under hydrogen. The mixture was filtered through a celite pad and washed with ethanol (100 mL). The filtrate was concentrated under reduced pressure to afford tert-butyl ((2S)-1-oxo-3-((S)-2-oxopyrrolidin-3-yl)-1-(tetrahydrofuran-2-yl)propan-2-yl)carbamate (290 mg, crude) as a white solid. LC-MS (ESI, m/z): 329 [M+H]$^+$.

To a mixture of tert-butyl ((2S)-1-oxo-3-((S)-2-oxopyrrolidin-3-yl)-1-(tetrahydrofuran-2-yl)propan-2-yl)carbamate (290 mg, 0.883 mmol, 1.0 eq.) in DMSO (3 mL) was added 2-iodoxybenzoic acid (494 mg, 1.76 mmol, 2.0 eq.). The mixture was stirred 24 h at rt. The reaction was quenched with sat. aq. sodium bicarbonate (10 mL) and extracted with EA (3×10 mL). The organic layers were combined, washed with brine (2×10 mL), dried over anhydrous sodium sulfate, filtered and concentrated under reduced pressure to afford the crude product. The crude product was purified by TLC (Mobile phase: methanol: dichloromethane=1:20; Rf=0.4; detection: UV) to provide tert-butyl ((2S)-1-oxo-3-((S)-2-oxopyrrolidin-3-yl)-1-(tetrahydrofuran-2-yl)propan-2-yl)carbamate (240 mg, 80%) as a pale yellow solid. LC-MS (ESI, m/z): 327 [M+H]$^+$.

To a mixture of tert-butyl ((2S)-1-oxo-3-((S)-2-oxopyrrolidin-3-yl)-1-(tetrahydrofuran-2-yl)propan-2-yl)carbamate (240 mg, 0.735 mmol, 1.0 eq.) in dioxane (3 mL) was added hydrogen chloride (1 mL, 4 M in 1,4-dioxane) at 0° C. The mixture was stirred for 1 h at rt, and then concentrated under reduced pressure to afford (3S)-3-((2S)-2-amino-3-oxo-3-(tetrahydrofuran-2-yl)propyl)pyrrolidin-2-one hydrochloride (200 mg, crude) as a white solid. LC-MS (ESI, m/z): 227 [M+H]$^+$.

To a mixture of (3S)-3-((2S)-2-amino-3-oxo-3-(tetrahydrofuran-2-yl)propyl)pyrrolidin-2-one hydrochloride (200 mg, 0.761 mmol, 1.0 eq.), (1S,3aR,6aS)-2-(4-methoxy-1H-indole-2-carbonyl)-hexahydro-1H-cyclopenta[c]pyrrole-1-carboxylic acid (250 mg, 0.761 mmol, 1.0 eq.) and N,N,N,N-tetramethylchloroformamidinium hexafluorophosphate (278 mg, 0.989 mmol, 1.3 eq.) in acetonitrile (3 mL) was added and 1-methyl-1H-imidazole (312 mg, 3.81 mmol, 5.0 eq.) at 0° C. The mixture was stirred for 1 h at rt, and the reaction was quenched with water (3 mL). The mixture was extracted with EA (3×10 mL). The organic layers were combined, washed with brine (2×10 mL), dried over anhydrous sodium sulfate, filtered and concentrated under reduced pressure to afford the crude product. The crude product purified by prep-HPLC (Column: XBridge Prep OBD C18 Column, 19*250 mm, 5 μm; Mobile Phase A: Water (0.1% TFA), Mobile Phase B: ACN; Flow rate: 25 mL/min; Gradient: 30% B to 45% B in 10 min: 254 nm; RT1 (min): 8.3, 9.5) to provide two isomers: 69_A (21.9 mg, 4%) as a white solid and 69_B (8.6 mg, 1%) as a white solid. 69_A: LC-MS (ESI, m/z): 537 [M+H]$^+$. 69_B: LC-MS (ESI, m/z): 537 [M+H]$^+$.

Example 71

COMPOUND 70A_1 AND COMPOUND 70_1
COMPOUND 70A_2 AND COMPOUND 70_2

273
-continued
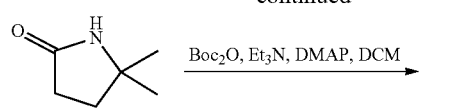
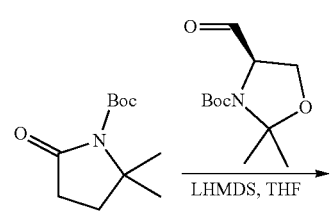
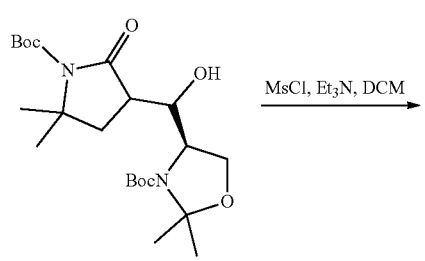
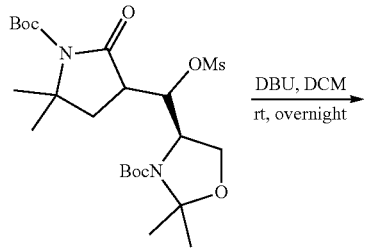
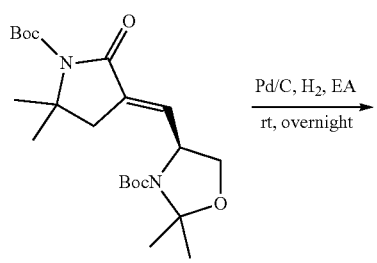
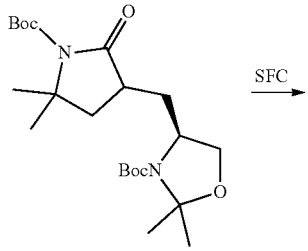
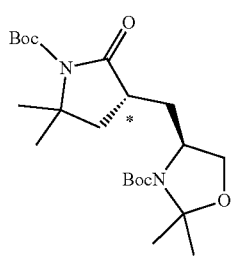
274
-continued
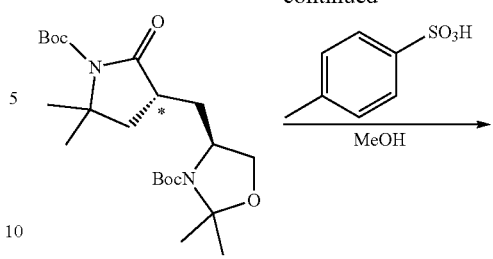
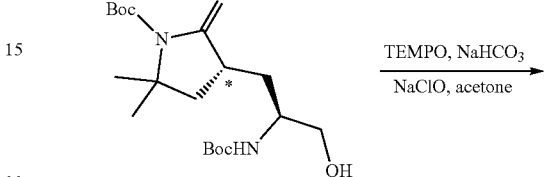
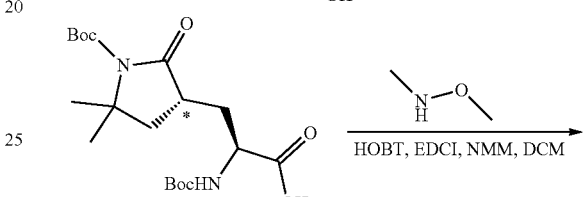
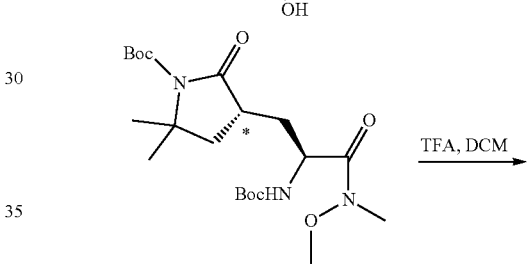
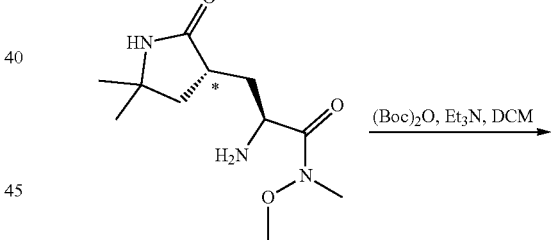
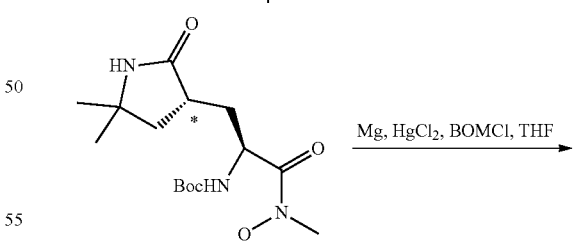
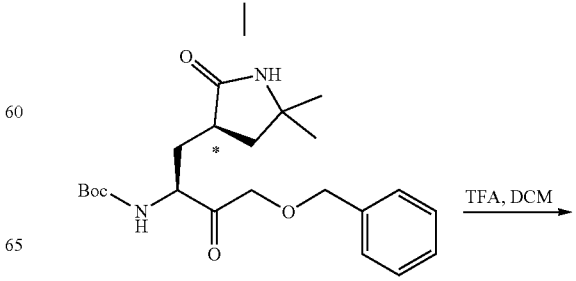

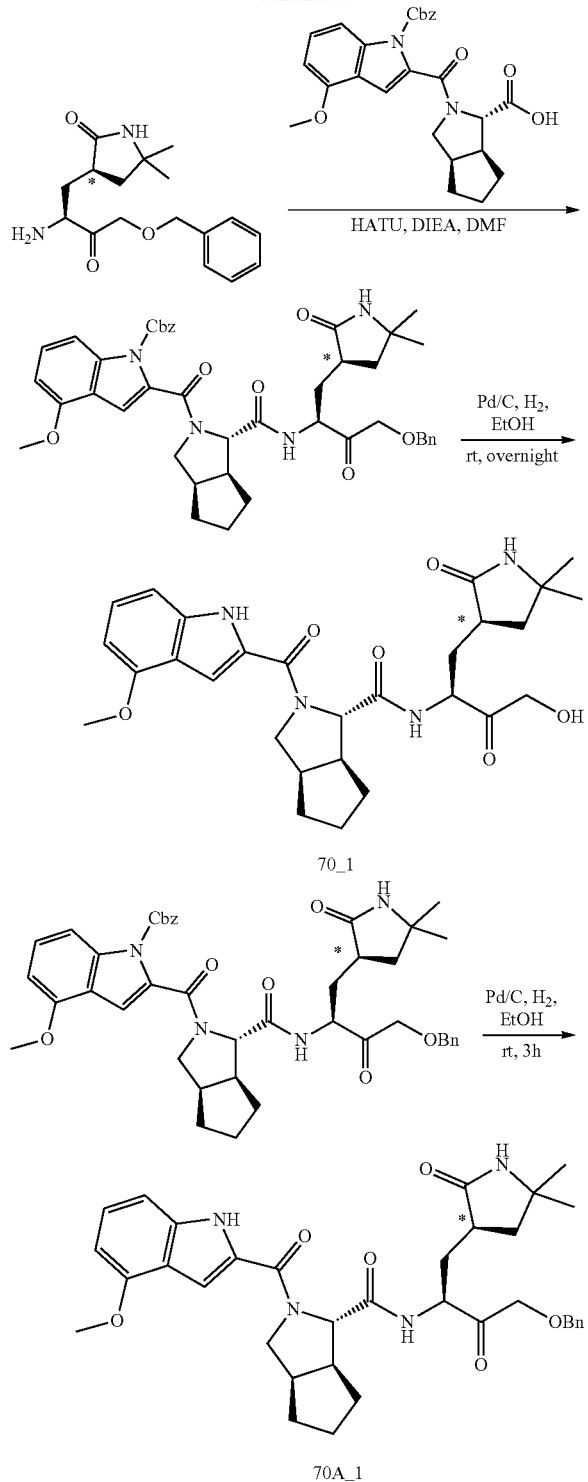

The chiral center noted with "*" is tentatively assigned.

A 100 mL round-bottom flask was charged with 5,5-dimethylpyrrolidin-2-one (3.5 g, 30.9 mmol, 1.0 eq.), DCM (50 mL), di-tert-butyl dicarbonate (10.8 g, 49.5 mmol, 1.6 eq.), triethylamine (6.24 g, 61.8 mmol, 2.0 eq.) and DMAP (0.38 g, 3.09 mmol, 0.1 eq.). The solution was stirred overnight at 40° C., and the reaction was quenched with water (150 mL). The solution was extracted with EA (5×300 mL). The organic layers were combined, washed with brine (2×100 mL), dried over anhydrous sodium sulfate, filtered and concentrated under reduced pressure. The residue was chromatographed on a silica gel column with EA:PE (13:87) to provide tert-butyl 2,2-dimethyl-5-oxopyrrolidine-1-carboxylate (4.0 g, 58%) as a white solid. LC-MS (ESI, m/z): 214 [M+H]$^+$.

A 100 mL round-bottom flask was charged with tert-butyl 2,2-dimethyl-5-oxopyrrolidine-1-carboxylate (3.6 g, 16.9 mmol, 1.00 eq.) and THF (50 mL). The solution was cooled to −78° C. and LiHMDS (20.2 mL, 1M in THF, 20.2 mmol, 1.2 eq.) was added. The mixture was stirred for 1 h at −78° C., and a solution of tert-butyl (4R)-4-formyl-2,2-dimethyl-1,3-oxazolidine-3-carboxylate (5.81 g, 25.3 mmol, 1.5 eq.) in THF (10 mL) was added under Ar. Stirring was continued at −78° C. for 1 h. The reaction was quenched with a sat. ammonium chloride solution (50 mL). The solution was extracted with dichloromethane (3×150 mL). The organic layers were combined, washed with brine (2×50 mL), dried over anhydrous sodium sulfate, filtered and concentrated under reduced pressure. The residue was chromatographed on a silica gel column with EA:PE (1:4) to provide tert-butyl (4R)-4-{[1-(tert-butoxycarbonyl)-5,5-dimethyl-2-oxopyrrolidin-3-yl](hydroxy)methyl}-2,2-dimethyl-1,3-oxazolidine-3-carboxylate (7.2 g, 89%) as a colorless oil. LC-MS (ESI, m/z): 443 [M+H]$^+$.

A 100 mL round-bottom flask was charged with tert-butyl (4R)-4-{[1-(tert-butoxycarbonyl)-5,5-dimethyl-2-oxopyrrolidin-3-yl](hydroxy)methyl}-2,2-dimethyl-1,3-oxazolidine-3-carboxylate (1 g, 2.26 mmol, 1.00 eq.), DCM (10 mL), triethylamine (1.14 g, 11.3 mmol, 5.0 eq.) and MsCl (0.31 g, 4.52 mmol, 2.0 eq.). The mixture was stirred overnight at rt, and the reaction was quenched with water (30 mL). The solution was extracted with dichloromethane (4×50 mL). The organic layers were combined, washed with brine (3×20 mL), dried over anhydrous sodium sulfate, filtered and concentrated under reduced pressure to provide tert-butyl (4R)-4-{[1-(tert-butoxycarbonyl)-5,5-dimethyl-2-oxopyrrolidin-3-yl](methanesulfonyloxy)methyl}-2,2-dimethyl-1,3-oxazolidine-3-carboxylate (960 mg, crude) as a yellow oil. LC-MS (ESI, m/z): 521 [M+H]$^+$.

A 100 mL round-bottom flask was charged with tert-butyl (4R)-4-{[1-(tert-butoxycarbonyl)-5,5-dimethyl-2-oxopyrrolidin-3-yl](methanesulfonyloxy)methyl}-2,2-dimethyl-1,3-oxazolidine-3-carboxylate (900 mg, 1.73 mmol, 1.0 eq.), DCM (20 mL) and DBU (1.32 g, 8.64 mmol, 5.0 eq.). The mixture was stirred overnight at rt, and the reaction was quenched with water (30 mL). The solution was extracted with dichloromethane (3×80 mL). The organic layers were combined, washed with brine (2×30 mL), dried over anhydrous sodium sulfate, filtered and concentrated under reduced pressure. The residue was chromatographed on a silica gel column with EA:PE (1:4) to provide tert-butyl (4S)-4-{[1-(tert-butoxycarbonyl)-5,5-dimethyl-2-oxopyrrolidin-3-ylidene]methyl}-2,2-dimethyl-1,3-oxazolidine-3-carboxylate (635 mg, 82%) as a colorless oil. LC-MS (ESI, m/z): 425 [M+H]$^+$.

A 250 mL round-bottom flask was charged with tert-butyl (4S)-4-{[1-(tert-butoxycarbonyl)-5,5-dimethyl-2-oxopyrrolidin-3-ylidene]methyl}-2,2-dimethyl-1,3-oxazolidine-3-carboxylate (4.4 g, 10.4 mmol, 1.0 eq.), EA (50 mL) and 10% palladium on activated carbon (5.51 g). The contents of the flask were placed under an atmosphere of hydrogen (3 atm). The mixture was stirred overnight at rt. The solids were filtered off. The organic layer was concentrated under reduced pressure to provide tert-butyl (4S)-4-{[1-(tert-butoxycarbonyl)-5,5-dimethyl-2-oxopyrrolidin-3-yl]methyl}-

2,2-dimethyl-1,3-oxazolidine-3-carboxylate (4.3 g, 78%) as a colorless oil. LC-MS (ESI, m/z): 427 [M+H]$^+$.

Tert-butyl (4S)-4-((1-(tert-butoxycarbonyl)-5,5-dimethyl-2-oxopyrrolidin-3-yl)methyl)-2,2-dimethyloxazolidine-3-carboxylate (3.6 g) was purified by prep-SFC using the following gradient conditions: Column: Lux Sum Cellulose-2, 3*25 cm, 5 μm; Mobile Phase A: $CO_2$, Mobile Phase B: IPA (0.5% 2M $NH_3$-MeOH); Flow rate: 60 mL/min; Gradient: isocratic 10% B; Column Temperature (° C.): 35; Back Pressure (bar): 100; Wave Length: 220 nm; RT1 (min): 4.81; RT2 (min): 6.43; Sample Solvent: MeOH—Preparative; Injection Volume: 1.5 mL; Number Of Runs: 27. Purification resulted in tert-butyl (S)-4-(((S*)-1-(tert-butoxycarbonyl)-5,5-dimethyl-2-oxopyrrolidin-3-yl)methyl)-2,2-dimethyloxazolidine-3-carboxylate (990 mg) as an off-white solid (Lux Celloluse-2 4.6*50 mm, 3 μm, 35° C. Co-Solvent: IPA (0.1% DEA), 10% to 50% in 2.0 min, hold 1.0 min at 50%): Rt: 0.969 min), and tert-butyl (S)-4-(((R*)-1-(tert-butoxycarbonyl)-5,5-dimethyl-2-oxopyrrolidin-3-yl)methyl)-2,2-dimethyloxazolidine-3-carboxylate (1.6 g) as an off-white solid Lux Celloluse-2 4.6*50 mm, 3 μm, 35° c. Co-Solvent: IPA (0.1% DEA), 10% to 50% in 2.0 min, hold 1.0 min at 50%): Rt: 1.411 min).

A 40 mL vial was charged with tert-butyl (S)-4-(((R*)-1-(tert-butoxycarbonyl)-5,5-dimethyl-2-oxopyrrolidin-3-yl)methyl)-2,2-dimethyloxazolidine-3-carboxylate (1.6 g, 3.75 mmol, 1.0 eq.), para-toluene sulfonate (64.6 mg, 0.375 mmol, 0.1 eq.) and MeOH (20 mL). The mixture was stirred overnight at rt. The reaction was quenched with water (20 mL). The solution was extracted with EA (3×30 mL). The organic layers were combined, washed with brine (50 mL), dried over anhydrous sodium sulfate, filtered and concentrated under reduced pressure to provide tert-butyl(S)-4-((S)-2-((tert-butoxycarbonyl)amino)-3-hydroxypropyl)-2,2-dimethyl-5-oxopyrrolidine-1-carboxylate (1.47 g, crude) as an off-white semi-solid. LC-MS (ESI, m/z): 387 [M+H]$^+$.

To a solution of tert-butyl (S)-4-((R*)-2-((tert-butoxycarbonyl)amino)-3-hydroxypropyl)-2,2-dimethyl-5-oxopyrrolidine-1-carboxylate (1.7 g, 4.40 mmol, 1.0 eq.) in acetone (22 mL) was added 5% sodium bicarbonate solution (22 mL, 13.1 mmol, 3.0 eq.) and 2,2,6,6-Tetramethylpiperidinooxy (0.14 g, 0.88 mmol, 0.2 eq.). Chlorosylsodium (1.15 g, 15.4 mmol, 3.5 eq.) was added dropwise at 0° C. The mixture was stirred at rt overnight, and the reaction was quenched with water (20 mL). The solution was washed with Et2O (2×20 mL). The pH value of the aqueous solution was adjusted to 2 with concentrated hydrochloric acid (1 mol/L). The solution was extracted with EtOAc (3×50 mL). The organic layers were combined, washed with brine (50 mL), dried over anhydrous sodium sulfate, filtered and concentrated under reduced pressure to provide (S)-3-((R*)-1-(tert-butoxycarbonyl)-5,5-dimethyl-2-oxopyrrolidin-3-yl)-2-((tert-butoxycarbonyl)amino)propanoic acid (1.2 g, 61%) as a white solid. LC-MS (ESI, m/z): 401 [M+H]$^+$.

To a solution of (S)-3-((R*)-1-(tert-butoxycarbonyl)-5,5-dimethyl-2-oxopyrrolidin-3-yl)-2-((tert-butoxycarbonyl)amino)propanoic acid (1.11 g, 2.77 mmol, 1.0 eq.) in DCM (20 mL) was added N,O-dimethylhydroxylamine (0.17 g, 2.77 mmol, 1.0 eq.), 1-Hydroxybenzotrizole (0.37 g, 2.77 mmol, 1.0 eq.), NMM (0.84 g, 8.32 mmol, 3.0 eq.) and N-(3-dimethylaminopropyl)-N'-ethylcarbodiimide hydrochloride (0.58 g, 3.05 mmol, 1.1 eq.). The mixture was stirred at rt for 1 h, and the reaction was quenched with water (20 mL). The mixture was extracted with DCM (3×50 mL). The organic layers were combined, dried over anhydrous sodium sulfate, filtered and concentrated under reduced pressure. The residue was chromatographed on a silica gel column with MeOH:DCM (1:25) to provide tert-butyl (R*)-4-((S)-2-((tert-butoxycarbonyl)amino)-3-(methoxy(methyl)amino)-3-oxopropyl)-2,2-dimethyl-5-oxopyrrolidine-1-carboxylate (1 g, 73%) as a white solid. LCMS (ESI, m/z): 444 [M+H]$^+$.

To a solution of tert-butyl (4R*)-4-[(2S)-2-[(tert-butoxycarbonyl)amino]-2-[methoxy(methyl)carbamoyl]ethyl]-2,2-dimethyl-5-oxopyrrolidine-1-carboxylate (700 mg, 1.578 mmol, 1.00 eq.) in DCM (9 mL) was added TFA (3 mL). The mixture was stirred at rt for 1 h, and then concentrated under reduced pressure to provide (2S)-2-amino-3-[(3R*)-5,5-dimethyl-2-oxopyrrolidin-3-yl]-N-methoxy-N-methylpropanamide (400 mg, 73%) as an off-white oil. LC-MS (ESI, m/z): 244 [M+H]$^+$.

To a solution of (2S)-2-amino-3-[(3R*)-5,5-dimethyl-2-oxopyrrolidin-3-yl]-N-methoxy-N-methylpropanamide (430 mg, 1.77 mmol, 1.0 eq.) in DCM (5 mL) was added triethylamine (894 mg, 8.83 mmol, 5.0 eq.) and di-tert-butyl dicarbonate (1.16 g, 5.3 mmol, 3.0 eq.). The mixture was stirred at rt overnight, and the reaction was quenched with water (5 mL). The mixture was extracted with DCM (3×20 mL). The organic layers were combined, dried over anhydrous sodium sulfate, filtered and concentrated under reduced pressure. The residue was chromatographed on a silica gel column with MeOH:DCM (1:25) to provide tert-butyl N-[(1S)-2-[(3R*)-5,5-dimethyl-2-oxopyrrolidin-3-yl]-1-[methoxy(methyl)carbamoyl]ethyl]carbamate (460 mg, 68%) of as a white solid. LCMS (ESI, m/z): 344 [M+H]$^+$.

A 40 mL vial was charged with Mg (283 mg, 11.6 mmol, 10.0 eq.) and mercury(II) chloride (190 mg, 0.70 mmol, 0.6 eq.) in THF (5 mL) at −45° C. under nitrogen. [(chloromethoxy)methyl]benzene (1.82 g, 11.7 mmol, 10.0 eq.) was added. The mixture was stirred for 5 h at −45° C. to 5° C., and then cooled to −45° C. Tert-butyl N-[(1S)-2-[(3S)-5,5-dimethyl-2-oxopyrrolidin-3-yl]-1-[methoxy(methyl)carbamoyl]ethyl]carbamate (400 mg, 1.17 mmol, 1.0 eq.) was added. The mixture was stirred overnight at rt. The reaction was quenched by water (5 mL). The solution was extracted with EA (3×20 mL). The organic layers were combined, washed with brine (20 mL), dried over anhydrous sodium sulfate, filtered and concentrated under reduced pressure. The residue was chromatographed on a silica gel column with DCM:MeOH (24:1) to provide tert-butyl N-[(2S)-4-(benzyloxy)-1-[(3R*)-5,5-dimethyl-2-oxopyrrolidin-3-yl]-3-oxobutan-2-yl]carbamate (300 mg, 54%) of as a white solid. LC-MS (ESI, m/z): 405 [M+H]$^+$.

To a solution of tert-butyl N-[(2S)-4-(benzyloxy)-1-[(3R*)-5,5-dimethyl-2-oxopyrrolidin-3-yl]-3-oxobutan-2-yl]carbamate (300 mg, 0.74 mmol, 1.0 eq.) in DCM (6 mL) was added TFA (2 mL). The mixture was stirred at rt for 1.5 h, and then concentrated under reduced pressure to provide (3R*)-3-[(2S)-2-amino-4-(benzyloxy)-3-oxobutyl]-5,5-dimethylpyrrolidin-2-one (200 mg, 62%) of as an off-white oil. LC-MS (ESI, m/z): 305 [M+H]$^+$.

To a solution of (1S,3aR,6aS)-2-{1-[(benzyloxy)carbonyl]-4-methoxyindole-2-carbonyl}-hexahydro-1H-cyclopenta[c]pyrrole-1-carboxylic acid (334 mg, 0.72 mmol, 1.1 eq.) N,N,N',N'-Tetramethyl-O-(7-azabenzotriazol-1-yl)uronium hexafluorophospate (275 mg, 0.72 mmol, 1.1 eq.) and N,N-diisopropylethylamine (764 mg, 5.91 mmol, 9.0 eq.). The mixture was stirred at 0° C. for 30 min, and (3R*)-3-[(2S)-2-amino-4-(benzyloxy)-3-oxobutyl]-5,5-dimethylpyrrolidin-2-one (200 mg, 0.66 mmol, 1.0 eq.) was added. The mixture was stirred at 0° C. for 1 h, and the reaction quenched with water (5 mL). The mixture was extracted with EA (3×20 mL). The organic layers were combined, dried over anhydrous sodium sulfate, filtered and concentrated under reduced pressure. The residue was chromatographed on a silica gel column with DCM:MeOH (24:1) to provide benzyl 2-[(1S,3aR,6aS)-1-{[(2S)-4-(benzyloxy)-1-[(3R*)-5,5-dimethyl-2-oxopyrrolidin-3-yl]-3-oxobutan-2-yl]carbamoyl}-hexahydro-1H-cyclopenta[c]pyrrole-2-carbonyl]-4-methoxyindole-1-carboxylate (185 mg, 32%) as an off-white solid. LC-MS (ESI, m/z): 749 [M+H]$^+$.

To a solution of benzyl 2-[(1S,3aR,6aS)-1-{[(2S)-4-(benzyloxy)-1-[(3R*)-5,5-dimethyl-2-oxopyrrolidin-3-yl]-3-oxobutan-2-yl]carbamoyl}-hexahydro-1H-cyclopenta[c]pyrrole-2-carbonyl]-4-methoxyindole-1-carboxylate (30 mg, 0.04 mmol, 1.0 eq.) in ethanol (3 mL) was added 10% palladium on activated carbon (20 mg). The mixture was stirred at rt for 3 h. The solution was filtered, and the filtrate was concentrated under reduced pressure to get a residue. The residue was purified by Prep-HPLC (Column: XBridge Shield RP18 OBD Column, 19*250 mm, 10 μm; Mobile Phase A: Water (0.1% TFA), Mobile Phase B: ACN; Flow rate: 25 mL/min; Gradient: 41% B to 57% B in 10 min, 57% B; Wave Length: 254 nm; RT1 (min): 9.88) to provide (1S,3aR,6aS)—N-[(2S)-4-(benzyloxy)-1-[(3R*)-5,5-dimethyl-2-oxopyrrolidin-3-yl]-3-oxobutan-2-yl]-2-(4-methoxy-1H-indole-2-carbonyl)-hexahydro-1H-cyclopenta[c]pyrrole-1-carboxamide (2 mg, 7%) as a white solid. LC-MS (ESI, m/z): 615 [M+H]$^+$.

To a solution of benzyl 2-[(1S,3aR,6aS)-1-{[(2S)-4-(benzyloxy)-1-[(3R*)-5,5-dimethyl-2-oxopyrrolidin-3-yl]-3-oxobutan-2-yl]carbamoyl}-hexahydro-1H-cyclopenta[c]pyrrole-2-carbonyl]-4-methoxyindole-1-carboxylate (120 mg, 0.16 mmol, 1.0 eq.) in ethanol (3 mL) was added 10% palladium on activated carbon (120 mg). The mixture was stirred at rt for overnight. The solution was filtered, and the filtrate was concentrated under reduced pressure to get a residue. The residue was purified by Prep-HPLC (Column: XBridge Shield RP18 OBD Column, 19*250 mm, 10 μm; Mobile Phase A: Water (0.1% TFA), Mobile Phase B: ACN; Flow rate: 25 mL/min; Gradient: 25% B to 42% B in 10 min, 42% B; Wave Length: 254 nm; RT1 (min): 10.47) to provide (1S,3aR,6aS)—N—((S)-1-((R*)-5,5-dimethyl-2-oxopyrrolidin-3-yl)-4-hydroxy-3-oxobutan-2-yl)-2-(4-methoxy-1H-indole-2-carbonyl)octahydrocyclopenta[c]pyrrole-1-carboxamide (11.2 mg, 13%) as a white solid. $^1$H NMR (400 MHz, DMSO-d$_6$, 80° C.) δ 11.22 (s, 1H), 8.41 (br, 1H), 7.48 (s, 1H), 7.05-7.14 (m, 2H), 6.90 (s, 1H), 6.51-6.53 (m, 1H), 4.47-4.82 (m, 3H), 4.23-4.31 (m, 2H), 4.15-4.19 (m, 1H), 3.90 (s, 3H), 3.74-3.77 (m, 1H), 2.61-2.93 (m, 2H), 2.57-2.60 (m, 1H), 1.95-2.05 (m, 3H), 1.86-1.88 (m, 1H), 1.65-1.85 (m, 4H), 1.60-1.63 (m, 2H), 1.17 (s, 3H), 1.03 (s, 3H). LC-MS (ESI, m/z): 525 [M+H]$^+$.

70A_2

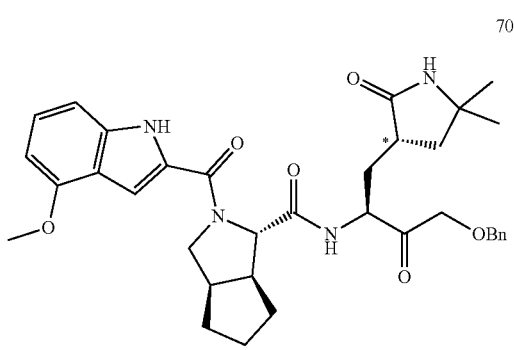

70_2

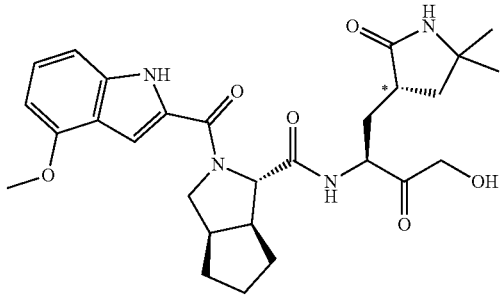

70A_2: (LC-MS (ESI, m/z): 615 [M+H]$^+$), and 70_2: (LC-MS (ESI, m/z): 525 [M+H]$^+$) were prepared similarly as described for 70A_1 and 70_1, using tert-butyl (S*)-4-((S)-2-((tert-butoxycarbonyl)amino)-3-(methoxy(methyl)amino)-3-oxopropyl)-2,2-dimethyl-5-oxopyrrolidine-1-carboxylate (as described in the synthesis of Compound 95) using tert-butyl (R*)-4-((S)-2-((tert-butoxycarbonyl)amino)-3-(methoxy(methyl)amino)-3-oxopropyl)-2,2-dimethyl-5-oxopyrrolidine-1-carboxylate.

Example 72

COMPOUND 71

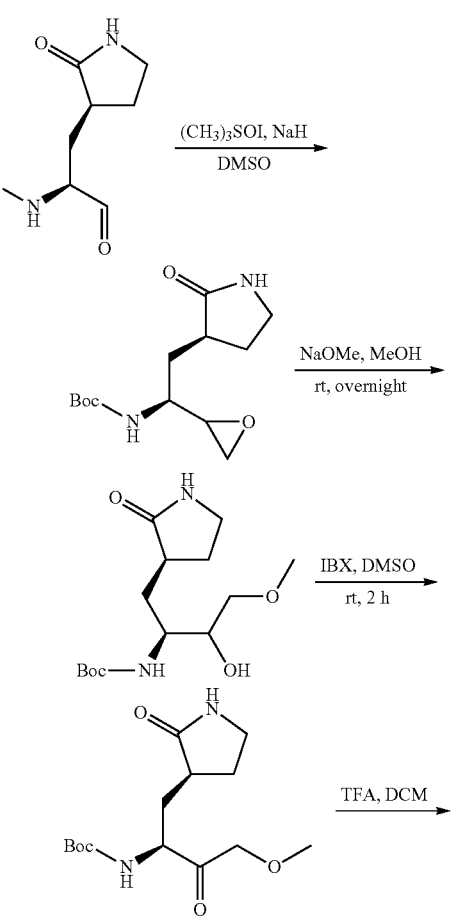

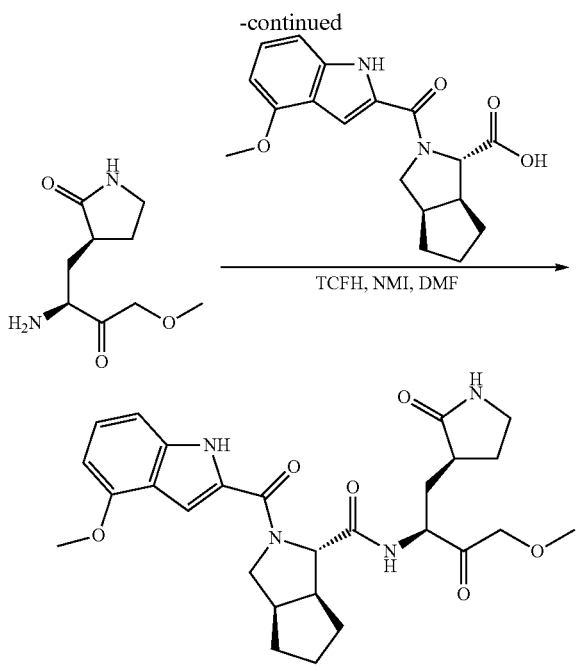

A 40 mL vial was charged with NaH (406 mg, 60% in mineral oil, 10.1 mmol, 2.0 eq.), DMSO (30 mL) and (CH₃)₃SOI (2.23 g, 10.1 mmol, 2.0 eq.). The mixture was stirred for 30 min at rt. Tert-butyl N-[(2S)-1-oxo-3-[(3S)-2-oxopyrrolidin-3-yl]propan-2-yl]carbamate (1.3 g, 5.07 mmol, 1.0 eq.) was added. The mixture was stirred for 2 h at rt, and the reaction was quenched with water (50 mL). The solution was extracted with dichloromethane (3×100 mL). The organic layers were combined, washed with brine (2×50 mL), dried over anhydrous sodium sulfate, filtered and concentrated under reduced pressure. The residue was chromatographed on a silica gel column with dichloromethane:methanol (94:6) to provide tert-butyl N-[(1S)-1-(oxiran-2-yl)-2-[(3S)-2-oxopyrrolidin-3-yl]ethyl]carbamate (850 mg, 53%) as a colorless oil. LC-MS (ESI, m/z): 271 [M+H]⁺.

A 40 mL vial was charged with tert-butyl N-[(1S)-1-(oxiran-2-yl)-2-[(3S)-2-oxopyrrolidin-3-yl]ethyl]carbamate (300 mg, 1.11 mmol, 1.0 eq.), methanol (10 mL) and sodium methoxide (2.00 g, 11.1 mmol, 10.0 eq.) was added at 0° C. The mixture was stirred overnight at rt. The mixture was then acidified to pH-5 with 1M hydrochloric acid and extracted with EA (3×50 mL). The organic layer was washed with brine (2×30 mL), dried over anhydrous sodium sulfate, filtered and concentrated under reduced pressure. The residue was chromatographed on a silica gel column with dichloromethane:methanol (96:4) to provide tert-butyl N-[(2S)-3-hydroxy-4-methoxy-1-[(3S)-2-oxopyrrolidin-3-yl]butan-2-yl]carbamate (230 mg, 58%) as a colorless oil. LC-MS (ESI, m/z): 303 [M+H]⁺.

A 40 mL vial was charged with tert-butyl N-[(2S)-3-hydroxy-4-methoxy-1-[(3S)-2-oxopyrrolidin-3-yl]butan-2-yl]carbamate (200 mg, 0.661 mmol, 1.0 eq.), DMSO (10 mL) and IBX (556 mg, 1.98 mmol, 3.0 eq.). The mixture was stirred for 2 h at rt, and the reaction was quenched with sodium thiosulfate (1M, 20 mL) and sat. sodium bicarbonate solution (20 mL). The solution was extracted with EA (5×100 mL). The organic layers was combined, washed with brine (2×50 mL), dried over anhydrous sodium sulfate, filtered and concentrated under reduced pressure. The residue was chromatographed on a silica gel column with dichloromethane:methanol (95:5) to provide tert-butyl N-[(2S)-4-methoxy-3-oxo-1-[(3S)-2-oxopyrrolidin-3-yl]butan-2-yl]carbamate (130 mg, 52%) as a colorless oil. LC-MS (ESI, m/z): 301 [M+H]⁺.

A 250 mL round-bottom flask was charged with tert-butyl N-[(2S)-4-methoxy-3-oxo-1-[(3S)-2-oxopyrrolidin-3-yl]butan-2-yl]carbamate (130 mg, 0.433 mmol, 1.0 eq.) and DCM (10 mL). TFA (3 mL) was added dropwise at 0° C. The mixture was stirred for 1.5 h at rt. The mixture was concentrated under reduced pressure to provide (3S)-3-[(2S)-2-amino-4-methoxy-3-oxobutyl]pyrrolidin-2-one (90 mg crude) as a yellow oil. LC-MS (ESI, m/z): 201 [M+H]⁺.

A 250 mL round-bottom flask was charged with (3S)-3-[(2S)-2-amino-4-methoxy-3-oxobutyl]pyrrolidin-2-one (150 mg, 0.749 mmol, 1.0 eq.), (1S,3aR,6aS)-2-(4-methoxy-1H-indole-2-carbonyl)-hexahydro-1H-cyclopenta[c]pyrrole-1-carboxylic acid (271 mg, 0.824 mmol, 1.1 eq.), DMF (50 mL) and NMI (554 mg, 6.74 mmol, 9.0 eq.). TCFH (273 mg, 0.974 mmol, 1.3 eq.) was added at 0° C. The mixture was stirred overnight at rt. The reaction was quenched with water (150 mL). The solution was extracted with EA (5×300 mL). The organic layers were combined, washed with brine (2×100 mL), dried over anhydrous sodium sulfate, filtered and concentrated under reduced pressure. The residue was chromatographed on a silica gel column with dichloromethane:methanol (96:4) to provide then crude product. The crude product (120 mg) was purified by prep-HPLC using the following gradient conditions: Column: XSelect CSH Prep C18 OBD Column, 19*250 mm, m; Mobile Phase A: Water (0.05% TFA), Mobile Phase B: ACN; Flow rate: 25 mL/min; Gradient: 30% B to 40% B in 10 min, 40% B; Wave Length: 254 nm; RT1 (min): 8.32, 9.68. Purification resulted in (1S,3aR,6aS)-2-(4-methoxy-1H-indole-2-carbonyl)-N-[(2S)-4-methoxy-3-oxo-1-[(3S)-2-oxopyrrolidin-3-yl]butan-2-yl]-hexahydro-1H-cyclopenta[c]pyrrole-1-carboxamide (32.2 mg, 8%) as a white solid. ¹H NMR (400 MHz, DMSO-d₆ 80° C.) δ 11.25 (s, 1H), 8.43 (s, 1H), 7.32 (s, 1H), 7.02-7.20 (m, 2H), 7.00 (s, 1H), 6.52 (d, J=6.8 Hz, 1H), 4.60 (br, 1H), 4.35-4.45 (m, 1H), 3.92-4.31 (m, 3H), 3.89 (s, 3H), 3.72-3.75 (m, 1H), 3.27 (s, 3H), 3.00-3.18 (m, 2H), 2.70-2.90 (m, 1H), 2.60-2.69 (m, 1H), 2.35-2.39 (m, 1H), 1.90-2.20 (m, 3H), 1.80-1.89 (m, 1H), 1.50-1.79 (m, 6H). LC-MS (ESI, m/z): 511 [M+H]⁺.

Example 73

COMPOUND 72

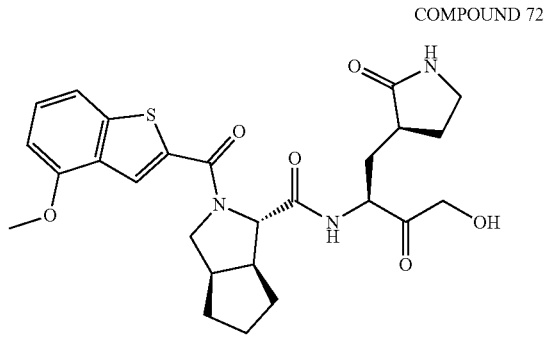 [SMILES: COc1cccc2sc(C(=O)N3C[C@@H]4CCC[C@@H]4[C@H]3C(=O)N[C@@H](C[C@@H]3CCNC3=O)C(=O)CO)cc12]

To a mixture of 4-methoxy-1-benzothiophene-2-carboxylic acid (75.0 mg, 0.361 mmol, 1.0 eq.), o-(7-azabenzotriazol-1-yl)-N,N,N',N'-tetramethyluronium hexafluorophosphate (165 mg, 0.433 mmol, 1.2 eq.) and N-ethyl-N-isopropylpropan-2-amine (140 mg, 1.08 mmol, 3.0 eq.) in DMF (3 mL) was added (1S,3aR,6aS)—N-[(2S)-4-hydroxy-3-oxo-1-[(3S)-2-oxopyrrolidin-3-yl]butan-2-yl]-octahydro-cyclopenta[c]pyrrole-1-carboxamide hydrochloride (130 mg, 0.361 mmol, 1.0 eq.) at 0° C. The mixture was stirred for 1 h at rt. The reaction was quenched with water (10 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by TLC (Mobile phase: MeOH:DCM=1:12; Rf=0.4; detection: UV) to afford the crude product. The crude product was purified by prep-HPLC (Column: Kinetex EVO prep C18, 30×150, 5 μm; Mobile Phase A: Water (0.1% TFA), Mobile Phase B: ACN; Flow rate: 60 mL/min; Gradient: 20% B to 45% B in 7 min, 45% B; Wave Length: 254 nm; RT: 5.42 min) to provide (1S,3aR,6aS)—N-[(2S)-4-hydroxy-3-oxo-1-[(3S)-2-oxopyrrolidin-3-yl]butan-2-yl]-2-(4-methoxy-1-benzothiophene-2-carbonyl)-hexahydro-1H-cyclopenta[c]pyrrole-1-carboxamide (26.0 mg, 14%) as a white solid. $^1$H NMR (400 MHz, DMSO-d$_6$) δ 8.30-8.48 (m, 1H), 7.78 (s, 1H), 7.52 (d, J=8.0 Hz, 1H), 7.41 (t, J=8.0 Hz, 1H), 7.31 (s, 1H), 6.94 (d, J=8.0 Hz, 1H), 4.53-4.78 (m, 1H), 4.38-4.50 (m, 2H), 4.13-4.30 (m, 2H), 3.98-4.12 (m, 1H), 3.96 (s, 3H), 3.60-3.75 (m, 1H), 2.85-3.20 (m, 2H), 2.70-2.84 (m, 1H), 2.55-2.69 (m, 1H), 2.16-2.40 (m, 1H), 1.88-2.15 (m, 3H), 1.66-1.87 (m, 3H), 1.55-1.65 (m, 3H), 1.43-1.54 (m, 1H). LC-MS (ESI, m/z): 514 [M+H]$^+$.

Example 74

COMPOUND 73

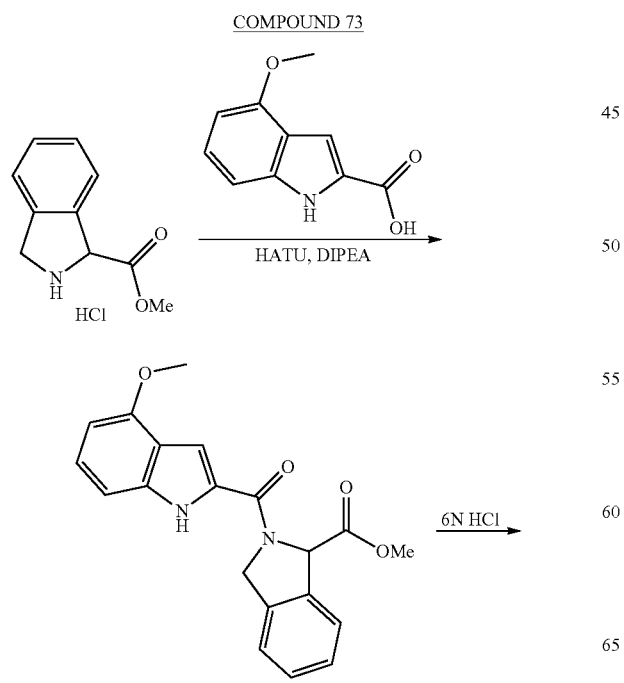

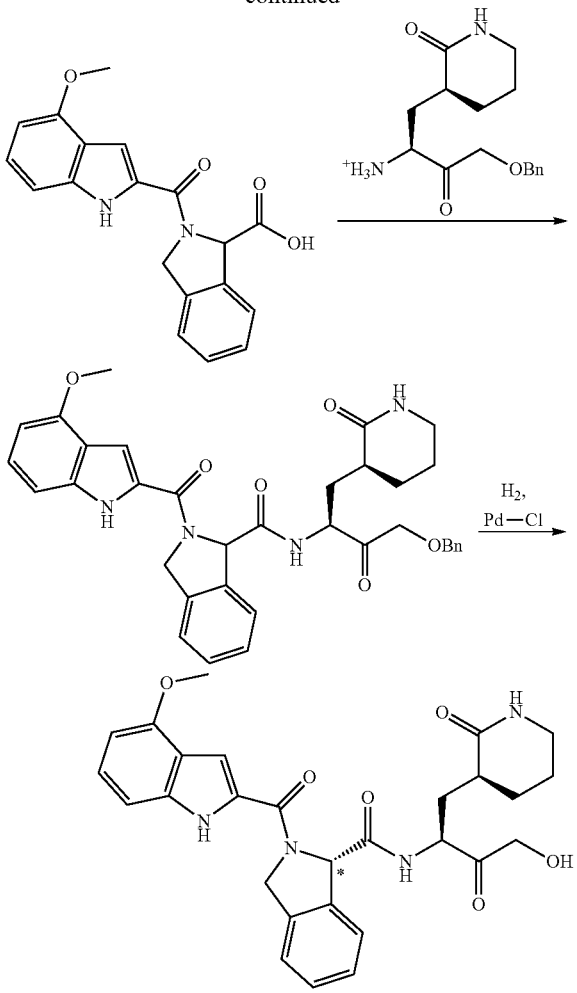

To a stirred at 0° C. solution of methyl isoindoline-1-carboxylate hydrochloride (220 mg, 1 mmol) and 4-methoxy-1H-indole-2-carbonylic acid (191 mg, 1 mmol) in DMF (5 mL) were added DIPEA (0.872 mL, 5 mmol) and HATU (456 mg, 1.2 mmol). After 1 h, the reaction was quenched with water, which afforded precipitation. The solid was filtered off, washed with water and acetonitrile, and dried under vacuum at 50° C. overnight to provide methyl 2-(4-methoxy-1H-indole-2-carbonyl)isoindoline-1-carboxylate 300 mg (86% yield). LC-MS (ESI, m/z): 351.10 [M+H]$^+$.

A mixture of Methyl 2-(4-methoxy-1H-indole-2-carbonyl)isoindoline-1-carboxylate (300 mg, 0.86 mmol) dioxane (6 mL) and 6N hydrochloric acid (0.6 mL) was heated at 95° C. for 4.5 h. The solvent was removed under vacuum, and the residue was crystallized from DCM (3 mL). The solid was collected by filtration and dried under vacuum, resulting in 2-(4-Methoxy-1H-indole-2-carbonyl)isoindoline-1-carboxylic acid (220 mg, 76%). LC-MS (ESI, m/z): 337.0 [M+H]⁺.

To a solution of tert-butyl ((S)-4-(benzyloxy)-3-oxo-1-((S)-2-oxopiperidin-3-yl)butan-2-yl)carbamate (85 mg, 0.22 mmol) in DCM (1 mL) was added TFA (0.2 mL). After 1 h, the mixture was diluted with DCM (15 mL), and the solvent was removed under reduced pressure. The crude was combined with (4-Methoxy-1H-indole-2-carbonyl)isoindoline-1-carboxylic acid (148 mg, 0.44 mmol) and DMF (2 mL). The solution was cooled to −25° C. and treated with DIPEA (0.192 mL, 1.1 mmol) and HATU (167 mg, 0.44 mmol). The mixture was gradually warmed to 0° C. over 1 h, and the reaction was quenched with 0.1 N hydrochloric acid (10 mL). The mixture was extracted with EA. The organic phase was washed with brine and a sodium bicarbonate solution. After drying over sodium sulfate, the solvent was removed under reduced pressure. The residue was purified by silica gel column chromatography (2 to 7% MeOH-DCM) resulting in N—((S)-4-(benzyloxy)-3-oxo-1-((S)-2-oxopiperidin-3-yl)butan-2-yl)-2-(4-methoxy-1H-indole-2-carbonyl)isoindoline-1-carboxamide (55 mg, 41%). LC-MS (ESI, m/z): 609.45 [M+H]⁺.

To a solution of N—((S)-4-(benzyloxy)-3-oxo-1-((S)-2-oxopiperidin-3-yl)butan-2-yl)-2-(4-methoxy-1H-indole-2-carbonyl)isoindoline-1-carboxamide (55 mg, 0.09 mmol) in ethanol (2 mL) was added 10% Pd—C(30 mg). The mixture was hydrogenated under atmospheric pressure (balloon) for 6 h. The catalyst was filtered off, and the filtrate was concentrated under vacuum. The residue was separated by prep-HPLC (phase,) in 25 to 95% 0.1% aqueous formic acid in acetonitrile over 25 min. 73_1 (first eluting peak): 6.5 mg; Rt: 2.42 min, LC-MS (ESI, m/z): 519.25 [M+H]⁺. 732 (second eluting peak): 10.4 mg; Rt: 2.50 min, LC-MS (ESI, m/z): 519.35 [M+H]⁺.

Example 75

COMPOUND 74

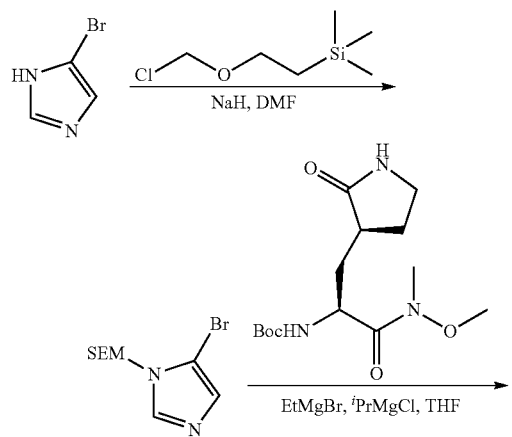

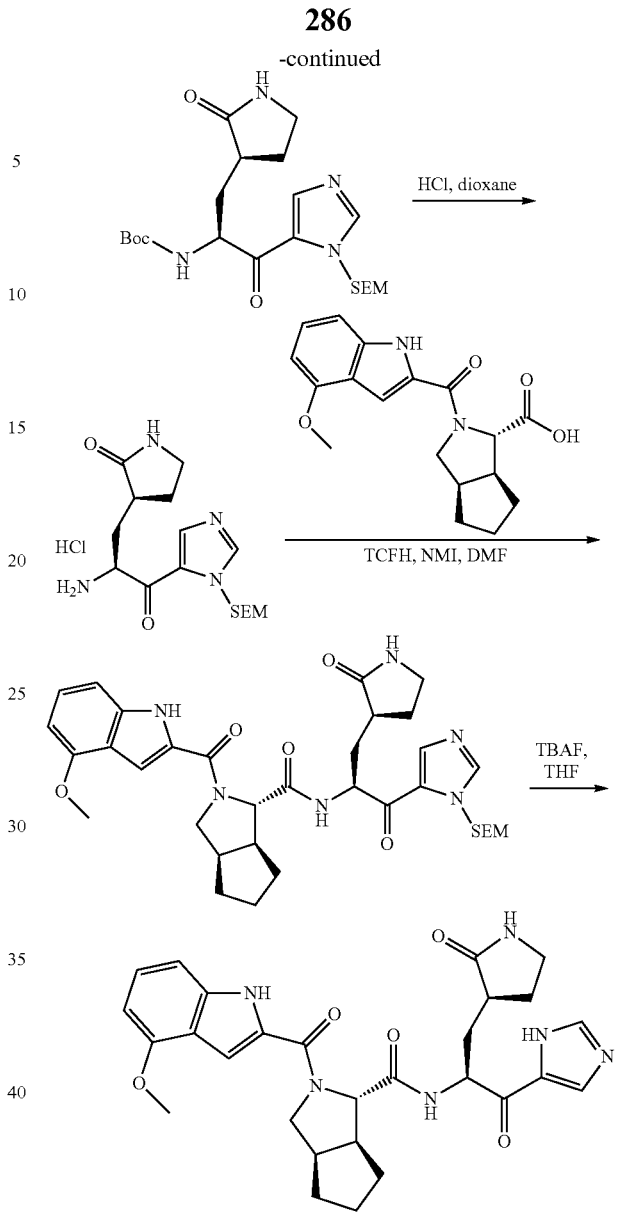

To a stirred mixture of DMF (15 mL) and NaH (720 mg, 27.2 mmol, 1.0 eq., 60% in mineral oil) at 0° C. was added 4-bromo-1H-imidazole (4.00 g, 27.2 mmol, 1.0 eq.) in one portion under nitrogen. The mixture was stirred for 5 min at 0° C. A solution of 2-(trimethylsilyl)ethoxymethyl chloride (6 mL, mmol 1.2 eq.) in DMF (4 mL) was added dropwise. After stirring for 1 h at 0° C., the mixture was warmed slowly to rt, and stirred overnight. The reaction was quenched with water and extracted with EA (3×100 mL). The organic layers were combined, washed with brine (2×100 mL), dried over anhydrous sodium sulfate, filtered and concentrated under reduced pressure to afford the crude product. The crude product was diluted with dichloromethane (20 mL), made into a slurry with 100~200 silica gel mesh (10 g) and loaded onto a column after removing the dichloromethane. The sample was purified by column chromatography (Column size 4×24 cm, column volume: 300 mL, silica gel size (100~200 mesh) quantity: 120 g) and eluted with EA:PE (5%~20% over 30 min). The collected fractions: 10%-15% EA:PE fractions were chosen as pure fractions, and those fractions were combined and concentrated under reduced pressure to provide 5-bromo-1-((2-(trimethylsilyl)ethoxy)methyl)-1H-imidazole as an oil (4.8 g, 63%). $^1$H NMR (300 MHz, DMSO-$d_6$) δ 7.51 (s, 1H), 7.05 (s, 1H), 5.25 (s, 2H), 3.48-3.58 (m, 2H), 0.90-0.99 (m, 2H), 0.01 (s, 9H). LC-MS (ESI, m/z): 277 [M+H]$^+$.

To a solution of 5-bromo-1-((2-(trimethylsilyl)ethoxy)methyl)-1H-imidazole (4.22 g, 15.2 mmol, 6.0 eq.) in THF (5 mL) was added EtMgBr (8.34 mL, 16.7 mmol, 6.6 eq., 2.0 M in Et$_2$O) slowly at 0° C. under nitrogen. The mixture was stirred for 1 h at 0° C. To a solution of tert-butyl ((S)-1-(methoxy(methyl)amino)-1-oxo-3-((S)-2-oxopyrrolidin-3-yl)propan-2-yl)carbamate (800 mg, 2.54 mmol, 1.0 eq.) in THF (10 mL) was added $^i$PrMgCl (2.5 mL, 5.07 mmol, 2.0 eq., 2.0 M in THF) slowly at −15° C. under nitrogen. The mixture was stirred for 20 min at −15° C. and then added into the above solution. The solution was stirred at rt overnight, and the reaction was quenched with sat. aq. ammonium chloride (10 mL). The mixture was extracted with EA (3×20 mL). The organic layers were combined, washed with brine (2×20 mL), dried over anhydrous sodium sulfate, filtered and concentrated under reduced pressure to afford the crude product. The crude product was purified by TLC (Mobile phase: methanol:dichloromethane=1:20; Rf=0.5; detection: UV) to provide tert-butyl ((S)-1-oxo-3-((S)-2-oxopyrrolidin-3-yl)-1-(1-((2-(trimethylsilyl)ethoxy)methyl)-1H-imidazol-5-yl)propan-2-yl)carbamate (200 mg, 23%) as a yellow solid. LC-MS (ESI, m/z): 453 [M+H]$^+$.

To a mixture of tert-butyl ((S)-1-oxo-3-((S)-2-oxopyrrolidin-3-yl)-1-(1-((2-(trimethylsilyl)ethoxy)methyl)-1H-imidazol-5-yl)propan-2-yl)carbamate (200 mg, 0.442 mmol, 1.0 eq.) in dioxane (3 mL) was added hydrogen chloride (3 mL, 4 M in 1,4-dioxane) at 0° C. The mixture was stirred for 1 h at rt and then concentrated under reduced pressure to afford (S)-3-((S)-2-amino-3-oxo-3-(1-((2-(trimethylsilyl)ethoxy)methyl)-1H-imidazol-5-yl)propyl)pyrrolidin-2-one hydrochloride (160 mg, crude) as a yellow solid. LC-MS (ESI, m/z): 353 [M+H]$^+$.

To a mixture of (S)-3-((S)-2-amino-3-oxo-3-(1-((2-(trimethylsilyl)ethoxy)methyl)-1H-imidazol-5-yl)propyl)pyrrolidin-2-one hydrochloride (160 mg, 0.411 mmol, 1.0 eq.), (1S,3aR,6aS)-2-(4-methoxy-1H-indole-2-carbonyl)-hexahydro-1H-cyclopenta[c]pyrrole-1-carboxylic acid (162 mg, 0.493 mmol, 1.0 eq.) and N,N,N,N-tetramethylchloroformamidinium hexafluorophosphate (139 mg, 0.493 mmol, 1.2 eq.) in DMF (3 mL) was added and 1-methyl-1H-imidazole (169 mg, 2.01 mmol, 5.0 eq.) at 0° C. The mixture was stirred for 1 h at rt, and the reaction was quenched with water (3 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by TLC (Mobile phase: methanol:dichloromethane=1:10; Rf=0.4; detection: UV) to provide (1S,3aR,6aS)-2-(4-methoxy-1H-indole-2-carbonyl)-N—((S)-1-oxo-3-((S)-2-oxopyrrolidin-3-yl)-1-(1-((2-(trimethylsilyl)ethoxy)methyl)-1H-imidazol-5-yl)propan-2-yl)octahydrocyclopenta[c]pyrrole-1-carboxamide (90 mg, 33%) as a yellow solid. LC-MS (ESI, m/z): 663 [M+H]$^+$.

To a mixture of (1S,3aR,6aS)-2-(4-methoxy-1H-indole-2-carbonyl)-N—((S)-1-oxo-3-((S)-2-oxopyrrolidin-3-yl)-1-(1-((2-(trimethylsilyl)ethoxy)methyl)-1H-imidazol-5-yl)propan-2-yl)octahydrocyclopenta[c]pyrrole-1-carboxamidete (90.0 mg, 0.136 mmol, 1.0 eq.) in THF (3 mL) was added tetrabutylammonium fluoride (1.4 mL, 1.36 mmol, 10.0 eq., 1 M in THF). The mixture was stirred overnight at 60° C., and the reaction was quenched with water (3 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by prep-HPLC (Column: XSelect CSH Prep C18 OBD Column, 19*250 mm, 5 μm; Mobile Phase A: Water (0.05% TFA), Mobile Phase B: ACN; Flow rate: 25 mL/min; Gradient: 22% B to 50% B in 10 min, 50% B; Wave Length: 254 nm; RT1 (min): 6.67) to provide (1S,3aR,6aS)—N-[(2S)-1-(3H-imidazol-4-yl)-1-oxo-3-[(3S)-2-oxopyrrolidin-3-yl]propan-2-yl]-2-(4-methoxy-1H-indole-2-carbonyl)-hexahydro-1H-cyclopenta[c]pyrrole-1-carboxamide (2.4 mg, 3%) as a white solid. LC-MS (ESI, m/z): 533 [M+H]$^+$.

Example 76

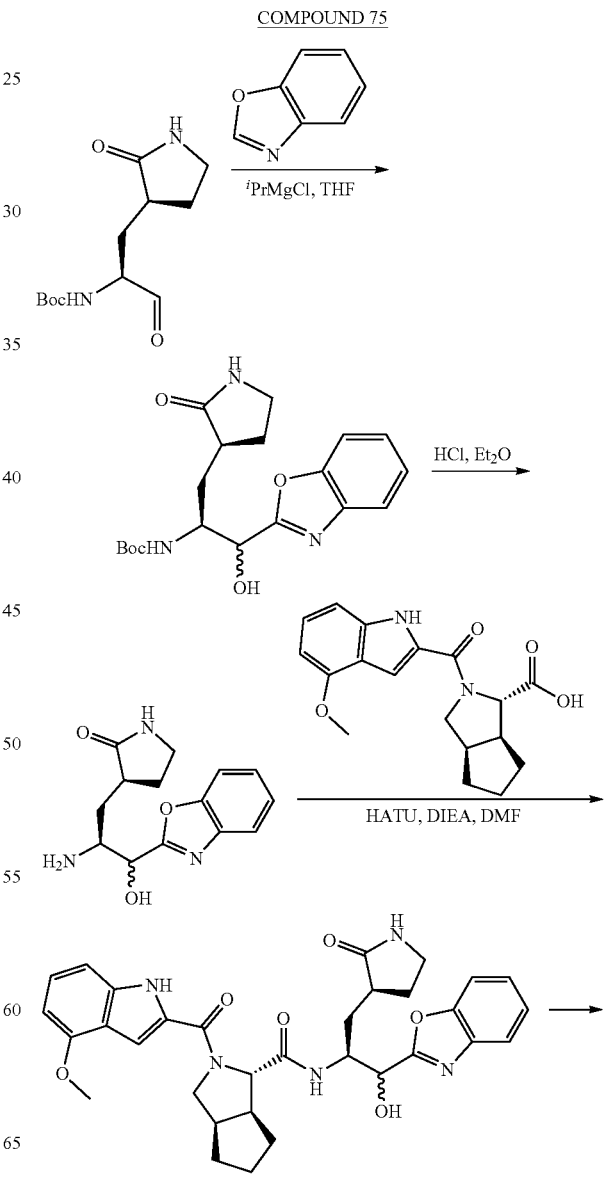

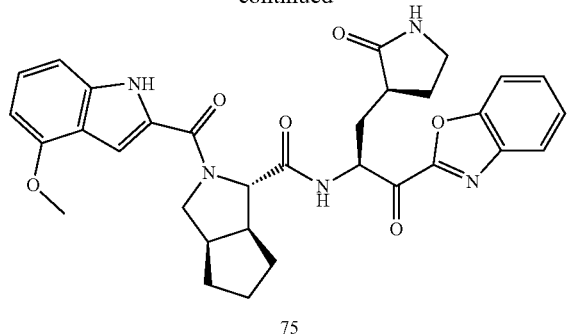

75

To a solution of benzoxazole (373 mg, 3.14 mmol, 3.0 eq.) in THF (4 mL) was added chloro(isopropyl)magnesium (1.05 mL, 2.09 mmol, 2.0 eq.) under nitrogen at −10° C. The mixture was stirred for 1 h at −10° C., and then tert-butyl N-[(2S)-1-oxo-3-[(3S)-2-oxopyrrolidin-3-yl]propan-2-yl] carbamate (268 mg, 1.05 mmol, 1.0 eq., in 3 mL THF) was added at −10° C. The mixture was allowed to warm to rt, and then stirred overnight. The reaction was quenched with water (10 mL). The mixture was extracted with EtOAc (3×15 mL). The organic layers were combined, washed with brine (2×15 mL), dried over anhydrous sodium sulfate, filtered and concentrated under reduced pressure to afford the crude product. The crude product was purified by silica gel column chromatography, eluted with DCM:MeOH=10:1 to afford tert-butyl N-[(2S)-1-(1,3-benzoxazol-2-yl)-1-hydroxy-3-[(3S)-2-oxopyrrolidin-3-yl]propan-2-yl]carbamate (116 mg, 28%). LC-MS (ESI, m/z): 376 [M+H]+.

To a solution of tert-butyl N-[(2S)-1-(1,3-benzoxazol-2-yl)-1-hydroxy-3-[(3S)-2-oxopyrrolidin-3-yl]propan-2-yl] carbamate (150 mg, 0.400 mmol, 1.0 eq.) in DCM (1.5 mL) was added HCl (2.0 mL, 2M in EtO2), and the mixture was stirred for 1 h at rt. The mixture was concentrated under reduced pressure to afford (3S)-3-[(2S)-2-amino-3-(1,3-benzoxazol-2-yl)-3-hydroxypropyl]pyrrolidin-2-one (130 mg, crude). LC-MS (ESI, m/z): 276 [M+H]+.

To a mixture of (3S)-3-[(2S)-2-amino-3-(1,3-benzoxazol-2-yl)-3-hydroxypropyl]pyrrolidin-2-one (110 mg, 0.400 mmol, 1.0 eq.) in DMF (2 mL) was added (1S,3aR,6aS)-2-(4-methoxy-1H-indole-2-carbonyl)-hexahydro-1H-cyclopenta[c]pyrrole-1-carboxylic acid (131 mg, 0.400 mmol, 1.0 eq.), o-(7-azabenzotriazol-1-yl)-N,N,N',N'-tetramethyluronium hexafluorophosphate (213 mg, 0.560 mmol, 1.4 eq.) and N-ethyl-N-isopropylpropan-2-amine (155 mg, 1.20 mmol, 3.0 eq.). The mixture was stirred for 1 h at rt, and the reaction was quenched with water (2 mL). The mixture was extracted with EtOAc (3×5 mL). The organic layers were combined, washed with brine (2×10 mL), dried over anhydrous sodium sulfate, filtered and concentrated under reduced pressure to afford the crude product. The crude product was purified by TLC (Mobile phase: MeOH:DCM ether=1:11; Rf=0.3; detection: UV) to provide (1S,3aR,6aS)—N-[(2S)-1-(1,3-benzoxazol-2-yl)-1-hydroxy-3-[(3S)-2-oxopyrrolidin-3-yl]propan-2-yl]-2-(4-methoxy-1H-indole-2-carbonyl)-hexahydro-1H-cyclopenta[c]pyrrole-1-carboxamide (136 mg, 58%). LC-MS (ESI, m/z): 586 [M+H]+.

To a solution of (1S,3aR,6aS)—N-[(2S)-1-(1,3-benzoxazol-2-yl)-1-hydroxy-3-[(3S)-2-oxopyrrolidin-3-yl]propan-2-yl]-2-(4-methoxy-1H-indole-2-carbonyl)-hexahydro-1H-cyclopenta[c]pyrrole-1-carboxamide (136 mg, 0.232 mmol, 1.00 eq.) in DMSO (2 mL) was added 2-iodoxybenzoic acid (195 mg, 0.696 mmol, 3.0 v). The mixture was stirred for 20 h at rt, and the reaction was quenched with sat. sodium bicarbonate (5 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by TLC (Mobile phase: MeOH:DCM=1:11; Rf=0.5; detection: UV) to provide (1S,3aR,6aS)—N-[(2S)-1-(1,3-benzoxazol-2-yl)-1-oxo-3-[(3S)-2-oxopyrrolidin-3-yl]propan-2-yl]-2-(4-methoxy-1H-indole-2-carbonyl)-hexahydro-1H-cyclopenta[c]pyrrole-1-carboxamide (53.2 mg, 39%) as an off-white solid. LC-MS (ESI, m/z): 584 [M+H]+.

Example 77

COMPOUND 76

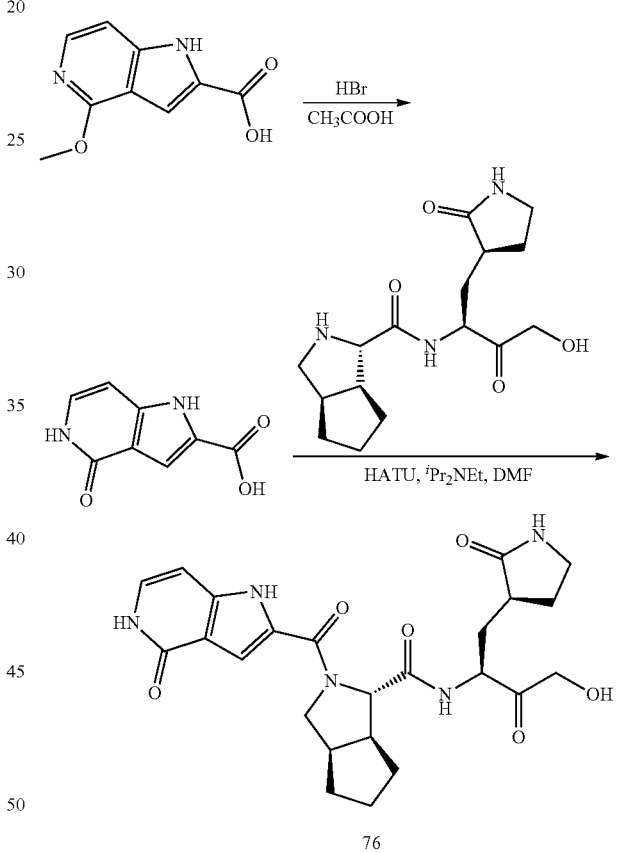

76

A mixture of 4-methoxy-1H-pyrrolo[3,2-c]pyridine-2-carboxylic acid (200 mg, 1.04 mmol, 1.0 eq.) and HBr (6.32 mL, 31.230 mmol, 30 eq., 40% in CH3COOH) was stirred for 2 h at 90° C. The mixture was filtered. The filter cake was washed with ethyl ether (50 mL) and concentrated under reduced pressure to afford 4-oxo-1H,5H-pyrrolo[3,2-c]pyridine-2-carboxylic acid (180 mg, crude) as a white solid. LC-MS (ESI, m/z): 179 [M+H]+.

To a stirred mixture of 4-oxo-1H,5H-pyrrolo[3,2-c]pyridine-2-carboxylic acid (65.4 mg, 0.367 mmol, 1.1 eq.) and N-ethyl-N-isopropylpropan-2-amine (129 mg, 1.00 mmol, 3.0 eq.) in DMF (4 mL) was added o-(7-Azabenzotriazol-1-yl)-N,N,N',N'-tetramethyluronium hexafluorophosphate (152 mg, 0.401 mmol, 1.2 eq.) at 0° C. (1S,3aR,6aS)—N-

[(2S)-4-hydroxy-3-oxo-1-[(3S)-2-oxopyrrolidin-3-yl]butan-2-yl]-octahydrocyclopenta[c]pyrrole-1-carboxamide (108 mg, 0.334 mmol, 1.0 eq.) was added at 0° C., and the mixture was stirred for 1 h at rt. The crude product was purified by TLC (Mobile phase: methanol:dichloromethane=1:1; Rf=0.4; detection: UV) to provide the crude product. The crude product was purified by Prep-HPLC with the following conditions (Column: Kinetex EVO C18 Column, 30*150, 5 μm; Mobile Phase A: Water (0.05% TFA), Mobile Phase B: ACN; Flow rate: 25 mL/min; Gradient: 5% B to 28% B in 10 min, 28% B; Wave Length: 254 nm; RT1 (min): 8.30, 8.60; Number Of Runs: 0) to afford (1S,3aR,6aS)—N-[(2S)-4-hydroxy-3-oxo-1-[(3S)-2-oxopyrrolidin-3-yl]butan-2-yl]-2-{4-oxo-1H,5H-pyrrolo[3,2-c]pyridine-2-carbonyl}-hexahydro-1H-cyclopenta[c]pyrrole-1-carboxamide (5.5 mg, 3%) as a white solid. $^1$H NMR (353K, 400 MHz, DMSO-d$_6$) δ 11.59 (s, 1H), 10.50 (s, 1H), 8.37 (s, 1H), 7.31 (s, 1H), 6.88-7.11 (m, 2H), 6.33-6.39 (m, 1H), 4.37-4.85 (m, 3H), 4.09-4.32 (m, 2H), 4.02 (brs, 1H), 3.62-3.72 (m, 1H), 3.12 (m, 2H), 2.70-2.85 (m, 1H), 2.55-2.70 (m, 1H), 2.31-2.42 (m, 1H), 2.01-2.17 (m, 1H), 1.88-1.99 (m, 2H), 1.77-1.87 (m, 1H), 1.55-1.78 (m, 5H), 1.44-1.54 (m, 1H). LC-MS (ESI, m/z): 484 [M+H]$^+$.

Example 78

COMPOUND 77

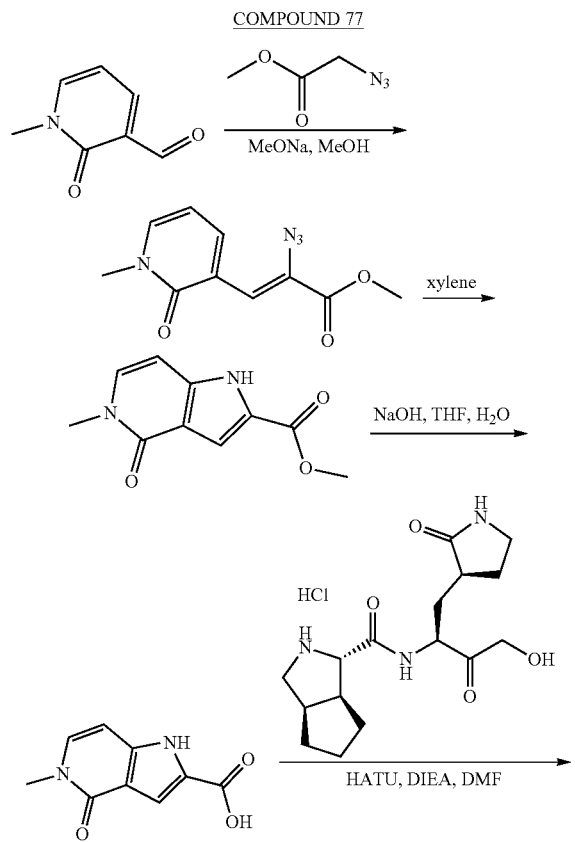

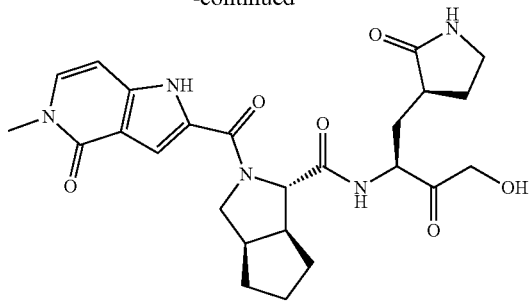

A 40 mL vial was charged with sodium methoxide (1.58 mL, 8.75 mmol, 4.0 eq.) in MeOH (4 mL). 1-methyl-2-oxo-1,2-dihydropyridine-3-carbaldehyde (300 mg, 2.19 mmol, 1.0 eq.) and methyl 2-azidoacetate (1.01 g, 8.75 mmol, 4.0 eq.) in MeOH (1 mL) was added in 1.5 h at −10° C. The mixture was stirred for 1.5 h at −10° C. and poured into ice-water (10 mL). The solution was extracted with EA (3×20 mL). The organic layers were combined, washed with brine (2×20 mL), dried over anhydrous sodium sulfate, filtered and concentrated under reduced pressure to provide methyl 2-azido-3-(1-methyl-2-oxo-1,2-dihydropyridin-3-yl) acrylate (300 mg, 58%) as a yellow solid. LC-MS (ESI, m/z): 235 [M+H]$^+$.

A 40 mL vial was charged with methyl (Z)-2-azido-3-(1-methyl-2-oxo-1,2-dihydropyridin-3-yl)acrylate (300 mg, 1.28 mmol, 1.0 eq.), xylene (8 mL) under nitrogen. The mixture was stirred for 1 h at 120° C., and then concentrated under reduced pressure to provide methyl 5-methyl-4-oxo-4,5-dihydro-1H-pyrrolo[3,2-c]pyridine-2-carboxylate (250 mg, 92%) as a yellow solid. $^1$H NMR (300 MHz, DMSO-d$_6$) δ 12.29 (s, 1H), 7.44 (d, J=7.3 Hz, 1H), 7.15 (s, 1H), 6.38 (d, J=7.3 Hz, 1H), 3.84 (s, 3H), 3.45 (s, 3H). LC-MS (ESI, m/z): 207 [M+H]$^+$.

A 50 mL round-bottom flask was charged with methyl 5-methyl-4-oxo-4,5-dihydro-1H-pyrrolo[3,2-c]pyridine-2-carboxylate (250 mg, 1.212 mmol, 1.00 eq.), THF (3 mL), NaOH (145 mg, 3.64 mmol, 3.0 eq.) and H$_2$O (3 mL). The mixture was stirred for 1 h at rt. The pH value of the solution was adjusted to 5 with acetate acid. The solution was concentrated under reduced pressure. The residue was diluted with water (5 mL) and filtered. The solids were dried under reduced pressure to provide 5-methyl-4-oxo-4,5-dihydro-1H-pyrrolo[3,2-c]pyridine-2-carboxylic acid (160 mg, 68%) as a light yellow solid. $^1$H NMR (300 MHz, DMSO-d$_6$) δ 12.86 (s, 1H), 12.08 (s, 1H), 7.39 (d, J=7.3 Hz, 1H), 7.07 (d, J=1.6 Hz, 1H), 6.34 (d, J=7.3 Hz, 1H), 3.42 (s, 3H). LC-MS (ESI, m/z): 193 [M+H]$^+$.

A 25 mL round-bottom flask was charged with 5-methyl-4-oxo-4,5-dihydro-1H-pyrrolo[3,2-c]pyridine-2-carboxylic acid (50.0 mg, 0.260 mmol, 1.0 eq.), N,N,N',N'-tetramethyl-O-(7-azabenzotriazol-1-yl)uronium hexafluorophospate (148 mg, 0.39 mmol, 1.5 eq.), N,N-diisopropylethylamine (101 mg, 0.780 mmol, 3.0 eq.) and DMF (5 mL). The mixture was stirred for 30 min at 0° C. (1S,3aR,6aS)—N—((S)-4-hydroxy-3-oxo-1-((S)-2-oxopyrrolidin-3-yl)butan-2-yl)octahydrocyclopenta[c]pyrrole-1-carboxamide hydrochloride (74.9 mg, 0.21 mmol, 0.8 eq.) was added. The mixture was stirred for 1 h at 0° C. The reaction was quenched with water (10 mL). The solution was extracted with EA (3×20 mL). The organic layers were combined, washed with brine (2×20 mL), dried over anhydrous sodium sulfate, filtered and concentrated under reduced pressure. The crude product was purified by prep-HPLC using the following gradient conditions: Column: XBridge Shield RP18 OBD Column, 30*150 mm, 5 μm; Mobile Phase A: Water (0.1% TFA), Mobile Phase B: ACN; Flow rate: 60 mL/min; Gradient: 5% B to 18% B in 10 min, Wave Length: 254 nm; RT1 (min): 10.52. Purification resulted in (1S,3aR, 6aS)—N—((S)-4-hydroxy-3-oxo-1-((S)-2-oxopyrrolidin-3-yl)butan-2-yl)-2-(5-methyl-4-oxo-4,5-dihydro-1H-pyrrolo [3,2-c]pyridine-2-carbonyl)octahydrocyclopenta[c]pyrrole-1-carboxamide (3.6 mg, 3%) as a white solid. LC-MS (ESI, m/z): 498 [M+H]⁺.

Example 79

COMPOUND 78

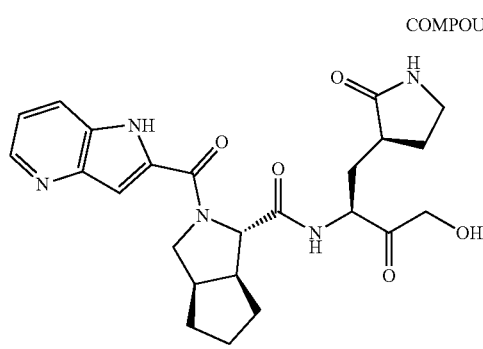

To a solution of 1H-pyrrolo[3,2-b]pyridine-2-carboxylic acid (82.73 mg, 0.510 mmol, 1.1 eq.) in DMF (3 mL), was added N,N-diisopropylethylamine (539 mg, 4.18 mmol, 9.0 eq.) and N,N,N',N'-Tetramethyl-O-(7-azabenzotriazol-1-yl) uronium hexafluorophospate (194 mg, 0.51 mmol, 1.1 eq.). The mixture was stirred at 0° C. for 30 min and (1S,3aR, 6aS)—N-[(2S)-4-hydroxy-3-oxo-1-[(3S)-2-oxopyrrolidin-3-yl]butan-2-yl]-octahydrocyclopenta[c]pyrrole-1-carboxamide (150 mg, 0.46 mmol, 1.0 eq.) was added. The mixture was stirred at 0° C. for 1 h, and the reaction was quenched with water (5 mL). The solution was extracted with EA (3×10 mL). The organic layers were combined, dried over anhydrous sodium sulfate, filtered and concentrated under reduced pressure. The residue was chromatographed on a C18 column with MeCN:H₂O (1:7) to get the crude product. The crude product was purified by Prep-HPLC (Column: XBridge Prep Phenyl OBD Column, 19*250 mm, 5 μm; Mobile Phase A: Water (10 mmol/L NH₄HCO₃+0.1% NH₃·H₂O), Mobile Phase B: ACN; Flow rate: 25 mL/min; Gradient: 15% B to 25% B in 10 min, 25% B; Wave Length: 254 nm; RT1 (min): 8.65) to provide (1S,3aR,6aS)—N—((S)-4-hydroxy-3-oxo-1-((S)-2-oxopyrrolidin-3-yl)butan-2-yl)-2-(1H-pyrrolo[3,2-b]pyridine-2-carbonyl)octahydrocyclopenta[c]pyrrole-1-carboxamide (4.8 mg, 2%) as a white solid. LC-MS (ESI, m/z): 468 [M+H]⁺.

Example 80

COMPOUND 79

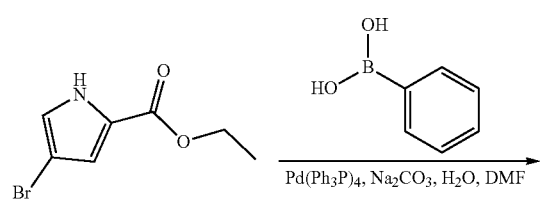

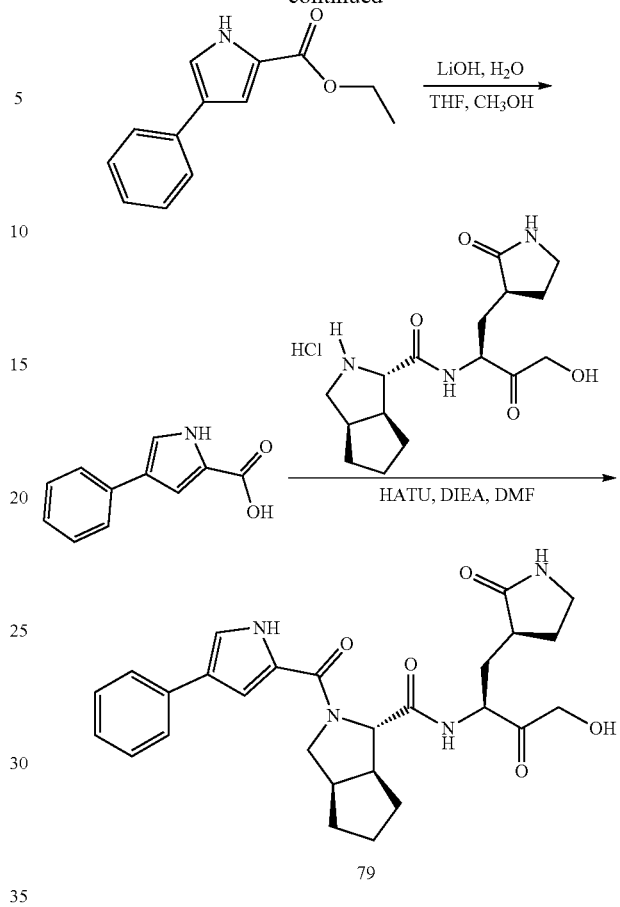

79

To a solution of ethyl 4-bromo-1H-pyrrole-2-carboxylate (1.5 g, 6.88 mmol, 1.0 eq.) in DMF (30 mL) was added phenylboronic acid (2.10 g, 17.2 mmol, 2.5 eq.) and palladium tetrakis-triphenylphosphine (400 mg, 0.334 mmol, 0.05 eq.), and the mixture was stirred under nitrogen at rt. The mixture was heated to 70° C. and sodium carbonate (6.56 g, 61.9 mmol, 9.0 eq., in 5 mL H₂O) was added. The mixture was stirred for 5 h at 110° C. and diluted with water (15 mL). The mixture was extracted with EA (3×30 mL). The combined organic layers were washed with brine, dried with anhydrous sodium sulfate, filtered and concentrated under reduced pressure to afford the crude product. The crude product was diluted with dichloromethane (10 mL), made into a slurry with 100~200 silica gel mesh (5 g) and loaded to a column after removing the dichloromethane. The sample was purified by column chromatography (Column size 4×24 cm, column volume: 300 mL, silica gel size (100~200 mesh) quantity: 80 g) and eluted with EA:PE (5%~15% over min). The collected fractions: 8%-11% EA:PE fractions were chosen as the pure fractions. Those fractions were combined and concentrated under reduced pressure to provide ethyl 4-phenyl-1H-pyrrole-2-carboxylate (650 mg, 43%) as a white solid. ¹H NMR (300 MHz, CDCl₃-d) δ 9.34 (br, 1H), 7.50-7.62 (m, 2H), 7.34-7.44 (m, 2H), 7.21-7.29 (m, 3H), 4.32-4.43 (m, 2H), 1.42 (t, J=7.1 Hz, 3H). LC-MS (ESI, m/z): 216 [M+H]⁺.

To a mixture of ethyl 4-phenyl-1H-pyrrole-2-carboxylate (300 mg, 1.39 mmol, 1.0 eq.) in THF (3 mL)/water (2 mL)/methanol (1 mL) was added lithium hydroxide (200 mg, 8.36 mmol, 6.0 eq.). The mixture was stirred 2 h at 60° C. and then concentrated under reduced pressure to remove the tetrahydrofuran and methanol. The pH of the mixture was adjusted to 5 with HCl (1 M). The mixture was extracted with EA (3×30 mL). The organic layers were combined, washed with brine (2×10 mL), dried over anhydrous sodium sulfate, filtered and concentrated under reduced pressure to provide 4-phenyl-1H-pyrrole-2-carboxylic acid (230 mg, 88%) as a white solid. $^1$H NMR (300 MHz, DMSO-d$_6$) δ 12.33 (s, 1H), 11.87 (s, 1H), 7.57-7.59 (m, 2H), 7.43 (s, 1H), 7.27-7.33 (m, 2H), 7.02-7.21 (m, 2H). LC-MS (ESI, m/z): 188 [M+H]$^+$.

To a mixture of 4-phenyl-1H-pyrrole-2-carboxylic acid (80.1 mg, 0.428 mmol, 1.1 eq.), (1S,3aR,6aS)—N—((S)-4-hydroxy-3-oxo-1-((S)-2-oxopyrrolidin-3-yl) butan-2-yl)octahydrocyclopenta[c]pyrrole-1-carboxamide hydrochloride (140 mg, 0.389 mmol, 1.0 eq.) and o-(7-aza-1H-benzotriazol-1-yl)-N,N,N',N'-tetramethyluronium hexafluorophosphate (178 mg, 0.467 mmol, 1.2 eq.) in DMF (3 mL) was added N,N-diisopropylethylamine (151 mg, 1.18 mmol, 3.0 eq.) at 0° C. The mixture was stirred for 1 h at 0° C., and the reaction was quenched with water (3 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by HPLC (Column: X Bridge Prep Phenyl OBD Column, 19*250 mm, 5 μm; Mobile Phase A: Water (0.05% TFA), Mobile Phase B: ACN; Flow rate: 25 mL/min; Gradient: 30% B to 38% B in 10 min, 38% B; Wave Length: 254 nm; RT1 (min): 9.42) to provide (1S,3aR,6aS)—N—((S)-4-hydroxy-3-oxo-1-((S)-2-oxopyrrolidin-3-yl)butan-2-yl)-2-(4-phenyl-1H-pyrrole-2-carbonyl) octahydrocyclopenta[c]pyrrole-1-carboxamide (16.2 mg, 8%) as a white solid. $^1$H NMR (400 MHz, DMSO-d$_6$) δ 11.31 (s, 1H), 8.35 (s, 1H), 7.54-7.57 (m, 2H), 7.29-7.32 (m, 4H), 7.13-7.15 (m, 1H), 6.94 (s, 1H), 4.77 (s, 1H), 4.49-4.52 (m, 1H), 4.38-4.46 (m, 1H), 4.17-4.23 (m, 2H), 3.96-4.00 (m, 1H), 3.63-3.69 (m, 1H), 2.96-3.09 (m, 2H), 2.59 (s, 1H), 2.71 (s, 1H), 2.28-2.34 (m, 1H), 1.44-2.03 (m, 10H). LC-MS (ESI, m/z): 493 [M+H]$^+$.

Example 81

COMPOUND 80

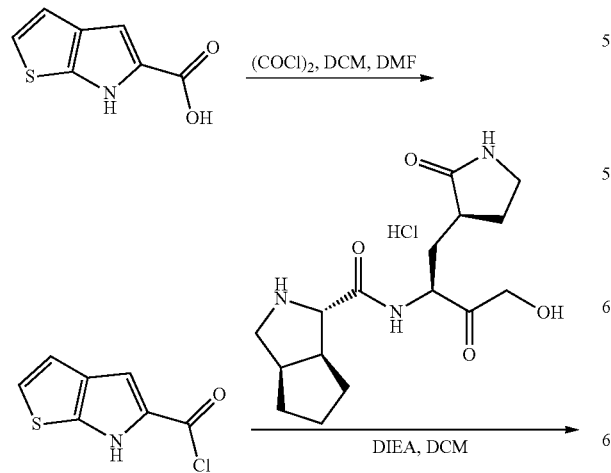

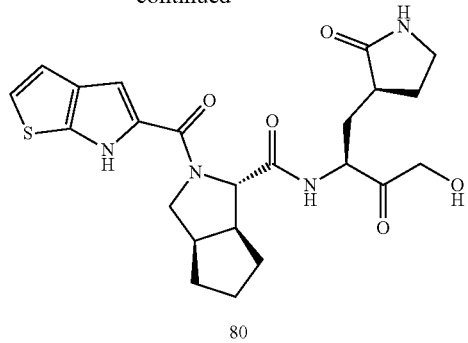

80

To a stirred mixture of (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (150 mg, 0.417 mmol, 1.0 eq.) in dichloromethane (5 mL) was added 6H-thieno[2,3-b]pyrrole-5-carbonyl chloride (77.5 mg, 0.417 mmol, 1.0 eq.) and N,N-diisopropylethylamine (188 mg, 1.46 mmol, 3.5 eq.) dropwise at 0° C. The mixture was stirred for 1 h at rt, and the reaction was quenched with water (10 mL) at rt. The mixture was extracted with dichloromethane (3×50 mL). The organic layers were combined washed with brine (2×30 mL), dried over anhydrous sodium sulfate, filtrated and concentrated under reduced pressure. The residue was purified by Prep-TLC (dichloromethane:methanol=12:1) to afford (1S,3aR,6aS)—N-[(2S)-4-hydroxy-3-oxo-1-[(3S)-2-oxopyrrolidin-3-yl]butan-2-yl]-2-{6H-thieno[2,3-b]pyrrole-5-carbonyl}-hexahydro-1H-cyclopenta[c]pyrrole-1-carboxamide (50 mg, crude) as a yellow oil. The crude product (50 mg) was purified by Prep-HPLC with the following conditions (Column: XSelect CSH Prep C18 OBD Column, 19*250 mm, 5 μm; Mobile Phase A: Water (10 mmol/L NH$_4$HCO$_3$+0.1% NH$_3$·H$_2$O), Mobile Phase B: ACN; Flow rate: 25 mL/min; Gradient: 24% B to 54% B in 7 min, 54% B; Wave Length: 254 nm; RT1 (min): 5.72, 6.10) to afford (1S,3aR,6aS)—N-[(2S)-4-hydroxy-3-oxo-1-[(3S)-2-oxopyrrolidin-3-yl]butan-2-yl]-2-{6H-thieno[2,3-b]pyrrole-5-carbonyl}-hexahydro-1H-cyclopenta[c]pyrrole-1-carboxamide (6.3 mg, 3%) as a white solid. $^1$H NMR (400 MHz, DMSO-d$_6$) δ 11.81 (s, 1H), 8.46-8.65 (m, 1H), 7.63 (brs, 1H), 6.71-7.05 (m, 3H), 5.02=5.14 (m, 1H), 4.33-4.75 (m, 2H), 3.58-4.29 (m, 4H), 2.92-3.22 (m, 2H), 2.67-2.88 (m, 1H), 2.10-2.39 (m, 2H), 1.41-1.99 (m, 10H). LC-MS (ESI, m/z): 473 [M+H]$^+$.

Example 82

COMPOUND 81

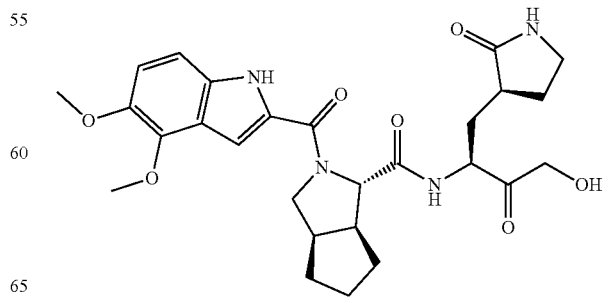

To a mixture of 4,5-dimethoxy-1H-indole-2-carboxylic acid (74.0 mg, 0.333 mmol, 1.0 eq.), (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (120 mg, 0.333 mmol, 1.0 eq.) and o-(7-azabenzotriazol-1-yl)-N,N,N',N'-tetramethyluronium hexafluorophosphate (190 mg, 0.500 mmol, 1.5 eq.) in DMF (3 mL) was added N-ethyl-N-isopropylpropan-2-amine (129 mg, 1.00 mmol, 3.0 eq.) at 0° C. The mixture was stirred for 1 h at rt, and the reaction was quenched with water (5 mL). The mixture was extracted with EtOAc (3×5 mL). The organic layers were combined, washed with brine (2×10 mL), dried over anhydrous sodium sulfate, filtered and concentrated under reduced pressure to afford the crude product. The crude product was purified by prep-HPLC (Column: XBridge Shield RP18 OBD Column, 19×250 mm, 10 μm; Mobile Phase A: Water (0.1% TFA), Mobile Phase B: ACN; Flow rate: 25 mL/min; Gradient: 20% B to 37% B in 10 min, 37% B; Wave Length: 254 nm; RT: 8.82 min) to provide (1S,3aR,6aS)-2-(4,5-dimethoxy-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (13.4 mg, 7%) as a white solid. $^1$H NMR (400 MHz, DMSO-d) δ 11.16 (s, 1H), 8.39 (s, 1H), 7.34 (s, 1H), 7.10 (d, J=8.8 Hz, 1H), 6.99 (d, J=8.4 Hz, 1H), 6.84 (s, 1H), 4.70-4.90 (m, 1H), 4.40-4.69 (m, 2H), 4.00-4.39 (m, 3H), 3.85-3.99 (m, 3H), 3.56-3.84 (m, 4H), 2.85-3.10 (m, 2H), 2.70-2.83 (m, 1H), 2.55-2.69 (m, 1H), 2.20-2.40 (m, 1H), 1.40-2.19 (m, 10H). LC-MS (ESI, m/z): 527 [M+H]$^+$.

Example 83

COMPOUND 82

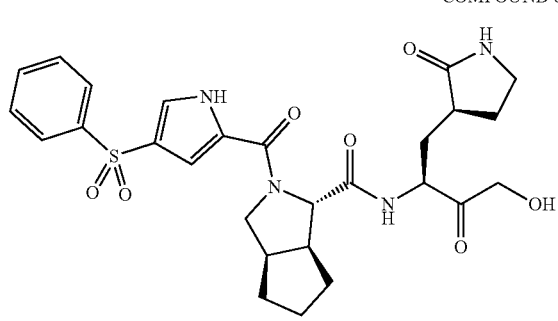

To a mixture of ethyl 4-(benzenesulfonyl)-1H-pyrrole-2-carboxylate (130 mg, 0.465 mmol, 1.0 eq., Gupton et al., Journal of Organic Chemistry (1990) 55(15):4735-4740) in THF (1 mL)/water (1 mL)/MeOH (1 mL) was added lithium hydroxide (56.0 mg, 2.33 mmol, 5.0 eq.). The mixture was stirred overnight at 80° C., and pH adjusted to 6 with hydrochloric acid (2 M). The mixture was extracted with EtOAc (3×2 mL). The organic layers were combined, washed with brine (2×2 mL), dried over anhydrous sodium sulfate, filtered and concentrated under reduced pressure to provide 4-(benzenesulfonyl)-1H-pyrrole-2-carboxylic acid (100 mg, 79%) as a yellow solid. LC-MS (ESI, m/z): 252 [M+H]$^+$.

To a mixture of (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (102 mg, 0.283 mmol, 1.0 eq.), 4-(benzenesulfonyl)-1H-pyrrole-2-carboxylic acid (71.0 mg, 0.283 mmol, 1.0 eq.) and o-(7-azabenzotriazol-1-yl)-N,N,N',N'-tetramethyluronium hexafluorophosphate (140 mg, 0.368 mmol, 1.3 eq.) in DMF (3 mL) was added N-ethyl-N-isopropylpropan-2-amine (110 mg, 0.849 mmol, 3.0 eq.) at 0° C. The mixture was stirred for 1 h at rt, and the reaction was quenched with water (5 mL). The mixture was extracted with EtOAc (3×5 mL). The organic layers were combined, washed with brine (2×5 mL), dried over anhydrous sodium sulfate, filtered and concentrated under reduced pressure to afford the crude product. The crude product was purified by prep-HPLC (Column: XBridge Shield RP18 OBD Column, 19×250 mm, 10 μm; Mobile Phase A: Water (0.1% TFA), Mobile Phase B: ACN; Flow rate: 25 mL/min; Gradient: 20% B to 40% B in 10 min, 40% B; Wave Length: 254 nm; RT: 9.22 min) to provide (1S,3aR,6aS)-2-[4-(benzenesulfonyl)-1H-pyrrole-2-carbonyl]-N-[(2S)-4-hydroxy-3-oxo-1-[(3S)-2-oxopyrrolidin-3-yl]butan-2-yl]-hexahydro-1H-cyclopenta[c]pyrrole-1-carboxamide (23.4 mg, 14%) as a white solid. LC-MS (ESI, m/z): 557 [M+H]$^+$.

Example 84

COMPOUND 83

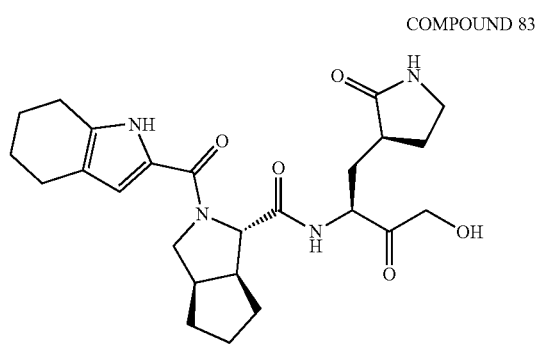 [SMILES: O=C1NCC[C@H]1C[C@H](NC(=O)[C@@H]1[C@H]2CCC[C@H]2CN1C(=O)c1cc2c([nH]1)CCCC2)C(=O)CO]

To a mixture of 4,5,6,7-tetrahydro-1H-indole-2-carboxylic acid (47.0 mg, 0.283 mmol, 1.0 eq.), (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (102 mg, 0.283 mmol, 1.0 eq.) and o-(7-azabenzotriazol-1-yl)-N,N,N',N'-tetramethyluronium hexafluorophosphate (140 mg, 0.368 mmol, 1.3 eq.) in DMF (3 mL) was added N-ethyl-N-isopropylpropan-2-amine (110 mg, 0.849 mmol, 3.0 eq.) at 0° C. The mixture was stirred for 1 h at rt, and the reaction was quenched with water (5 mL). The mixture was extracted with EtOAc (3×5 mL). The organic layers were combined, washed with brine (2×5 mL), dried over anhydrous sodium sulfate, filtered and concentrated under reduced pressure to afford the crude product. The crude product was purified by prep-HPLC (Column: XBridge Prep OBD C18 Column, 19×250 mm, 5 μm; Mobile Phase A: Water (0.1% TFA), Mobile Phase B: ACN; Flow rate: 25 mL/min; Gradient: 23% B to 43% B in 10 min, 43% B; Wave Length: 254 nm; RT: 9.5 min) to provide (1S,3aR,6aS)—N-[(2S)-4-hydroxy-3-oxo-1-[(3S)-2-oxopyrrolidin-3-yl]butan-2-yl]-2-(4,5,6,7-tetrahydro-1H-indole-2-carbonyl)-hexahydro-1H-cyclopenta[c]pyrrole-1-carboxamide (15.1 mg, 11%) as a white solid. LC-MS (ESI, m/z): 471 [M+H]$^+$.

Example 85

COMPOUND 84

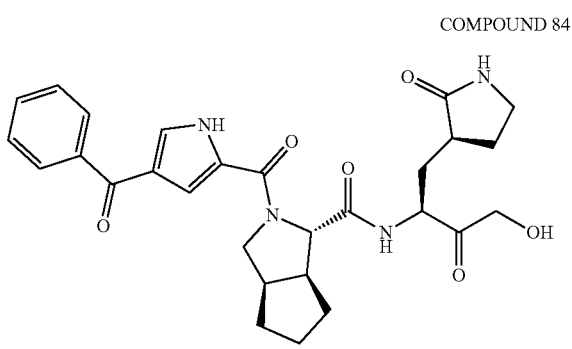 [SMILES: O=C(c1ccccc1)c1c[nH]c(C(=O)N2C[C@@H]3CCC[C@@H]3[C@H]2C(=O)N[C@@H](C[C@@H]2CCNC2=O)C(=O)CO)c1]

To a stirred mixture of 4-benzoyl-1H-pyrrole-2-carboxylic acid (65.7 mg, 0.306 mmol, 1.1 eq.) and (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (100 mg, 0.278 mmol, 1.0 eq.) in DMF (3 mL) was added o-(7-Azabenzotriazol-1-yl)-N,N,N',N'-tetramethyluronium hexafluorophosphate (126 mg, 0.334 mmol, 1.2 eq.) at 0° C. N-ethyl-N-isopropylpropan-2-amine (107 mg, 0.834 mmol, 3.0 eq.) was added at 0° C. The mixture was stirred for 1 h at rt, and the reaction was quenched with water (30 mL). The mixture was extracted with dichloromethane (3×30 mL). The organic layers were combined, washed with brine (2×30 mL), dried over anhydrous sodium sulfate, filtered and concentrated under reduced pressure to afford the crude product. The crude product was purified by Prep-HPLC with the following conditions (Column: XBridge Prep OBD C18 Column, 19*250 mm, 5 μm; Mobile Phase A: Water (0.1% TFA), Mobile Phase B: ACN; Flow rate: 25 mL/min; Gradient: 20% B to 38% B in 10 min, 38% B; Wave Length: 254 nm; RT1 (min): 8.28; Number Of Runs: 0) to afford (1S,3aR,6aS)-2-(4-benzoyl-1H-pyrrole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (37.4 mg, 25%) as a white solid. $^1$H NMR (400 MHz, 80° C., DMSO-$d_6$) δ 11.92 (s, 1H), 8.35 (s, 1H), 7.70-7.77 (m, 2H), 7.43-7.61 (m, 3H), 7.33 (s, 2H), 6.99 (s, 1H), 4.73 (brs, 1H), 4.34-4.56 (m, 2H), 4.05-4.30 (m, 2H), 3.98 (brs, 1H), 3.54-3.66 (m, 1H), 3.06-3.13 (m, 2H), 2.67-2.82 (m, 1H), 2.55-2.65 (m, 1H), 2.24-2.39 (m, 1H), 2.00-2.18 (m, 1H), 1.86-1.98 (m, 2H), 1.52-1.85 (m, 6H), 1.41-1.52 (m, 1H). LC-MS (ESI, m/z): 521 [M+H]$^+$.

Example 86

COMPOUND 85

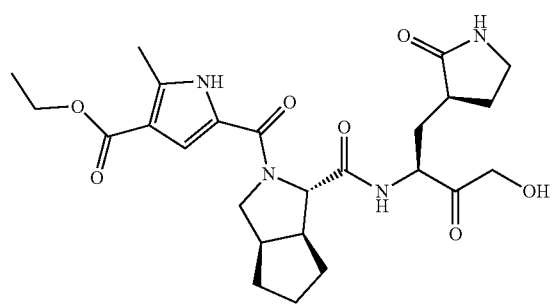

To a mixture of 4-(ethoxycarbonyl)-5-methyl-1H-pyrrole-2-carboxylic acid (56.0 mg, 0.283 mmol, 1.0 eq.), (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (102 mg, 0.283 mmol, 1.0 eq.) and o-(7-azabenzotriazol-1-yl)-N,N,N',N'-tetramethyluronium hexafluorophosphate (140 mg, 0.368 mmol, 1.3 eq.) in DMF (3 mL) was added N-ethyl-N-isopropylpropan-2-amine (110 mg, 0.849 mmol, 3.0 eq.) at 0° C. The mixture was stirred for 1 h at rt, and the reaction was quenched with water (5 mL). The mixture was extracted with EtOAc (3×5 mL). The organic layers were combined, washed with brine (2×5 mL), dried over anhydrous sodium sulfate, filtered and concentrated under reduced pressure to afford the crude product. The crude product was purified by prep-HPLC (Column: XBridge Prep OBD C18 Column, 19×250 mm, 5 μm; Mobile Phase A: Water (0.1% TFA), Mobile Phase B: ACN; Flow rate: 25 mL/min; Gradient: 20% B to 37% B in 10 min, 37% B; Wave Length: 254 nm; RT: 9.33 min) to provide ethyl 5-[(1S,3aR,6aS)-1-{[(2S)-4-hydroxy-3-oxo-1-[(3S)-2-oxopyrrolidin-3-yl]butan-2-yl]carbamoyl}-hexahydro-1H-cyclopenta[c]pyrrole-2-carbonyl]-2-methyl-1H-pyrrole-3-carboxylate (24.4 mg, 16%) as a white solid. LC-MS (ESI, m/z): 503 [M+H]$^+$.

Example 87

COMPOUND 86

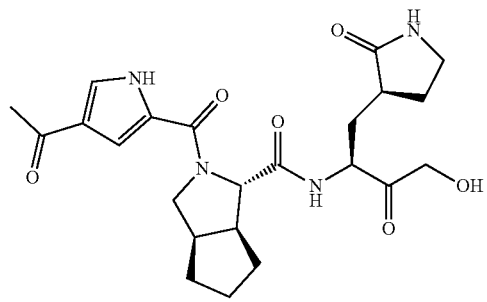

To a stirred mixture of 4-acetyl-1H-pyrrole-2-carboxylic acid (36.0 mg, 0.235 mmol, 1.0 eq.) in dichloromethane (3 mL) was added oxalyl chloride (35.8 mg, 0.282 mmol, 1.2 eq.) and N,N-dimethylformamide (1.72 mg, 0.024 mmol, 0.1 eq.) dropwise at 0° C. The mixture was stirred for 1 h at 0° C. The resulting mixture was used in the next step directly without further purification.

To a stirred mixture of (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (85.0 mg, 0.236 mmol, 1.0 eq.) in dichloromethane (8 mL) was added 4-acetyl-1H-pyrrole-2-carbonyl chloride (40.5 mg, 0.236 mmol, 1.0 eq.) dropwise at 0° C. N,N-diisopropylethylamine (122 mg, 0.944 mmol, 4.0 eq.) was then added. The mixture was stirred for 1 h at rt, and then concentrated under reduced pressure. The residue was purified by Prep-TLC (dichloromethane:methanol=12:1) to afford (1S,3aR,6aS)-2-(4-acetyl-1H-pyrrole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (110 mg, crude) as a yellow solid. The crude product was purified by Prep-HPLC with the following conditions (Column: XBridge Shield RP18 OBD Column, 19*250 mm, 10 μm; Mobile Phase A: Water (0.05% TFA), Mobile Phase B:

ACN; Flow rate: 25 mL/min; Gradient: 12% B to 31% B in 10 min, 31% B; Wave Length: 254 nm; RT1 (min): 8.05, 8.53) to afford (1S,3aR,6aS)-2-(4-acetyl-1H-pyrrole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (34.1 mg, 31%) as a white solid. $^{1}$H NMR (400 MHz, 100° C., DMSO-$d_6$) δ 11.64 (s, 1H), 8.17-8.31 (m, 1H), 7.47-7.52 (m, 1H), 7.15-7.30 (m, 1H), 6.82-6.93 (m, 1H), 4.40-4.51 (m, 2H), 4.10-4.21 (m, 2H), 3.85-3.96 (m, 2H), 3.55-3.63 (m, 1H), 3.04-3.15 (m, 2H), 2.67-2.78 (m, 1H), 2.54-2.65 (m, 1H), 2.24-2.31 (m, 4H), 2.00-2.12 (m, 1H), 1.85-1.97 (m, 2H), 1.76-1.84 (m, 1H), 1.53-1.73 (m, 5H), 1.41-1.50 (m, 1H). LCMS (ESI, m/z): 459 [M+H]$^+$.

Example 88

COMPOUND 87

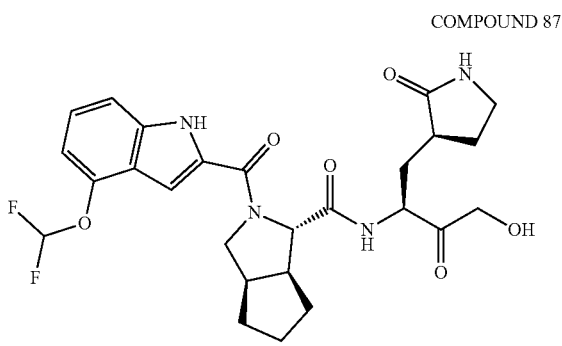 [SMILES: O=C1NCC[C@H]1C[C@H](NC(=O)[C@@H]1[C@H]2CCC[C@H]2CN1C(=O)c1cc2c(OC(F)F)cccc2[nH]1)C(=O)CO]

To a stirred mixture of 4-(difluoromethoxy)-1H-indole-2-carboxylic acid (64.2 mg, 0.283 mmol, 1.0 eq.) and (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (102 mg, 0.283 mmol, 1.0 eq.) in N,N-dimethylformamide (10 mL) was added O-(7-Aza-1H-benzotriazol-1-yl)-N,N,N',N'-tetramethyluronium hexafluorophosphate (140 mg, 0.368 mmol, 1.3 eq.) and N,N-diisopropylethylamine (146 mg, 1.13 mmol, 4.0 eq.) at 0° C. The mixture was stirred for 2 h at rt, and the reaction was quenched with water (15 mL). The mixture was extracted with EA (3×30 mL). The organic layers were combined, washed with brine (3×20 mL), dried over anhydrous sodium sulfate, filtered and concentrated under reduced pressure. The crude product (300 mg) was purified by Prep-HPLC with the following conditions (Column: XBridge Prep OBD C18 Column, 30*150 mm, 5 μm; Mobile Phase A: Water (0.05% TFA), Mobile Phase B: ACN; Flow rate: 60 mL/min; Gradient: 22% B to 52% B in 7 min, 52% B; Wave Length: 254 nm; RT1 (min): 5.9) to afford (1S,3aR,6aS)-2-[4-(difluoromethoxy)-1H-indole-2-carbonyl]-N-[(2S)-4-hydroxy-3-oxo-1-[(3S)-2-oxopyrrolidin-3-yl]butan-2-yl]-hexahydro-1H-cyclopenta[c]pyrrole-1-carboxamide (25.9 mg, 16%) as a white solid. $^{1}$H-NMR (400 MHz, 100° C., DMSO-$d_6$) δ 11.50 (s, 1H), 8.21-8.35 (m, 1H), 6.77-7.35 (m, 6H), 4.57-4.78 (m, 1H), 4.49-4.57 (m, 1H), 4.36-4.47 (m, 1H), 3.99-4.24 (m, 3H), 3.67-3.80 (m, 1H), 3.00-3.15 (m, 2H), 2.69-2.82 (m, 1H), 2.56-2.69 (m, 1H), 2.18-2.34 (m, 1H), 1.80-2.15 (m, 4H), 1.52-1.79 (m, 5H), 1.42-1.52 (m, 1H). LCMS (ESI, m/z): 533 [M+H]$^+$.

Example 89

COMPOUND 88

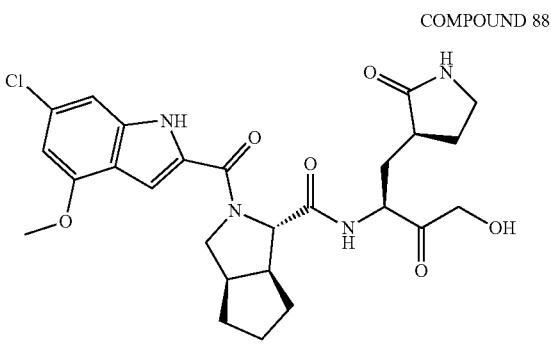 [SMILES: COc1cc(Cl)cc2[nH]c(C(=O)N3C[C@@H]4CCC[C@@H]4[C@H]3C(=O)N[C@@H](C[C@@H]3CCNC3=O)C(=O)CO)cc12]

To a stirred mixture of 6-chloro-4-methoxy-1H-indole-2-carboxylic acid (64.0 mg, 0.28 mmol, 1.0 eq.) and (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (102 mg, 0.28 mmol, 1.0 eq.) in N,N-Dimethylformamide (10 mL) was added O-(7-Aza-1H-benzotriazol-1-yl)-N,N,N',N'-tetramethyluronium hexafluorophosphate (140 mg, 0.37 mmol, 1.3 eq.) and N,N-diisopropylethylamine (147 mg, 1.14 mmol, 4.0 eq.) at 0° C. The mixture was stirred for 2 h at rt, and the reaction was quenched with water (15 mL). The mixture was extracted with EA (3×30 mL). The organic layers were combined, washed with brine (3×20 mL), dried over anhydrous sodium sulfate, filtered and concentrated under reduced pressure. The crude product (300 mg) was purified by Prep-HPLC with the following conditions (Column: XBridge Prep OBD C18 Column, 30*150 mm, 5 μm; Mobile Phase A: Water (0.05% TFA), Mobile Phase B: ACN; Flow rate: 60 mL/min; Gradient: 22% B to 52% B in 7 min, 52% B; Wave Length: 254 nm; RT1 (min): 5.93) to afford (1S,3aR,6aS)-2-(6-chloro-4-methoxy-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (50.5 mg, 32%) as a white solid. $^{1}$H-NMR (400 MHz, 100° C., DMSO-$d_6$) δ 11.31 (s, 1H), 8.22-8.40 (m, 1H), 7.23 (s, 1H), 7.05-7.07 (m, 1H), 6.87 (s, 1H), 6.52 (s, 1H), 4.47-4.70 (m, 2H), 4.40-4.46 (m, 1H), 4.09-4.22 (m, 2H), 3.92-4.06 (m, 1H), 3.87 (s, 3H), 3.64-3.68 (m, 1H), 2.99-3.16 (m, 2H), 2.67-2.78 (m, 1H), 2.58-2.66 (m, 1H), 2.24-2.39 (m, 1H), 1.84-2.07 (m, 3H), 1.75-1.84 (m, 1H), 1.52-1.74 (m, 5H), 1.43-1.51 (m, 1H). LC-MS (ESI, m/z): 531 [M+H]$^+$.

Example 90

COMPOUND 89

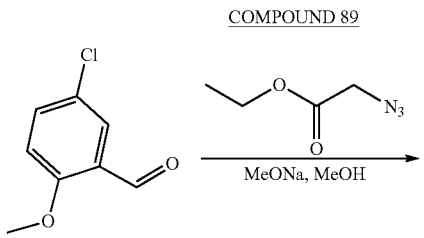

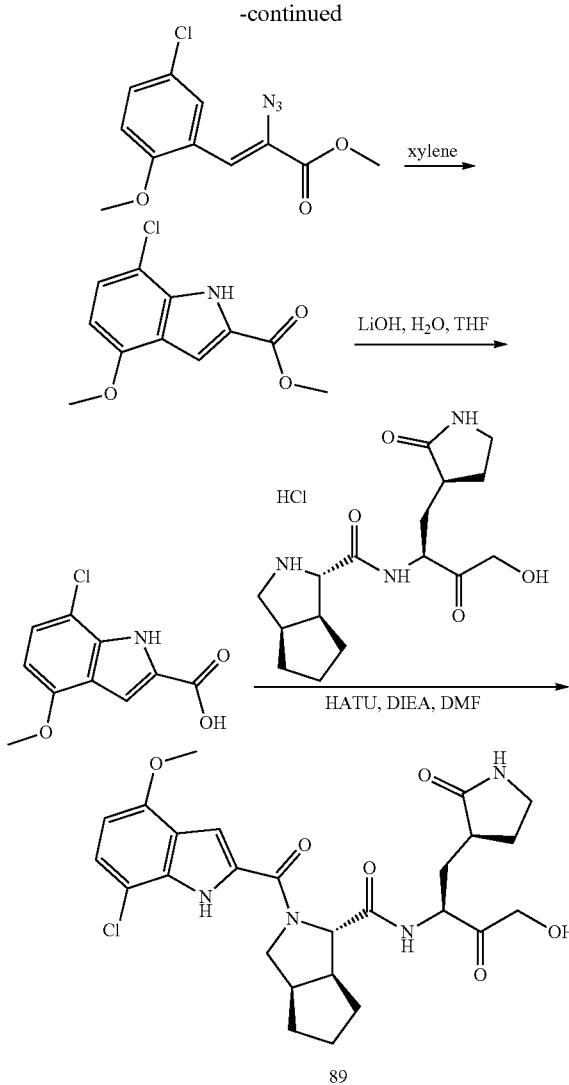

89

To a solution of sodium methoxide (8.45 g, 46.9 mmol, 4.0 eq., 30% in MeOH) was added a mixture of 5-chloro-2-methoxybenzaldehyde (2.00 g, 11.7 mmol, 1.0 eq., in 20 mL MeOH) and ethyl 2-azidoacetate (6.06 g, 46.9 mmol, 4.0 eq.) stirred at −10° C. The mixture was stirred for 6 h at rt, and the reaction was quenched with water/ice (10 mL). The mixture was extracted with EtOAc (3×20 mL). The organic layers were combined, dried over anhydrous sodium sulfate, filtered and concentrated under reduced pressure to afford the crude product. The crude product was purified by silica gel column chromatography, eluted with EtOAc:PE=4:96 to afford methyl 2-azido-3-(5-chloro-2-methoxyphenyl)acrylate (532 mg, 17.0%).

A solution of methyl 2-azido-3-(5-chloro-2-methoxyphenyl)prop-2-enoate (384 mg, 1.44 mmol, 1.0 eq.) in xylene (3 mL) was stirred for overnight at 120° C. The mixture was concentrated under reduced pressure to afford the crude product. The crude product was purified by silica gel column chromatography, eluted with EtOAc:PE=4:96 to afford methyl 7-chloro-4-methoxy-1H-indole-2-carboxylate (204 mg, 59.3%). $^1$H NMR (300 MHz, DMSO-d6) δ 12.17 (s, 1H), 7.23-7.31 (m, 1H), 7.17-7.22 (m, 1H), 6.54-6.63 (m, 1H), 3.85-3.93 (m, 6H). LC-MS (ESI, m/z): 240 [M+H]$^+$.

To a solution of methyl 7-chloro-4-methoxy-1H-indole-2-carboxylate (200 mg, 0.835 mmol, 1.0 eq.) in THF (2 mL) was added lithium hydroxide (100 mg, 4.18 mmol, 5.0 eq., in 2 mL water) at rt. The mixture was stirred for 4 h at rt and acidified to pH=5 with hydrochloric acid (1M). The mixture was extracted with EA (3×5 mL). The organic layers were combined, dried over anhydrous sodium sulfate, filtered and concentrated under reduced pressure to afford 7-chloro-4-methoxy-1H-indole-2-carboxylic acid (180 mg, crude). LC-MS (ESI, m/z): 226 [M+H]$^+$.

To a solution of 7-chloro-4-methoxy-1H-indole-2-carboxylic acid (53.4 mg, 0.236 mmol, 1.0 eq.) in DMF (2 mL) was added (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide (85.0 mg, 0.236 mmol, 1.0 eq.), o-(7-azabenzotriazol-1-yl)-N,N,N',N'-tetramethyluronium hexafluorophosphate (108 mg, 0.283 mmol, 1.2 eq.) and N-ethyl-N-isopropylpropan-2-amine (152 mg, 1.18 mmol, 5.0 eq.) at 0° C. The mixture was stirred for 1 h at rt, and the reaction was quenched with water (1 mL). The mixture was extracted with EA (3×2 mL). The organic layers were combined, washed with brine (2×5 mL), dried over anhydrous sodium sulfate, filtered and concentrated under reduced pressure to afford the crude product. The crude product was purified by prep-HPLC (Column: XSelect CSH Prep C18 OBD Column, 19*250 mm, 5 μm; Mobile Phase A: Water (0.05% TFA), Mobile Phase B: ACN; Flow rate: 25 mL/min; Gradient: 32% B to 62% B in 7 min, 62% B; Wave Length: 254 nm; RT1 (min): 5.12) to provide (1S,3aR,6aS)-2-(7-chloro-4-methoxy-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (15.2 mg, 10.5%) as a white solid. LC-MS (ESI, m/z): 531 [M+H]$^+$.

Example 91

COMPOUND 90

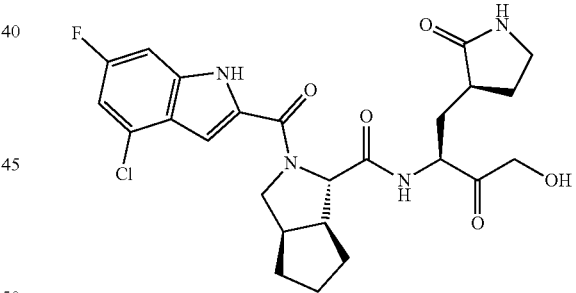

To a mixture of (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (102 mg, 0.283 mmol, 1.0 eq.), 4-chloro-6-fluoro-1H-indole-2-carboxylic acid (61.0 mg, 0.283 mmol, 1.0 eq.) and o-(7-azabenzotriazol-1-yl)-N,N,N',N'-tetramethyluronium hexafluorophosphate (140 mg, 0.368 mmol, 1.3 eq.) in DMF (3 mL) was added N-ethyl-N-isopropylpropan-2-amine (110 mg, 0.849 mmol, 3.0 eq.) at 0° C. The mixture was stirred for 1 h at rt, and the reaction was quenched with water (5 mL). The mixture was extracted with EtOAc (3×5 mL). The organic layers were combined, washed with brine (2×5 mL), dried over anhydrous sodium sulfate, filtered and concentrated under reduced pressure to afford the crude product. The crude product was purified by prep-HPLC (Column: XBridge Shield RP18 OBD Column, 30×150 mm, 5 μm;

Mobile Phase A: Water (0.1% TFA), Mobile Phase B: ACN; Flow rate: 60 mL/min; Gradient: 28% B to 37% B in 10 min, 37% B; Wave Length: 254 nm; RT: 9.15 min); to provide (1S,3aR,6aS)-2-(4-chloro-6-fluoro-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (23.4 mg, 15%) as a white solid. $^1$H-NMR (400 MHz, 100° C., DMSO-$d_6$) δ 11.65 (br.s, 1H), 8.35 (br.s, 1H), 7.25 (br.s, 1H), 7.11-7.20 (m, 1H), 6.97-7.09 (m, 1H), 6.65-6.96 (m, 1H), 4.50-5.10 (m, 2H), 4.35-4.49 (m, 1H), 4.10-4.25 (m, 2H), 3.90-4.09 (m, 1H), 3.60-3.80 (m, 1H), 3.05-3.30 (m, 2H), 2.70-2.85 (m, 1H), 2.59-2.69 (m, 1H), 2.20-2.35 (m, 1H), 1.40-2.19 (m, 10H). LC-MS (ESI, m/z): 519 [M+H]$^+$.

Example 92

COMPOUND 91

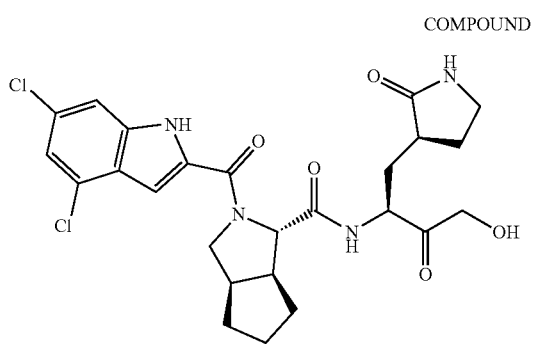

To a stirred mixture of 4,6-dichloro-1H-indole-2-carboxylic acid (65.0 mg, 0.283 mmol, 1.0 eq.) and (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (102 mg, 0.283 mmol, 1.0 eq.) in N,N-dimethylformamide (8 mL) was added O-(7-Aza-1H-benzotriazol-1-yl)-N,N,N',N'-tetramethyluronium hexafluorophosphate (140 mg, 0.368 mmol, 1.3 eq.) and N,N-diisopropylethylamine (146 mg, 1.13 mmol, 4.0 eq.) at 0° C. The mixture was stirred for 1.5 h at rt, and the reaction was quenched with water (16 mL). The mixture was extracted with EA (3×40 mL). The organic layers were combined, washed with brine (2×30 mL), dried over anhydrous sodium sulfate, filtered and concentrated under reduced pressure. The crude product (300 mg) was purified by Prep-HPLC with the following conditions (Column: XBridge Shield RP18 OBD Column, 30*150 mm, 5 μm; Mobile Phase A: Water (0.1% TFA), Mobile Phase B: ACN; Flow rate: 60 mL/min; Gradient: 30% B to 42% B in 10 min, 42% B; Wave Length: 254 nm; RT1 (min): 9.22) to afford (1S,3aR, 6aS)-2-(4,6-dichloro-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (24.9 mg, 16%) as a white solid. $^1$H-NMR (400 MHz, 80° C., DMSO-$d_6$) δ 11.82 (br. s, 1H), 8.42 (br, s, 1H), 7.45 (s, 1H), 7.35 (s, 1H), 7.13-7.15 (m, 1H), 6.91 (br. s, 1H), 4.70-4.85 (m, 1H), 4.31-4.62 (m, 2H), 3.82-4.26 (m, 3H), 3.61-3.79 (m, 1H), 3.01-3.18 (m, 2H), 2.54-2.81 (m, 2H), 1.43-2.35 (m, 11H). LC-MS (ESI, m/z): 535 [M+H]$^+$.

Example 93

COMPOUND 92

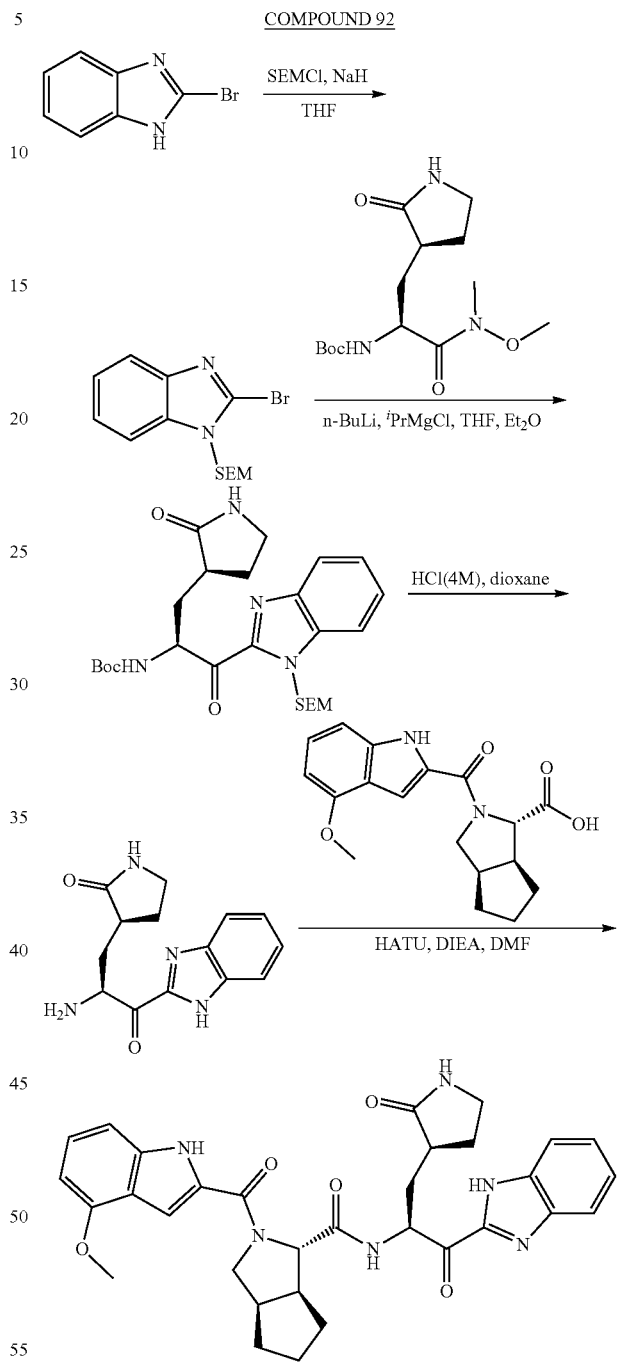

To a solution of 2-bromo-1H-1,3-benzodiazole (1.65 g, 8.35 mmol, 1.00 eq.) in THF (25 mL) was added NaH (0.20 g, 8.35 mmol, 1.0 eq., 60% in mineral oil) at 0° C. and stirred for 15 min. [2-(chloromethoxy)ethyl]trimethylsilane (1.39 g, 8.35 mmol, 1.0 eq.) was then added. The mixture was stirred for 1 h at rt, and the reaction was quenched with water (5 mL). The mixture was extracted with EA (3×5 mL). The organic layers were combined, washed with brine (2×5 mL), dried over anhydrous sodium sulfate, filtered and concentrated under reduced pressure to afford the crude product.

The crude product was purified by silica gel column chromatography, eluted with DCM:MeOH=9:1 to afford 2-bromo-1-{[2-(trimethylsilyl)ethoxy]methyl}-1,3-benzodiazole (1.6 g, 60%) as a white solid. LC-MS (ESI, m/z): 327 [M+H]$^+$.

To a solution of 2-bromo-1-{[2-(trimethylsilyl)ethoxy]methyl}-1,3-benzodiazole (1.08 g, 3.29 mmol, 5.00 eq.) in THF (10 mL) was added butyllithium (1.32 mL, 3.29 mmol, 5.0 eq., 2.5M in THF) at −78° C., and then the mixture was stirred for 30 min at −78° C. under nitrogen. A solution of tert-butyl N-[(1S)-1-[methoxy(methyl)carbamoyl]-2-[(3S)-2-oxopyrrolidin-3-yl]ethyl]carbamate (208 mg, 0.659 mmol, 1.00 eq.) in THF (2 mL) was added isopropylmagnesium chloride (0.66 mL, 1.318 mmol, 2.0 eq., 2 M in THF) at −15° C. under nitrogen, and the mixture was stirred for 5 min at 0° C. The mixture was added to the above solution, and the resulting mixture was stirred for 3 h at −78° C. under nitrogen. The reaction was quenched with a sat. ammonium chloride solution (5 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by silica gel column chromatography, eluted with PE:EtOAc=2:3 to afford tert-butyl N-[(2S)-1-oxo-3-[(3S)-2-oxopyrrolidin-3-yl]-1-(1-{[2-(trimethylsilyl)ethoxy]methyl}-1,3-benzodiazol-2-yl)propan-2-yl]carbamate (276 mg, 83%).

The mixture of tert-butyl N-[(2S)-1-oxo-3-[(3S)-2-oxopyrrolidin-3-yl]-1-(1-{[2-(trimethylsilyl)ethoxy]methyl}-1,3-benzodiazol-2-yl)propan-2-yl]carbamate (100 mg) and hydrogen chloride (2 mL, 4M in 1,4-dioxane) was stirred for 2 h at rt, and then concentrated under reduced pressure to afford (3S)-3-[(2S)-2-amino-3-(1H-1,3-benzodiazol-2-yl)-3-oxopropyl]pyrrolidin-2-one (60 mg, crude). LC-MS (ESI, m/z): 273 [M+H]$^+$.

To a solution of (3S)-3-[(2S)-2-amino-3-(1H-1,3-benzodiazol-2-yl)-3-oxopropyl]pyrrolidin-2-one (54.0 mg, 0.198 mmol, 1.00 eq.) in DMF (2 mL) was added (1S,3aR,6aS)-2-(4-methoxy-1H-indole-2-carbonyl)-hexahydro-1H-cyclopenta[c]pyrrole-1-carboxylic acid (65.0 mg, 0.198 mmol, 1.0 eq.), o-(7-azabenzotriazol-1-yl)-N,N,N',N'-tetramethyluronium hexafluorophosphate (106 mg, 0.277 mmol, 1.4 eq.) and N-ethyl-N-isopropylpropan-2-amine (128 mg, 0.990 mmol, 5.0 eq.) at 0° C. The mixture was stirred for 1 h at rt, and the reaction was quenched with water (10 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by prep-HPLC (Column: XBridge Prep Phenyl OBD Column, 19*250 mm, 5 μm; Mobile Phase A: Water (10 mmol/L NH$_4$HCO$_3$+0.1% NH$_3$H$_2$O), Mobile Phase B: MeOH-HPLC; Flow rate: 25 mL/min; Gradient: 65% B to 74% B in 10 min, 74% B; Wave Length: 254 nm; RT1 (min): 7.98) to provide (1S,3aR,6aS)—N-[(2S)-1-(1H-1,3-benzodiazol-2-yl)-1-oxo-3-[(3S)-2-oxopyrrolidin-3-yl]propan-2-yl]-2-(4-methoxy-1H-indole-2-carbonyl)-hexahydro-1H-cyclopenta[c]pyrrole-1-carboxamide (5.0 mg, 4.%) as a white solid. LC-MS (ESI, m/z): 583 [M+H]$^+$.

Example 94

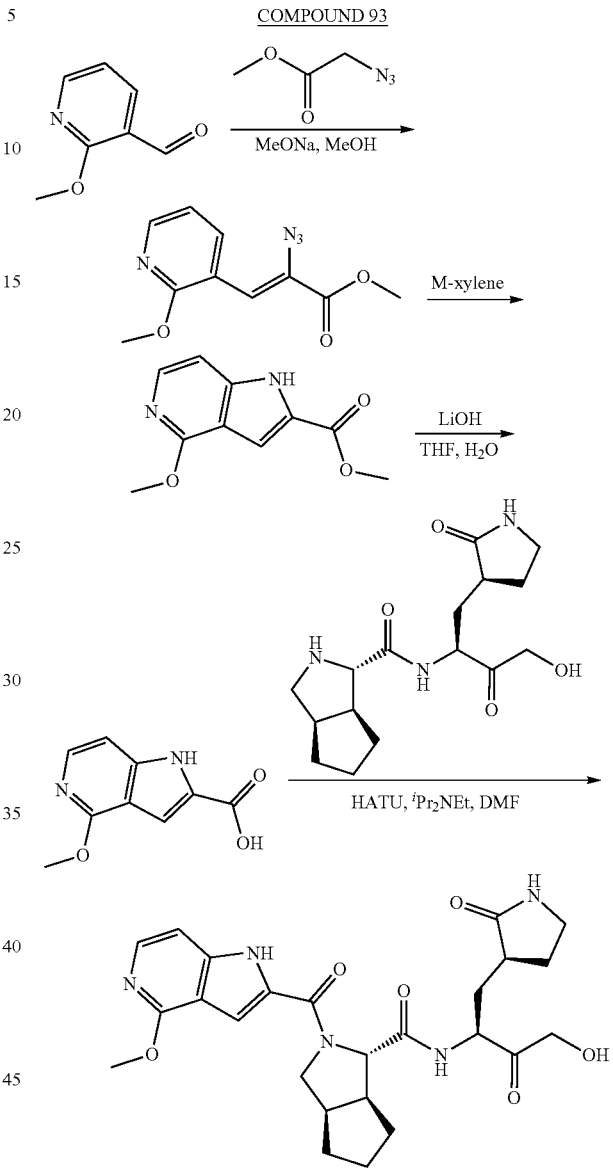

A solution of sodium methanolate (5.25 g, 30% wt, 29.1 mmol, 4.0 eq.) in MeOH (10 mL) was cooled to −10° C. The mixture of 2-methoxypyridine-3-carbaldehyde (1.00 g, 7.29 mmol, 1.0 eq.) and methyl 2-azidoacetate (3.36 g, 29.1 mmol, 4.0 eq.) in MeOH (10 mL) was added dropwise to the solution over 1.5 h. The mixture was stirred for 1.5 h at −10° C., then poured into ice-water (100 mL) and extracted with ethyl ether (3×100 mL). The organic layers were combined, washed with brine (2×30 mL), dried over anhydrous sodium sulfate, filtered and concentrated under reduced pressure to afford the crude product. The crude product was diluted with EA (20 mL), made into a slurry with 100~200 silica gel mesh (4 g) and loaded to a column after removing the dichloromethane. The sample was purified by column chromatography (Column size 5×24 cm, column volume: 300 mL, silica gel size (100~200 mesh) quantity: 120 g) and eluted with EA:PE (0%~30% over 30 min). The collected fractions: 11%-12% EA:PE fractions were chosen as pure fractions. Those fractions were combined and concentrated under reduced pressure to provide methyl (2Z)-2-azido-3-(2-methoxypyridin-3-yl)prop-2-enoate (400 mg, 23%) as a light yellow solid. LC-MS (ESI, m/z): 235 [M+H]+.

A solution of methyl (2Z)-2-azido-3-(2-methoxypyridin-3-yl)prop-2-enoate (400 mg, 1.70 mmol, 1.0 eq.) in M-xylene (20 mL) was stirred for 1 h at 120° C. under nitrogen and then concentrated under reduced pressure. The crude product was diluted with EA (20 mL), made into a slurry with 100~200 silica gel mesh (2 g) and loaded to a column after removing the dichloromethane. The sample was purified by column chromatography (Column size 5×24 cm, column volume: 300 mL, silica gel size (100~200 mesh) quantity: 120 g) and eluted with EA:PE (0%~30% over 30 min). The collected fractions: 20%-21% EA:PE fractions were chosen as pure fractions. Those fractions were combined and concentrated under reduced pressure to provide methyl 4-methoxy-1H-pyrrolo[3,2-c]pyridine-2-carboxylate (180 mg, 48%) as a white solid. $^1$H NMR (400 MHz, DMSO-d$_6$) δ 12.37 (s, 1H), 7.84 (d, J=4.0 Hz, 1H), 7.11-7.15 (m, 1H), 7.00-7.04 (m, 1H), 3.98 (s, 3H), 3.88 (s, 3H). LC-MS (ESI, m/z): 207 [M+H]+.

To a stirred mixture of methyl 4-methoxy-1H-pyrrolo[3,2-c]pyridine-2-carboxylate (170 mg, 0.821 mmol, 1.0 eq.) in THF (2 mL) and H$_2$O (0.5 mL) was added lithium hydroxide (99.0 mg, 4.11 mmol, 5.0 eq.). The mixture was stirred for 2 h at 60° C. The mixture was acidified to pH 3 with acetic acid. The residue was purified by filter with ethyl ether (30 mL) to afford 4-methoxy-1H-pyrrolo[3,2-c]pyridine-2-carboxylic acid (120 mg, crude) as a white solid. $^1$H NMR (400 MHz, DMSO-d$_6$) δ 12.13 (s, 1H), 7.80 (d, J=4.0 Hz, 1H), 6.98-7.06 (m, 2H), 3.98 (s, 3H). LC-MS (ESI, m/z): 193 [M+H]+.

To a stirred mixture of 4-methoxy-1H-pyrrolo[3,2-c]pyridine-2-carboxylic acid (70.6 mg, 0.367 mmol, 1.1 eq.) and N-ethyl-N-isopropylpropan-2-amine (129 mg, 1.00 mmol, 3.0 eq.) in DMF (4 mL) was added o-(7-Azabenzotriazol-1-yl)-N,N,N',N'-tetramethyluronium hexafluorophosphate (152 mg, 0.401 mmol, 1.2 eq.) at 0° C. (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide (108 mg, 0.334 mmol, 1.0 eq.) was added at 0° C., and the mixture stirred for 1 h at rt. The residue was purified by reverse flash chromatography with the following conditions: column, C18 silica gel; Mobile Phase A: Water (0.05% TFA), Mobile Phase B: ACN; Flow rate: 40 mL/min; Gradient: 0% B to 20% B in 30 min, 10% B; Wave Length: 220 nm to afford the crude product as a yellow solid. The crude product (70 mg) was purified by Prep-HPLC with the following conditions (Column: XBridge Prep Phenyl OBD Column, 19*250 mm, 5 μm; Mobile Phase A: Water (0.05% TFA), Mobile Phase B: ACN; Flow rate: 25 mL/min; Gradient: 15% B to 30% B in 10 min, 30% B; Wave Length: 254 nm; RT1 (min): 6.7) to afford (1S,3aR,6aS)—N-[(2S)-4-hydroxy-3-oxo-1-[(3S)-2-oxopyrrolidin-3-yl]butan-2-yl]-2-{4-methoxy-1H-pyrrolo[3,2-c]pyridine-2-carbonyl}-hexahydro-1H-cyclopenta[c]pyrrole-1-carboxamide (6.0 mg, 3%) as a white solid. LC-MS (ESI, m/z): 498 [M+H]+.

Example 95

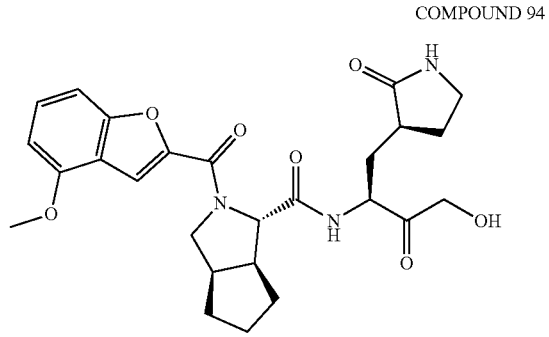

COMPOUND 94

To a mixture of 4-methoxy-1-benzofuran-2-carboxylic acid (70.0 mg, 0.361 mmol, 1.0 eq.), o-(7-azabenzotriazol-1-yl)-N,N,N',N'-tetramethyluronium hexafluorophosphate (165 mg, 0.433 mmol, 1.2 eq.) and N-ethyl-N-isopropylpropan-2-amine (140 mg, 1.08 mmol, 3.0 eq.) in DMF (3 mL) was added (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (130 mg, 0.361 mmol, 1.0 eq.) at 0° C. The mixture was stirred for 1 h at rt, and the reaction was quenched with water (10 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by TLC (Mobile phase: MeOH:DCM=1:12; Rf=0.4; detection: UV) to afford the crude product. The crude product was purified by prep-HPLC (Column: Kinetex EVO prep C18, 30×150, 5 μm; Mobile Phase A: Water (0.1% TFA), Mobile Phase B: ACN; Flow rate: 60 mL/min; Gradient: 18% B to 43% B in 7 min, 43% B; Wave Length: 254 nm; RT: 5.18 min) to provide (1S,3aR,6aS)—N-[(2S)-4-hydroxy-3-oxo-1-[(3S)-2-oxopyrrolidin-3-yl]butan-2-yl]-2-(4-methoxy-1-benzofuran-2-carbonyl)-hexahydro-1H-cyclopenta[c]pyrrole-1-carboxamide (31.3 mg, 17%) as a white solid. $^1$H NMR (400 MHz, DMSO-d$_6$) δ 8.20-8.50 (m, 1H), 7.35-7.50 (m, 2H), 7.31 (s, 1H), 7.18-7.23 (m, 1H), 6.84 (d, J=8.0 Hz, 1H), 4.31-4.89 (m, 3H), 4.10-4.30 (m, 2H), 3.84-4.09 (m, 4H), 3.50-3.83 (m, 1H), 2.95-3.25 (m, 2H), 2.55-2.82 (m, 2H), 2.05-2.40 (m, 1H), 1.45-2.02 (m, 10H). LC-MS (ESI, m/z): 498 [M+H]+.

Example 96

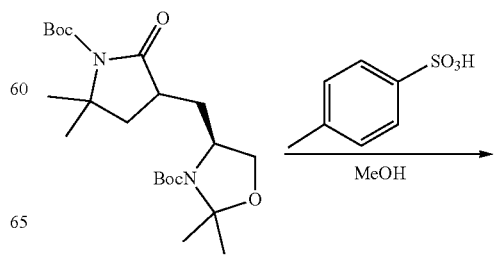

COMPOUND 95

311
-continued

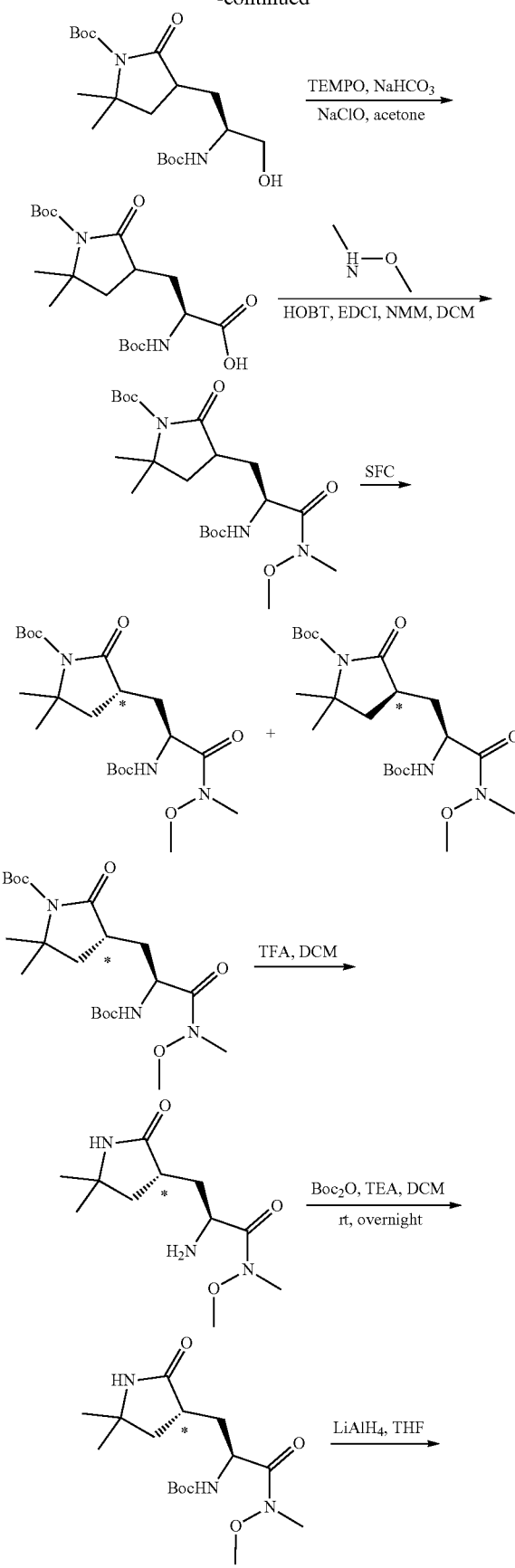

312
-continued

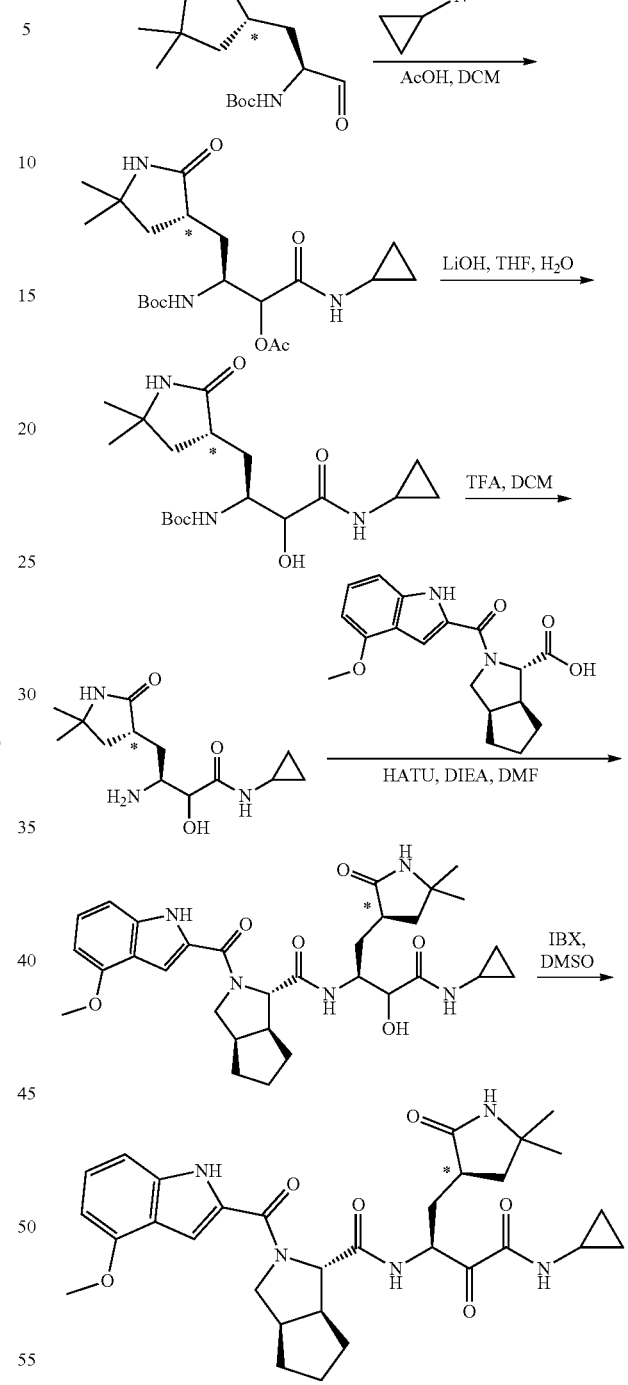

The absolute configuration of the chiral centers noted with "*" is tentatively assigned A 40 mL vial was charged with tert-butyl (4S)-4-((1-(tert-butoxycarbonyl)-5,5-dimethyl-2-oxopyrrolidin-3-yl)methyl)-2,2-dimethyloxazolidine-3-carboxylate (4 g, 9.38 mmol, 1.0 eq.), 4-methylbenzenesulfonic acid (0.16 g, 0.94 mmol, 0.1 eq.) and MeOH (40 mL). The mixture was stirred overnight at rt, and the reaction was quenched with water (30 mL). The solution was extracted with EA (3×50 mL). The organic layers were combined, washed with brine (2×20 mL), dried over anhydrous sodium sulfate, filtered and concentrated under reduced pressure to provide tert-butyl 4-((S)-2-((tert-butoxycarbonyl)amino)-3-hydroxypropyl)-2,2-dimethyl-5-oxopyrrolidine-1-carboxylate (3.3 g, crude) as an off-white semi-solid. LC-MS (ESI, m/z): 387 [M+H]$^+$.

To a solution of tert-butyl 4-((S)-2-((tert-butoxycarbonyl)amino)-3-hydroxypropyl)-2,2-dimethyl-5-oxopyrrolidine-1-carboxylate (3.3 g, 8.54 mmol, 1.0 eq.) in acetone (33 mL) was added 5% sodium bicarbonate solution (43 mL, 25.6 mmol, 3.0 eq.) and 2,2,6,6-Tetramethylpiperidinooxy (0.27 g, 1.71 mmol, 0.2 eq.). Chlorosylsodium (2.22 g, 29.9 mmol, 3.5 eq.) was added at 0° C. dropwise. The mixture was stirred at rt overnight, and the reaction was quenched with water (30 mL). The solution was washed with Et$_2$O (2×50 mL). The pH value of the aqueous solution was adjusted to 2 with hydrochloric acid (1 mol/L). The solution was extracted with EtOAc (3×50 mL). The organic layers were combined, washed with brine (50 mL), dried over anhydrous sodium sulfate, filtered and concentrated under reduced pressure to provide (2S)-3-(1-(tert-butoxycarbonyl)-5,5-dimethyl-2-oxopyrrolidin-3-yl)-2-((tert-butoxycarbonyl)amino)propanoic acid (3.1 g, 73%) as a white solid. LC-MS (ESI, m/z): 401 [M+H]$^+$.

To a solution of (2S)-3-(1-(tert-butoxycarbonyl)-5,5-dimethyl-2-oxopyrrolidin-3-yl)-2-((tert-butoxycarbonyl)amino)propanoic acid (3.1 g, 7.74 mmol, 1.0 eq.) in DCM (50 mL) was added N,O-dimethylhydroxylamine (0.47 g, 7.74 mmol, 1.0 eq.), 1-Hydroxybenzotrizole (1.05 g, 7.74 mmol, 1.0 eq.), NMM (2.35 g, 23.2 mmol, 3.0 eq.) and N-(3-dimethylaminopropyl)-N'-ethylcarbodiimide hydrochloride (1.63 g, 8.52 mmol, 1.1 eq.). The mixture was stirred at rt for 1 h, and the reaction was quenched with water (30 mL). The mixture was extracted with DCM (3×50 mL). The organic layers were combined, dried over anhydrous sodium sulfate, filtered and concentrated under reduced pressure. The residue was chromatographed on a silica gel column with MeOH:DCM (1:25) to provide tert-butyl 4-((S)-2-((tert-butoxycarbonyl)amino)-3-(methoxy(methyl)amino)-3-oxopropyl)-2,2-dimethyl-5-oxopyrrolidine-1-carboxylate (1.9 g, 50%) as a white solid. LCMS (ESI, m/z): 444 [M+H]$^+$.

Tert-butyl 4-((S)-2-((tert-butoxycarbonyl)amino)-3-(methoxy(methyl)amino)-3-oxopropyl)-2,2-dimethyl-5-oxopyrrolidine-1-carboxylate (1.9 g) was purified by prep-SFC using the following gradient conditions: Column: Column: Lux 5 um i-Cellulose-5, 3*25 cm, 5 μm; Mobile Phase A: CO$_2$, Mobile Phase B: MeOH (0.1% 2M NH$_3$-MeOH); Flow rate: 80 mL/min; Gradient: isocratic 30% B; Column Temperature (° C.): 35; Back Pressure (bar): 100; Wave Length: 220 nm; RT1 (min): 3.82; RT2 (min): 5.33; Sample Solvent: MeOH-Preparative; Injection Volume: 0.7 mL; Number Of Runs: 23. Purification resulted in tert-butyl (S*)-4-((S)-2-((tert-butoxycarbonyl)amino)-3-(methoxy(methyl)amino)-3-oxopropyl)-2,2-dimethyl-5-oxopyrrolidine-1-carboxylate (550 mg) as an off-white solid. $^1$H NMR (300 MHz, DMSO-d$_6$) δ 7.03-7.06 (m, 1H), 4.64-4.67 (m, 1H), 3.74 (s, 3H), 3.12 (s, 3H), 2.51-2.66 (m, 1H), 1.98-2.06 (m, 2H), 1.51-1.67 (m, 2H), 1.42-1.46 (m, 12H), 1.35-1.38 (m, 12H). LC-MS (ESI, m/z): 444 [M+H]$^+$. SFC (MeOH (1% 2M NH$_3$-MeOH), CHIRALPAK IF-3 3.0*50 mm, 3 μm, Rt: 0.594 min. and tert-butyl (R*)-4-((S)-2-((tert-butoxycarbonyl)amino)-3-(methoxy(methyl)amino)-3-oxopropyl)-2,2-dimethyl-5-oxopyrrolidine-1-carboxylate (850 mg) as an off-white solid. $^1$H NMR (300 MHz, DMSO-d$_6$) δ 7.14-7.17 (m, 1H), 4.30-4.45 (m, 1H), 3.72 (s, 3H), 3.11 (s, 3H), 2.51-2.62 (m, 1H), 1.97-2.12 (m, 2H), 1.35-1.53 (m, 26H). LC-MS (ESI, m/z): 444 [M+H]$^+$. SFC (MeOH (1% 2M NH$_3$-MeOH), CHIRALPAK IF-3 3.0*50 mm, 3 μm, Rt: 0.728 min.

To a solution of tert-butyl (R*)-4-((S)-2-((tert-butoxycarbonyl)amino)-3-(methoxy(methyl)amino)-3-oxopropyl)-2,2-dimethyl-5-oxopyrrolidine-1-carboxylate (850 mg, 1.92 mmol, 1.0 eq.) in DCM (12 mL) was added TFA (4 mL). The mixture was stirred at rt for 2 h and then concentrated under reduced pressure to provide (2S)-2-amino-3-[(3R*)-5,5-dimethyl-2-oxopyrrolidin-3-yl]-N-methoxy-N-methylpropanamide (500 mg, 75%) of as an off-white oil. LC-MS (ESI, m/z): 244 [M+H]$^+$.

To a solution of (2S)-2-amino-3-[(3R*)-5,5-dimethyl-2-oxopyrrolidin-3-yl]-N-methoxy-N-methylpropanamide (500 mg, 2.06 mmol, 1.0 eq.) in DCM (8 mL) was added triethylamine (1.04 g, 10.3 mmol, 5.0 eq.) and di-tert-butyl dicarbonate (1.35 g, 6.17 mmol, 3.0 eq.). The mixture was stirred at rt overnight, and the reaction was quenched with water (5 mL). The mixture was extracted with DCM (3×15 mL). The organic layers were combined, dried over anhydrous sodium sulfate, filtered and concentrated under reduced pressure. The residue was chromatographed on a silica gel column with MeOH:DCM (1:25) to provide tert-butyl N-[(1S)-2-[(3R*)-5,5-dimethyl-2-oxopyrrolidin-3-yl]-1-[methoxy(methyl)carbamoyl]ethyl]carbamate (650 mg, 68%) as a white solid. LCMS (ESI, m/z): 344 [M+H]$^+$.

To a solution of tert-butyl N-[(1S)-2-[(3R*)-5,5-dimethyl-2-oxopyrrolidin-3-yl]-1-[methoxy(methyl)carbamoyl]ethyl]carbamate (400 mg, 1.165 mmol, 1.00 eq.) in THF (6 mL) was added lithium aluminum hydride (79.8 mg, 2.1 mmol, 1.8 eq.). The mixture was stirred at −10° C. for 1 h, and the reaction was quenched with hydrochloric acid (1M). The mixture was extracted with EA (3×15 mL). The organic layers were combined, dried over anhydrous sodium sulfate, filtered and concentrated under reduced pressure to provide tert-butyl N-[(2S)-1-[(3R*)-5,5-dimethyl-2-oxopyrrolidin-3-yl]-3-oxopropan-2-yl]carbamate (300 mg, 54%) as a white solid. LCMS (ESI, m/z): 285 [M+H]$^+$.

To a solution of tert-butyl N-[(2S)-1-[(3R*)-5,5-dimethyl-2-oxopyrrolidin-3-yl]-3-oxopropan-2-yl]carbamate (300 mg, 1.06 mmol, 1.0 eq.) in DCM (5 mL) was added isocyanocyclopropane (142 mg, 2.11 mmol, 2.0 eq.) and AcOH (190 mg, 3.17 mmol, 3.0 eq.) at 0° C. The mixture was stirred overnight at rt. The mixture was concentrated under reduced pressure to provide (2S)-2-[(tert-butoxycarbonyl)amino]-1-(cyclopropylcarbamoyl)-3-[(3R*)-5,5-dimethyl-2-oxopyrrolidin-3-yl]propyl acetate (400 mg, crude) as an yellow oil. L CMS (ESI, m/z): 412 [M+H]$^+$.

To a solution of (2S)-2-[(tert-butoxycarbonyl)amino]-1-(cyclopropylcarbamoyl)-3-[(3R*)-5,5-dimethyl-2-oxopyrrolidin-3-yl]propyl acetate (400 mg, 0.97 mmol, 1.0 eq.) in THF (4 mL) was added LiOH (70 mg, 2.92 mmol, 3.0 eq.) in H$_2$O (4 mL) at 0° C. The mixture was stirred at rt for 1 h, and the reaction was quenched with hydrochloric acid (2 mL, 2 mol/L). The solution was extracted with EA (3×10 mL). The organic layers were combined, dried over anhydrous sodium sulfate, filtered and concentrated under reduced pressure. The residue was chromatographed on a silica gel column with MeOH:DCM (1:18) to provide tert-butyl N-[(2S)-1-(cyclopropylcarbamoyl)-3-[(3R*)-5,5-dimethyl-2-oxopyrrolidin-3-yl]-1-hydroxypropan-2-yl]carbamate (290 mg, 73%) as a white solid. LC-MS (ESI, m/z): 370 [M+H]$^+$.

To a solution of tert-butyl N-[(2S)-1-(cyclopropylcarbamoyl)-3-[(3R*)-5,5-dimethyl-2-oxopyrrolidin-3-yl]-1-hydroxypropan-2-yl]carbamate (700 mg, 1.578 mmol, 1.00 eq.) in DCM (9 mL) was added TFA (3 mL). The mixture was stirred at rt for 1 h, and then concentrated under reduced pressure to provide (3S)-3-amino-N-cyclopropyl-4-((R*)-5,5-dimethyl-2-oxopyrrolidin-3-yl)-2-hydroxybutanamide (400 mg, 73%) as an off-white oil. LC-MS (ESI, m/z): 270 [M+H]⁺.

To a solution of (3S)-3-amino-N-cyclopropyl-4-((R*)-5,5-dimethyl-2-oxopyrrolidin-3-yl)-2-hydroxybutanamide (130 mg, 0.48 mmol, 1.0 eq.) in DMF (4 mL) was added (1S,3aR,6aS)-2-(4-methoxy-1H-indole-2-carbonyl)-hexahydro-1H-cyclopenta[c]pyrrole-1-carboxylic acid (174 mg, 0.53 mmol, 1.1 eq.), N,N-diisopropylethylamine (437 mg, 3.38 mmol, 7.0 eq.) and N,N,N',N'-Tetramethyl-O-(7-azabenzotriazol-1-yl)uronium hexafluorophospate (202 mg, 0.53 mmol, 1.1 eq.). The mixture was stirred at 0° C. for 1 h, and the reaction was quenched with water (4 mL). The mixture was extracted with EA (3×10 mL). The organic layers were combined, dried over anhydrous sodium sulfate, filtered and concentrated under reduced pressure. The residue was chromatographed on a silica gel column with DCM:MeOH (17:1) to provide (3S)-3-{[(1S,3aR,6aS)-2-(4-methoxy-1H-indole-2-carbonyl)-hexahydro-1H-cyclopenta[c]pyrrol-1-yl]formamido}-N-cyclopropyl-4-[(3R*)-5,5-dimethyl-2-oxopyrrolidin-3-yl]-2-hydroxybutanamide (150 mg, 48%) as a white solid. LC-MS (ESI, m/z): 580 [M+H]⁺.

To a solution of (3S)-3-{[(1S,3aR,6aS)-2-(4-methoxy-1H-indole-2-carbonyl)-hexahydro-1H-cyclopenta[c]pyrrol-1-yl]formamido}-N-cyclopropyl-4-[(3S)-5,5-dimethyl-2-oxopyrrolidin-3-yl]-2-hydroxybutanamide (140 mg, 0.24 mmol, 1.0 eq.) in DMSO (3 mL) was added IBX (135 mg, 0.48 mmol, 2.0 eq.). The mixture was stirred at rt for 6 h, and the reaction was quenched with sodium bicarbonate solution (2 mL). The solution was extracted with EA (3×8 mL). The organic layers were combined, dried over anhydrous sodium sulfate, filtered and concentrated under reduced pressure. The residue was purified by prep-TLC with MeOH:DCM (1:18) to provide (3S)-3-{[(1S,3aR,6aS)-2-(4-methoxy-1H-indole-2-carbonyl)-hexahydro-1H-cyclopenta[c]pyrrol-1-yl]formamido}-N-cyclopropyl-4-[(3R*)-5,5-dimethyl-2-oxopyrrolidin-3-yl]-2-oxobutanamide (15.2 mg, 11%) as a white solid. LC-MS (ESI, m/z): 578 [M+H]⁺.

Example 97

COMPOUND 96

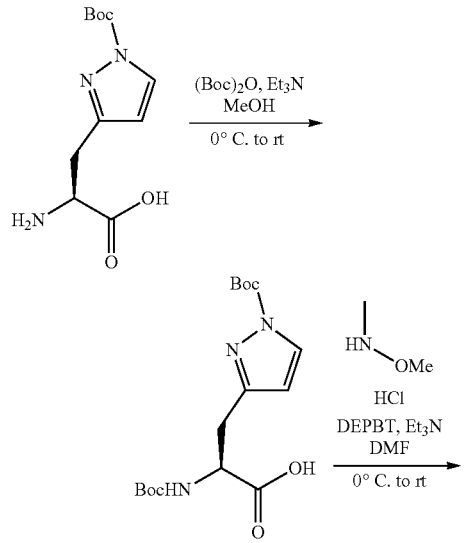

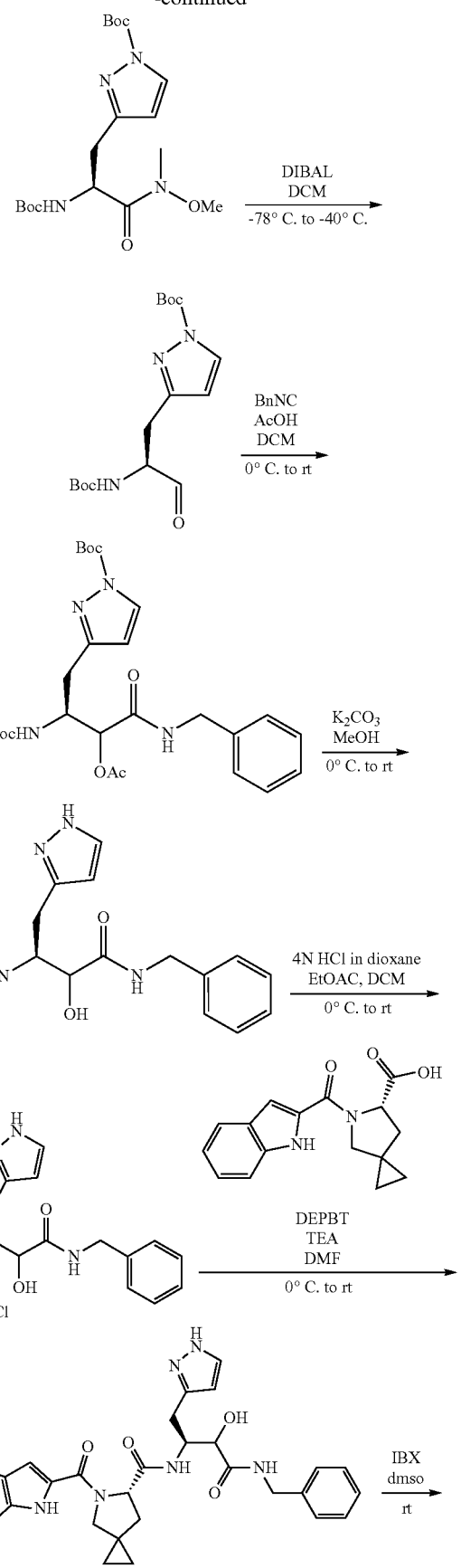

-continued

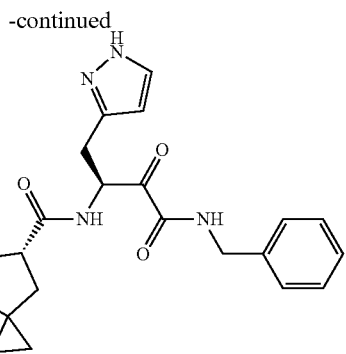

96

To a solution of (S)-2-amino-3-(1-(tert-butoxycarbonyl)-1H-pyrazol-3-yl)propanoic acid 4 (1.9 g, 7.45 mmol, 1.0 eq.) in MeOH (38 mL) was cooled to 0° C., and NEt$_3$ (3.1 mL, 22.3 mmol, 3.0 eq.) and (Boc)$_2$O (3.25 g, 14.9 mmol, 2.0 eq.) were added. The mixture was allowed to warm to rt, and stirred at rt for 3 h. The mixture was concentrated under reduced pressure. The residue was purified by flash chromatography on silica gel (24 g column) using a gradient of MeOH (5 to 6%) in DCM to afford (S)-3-(1-(tert-butoxycarbonyl)-1H-pyrazol-3-yl)-2-((tert-butoxycarbonyl)amino)propanoic acid (2.5 g, 94%) as a colorless oil. LCMS (ESI, m/z): 356 [M+H]$^+$.

To a solution of (S)-3-(1-(tert-butoxycarbonyl)-1H-pyrazol-3-yl)-2-((tert-butoxycarbonyl)amino)propanoic acid (50 mg, 0.141 mmol, 1.0 eq.) in DMF (0.5 mL) was cooled to 0° C., DEPBT (46 mg, 0.154 mmol, 1.1 eq.), NEt$_3$ (0.060 mL, 0.433 mmol, 3.0 eq.) and N,O-dimethylhydroxylamine hydrochloride (17 mg, 0.174 mmol, 2.0 eq.) were added. The mixture was slowly allowed to warm to rt, and then stirred at rt for 5 h. The mixture was diluted with water (5 mL) and extracted with EA (3×15 mL). The organic phases were combined, dried over Na$_2$SO$_4$, filtered and concentrated under reduced pressure. The residue was purified by flash chromatography on silica gel (4 g column) using 30% EA in PE as eluent to afford tert-butyl (S)-3-(2-((tert-butoxycarbonyl)amino)-3-(methoxy(methyl)amino)-3-oxopropyl)-1H-pyrazole-1-carboxylate (20 mg, 35%) as a colorless oil. LCMS (ESI, m/z): 399 [M+H]$^+$.

To a solution of tert-butyl (S)-3-(2-((tert-butoxycarbonyl)amino)-3-(methoxy(methyl)amino)-3-oxopropyl)-1H-pyrazole-1-carboxylate (1.1 g, 2.76 mmol, 1.0 eq.) in DCM (13 mL) was cooled to −78° C., and 1M DIBAL-H in hexane (6.9 mL, 6.90 mmol, 2.5 eq.) was added. The mixture was stirred at −78° C. for 4 h. The reaction was quenched by the addition of MeOH (15 mL) at −40° C. The mixture was allowed to warm to rt. The mixture was diluted with 10% MeOH in DCM (100 mL) and filtered through celite. The filtrate was concentrated under reduced pressure to afford tert-butyl (S)-3-(2-((tert-butoxycarbonyl)amino)-3-oxopropyl)-1H-pyrazole-1-carboxylate (800 mg, 85%) as an off white solid. $^1$H NMR (500 MHz, CDCl$_3$) δ 9.68 (s, 1H), 7.97 (s, 1H), 6.23 (s, 1H), 5.62 (brs 1H), 4.48 (brs, 1H), 3.50-3.60 (m, 1H), 2.60-2.62 (m, 1H), 1.45 (s, 18H).

To a solution of tert-butyl (S)-3-(2-((tert-butoxycarbonyl)amino)-3-oxopropyl)-1H-pyrazole-1-carboxylate (600 mg, 1.77 mmol, 1.0 eq.) in DCM (50 mL) was cooled to 0° C., and benzyl isocyanide (0.258 mL, 2.12 mmol, 1.2 eq.) and acetic acid (0.300 mL, 5.30 mmol, 3 eq.) were added. The mixture was stirred at rt for 8 h. The mixture was diluted with DCM (100 mL) and washed with sat. NaHCO$_3$ (20 mL). The phases were separated. The organic phase was washed with brine (20 mL), dried over Na$_2$SO$_4$, filtered and concentrated under reduced pressure. The residue was purified by flash chromatography on silica gel (12 g column) using a gradient of MeOH (3 to 5%) in DCM to afford a mixture of tert-butyl 3-((2S)-3-acetoxy-4-(benzylamino)-2-((tert-butoxycarbonyl)amino)-4-oxobutyl)-1H-pyrazole-1-carboxylate and a compound resulting from the removal of one Boc protecting group (580 mg). The mixture was dissolved in MeOH (15 mL). After cooling to 0° C., K$_2$CO$_3$ was added (176 mg, 1.28 mmol, 1.2 eq.). The mixture was stirred at rt for 4 h and then concentrated under reduced pressure (rotavapor bath temperature at rt). The mixture was taken up with 10% MeOH in DCM (50 mL) and then filtered. The filtrate was concentrated under reduced pressure to afford tert-butyl ((2S)-4-(benzylamino)-3-hydroxy-4-oxo-1-(1H-pyrazol-3-yl)butan-2-yl)carbamate (400 mg, 79%) as an off-white solid. LCMS (ESI, m/z): 375 [M+H]$^+$.

To a solution of tert-butyl ((2S)-4-(benzylamino)-3-hydroxy-4-oxo-1-(1H-pyrazol-3-yl)butan-2-yl)carbamate (400 mg, 1.07 mmol, 1.0 eq.) in EA (4 mL) and DCM (4 mL) was cooled to 0° C. 4N HCl in dioxane (2.14 mL, 8.54 mmol, 8.0 eq.) was added. The mixture was stirred at rt for 24 h. The mixture was concentrated under reduced pressure. The residue was triturated with diethyl ether to afford ((3S)-3-amino-N-benzyl-2-hydroxy-4-(1H-pyrazol-3-yl)butanamide hydrochloride (350 mg, crude) as a pale brown solid.

To a solution of ((3S)-3-amino-N-benzyl-2-hydroxy-4-(1H-pyrazol-3-yl)butanamide hydrochloride (300 mg, 0.967 mmol, 1.0 eq.) and (S)-5-(1H-indole-2-carbonyl)-5-azaspiro[2.4]heptane-6-carboxylic acid (384 mg, 1.35 mmol, 1.4 eq., prepared in a similar manner as described for (1S,3aR,6aS)-2-(1H-indole-2-carbonyl)octahydrocyclopenta[c]pyrrole-1-carboxylic acid in Example 3) in DMF (5 mL) was cooled to 0° C. DEPBT (404 mg, 1.35 mmol, 1.4 eq.) and NEt$_3$ (0.401 mL, 2.89 mmol, 3.0 eq.) were added. The mixture was slowly allowed to warm to rt, and then stirred at rt for 5 h. The mixture was diluted with cold water (20 mL) and extracted with EA (3×50 mL). The organic phases were combined, washed with water (20 mL) and brine, dried over Na$_2$SO$_4$, filtered and concentrated under reduced pressure. The residue was purified by flash chromatography on silica gel (12 g column) using a gradient of MeOH (2 to 4%) in DCM to afford (6S)—N-((2S)-4-(benzylamino)-3-hydroxy-4-oxo-1-(1H-pyrazol-3-yl)butan-2-yl)-5-(1H-indole-2-carbonyl)-5-azaspiro[2.4]heptane-6-carboxamide (170 mg, 32%) as an off-white solid. LCMS (ESI, m/z): 541 [M+H]$^+$.

To a solution of (6S)—N-((2S)-4-(benzylamino)-3-hydroxy-4-oxo-1-(1H-pyrazol-3-yl)butan-2-yl)-5-(1H-indole-2-carbonyl)-5-azaspiro[2.4]heptane-6-carboxamide (170 mg, 0.314 mmol, 1.0 eq.) in DMSO (9 mL) was added IBX (352 mg, 1.26 mmol, 4.0 eq.), and the mixture was stirred at rt for 5 h. The mixture was diluted with cold water (20 mL). The resulting solid was collected by filtration and was purified by prep-HPLC (Column: HICHROM 5 C18, 21.2× 250 mm 5 µm; Mobile Phase A: 10 mM NH$_4$HCO$_3$ in water, Mobile Phase B: ACN; Flow rate: 17 mL/min; Gradient: 20% B to 70% B in 8 min) to afford (S)—N—((S)-4-(benzylamino)-3,4-dioxo-1-(1H-pyrazol-3-yl)butan-2-yl)-5-(1H-indole-2-carbonyl)-5-azaspiro[2.4]heptane-6-carboxamide (36 mg, 21%) as a pale yellow solid. $^1$H NMR (500 MHz, 363K, DMSO-d$_6$) δ ppm 12.30 (br s, 1H), 11.18 (s, 1H), 8.70-8.82 (m, 1H), 7.90-8.20 (m, 1H), 7.55-7.65 (m, 1H), 7.40-7.50 (m, 2H), 7.10-7.30 (m, 6H), 6.98-7.08 (m, 1H), 6.80-6.92 (m, 1H), 5.90-6.12 (m, 1H), 5.25 (brs, 1H), 4.85 (brs, 1H), 4.20-4.40 (m, 2H), 3.60-3.90 (m, 2H), 3.00-3.20 (m, 2H), 2.10-2.30 (m, 1H), 1.70-1.90 (m, 1H), 0.52-0.72 (m, 4H). LCMS (ESI, m/z): 539 [M+H]+.

Example 98

COMPOUND 97

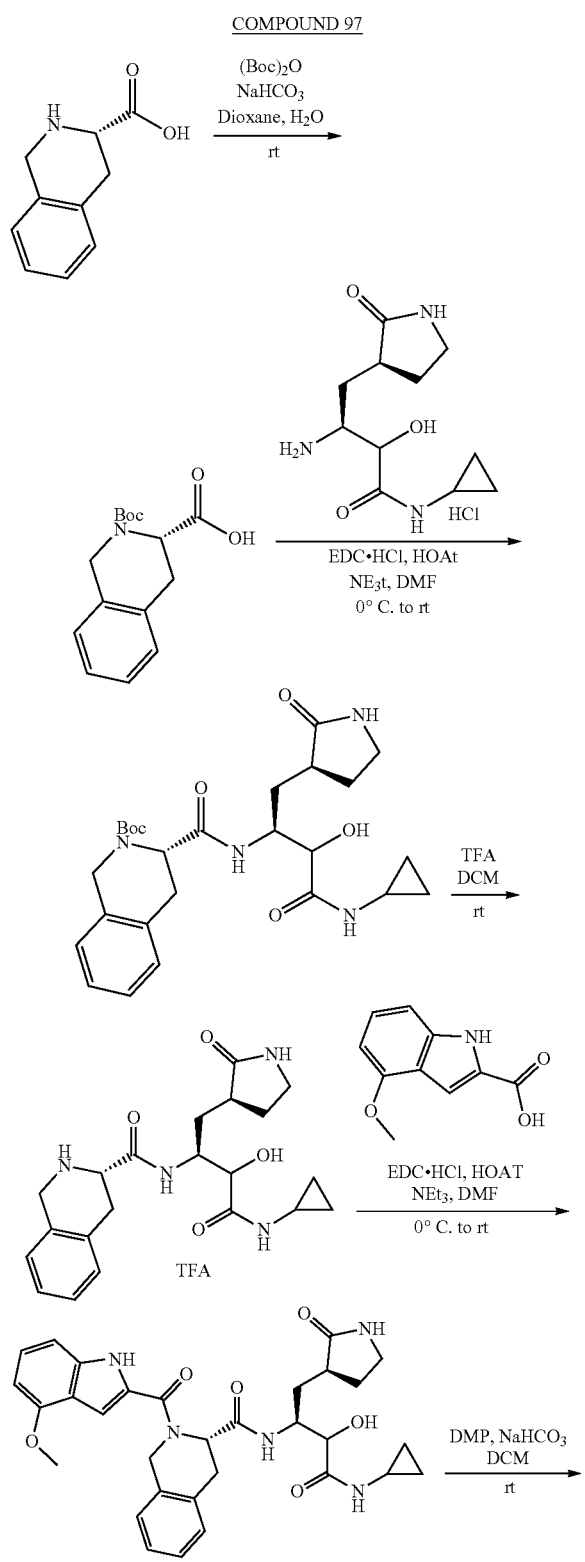

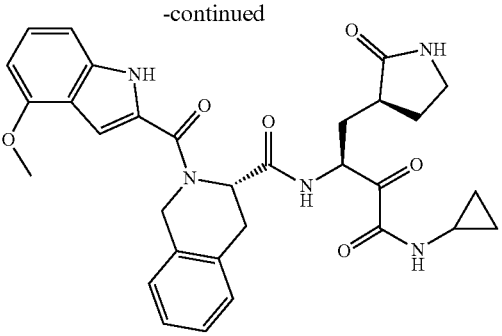

97

A solution of (S)-1,2,3,4-tetrahydroisoquinoline-3-carboxylic acid (2.0 g, 11.3 mmol, 1.0 eq.) and NaHCO3 (1.90 g, 22.6 mmol, 2.0 eq.) in dioxane (20 mL) and water (10 mL) was cooled to 0° C. (Boc)2O (2.7 g, 12.4 mmol, 1.1 eq.) was added. The mixture was stirred at rt for 16 h, and then concentrated under reduced pressure to remove the organic solvent. The residue was diluted with water (10 mL) and was extracted with DCM (5×20 mL). The organic phases were combined, washed with brine (3×15 mL), dried over Na2SO4, filtered and concentrated under reduced pressure to afford (S)-2-(tert-butoxycarbonyl)-1,2,3,4-tetrahydroisoquinoline-3-carboxylic acid (2.0 g, 64%) as an off-white solid (2 g, 64%). LCMS (ESI, m/z): 278 [M+H]+.

A solution of (S)-2-(tert-butoxycarbonyl)-1,2,3,4-tetrahydroisoquinoline-3-carboxylic acid (500 mg, 1.81 mmol, 1.0 eq.) in DMF (5 mL) was cooled to 0° C. EDC·HCl (689 mg, 3.61 mmol, 2.0 eq.), HOAt (245 mg, 1.81 mmol, 1.0 eq.) and NEt3 (0.753 mL, 5.4 mmol, 3.0 eq.) were added. The mixture was stirred at 0° C. for 30 min. (3S)-3-Amino-N-cyclopropyl-2-hydroxy-4-((S)-2-oxopyrrolidin-3-yl)butanamide hydrochloride (548 g, 1.99 mmol, 1.1 eq.) was added, and the mixture was stirred at rt for 16 h. The mixture was diluted with water (20 mL) and extracted with EtOAc (5×20 mL). The organic phases were combined, washed with brine (30 mL), dried over Na2SO4, filtered and concentrated under reduced pressure. The residue was purified by flash chromatography on C18 (12 g column) using a gradient of 0.1% TFA in water (30 to 40%) in ACN to afford tert-butyl (3S)-3-(((2S)-4-(cyclopropylamino)-3-hydroxy-4-oxo-1-((S)-2-oxopyrrolidin-3-yl)butan-2-yl)carbamoyl)-3,4-dihydroisoquinoline-2(1H)-carboxylate (210 mg, 58%) as an off-white solid. LCMS (ESI, m/z): 499 [M−H]−.

To a solution of tert-butyl (3S)-3-(((2S)-4-(cyclopropylamino)-3-hydroxy-4-oxo-1-((S)-2-oxopyrrolidin-3-yl)butan-2-yl)carbamoyl)-3,4-dihydroisoquinoline-2(1H)-carboxylate (200 mg, 0.400 mmol, 1.0 eq.) in DCM (5 mL) was added TFA (2 mL). The mixture was stirred at rt for 5 h. The mixture was concentrated under reduced pressure and coevaporated with diethyl ether to afford (3S)—N-((2S)-4-(cyclopropylamino)-3-hydroxy-4-oxo-1-((S)-2-oxopyrrolidin-3-yl)butan-2-yl)-1,2,3,4-tetrahydroisoquinoline-3-carboxamide TFA salt (150 mg, 93%) as an off-white solid. LCMS (ESI, m/z): 401 [M+H]+.

A solution of 4-methoxy-1H-indole-2-carboxylic acid (150 mg, 0.375 mmol, 1.0 eq.) in DMF (10 mL) was cooled to 0° C. EDC·HCl (143 mg, 0.746 mmol, 2.0 eq.), HOAt (51 mg, 0.375 mmol, 1.0 eq.) and NEt3 (0.156 mL, 1.125 mmol, 3.0 eq.) were added. The mixture was stirred at 0° C. for 30 min. (3S)—N-((2S)-4-(cyclopropylamino)-3-hydroxy-4-oxo-1-((S)-2-oxopyrrolidin-3-yl)butan-2-yl)-1,2,3,4-tetrahydroisoquinoline-3-carboxamide TFA salt (200 mg, 0.687 mmol, 1.0 eq.) was added. The mixture was stirred at rt for 16 h. The mixture was diluted with water (10 mL) and extracted with EA (2×10 mL). The organic phases were combined, washed with brine (20 mL), dried over Na$_2$SO$_4$, filtered and concentrated under reduced pressure. The residue was purified by flash chromatography on C18 (12 g column) using a gradient of 0.1% TFA in water (30 to 40%) in ACN to afford (3S)—N-((2S)-4-(cyclopropylamino)-3-hydroxy-4-oxo-1-((S)-2-oxopyrrolidin-3-yl)butan-2-yl)-2-(4-methoxy-1H-indole-2-carbonyl)-1,2,3,4-tetrahydroisoquinoline-3-carboxamide (80 mg, 32%) as an off-white solid. LCMS (ESI, m/z): 574 [M+H]$^+$.

To a solution of (3S)—N-((2S)-4-(cyclopropylamino)-3-hydroxy-4-oxo-1-((S)-2-oxopyrrolidin-3-yl)butan-2-yl)-2-(4-methoxy-1H-indole-2-carbonyl)-1,2,3,4-tetrahydroisoquinoline-3-carboxamide (70 mg, 0.122 mmol, 1.0 eq.) in DCM (5 mL) were added NaHCO$_3$ (12 mg, 0.146 mmol, 1.2 eq.) and Dess-Martin periodinane (62 mg, 0.146 mmol, 1.2 eq.). The mixture was stirred at rt for 2 h, and then filtered through celite. The filtrate was washed with sat. Na$_2$S$_2$O$_3$ (3×5 mL), sat. NaHCO$_3$ (3×5 mL) and brine (3×5 mL), dried over Na$_2$SO$_4$, filtered and concentrated under reduced pressure. The residue was purified by flash chromatography on silica gel (24 g column) using a gradient of MeOH (1 to 10%) in DCM and by prep-HPLC (Column: X-SELECT-C18, 19×250 mm 5 µm; Mobile Phase A: 10 mM NH$_4$HCO$_3$ in water, Mobile Phase B: ACN; Flow rate: 17 mL/min; Gradient: 20% B to 65% B in 10 min) to afford (S)—N-((S)-4-(cyclopropylamino)-3,4-dioxo-1-((S)-2-oxopyrrolidin-3-yl)butan-2-yl)-2-(4-methoxy-1H-indole-2-carbonyl)-1,2,3,4-tetrahydroisoquinoline-3-carboxamide (40 mg, 57%) as an off-white solid. $^1$H NMR (500 MHz, 373K, DMSO-d$_6$) δ ppm 11.26 (s, 1H), 8.35 (d, 2H), 7.05-7.29 (m, 7H), 6.92 (s, 1H), 6.51 (d, 1H), 5.22 (s, 1H), 5.04-5.08 (m, 1H), 4.83-4.89 (m, 2H), 3.88 (s, 3H), 3.18-3.21 (m, 2H), 3.07-3.10 (m, 2H), 2.68 (d, 1H), 2.01-2.04 (m, 1H), 1.86-1.89 (m, 2H), 1.56-1.61 (m, 2H), 0.55-0.62 (m, 4H). LCMS (ESI, m/z): 572 [M+H]$^+$.

Example 99

COMPOUND 98

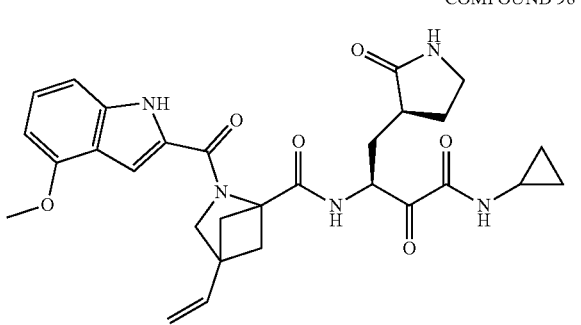

Compound 98 was prepared similarly as described for Compound 97 using 4-vinyl-2-azabicyclo[2.1.1]hexane-1-carboxylic acid hydrochloride in place of (S)-1,2,3,4-tetrahydroisoquinoline-3-carboxylic acid. LCMS (ESI, m/z): 548 [M+H]$^+$.

4-Vinyl-2-azabicyclo[2.1.1]hexane-1-carboxylic acid hydrochloride: A solution of methyl 2-benzoyl-4-(hydroxymethyl)-2-azabicyclo[2.1.1]hexane-1-carboxylate (Cox et al., ACS Med. Chem. Lett. (2020) 11(6):1185-1190) (1.5 g, 5.45 mmol, 1.0 eq.) in DCM (50 mL) was cooled to 0° C. Dess-Martin Periodinane (4.6 g, 10.90 mmol, 2.0 eq.) was added. The mixture was refluxed for 6 h. After cooling to rt, the mixture was diluted with 10% MeOH in DCM (50 mL) and filtered through celite. The filtrate was concentrated under reduced pressure. The residue was purified by flash chromatography on silica gel (24 g column) using a gradient of MeOH (6 to 8%) in DCM to afford methyl 2-benzoyl-4-formyl-2-azabicyclo[2.1.1]hexane-1-carboxylate (1.2 g, 80%) as a white foam.

A suspension of methyltriphenylphosphonium bromide (6.3 g, 17.6 mmol, 4.0 eq.) in THF (40 mL) was cooled to 0° C. 1.6 M n-BuLi in hexane (9.6 mL, 15.4 mmol, 3.5 eq.) was added, and the mixture was stirred at 0° C. for 40 min. After cooling to −78° C., a solution of methyl 2-benzoyl-4-formyl-2-azabicyclo[2.1.1]hexane-1-carboxylate (1.2 g, 4.39 mmol, 1.0 eq.) in THF (40 mL) was added. The mixture was stirred at −78° C. for 1 h, and then slowly allowed to warm to rt over 2 h. The mixture was stirred at rt for 1 h. The reaction was quenched by the addition of sat. NaHCO$_3$ (50 mL) and water (20 mL). The mixture was extracted with EA (3×100 mL). The organic phases were combined, washed with brine (20 mL), dried over Na$_2$SO$_4$, filtered and concentrated under reduced pressure. The residue was purified by flash chromatography on silica gel (24 g column) using a gradient of MeOH (2 to 3%) in DCM to afford methyl 2-benzoyl-4-vinyl-2-azabicyclo[2.1.1]hexane-1-carboxylate (300 mg, 25%) as an off white solid. LCMS (ESI, m/z): 272 [M+H]$^+$.

A mixture of methyl 2-benzoyl-4-vinyl-2-azabicyclo[2.1.1]hexane-1-carboxylate (300 mg, 1.10 mmol, 1.0 eq.) in 6M HCl (6.0 mL, 36.0 mmol) was heated in a sealed tube at 100° C. for 6 h. After cooling to rt, the mixture was extracted with DCM (3×5 mL). The aqueous layer was concentrated under reduced pressure to afford 4-vinyl-2-azabicyclo[2.1.1]hexane-1-carboxylic acid hydrochloride (180 mg, 86%) as a pale brown solid.

Example 100

COMPOUND 99

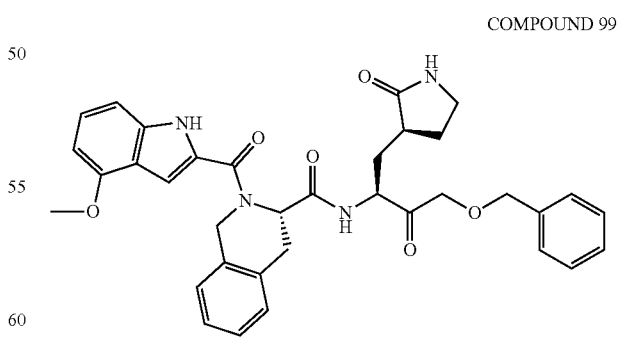

Compound 99 was prepared in a similar manner as described for Compound 31A using (S)-2-(tert-butoxycarbonyl)-1,2,3,4-tetrahydroisoquinoline-3-carboxylic acid in place of (S)-5-(tert-butoxycarbonyl)-5-azaspiro[2.4]heptane-6-carboxylic acid. LCMS (ESI, m/z): 609 [M+H]$^+$.

Example 101

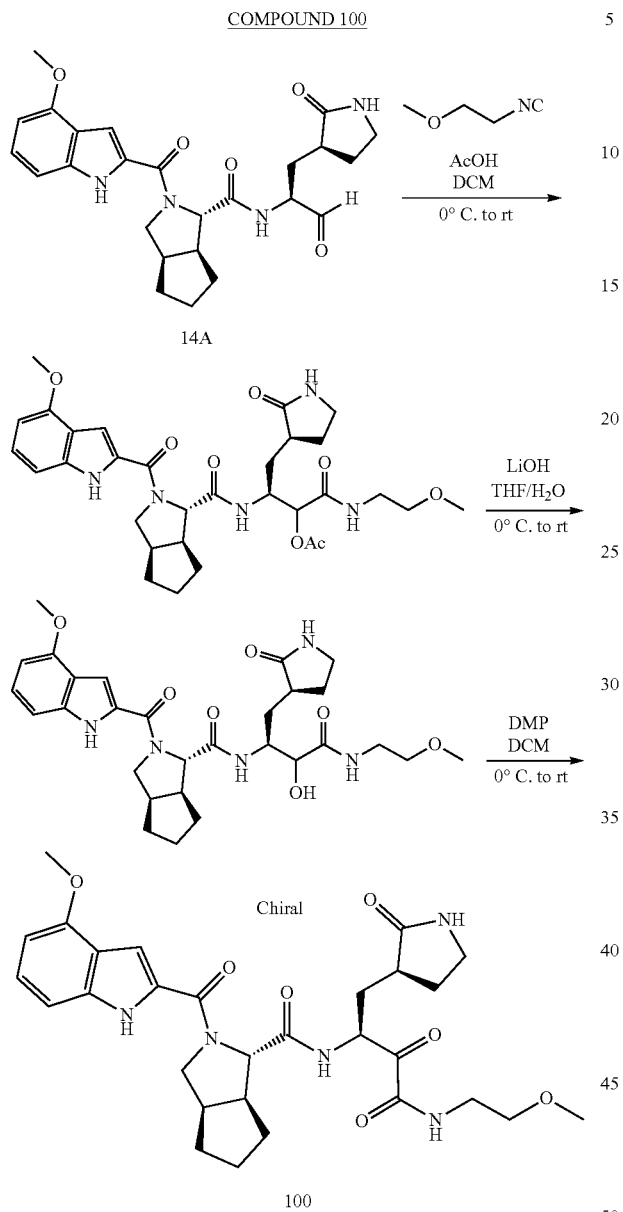

To a solution of Compound 14A (400 mg, 0.857 mmol, 1.0 eq.) in DCM (10 mL) were added AcOH (0.160 mL, 2.57 mmol, 3.0 eq.) and 1-isocyano-2-methoxyethane (109 mg, 1.28 mmol, 1.5 eq.). The mixture was stirred at rt for 2 h. The mixture was diluted with EA (50 mL) and washed with sat. NaHCO$_3$ (20 mL). The phases were separated. The organic phase was washed with brine (20 mL), dried over Na$_2$SO$_4$, filtered and concentrated under reduced pressure. The residue was purified by flash chromatography on silica gel (24 g column) using a gradient of MeOH (1 to 10%) in DCM to afford (3S)-3-((1S,3aR,6aS)-2-(4-methoxy-1H-indole-2-carbonyl)octahydrocyclopenta[c]pyrrole-1-carboxamido)-1-((2-methoxyethyl)amino)-1-oxo-4-((S)-2-oxopyrrolidin-3-yl)butan-2-yl acetate (350 mg, 66%) as an off-white solid. LCMS (ESI, m/z): 612 [M+H]$^+$.

A solution of (3S)-3-((1S,3aR,6aS)-2-(4-methoxy-1H-indole-2-carbonyl)octahydrocyclopenta[c]pyrrole-1-carboxamido)-1-((2-methoxyethyl)amino)-1-oxo-4-((S)-2-oxopyrrolidin-3-yl)butan-2-yl acetate (350 mg, 0.572 mmol, 1.0 eq.) in THF (6 mL) and water (6 mL) was cooled to 0° C. LiOH (48 mg, 1.14 mmol, 2.0 eq.) was added, and the mixture was stirred at rt for 1 h. The mixture was diluted with water (10 mL) and extracted with 10% MeOH in DCM (2×10 mL). The organic phases were combined, dried over Na$_2$SO$_4$, filtered and concentrated under reduced pressure. The residue was purified by flash chromatography on silica gel (24 g column) using a gradient of MeOH (1 to 10%) in DCM to afford (1S,3aR,6aS)—N-((2S)-3-hydroxy-4-((2-methoxyethyl)amino)-4-oxo-1-((S)-2-oxopyrrolidin-3-yl)butan-2-yl)-2-(4-methoxy-1H-indole-2-carbonyl) octahydrocyclopenta[c]pyrrole-1-carboxamide (300 mg, 92%) as an off-white solid. LCMS (ESI, m/z): 570 [M+H]$^+$.

To a stirred solution of (1S,3aR,6aS)—N-((2S)-3-hydroxy-4-((2-methoxyethyl)amino)-4-oxo-1-((S)-2-oxopyrrolidin-3-yl)butan-2-yl)-2-(4-methoxy-1H-indole-2-carbonyl)octahydrocyclopenta[c]pyrrole-1-carboxamide (270 mg, 0.474 mmol, 1.0 eq.) in DCM (5 mL) was added Dess-Martin periodinane (301 mg, 0.710 mmol, 1.5 eq.). The mixture was stirred at rt for 3 h. The mixture was diluted with DCM (15 mL) and was filtered through celite. The filtrate was concentrated under reduced pressure. The residue was purified by prep-HPLC (Column: X-SELECT-C18, 19×250 mm 5 µm; Mobile Phase A: 10 mM NH$_4$HCO$_3$ in water, Mobile Phase B: ACN; Flow rate: 17 mL/min; Gradient: 10% B to 60% B in 8 min) to afford (1S,3aR,6aS)-2-(4-methoxy-1H-indole-2-carbonyl)-N—((S)-4-((2-methoxyethyl)amino)-3,4-dioxo-1-((S)-2-oxopyrrolidin-3-yl)butan-2-yl)octahydrocyclopenta[c]pyrrole-1-carboxamide (55 mg, 20%) as an off-white solid. $^1$H NMR (500 MHz, 363K, DMSO-d$_6$) δ ppm 11.15 (s, 1H), 8.41 (s, 1H), 8.21 (s, 1H), 7.25 (s, 1H), 7.02-7.10 (m, 2H), 6.85 (s, 1H), 6.48 (d, 1H), 4.95 (s, 1H), 4.62 (s, 1H), 3.98 (s, 1H), 3.86 (s, 3H), 3.69 (d, 1H), 3.39-3.42 (m, 2H), 3.27-3.30 (m, 2H), 3.23 (s, 3H), 3.08-3.12 (m, 1H), 2.62-2.75 (m, 2H), 2.42-2.48 (m, 2H), 1.80-1.98 (m, 4H), 1.57-1.70 (m, 5H), 1.45-1.52 (m, 1H). LCMS (ESI, m/z): 568 [M+H]$^+$.

Example 102

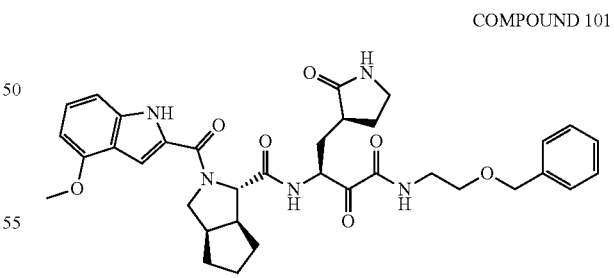

COMPOUND 101

Compound 101 was prepared similarly as described for Compound 100 using ((2-isocyanoethoxy)methyl)benzene in place of 1-isocyano-2-methoxyethane. LCMS (ESI, m/z): 644 [M+H]$^+$.

((2-Isocyanoethoxy)methyl)benzene: A solution of 2-(benzyloxy)ethan-1-amine (2.0 g, 23.0 mmol, 1.0 eq.) in triethyl orthoformate (2.45 mL, 29.9 mmol, 1.3 eq.) was heated at 60° C. overnight. After cooling to rt, the mixture was concentrated under reduced pressure. The residue was purified by flash chromatography on silica gel (40 g column) using a gradient of MeOH (1 to 10%) in DCM to afford N-(2-(benzyloxy)ethyl)formamide (2.0 g, 84%) as a pale brown liquid. LCMS (ESI, m/z): 180 [M+H]+.

To a solution of N-(2-(benzyloxy)ethyl)formamide (1.67 g, 9.32 mmol, 1.0 eq.) in DCM (20 mL) were added PPh3 (2.68 g, 10.3 mmol, 3.0 eq.), CCl4 (0.890 mL, 9.33 mmol, 3.0 eq.) and NEt3 (1.3 mL, 9.33 mmol, 1.0 eq.). The mixture was heated at 45° C. overnight. After cooling to rt, the mixture was concentrated under reduced pressure. The residue was taken up with Et2O (20 mL). The solids were filtered, and the filtrate was concentrated. The residue was purified by flash chromatography on silica gel (40 g column) using a gradient of EA (20 to 40%) in PE to afford ((2-isocyanoethoxy)methyl)benzene (1.0 g, 66%) as a pale brown liquid. LCMS (ESI, m/z): 162 [M+H]+.

Example 103

COMPOUND 102

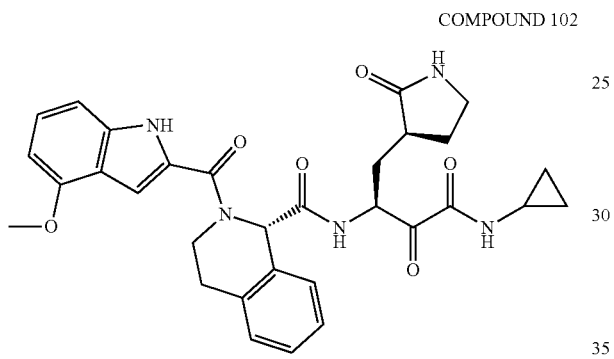

Compound 102 was prepared similarly as described for Compound 97 using (S)-1,2,3,4-tetrahydroisoquinoline-1-carboxylic acid in place of (S)-1,2,3,4-tetrahydroisoquinoline-3-carboxylic acid. LCMS (ESI, m/z): 572 [M+H]+.

Example 104

COMPOUND 103

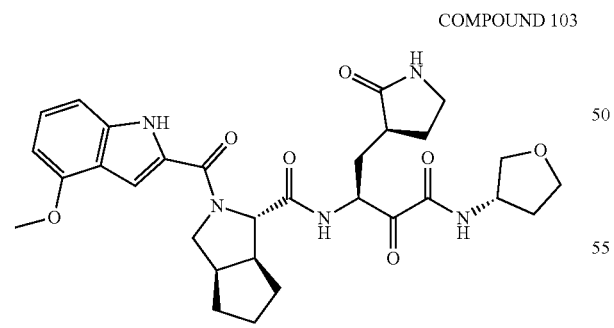

Compound 103 was prepared similarly as described for Compound 101 using (S)-3-isocyanotetrahydrofuran in place of ((2-isocyanoethoxy)methyl)benzene. LCMS (ESI, m/z): 580 [M+H]+.

(S)-3-Isocyanotetrahydrofuran was prepared similarly as described for ((2-isocyanoethoxy)methyl)benzene using (S)-tetrahydrofuran-3-amine in place of 2-(benzyloxy)ethan-1-amine.

Example 105

COMPOUND 104

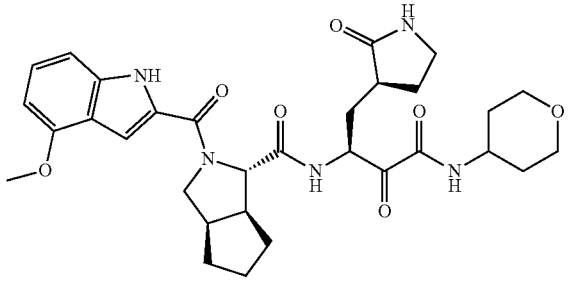

Compound 104 was prepared similarly as described for Compound 101 using 4-isocyanotetrahydro-2H-pyran in place of ((2-isocyanoethoxy)methyl)benzene. LCMS (ESI, m/z): 594 [M+H]+.

4-Isocyanotetrahydro-2H-pyran was prepared similarly as described for ((2-isocyanoethoxy)methyl)benzene using tetrahydro-2H-pyran-4-amine in place of 2-(benzyloxy)ethan-1-amine.

Example 106

COMPOUND 105

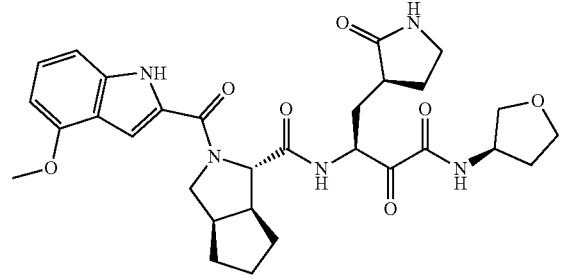

Compound 105 was prepared similarly as described for Compound 101 using (R)-3-isocyanotetrahydrofuran in place of ((2-isocyanoethoxy)methyl)benzene. LCMS (ESI, m/z): 580 [M+H]+.

(R)-3-Isocyanotetrahydrofuran was prepared similarly as described for ((2-isocyanoethoxy)methyl)benzene using (R)-tetrahydrofuran-3-amine in place of 2-(benzyloxy)ethan-1-amine.

Example 107

COMPOUND 106

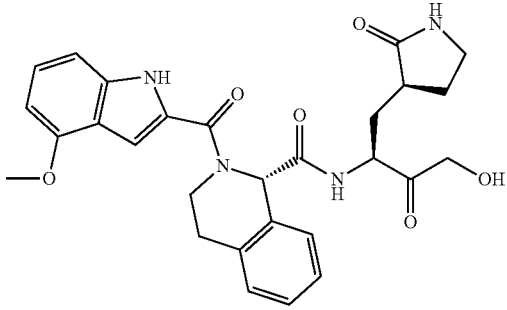

Compound 106 was prepared in a similar manner as described for Compound 31 using (S)-2-(tert-butoxycarbonyl)-1,2,3,4-tetrahydroisoquinoline-1-carboxylic acid in place of (S)-5-(tert-butoxycarbonyl)-5-azaspiro[2.4]heptane-6-carboxylic acid. LCMS (ESI, m/z): 519 [M+H]⁺.

Example 108

COMPOUND 107

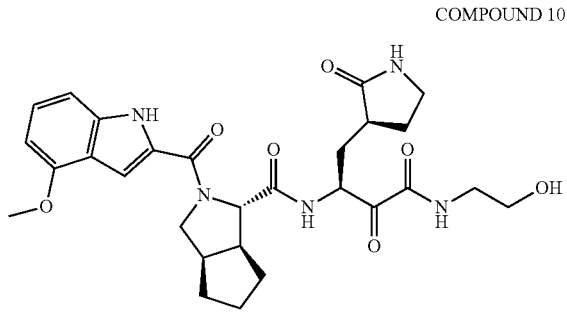

To a solution of Compound 101 (120 mg, 0.180 mmol, 1.0 eq.) in DCM (5 mL) was added DDQ (103 mg, 0.452 mmol, 1.5 eq.). The mixture was stirred at rt for 16 h. The mixture was filtered through celite, and the filtrate was concentrated under reduced pressure. The residue was purified by prep-HPLC (Column: X-SELECT-C18, 19×250 mm 5 μm; Mobile Phase A: 10 mM NH₄HCO₃ in water, Mobile Phase B: ACN; Flow rate: 17 mL/min; Gradient: 20% B to 60% B in 8 min) to afford (1S, 3aR, 6aS)—N—((S)-4-((2-hydroxyethyl)amino)-3,4-dioxo-1-((S)-2-oxopyrrolidin-3-yl)butan-2-yl)-2-(4-methoxy-1H-indole-2-carbonyl)octahydrocyclopenta[c]pyrrole-1-carboxamide (23 mg, 18%) as an off-white solid. ¹H NMR (500 MHz, 363K, DMSO-d₆) δ ppm 11.10 (s, 1H), 8.12-8.40 (m, 1H), 7.25-7.67 (m, 2H), 7.01-7.10 (m, 2H), 6.85 (s, 1H), 6.48 (t, 1H), 4.95-5.08 (m, 1H), 4.60-4.68 (m, 1H), 4.34-4.38 (m, 1H), 3.90-3.95 (m, 1H), 3.86 (s, 3H), 3.60-3.70 (m, 1H), 3.45-3.49 (m, 2H), 3.19-3.23 (m, 1H), 3.10-3.19 (m, 1H), 2.61-2.66 (m, 2H), 2.40-2.45 (m, 1H), 1.46-2.33 (m, 11H). LCMS (ESI, m/z): 554 [M+H]⁺.

Example 109

COMPOUND 108

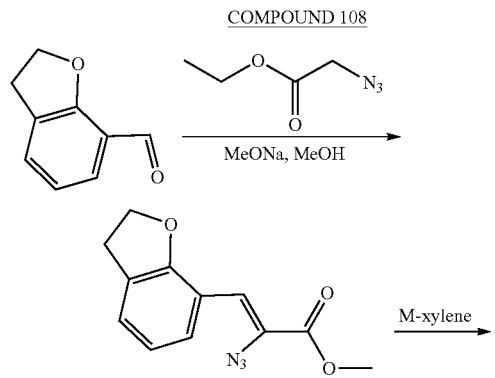

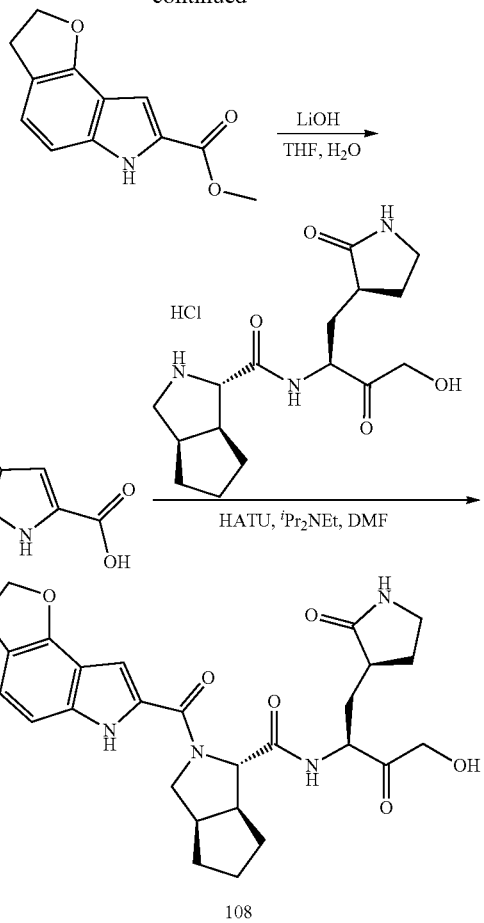

A solution of sodium methanolate (1.94 g, 10.8 mmol, 4.0 eq., 30% in MeOH) in MeOH (5 mL) was cooled to −10° C. A mixture of 2,3-dihydro-1-benzofuran-7-carbaldehyde (400 mg, 2.70 mmol, 1.0 eq.) and ethyl propionate (1.10 g, 10.8 mmol, 4.0 eq.) in MeOH (10 mL) was added dropwise to the above solution over 1.5 h. The mixture was stirred for 3 h at −10° C., poured into ice-water (100 mL) and extracted with ethyl ether (3×100 mL). The organic layers were combined, washed with brine (2×100 mL), dried over anhydrous sodium sulfate, filtered and concentrated under reduced pressure to afford the crude product. The crude product was diluted with EA (20 mL), made into a slurry with 100~200 silica gel mesh (4 g) and loaded to a column after removing the EA. The sample was purified by column chromatography (Column size 5×24 cm, column volume: 300 mL, silica gel size (100~200 mesh) quantity: 120 g) and eluted with EA:PE (0%~30% over 30 min). The collected fractions: 7%-8% EA:PE fractions were chosen as the pure fractions. Those fractions were combined and concentrated under reduced pressure to provide methyl 2-azido-3-(2,3-dihydro-1-benzofuran-7-yl)prop-2-enoate (240 mg, 36%) as a light yellow solid.

A solution of 2-azido-3-(2,3-dihydro-1-benzofuran-7-yl)prop-2-enoic acid (240 mg, 1.03 mmol, 1.0 eq.) in M-xylene (15 mL) was stirred for 2 h at 120° C. under nitrogen atmosphere. The mixture was concentrated under vacuum. The crude product was diluted with dichloromethane (20 mL), made into a slurry with 100~200 silica gel mesh (2 g) and loaded to a column after removing the dichloromethane.

The sample was purified by column chromatography (Column size 5×24 cm, column volume: 300 mL, silica gel size (100~200 mesh) quantity: 120 g) and eluted with EA:PE (0%~30% over 30 min). The collected fractions: 10%-11% EA:PE fractions were chosen as the pure fractions. Those fractions were combined and concentrated under reduced pressure to provide methyl 2H,3H,6H-furo[2,3-e]indole-7-carboxylate (105 mg, 43%) as a white solid. $^1$H NMR (400 MHz, DMSO-$d_6$) δ 11.91 (s, 1H), 7.16-7.19 (m, 1H), 7.00-6.91 (m, 2H), 4.66 (t, J=8.0 Hz, 2H), 3.87 (s, 3H), 3.23 (t, J=10.0 Hz, 2H). LC-MS (ESI, m/z): 218 $[M+H]^+$.

To a stirred mixture of methyl 2H,3H,6H-furo[2,3-e]indole-7-carboxylate (105 mg, 0.483 mmol, 1.0 eq.) in THF (2 mL) and $H_2O$ (2 mL) was added lithium hydroxide (57.8 mg, 2.41 mmol, 5.0 eq.) at rt. The mixture was stirred for 2 h at rt, and then diluted with water (20 mL). The mixture was extracted with EA (3×20 mL). The organic layers were combined, washed with brine (2×20 mL), dried over anhydrous sodium sulfate, filtered and concentrated under reduced pressure to afford 2H,3H,6H-furo[2,3-e]indole-7-carboxylic acid (90 mg, crude) as a white solid $^1$H NMR (400 MHz, DMSO-$d_6$) δ 12.95 (s, 1H), 11.72 (s, 1H), 7.12 (d, J=8.0 Hz, 1H), 6.87-6.97 (m, 2H), 4.65 (t, J=8.0 Hz, 2H), 3.22 (t, J=8.0 Hz, 2H)/LC-MS (ESI, m/z): 204 $[M+H]^+$.

To a stirred mixture of 2H,3H,6H-furo[2,3-e]indole-7-carboxylic acid (68.3 mg, 0.337 mmol, 1.1 eq.), (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (110 mg, 0.306 mmol, 1.0 eq.) and o-(7-Azabenzotriazol-1-yl)-N,N,N',N'-tetramethyluronium hexafluorophosphate (139 mg, 0.367 mmol, 1.2 eq.) in DMF (3 mL) was added N-ethyl-N-isopropylpropan-2-amine (118 mg, 0.918 mmol, 3.0 eq.) at 0° C. The mixture was stirred for 1 h at rt, and the reaction was quenched with water (30 mL). The mixture was extracted with dichloromethane (3×30 mL). The organic layers were combined, washed with brine (2×30 mL), dried over anhydrous sodium sulfate, filtered and concentrated under reduced pressure to afford the crude product. The crude product was purified by Prep-HPLC with the following conditions (Column: XBridge Shield RP18 OBD Column, 30*150 mm, 5 μm; Mobile Phase A: Water (0.1% TFA), Mobile Phase B: ACN; Flow rate: 60 mL/min; Gradient: 20% B to 42% B in 7 min, 42% B; Wave Length: 254 nm; RT1 (min): 5.63) to afford (1S,3aR,6aS)-2-{2H,3H,6H-furo[2,3-e]indole-7-carbonyl}-N-[(2S)-4-hydroxy-3-oxo-1-[(3S)-2-oxopyrrolidin-3-yl]butan-2-yl]-hexahydro-1H-cyclopenta[c]pyrrole-1-carboxamide (25.7 mg, 15%) as a white solid. LC-MS (ESI, m/z): 509 $[M+H]^+$.

Example 110

COMPOUND 109A AND COMPOUND 109B

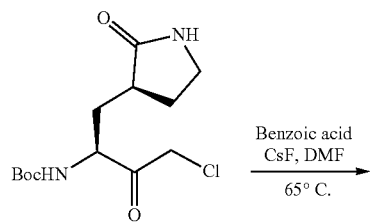

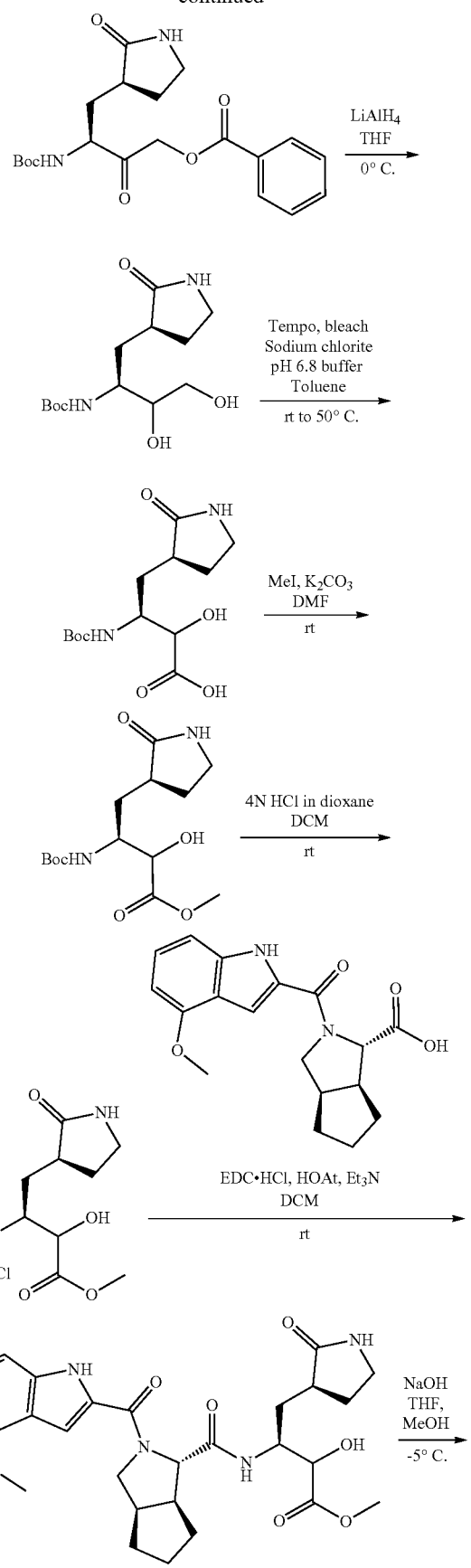

-continued

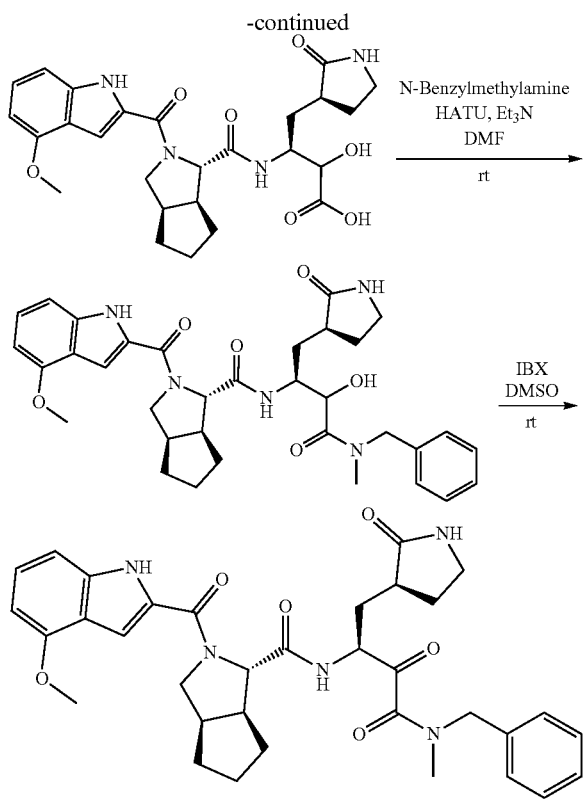

A mixture of tert-butyl N-[(1S)-3-chloro-2-oxo-1-[[(3S)-2-oxopyrrolidin-3-yl]methyl]propyl]carbamate (1.04 g, 3.41 mmol, 1.0 eq.) and CsF (930 mg, 6.14 mmol, 1.8 eq.) in dry DMF (35 mL) was purged with nitrogen. Benzoic acid (430 mg, 3.48 mmol, 1.0 eq.) was added. The mixture was heated at 65° C. for 3 h and then kept at rt overnight. The mixture was diluted with water and extracted (2×) with DCM. The organic phases were combined, dried over $Na_2SO_4$, filtered and concentrated under reduced pressure. The residue was purified by flash chromatography on silica gel (80 g column) using a gradient of MeOH (0 to 5%) in DCM to afford [(3S)-3-(tert-butoxycarbonylamino)-2-oxo-4-[(3S)-2-oxopyrrolidin-3-yl]butyl]benzoate (1.12 g, 84%) as an oil. LCMS (ESI, m/z): 291 [M+2H-Boc]$^+$.

To a solution of [(3S)-3-(tert-butoxycarbonylamino)-2-oxo-4-[(3S)-2-oxopyrrolidin-3-yl]butyl]benzoate (3.40 g, 8.71 mmol, 1.0 eq.) in THF (140 mL) cooled to 0° C. was added 2.4M $LiAlH_4$ in THF (7.3 mL, 17.4 mmol, 2.0 eq.). The mixture was stirred at 0° C. for 2 h. The mixture was diluted with EA (250 mL) and sodium sulfate decahydrate was added (70 g). The resulting suspension was stirred vigorously at rt overnight. The solids were filtered off, and the filtrated was concentrated under reduced pressure. The residue was purified by flash chromatography on silica gel (40 g column) using a gradient of MeOH (1 to 20%) in DCM to afford tert-butyl N-[(1S)-2,3-dihydroxy-1-[[(3S)-2-oxopyrrolidin-3-yl]methyl]propyl]carbamate (1.79 g, 71%) as a white solid. LCMS (ESI, m/z): 189 [M+2H-Boc]$^+$.

To a mixture of tert-butyl N-[(1S)-2,3-dihydroxy-1-[[(3S)-2-oxopyrrolidin-3-yl]methyl]propyl]carbamate (0.895 g, 3.10 mmol, 1.0 eq.) and TEMPO (0.025 g, 0.155 mmol, 0.05 eq.) in toluene (15.5 mL), and 0.1M sodium phosphate pH 6.8 buffer (2.2 mL) were added 3.5M sodium chlorite in water (4.43 mL, 15.5 mmol, 5.0 eq.) and diluted bleach (3.01 mL, prepared by diluting 10× the technical commercial bleach containing 14% $Cl_2$ in aqueous solution) over 1 h using a syringe driver. The mixture was stirred at rt for 11 h and then heated at 50° C. for 11 h. TEMPO (0.025 g, 0.155 mmol, 0.05 eq) and diluted bleach (3.01 mL) were added, and heating was maintained at 50° C. for 36 h. After cooling to rt, the mixture was diluted with water, acidified with 1N HCl until pH ~2-3 and extracted with 10% tBuOH in DCM (10×50 mL). The organic phases were combined, dried over $MgSO_4$, filtered and concentrated under reduced pressure to afford (3S)-3-(tert-butoxycarbonylamino)-2-hydroxy-4-[(3S)-2-oxopyrrolidin-3-yl]butanoic acid (938 mg, crude) as a beige solid. LCMS (ESI, m/z): 301 [M−H]$^-$.

To a solution of (3S)-3-(tert-butoxycarbonylamino)-2-hydroxy-4-[(3S)-2-oxopyrrolidin-3-yl]butanoic acid (930 mg, 3.08 mmol, 1.0 eq.) in DMF (17 mL) were added $K_2CO_3$ (595 mg, 4.31 mmol, 1.4 eq.) and iodomethane (0.34 mL, 5.54 mmol, 1.8 eq.). The mixture was stirred at rt overnight. The mixture was diluted with water, acidified with 1N HCl until pH ~5-6 and extracted (2×) with DCM. The organic phases were combined, dried over $MgSO_4$, filtered and concentrated under reduced pressure. The residue was purified by flash chromatography on silica gel (80 g column) using a gradient of MeOH (0 to 10%) in DCM to afford methyl (3S)-3-(tert-butoxycarbonylamino)-2-hydroxy-4-[(3S)-2-oxopyrrolidin-3-yl]butanoate (596 mg, 61%) as a beige solid. LCMS (ESI, m/z): 217 [M+H-Boc]$^+$.

To a solution of methyl (3S)-3-(tert-butoxycarbonylamino)-2-hydroxy-4-[(3S)-2-oxopyrrolidin-3-yl]butanoate (190 mg, 0.606 mmol, 1.0 eq.) in DCM (6 mL) was added 4N HCl in dioxane (1.5 mL, 6.00 mmol, 10.0 eq.). The mixture was stirred at rt overnight and then concentrated under reduced pressure to afford quantitatively methyl (3S)-3-amino-2-hydroxy-4-[(3S)-2-oxopyrrolidin-3-yl]butanoate hydrochloride.

To a solution of (3S,3aS,6aR)-2-(4-methoxy-1H-indole-2-carbonyl)-3,3a,4,5,6,6a-hexahydro-1H-cyclopenta[c]pyrrole-3-carboxylic acid (680 mg, 2.07 mmol, 1.0 eq.) and methyl (3S)-3-amino-2-hydroxy-4-[(3S)-2-oxopyrrolidin-3-yl]butanoate hydrochloride (471 mg, 1.86 mmol, 0.9 eq.) in DMF (17 mL) were added EDC·HCl (802 mg, 4.14 mmol; 2.0 eq.), HOAt (291 mg, 2.07 mmol, 1.0 eq.) and $NEt_3$ (1.44 mL, 10.4 mmol, 5.0 eq.). The mixture was stirred at rt for 24 h. The mixture was diluted water and extracted (2×) with 10% tBuOH in DCM. The organic phases were combined, dried over $MgSO_4$, filtered and concentrated under reduced pressure. The residue was purified by flash chromatography on silica gel (40 g column) using a gradient of MeOH (0 to 10%) in DCM to afford methyl (3S)-3-[[(3S,3aS,6aR)-2-(4-methoxy-1H-indole-2-carbonyl)-3,3a,4,5,6,6a-hexahydro-1H-cyclopenta[c]pyrrole-3-carbonyl]amino]-2-hydroxy-4-[(3S)-2-oxopyrrolidin-3-yl]butanoate (860 mg, 79%) as a white solid. LCMS (ESI, m/z): 527 [M+H]$^+$.

To a solution of methyl (3S)-3-[[(3S,3aS,6aR)-2-(4-methoxy-1H-indole-2-carbonyl)-3,3a,4,5,6,6a-hexahydro-1H-cyclopenta[c]pyrrole-3-carbonyl]amino]-2-hydroxy-4-[(3S)-2-oxopyrrolidin-3-yl]butanoate (860 mg, 1.63 mmol, 1.0 eq) in MeOH (9 mL) and THF (9 mL) cooled to −5° C. was added dropwise a cooled solution of NaOH (261 mg, 6.53 mmol, 4.0 eq.) in water (9 mL). The mixture was stirred at −5° C. for 2 h. The mixture was neutralized at −5° C. by the addition of 1N HCl until pH ~ 2-3. The mixture was extracted (2×) with 10% tBuOH in DCM. The organic phases were combined, dried over $MgSO_4$, filtered and concentrated under reduced pressure to afford quantitatively (3S)-3-[[(3S,3aS,6aR)-2-(4-methoxy-1H-indole-2-carbonyl)-3,3a,4,5,6,6a-hexahydro-1H-cyclopenta[c]pyrrole-3- carbonyl]amino]-2-hydroxy-4-[(3S)-2-oxopyrrolidin-3-yl]butanoic acid as a white solid. LCMS (ESI, m/z): 513 [M+H]⁺.

A mixture of (3S)-3-[[(3S,3aS,6aR)-2-(4-methoxy-1H-indole-2-carbonyl)-3,3a,4,5,6,6a-hexahydro-1H-cyclopenta[c]pyrrole-3-carbonyl]amino]-2-hydroxy-4-[(3S)-2-oxopyrrolidin-3-yl]butanoic acid (90 mg, 0.180 mmol, 1.0 eq.), HATU (80 mg, 0.211 mmol, 1.2 eq.) and NEt₃ (0.074 mL, 0.527 mmol, 3.0 eq.) in DMF (1.5 mL) was stirred at rt for 5 min. N-Benzylmethylamine (0.050 mL, 0.351 mmol, 2.0 eq.) was added, and the mixture was stirred at rt overnight. The mixture was diluted with DCM and washed with sat. NaHCO₃. The phases were separated. The organic phase was washed with water, dried over Na₂SO₄, filtered and concentrated under reduced pressure. The residue was purified by flash chromatography on silica gel (12 g column) using a gradient of MeOH (0 to 7%) in DCM to afford (3S,3aS,6aR)—N-[(1S)-3-[benzyl(methyl)amino]-2-hydroxy-3-oxo-1-[[(3S)-2-oxopyrrolidin-3-yl]methyl]propyl]-2-(4-methoxy-1H-indole-2-carbonyl)-3,3a,4,5,6,6a-hexahydro-1H-cyclopenta[c]pyrrole-3-carboxamide (64 mg, 59%) as a white solid. LCMS (ESI, m/z): 616 [M+H]⁺.

To a solution of (3S,3aS,6aR)—N-[(1S)-3-[benzyl(methyl)amino]-2-hydroxy-3-oxo-1-[[(3S)-2-oxopyrrolidin-3-yl]methyl]propyl]-2-(4-methoxy-1H-indole-2-carbonyl)-3,3a,4,5,6,6a-hexahydro-1H-cyclopenta[c]pyrrole-3-carboxamide (64 mg, 0.104 mmol, 1.0 eq.) in DMSO (3 mL) was added IBX (58 mg, 0.208 mmol, 2.0 eq.). The mixture was stirred at rt for 4 h. IBX (31 mg, 0.111 mmol, 1.1 eq.) was added. After 16 h at rt, a second batch of IBX (31 mg, 0.111 mmol, 1.1 eq.) was added. The mixture was stirred at rt for 4 h. The mixture was diluted with sat. NaHCO₃ and extracted (2×) with 10% tBuOH in DCM. The organic phases were combined, dried over MgSO₄, filtered and concentrated under reduced pressure. The residue was dissolved in EA and washed with sat. NaHCO₃. The phases were separated. The organic phase was washed with water, dried over MgSO₄, filtered and concentrated under reduced pressure. The residue was purified by flash chromatography on silica gel (12 g column) using a gradient of MeOH (0 to 7%) in DCM to provide two atropoisomers. 109A (8 mg, 12%) as a white solid and 109B (11 mg, 16%) as a white solid. 109A: LC-MS (ESI, m/z): 614 [M+H]⁺. 109B: LC-MS (ESI, m/z): 614 [M+H]⁺.

Example 111

COMPOUND 110

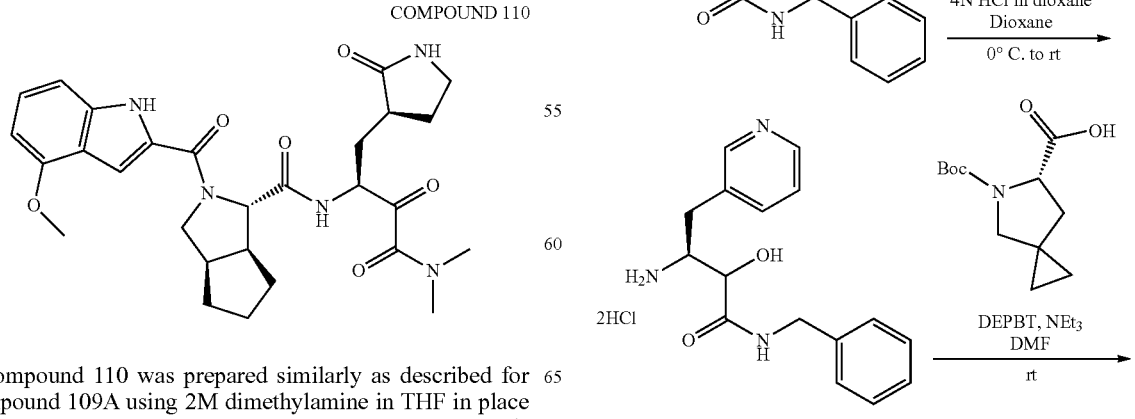

Compound 110 was prepared similarly as described for Compound 109A using 2M dimethylamine in THF in place of N-benzylmethylamine. LCMS (ESI, m/z): 538 [M+H]⁺.

Example 112

COMPOUND 111

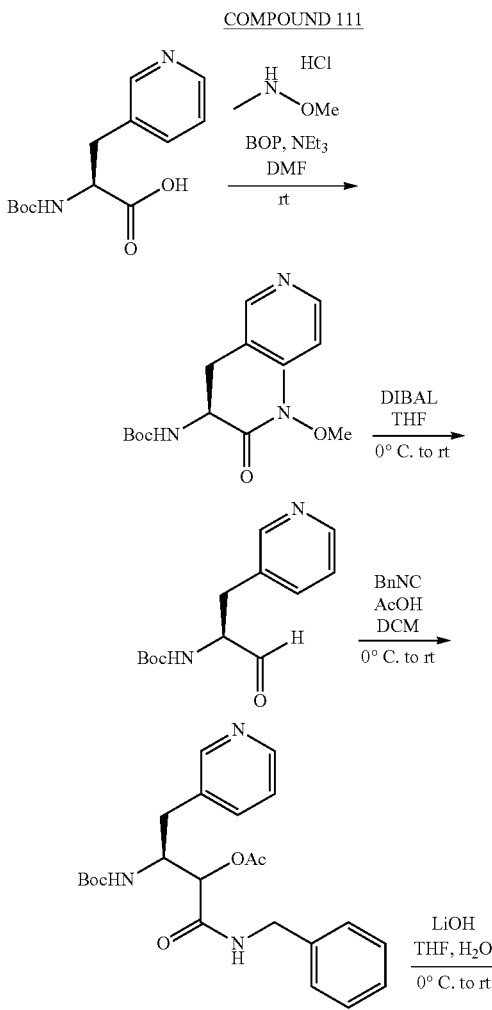

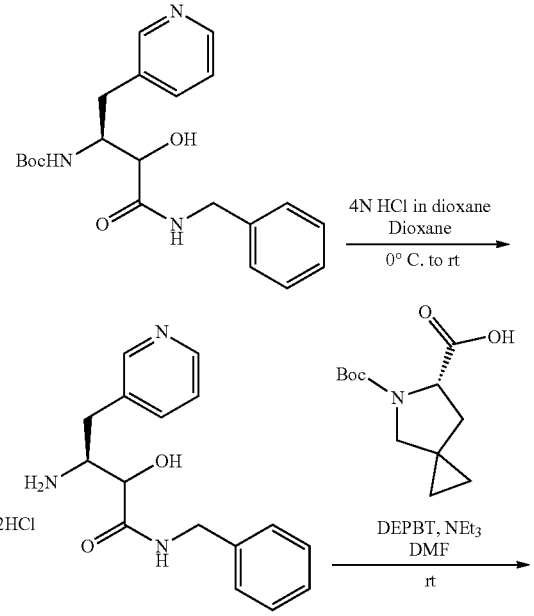

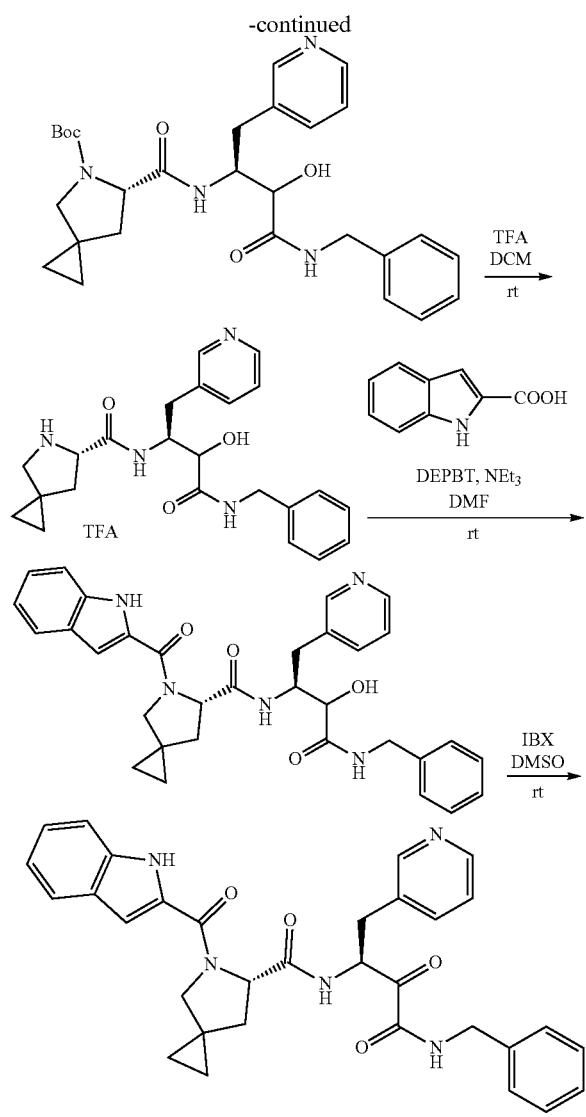

To a solution of (S)-2-((tert-butoxycarbonyl)amino)-3-(pyridin-3-yl)propanoic acid (3.5 g, 13.2 mmol, 1.0 eq.) in DMF (35 mL) cooled to 0° C. were added BOP (8.7 g, 19.7 mmol, 1.5 eq.) and NEt₃ (5.3 mL, 39.5 mmol, 3.0 eq.). The mixture was stirred at 0° C. for 30 min, and N,O-dimethylhydroxylamine hydrochloride (1.9 g, 19.7 mmol, 1.5 eq.) was added. The mixture was stirred at rt for 16 h. The mixture was diluted with water (50 mL) and extracted with EA (2×100 mL). The organic phases were combined, washed with water (3×100 mL), dried over Na₂SO₄, filtered and concentrated under reduced pressure. The residue was purified by flash chromatography on silica gel (80 g column) using a gradient of MeOH (40 to 50%) in DCM to afford tert-butyl (S)-(1-(methoxy(methyl)amino)-1-oxo-3-(pyridin-3-yl)propan-2-yl)carbamate (2.5 g, 61%) as a white solid. LC-MS (ESI, m/z): 310 [M+H]⁺.

To a solution of tert-butyl (S)-(1-(methoxy(methyl)amino)-1-oxo-3-(pyridin-3-yl)propan-2-yl)carbamate (1.0 g, 0.324 mmol, 1.0 eq.) in THF (20 mL) cooled to −78° C. was added 1M DIBAL in hexane (0.647 mL, 0.647 mmol, 2.0 eq.). The mixture was stirred at −78° C. for 2 h. After warming to rt, the reaction was quenched by addition of sat. NH₄Cl (20 mL). The phases were separated. The aqueous phase was extracted with DCM (2×50 mL). The organic phases were combined, dried over Na₂SO₄, filtered and concentrated under reduced pressure to afford tert-butyl (S)-(1-oxo-3-(pyridin-3-yl)propan-2-yl)carbamate (1.5 g, crude) as an off-white solid.

To a solution of tert-butyl (S)-(1-oxo-3-(pyridin-3-yl)propan-2-yl)carbamate (650 mg, 2.60 mmol, 1.0 eq.) in DCM (10 mL) cooled to 0° C. were added benzyl isocyanide (0.37 mL, 3.12 mmol, 1.2 eq.) and acetic acid (0.46 mL, 7.80 mmol, 3.0 eq.). The mixture was stirred at rt for 16 h. The mixture was diluted with water (30 mL) and extracted with DCM (2×50 mL). The organic phases were combined, dried over Na₂SO₄, filtered and concentrated under reduced pressure. The residue was purified by flash chromatography on silica gel (40 g column) using a gradient of MeOH (20 to 30%) in DCM to afford (3S)-1-(benzylamino)-3-((tert-butoxycarbonyl)amino)-1-oxo-4-(pyridin-3-yl)butan-2-yl acetate (600 mg, 54%) as a white solid. LC-MS (ESI, m/z): 428 [M+H]⁺.

To a stirred solution of (3S)-1-(benzylamino)-3-((tert-butoxycarbonyl)amino)-1-oxo-4-(pyridin-3-yl)butan-2-yl acetate (500 mg, 0.160 mmol, 1.0 eq.) in THF (6 mL) and water (2 mL) cooled to 0° C. was added LiOH (7 mg, 0.320 mmol, 2.0 eq.). The mixture was stirred at rt for 2 h. The mixture was diluted with cold water (250 mL) and extracted with DCM (2×250 mL). The organic phases were combined, dried over Na₂SO₄, filtered and concentrated under reduced pressure. The residue was purified by flash chromatography on silica gel (24 g column) using a gradient of MeOH (40 to 50%) in DCM to afford tert-butyl ((2S)-4-(benzylamino)-3-hydroxy-4-oxo-1-(pyridin-3-yl)butan-2-yl)carbamate (300 mg, 48%). LC-MS (ESI, m/z): 386 [M+H]⁺.

To a stirred solution of tert-butyl ((2S)-4-(benzylamino)-3-hydroxy-4-oxo-1-(pyridin-3-yl)butan-2-yl)carbamate (500 mg, 0.160 mmol, 1.0 eq.) in dioxane (2 mL) cooled to 0° C. was added 4N HCl in dioxane (0.200 mL, 0.800 mmol, 5.0 eq). The reaction mixture was stirred at rt for 16 h and was concentrated under reduced pressure to afford (3S)-3-amino-N-benzyl-2-hydroxy-4-(pyridin-3-yl)butanamide dihydrochloride (450 mg) as an oil. LC-MS (ESI, m/z): 286 [M+H]⁺.

To a solution of (3S)-3-amino-N-benzyl-2-hydroxy-4-(pyridin-3-yl)butanamide dihydrochloride (650 mg, 1.72 mmol, 1.0 eq.) in DMF (10 mL) cooled to 0° C. were added (S)-5-(tert-butoxycarbonyl)-5-azaspiro[2.4]heptane-6-carboxylic acid (621 mg, 2.57 mmol, 1.5 eq.), DEPBT (565 mg, 1.89 mmol, 1.1 eq.) and NEt₃ (0.7 mL, 5.16 mmol, 3.0 eq.). The reaction mixture was stirred at 0° C. for 30 min, was allowed to warm to rt and was stirred at rt for 16 h. The reaction mixture was diluted with water (50 mL) and extracted with EA (2×150 mL). The organic phases were combined, washed with water (3×50 mL), dried over Na₂SO₄, filtered and concentrated under reduced pressure. The residue was purified by flash chromatography on silica gel (120 g column) using a gradient of MeOH (40 to 50%) in DCM to afford tert-butyl (6S)-6-(((2S)-4-(benzylamino)-3-hydroxy-4-oxo-1-(pyridin-3-yl)butan-2-yl)carbamoyl)-5-azaspiro[2.4]heptane-5-carboxylate (400 mg, 46%) as a white oil. LC-MS (ESI, m/z): 509 [M+H]⁺.

To a solution of tert-butyl (6S)-6-(((2S)-4-(benzylamino)-3-hydroxy-4-oxo-1-(pyridin-3-yl)butan-2-yl)carbamoyl)-5-azaspiro[2.4]heptane-5-carboxylate (300 mg, 0.588 mmol, 1.0 eq.) in DCM (5 mL) cooled to 0° C. was added TFA (336 mg, 2.95 mmol, 5.0 eq.) and the reaction mixture was stirred at rt for 16 h. The reaction mixture was concentrated under reduced pressure to afford (6S)—N-((2S)-4-(benzylamino)-3-hydroxy-4-oxo-1-(pyridin-3-yl)butan-2-yl)-5-azaspiro

[2.4]heptane-6-carboxamide under its TFA salt form (250 mg, crude) as an oil. LC-MS (ESI, m/z): 409 [M+H]+.

To a solution of (6S)—N-((2S)-4-(benzylamino)-3-hydroxy-4-oxo-1-(pyridin-3-yl)butan-2-yl)-5-azaspiro[2.4]heptane-6-carboxamide (240 mg, 0.588 mmol, 1.0 eq., TFA salt) in DMF (5 mL) were added 1H-indole-2-carboxylic acid (104 mg, 0.647 mmol, 1.1 eq.), DEPBT (193 mg, 0.647 mmol, 1.1 eq.) and NEt₃ (0.24 mL, 1.76 mmol, 3.0 eq.). The reaction mixture was stirred at 0° C. for 30 min, was allowed to warm to rt and was stirred at rt for 16 h. The reaction mixture was diluted with water (20 mL) and was extracted with EA (3×20 mL). The organic phases were combined, dried over Na₂SO₄, filtered and concentrated under reduced pressure. The residue was purified by flash chromatography on silica gel (24 g column) using a gradient of MeOH (40 to 50%) in DCM to afford (6S)—N-((2S)-4-(benzylamino)-3-hydroxy-4-oxo-1-(pyridin-3-yl)butan-2-yl)-5-(1H-indole-2-carbonyl)-5-azaspiro[2.4]heptane-6-carboxamide (200 mg, 62%) as a white solid. LC-MS (ESI, m/z): 552 [M+H]+.

To a solution of (6S)—N-((2S)-4-(benzylamino)-3-hydroxy-4-oxo-1-(pyridin-3-yl)butan-2-yl)-5-(1H-indole-2-carbonyl)-5-azaspiro[2.4]heptane-6-carboxamide (150 mg, 0.272 mmol, 1.0 eq.) in DMSO (3 mL) was added IBX (144 mg, 1.63 mmol, 6.0 eq.). The reaction mixture was stirred at rt for 1 h. The reaction mixture was diluted with H₂O (20 ml) and extracted with EA (3×20 mL). The organic phases were combined, washed with brine (10 mL), dried over Na₂SO₄, filtered and concentrated under reduced pressure. The residue was purified by flash chromatography on silica gel (24 g column) using a gradient of MeOH (30 to 50%) in DCM and by preparative HPLC (Column: X-BRIDGE-C18, 10×250 mm, 5 um; Mobile Phase A: 10 mM NH₄HCO₃ in water, Mobile Phase B: ACN; Flow rate: 17 mL/min; Gradient: 20% B to 75% B in 8 min) to afford (S)—N—((S)-4-(benzylamino)-3,4-dioxo-1-(pyridin-3-yl)butan-2-yl)-5-(1H-indole-2-carbonyl)-5-azaspiro[2.4]heptane-6-carboxamide (35 mg, 23%) as an off-white solid. ¹H NMR (500 MHz, 364K, DMSO-d₆) δ ppm 11.16 (s, 1H), 8.81-8.84 (m, 1H), 8.42 (d, 1H), 8.36 (t, 1H), 8.17 (s, 1H), 7.58-7.61 (t, 2H), 7.45 (d, 1H), 7.12-7.30 (m, 7H), 7.00-7.03 (m, 1H), 6.82 (s, 1H), 5.21-5.25 (m, 1H), 4.80 (d, 1H), 4.33 (dd, 2H), 3.79-3.80 (m, 1H), 3.69 (s, 1H), 3.18 (m, 1H), 2.96 (m, 1H), 2.15 (m, 1H), 1.63-1.79 (dd, 1H), 0.61-0.50 (m, 4H). LCMS (ESI, m/z): 550 [M+H]+.

Example 113

COMPOUND 112

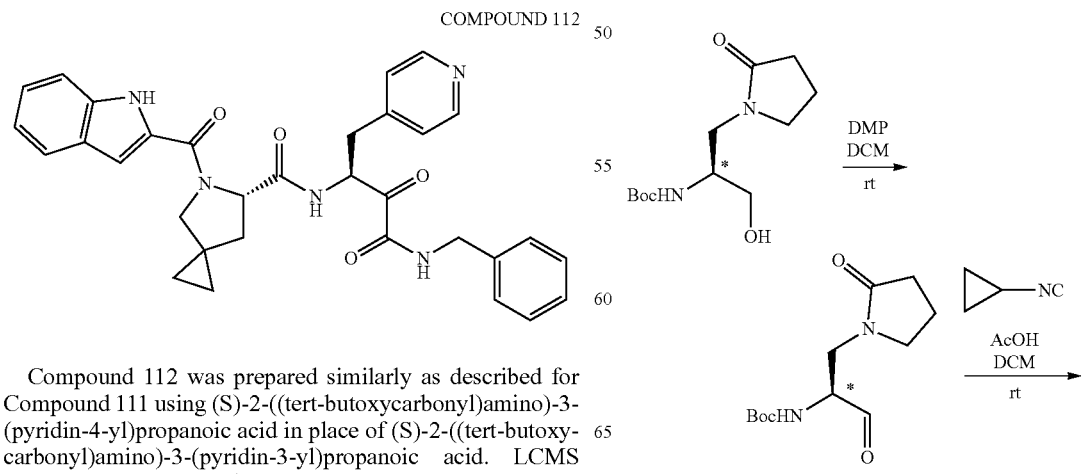

Compound 112 was prepared similarly as described for Compound 111 using (S)-2-((tert-butoxycarbonyl)amino)-3-(pyridin-4-yl)propanoic acid in place of (S)-2-((tert-butoxycarbonyl)amino)-3-(pyridin-3-yl)propanoic acid. LCMS (ESI, m/z): 550 [M+H]+.

Example 114

COMPOUND 113A AND COMPOUND 113B

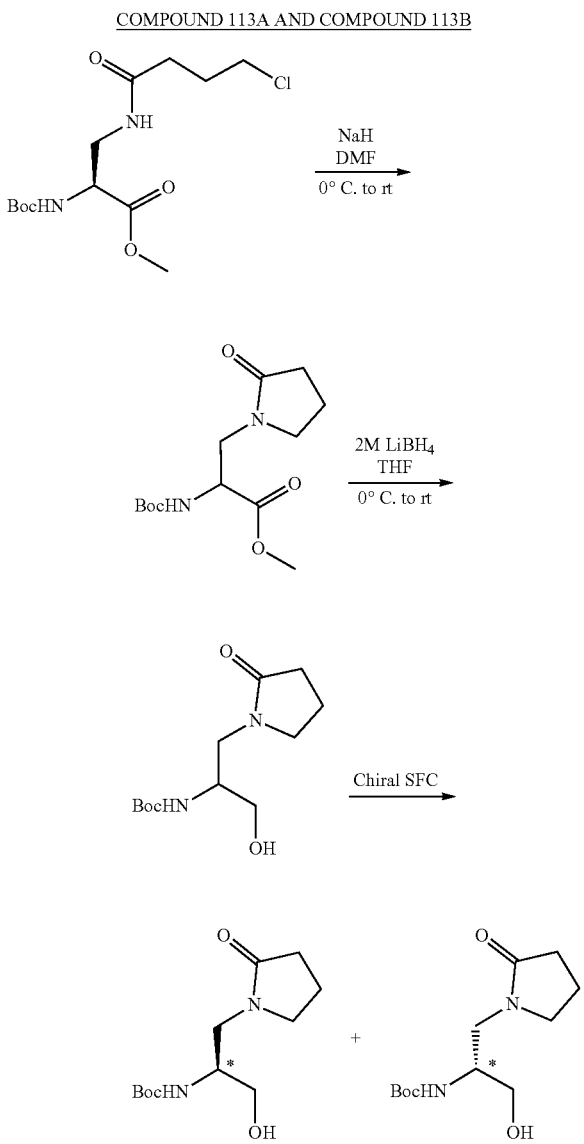

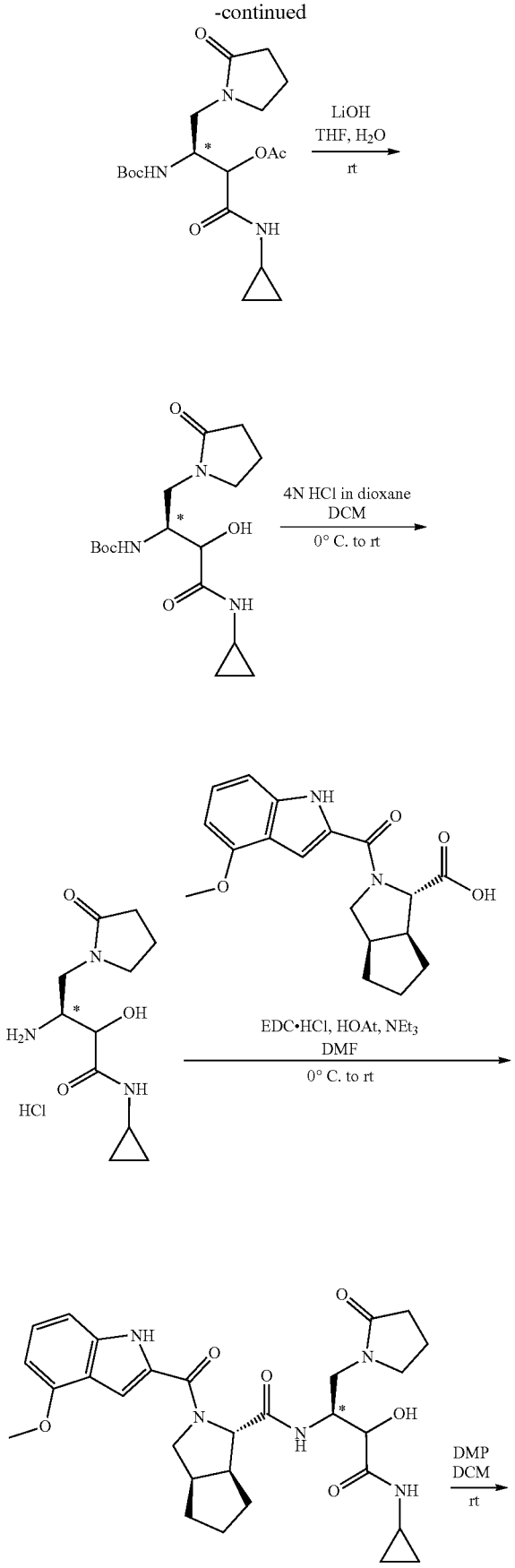

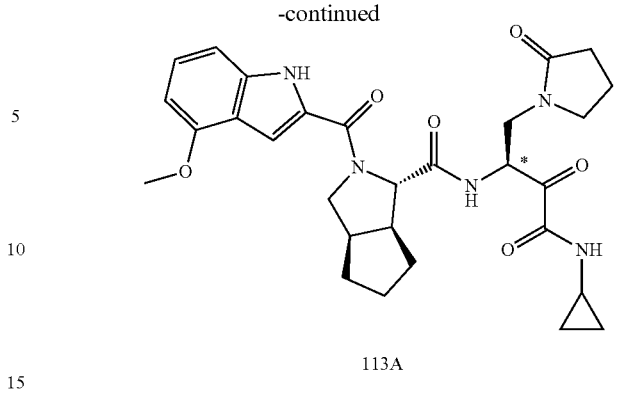

113A

The chiral center noted with "*" is tentatively assigned.

To a solution of methyl (S)-2-((tert-butoxycarbonyl)amino)-3-(4-chlorobutanamido)propanoate (1.8 g, 5.59 mmol, 1.0 eq., CAS [1629681-11-3]) in DMF (20 mL) cooled to 0° C. was added NaH (246 mg, 6.14 mmol, 1.1 eq.), and the mixture was stirred at rt for 16 h. After cooling to 0° C., the reaction was quenched by the addition of AcOH (2 mL) and water. The mixture was extracted with 10% MeOH in DCM (2×50 mL). The organic phases were combined, dried over $Na_2SO_4$, filtered and concentrated under reduced pressure. The residue was purified by flash chromatography on silica gel (40 g column) using a gradient of MeOH (1 to 5%) in DCM to afford methyl 2-((tert-butoxycarbonyl)amino)-3-(2-oxopyrrolidin-1-yl)propanoate (1.2 g, 75%) as a pale yellow liquid. LCMS (ESI, m/z): 287 $[M+H]^+$.

To a solution of methyl 2-((tert-butoxycarbonyl)amino)-3-(2-oxopyrrolidin-1-yl)propanoate (1.15 g, 4.02 mmol, 1.0 eq.) in THF (15 mL) cooled to 0° C. was added 2 M $LiBH_4$ in THF (4.0 mL, 8.00 mmol, 2.0 eq.). The mixture was stirred at rt for 2 h. After cooling to 0° C., the reaction was quenched by addition of cold water (20 mL). The mixture was extracted with 10% MeOH in DCM (2×25 mL). The organic phases were combined, washed with brine (25 mL), dried over $Na_2SO_4$, filtered and concentrated under reduced pressure. The residue was purified by flash chromatography on silica gel (40 g column) using a gradient of MeOH (5 to 10%) in DCM to afford tert-butyl (1-hydroxy-3-(2-oxopyrrolidin-1-yl)propan-2-yl)carbamate (750 mg, 72%) as a white solid. LCMS (ESI, m/z): 259 $[M+H]^+$.

Tert-butyl (1-hydroxy-3-(2-oxopyrrolidin-1-yl)propan-2-yl)carbamate (700 mg) was purified by prep-SFC using the following conditions: Column: Chiralpak IC, 3*25 cm, 5 μm; Mobile Phase A: $CO_2$, Mobile Phase B: IPA; Flow rate: 60 mL/min; Gradient: isocratic 30% B; Column Temperature (° C.): 30; Back Pressure (bar): 100; Wave Length: 214 nm; Sample Solvents: IPA, ACN, DCM and THF (33 mL); Load/Injection: 39.5 mg/injection; Number of Runs: 20. Purification resulted in tert-butyl (S*)-(1-hydroxy-3-(2-oxopyrrolidin-1-yl)propan-2-yl)carbamate (280 mg) as an off-white solid (Chiralpak IC 4.6*250 mm, 5 μm, 30° C. Co-Solvent: IPA, hold 15 min at 25%; Rt: 5.56 min), and tert-butyl (R*)-(1-hydroxy-3-(2-oxopyrrolidin-1-yl)propan-2-yl)carbamate (275 mg) as an off-white solid (Chiralpak IC 4.6*250 mm, 5 μm, 30° C. Co-Solvent: IPA, hold 15 min at 25%; Rt: 9.16 min).

To a solution of tert-butyl (S*)-(1-hydroxy-3-(2-oxopyrrolidin-1-yl)propan-2-yl)carbamate (270 mg, 1.05 mmol, 1.0 eq.) in DCM (5 mL) was added Dess-Martin periodinane (532 mg, 1.26 mmol, 1.2 eq.) and the reaction mixture stirred at rt for 2 h. AcOH (0.18 mL, 3.14 mmol, 3.0 eq.) and isocyanocyclopropane (105 mg, 1.57 mmol, 1.5 eq.) were added and the reaction mixture stirred at rt for 16 h. The reaction mixture was diluted with 10% MeOH in DCM (20 mL) and washed with sat. NaHCO$_3$ (10 mL). The phases were separated. The organic phase was washed with brine (10 mL), dried over Na$_2$SO$_4$, filtered and concentrated under reduced pressure. The residue was purified by flash chromatography on silica gel (24 g column) using a gradient of MeOH (1 to 10%) in DCM to afford (3S*)-3-((tert-butoxycarbonyl)amino)-1-(cyclopropylamino)-1-oxo-4-(2-oxopyrrolidin-1-yl)butan-2-yl acetate (355 mg, 89%) as an off-white solid. LCMS (ESI, m/z): 384 [M+H]$^+$.

To a solution of (3S*)-3-((tert-butoxycarbonyl)amino)-1-(cyclopropylamino)-1-oxo-4-(2-oxopyrrolidin-1-yl)butan-2-yl acetate (330 mg, 0.861 mmol, 1.0 eq.) in THF (5 mL) and water (5 mL) was added LiOH (41 mg, 1.72 mmol, 2.0 eq.), and the mixture was stirred at rt for 2 h. The mixture was diluted with water (5 mL) and extracted with 10% MeOH in DCM (2×10 mL). The organic phases were combined, dried over Na$_2$SO$_4$, filtered and concentrated under reduced pressure. The residue was purified by flash chromatography on silica gel (24 g column) using a gradient of MeOH (1 to 10%) in DCM to afford tert-butyl ((2S*)-4-(cyclopropylamino)-3-hydroxy-4-oxo-1-(2-oxopyrrolidin-1-yl)butan-2-yl)carbamate (270 mg, 84%) as an off-white solid. LCMS (ESI, m/z): 342 [M+H]$^+$.

To a stirred solution of tert-butyl ((2S*)-4-(cyclopropylamino)-3-hydroxy-4-oxo-1-(2-oxopyrrolidin-1-yl)butan-2-yl)carbamate (260 mg, 0.762 mmol, 1.0 eq.) in DCM (5 mL) cooled to 0° C. was added 4N HCl in dioxane (0.70 mL, 2.80 mmol, 4.0 eq.), and the mixture was stirred at rt. The mixture was concentrated under reduced pressure to afford (3S*)-3-amino-N-cyclopropyl-2-hydroxy-4-(2-oxopyrrolidin-1-yl)butanamide hydrochloride (165 mg, crude) as an off-white solid. LCMS (ESI, m/z): 242 [M+H]$^+$.

To a solution of (1S,3aR,6aS)-2-(4-methoxy-1H-indole-2-carbonyl)octahydrocyclopenta[c]pyrrole-1-carboxylic acid (160 mg, 0.487 mmol, 1.0 eq.) in DMF (4 mL) cooled to 0° C. were added EDC·HCl (186 mg, 0.974 mmol, 2.0 eq.), HOAt (66 mg, 0.487 mmol, 1.0 eq.) and NEt$_3$ (0.27 mL, 1.95 mmol, 4.0 eq.). The mixture was stirred at rt for 30 min. (3S*)-3-Amino-N-cyclopropyl-2-hydroxy-4-(2-oxopyrrolidin-1-yl)butanamide hydrochloride (162 mg, 0.585 mmol, 1.2 eq.) was added, and the mixture was stirred at rt for 16 h. The mixture was diluted with water (10 mL) and extracted with 10% MeOH in DCM (3×10 mL). The organic phases were combined, dried over Na$_2$SO$_4$, filtered and concentrated under reduced pressure. The residue was purified by flash chromatography on silica gel (24 g column) using a gradient of MeOH (1 to 10%) in DCM to afford (1S,3aR,6aS)—N-((2S*)-4-(cyclopropylamino)-3-hydroxy-4-oxo-1-(2-oxopyrrolidin-1-yl)butan-2-yl)-2-(4-methoxy-1H-indole-2-carbonyl)octahydrocyclo penta[c]pyrrole-1-carboxamide (140 mg, 52%) as an off-white solid. LCMS (ESI, m/z): 552 [M+H]$^+$.

To a solution of (1S,3aR,6aS)—N-((2S*)-4-(cyclopropylamino)-3-hydroxy-4-oxo-1-(2-oxopyrrolidin-1-yl)butan-2-yl)-2-(4-methoxy-1H-indole-2-carbonyl)octahydro cyclopenta[c]pyrrole-1-carboxamide (130 mg, 0.235 mmol, 1.0 eq.) in DCM (5 mL) was added Dess-Martin periodinane (150 mg, 0.353 mmol, 1.5 eq.), and the mixture was stirred at rt for 2 h. The mixture was diluted with 10% MeOH in DCM (20 mL) and washed with sat. Na$_2$S$_2$O$_3$ (5 mL). The phases were separated. The organic phase was washed with sat. NaHCO$_3$ (5 mL), dried over Na$_2$SO$_4$, filtered and concentrated under reduced pressure. The residue was purified by prep-HPLC (Column: X-SELECT-C18, 19×150 mm, 5 um; Mobile Phase A: 10 mM NH$_4$HCO$_3$ in water, Mobile Phase B: ACN; Flow rate: 17 mL/min; Gradient: 5% B to 55% B in 8 min) to afford (1S,3aR,6aS)—N—((S*)-4-(cyclopropylamino)-3,4-dioxo-1-(2-oxopyrrolidin-1-yl)butan-2-yl)-2-(4-methoxy-1H-indole-2-carbonyl)octahydrocyclopenta[c]pyrrole-1-carboxamide (50 mg, 39%) as an off-white solid. $^1$H NMR (500 MHz, 363K, DMSO-d$_6$) δ ppm 11.18 (s, 1H), 8.23-8.27 (m, 1H), 8.11 (br s, 1H), 7.03-7.11 (m, 2H), 6.88 (br s, 1H), 6.49 (d, 1H), 5.13-5.16 (m, 1H), 4.58-4.61 (m, 1H), 4.01-4.09 (m, 1H), 3.88 (s, 3H), 3.70-3.74 (m, 1H), 3.54-3.57 (m, 2H), 3.31-3.34 (m, 2H), 2.64-2.72 (m, 3H), 2.08-2.12 (m, 2H), 1.70-1.92 (m, 5H), 1.48-1.59 (m, 3H), 0.59-0.65 (m, 4H). LCMS (ESI, m/z): 550 [M+H]$^+$.

113B

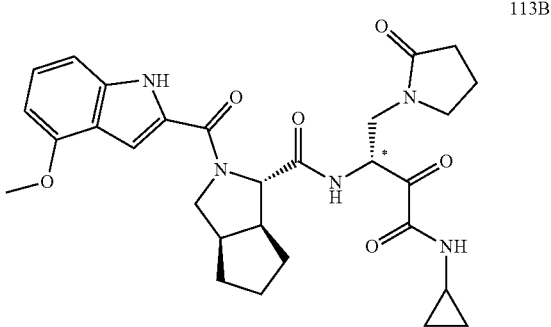 [SMILES: COc1cccc2[nH]c(C(=O)N3C[C@@H]4CCC[C@@H]4[C@H]3C(=O)N[C@H](CN3CCCC3=O)C(=O)C(=O)NC3CC3)cc12]

Compound 113B was prepared similarly as described for Compound 113A using tert-butyl (R*)-(1-hydroxy-3-(2-oxopyrrolidin-1-yl)propan-2-yl)carbamate in place of tert-butyl (S*)-(1-hydroxy-3-(2-oxopyrrolidin-1-yl)propan-2-yl)carbamate. LCMS (ESI, m/z): 550 [M+H]$^+$.

Example 115

COMPOUND 114

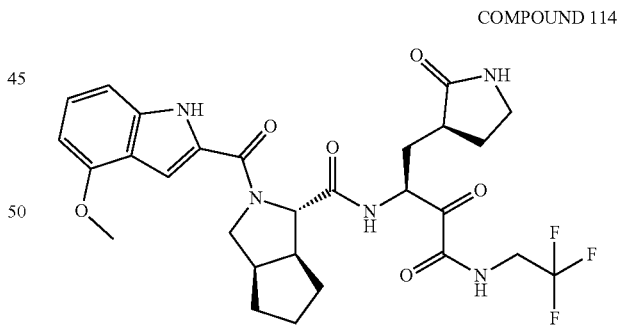

Compound 121 was prepared similarly as described for Compound 16 using (3S)-3-amino-2-hydroxy-4-((S)-2-oxopyrrolidin-3-yl)-N-(2,2,2-trifluoroethyl)butanamide hydrochloride in place of (3S)-3-amino-N-benzyl-2-hydroxy-4-[(3S)-2-oxopyrrolidin-3-yl]butanamide hydrochloride. LCMS (ESI, m/z): 592 [M+H]$^+$.

(3S)-3-Amino-2-hydroxy-4-((S)-2-oxopyrrolidin-3-yl)-N-(2,2,2-trifluoroethyl)butanamide hydrochloride was prepared similarly as described for Intermediate 1 using 1,1,1-trifluoro-2-isocyanoethane in place of (isocyanomethyl)benzene.

Example 116
COMPOUND 115
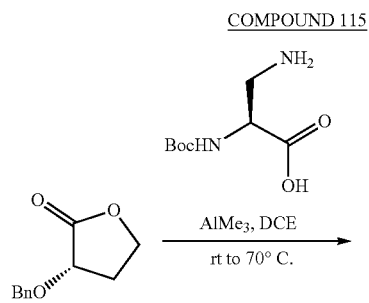
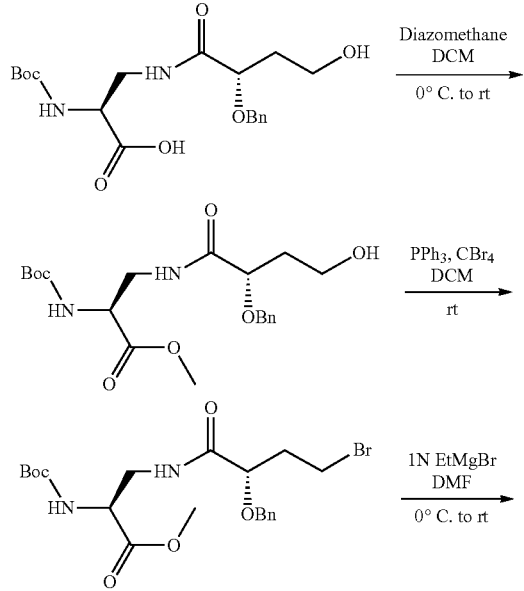
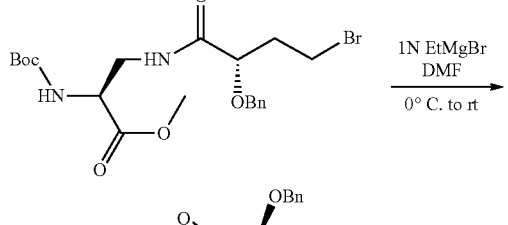
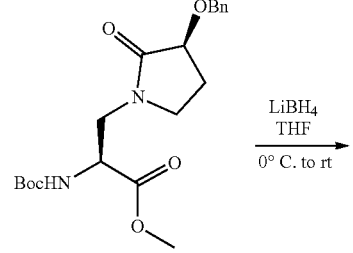
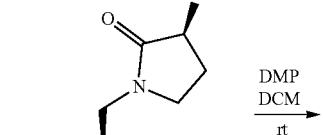
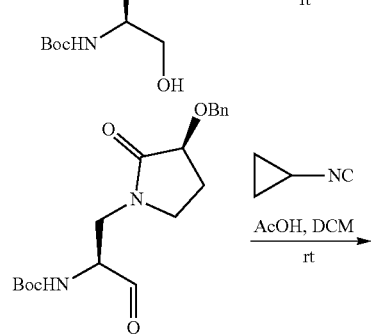
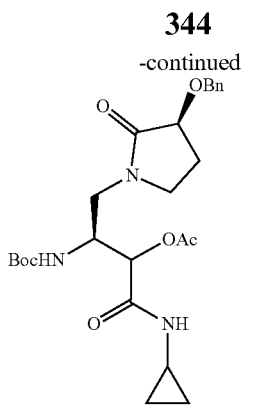
-continued
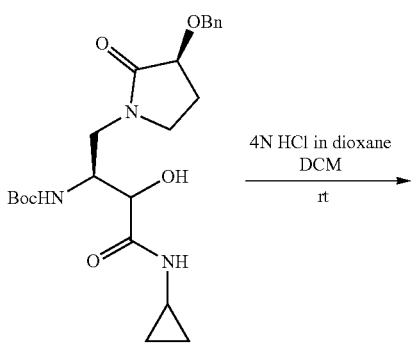
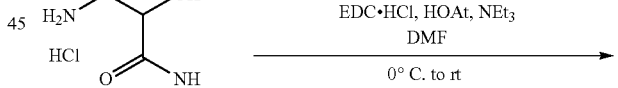
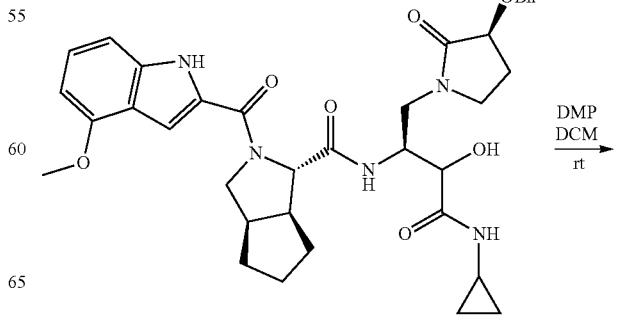

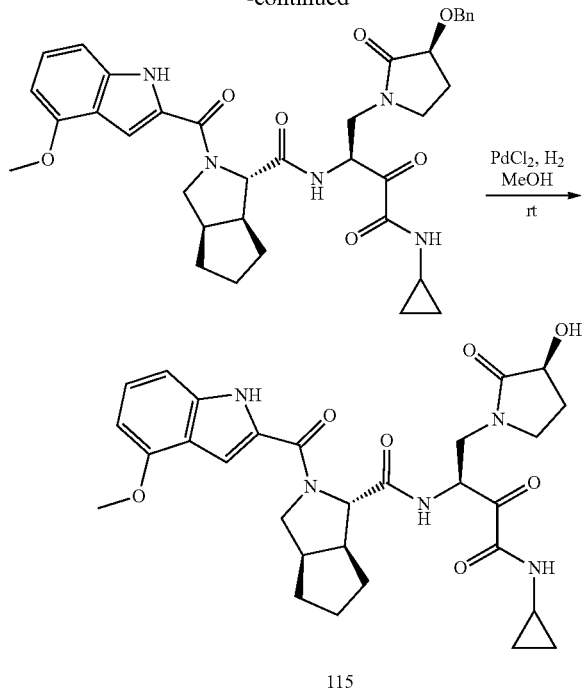

115

To a solution of (S)-3-amino-2-((tert-butoxycarbonyl)amino)propanoic acid (11 g, 54.7 mmol, 1.5 eq.) in DCE (50 mL) was added dropwise 2M AlMe$_3$ in toluene (36.4 mL, 72.8 mmol, 2.0 eq.), and the mixture was stirred at rt for 40 min. A solution (S)-3-(benzyloxy)dihydrofuran-2(3H)-one (Liu et al., Org. Lett. (2012) 14(14):3648-3651) (7.0 g, 36.5 mmol, 1.0 eq.) in DCE (20 mL) was added, and the mixture was heated at 70° C. overnight. After cooling to 0° C., the reaction was quenched by addition of 1N HCl until pH~5. The mixture was filtered through Celite. The solids were washed with 10% MeOH in DCM (3×50 mL). The phases of the filtrate were separated. The organic phase was dried over Na$_2$SO$_4$, filtered and concentrated under reduced pressure. The residue was purified by flash chromatography on silica gel using a gradient of MeOH (1 to 10%) in DCM to provide (S)-3-((S)-2-(benzyloxy)-4-hydroxybutanamido)-2-((tert-butoxycarbonyl)amino)propanoic acid (7.0 g, 48%) as a pale brown liquid. $^1$H NMR (400 MHz, DMSO-d$_6$) δ ppm 12.63 (d, 1H), 7.95 (br s, 1H), 7.16-7.35 (m, 5H), 7.06 (d, 1H), 4.54 (d, 1H), 4.47 (s, 1H), 4.34 (d, 1H), 4.05-4.08 (m, 2H), 3.86 (s, 1H), 3.46 (s, 3H), 1.66-1.75 (m, 2H), 1.35 (s, 9H).

To a solution of (S)-3-((S)-2-(benzyloxy)-4-hydroxybutanamido)-2-((tert-butoxycarbonyl)amino)propanoic acid (7.0 g, 17.7 mmol, 1.0 eq.) in DCM (70 mL) cooled to 0° C. was added 0.5M diazomethane in ether (90 mL, 45.0 mmol, 2.5 eq.). The mixture was stirred at rt for 5 h and then concentrated under reduced pressure. The residue was purified by flash chromatography on silica gel (80 g column) using a gradient of MeOH (1 to 10%) in DCM to afford methyl (S)-3-((S)-2-(benzyloxy)-4-hydroxybutanamido)-2-((tert-butoxycarbonyl)amino)propanoate (7.0 g, 97%) as a pale yellow liquid. $^1$H NMR (400 MHz, DMSO-d$_6$) δ ppm 8.00-8.05 (m, 1H), 7.36 (d, 1H), 7.26-7.32 (m, 5H), 4.53 (d, 1H), 4.48 (t, 1H), 4.34 (d, 1H), 4.14 (d, 2H), 3.83-3.87 (m, 1H), 3.59 (s, 3H), 3.41-3.49 (m, 3H), 1.66-1.75 (m, 2H), 1.36 (s, 9H).

To a solution of methyl (S)-3-((S)-2-(benzyloxy)-4-hydroxybutanamido)-2-((tert-butoxycarbonyl)amino)propanoate (7.0 g, 17.1 mmol, 1.0 eq.) in DCM (70 mL) were added portionwise triphenylphosphine (6.7 g, 25.6 mmol, 1.5 eq.) and CBr$_4$ (8.4 g, 25.6 mmol, 1.5 eq.). The mixture was stirred at rt for 1 h and then concentrated under reduced pressure. The residue was purified by flash chromatography on silica gel (80 g column) using a gradient of EA (40 to 60%) in PE to afford methyl (S)-3-((S)-2-(benzyloxy)-4-bromobutanamido)-2-((tert-butoxycarbonyl)amino)propanoate (6.5 g, 81%) as a pale brown liquid. LCMS (ESI, m/z): 473 [M+H]$^+$.

To a solution of methyl (S)-3-((S)-2-(benzyloxy)-4-bromobutanamido)-2-((tert-butoxycarbonyl)amino)propanoate (2.0 g, 4.24 mmol, 1.0 eq.) in DMF (20 mL) cooled to 0° C. was added dropwise 1M EtMgBr in THF (8.5 mL, 8.50 mmol, 2.0 eq.), and the mixture was stirred at rt for 5 h. After cooling to 0° C., the reaction was quenched by the addition of ice:water (20 mL). The mixture was extracted with EA (2×20 mL). The organic phases were combined, washed with brine (2×20 mL), dried over Na$_2$SO$_4$, filtered and concentrated under reduced pressure. The residue was purified by flash chromatography on silica gel (40 g column) using a gradient of EA (50 to 70%) in PE to afford methyl (S)-3-((S)-3-(benzyloxy)-2-oxopyrrolidin-1-yl)-2-((tert-butoxycarbonyl)amino)propanoate (1.3 g, 76%) as a pale yellow liquid. LC-MS (ESI, m/z): 337 [M-tBu+2H]$^+$.

To a solution of methyl (S)-3-((S)-3-(benzyloxy)-2-oxopyrrolidin-1-yl)-2-((tert-butoxycarbonyl)amino)propanoate (1.3 g, 3.32 mmol, 1.0 eq.) in THF (15 mL) cooled to 0° C. was added dropwise 2M LiBH$_4$ in THF (3.3 mL, 6.60 mmol, 2.0 eq.). The mixture was stirred at rt for 2 h. After cooling to 0° C., the reaction was quenched by the addition of ice:water (20 mL), and the mixture was extracted with EA (2×20 mL). The organic phases were combined, dried over Na$_2$SO$_4$, filtered and concentrated under reduced pressure. The residue was purified by flash chromatography on silica gel (40 g column) using a gradient of MeOH (1 to 10%) in DCM to afford tert-butyl ((S)-1-((S)-3-(benzyloxy)-2-oxopyrrolidin-1-yl)-3-hydroxypropan-2-yl)carbamate (1.0 g, 83%) as a white solid. LC-MS (ESI, m/z): 365 [M+H]$^+$.

To a solution of tert-butyl ((S)-1-((S)-3-(benzyloxy)-2-oxopyrrolidin-1-yl)-3-hydroxypropan-2-yl)carbamate (1.0 g, 2.76 mmol, 1.0 eq.) in DCM (10 mL) was added Dess-Martin periodinane (1.7 g, 4.14 mmol, 1.0 eq.). The mixture was stirred at rt for 1 h. AcOH (0.49 mL, 8.28 mmol, 3.0 eq.) and cyclopropyl isocyanide (0.37 mL, 5.54 mmol, 2.0 eq.) were added, and the mixture was stirred at rt for 16 h. The mixture was diluted with EA (20 mL) and washed with sat. NaHCO$_3$ (20 mL). The phases were separated. The organic phase was washed with brine (50 mL), dried over Na$_2$SO$_4$, filtered and concentrated under reduced pressure. The residue was purified by flash chromatography on silica gel (40 g column) using a gradient of MeOH (1 to 10%) in DCM to afford (3S)-4-((S)-3-(benzyloxy)-2-oxopyrrolidin-1-yl)-3-((tert-butoxycarbonyl)amino)-1-(cyclopropylamino)-1-oxobutan-2-yl acetate (1.0 g, 77%) as an off-white solid. LC-MS (ESI, m/z): 490 [M+H]$^+$.

To a solution of (3S)-4-((S)-3-(benzyloxy)-2-oxopyrrolidin-1-yl)-3-((tert-butoxycarbonyl)amino)-1-(cyclopropylamino)-1-oxobutan-2-yl acetate (1.0 g, 2.04 mmol, 1.0 eq.) in THF (5 mL) and water (5 mL) was added LiOH (94 mg, 4.08 mmol, 2.0 eq.). The mixture was stirred at rt for 2 h. The mixture was diluted with water (10 mL) and extracted with EA (2×10 mL). The organic phases were combined, washed with brine (20 mL), dried over Na$_2$SO$_4$, filtered and concentrated under reduced pressure. The residue was purified by flash chromatography on silica gel (24 g column) using a gradient of MeOH (1 to 10%) in DCM to afford tert-butyl ((2S)-1-((S)-3-(benzyloxy)-2-oxopyrrolidin-1-yl)-4-(cyclopropylamino)-3-hydroxy-4-oxobutan-2-yl)carbamate (700 mg, 74%) as an off-white solid. LC-MS (ESI, m/z): 448 [M+H]$^+$.

To a solution of tert-butyl ((2S)-1-((S)-3-(benzyloxy)-2-oxopyrrolidin-1-yl)-4-(cyclopropylamino)-3-hydroxy-4-oxobutan-2-yl)carbamate (700 mg, 1.56 mmol, 1.0 eq.) in DCM (10 mL) cooled to 0° C. was added 4N HCl in dioxane (1.56 mL, 6.26 mmol, 4.0 eq.). The mixture was stirred at rt for 16 h and then concentrated under reduced pressure to afford (3S)-3-amino-4-((S)-3-(benzyloxy)-2-oxopyrrolidin-1-yl)-N-cyclopropyl-2-hydroxybutanamide hydrochloride (500 mg, crude) as an off-white solid. LC-MS (ESI, m/z): 348 [M+H]$^+$.

To a solution of (3S)-3-amino-4-((S)-3-(benzyloxy)-2-oxopyrrolidin-1-yl)-N-cyclopropyl-2-hydroxybutanamide hydrochloride (300 mg, 0.787 mmol, 1.0 eq.) and (1S,3aR,6aS)-2-(4-methoxy-1H-indole-2-carbonyl)octahydrocyclopenta[c]pyrrole-1-carboxylic acid (309 mg, 0.944 mmol, 1.2 eq.) in DMF (5 mL) cooled to 0° C. were added EDC·HCl (300 mg, 1.57 mmol, 2.0 eq.), HOAt (107 mg, 0.787 mmol, 1.0 eq.) and NEt$_3$ (0.33 mL, 2.36 mmol, 3.0 eq.). The mixture was stirred at rt for 16 h. The mixture was diluted with water (10 mL) and extracted with EA (2×10 mL). The organic phases were combined, washed with brine (20 mL), dried over Na$_2$SO$_4$, filtered and concentrated under reduced pressure. The residue was purified by flash chromatography on silica gel (24 g column) using a gradient of MeOH (1 to 10%) in DCM to afford (1S,3aR,6aS)—N-((2S)-1-((S)-3-(benzyloxy)-2-oxopyrrolidin-1-yl)-4-(cyclopropylamino)-3-hydroxy-4-oxobutan-2-yl)-2-(4-methoxy-1H-indole-2-carbonyl)octahydrocyclopenta[c]pyrrole-1-carboxamide (300 mg, 58%) as an off-white solid. LC-MS (ESI, m/z): 658 [M+H]$^+$.

To a solution of (1S,3aR,6aS)—N-((2S)-1-((S)-3-(benzyloxy)-2-oxopyrrolidin-1-yl)-4-(cyclopropylamino)-3-hydroxy-4-oxobutan-2-yl)-2-(4-methoxy-1H-indole-2-carbonyl)octahydrocyclopenta[c]pyrrole-1-carboxamide (200 mg, 0.304 mmol, 1.0 eq.) in DCM (5 mL) was added Dess-Martin periodinane (193 mg, 0.456 mmol, 1.5 eq.). The mixture was stirred at rt for 2 h. The mixture was washed with sat. Na$_2$S$_2$O$_3$ (5 mL), and the phases were separated. The organic phase was washed with sat. Na$_2$S$_2$O$_3$ (2×5 mL), sat. NaHCO$_3$ (3×5 mL) and brine (3×5 mL), dried over Na$_2$SO$_4$, filtered and concentrated under reduced pressure. The residue was purified by flash chromatography on silica gel (24 g column) using a gradient of MeOH (1 to 10%) in DCM to afford (1S,3aR,6aS)—N—((S)-1-((S)-3-(benzyloxy)-2-oxopyrrolidin-1-yl)-4-(cyclopropylamino)-3,4-dioxobutan-2-yl)-2-(4-methoxy-1H-indole-2-carbonyl)octahydrocyclopenta[c]pyrrole-1-carboxamide (180 mg, 90%) as an off-white solid. LC-MS (ESI, m/z): 656 [M+H]$^+$.

To a solution of (1S,3aR,6aS)—N—((S)-1-((S)-3-(benzyloxy)-2-oxopyrrolidin-1-yl)-4-(cyclopropylamino)-3,4-dioxobutan-2-yl)-2-(4-methoxy-1H-indole-2-carbonyl)octahydrocyclopenta[c]pyrrole-1-carboxamide (150 mg, 0.133 mmol, 1.0 eq.) in MeOH (5 mL) was added PdCl$_2$ (61 mg, 0.343 mmol, 1.5 eq.). The mixture was stirred at rt for 1 h under hydrogen atmosphere. The mixture was filtered through Celite, and the filtrate was concentrated under reduced pressure. The residue was purified by flash chromatography on silica gel (12 g column) using a gradient of MeOH (1 to 10%) in DCM to afford (1S,3aR,6aS)—N—((S)-4-(cyclopropylamino)-1-((S)-3-hydroxy-2-oxopyrrolidin-1-yl)-3,4-dioxobutan-2-yl)-2-(4-methoxy-1H-indole-2-carbonyl)octahydrocyclopenta[c]pyrrole-1-carboxamide (100 mg, 77%) as an off-white solid. LCMS (ESI, m/z): 566 [M+H]$^+$.

Example 117

COMPOUND 116A AND 116B

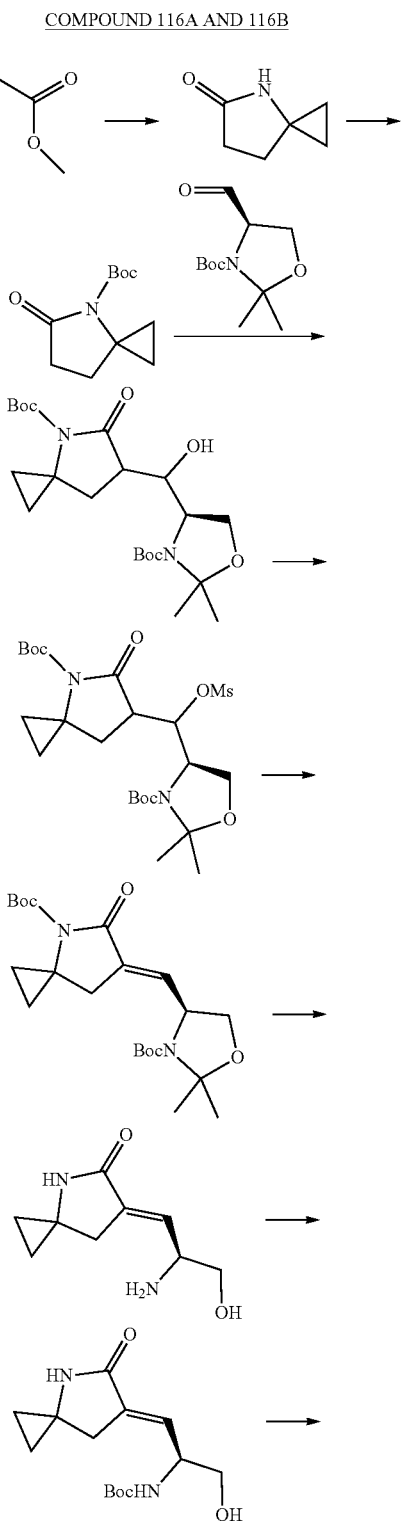

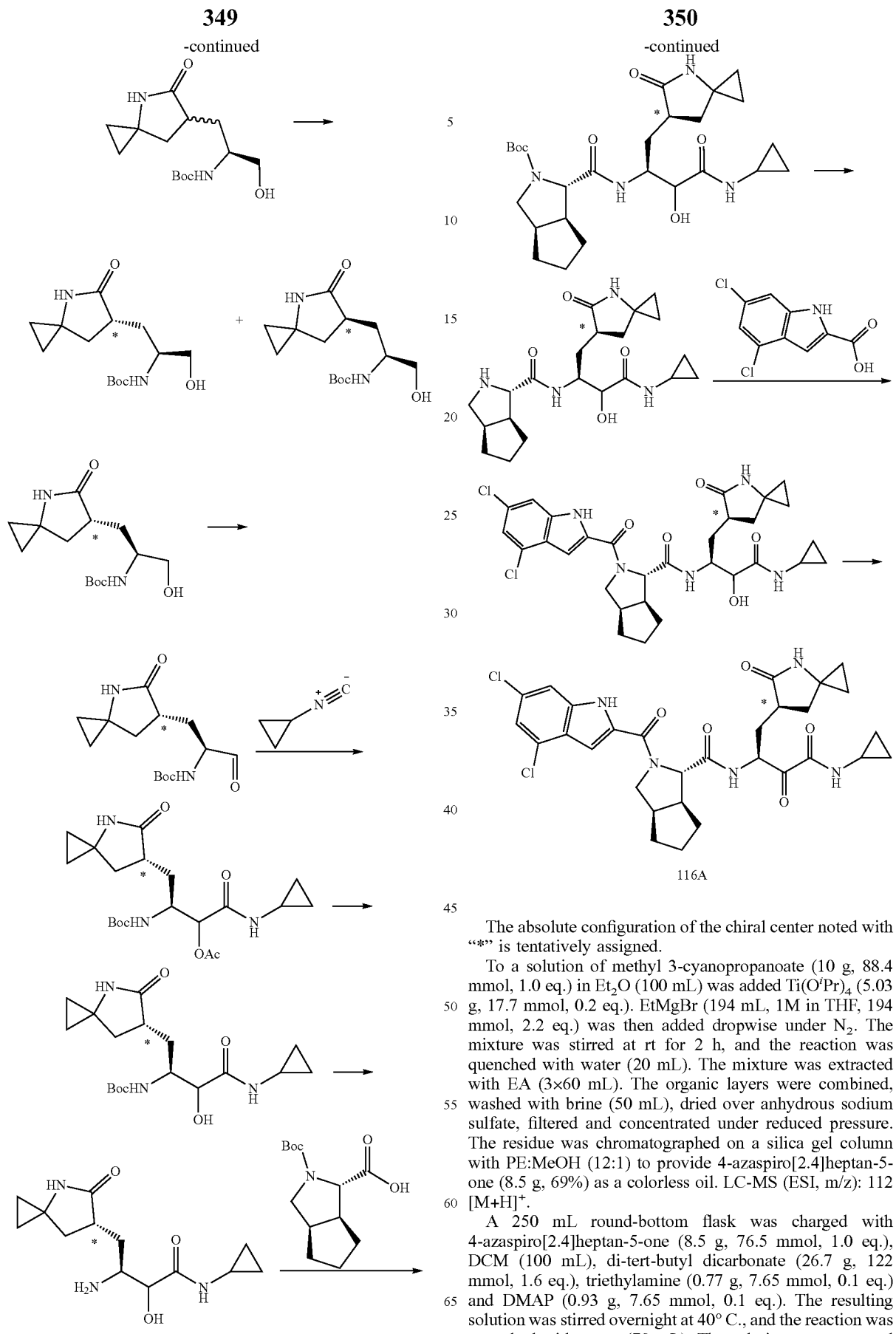

The absolute configuration of the chiral center noted with "*" is tentatively assigned.

To a solution of methyl 3-cyanopropanoate (10 g, 88.4 mmol, 1.0 eq.) in Et$_2$O (100 mL) was added Ti(O$^i$Pr)$_4$ (5.03 g, 17.7 mmol, 0.2 eq.). EtMgBr (194 mL, 1M in THF, 194 mmol, 2.2 eq.) was then added dropwise under N$_2$. The mixture was stirred at rt for 2 h, and the reaction was quenched with water (20 mL). The mixture was extracted with EA (3×60 mL). The organic layers were combined, washed with brine (50 mL), dried over anhydrous sodium sulfate, filtered and concentrated under reduced pressure. The residue was chromatographed on a silica gel column with PE:MeOH (12:1) to provide 4-azaspiro[2.4]heptan-5-one (8.5 g, 69%) as a colorless oil. LC-MS (ESI, m/z): 112 [M+H]$^+$.

A 250 mL round-bottom flask was charged with 4-azaspiro[2.4]heptan-5-one (8.5 g, 76.5 mmol, 1.0 eq.), DCM (100 mL), di-tert-butyl dicarbonate (26.7 g, 122 mmol, 1.6 eq.), triethylamine (0.77 g, 7.65 mmol, 0.1 eq.) and DMAP (0.93 g, 7.65 mmol, 0.1 eq.). The resulting solution was stirred overnight at 40° C., and the reaction was quenched with water (70 mL). The solution was extracted with DCM (3×100 mL). The organic layers were combined, washed with brine (80 mL), dried over anhydrous sodium sulfate, filtered and concentrated under reduced pressure. The residue was chromatographed on a silica gel column with EA:PE (1:12) to provide tert-butyl 5-oxo-4-azaspiro[2.4]heptane-4-carboxylate (11 g, 58%) as a white solid. LC-MS (ESI, m/z): 212 [M+H]$^+$.

A 500 mL round-bottom flask was charged with tert-butyl 5-oxo-4-azaspiro[2.4]heptane-4-carboxylate (11 g, 52.1 mmol, 1.0 eq.) and THF (150 mL). The solution was cooled to −78° C. and LiHMDS (62.5 mL, 1M in THF, 62.5 mmol, 1.2 eq.) was added. The mixture was stirred for 1 h at −78° C. and a solution of tert-butyl (4R)-4-formyl-2,2-dimethyl-1,3-oxazolidine-3-carboxylate (17.9 g, 78.1 mmol, 1.5 eq.) in THF (50 mL) under Ar was added. Stirring was continued at −78° C. for 1 h. The reaction was quenched with sat. ammonium chloride solution (100 mL). The solution was extracted with EA (3×200 mL). The organic layers were combined, washed with brine (200 mL), dried over anhydrous sodium sulfate, filtered and concentrated under reduced pressure. The residue was chromatographed on a silica gel column with EA:PE (1:8) to provide tert-butyl (4R)-4-((4-(tert-butoxycarbonyl)-5-oxo-4-azaspiro[2.4]heptan-6-yl)(hydroxy)methyl)-2,2-dimethyloxazolidine-3-carboxylate (19.7 g, 69%) as a colorless oil. LC-MS (ESI, m/z): 441 [M+H]$^+$.

A 500 mL round-bottom flask was charged with tert-butyl (4R)-4-((4-(tert-butoxycarbonyl)-5-oxo-4-azaspiro[2.4]heptan-6-yl)(hydroxy)methyl)-2,2-dimethyloxazolidine-3-carboxylate (19.7 g, 44.7 mmol, 1.0 eq.), DCM (250 mL), triethylamine (27.2 g, 268 mmol, 6.0 eq.) and MsCl (20.5 g, 179 mmol, 4.0 eq.). The mixture was stirred overnight at rt, and the reaction was quenched with water (100 mL). The solution was extracted with DCM (4×150 mL). The organic layers were combined, washed with brine (100 mL), dried over anhydrous sodium sulfate, filtered and concentrated under reduced pressure to provide tert-butyl (4R)-4-((4-(tert-butoxycarbonyl)-5-oxo-4-azaspiro[2.4]heptan-6-yl)((methylsulfonyl)oxy)methyl)-2,2-dimethyloxazolidine-3-carboxylate (22 g, crude) as an orange oil. LC-MS (ESI, m/z): 519 [M+H]$^+$.

A 500 mL round-bottom flask was charged with tert-butyl (4R)-4-((4-(tert-butoxycarbonyl)-5-oxo-4-azaspiro[2.4]heptan-6-yl)((methylsulfonyl)oxy)methyl)-2,2-dimethyloxazolidine-3-carboxylate (22 g, 42.4 mmol, 1.0 eq.), DCM (200 mL) and DBU (14.2 g, 93.3 mmol, 2.2 eq.). The mixture was stirred overnight at rt, and the reaction was quenched with water (80 mL). The solution was extracted with DCM (3×100 mL). The organic layers were combined, washed with brine (80 mL), dried over anhydrous sodium sulfate, filtered and concentrated under reduced pressure. The residue was chromatographed on a silica gel column with EA:PE (1:12) to provide tert-butyl 6-{[(4S)-3-(tert-butoxycarbonyl)-2,2-dimethyl-1,3-oxazolidin-4-yl]methylidene}-5-oxo-4-azaspiro[2.4]heptane-4-carboxylate (11.3 g, 57%) as a colorless oil. LC-MS (ESI, m/z): 423 [M+H]$^+$.

A 250 mL vial was charged with tert-butyl 6-{[(4S)-3-(tert-butoxycarbonyl)-2,2-dimethyl-1,3-oxazolidin-4-yl]methylidene}-5-oxo-4-azaspiro[2.4]heptane-4-carboxylate (11.3 g, 26.7 mmol, 1.0 eq.), 4-methylbenzenesulfonic acid (5.53 g, 32.1 mmol, 1.2 eq.) and MeOH (120 mL). The mixture was stirred overnight at rt, and then concentrated under reduced pressure to provide 6-[(2S)-2-amino-3-hydroxypropylidene]-4-azaspiro[2.4]heptan-5-one (5.8 g, crude) as an orange oil. LC-MS (ESI, m/z): 183 [M+H]$^+$.

To a solution of 6-[(2S)-2-amino-3-hydroxypropylidene]-4-azaspiro[2.4]heptan-5-one (5.8 g, 31.829 mmol, 1.00 eq.) in DCM (90 mL) was added triethylamine (25.8 g, 255 mmol, 8.0 eq.) and di-tert-butyl dicarbonate (20.8 g, 95.5 mmol, 3.0 eq.). The mixture was stirred at rt overnight, and the reaction was quenched with water (30 mL). The mixture was extracted with CDCl$_3$:isopropyl alcohol=3:1 (3×50 mL). The organic layers were combined, dried over anhydrous sodium sulfate, filtered and concentrated under reduced pressure. The residue was chromatographed on a silica gel column with MeOH:DCM (1:25) to provide tert-butyl N-[(2S)-1-hydroxy-3-[(6E)-5-oxo-4-azaspiro[2.4]heptan-6-ylidene]propan-2-yl]carbamate (3.9 g, 39%) as a brown yellow solid. LCMS (ESI, m/z): 283 [M+H]$^+$.

To a solution of tert-butyl N-[(2S)-1-hydroxy-3-[5-oxo-4-azaspiro[2.4]heptan-6-ylidene]propan-2-yl]carbamate (3.9 g, 13.8 mmol, 1.0 eq.) in THF (30 mL) and MeOH (90 mL) was added NiCl$_2$·6H$_2$O (23 g, 96.7 mmol, 7.0 eq.). NaBH$_4$ (11 g, 290 mmol, 21.0 eq.) was added in several portions at 0° C. The mixture was stirred at rt overnight, and the reaction was quenched with water (30 mL). The mixture was extracted with CDCl$_3$:isopropyl alcohol=3:1 (3×60 mL). The organic layers were combined, dried over anhydrous sodium sulfate, filtered and concentrated under reduced pressure. The residue was chromatographed on a C18 column with MeCN:H$_2$O (4:1) to provide tert-butyl N-[(2S)-1-hydroxy-3-{5-oxo-4-azaspiro[2.4]heptan-6-yl}propan-2-yl]carbamate (1.7 g, 39%) as a brown yellow solid. LCMS (ESI, m/z): 285 [M+H]$^+$.

Tert-butyl N-[(2S)-1-hydroxy-3-{5-oxo-4-azaspiro[2.4]heptan-6-yl}propan-2-yl]carbamate (1.7 g) was purified by SFC using the following gradient conditions: Column: NB-Lux 5 um i-Cellulose-5, 2.12*25 cm, 5 μm; Mobile Phase A: CO$_2$, Mobile Phase B: MeOH (0.1% 2M NH$_3$-MeOH); Flow rate: 100 mL/min; Gradient: isocratic 25% B; Column Temperature (° C.): 35; Back Pressure (bar): 100; Wave Length: 220 nm; RT1 (min): 3.37; RT2 (min): 4.02; Sample Solvent: MeOH-Preparative; Injection Volume: 1 mL; Number Of Runs: 40. Purification resulted in 590 mg of first eluding tert-butyl ((S)-1-hydroxy-3-((R*)-5-oxo-4-azaspiro[2.4]heptan-6-yl)propan-2-yl)carbamate as a brown yellow solid and 640 mg of last eluding tert-butyl ((S)-1-hydroxy-3-((S*)-5-oxo-4-azaspiro[2.4]heptan-6-yl)propan-2-yl)carbamate as a brown yellow solid.

To a solution of tert-butyl ((S)-1-hydroxy-3-((R*)-5-oxo-4-azaspiro[2.4]heptan-6-yl)propan-2-yl)carbamate (540 mg, 1.9 mmol, 1.0 eq.) in DMSO (10 mL) was added IBX (1.6 g, 5.7 mmol, 3.0 eq.). The mixture was stirred at rt overnight, and the reaction was quenched with sodium bicarbonate solution (4 mL). The solution was extracted with CDCl$_3$:isopropyl alcohol=3:1 (3×15 mL). The organic layers were combined, washed with brine (3×10 mL), dried over anhydrous sodium sulfate, filtered and concentrated under reduced pressure to provide tert-butyl N-[(2S)-1-oxo-3-[(6R*)-5-oxo-4-azaspiro[2.4]heptan-6-yl]propan-2-yl]carbamate (480 mg, crude) as an off-white solid. LC-MS (ESI, m/z): 283 [M+H]$^+$.

To a solution of tert-butyl N-[(2S)-1-oxo-3-[(6R*)-5-oxo-4-azaspiro[2.4]heptan-6-yl]propan-2-yl]carbamate (540 mg, 1.93 mmol, 1.0 eq.) in DCM (8 mL) was added isocyanocyclopropane (257 mg, 3.83 mmol, 2.0 eq.) and AcOH (345 mg, 5.74 mmol, 3.0 eq.) at 0° C. The mixture was stirred overnight at rt. The mixture was concentrated under reduced pressure to provide (3S)-3-((tert-butoxycarbonyl)amino)-1-(cyclopropylamino)-1-oxo-4-((R*)-5-oxo-4-azaspiro[2.4]heptan-6-yl)butan-2-yl acetate (440 mg, crude) as a brown oil. LC-MS (ESI, m/z): 410 [M+H]$^+$.

To a solution of (3S)-3-((tert-butoxycarbonyl)amino)-1-(cyclopropylamino)-1-oxo-4-((R*)-5-oxo-4-azaspiro[2.4]

heptan-6-yl)butan-2-yl acetate (440 mg, 1.08 mmol, 1.0 eq.) in THF (6 mL) was added LiOH (129 mg, 5.38 mmol, 5.0 eq.) in H$_2$O (6 mL) at 0° C. The mixture was stirred at rt for 2 h, and the reaction was quenched with hydrochloric acid (4 mL, 2 mol/L). The solution was extracted with EA (3×10 mL). The organic layers were combined, dried over anhydrous sodium sulfate, filtered and concentrated under reduced pressure. The residue was chromatographed on a silica gel column with MeOH:DCM (1:18) to provide tert-butyl ((2S)-4-(cyclopropylamino)-3-hydroxy-4-oxo-1-((R*)-5-oxo-4-azaspiro[2.4]heptan-6-yl)butan-2-yl)carbamate (320 mg, 73%) as a brown yellow solid. LCMS (ESI, m/z): 368 [M+H]$^+$.

To a solution of tert-butyl N-[(2S)-1-(cyclopropylcarbamoyl)-1-hydroxy-3-[(6R*)-5-oxo-4-azaspiro[2.4]heptan-6-yl]propan-2-yl]carbamate (300 mg, 0.82 mmol, 1.0 eq.) in hydrochloric acid (6 mL, 4 mol/L in dioxane) was stirred at rt for 1 h and then concentrated under reduced pressure to provide (3S)-3-amino-N-cyclopropyl-2-hydroxy-4-[(6R*)-5-oxo-4-azaspiro[2.4]heptan-6-yl]butanamide (220 mg, crude) as a brown oil. LC-MS (ESI, m/z): 268 [M+H]$^+$.

To a solution of (3S)-3-amino-N-cyclopropyl-2-hydroxy-4-[(6R*)-5-oxo-4-azaspiro[2.4]heptan-6-yl]butanamide (200 mg, 0.75 mmol, 1.0 eq.) in DMF (4 mL) was added (1S,3aR,6aS)-2-(tert-butoxycarbonyl)-hexahydro-1H-cyclopenta[c]pyrrole-1-carboxylic acid (287 mg, 1.12 mmol, 1.5 eq.), 1-Methylimidazole (307 mg, 3.74 mmol, 5.0 eq.) and N,N,N,N-Tetramethylchloroformamidinium hexafluorophosphate (315 mg, 1.12 mmol, 1.5 eq.). The mixture was stirred at 0° C. for 2 h, and the reaction was quenched with water (3 mL). The mixture was extracted with EA (3×10 mL). The organic layers were combined, washed with brine (3×10 mL), dried over anhydrous sodium sulfate, filtered and concentrated under reduced pressure. The residue was chromatographed on a silica gel column with DCM:MeOH (16:1) to provide tert-butyl (1S,3aR,6aS)-1-(((2S)-4-(cyclopropylamino)-3-hydroxy-4-oxo-1-((R*)-5-oxo-4-azaspiro[2.4]heptan-6-yl)butan-2-yl)carbamoyl)hexahydrocyclopenta[c]pyrrole-2(1H)-carboxylate (320 mg, 72%) as a brown yellow solid. LC-MS (ESI, m/z): 505 [M+H]$^+$.

To a solution of tert-butyl (1S,3aR,6aS)-1-{[(2S)-1-(cyclopropylcarbamoyl)-1-hydroxy-3-[(6R*)-5-oxo-4-azaspiro[2.4]heptan-6-yl]propan-2-yl]carbamoyl}-hexahydro-1H-cyclopenta[c]pyrrole-2-carboxylate (160 mg, 0.32 mmol, 1.00 eq.) in DCM (3 mL) was added TFA (1 mL). The mixture was stirred at rt for 1 h and then concentrated under reduced pressure to provide (3S)-3-[(1S,3aR,6aS)-octahydrocyclopenta[c]pyrrol-1-ylformamido]-N-cyclopropyl-2-hydroxy-4-[(6R*)-5-oxo-4-azaspiro[2.4]heptan-6-yl]butanamide (130 mg, crude) as a brown oil. LC-MS (ESI, m/z): 405 [M+H]$^+$.

To a solution of 4,6-dichloro-1H-indole-2-carboxylic acid (81.3 mg, 0.35 mmol, 1.1 eq.) in DMF (4 mL) was added N,N,N',N'-Tetramethyl-O-(7-azabenzotriazol-1-yl)uronium hexafluorophospate (134 mg, 0.35 mmol, 1.1 eq.) and N,N-diisopropylethylamine (291 mg, 2.25 mmol, 7.0 eq.). The mixture was stirred at 0° C. for 30 min and (3S)-3-[(1S,3aR,6aS)-octahydrocyclopenta[c]pyrrol-1-ylformamido]-N-cyclopropyl-2-hydroxy-4-[(6R*)-5-oxo-4-azaspiro[2.4]heptan-6-yl]butanamide (130 mg, 0.32 mmol, 1.0 eq.) was added. The mixture was stirred at rt for 2 h, and the reaction was quenched with water (3 mL). The mixture was extracted with EA (3×10 mL). The organic layers were combined, dried over anhydrous sodium sulfate, filtered and concentrated under reduced pressure. The residue was chromatographed on a silica gel column with DCM:MeOH (12:1) to provide (1S,3aR,6aS)—N-((2S)-4-(cyclopropylamino)-3-hydroxy-4-oxo-1-((R*)-5-oxo-4-azaspiro[2.4]heptan-6-yl)butan-2-yl)-2-(4,6-dichloro-1H-indole-2-carbonyl)octahydrocyclopenta[c]pyrrole-1-carboxamide (140 mg, 63%) as a brown yellow solid. LC-MS (ESI, m/z): 616 [M+H]$^+$.

To a solution of (1S,3aR,6aS)—N-((2S)-4-(cyclopropylamino)-3-hydroxy-4-oxo-1-((R*)-5-oxo-4-azaspiro[2.4]heptan-6-yl)butan-2-yl)-2-(4,6-dichloro-1H-indole-2-carbonyl)octahydrocyclopenta[c]pyrrole-1-carboxamide (130 mg, 0.21 mmol, 1.0 eq.) in DMSO (3 mL) was added IBX (177 mg, 0.63 mmol, 3.0 eq.). The mixture was stirred at rt overnight, and the reaction was quenched with sodium bicarbonate solution (2 mL). The solution was extracted with EA (3×8 mL). The organic layers were combined, dried over anhydrous sodium sulfate, filtered and concentrated under reduced pressure. The residue was purified by pre-TLC with MeOH:DCM (1:12) to provide (1S,3aR,6aS)—N-(4-(cyclopropylamino)-3,4-dioxo-1-((R*)-5-oxo-4-azaspiro[2.4]heptan-6-yl)butan-2-yl)-2-(4,6-dichloro-1H-indole-2-carbonyl)octahydrocyclopenta[c]pyrrole-1-carboxamide (30.8 mg, 23%) as a white solid. LC-MS (ESI, m/z): 614 [M+H]$^+$.

Compound 117B ((1S,3aR,6aS)—N-(4-(cyclopropylamino)-3,4-dioxo-1-((S*)-5-oxo-4-azaspiro[2.4]heptan-6-yl)butan-2-yl)-2-(4,6-dichloro-1H-indole-2-carbonyl)octahydrocyclopenta[c]pyrrole-1-carboxamide; LC-MS (ESI, m/z): 614 [M+H]+) was prepared using a similar procedure for preparing 117A using tert-butyl ((S)-1-hydroxy-3-((S*)-5-oxo-4-azaspiro[2.4]heptan-6-yl)propan-2-yl)carbamate.

Example 118

COMPOUND 117

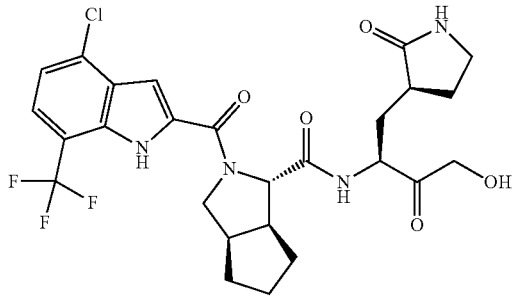

To a mixture of sodium methoxide (6.91 g, 38.4 mmol, 4.0 eq., 30% in MeOH) in MeOH (15 mL) was added a solution of 2-chloro-5-(trifluoromethyl)benzaldehyde (2.00 g, 9.59 mmol, 1.0 eq.) and ethyl 2-azidoacetate (4.95 g, 38.4 mmol, 4.0 eq.) in MeOH (15 mL) at −10° C. The mixture was stirred for 2 h at 0° C., and the reaction was quenched with water (50 mL). The mixture was extracted with EtOAc (3×50 mL). The organic layers were combined, washed with brine (2×30 mL), dried over anhydrous sodium sulfate, filtered and concentrated under reduced pressure to afford the crude product. The crude product was diluted with DCM (30 mL) and made into a slurry with 100~200 silica gel mesh (3 g), and the slurry was loaded to a column chromatography after removing the DCM. The sample was purified by column chromatography (Column size 5×24 cm, column volume: 300 mL, silica gel size (100~200 mesh) quantity: 120 g) and eluted with EtOAc:PE (0%-10% over 30 min). The collected fractions: 3%-4% EtOAc:PE fractions were chosen as the pure fractions and those fractions were combined and concentrated under reduced pressure to provide methyl 2-azido-3-[2-chloro-5-(trifluoromethyl)phenyl]prop-2-enoate (1.03 g, 33%) as a light yellow solid. $^1$H NMR (300 MHz, CDCl$_3$-d) δ 8.46-8.50 (m, 1H), 7.47-7.59 (m, 2H), 7.26 (s, 1H), 3.98 (s, 3H).

A mixture of methyl (2Z)-2-azido-3-[2-chloro-5-(trifluoromethyl)phenyl]prop-2-enoate (1.00 g, 3.27 mmol, 1.0 eq.) in xylene (10 mL) was stirred for 4 h at 120° C. and then concentrated under reduced pressure to afford the crude product. The crude product was diluted with DCM (20 mL) and made into a slurry with 100~200 silica gel mesh (2 g). The slurry was loaded to a column chromatography after removing the DCM. The sample was purified by column chromatography (Column size 4×24 cm, column volume: 200 mL, silica gel size (100~200 mesh) quantity: 80 g) and eluted with EtOAc:PE (0%~10% over 20 min). The collected fractions: 4%-5% EtOAc:PE fractions were chosen as the pure fractions and those fractions were combined and concentrated under reduced pressure to provide methyl 4-chloro-7-(trifluoromethyl)-1H-indole-2-carboxylate (390 mg, 41%) as an off-white solid. $^1$H NMR (300 MHz, CDCl$_3$-d) δ 9.26 (br, 1H), 7.48-7.57 (m, 1H), 7.39-7.43 (m, 1H), 7.23-7.28 (m, 1H), 4.01 (s, 3H).

To a mixture of methyl 4-chloro-7-(trifluoromethyl)-1H-indole-2-carboxylate (390 mg, 1.41 mmol, 1.0 eq.) in THF (2 mL)/water (2 mL) was added lithium hydroxide (168, 7.03 mmol, 5.0 eq.). The mixture was stirred for 4 h at 60° C. The mixture was concentrated under reduced pressure to remove the THF. The pH was adjusted to 6 with hydrochloric acid (2 M). 4-chloro-7-(trifluoromethyl)-1H-indole-2-carboxylic acid (300 mg, 80%) was obtained by filtration as a white solid. $^1$H NMR (300 MHz, DMSO-d$_6$) δ 13.50 (br, 1H), 12.43 (s, 1H), 7.60-7.68 (m, 1H), 7.32-7.40 (m, 1H), 7.23-7.28 (m, 1H). LC-MS (ESI, m/z): 262 [M−H]$^-$.

To a mixture of (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (102 mg, 0.283 mmol, 1.0 eq.), 4-chloro-7-(trifluoromethyl)-1H-indole-2-carboxylic acid (75.0 mg, 0.283 mmol, 1.0 eq.) and o-(7-azabenzotriazol-1-yl)-N,N,N',N'-tetramethyluronium hexafluorophosphate (140 mg, 0.368 mmol, 1.3 eq.) in DMF (3 mL) was added N-ethyl-N-isopropylpropan-2-amine (183 mg, 1.42 mmol, 5.0 eq.) at 0° C. The mixture was stirred for 1 h at rt, and the reaction was quenched with water (5 mL). The mixture was extracted with EtOAc (3×5 mL). The organic layers were combined, washed with brine (2×5 mL), dried over anhydrous sodium sulfate, filtered and concentrated under reduced pressure to afford the crude product. The crude product was purified by prep-HPLC (Column: YMC-Actus Triart C18, 20×250 mm, 5 µm, 12 nm; Mobile Phase A: Water (0.1% FA), Mobile Phase B: ACN; Flow rate: 25 mL/min; Gradient: 40% B to 58% B in 10 min, 58% B; Wave Length: 254 nm; RT: 7.48 min) to provide (1S,3aR,6aS)-2-[4-chloro-7-(trifluoromethyl)-1H-indole-2-carbonyl]-N-[(2S)-4-hydroxy-3-oxo-1-[(3S)-2-oxopyrrolidin-3-yl]butan-2-yl]-hexahydro-1H-cyclopenta[c]pyrrole-1-carboxamide (21.9 mg, 13%) as a white solid. LC-MS (ESI, m/z): 569 [M+H]$^+$.

Example 119

COMPOUND 118

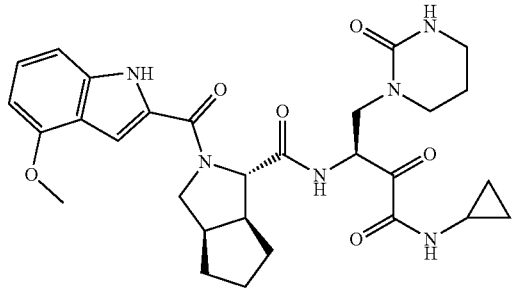

Compound 118 was prepared similarly as described for Compound 16 using (3S)-3-amino-N-cyclopropyl-2-hydroxy-4-(2-oxotetrahydropyrimidin-1(2H)-yl)butanamide hydrochloride in place of (3S)-3-amino-N-benzyl-2-hydroxy-4-[(3S)-2-oxopyrrolidin-3-yl]butanamide hydrochloride. LCMS (ESI, m/z): 565 [M+H]$^+$.

(3S)-3-Amino-N-cyclopropyl-2-hydroxy-4-(2-oxotetrahydropyrimidin-1(2H)-yl)butanamide hydrochloride: To a cold solution of tert-butyl (S)-(3-amino-1-(methoxy(methyl)amino)-1-oxopropan-2-yl)carbamate (Eiden et al., J. Org. Chem. (2017) 82(15):7806-7819) (750 mg, 3.03 mmol, 1.0 eq.) in ACN (15 mL) cooled to 0° C. were added Et$_3$N (0.42 mL, 3.03 mmol, 1/0 eq.) and 1-chloro-3-isocyanatopropane (0.37 mL, 3.63 mmol, 1.2 eq.). The mixture was stirred at rt for 2 h and then concentrated under reduced pressure to afford tert-butyl (S)-(12-chloro-3-methyl-4,8-dioxo-2-oxa-3,7,9-triazadodecan-5-yl)carbamate (900 mg, 81%) as a colorless oil. LCMS (ESI, m/z): 367 [M+H]$^+$.

To a solution of tert-butyl (S)-(12-chloro-3-methyl-4,8-dioxo-2-oxa-3,7,9-triazadodecan-5-yl)carbamate (600 mg, 1.63 mmol, 1.0 eq.) in dry DMF (6 mL) was added Cs$_2$CO$_3$ (1.07 g, 3.27 mmol, 2.0 eq.). The reaction mixture was heated at 100° C. under microwave irradiation for 2 h. After cooling to rt, the reaction mixture was diluted with cold water (20 mL) and extracted with 10% MeOH in DCM (3×30 mL). The organic phases were combined, dried over Na$_2$SO$_4$, filtered and concentrated under reduced pressure. The residue was purified by flash chromatography on silica gel using 4% MeOH in DCM as eluent to afford tert-butyl (S)-(1-(methoxy(methyl)amino)-1-oxo-3-(2-oxotetrahydropyrimidin-1(2H)-yl)propan-2-yl)carbamate (350 mg, 64%) as a colorless oil. LC-MS (ESI, m/z): 331 [M+H]$^+$.

To a solution of tert-butyl (S)-(1-(methoxy(methyl)amino)-1-oxo-3-(2-oxotetrahydropyrimidin-1(2H)-yl)propan-2-yl)carbamate (350 mg, 1.05 mmol, 1.0 eq.) in DCM (5 mL) cooled to −78° C. was added 1M DIBAL in hexane (2.65 mL, 2.65 mmol, 2.5 eq.). The mixture was stirred at −78° C. for 5 h. The reaction was quenched by the addition of MeOH (2.6 mL) at −78° C., and the mixture was allowed to warm to rt. 5% MeOH in DCM (30 mL) was added, and the insoluble material was filtered through Celite. The filtrate was concentrated under reduced pressure to afford tert-butyl (S)-(1-oxo-3-(2-oxotetrahydropyrimidin-1(2H)-yl)propan-2-yl)carbamate (300 mg, crude) as a colourless gum.

To a solution of tert-butyl (S)-(1-oxo-3-(2-oxotetrahydropyrimidin-1(2H)-yl)propan-2-yl)carbamate (300 mg, 1.05 mmol, 1.0 eq.) in DCM (5 mL) cooled to 0° C. were added AcOH (0.19 mL, 3.31 mmol, 3.2 eq.) and isocyanocyclopropane (111 mg, 1.65 mmol, 1.6 eq.). The mixture was stirred at rt for 18 h. The mixture was diluted with EA (100 mL) and washed with sat. NaHCO₃ (20 mL). The phases were separated. The organic phase was washed with brine, dried over Na₂SO₄, filtered and concentrated under reduced pressure. The residue was purified by flash chromatography on silica gel using a gradient of MeOH (4 to 6%) in DCM to provide (3S)-3-((tert-butoxycarbonyl)amino)-1-(cyclopropylamino)-1-oxo-4-(2-oxotetrahydropyrimidin-1(2H)-yl)butan-2-yl acetate as an off-white semi solid (290 mg, 57% over two steps). LC-MS (ESI, m/z): 399 [M+H]⁺.

To a solution of (3S)-3-((tert-butoxycarbonyl)amino)-1-(cyclopropylamino)-1-oxo-4-(2-oxotetrahydropyrimidin-1(2H)-yl)butan-2-yl acetate (290 mg, 0.728 mmol, 1.0 eq.) in THF (3 mL) and water (3 mL) cooled to 0° C. was added LiOH (35 mg, 1.45 mmol, 2.0 eq.). The mixture was stirred at rt for 4 h and then concentrated under reduced pressure. The residue was purified by flash chromatography on silica gel using a gradient of MeOH (5 to 6%) in DCM to afford tert-butyl ((2S)-4-(cyclopropylamino)-3-hydroxy-4-oxo-1-(2-oxotetrahydropyrimidin-1(2H)-yl)butan-2-yl)carbamate (240 mg, 92%) as a pale brown solid. LC-MS (ESI, m/z): 357 [M+H]⁺.

To a solution of tert-butyl ((2S)-4-(cyclopropylamino)-3-hydroxy-4-oxo-1-(2-oxotetrahydropyrimidin-1(2H)-yl)butan-2-yl)carbamate (290 mg, 0.814 mmol, 1.0 eq.) in DCM (3 mL) cooled to 0° C. was added 4N HCl in dioxane (0.830 mL, 3.25 mmol, 4.0 eq.). The mixture was stirred at rt for 4 h and then concentrated under reduced pressure. The residue was triturated with diethyl ether to afford (3S)-3-amino-N-cyclopropyl-2-hydroxy-4-(2-oxotetrahydropyrimidin-1(2H)-yl)butanamide hydrochloride (220 mg, 92%) as an off-white solid. LC-MS (ESI, m/z): 257 [M+H]⁺.

Example 120

COMPOUND 119

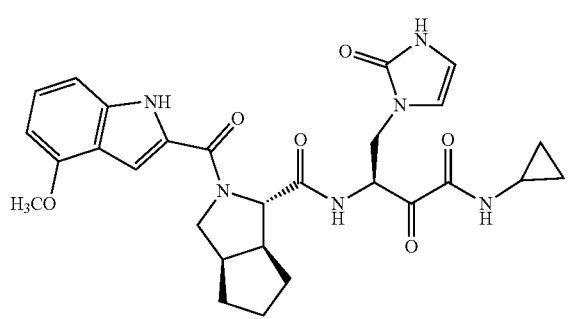

Compound 119 was prepared similarly as described for Compound 100 using (1S,3aR,6aS)-2-(4-methoxy-1H-indole-2-carbonyl)-N—((S)-1-oxo-3-(2-oxo-2,3-dihydro-1H-imidazol-1-yl)propan-2-yl)octahydrocyclopenta[c]pyrrole-1-carboxamide in place of Compound 14A, and isocyanocyclopropane in place of 1-isocyano-2-methoxy-ethane. LCMS (ESI, m/z): 549 [M+H]⁺.

(1S,3aR,6aS)-2-(4-Methoxy-1H-indole-2-carbonyl)-N—((S)-1-oxo-3-(2-oxo-2,3-dihydro-1H-imidazol-1-yl)propan-2-yl)octahydrocyclopenta[c]pyrrole-1-carboxamide: To a solution of N-alpha-Fmoc-L-2,3-diaminopropionic acid (5.0 g, 15.3 mmol, 1.0 eq.) in MeOH (50 mL) cooled to 0° C. was added thionyl chloride (1.1 mL, 23.0 mmol, 1.5 eq.). The mixture was stirred at rt for 16 h and then concentrated under reduced pressure to afford methyl (S)-2-((((9H-fluoren-9-yl)methoxy)carbonyl)amino)-3-aminopropanoate hydrochloride (5.1 g, 98%). LC-MS (ESI, m/z): 341 [M+H]⁺.

To a solution of methyl (S)-2-((((9H-fluoren-9-yl)methoxy)carbonyl)amino)-3-aminopropanoate hydrochloride (2.5 g, 6.63 mmol, 1.0 eq.) in ACN (25 mL) were added NEt₃ (1.5 mL, 11.0 mmol, 1.7 eq.) and 1,1-diethoxy-2-isocyanatoethane (1.4 g, 8.82 mmol, 1.3 eq.). The mixture was stirred at rt for 30 min and then concentrated under reduced pressure. The residue was purified by flash chromatography on silica gel using a gradient of MeOH (1 to 2%) in DCM to afford methyl (S)-2-((((9H-fluoren-9-yl)methoxy)carbonyl)amino)-3-(3-(2,2-diethoxyethyl)ureido)propanoate (1.6 g, 48%) as a brown oil. LC-MS (ESI, m/z): 500 [M+H]⁺.

A solution of methyl (S)-2-((((9H-fluoren-9-yl)methoxy)carbonyl)amino)-3-(3-(2,2-diethoxyethyl)ureido)propanoate (1.6 g, 3.93 mmol, 1.0 eq.) in formic acid (16 mL) was heated at 80° C. for 1 h and then concentrated under reduced pressure. The residue was partitioned between sat. NaHCO₃ (20 mL) and DCM (50 mL). The phases were separated. The aqueous phase was extracted with DCM (2×50 mL). The organic phases were combined, dried over Na₂SO₄, filtered and concentrated under reduced pressure. The residue was purified by flash chromatography on silica gel (24 g column) using a gradient of MeOH (3 to 5%) in DCM to afford methyl (S)-2-((((9H-fluoren-9-yl)methoxy)carbonyl)amino)-3-(2-oxo-2,3-dihydro-1H-imidazol-1-yl)propanoate (960 mg, 74%) as a white foam. LC-MS (ESI, m/z): 408 [M+H]⁺.

To a solution of methyl (S)-2-((((9H-fluoren-9-yl)methoxy)carbonyl)amino)-3-(2-oxo-2,3-dihydro-1H-imidazol-1-yl)propanoate (1.0 g, 2.45 mmol, 1.0 eq.) and N,O-dimethyl hydroxylamine hydrochloride (358 mg, 3.68 mmol, 1.5 eq.) in DCM (10 mL) cooled to 0° C. was added 2M iPrMgCl in THF (12.3 mL, 24.5 mmol, 10 eq.). The mixture was stirred at 0° C. for 1 h. The reaction was quenched by the addition of sat. NH₄Cl solution (20 mL), and the mixture was extracted with EA (3×25 mL). The organic phases were combined, washed with brine (20 mL), dried over Na₂SO₄, filtered and concentrated under reduced pressure. The residue was purified by flash chromatography on silica gel (12 g column) using a gradient of MeOH (1 to 5%) in DCM to afford ((9H-fluoren-9-yl)methyl (S)-(1-(methoxy(methyl)amino)-1-oxo-3-(2-oxo-2,3-dihydro-1H-imidazol-1-yl)propan-2-yl)carbamate (600 mg, 60%) as a white foam. LC-MS (ESI, m/z): 437 [M+H]⁺.

To a solution of ((9H-fluoren-9-yl)methyl (S)-(1-(methoxy(methyl)amino)-1-oxo-3-(2-oxo-2,3-dihydro-1H-imidazol-1-yl)propan-2-yl)carbamate (600 mg, 1.37 mmol, 1.0 eq.) in THF (6 mL) was added diethylamine (3.0 mL, 29.0 mmol, 21 eq.). The mixture was stirred at rt for 16 h and then concentrated under reduced pressure. The residue was dissolved in ACN (10 mL) and washed with hexane (3×10 mL). The acetonitrile phase was concentrated under reduced pressure to afford quantitatively (S)-2-amino-N-methoxy-N-methyl-3-(2-oxo-2,3-dihydro-1H-imidazol-1-yl)propanamide as a pale yellow liquid. LC-MS (ESI, m/z): 215 [M+H]⁺.

To a solution of (1S,3aR,6aS)-2-(4-methoxy-1H-indole-2-carbonyl)octahydrocyclopenta[c]pyrrole-1-carboxylic acid (460 mg, 1.40 mmol, 1.0 eq.) and (S)-2-amino-N-methoxy-N-methyl-3-(2-oxo-2,3-dihydro-1H-imidazol-1-yl)propanamide (300 mg, 1.40 mmol, 1.0 eq.) in DMF (5 mL) cooled to 0° C. were added EDC·HCl (535 mg, 2.80 mmol, 2.0 eq.), HOAt (190 mg, 1.40 mmol, 1.0 eq.) and NEt₃ (0.400 mL, 2.80 mmol, 2.0 eq.). The mixture was stirred at rt for 16 h. The mixture was diluted with water (15 mL) and extracted with EA (3×25 mL). The organic phases were combined, washed with brine (20 mL), dried over Na$_2$SO$_4$, filtered and concentrated under reduced pressure. The residue was purified by flash chromatography on silica gel (24 g column) using a gradient of MeOH (1 to 5%) in DCM to afford (1S,3aR,6aS)—N—((S)-1-(methoxy(methyl)amino)-1-oxo-3-(2-oxo-2,3-dihydro-1H-imidazol-1-yl)propan-2-yl)-2-(4-methoxy-1H-indole-2-carbonyl)octahydrocyclopenta[c]pyrrole-1-carboxamide (600 mg, 61%) as an off-white foam. LC-MS (ESI, m/z): 525 [M+H]$^+$.

To a solution of (1S,3aR,6aS)—N—((S)-1-(methoxy(methyl)amino)-1-oxo-3-(2-oxo-2,3-dihydro-1H-imidazol-1-yl)propan-2-yl)-2-(4-methoxy-1H-indole-2-carbonyl)octahydrocyclopenta[c]pyrrole-1-carboxamide (600 mg, 1.14 mmol, 1.0 eq.) in DCM (10 mL) cooled to −78° C. was added 1M DIBAL in hexane (3.43 mL, 3.43 mmol, 3.0 eq.). The mixture was stirred at −78° C. for 2 h. The reaction was quenched by then addition of methanol at −78° C., and the mixture was allowed to warm to rt. The reaction mixture was filtered through Celite, and the filtrate was concentrated under reduced pressure to afford (1S,3aR,6aS)-2-(4-methoxy-1H-indole-2-carbonyl)-N—((S)-1-oxo-3-(2-oxo-2,3-dihydro-1H-imidazol-1-yl)propan-2-yl)octahydrocyclopenta[c]pyrrole-1-carboxamide (610 mg, crude). LC-MS (ESI, m/z): 466 [M+H]$^+$.

Example 121

COMPOUND 120

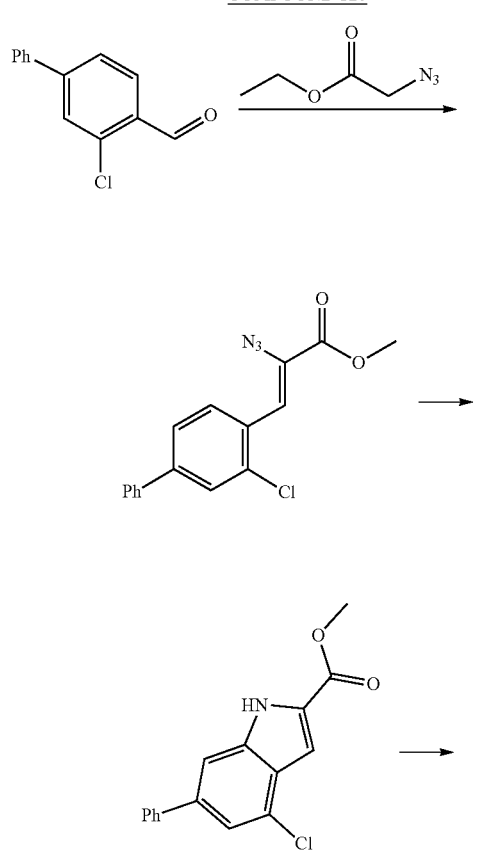

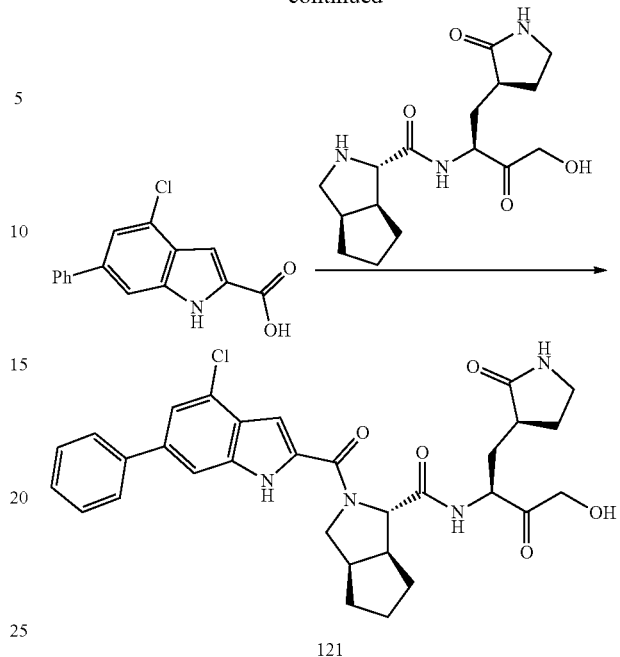

121

A 100 mL vial was charged with sodium methoxide (399 mg, 7.38 mmol, 4.0 eq.) in MeOH (6 mL). 3-chloro-[1,1'-biphenyl]-4-carbaldehyde (400 mg, 1.85 mmol, 1.0 eq.) and ethyl 2-azidoacetate (954 mg, 7.38 mmol, 4.0 eq.) in MeOH (6 mL) was added at −10° C. The mixture was stirred for 1 h at −10° C. and then warmed to rt for 1.5 h. Ice-water (15 mL) was poured into mixture, and the resulting solution was extracted with EA (3×30 mL). The organic layers were combined, washed with brine (20 mL), dried over anhydrous sodium sulfate, filtered and concentrated under reduced pressure. The residue was chromatographed on a silica gel column with EA:PE (1:13) to provide methyl 2-azido-3-{3-chloro-[1,1'-biphenyl]-4-yl}prop-2-enoate (210 mg, 33%) as an off-white oil. $^1$H NMR (300 MHz, DMSO-d$_6$) δ 8.31-8.33 (m, 1H), 7.95-7.97 (m, 1H), 7.81-7.88 (m, 3H), 7.40-7.56 (m, 3H), 7.18 (s, 1H), 3.99 (s, 3H).

A 50 mL vial was charged with methyl 2-azido-3-{3-chloro-[1,1'-biphenyl]-4-yl}prop-2-enoate (210 mg, 0.67 mmol, 1.0 eq.) and xylene (6 mL) under nitrogen. The mixture was stirred for 1 h at 120° C. The mixture was then concentrated under reduced pressure to provide methyl 4-chloro-6-phenyl-1H-indole-2-carboxylate (180 mg, 94%) as an off-white oil. LC-MS (ESI, m/z): 284 [M–H]$^-$.

A 50 mL round-bottom flask was charged with methyl 4-chloro-6-phenyl-1H-indole-2-carboxylate (192 mg, 0.67 mmol, 1.0 eq.), THF (3 mL), NaOH (80.6 mg, 2.02 mmol, 3.0 eq.) and H$_2$O (3 mL). The mixture was stirred at 40° C. for 1 h. Water (2 mL) was added, and the mixture was washed with EA (3×10 mL). The pH value of the aqueous phase was adjusted to 4 with acetate acid. The solution was extracted with EA (3×10 mL). The organic layers were combined, dried over anhydrous sodium sulfate, filtered and concentrated under reduced pressure to provide 4-chloro-6-phenyl-1H-indole-2-carboxylic acid (120 mg. 56%) as a light yellow oil. LC-MS (ESI, m/z): 270 [M–H]$^-$.

To a solution of 4-chloro-6-phenyl-1H-indole-2-carboxylic acid (84.7 mg, 0.31 mmol, 1.1 eq.) in DMF (2 mL) was added N,N,N',N'-Tetramethyl-O-(7-azabenzotriazol-1-yl)uronium hexafluorophospate (129 mg, 0.34 mmol, 1.2 eq.)

and N,N-diisopropylethylamine (220 mg, 1.7 mmol, 6.0 eq.). The mixture was stirred at 0° C. for 30 min. (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide (91.6 mg, 0.28 mmol, 1.0 eq.) was added. The mixture was stirred at rt for 2 h, and the reaction was quenched with water (3 mL). The mixture was extracted with EA (3×10 mL). The organic layers were combined, dried over anhydrous sodium sulfate, filtered and concentrated under reduced pressure. The residue was purified by Prep-HPLC (Column: XBridge Shield RP18 OBD Column, 30*150 mm, 5 μm; Mobile Phase A: Water (0.1% FA), Mobile Phase B: ACN; Flow rate: 60 mL/min; Gradient: 35% B to 49% B in 10 min, 49% B; Wave Length: 254 nm; RT1 (min): 9.1); to provide (1S,3aR,6aS)-2-(4-chloro-6-phenyl-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (53 mg, 31%) as a white solid. LC-MS (ESI, m/z): 577 [M+H]$^+$.

Example 122

COMPOUND 121

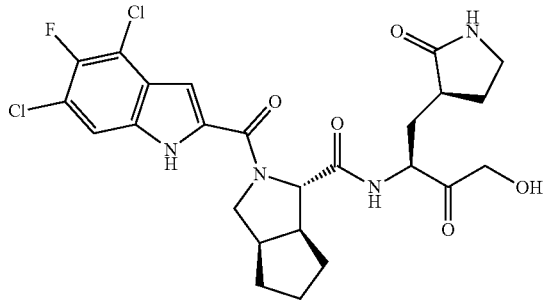

To a solution of sodium methanolate (7.46 g, 20.7 mmol, 4.0 eq., 30% in MeOH) in MeOH (10 mL) was added a solution of 2,4-dichloro-3-fluorobenzaldehyde (2.00 g, 10.4 mmol, 1.0 eq.) and ethyl 2-azidoacetate (5.35 g, 41.4 mmol, 4.0 eq.) in MeOH (10 mL). The mixture was stirred for 2 h at −10° C., and the reaction quenched with water (20 mL). The mixture was extracted with EA (3×50 mL). The organic layers were combined, washed with brine (2×20 mL), dried over anhydrous sodium sulfate, filtered and concentrated under reduced pressure to afford the crude product. The crude product was diluted with dichloromethane (10 mL) and made into a slurry with 100~200 silica gel mesh (2.5 g). The slurry was loaded to a column after removing the dichloromethane. The sample was purified by column chromatography (Column size 6×12 cm, column volume: 300 mL, silica gel size (100~200 mesh) quantity: 120 g) and eluted with EA:PE (0%~10%) to provide 2-azido-3-(2,4-dichloro-3-fluorophenyl)acrylate (1.10 g, 36%) as a yellow solid. $^1$H-NMR (300 MHz, DMSO-d$_6$) δ 8.05-8.09 (m, 1H), 7.66-7.70 (m, 1H), 7.01 (s, 1H), 3.80 (s, 3H).

A solution of methyl (Z)-2-azido-3-(2,4-dichloro-3-fluorophenyl)acrylate (1.1 g, 3.79 mmol, 1.0 eq.) in xylene (10 mL) was stirred for 3 h at 120° C. The mixture was concentrated under reduced pressure to afford the crude product. The crude product was diluted with dichloromethane (10 mL) and made into a slurry with 100~200 silica gel mesh (2.5 g) and the slurry was loaded to a column after removing the dichloromethane. The sample was purified by column chromatography (Column size 4×12 cm, column volume: 120 mL, silica gel size (100~200 mesh) quantity: 80 g) and eluted with EA:PE (0%~20% over min). The collected fractions: 6%-7% EA:PE fractions were chosen as the pure fractions. Those fractions were combined and concentrated under reduced pressure to provide methyl 4,6-dichloro-5-fluoro-1H-indole-2-carboxylate (750 mg, 75%) as a yellow solid. $^1$H NMR (300 MHz, DMSO-d$_6$) δ 12.55 (s, 1H), 7.55-7.57 (m, 1H), 7.15-7.16 (m, 1H), 3.91 (s, 3H). LC-MS (ESI, m/z): 260 [M−H]$^−$.

To a mixture of methyl 4,6-dichloro-5-fluoro-1H-indole-2-carboxylate (400 mg, 1.53 mmol, 1.0 eq.) in THF (5 mL) was added sodium hydroxide (305 mg, 7.63 mmol, 5.0 eq., in 1 mL water). The mixture was stirred for 2 h at 50° C. and concentrated under reduced pressure to remove the THF. The pH was adjusted to 3 with HCl (2M). The mixture was extracted with EA (3×10 mL). The organic layers were combined, washed with brine (2×10 mL), dried over anhydrous sodium sulfate, filtered and concentrated under reduced pressure to afford 4,6-dichloro-5-fluoro-1H-indole-2-carboxylic acid (240 mg, crude) as a white solid. $^1$H NMR (300 MHz, DMSO-d$_6$) δ 13.47 (br, 1H), 12.38 (s, 1H), 7.54-7.56 (m, 1H), 7.09-7.10 (m, 1H). LC-MS (ESI, m/z): 246 [M−H]$^−$.

To a mixture of 4,6-dichloro-5-fluoro-1H-indole-2-carboxylic acid (86.9 mg, 0.350 mmol, 1.2 eq.), (1S,3aR,6aS)—N—((S)-4-hydroxy-3-oxo-1-((S)-2-oxopyrrolidin-3-yl)butan-2-yl)octahydrocyclopenta[c]pyrrole-1-carboxamide hydrochloride (105 mg, 0.292 mmol, 1.0 eq.) and 2-(7-azabenzotriazol-1-yl)-N,N,N',N'-tetramethyluronium hexafluorophosphate (133 mg, 0.350 mmol, 1.2 eq.) in DMF (2 mL) was added N,N-diisopropylethylamine (113 mg, 0.876 mmol, 3.0 eq.) at 0° C. The mixture was stirred for 1 h at rt, and the reaction was quenched with water (2 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by HPLC (Column: X Select CSH Prep C18 OBD Column, 19*250 mm, 5 μm; Mobile Phase A: Water (0.05% FA), Mobile Phase B: ACN; Flow rate: 25 mL/min; Gradient: 40% B to 70% B in 7 min, 70% B; Wave Length: 254 nm; RT1 (min): 5.7, 6 (min)) to provide (1S,3aR,6aS)-2-(4,6-dichloro-5-fluoro-1H-indole-2-carbonyl)-N—((S)-4-hydroxy-3-oxo-1-((S)-2-oxopyrrolidin-3-yl)butan-2-yl)octahydrocyclopenta[c]pyrrole-1-carboxamide (42.4 mg, 25%) as a white solid. LC-MS (ESI, m/z): 553 [M+H]$^+$.

Example 123

COMPOUND 122

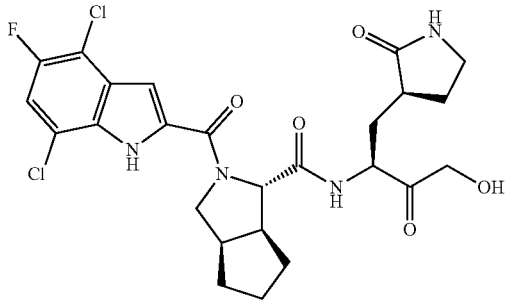

A 100 mL vial was charged with sodium methoxide (672 mg, 12.4 mmol, 4.0 eq.) in MeOH (10 mL). 2,5-dichloro-3-fluorobenzaldehyde (600 mg, 3.11 mmol, 1.0 eq.) and 2,5-dichloro-4-fluorobenzaldehyde (1.61 g, 12.4 mmol, 4.0 eq.) in MeOH (10 mL) was added in at −10° C. The mixture was stirred for 1 h at −10° C. and then warmed to rt for 1.5 h. Ice-water (15 mL) was poured into the mixture, and the resulting solution was extracted with EA (3×40 mL). The organic layers were combined, washed with brine (20 mL), dried over anhydrous sodium sulfate, filtered and concentrated under reduced pressure. The residue was chromatographed on a silica gel column with EA:PE (1:18) to provide methyl 2-azido-3-(2,5-dichloro-4-fluorophenyl)acrylate (270 mg, 24%) as a light yellow solid. $^1$H-NMR (300 MHz, DMSO-$d_6$) δ 8.06 (s, 1H), 7.73-7.76 (m, 1H), 6.99 (s, 1H), 3.90 (s, 3H).

A 50 mL vial was charged with methyl (E)-2-azido-3-(2,5-dichloro-4-fluorophenyl)acrylate (270 mg, 0.93 mmol, 1.0 eq.) and xylene (6 mL) under nitrogen. The mixture was stirred for 2 h at 120° C. and then concentrated under reduced pressure to provide methyl 4,7-dichloro-5-fluoro-1H-indole-2-carboxylate (195 mg, 64%) as a yellow solid. LC-MS (ESI, m/z): 260 [M−H]$^−$.

A 50 mL round-bottom flask was charged with methyl 4,7-dichloro-5-fluoro-1H-indole-2-carboxylate (195 mg, 0.74 mmol, 1.0 eq.), THF (2 mL), NaOH (89.3 mg, 2.23 mmol, 3.0 eq.) and H$_2$O (2 mL). The mixture was stirred at 40° C. for 1 h. Water (2 mL) was added, and the mixture was washed with EA (3×8 mL). The pH value of the aqueous phase was adjusted to 4 with acetate acid. The solution was extracted with EA (3×10 mL). The organic layers were combined, dried over anhydrous sodium sulfate, filtered and concentrated under reduced pressure to provide 4,7-dichloro-5-fluoro-1H-indole-2-carboxylic acid (102 mg, 50%) as a yellow solid. LC-MS (ESI, m/z): 246 [M−H]$^−$.

To a solution of 4,7-dichloro-5-fluoro-1H-indole-2-carboxylic acid (77.3 mg, 0.31 mmol, 1.1 eq.) in DMF (2 mL) was added N,N,N',N'-Tetramethyl-O-(7-azabenzotriazol-1-yl)uronium hexafluorophospate (119 mg, 0.31 mmol, 1.1 eq.) and N,N-diisopropylethylamine (220 mg, 1.7 mmol, 6.0 eq.). The mixture was stirred at 0° C. for 30 min and then (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide (91.6 mg, 0.28 mmol, 1.0 eq.) was added. The mixture was stirred at 0° C. for 1.5 h, and the reaction was quenched with water (3 mL). The mixture was extracted with EA (3×10 mL). The organic layers were combined, dried over anhydrous sodium sulfate, filtered and concentrated under reduced pressure. The residue was purified by Prep-HPLC (Column: XSelect CSH Prep C18 OBD Column, 19*250 mm, 5 μm; Mobile Phase A: Water (0.05% FA), Mobile Phase B: ACN; Flow rate: 25 mL/min; Gradient: 40% B to 70% B in 7 min, 70% B; Wave Length: 254 nm; RT1 (min): 5.2, 5.7 (min)); to provide (1S,3aR,6aS)-2-(4,7-dichloro-5-fluoro-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (30.1 mg, 19%) as a white solid. LC-MS (ESI, m/z): 553 [M+H]$^+$.

Example 124

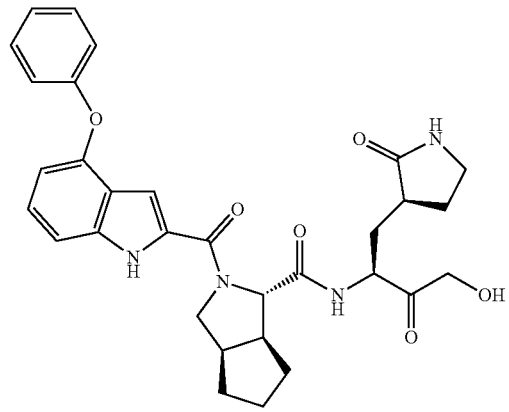

COMPOUND 123

To a solution of sodium methoxide (3.63 g, 20.2 mmol, 4.0 eq., 30% in MeOH) in MeOH (10 mL) was added dropwise a mixture of 2-phenoxybenzaldehyde (1 g, 5.05 mmol, 1.0 eq.) and ethyl 2-azidoacetate (2.61 g, 20.2 mmol, 4.0 eq.) in MeOH (10 mL) at −10° C. The mixture was stirred for 4 h at −10° C. The reaction was quenched with water (5 mL) and then extracted with EtOAc (3×20 mL). The organic layers were combined, dried over anhydrous sodium sulfate, filtered and concentrated under reduced pressure to afford the crude product. The crude product was purified by silica gel column chromatography with EtOAc:PE (4:96) to afford methyl 2-azido-3-(2-phenoxyphenyl)prop-2-enoate (980 mg, 66%). $^1$H NMR (300 MHz, DMSO-$d_6$) δ 8.21-8.40 (m, 1H), 7.31-7.51 (m, 3H), 7.10-7.30 (m, 3H), 6.95-7.08 (m, 2H), 6.83-6.93 (m, 1H), 3.82 (s, 3H).

A solution of methyl (2-azido-3-(2-phenoxyphenyl)prop-2-enoate (900 mg, 3.05 mmol, 1.0 eq.) in xylene (10 mL) was stirred overnight at 120° C. and then concentrated under reduced pressure to afford the crude product. The crude product was purified by silica gel column chromatography with EtOAc:PE (4:96) to afford methyl 4-phenoxy-1H-indole-2-carboxylate (555 mg, 68%). $^1$H NMR (300 MHz, DMSO-$d_6$) δ 12.16 (s, 1H), 7.34-7.45 (m, 2H), 7.21-7.30 (m, 2H), 7.11-7.18 (m, 1H), 6.99-7.08 (m, 2H), 6.79-6.88 (m, 1H), 6.59-6.68 (m, 1H), 3.84 (s, 3H). LCMS (ESI, m/z): 268 [M+H]$^+$.

To a solution of methyl 4-phenoxy-1H-indole-2-carboxylate (300 mg, 1.12 mmol, 1.0 eq.) in THF (3 mL) was added lithium hydroxide (134 mg, 5.61 mmol, 5.0 eq., in 3 mL water). The mixture was stirred for 3 h at 60° C., and then acidified to pH=5 with hydrochloric acid (1M). The mixture was extracted with EtOAc (3×10 mL). The organic layers were combined, dried over anhydrous sodium sulfate, filtered and concentrated under reduced pressure to afford 4-phenoxy-1H-indole-2-carboxylic acid (280 mg, crude). $^1$H NMR (300 MHz, DMSO-$d_6$) δ 13.02 (s, 1H), 11.98 (s, 1H), 7.35-7.44 (m, 2H), 7.11-7.27 (m, 3H), 6.99-7.08 (m, 2H), 6.73-6.88 (m, 1H), 6.57-6.66 (m, 1H). LCMS (ESI, m/z): 254 [M+H]$^+$.

To a solution of (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (102 mg, 0.283 mmol, 1.0 eq.) in DMF (1 mL) was added 4-phenoxy-1H-indole-2-carboxylic acid (79.0 mg, 0.311 mmol, 1.1 eq.), o-(7-azabenzotriazol-1-yl)-N,N,N',N'-tetramethyluronium hexafluorophosphate (141 mg, 0.369 mmol, 1.3 eq.) and N-ethyl-N-isopropylpropan-2-amine (184 mg, 1.42 mmol, 5.0 eq.). The mixture was stirred at 0° C., and then stirred for 1 h at rt. The reaction was quenched with water (1 mL). The mixture was extracted with EtOAc (3×5 mL). The organic layers were combined, washed with brine (2×3 mL), dried over anhydrous sodium sulfate, filtered and concentrated under reduced pressure to afford the crude product. The crude product was purified by prep-HPLC (Column: XSelect CSH Prep C18 OBD Column, 19*250 mm, 5 μm; Mobile Phase A: Water (0.05% FA), Mobile Phase B: ACN; Flow rate: 25 mL/min; Gradient: 43% B to 53% B in 10 min, 53% B; Wave Length: 254 nm; RT1 (min): 6.8.) to provide (1S,3aR,6aS)—N-[(2S)-4-hydroxy-3-oxo-1-[(3S)-2-oxopyrrolidin-3-yl]butan-2-yl]-2-(4-phenoxy-1H-indole-2-carbonyl)-hexahydro-1H-cyclopenta[c]pyrrole-1-carboxamide (61.1 mg, 38%) as a white solid. $^1$H NMR (400 MHz, 80° C., DMSO-$d_6$) δ 11.46 (s, 1H), 8.36 (s, 1H), 7.00-7.40 (m, 8H), 6.71 (s, 1H), 6.50 (s, 1H), 4.35-4.65 (m, 2H), 4.10-4.27 (m, 2H), 3.90-4.09 (m, 1H), 3.70-3.89 (m, 1H), 3.54-3.70 (m, 1H), 2.81-3.23 (m, 2H), 2.55-2.80 (m, 2H), 1.21-2.40 (m, 11H). LCMS (ESI, m/z): 559 [M+H]$^+$.

Example 125

COMPOUND 124

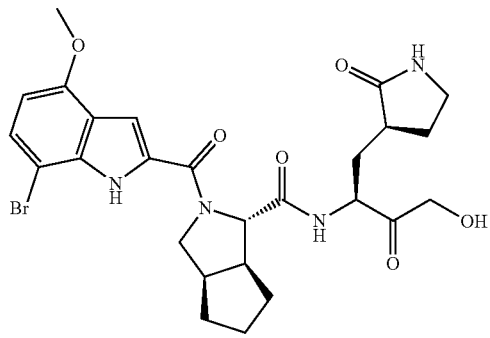

To a mixture of sodium methoxide (6.70 g, 37.2 mmol, 4.0 eq., 30% in MeOH) in MeOH (15 mL) was added a solution of 5-bromo-2-methoxybenzaldehyde (2.00 g, 9.30 mmol, 1.0 eq.) and ethyl 2-azidoacetate (4.80 g, 37.2 mmol, 4.0 eq.) in MeOH (15 mL) at −10° C. The mixture was stirred for 2 h at −10° C., and the reaction was quenched with ice-water (50 mL). The mixture was extracted with EtOAc (3×50 mL). The organic layers were combined, washed with brine (2×50 mL), dried over anhydrous sodium sulfate, filtered and concentrated under reduced pressure to afford the crude product. The crude product was diluted with DCM (40 mL) and made into a slurry with 100~200 silica gel mesh (3 g). The slurry was loaded to a column after removing the DCM. The sample was purified by column chromatography (Column size 5×24 cm, column volume: 300 mL, silica gel size (100~200 mesh) quantity: 120 g) and eluted with EtOAc:PE (0%~15% over 20 min). The collected fractions: 8%-9% EtOAc:PE fractions were chosen as the pure fractions, and those fractions were combined and concentrated under reduced pressure to provide methyl 2-azido-3-(5-bromo-2-methoxyphenyl)prop-2-enoate (800 mg, 25%) as a light yellow solid. $^1$H NMR (300 MHz, CDCl$_3$-d) δ 8.34-8.36 (m, 1H), 7.39-7.45 (m, 1H), 7.28 (s, 1H), 6.74-6.81 (m, 1H), 3.94 (s, 3H), 3.87 (s, 3H).

A mixture of methyl (2Z)-2-azido-3-(5-bromo-2-methoxyphenyl)prop-2-enoate (800 mg, 2.56 mmol, 1.0 eq.) in xylene (10 mL) was stirred for 1 h at 120° C. The mixture was concentrated under reduced pressure to afford the crude product. The crude product was diluted with DCM (20 mL) and made into a slurry with 100~200 silica gel mesh (2 g). The slurry was loaded to a column after removing the DCM. The sample was purified by column chromatography (Column size 5×24 cm, column volume: 300 mL, silica gel size (100~200 mesh) quantity: 120 g) and eluted with EtOAc:PE (0%~30% over 30 min). The collected fractions: 18%-20% EtOAc:PE fractions were chosen as the pure fractions, and those fractions were combined and concentrated under reduced pressure to provide methyl 7-bromo-4-methoxy-1H-indole-2-carboxylate (550 mg, 64%) as a white solid.

To a mixture of methyl 7-bromo-4-methoxy-1H-indole-2-carboxylate (300 mg, 1.06 mmol, 1.0 eq.) in THF (2 mL)/water (2 mL) was added lithium hydroxide (127 mg, 5.28 mmol, 5.0 eq.). The mixture was stirred for 4 h at rt. The mixture was concentrated under reduced pressure to removed the THF and then the pH was adjusted to 6 with hydrochloric acid (2 M). 7-bromo-4-methoxy-1H-indole-2-carboxylic acid (190 mg, 64%) was obtained by filtration as a white solid. $^1$H NMR (300 MHz, DMSO-$d_6$) δ 10.09 (br, 1H), 11.69 (s, 1H), 7.35-7.42 (m, 1H), 7.13-7.18 (m, 1H), 6.51-6.58 (m, 1H), 3.89 (s, 3H). LC-MS (ESI, m/z): 268 [M−H]$^-$.

To a mixture of (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (102 mg, 0.283 mmol, 1.0 eq.), 7-bromo-4-methoxy-1H-indole-2-carboxylic acid (77.0 mg, 0.283 mmol, 1.0 eq.) and o-(7-azabenzotriazol-1-yl)-N,N,N',N'-tetramethyluronium hexafluorophosphate (140 mg, 0.368 mmol, 1.3 eq.) in DMF (3 mL) was added N-ethyl-N-isopropylpropan-2-amine (183 mg, 1.42 mmol, 5.0 eq.) at 0° C. The mixture was stirred for 1 h at rt, and the reaction was quenched with water (5 mL). The mixture was extracted with EtOAc (3×5 mL). The organic layers were combined, washed with brine (2×5 mL), dried over anhydrous sodium sulfate, filtered and concentrated under reduced pressure to afford the crude product. The crude product was purified by prep-HPLC (Column: Xselect CSH F-Phenyl OBD column, 19×250 mm, 5 μm; Mobile Phase A: Water (0.1% FA), Mobile Phase B: ACN; Flow rate: 25 mL/min; Gradient: 25% B to 44% B in 10 min, 44% B; Wave Length: 254 nm; RT: 8.97 min) to provide (1S,3aR,6aS)-2-(7-bromo-4-methoxy-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (45.2 mg, 27%) as a white solid. $^1$H NMR (400 MHz, 80° C., DMSO-$d_6$) δ 10.68 (s, 1H), 8.25-8.50 (m, 1H), 7.22-7.45 (m, 2H), 6.96 (s, 1H), 6.41-6.66 (m, 1H), 4.38-4.90 (m, 3H), 4.10-4.30 (m, 2H), 3.75-4.09 (m, 4H), 3.60-3.74 (m, 1H), 3.05-3.20 (m, 2H), 2.55-2.80 (m, 2H), 2.20-2.38 (m, 1H), 1.45-2.05 (m, 10H). LC-MS (ESI, m/z): 575 [M+H]$^+$.

Example 126

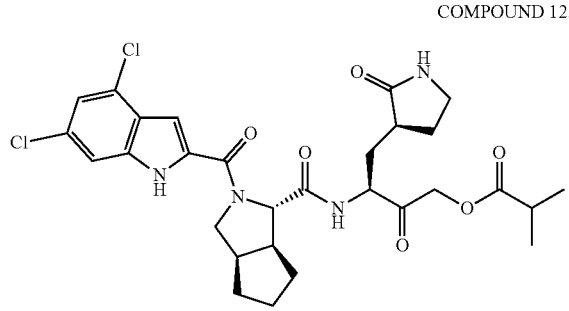

COMPOUND 125

To a mixture of isobutyric acid (7.00 mg, 0.073 mmol, 1.1 eq.) in DCM (0.5 mL) was added dicyclohexylcarbodiimide (41.0 mg, 0.195 mmol, 3.0 eq.), (1S,3aR,6aS)-2-(4,6-dichloro-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (35.0 mg, 0.065 mmol, 1.0 eq.) and N,N-dimethylpyridin-4-amine (2.00 mg, 0.014 mmol, 0.2 eq.) at 0° C. The mixture was stirred for 3 h at rt, and the reaction was quenched with water (5 mL). The mixture was extracted with DCM (3×5 mL). The organic layers were combined, washed with brine (2×5 mL), dried over anhydrous sodium sulfate, filtered and concentrated under reduced pressure to afford the crude product. The crude product was purified by prep-HPLC (Column: YMC-Actus Triart C18, 30×150 mm, 5 μm; Mobile Phase A: Water (0.1% FA), Mobile Phase B: ACN; Flow rate: 60 mL/min; Gradient: 45% B to 64% B in 10 min, 64% B; Wave Length: 254 nm; RT: 9.3 min) to provide (3S)-3-{[(1S,3aR,6aS)-2-(4,6-dichloro-1H-indole-2-carbonyl)-hexahydro-1H-cyclopenta[c]pyrrol-1-yl]formamido}-2-oxo-4-[(3S)-2-oxopyrrolidin-3-yl]butyl 2-methylpropanoate (10.0 mg, 25%) as a white solid. $^1$H NMR (400 MHz, 80° C., DMSO-d$_6$) δ 11.80 (s, 1H), 8.56 (br, 1H), 7.45 (s, 1H), 7.37 (s, 1H), 7.16 (s, 1H), 6.92 (br, 1H), 4.70-5.02 (m, 2H), 4.30-4.69 (m, 2H), 3.90-4.29 (m, 1H), 3.60-3.89 (m, 1H), 3.05-3.28 (m, 2H), 2.50-2.90 (m, 3H), 2.20-2.40 (m, 1H), 1.40-2.08 (m, 10H), 1.12 (d, J=6.4 Hz, 6H). LC-MS (ESI, m/z): 605 [M+H]$^+$.

Example 127

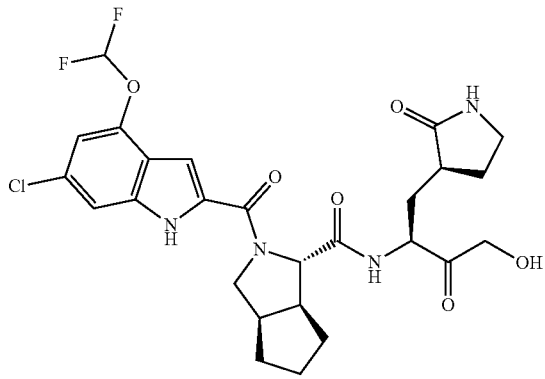

COMPOUND 126

To a solution of sodium methoxide (1.05 g, 5.81 mmol, 4.0 eq., 30% in MeOH) in MeOH (3 mL) was added a mixture of 4-chloro-2-(difluoromethoxy)benzaldehyde (300 mg, 1.45 mmol, 1.0 eq.) and ethyl 2-azidoacetate (750 mg, 5.81 mmol, 4.0 eq.) in MeOH (5 mL) at −10° C. The mixture was stirred for 4 h at −10° C., and the reaction was quenched with water (15 mL) and extracted with EtOAc (3×20 mL). The organic layers were combined, dried over anhydrous sodium sulfate, filtered and concentrated under reduced pressure to afford the crude product. The crude product was purified by TLC (Mobile phase: EtOAc:PE=1:15; Rf=0.5) to provide methyl 2-azido-3-[4-chloro-2-(difluoromethoxy)phenyl]prop-2-enoate (247 mg, 53%).

A solution of methyl 2-azido-3-[4-chloro-2-(difluoromethoxy)phenyl]prop-2-enoate (245 mg, 0.807 mmol, 1.0 eq.) in xylene (3 mL) was stirred for 2 h at 120° C. and then concentrated under reduced pressure to afford the crude product. The crude product was purified by TLC (Mobile phase: EtOAc:PE=1:12; Rf=0.5) to provide methyl 6-chloro-4-(difluoromethoxy)-1H-indole-2-carboxylate (130 mg, 58%). LCMS (ESI, m/z): 274 [M−H]$^−$.

To a solution of methyl 6-chloro-4-(difluoromethoxy)-1H-indole-2-carboxylate (120 mg, 0.435 mmol, 1.0 eq.) in THF (1 mL) was added lithium hydroxide (52.1 mg, 2.18 mmol, 5.0 eq., in 1 mL water), and the mixture was stirred for 2 h at 60° C. The mixture was acidified to pH=5 with hydrochloric acid (1M) and extracted with EtOAc (3×10 mL). The organic layers were combined, dried over anhydrous sodium sulfate, filtered and concentrated under reduced pressure to afford 6-chloro-4-(difluoromethoxy)-1H-indole-2-carboxylic acid (113 mg, crude). LCMS (ESI, m/z): 260 [M−H]$^−$.

To a solution of (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (102 mg, 0.283 mmol, 1.0 eq.) in DMF (1 mL) was added 6-chloro-4-(difluoromethoxy)-1H-indole-2-carboxylic acid (81.6 mg, 0.311 mmol, 1.1 eq.), o-(7-azabenzotriazol-1-yl)-N,N,N',N'-tetramethyluronium hexafluorophosphate (141 mg, 0.369 mmol, 1.3 eq.) and N-ethyl-N-isopropylpropan-2-amine (184 mg, 1.42 mmol, 5.0 eq.) stirred at 0° C. The mixture was stirred for 1 h at rt, and the reaction was quenched with water (5 mL). The mixture was extracted with EA (3×15 mL). The organic layers were combined, washed with brine (2×15 mL), dried over anhydrous sodium sulfate, filtered and concentrated under reduced pressure to afford the crude product. The crude product was purified by preparative HPLC (Column: XSelect CSH Prep C18 OBD Column, 19*150 mm, 5 μm; Mobile Phase A: Water (0.05% FA), Mobile Phase B: ACN; Flow rate: 25 mL/min; Gradient: 37% B to 45% B in 10 min, 45% B; Wave Length: 254 nm; RT1 (min): 6.4.) to provide (1S,3aR,6aS)-2-[6-chloro-4-(difluoromethoxy)-1H-indole-2-carbonyl]-N-[(2S)-4-hydroxy-3-oxo-1-[(3S)-2-oxopyrrolidin-3-yl]butan-2-yl]-hexahydro-1H-cyclopenta[c]pyrrole-1-carboxamide (24.7 mg, 14%) as a white solid.

To a solution of (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (102 mg, 0.283 mmol, 1.0 eq.) in DMF (1 mL) was added 6-chloro-4-(difluoromethoxy)-1H-indole-2-carboxylic acid (81.6 mg, 0.311 mmol, 1.1 eq.), o-(7-azabenzotriazol-1-yl)-N,N,N',N'-tetramethyluronium hexafluorophosphate (141 mg, 0.369 mmol, 1.3 eq.) and N-ethyl-N-isopropylpropan-2-amine (184 mg, 1.42 mmol, 5.0 eq.) stirred at 0° C. The mixture was stirred for 1 h at rt, and the reaction was quenched with water (5 mL). The mixture was extracted with EA (3×15 mL). The organic layers were combined, washed with brine (2×15 mL), dried over anhydrous sodium sulfate, filtered and concentrated under reduced pressure to afford the crude product. The crude product was purified by prep-HPLC (Column: XSelect CSH Prep C18 OBD Column, 19*150 mm, 5 μm; Mobile Phase A: Water (0.05% FA), Mobile Phase B: ACN; Flow rate: 25 mL/min; Gradient: 37% B to 45% B in 10 min, 45% B; Wave Length: 254 nm; RT1 (min): 6.4.) to provide (1S,3aR,6aS)-2-[6-chloro-4-(difluoromethoxy)-1H-indole-2-carbonyl]-N-[(2S)-4-hydroxy-3-oxo-1-[(3S)-2-oxopyrrolidin-3-yl]butan-2-yl]-hexahydro-1H-cyclopenta[c]pyrrole-1-carboxamide (24.7 mg, 14%) as a white solid. LCMS (ESI, m/z): 567 [M+H]$^+$.

Example 128

COMPOUND 127

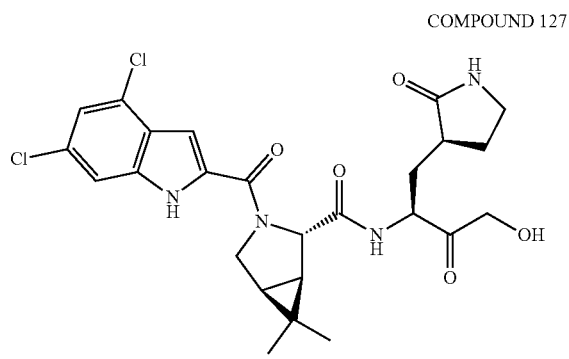 [SMILES: CC1(C)[C@@H]2[C@@H](C(=O)N[C@@H](C[C@@H]3CCNC3=O)C(=O)CO)N(C(=O)c3cc4c(Cl)cc(Cl)cc4[nH]3)C[C@@H]21]

To a solution of (3S)-3-[(2S)-2-amino-4-(benzyloxy)-3-oxobutyl]pyrrolidin-2-one hydrochloride (350 mg, 1.11 mmol, 1.0 eq.), (1R,2S,5S)-3-(tert-butoxycarbonyl)-6,6-dimethyl-3-azabicyclo[3.1.0]hexane-2-carboxylic acid (314 mg, 1.23 mmol, 1.1 eq.) and o-(7-Azabenzotriazol-1-yl)-N,N,N',N'-tetramethyluronium hexafluorophosphate (510 mg, 1.34 mmol, 1.2 eq.) in DMF (3 mL) was added N-ethyl-N-isopropylpropan-2-amine (433 mg, 3.35 mmol, 3.0 eq.) at 0° C. The mixture was stirred for 1 h at rt, and the reaction quenched with water (20 mL). The mixture was extracted with EA (3×20 mL). The organic layers were combined, washed with brine (2×20 mL), dried over anhydrous sodium sulfate, filtered and concentrated under reduced pressure to afford the crude product. The crude product was diluted with dichloromethane (20 mL) and made into a slurry with 100~200 silicagel mesh (2 g). The slurry was loaded to a column after removing the dichloromethane. The sample was purified by column chromatography (Column size 5×24 cm, column volume: 300 mL, silica gel size (100~200 mesh) quantity: 120 g) and eluted with methanol:dichloromethane (0%~10% over 40 min). The collected fractions: 3%-4% methanol:dichloromethane fractions were chosen as the pure fractions, and those fractions were combined and concentrated under reduced pressure to provide tert-butyl (1R,2S,5S)-2-{[(2S)-4-(benzyloxy)-3-oxo-1-[(3S)-2-oxopyrrolidin-3-yl]butan-2-yl]carbamoyl}-6,6-dimethyl-3-azabicyclo[3.1.0]hexane-3-carboxylate (360 mg, 56%) as a yellow solid. LC-MS (ESI, m/z): 514 [M+H]$^+$.

To a stirred mixture of tert-butyl (1R,2S,5S)-2-{[(2S)-4-(benzyloxy)-3-oxo-1-[(3S)-2-oxopyrrolidin-3-yl]butan-2-yl]carbamoyl}-6,6-dimethyl-3-azabicyclo[3.1.0]hexane-3-carboxylate (400 mg, 0.779 mmol, 1.0 eq.) in EtOH (20 mL) was added 10% Palladium on activated carbon (200 mg) at rt. The mixture was stirred for 2 days at rt under hydrogen and then filtered. The residue was washed with EtOH (3×30 mL) and then concentrated under reduced pressure to afford the crude product. The crude product was diluted with dichloromethane (10 mL) and made into a slurry with 100~200 silicagel mesh (2 g). The slurry was loaded to a column after removing the dichloromethane. The sample was purified by column chromatography (Column size 5×24 cm, column volume: 300 mL, silicagel size (100~200 mesh) quantity: 120 g) and eluted with methanol:dichloromethane (0%~10% over 90 min). The collected fractions: 5%-6% methanol:dichloromethane fractions were chosen as the pure fractions, and those fractions were combined and concentrated under reduced pressure to provide tert-butyl (1R,2S,5S)-2-{[(2S)-4-hydroxy-3-oxo-1-[(3S)-2-oxopyrrolidin-3-yl]butan-2-yl]carbamoyl}-6,6-dimethyl-3-azabicyclo[3.1.0] hexane-3-carboxylate (160 mg, 46%) as a light yellow solid. LC-MS (ESI, m/z): 424 [M+H]$^+$.

To a stirred mixture of tert-butyl (1R,2S,5S)-2-{[(2S)-4-hydroxy-3-oxo-1-[(3S)-2-oxopyrrolidin-3-yl]butan-2-yl]carbamoyl}-6,6-dimethyl-3-azabicyclo[3.1.0]hexane-3-carboxylate (160 mg, 0.378 mmol, 1.0 eq.) and DCM (0.5 mL) was added hydrochloric acid (2 mL, 2M in Et$_2$O). The mixture was stirred for 1 h at rt and concentrated under reduced pressure to afford (1R,2S,5S)—N-[(2S)-4-hydroxy-3-oxo-1-[(3S)-2-oxopyrrolidin-3-yl]butan-2-yl]-6,6-dimethyl-3-azabicyclo[3.1.0]hexane-2-carboxamide (150 mg, crude) as a yellow semi-solid. LC-MS (ESI, m/z): 324 [M+H]$^+$.

To a stirred mixture of 4,6-dichloro-1H-indole-2-carboxylic acid (105 mg, 0.459 mmol, 1.1 eq.), o-(7-Azabenzotriazol-1-yl)-N,N,N',N'-tetramethyluronium hexafluorophosphate (190 mg, 0.500 mmol, 1.2 eq.) and (1R,2S,5S)—N-[(2S)-4-hydroxy-3-oxo-1-[(3S)-2-oxopyrrolidin-3-yl]butan-2-yl]-6,6-dimethyl-3-azabicyclo[3.1.0]hexane-2-carboxamide hydrochloride (150 mg, 0.417 mmol, 1.0 eq.) in DMF (2 mL) was added N-ethyl-N-isopropylpropan-2-amine (269 mg, 2.09 mmol, 5.0 eq.) at 0° C. The mixture was stirred for 1 h at rt, and the reaction was quenched with water (10 mL). The mixture was extracted with EA (3×10 mL). The organic layers were combined, washed with brine (2×10 mL), dried over anhydrous sodium sulfate, filtered and concentrated under reduced pressure to afford the crude product. The crude product was diluted with dichloromethane (5 mL) and made into a slurry with 100~200 silicagel mesh (1 g). The slurry was loaded to a column after removing the dichloromethane. The sample was purified by column chromatography (Column size 5×24 cm, column volume: 300 mL, silica gel size (100~200 mesh) quantity: 120 g) and eluted with methanol:dichloromethane (0%~10% over min). The collected fractions: 5%-6% methanol:dichloromethane fractions were chosen as the pure fractions. Those fractions were combined and concentrated under reduced pressure to provide the crude product. The crude product (80 mg) was purified by Prep-Achiral-SFC with the following conditions (Column: GreenSep Basic, 3*15 cm, 5 μm; Mobile Phase A: C$_{O2}$, Mobile Phase B: IPA (0.5% 2M NH$_3$-MeOH); Flow rate: 75 mL/min; Gradient: isocratic 30% B; Column Temperature (° C.): 35; Back Pressure (bar): 100; Wave Length: 220 nm; RT1 (min): 4.02) to afford (1R,2S,5S)-3-(4,6-dichloro-1H-indole-2-carbonyl)-N-[(2S)-4-hydroxy-3-oxo-1-[(3S)-2-oxopyrrolidin-3-yl]butan-2-yl]-6,6-dimethyl-3-azabicyclo[3.1.0]hexane-2-carboxamide (19.1 mg, 7%) as an off-white solid. LC-MS (ESI, m/z): 535 [M+H]$^+$. LC-MS (ESI, m/z): 535 [M+H]$^+$.

Example 129

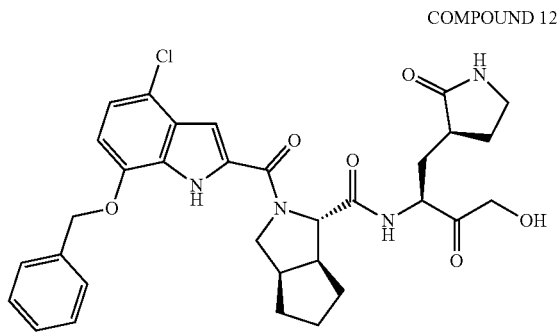

COMPOUND 128

To a stirred mixture of sodium methylate (3.79 g, 21.1 mmol, 4.0 eq., 30% in MeOH) in MeOH (30 mL) was added a solution of 5-(benzyloxy)-2-chlorobenzaldehyde (1.30 g, 5.27 mmol, 1.0 eq.) and ethyl 2-azidoacetate (2.72 g, 21.1 mmol, 4.0 eq.) in MeOH (10 mL) at 0° C. The mixture was stirred for 4 h at rt, and the reaction was quenched with water (50 mL). The mixture was extracted with EA (3×100 mL). The organic layers were combined, washed with brine (2×30 mL), dried over anhydrous sodium sulfate, filtered and concentrated under reduced pressure. The residue was purified by silica gel column chromatography, eluted with PE:EA (15:1) to afford methyl (2E)-2-azido-3-[5-(benzyloxy)-2-chlorophenyl]prop-2-enoate (1.35 g, 68%) as a yellow solid.

A mixture of methyl (2E)-2-azido-3-[5-(benzyloxy)-2-chlorophenyl]prop-2-enoate (1.30 g, 3.78 mmol, 1.0 eq.) in xylene (20 mL) was stirred for 3 h at 120° C. and then concentrated under reduced pressure. The residue was purified by silica gel column chromatography, eluted with PE:EA (15:1) to afford methyl 7-(benzyloxy)-4-chloro-1H-indole-2-carboxylate (1.02 g, 78%) as a yellow solid. LC-MS (ESI, m/z): 316 [M+H]$^+$.

To a stirred mixture of methyl 7-(benzyloxy)-4-chloro-1H-indole-2-carboxylate (500 mg, 1.58 mmol, 1.0 eq.) in tetrahydrofuran (10 mL) and water (5 mL) was added lithium hydroxide (189 mg, 7.92 mmol, 5.0 eq.) dropwise at rt. The mixture was stirred for 2 h at 40° C. The reaction was diluted with water (20 mL) at rt. The mixture was extracted with EA (30 mL). The water layers were acidified to pH=3 with hydrochloric acid (2M). The mixture was extracted with EA (3×40 mL). The organic layers were combined, washed with brine (2×30 mL), dried over anhydrous sodium sulfate, filtered and concentrated under reduced pressure to afford 7-(benzyloxy)-4-chloro-1H-indole-2-carboxylic acid (240 mg, 50%) as a yellow solid. LC-MS (ESI, m/z): 300 [M−H]$^-$.

To a stirred mixture of 7-(benzyloxy)-4-chloro-1H-indole-2-carboxylic acid (71.0 mg, 0.235 mmol, 1.0 eq.) and (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (84.7 mg, 0.235 mmol, 1.0 eq.) in N,N-dimethylformamide (8 mL) was added O-(7-Aza-1H-benzotriazol-1-yl)-N,N,N',N'-tetramethyluronium hexafluorophosphate (116 mg, 0.305 mmol, 1.3 eq.) and N,N-diisopropylethylamine (122 mg, 0.940 mmol, 4.0 eq.) at 0° C. The mixture was stirred for 2 h at rt, and the reaction was quenched with water (15 mL) at rt. The mixture was extracted with EA (3×40 mL). The organic layers were combined, washed with brine (2×30 mL), dried over anhy-drous sodium sulfate, filtered and concentrated under reduced pressure. The crude product (200 mg) was purified by Prep-HPLC with the following conditions (Column: XBridge Prep Phenyl OBD Column, 19*250 mm, 5 μm; Mobile Phase A: Water (0.05% FA), Mobile Phase B: ACN; Flow rate: 25 mL/min; Gradient: 45% B to 75% B in 7 min, 75% B; Wave Length: 254 nm; RT1 (min): 5.5) to afford (1S,3aR,6aS)-2-[7-(benzyloxy)-4-chloro-1H-indole-2-carbonyl]-N-[(2S)-4-hydroxy-3-oxo-1-[(3S)-2-oxopyrrolidin-3-yl]butan-2-yl]-hexahydro-1H-cyclopenta[c]pyrrole-1-carboxamide (38.5 mg, 27%) as a white solid. $^1$H NMR (400 MHz, 80° C., DMSO-d$_6$) δ 11.43 (br, 1H), 8.34-8.38 (m, 1H), 7.53-7.57 (m, 2H), 7.33-7.38 (m, 2H), 7.26-7.32 (m, 2H), 6.95-6.98 (m, 1H), 6.75-6.80 (m, 2H), 5.23 (s, 2H), 3.72-4.88 (m, 6H), 3.61-3.68 (m, 1H), 2.89-3.03 (m, 2H), 2.55-2.77 (m, 2H), 1.40-2.32 (m, 11H). LC-MS (ESI, m/z): 607 [M+H]$^+$.

Example 130

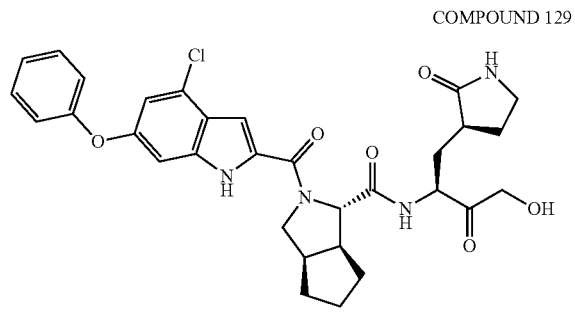 [SMILES: O=C1NCC[C@H]1C[C@H](NC(=O)[C@@H]1[C@H]2CCC[C@H]2CN1C(=O)c1cc2c(Cl)cc(Oc3ccccc3)cc2[nH]1)C(=O)CO]

COMPOUND 129

To a solution of sodium methoxide (3.10 g, 17.2 mmol, 4.0 eq., 30% in MeOH) in MeOH (10 mL) was added a mixture of 2-chloro-4-phenoxybenzaldehyde (1.00 g, 4.30 mmol, 1.0 eq.) and ethyl 2-azidoacetate (2.22 g, 17.2 mmol, 4.0 eq.) in MeOH (10 mL) at −10° C. The mixture was stirred for 2 h at 0° C., and the reaction was quenched with water (25 mL) and extracted with EtOAc (3×40 mL). The organic layers were combined, dried over anhydrous sodium sulfate, filtered and concentrated under reduced pressure to afford the crude product. The crude product was purified by silica gel column chromatography with EtOAc:PE=1:99 to afford methyl 2-azido-3-(2-chloro-4-phenoxyphenyl)prop-2-enoate (600 mg, 42%).

A solution of methyl 2-azido-3-(2-chloro-4-phenoxyphenyl)prop-2-enoate (600 mg, 1.82 mmol, 1.0 eq.) in xylene (6 mL) was stirred for 4 h at 120° C. and then concentrated under reduced pressure to afford the crude product. The crude product was purified by silica gel column chromatography with EtOAc:PE=2:98 to afford methyl 4-chloro-6-phenoxy-1H-indole-2-carboxylate (350 mg, 63%). $^1$H NMR (400 MHz, DMSO-d$_6$) δ 12.10-12.28 (m, 1H), 7.39-7.47 (m, 2H), 7.17-7.22 (m, 1H), 7.06-7.13 (m, 3H), 6.98-7.02 (m, 1H), 6.89-6.93 (m, 1H), 3.88 (s, 3H). LCMS (ESI, m/z): 300 [M−H]$^-$.

To a solution of methyl 4-chloro-6-phenoxy-1H-indole-2-carboxylate (350 mg, 1.16 mmol, 1.0 eq.) in THF (3 mL) was added lithium hydroxide (139 mg, 5.80 mmol, 5.0 eq., in 3 mL water), and the mixture was stirred for 2 h at 60° C. The mixture was acidified to pH=5 with hydrochloric acid (1M) and extracted with EtOAc (3×10 mL). The organic layers were combined, dried over anhydrous sodium sulfate, filtered and concentrated under reduced pressure to afford 4-chloro-6-phenoxy-1H-indole-2-carboxylic acid (320 mg, crude). $^1$H NMR (300 MHz, DMSO-d$_6$) δ 13.19 (s, 1H), 11.92-12.12 (m, 1H), 7.37-7.49 (m, 2H), 7.14-7.23 (m, 1H), 7.02-7.13 (m, 3H), 6.95-7.00 (m, 1H), 6.86-6.94 (m, 1H). LCMS (ESI, m/z): 286 [M−H]$^−$.

To a solution of (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (102 mg, 0.283 mmol, 1.0 eq.) in DMF (1 mL) was added 4-chloro-6-phenoxy-1H-indole-2-carboxylic acid (89.7 mg, 0.311 mmol, 1.1 eq.), o-(7-azabenzotriazol-1-yl)-N,N,N',N'-tetramethyluronium hexafluorophosphate (141 mg, 0.369 mmol, 1.3 eq.) and N-ethyl-N-isopropylpropan-2-amine (184 mg, 1.42 mmol, 5.0 eq.) stirred at 0° C. The mixture was stirred for 1 h at rt, and the reaction was quenched with water (5 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by prep-HPLC (Column: XSelect CSH Prep C18 OBD Column, 19*250 mm, 5 μm; Mobile Phase A: Water (0.05% FA), Mobile Phase B: ACN; Flow rate: 25 mL/min; Gradient: 45% B to 55% B in 10 min, 55% B; Wave Length: 254 nm; RT1 (min): 9.8.) to provide (1S,3aR,6aS)-2-(4-chloro-6-phenoxy-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (44.2 mg, 26%) as a white solid. LCMS (ESI, m/z): 593 [M+H]$^+$.

Example 131

COMPOUND 130

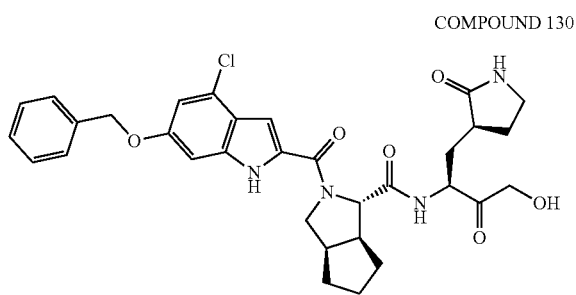 [SMILES: O=C1NCC[C@H]1C[C@H](NC(=O)[C@@H]1[C@H]2CCC[C@H]2CN1C(=O)c1cc2c(Cl)cc(OCc3ccccc3)cc2[nH]1)C(=O)CO]

To a solution of sodium methanolate (4.37 g, 24.3 mmol, 4.0 eq., 30% in MeOH) in MeOH (15 mL) was add a solution of 4-(benzyloxy)-2-chlorobenzaldehyde (1.50 g, 6.08 mmol, 1.0 eq.) and ethyl 2-azidoacetate (3.14 g, 24.3 mmol, 4.0 eq.) in MeOH (15 mL) at −10° C. The mixture was stirred for overnight at rt, and the reaction quenched with water (20 mL). The mixture was extracted with EA (3×50 mL). The organic layers were combined, washed with brine (2×20 mL), dried over anhydrous sodium sulfate, filtered and concentrated under reduced pressure to afford the crude product. The crude product was diluted with dichloromethane (10 mL) and made into a slurry with 100~200 silica gel mesh (5 g). The slurry was loaded to a column after removing the dichloromethane. The sample was purified by column chromatography (Column size 6×12 cm, column volume: 300 mL, silica gel size (100~200 mesh) quantity: 120 g) and eluted with EA:PE (0%-10% over 20 min). The collected fractions: 3%-5% EA:PE fractions were chosen as the pure fractions. Those fractions were combined and concentrated under reduced pressure to provide methyl 2-azido-3-[4-(benzyloxy)-2-chlorophenyl]prop-2-enoate (800 mg, 38%) as a white solid. $^1$H NMR (300 MHz, DMSO-d$_6$) δ 8.21-8.24 (m, 1H), 7.32-7.47 (m, 5H), 7.24-7.25 (m, 1H), 7.07-7.18 (m, 2H), 5.19 (s, 2H), 3.86 (s, 3H).

A solution of methyl 2-azido-3-[4-(benzyloxy)-2-chlorophenyl]prop-2-enoate (800 mg, 1.45 mmol, 1.0 eq.) in xylene (8 mL) was stirred for 3 h at 120° C. The mixture was concentrated under reduced pressure to afford the crude product. The crude product was diluted with dichloromethane (10 mL) and made into a slurry with 100~200 silica gel mesh (2 g). The slurry was loaded to a column after removing the dichloromethane. The sample was purified by column chromatography (Column size 4×12 cm, column volume: 120 mL, silicagel size (100~200 mesh) quantity: 80 g) and eluted with EA:PE (0%-10% over 30 min). The collected fractions: 5%-6% EA:petroleum ether fractions were chosen as the pure fractions, and those fractions were combined and concentrated under reduced pressure to provide methyl 6-(benzyloxy)-4-chloro-1H-indole-2-carboxylate (500 mg, 68%) as a white solid. $^1$H NMR (300 MHz, DMSO-d$_6$) δ 12.12 (s, 1H), 7.27-7.50 (m, 5H), 7.05-7.06 (m, 1H), 6.97-6.98 (m, 1H), 6.94-6.95 (m, 1H), 5.16 (s, 2H), 3.87 (s, 3H). LC-MS (ESI, m/z): 314 [M−H]$^−$.

To a mixture of methyl 6-(benzyloxy)-4-methoxy-1H-indole-2-carboxylate (300 mg, 0.950 mmol, 1.0 eq.) in THF (5 mL) was added sodium hydroxide (190 mg, 4.75 mmol, 5.0 eq., in 1 mL water). The mixture was stirred for 2 h at 50° C. The mixture was concentrated under reduced pressure to remove the THF, and the pH was adjusted to 3-4 with HCl (2 M). The mixture was extracted with EA (3×10 mL). The organic layers were combined, washed with brine (2×10 mL), dried over anhydrous sodium sulfate, filtered and concentrated under reduced pressure to afford 6-(benzyloxy)-4-methoxy-1H-indole-2-carboxylic acid (240 mg, crude) as a white solid. $^1$H NMR (300 MHz, DMSO-d$_6$) δ 12.96 (br, 1H), 11.94-11.95 (m, 1H), 7.31-7.50 (m, 5H), 6.94-6.99 (m, 3H), 5.15 (s, 2H). LC-MS (ESI, m/z): 300 [M−H]$^−$.

To a mixture of 6-(benzyloxy)-4-methoxy-1H-indole-2-carboxylic acid (106 mg, 0.350 mmol, 1.2 eq.), (1S,3aR,6aS)—N—((S)-4-hydroxy-3-oxo-1-((S)-2-oxopyrrolidin-3-yl)butan-2-yl)octahydrocyclopenta[c]pyrrole-1-carboxamide hydrochloride (105 mg, 0.292 mmol, 1.0 eq.) and 2-(7-azabenzotriazol-1-yl)-N,N,N',N'-tetramethyluronium hexafluorophosphate (133 mg, 0.350 mmol, 1.2 eq.) in DMF (2 mL) was added N,N-diisopropylethylamine (113 mg, 0.876 mmol, 3.0 eq.) at 0° C. The mixture was stirred for 1 h at rt, and the reaction was quenched with water (5 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by HPLC (Column: XSelect CSH Prep C18 OBD Column, 19*250 mm, 5 μm; Mobile Phase A: Water (0.05% FA), Mobile Phase B: ACN; Flow rate: 25 mL/min; Gradient: 45% B to 73% B in 7 min, 73% B; Wave Length: 254 nm; RT1 (min): 6); to provide (1S,3aR,6aS)-2-(6-(benzyloxy)-4-chloro-1H-indole-2-carbonyl)-N—((S)-4-hydroxy-3-oxo-1-((S)-2-oxopyrrolidin-3-yl)butan-2-yl)octahydrocyclopenta[c]pyrrole-1-carboxamide (45.3 mg, 25%) as a white solid. $^1$H-NMR (400 MHz, 80° C., DMSO-d$_6$) δ 11.43 (s, 1H), 8.40 (br, 1H), 7.38-7.44 (m, 2H), 7.28-7.36 (m, 4H), 7.00 (s, 1H), 6.89-6.90 (m, 1H), 6.80 (br, 1H), 5.13 (s, 2H), 4.73-4.76 (m, 2H), 4.51-4.55 (m, 1H), 4.03-4.22 (m, 3H), 3.69-3.71 (m, 1H), 2.93-3.00 (m, 2H), 2.62-2.74 (m, 2H), 2.29-2.34 (m, 1H), 1.77-2.01 (m, 4H), 1.55-1.75 (m, 5H), 1.43-1.50 (m, 1H). LC-MS (ESI, m/z): 607 [M+H]⁺.

Example 132

COMPOUND 131

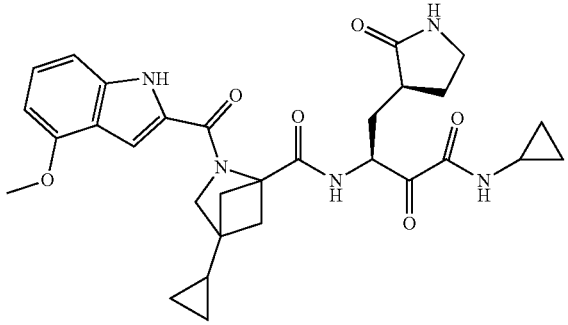

Compound 131 was prepared similarly as described for Compound 97 using 4-cyclopropyl-2-azabicyclo[2.1.1]hexane-1-carboxylic acid hydrochloride in place of (S)-1,2,3,4-tetrahydroisoquinoline-3-carboxylic acid. LCMS (ESI, m/z): 562 [M+H]⁺. 4-Cyclopropyl-2-azabicyclo[2.1.1]hexane-1-carboxylic acid hydrochloride: To a solution of methyl 2-benzoyl-4-vinyl-2-azabicyclo[2.1.1]hexane-1-carboxylate (220 mg, 0.811 mmol, 1.0 eq.) in diethyl ether (1.5 mL) cooled to −10° C. were added freshly prepared diazomethane solution (5 mL) and Pd(OAc)₂ (27 mg, 0.120 mmol, 0.15 eq.). The mixture was stirred at −10° C. to 0° C. for 3 h. After cooling to −10° C., freshly prepared diazomethane solution (5 mL) and Pd(OAc)₂ (27 mg, 0.120 mmol, 0.15 eq.) were added a second time. The mixture was stirred at −10° C. to 0° C. for 3 h. The mixture was diluted with 5% MeOH in DCM (20 mL) and then filtered through Celite. The filtrate was concentrated under reduced pressure. The residue was purified by flash chromatography on silica gel (12 g column) using a gradient of MeOH (1 to 2%) in DCM to afford methyl 2-benzoyl-4-cyclopropyl-2-azabicyclo[2.1.1]hexane-1-carboxylate (205 mg, 88%) as a pale brown oil. LC-MS (ESI, m/z): 286 [M+H]⁺.

Preparation of the diazomethane solution: A solution of KOH (1.2 g) in water (2 mL) and ethanol (6 mL) was heated to 70° C. A solution of Diazald in diethyl ether (30 mL) was added dropwise, and the generated diazomethane was collected as an ethereal solution at −50° C. for 30 min.

To a solution of methyl 2-benzoyl-4-cyclopropyl-2-azabicyclo[2.1.1]hexane-1-carboxylate (300 mg, 1.05 mmol, 1.0 eq.) in dioxane (3 mL) was added conc. HCl (3 mL). The mixture was heated in a sealed-tube at 80° C. for 20 h. After cooling to rt, the mixture was concentrated under reduced pressure. The residue was dissolved in water (5 mL) and then extracted with DCM (2×10 mL). The aqueous layer was concentrated under reduced pressure to afford 4-cyclopropyl-2-azabicyclo[2.1.1]hexane-1-carboxylic acid hydrochloride (210 mg, 98%) as a pale brown solid. LC-MS (ESI, m/z): 168 [M+H]⁺.

Example 133

COMPOUND 132

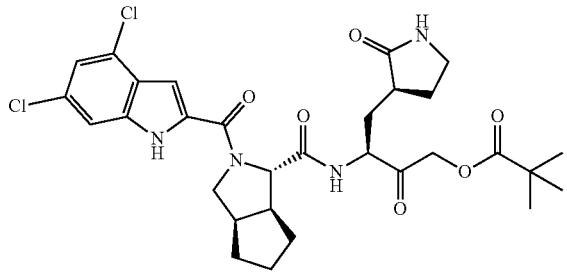

To a mixture of pivalic acid (42.0 mg, 0.411 mmol, 1.1 eq.) in DCM (5 mL) was added dicyclohexylcarbodiimide (231 mg, 1.12 mmol, 3.0 eq.), (1S,3aR,6aS)-2-(4,6-dichloro-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (200 mg, 0.374 mmol, 1.0 eq.) and N,N-dimethylpyridin-4-amine (9.00 mg, 0.075 mmol, 0. eq.) at 0° C. The mixture was stirred overnight at rt, and the reaction was quenched with water (10 mL). The mixture was extracted with DCM (3×10 mL). The organic layers were combined, washed with brine (2×10 mL), dried over anhydrous sodium sulfate, filtered and concentrated under reduced pressure to afford the crude product. The crude product was purified by TLC (Mobile phase: MeOH: DCM=1:15; Rf=0.6; detection: UV) to afford the crude product (150 mg). The crude product was purified by prep-HPLC (Column: XBridge Prep Phenyl OBD Column, 19×250 mm, 5 μm; Mobile Phase A: Water (0.1% FA), Mobile Phase B: ACN; Flow rate: 25 mL/min; Gradient: 55% B to 72% B in 7 min, 72% B; Wave Length: 254 nm; RT: 6.8 min) to provide (3S)-3-{[(1S,3aR,6aS)-2-(4,6-dichloro-1H-indole-2-carbonyl)-hexahydro-1H-cyclopenta[c]pyrrol-1-yl]formamido}-2-oxo-4-[(3S)-2-oxopyrrolidin-3-yl]butyl 2,2-dimethylpropanoate (90.3 mg, 38%) as a white solid. ¹H NMR (400 MHz, 80° C., DMSO-d₆) δ 10.80 (s, 1H), 8.58 (br, 1H), 7.30-7.55 (m, 2H), 7.16 (s, 1H), 6.92 (br, 1H), 4.65-5.03 (m, 2H), 4.28-4.64 (m, 2H), 3.80-4.27 (m, 1H), 3.55-3.79 (m, 1H), 3.05-3.28 (m, 2H), 2.55-2.88 (m, 2H), 1.90-2.40 (m, 4H), 1.40-1.89 (m, 7H), 1.00-1.28 (m, 9H). LC-MS (ESI, m/z): 619 [M+H]⁺.

Example 134

COMPOUND 133

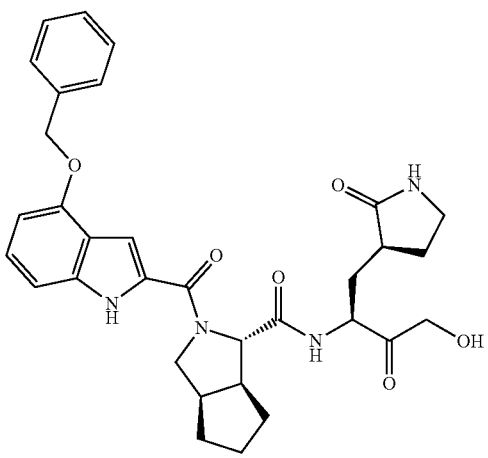

To a solution of (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (102 mg, 0.283 mmol, 1.0 eq.) in DMF (1 mL) was added 4-(benzyloxy)-1H-indole-2-carboxylic acid (83.3 mg, 0.311 mmol, 1.1 eq.), o-(7-azabenzotriazol-1-yl)-N,N,N',N'-tetramethyluronium hexafluorophosphate (141 mg, 0.369 mmol, 1.3 eq.) and N-ethyl-N-isopropylpropan-2-amine (184 mg, 1.42 mmol, 5.0 eq.) stirred at 0° C. The mixture was stirred for 1 h at rt, and the reaction was quenched with water (5 mL). The mixture was extracted with EA (3×15 mL). The organic layers were combined, washed with brine (2×20 mL), dried over anhydrous sodium sulfate, filtered and concentrated under reduced pressure to afford the crude product. The crude product was purified by prep-HPLC (Column: XSelect CSH Prep C18 OBD Column, 19*250 mm, 5 μm; Mobile Phase A: Water (0.05% FA), Mobile Phase B: ACN; Flow rate: 25 mL/min; Gradient: 45% B to 50% B in 10 min, 50% B; Wave Length: 254 nm; RT1 (min): 6.4.) to provide (1S,3aR,6aS)-2-[4-(benzyloxy)-1H-indole-2-carbonyl]-N-[(2S)-4-hydroxy-3-oxo-1-[(3S)-2-oxopyrrolidin-3-yl]butan-2-yl]-hexahydro-1H-cyclopenta[c]pyrrole-1-carboxamide (64.8 mg, 39%) as a white solid. LCMS (ESI, m/z): 573 [M+H]$^+$.

Example 135

COMPOUND 134

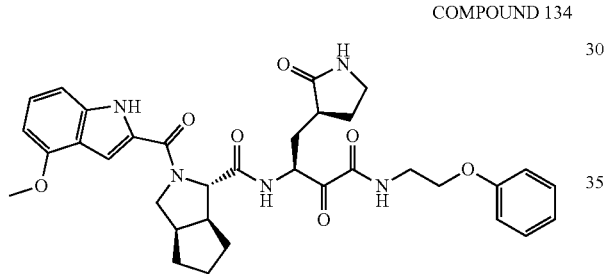

Compound 134 was prepared similarly as described for Compound 16 using (3S)-3-amino-2-hydroxy-4-((S)-2-oxopyrrolidin-3-yl)-N-(2-phenoxyethyl)butanamide hydrochloride in place of (3S)-3-amino-N-benzyl-2-hydroxy-4-[(3S)-2-oxopyrrolidin-3-yl]butanamide hydrochloride. LCMS (ESI, m/z): 630 [M+H]$^+$.

(3S)-3-Amino-2-hydroxy-4-((S)-2-oxopyrrolidin-3-yl)-N-(2-phenoxyethyl)butanamide hydrochloride was prepared similarly as described for Intermediate 1 using (2-isocyanoethoxy)benzene in place of (isocyanomethyl)benzene.

Example 136

COMPOUND 135

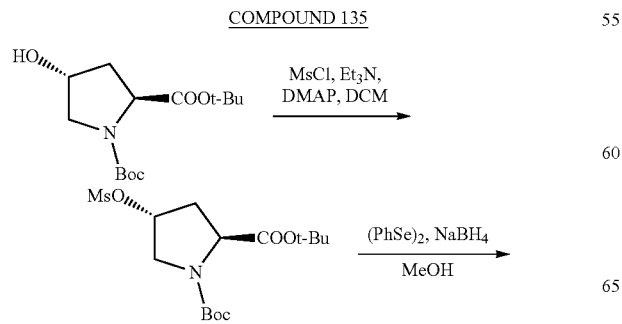

-continued

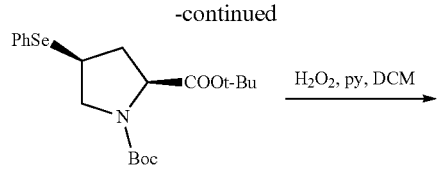

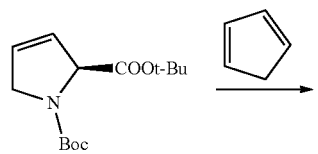

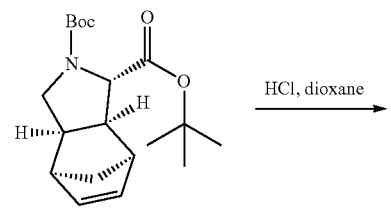

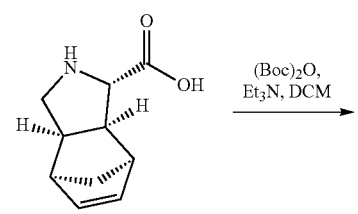

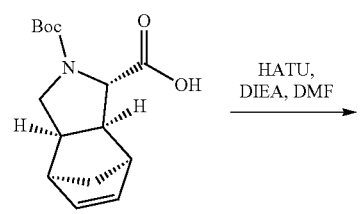

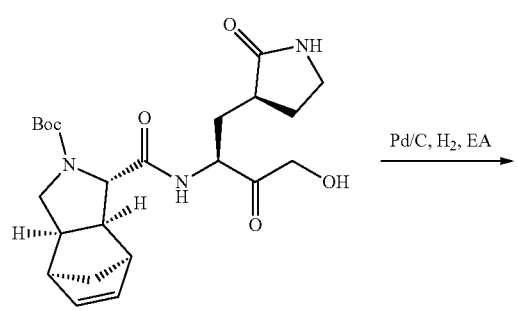

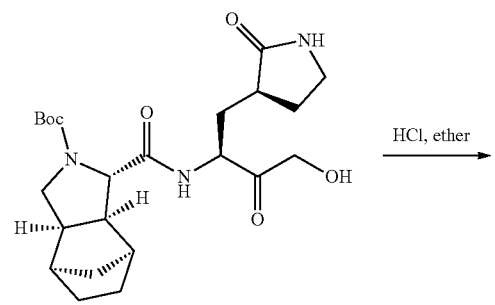

-continued

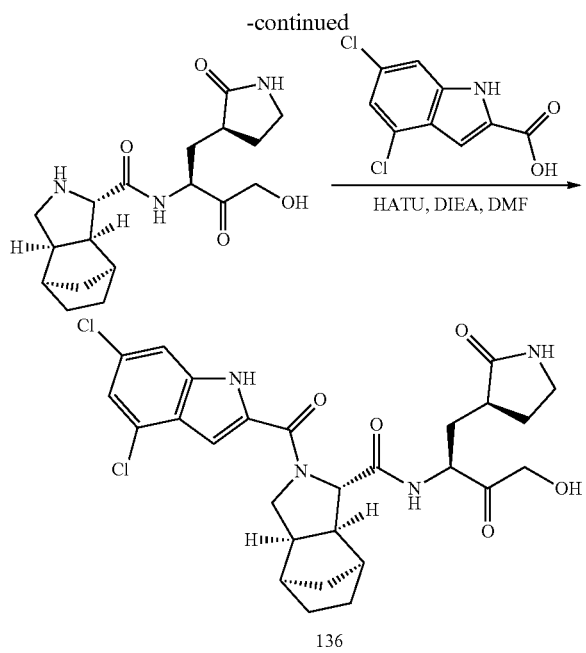

136

To a solution of 1,2-di-tert-butyl (2S,4R)-4-hydroxypyrrolidine-1,2-dicarboxylate (15 g, 52.2 mmol, 1.0 eq.) in DCM (250 mL) was added triethylamine (9.51 g, 93.9 mmol, 1.8 eq.) and DMAP (1.91 g, 15.7 mmol, 0.3 eq.). MsCl (8.97 g, 78.3 mmol, 1.5 eq.) was added dropwise at 0° C. The mixture was stirred at rt for 2 h, and the reaction was quenched with water (100 mL). The solution was extracted with DCM (3×150 mL). The organic layers were combined, washed with brine (100 mL), dried over anhydrous sodium sulfate, filtered and concentrated under reduced pressure. The residue was chromatographed on a silica gel column with EA:PE (1:10) to provide 1,2-di-tert-butyl (2S,4R)-4-(methanesulfonyloxy)pyrrolidine-1,2-dicarboxylate (17.8 g, 89%) as a colorless oil. LC-MS (ESI, m/z): 366 [M+H]$^+$.

To a solution of 1,2-di-tert-butyl (2S,4R)-4-(methanesulfonyloxy)pyrrolidine-1,2-dicarboxylate (17.8 g, 48.7 mmol, 1.0 eq.) in MeOH (400 mL) was added (phenyldiselanyl)benzene (9.12 g, 29.2 mmol, 0.6 eq.). SodiumBorohydride (2.4 g, 63.3 mmol, 1.3 eq.) was added at 0° C. in several portions. The mixture was refluxed overnight and then concentrated under reduced pressure. Water (100 mL) was added, and the mixture was extracted with EA (3×150 mL). The organic layers were combined, washed with brine (100 mL), dried over anhydrous sodium sulfate, filtered and concentrated under reduced pressure. The residue was chromatographed on a silica gel column with EA:PE (1:5) to provide 1,2-di-tert-butyl (2S,4S)-4-(phenylselanyl)pyrrolidine-1,2-dicarboxylate (7.5 g (yield 32%) as a colorless oil. LC-MS (ESI, m/z): 428 [M+H]$^+$.

To a solution of 1,2-di-tert-butyl (2S,4S)-4-(phenylselanyl)pyrrolidine-1,2-dicarboxylate (7.5 g, 17.6 mmol, 1.0 eq.) in DCM (100 mL) was added pyridine (2.4 mL, 30.5 mmol, 1.7 eq.) and 30% aqueous H$_2$O$_2$ (5.6 mL, 71.6 mmol, 4.0 eq.). The mixture was stirred at rt for 12 h, and the reaction was quenched with water (20 mL). The solution was extracted with DCM (3×150 mL). The organic layers were combined, washed with 1 M citric acid (80 mL), sat. aq. Na$_2$SO$_3$ (100 mL) and brine (100 mL), dried over anhydrous sodium sulfate, filtered and concentrated under reduced pressure. The residue was chromatographed on a silica gel column with EA:PE (1:9) to provide 1,2-di-tert-butyl (2S)-2,5-dihydropyrrole-1,2-dicarboxylate (2.8 g, 53%) as a colorless oil. $^1$H NMR (300 MHz, DMSO-d$_6$) δ 6.02-6.09 (m, 1H), 5.76-5.83 (m, 1H), 4.72-4.78 (m, 1H), 4.05-4.09 (m, 2H), 1.17-1.42 (m, 18H). LC-MS (ESI, m/z): 270 [M+H]$^+$.

A solution of 1,2-di-tert-butyl (2S)-2,5-dihydropyrrole-1,2-dicarboxylate (2.8 g, 10.4 mmol, 1.0 eq.) in cyclopenta-1,3-diene (60 mL) was stirred at 170° C. for 48 h under nitrogen and then resolved with DCM (200 mL). After removal of the solvent, the resulting residue was chromatographed on a silica gel column with EA:PE (1:9) to provide the product (2.5 g, crude) as a yellow oil. The crude oil was chromatographed on a C18 column with H$_2$O:MeCN (2:1) to provide di-tert-butyl (1S,3aR,4S,7R,7aS)-1,3,3a,4,7,7a-hexahydro-2H-4,7-methanoisoindole-1,2-dicarboxylate (690 mg, 19%) as a white solid. LC-MS (ESI, m/z): 270 [M+H]$^+$.

To a solution of i-tert-butyl (1S,3aR,4S,7R,7aS)-1,3,3a,4,7,7a-hexahydro-2H-4,7-methanoisoindole-1,2-dicarboxylate (690 mg, 2.1 mmol, 1.0 eq.) in dioxane (10 mL) was added hydrochloric acid (10 mL, 9M). The mixture was stirred at rt overnight and then concentrated under reduced pressure to provide (1S,3aR,4S,7R,7aS)-2,3,3a,4,7,7a-hexahydro-1H-4,7-methanoisoindole-1-carboxylic acid (320 mg, crude) as a black solid. LC-MS (ESI, m/z): 180 [M+H]$^+$.

To a solution of (1S,3aR,4S,7R,7aS)-2,3,3a,4,7,7a-hexahydro-1H-4,7-methanoisoindole-1-carboxylic acid (320 mg, 1.79 mmol, 1.0 eq.) in DCM (8 mL) was added di-tert-butyl dicarbonate (429 mg, 1.97 mmol, 1.1 eq.) and triethylamine (542 mg, 5.34 mmol, 3.0 eq.). The mixture was stirred at rt for 3 h and then concentrated under reduced pressure to provide (1S,3aR,4S,7R,7aS)-2-(tert-butoxycarbonyl)-2,3,3a,4,7,7a-hexahydro-1H-4,7-methanoisoindole-1-carboxylic acid (430 mg, crude) as a brown solid. LC-MS (ESI, m/z): 280 [M+H]$^+$.

To a solution of tert-butyl N-[(2S)-4-hydroxy-3-oxo-1-[(3S)-2-oxopyrrolidin-3-yl]butan-2-yl]carbamate (630 mg, 2.2 mmol, 1.0 eq.) in hydrochloric acid (12 mL, 4 mol/L in dioxane) was stirred at rt for 1 h and then concentrated under reduced pressure to provide (3S)-3-[(2S)-2-amino-4-hydroxy-3-oxobutyl]pyrrolidin-2-one (330 mg, crude) as a white solid. LCMS (ESI, m/z): 187 [M+H]$^+$.

To a solution of (1S,3aR,4S,7R,7aS)-2-(tert-butoxycarbonyl)-2,3,3a,4,7,7a-hexahydro-1H-4,7-methanoisoindole-1-carboxylic acid (430 mg, 1.54 mmol, 1.0 eq.) in DMF (8 mL) was added N,N,N',N'-Tetramethyl-O-(7-azabenzotriazol-1-yl)uronium hexafluorophospate (761 mg, 2.0 mmol, 1.3 eq.) and N,N-diisopropylethylamine (1.39 g, 10.8 mmol, 7.0 eq.). The mixture was stirred at 0° C. for 30 min and (3S)-3-[(2S)-2-amino-4-hydroxy-3-oxobutyl]pyrrolidin-2-one (330 mg, 1.77 mmol, 1.1 eq.) was added. The mixture was stirred at rt for 2 h, and the reaction was quenched with water (5 mL). The mixture was extracted with EA (3×15 mL). The organic layers were combined, washed with brine (3×10 mL), dried over anhydrous sodium sulfate, filtered and concentrated under reduced pressure. The residue was chromatographed on a silica gel column with DCM:MeOH (19:1) to provide tert-butyl (1S,3aR,4S,7R,7aS)-1-(((S)-4-hydroxy-3-oxo-1-((S)-2-oxopyrrolidin-3-yl)butan-2-yl)carbamoyl)-1,3,3a,4,7,7a-hexahydro-2H-4,7-methanoisoindole-2-carboxylate (370 mg, 45%) as a brown yellow solid. LC-MS (ESI, m/z): 448 [M+H]$^+$.

A 50 mL round-bottom flask was charged with tert-butyl (1S,3aR,4S,7R,7aS)-1-(((S)-4-hydroxy-3-oxo-1-((S)-2-oxopyrrolidin-3-yl)butan-2-yl)carbamoyl)-1,3,3a,4,7,7a-hexahydro-2H-4,7-methanoisoindole-2-carboxylate (180 mg, 0.4 mmol, 1.0 eq.), EA (5 mL) and 10% Palladium on activated carbon (90 mg). The contents of the flask were placed under an atmosphere of hydrogen (3 atm). The mixture was stirred at rt for 2 h. The solids were filtered out. The organic layer was concentrated under reduced pressure to provide (1S,3aR,4R,7S,7aS)—N—((S)-4-hydroxy-3-oxo-1-((S)-2-oxopyrrolidin-3-yl)butan-2-yl)octahydro-1H-4,7-methanoisoindole-1-carboxamide (165 g, 82%) as an off-white solid. LC-MS (ESI, m/z): 450 [M+H]+.

To a solution of (1S,3aR,4R,7S,7aS)—N—((S)-4-hydroxy-3-oxo-1-((S)-2-oxopyrrolidin-3-yl)butan-2-yl)octahydro-1H-4,7-methanoisoindole-1-carboxamide (165 mg, 0.37 mmol, 1.0 eq.) in hydrochloric acid (4 mL, 2 mol/L in ether) was stirred at rt for 2 h and then concentrated under reduced pressure to provide (1S,3aR,4R,7S,7aS)—N—((S)-4-hydroxy-3-oxo-1-((S)-2-oxopyrrolidin-3-yl)butan-2-yl)octahydro-1H-4,7-methanoisoindole-1-carboxamide (80 mg, crude) as a light yellow solid. LC-MS (ESI, m/z): 350 [M+H]+.

To a solution of 4,6-dichloro-1H-indole-2-carboxylic acid (57.3 mg, 0.25 mmol, 1.1 eq.) in DMF (2 mL) was added N,N,N',N'-Tetramethyl-O-(7-azabenzotriazol-1-yl)uronium hexafluorophospate (103 mg, 0.3 mmol, 1.3 eq.) and N,N-diisopropylethylamine (208 mg, 1.61 mmol, 7.0 eq.). The mixture was stirred at 0° C. for 30 min and (1S,3aR,4R,7S,7aS)—N—((S)-4-hydroxy-3-oxo-1-((S)-2-oxopyrrolidin-3-yl)butan-2-yl)octahydro-1H-4,7-methanoisoindole-1-carboxamide (80 mg, 0.23 mmol, 1.0 eq.) was added. The mixture was stirred at rt for 2 h, and the reaction was quenched with water (3 mL). The mixture was extracted with EA (3×10 mL). The organic layers were combined, dried over anhydrous sodium sulfate, filtered and concentrated under reduced pressure. The residue was purified by Pre-HPLC (Column: Kinetex EVO C18, 21.2*250 mm, 5 μm; Mobile Phase A: Water (0.1% FA), Mobile Phase B: ACN; Flow rate: 25 mL/min; Gradient: 40% B to 70% B in 7 min, 70% B; Wave Length: 254 nm; RT1 (min): 5.65) to provide (1S,3aR,4R,7S,7aS)-2-(4,6-dichloro-1H-indole-2-carbonyl)-N—((S)-4-hydroxy-3-oxo-1-((S)-2-oxopyrrolidin-3-yl)butan-2-yl)octahydro-1H-4,7-methanoisoindole-1-carboxamide (13.4 mg, 11%) as a white solid. LC-MS (ESI, m/z): 561 [M+H]+.

Example 137

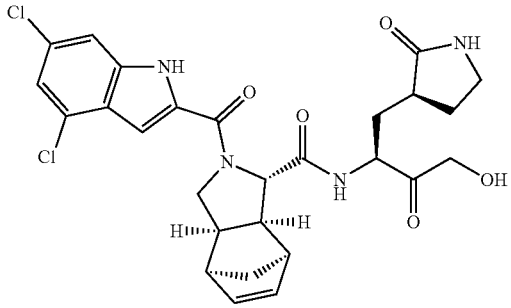 [SMILES: O=C1NCC[C@H]1C[C@H](NC(=O)[C@@H]1[C@@H]2[C@H](CN1C(=O)c1cc3c(Cl)cc(Cl)cc3[nH]1)[C@@H]1C=C[C@H]2C1)C(=O)CO]

To a solution of tert-butyl (1S,3aR,4S,7R,7aS)-1-(((S)-4-hydroxy-3-oxo-1-((S)-2-oxopyrrolidin-3-yl)butan-2-yl)carbamoyl)-1,3,3a,4,7,7a-hexahydro-2H-4,7-methanoisoindole-2-carboxylate (180 mg, 0.4 mmol, 1.0 eq.) in hydrochloric acid in ether (4 mL, 2 mol/L), was stirred at rt for 2 h and then concentrated under reduced pressure to provide (1S,3aR,4S,7R,7aS)—N—((S)-4-hydroxy-3-oxo-1-((S)-2-oxopyrrolidin-3-yl)butan-2-yl)-2,3,3a,4,7,7a-hexahydro-1H-4,7-methanoisoindole-1-carboxamide (95 mg, crude) as a light yellow solid. LC-MS (ESI, m/z): 348 [M+H]+.

To a solution of 4,6-dichloro-1H-indole-2-carboxylic acid (69.2 mg, 0.3 mmol, 1.1 eq.) in DMF (2 mL) was added N,N,N',N'-Tetramethyl-O-(7-azabenzotriazol-1-yl)uronium hexafluorophospate (135 mg, 0.35 mmol, 1.3 eq.) and N,N-diisopropylethylamine (247 mg, 1.91 mmol, 7.0 eq.). The mixture was stirred at 0° C. for 30 min and (1R,2S,3S,6R,7S)—N-[(2S)-4-hydroxy-3-oxo-1-[(3S)-2-oxopyrrolidin-3-yl]butan-2-yl]-4-azatricyclo[5.2.1.0^{2,6}]dec-8-ene-3-carboxamide (95 mg, 0.27 mmol, 1.0 eq.) was added. The mixture was stirred at rt for 2 h, and the reaction was quenched with water (3 mL). The mixture was extracted with EA (3×10 mL). The organic layers were combined, dried over anhydrous sodium sulfate, filtered and concentrated under reduced pressure. The residue was purified by Prep-HPLC (Column: Kinetex EVO C18, 21.2*250 mm, 5 μm; Mobile Phase A: Water (0.1% FA), Mobile Phase B: ACN; Flow rate: 25 mL/min; Gradient: 40% B to 70% B in 7 min, 70% B; Wave Length: 254 nm; RT1 (min): 5.18) to provide (1R,2S,3S,6R,7S)-4-(4,6-dichloro-1H-indole-2-carbonyl)-N-[(2S)-4-hydroxy-3-oxo-1-[(3S)-2-oxopyrrolidin-3-yl]butan-2-yl]-4-azatricyclo[5.2.1.0^{2,6}]dec-8-ene-3-carboxamide (23.0 mg, 15%) as a white solid. LC-MS (ESI, m/z): 559 [M+H]+.

Example 138

COMPOUND 137

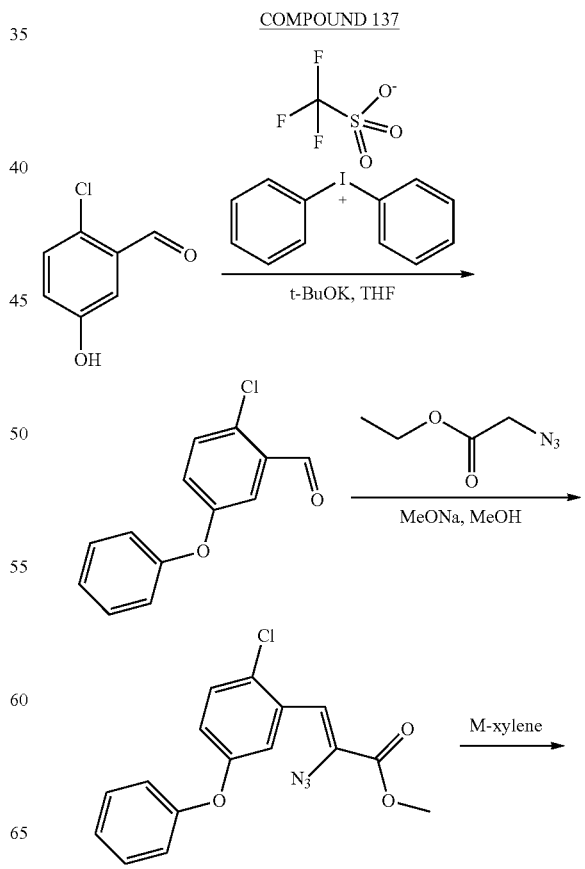

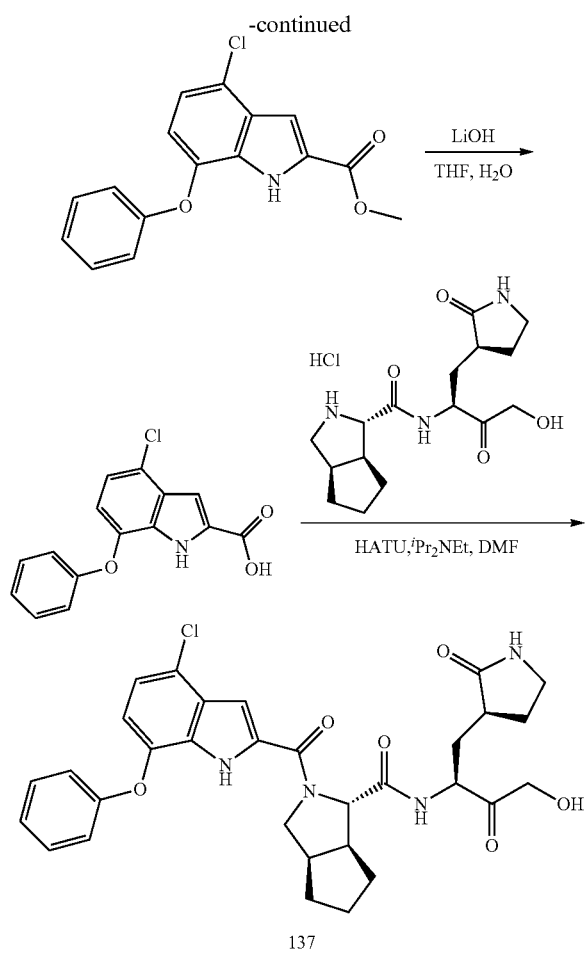

137

To a stirred mixture of 2-chloro-5-hydroxybenzaldehyde (1.00 g, 6.38 mmol, 1.0 eq.) in THF (15 mL) was added potassium tert-butoxide (0.790 g, 7.02 mmol, 1.1 eq.) at 0° C., and the mixture was stirred for 15 min at 0° C. Diphenyliodanium triflate (3.30 g, 7.66 mmol, 1.2 eq.) was then added at 0° C. The mixture was stirred for 4 h at 40° C., and the reaction was quenched with water (100 mL). The resulting mixture was extracted with EA (3×100 mL). The organic layers were combined, washed with brine (2×100 mL), dried over anhydrous sodium sulfate, filtered and concentrated under reduced pressure to afford the crude product. The crude product was diluted with dichloromethane (20 mL) and made into a slurry with 100~200 silica gel mesh (4 g). The slurry was loaded to a column after removing the dichloromethane. The sample was purified by column chromatography (Column size 5×24 cm, column volume: 300 mL, silica gel size (100~200 mesh) quantity: 120 g) using EA:PE (0%~10% over 30 min) as the eluent. The collected fractions: 4%-5% EA:PE fractions were chosen as the pure fractions. Those fractions were combined and concentrated under reduced pressure to provide 2-chloro-5-phenoxybenzaldehyde (1.3 g, 83%) as a colorless oil. $^1$H NMR (400 MHz, DMSO-d$_6$) δ 10.26 (s, 1H), 7.65 (d, J=8.0 Hz, 1H), 7.43-7.50 (m, 2H), 7.33-7.42 (m, 1H), 7.29-7.33 (m, 1H), 7.22-7.28 (m, 1H), 7.08-7.15 (m, 2H).

A solution of sodium methanolate (4.03 g, 22.4 mmol, 4.0 eq., 30% in MeOH) in MeOH (10 mL) was cooled to −10° C. A mixture of 2-chloro-5-phenoxybenzaldehyde (1.30 g, 5.58 mmol, 1.0 eq.) and ethyl 2-azidoacetate (2.89 g, 22.4 mmol, 4.0 eq.) in MeOH (10 mL) was added dropwise to the sodium methanolate solution over 0.5 h. The mixture was stirred for 4 h at −10° C., and then poured into ice-water (100 mL). The mixture was extracted with ethyl ether (3×100 mL). The organic layers were combined, washed with brine (2×100 mL), dried over anhydrous sodium sulfate, filtered and concentrated under reduced pressure to afford the crude product. The crude product was diluted with EA (20 mL) and made into a slurry with 100~200 silica gel mesh (4 g). The slurry was loaded to a column after removing the dichloromethane. The sample was purified by column chromatography (Column size 5×24 cm, column volume: 300 mL, silica gel size (100~200 mesh) quantity: 120 g) using EA:PE (0%~10% over 30 min) as the eluent. The collected fractions: 3%-4% EA:PE fractions were chosen as the pure fractions. Those fractions were combined and concentrated under reduced pressure to provide methyl (2Z)-2-azido-3-(2-chloro-5-phenoxyphenyl)prop-2-enoate (680 mg, 33%) as a light yellow solid.

The mixture of methyl 2-azido-3-(2-chloro-5-phenoxyphenyl)prop-2-enoate (680 mg, 2.06 mmol, 1.0 eq.) and m-xylene (10 mL) was stirred for 2 h at 120° C. under nitrogen. The mixture was concentrated under reduced pressure to afford the crude product. The crude product was diluted with dichloromethane (10 mL) and made into a slurry with 100~200 silica gel mesh (1 g). The slurry was loaded to a column after removing the dichloromethane. The sample was purified by column chromatography (Column size 5×24 cm, column volume: 300 mL, silica gel size (100~200 mesh) quantity: 120 g) using EA:PE (0%-20% over 30 min) as the eluent. The collected fractions: 7%-8% EA:PE fractions were chosen as the pure fractions. Those fractions were combined and concentrated under reduced pressure to provide methyl 4-chloro-7-phenoxy-1H-indole-2-carboxylate (160 mg, 23%) as a white solid. LC-MS (ESI, m/z): 300 [M−H]$^-$.

To a stirred mixture of methyl 4-chloro-7-phenoxy-1H-indole-2-carboxylate (160 mg, 0.530 mmol, 1.0 eq.) in H$_2$O (2 mL) and THF (2 mL) was added lithium hydroxide (63.5 mg, 2.65 mmol, 5.0 eq.), and the mixture was stirred for 2 h at 60° C. The mixture was acidified to pH=3 with hydrochloric acid (2M). The mixture was extracted with EA (3×10 mL). The organic layers were combined, washed with brine (2×10 mL), dried over anhydrous sodium sulfate, filtered and concentrated under reduced pressure to afford 4-chloro-7-phenoxy-1H-indole-2-carboxylic acid (140 mg, crude). LC-MS (ESI, m/z): 286 [M−H]$^-$.

To a stirred mixture of (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (90.0 mg, 0.250 mmol, 1.0 eq.), 4-chloro-7-phenoxy-1H-indole-2-carboxylic acid (79.1 mg, 0.275 mmol, 1.1 eq.) and o-(7-Azabenzotriazol-1-yl)-N,N,N',N'-tetramethyluronium hexafluorophosphate (114 mg, 0.300 mmol, 1.2 eq.) in DMF (4 mL) was added N-ethyl-N-isopropylpropan-2-amine (193 mg, 1.50 mmol, 6.0 eq.) at 0° C. The mixture was stirred for 1 h at rt, and the reaction was quenched with water (10 mL). The mixture was extracted with EA (3×10 mL). The organic layers were combined, washed with brine (2×10 mL), dried over anhydrous sodium sulfate, filtered and concentrated under reduced pressure to afford the crude product. The crude product (100 mg) was purified by prep-HPLC with the following conditions (Column: XBridge Prep C18 OBD Column, 19*150 mm, 5 μm; Mobile Phase A: Water (0.05% FA), Mobile Phase B: ACN; Flow rate: 25 mL/min; Gradient: 33% B to 63% B in 7 min, 63% B; Wave Length: 254 nm; RT1 (min): 6.3) to afford (1S,3aR,6aS)-2-(4-chloro-7- phenoxy-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (42.2 mg, 27%) as a white solid. LC-MS (ESI, m/z): 593 [M+H]$^+$.

Example 139

COMPOUND 138

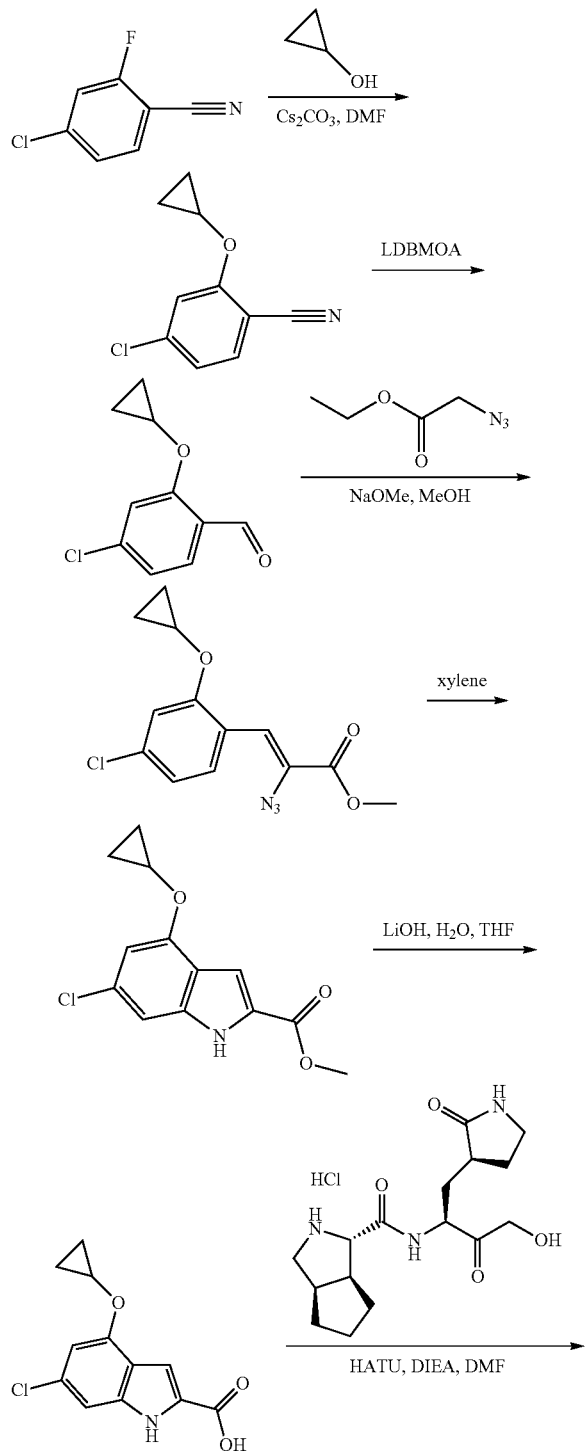

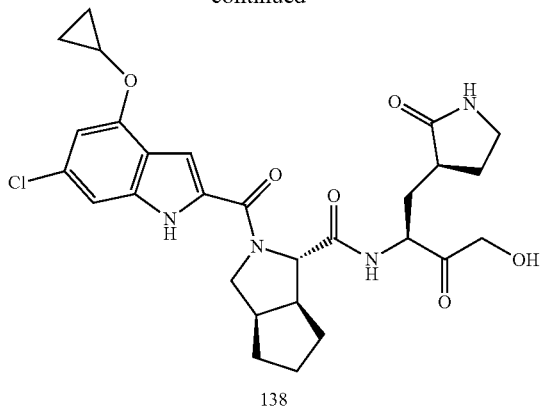

138

To a solution of 4-chloro-2-fluorobenzonitrile (1.00 g, 6.43 mmol, 1.0 eq.) in DMF (10 mL) was added cesium carbonate (4.20 g, 12.9 mmol, 2.0 eq.) and cyclopropanol (1.12 g, 19.3 mmol, 3.0 eq.) at rt. The mixture was stirred overnight at 80° C., and the reaction was quenched with water (30 mL). The mixture was extracted with EA (3×30 mL). The organic layers were combined, washed with brine (2×20 mL), dried over anhydrous sodium sulfate, filtered and concentrated under reduced pressure to afford the crude product. The crude product was purified by silica gel column chromatography with EA:PE (5:95) to afford 4-chloro-2-cyclopropoxybenzonitrile (750 mg, 60%). $^1$H NMR (400 MHz, DMSO-d$_6$) δ 7.75-7.83 (m, 1H), 7.56-7.60 (m, 1H), 7.20-7.26 (m 1H), 4.09-4.16 (m, 1H), 0.84-0.93 (m, 2H), 0.74-0.81 (m, 2H).

To a solution of morpholine (1.1 mL, 12.5 mmol) in THF (6.4 mL) was added n-BuLi (5 mL, 2.5M in THF, 12.5 mmol) slowly under nitrogen at 0° C. The mixture was stirred for 1 h at 0° C., and then diisobutylaluminium hydride (12.5 mmol, 1.0 M in hexanes) was dropwise to the mixture at 0° C. under nitrogen. The mixture was stirred for 2 h at rt, and the crude product (LDBMOA) was used directly into the next step.

To a solution of 4-chloro-2-cyclopropoxybenzonitrile (900 mg, 4.65 mmol, 1.0 eq.) in THF (9 mL) was added dropwise LDBMOA (18.6 mL, 9.30 mmol, 2.0 eq., 0.5M) at 0° C. under nitrogen. The mixture was stirred overnight at rt, and the reaction was quenched with water (10 mL). The mixture was extracted with EA (3×20 mL). The organic layers were combined, dried over anhydrous sodium sulfate, filtered and concentrated under reduced pressure to afford the crude product. The crude product was purified by silica gel column chromatography with EA:P (2:98) to afford 4-chloro-2-cyclopropoxybenzaldehyde (450 mg, 49%). $^1$H NMR (400 MHz, DMSO-d$_6$) δ 10.20 (s, 1H), 7.67-7.73 (m, 1H), 7.54-7.59 (m, 1H), 7.15-7.22 (m, 1H), 4.09-4.17 (m, 1H), 0.77-0.91 (m, 4H). LCMS (ESI, m/z): 197 [M+H]$^+$.

To a solution of sodium methoxide (1.98 g, 11.0 mmol, 4.0 eq., 30% in MeOH) in MeOH (5 mL) was added dropwise a mixture of 4-chloro-2-cyclopropoxybenzaldehyde (540 mg, 2.75 mmol, 1.0 eq.) and ethyl 2-azidoacetate (1.42 g, 11.0 mmol, 4.0 eq.) in MeOH (5 mL) at −10° C. The mixture was stirred for 4 h at −10° C., and the reaction was quenched with water (30 mL) and extracted with EtOAc (3×30 mL). The organic layers were combined, dried over anhydrous sodium sulfate, filtered and concentrated under reduced pressure to afford the crude product. The crude product was purified by silica gel column chromatography with EtOAc:PE (1:99) to afford methyl 2-azido-3-(4-chloro-2-cyclopropoxyphenyl)prop-2-enoate (420 mg, 52%).

A solution of methyl 2-azido-3-(4-chloro-2-cyclopropoxyphenyl)prop-2-enoate (370 mg, 1.26 mmol, 1.0 eq.) in xylene (4 mL) was stirred for 2 h at 120° C., and then concentrated under reduced pressure to afford the crude product. The crude product was purified by silica gel column chromatography with EtOAc:PE (2:98) to afford methyl 6-chloro-4-cyclopropoxy-1H-indole-2-carboxylate (211 mg, 63%). $^1$H NMR (300 MHz, DMSO-d$_6$) δ 12.11 (br, 1H), 6.99-7.12 (m, 2H), 6.80-6.88 (m, 1H), 3.96-4.07 (m, 1H), 3.86 (s, 3H), 0.71-0.90 (m, 4H).

To a solution of methyl 6-chloro-4-cyclopropoxy-1H-indole-2-carboxylate (211 mg, 0.794 mmol, 1.0 eq.) in THF (2 mL) was added lithium hydroxide (95.1 mg, 3.97 mmol, 5.0 eq., in 1 mL water), and the mixture was stirred for 2 h at 60° C. The mixture was acidified to pH=5 with hydrochloric acid (1M) and extracted with EtOAc (3×10 mL). The organic layers were combined, dried over anhydrous sodium sulfate, filtered and concentrated under reduced pressure to afford 6-chloro-4-cyclopropoxy-1H-indole-2-carboxylic acid (199 mg, crude). LCMS (ESI, m/z): 250 [M−H]$^−$.

To a solution of (1S,3aR,6aS)—N—((S)-4-hydroxy-3-oxo-1-((S)-2-oxopyrrolidin-3-yl)butan-2-yl)octahydrocyclopenta[c]pyrrole-1-carboxamide hydrochloride (102 mg, 0.284 mmol, 1.0 eq.) in DMF (1 mL) was added 6-chloro-4-cyclopropoxy-1H-indole-2-carboxylic acid (78.5 mg, 0.311 mmol, 1.1 eq.), o-(7-azabenzotriazol-1-yl)-N,N,N',N'-tetramethyluronium hexafluorophosphate (141 mg, 0.369 mmol, 1.3 eq.) and N-ethyl-N-isopropylpropan-2-amine (184 mg, 1.42 mmol, 5.0 eq.) at 0° C. The mixture was stirred for 1 h at rt, and the reaction was quenched with water (5 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by prep-HPLC (Column: XBridge Prep C18 OBD Column, 19*150 mm, 5 μm; Mobile Phase A: Water (0.05% FA), Mobile Phase B: ACN; Flow rate: 25 mL/min; Gradient: 37% B to 43% B in 10 min, 43% B; Wave Length: 254 nm; RT1 (min): 6.0) to provide (1S,3aR,6aS)-2-(6-chloro-4-cyclopropoxy-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (33.9 mg, 21%) as a white solid. LCMS (ESI, m/z): 557 [M+H]$^+$.

Example 140

COMPOUND 139

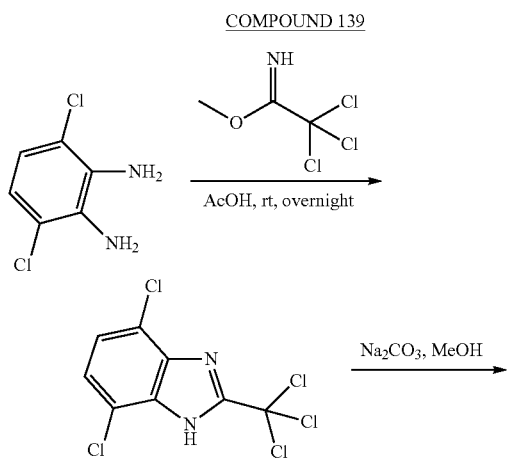

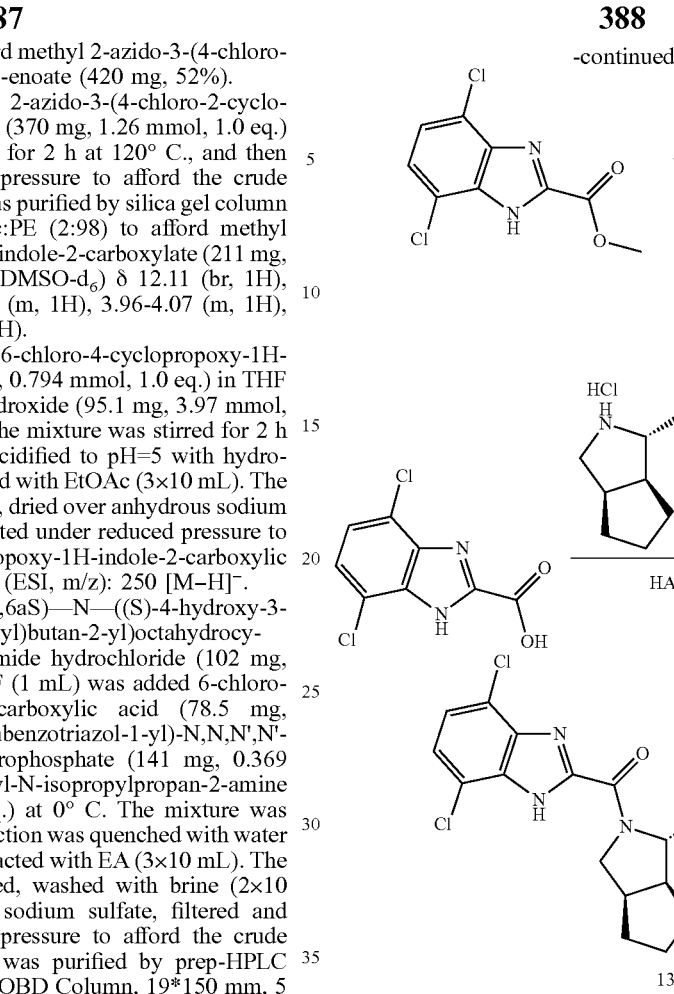

To a mixture of 3,6-dichlorobenzene-1,2-diamine (300 mg, 1.69 mmol, 1.0 eq.) in acetic acid (10 mL) was added methyl 2,2,2-trichloroethanimidate (329 mg, 1.86 mmol, 1.1 e eq.). The mixture was stirred overnight at rt and then poured into water (20 mL). 4,7-dichloro-2-(trichloromethyl)-1H-1,3-benzodiazole (400 mg, 73%) was obtained by filtration as a light yellow solid. $^1$H NMR (300 MHz, CDCl$_3$-d) δ 9.88 (br, 1H), 7.33-7.38 (m, 2H). LC-MS (ESI, m/z): 303 [M+H]$^+$.

To a mixture of 4,7-dichloro-2-(trichloromethyl)-1H-1,3-benzodiazole (400 mg, 1.31 mmol, 1.0 eq.) in MeOH (10 mL) was added sodium carbonate (141 mg, 1.31 mmol, 1.0 eq.). The mixture was stirred overnight at 70° C. The mixture was filtered through a Celite pad and then concentrated under reduced pressure to afford the crude product. The crude product was diluted with DCM (10 mL) and made into a slurry with 100~200 silicagel mesh (1 g). The slurry was loaded to a column after removing the DCM. The sample was purified by column chromatography (Column size 4×24 cm, column volume: 200 mL, silicagel size (100~200 mesh) quantity: 80 g) and eluted with MeOH:DCM (0% 3% over 20 min). The collected fractions: 1%-2% MeOH:DCM fractions were chosen as the pure fractions. Those fractions were combined and concentrated under reduced pressure to provide methyl 4,7-dichloro-1H-1,3-benzodiazole-2-carboxylate (240 mg, 71%) as a yellow solid. LC-MS (ESI, m/z): 245 [M+H]$^+$.

To a mixture of methyl 4,7-dichloro-1H-1,3-benzodiazole-2-carboxylate (140 mg, 0.571 mmol, 1.0 eq.) in THF (1.5 mL):water (1.5 mL) was added lithium hydroxide (68.0 mg, 2.85 mmol, 5.0 eq.). The mixture was stirred for 3 h at 40° C. The mixture was concentrated under reduced pressure to the THF. The pH was adjusted to 6 with hydrochloric acid (2 M). The 4,7-dichloro-1H-1,3-benzodiazole-2-carboxylic acid (90.0 mg, 66%) was obtained by filtration as a white solid. LC-MS (ESI, m/z): 229 [M–H]⁻.

To a mixture of (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (102 mg, 0.283 mmol, 1.0 eq.), 4,7-dichloro-1H-1,3-benzodiazole-2-carboxylic acid (72.0 mg, 0.311 mmol, 1.1 eq.) and o-(7-azabenzotriazol-1-yl)-N,N,N',N'-tetramethyluronium hexafluorophosphate (140 mg, 0.368 mmol, 1.3 eq.) in DMF (3 mL) was added N-ethyl-N-isopropylpropan-2-amine (183 mg, 1.42 mmol, 5.0 eq.) at 0° C. The mixture was stirred for 1 h at rt. The mixture was purified by C18 column with CH₃CN:Water (0.05% TFA) to afford the crude product (110 mg). The crude product was further purified by prep-HPLC (Column: XBridge Prep Phenyl OBD Column, 19×250 mm, 5 μm; Mobile Phase A: Water (0.1% FA), Mobile Phase B: ACN; Flow rate: 25 mL/min; Gradient: 25% B to 50% B in 7 min, 50% B; Wave Length: 254 nm; RT: 6.65 min) to provide (1S,3aR,6aS)-2-(4,7-dichloro-1H-1,3-benzodiazole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (54.6 mg, 34%) as a white solid. ¹H NMR (400 MHz, 80° C., DMSO-d₆) δ 13.68 (br, 1H), 8.30-8.58 (m, 1H), 7.05-7.55 (m, 3H), 4.60-5.56 (m, 1H), 4.38-4.59 (m, 1H), 3.50-4.37 (m, 5H), 3.05-3.20 (m, 1H), 2.90-3.03 (m, 1H), 2.75-2.89 (m, 1H), 2.55-2.74 (m, 1H), 2.10-2.45 (m, 1H), 1.28-2.09 (m, 10H). LC-MS (ESI, m/z): 536 [M+H]⁺.

Example 141

COMPOUND 140

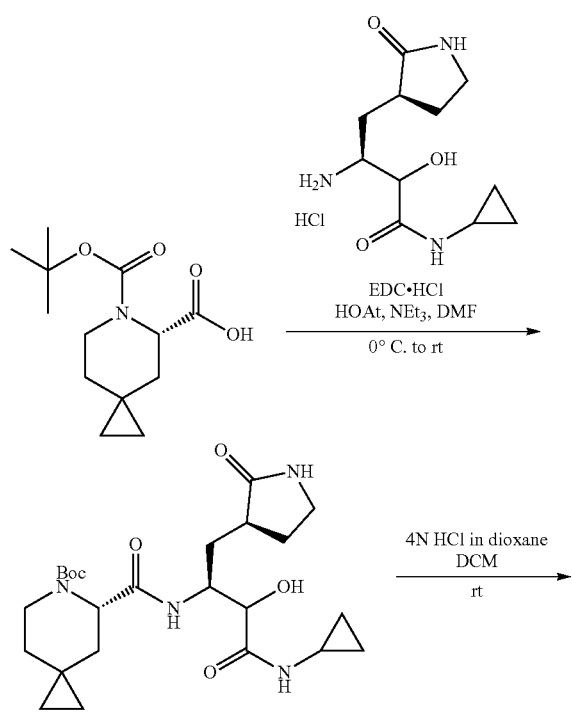

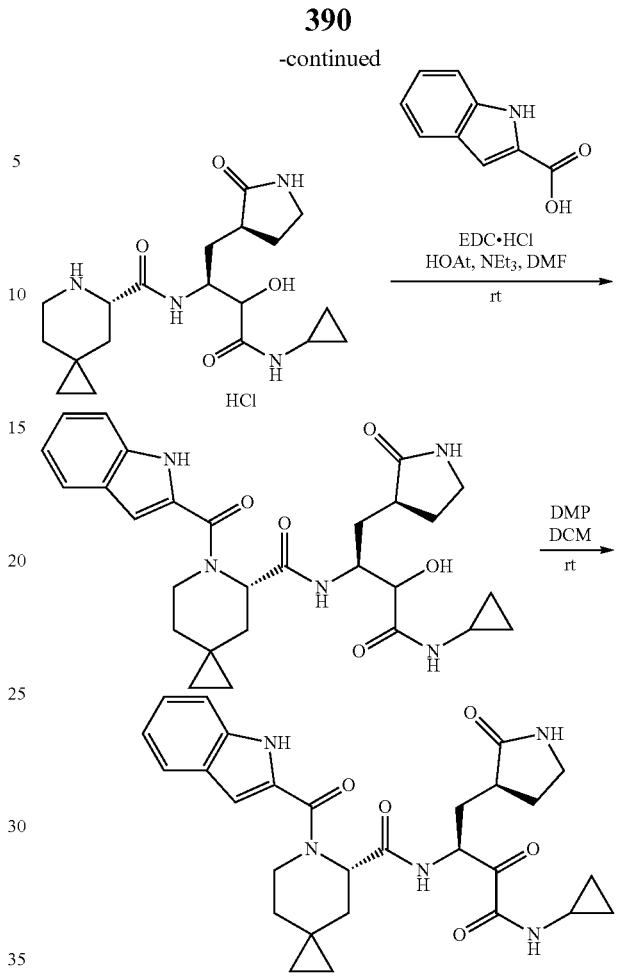

To a solution of (S)-6-(tert-butoxycarbonyl)-6-azaspiro[2.5]octane-5-carboxylic acid (1.79 g, 7.03 mmol, 1.0 eq.) in DMF (18 mL) cooled to 0° C. were added (3S)-3-amino-N-cyclopropyl-2-hydroxy-4-((S)-2-oxopyrrolidin-3-yl)butanamide hydrochloride (2.03 g, 8.44 mmol, 1.2 eq.), EDC·HCl (2.68 g, 14.1 mmol, 2.0 eq.), HOAt (956 mg, 7.03 mmol, 1.0 eq.) and NEt₃ (3.3 mL, 21.1 mmol, 3.0 eq.). The mixture was stirred at rt for 16 h. The mixture was diluted with water (20 mL) and extracted with EA (5×20 mL). The organic phases were combined, washed with brine (30 mL), dried over Na₂SO₄, filtered and concentrated under reduced pressure. The residue was purified by flash chromatography on silica gel (40 g column) using 10% MeOH in DCM as the eluent to afford tert-butyl (5S)-5-(((2S)-4-(cyclopropylamino)-3-hydroxy-4-oxo-1-((S)-2-oxopyrrolidin-3-yl)butan-2-yl)carbamoyl)-6-azaspiro[2.5]octane-6-carboxylate (1.4 g, 38%) as an off-white solid. LC-MS (ESI, m/z): 479 [M+H]⁺.

To a solution of tert-butyl (5S)-5-(((2S)-4-(cyclopropylamino)-3-hydroxy-4-oxo-1-((S)-2-oxopyrrolidin-3-yl)butan-2-yl)carbamoyl)-6-azaspiro[2.5]octane-6-carboxylate (1.4 g, 2.92 mmol, 1.0 eq.) in DCM (14 mL) was added 4N HCl in dioxane (7.0 mL, 28.0 mmol, 9.6 eq.). The mixture was stirred at rt for 5 h. The mixture was concentrated under reduced pressure and coevaporated with diethyl ether to afford (5S)—N-((2S)-4-(cyclopropylamino)-3-hydroxy-4-oxo-1-((S)-2-oxopyrrolidin-3-yl)butan-2-yl)-6-azaspiro[2.5]octane-5-carboxamide hydrochloride (1.35 g, crude) as an off-white solid. LC-MS (ESI, m/z): 379 [M+H]⁺.

To a solution of (5S)—N-((2S)-4-(cyclopropylamino)-3-hydroxy-4-oxo-1-((S)-2-oxopyrrolidin-3-yl)butan-2-yl)-6-azaspiro[2.5]octane-5-carboxamide hydrochloride (150 mg, 0.363 mmol, 1.0 eq.) in DMF (1.5 mL) cooled to 0° C. were added 1H-indole-2-carboxylic acid (62 mg, 0.385 mmol, 1.1 eq.), EDC·HCl (111 mg, 0.581 mmol, 1.6 eq.), HOAt (40 mg, 0.290 mmol, 0.8 eq.) and NEt$_3$ (0.12 mL, 0.871 mmol, 2.4 eq.). The mixture was stirred at rt for 16 h. The mixture was diluted with water (5 mL) and extracted with DCM (2×10 mL). The organic phases were combined, washed with brine (5 mL), dried over Na$_2$SO$_4$, filtered and concentrated under reduced pressure. The residue was purified by flash chromatography on silica gel (12 g column) using a gradient of MeOH (1 to 10%) in DCM to afford (5S)—N-((2S)-4-(cyclopropylamino)-3-hydroxy-4-oxo-1-((S)-2-oxopyrrolidin-3-yl)butan-2-yl)-6-(1H-indole-2-carbonyl)-6-azaspiro[2.5]octane-5-carboxamide (84 mg, 44%) as an off-white solid. LC-MS (ESI, m/z): 522 [M+H]$^+$.

To a solution of (5S)—N-((2S)-4-(cyclopropylamino)-3-hydroxy-4-oxo-1-((S)-2-oxopyrrolidin-3-yl)butan-2-yl)-6-(1H-indole-2-carbonyl)-6-azaspiro[2.5]octane-5-carboxamide (80 mg, 0.161 mmol, 1.0 eq.) in DCM (1 mL) was added Dess-Martin periodinane (78 mg, 0.184 mmol, 1.2 eq.). The mixture was stirred at rt for 2 h, and then filtered through Celite. The filtrate was washed with sat. Na$_2$S$_2$O$_3$ (3×5 mL), sat. NaHCO$_3$ (3×5 mL) and brine (3×5 mL), dried over Na$_2$SO$_4$, filtered and concentrated under reduced pressure. The residue was purified by prep-TLC using 10% MeOH in DCM as the eluent and by prep-HPLC (Column: X-SELECT-C18, 19×250 mm, 5 um; Mobile Phase A: 10 mM NH$_4$HCO$_3$ in water, Mobile Phase B: ACN; Flow rate: 17 mL/min; Gradient: 10% B to 50% B in 8 min) to afford (S)—N—((S)-4-(cyclopropylamino)-3,4-dioxo-1-((S)-2-oxopyrrolidin-3-yl)butan-2-yl)-6-(1H-indole-2-carbonyl)-6-azaspiro[2.5] octane-5-carboxamide (21 mg, 26%) as an off-white solid. $^1$H NMR (500 MHz, 363K, DMSO-d$_6$) δ ppm 11.20 (s, 1H), 8.34 (dd, 2H), 7.54 (d, 1H), 7.43 (d, 1H), 7.37 (s, 1H), 7.15 (t, 1H), 7.01 (t, 1H), 6.75 (s, 1H), 5.12 (m, 2H), 4.39 (d, 1H), 3.45 (t, 1H), 3.17-3.30 (m, 2H), 2.75 (d, 1H), 2.45 (t, 1H), 2.22 (m, 1H), 2.04 (m, 1H), 1.96 (t, 1H), 1.87 (t, 1H), 1.65-1.77 (m, 3H), 0.96 (d, 1H), 0.64 (t, 4H), 0.50 (d, 1H), 0.27 (d, 3H). LCMS (ESI, m/z): 518 [M–H]$^-$.

Example 142

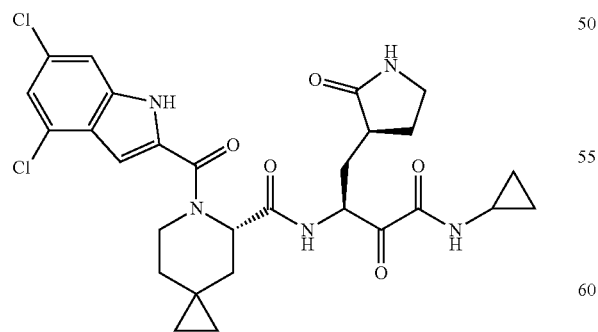

Compound 141 was prepared similarly as described for Compound 140 using 4,6-dichloro-1H-indole-2-carboxylic acid in place of 1H-indole-2-carboxylic acid. LCMS (ESI, m/z): 586 [M–H]$^-$.

Example 143

COMPOUND 142

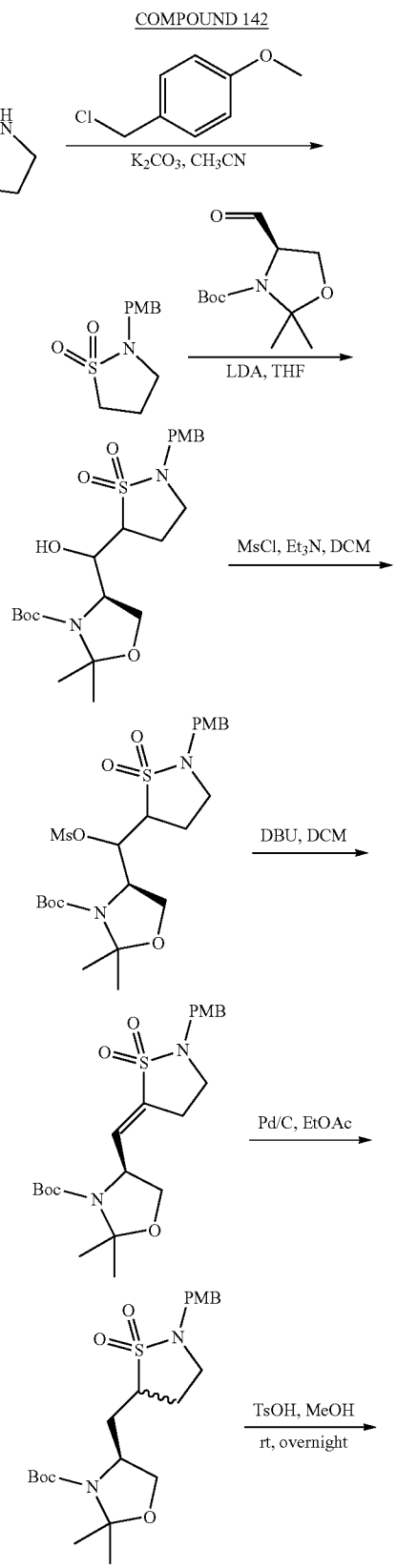

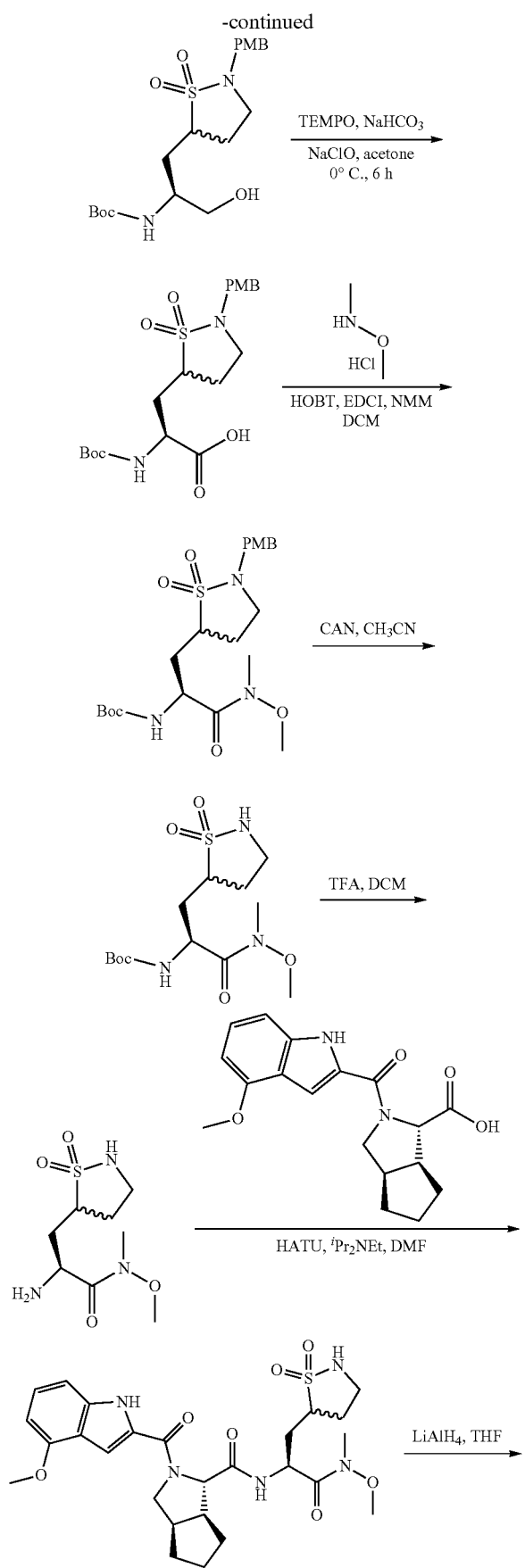

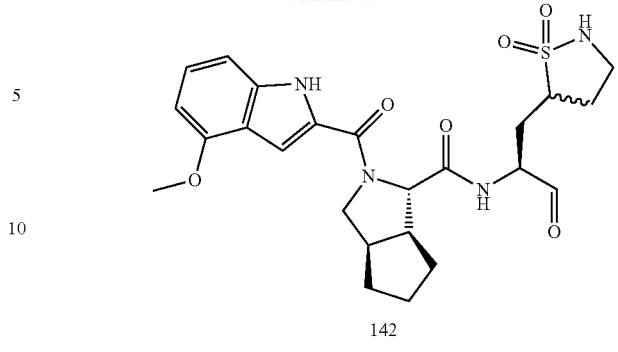

142

To a solution of isothiazolidine 1,1-dioxide (7.20 g, 59.4 mmol, 1.0 eq.) in MeCN (150 mL) was added 1-(chloromethyl)-4-methoxybenzene (11.2 g, 71.3 mmol, 1.2 eq.) and potassium carbonate (24.6 g, 178 mmol, 3.0 eq.) at 80° C. The mixture was stirred overnight at 80° C. and then filtered. The filtrate cake was washed with MeCN (3×30 mL). The filtrate was concentrated under reduced pressure to afford the crude product. The crude product was diluted with dichloromethane (50 mL) and made into a slurry with 100~200 silicagel mesh (25 g). The slurry was loaded to a column after removing the dichloromethane. The sample was purified by column chromatography (Column size 6×24 cm, column volume: 600 mL, silicagel size (100~200 mesh) quantity: 330 g) using EA:PE (0%-60% over 40 min) as the eluent. The collected fractions: 41%-43% EA:PE fractions were chosen as pure fractions. Those fractions were combined and concentrated under reduced pressure to provide 2-(4-methoxybenzyl)isothiazolidine 1,1-dioxide (12.7 g, 88%) as a light yellow solid.

To a mixture of 2-(4-methoxybenzyl)isothiazolidine 1,1-dioxide (12.7 g, 52.6 mmol, 1.0 eq.) in tetrahydrofuran (150 mL) was added dropwise lithium diisopropylamide (31.6 mL, 63.2 mmol, 1.2 eq., 2 M in THF) at −78° C. under nitrogen. After stirred for 0.5 h at −78° C., tert-butyl (R)-4-formyl-2,2-dimethyloxazolidine-3-carboxylate (14.5 g, 63.2 mmol, 1.2 eq.) was added. The mixture was stirred for 1 h at −78° C. under nitrogen. The reaction was quenched with hydrochloric acid (0.5 M) and acidified to pH=6. The mixture was extracted with EA (3×150 mL). The organic layers were combined, washed with brine (2×100 mL), dried over anhydrous sodium sulfate, filtered and concentrated under reduced pressure to afford the crude product. The crude product was diluted with dichloromethane (100 mL) and made into a slurry with 100~200 silicagel mesh (40 g). The slurry was loaded to a column after removing the dichloromethane. The sample was purified by column chromatography (Column size 6×24 cm, column volume: 600 mL, silicagel size (100~200 mesh) quantity: 330 g) using EA:PE (0%-50% over 60 min) as the eluent. The collected fractions: 37%-43% E:PE fractions were chosen as the pure fractions. Those fractions were combined and concentrated under reduced pressure to provide tert-butyl (4R)-4-(hydroxy(2-(4-methoxybenzyl)-1,1-dioxidoisothiazolidin-5-yl)methyl)-2,2-dimethyloxazolidine-3-carboxylate (14.8 g, 59%) as a yellow oil. LC-MS (ESI, m/z): 471 [M+H]⁺.

To a mixture of tert-butyl (4R)-4-(hydroxy(2-(4-methoxybenzyl)-1,1-dioxidoisothiazolidin-5-yl)methyl)-2,2-dimethyloxazolidine-3-carboxylate (14.8 g, 31.5 mmol, 1.0 eq.) in DCM (250 mL) was added methanesulfonyl chloride (14.4 g, 126 mmol, 4.0 eq.) and triethylamine (19.1 g, 189 mmol, 6.0 eq.) at 0° C. The mixture was stirred at 40° C. for 3 h, and the reaction was quenched with water (50 mL). The mixture was extracted with DCM (3×100 mL). The organic layers were combined, washed with brine (2×50 mL), dried over anhydrous sodium sulfate, filtered and concentrated under reduced pressure to afford tert-butyl (4R)-4-((2-(4-methoxybenzyl)-1,1-dioxidoisothiazolidin-5-yl)((methylsulfonyl)oxy)methyl)-2,2-dimethyloxazolidine-3-carboxylate (17 g, crude) as an orange red semi-solid. LC-MS (ESI, m/z): 549 [M+H]$^+$.

To a mixture of tert-butyl (4R)-4-((2-(4-methoxybenzyl)-1,1-dioxidoisothiazolidin-5-yl)((methylsulfonyl)oxy)methyl)-2,2-dimethyloxazolidine-3-carboxylate (17.0 g, 31.0 mmol, 1.0 eq.) in DCM (200 mL) was added 1,8-diazabicyclo[5.4.0]undec-7-ene (11.8 g, 77.5 mmol, 2.5 eq.). The mixture was stirred 3 h at rt, and the reaction was then quenched with water (50 mL). The mixture was extracted with DCM (3×100 mL). The organic layers were combined, washed with brine (2×50 mL), dried over anhydrous sodium sulfate, filtered and concentrated under reduced pressure to afford the crude product. The crude product was diluted with dichloromethane (50 mL) and made into a slurry with 100~200 silica gel mesh (40 g). The slurry was loaded to a column after removing the dichloromethane. The sample was purified by column chromatography (Column size 6×24 cm, column volume: 600 mL, silicagel size (100~200 mesh) quantity: 330 g) using EA:PE (0%-50% over 60 min) as the eluent. The collected fractions: 37%-40% EA:PE fractions were chosen as the pure fractions. Those fractions were combined and concentrated under reduced pressure to provide tert-butyl (S)-4-((2-(4-methoxybenzyl)-1,1-dioxidoisothiazolidin-5-ylidene)methyl)-2,2-dimethyloxazolidine-3-carboxylate (10.7 g, 76%) as a yellow oil. LC-MS (ESI, m/z): 453 [M+H]$^+$.

To a mixture of tert-butyl (S,E)-4-((2-(4-methoxybenzyl)-1,1-dioxidoisothiazolidin-5-ylidene)methyl)-2,2-dimethyloxazolidine-3-carboxylate (10.7 g, 23.6 mmol, 1.0 eq.) in EA (120 mL) was added 10% palladium on activated carbon (5.7 g). The mixture was stirred 2 h at rt under hydrogen. The mixture was filtered through a Celite pad and washed with EA (150 mL). The filtrate was concentrated under reduced pressure to afford tert-butyl (4S)-4-((2-(4-methoxybenzyl)-1,1-dioxidoisothiazolidin-5-yl)methyl)-2,2-dimethyloxazolidine-3-carboxylate (9.5 g, crude) as a white solid. LC-MS (ESI, m/z): 455 [M+H]$^+$.

To a mixture of tert-butyl (4S)-4-((2-(4-methoxybenzyl)-1,1-dioxidoisothiazolidin-5-yl)methyl)-2,2-dimethyloxazolidine-3-carboxylate (3.00 g, 6.60 mmol, 1.0 eq.) in MeOH (30 mL) was added p-toluenesulfonic acid (455 mg, 2.64 mmol, 0.4 eq.) at 0° C. The mixture was stirred overnight at rt. The reaction was quenched with water (10 mL). The mixture was concentrated under reduced pressure to remove the MeOH and then extracted with DCM (3×10 mL). The organic layers were combined, washed with brine (2×30 mL), dried over anhydrous sodium sulfate, filtered and concentrated under reduced pressure to afford the crude product. The crude product was diluted with DCM (20 mL) and made into a slurry with 100~200 silica gel mesh (15 g). The slurry was loaded to a column after removing the DCM. The sample was purified by column chromatography (Column size 4×12 cm, column volume: 300 mL, silica gel size (100~200 mesh) quantity: 120 g) MeOH:DCM (0%-10% over 30 min) as the eluent. The collected fractions: 6% MeOH:DCM fractions were chosen as pure fractions, and those fractions were combined and concentrated under reduced pressure to provide tert-butyl ((2S)-1-hydroxy-3-(2-(4-methoxybenzyl)-1,1-dioxidoisothiazolidin-5-yl)propan-2-yl)carbamate (2.2 g, 80%) as a colorless oil. LC-MS (ESI, m/z): 415 [M+H]$^+$.

To a stirred mixture of tert-butyl ((2S)-1-hydroxy-3-(2-(4-methoxybenzyl)-1,1-dioxidoisothiazolidin-5-yl)propan-2-yl)carbamate (2.2 g, 5.31 mmol, 1.0 eq.) and 2,2,6,6-tetramethylpiperidine-1-oxyl (166 mg, 1.06 mmol, 0.2 eq.) in acetone (30 mL) was added aqueous sodium bicarbonate (30 mL) at 0° C. Sodium hypochlorite (5.60 g, 9.78 mmol, 3.5 eq., 13%) was added. The mixture was stirred for 6 h at 0° C. The mixture was extracted with EA (3×30 mL), and the aqueous layer was acidified to pH=5 with hydrochloric acid (2 M). The aqueous layer was extracted with EA (3×50 mL). The organic layers were combined and concentrated under reduced pressure to afford (2S)-2-[(tert-butoxycarbonyl)amino]-3-{2-[(4-methoxyphenyl)methyl]-1,1-dioxo-1lambda6,2-thiazolidin-5-yl}propanoic acid (1.6 g, crude) as a yellow solid. $^1$H NMR (300 MHz, CDCl$_3$) δ 7.20-7.24 (m, 2H), 6.81-6.89 (m, 2H), 3.98-4.39 (m, 3H), 3.74-3.81 (m, 3H), 3.29-3.51 (m, 1H), 2.93-3.03 (m, 2H), 1.92-2.55 (m, 4H), 1.35-1.49 (m, 9H). LC-MS (ESI, m/z): 427 [M–H]$^-$.

To a mixture of (2S)-2-[(tert-butoxycarbonyl)amino]-3-{2-[(4-methoxyphenyl)methyl]-1,1-dioxo-1lambda6,2-thiazolidin-5-yl}propanoic acid (1.50 g, 3.50 mmol, 1.0 eq.), N,O-dimethylhydroxylamine hydrochloride (341 mg, 3.50 mmol, 1.0 eq.), 1-hydroxybenzotriazole (473 mg, 3.50 mmol, 1.0 eq.) and 1-(3-dimethylaminopropyl)-3-ethylcarbodiimide hydrochloride (738 mg, 4.11 mmol, 1.1 eq.) in DCM (20 mL) was added N-methylmorpholine (1.77 g, 17.5 mmol, 5. eq.) at 0° C. The mixture was stirred for 1 h at rt, and the reaction was quenched with water (10 mL). The mixture was extracted with DCM (3×50 mL). The organic layers were combined, washed with brine (2×30 mL), dried over anhydrous sodium sulfate, filtered and concentrated under reduced pressure to afford the crude product. The crude product was diluted with dichloromethane (20 mL) and made into a slurry with 100~200 silicagel mesh (5 g). The slurry was loaded to a column after removing the dichloromethane. The sample was purified by column chromatography (Column size 4×24 cm, column volume: 300 mL, silicagel size (100~200 mesh) quantity: 120 g) using EA:PE (0%-70% over 50 min) as the eluent. The collected fractions: 49%-53% EA:PE fractions were chosen as the pure fractions, and those fractions were combined and concentrated under reduced pressure to provide tert-butyl ((2S)-1-(methoxy(methyl)amino)-3-(2-(4-methoxybenzyl)-1,1-dioxidoisothiazolidin-5-yl)-1-oxopropan-2-yl)carbamate (950 mg, 57%) as a pale yellow solid. LC-MS (ESI, m/z): 472 [M+H]$^+$.

A solution of tert-butyl ((2S)-1-(methoxy(methyl)amino)-3-(2-(4-methoxybenzyl)-1,1-dioxidoisothiazolidin-5-yl)-1-oxopropan-2-yl)carbamate (900 mg, 1.91 mmol, 1.0 eq.) in CH$_3$CN (10 mL) and H$_2$O (2 mL) was added ammonium cerium(IV) nitrate (3.15 g, 5.73 mmol, 3.0 eq.) at rt. The mixture was stirred for 1 h at rt, and then diluted with H$_2$O (30 mL). The mixture was extracted with EA (3×50 mL). The organic layers were combined, washed with brine (2×30 mL), dried over anhydrous sodium sulfate, filtered and concentrated under reduced pressure to afford the crude product. The crude product was made into a slurry with 100~200 silica gel mesh (2 g). The slurry was loaded to a column. The sample was purified by column chromatography (Column size 3×12 cm, column volume: 120 mL, silica gel size (100~200 mesh) quantity: 80 g) using MeOH:DCM (0%-10% over 30 min) as the eluent. The collected fractions: 2%-4% MeOH:DCM fractions were chosen as the pure fractions. Those fractions were combined and concentrated under reduced pressure to provide tert-butyl ((2S)-3-(1,1-dioxidoisothiazolidin-5-yl)-1-(methoxy(methyl)amino)-1-oxopropan-2-yl)carbamate (460 mg, 68%) as a white solid. LC-MS (ESI, m/z): 352 [M+H]⁺.

To a mixture of tert-butyl ((2S)-3-(1,1-dioxidoisothiazolidin-5-yl)-1-(methoxy(methyl)amino)-1-oxopropan-2-yl)carbamate (450 mg, 1.28 mmol, 1.0 eq.) in DCM (4.5 mL) was add trifluoroacetic acid (1.5 mL) at rt. The mixture was stirred for 3 h at rt and concentrated under reduced pressure to afford (2S)-2-amino-3-(1,1-dioxidoisothiazolidin-5-yl)-N-methoxy-N-methylpropanamide (370 mg, crude) as a red semi-solid. LC-MS (ESI, m/z): 252 [M+H]⁺.

To a mixture of (2S)-2-amino-3-(1,1-dioxidoisothiazolidin-5-yl)-N-methoxy-N-methylpropanamide (370 mg, 1.47 mmol, 1.0 eq.), (1S,3aR,6aS)-2-(4-methoxy-1H-indole-2-carbonyl)octahydrocyclopenta[c]pyrrole-1-carboxylic acid (483 mg, 1.47 mmol, 1.0 eq.) and o-(7-azabenzotriazol-1-yl)-N,N,N',N'-tetramethyluronium hexafluorophosphate (672 mg, 1.77 mmol, 1.2 eq.) in DMF (10 mL) was added N-ethyl-N-isopropylpropan-2-amine (951 mg, 7.36 mmol, 5.0 eq.) at 0° C. The mixture was stirred for 1 h at rt, and the reaction was quenched with water (20 mL). The mixture was extracted with EA (3×50 mL). The organic layers were combined, washed with brine (2×50 mL), dried over anhydrous sodium sulfate, filtered and concentrated under reduced pressure to afford the crude product. The crude product was diluted with DCM (50 mL) and made into a slurry with 100-200 silica gel mesh (8 g). The slurry was loaded to a column after removing the DCM. The sample was purified by column chromatography (Column size 3×24 cm, column volume: 120 mL, silica gel size (100~200 mesh) quantity: 80 g) using MeOH:DCM (0%-10% over 30 min) as the eluent. The collected fractions: 2%-4% MeOH:DCM fractions were chosen as the pure fractions, and those fractions were combined and concentrated under reduced pressure to provide (1S,3aR,6aS)—N-((2S)-3-(1,1-dioxidoisothiazolidin-5-yl)-1-(methoxy(methyl)amino)-1-oxopropan-2-yl)-2-(4-methoxy-1H-indole-2-carbonyl)octahydrocyclopenta[c]pyrrole-1-carboxamide (220 mg, 26%) as an off-white solid. LC-MS (ESI, m/z): 562 [M+H]⁺.

A mixture of (1S,3aR,6aS)—N-((2S)-3-(1,1-dioxidoisothiazolidin-5-yl)-1-(methoxy(methyl)amino)-1-oxopropan-2-yl)-2-(4-methoxy-1H-indole-2-carbonyl)octahydrocyclopenta[c]pyrrole-1-carboxamide (70.0 mg, 0.125 mmol, 1.0 eq.) in THF (2 mL) was added lithiumaluminium tetrahydride (0.1 ml, 0.237 mmol, 1.9 eq., 2.5 M in THF) at −5° C. under nitrogen. The mixture was stirred at −5° C. for 1 h, and the reaction was quenched with water (5 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by HPLC (Column: XSelect CSH Prep C18 OBD Column, 19*150 mm, 5 µm; Mobile Phase A: Water (10 mmol/L NH₄HCO₃), Mobile Phase B: ACN; Flow rate: 25 mL/min; Gradient: 23% B to 53% B in 7 min, 53% B; Wave Length: 254 nm; RT1 (min): 6); to provide (1S,3aR,6aS)—N-((2S)-1-(1,1-dioxidoisothiazolidin-5-yl)-3-oxopropan-2-yl)-2-(4-methoxy-1H-indole-2-carbonyl)octahydrocyclopenta[c]pyrrole-1-carboxamide (2.6 mg, 4%) as a white solid. LC-MS (ESI, m/z): 503 [M+H]⁺.

Example 144

COMPOUND 143

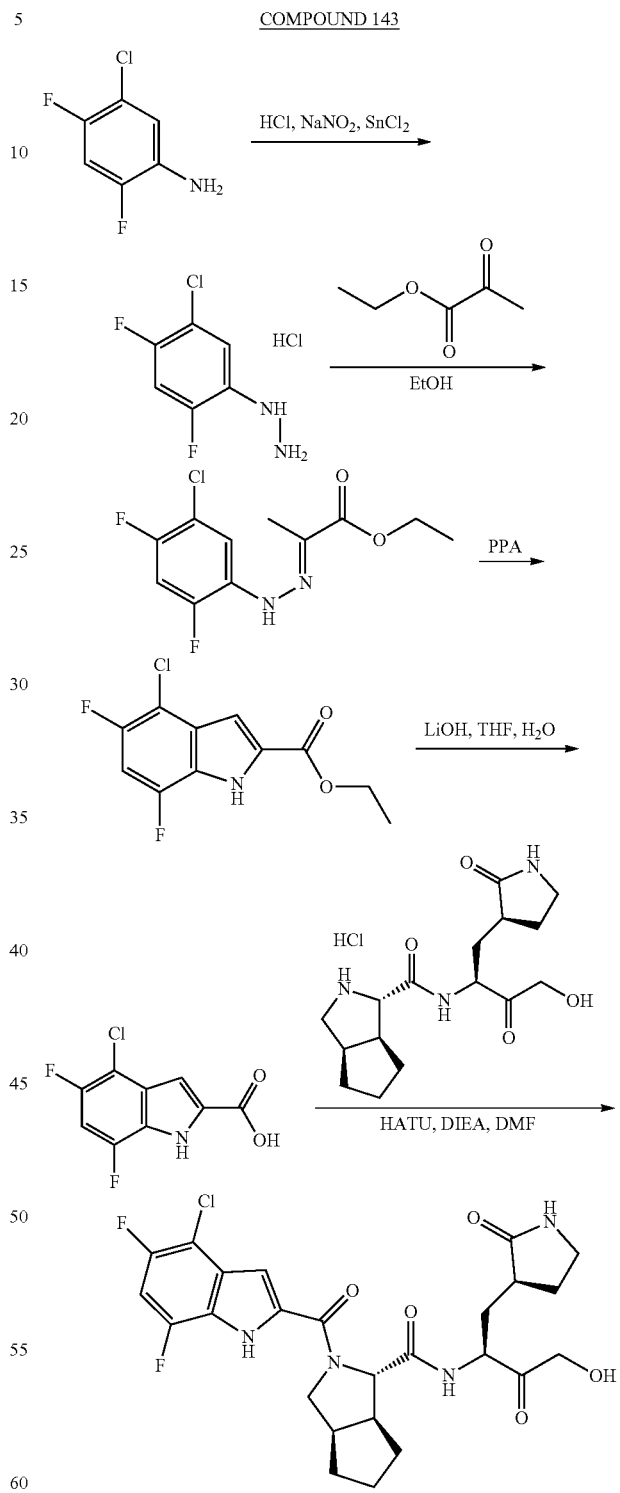

To a solution of 5-chloro-2,4-difluoroaniline (3.42 g, 20.9 mmol, 1.0 eq.) in hydrochloric acid (63 mL) was added sodium nitrite (1.51 g, 22.0 mmol, 1.05 eq.) at −10° C. The mixture was stirred for 2 h at −10° C. A solution of stannous chloride dihydrate (14.2 g, 62.7 mmol, 3.0 eq.) in hydrochloric acid (52 mL, 18M) was added dropwise at −30° C. The mixture was stirred for 1 h at −20° C., warmed to rt, and filtered to afford (5-chloro-2,4-difluorophenyl)hydrazine hydrochloride (4.0 g, crude). LCMS (ESI, m/z): 179 [M+H]⁺.

To a solution of (5-chloro-2,4-difluorophenyl)hydrazine hydrochloride (4.50 g, 20.9 mmol, 1.0 eq.) in EtOH (50 mL) was added dropwise ethyl pyruvate (2.55 g, 22.0 mmol, 1.05 eq.) at rt. The mixture was stirred for 1.5 h at rt, and then concentrated under reduced pressure to afford the crude product. The crude product was purified by silica gel column chromatography with EtOAc:PE (10:90) to afford ethyl (2E)-2-[2-(5-chloro-2,4-difluorophenyl)hydrazin-1-ylidene]propanoate (900 mg, 15%). $^1$H NMR (400 MHz, DMSO-d) δ 9.48 (s, 1H), 7.56-7.64 (m, 1H), 7.47-7.54 (m, 1H), 4.19-4.25 (m, 2H), 2.11 (s, 3H), 1.25-1.30 (m, 3H). LCMS (ESI, m/z): 277 [M+H]⁺.

A mixture of ethyl (2E)-2-[2-(5-chloro-2,4-difluorophenyl)hydrazin-1-ylidene]propanoate (100 mg, 0.361 mmol, 1.0 eq.) in polyphosphoric acid (5 g) was stirred for 5 h at 105° C. The reaction was quenched with water (10 mL), and the mixture was extracted with EA (3×20 mL). The organic layers were combined, dried over anhydrous sodium sulfate, filtered and concentrated under reduced pressure to afford ethyl 4-chloro-5,7-difluoro-1H-indole-2-carboxylate (65 mg, crude). LCMS (ESI, m/z): 258 [M−H]⁻.

To a solution of ethyl 4-chloro-5,7-difluoro-1H-indole-2-carboxylate (65.0 mg, 0.250 mmol, 1.0 eq.) in THF (0.5 mL) was added lithium hydroxide (24.0 mg, 1.0 mmol, 4.0 eq., in 0.3 mL water) at rt, and the mixture was stirred for 2 h at 65° C. The mixture was acidified to pH=5 with hydrochloric acid (1M) and extracted with EtOAc extracted (3×5 mL). The organic layers were combined, dried over anhydrous sodium sulfate, filtered and concentrated under reduced pressure to afford 4-chloro-5,7-difluoro-1H-indole-2-carboxylic acid (55 mg, crude). LCMS (ESI, m/z): 230 [M−H]⁻.

To a solution of (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (77.7 mg, 0.216 mmol, 1.0 eq.) in DMF (1 mL) was added 4-chloro-5,7-difluoro-1H-indole-2-carboxylic acid (50.0 mg, 0.216 mmol, 1.0 eq.), o-(7-azabenzotriazol-1-yl)-N,N,N',N'-tetramethyluronium hexafluorophosphate (94.4 mg, 0.248 mmol, 1.15 eq.) and N-ethyl-N-isopropylpropan-2-amine (139 mg, 1.08 mmol, 5.0 eq.) at 0° C. The mixture was stirred for 1 h at rt, and the reaction was quenched with water (10 mL). The mixture was extracted with EtOAc (3×15 mL). The organic layers were combined, washed with brine (2×20 mL), dried over anhydrous sodium sulfate, filtered and concentrated under reduced pressure to afford the crude product. The crude product was purified by prep-HPLC (Column: XSelect CSH Prep C18 OBD Column, 19*150 mm, 5 μm; Mobile Phase A: Water (0.05% FA), Mobile Phase B: ACN; Flow rate: 25 mL/min; Gradient: 38% B to 45% B in 10 min, 45% B; Wave Length: 254 nm; RT1 (min): 7.97) to provide (1S,3aR,6aS)-2-(4-chloro-5,7-difluoro-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (2.7 mg, 2%) as a white solid. LCMS (ESI, m/z): 537 [M+H]⁺.

Example 145

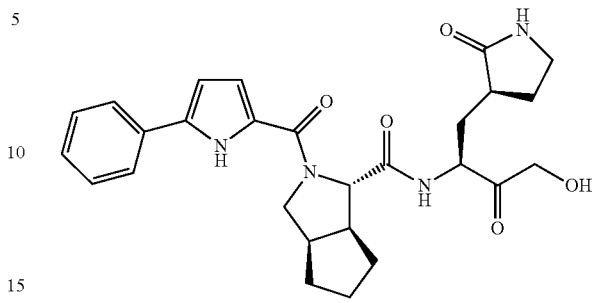

To a solution of (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (102 mg, 0.283 mmol, 1.0 eq.) in DMF (1 mL) was added 5-phenyl-1H-pyrrole-2-carboxylic acid (58.4 mg, 0.311 mmol, 1.1 eq.), o-(7-azabenzotriazol-1-yl)-N,N,N',N'-tetramethyluronium hexafluorophosphate (141 mg, 0.369 mmol, 1.3 eq.) and N-ethyl-N-isopropylpropan-2-amine (184 mg, 1.42 mmol, 5.0 eq.) stirred at 0° C. The mixture was stirred for 1 h at rt, and the reaction was quenched with water (5 mL). The mixture was extracted with EtOAc (3×15 mL). The organic layers were combined, washed with brine (2×20 mL), dried over anhydrous sodium sulfate, filtered and concentrated under reduced pressure to afford the crude product. The crude product was purified by prep-HPLC (Column: XSelect CSH Prep C18 OBD Column, 19*150 mm, 5 μm; Mobile Phase A: Water (0.05% FA), Mobile Phase B: ACN; Flow rate: 25 mL/min; Gradient: 40% B to 47% B in 10 min, 47% B; Wave Length: 254 nm; RT1 (min): 5.7) to provide (1S,3aR,6aS)—N-[(2S)-4-hydroxy-3-oxo-1-[(3S)-2-oxopyrrolidin-3-yl]butan-2-yl]-2-(5-phenyl-1H-pyrrole-2-carbonyl)-hexahydro-1H-cyclopenta[c]pyrrole-1-carboxamide (10.4 mg, 7%) as a white solid. LCMS (ESI, m/z): 493 [M+H]⁺.

Example 146

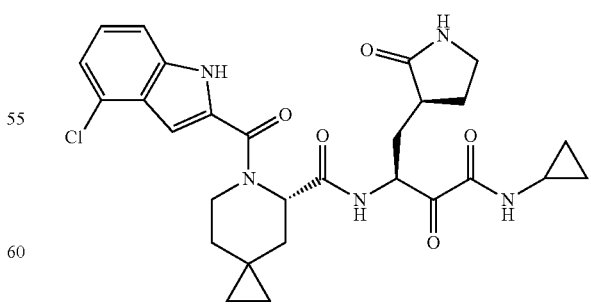

Compound 145 was prepared similarly as described for Compound 140 using 4-chloro-1H-indole-2-carboxylic acid in place of 1H-indole-2-carboxylic acid. LCMS (ESI, m/z): 552 [M−H]⁻.

Example 147

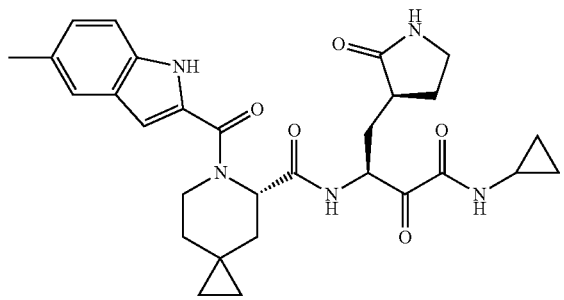 [SMILES: Cc1ccc2[nH]c(C(=O)N3CCC4(CC4)C[C@H]3C(=O)N[C@@H](C[C@@H]3CCNC3=O)C(=O)C(=O)NC3CC3)cc2c1]

Compound 146 was prepared similarly as described for Compound 140 using 5-methyl-1H-indole-2-carboxylic acid in place of 1H-indole-2-carboxylic acid. LCMS (ESI, m/z): 532 [M−H]⁻.

Example 148

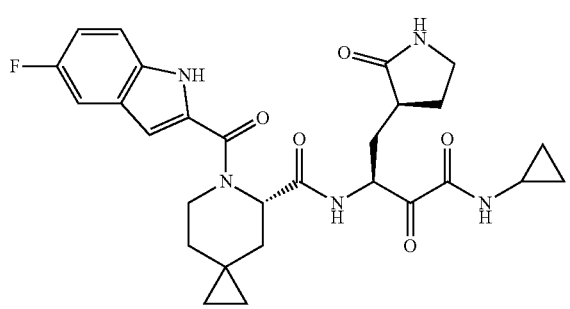

Compound 147 was prepared similarly as described for Compound 140 using 5-fluoro-1H-indole-2-carboxylic acid in place of 1H-indole-2-carboxylic acid. LCMS (ESI, m/z): 538 [M+H]⁺.

Example 149

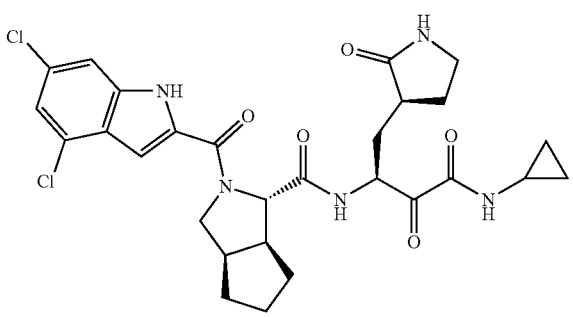 [SMILES: O=C(NC1CC1)C(=O)[C@H](C[C@@H]1CCNC1=O)NC(=O)[C@@H]1[C@H]2CCC[C@H]2CN1C(=O)c1cc2c(Cl)cc(Cl)cc2[nH]1]

Compound 148 was prepared similarly as described for Compound 140 using (1S,3aR,6aS)-2-(tert-butoxycarbonyl)octahydrocyclopenta[c]pyrrole-1-carboxylic acid in place of (S)-6-(tert-butoxycarbonyl)-6-azaspiro[2.5]octane-5-carboxylic acid and 4,6-dichloro-1H-indole-2-carboxylic acid in place of 1H-indole-2-carboxylic acid. LCMS (ESI, m/z): 588 [M+H]⁺.

Example 150

COMPOUND 149

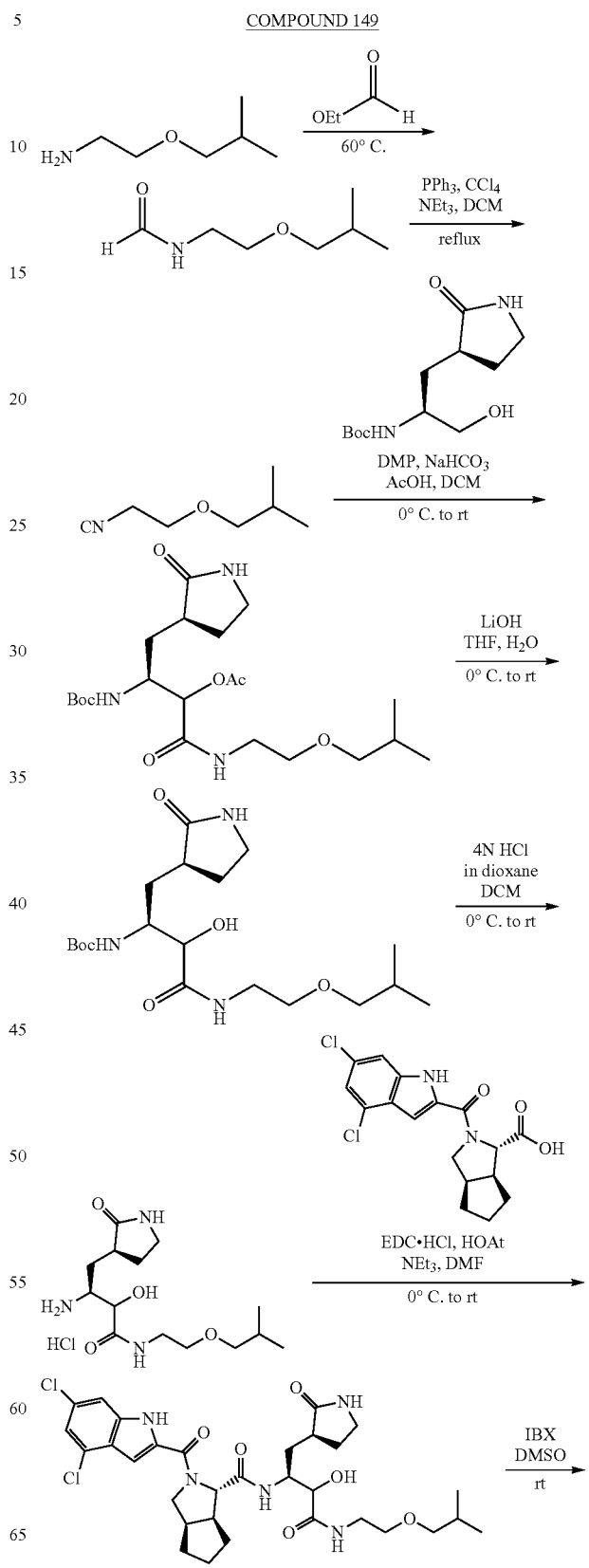

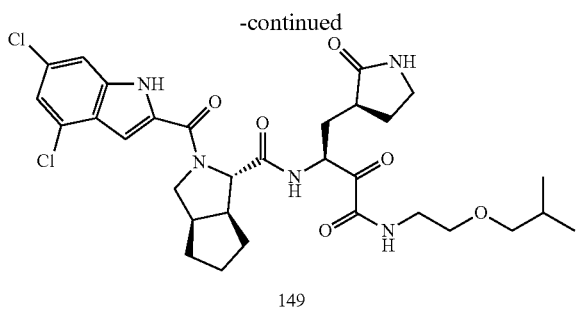

149

A mixture of 2-isobutoxyethan-1-amine (0.900 g, 7.62 mmol, 1.0 eq.) and ethyl formate (10 mL, 76.9 mmol, 10.0 eq.) was heated at 60° C. for 16 h, and the mixture was concentrated under reduced pressure to afford N-(2-isobutoxyethyl)formamide (0.9 g, 81%) as a brown liquid. $^1$H NMR (400 MHz, CDCl$_3$) δ ppm 8.20 (d, 1H), 6.09 (br s, 1H), 3.45-3.55 (m, 4H), 3.18-3.22 (m, 2H), 1.80-1.90 (m, 1H), 0.91 (d, 6H).

To a solution of N-(2-isobutoxyethyl)formamide (900 mg, 6.21 mmol, 1.0 eq.) in DCM (10 mL) cooled to 0° C. were added PPh$_3$ (3.26 g, 12.4 mmol, 2.0 eq.), CCl$_4$ (1.2 mL, 12.4 mmol, 2.0 eq.) and NEt$_3$ (1.7 mL, 12.4 mmol, 2.0 eq.). The mixture was refluxed for 18 h. After cooling to rt, pentane was added, and the insoluble materials were filtered. The filtrate was concentrated under reduced pressure (rotavapor bath at rt) to afford 1-(2-isocyanoethoxy)-2-methylpropane (600 mg, 77%) as a brown liquid. $^1$H NMR (400 MHz, CDCl$_3$) δ ppm 3.60-3.65 (m, 2H), 3.52-3.58 (m, 2H), 3.26 (d, 2H), 1.82-1.93 (m, 1H), 0.92 (d, 6H).

To a solution of tert-butyl ((S)-1-hydroxy-3-((S)-2-oxopyrrolidin-3-yl)propan-2-yl)carbamate (300 mg, 1.16 mmol, 1.0 eq.) in DCM (3 mL) were added NaHCO$_3$ (98 mg, 1.16 mmol, 1.0 eq.) and Dess-Martin periodinane (492 mg, 1.16 mmol, 1.0 eq.). The mixture was stirred at rt for 2 h. After cooling to 0° C., AcOH (0.19 mL, 3.48 mmol, 3.0 eq.) and 1-(2-isocyanoethoxy)-2-methylpropane (221 mg, 1.74 mmol, 1.5 eq.) were added, and the mixture was stirred at rt for 16 h. The mixture was diluted with 10% MeOH in DCM (20 mL) and washed with sat. NaHCO$_3$ (10 mL). The phases were separated. The organic phase was washed with brine (10 mL), dried over Na$_2$SO$_4$, filtered and concentrated under reduced pressure. The residue was purified by flash chromatography on silica gel using a gradient of MeOH (1 to 5%) in DCM to afford (6S)-2,2,14-trimethyl-4,8-dioxo-6-(((S)-2-oxopyrrolidin-3-yl)methyl)-3,12-dioxa-5,9-diazapentadecan-7-yl acetate (400 mg, 77%) as a white oil. LCMS (ESI, m/z): 444 [M+H]$^+$.

To a solution of (6S)-2,2,14-trimethyl-4,8-dioxo-6-(((S)-2-oxopyrrolidin-3-yl)methyl)-3,12-dioxa-5,9-diazapentadecan-7-yl acetate (430 mg, 0.971 mmol, 1.0 eq.) in THF (4.3 mL) and water (4.3 mL) cooled to 0° C. was added LiOH (46 mg, 1.94 mmol, 2.0 eq.). The mixture was stirred at rt for 2 h and then concentrated under reduced pressure. The residue was purified by flash chromatography on silica gel using a gradient of MeOH (1 to 10%) in DCM to afford tert-butyl ((2S)-3-hydroxy-4-((2-isobutoxyethyl)amino)-4-oxo-1-((S)-2-oxopyrrolidin-3-yl)butan-2-yl)carbamate (300 mg, 77%) as an off-white solid. LCMS (ESI, m/z): 402 [M+H]$^+$.

To a solution of tert-butyl ((2S)-3-hydroxy-4-((2-isobutoxyethyl)amino)-4-oxo-1-((S)-2-oxopyrrolidin-3-yl)butan-2-yl)carbamate (300 mg, 0.747 mmol, 1.0 eq.) in DCM (3 mL) cooled to 0° C. was added 4N HCl in dioxane (0.747 mL, 2.99 mmol, 4.0 eq.). The mixture was stirred at rt for 2 h and then concentrated under reduced pressure. The residue was triturated with Et$_2$O, and the solid was filtered to afford (3S)-3-amino-2-hydroxy-N-(2-isobutoxyethyl)-4-((S)-2-oxopyrrolidin-3-yl)butanamide hydrochloride (190 mg, 75%) as an off-white solid. LCMS (ESI, m/z): 302 [M+H]$^+$.

To a solution of (3S)-3-amino-2-hydroxy-N-(2-isobutoxyethyl)-4-((S)-2-oxopyrrolidin-3-yl)butanamide hydrochloride (182 mg, 0.539 mmol, 1.1 eq.) and (1S,3aR,6aS)-2-(4,6-dichloro-1H-indole-2-carbonyl)octahydrocyclopenta[c]pyrrole-1-carboxylic acid (180 mg, 0.490 mmol, 1.0 eq., prepared similarly to (1S,3aR,6aS)-2-(4-methoxy-1H-indole-2-carbonyl)-hexahydro-1H-cyclopenta[c]pyrrole-1-carboxylic acid in Example 15) in DMF (2 mL) cooled to 0° C. were added EDC·HCl (187 mg, 0.975 mmol, 2.0 eq.), HOAt (67 mg, 0.496 mmol, 1.0 eq.) and Et$_3$N (0.20 mL, 1.47 mmol, 3.0 eq.). The mixture was stirred at rt for 16 h. The mixture was diluted with water (10 mL) and extracted with 10% MeOH in DCM (3×10 mL). The organic phases were combined, dried over Na$_2$SO$_4$, filtered and concentrated under reduced pressure. The residue was purified by flash chromatography on silica gel (12 g column) using a gradient of MeOH (0 to 8%) in DCM to afford (1S,3aR,6aS)-2-(4,6-dichloro-1H-indole-2-carbonyl)-N-((2S)-3-hydroxy-4-((2-isobutoxyethyl)amino)-4-oxo-1-((S)-2-oxopyrrolidin-3-yl)butan-2-yl)octahydrocyclopenta[c]pyrrole-1-carboxamide (160 mg, 50%) as an off-white solid. LC-MS (ESI, m/z): 650 [M+H]$^+$.

To a solution of (1S,3aR,6aS)-2-(4,6-dichloro-1H-indole-2-carbonyl)-N-((2S)-3-hydroxy-4-((2-isobutoxyethyl)amino)-4-oxo-1-((S)-2-oxopyrrolidin-3-yl)butan-2-yl)octahydrocyclopenta[c]pyrrole-1-carboxamide (100 mg, 0.154 mmol, 1.0 eq.) in DMSO (5 mL) was added 2-iodoxybenzoic acid (129 mg, 0.462 mmol, 3.0 eq.), and the mixture was stirred at rt for 6 h. 2-Iodoxybenzoic acid (43 mg, 0.154 mmol, 1.0 eq.) was added, and the mixture was stirred at rt overnight. The mixture was diluted with EA (50 mL) and washed with sat. NaHCO$_3$. The phases were separated. The organic phase was washed with water, dried over Na$_2$SO$_4$, filtered and concentrated under reduced pressure. The residue was purified by prep-HPLC (Column: X-SELECT-C18, 19×250 mm, 5 um; Mobile Phase A: 10 mM NH$_4$HCO$_3$ in water, Mobile Phase B: ACN; Flow rate: 17 mL/min; Gradient: 10% B to 60% B in 8 min) to afford (1S,3aR,6aS)-2-(4,6-dichloro-1H-indole-2-carbonyl)-N—((S)-4-((2-isobutoxyethyl)amino)-3,4-dioxo-1-((S)-2-oxopyrrolidin-3-yl)butan-2-yl)octahydrocyclopenta[c]pyrrole-1-carboxamide (31 mg, 31%) as an off-white solid. $^1$H NMR (500 MHz, 362K, DMSO-d$_6$) δ ppm 11.73 (br s, 1H), 8.47 (br s, 1H), 8.08-8.22 (m, 1H), 7.45 (s, 1H), 7.28-7.34 (m, 1H), 7.15 (s, 1H), 6.84-6.92 (m, 1H), 4.90-5.10 (m, 1H), 4.50-4.68 (m, 1H), 3.90-4.12 (m, 1H), 3.65-3.75 (m, 1H), 3.40-3.48 (m, 2H), 3.22-3.35 (m, 2H), 3.08-3.20 (m, 4H), 2.60-2.80 (m, 2H), 2.10-2.30 (m, 1H), 1.90-2.00 (m, 2H), 1.48-1.88 (m, 9H), 0.83 (d, 6H). LCMS (ESI, m/z): 648 [M+H]$^+$.

Example 151

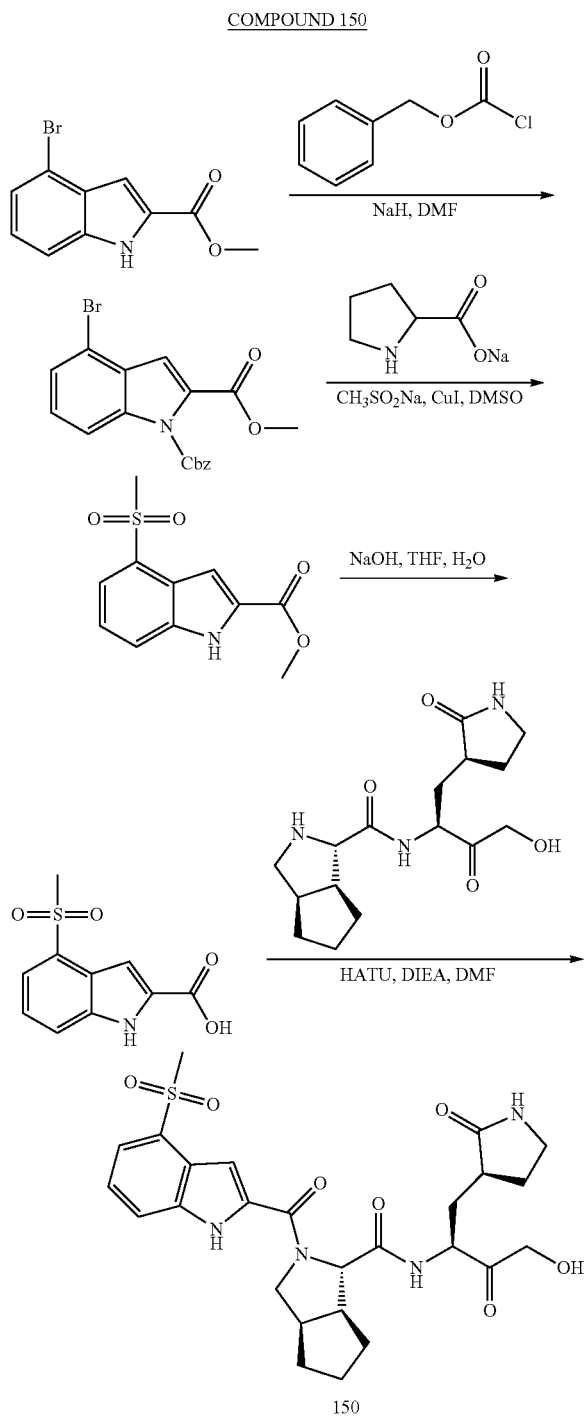

A 100 mL round-bottom flask was charged with methyl 4-bromo-1H-indole-2-carboxylate (2 g, 7.87 mmol, 1.0 eq.), DMF (40 mL) and NaH (0.630 g, 60% in mineral oil, 15.7 mmol, 2.0 eq.). The mixture was stirred for 20 min at rt. Benzyl chloroformate (2.69 g, 15.7 mmol, 2.0 eq.) was added, and the mixture was stirred for 2 h at rt. The reaction was quenched with water (50 mL). The resulting solution was extracted with EA (3×100 mL). The organic layers were combined, washed with brine (2×50 mL), dried over anhydrous sodium sulfate, filtered and concentrated under reduced pressure. The residue was chromatographed on a silica gel column with EA:PE (3:7) to provide 1-benzyl 2-methyl 4-bromoindole-1,2-dicarboxylate (2.9 g, 85%) as a white solid. LC-MS (ESI, m/z): 388 [M+H]$^+$.

A 100 mL round-bottom flask was charged with 1-benzyl 2-methyl 4-bromoindole-1,2-dicarboxylate (1 g, 2.57 mmol, 1.0 eq.), sodium pyrrolidine-2-carboxylate (741 mg, 5.41 mmol, 2.1 eq.), sodium methanesulfinate (815 mg, 7.98 mmol, 3.1 eq.) and DMSO (20 mL), copper(I) iodide (1.52 g, 7.98 mmol, 3.1 eq.). The mixture was stirred overnight at 130° C. under nitrogen. The reaction was quenched with water (50 mL). The resulting solution was extracted with EA (3×100 mL). The organic layers were combined, washed with brine (3×50 mL), dried over anhydrous sodium sulfate, filtered and concentrated under reduced pressure. The residue was chromatographed on a silica gel column with EA:PE (3:7) to provide 1-benzyl 2-methyl 4-methanesulfonylindole-1,2-dicarboxylate (480 mg, 46%) as a yellow solid. $^1$H NMR (300 MHz, DMSO-d$_6$) δ 12.65 (s, 1H), 7.90-7.79 (m, 1H), 7.68-7.70 (m, 1H), 7.61-7.36 (m, 2H), 3.93 (s, 3H), 3.24 (s, 3H). LC-MS (ESI, m/z): 254 [M+H]$^+$.

A 100 mL round-bottom flask was charged with methyl 4-methanesulfonyl-1H-indole-2-carboxylate (200 mg, 0.790 mmol, 1.0 eq.) and THF (4 mL), H$_2$O (4 mL). NaOH (189 mg, 4.74 mmol, 6.0 eq.) was added dropwise at 0° C. The mixture was stirred overnight at 60° C. The reaction was quenched with water (10 mL). The resulting solution was extracted with EA (3×50 mL). The organic layers were combined, washed with brine (2×20 mL), dried over anhydrous sodium sulfate, filtered and concentrated under reduced pressure to provide 4-methanesulfonyl-1H-indole-2-carboxylic acid (180 mg, 76%) as a white solid. LC-MS (ESI, m/z): 240 [M+H]$^+$.

A 50 mL round-bottom flask was charged with 4-methanesulfonyl-1H-indole-2-carboxylic acid (60 mg, 0.251 mmol, 1.0 eq.), (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide (81.1 mg, 0.251 mmol, 1.0 eq.), DMF (3 mL), HATU (133. mg, 0.351 mmol, 1.4 eq.) and DIEA (97.2 mg, 0.753 mmol, 3.0 eq.). The mixture was stirred for 2 h at rt. The reaction was quenched with water (10 mL). The resulting solution was extracted with EA (3×20 mL). The organic layers were combined, washed with brine (10 mL×2), dried over anhydrous sodium sulfate, filtered and concentrated under reduced pressure to provide the crude product. The crude product was purified by prep-HPLC using the following gradient conditions: Column: YMC-Actus Triart C18 ExRS, 30*150 mm, 5 μm; Mobile Phase A: Water (0.1% FA), Mobile Phase B: ACN; Flow rate: 60 mL/min; Gradient: 18% B to 36% B in 10 min, 36% B; Wave Length: 254 nm; RT1 (min): 7.68. Purification resulted in (1S,3aR,6aS)—N-[(2S)-4-hydroxy-3-oxo-1-[(3S)-2-oxopyrrolidin-3-yl]butan-2-yl]-2-(4-methanesulfonyl-1H-indole-2-carbonyl)-hexahydro-1H-cyclopenta[c]pyrrole-1-carboxamide (5.1 mg, 4%) as a white solid. LC-MS (ESI, m/z): 545 [M+H]$^+$.

Example 152

COMPOUND 151

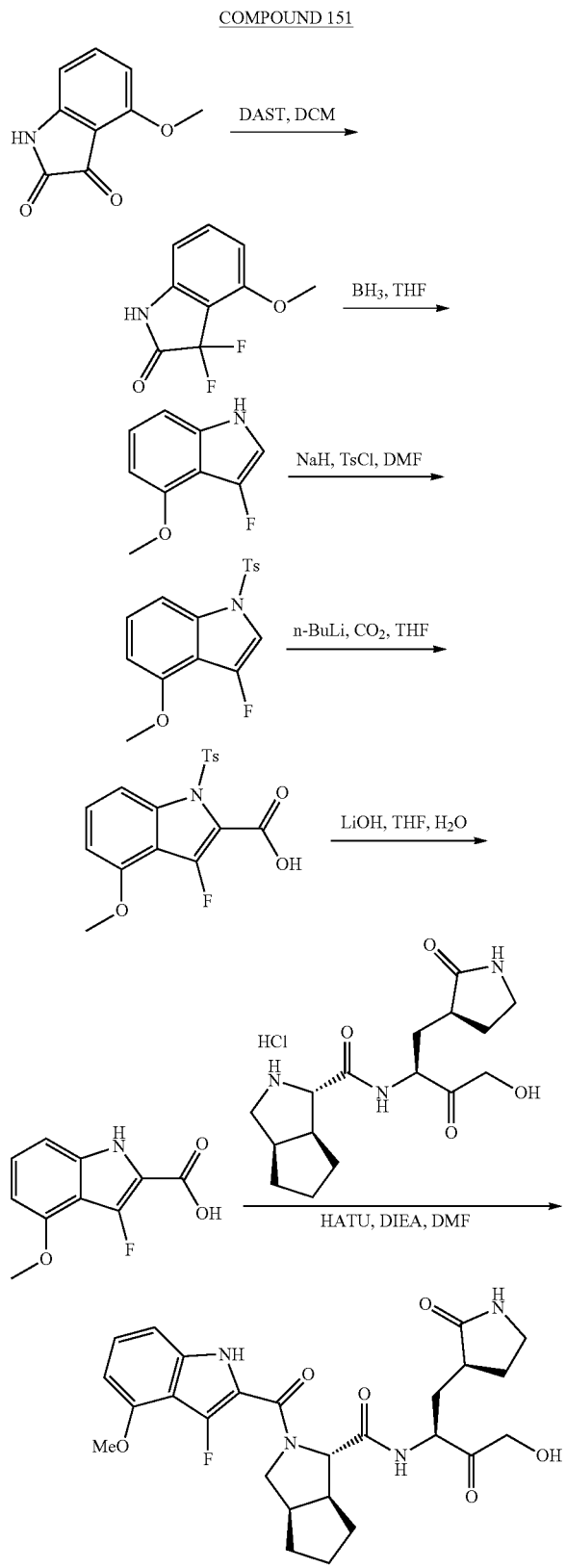

A 100 mL round-bottom flask was charged with 4-methoxyindoline-2,3-dione (600 mg, 3.39 mmol, 1.0 eq.) in DCM (10 mL). Diethylaminosulfur trifluoride (4.09 g, 25.4 mmol, 7.5 eq.) was added. The mixture was stirred for 2 d at rt, and the reaction was quenched with water (15 mL). The resulting solution was extracted with dichloromethane (3×20 mL). The organic layers were combined, dried over anhydrous sodium sulfate, filtered and concentrated under reduced pressure. The residue was chromatographed on a silica gel column with EA:PE (1:4) to provide 3,3-difluoro-4-methoxyindolin-2-one (100 mg, 28%) as a yellow solid. $^1$H NMR (300 MHz, DMSO-$d_6$) δ 11.12 (s, 1H), 7.48 (t, J=8.2 Hz, 1H), 6.81 (d, J=8.7 Hz, 1H), 6.52-6.61 (m, 1H), 3.88 (s, 3H). LC-MS (ESI, m/z): 198 [M–H]$^-$.

A 8 mL vial was charged with 3,3-difluoro-4-methoxy-indolin-2-one (300 mg, 1.51 mmol, 1.0 eq.) and THF (10 mL). Borane tetrahydrofuran complex solution 1 M in THF (6.03 mL, 6.02 mmol, 4.0 eq.) was added at 0° C. under nitrogen. The mixture was stirred overnight at rt. The reaction was quenched with water (10 mL). The resulting solution was extracted with dichloromethane (3×20 mL). The organic layers were combined, washed with brine (2×10 mL), dried over anhydrous sodium sulfate, filtered and concentrated under reduced pressure to provide 3-fluoro-4-methoxy-1H-indole (270 mg, crude) as dark green oil. $^1$H NMR (300 MHz, DMSO-$d_6$) δ 10.78 (s, 1H), 7.14 (t, J=2.7 Hz, 1H), 7.02 (t, J=8.0 Hz, 1H), 6.90-6.93 (m, 1H), 6.49 (d, J=7.6 Hz, 1H), 3.85 (s, 3H). LC-MS (ESI, m/z): 166 [M+H]$^+$.

A 40 mL vial was charged with 3-fluoro-4-methoxy-1H-indole (270 mg, 1.14 mmol, 1.0 eq.), DMF (7 mL). Sodium hydride (68.6 mg, 1.72 mmol, 1.5 eq., 60% in mineral oil) was added at 0° C. The mixture was stirred for 10 min at 0° C. Tosyl chloride (436 mg, 2.29 mmol, 2.0 eq.) was added, and the mixture was then stirred for 2 h at rt. The reaction was quenched with water (10 mL). The resulting solution was extracted with EA (3×20 mL). The organic layers were combined, washed with brine (2×20 mL), dried over anhydrous sodium sulfate, filtered and concentrated under reduced pressure. The residue was chromatographed on a silica gel column with EA:PE (1:5) to provide 3-fluoro-4-methoxy-1-tosyl-1H-indole (240 mg, 61%) as an off-white solid. $^1$H NMR (400 MHz, CDCl$_3$-d) δ 7.71-7.78 (m, 2H), 7.62-7.64 (m, 1H), 7.30 (s, 1H), 7.22-7.27 (m, 3H), 6.68 (d, J=8.1 Hz, 1H), 3.92 (s, 3H), 2.37 (s, 3H). LC-MS (ESI, m/z): 320 [M+H]$^+$.

A 40 mL vial was charged with 3-fluoro-4-methoxy-1-tosyl-1H-indole (250 mg, 0.783 mmol, 1.0 eq.) in THF (5 mL) under nitrogen. n-BuLi (0.33 mL, 2.5 M in hexane, 0.822 mmol, 1.05 eq.) was added dropwise at –75° C. The mixture was stirred for 30 min at –75° C. CO$_2$ was bubbled through the reaction for 15 min at –75° C. The mixture was warmed to rt. The reaction was quenched by water (10 mL). The mixture was purified by C18 column with MeCN:H$_2$O (1:1) to provide 3-fluoro-4-methoxy-1-tosyl-1H-indole-2-carboxylic acid (210 mg, 70%) as a white solid. $^1$H NMR (300 MHz, DMSO-$d_6$) δ 13.93 (s, 1H), 7.71-7.80 (m, 2H), 7.56-7.60 (m, 1H), 7.48 (t, J=8.3 Hz, 1H), 7.39 (d, J=8.1 Hz, 2H), 6.91 (d, J=8.1 Hz, 1H), 3.85 (s, 3H), 2.33 (s, 3H). LC-MS (ESI, m/z): 364 [M+H]$^+$.

A 8 mL vial was charged with 3-fluoro-4-methoxy-1-tosyl-1H-indole-2-carboxylic acid (180 mg, 0.495 mmol, 1.0 eq.), lithium hydroxide (119 mg, 4.95 mmol, 10.0 eq.), THF (1.2 mL) and H$_2$O (3.6 mL). The mixture was stirred for 2 days at 60° C. The pH value of the solution was adjusted to 5 with conc. hydrochloric acid (1 mol/L). The resulting solution was extracted with dichloromethane (3×10 mL). The organic layers were combined, washed with brine (2×5 mL), dried over anhydrous sodium sulfate, filtered and concentrated under reduced pressure to provide 3-fluoro-4-methoxy-1H-indole-2-carboxylic acid (100 mg, 80%) as a yellow solid. $^1$H NMR (300 MHz, DMSO-$d_6$) δ 13.07 (s, 1H), 11.50 (s, 1H), 7.19 (t, J=8.1 Hz, 1H), 6.92-6.96 (m, 1H), 6.53 (d, J=7.7 Hz, 1H), 3.88 (s, 3H). LC-MS (ESI, m/z): 208 [M−H]$^-$.

A 8 mL vial was charged with 3-fluoro-4-methoxy-1H-indole-2-carboxylic acid (60 mg, 0.287 mmol, 1.0 eq.), N,N,N',N'-tetramethyl-O-(7-azabenzotriazol-1-yl)uronium hexafluorophospate (164 mg, 0.430 mmol, 1.5 eq.), DMF (3 mL) and N,N-diisopropylethylamine (111 mg, 0.861 mmol, 3.0 eq.). The mixture was stirred for 30 min at 0° C. (1S,3aR,6aS)—N—((S)-4-hydroxy-3-oxo-1-((S)-2-oxopyrrolidin-3-yl)butan-2-yl)octahydrocyclopenta[c]pyrrole-1-carboxamide (82.6 mg, 0.230 mmol, 0.8 eq.) was added. The mixture was stirred for 1 h at 0° C. The reaction was quenched with water (10 mL). The resulting solution was extracted with EA (3×20 mL). The organic layers were combined, washed with brine (2×20 mL), dried over anhydrous sodium sulfate, filtered and concentrated under reduced pressure. The residue was purified by C18 column with MeCN:H$_2$O (0.05% TFA) (3:7) to provide the crude product. The crude product was purified by prep-HPLC using the following gradient conditions: Column: XBridge Shield RP18 OBD Column, 19*250 mm, 10 μm; Mobile Phase A: Water (0.1% FA), Mobile Phase B: ACN; Flow rate: 25 mL/min; Gradient: 30% B to 47% B in 7 min, 47% B; Wave Length: 254 nm; RT1 (min): 5.27. Purification resulted in (1S,3aR,6aS)-2-(3-fluoro-4-methoxy-1H-indole-2-carbonyl)-N—((S)-4-hydroxy-3-oxo-1-((S)-2-oxopyrrolidin-3-yl)butan-2-yl)octahydrocyclopenta[c]pyrrole-1-carboxamide (4.7 mg) as a white solid. LC-MS (ESI, m/z): 515 [M+H]$^+$.

Example 153

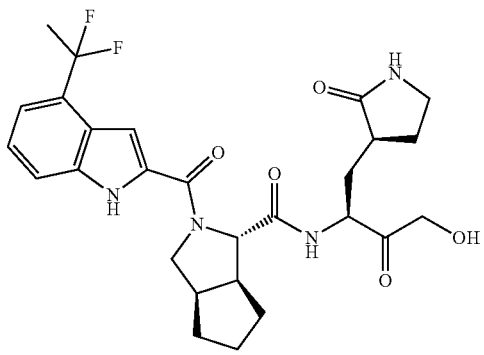 [SMILES: CC(F)(F)c1cccc2[nH]c(C(=O)N3C[C@@H]4CCC[C@@H]4[C@H]3C(=O)N[C@@H](C[C@@H]3CCNC3=O)C(=O)CO)cc12]

To a stirred mixture of 4-(1,1-difluoroethyl)-1H-indole-2-carboxylic acid (64.0 mg, 0.284 mmol, 1.0 eq.) and (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (102 mg, 0.284 mmol, 1.0 eq.) in N,N-dimethylformamide (6 mL) was added O-(7-Aza-1H-benzotriazol-1-yl)-N,N,N',N'-tetramethyluronium hexafluorophosphate (140 mg, 0.369 mmol, 1.3 eq.) and N,N-diisopropylethylamine (147 mg, 1.14 mmol, 4.0 eq.) at 0° C. The mixture was stirred for 2 h at rt, and the reaction was quenched with water (20 mL) at rt. The mixture was extracted with EA (3×40 mL). The combined organic layers were washed with brine (3×20 mL), dried over anhydrous sodium sulfate. After filtration, the filtrate was concentrated under reduced pressure to provide the crude product. The crude product (350 mg) was purified by prep-HPLC with the following conditions (Column: XBridge Shield RP18 OBD Column, 30*150 mm, 5 μm; Mobile Phase A: Water (0.1% FA), Mobile Phase B: ACN; Flow rate: 60 mL/min; Gradient: 24% B to 40% B in 10 min, 40% B; Wave Length: 254 nm; RT1 (min): 8.82) to afford (1S,3aR,6aS)-2-[4-(1,1-difluoroethyl)-1H-indole-2-carbonyl]-N-[(2S)-4-hydroxy-3-oxo-1-[(3S)-2-oxopyrrolidin-3-yl]butan-2-yl]-hexahydro-1H-cyclopenta[c]pyrrole-1-carboxamide (9.7 mg, 6%) as a white solid. $^1$H NMR (400 MHz, 80° C., DMSO-$d_6$) δ 11.58 (s, 1H), 8.35-8.39 (m, 1H), 7.54-7.56 (m, 1H), 7.16-7.26 (m, 3H), 6.89 (s, 1H), 4.69-4.76 (m, 1H), 4.38-4.60 (m, 2H), 3.95-4.24 (m, 3H), 3.68-3.71 (m, 1H), 3.05-3.17 (m, 2H), 2.69-2.85 (m, 1H), 2.55-2.68 (m, 1H), 2.17-2.35 (m, 1H), 1.41-2.09 (m, 13H). LC-MS (ESI, m/z): 531 [M+H]$^+$.

Example 154

COMPOUND 153

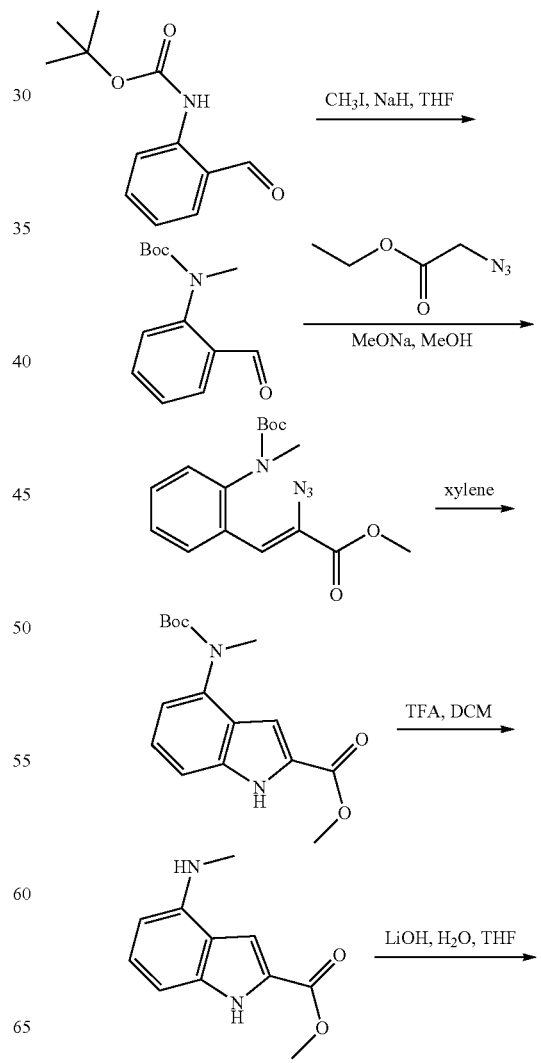

-continued

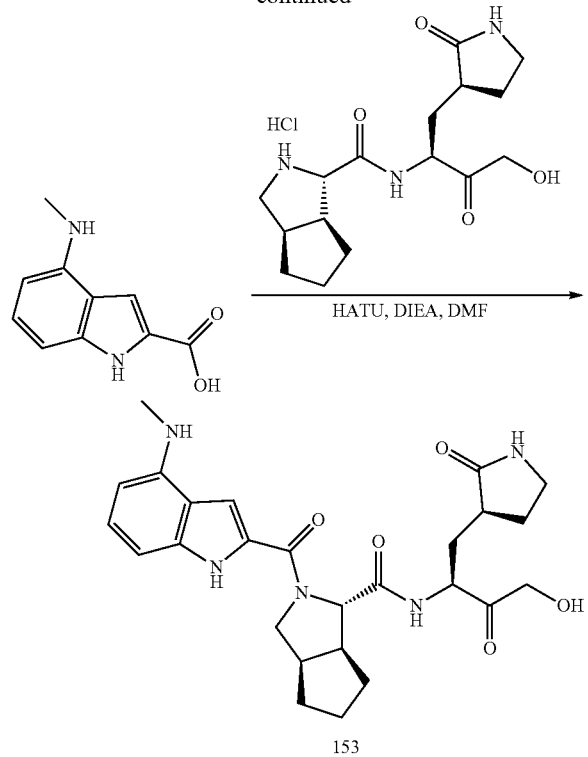

153

To a solution of tert-butyl N-(2-formylphenyl)carbamate (1.50 g, 6.78 mmol, 1.0 eq.) in THF (15 mL) was added sodium hydride (542 mg, 13.6 mmol, 2.0 eq., 60% in mineral oil) stirred at 0° C. for 30 min. Iodomethane (1.25 g, 8.81 mmol, 1.3 eq.) was added, and the mixture was stirred for 7 h at 0° C. The reaction was quenched with water (10 mL). The mixture was extracted with EtOAc (3×10 mL). The organic layers were combined, dried over anhydrous sodium sulfate, filtered and concentrated under reduced pressure to afford the crude product. The crude product was purified by silica gel column chromatography, eluted with EtOAc:PE (3:97) to afford tert-butyl N-(2-formylphenyl)-N-methylcarbamate (1.07 g, 66%).

To a solution of sodium methoxide (0.980 g, 18.2 mmol, 4.0 eq., 30% in MeOH) was added dropwise a mixture of tert-butyl N-(2-formylphenyl)-N-methylcarbamate (1.07 g, 4.55 mmol, 1.0 eq.) and ethyl 2-azidoacetate (2.35 g, 18.2 mmol, 4.0 eq.). The mixture was stirred for 3 h at −10° C., and the reaction was quenched with water (5 mL). The mixture was extracted with EtOAc (3×20 mL). The organic layers were combined, dried over anhydrous sodium sulfate, filtered and concentrated under reduced pressure to afford the crude product. The crude product was purified by silica gel column chromatography with EtOAc:PE (4:96) to afford methyl 2-azido-3-{2-[(tert-butoxycarbonyl)(methyl)amino]phenyl}prop-2-enoate (300 mg, 20%). LC-MS (ESI, m/z): 331 [M−H]⁻.

A solution of methyl (2Z)-2-azido-3-{2-[(tert-butoxycarbonyl)(methyl)amino]phenyl}prop-2-enoate (300 mg, 0.901 mmol, 1.0 eq.) in xylene (3 mL) was stirred for overnight at 120° C. and then concentrated under reduced pressure to afford the crude product. The crude product was purified by TLC (Mobile phase: EtOAc:PE (1:16); Rf=0.6; detection: UV) to provide methyl 4-[(tert-butoxycarbonyl)(methyl)amino]-1H-indole-2-carboxylate (134 mg, 49%). ¹H NMR (400 MHz, DMSO-d₆) δ 12.06 (s, 1H), 7.22-7.37 (m, 2H), 6.88-7.00 (m, 2H), 3.86 (s, 3H), 3.24 (s, 3H), 1.34 (s, 9H).

To a solution of methyl 4-[(tert-butoxycarbonyl)(methyl)amino]-1H-indole-2-carboxylate (130 mg, 0.427 mmol, 1.0 eq.) in DCM (2.5 mL) was added trifluoroacetaldehyde (0.5 mL) at rt. The mixture was stirred for 1 h at rt and then concentrated under reduced pressure to afford methyl 4-(methylamino)-1H-indole-2-carboxylate (90 mg, crude). LC-MS (ESI, m/z): 205 [M+H]⁺.

To a solution of methyl 4-(methylamino)-1H-indole-2-carboxylate (120 mg, 0.588 mmol, 1.0 eq.) in THF (1.5 mL) was added lithium hydroxide (70.4 mg, 2.94 mmol, 5.0 eq., in 1 mL water) at rt. The mixture was stirred for 3 h at 60° C. The mixture was acidified to pH=5 with hydrochloric acid (1M) and extracted with EtOAc extracted (3×5 mL). The organic layers were combined, dried over anhydrous sodium sulfate, filtered and concentrated under reduced pressure to afford 4-(methylamino)-1H-indole-2-carboxylic acid (80 mg, crude). LC-MS (ESI, m/z): 191 [M+H]⁺.

To a solution of (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (102 mg, 0.284 mmol, 1.0 eq.) in DMF (1 mL) was added 4-(methylamino)-1H-indole-2-carboxylic acid (64.9 mg, 0.341 mmol, 1.2 eq.), o-(7-azabenzotriazol-1-yl)-N,N,N',N'-tetramethyluronium hexafluorophosphate (141 mg, 0.369 mmol, 1.3 eq.) and N-ethyl-N-isopropylpropan-2-amine (183 mg, 1.42 mmol, 5.0 eq.) stirred at 0° C. The mixture was stirred for 1 h at rt, and the reaction was quenched with water (1 mL). The mixture was extracted with EtOAc (3×5 mL). The organic layers were combined, washed with brine (2×5 mL), dried over anhydrous sodium sulfate, filtered and concentrated under reduced pressure to afford the crude product. The crude product was purified by prep-HPLC (Column: XBridge Shield RP18 OBD Column, 19*250 mm, 10 μm; Mobile Phase A: Water (0.1% FA), Mobile Phase B: ACN; Flow rate: 25 mL/min; Gradient: 15% B to 30% B in 10 min, 30% B; Wave Length: 254 nm; RT1 (min): 7.88.) to provide (1S,3aR,6aS)—N-[(2S)-4-hydroxy-3-oxo-1-[(3S)-2-oxopyrrolidin-3-yl]butan-2-yl]-2-[4-(methylamino)-1H-indole-2-carbonyl]-hexahydro-1H-cyclopenta[c]pyrrole-1-carboxamide (26.8 mg, 18%) as an off-white solid. LC-MS (ESI, m/z): 496 [M+H]⁺.

Example 155

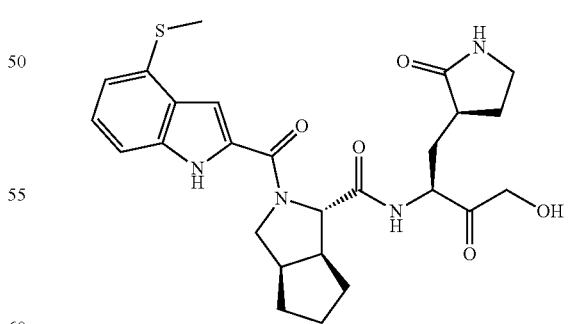

A 50 mL round-bottom flask was charged with 4-(methylsulfanyl)-1H-indole-2-carboxylic acid (60 mg, 0.288 mmol, 1.0 eq.), DMF (5 mL), N,N,N',N'-tetramethyl-O-(7-azabenzotriazol-1-yl)uronium hexafluorophospate (165 mg, 0.434 mmol, 1.5 eq.) and N,N-diisopropylethylamine (112 mg, 0.870 mmol, 3.0 eq.). The mixture was stirred for 20 min at rt. (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide (102 mg, 0.318 mmol, 1.1 eq.) was added. The mixture was stirred for 2 h at rt. The reaction was quenched with water (10 mL). The resulting solution was extracted with EA (3×20 mL). The organic layers were combined, washed with brine (20 mL), dried over anhydrous sodium sulfate, filtered and concentrated under reduced pressure. The crude product was purified by prep-HPLC using the following gradient conditions: Column: XSelect CSH Prep C18 OBD Column, 19*250 mm, 5 μm; Mobile Phase A: Water (0.05% FA), Mobile Phase B: ACN; Flow rate: 25 mL/min; Gradient: 33% B to 38% B in 10 min, 38% B; Wave Length: 254 nm; RT1 (min): 7.5. Purification resulted in (1S,3aR,6aS)—N—((S)-4-hydroxy-3-oxo-1-((S)-2-oxopyrrolidin-3-yl)butan-2-yl)-2-(4-(methylthio)-1H-indole-2-carbonyl)octahydrocyclopenta[c]pyrrole-1-carboxamide (2.2 mg, 2%) as a white solid. LC-MS (ESI, m/z): 513 [M+H]$^+$.

Example 156

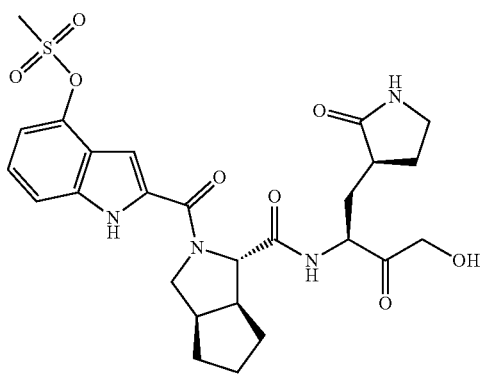 [SMILES: CS(=O)(=O)Oc1cccc2[nH]c(C(=O)N3C[C@@H]4CCC[C@@H]4[C@H]3C(=O)N[C@@H](C[C@@H]3CCNC3=O)C(=O)CO)cc12]

To a solution of methyl 4-hydroxy-1H-indole-2-carboxylate (130 mg, 0.680 mmol, 1.0 eq.) in DCM (2 mL) was added triethylamine (138 mg, 1.360 mmol, 2.0 eq.) and methanesulfonyl chloride (110 mg, 0.952 mmol, 1.4 eq.) stirred at 0° C. The mixture was stirred for 3 h at rt, and the reaction was quenched with water (1 mL). The resulting mixture was extracted with DCM (3×5 mL). The organic layers were combined, washed with brine (2×2 mL), dried over anhydrous sodium sulfate, filtered and concentrated under reduced pressure to afford the crude product. The crude product was purified by silica gel column chromatography, eluted with DCM:MeOH (99:1) to afford methyl 4-(methanesulfonyloxy)-1H-indole-2-carboxylate (154 mg, 83%). $^1$H NMR (400 MHz, DMSO-d$_6$) δ 12.27-12.39 (m, 1H), 7.42-7.49 (m, 1H), 7.30-7.37 (m, 1H), 7.23-7.28 (m, 1H), 7.06-7.12 (m, 1H), 3.90 (s, 3H), 3.47 (s, 3H). LCMS (ESI, m/z): 270 [M+H]$^+$.

To a solution of methyl 4-(methanesulfonyloxy)-1H-indole-2-carboxylate (140 mg, 0.520 mmol, 1.0 eq.) in THF (2 mL) was added lithium hydroxide (62.3 mg, 2.600 mmol, 5.0 eq., in 2 mL water), and the mixture was stirred for 4 h at rt. The mixture was acidified to pH=5 with hydrochloric acid (1M), and extracted with EA (3×5 mL). The organic layers were combined, dried over anhydrous sodium sulfate, filtered and concentrated under reduced pressure to afford crude 4-(methanesulfonyloxy)-1H-indole-2-carboxylic acid. $^1$H NMR (400 MHz, DMSO-d$_6$) δ 13.25 (br, 1H), 12.02-12.23 (m, 1H), 7.39-7.49 (m, 1H), 7.25-7.35 (m, 1H), 7.13-7.20 (m, 1H), 7.03-7.10 (m, 1H), 3.46 (s, 3H).

To a solution of (1S,3aR,6aS)—N—((S)-4-hydroxy-3-oxo-1-((S)-2-oxopyrrolidin-3-yl)butan-2-yl)octahydrocyclopenta[c]pyrrole-1-carboxamide hydrochloride (102 mg, 0.284 mmol, 1.0 eq.) in DMF (1 mL) was added 4-(methanesulfonyloxy)-1H-indole-2-carboxylic acid (76.3 mg, 0.298 mmol, 1.05 eq.), o-(7-azabenzotriazol-1-yl)-N,N,N',N'-tetramethyluronium hexafluorophosphate (141 mg, 0.369 mmol, 1.3 eq.) and N-ethyl-N-isopropylpropan-2-amine (184 mg, 1.42 mmol, 5.0 eq.) stirred at 0° C. The mixture was stirred for 1 h at rt, and the reaction was quenched with water (1 mL). The resulting mixture was extracted with EA (3×5 mL). The organic layers were combined, washed with brine (2×3 mL), dried over anhydrous sodium sulfate, filtered and concentrated under reduced pressure to afford the crude product. The crude product was purified by prep-HPLC (Column: XBridge Shield RP18 OBD Column, 30*150 mm, 5 μm; Mobile Phase A: Water (0.1% FA), Mobile Phase B: ACN; Flow rate: 60 mL/min; Gradient: 15% B to 32% B in 10 min, hold 1 min, 32% B; Wave Length: 254 nm; RT1 (min): 10.08.) to provide 2-[(1S,3aR,6aS)-1-{[(2S)-4-hydroxy-3-oxo-1-[(3S)-2-oxopyrrolidin-3-yl]butan-2-yl]carbamoyl}-hexahydro-1H-cyclopenta[c]pyrrole-2-carbonyl]-1H-indol-4-yl methanesulfonate (44.9 mg, 27%) as a white solid. $^1$H NMR (400 MHz, 80° C., DMSO-d$_6$) 11.67 (s, 1H), 8.19-8.60 (m, 1H), 7.40-7.50 (m, 1H), 7.28-7.39 (m, 1H), 7.16-7.26 (m, 1H), 7.01-7.11 (m, 1H), 6.87-7.00 (m, 1H), 4.71-4.83 (m, 1H), 4.36-4.61 (m, 2H), 4.00-4.35 (m, 3H), 3.72 (br, 1H), 3.38 (s, 3H), 3.08-3.25 (m, 2H), 2.70-2.90 (m, 1H), 2.57-2.70 (m, 1H), 1.37-2.43 (m, 11H). LC-MS (ESI, m/z): 561 [M+H]$^+$.

Example 157

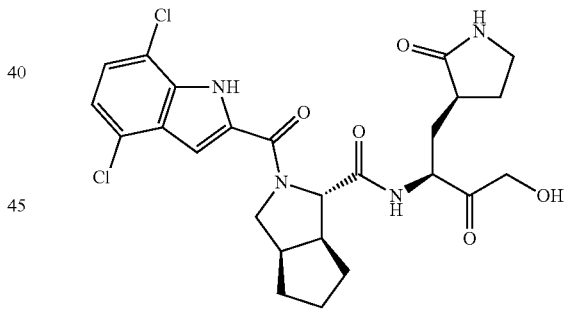

To a stirred mixture of 4,7-dichloro-1H-indole-2-carboxylic acid (65.0 mg, 0.280 mmol, 1.0 eq.) and (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (101 mg, 0.280 mmol, 1.0 eq.) in N,N-dimethylformamide (6 mL) was added O-(7-Aza-1H-benzotriazol-1-yl)-N,N,N',N'-tetramethyluronium hexafluorophosphate (139 mg, 0.370 mmol, 1.3 eq.) and N,N-diisopropylethylamine (128 mg, 0.990 mmol, 3.5 eq.) at 0° C. The mixture was stirred for 2 h at rt, and the reaction was quenched with water (15 mL) at rt. The mixture was extracted with EA (3×40 mL). The organic layers were combined, washed with brine (3×20 mL), dried over anhydrous sodium sulfate, filtered and concentrated under reduced pressure. The residue was purified by prep-TLC (dichloromethane:methanol=10:1) to afford (1S,3aR,6aS)-2-(4,7-dichloro-1H-indole-2-carbonyl)-N-[(2S)-4-hydroxy-3- oxo-1-[(3S)-2-oxopyrrolidin-3-yl]butan-2-yl]-hexahydro-1H-cyclopenta[c]pyrrole-1-carboxamide as a yellow solid. The crude product (70 mg) was purified by prep-HPLC with the following conditions (Column: XBridge Shield RP18 OBD Column, 30*150 mm, 5 μm; Mobile Phase A: Water (0.1% FA), Mobile Phase B: ACN; Flow rate: 60 mL/min; Gradient: 24% B to 40% B in 13 min, 40% B; Wave Length: 254 nm; RT1 (min): 10.1) to afford (1S,3aR,6aS)-2-(4,7-dichloro-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (10.5 mg, 7%) as a white solid. $^1$H NMR (400 MHz, 80° C., DMSO-d$_6$) δ 11.68 (s, 1H), 8.40-8.42 (m, 1H), 7.31 (s, 1H), 7.23-7.26 (m, 1H), 7.09-7.13 (m, 1H), 6.88 (br, 1H), 4.70-4.95 (m, 1H), 4.37-4.57 (m, 2H), 3.76-4.24 (m, 3H), 3.58-3.72 (m, 1H), 3.00-3.23 (m, 2H), 2.58-2.78 (m, 2H), 1.36-2.40 (m, 11H). LC-MS (ESI, m/z): 535 [M+H]$^+$.

Example 158

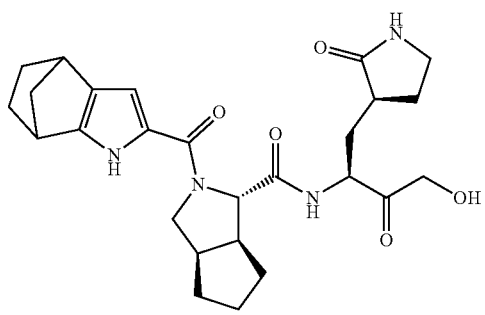 [SMILES: O=C1NCC[C@H]1C[C@H](NC(=O)[C@@H]1[C@H]2CCC[C@H]2CN1C(=O)c1cc2c([nH]1)C1CCC2C1)C(=O)CO]

To a solution of (1S,3aR,6aS)—N—((S)-4-hydroxy-3-oxo-1-((S)-2-oxopyrrolidin-3-yl)butan-2-yl)octahydrocyclopenta[c]pyrrole-1-carboxamide hydrochloride (102 mg, 0.284 mmol, 1.0 eq.) in DMF (1 mL) was added 3-azatricyclo[5.2.1.0^{2,6}]deca-2(6),4-diene-4-carboxylic acid (50.2 mg, 0.283 mmol, 1.0 eq.), N,N,N',N'-Tetramethylchloroformamidinium hexafluorophosphate (103 mg, 0.368 mmol, 1.3 eq.) and N-methylimidazole (186 mg, 2.264 mmol, 8.0 eq.) stirred at 0° C. The mixture was stirred for 1 h at rt, and the reaction was quenched with water (1 mL). The mixture was extracted with EA (3×5 mL). The organic layers were combined, washed with brine (2×3 mL), dried over anhydrous sodium sulfate, filtered and concentrated under reduced pressure to afford the crude product. The crude product was purified by prep-HPLC (Column: XBridge Prep Phenyl OBD Column, 19*150 mm, 5 μm; Mobile Phase A: Water (0.05% FA), Mobile Phase B: ACN; Flow rate: 25 mL/min; Gradient: 22% B to 52% B in 7 min, 52% B; Wave Length: 254 nm; RT1 (min): 6.) to provide (1S,3aR,6aS)-2-{3-azatricyclo[5.2.1.0^{2,6}]deca-2(6),4-diene-4-carbonyl}-N-[(2S)-4-hydroxy-3-oxo-1-[(3S)-2-oxopyrrolidin-3-yl]butan-2-yl]-hexahydro-1H-cyclopenta[c]pyrrole-1-carboxamide (2.4 mg, 1.7%) as a light yellow solid. $^1$H NMR (400 MHz, 80° C., DMSO-d$_6$) δ 10.72 (s, 1H), 8.17-8.20 (m, 1H), 7.28 (s, 1H), 6.18-6.25 (m, 1H), 4.05-4.86 (m, 5H), 3.70-3.91 (m, 1H), 3.38-3.60 (m, 1H), 3.10-3.35 (m, 2H), 2.55-2.71 (m, 1H), 2.44-2.54 (m, 1H), 1.24-2.35 (m, 17H), 0.79-0.90 (m, 2H). LCMS (ESI, m/z): 483 [M+H]$^+$.

Example 159

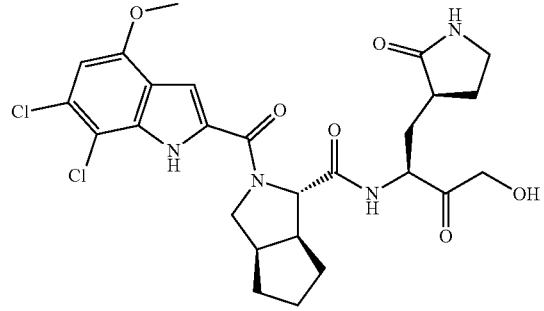 [SMILES: COc1cc(Cl)c(Cl)c2[nH]c(C(=O)N3C[C@@H]4CCC[C@@H]4[C@H]3C(=O)N[C@@H](C[C@@H]3CCNC3=O)C(=O)CO)cc12]

A 100 mL vial was charged with sodium methoxide (1.05 g, 19.5 mmol, 4.0 eq.) in MeOH (10 mL). 4,5-dichloro-2-methoxybenzaldehyde (1.00 g, 4.89 mmol, 1.0 eq.) and ethyl 2-azidoacetate (2.52 g, 19.5 mmol, 4.0 eq.) in MeOH (15 mL) was added to the via over 1.5 h at −10° C. The mixture was stirred for 1.5 h at −10° C. and then poured into ice-water (15 mL). The resulting solution was extracted with EA (3×30 mL). The organic layers were combined, washed with brine (20 mL), dried over anhydrous sodium sulfate, filtered and concentrated under reduced pressure. The residue was chromatographed on a silica gel column with EA:PE (1:13) to provide methyl 2-azido-3-(4,5-dichloro-2-methoxyphenyl)prop-2-enoate (270 mg, 16%) as a yellow solid. $^1$H NMR (300 MHz, DMSO-d$_6$) δ 8.30 (s, 1H), 7.38 (s, 1H), 7.06 (s, 1H), 3.58-3.97 (m, 6H).

A 50 mL vial was charged with methyl 2-azido-3-(4,5-dichloro-2-methoxyphenyl)prop-2-enoate (270 mg, 0.894 mmol, 1.0 eq.), xylene (4 mL) under nitrogen. The mixture was stirred for 3 h at 120° C. The reaction was concentrated under reduced pressure to provide methyl 6,7-dichloro-4-methoxy-1H-indole-2-carboxylate (220 mg, 72%) as a yellow solid. $^1$H NMR (300 MHz, DMSO-d6) δ 10.22 (br, 1H), 7.16-7.18 (m, 1H), 6.81 (s, 1H), 3.95 (s, 3H), 3.87 (s, 3H). LC-MS (ESI, m/z): 272 [M−H]$^-$.

A 50 mL round-bottom flask was charged with methyl 6,7-dichloro-4-methoxy-1H-indole-2-carboxylate (245 mg, 0.89 mmol, 1.0 eq.), THF (3 mL), NaOH (107 mg, 2.68 mmol, 3.0 eq.) and water (3 mL). The mixture was stirred at rt overnight. Water (2 mL) was added, and the mixture was washed with EA (3×10 mL). The combined organic layers were discarded. The pH value of the aqueous phase was adjusted to 4 with hydrochloric acid (1 mol/L). The resulting solution was extracted with EA (3×10 mL). The organic layers were combined, dried over anhydrous sodium sulfate, filtered and concentrated under reduced pressure to provide 6,7-dichloro-4-methoxy-1H-indole-2-carboxylic acid (180 mg, 69%) as a yellow solid. $^1$H NMR (300 MHz, DMSO-d$_6$) δ 13.11 (br, 1H), 12.20 (s, 1H), 7.12 (s, 1H), 6.80 (s, 1H), 3.87 (s, 3H). LC-MS (ESI, m/z): 258 [M−H]$^-$.

To a solution of 6,7-dichloro-4-methoxy-1H-indole-2-carboxylic acid (81 mg, 0.31 mmol, 1.1 eq.) in DMF (2 mL) was added N,N,N',N'-tetramethyl-O-(7-azabenzotriazol-1-yl)uronium hexafluorophospate (140 mg, 0.37 mmol, 1.3 eq.) and N,N-diisopropylethylamine (220 mg, 1.7 mmol, 6.0 eq.). The mixture was stirred at 0° C. for 30 min and (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide (91.6 mg, 0.28 mmol, 1.0 eq.) was added. The mixture was stirred at 0° C. for 1 h, and the reaction was quenched with water (3 mL). The mixture was extracted with EA (3×10 mL). The organic layers were combined, dried over anhydrous sodium sulfate, filtered and concentrated under reduced pressure. The residue was purified by prep-HPLC (Column: XBridge Shield RP18 OBD Column, 30*150 mm, 5 μm; Mobile Phase A: Water (0.1% FA), Mobile Phase B: ACN; Flow rate: 60 mL/min; Gradient: 28% B to 46% B in 10 min, 46% B; Wave Length: 254 nm; RT1 (min): 7.67) to provide (1S,3aR,6aS)-2-(6,7-dichloro-4-methoxy-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (46.3 mg, 28%) as a white solid. LC-MS (ESI, m/z): 565 [M+H]+.

Example 160

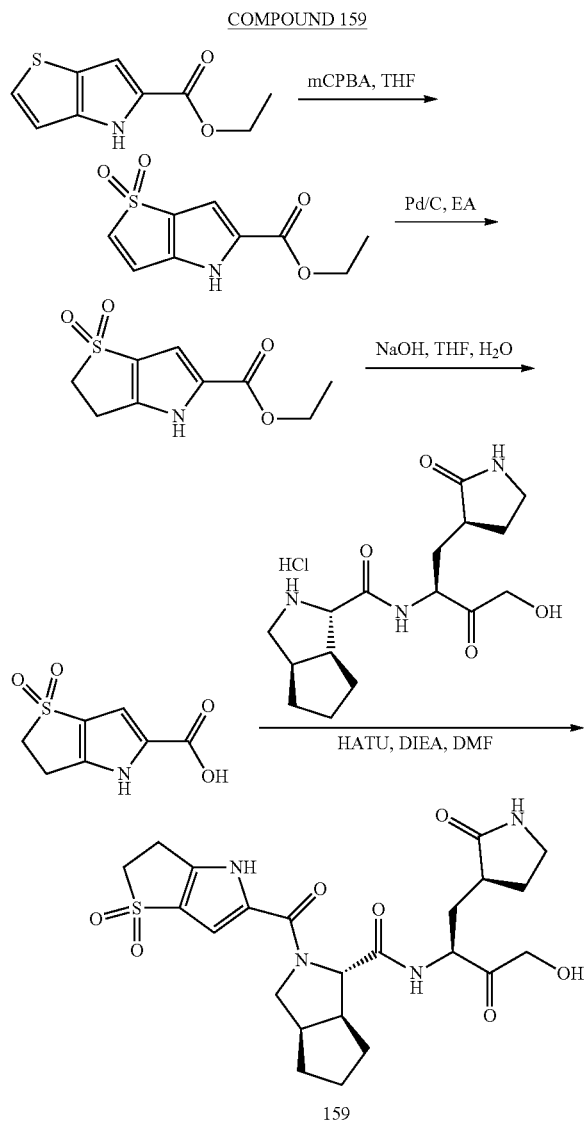

159

To a stirred mixture of ethyl 4H-thieno[3,2-b]pyrrole-5-carboxylate (2.00 g, 10.2 mmol, 1.0 eq.) in tetrahydrofuran (50 mL) was added 3-chloroperoxybenzoic acid (7.95 g, 46.1 mmol, 4.5 eq.) in portions at 0° C. The mixture was stirred for 6 h at rt, and the reaction was quenched with water (100 mL) at rt. The mixture was extracted with EA (3×200 mL). The organic layers were combined, washed with brine (2×80 mL), dried over anhydrous sodium sulfate, filtered and concentrated under reduced pressure to afford ethyl 1,1-dioxo-4H-1lambda6-thieno[3,2-b]pyrrole-5-carboxylate (8 g, crude) as a yellow solid. LC-MS (ESI, m/z): 226 [M−H]−.

To a stirred mixture of ethyl 1,1-dioxo-4H-1lambda6-thieno[3,2-b]pyrrole-5-carboxylate (8 g, crude) in EA (80 mL) was added 10% palladium on activated carbon (251 mg) at rt. The mixture was stirred for 3 h at rt under hydrogen, and then filtered. The filter cake was washed with EA (3×50 mL). The filtrate was concentrated under reduced pressure. The residue was purified by silica gel column chromatography with dichloromethane:methanol (49:1) to afford ethyl 1,1-dioxo-2H,3H,4H-1lambda6-thieno[3,2-b]pyrrole-5-carboxylate (400 mg) as a yellow solid. The residue was purified by TLC with PE:EA (1:3) to afford ethyl 1,1-dioxo-2H,3H,4H-1λ6-thieno[3,2-b]pyrrole-5-carboxylate (230 mg) as a yellow solid. The residue was dissolved in EA (30 mL) and water (20 mL). The residue was basified to pH=8 with sat. sodium bicarbonate (aq.). The mixture was extracted with EA (3×30 mL). The combined organic layers were washed with brine (2×20 mL), dried over anhydrous sodium sulfate, filtered and concentrated under reduced pressure to afford ethyl 1,1-dioxo-2H,3H,4H-1lambda6-thieno[3,2-b]pyrrole-5-carboxylate (120 mg, 13%) as a yellow solid. $^1$H NMR (400 MHz, CDCl$_3$-d) δ 9.48-9.60 (m, 1H), 7.00-7.04 (m, 1H), 4.35-4.40 (m, 2H), 3.85-3.90 (m, 2H), 3.32-3.36 (m, 2H), 1.38-1.41 (m, 3H). LC-MS (ESI, m/z): 228 [M−H]−.

To a stirred mixture of ethyl 1,1-dioxo-2H,3H,4H-1lambda6-thieno[3,2-b]pyrrole-5-carboxylate (120 mg, 0.523 mmol, 1.0 eq.) in tetrahydrofuran (8 mL) was added sodium hydroxide (126 mg, 3.14 mmol, 6.0 eq.) in water (2 mL) at rt. The mixture was stirred for 4 h at 50° C. and diluted with water (10 mL) at rt. The mixture was extracted with EA (2×20 mL). The water layers were acidified to pH=3 with hydrochloric acid (2M). The mixture was extracted with EA (3×30 mL). The organic layers were combined, washed with brine (2×20 mL), dried over anhydrous sodium sulfate, filtered and concentrated under reduced pressure to afford 1,1-dioxo-2H,3H,4H-1lambda6-thieno[3,2-b]pyrrole-5-carboxylic acid (87 mg, 77%) as a yellow solid. LC-MS (ESI, m/z): 200 [M−H]−.

To a stirred mixture of 1,1-dioxo-2H,3H,4H-1lambda6-thieno[3,2-b]pyrrole-5-carboxylic acid (47.0 mg, 0.234 mmol, 1.0 eq.) and (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (84.1 mg, 0.234 mmol, 1.0 eq.) in N,N-dimethylformamide (8 mL) was added O-(7-Aza-1H-benzotriazol-1-yl)-N,N,N',N'-tetramethyluronium hexafluorophosphate (115 mg, 0.304 mmol, 1.3 eq.) and N,N-diisopropylethylamine (121 mg, 0.936 mmol, 4.0 eq.) at 0° C. The mixture was stirred for 2 h at rt, and the reaction was quenched with water (10 mL) at rt. The mixture was extracted with EA (3×30 mL). The organic layers were combined, washed with brine (3×20 mL), dried over anhydrous sodium sulfate, filtered and concentrated under reduced pressure. The residue was purified by TLC with dichloromethane:methanol (9:1) to afford (1S,3aR,6aS)-2-{1,1-dioxo-2H,3H,4H-1lambda6-thieno[3,2-b]pyrrole-5-carbonyl}-N-[(2S)-4-hydroxy-3-oxo-1-[(3S)-2-oxopyrrolidin-3-yl]butan-2-yl]-hexahydro-1H-cyclopenta[c]pyrrole-1-carboxamide as a yellow solid. The crude product (100 mg) was purified by prep-HPLC with the following conditions (Column: XBridge Prep Phenyl OBD Column, 19*250 mm, 5 μm; Mobile Phase A: Water (0.05% FA), Mobile Phase B: ACN; Flow rate: 25 mL/min; Gradient: 20% B to 22% B in 10 min, 22% B; Wave Length: 254 nm; RT1 (min): 8) to afford (1S,3aR,6aS)-2-{1,1-dioxo-2H,3H,4H-1λ6-thieno[3,2-b]pyrrole-5-carbonyl}-N-[(2S)-4-hydroxy-3-oxo-1-[(3S)-2-oxopyrrolidin-3-yl]butan-2-yl]-hexahydro-1H-cyclopenta[c]pyrrole-1-carboxamide (10.8 mg, 9%) as a white solid. $^1$H NMR (400 MHz, 80° C., DMSO-$d_6$) δ 11.83 (br, 1H), 8.32 (br, 1H), 7.35 (s, 1H), 6.73 (br, 1H), 4.73 (br, 1H), 4.38-4.44 (m, 2H), 4.09-4.22 (m, 2H), 3.84-4.10 (m, 1H), 3.70-3.75 (m, 2H), 3.55-3.60 (m, 1H), 3.10-3.20 (m, 4H), 2.65-2.78 (m, 1H), 2.50-2.62 (m, 1H), 1.41-2.35 (m, 11H). LC-MS (ESI, m/z): 507 [M+H]$^+$.

Example 161

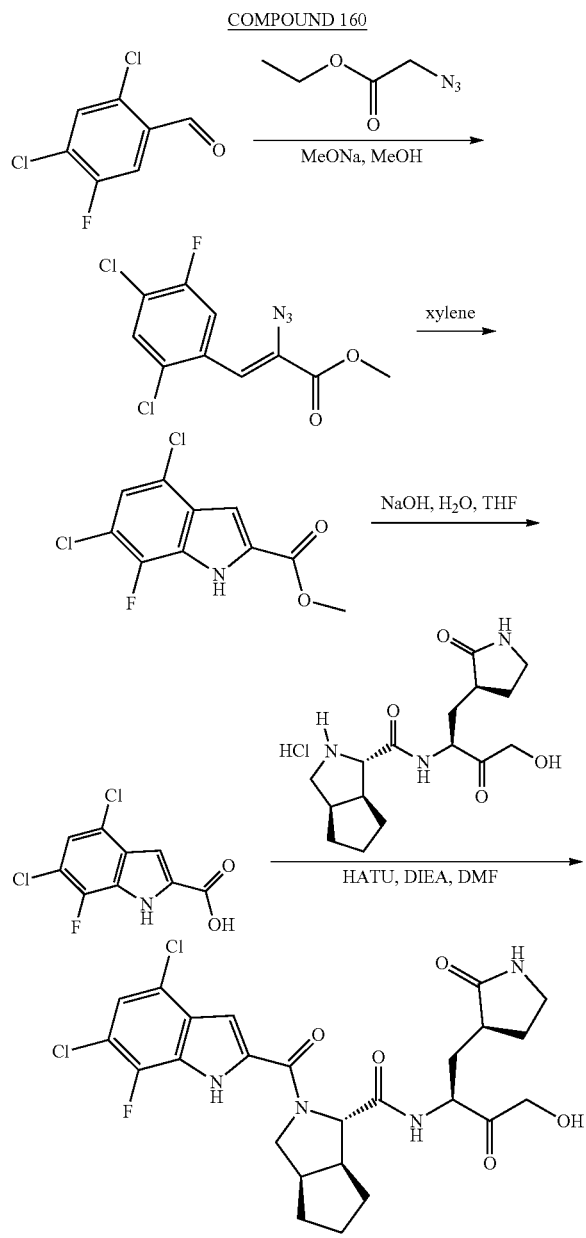

COMPOUND 160

To a solution of sodium methanolate (3.73 g, 20.7 mmol, 4.0 eq., 30% in MeOH) in MeOH (20 mL) was added a solution of 2,4-dichloro-5-fluorobenzaldehyde (1.00 g, 4.90 mmol, 1.0 eq.) and ethyl 2-azidoacetate (2.68 g, 20.7 mmol, 4.0 eq.) in MeOH (10 mL) at -10° C. The mixture was stirred for 2 h at -10° C., and the reaction was quenched with water (20 mL). The mixture was extracted with EA (3×50 mL). The organic layers were combined, washed with brine (2×20 mL), dried over anhydrous sodium sulfate, filtered and concentrated under reduced pressure to afford the crude product. The crude product was diluted with dichloromethane (10 mL) and made into a slurry with 100~200 silicagel mesh (2.5 g). The slurry was loaded to a column after removing the dichloromethane. The sample was purified by column chromatography (Column size 6×12 cm, column volume: 300 mL, silicagel size (100~200 mesh) quantity: 120 g) using EA:PE (0%-10% over min) as the eluent. The collected fractions: 6% EA:PE fractions were chosen as pure fractions, and those fractions were combined and concentrated under reduced pressure to provide methyl 2-azido-3-(2,4-dichloro-5-fluorophenyl)prop-2-enoate (420 mg, 27%) as a yellow solid. $^1$H-NMR (300 MHz, CDCl$_3$) δ 8.14-8.18 (m, 1H), 7.48-7.50 (m, 1H), 7.18 (s, 1H), 3.97 (s, 3H).

A solution of methyl (2Z)-2-azido-3-(2,4-dichloro-5-fluorophenyl)prop-2-enoate (420 mg, 1.45 mmol, 1.0 eq.) in xylene (5 mL) was stirred for 3 h at 120° C. The mixture was concentrated under reduced pressure to afford the crude product. The crude product was diluted with dichloromethane (10 mL) and made into slurry with 100~200 silicagel mesh (1 g). The slurry was loaded to a column after removing the dichloromethane. The sample was purified by column chromatography (Column size 4×12 cm, column volume: 120 mL, silicagel size (100~200 mesh) quantity: 80 g) using EA:PE (0%-20% over min) as the eluent. The collected fractions:12% EA:PE fractions were chosen as pure fractions. Those fractions were combined and concentrated under reduced pressure to provide methyl 4,6-dichloro-7-fluoro-1H-indole-2-carboxylate (200 mg, 52%) as a yellow solid. $^1$H NMR (300 MHz, DMSO-$d_6$) δ 13.14 (s, 1H), 7.70-7.13 (m, 1H), 7.17-7.19 (m, 1H), 3.91 (s, 3H). LC-MS (ESI, m/z): 260 [M–H]$^-$.

To a mixture of methyl 4,6-dichloro-7-fluoro-1H-indole-2-carboxylate (200 mg, 0.763 mmol, 1.0 eq.) in THF (2 mL) was added sodium hydroxide (153 mg, 3.82 mmol, 5.0 eq., in 0.3 mL water). The mixture was stirred for overnight at 50° C. The mixture was concentrated under reduced pressure to remove the THF. The pH was adjusted to 3 with 2 M HCl. The mixture was extracted with EA (3×20 mL). The organic layers were combined, washed with brine (2×10 mL), dried over anhydrous sodium sulfate, filtered and concentrated under reduced pressure to afford 4,6-dichloro-7-fluoro-1H-indole-2-carboxylic acid (110 mg, crude) as a white solid. $^1$H NMR (300 MHz, DMSO-$d_6$) δ 13.43 (s, 1H), 12.97 (s, 1H), 7.7-7.39 (m, 1H), 7.11-7.13 (m, 1H). LC-MS (ESI, m/z): 246 [M–H]$^-$.

To a mixture of imidazo[1,2-a]pyridin-5-ylglycine (86.9 mg, 0.350 mmol, 1.2 eq.), (1S,3aR,6aS)—N—((S)-4-hydroxy-3-oxo-1-((S)-2-oxopyrrolidin-3-yl)butan-2-yl)octahydrocyclopenta[c]pyrrole-1-carboxamide hydrochloride (105 mg, 0.292 mmol, 1.0 eq.) and 2-(7-azabenzotriazol-1-yl)-N,N,N',N'-tetramethyluronium hexafluorophosphate (133 mg, 0.350 mmol, 1.2 eq.) in DMF (2 mL) was added N,N-diisopropylethylamine (113 mg, 0.876 mmol, 3.0 eq.) at 0° C. The mixture was stirred for 1 h at rt, and the reaction was quenched with water (2 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by HPLC (Column: X Bridge Prep Phenyl OBD Column, 19*250 mm, 5 μm; Mobile Phase A: Water (0.05% FA), Mobile Phase B: ACN; Flow rate: 25 mL/min; Gradient: 40% B to 70% B in 7 min, 70% B; Wave Length: 254 nm; RT1 (min): 5.32); to provide (1S,3aR,6aS)-2-(4,6-dichloro-7-fluoro-1H-indole-2-carbonyl)-N—((S)-4-hydroxy-3-oxo-1-((S)-2-oxopyrrolidin-3-yl)butan-2-yl)octahydrocyclopenta[c]pyrrole-1-carboxamide (20.0 mg, 12%) as a white solid. $^{1}$H-NMR (400 MHz, 80° C., DMSO-$d_6$) δ 12.35 (br, 1H), 8.41 (br, 1H), 7.25-7.34 (m, 2H), 6.93 (br, 1H), 4.78 (br, 1H), 4.41-4.52 (m, 2H), 4.12-4.24 (m, 3H), 3.69 (br, 1H), 2.95-2.96 (m, 1H), 2.92-2.95 (m, 1H), 2.62-2.74 (m, 2H), 1.60-2.29 (m, 11H). LC-MS (ESI, m/z): 553 [M+H]$^+$.

Example 162

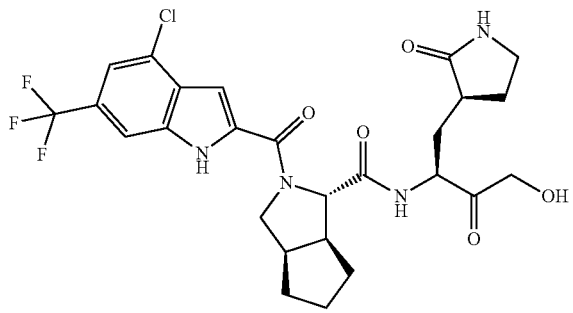 [SMILES: O=C1NCC[C@H]1C[C@H](NC(=O)[C@@H]1[C@H]2CCC[C@H]2CN1C(=O)c1cc2c(Cl)cc(C(F)(F)F)cc2[nH]1)C(=O)CO]

To a stirred mixture of sodium methylate (3.44 g, 19.1 mmol, 4.0 eq., 30% in MeOH) in methanol (20 mL) was added 2-chloro-4-trifluoromethylbenzaldehyde (1.00 g, 4.78 mmol, 1.0 eq.) and ethyl 2-azidoacetate (2.46 g, 19.1 mmol, 4.0 eq.) dropwise at 0° C. The mixture was stirred for overnight at rt, and the reaction was quenched with water (30 mL) at 0° C. The mixture was extracted with EA (3×60 mL). The combined organic layers were washed with brine (2×40 mL), dried over anhydrous sodium sulfate, filtered and concentrated under reduced pressure. The residue was purified by TLC with PE:EA (8:1) to afford methyl 2-azido-3-[2-chloro-4-(trifluoromethyl)phenyl]prop-2-enoate (270 mg, 18%) as a yellow solid. $^{1}$H NMR (300 MHz, CDCl$_3$-d) δ 8.28-8.31 (m, 1H), 7.65-7.70 (m, 1H), 7.52-7.65 (m, 1H), 7.24 (s, 1H), 3.96 (s, 3H).

A mixture of methyl (2Z)-2-azido-3-[2-chloro-4-(trifluoromethyl)phenyl]prop-2-enoate (270 mg, 0.883 mmol, 1.0 eq.) in xylene (10 mL) was stirred for 5 h at 120° C. and then concentrated under reduced pressure. The residue was purified by silica gel column chromatography with PE:EA (9:1) to afford methyl 4-chloro-6-(trifluoromethyl)-1H-indole-2-carboxylate (91 mg, 34%) as a yellow solid. $^{1}$H NMR (400 MHz, CDCl$_3$-d) δ 9.24 (s, 1H), 7.67 (s, 1H), 7.43-7.46 (m, 1H), 7.37-7.40 (m, 1H), 4.02 (m, 3H). LC-MS (ESI, m/z): 276 [M−H]$^-$.

To a stirred mixture of methyl 4-chloro-6-(trifluoromethyl)-1H-indole-2-carboxylate (80.0 mg, 0.288 mmol, 1.0 eq.) in tetrahydrofuran (8 mL) and water (3 mL) was added lithium hydroxide (55.2 mg, 2.30 mmol, 8.0 eq.) at rt. The mixture was stirred for 4 h at 40° C. and then acidified to pH 3 with hydrochloric acid (2M). The mixture was extracted with EA (3×30 mL). The combined organic layers were washed with brine (3×20 mL), dried over anhydrous sodium sulfate, filtered and concentrated under reduced pressure to afford 4-chloro-6-(trifluoromethyl)-1H-indole-2-carboxylic acid (70 mg, 87%) as a yellow solid. LC-MS (ESI, m/z): 262 [M−H]$^-$.

To a stirred mixture of 4-chloro-6-(trifluoromethyl)-1H-indole-2-carboxylic acid (63.0 mg, 0.239 mmol, 1.0 eq.) and (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (86.0 mg, 0.239 mmol, 1.0 eq.) in N,N-dimethylformamide (8 mL) was added O-(7-Aza-1H-benzotriazol-1-yl)-N,N,N',N'-tetramethyluronium hexafluorophosphate (118 mg, 0.311 mmol, 1.3 eq.) and N,N-diisopropylethylamine (123 mg, 0.956 mmol, 4.0 eq.) dropwise at 0° C. The mixture was stirred for 2 h at rt, and the reaction was quenched with water (15 mL) at rt. The mixture was extracted with EA (3×30 mL). The combined organic layers were washed with brine (3×30 mL), dried over anhydrous sodium sulfate, filtered and concentrated under reduced pressure. The residue was purified by TLC with dichloromethane:methanol (9:1) to afford (1S,3aR,6aS)-2-[4-chloro-6-(trifluoromethyl)-1H-indole-2-carbonyl]-N-[(2S)-4-hydroxy-3-oxo-1-[(3S)-2-oxopyrrolidin-3-yl]butan-2-yl]-hexahydro-1H-cyclopenta[c]pyrrole-1-carboxamide as a yellow solid. The crude product (100 mg) was purified by prep-HPLC with the following conditions (Column: XSelect CSH Prep C18 OBD Column, 19*250 mm, 5 μm; Mobile Phase A: Water (0.1% FA), Mobile Phase B: ACN; Flow rate: 25 mL/min; Gradient: 35% B to 60% B in 10 min, 60% B; Wave Length: 254 nm; RT1 (min): 8.83) to afford (1S,3aR,6aS)-2-[4-chloro-6-(trifluoromethyl)-1H-indole-2-carbonyl]-N-[(2S)-4-hydroxy-3-oxo-1-[(3S)-2-oxopyrrolidin-3-yl]butan-2-yl]-hexahydro-1H-cyclopenta[c]pyrrole-1-carboxamide (15.4 mg, 11%) as a white solid. LC-MS (ESI, m/z): 569 [M+H]$^+$.

Example 163

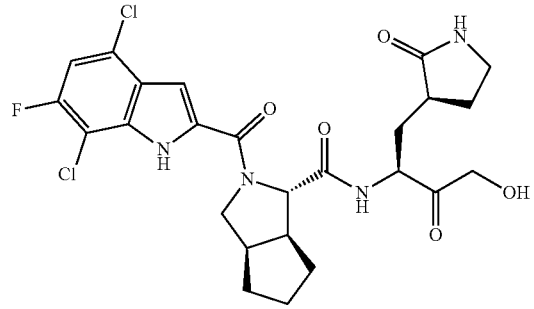 [SMILES: O=C1NCC[C@H]1C[C@H](NC(=O)[C@@H]1[C@H]2CCC[C@H]2CN1C(=O)c1cc2c(Cl)cc(F)c(Cl)c2[nH]1)C(=O)CO]

A solution of sodium methanolate (3.73 g, 30% wt, 20.7 mmol, 4.0 eq.) in MeOH (10 mL) was add a solution of 2,5-dichloro-4-fluorobenzaldehyde (1 g, 5.18 mmol, 1.0 eq.) and ethyl 2-azidoacetate (2.68 g, 20.7 mmol, 4.0 eq.) in MeOH (10 mL) at −10° C. The mixture was stirred for 4 h at rt, and the reaction was quenched with water (50 mL). The mixture was extracted with ethyl ether (3×50 mL). The organic layers were combined, washed with brine (2×50 mL), dried over anhydrous sodium sulfate, filtered and concentrated under reduced pressure to afford the crude product. The crude product was diluted with EA (20 mL) and made into a slurry with 100~200 silica gel mesh (4 g). The slurry was loaded to a column after removing the EA. The sample was purified by column chromatography (Column size 5×24 cm, column volume: 300 mL, silica gel size (100~200 mesh) quantity: 120 g) using EA:PE (0%-10% over 30 min) as the eluent. The collected fractions: 3%-4% EA:PE fractions were chosen as pure fractions, and those fractions were combined and concentrated under reduced pressure to provide methyl 2-azido-3-(2,5-dichloro-4-fluorophenyl)prop-2-enoate (500 mg, 29%) as a light yellow solid. $^1$H NMR (400 MHz, CDCl$_3$-d) δ 8.36-8.38 (m, 1H), 7.27-7.31 (m, 1H), 7.16 (s, 1H), 3.80-4.00 (m, 3H).

A solution of methyl (2Z)-2-azido-3-(2,5-dichloro-4-fluorophenyl)prop-2-enoate (500 mg, 1.72 mmol, 1.0 eq.) in m-xylene (10 mL) was stirred for 2 h at 120° C. and then concentrated under reduced pressure. The crude product was diluted with dichloromethane (20 mL) and made into a slurry with 100~200 silica gel mesh (2 g). The slurry was loaded to a column after removing the dichloromethane. The sample was purified by column chromatography (Column size 5×24 cm, column volume: 300 mL, silica gel size (100~200 mesh) quantity: 120 g) using EA:PE (0%-10% over 30 min) as the eluent. The collected fractions: 1% EA:PE fractions were chosen as pure fractions, and those fractions were combined and concentrated under reduced pressure to provide methyl 4,7-dichloro-6-fluoro-1H-indole-2-carboxylate (300 mg, 57%) as a white solid. $^1$H NMR (400 MHz, DMSO-d$_6$) δ 12.88 (m, 1H), 7.47 (d, J=8.0 Hz, 1H), 7.18-7.28 (m, 1H), 3.87-3.94 (m, 3H). LC-MS (ESI, m/z): 260 [M−H]$^-$.

To a stirred mixture of methyl 4,7-dichloro-6-fluoro-2,3-dihydro-1H-indole-2-carboxylate (100 mg, 0.379 mmol, 1.0 eq.) in THF (2 mL) and H$_2$O (2 mL) was added lithium hydroxide (45.3 mg, 1.89 mmol, 5.0 eq.). The mixture was stirred for 2 h at 60° C. and then acidified to pH=3 with hydrochloric acid (2M). The mixture was extracted with EA (3×30 mL). The organic layers were combined, washed with brine (2×30 mL), dried over anhydrous sodium sulfate, filtered and concentrated under reduced pressure to afford 4,7-dichloro-6-fluoro-2,3-dihydro-1H-indole-2-carboxylic acid (91 mg, crude) as a light yellow solid. LC-MS (ESI, m/z): 246 [M−H]$^-$.

To a stirred mixture of 4,7-dichloro-6-fluoro-1H-indole-2-carboxylic acid (90.9 mg, 0.366 mmol, 1.1 eq.), (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (120 mg, 0.333 mmol, 1.0 eq.) and o-(7-Azabenzotriazol-1-yl)-N,N,N',N'-tetramethyluronium hexafluorophosphate (152 mg, 0.400 mmol, 1.2 eq.) in DMF (2 mL) was added N-ethyl-N-isopropylpropan-2-amine (129 mg, 0.999 mmol, 3.0 eq.) at 0° C. The mixture was stirred for 1 h at rt, and the reaction was quenched with water (10 mL). The mixture was extracted with EA (3×10 mL). The organic layers were combined, washed with brine (2×10 mL), dried over anhydrous sodium sulfate, filtered and concentrated under reduced pressure to afford the crude product. The crude product (80 mg) was purified by prep-HPLC with the following conditions (Column: XSelect CSH Prep C18 OBD Column, 19*250 mm, 5 μm; Mobile Phase A: Water (0.05% FA), Mobile Phase B: ACN; Flow rate: 25 mL/min; Gradient: 40% B to 70% B in 7 min, 70% B; Wave Length: 254 nm; RT1 (min): 5.2) to afford (1S,3aR,6aS)-2-(4,7-dichloro-6-fluoro-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (26.9 mg, 14%) as a white solid. $^1$H NMR (400 MHz, 80° C., DMSO-d$_6$) δ 11.97 (br, 1H), 8.42 (s, 1H), 7.51-7.13 (m, 2H), 6.90 (br, 1H), 4.77 (s, 1H), 4.29-4.77 (m, 2H), 4.09-4.25 (m, 2H), 3.72-4.09 (m, 1H), 3.58-3.72 (m, 1H), 3.12-3.38 (m, 2H), 2.55-2.85 (m, 2H), 1.29-2.40 (m, 11H). LC-MS (ESI, m/z): 553 [M+H]$^+$.

Example 164

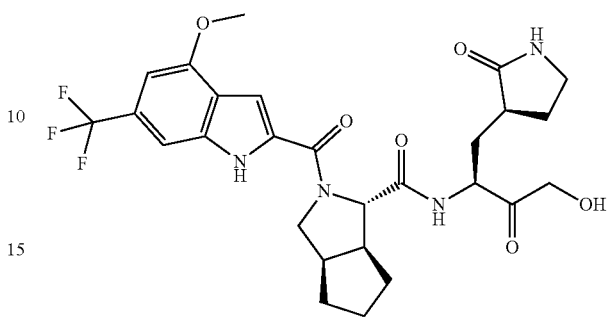

COMPOUND 163

To a solution of sodium methanolate (3.53 g, 19.6 mmol, 4.0 eq., 30% in MeOH) in MeOH (5 mL) was added a solution of 2-methoxy-4-(trifluoromethyl)benzaldehyde (1.00 g, 4.90 mmol, 1.0 eq.) and ethyl 2-azidoacetate (2.53 g, 19.6 mmol, 4.0 eq.) in MeOH (10 mL) stirred at −10° C. The mixture was stirred for 4 h at −10° C., and the reaction was quenched with water (10 mL). The mixture was extracted with EA (3×50 mL). The organic layers were combined, washed with brine (2×20 mL), dried over anhydrous sodium sulfate, filtered and concentrated under reduced pressure to afford the crude product. The crude product was diluted with dichloromethane (10 mL) and made into slurry with 100~200 silica gel mesh (2.5 g). The slurry was loaded to a column chromatography after removing the dichloromethane. The sample was purified by column chromatography (Column size 4×12 cm, column volume: 300 mL, silica gel size (100~200 mesh) quantity: 80 g) using EA:PE (0%-10% over 30 min) as the eluent. The collected fractions: 3%-4% EA:PE fractions were chosen as pure fractions, and those fractions were combined and concentrated under reduced pressure to methyl 2-azido-3-[2-methoxy-4-(trifluoromethyl)phenyl]prop-2-enoate (650 mg, 44%) as a yellow solid. $^1$H-NMR (300 MHz, CDCl$_3$-d) δ 8.29-8.32 (m, 1H), 7.34 (s, 1H), 7.25-7.26 (m, 1H), 7.10-7.11 (m, 1H), 3.95 (s, 3H), 3.94 (s, 3H).

A solution of methyl 2-azido-3-[2-methoxy-4-(trifluoromethyl)phenyl]prop-2-enoate (480 mg, 1.59 mmol, 1.0 eq.) in xylene (5 mL) was stirred for 3 h at 120° C. The mixture was concentrated under reduced pressure to afford the crude product. The crude product was diluted with dichloromethane (10 mL) and made into a slurry with 100~200 silica gel mesh (2.5 g). The slurry was loaded to a column after removing the dichloromethane. The sample was purified by column chromatography (Column size 4×12 cm, column volume: 120 mL, silica gel size (100~200 mesh) quantity: 80 g) using EA:PE (0%-20% over 30 min) as the eluent. The collected fractions: 5%-7% EA:PEA fractions were chosen as pure fractions, and those fractions were combined and concentrated under reduced pressure to provide methyl 4-methoxy-6-(trifluoromethyl)-1H-indole-2-carboxylate (310 mg, 71%) as a white solid. $^1$H NMR (300 MHz, DMSO-d$_6$) δ 12.44 (br, 1H), 7.37-7.38 (m, 1H), 7.17-7.18 (m, 1H), 6.77 (s, 1H), 4.37 (s, 3H), 4.33 (s, 3H). LC-MS (ESI, m/z): 272 [M−H]$^-$.

A solution of methyl (2Z)-2-azido-3-[2-methoxy-4-(trifluoromethyl)phenyl]prop-2-enoate (480 mg, 1.59 mmol, 1.0 eq.) in xylene (5 mL) was stirred for 3 h at 120° C. The mixture was concentrated under reduced pressure to afford the crude product. The crude product was diluted with dichloromethane (10 mL) and made into a slurry with 100~200 silica gel mesh (2.5 g). The slurry was loaded to a column chromatography after removing the dichloromethane. The sample was purified by column chromatography (Column size 4×12 cm, column volume: 120 mL, silica gel size (100~200 mesh) quantity: 80 g) and using EA:PE (0%-20% over 30 min) as the eluent. The collected fractions: 5%-7% EA:PE fractions were chosen as pure fractions, and those fractions were combined and concentrated under reduced pressure to provide methyl 4-methoxy-6-(trifluoromethyl)-1H-indole-2-carboxylate (310 mg, 71%) as a white solid. $^1$H NMR (300 MHz, DMSO-d$_6$) δ 12.44 (br, 1H), 7.37-7.38 (m, 1H), 7.17-7.18 (m, 1H), 6.77 (s, 1H), 4.37 (s, 3H), 4.33 (s, 3H). LC-MS (ESI, m/z): 272 [M–H]$^-$.

To a mixture of methyl 4-methoxy-6-(trifluoromethyl)-1H-indole-2-carboxylate (300 mg, 1.10 mmol, 1.0 eq.) in THF (5 mL) was added sodium hydroxide (219 mg, 5.49 mmol, 5.0 eq., in 1 mL water). The mixture was stirred for 2 h at 50° C. The mixture was concentrated under reduced pressure to remove the THF, and the pH was adjusted to 3-4 with HCl (2M). The mixture was extracted with EA (3×10 mL). The organic layers were combined, washed with brine (2×10 mL), dried over anhydrous sodium sulfate, filtered and concentrated under reduced pressure to afford 4-methoxy-6-(trifluoromethyl)-1H-indole-2-carboxylic acid (180 mg, crude) as a white solid. $^1$H NMR (300 MHz, DMSO-d$_6$) δ 12.68 (br, 1H), 12.27 (s, 1H), 7.78 (s, 1H), 7.37 (s, 1H), 6.75 (s, 1H), 3.91 (s, 3H). LC-MS (ESI, m/z): 258 [M–H]$^-$.

To a mixture of 4-methoxy-6-(trifluoromethyl)-1H-indole-2-carboxylic acid (90.8 mg, 0.350 mmol, 1.2 eq.), (1S,3aR,6aS)—N—((S)-4-hydroxy-3-oxo-1-((S)-2-oxopyrrolidin-3-yl)butan-2-yl)octahydrocyclopenta[c]pyrrole-1-carboxamide hydrochloride (105 mg, 0.292 mmol, 1.0 eq.) and 2-(7-azabenzotriazol-1-yl)-N,N,N',N'-tetramethyluronium hexafluorophosphate (133 mg, 0.350 mmol, 1.2 eq.) in DMF (2 mL) was added N,N-diisopropylethylamine (188 mg, 1.46 mmol, 5.0 eq.) at 0° C. The mixture was stirred for 1 h at rt, and the reaction was quenched with water (2 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by HPLC (Column: X Select CSH Prep C18 OBD Column, 19*250 mm, 5 μm; Mobile Phase A: Water (0.05% FA), Mobile Phase B: ACN; Flow rate: 25 mL/min; Gradient: 34% B to 64% B in 7 min, 64% B; Wave Length: 254 nm; RT1 (min): 6); to provide (1S, 3aR,6aS)—N—((S)-4-hydroxy-3-oxo-1-((S)-2-oxopyrrolidin-3-yl)butan-2-yl)-2-(4-methoxy-6-(trifluoromethyl)-1H-indole-2-carbonyl)octahydrocyclopenta[c]pyrrole-1-carboxamide (9.1 mg, 5%) as a white solid. LC-MS (ESI, m/z): 565 [M+H]$^+$.

Example 165

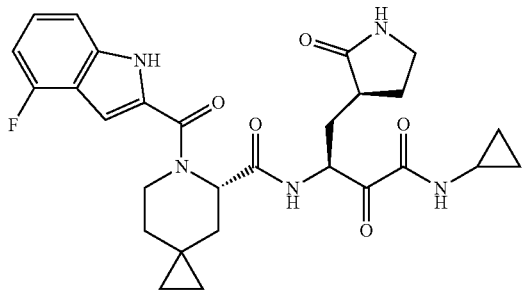

COMPOUND 164

Compound 164 was prepared similarly as described for Compound 140 using 4-fluoro-1H-indole-2-carboxylic acid in place of 1H-indole-2-carboxylic acid. LCMS (ESI, m/z): 536 [M–H]$^-$.

Example 166

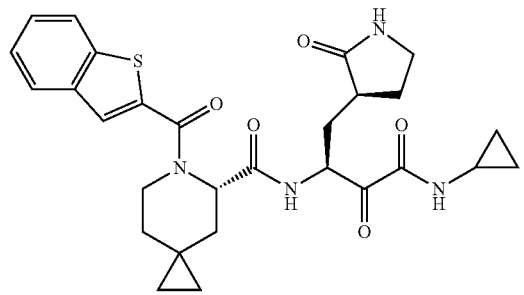

COMPOUND 165

Compound 165 was prepared similarly as described for Compound 140 using benzo[b]thiophene-2-carboxylic acid in place of 1H-indole-2-carboxylic acid. $^1$H NMR (500 MHz, 364K, DMSO-d$_6$) δ ppm 8.34-8.43 (m, 2H), 7.93 (dd, 2H), 7.66 (s, 1H), 7.37-7.48 (m, 2H), 7.35 (brs, 1H), 4.95-5.09 (m, 2H), 4.26 (m, 1H), 3.44 (t, 1H), 3.09-3.28 (m, 2H), 2.76 (m, 1H), 2.34 (m, 1H), 2.23 (m, 1H), 2.09 (dd, 1H), 1.81-2.03 (m, 2H), 1.76 (m, 2H), 1.64 (d, 1H), 0.97 (d, 1H), 0.57-0.74 (m, 4H), 0.52 (m, 1H), 0.23-0.35 (m, 3H). LCMS (ESI, m/z): 537 [M+H]$^+$. LCMS (ESI, m/z): 537 [M+H]$^+$.

Example 167

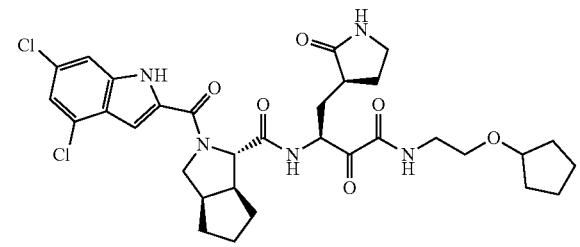

COMPOUND 166

Compound 166 was prepared similarly as described for Compound 149 using 2-(cyclopentyloxy)ethan-1-amine in place of 2-isobutoxyethan-1-amine. LCMS (ESI, m/z): 660 [M+H]⁺.

Example 168

COMPOUND 167

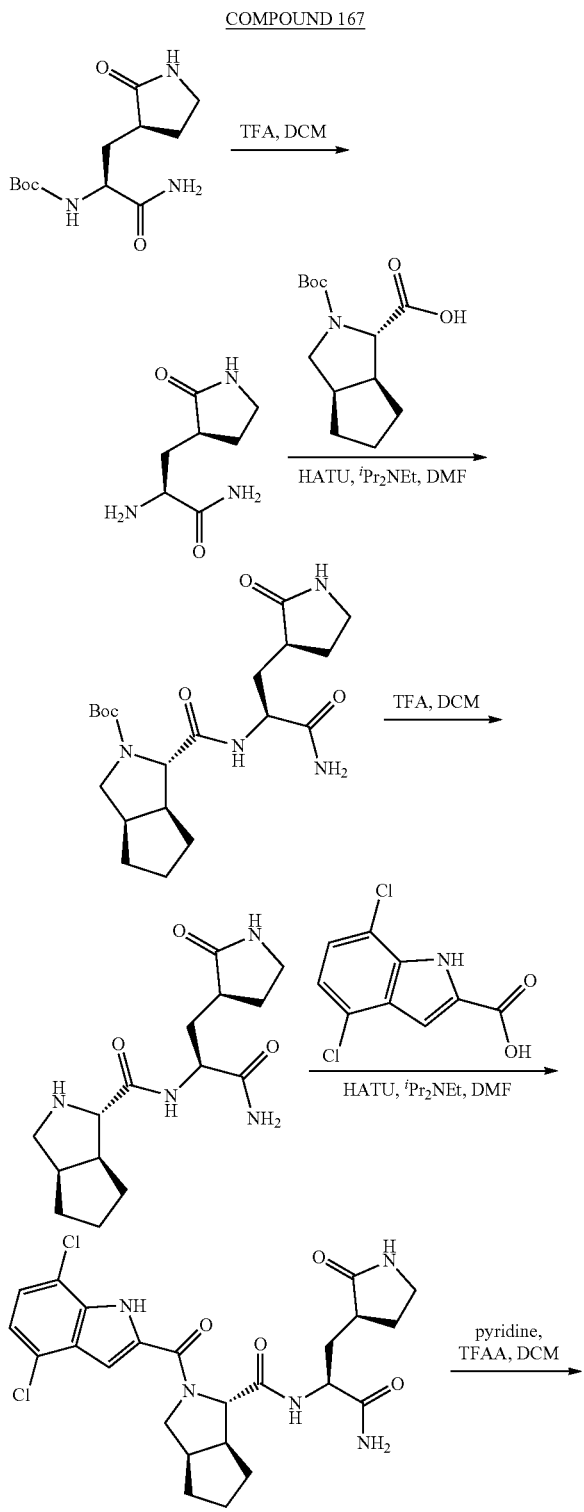

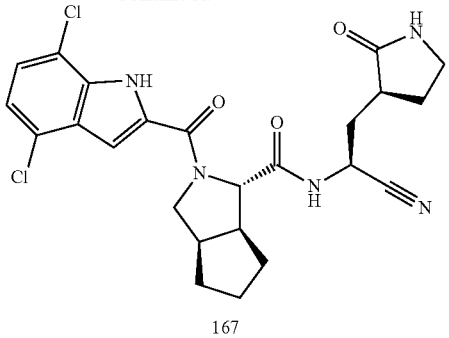

167

To a mixture of tert-butyl N-[(1S)-1-carbamoyl-2-[(3S)-2-oxopyrrolidin-3-yl]ethyl]carbamate (2.00 g, 7.37 mmol, 1.0 eq.) in DCM (18 mL) was added trifluoroacetic acid (6 mL). The mixture was stirred for 1 h at rt and then concentrated under reduced pressure to afford (2S)-2-amino-3-[(3S)-2-oxopyrrolidin-3-yl]propanamide (1.30 g, crude) as a brown oil. LC-MS (ESI, m/z): 172 [M+H]⁺.

To a mixture of (2S)-2-amino-3-[(3S)-2-oxopyrrolidin-3-yl]propanamide (1.30 g, 7.59 mmol, 1.0 eq.), (1S,3aR,6aS)-2-(tert-butoxycarbonyl)-hexahydro-1H-cyclopenta[c]pyrrole-1-carboxylic acid (2.13 g, 8.35 mmol, 1.1 eq.) and o-(7-azabenzotriazol-1-yl)-N,N,N',N'-tetramethyluronium hexafluorophosphate (3.75 g, 9.87 mmol, 1.3 eq.) in DMF (10 mL) was added N-ethyl-N-isopropylpropan-2-amine (5.89 g, 45.6 mmol, 6.0 eq.) at 0° C. The mixture was stirred for 1 h at rt. The mixture was purified by C18 column with CH₃CN:Water (0.05% TFA), and the fraction was concentrated under reduced pressure to provide tert-butyl (1S,3aR,6aS)-1-{[(1S)-1-carbamoyl-2-[(3S)-2-oxopyrrolidin-3-yl]ethyl]carbamoyl}-hexahydro-1H-cyclopenta[c]pyrrole-2-carboxylate (1.97 g, 61%) as a yellow solid. LC-MS (ESI, m/z): 409 [M+H]⁺.

To a mixture of tert-butyl (1S,3aR,6aS)-1-{[(1S)-1-carbamoyl-2-[(3S)-2-oxopyrrolidin-3-yl]ethyl]carbamoyl}-hexahydro-1H-cyclopenta[c]pyrrole-2-carboxylate (160 mg, 0.392 mmol, 1.0 eq.) in DCM (3 mL) was added trifluoroacetic acid (1 mL). The mixture was stirred for 1 h at rt. The mixture was concentrated under reduced pressure to afford (2S)-2-[(1S,3aR,6aS)-octahydrocyclopenta[c]pyrrol-1-ylformamido]-3-[(3S)-2-oxopyrrolidin-3-yl]propanamide (120 mg, crude) as a yellow oil. LC-MS (ESI, m/z): 309 [M+H]⁺.

To a mixture of (2S)-2-[(1S,3aR,6aS)-octahydrocyclopenta[c]pyrrol-1-ylformamido]-3-[(3S)-2-oxopyrrolidin-3-yl]propanamide (120 mg, 0.392 mmol, 1.0 eq.), 4,7-dichloro-1H-indole-2-carboxylic acid (90.0 mg, 0.392 mmol, 1.0 eq.) and o-(7-azabenzotriazol-1-yl)-N,N,N',N'-tetramethyluronium hexafluorophosphate (194 mg, 0.510 mmol, 1.3 eq.) in DMF (3 mL) was added N-ethyl-N-isopropylpropan-2-amine (203 mg, 1.57 mmol, 4.0 eq.) at 0° C. The mixture was stirred for 1 h at rt. The mixture was purified by C18 column with CH₃CN:Water (0.05% TFA), and the fraction was concentrated under reduced pressure to provide (2S)-2-{[(1S,3aR,6aS)-2-(4,7-dichloro-1H-indole-2-carbonyl)-hexahydro-1H-cyclopenta[c]pyrrol-1-yl]formamido}-3-[(3S)-2-oxopyrrolidin-3-yl]propanamide (110 mg, 52%) as a light yellow solid. LC-MS (ESI, m/z): 520 [M+H]⁺.

To a mixture of (2S)-2-{[(1S,3aR,6aS)-2-(4,7-dichloro-1H-indole-2-carbonyl)-hexahydro-1H-cyclopenta[c]pyrrol-1-yl]formamido}-3-[(3S)-2-oxopyrrolidin-3-yl]propanamide (100 mg, 0.192 mmol, 1.0 eq.) in DCM (2 mL) was added pyridine (53.0 mg, 0.672 mmol, 3.5 eq.) and trifluoroacetic anhydride (57.0 mg, 0.269 mmol, 1.4 eq.). The mixture was stirred for 2 h at rt, and the reaction was quenched with water (4 mL). The mixture was extracted with DCM (3×3 mL). The organic layers were combined, washed with brine (2×4 mL), dried over anhydrous sodium sulfate, filtered and concentrated under reduced pressure to afford the crude product. The crude product was purified by prep-HPLC (Column: XSelect CSH Prep C18 OBD Column, 19×250 mm, 5 μm; Mobile Phase A: Water (0.1% FA), Mobile Phase B: ACN; Flow rate: 25 mL/min; Gradient: 42% B to 57% B in 10 min, 57% B; Wave Length: 254 nm; RT: 8.6 min) to provide (1S,3aR,6aS)—N-[(1S)-1-cyano-2-[(3S)-2-oxopyrrolidin-3-yl]ethyl]-2-(4,7-dichloro-1H-indole-2-carbonyl)-hexahydro-1H-cyclopenta[c]pyrrole-1-carboxamide (18.0 mg, 18%) as a white solid. $^1$H NMR (400 MHz, 80° C., DMSO-$d_6$) δ 11.40-11.90 (m, 1H), 8.79 (br, 1H), 7.43 (s, 1H), 7.20-7.35 (m, 1H), 7.10-7.19 (m, 1H), 6.94 (br, 1H), 4.80-5.08 (m, 1H), 4.30-4.55 (m, 1H), 3.80-4.20 (m, 1H), 3.50-3.79 (m, 1H), 3.08-3.22 (m, 2H), 2.70-2.90 (m, 1H), 2.50-2.69 (m, 1H), 2.22-2.45 (m, 1H), 1.40-2.20 (m, 10H). LC-MS (ESI, m/z): 502 [M+H]$^+$.

Example 169

COMPOUND 168

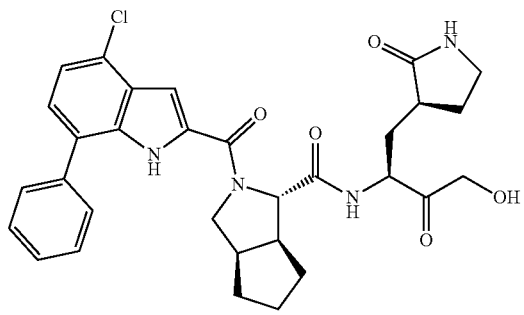

To a solution of (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (102 mg, 0.283 mmol, 1.0 eq.) in DMF (1 mL) was added 4-chloro-7-phenyl-1H-indole-2-carboxylic acid (84.7 mg, 0.311 mmol, 1.1 eq.), o-(7-azabenzotriazol-1-yl)-N,N,N',N'-tetramethyluronium hexafluorophosphate (141 mg, 0.369 mmol, 1.3 eq.) and N-ethyl-N-isopropylpropan-2-amine (184 mg, 1.42 mmol, 5.0 eq.) at 0° C. The mixture was stirred for 1 h at rt, and the reaction was quenched with water (5 mL). The mixture was extracted with EA (3×15 mL). The organic layers were combined, washed with brine (2×20 mL), dried over anhydrous sodium sulfate, filtered and concentrated under reduced pressure to afford the crude product. The crude product was purified by prep-HPLC (Column: XSelect CSH Prep C18 OBD Column, 19*150 mm, 5 μm; Mobile Phase A: Water (0.05% FA), Mobile Phase B: ACN; Flow rate: 25 mL/min; Gradient: 38% B to 50% B in 10 min, 50% B; Wave Length: 254 nm; RT1 (min): 9.47) to provide (1S,3aR,6aS)-2-(4-chloro-7-phenyl-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (43.3 mg, 26%) as a white solid. LCMS (ESI, m/z): 577 [M+H]$^+$.

Example 170

COMPOUND 169

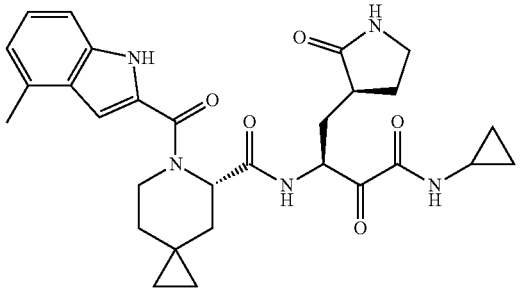

Compound 169 was prepared similarly as described for Compound 140 using 4-methyl-1H-indole-2-carboxylic acid in place of 1H-indole-2-carboxylic acid. LCMS (ESI, m/z): 534 [M+H]$^+$.

Example 171

COMPOUND 170

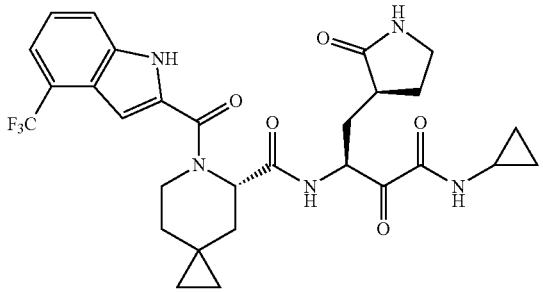

Compound 170 was prepared similarly as described for Compound 140 using 4-(trifluoromethyl)-1H-indole-2-carboxylic acid in place of 1H-indole-2-carboxylic acid. LCMS (ESI, m/z): 588 [M+H]$^+$.

4-(Trifluoromethyl)-1H-indole-2-carboxylic acid: To a solution of methyl 4-(trifluoromethyl)-1H-indole-2-carboxylate (200 mg, 0.822 mmol, 1.0 eq.) in MeOH (1.6 mL) and H$_2$O (1.6 mL) was added 10% KOH aqueous solution (3.2 mL). The mixture was heated at 50° C. until the mixture turned clear. After cooling to 0° C., the mixture was diluted with cold water (5 mL) and acidified with 1N HCl. The solid was filtered, washed with cold water and dried under high vacuum to afford 4-(trifluoromethyl)-1H-indole-2-carboxylic acid (170 mg, 90%) as an off-white solid. LCMS (ESI, m/z): 228 [M−H]$^-$.

Example 172

COMPOUND 171

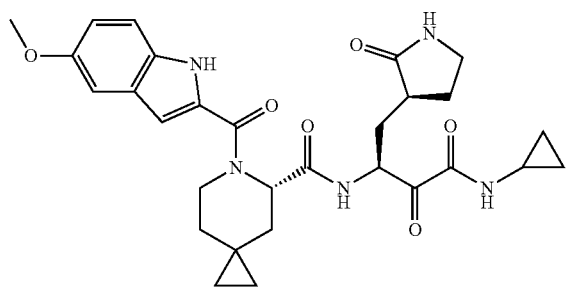

Compound 171 was prepared similarly as described for Compound 140 using 5-methoxy-1H-indole-2-carboxylic acid in place of 1H-indole-2-carboxylic acid. LCMS (ESI, m/z): 550 [M+H]⁺.

Example 173

COMPOUND 172

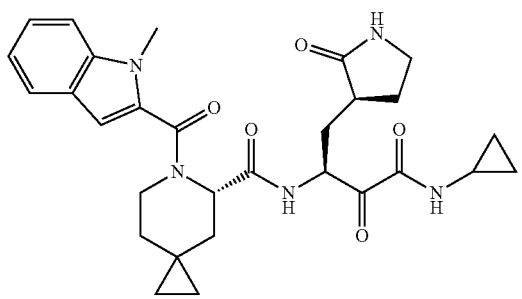

Compound 172 was prepared similarly as described for Compound 140 using 1-methyl-1H-indole-2-carboxylic acid in place of 1H-indole-2-carboxylic acid. $^1$H NMR (500 MHz, 362K, DMSO-d$_6$) δ 8.33-8.36 (m, 2H), 7.55 (d, 1H), 7.45 (d, 1H), 7.36 (s, 1H), 7.21 (t, 1H), 7.06 (t, 1H), 6.62 (s, 1H), 5.05-5.11 (m, 1H), 4.96 (brs, 1H), 4.25 (s, 1H), 3.75 (s, 3H), 3.42 (t, 1H), 3.13-3.24 (m, 2H), 2.79 (m, 1H), 2.19-2.38 (m, 2H), 2.13 (dd, 1H), 1.83-2.00 (m, 2H), 1.62-1.80 (m, 3H), 0.98 (d, 1H), 0.59-0.72 (m, 4H), 0.54 (m, 1H), 0.24-0.36 (m, 3H). LCMS (ESI, m/z): 534 [M+H]⁺.

Example 174

COMPOUND 173

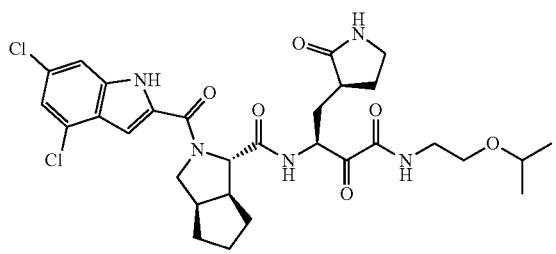

Compound 173 was prepared similarly as described for Compound 149 using 2-isopropoxyethan-1-amine in place of 2-isobutoxyethan-1-amine. LCMS (ESI, m/z): 634 [M+H]⁺.

Example 175

COMPOUND 174

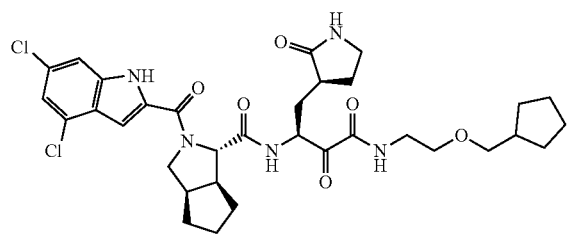

Compound 174 was prepared similarly as described for Compound 149 using 2-(cyclopentylmethoxy)ethan-1-amine in place of 2-isobutoxyethan-1-amine. LCMS (ESI, m/z): 674 [M+H]⁺.

Example 176

COMPOUND 175

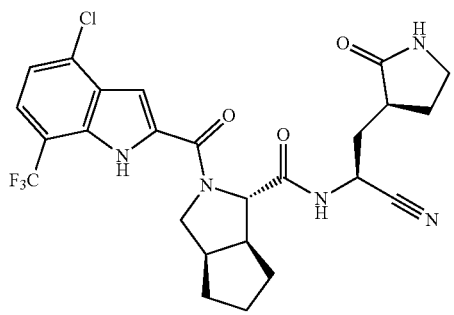

Compound 175 was prepared similarly as described for Compound 167, using 4-chloro-7-(trifluoromethyl)-1H-indole-2-carboxylic acid in place of 4,7-dichloro-1H-indole-2-carboxylic acid. LC-MS (ESI, m/z): 536 [M+H]⁺.

Example 177

COMPOUND 176

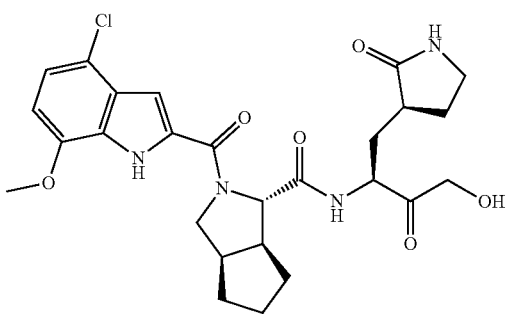

Compound 176 was prepared similarly as described for Compound 163, starting from 2-chloro-5-methoxybenzaldehyde in place of 2-methoxy-4-(trifluoromethyl)benzaldehyde. $^1$H NMR (400 MHz, 80° C., DMSO-d$_6$) δ 11.26 (br, 1H), 8.38 (br, 1H), 7.34 (br, 1H), 6.94-7.02 (m, 1H), 6.63-6.86 (m, 2H), 4.75 (br, 1H), 4.31-4.61 (m, 2H), 3.92-4.25 (m, 3H), 3.91 (s, 3H), 3.57-3.68 (m, 1H), 3.06-3.16 (m, 2H), 2.53-2.81 (m, 2H), 1.18-2.41 (m, 11H). LCMS (ESI, m/z): 531 [M+H]$^+$.

Example 178

COMPOUND 177

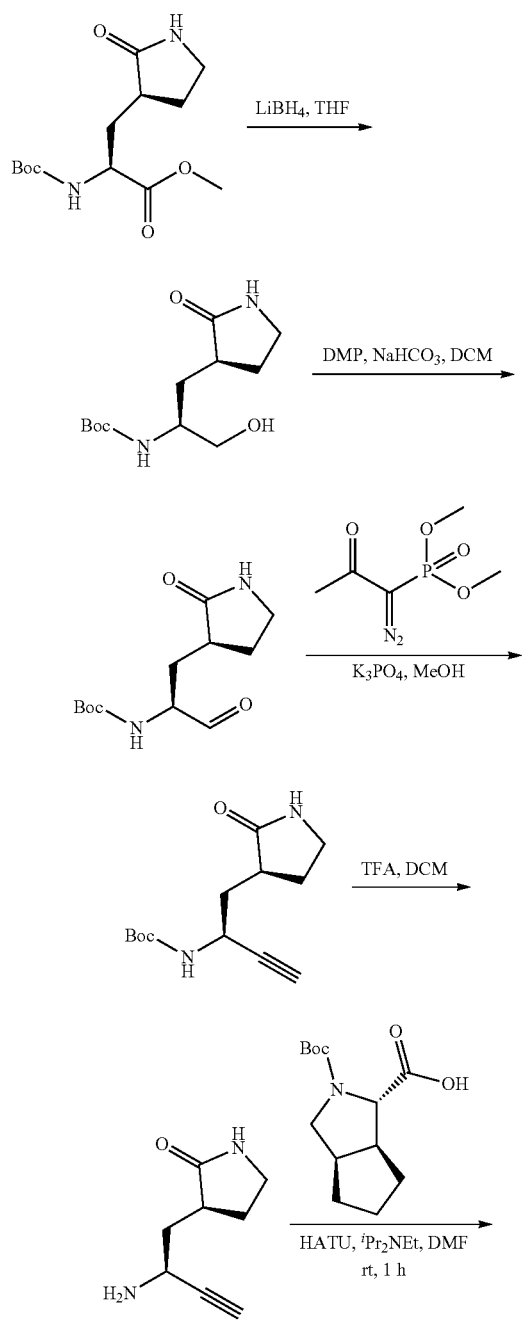

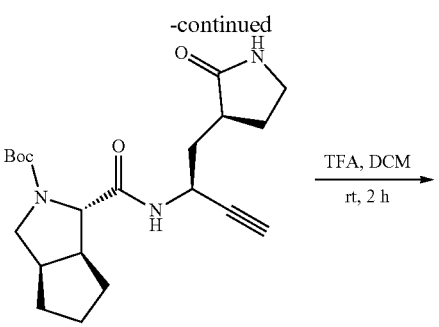

To a stirred mixture of methyl (2S)-2-[(tert-butoxycarbonyl)amino]-3-[(3S)-2-oxopyrrolidin-3-yl]propanoate (1.00 g, 3.49 mmol, 1.0 eq.) in THF (10 mL) was added lithium borohydride (8.7 mL, 17.4 mmol, 5.0 V, 2 M in tetrahydrofuran) dropwise at 0° C. The mixture was stirred for 2 h at rt, and the reaction was quenched with water (100 mL). The mixture was extracted with chloroform:isopropyl alcohol (3:1, 3×100 mL). The organic layers were combined, washed with brine (2×100 mL), dried over anhydrous sodium sulfate, filtered and concentrated under reduced pressure to afford the crude product. The crude product was diluted with dichloromethane (20 mL) and made into a slurry with 100~200 silicagel mesh (3 g). The slurry was loaded to a column after removing the dichloromethane. The sample was purified by column chromatography (Column size 5×24 cm, column volume: 300 mL, silica gel size (100~200 mesh) quantity: 120 g) using methanol:dichloromethane (0%-15% over min) as the eluent. The collected fractions: 12%-13% methanol:dichloromethane fractions were chosen as pure fractions, and those fractions were combined and concentrated under reduced pressure to provide tert-butyl N-[(2S)-1-hydroxy-3-[(3S)-2-oxopyrrolidin-3-yl]propan-2-yl]carbamate (750 mg, 74%) as a white solid. LC-MS (ESI, m/z): 159 [M−100+H]$^+$.

To a stirred mixture of tert-butyl N-[(2S)-1-hydroxy-3-[(3S)-2-oxopyrrolidin-3-yl]propan-2-yl]carbamate (650 mg, 2.51 mmol, 1.0 eq.) in DCM (7 mL) was added Dess-Martin periodinane (1.07 g, 2.51 mmol, 1.0 eq.) and sodium bicarbonate (211 mg, 2.51 mmol, 1.0 eq.) at rt. The mixture was stirred for 2 h at rt, and the reaction was quenched with water (100 mL). The mixture was extracted with chloroform: isopropyl alcohol (5:1, 3×100 mL). The organic layers were combined, washed with brine (2×100 mL), dried over anhydrous sodium sulfate, filtered and concentrated under reduced pressure to afford tert-butyl N-[(2S)-1-oxo-3-[(3S)-2-oxopyrrolidin-3-yl]propan-2-yl]carbamate (600 mg, crude) as a white semi-solid. LC-MS (ESI, m/z): 257 [M+H]$^+$.

To a stirred mixture of tert-butyl N-[(2S)-1-oxo-3-[(3S)-2-oxopyrrolidin-3-yl]propan-2-yl]carbamate (600 mg, 2.34 mmol, 1.0 eq.) and potassium phosphate (993 mg, 4.68 mmol, 2.0 eq.) in MeOH (10 mL) was added dimethyl (1-diazo-2-oxopropyl)phosphonate (899 mg, 4.68 mmol, 2.0 eq.) dropwise at rt under nitrogen. The mixture was stirred overnight at rt, and the reaction was quenched with water (50 mL). The mixture was extracted with EA (3×100 mL). The organic layers were combined, washed with brine (2×100 mL), dried over anhydrous sodium sulfate, filtered and concentrated under reduced pressure to afford the crude product. The crude product was diluted with dichloromethane (20 mL) and made into a slurry with 100~200 silicagel mesh (4 g). The slurry was loaded to a column after removing the dichloromethane. The sample was purified by column chromatography (Column size 5×24 cm, column volume: 300 mL, silica gel size (100~200 mesh) quantity: 120 g) using EA:PE (0%-100% over 30 min) as the eluent. The collected fractions: 90%-100% EA:PE fractions were chosen as pure fractions, and those fractions were combined and concentrated under reduced pressure to provide tert-butyl N-[(2S)-1-oxo-3-[(3S)-2-oxopyrrolidin-3-yl]propan-2-yl]carbamate (700 mg, crude) as a light brown oil. LC-MS (ESI, m/z): 253 [M+H]$^+$.

To a stirred mixture of tert-butyl N-[(2S)-1-[(3S)-2-oxopyrrolidin-3-yl]but-3-yn-2-yl]carbamate (700 mg, 2.77 mmol, 1.0 eq.) in DCM (6 mL) was added trifluoroacetic acid (2 mL). The mixture was stirred for 2 h at rt, and then concentrated under reduced pressure to afford (3S)-3-[(2S)-2-aminobut-3-yn-1-yl]pyrrolidin-2-one (700 mg, crude) as a light brown oil. LC-MS (ESI, m/z): 153 [M+H]$^+$.

To a stirred mixture of (3S)-3-[(2S)-2-aminobut-3-yn-1-yl]pyrrolidin-2-one (530 mg, 3.48 mmol, 1.0 eq.) and (1S,3aR,6aS)-2-(tert-butoxycarbonyl)-hexahydro-1H-cyclopenta[c]pyrrole-1-carboxylic acid (978 mg, 3.83 mmol, 1.1 eq.) in DMF (2 mL) was added o-(7-Azabenzotriazol-1-yl)-N,N,N',N'-tetramethyluronium hexafluorophosphate (1.59 g, 4.17 mmol, 1.2 eq.) and N-ethyl-N-isopropylpropan-2-amine (2.70 g, 20.8 mmol, 6.0 eq.). The mixture was stirred for 1 h at rt, and the reaction was quenched with water (50 mL). The mixture was extracted with EA (3×100 mL). The organic layers were combined, washed with brine (2×100 mL), dried over anhydrous sodium sulfate, filtered and concentrated under reduced pressure to afford the crude product. The crude product was diluted with dichloromethane (20 mL) and made into a slurry with 100~200 silicagel mesh (2 g). The slurry was loaded to a column after removing the dichloromethane. The sample was purified by column chromatography (Column size 5×24 cm, column volume: 300 mL, silicagel size (100~200 mesh) quantity: 120 g) using EA:PE (0%-100% over 30 min) as the eluent. The collected fractions: 96%-100% EA:PE fractions were chosen as pure fractions, and those fractions were combined and concentrated under reduced pressure to provide tert-butyl (1S,3aR,6aS)-1-{[(2S)-1-[(3S)-2-oxopyrrolidin-3-yl]but-3-yn-2-yl]carbamoyl}-hexahydro-1H-cyclopenta[c]pyrrole-2-carboxylate (500 mg, crude) as a light yellow oil. LC-MS (ESI, m/z): 390 [M+H]$^+$.

To a stirred mixture of tert-butyl (1S,3aR,6aS)-1-{[(2S)-1-[(3S)-2-oxopyrrolidin-3-yl]but-3-yn-2-yl]carbamoyl}-hexahydro-1H-cyclopenta[c]pyrrole-2-carboxylate (160 mg, 0.411 mmol, 1.0 eq.) in DCM (6 mL) was added trifluoroacetic acid (2 mL). The mixture was stirred for 2 h at rt, and then concentrated under reduced pressure to afford (1S,3aR,6aS)—N-[(2S)-1-[(3S)-2-oxopyrrolidin-3-yl]but-3-yn-2-yl]-octahydrocyclopenta[c]pyrrole-1-carboxamide (130 mg, crude) as a light brown oil. LC-MS (ESI, m/z): 290 [M+H]$^+$.

To a stirred mixture of (1S,3aR,6aS)—N-[(2S)-1-[(3S)-2-oxopyrrolidin-3-yl]but-3-yn-2-yl]-octahydrocyclopenta[c]pyrrole-1-carboxamide (103 mg, 0.359 mmol, 1.1 eq.), 4,7-dichloro-1H-indole-2-carboxylic acid (75.0 mg, 0.326 mmol, 1.0 eq.) and o-(7-Azabenzotriazol-1-yl)-N,N,N',N'-tetramethyluronium hexafluorophosphate (148 mg, 0.391 mmol, 1.2 eq.) in DMF (2 mL) was added N-ethyl-N-isopropylpropan-2-amine (252 mg, 1.95 mmol, 6.0 eq.). The mixture was stirred for 2 h at rt, and the reaction was quenched with water (10 mL). The mixture was extracted with EA (3×10 mL). The organic layers were combined, washed with brine (2×10 mL), dried over anhydrous sodium sulfate, filtered and concentrated under reduced pressure to afford the crude product. The crude product was purified by prep-HPLC with the following conditions (Column: XBridge Prep Phenyl OBD Column, 19*150 mm, 5 μm; Mobile Phase A: Water (0.05% FA), Mobile Phase B: ACN; Flow rate: 25 mL/min; Gradient: 35% B to 45% B in 10 min, 45% B; Wave Length: 254 nm; RT1 (min): 9) to afford (1S,3aR,6aS)-2-(4,7-dichloro-1H-indole-2-carbonyl)-N-[(2S)-1-[(3S)-2-oxopyrrolidin-3-yl]but-3-yn-2-yl]-hexahydro-1H-cyclopenta[c]pyrrole-1-carboxamide (5.6 mg, 3%) as a white solid. $^1$H NMR (400 MHz, 80° C., DMSO-d$_6$) δ 10.85-12.55 (br, 1H), 8.20-8.70 (br, 1H), 7.20-7.40 (m, 2H), 7.00-7.20 (m, 1H), 6.60-7.00 (m, 1H), 4.32-4.82 (m, 2H), 3.66-4.22 (m, 2H), 3.00-3.05 (m, 2H), 2.72 (s, 1H), 2.53-2.67 (m, 1H), 1.35-2.39 (m, 12H). LC-MS (ESI, m/z): 501 [M+H]$^+$.

Example 179

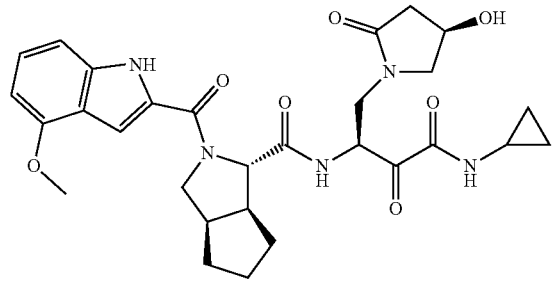

COMPOUND 1778

Compound 178 was prepared similarly as described for Compound 115 using (R)-4-(benzyloxy)dihydrofuran-2 (3H)-one in place of (S)-3-(benzyloxy)dihydrofuran-2(3H)-one. LCMS (ESI, m/z): 566 [M+H]$^+$.

(R)-4-(benzyloxy)dihydrofuran-2(3H)-one: A solution of L-carnitine (25 g, 155 mmol, 1.0 eq.) in DMF (250 mL) was heated at 150° C. for 16 h. The mixture was concentrated under reduced pressure. The residue was purified by flash chromatography on silica gel (80 g column) using a gradient of EA (70 to 100%) in PE to afford (R)-4-hydroxydihydrofuran-2(3H)-one (11.2 g, 71%) as a brown liquid. $^1$H NMR (400 MHz, DMSO-d$_6$) δ 5.43 (d, 1H), 4.41-4.44 (m, 1H), 4.30-4.33 (m, 1H), 4.08 (d, 1H), 2.77 (dd, 1H), 2.22 (d, 1H).

To a solution of (R)-4-hydroxydihydrofuran-2(3H)-one (10.0 g, 98.0 mmol, 1.0 eq.) and benzyl 2,2,2-trichloroacetimidate (27.5 mmol, 147 mmol, 1.2 eq.) in cyclohexane (80 mL) and DCM (20 mL) cooled to 0° C. was added TMSOTf (3.4 mL, 19.6 mmol, 0.2 eq.). The mixture was stirred at rt for 2 h., and then filtered. The filtrate was concentrated under reduced pressure. The residue was purified by flash chromatography on silica gel (80 g column) using a gradient of EA (10 to 30%) in PE to afford (R)-4-(benzyloxy)dihydrofuran-2(3H)-one (12.6 g, 69%) as an off-white solid. $^1$H NMR (500 MHz, CDCl$_3$) δ 7.35-7.38 (m, 2H), 7.30-7.33 (m, 3H), 4.54 (dd, 2H), 4.35-4.40 (m, 3H), 2.61-2.71 (m, 2H).

Example 180

COMPOUND 179

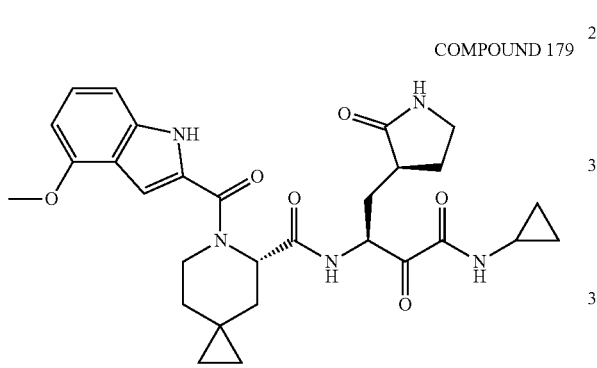

Compound 179 was prepared similarly as described for Compound 140 using 4-methoxy-1H-indole-2-carboxylic acid in place of 1H-indole-2-carboxylic acid. LCMS (ESI, m/z): 548 [M−H]$^-$.

Example 181

COMPOUND 180

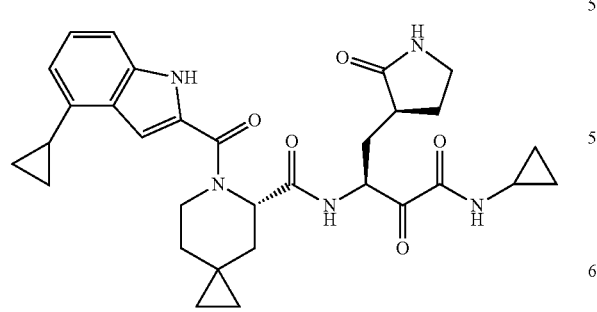

Compound 180 was prepared similarly as described for Compound 140 using 4-cyclopropyl-1H-indole-2-carboxylic acid in place of 1H-indole-2-carboxylic acid. LCMS (ESI, m/z): 560 [M+H]$^+$.

Example 182

COMPOUND 181

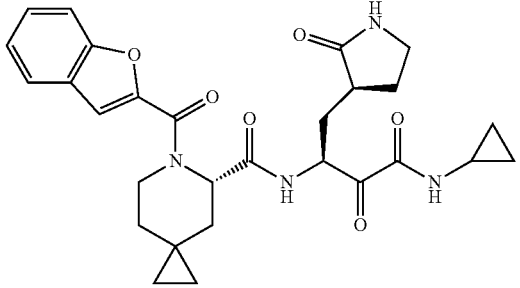

Compound 181 was prepared similarly as described for Compound 140 using benzofuran-2-carboxylic acid in place of 1H-indole-2-carboxylic acid. LCMS (ESI, m/z): 521 [M+H]$^+$.

Example 183

COMPOUND 182

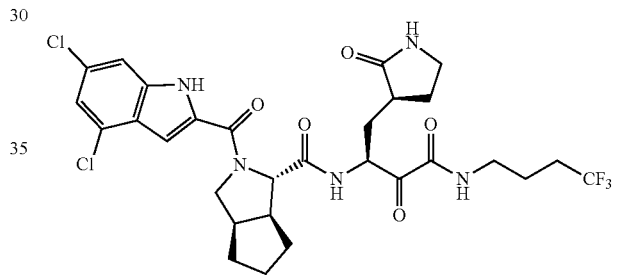

Compound 182 was prepared similarly as described for Compound 149 using 4,4,4-trifluorobutan-1-amine in place of 2-isobutoxyethan-1-amine. LCMS (ESI, m/z): 658 [M+H]$^+$.

Example 184

COMPOUND 183

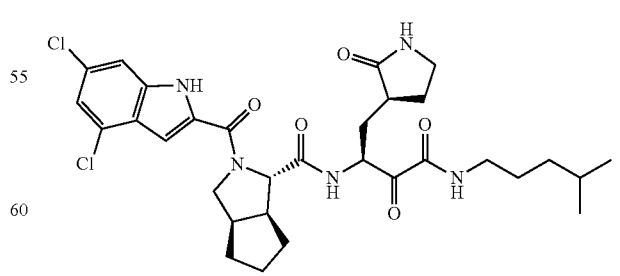

Compound 183 was prepared similarly as described for Compound 149 using 4-methylpentan-1-amine in place of 2-isobutoxyethan-1-amine. LCMS (ESI, m/z): 632 [M+H]$^+$.

Example 183

COMPOUND 184

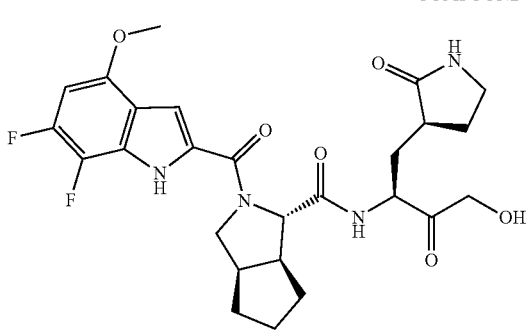

To a solution of sodium methoxide (4.18 g, 23.2 mmol, 4.0 eq., 30% in MeOH) in MeOH (5 mL) was added dropwise the mixture of 4,5-difluoro-2-methoxybenzaldehyde (1.00 g, 5.81 mmol, 1.0 eq.) and ethyl 2-azidoacetate (3.00 g, 23.2 mmol, 4.0 eq.) in MeOH (5 mL) at −10° C. The mixture was stirred for 4 h at −10° C., and the reaction was quenched with water (10 mL). The mixture was extracted with EtOAc (3×20 mL). The organic layers were combined, dried over anhydrous sodium sulfate, filtered and concentrated under reduced pressure to afford the crude product. The crude product was purified by silica gel column chromatography with EtOAc:PE (1:99) to afford methyl (2Z)-2-azido-3-(4,5-difluoro-2-methoxyphenyl)prop-2-enoate (900 mg, 57%). $^1$H NMR (300 MHz, DMSO-$d_6$) δ 8.12-8.24 (m, 1H), 7.20-7.32 (m, 1H), 7.06-7.13 (m, 1H), 3.82-3.88 (m, 6H).

A solution of methyl (2Z)-2-azido-3-(4,5-difluoro-2-methoxyphenyl)prop-2-enoate (900 mg, 3.34 mmol, 1.0 eq.) in xylene (10 mL) was stirred for 2 h at 120° C. and then concentrated under reduced pressure to afford methyl 6,7-difluoro-4-methoxy-1H-indole-2-carboxylate (700 mg, crude).

To a solution of methyl 6,7-difluoro-4-methoxy-1H-indole-2-carboxylate (300 mg, 1.24 mmol, 1.0 eq.) in THF (3 mL) was added lithium hydroxide (119 mg, 4.98 mmol, 4.0 eq., in 2 mL water) at rt. The mixture was stirred for 2 h at 60° C. and then acidified to pH=5 with hydrochloric acid (1M). The mixture was extracted with EtOAc (3×10 mL). The organic layers were combined, dried over anhydrous sodium sulfate, filtered and concentrated under reduced pressure to afford 6,7-difluoro-4-methoxy-1H-indole-2-carboxylic acid (270 mg, crude). LCMS (ESI, m/z): 226 [M−H]$^-$.

To a solution of (1S,3aR,6aS)—N-[(2S)-4-hydroxy-3-oxo-1-[(3S)-2-oxopyrrolidin-3-yl]butan-2-yl]-octahydrocyclopenta[c]pyrrole-1-carboxamide hydrochloride (102 mg, 0.283 mmol, 1.0 eq.) in DMF (1 mL) was added 6,7-difluoro-4-methoxy-1H-indole-2-carboxylic acid (77.3 mg, 0.340 mmol, 1.2 eq.), o-(7-azabenzotriazol-1-yl)-N,N,N',N'-tetramethyluronium hexafluorophosphate (141 mg, 0.369 mmol, 1.3 eq.) and N-ethyl-N-isopropylpropan-2-amine (184 mg, 1.42 mmol, 5.0 eq.) stirred at 0° C. The mixture was stirred for 1 h at rt, and the reaction was quenched with water (5 mL). The mixture was extracted with EA (3×15 mL). The organic layers were combined, washed with brine (2×20 mL), dried over anhydrous sodium sulfate, filtered and concentrated under reduced pressure to afford the crude product. The crude product was purified by prep-HPLC (Column: XSelect CSH Prep C18 OBD Column, 19*250 mm, 5 μm; Mobile Phase A: Water (0.05% FA), Mobile Phase B: ACN; Flow rate: 25 mL/min; Gradient: 30% B to 40% B in 10 min, 40% B; Wave Length: 254 nm; RT1 (min): 8.68) to provide (1S,3aR,6aS)-2-(6,7-difluoro-4-methoxy-1H-indole-2-carbonyl)-N-[(2S)-4-hydroxy-3-oxo-1-[(3S)-2-oxopyrrolidin-3-yl]butan-2-yl]-hexahydro-1H-cyclopenta[c]pyrrole-1-carboxamide (9.6 mg, 6%) as a white solid. $^1$H NMR (400 MHz, DMSO-$d_6$) δ 11.87 (br, 1H), 8.39 (br, 1H), 7.32 (s, 1H), 6.89 (s, 1H), 6.45-6.57 (m, 1H), 4.28-5.05 (m, 3H), 4.07-4.27 (m, 2H), 3.73-4.06 (m, 4H), 3.52-3.71 (m, 1H), 3.14-3.36 (m 2H), 2.52-2.82 (m, 2H), 1.40-2.40 (m, 11H). LCMS (ESI, m/z): 533 [M+H]$^+$.

Example 184

COMPOUND 185

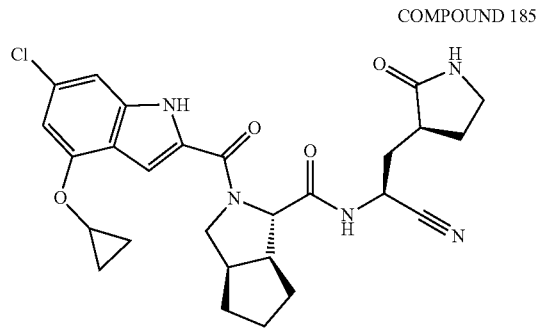 [SMILES: N#C[C@H](C[C@@H]1CCNC1=O)NC(=O)[C@@H]1[C@H]2CCC[C@H]2CN1C(=O)c1cc2c(OC3CC3)cc(Cl)cc2[nH]1]

To a solution of (2S)-2-[(1S,3aR,6aS)-octahydrocyclopenta[c]pyrrol-1-ylformamido]-3-[(3S)-2-oxopyrrolidin-3-yl]propanamide (135 mg, 0.438 mmol, 1.0 eq.) in DMF (1.5 mL) was added 6-chloro-4-cyclopropoxy-1H-indole-2-carboxylic acid (121 mg, 0.482 mmol, 1.1 eq.), o-(7-azabenzotriazol-1-yl)-N,N,N',N'-tetramethyluronium hexafluorophosphate (217 mg, 0.569 mmol, 1.3 eq.) and N-ethyl-N-isopropylpropan-2-amine (283 mg, 2.19 mmol, 5.0 eq.) stirred at 0° C. The mixture was stirred for 2 h at rt. The mixture was purified by C18 column with CH$_3$CN:Water (0.05% FA), and the fraction was concentrated under reduced pressure to provide (2S)-2-{[(1S,3aR,6aS)-2-(6-chloro-4-cyclopropoxy-1H-indole-2-carbonyl)-hexahydro-1H-cyclopenta[c]pyrrol-1-yl]formamido}-3-[(3S)-2-oxopyrrolidin-3-yl]propanamide (150 mg, 63%) as a white solid. LCMS (ESI, m/z): 542 [M+H]$^+$.

To a solution of (2S)-2-{[(1S,3aR,6aS)-2-(6-chloro-4-cyclopropoxy-1H-indole-2-carbonyl)-hexahydro-1H-cyclopenta[c]pyrrol-1-yl]formamido}-3-[(3S)-2-oxopyrrolidin-3-yl]propanamide (150 mg, 0.277 mmol, 1.0 eq.) in DMF (2 mL) was added pyridine (76.6 mg, 0.970 mmol, 3.5 eq.) and trifluoroacetic anhydride (116 mg, 0.554 mmol, 2.0 eq.). The mixture was stirred for 2 h at rt, and the reaction was quenched with water (5 mL). The mixture was extracted with EtOAc (3×15 mL). The organic layers were combined, dried over anhydrous sodium sulfate, filtered and concentrated under reduced pressure to afford the crude product. The crude product was purified by prep-HPLC (Column: XBridge Prep Phenyl OBD Column, 19*150 mm, 5 μm; Mobile Phase A: Water (0.05% FA), Mobile Phase B: ACN; Flow rate: 25 mL/min; Gradient: 40% B to 50% B in 10 min, 50% B; Wave Length: 254 nm; RT1 (min): 9) to provide (1S,3aR,6aS)-2-(6-chloro-4-cyclopropoxy-1H-indole-2-carbonyl)-N-[(1S)-1-cyano-2-[(3S)-2-oxopyrrolidin-3-yl]ethyl]-hexahydro-1H-cyclopenta[c]pyrrole-1-carboxamide (63.6 mg, 43%) as a white solid. $^1$H NMR (400 MHz, 80° C., DMSO-d$_6$) δ 11.46 (s, 1H), 8.76 (br, 1H), 7.34-7.51 (m, 1H), 7.09 (s, 1H), 6.70-6.90 (m, 2H), 4.81-4.96 (m, 1H), 4.45 (br, 1H), 3.88-4.17 (m, 2H), 3.59-3.73 (m, 1H), 3.05-3.18 (m, 2H), 2.77 (br, 1H), 2.56 (br, 1H), 1.42-2.41 (m, 11H), 0.69-0.87 (m, 4H). LCMS (ESI, m/z): 524 [M+H]$^+$.

Example 185

COMPOUND 186

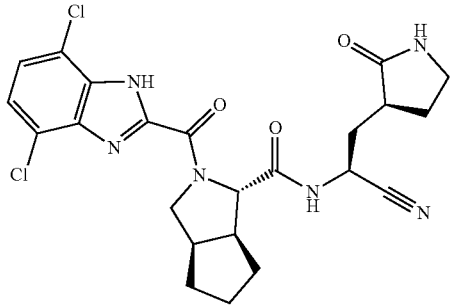

Compound 186 was prepared similarly as described for Compound 185, using 4,7-dichloro-1H-1,3-benzodiazole-2-carboxylic acid in place of 6-chloro-4-cyclopropoxy-1H-indole-2-carboxylic acid. $^1$H NMR (400 MHz, 80° C., DMSO-d$_6$) δ 13.30-14.40 (m, 1H), 8.60-9.35 (m, 1H), 7.10-7.60 (m, 3H), 4.05-5.50 (m, 3H), 3.48-3.90 (m, 1H), 3.10-3.35 (m, 2H), 2.50-2.90 (m, 2H), 1.35-2.45 (m, 11H). LC-MS (ESI, m/z): 503 [M+H]$^+$.

Example 186

COMPOUND 187

Compound 187 was prepared similarly as described for Compound 185, using 4-chloro-6-fluoro-1H-indole-2-carboxylic acid in place of 6-chloro-4-cyclopropoxy-1H-indole-2-carboxylic acid. $^1$H NMR (400 MHz, 80° C., DMSO-d$_6$) δ 11.76 (s, 1H), 8.79 (br, 1H), 7.43 (s, 1H), 7.11-7.19 (m, 1H), 7.01-7.09 (m, 1H), 6.65-7.00 (m, 1H), 4.78-5.08 (m, 1H), 3.90-4.75 (m, 2H), 3.60-3.85 (m, 1H), 3.10-3.35 (m, 2H), 2.52-2.90 (m, 2H), 2.25-2.42 (m, 1H), 1.40-2.23 (m, 10H). LC-MS (ESI, m/z): 486 [M+H]$^+$.

Example 187

COMPOUND 188

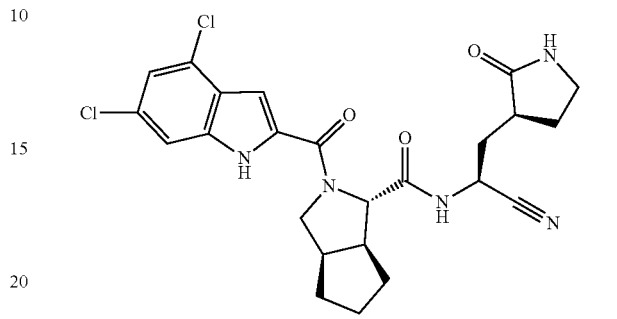

Compound 188 was prepared similarly as described for Compound 185, using 4,6-dichloro-1H-indole-2-carboxylic acid in place of 6-chloro-4-cyclopropoxy-1H-indole-2-carboxylic acid. $^1$H NMR (400 MHz, 80° C., DMSO-d$_6$) δ 11.82 (s, 1H), 8.80 (br, 1H), 7.35-7.51 (m, 2H), 7.17 (s, 1H), 6.72-7.00 (m, 1H), 4.81-4.96 (m, 1H), 4.47 (br, 1H), 4.14 (br, 1H), 3.63-3.80 (m, 1H), 3.06-3.21 (m, 2H), 2.79 (br, 1H), 2.58 (br, 1H), 1.43-2.42 (m, 11H). LCMS (ESI, m/z): 502 [M+H]$^+$.

Example 188

COMPOUND 189

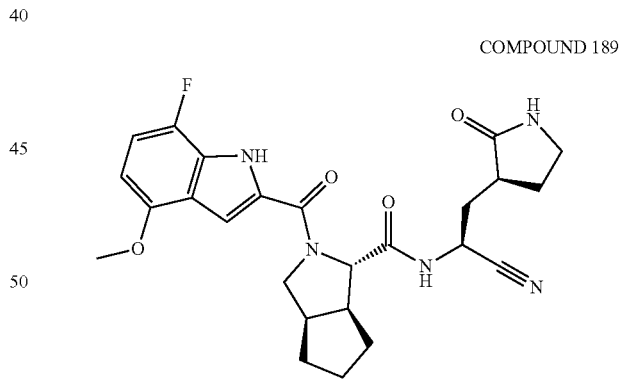

Compound 189 was prepared similarly as described for Compound 185, using 7-fluoro-4-methoxy-1H-indole-2-carboxylic acid in place of 6-chloro-4-cyclopropoxy-1H-indole-2-carboxylic acid. $^1$H NMR (400 MHz, 80° C., DMSO-d$_6$) δ 11.67 (s, 1H), 8.78 (br, 1H), 7.42 (s, 1H), 6.70-7.10 (m, 2H), 6.30-6.55 (m, 1H), 4.80-5.05 (m, 1H), 4.30-4.65 (m, 1H), 3.95-4.20 (m, 1H), 3.86 (s, 3H), 3.55-3.75 (m, 1H), 3.05-3.20 (m, 2H), 2.52-2.88 (m, 2H), 2.20-2.45 (m, 1H), 1.40-2.19 (m, 10H). LC-MS (ESI, m/z): 482 [M+H]$^+$.

Example 189

COMPOUND 190

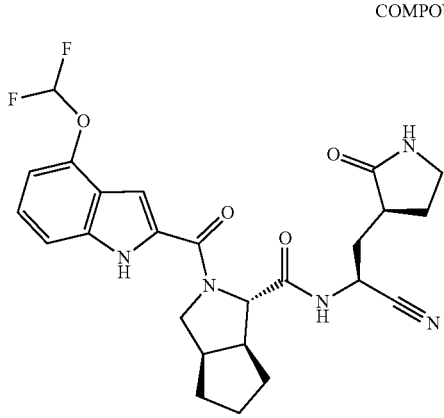

Compound 190 was prepared similarly as described for Compound 185, using 4-(difluoromethoxy)-1H-indole-2-carboxylic acid in place of 6-chloro-4-cyclopropoxy-1H-indole-2-carboxylic acid. $^1$H NMR (400 MHz, 80° C., DMSO-d$_6$) δ 11.60 (s, 1H), 8.74-8.96 (m, 1H), 7.37-7.48 (m, 1H), 7.29-7.33 (m, 1H), 7.02-7.20 (m, 2H), 6.87 (br, 1H), 6.77-6.80 (m, 1H), 4.84-4.94 (m, 1H), 4.44 (s, 1H), 4.08 (br, 1H), 3.68-3.77 (m, 1H), 3.05-3.20 (m, 2H), 2.71-2.86 (m, 1H), 2.52-2.63 (m, 1H), 1.45-2.39 (m, 11H). LC-MS (ESI, m/z): 500 [M+H]$^+$.

Example 190

COMPOUND 191

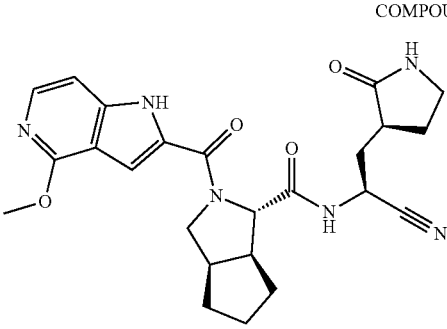

Compound 191 was prepared similarly as described for Compound 185, using 4-methoxy-1H-pyrrolo[3,2-c]pyridine-2-carboxylic acid in place of 6-chloro-4-cyclopropoxy-1H-indole-2-carboxylic acid. LC-MS (ESI, m/z): 465 [M+H]$^+$.

Example 191

COMPOUND 192

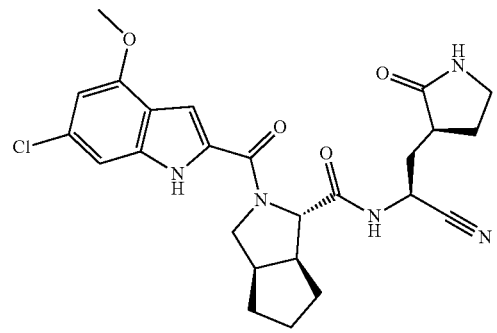

Compound 192 was prepared similarly as described for Compound 185, using 6-chloro-4-methoxy-1H-indole-2-carboxylic acid in place of 6-chloro-4-cyclopropoxy-1H-indole-2-carboxylic acid. $^1$H NMR (400 MHz, 80° C., DMSO-d$_6$) δ 11.46 (s, 1H), 8.79 (br, 1H), 7.40-7.48 (m, 1H), 7.04-7.06 (m, 1H), 6.85 (br, 1H), 6.49-6.52 (m, 1H), 4.83-4.93 (m, 1H), 4.26-4.61 (m, 1H), 3.94-4.16 (m, 1H), 3.82-3.91 (m, 3H), 3.65-3.74 (m, 1H), 3.06-3.20 (m, 2H), 2.68-2.84 (m, 1H), 2.50-2.61 (m, 1H), 1.45-2.39 (m, 11H). LC-MS (ESI, m/z): 498 [M+H]$^+$.

Example 192

COMPOUND 193

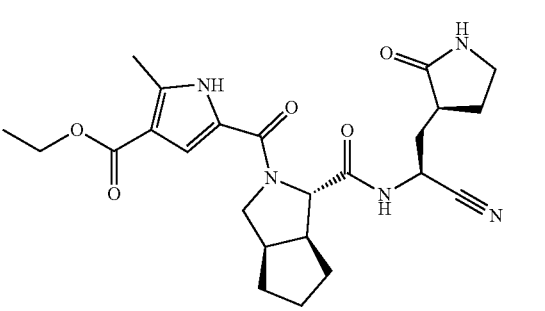

Compound 193 was prepared similarly as described for Compound 185, using 4-(ethoxycarbonyl)-5-methyl-1H-pyrrole-2-carboxylic acid in place of 6-chloro-4-cyclopropoxy-1H-indole-2-carboxylic acid. $^1$H NMR (400 MHz, 80° C., DMSO-d$_6$) δ 11.63 (s, 1H), 8.71 (s, 1H), 7.44-7.50 (m, 1H), 6.80 (s, 1H), 4.89-4.95 (m, 1H), 4.36 (s, 1H), 4.17-4.19 (m, 2H), 3.96 (s, 1H), 3.58-3.60 (m, 1H), 3.12-3.17 (m, 2H), 2.65-2.85 (m, 1H), 2.45-2.60 (m, 1H), 2.42 (s, 3H), 2.31-2.47 (m, 1H), 2.08-2.15 (m, 2H), 1.92 (s, 1H), 1.68-1.85 (m, 4H), 1.48-1.58 (m, 3H), 1.26 (t, J=7 Hz, 3H). LC-MS (ESI, m/z): 470 [M+H]$^+$.

Example 193

LC-MS Methods

| Compound No. | Rt (min) | [M + H]⁺ or [M − H]⁻ | LCMS Method |
|---|---|---|---|
| 1 | 1.343, 1.395 | [M + H]⁺ = 544 | 1 |
| 2 | 1.010, 1.078 | [M + H]⁺ = 570 | 3 |
| 3 | 1.138 | [M + H]⁺ = 532 | 7 |
| 4 | 1.373, 1.447 | [M + H]⁺ = 570 | 7 |
| 5 | 1.419 | [M + H]⁺ = 622 | 7 |
| 6 | 1.425 | [M + H]⁺ = 636 | 7 |
| 7 | 1.459 | [M + H]⁺ = 606 | 7 |
| 8 | 1.242 | [M + H]⁺ = 556 | 7 |
| 9 | 2.609 | [M + H]⁺ = 556 | 13 |
| 10 | 1.383 | [M + H]⁺ = 602 | 7 |
| 11 | 1.313 | [M + H]⁺ = 558 | 7 |
| 12 | 1.120 | [M + H]⁺ = 560 | 7 |
| 13 | 1.029 | [M + H]⁺ = 437 | 7 |
| 14a | 1.032 | [M + H]⁺ = 467 | 7 |
| 14b | 1.130 | [M + H]⁺ = 467 | 7 |
| 15 | 1.090 | [M + H]⁺ = 451 | 7 |
| 16 | 1.332 | [M + H]⁺ = 600 | 7 |
| 17 | 1.400 | [M + H]⁺ = 584 | 7 |
| 18 | 1.282 | [M + H]⁺ = 536 | 7 |
| 19 | 1.359 | [M + H]⁺ = 598 | 7 |
| 20 | 1.635 | [M + H]⁺ = 612 | 7 |
| 21 | 1.390 | [M + H]⁺ = 570 | 7 |
| 22 | 0.946 | [M + H]⁺ = 592 | 16 |
| 23 | 2.718 | [M + H]⁺ = 592 | 13 |
| 24 | 1.015 | [M + H]⁺ = 570 | 16 |
| 25 | 0.912 | [M + H]⁺ = 544 | 16 |
| 26 | 1.000, 1.0347 | [M + H]⁺ = 572 | 16 |
| 27A | 0.919 | [M + H]+ = 587 | 18 |
| 27 | 1.233 | [M + H]⁺ = 497 | 19 |
| 28 | 0.929 | [M + H]⁺ = 558 | 16 |
| 29 | 0.742 | [M + H]⁺ = 503 | 16 |
| 30 | 1.403 & 1.501 | [M + H]⁺ = 556 | 20 |
| 31 | 0.719 | [M + H]⁺ = 483 | 16 |
| 32 | 1.331 | [M + H]⁺ = 533 | 21 |
| 33 | 0.944, 0.999 | [M + H]⁺ = 636 | 16 |
| 34 | 0.862, 0.927 | [M + H]⁺ = 588 | 16 |
| 35 | 0.854 | [M + H]⁺ = 571 | 16 |
| 36 | 0.856 | [M + H]⁺ = 601 | 16 |
| 37 | 0.649 | [M + H]⁺ = 498 | 16 |
| 38 | 2.536, 2.635 | [M + H]⁺ = 586 | 13 |
| 39 | 0.831 | [M + H]⁺ = 519 | 18 |
| 40 | 0.941 | [M + H]⁺ = 570 | 16 |
| 41 | 0.782 | [M + H]⁺ = 511 | 18 |
| 42 | 0.897 | [M + H]⁺ = 497 | 23 |
| 43 | 4.568 | [M + H]⁺ = 497 | 24 |
| 44 | 1.331 | [M + H]⁺ = 511 | 26 |
| 45 | 1.299 | [M + H]⁺ = 539 | 25 |
| 45A | 1.575 | [M + H]⁺ = 629 | 27 |
| 46 | 0.869, 0.941 | [M + H]⁺ = 546 | 23 |
| 47A | 1.530 | [M + H]⁺ = 623 | 27 |
| 47 | 0.719 | [M + H]⁺ = 533 | 11 |
| 48 | 1.144 | [M + H]⁺ = 572 | 23 |
| 49 | 2.578 | [M + H]⁺ = 511 | 13 |
| 49A | 0.938 | [M + H]⁺ = 601 | 18 |
| 50 | 0.938 | [M + H]+ = 600 | 29 |
| 51 | 0.833 | [M + H]+ = 510 | 30 |
| 52 | 1.359, 1.498 | [M + H]+ = 550 | 31 |
| 54 | 1.344, 1.418 | [M + H]+ = 533 | 31 |
| 55 | 0.929, 0.983 | [M + H]⁺ = 564 | 30 |
| 56 | 0.818, 0.888 | [M + H]⁺ = 510 | 30 |
| 57 | 0.960, 1.014 | [M + H]⁺ = 564 | 30 |
| 59_1 | 2.466 | [M + H]⁺ = 525 | A |
| 59_2 | 2.499 | [M + H]⁺ = 525 | A |
| 59A_1 | 2.867 | [M + H]⁺ = 615 | A |
| 59A_2 | 2.900 | [M + H]⁺ = 615 | A |
| 60 | 0.935 | [M + H]⁺ = 501 | 30 |
| 60A | 0.953 | [M + H]⁺ = 591 | 29 |
| 61 | 0.643 | [M + H]⁺ = 576 | 29 |
| 62 | 2.189, 2.308, 2.348 | [M + H]⁺ = 511 | 28 |
| 63 | 1.446 | [M + H]⁺ = 535 | 26 |
| 64 | 0.877 | [M + H]⁺ = 551 | 29 |
| 65 | 0.747 | [M + H]⁺ = 515 | 29 |
| 66 | 1.227 | [M + H]⁺ = 492 | 34 |
| 66A | 0.883 | [M + H]⁺ = 582 | 29 |
| 67 | 0.531 | [M + H]⁺ = 498 | 29 |
| 68 | 1.386 | [M + H]⁺ = 531 | 19 |
| 69_A | 1.306, 1.333 | [M + H]⁺ = 537 | 35 |
| 69_B | 1.259, 1.285 | [M + H]⁺ = 537 | 36 |
| 70_1 | 1.311 | [M + H]⁺ = 525 | 35 |
| 70_2 | 0.821 | [M + H]⁺ = 525 | 18 |
| 70A_1 | 1.138 | [M + H]⁺ = 615 | 37 |
| 70A_2 | 1.004 | [M + H]⁺ = 615 | 18 |
| 71 | 0.790 | [M + H]⁺ = 511 | 18 |
| 72 | 0.743 | [M + H]⁺ = 514 | 29 |
| 73_1 | 2.413 | [M + H]⁺ = 519 | A |
| 73_2 | 2.502 | [M + H]⁺ = 519 | A |
| 74 | 0.911 | [M + H]⁺ = 533 | 30 |
| 75 | 1.116, 1.140 | [M + H]⁺ = 584 | 30 |
| 76 | 0.594 | [M + H]⁺ = 484 | 30 |
| 77 | 0.547 | [M + H]⁺ = 498 | 29 |
| 78 | 1.097 | [M + H]⁺ = 468 | 38 |
| 79 | 0.740 | [M + H]⁺ = 493 | 11 |
| 80 | 1.196 | [M + H]⁺ = 473 | 40 |
| 81 | 0.685 | [M + H]⁺ = 527 | 29 |
| 82 | 0.695 | [M + H]⁺ = 557 | 29 |
| 83 | 0.744 | [M + H]⁺ = 471 | 29 |
| 84 | 1.251 | [M + H]⁺ = 521 | 31 |
| 85 | 0.690 | [M + H]⁺ = 503 | 29 |
| 86 | 0.961 | [M + H]⁺ = 459 | 31 |
| 87 | 1.424 | [M + H]⁺ = 533 | 42 |
| 88 | 0.801 | [M + H]⁺ = 531 | 41 |
| 89 | 0.748 | [M + H]⁺ = 531 | 11 |
| 90 | 0.827 | [M + H]⁺ = 519 | 41 |
| 91 | 0.879 | [M + H]⁺ = 535 | 41 |
| 92 | 0.991 | [M + H]⁺ = 583 | 30 |
| 93 | 0.789 | [M + H]⁺ = 498 | 30 |
| 94 | 0.706 | [M + H]⁺ = 498 | 29 |
| 95 | 1.011 | [M + H]⁺ = 578 | 30 |
| 96 | 2.246 | [M + H]⁺ = 539 | B |
| 97 | 2.083 | [M + H]⁺ = 572 | B |
| 98 | 2.123 | [M + H]⁺ = 548 | B |
| 99 | 2.270 | [M + H]⁺ = 609 | B |
| 100 | 2.103 | [M + H]⁺ = 568 | B |
| 101 | 2.291 | [M + H]⁺ = 644 | B |
| 102 | 2.250 | [M + H]⁺ = 572 | B |
| 103 | 2.084 | [M + H]⁺ = 580 | B |
| 104 | 2.209 | [M + H]⁺ = 594 | B |
| 105 | 2.174 | [M + H]⁺ = 580 | B |
| 106 | 2.111 | [M + H]⁺ = 519 | B |
| 107 | 2.016 | [M + H]⁺ = 554 | B |
| 108 | 1.274 | [M + H]⁺ = 509 | 31 |
| 109A | 3.60 | [M + H]⁺ = 614 | C |
| 109B | 3.34 | [M + H]⁺ = 614 | C |
| 110 | 2.65, 2.89 | [M + H]⁺ = 538 | C |
| 111 | 2.118 | [M + H]⁺ = 550 | B |
| 112 | 2.111 | [M + H]⁺ = 550 | B |
| 113A | 2.206 | [M + H]⁺ = 550 | B |
| 113B | 2.218 | [M + H]⁺ = 550 | B |
| 114 | 2.243 | [M + H]⁺ = 592 | B |
| 115 | 2.144 | [M + H]⁺ = 566 | B |
| 116A | 1.166 | [M + H]⁺ = 614 | 45 |
| 116B | 1.255 | [M + H]⁺ = 614 | 45 |
| 117 | 1.042 | [M + H]⁺ = 569 | 30 |
| 118 | 2.190 | [M + H]+ = 565 | B |
| 119 | 2.104 | [M + H]⁺ = 549 | B |
| 120 | 1.329 | [M + H]⁺ = 577 | 45 |
| 121 | 1.156 | [M + H]⁺ = 533 | 45 |
| 122 | 1.1 | [M + H]⁺ = 553 | 45 |
| 123 | 1.165 | [M + H]⁺ = 559 | 30 |
| 124 | 1.164 | [M + H]⁺ = 575 | 47 |
| 125 | 1.569 | [M + H]⁺ = 605 | 48 |
| 126 | 1.087 | [M + H]⁺ = 567 | 48 |
| 127 | 1.186 | [M + H]⁺ = 535 | 23 |
| 128 | 1.321 | [M + H]⁺ = 607 | 48 |
| 129 | 1.351 | [M + H]⁺ = 593 | 48 |
| 130 | 1.346 | [M + H]⁺ = 607 | 48 |
| 131 | 2.148 | [M + H]⁺ = 562 | B |
| 132 | 1.465, 1.508 | [M + H]+ = 619 | 49 |

-continued

| Compound No. | Rt (min) | [M + H]⁺ or [M − H]⁻ | LCMS Method |
|---|---|---|---|
| 133 | 0.867 | [M + H]+ = 573 | 41 |
| 134 | 2.238 | [M + H]⁺ = 630 | B |
| 135 | 1.518, 1.572 | [M + H]+ = 561 | 27 |
| 136 | 1.454, 4.507 | [M + H]+ = 559 | 27 |
| 137 | 1.326 | [M + H]+ = 593 | 48 |
| 138 | 1.133 | [M + H]+ = 557 | 48 |
| 139 | 0.874 | [M + H]+ = 536 | 23 |
| 140 | 2.128 | [M − H]⁻ = 518 | B |
| 141 | 2.320 | [M − H]⁻ = 586 | B |
| 142 | 0.894, 1.002 | [M + H]+ = 503 | 50 |
| 143 | 1.001 | [M + H]+ = 537 | 48 |
| 144 | 0.903 | [M + H]+ = 493 | 48 |
| 145 | 2.191 | [M − H]⁻ = 552 | B |
| 146 | 2.181 | [M − H]⁻ = 532 | B |
| 147 | 2.143 | [M + H]⁺ = 538 | B |
| 148 | 2.269 | [M + H]⁺ = 588 | B |
| 149 | 2.406 | [M + H]⁺ = 648 | B |
| 150 | 0.612 | [M + H]+ = 545 | 11 |
| 151 | 0.847 | [M + H]+ = 515 | 30 |
| 152 | 0.827 | [M + H]+ = 531 | 41 |
| 153 | 1.219 | [M + H]+ = 496 | 31 |
| 154 | 0.666 | [M − H]- = 511 | 45 |
| 155 | 0.735 | [M + H]+ = 561 | 41 |
| 156 | 0.863 | [M + H]+ = 535 | 41 |
| 157 | 0.769, 0.778 | [M + H]+ = 483 | 41 |
| 158 | 0.996 | [M + H]+ = 565 | 30 |
| 159 | 0.657 | [M + H]+ = 507 | 30 |
| 160 | 1.042 | [M + H]+ = 553 | 30 |
| 161 | 1.059 | [M + H]+ = 569 | 45 |
| 162 | 1.117 | [M + H]+ = 553 | 48 |
| 163 | 1.046 | [M + H]+ = 565 | 48 |
| 164 | 2.124 | [M − H]⁻ = 536 | B |
| 165 | 2.148 | [M + H]⁺ = 537 | B |
| 166 | 2.400 | [M + H]⁺ = 660 | B |
| 167 | 1.227 | [M + H]+ = 502 | 23 |
| 168 | 1.549 | [M + H]+ = 577 | 51 |
| 169 | 2.180 | [M + H]⁺ = 534 | B |
| 170 | 2.249 | [M + H]⁺ = 588 | B |
| 171 | 2.183 | [M + H]⁺ = 550 | B |
| 172 | 2.251 | [M + H]⁺ = 534 | B |
| 173 | 2.366 | [M + H]⁺ = 634 | B |
| 174 | 2.582 | [M + H]⁺ = 674 | B |
| 175 | 1.391 | [M + H]+ = 536 | 48 |
| 176 | 1.069 | [M + H]+ = 531 | 23 |
| 177 | 1.235 | [M + H]+ = 501 | 23 |
| 178 | 2.107 | [M + H]⁺ = 566 | B |
| 179 | 2.108 | [M − H]⁻ = 548 | B |
| 180 | 2.286 | [M + H]⁺ = 560 | B |
| 181 | 2.170 | [M + H]⁺ = 521 | B |
| 182 | 2.479 | [M + H]⁺ = 658 | B |
| 183 | 2.584 | [M + H]⁺ = 632 | B |
| 184 | 1.039 | [M + H]+ = 533 | 23 |
| 185 | 0.825 | [M + H]+ = 524 | 52 |
| 186 | 1.061, 1.117 | [M + H]+ = 503 | 47 |
| 187 | 0.784 | [M + H]+ = 486 | 52 |
| 188 | 1.365 | [M + H]+ = 502 | 48 |
| 189 | 0.804 | [M + H]+ = 482 | 41 |
| 190 | 1.157 | [M + H]+ = 500 | 23 |
| 191 | 1.027 | [M + H]+ = 465 | 47 |
| 192 | 1.174 | [M + H]+ = 498 | 48 |
| 193 | 0.754 | [M + H]+ = 470 | 41 |

Final compounds can be obtained in some cases as a mixture with a corresponding stereoisomer. Retention times of the main isomers are depicted in the table above.

Description of LC-MS Methods

| LC Method | Instrument | Column | Mobile Phase | Gradient | Flow | Col T | Run Time |
|---|---|---|---|---|---|---|---|
| 1 | Shimadzu LCMS-2020 | Titank C18 (1.8 μm, 2.1*30 mm) | A: Water/ 0.04% NH₄OH; B: Acetonitrile | From 90% A to 5% A in 1.39 min, held for 0.5 min, to 90% A in 0.02 min, held for 0.08 min | 0.8 mL/min | 40 | 2 min |
| 3 | Shimadzu LCMS-2020 | Titank C18 (1.8 μm, 2.1*30 mm) | A: water/ 0.04% NH₄OH; B: Acetonitrile | From 70% A to 5% A in 1.39 min, held for 0.5 min, to 90% A in 0.02 min, held for 0.08 min | 0.8 mL/min | 40 | 2 min |
| 7 | Shimadzu LCMS-2020 | kinetex EVO-C18 (2.6 μm 3.0*50 mm) | A: Water/ 6.5 mM NH₄HCO₃ + Ammonia Hydroxide (pH = 10) B: Acetonitrile | From 90% A to 5% A in 1.99 min, held for 0.7 min, to 90% A in 0.05 min, held for 0.25 min | 1.2 mL/min | 40 | 3 min |
| 11 | Shimadzu LCMS-2020 | HALO 2.0 μm C18 90A (2.0 μm, 3.0*30 mm) | A: Water/ 0.1% TFA B: Acetonitrile/ 0.1% TFA | From 95% A to 0% A in 1.09 min, held for 0.6 min, to 95% A in 0.05 min, held for 0.10 min | 1.5 ml/min | 40 | 1.85 min |
| 13 | Shimadzu LC20AD | XSelect CSH C18 (2.5 μm, 3.0*50 mm) | A: 5 mM Ammonium acetate B: MeOH | From 95% A to 5% A in 2.99 min, held for 1.5 min, to 95% in 0.2 min held for 0.3 min | 1.0 mL/min | 70 | 5 min |

-continued

| LC Method | Instrument | Column | Mobile Phase | Gradient | Flow | Col T | Run Time |
|---|---|---|---|---|---|---|---|
| 16 | Shimadzu LCMS-2020 | kinetex EVO-C18 (2.6 μm, 3.0*30 mm) | A: Water/ 6.5 mM NH₄HCO₃ + Ammonia Hydroxide (pH = 10) B: Acetonitrile | From 90% A to 5% A in 1.19 min, held for 0.6 min, to 90% A in 0.02 min, held for 0.18 min | 1.2 mL/Min | 40 | 2 min |
| 18 | Shimadzu LCMS-2020 | HALO 90 C18 (2.0 μm, 3.0*30 mm) | A: Water + 0.05% TFA B: ACN + 0.05% TFA | From 95% A to 0% A in 1.19 min, held for 0.5 min, to 95% A in 0.05 min, held for 0.25 min | 1.5 mL/min | 40 | 2 min |
| 19 | Shimadzu LCMS-2020 | HALO 90A C18 (2.0 μm, 3.0*30 mm) | A: Water + 0.05% TFA B: ACN + 0.05% TFA | From 95% A to 45% A in 1.69 min, to 5% A in 0.6 min, held for 0.5 min, to 95% A in 0.03 min, held for 0.17 min | 1.5 mL/Min | 40 | 3 min |
| 20 | Shimadzu LCMS-2020 | kinetex EVO-C18 (2.6 μm, 3.0*30 mm) | A: Water/ 6.5 mM NH₄HCO₃ + Ammonia Hydroxide (pH = 10) B: Acetonitrile | From 90% A to 40% A in 1.69 min, to 5% A in 0.6 min, held for 0.5 min, to 90% A in 0.03 min, held for 0.17 min | 1.2 mL/min | 40 | 3 min |
| 21 | Shimadzu LCMS-2020 | Poroshell HPH-C18 (2.7 μm, 3.0*50 mm) | A: Water- 5 mM NH₄HCO₃ B: Acetonitrile | From 90% A to 5% A in 1.99 min, held for 0.7 min, to 90% in 0.05 min, held for 0.1 min | 1.2 mL/min | 40 | 2.85 min |
| 23 | Shimadzu LCMS-2020 | Shim-pack Scepter SP-C18 (3 μm, 3.0*33 mm) | A: Water/ 6.5 mM NH₄HCO₃ + Ammonia Hydroxide (pH = 10) B: Acetonitrile | From 90% A to 5% A in 1.19 min, held for 0.6 min, to 90% A in 0.02 min, held for 0.18 min | 1.2 mL/min | 40 | 2 min |
| 24 | Shimadzu LC20AD | XSelect HSS T3 (2.5 μm, 4.6*100 mm) | A: Water + 0.05% TFA B: ACN + 0.05% TFA | From 90% A to 5% A in 7.99 min, held for 2 min, to 90% A in 0.5 min, held for 3 min | 1.2 mL/min | 40 | 13.5 min |
| 25 | Shimadzu LCMS-2020 | HALO 2.0 μm C18 90A (2.0 μm, 3.0*30 mm) | A: Water/ 0.1% TFA B: ACN/ 0.1% TFA | From 95% A to 45% A in 1.69 min, to 0% A in 0.6 min, held for 0.5 min, to 95% A in 0.03 min, held for 0.17 min | 1.5 mL/min | 40 | 3 min |
| 26 | Shimadzu LCMS-2020 | HALO 90 C18 (2.0 μm, 3.0*30 mm) | A: Water/ 0.05% TFA B: Acetonitrile/ 0.05% TFA | From 95% A to 40% A in 1.69 min, to 0% A in 0.6 min, held for 0.5 min, to 95% A in 0.03 min, held for 0.17 min | 1.5 mL/min | 40 | 3 min |
| 27 | Shimadzu LCMS-2020 | HALO 2.0 μm C18 90A (2.0 μm, 3.0*30 mm) | A: Water/ 0.1% TFA B: ACN/ 0.1% TFA | From 95% A to 35% A in 1.69 min, to 0% A in 0.6 min, held for 0.5 min, to 95% A in 0.03 min, held for 0.17 min | 1.5 mL/min | 40 | 3 min |

| LC Method | Instrument | Column | Mobile Phase | Gradient | Flow | Col T | Run Time |
|---|---|---|---|---|---|---|---|
| 28 | Shimadzu LCMS-2020 | Poroshell HPH-C18 (2.7 μm, 3.0*50 mm) | A: Water-5 mM NH$_4$HCO$_3$ B: Acetonitrile | From 90% A to 40% A in 2.99 min, to 5% A in 0.3 min, held for 0.45 min, to 90% in 0.05 min, held for 0.2 min | 1.2 mL/min | 40 | 4 min |
| 29 | Shimadzu LCMS-2020 | HALO 90A C18 (2.0 μm, 3.0*30 mm) | A: Water + 0.05% TFA B: ACN + 0.05% TFA | From 95% A to 0% A in 1.19 min, held for 0.5 min, to 95% A in 0.05 min, held for 0.25 min | 1.5 mL/Min | 40 | 2 min |
| 30 | Shimadzu LCMS-2020 | L-column3 C18 (2.0 μm, 3.0*30 mm) | A: Water/ 6.5 mM NH$_4$HCO$_3$+ Ammonia Hydroxide (pH = 10) B: Acetonitrile | From 90% A to 5% A in 1.19 min, held for 0.6 min, to 90% A in 0.02 min, held for 0.18 min | 1.2 mL/min | 40 | 2 min |
| 31 | Shimadzu LCMS-2020 | L-column3 C18 (2.0 μm, 3.0*30 mm) | A: Water/ 6.5 mM NH$_4$HCO$_3$+ Ammonia Hydroxide (pH = 10) B: Acetonitrile | From 90% A to 40% A in 1.69 min, to 5% A in 0.6 min, held for 0.5 min, to 90% A in 0.03 min, held for 0.17 min | 1.2 mL/min | 40 | 3 min |
| 34 | Shimadzu LCMS-2020 | Shim-pack Velox SP-C18 (2.7 μm, 3.0*30 mm) | A: Water + 0.05% TFA B: ACN + 0.05% TFA | From 95% A to 50% A in 1.69 min, to 0% A in 0.6 min, held for 0.5 min, to 95% A in 0.03 min, held for 0.17 min | 1.5 mL/min | 40 | 3 min |
| 35 | Shimadzu LCMS-2020 | HALO 2.0 μm C18 90A (2.0 μm, 3.0*30 mm) | A: Water/ 0.1% TFA B: ACN/ 0.1% TFA | From 95% A to 40% A in 1.69 min, to 0% A in 0.6 min, held for 0.5 min, to 95% A in 0.03 min, held for 0.17 min | 1.5 mL/min | 40 | 3 min |
| 36 | Shimadzu LCMS-2020 | HALO 90 C18 (2.0 μm, 3.0*30 mm) | A: Water + 0.05% TFA B: ACN + 0.05% TFA | From 95% A to 30% A in 1.69 min, to 0% A in 0.6 min, held for 0.5 min, to 95% A in 0.03 min, held for 0.17 min | 1.5 mL/min | 40 | 3 min |
| 37 | Shimadzu LCMS-2020 | HALO 2.0 μm C18 90A (2.0 μm, 3.0*30 mm) | A: Water/ 0.1% TFA B: ACN/ 0.1% TFA | From 70% A to 30% A in 1.69 min, to 0% A in 0.6 min, held for 0.5 min, to 95% A in 0.03 min, held for 0.17 min | 1.5 mL/min | 40 | 3 min |
| 38 | Shimadzu LCMS-2020 | L-column3 C18 (2.0 μm, 3.0*30 mm) | A: Water/ 6.5 mM NH$_4$HCO$_3$ + Ammonia Hydroxide (pH = 10) B: Acetonitrile | From 90% A to 50% A in 1.69 min, to 5% A in 0.6 min, held for 0.5 min, to 90% A in 0.03 min, held for 0.17 min | 1.2 mL/min | 40 | 3 min |

-continued

| LC Method | Instrument | Column | Mobile Phase | Gradient | Flow | Col T | Run Time |
|---|---|---|---|---|---|---|---|
| 40 | Shimadzu LCMS-2020 | L-column3 C18 (2.0 μm, 3.0*30 mm) | A: Water/ 6.5 mM NH$_4$HCO$_3$ + Ammonia Hydroxide (pH = 10) B: Acetonitrile | From 90% A to 30% A in 1.69 min, to 5% A in 0.6 min, held for 0.5 min, to 90% A in 0.03 min, held for 0.17 min | 1.2 mL/min | 40 | 3 min |
| 41 | Shimadzu LCMS-2020 | HALO C18 (2.0 μm, 3.0*30 mm) | A: Water + 0.05% TFA B: ACN + 0.05% TFA | From 95% A to 0% A in 1.19 min, held for 0.5 min, to 95% A in 0.05 min, held for 0.25 min | 1.5 mL/min | 40 | 2 min |
| 42 | Shimadzu LCMS-2020 | HALO C18 (2.0 μm, 3.0*30 mm) | A: Water + 0.05% TFA B: ACN + 0.05% TFA | From 95% A to 45% A in 1.69 min, to 5% A in 0.6 min, held for 0.5 min, to 95% A in 0.03 min, held for 0.17 min | 1.5 mL/min | 40 | 3 min |
| 45 | Shimadzu LCMS-2020 | L-column3 C18 (2.0 μm, 3.0*30 mm) | A: Water/ 6.5 mM NH4HCO3 + Ammonia Hydroxide (pH = 10) B: Acetonitrile | From 70% A to 5% A in 1.99 min, held for 0.7 min, to 90% A in 0.05 min, held for 0.25 min | 1.2 ml/min | 40 | 3 min |
| 47 | Shimadzu LCMS-2020 | Shim-pack Scepter SP-C18 (3 μm, 3.0*33 mm) | A: Water/ 6.5 mM NH$_4$HCO$_3$ + Ammonia Hydroxide (pH = 10) B: Acetonitrile | From 80% A to 5% A in 1.99 min, held for 0.7 min, to 90% A in 0.05 min, held for 0.25 min | 1.2 mL/min | 40 | 3 min |
| 48 | Shimadzu LCMS-2020 | Shim-pack Scepter SP-C18 (3 μm, 3.0*33 mm) | A: Water/ 6.5 mM NH$_4$HCO$_3$ + Ammonia Hydroxide (pH = 10) B: Acetonitrile | From 70% A to 5% A in 1.99 min, held for 0.7 min, to 90% A in 0.05 min, held for 0.25 min | 1.2 mL/min | 40 | 3 min |
| 49 | Shimadzu LCMS-2020 | Shim-pack Scepter SP-C18 (3 μm, 3.0*33 mm) | A: Water/ 6.5 mM NH$_4$HCO$_3$ + Ammonia Hydroxide (pH = 10) B: Acetonitrile | From 60% A to 5% A in 1.99 min, held for 0.7 min, to 90% A in 0.05 min, held for 0.25 min | 1.2 mL/min | 40 | 3 min |
| 50 | Shimadzu LCMS-2020 | Shim-pack Scepter SP-C18 (3 μm, 3.0*33 mm) | A: Water/ 5 mM NH$_4$HCO$_3$ B: Acetonitrile | From 90% A to 5% A in 1.19 min, held for 0.6 min, to 90% A in 0.02 min, held for 0.18 min | 1.5 mL/min | 40 | 2 min |
| 51 | Shimadzu LCMS-2020 | HALO C18 (2.0 μm, 3.0*30 mm) | A: Water + 0.05% TFA B: ACN + 0.05% TFA | From 95% A to 30% A in 1.69 min, to 5% A in 0.6 min, held for 0.5 min, to 95% A in 0.03 min, held for 0.17 min | 1.5 ml/min | 40 | 3 min |
| 52 | Shimadzu LCMS-2020 | HALO C18 (2.7 μm, 3.0*50 mm) | A: Water + 0.05% TFA B: ACN + 0.05% TFA | From 95% A to 0% A in 1.09 min, held for 0.6 min, to 95% A in 0.05 min, held for 0.25 min | 1.5 mL/min | 40 | 2 min |

-continued

| LC Method | Instrument | Column | Mobile Phase | Gradient | Flow | Col T | Run Time |
|---|---|---|---|---|---|---|---|
| A | Shimadzu LCMS-2020 | Cortex C18; 2.7 μm, 3.0*75 mm | A: water/ 0.05% TFA; B: Acetonitrile/ 0.05% TFA | From 5 to 95% B in 3.5 min | 0.1 mL/min | 40 | 4 min |
| B | Agilent 6150 SQ Mass Spectrometer coupled to an Agilent 1290 Infinity LC System | Acquity UPLC BEH C18 (1.7 μm, 2.1*50 mm) | A: 0.1% FA in Water, B: 0.1% FA in Acetonitrile | 98% A held for 0.2 min, to 2% A in 1.3 min, held for 1.8 min, to 98% A in 0.1 min, held for 0.4 min | 0.6 mL/min | 70 | 3.8 min |
| C | Waters Acquity UPLC H-Class | Acquity UPLC BEH C18 (1.7 μm, 2.1*50 mm) | A: 10 mM NH$_4$HCO$_3$ in H$_2$O (pH 7)/ CH$_3$CN (95/5) B: CH$_3$CN | From 84% A to 42% A in 3.4 min, to 10% A in 0.6 min, held for 1 min | 0.5 mL/min | 60 | 5.0 min |

Example 194

Other compounds that can be prepared applying similar procedures as those described herein

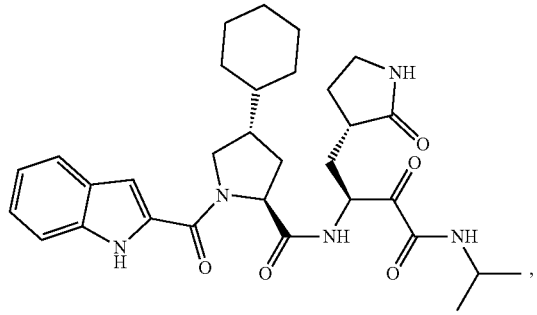

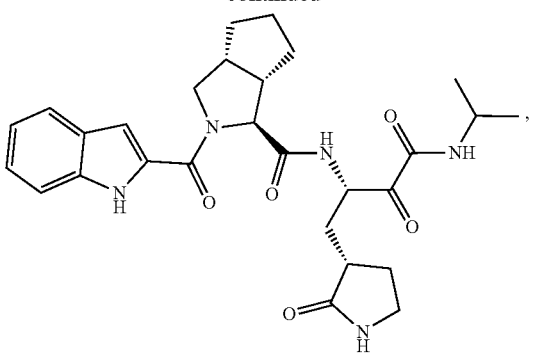

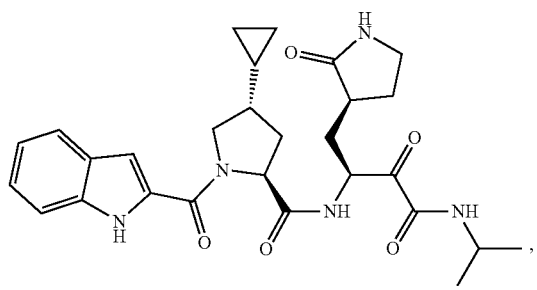

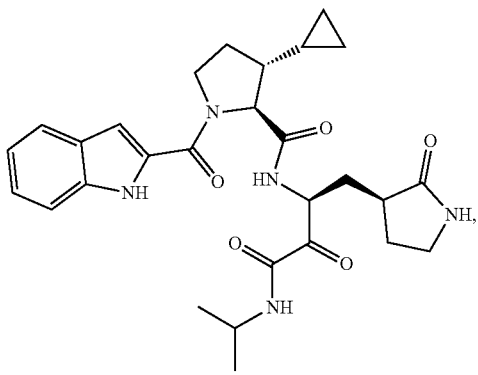

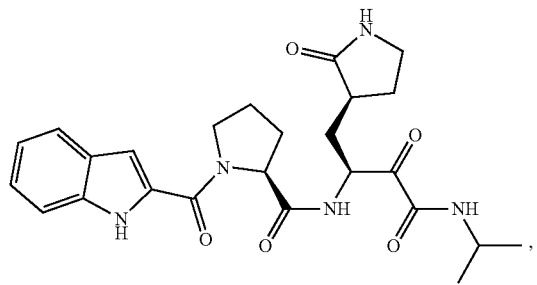

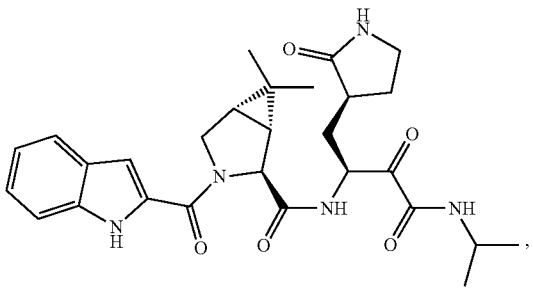

457
-continued
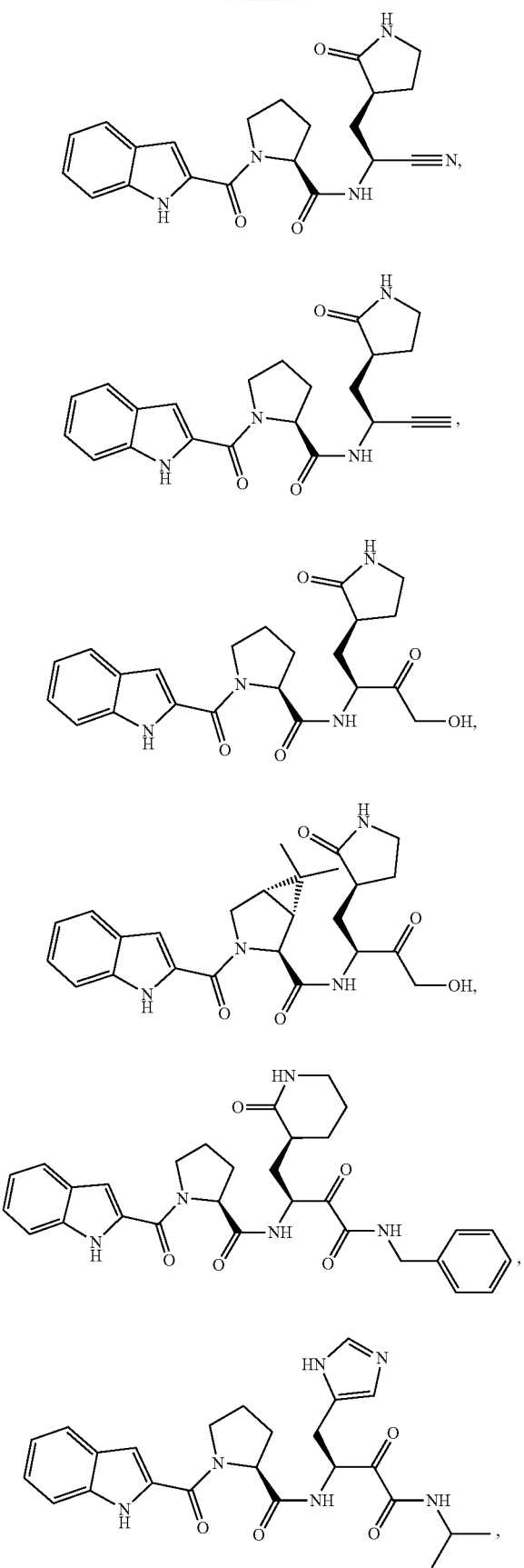
458
-continued
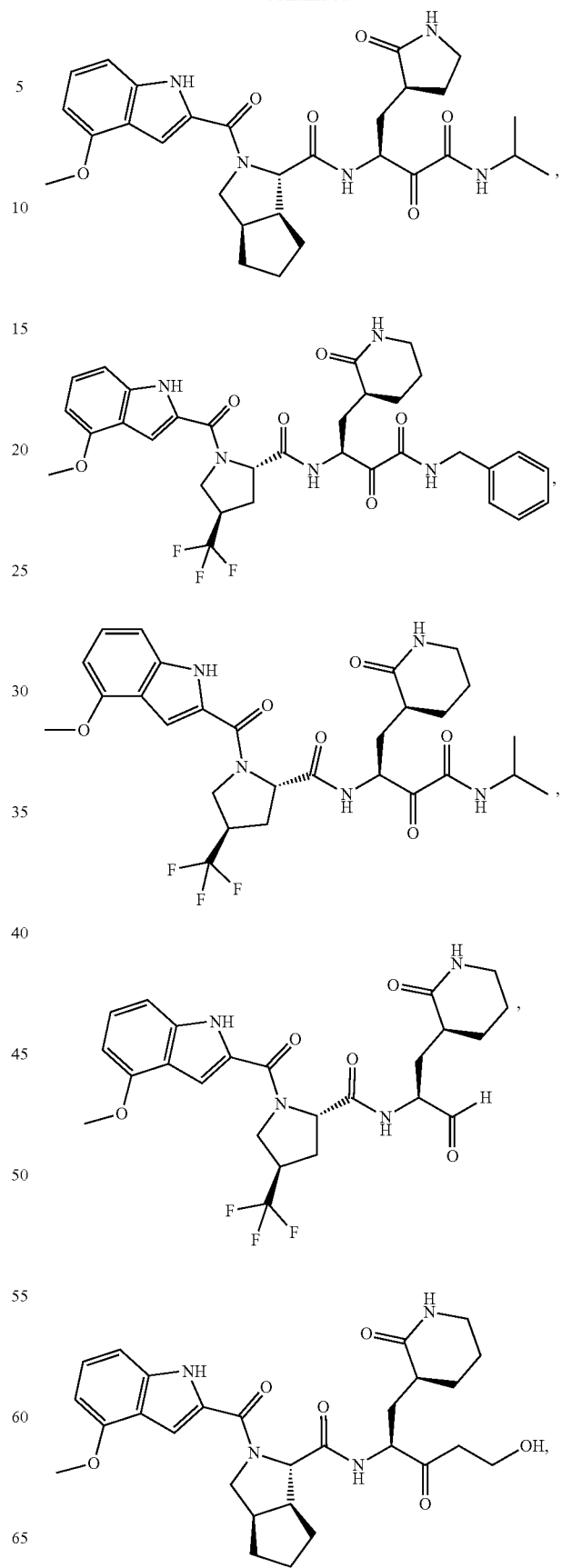

459
-continued
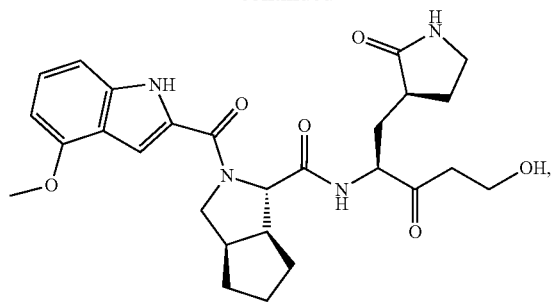
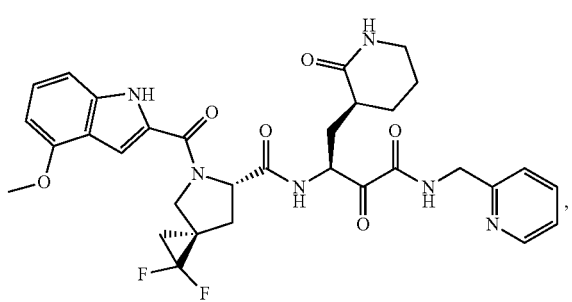
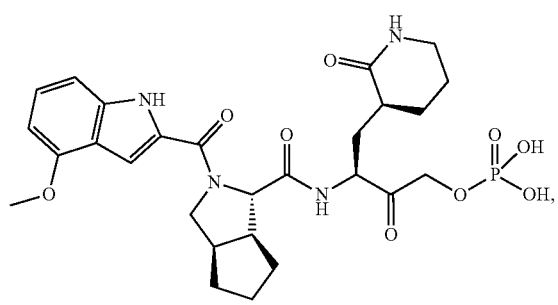
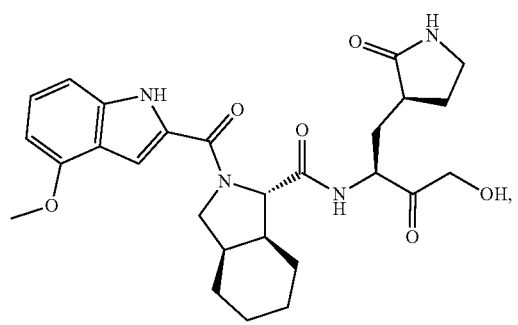
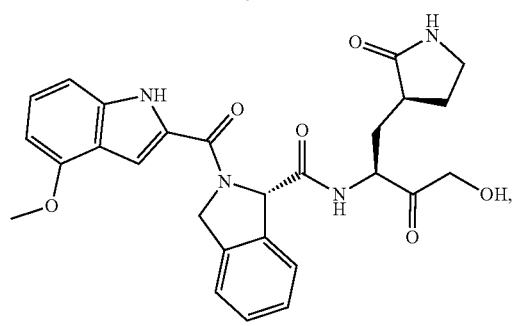
460
-continued
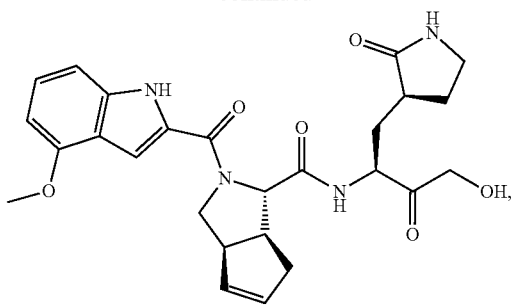
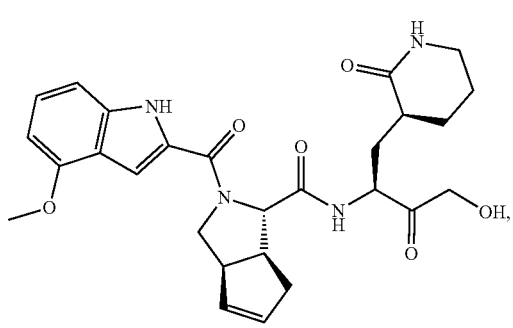
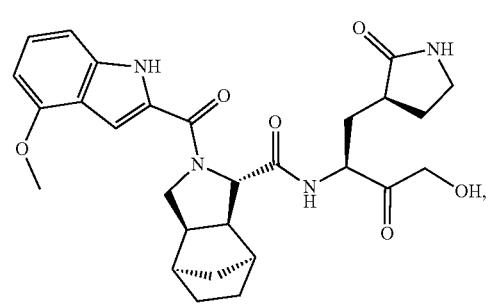
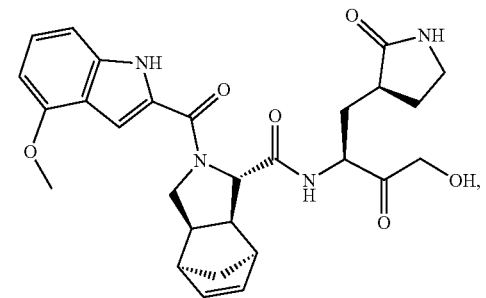
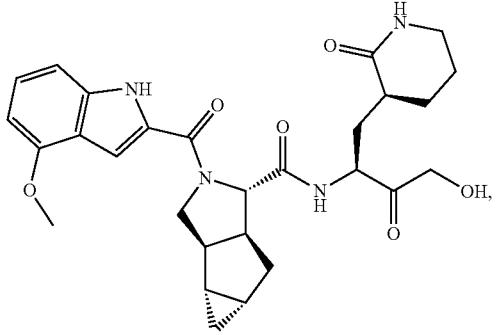

461
-continued
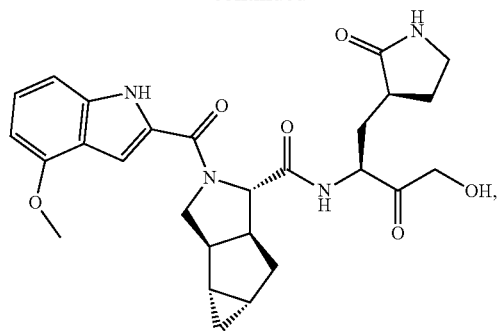
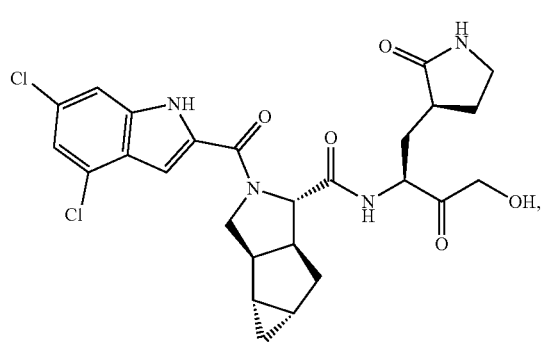
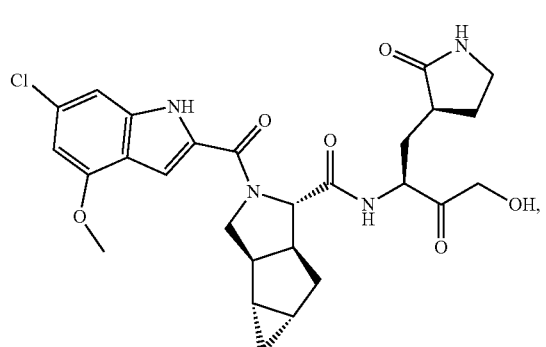
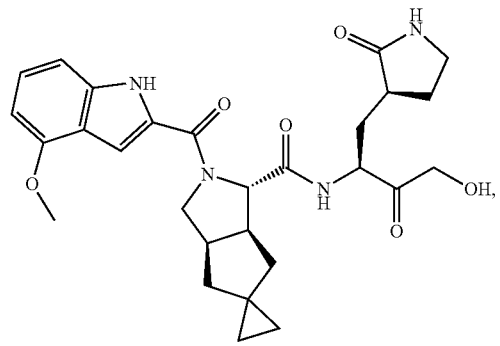
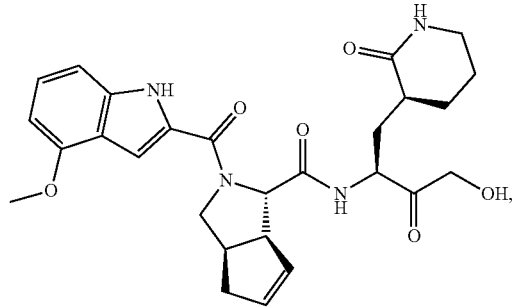
462
-continued
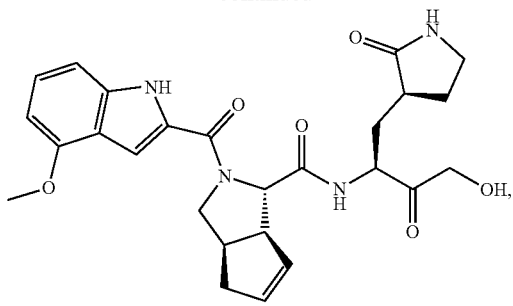
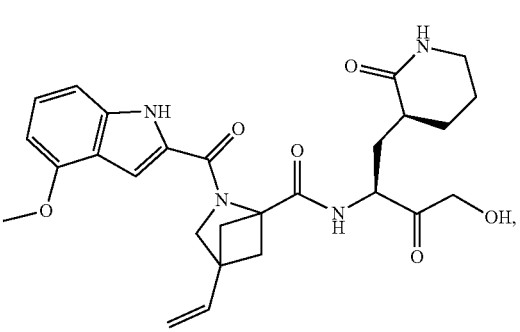
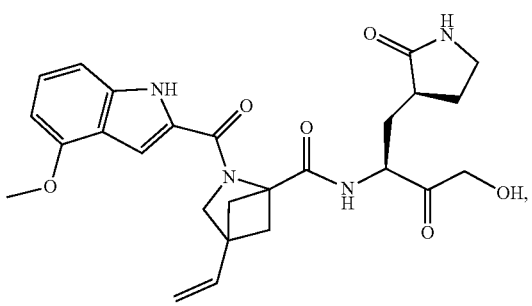
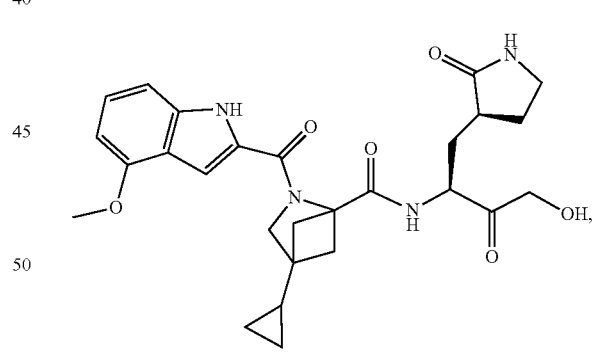
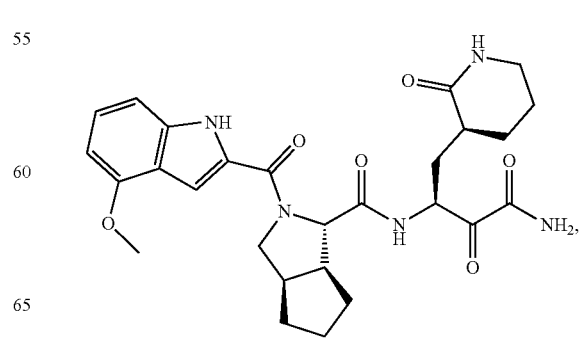

463
-continued
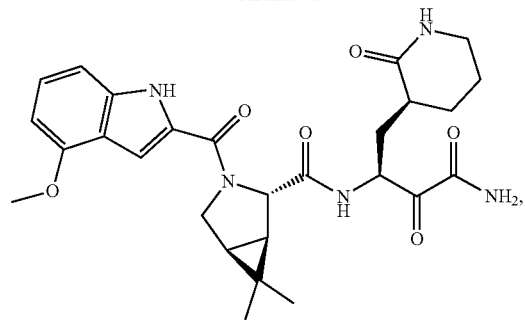
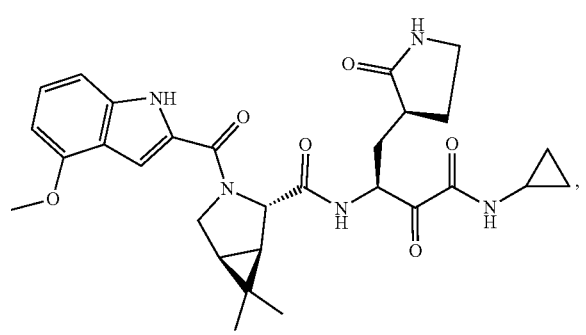
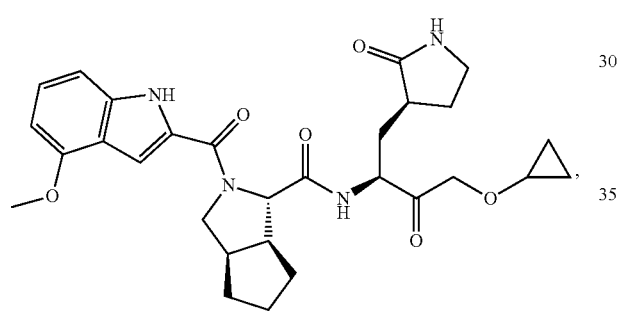
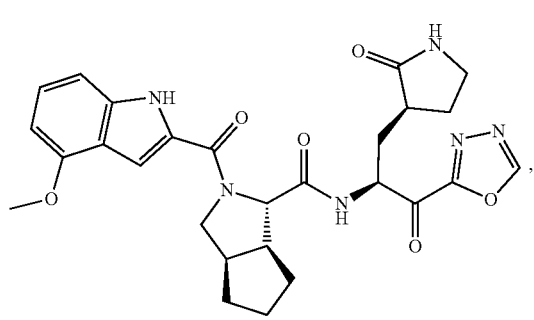
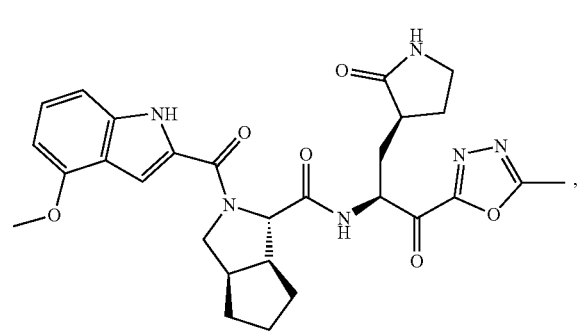
464
-continued
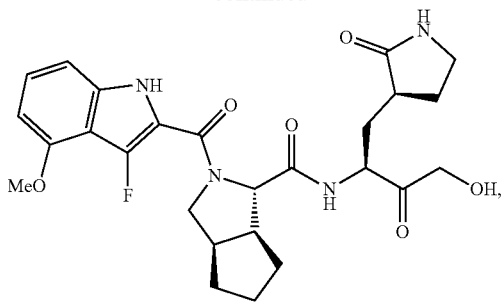
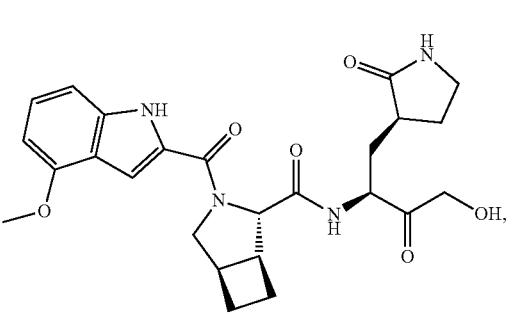
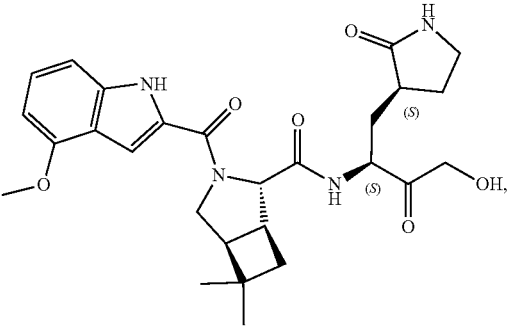
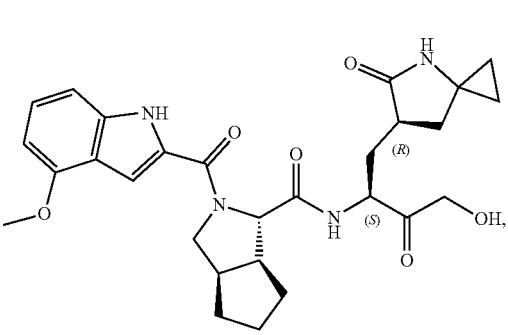
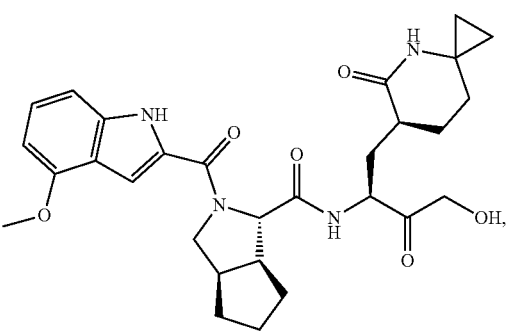

465
-continued
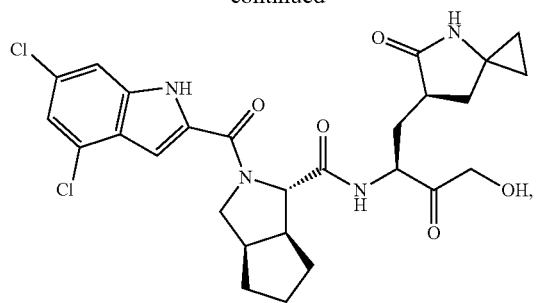
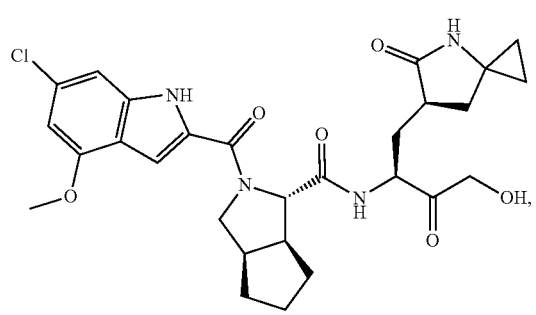
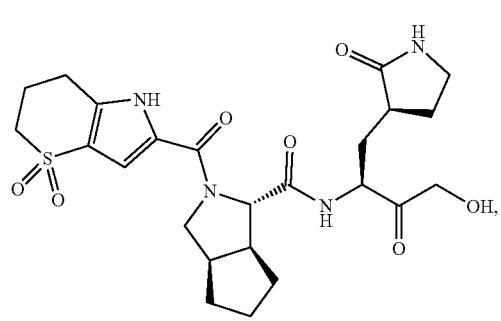
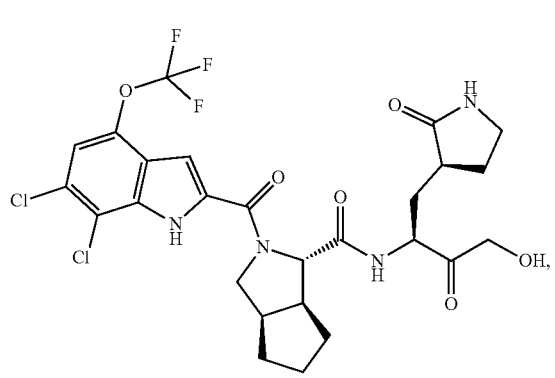
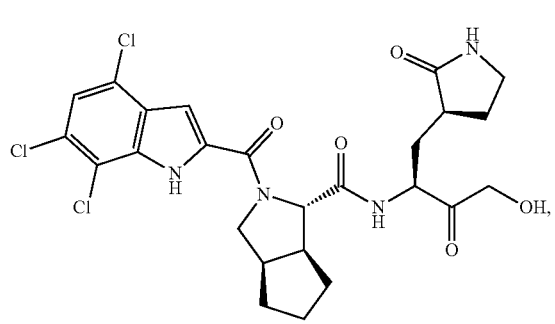
466
-continued
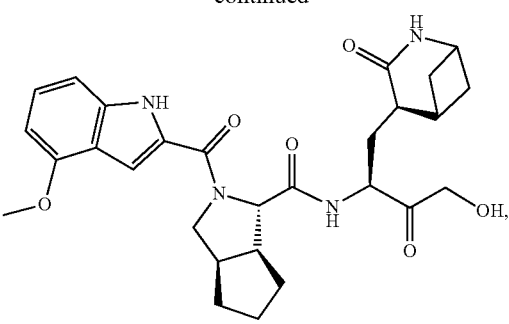
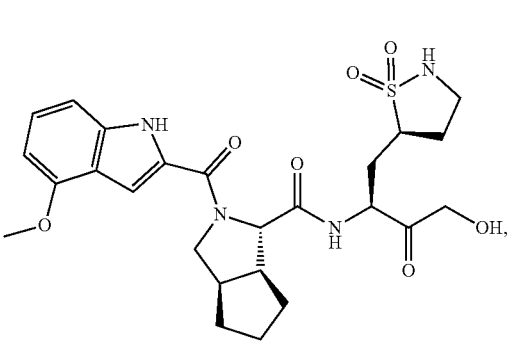
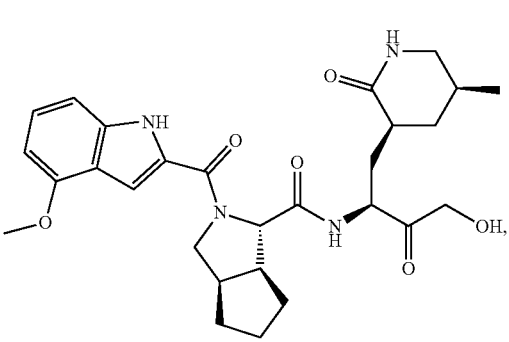
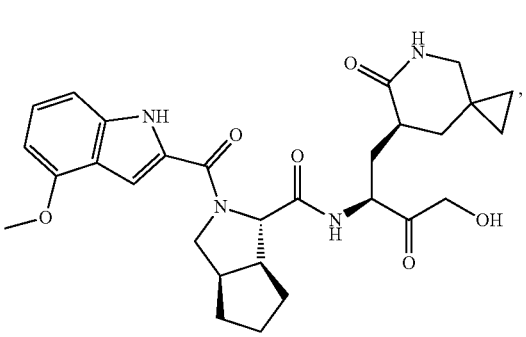
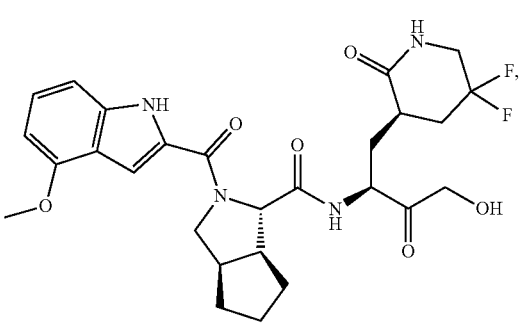

467
-continued
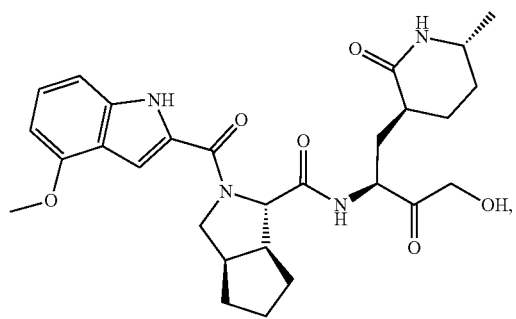
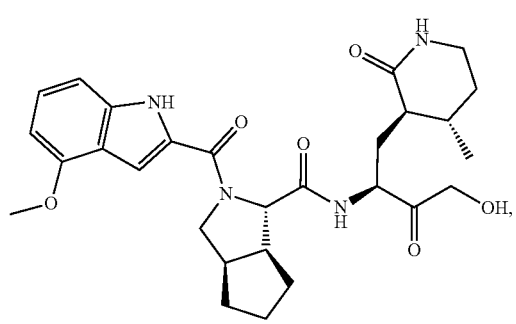
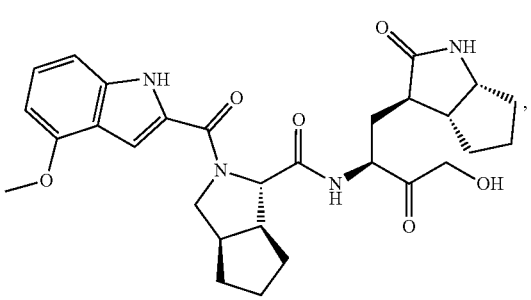
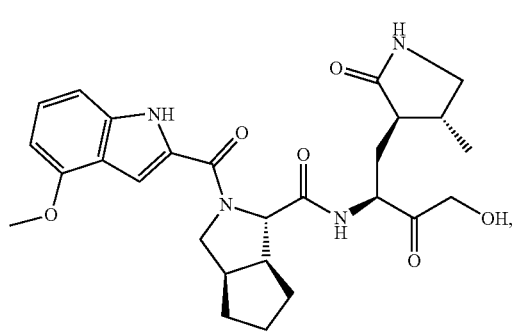
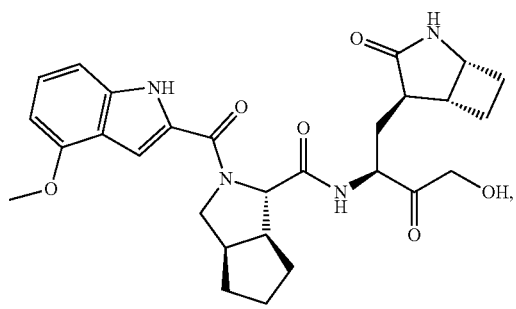
468
-continued
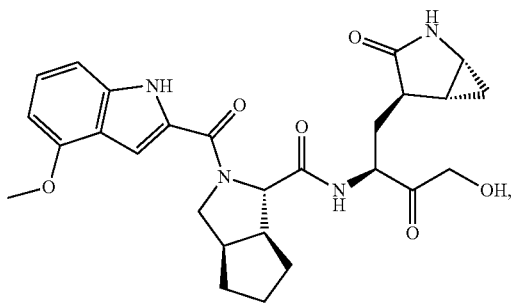
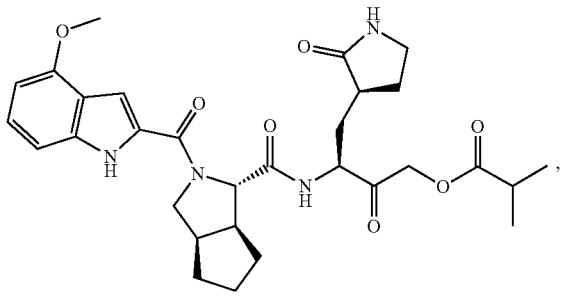
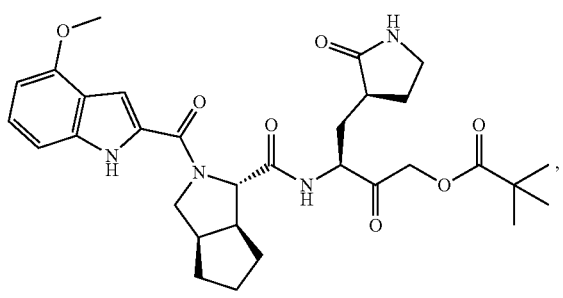
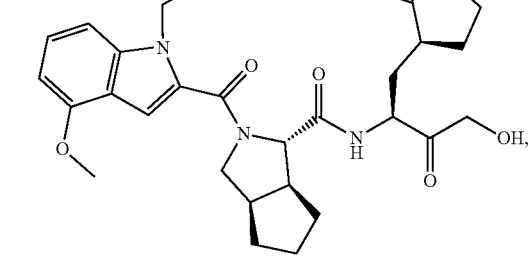
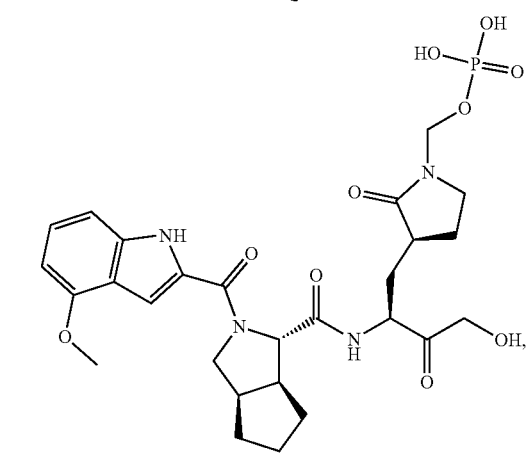

-continued

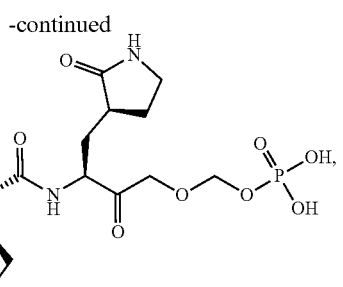

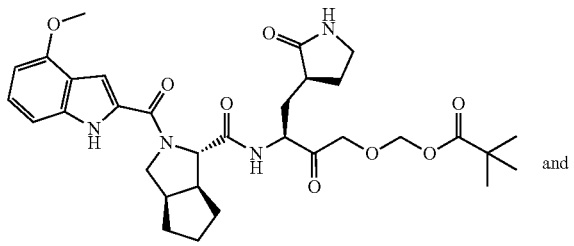
and
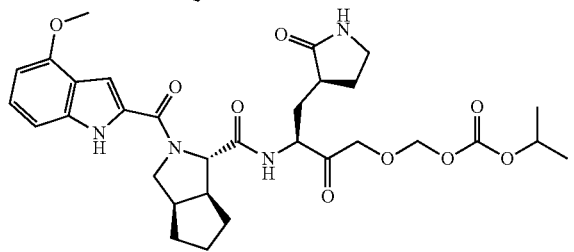

(including pharmaceutically acceptable salts of any of the foregoing.

Example A

SARS-Cov-2 3CLpro and HRV3C Duplex Assay

Protease assays were performed in 384-well low volume polypropylene microtiter plates at ambient temperature. For the duplex assay, 3CLpro and HRV3C was added using a Multidrop Combi (Thermo Scientific; Waltham, MA) and preincubated for 30 mins with small molecules. The reactions were initiated by the addition of the two peptide substrates. The reactions were incubated for 30 mins and quenched by the addition of 0.5% formic acid (final) with subsequent neutralization using 1% sodium bicarbonate (final). Internal standard peptides were added in 20 mM Hepes pH 8.0 for quantitation of the protease products. For SAMDI-MS analysis, 2 μL of each reaction mixture was transferred using a 384-channel automated liquid handler to SAMDI biochip arrays functionalized with a neutravidin-presenting self-assembled monolayer. The SAMDI arrays were incubated for 1 h in a humidified chamber to allow the specific immobilization of the biotinylated peptide substrates, cleaved products and internal standards. The samples were purified by washing the SAMDI arrays with deionized ultrafiltered water and dried with compressed air. A matrix comprising alpha-cyano cinnamic acid in 80% acetonitrile:20% aqueous ammonium citrate was applied in an automated format by dispensing 50 nL to each spot in the array. SAMDI-MS was performed using reflector-positive mode on an AB Sciex TOF-TOF 5800 System (AB Sciex, Framingham, MA) with 400 shots/spot analyzed in a random raster sampling. For data analysis, area under the curves (peaks) (AUCs) for the product and internal standard were calculated using the TOF/TOF Series Explorer (AB Sciex), and the amount of product formed was calculated using the equation (AUC product/AUC internal standard). The amount of product generated was calculated using the ratio of product area under the curve (AUC) divided by the AUC of the internal standard. Negative controls were prequenched with 0.5% formic acid final. Assay robustness was determined by Z-Factor. The $IC_{50}$s were determined by fitting the curves using a four-parameter equation in Graphpad Prism 8.

Table 1 indicates related $IC_{50}$ values for the tested compounds where 'A' indicates an $EC_{50} < 20$ nM, 'B' indicates an $IC_{50}$ of $\geq 20$ nM and $<200$ nM, 'C' indicates an $IC_{50} \geq 200$ nM and $<2000$ nM, 'D' indicates an $IC_{50} \geq 2000$ nM and $<20000$ nM and 'E' indicates an $IC_{50} \geq 20000$ nM and $<100000$ nM. As shown by the data in Table 1, compounds described herein (including pharmaceutically acceptable salts thereof) can effectively inhibit and be used to treat a coronavirus and rhinovirus.

TABLE 1

| Compound | SARS-Cov-2 | HRV |
| --- | --- | --- |
| 1 | D | E |
| 2 | C | D |
| 3 | E | D |
| 4 | C | D |
| 5 | E | C |
| 6 | D | C |
| 7 | C | C |
| 8 | C | D |
| 9 | B | D |
| 10 | D | C |
| 11 | C | D |
| 12 | D | E |
| 13 | A | C |
| 14a | B | C |
| 14b | C | C |
| 15 | A | B |
| 16 | B | C |
| 17 | B | D |
| 18 | B | C |
| 19 | C | D |
| 20 | C | C |
| 21 | C | D |
| 22 | C | D |
| 23 | B | D |
| 24 | B | E |
| 25 | D | D |
| 26 | B | D |
| 27 | A | D |
| 27A | B | D |
| 28 | C | D |
| 29 | B | B |
| 30 | B | C |
| 31 | A | E |
| 32 | B | C |
| 33 | B | C |
| 34 | B | C |
| 35 | B | D |
| 36 | B | E |
| 37 | B | E |
| 38 | B | C |
| 39 | B | >10 μM |
| 40 | C | C |
| 41 | A | >10 μM |
| 42 | B | D |
| 43 | B | >10 μM |
| 44 | B | >10 μM |
| 45 | B | D |
| 45A | B | D |
| 46 | B | C |
| 47 | B | D |
| 47A | B | D |
| 48 | C | D |
| 49 | A | >10 μM |
| 49A | B | >10 μM |

TABLE 1-continued

| Compound | SARS-Cov-2 | HRV |
|---|---|---|
| 50 | B | >10 µM |
| 51 | A | C |
| 52 | A | C |
| 53 | A | B |
| 54 | D | >10 |
| 55 | A | B |
| 56 | B | C |
| 57 | B | C |
| 58 | A | B |
| 59_1 | A | D |
| 59_2 | C | >10 µM |
| 59A_1 | B | D |
| 59A_2 | C | >10 µM |
| 60 | A | >10 µM |
| 60A | C | >10 µM |
| 61 | C | >10 µM |
| 62 | C | >10 µM |
| 63 | B | >10 µM |
| 64 | B | >10 µM |
| 65 | A | C |
| 66 | B | >10 µM |
| 66A | C | >10 µM |
| 67 | B | >10 µM |
| 68 | B | >10 µM |
| 69_A | C | >10 µM |
| 69_B | >10 µM | >10 µM |
| 70_1 | A | C |
| 70_2 | C | >10 |
| 70A_1 | B | D |
| 70A_2 | >10 µM | >10 µM |
| 71 | C | >10 µM |
| 72 | C | >10 µM |
| 73_1 | B | >10 µM |
| 73_2 | D | >10 µM |
| 74 | >10 µM | >10 µM |
| 75 | B | >10 µM |
| 76 | B | C |
| 77 | B | D |
| 78 | B | D |
| 79 | B | D |
| 80 | B | D |
| 81 | B | D |
| 82 | B | D |
| 83 | B | >10 µM |
| 84 | B | D |
| 85 | B | D |
| 86 | B | D |
| 87 | A | D |
| 88 | A | D |
| 89 | A | >10 µM |
| 90 | A | D |
| 91 | A | D |
| 92 | C | >10 µM |
| 93 | A | >10 µM |
| 94 | C | >10 µM |
| 95 | B | C |
| 96 | D | >10 µM |
| 97 | C | B |
| 98 | C | B |
| 99 | D | >10 µM |
| 100 | B | C |
| 101 | A | C |
| 102 | C | >10 µM |
| 103 | B | C |
| 104 | C | C |
| 105 | B | C |
| 106 | C | D |
| 107 | A | C |
| 108 | B | >10 µM |
| 109A | D | >10 µM |
| 109B | C | >10 µM |
| 110 | >10 µM | >10 µM |
| 111 | >10 µM | >10 µM |
| 112 | >10 µM | >10 µM |
| 113A | C | >10 µM |
| 113B | D | D |
| 114 | C | D |
| 115 | D | >10 µM |
| 116A | B | C |
| 116B | C | >10 µM |
| 117 | B | >10 µM |
| 118 | D | >10 µM |
| 119 | C | >10 µM |
| 120 | A | >10 µM |
| 121 | B | >10 µM |
| 122 | B | >10 µM |
| 123 | B | >10 µM |
| 124 | A | D |
| 125 | C | >10 µM |
| 126 | A | D |
| 127 | B | D |
| 128 | B | >10 µM |
| 129 | A | >10 µM |
| 130 | B | >10 µM |
| 131 | B | B |
| 132 | C | >10 µM |
| 133 | A | >10 µM |
| 134 | A | D |
| 135 | B | D |
| 136 | A | D |
| 137 | B | >10 µM |
| 138 | A | D |
| 139 | A | >10 µM |
| 140 | B | D |
| 141 | B | D |
| 142 | C | >10 µM |
| 143 | B | >10 µM |
| 144 | B | D |
| 145 | A | B |
| 146 | A | D |
| 147 | A | D |
| 148 | B | C |
| 149 | B | D |
| 150 | C | >10 µM |
| 151 | B | >10 µM |
| 152 | B | >10 µM |
| 153 | B | >10 µM |
| 154 | A | D |
| 155 | B | >10 µM |
| 156 | A | >10 µM |
| 157 | B | — |
| 158 | A | D |
| 159 | B | >10 µM |
| 160 | A | >10 µM |
| 161 | B | >10 µM |
| 162 | A | D |
| 163 | A | D |
| 164 | A | C |
| 165 | B | C |
| 166 | A | >10 µM |
| 167 | C | >10 µM |
| 168 | C | >10 µM |
| 169 | B | C |
| 170 | B | C |
| 171 | B | D |
| 172 | A | D |
| 173 | B | >10 µM |
| 174 | B | D |
| 175 | C | >10 µM |
| 176 | B | >10 µM |
| 177 | D | >10 µM |
| 178 | D | >10 µM |
| 179 | A | C |
| 180 | B | C |
| 181 | B | C |
| 182 | C | >10 µM |
| 183 | B | >10 µM |
| 184 | A | D |
| 185 | C | >10 µM |
| 186 | C | >10 µM |
| 187 | C | >10 µM |
| 188 | C | >10 µM |
| 189 | C | >10 µM |
| 190 | C | >10 µM |

TABLE 1-continued

| Compound | SARS-Cov-2 | HRV |
|---|---|---|
| 191 | C | >10 μM |
| 192 | C | >10 μM |
| 193 | C | >10 μM |

Example B

Coronavirus Assay

OC43 Coronavirus Assay in HeLa Cells

The human beta-coronavirus OC43 was purchased from ATCC (Manassas, VA) and propagated using HCT-8 human colorectal epithelial cells (ATCC). HeLa human cervical epithelial cells (ATCC) were used as susceptible host cell lines and were cultured using EMEM media, supplemented with 10% fetal bovine serum (FBS), 1% (v/v) penicillin/streptomycin (P/S), 1% (v/v) HEPES and 1% (v/v) Cellgro Glutagro™ supplement (all Corning, Manassas, VA) at 37° C. For the OC43 antiviral assay, $1.5 \times 10^4$ HeLa cells per well were plated in 100 μL complete media in white 96-well plates with clear bottoms at 37° C. for up to 24 h to facilitate attachment and allow cells to recover from seeding stresses. Next day, the cell culture medium was removed. Serially diluted compounds in 100 μL assay media (EMEM, 2% FBS, 1% P/S, 1% Cellgro Glutagro™ supplement, 1% HEPES) were added to the cells and incubated for 4H at 37° C. in a humidified 5% $CO_2$ incubator. 100 μL of OC43 virus stock was diluted to a concentration known to produce optimal cytopathic effect, inducing 80-90% reduction in cell viability. 96-well plates were incubated for 6 (HeLa) days at 33° C.; each plate contains uninfected control wells as well as virus-infected wells that were not treated with compound. Cytotoxicity plates without the addition of OC43 virus were carried out in parallel. At the end of the incubation period, 100 μL cell culture supernatant was replaced with 100 μL cell-titer-glo reagent (Promega, Madison, WI) and incubated for at least 10 min at rt prior to measuring luminescence. Luminescence was measured on a Perkin Elmer (Waltham, MA) Envision plate reader. Antiviral % inhibition was calculated as follows: [(Compound treated cells infected sample)−(no compound infected control)]/[(Uninfected control)−(no compound infected control)]*100; Using GraphPad (San Diego, CA) prism software version 8.3.1, the antiviral dose-response plot was generated as a sigmoidal fit, log(inhibitor) vs response-variable slope (four parameters) model and the $EC_{50}$ was calculated which is the predicted compound concentration corresponding to a 50% inhibition of the viral cytopathic effect.

Table 2 indicates related $EC_{50}$ and $CC_{50}$ values for the tested compounds 'A' indicates an $EC_{50}$<100 nM, 'B' indicates an $EC_{50}$ of ≥100 nM and <1000 nM, 'C' indicates an $EC_{50}$≥1000 nM and <10000 nM and 'D' indicates an $EC_{50}$≥10000 nM and <100000 nM. For $CC_{50}$, 'A' indicates a $CC_{50}$≥10000 nM, 'B' indicates an $CC_{50}$ of ≥1000 nM and <10000 nM and 'C' indicates an $CC_{50}$<1000 nM.

TABLE 2

| Compound | $EC_{50}$ | $CC_{50}$ |
|---|---|---|
| 1 | C | A |
| 2 | B | A |
| 3 | D | A |
| 4 | C | A |
| 5 | C | A |
| 6 | C | A |
| 7 | B | A |
| 8 | C | A |
| 9 | B | A |
| 10 | C | A |
| 11 | C | A |
| 12 | D | A |
| 13 | C | A |
| 14a | C | A |
| 14b | C | A |
| 15 | B | A |
| 16 | B | A |
| 17 | B | A |
| 18 | B | A |
| 19 | B | A |
| 20 | A | A |
| 21 | B | A |
| 22 | C | A |
| 23 | B | A |
| 24 | B | A |
| 25 | C | A |
| 26 | B | A |
| 27 | B | A |
| 27A | A | A |
| 28 | B | A |
| 29 | C | A |
| 30 | B | A |
| 31 | B | A |
| 32 | B | A |
| 33 | B | A |
| 34 | B | A |
| 35 | C | A |
| 36 | D | A |
| 37 | C | A |
| 38 | B | A |
| 39 | B | A |
| 40 | B | A |
| 41 | A | A |
| 42 | B | A |
| 43 | B | A |
| 44 | C | A |
| 45 | B | A |
| 45A | B | A |
| 46 | D | A |
| 47 | B | A |
| 47A | A | A |
| 48 | B | A |
| 49 | B | A |
| 49A | B | A |
| 50 | B | A |
| 51 | C | A |
| 52 | C | A |
| 53 | B | A |
| 54 | D | A |
| 55 | B | A |
| 56 | D | A |
| 57 | B | A |
| 58 | B | A |
| 59_1 | B | A |
| 59_2 | C | A |
| 59A_1 | B | A |
| 59A_2 | C | A |
| 60 | A | A |
| 60A | A | A |
| 61 | B | A |
| 62 | C | A |
| 63 | B | A |
| 64 | A | A |
| 65 | B | A |
| 66 | C | A |
| 66A | B | A |
| 67 | C | A |
| 68 | B | A |
| 69_A | C | A |
| 69_B | D | A |
| 70_1 | B | A |
| 70_2 | C | A |

TABLE 2-continued

| Compound | EC$_{50}$ | CC$_{50}$ |
|---|---|---|
| 70A_1 | A | A |
| 70A_2 | >10 μM | A |
| 71 | B | A |
| 72 | B | A |
| 73_1 | B | A |
| 73_2 | D | A |
| 74 | >10 μM | A |
| 75 | B | A |
| 76 | >10 μM | A |
| 77 | >10 μM | A |
| 78 | C | A |
| 79 | B | A |
| 80 | C | A |
| 81 | C | A |
| 82 | >10 μM | A |
| 83 | B | A |
| 84 | C | A |
| 85 | C | A |
| 86 | C | A |
| 87 | A | A |
| 88 | A | A |
| 89 | B | A |
| 90 | A | A |
| 91 | A | A |
| 92 | >10 μM | A |
| 93 | C | A |
| 94 | C | A |
| 95 | B | A |
| 96 | C | A |
| 97 | >10 μM | A |
| 98 | >10 μM | A |
| 99 | >10 μM | A |
| 100 | C | A |
| 101 | B | A |
| 102 | C | A |
| 103 | >10 μM | A |
| 104 | >10 μM | A |
| 105 | >10 μM | A |
| 106 | C | A |
| 107 | >10 μM | A |
| 108 | B | A |
| 109A | C | A |
| 109B | C | A |
| 110 | >10 μM | A |
| 111 | D | A |
| 112 | >10 μM | A |
| 113A | C | A |
| 113B | C | A |
| 114 | C | A |
| 115 | >10 μM | A |
| 116A | B | A |
| 116B | C | A |
| 117 | B | A |
| 118 | >10 μM | A |
| 119 | >10 μM | A |
| 120 | A | A |
| 121 | A | A |
| 122 | A | A |
| 123 | B | A |
| 124 | B | A |
| 125 | A | A |
| 126 | A | A |
| 127 | B | A |
| 128 | A | A |
| 129 | A | A |
| 130 | A | A |
| 131 | >10 μM | A |
| 132 | A | B |
| 133 | A | A |
| 134 | B | A |
| 135 | B | A |
| 136 | A | A |
| 137 | A | A |
| 138 | A | A |
| 139 | B | A |
| 140 | B | A |
| 141 | B | A |
| 142 | >10 μM | A |
| 143 | B | A |
| 144 | B | A |
| 145 | C | A |
| 146 | B | A |
| 147 | B | A |
| 148 | B | A |
| 149 | B | A |
| 150 | >10 μM | A |
| 151 | C | A |
| 152 | C | A |
| 153 | C | A |
| 154 | B | A |
| 155 | C | A |
| 156 | B | A |
| 157 | B | A |
| 158 | B | A |
| 159 | >10 μM | A |
| 160 | B | A |
| 161 | A | A |
| 162 | A | A |
| 163 | A | A |
| 164 | C | A |
| 165 | B | A |
| 166 | B | A |
| 167 | B | A |
| 168 | C | A |
| 169 | C | A |
| 170 | C | A |
| 171 | C | A |
| 172 | C | A |
| 173 | B | A |
| 174 | B | A |
| 175 | C | A |
| 176 | B | A |
| 177 | >10 μM | A |

SARS-CoV-2 Infection Model in Huh7 Cells

Assay medium, used for producing virus stocks and antiviral testing in Huh-7 cells, is prepared by supplementing DMEM with 4% FBS, 2% HEPES 1M, 5 mL sodium bicarbonate 7.5% and 1% NEAA. For antiviral testing Huh7 cells were seeded in 96-well plates (Corning® CellBIND® 96-well Microplate cat no 3300) at a density of 6000 cells per well in assay medium. After overnight growth, the cells were treated with the indicated compound concentrations and infected with Huh-7-adapted SARS-CoV-2-GHB-03021/2020 at a MOI of 0.005 TCID$_{50}$/cell (final volume 200 μL/well in assay medium). On day 4 p.i. differences in cell viability caused by virus-induced CPE or by compound-specific side effects were analyzed using MTS as described previously (PMID: 22575574).

SARS-CoV-2 Infection Model in VeroE6 Cells

The SARS-CoV-2 antiviral assay is derived from the previously established SARS-CoV assay (PMID: 15961169). In this assay, fluorescence of Vero E6-eGFP cells declines after infection with SARS-CoV-2 due to the cytopathogenic effect of the virus. In the presence of an antiviral compound, the cytopathogenicity is inhibited and the fluorescent signal rescued. On day −1, the test compounds were serially diluted in assay medium (DMEM supplemented with 2% v/v FCS). The plates were incubated (37° C., 5% CO$_2$ and 95% relative humidity) overnight. On day 0, the diluted compounds were mixed with Vero E6-eGFP cells (25,000 cells/well), SARS-CoV-2-GHB-03021/2020 (20 TCID$_{50}$/well) and the MDR1-inhibitor CP-100356 (final concentration 0.5 μM) in 96-well blackview plates (Greiner Bio-One, Vilvoorde, Belgium). The plates were incubated in a humidified incubator at 37° C. and 5% CO$_2$. At 4 days p.i., the wells were examined for eGFP expression using an argon laser-scanning microscope.

The microscope settings were excitation at 488 nm and emission at 510 nm and the fluorescence images of the wells were converted into signal values. The results were expressed as $EC_{50}$ values defined as the concentration of compound achieving 50% rescue from the virus-reduced eGFP signals as compared to the untreated virus-infected control cells. Toxicity of compounds in the absence of virus was evaluated in a standard MTS-assay as described previously (PMID: 22575574).

Table 3 indicates related $EC_{50}$ and $CC_{50}$ values for the tested compounds 'A' indicates an $EC_{50}<1000$ nM, 'B' indicates an $EC_{50}$ of $\geq 1000$ nM and $<10000$ nM, 'C' indicates an $EC_{50} \geq 10000$ nM and $<100000$ nM. For $CC_{50}$, 'A' indicates a $CC_{50} \geq 10000$ nM, 'B' indicates an $CC_{50}$ of $\geq 1000$ nM and $<10000$ nM, 'C' indicates an $CC_{50}<1000$ nM. >100 refers to >100 μM, >50 refers to >50 μM and >10 refers to >10 μM.

TABLE 3

| Compound | Huh-7 (EC$_{50}$) | Huh-7 (CC$_{50}$) | VeroE6 + CP (EC$_{50}$) | VeroE6 + CP (CC$_{50}$) |
|---|---|---|---|---|
| 1 | | | >100 | >100 |
| 2 | | | B | A |
| 3 | | | >100 | >100 |
| 4 | | | B | >100 |
| 5 | | | C | >100 |
| 6 | | | >100 | >100 |
| 7 | B | A | B | A |
| 8 | | | C | >100 |
| 9 | | | B | >100 |
| 10 | | | >100 | >100 |
| 11 | | | C | >100 |
| 12 | | | >100 | >100 |
| 13 | | | B | >100 |
| 14A | | | C | >100 |
| 15 | B | >100 | B | >100 |
| 16 | B | A | B | A |
| 17 | B | A | | |
| 18 | B | >100 | B | >100 |
| 19 | B | A | B | >100 |
| 20 | >100 | B | B | |
| 21 | | | C | |
| 22 | B | >100 | C | >100 |
| 23 | B | >100 | B | >100 |
| 24 | B | A | B | >100 |
| 25 | C | >100 | C | >100 |
| 26 | C | >100 | C | >100 |
| 27 | B | >100 | B | >100 |
| 27A | B | A | B | >100 |
| 28 | A | A | B | >100 |
| 29 | B | >100 | B | >100 |
| 30 | B | >100 | B | >100 |
| 31 | C | >100 | B | >100 |
| 32 | B | >100 | B | >100 |
| 33 | B | >100 | A | >100 |
| 34 | C | >100 | B | >100 |
| 35 | C | >100 | C | >100 |
| 36 | C | >100 | C | >100 |
| 37 | B | >100 | | |
| 38 | B | >100 | B | >100 |
| 39 | B | >100 | B | >100 |
| 40 | B | A | B | >100 |
| 41 | B | >100 | B | >100 |
| 42 | B | >100 | B | >100 |
| 43 | B | >100 | B | >100 |
| 44 | C | A | C | >100 |
| 45 | B | >100 | A | >100 |
| 45A | B | A | B | A |
| 46 | C | A | C | >100 |
| 47 | B | >100 | B | >100 |
| 47A | B | A | B | >100 |
| 48 | B | A | B | >100 |
| 49 | B | >100 | B | >100 |
| 49A | B | A | B | A |
| 50 | B | A | B | >100 |
| 51 | >100 | >100 | >100 | >100 |
| 52 | C | >100 | B | >100 |
| 53 | A | >100 | B | >100 |
| 54 | >100 | >100 | >100 | >100 |
| 55 | B | >100 | B | >100 |
| 56 | C | >100 | | |
| 57 | B | >100 | | |
| 58 | A | >100 | A | >100 |
| 59A_1 | A | A | A | A |
| 60 | A | >100 | A | A |
| 60A | B | B | B | >100 |
| 61 | B | >100 | B | >100 |
| 62 | C | >100 | C | A |
| 63 | A | A | A | A |
| 64 | A | A | A | A |
| 65 | A | >100 | A | A |
| 66 | C | >100 | | |
| 66A | B | A | | |
| 67 | C | >100 | | |
| 68 | B | >100 | | |
| 69_A | C | >100 | | |
| 69_B | >100 | >100 | | |
| 70_1 | B | A | A | A |
| 70_2 | C | >50 | C | >50 |
| 70A_1 | B | A | B | A |
| 70A_2 | >50 | A | >50 | A |
| 71 | B | >100 | | |
| 72 | B | >100 | B | >100 |
| 74 | | | C | A |
| 75 | | | B | >100 |
| 76 | | | C | >100 |
| 77 | | | C | A |
| 78 | | | C | >100 |
| 79 | B | >50 | B | >50 |
| 80 | B | >50 | B | >50 |
| 81 | C | >50 | B | >50 |
| 82 | >50 | >50 | C | >50 |
| 83 | A | >50 | A | >50 |
| 84 | >50 | >50 | B | >50 |
| 85 | C | >50 | B | >50 |
| 86 | C | >50 | C | >50 |
| 87 | B | A | A | >100 |
| 88 | A | A | A | >100 |
| 89 | A | >50 | A | >100 |
| 90 | A | >50 | A | >100 |
| 91 | A | A | A | A |
| 92 | | | C | >100 |
| 93 | C | >100 | C | >50 |
| 94 | C | >100 | | |
| 95 | B | >50 | B | >50 |
| 96 | >100 | A | | |
| 97 | >100 | >100 | | |
| 98 | >50 | >50 | C | A |
| 99 | | | C | A |
| 100 | C | >50 | C | >100 |
| 101 | B | >50 | B | A |
| 102 | C | >100 | B | >100 |
| 103 | C | >100 | C | >100 |
| 104 | C | >100 | C | >100 |
| 105 | C | >100 | C | >100 |
| 106 | C | A | C | >50 |
| 107 | C | >50 | C | >100 |
| 108 | C | >50 | B | >50 |
| 109A | >50 | A | B | A |
| 109B | C | A | C | >50 |
| 110 | >50 | >50 | >50 | >50 |
| 111 | B | A | >100 | >100 |
| 112 | >100 | A | | |
| 113A | C | >50 | C | >50 |
| 113B | >50 | >50 | C | >50 |
| 114 | | | C | >50 |
| 115 | >50 | A | >50 | >50 |
| 116A | A | A | B | >50 |
| 116B | B | A | B | A |
| 117 | A | >50 | A | >50 |
| 118 | >50 | A | >50 | >50 |
| 119 | >50 | >50 | >50 | >50 |

TABLE 3-continued

| Compound | Huh-7 (EC$_{50}$) | Huh-7 (CC$_{50}$) | VeroE6 + CP (EC$_{50}$) | VeroE6 + CP (CC$_{50}$) |
|---|---|---|---|---|
| 120 | A | B | A | A |
| 121 | A | >50 | B | >50 |
| 122 | A | >50 | A | >50 |
| 123 | B | >50 | B | >50 |
| 124 | A | >50 | A | >50 |
| 125 | A | A | A | >50 |
| 126 | B | >50 | B | >50 |
| 127 | A | A | A | >50 |
| 128 | A | A | B | A |
| 129 | A | A | A | A |
| 130 | A | A | A | A |
| 132 | A | A | A | A |
| 133 | A | >50 | A | >50 |
| 134 | B | >50 | B | >50 |
| 135 | A | A | A | A |
| 136 | A | >50 | A | >50 |
| 137 | A | A | B | >50 |
| 138 | A | >50 | B | >50 |
| 139 | A | >50 | A | >50 |
| 140 | B | A | B | >50 |
| 141 | >50 | A | >50 | >50 |
| 142 | >10 | >10 | >50 | >50 |
| 143 | A | >10 | A | >50 |
| 144 | B | >10 | A | >50 |
| 145 | C | >50 | C | >50 |
| 146 | B | A | B | >50 |
| 147 | C | >50 | C | >50 |
| 148 | A | A | A | >50 |
| 149 | A | B | A | A |
| 150 | >50 | >50 | >50 | >50 |
| 151 | B | >50 | C | >50 |
| 152 | C | >50 | C | >50 |
| 153 | C | A | C | >50 |
| 154 | A | >50 | B | >50 |
| 155 | >50 | >50 | C | >50 |
| 156 | A | >50 | A | >50 |
| 157 | B | >50 | B | >50 |
| 158 | A | A | A | >50 |
| 159 | >10 | >50 | C | >50 |
| 160 | A | A | A | >50 |
| 161 | A | A | B | >50 |
| 162 | A | >50 | A | >50 |
| 163 | B | >50 | B | >50 |
| 164 | >10 | B | C | >50 |
| 165 | A | >10 | A | >50 |
| 166 | A | B | A | A |
| 167 | A | >10 | A | >50 |
| 168 | B | >10 | B | >50 |
| 169 | B | >10 | B | >50 |
| 170 | B | >10 | C | >50 |
| 171 | B | >10 | B | >50 |
| 172 | A | >10 | A | >50 |
| 173 | B | B | A | >50 |
| 174 | A | B | A | B |
| 178 | >10 | >10 | >50 | >50 |
| 179 | >10 | >10 | C | >50 |
| 180 | B | >10 | B | >50 |
| 181 | B | >10 | B | >50 |
| 182 | >10 | B | B | A |
| 183 | B | B | A | B |

Tables 2 and 3 demonstrate that compounds described herein (including pharmaceutically acceptable salts thereof) can effectively inhibit and treat a coronavirus.

Example C

Picornavirus & Norovirus Assays

Compounds of Formula (I), including pharmaceutically acceptable salts thereof, are tested following a protocol similar to the protocol described in one of the following articles: Kim et al., Journal of Virology (2012) 86(21): 11754-11762, Zhang et al, JACS (2020) (https://dx.doi.org/10.1021/acs.jmedchem.9b01828), and U.S. Pat. No. 9,603,864.

The protocols of Kim et al., and Zhang et al., can be used to test for activity against a coronavirus.

Example D

For the cathepsin L assay, 10 pM of human cathepsin L (R&D Systems; Minneapolis, MN) was preincubated for 30 mins with test compounds. Reactions were initiated by the addition of a peptide substrate Z-FR-AMC (final concentration 2 μM, Anaspec; Fremont, CA). Fluorescence was measured at 2-minute intervals for 30 mins using a 355/460 excitation/emission filter module on an Envision plate reader (Perkin Elmer; Waltham, MA). The $IC_{50}$ values were calculated for each assay by fitting the curves using a four-parameter equation in GraphPad Prism.

Table 4 indicates related $IC_{50}$ values for the tested compounds where 'A' indicates an $IC_{50}$≥10000 nM, 'B' indicates an $IC_{50}$ of ≥1000 nM and <10000 nM, 'C' indicates an $IC_{50}$≥100 nM and <1000 nM, 'D' indicates an $IC_{50}$<100 nM.

TABLE 4

| Compound | Cathepsin L $IC_{50}$ |
|---|---|
| 2 | B |
| 4 | C |
| 7 | D |
| 8 | C |
| 9 | C |
| 11 | D |
| 13 | B |
| 14A | A |
| 14B | A |
| 15 | B |
| 16 | A |
| 17 | B |
| 18 | A |
| 19 | C |
| 20 | A |
| 22 | C |
| 23 | C |
| 24 | C |
| 25 | C |
| 26 | D |
| 27 | A |
| 27A | A |
| 28 | D |
| 29 | C |
| 30 | D |
| 31 | A |
| 32 | A |
| 33 | C |
| 34 | A |
| 35 | A |
| 36 | A |
| 37 | A |
| 38 | D |
| 39 | A |
| 40 | C |
| 41 | A |
| 42 | A |
| 43 | A |
| 44 | A |
| 45 | A |
| 45A | A |
| 46 | B |
| 47 | A |
| 47A | A |
| 48 | C |
| 49 | >3.3 μM |
| 49A | A |
| 50 | A |

TABLE 4-continued

| Compound | Cathepsin L IC$_{50}$ |
|---|---|
| 51 | C |
| 52 | A |
| 53 | A |
| 54 | A |
| 55 | A |
| 56 | A |
| 57 | A |
| 58 | B |
| 59_1 | A |
| 59_2 | A |
| 59A_1 | A |
| 59A_2 | A |
| 60 | A |
| 60A | A |
| 61 | A |
| 62 | A |
| 63 | A |
| 64 | A |
| 65 | A |
| 66 | A |
| 66A | A |
| 67 | A |
| 68 | A |
| 69_A | A |
| 69_B | A |
| 70_1 | A |
| 70_2 | A |
| 70A_1 | A |
| 70A_2 | A |
| 71 | A |
| 72 | >3.3 μM |
| 73_1 | A |
| 73_2 | A |
| 74 | A |
| 75 | A |
| 76 | A |
| 77 | A |
| 78 | A |
| 79 | A |
| 80 | A |
| 81 | A |
| 82 | A |
| 83 | A |
| 84 | A |
| 85 | A |
| 86 | A |
| 87 | A |
| 88 | A |
| 89 | A |
| 90 | A |
| 91 | A |
| 92 | A |
| 93 | A |
| 94 | A |
| 95 | A |
| 96 | B |
| 97 | A |
| 98 | A |
| 99 | A |
| 100 | A |
| 101 | A |
| 102 | A |
| 103 | A |
| 104 | A |
| 105 | A |
| 106 | A |
| 107 | A |
| 108 | A |
| 109A | A |
| 109B | A |
| 110 | A |
| 111 | D |
| 112 | B |
| 113A | A |
| 113B | A |
| 114 | A |
| 115 | A |
| 116A | A |
| 116B | A |
| 117 | A |
| 118 | A |
| 119 | A |
| 120 | A |
| 121 | A |
| 122 | A |
| 123 | A |
| 124 | A |
| 125 | A |
| 126 | A |
| 127 | A |
| 128 | A |
| 129 | A |
| 130 | A |
| 131 | A |
| 132 | A |
| 133 | A |
| 134 | A |
| 135 | A |
| 136 | A |
| 137 | A |
| 138 | A |
| 139 | A |
| 140 | A |
| 141 | C |
| 142 | A |
| 143 | A |
| 144 | A |
| 145 | C |
| 146 | B |
| 147 | A |
| 148 | A |
| 149 | B |
| 150 | A |
| 151 | A |
| 152 | A |
| 153 | A |
| 154 | A |
| 155 | A |
| 156 | A |
| 157 | A |
| 158 | A |
| 159 | A |
| 160 | A |
| 161 | A |
| 162 | A |
| 163 | A |
| 164 | B |
| 165 | B |
| 166 | B |
| 167 | A |
| 168 | A |
| 169 | B |
| 170 | C |
| 171 | A |
| 172 | B |
| 173 | A |
| 174 | B |
| 175 | A |
| 176 | A |
| 177 | A |
| 178 | A |
| 179 | B |
| 180 | B |
| 181 | B |
| 182 | A |
| 183 | B |
| 184 | A |
| 185 | A |
| 186 | A |
| 187 | A |
| 188 | A |
| 189 | A |
| 190 | A |
| 191 | A |

TABLE 4-continued

| Compound | Cathepsin L IC$_{50}$ |
|---|---|
| 192 | A |
| 193 | A |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the present disclosure.

What is claimed is:

1. A compound of Formula (I), or a pharmaceutically acceptable salt thereof, having the structure:

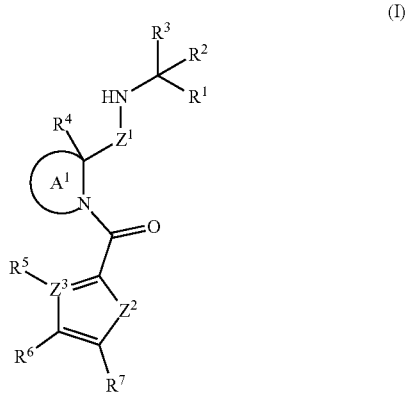

(I)

wherein:

$Z^1$ is —C(=O)— or —CH(CF$_3$)—;

$Z^2$ is O, S or NR$^8$, wherein R$^8$ is H or an unsubstituted C$_{1-4}$ alkyl;

$Z^3$ is N or C, and when $Z^3$ is N, then R$^5$ is absent;

Ring A$^1$ is selected from the group consisting of an unsubstituted or a substituted azetidine, an unsubstituted or a substituted pyrrolidine and an unsubstituted or a substituted piperidine, wherein the azetidine, the pyrrolidine and the piperidine can be optionally substituted with one or more R$^x$ groups independently selected from the group consisting of deuterium, halogen, an unsubstituted or a substituted C$_{1-4}$ alkyl, an unsubstituted or a substituted C$_{2-4}$ alkenyl, an unsubstituted or a substituted C$_{1-8}$ alkoxy, an unsubstituted or a substituted C$_{3-6}$ cycloalkyl, an unsubstituted or a substituted aryl, an unsubstituted or a substituted heteroaryl, an unsubstituted or a substituted heterocyclyl and an unsubstituted C$_{1-4}$ haloalkyl, and wherein the azetidine, the pyrrolidine and the piperidine can be connected to a cyclic moiety selected from the group consisting of a monocyclic C$_{3-7}$ cycloalkyl, a bicyclic C$_{5-9}$ cycloalkyl, a monocyclic C$_{3-7}$ cycloalkenyl, a bicyclic C$_{5-9}$ cycloalkenyl and phenyl, wherein the cyclic moiety is connected to the azetidine, the pyrrolidine and the piperidine in a fused-fashion or a spiro-fashion that can be optionally substituted with one or more moieties independently selected from the group consisting of halogen, an unsubstituted C$_{1-4}$ alkyl, an unsubstituted C$_{2-4}$ alkenyl and an unsubstituted or a substituted C$_{3-6}$ monocyclic cycloalkyl;

R$^1$ is selected from the group consisting of cyano, an unsubstituted or a substituted C$_{2-5}$ alkynyl, an unsubstituted or a substituted ketoamide, an unsubstituted or a substituted —C(=O)—N-sulfonamido, CH(OH)((P=O)(OR$^9$)$_2$), —C(=O)CH$_2$'O—(P=O)(OR$^{10}$)$_2$), —C(=O)CH$_2$—O—C(R$^{11A}$)$_2$—O—((P=O)(OR$^{11B}$)$_2$), —C(=O)CH$_2$—O—C(R$^{12A}$)$_2$—O—C(=O)—OR$^{12B}$ and —C(=O)CH$_2$—O—C(R$^{13A}$)$_2$—O—C(=O)—R$^{13B}$, wherein each R$^9$, each R$^{10}$, each R$^{11B}$ and R$^{12B}$ and R$^{13B}$ are independently hydrogen, an unsubstituted C$_{1-6}$ alkyl, an unsubstituted C$_{2-6}$ alkenyl, an unsubstituted C$_{1-6}$ haloalkyl, an unsubstituted or a substituted aryl or an unsubstituted or a substituted aryl(C$_{1-4}$ alkyl);

each R$^{11A}$, each R$^{12A}$ and each R$^{13A}$ are independently hydrogen or an unsubstituted C$_{1-4}$ alkyl;

R$^2$ is hydrogen, deuterium or halogen;

R$^3$ is an unsubstituted or a substituted C-amido(C$_{1-4}$ alkyl), an unsubstituted or a substituted monocyclic nitrogen-containing heteroaryl(C$_{1-4}$ alkyl), an unsubstituted or a substituted monocyclic nitrogen-containing heterocyclyl(C$_{1-4}$ alkyl), an unsubstituted or a substituted bicyclic nitrogen-containing heteroaryl(C$_{1-4}$ alkyl) or an unsubstituted or a substituted bicyclic nitrogen-containing heterocyclyl(C1-4 alkyl);

R$^4$ is hydrogen, deuterium or halogen;

R$^5$ is selected from the group consisting of hydrogen, deuterium, halogen, an unsubstituted C$_{1-6}$ alkyl and an unsubstituted C14 haloalkyl; and R$^6$ and R$^7$ are independently selected from the group consisting of hydrogen, deuterium, halogen, an unsubstituted or a substituted C$_{1-6}$ alkyl, an unsubstituted or a substituted phenyl, an unsubstituted or a substituted acyl, an unsubstituted or a substituted C-carboxy and an unsubstituted or a substituted sulfonyl; or R$^6$ and R$^7$ are taken together with the carbon to which R$^6$ and R$^7$ are each attached to form an optionally substituted 4-9 membered saturated or unsaturated ring or ring system that can optionally contain 1 or 2 ring heteroatoms selected from the group consisting of O, N and S.

2. The compound of claim 1, wherein R$^1$ is an unsubstituted or a substituted ketoamide.

3. The compound of claim 1, wherein R$^1$ is CH(OH)((P=O)(OR$^9$)$_2$), wherein each R$^9$ are independently hydrogen, an unsubstituted C$_{1-6}$ alkyl, an unsubstituted C$_{2-6}$ alkenyl, an unsubstituted C$_{1-6}$ haloalkyl, an unsubstituted or a substituted aryl or an unsubstituted or a substituted aryl(C$_{1-4}$ alkyl), or —C(=O)CH$_2$—O—((P=O)(OR$^{10}$)$_2$), wherein each R$^{10}$ are independently hydrogen, an unsubstituted C$_{1-6}$ alkyl, an unsubstituted C$_{2-6}$ alkenyl, an unsubstituted C$_{1-6}$ haloalkyl, an unsubstituted or a substituted aryl or an unsubstituted or a substituted aryl(C$_{1-4}$ alkyl).

4. The compound of claim 1, wherein $Z^1$ is —C(=O)—.

5. The compound of claim 1, wherein Ring A$^1$ is an unsubstituted or a substituted pyrrolidine.

6. The compound of claim 1, wherein Ring A$^1$ is an unsubstituted or a substituted azetidine, wherein the azetidine is connected to a cyclic moiety selected from the group consisting of a monocyclic C$_{3-7}$ cycloalkyl, a bicyclic C$_{5-9}$ cycloalkyl, a monocyclic C$_{3-7}$ cycloalkenyl, a bicyclic C$_{5-9}$ cycloalkenyl and phenyl, wherein the cyclic moiety is connected to the azetidine in a fused-fashion or a spiro-fashion that can be optionally substituted with one or more moieties independently selected from the group consisting of halogen, an unsubstituted $C_{1-4}$ alkyl and an unsubstituted $C_{2-4}$ alkenyl, or an unsubstituted or a substituted pyrrolidine, wherein the pyrrolidine is connected to a cyclic moiety selected from the group consisting of a monocyclic $C_{3-7}$ cycloalkyl, a bicyclic $C_{5-9}$ cycloalkyl, a monocyclic $C_{3-7}$ cycloalkenyl, a bicyclic $C_{5-9}$ cycloalkenyl and phenyl, wherein the cyclic moiety is connected to the pyrrolidine in a fused-fashion or a spiro-fashion that can be optionally substituted with one or more moieties independently selected from the group consisting of halogen, an unsubstituted $C_{1-4}$ alkyl and an unsubstituted $C_{2-4}$ alkenyl, or an unsubstituted or a substituted piperidine, wherein the piperidine is connected to a cyclic moiety selected from the group consisting of a monocyclic $C_{3-7}$ cycloalkyl, a bicyclic $C_{5-9}$ cycloalkyl, a monocyclic $C_{3-7}$ cycloalkenyl, a bicyclic $C_{5-9}$ cycloalkenyl and phenyl, wherein the cyclic moiety is connected to the piperidine in a fused-fashion or a spiro-fashion that can be optionally substituted with one or more moieties independently selected from the group consisting of halogen, an unsubstituted $C_{1-4}$ alkyl and an unsubstituted $C_{2-4}$ alkenyl.

7. The compound of claim 1, wherein $Z^2$ is $NR^8$; and $Z^3$ is $CR^5$.

8. The compound of claim 1, wherein $R^6$ and $R^7$ are taken together with the carbon to which $R^6$ and $R^7$ are each attached to form an optionally substituted 4-7 membered unsaturated ring that can optionally contain 1 or 2 ring heteroatoms selected from the group consisting of O, N and S.

9. The compound of claim 8, wherein $R^6$ and $R^7$ are taken together with the carbon to which $R^6$ and $R^7$ are each attached to form an optionally substituted phenyl ring.

10. The compound of claim 1, wherein $R^3$ is an unsubstituted or a substituted monocyclic nitrogen-containing heterocyclyl($C_{1-4}$ alkyl) or an unsubstituted or a substituted bicyclic nitrogen-containing heterocyclyl($C_{1-4}$ alkyl).

11. The compound of claim 1, wherein $R^2$ is hydrogen; and $R^4$ is hydrogen.

12. The compound of claim 1, wherein the compound is selected from the group consisting of:

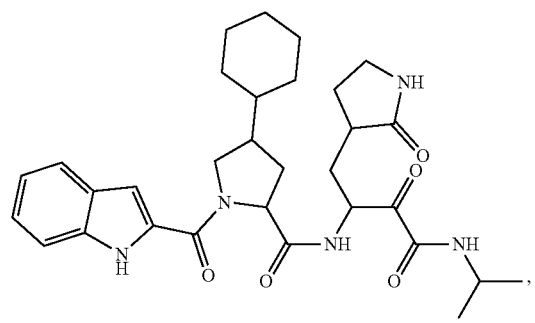

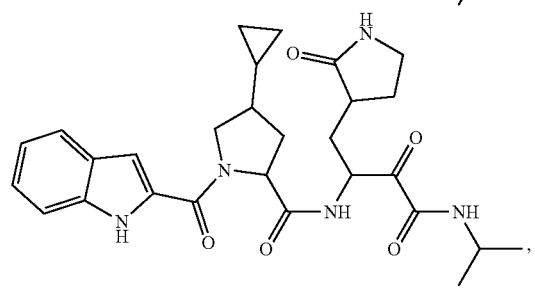

-continued

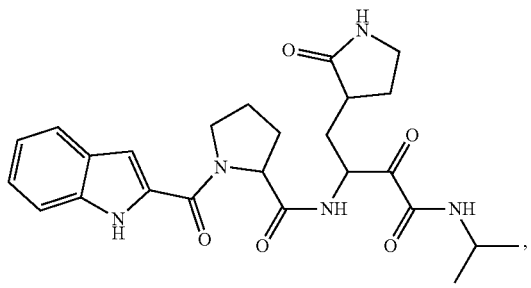

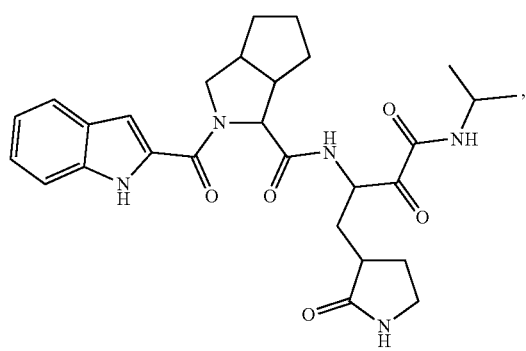

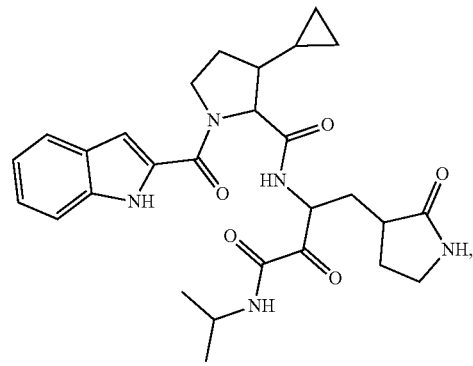

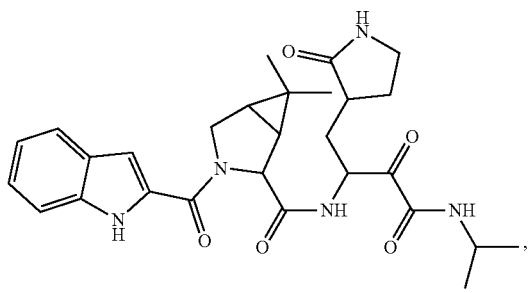

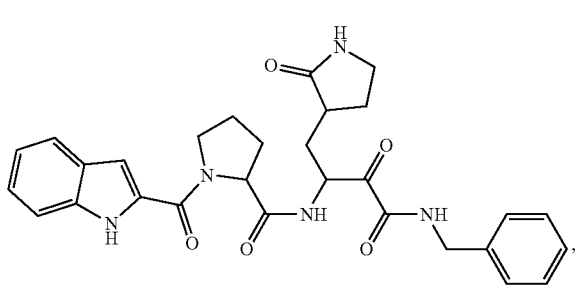

487
-continued
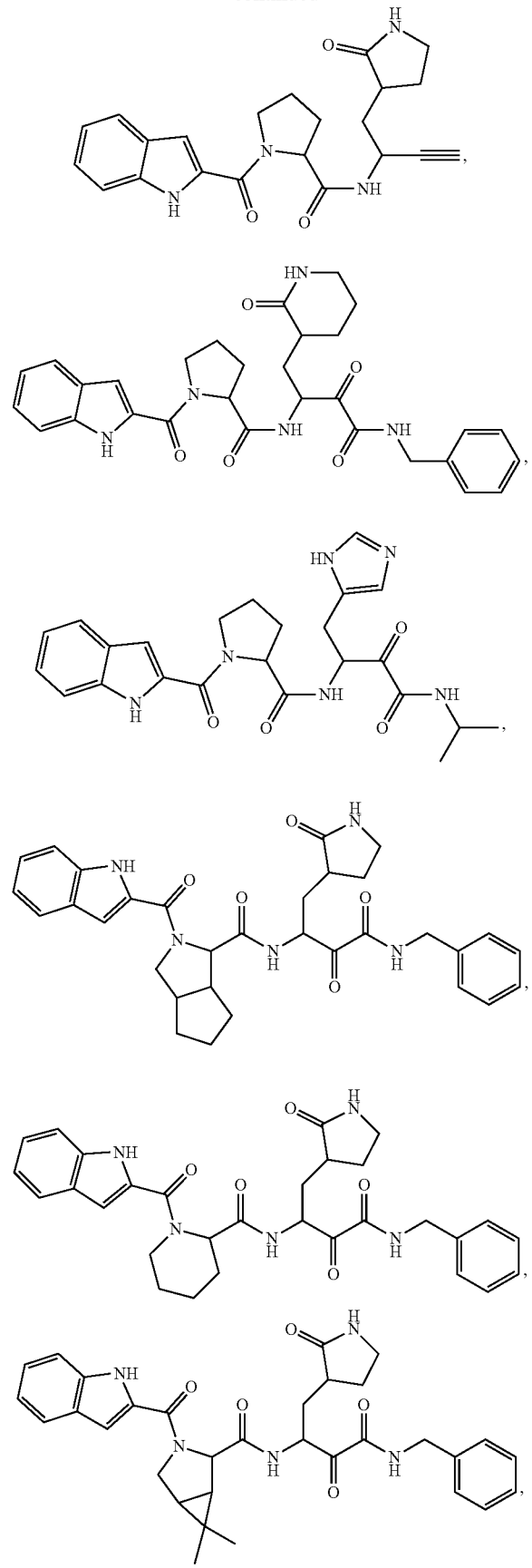
488
-continued
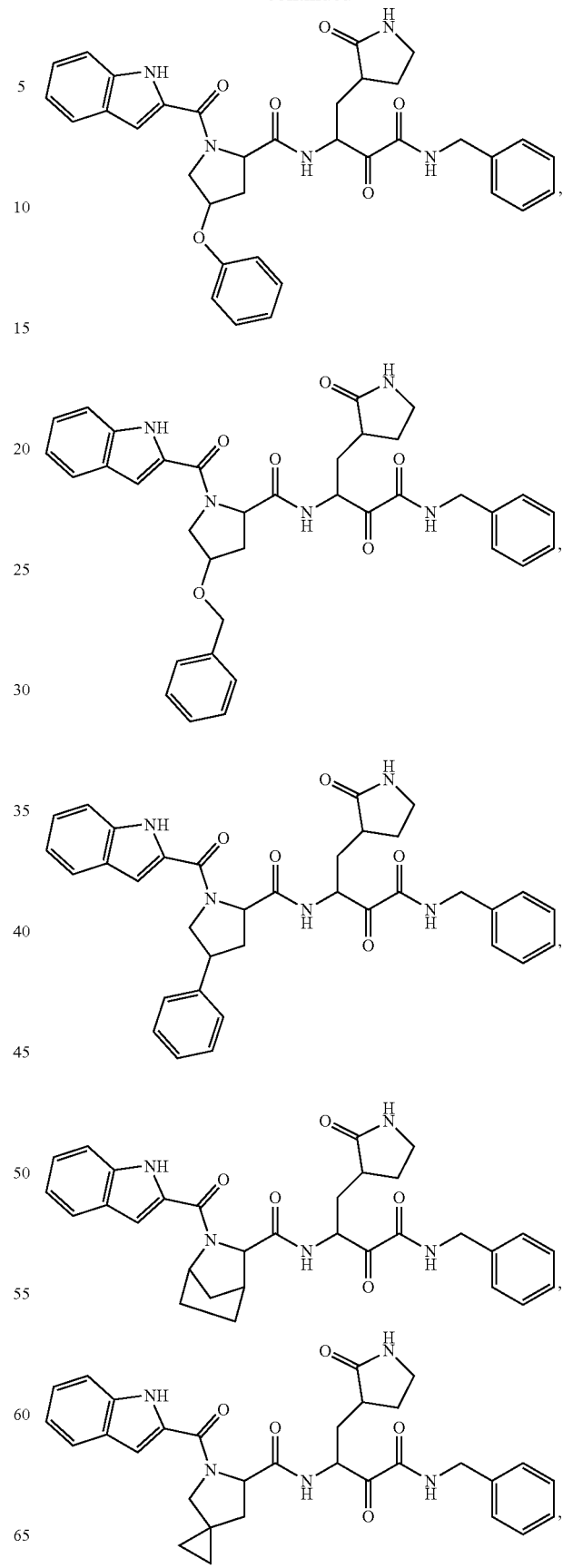

489
-continued
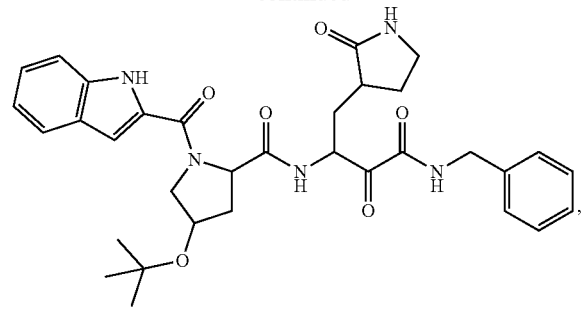
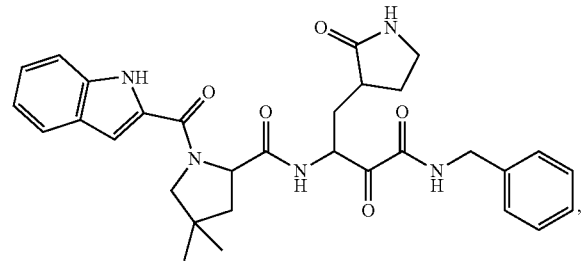
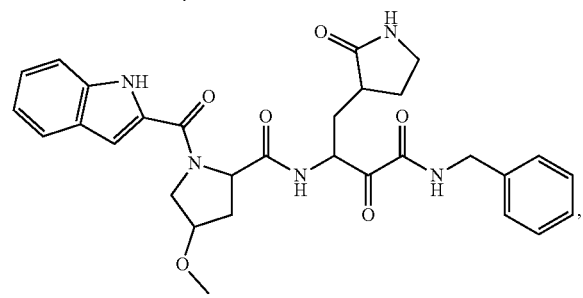
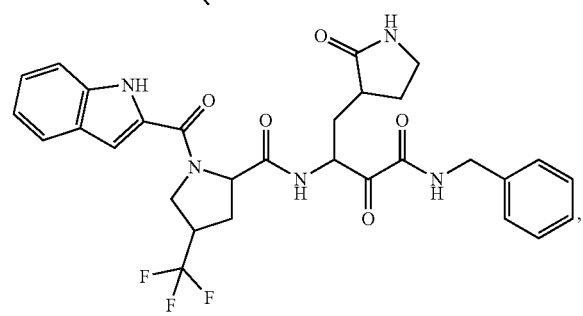
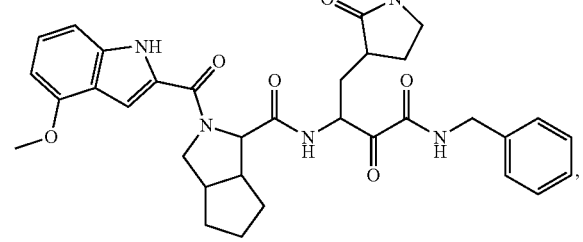
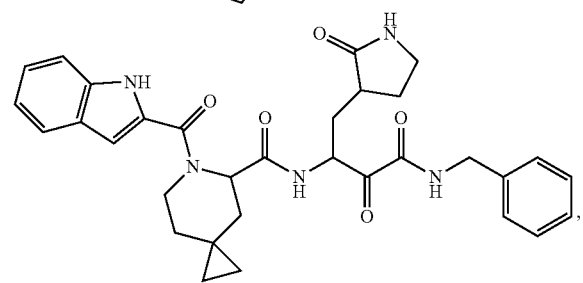
490
-continued
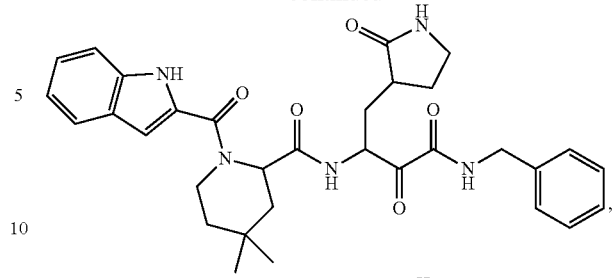
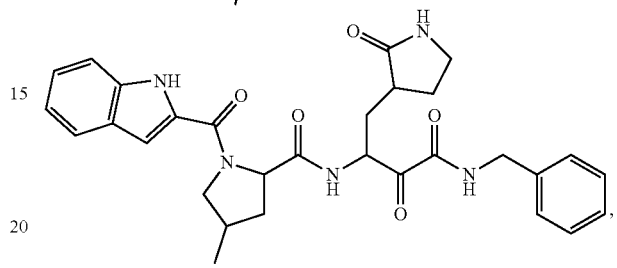
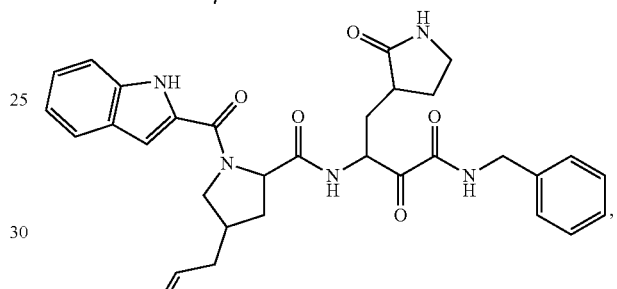
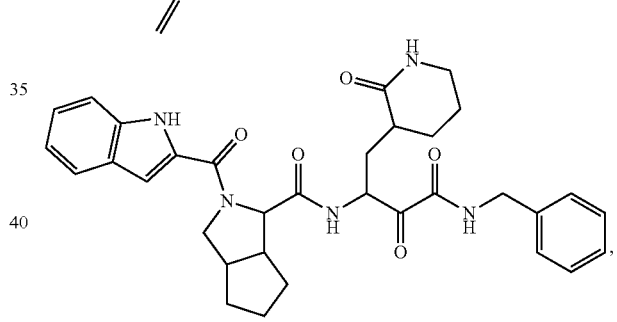
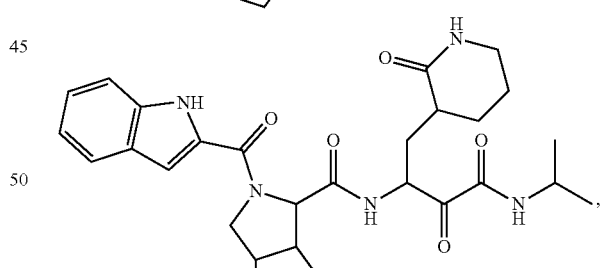
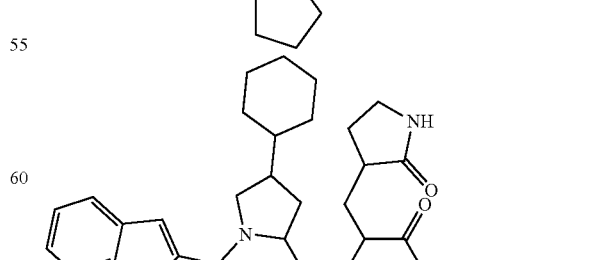

491
-continued
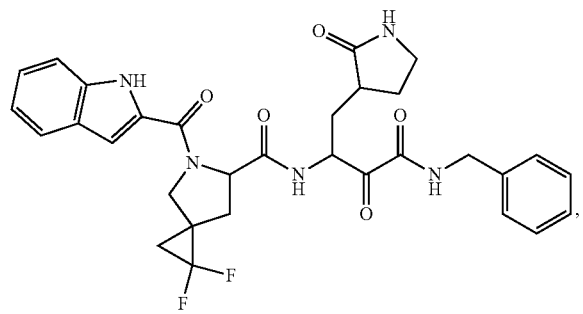
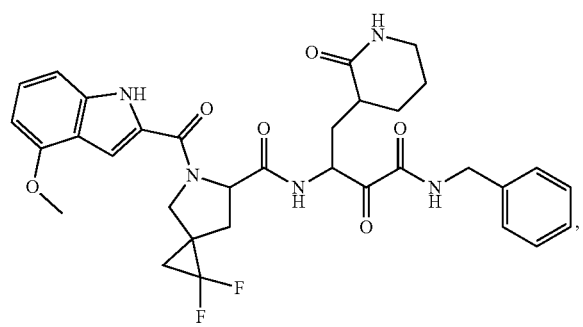
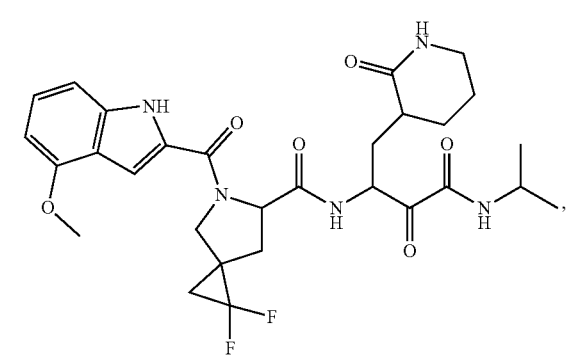
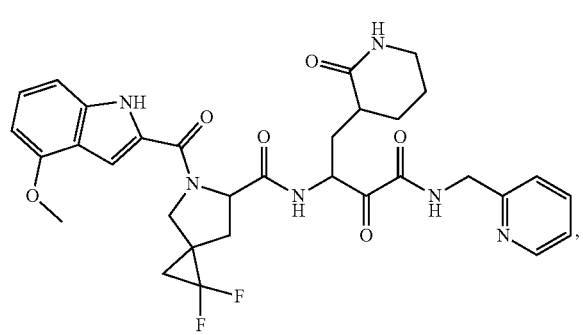
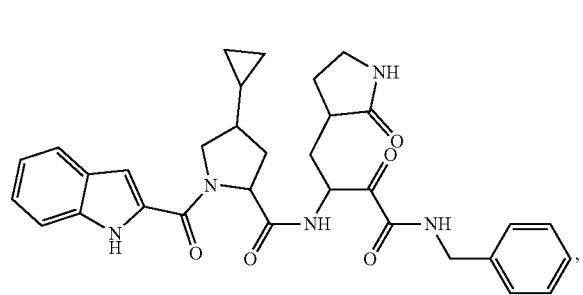
492
-continued
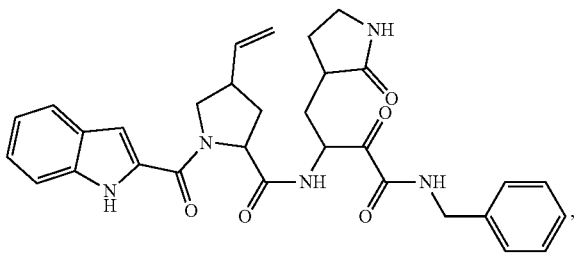
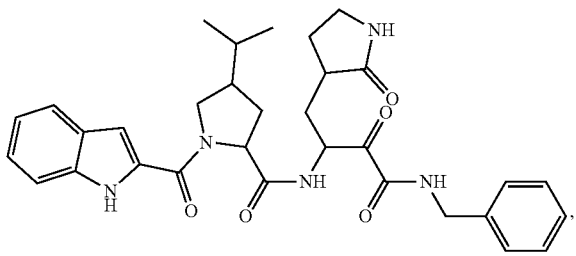
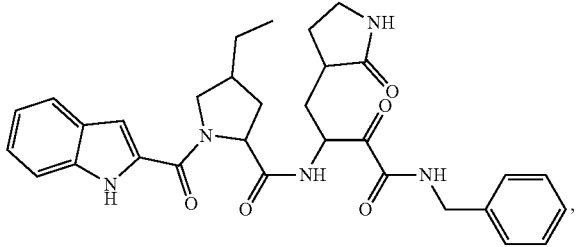
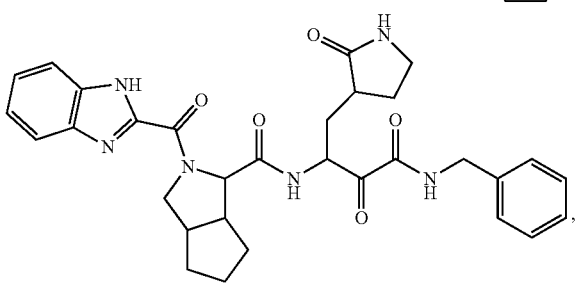
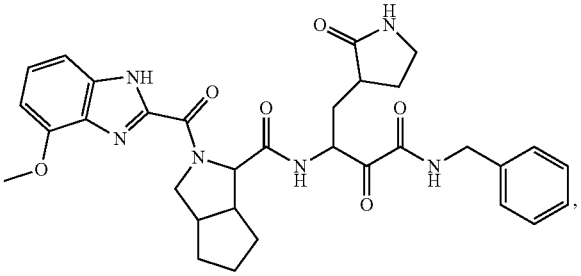
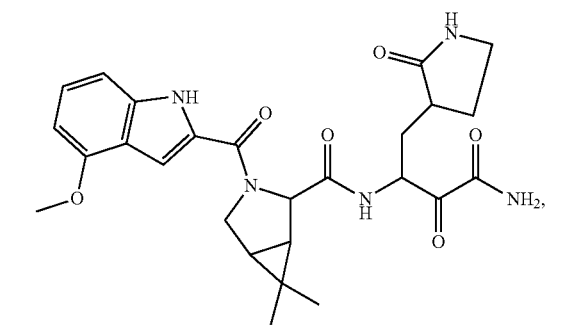

493
-continued
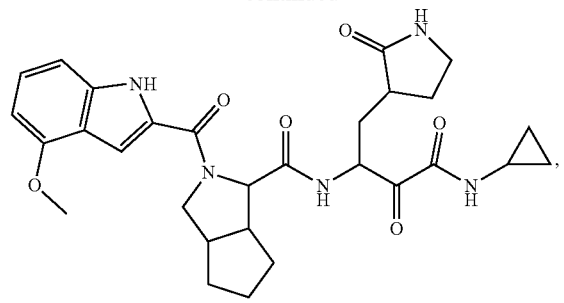
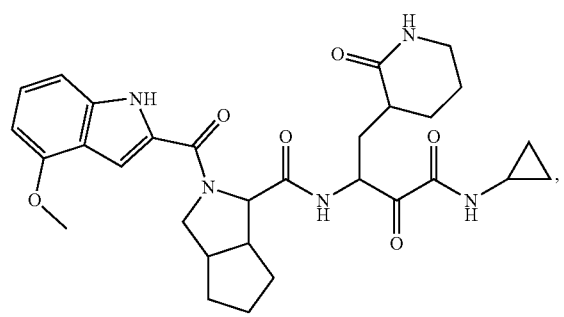
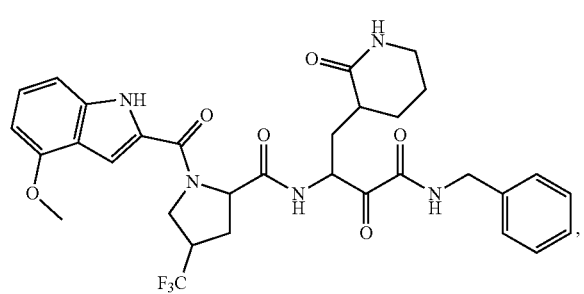
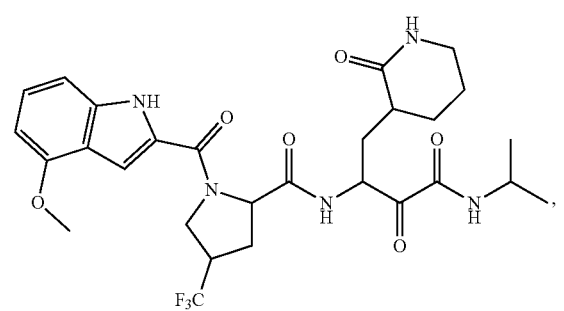
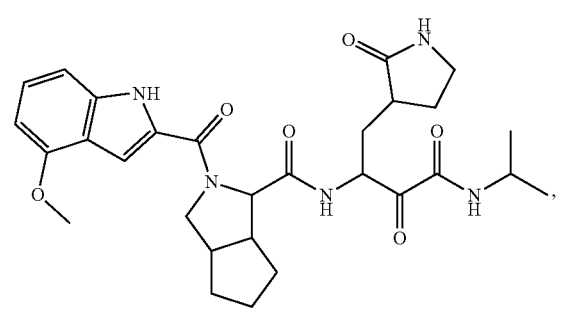
494
-continued
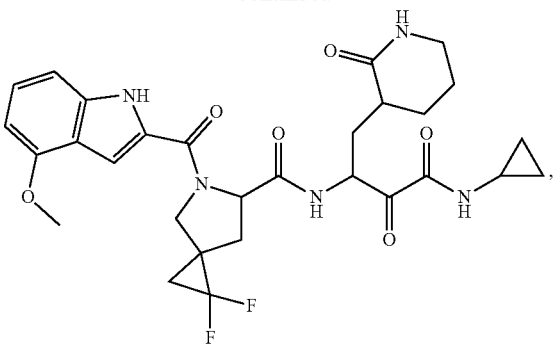
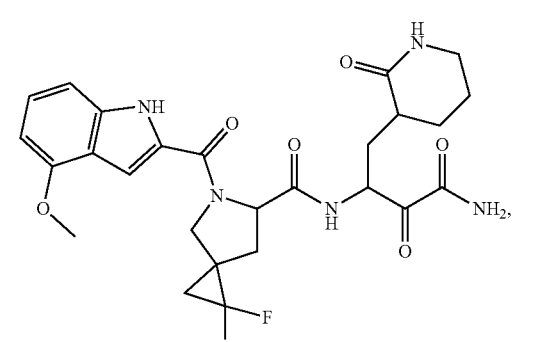
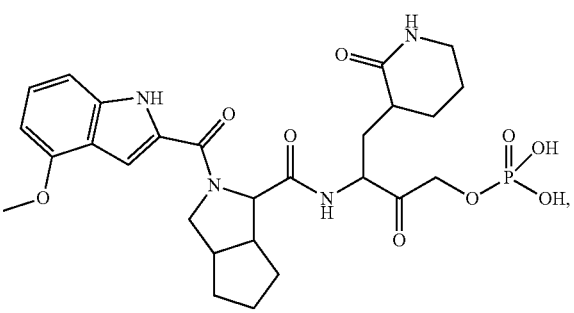
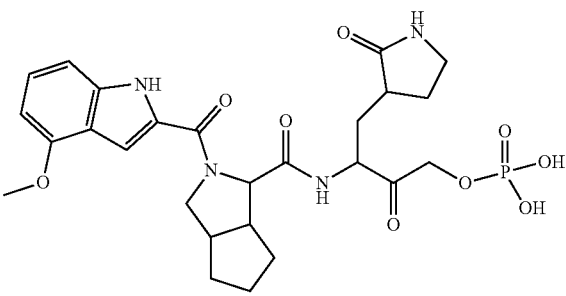
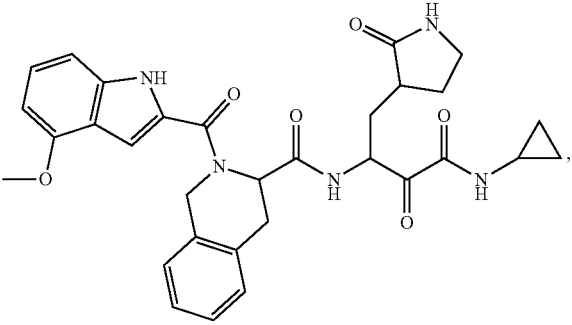

495
-continued
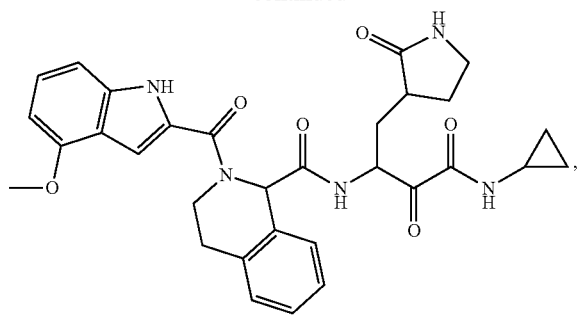
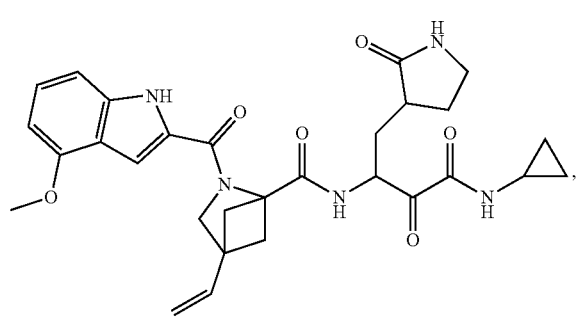
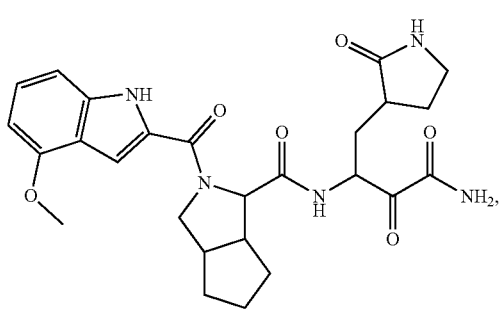
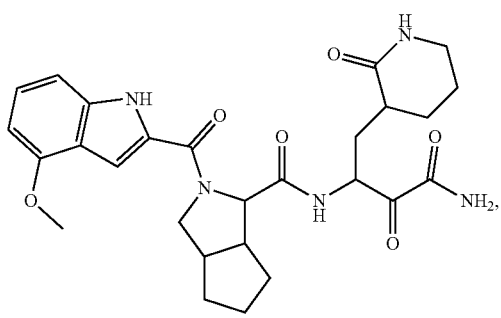
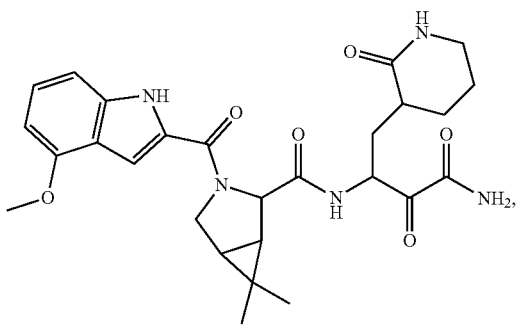
496
-continued
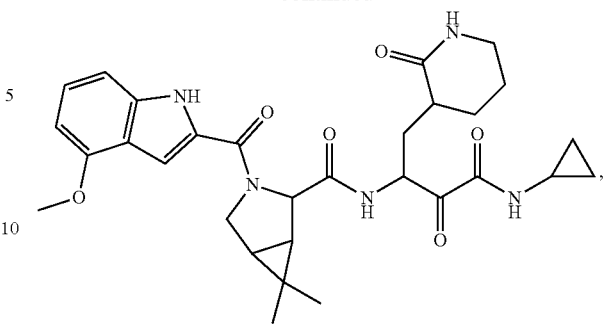
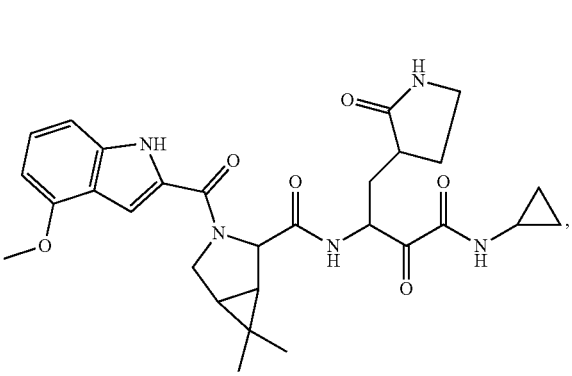
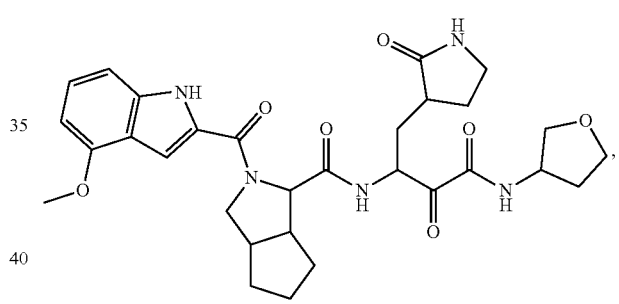
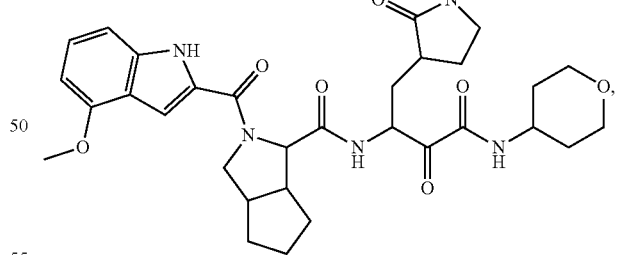
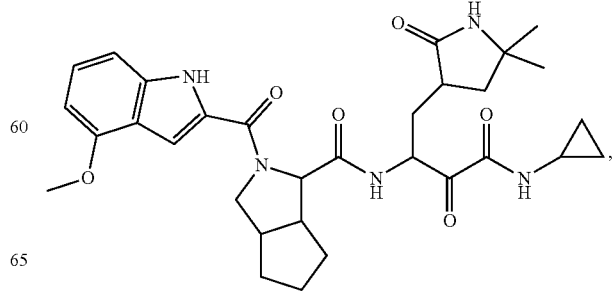

497
-continued
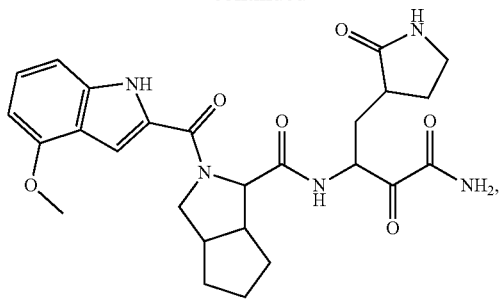
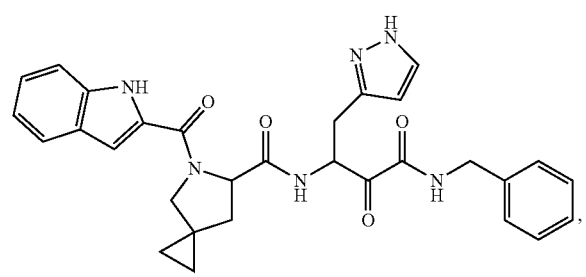
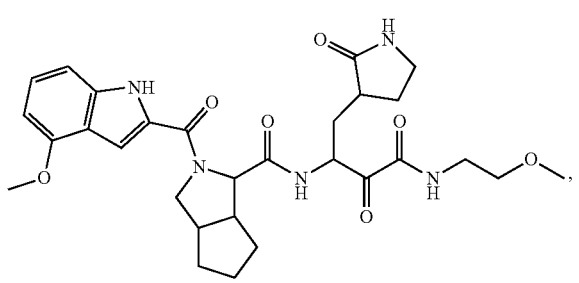
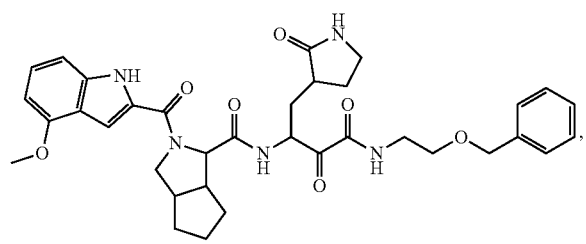
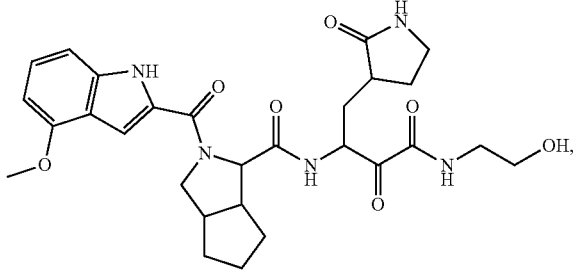
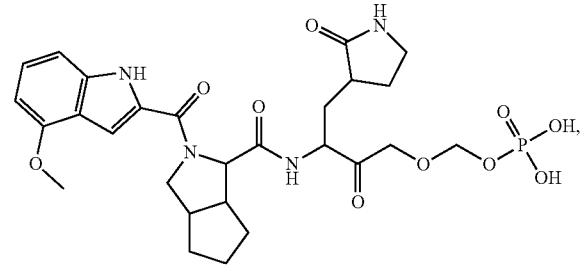
498
-continued
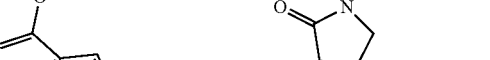
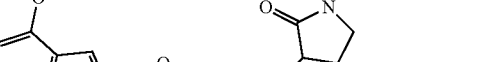

499
-continued
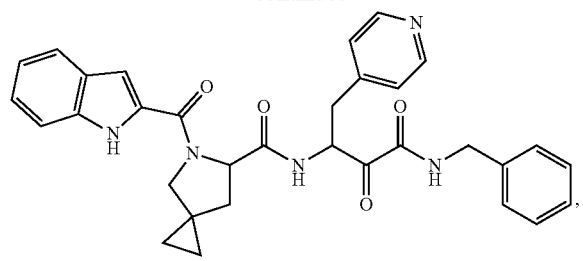
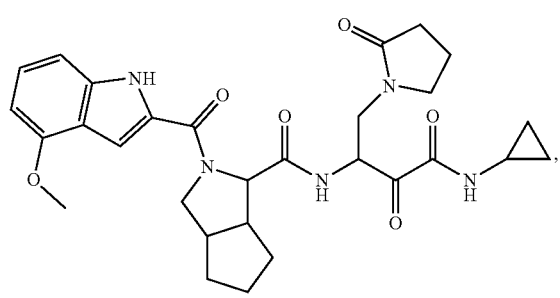
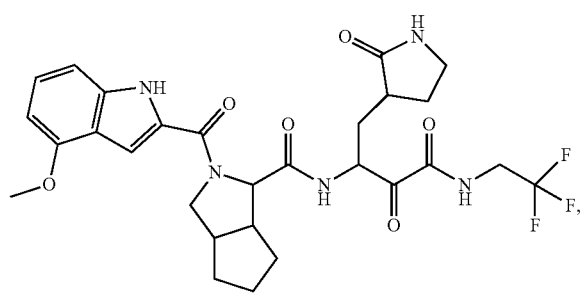
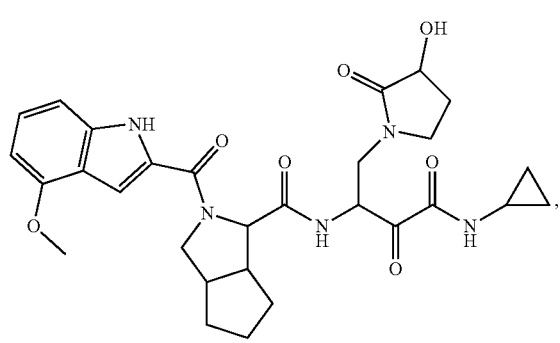
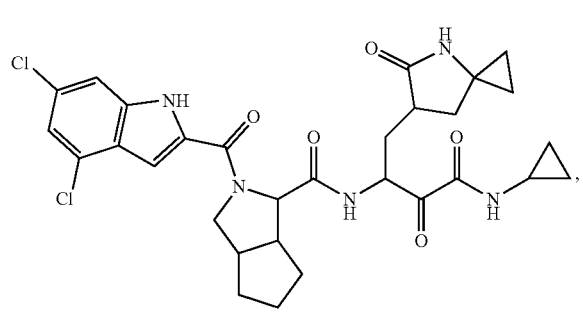
500
-continued
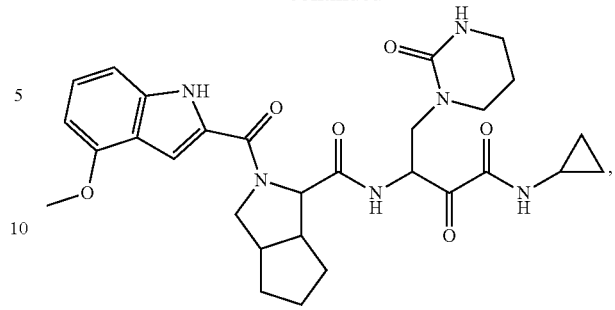
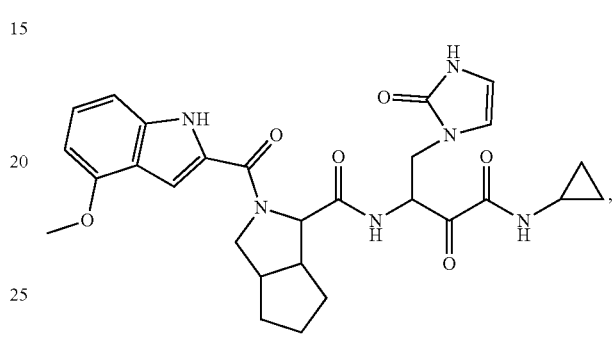
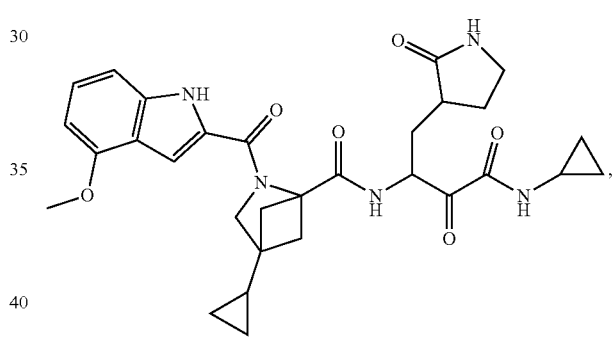
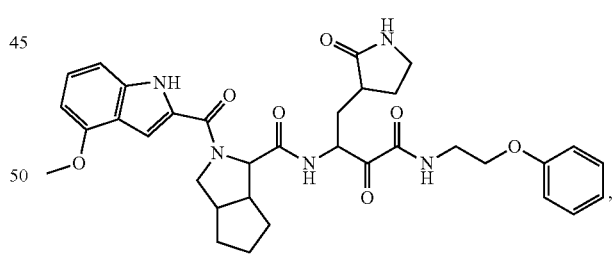
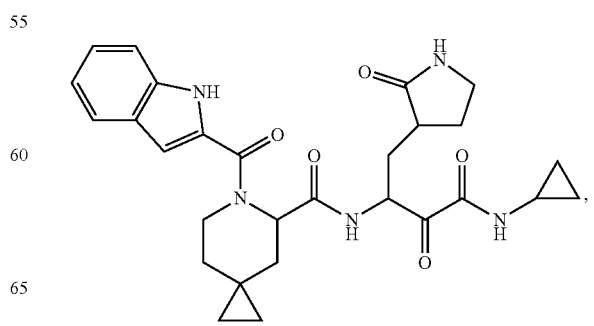

-continued
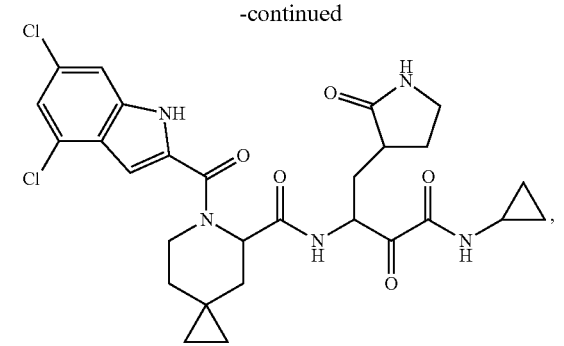
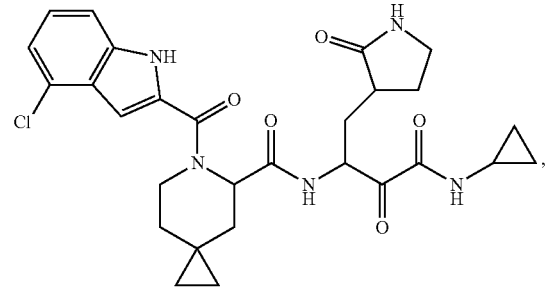
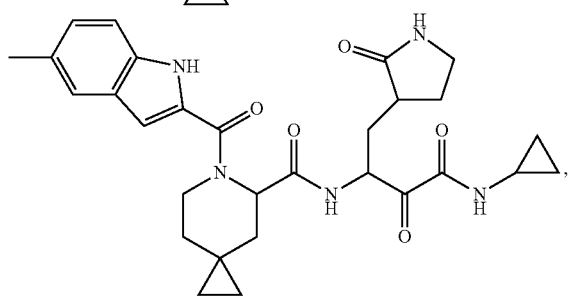
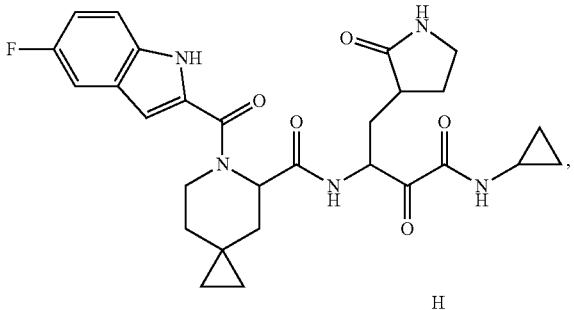
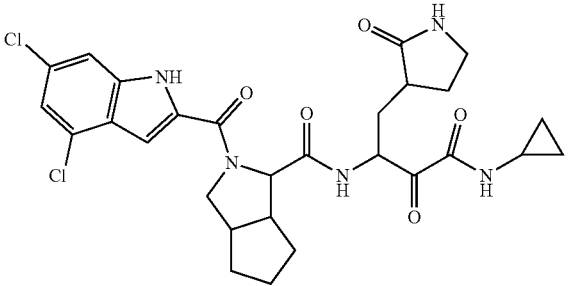
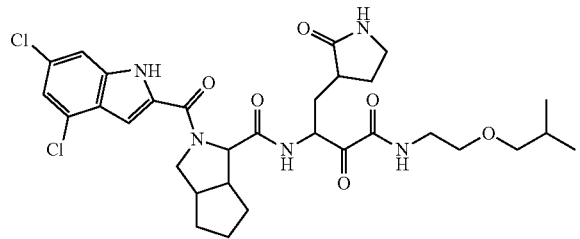
-continued
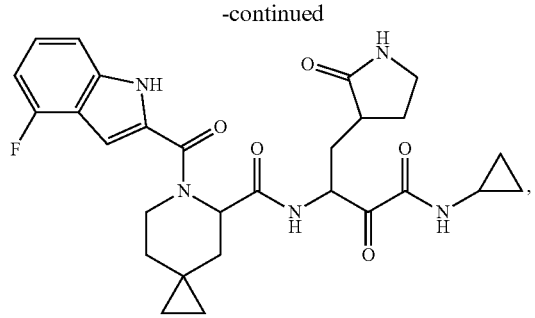
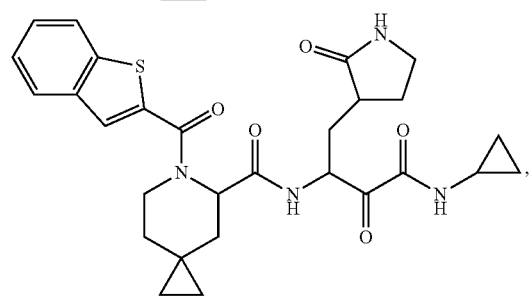
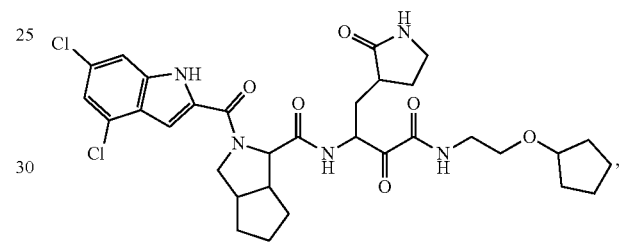
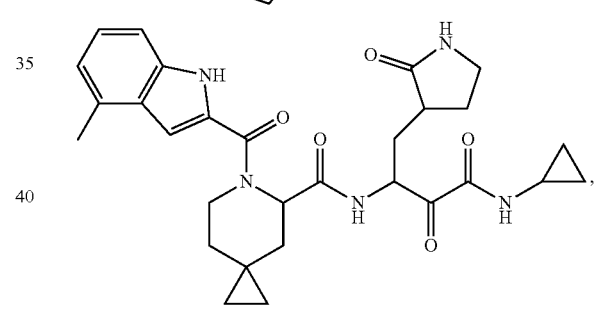
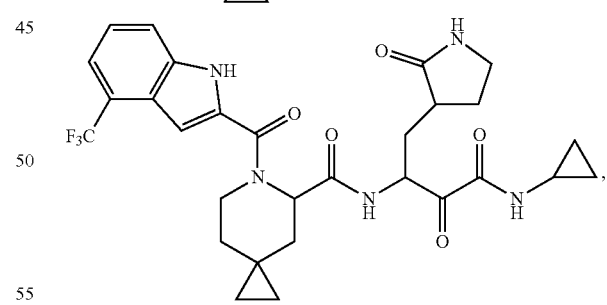
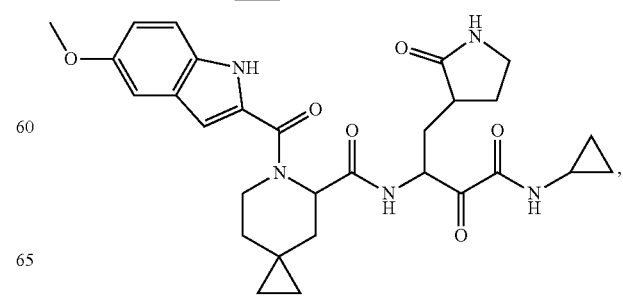

503
-continued
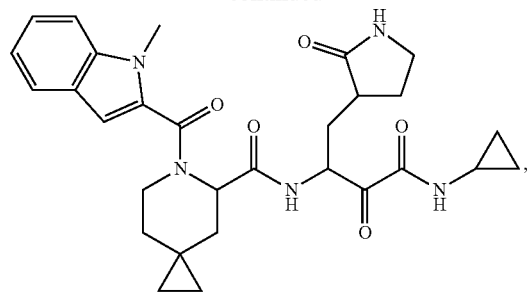
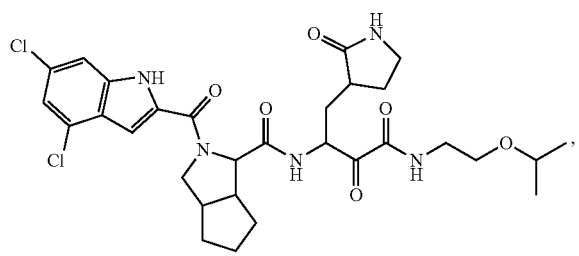 [SMILES: CC(C)CCCNC(=O)C(=O)C(CC1CCNC1=O)NC(=O)C1C2CCCC2CN1C(=O)c1cc2c(Cl)cc(Cl)cc2[nH]1]
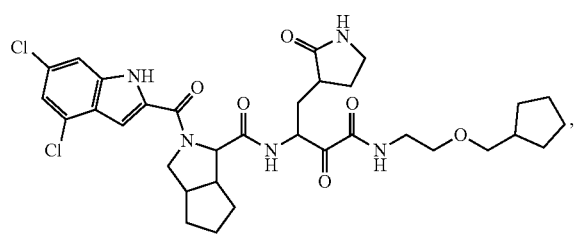
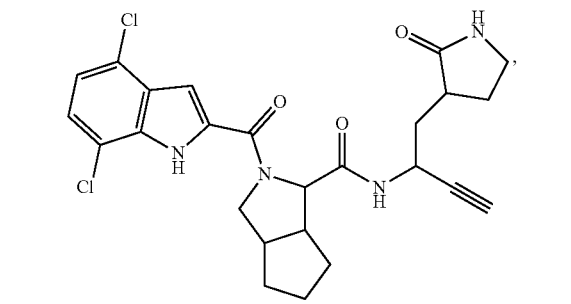
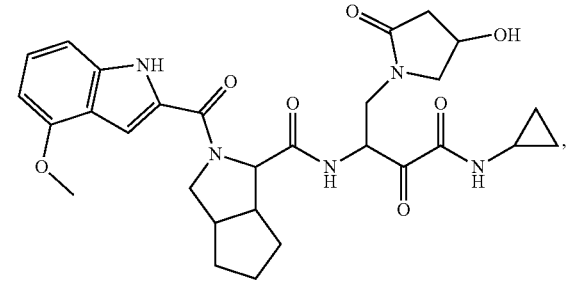
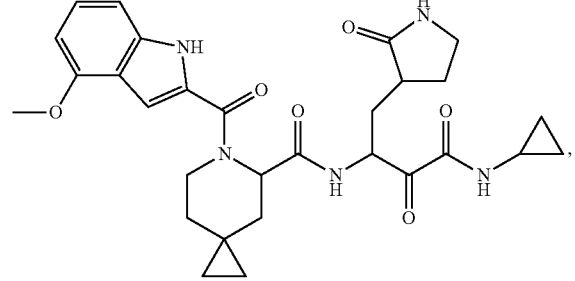
504
-continued
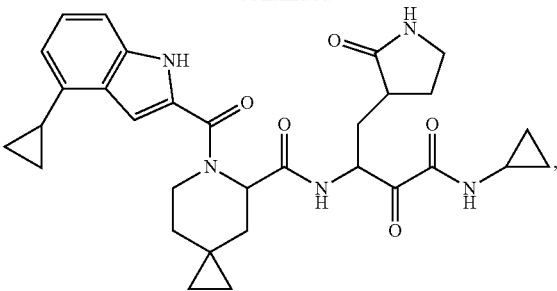
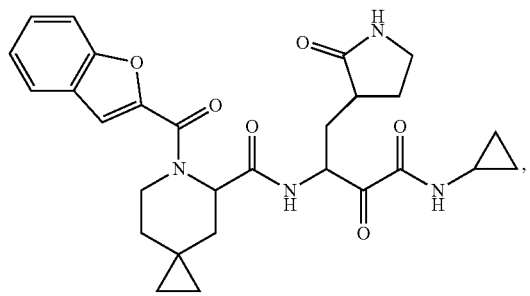
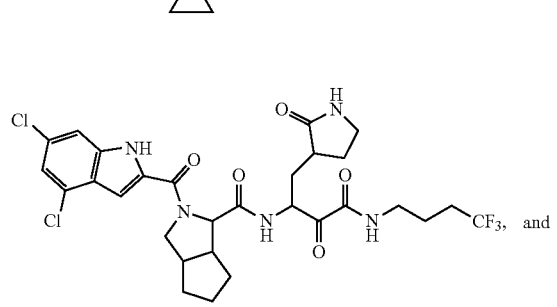
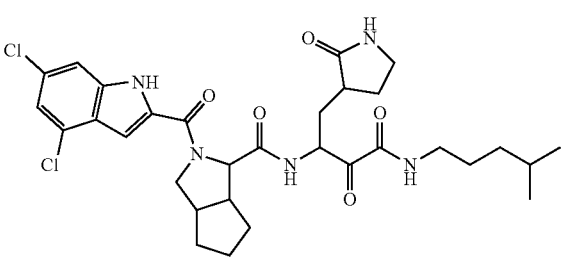
or pharmaceutically acceptable salt of any of the foregoing.
13. The compound of claim 1, wherein the compound is selected from the group consisting of:
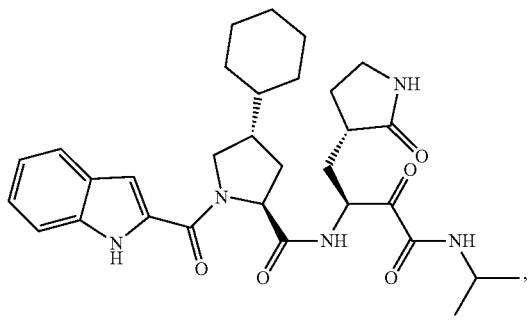

505
-continued
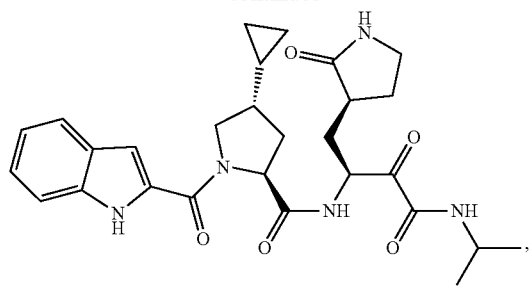
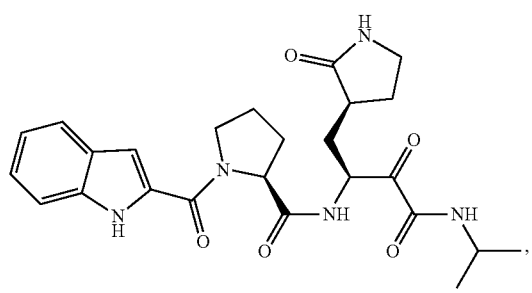
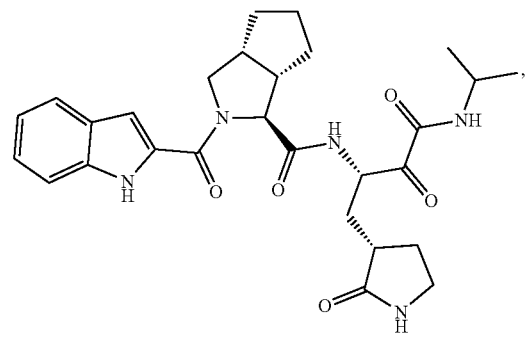
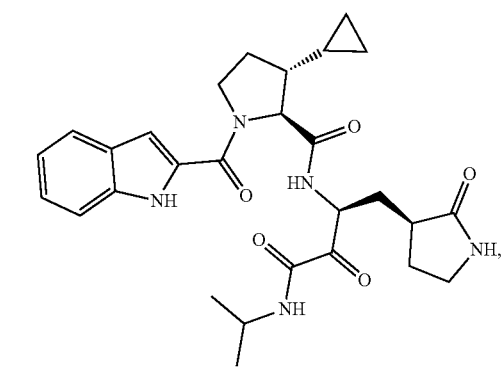
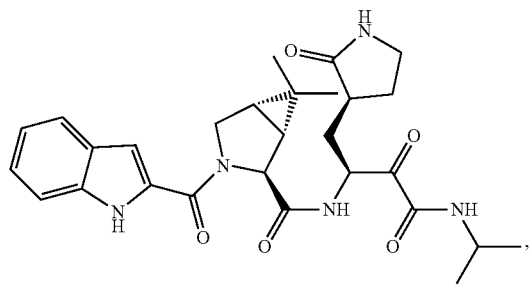
506
-continued
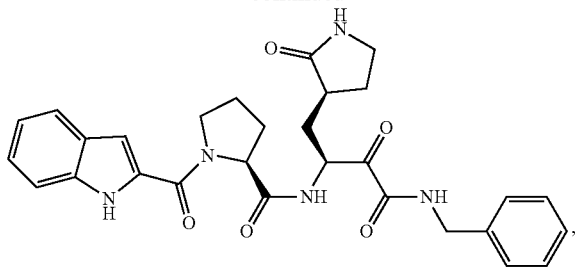
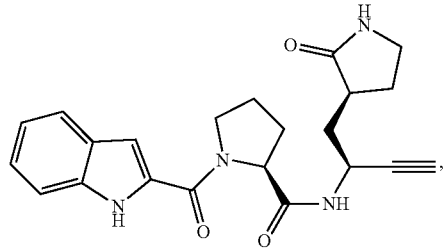
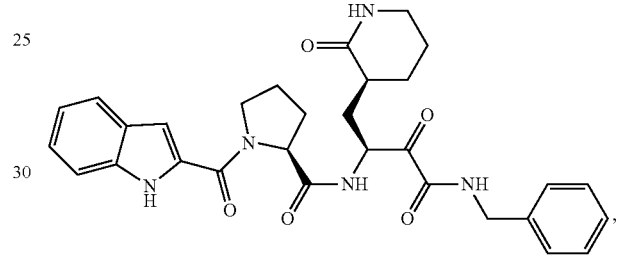
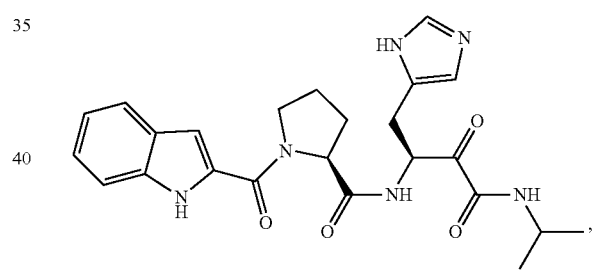
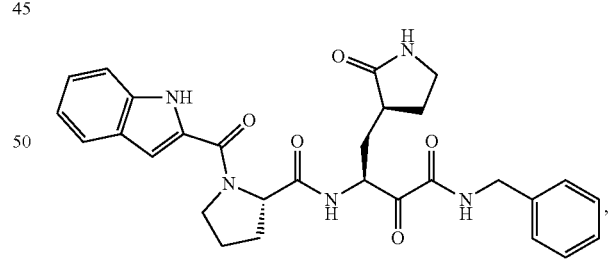
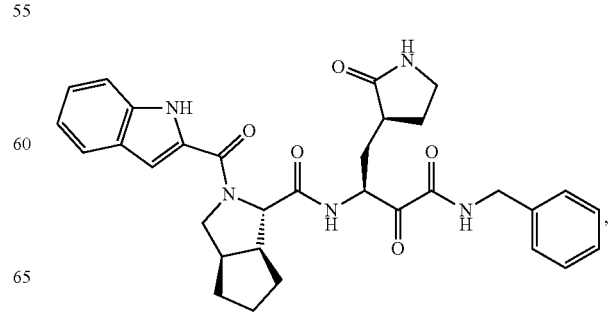

507
-continued
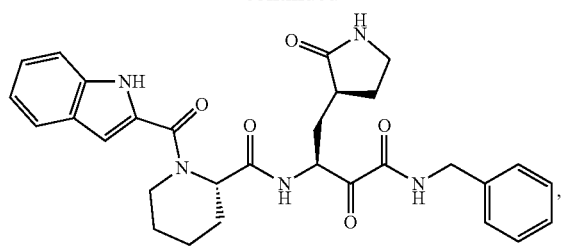
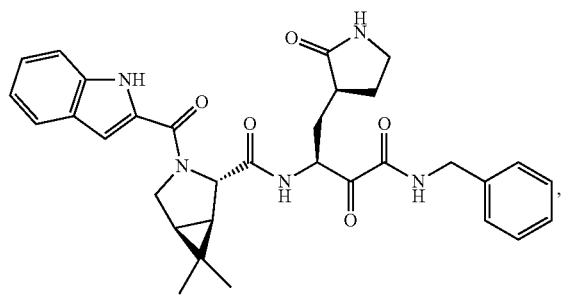
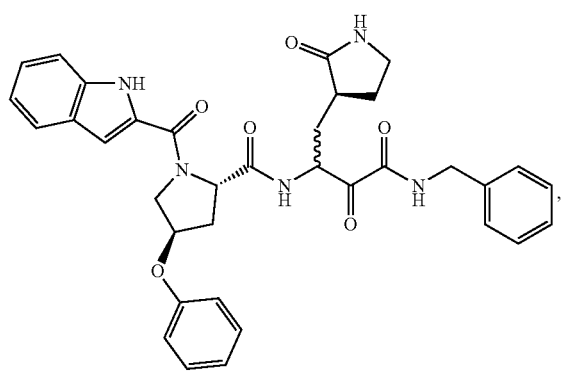
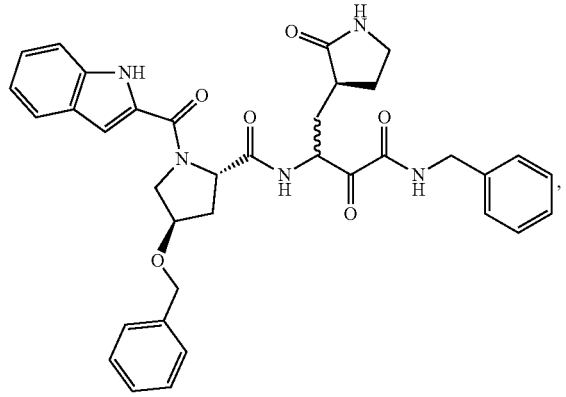
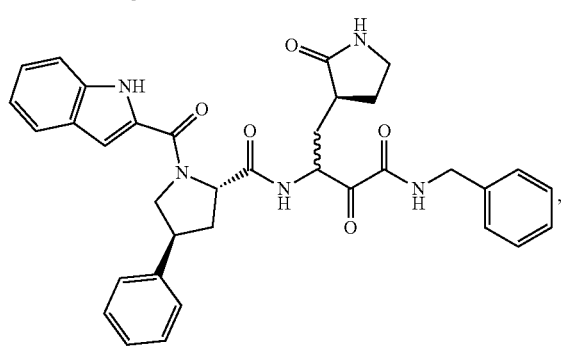
508
-continued
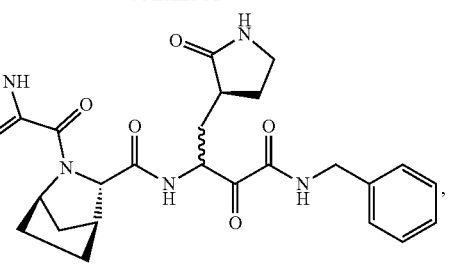
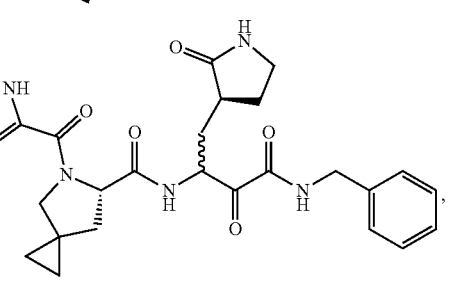
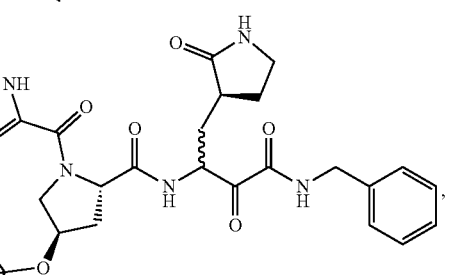
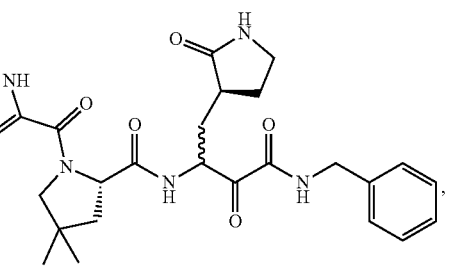
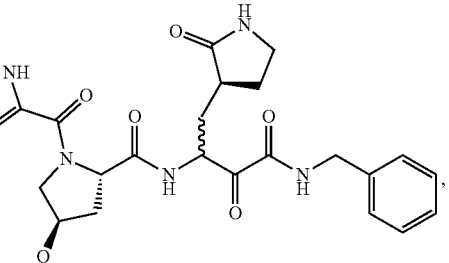
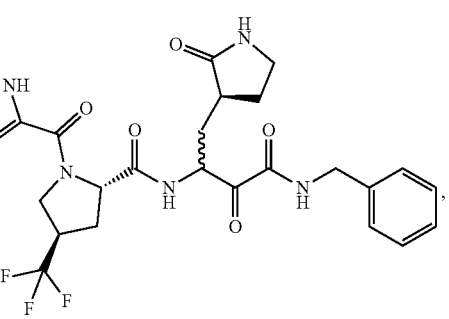

509
-continued
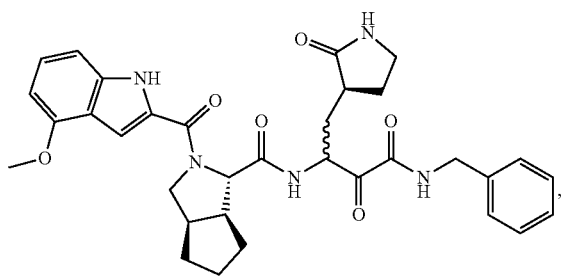
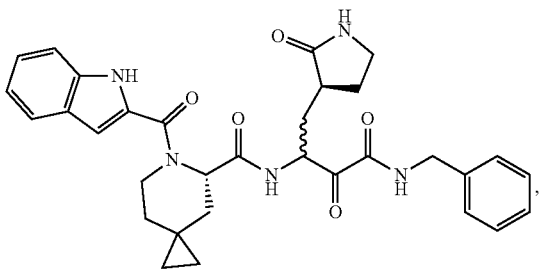
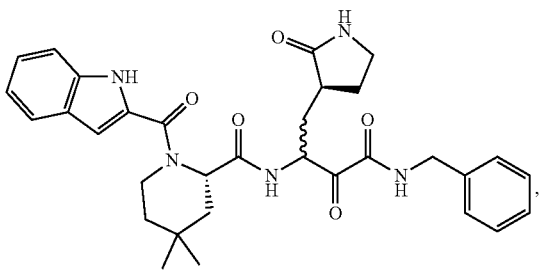
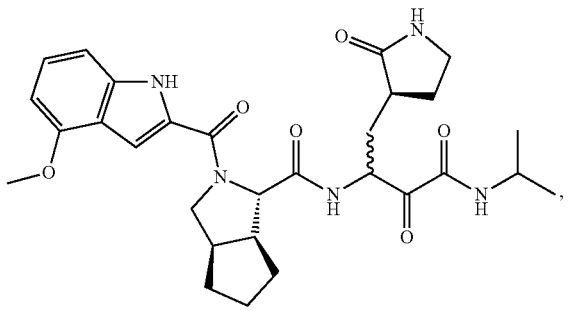
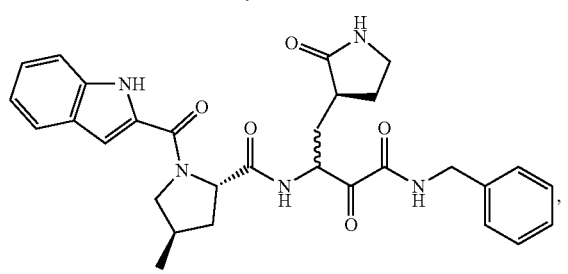
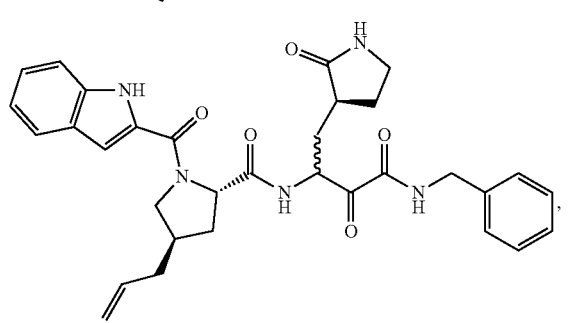
510
-continued
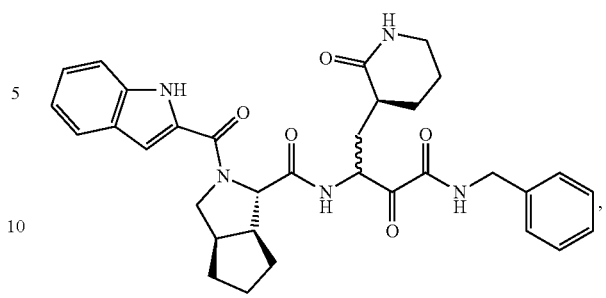
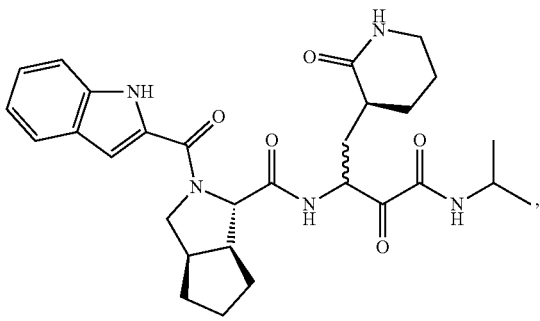
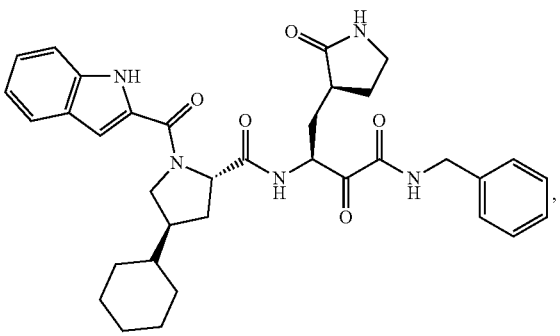
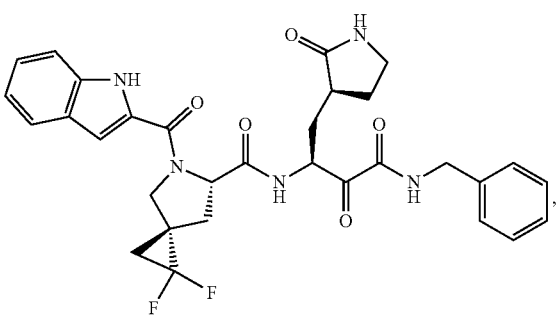
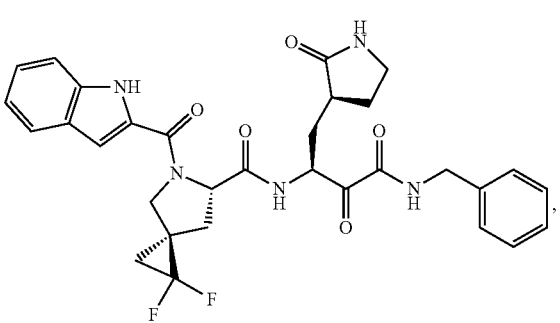

511
-continued
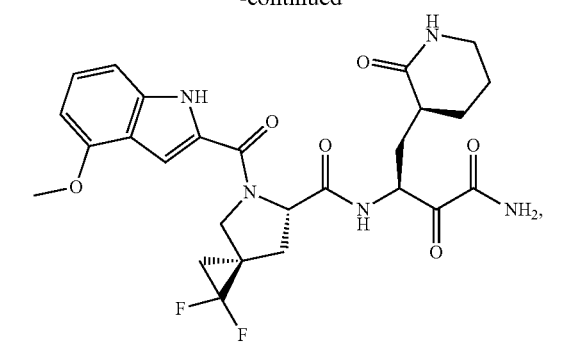
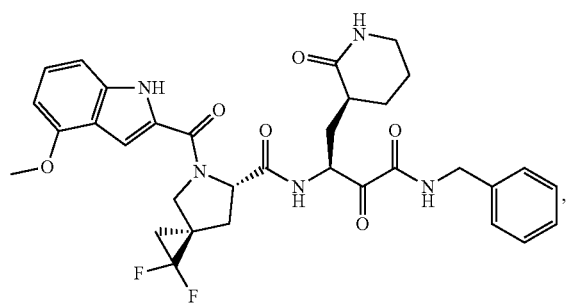
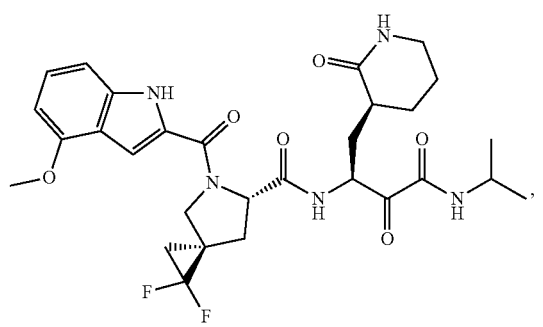
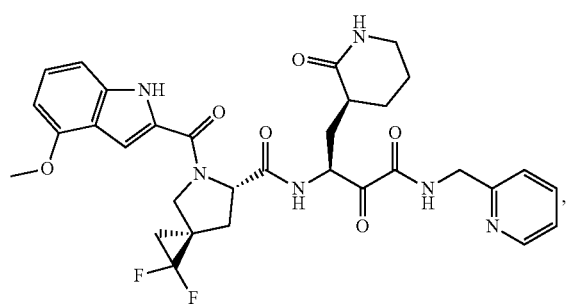
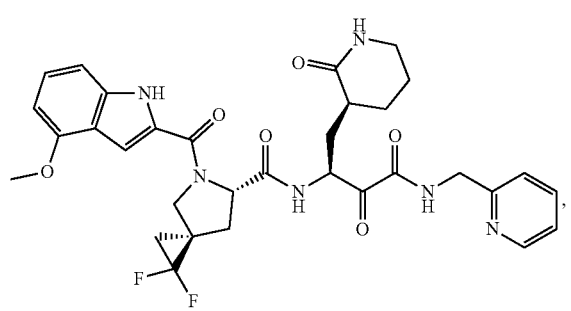
512
-continued
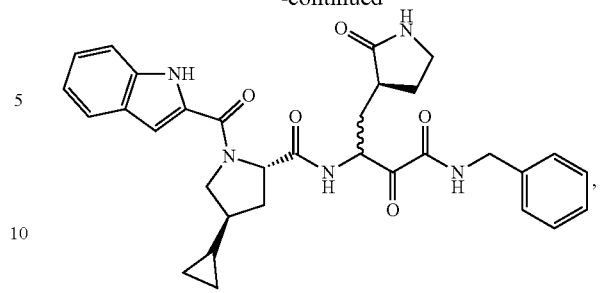
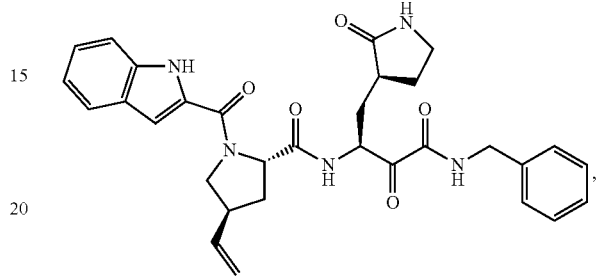
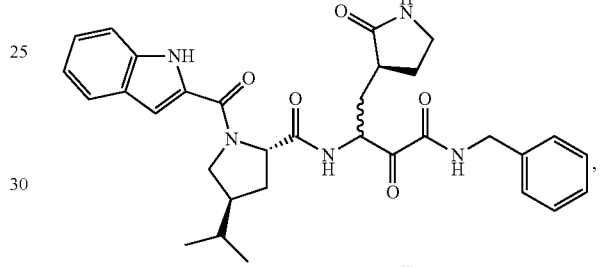
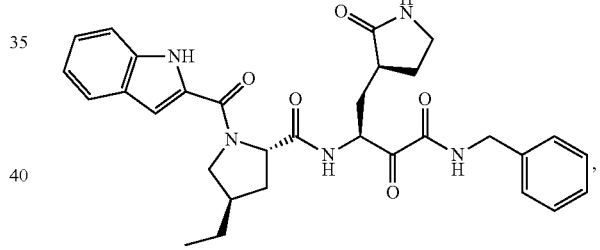
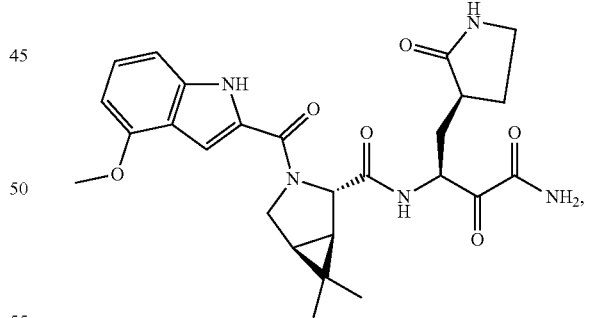
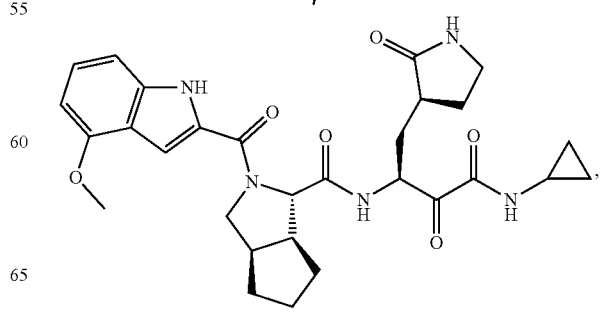

513
-continued
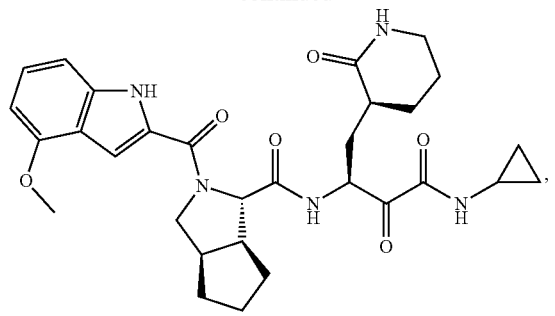
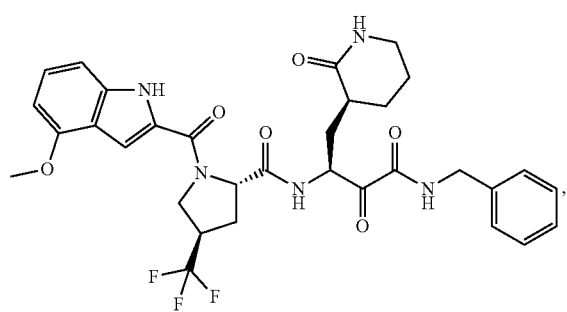
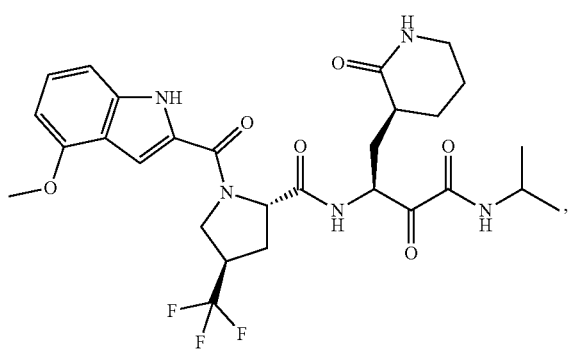
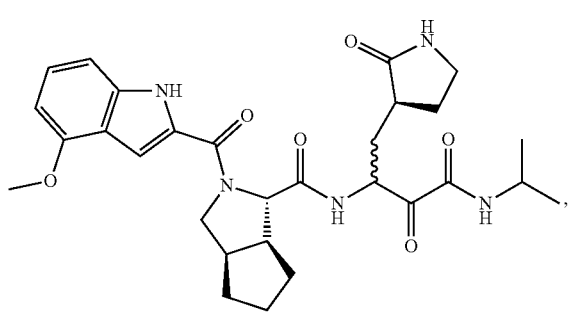
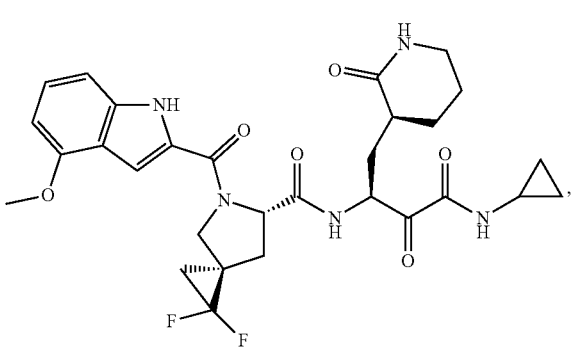
514
-continued
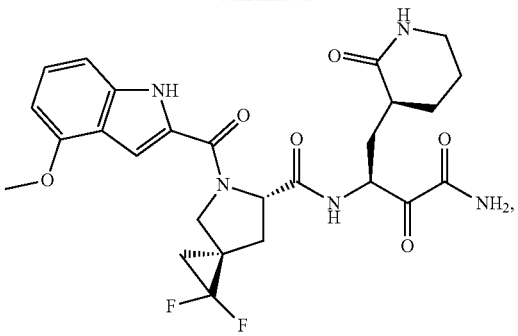
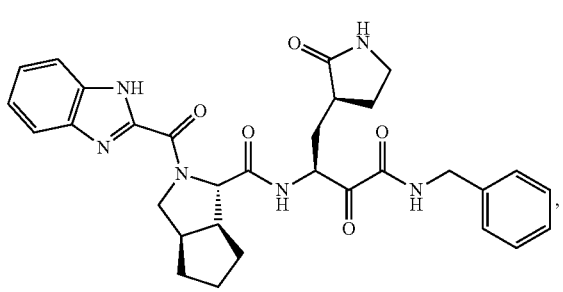
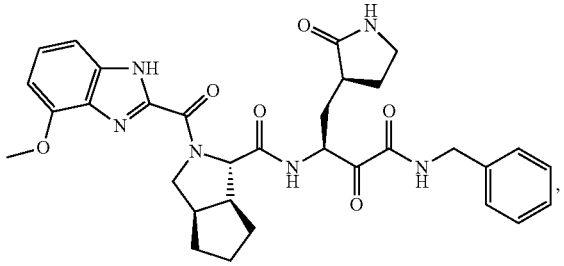
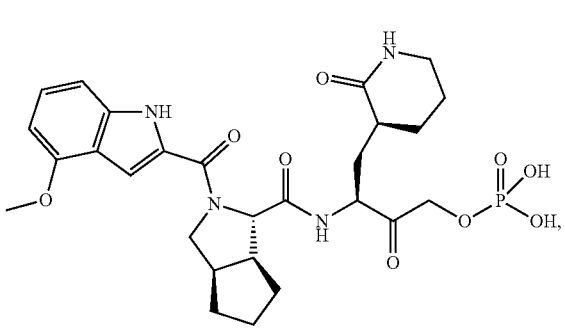
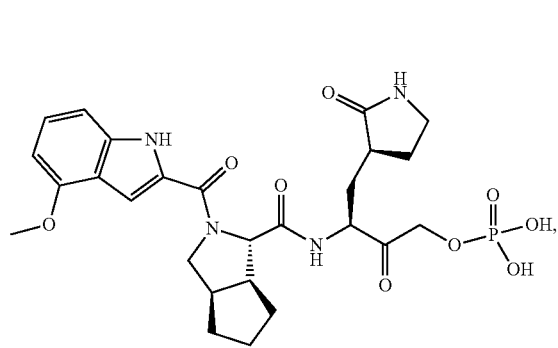

515
-continued
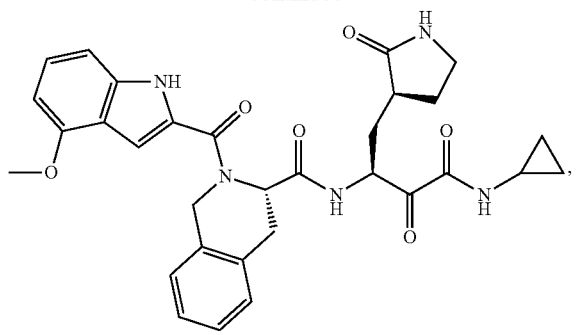
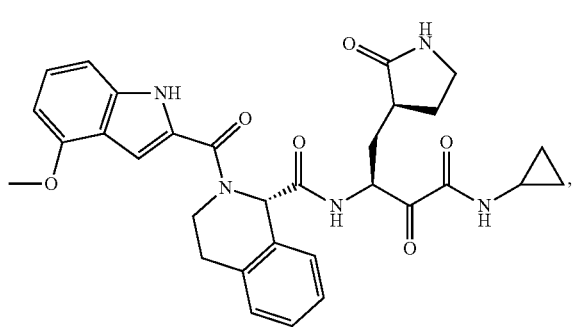
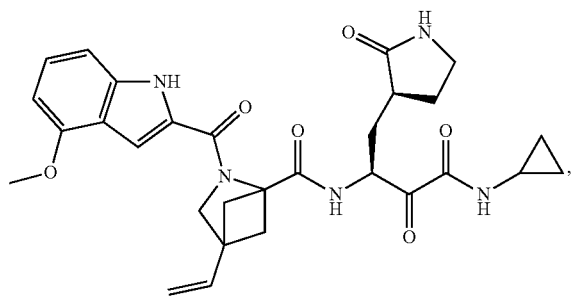
516
-continued
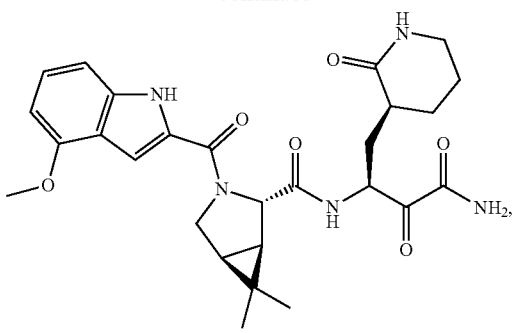
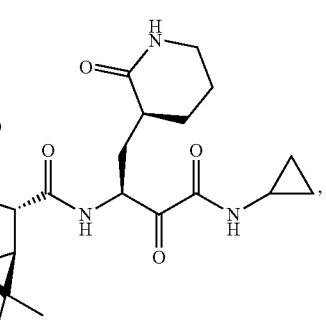
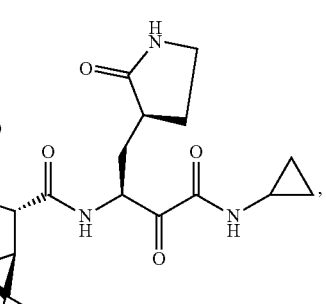
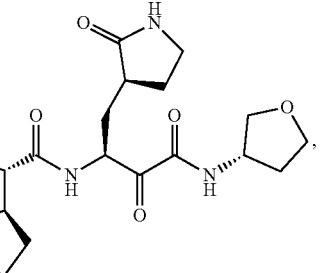
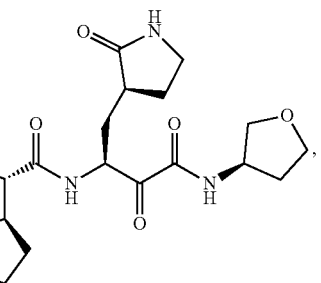

517
-continued
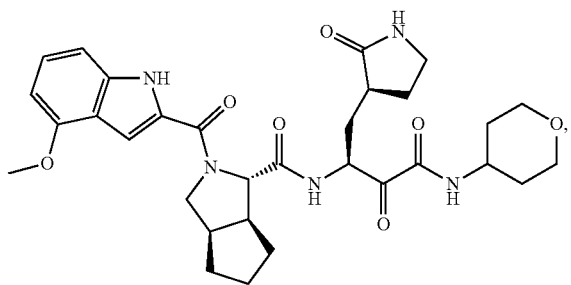
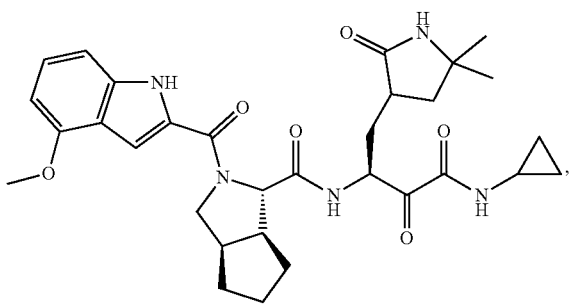
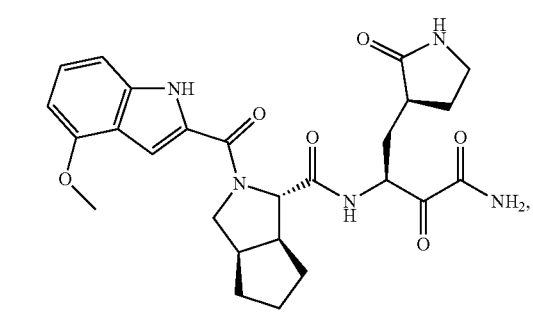
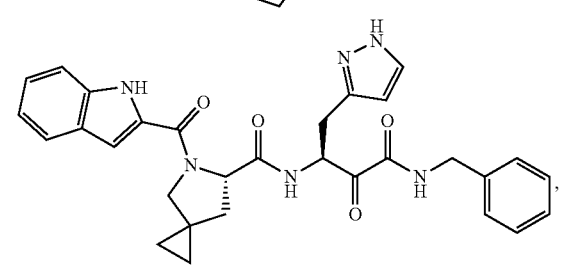
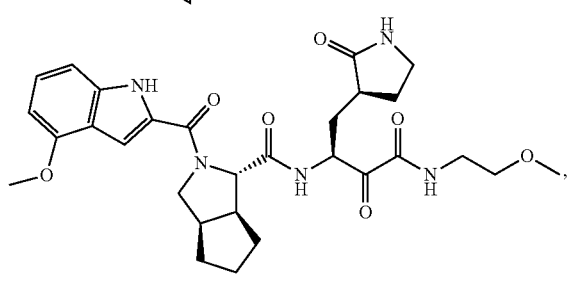
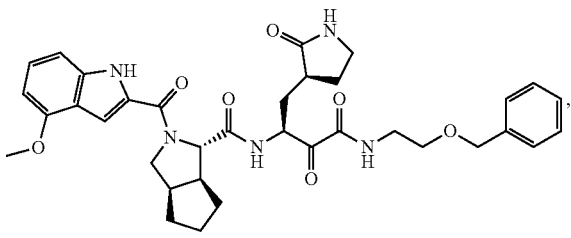
518
-continued
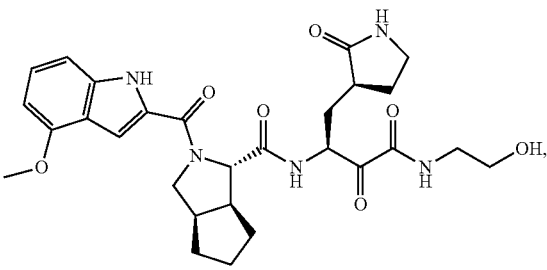
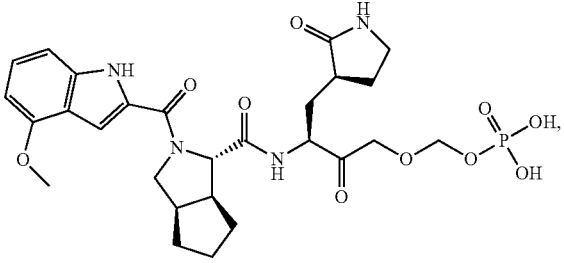
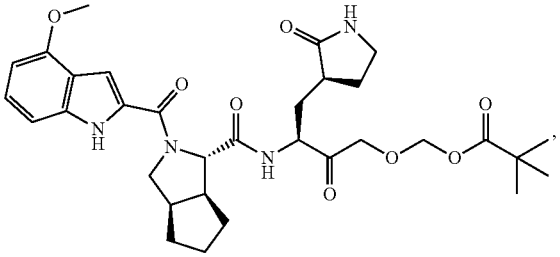
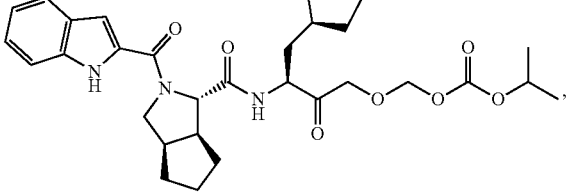
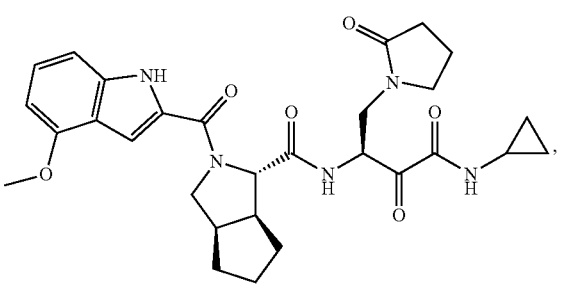
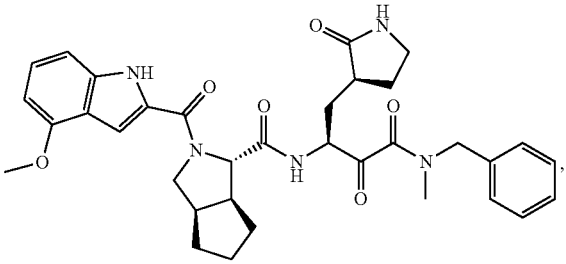

519
-continued
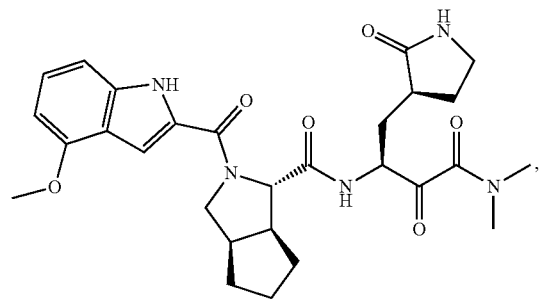
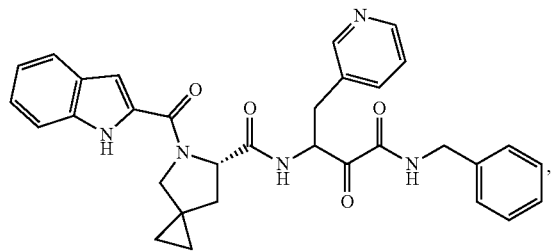
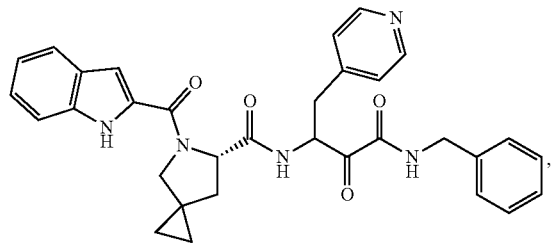
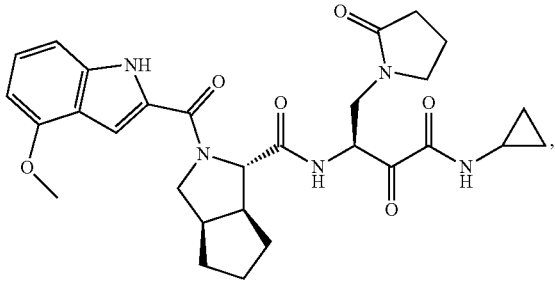
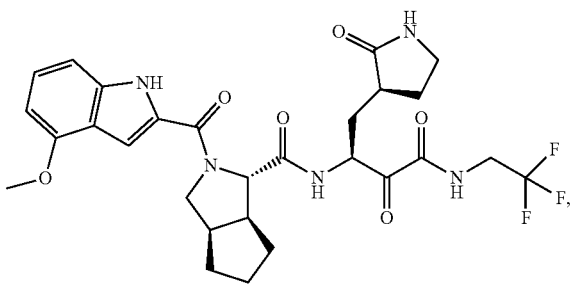
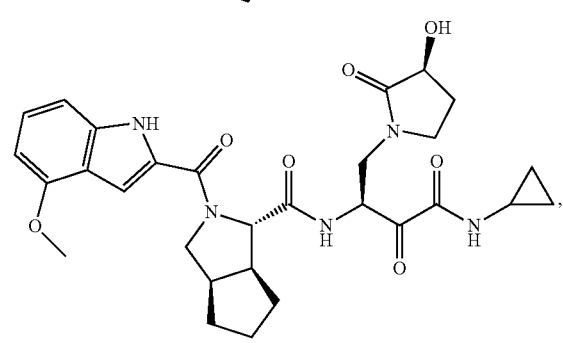
520
-continued
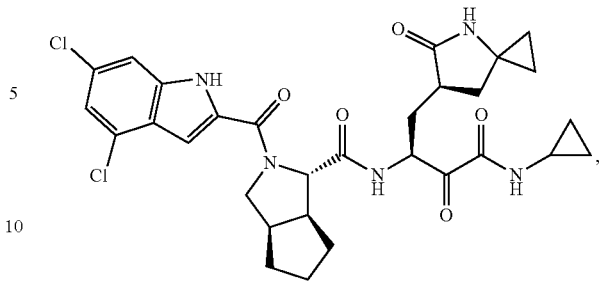
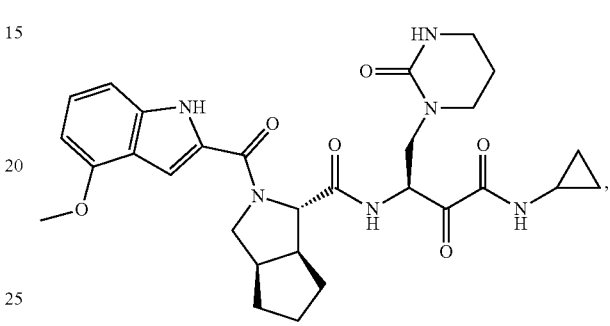
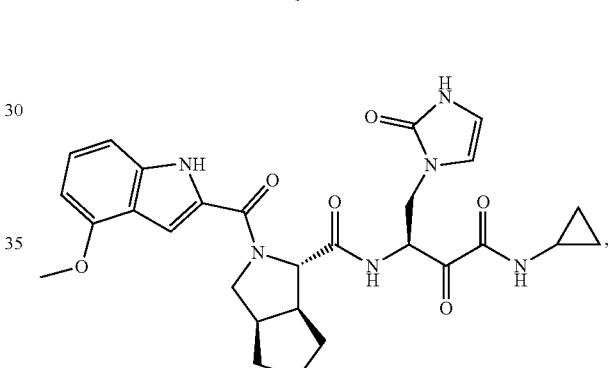
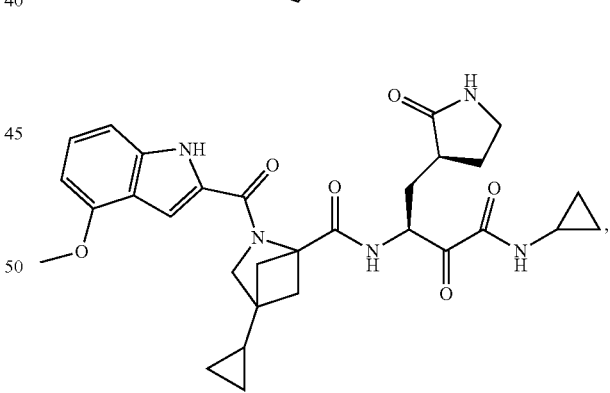
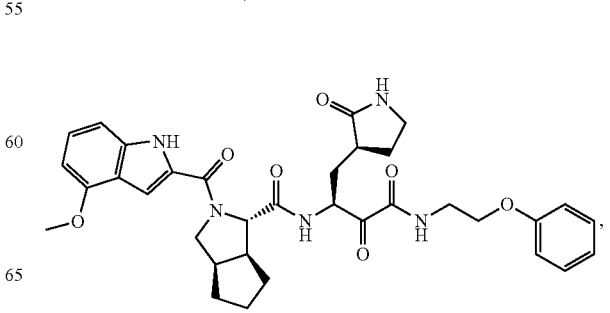

521
-continued
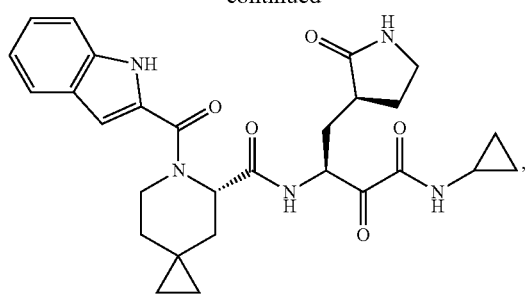
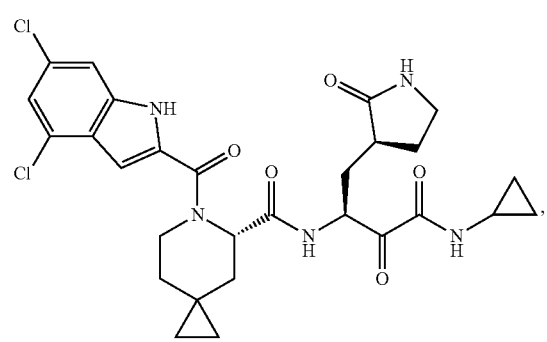
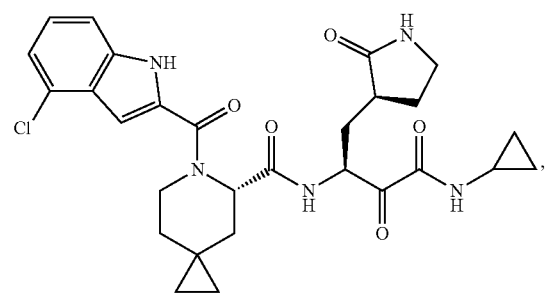
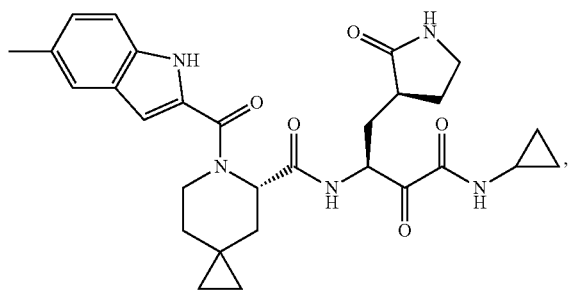
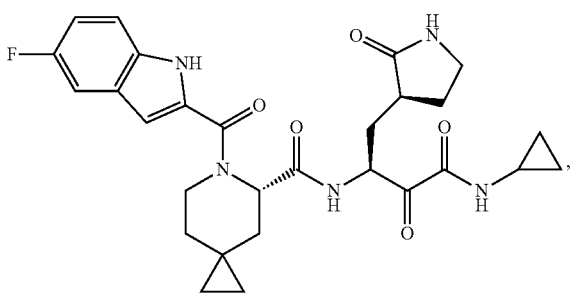
522
-continued
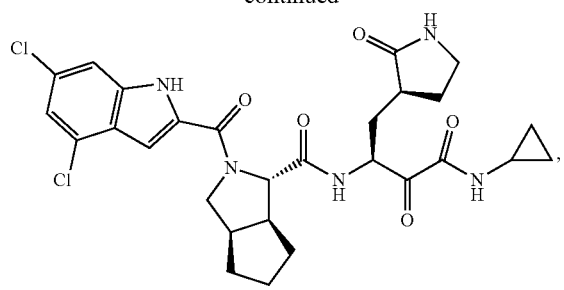
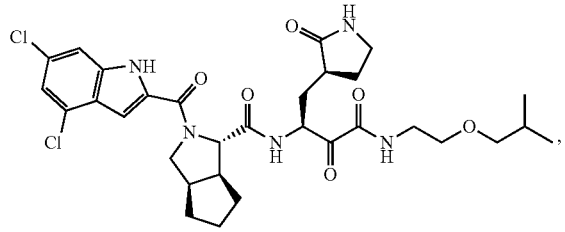
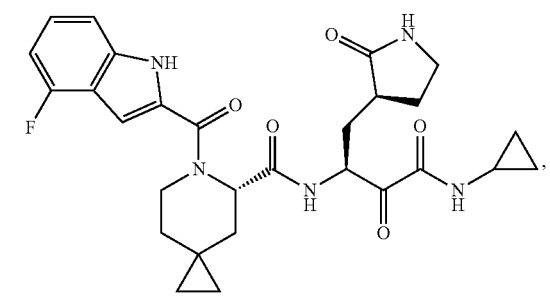
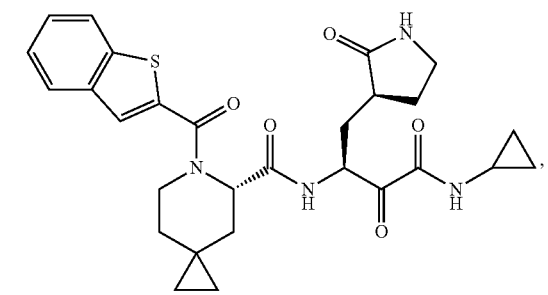
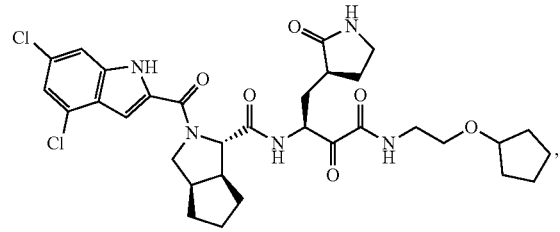
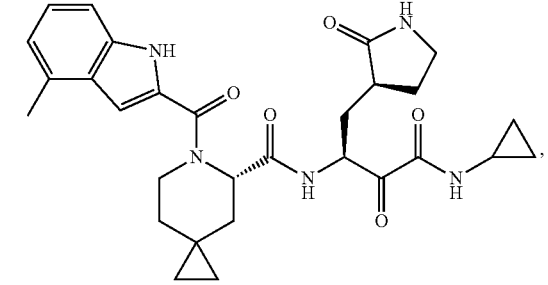

523
-continued
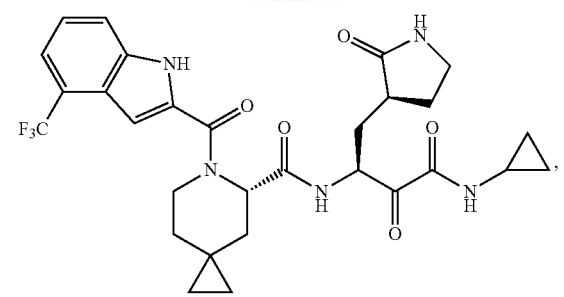
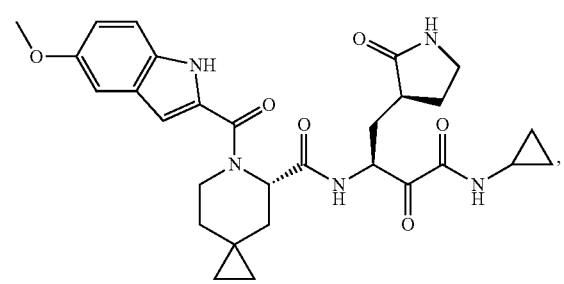
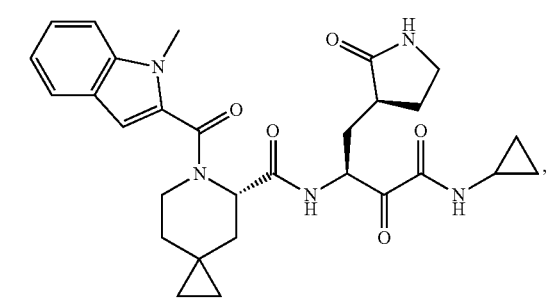
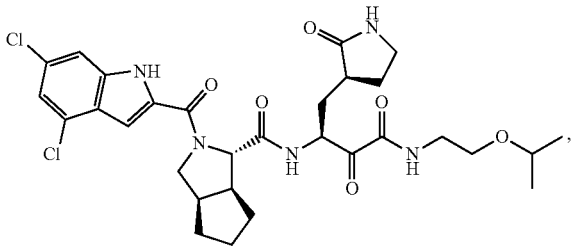
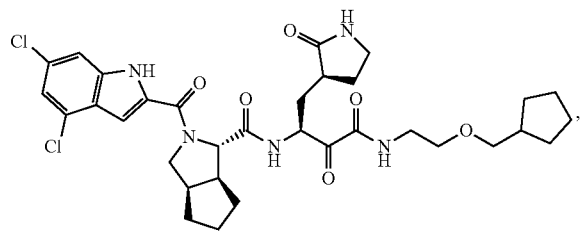
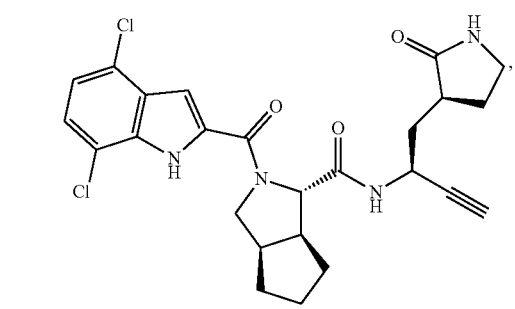
524
-continued
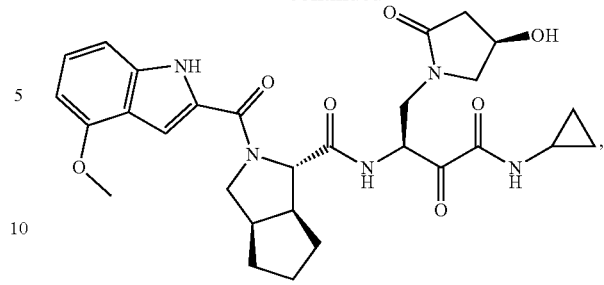
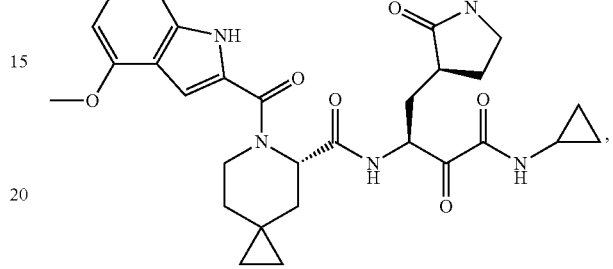
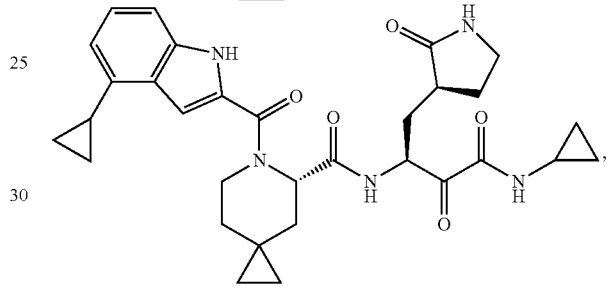
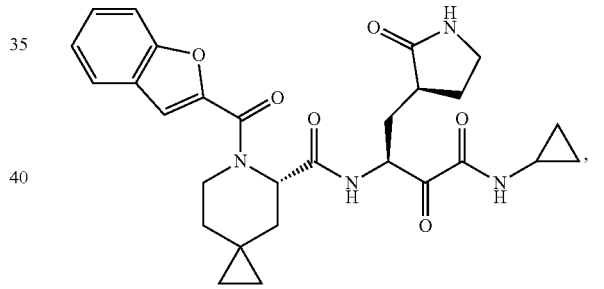
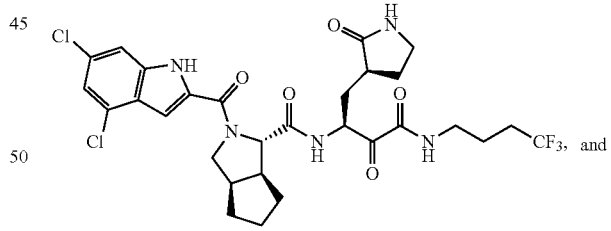
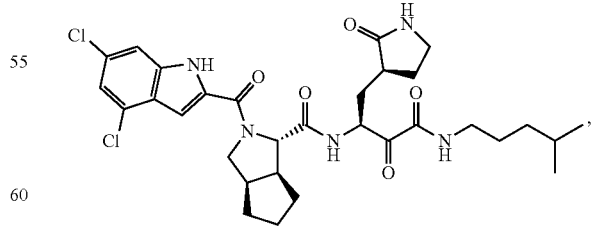
or pharmaceutically acceptable salt of any of the foregoing.
14. A pharmaceutical composition comprising an effective amount of a compound of claim 1, or a pharmaceutically acceptable salt thereof, and excipient.

15. A method for treating a coronavirus infection in a subject comprising administering to the subject in need thereof an effective amount of a compound of claim 1, or a pharmaceutically acceptable salt thereof.

16. The method of claim 15, further comprising administering an additional agent selected from the group consisting of an ACE inhibitor, an anticoagulant, an anti-inflammatory, an ARB, an ASO, a Covid-19 convalescent plasma, an entry inhibitor, an $H_2$ pump antagonist, an H-conducting channel, an HIV protease inhibitor, an HMG-CoA reductase inhibitor, an immune globulin, an immunosuppressant, an immunotherapeutic agent, a neuraminidase inhibitor, a nucleoside inhibitor, a nucleoside analog inhibitor, a polymerase inhibitor, a protease inhibitor, an siRNA, a statin, a tissue plasminogen activator, an antibiotic, an antimicrobial and a vaccine.

17. A method for treating a infection in a subject comprising administering to the subject in need thereof an effective amount of a compound of claim 1, or a pharmaceutically acceptable salt thereof, wherein the infection is selected from the group consisting of a picornavirus infection and a norovirus infection.

18. A method for inhibiting a coronavirus protease comprising contacting a cell infected with a coronavirus with an effective amount of a compound of claim 1, or a pharmaceutically acceptable salt thereof, wherein the compound, or a pharmaceutically acceptable salt thereof, selectively inhibits the coronavirus protease compared to a host protease.

* * * * *